US012679843B2

(12) United States Patent
Kotian et al.

(10) Patent No.: US 12,679,843 B2
(45) Date of Patent: Jul. 14, 2026

(54) PYRROLOPYRIMIDINE AMINES AS COMPLEMENT INHIBITORS

(71) Applicant: BioCryst Pharmaceuticals, Inc., Durham, NC (US)

(72) Inventors: Pravin L. Kotian, Hoover, AL (US); Yarlagadda S. Babu, Birmingham, AL (US); Minwan Wu, Vestavia Hills, AL (US); Zhao Dang, Vestavia Hills, AL (US); Trung Xuan Nguyen, Hoover, AL (US); Krishnan Raman, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 850 days.

(21) Appl. No.: 17/915,179

(22) PCT Filed: Apr. 2, 2021

(86) PCT No.: PCT/US2021/025547
§ 371 (c)(1),
(2) Date: Sep. 28, 2022

(87) PCT Pub. No.: WO2021/202977
PCT Pub. Date: Oct. 7, 2021

(65) Prior Publication Data

US 2023/0159536 A1 May 25, 2023

Related U.S. Application Data

(60) Provisional application No. 63/004,799, filed on Apr. 3, 2020.

(51) Int. Cl.

*C07D 487/04* (2006.01)
*C07D 401/14* (2006.01)
*C07D 471/04* (2006.01)
*C07D 471/14* (2006.01)

(52) U.S. Cl.
CPC ......... *C07D 487/04* (2013.01); *C07D 401/14* (2013.01); *C07D 471/04* (2013.01); *C07D 471/14* (2013.01)

(58) Field of Classification Search
CPC .. C07D 487/04; C07D 401/14; C07D 471/04; C07D 471/14
See application file for complete search history.

(56) References Cited

U.S. PATENT DOCUMENTS

| | | | |
|---|---|---|---|
| 5,106,873 | A | 4/1992 | O'Brien et al. |
| 5,756,517 | A | 5/1998 | Schohe-Loop et al. |
| 5,756,528 | A | 5/1998 | Anthony et al. |
| 5,767,116 | A | 6/1998 | Kerrigan et al. |
| 5,972,984 | A | 10/1999 | Anthony et al. |
| 6,080,870 | A | 6/2000 | Anthony et al. |
| 6,124,317 | A | 9/2000 | Bigge et al. |
| 6,124,323 | A | 9/2000 | Bigge et al. |
| 6,140,351 | A | 10/2000 | Arnaiz et al. |
| 6,194,409 | B1 | 2/2001 | van Boeckel et al. |
| 6,380,221 | B1 | 4/2002 | Arnaiz et al. |
| 6,498,185 | B1 | 12/2002 | Arnaiz et al. |
| 6,509,110 | B1 | 1/2003 | Salbeck et al. |
| 6,528,529 | B1 | 3/2003 | Brann et al. |
| 6,534,525 | B1 | 3/2003 | Bigge et al. |
| 6,562,817 | B1 | 5/2003 | Tanimoto et al. |
| 6,903,123 | B2 | 6/2005 | Burnett et al. |
| 6,943,175 | B2 | 9/2005 | Berge et al. |
| 6,969,711 | B2 | 11/2005 | Shibuya et al. |
| 6,995,268 | B2 | 2/2006 | Dutta |
| 7,012,077 | B2 | 3/2006 | Ackermann et al. |
| 7,125,896 | B2 | 10/2006 | Faull et al. |
| 7,129,264 | B2 | 10/2006 | Smallheer et al. |

(Continued)

FOREIGN PATENT DOCUMENTS

| | | |
|---|---|---|
| EP | 1502916 A1 | 2/2005 |
| FR | 3017386 B1 | 3/2016 |

(Continued)

OTHER PUBLICATIONS

Extended European Search Report for EP Application No. 21781014.2 dated Apr. 4, 2024.

Yang et al., "Buried hydrogen bond interactions contribute to the high potency of complement factor D inhibitors." ACS Medicinal Chemistry Letters 7(12) (2016): 1092-1096.

Makrides, "Therapeutic Inhibition of the Complement System", Pharmacological Reviews, 50(1): 59-88, (1998).

(Continued)

*Primary Examiner* — Timothy R Rozof

(74) *Attorney, Agent, or Firm* — Foley Hoag LLP; Dana M. Gordon; Laura A. Wzorek

(57) ABSTRACT

Disclosed are compounds of formula (I), and pharmaceutically acceptable salts thereof, which are inhibitors of the complement system. Also provided are pharmaceutical compositions comprising such a compound, and methods of using the compounds and compositions in the treatment or prevention of a disease or condition characterized by aberrant complement system activity.

(I)

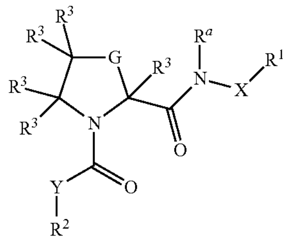

57 Claims, No Drawings

(56) References Cited

U.S. PATENT DOCUMENTS 7,138,412 B2 11/2006 Quan et al.
7,220,757 B2 5/2007 Berge et al.
7,485,651 B2 2/2009 Brann et al.
7,498,326 B2 3/2009 Axten et al.
7,501,418 B2 3/2009 Andres-Gil et al.
7,517,875 B2 4/2009 Matsumoto et al.
7,622,481 B2 11/2009 Axten et al.
7,648,980 B2 1/2010 Miller et al.
7,655,648 B2 2/2010 Miller et al.
7,691,850 B2 4/2010 Miller et al.
7,709,472 B2 5/2010 Miller et al.
7,709,646 B2 5/2010 Quan et al.
7,956,084 B2 6/2011 Faull et al.
8,017,791 B2 9/2011 Dutta
8,278,311 B2 10/2012 Liu et al.
8,278,313 B2 10/2012 Liu et al.
8,362,277 B2 1/2013 McKnight et al.
8,383,637 B2 2/2013 Baxter et al.
8,426,429 B2 4/2013 Baxter et al.
8,436,006 B2 5/2013 Bischoff et al.
8,546,407 B2 10/2013 Berdini et al.
8,604,074 B2 12/2013 McKnight et al.
8,673,940 B2 3/2014 Froestl et al.
8,735,411 B2 5/2014 Altenbach et al.
8,735,440 B2 5/2014 McKnight et al.
8,748,473 B2 6/2014 McKnight et al.
8,765,740 B2 7/2014 Li et al.
8,791,149 B2 7/2014 McKnight et al.
8,809,336 B2 8/2014 Berdini et al.
8,841,464 B2 9/2014 Dutta
8,877,797 B2 11/2014 McKnight et al.
8,889,669 B2 11/2014 Li et al.
9,006,177 B2 4/2015 Barawkar et al.
9,006,430 B2 4/2015 Berdini et al.
9,085,555 B2 7/2015 Altmann et al.
9,095,571 B2 8/2015 McKnight et al.
9,095,572 B2 8/2015 McKnight et al.
9,156,787 B2 10/2015 McKnight et al.
9,162,980 B2 10/2015 McKnight et al.
9,169,272 B2 10/2015 Li et al.
9,243,281 B2 1/2016 McKnight et al.
9,249,102 B2 2/2016 Meng et al.
9,278,923 B2 3/2016 McKnight et al.
9,353,127 B2 5/2016 Fishkin et al.
9,434,748 B2 9/2016 Li et al.
9,446,042 B2 9/2016 McKnight et al.
9,447,078 B2 9/2016 Kuksa et al.
9,534,000 B2 1/2017 Chari
9,616,048 B2 4/2017 McKnight et al.
9,645,139 B2 5/2017 McKnight et al.
9,840,564 B2 12/2017 Li et al.
9,868,791 B2 1/2018 Fishkin et al.
9,878,975 B2 1/2018 Kadyrov
9,884,820 B2 2/2018 McKnight et al.
9,902,713 B2 2/2018 McKnight et al.
9,962,368 B2 5/2018 McKnight et al.
10,023,602 B2 7/2018 Coenye et al.
10,077,271 B2 9/2018 Grembecka et al.
10,092,584 B2 * 10/2018 Wiles .................. A61K 31/549
10,155,725 B2 12/2018 Meng et al.
10,172,827 B2 1/2019 McKnight et al.
10,174,041 B2 1/2019 Grembecka et al.
10,179,818 B2 1/2019 Li et al.
10,183,011 B2 1/2019 McKnight et al.
2003/0144285 A1 7/2003 Brann et al.
2003/0186984 A1 10/2003 Ackermann et al.
2003/0195185 A1 10/2003 Burnett et al.
2003/0225133 A1 12/2003 Dutta
2004/0038987 A1 2/2004 Shibuya et al.
2004/0147548 A1 7/2004 Berge et al.
2004/0157822 A1 8/2004 Burnett et al.
2004/0220206 A1 11/2004 Smallheer et al.
2004/0235847 A1 11/2004 Quan et al.
2004/0242573 A1 12/2004 Faull et al.
2005/0119266 A1 6/2005 Shi et al.
2005/0197350 A1 9/2005 Sekiguchi et al.
2006/0014748 A1 1/2006 Berge et al.
2006/0058287 A1 3/2006 Axten et al.
2006/0074103 A1 4/2006 Corte et al.
2006/0079686 A1 4/2006 Baxter et al.
2006/0079687 A1 4/2006 Baxter et al.
2006/0116378 A1 6/2006 Andres-Gil et al.
2006/0122263 A1 6/2006 Dutta
2006/0178383 A1 8/2006 Bischoff et al.
2006/0189604 A1 8/2006 Axten et al.
2006/0223854 A1 10/2006 Quan et al.
2007/0010671 A1 1/2007 Sekiguchi et al.
2007/0015819 A1 1/2007 Faull et al.
2007/0032525 A1 2/2007 Matsumoto et al.
2007/0185079 A1 8/2007 Evertsson et al.
2007/0213362 A1 9/2007 Berge et al.
2007/0244091 A1 10/2007 Miller et al.
2007/0254872 A1 11/2007 Miller et al.
2007/0270417 A1 11/2007 Miller et al.
2007/0287701 A1 12/2007 Miller et al.
2008/0090863 A1 4/2008 Sekiguchi et al.
2008/0108618 A1 5/2008 Brann et al.
2008/0146551 A1 6/2008 Miller et al.
2008/0167478 A1 7/2008 Dutta
2008/0188452 A1 8/2008 Altenbach et al.
2008/0234256 A1 9/2008 Miller et al.
2008/0255155 A1 10/2008 Raeppel et al.
2008/0255213 A1 10/2008 Miller et al.
2009/0036448 A1 2/2009 Sekiguchi et al.
2009/0042874 A1 2/2009 Failli et al.
2009/0233904 A1 9/2009 Liu et al.
2009/0247538 A1 10/2009 Berdini et al.
2009/0270364 A1 10/2009 Liu et al.
2010/0069417 A1 3/2010 Bouaboula et al.
2010/0081650 A1 4/2010 Axten et al.
2010/0093668 A1 4/2010 Babin et al.
2010/0099694 A1 4/2010 Babin et al.
2010/0160626 A1 6/2010 Anderson et al.
2010/0183513 A1 7/2010 Froestl et al.
2011/0152234 A1 6/2011 Faull et al.
2012/0004428 A1 1/2012 Dutta
2012/0022096 A1 1/2012 McKnight et al.
2012/0122923 A1 5/2012 Cosledan et al.
2012/0238731 A1 9/2012 Fishkin et al.
2012/0244171 A1 9/2012 Li et al.
2012/0295884 A1 11/2012 Altmann et al.
2012/0309791 A1 12/2012 Froestl et al.
2013/0040977 A1 2/2013 McKnight et al.
2013/0184300 A1 7/2013 McKnight et al.
2013/0184301 A1 7/2013 McKnight et al.
2013/0190273 A1 7/2013 McKnight et al.
2013/0190339 A1 7/2013 McKnight et al.
2013/0225619 A1 8/2013 Kuksa et al.
2013/0252885 A1 9/2013 Dinesh et al.
2013/0302359 A1 11/2013 Li et al.
2014/0031547 A1 1/2014 Sheridan et al.
2014/0039187 A1 2/2014 Shim et al.
2014/0088089 A1 3/2014 Chari
2014/0094480 A1 4/2014 McKnight et al.
2014/0107137 A1 4/2014 Berdini et al.
2014/0142114 A1 5/2014 Meng et al.
2014/0303177 A1 10/2014 Berdini et al.
2014/0343018 A1 11/2014 McKnight et al.
2015/0057301 A1 2/2015 McKnight et al.
2015/0099874 A1 4/2015 Li et al.
2015/0126656 A1 5/2015 Park et al.
2015/0132783 A1 5/2015 McKnight et al.
2015/0290195 A1 10/2015 McKnight et al.
2016/0002174 A1 1/2016 Shim et al.
2016/0074361 A1 3/2016 McKnight et al.
2016/0108129 A1 4/2016 Li et al.
2016/0185726 A1 6/2016 Meng et al.
2016/0206594 A1 7/2016 McKnight et al.
2016/0206596 A1 7/2016 McKnight et al.
2016/0229834 A1 8/2016 Halby et al.
2016/0272571 A1 9/2016 Kadyrov
2016/0272619 A1 9/2016 McKnight et al.
2016/0324980 A1 11/2016 Fishkin et al.
2016/0354375 A1 12/2016 Sheridan et al.

(56) References Cited

U.S. PATENT DOCUMENTS

| | | | |
|---|---|---|---|
| 2016/0362372 A1 | 12/2016 | McKnight et al. |
| 2016/0362373 A1 | 12/2016 | McKnight et al. |
| 2017/0030897 A1 | 2/2017 | McKnight et al. |
| 2017/0044266 A1 | 2/2017 | Li et al. |
| 2017/0157092 A1 | 6/2017 | McKnight et al. |
| 2017/0158727 A1 | 6/2017 | Coenye et al. |
| 2017/0307592 A1 | 10/2017 | McKnight et al. |
| 2018/0002440 A1 | 1/2018 | Li et al. |
| 2018/0037659 A1 | 2/2018 | Fishkin et al. |
| 2018/0105531 A1 | 4/2018 | Grembecka et al. |
| 2018/0118717 A1 | 5/2018 | Halby et al. |
| 2018/0243303 A1 | 8/2018 | Grembecka et al. |
| 2018/0318255 A1 | 11/2018 | McKnight et al. |
| 2018/0327414 A1 | 11/2018 | Grembecka et al. |
| 2019/0023656 A1 | 1/2019 | Holson et al. |
| 2019/0092784 A1 | 3/2019 | Wu et al. |
| 2019/0218203 A1 | 7/2019 | McKnight et al. |

FOREIGN PATENT DOCUMENTS

| | | | |
|---|---|---|---|
| GB | 2245582 | A | 1/1992 |
| JP | H11292840 | A | 10/1999 |
| JP | 2007/91649 | A | 4/2007 |
| JP | 2007/291087 | A | 11/2007 |
| WO | WO-95/07274 | A1 | 3/1995 |
| WO | WO-97/23215 | A1 | 7/1997 |
| WO | WO-97/23216 | A1 | 7/1997 |
| WO | WO-97/36875 | A1 | 10/1997 |
| WO | WO-97/36876 | A1 | 10/1997 |
| WO | WO-98/47876 | A1 | 10/1998 |
| WO | WO-9854153 | A1 | 12/1998 |
| WO | WO-99/19419 | A1 | 4/1999 |
| WO | WO-99/32477 | A1 | 7/1999 |
| WO | WO-9938829 | A1 | 8/1999 |
| WO | WO-99/50247 | A1 | 10/1999 |
| WO | WO-00/71522 | A1 | 11/2000 |
| WO | WO-01/05763 | A2 | 1/2001 |
| WO | WO-01/22963 | A1 | 4/2001 |
| WO | WO-03/010158 | A1 | 2/2003 |
| WO | WO-03/043980 | A1 | 5/2003 |
| WO | WO-03/053933 | A1 | 7/2003 |
| WO | WO-2003087089 | A1 | 10/2003 |
| WO | WO-2004/002490 | A2 | 1/2004 |
| WO | WO-2004/002992 | A1 | 1/2004 |
| WO | WO-2004/018483 | A1 | 3/2004 |
| WO | WO-2004/052288 | A2 | 6/2004 |
| WO | WO-2004/080971 | A1 | 9/2004 |
| WO | WO-2004/087680 | A1 | 10/2004 |
| WO | WO-2004087669 | A1 | 10/2004 |
| WO | WO-2004/094372 | A2 | 11/2004 |
| WO | WO-2004/099127 | A1 | 11/2004 |
| WO | WO-2005/032472 | A2 | 4/2005 |
| WO | WO-2005/066132 | A1 | 7/2005 |
| WO | WO-2005/095357 | A2 | 10/2005 |
| WO | WO-2005/105075 | A1 | 11/2005 |
| WO | WO-2006/002047 | A2 | 1/2006 |
| WO | WO-2006/012396 | A1 | 2/2006 |
| WO | WO-2006/014580 | A1 | 2/2006 |
| WO | WO-2006/017468 | A2 | 2/2006 |
| WO | WO-2006/017836 | A2 | 2/2006 |
| WO | WO-2006/017844 | A1 | 2/2006 |
| WO | WO-2006/024932 | A1 | 3/2006 |
| WO | WO-2006/035967 | A1 | 4/2006 |
| WO | WO-2006/041831 | A2 | 4/2006 |
| WO | WO-2006/046024 | A1 | 5/2006 |
| WO | WO-2006/074428 | A2 | 7/2006 |
| WO | WO-2006/081178 | A2 | 8/2006 |
| WO | WO-2006/081179 | A1 | 8/2006 |
| WO | WO-2006/137769 | A1 | 12/2006 |
| WO | WO-2007/140222 | A2 | 12/2007 |
| WO | WO-2007/144487 | A2 | 12/2007 |
| WO | WO-2008/046216 | A1 | 4/2008 |
| WO | WO-2008/060767 | A2 | 5/2008 |
| WO | WO-2008/061795 | A2 | 5/2008 |
| WO | WO-2008/099073 | A1 | 8/2008 |
| WO | WO-2008/099074 | A1 | 8/2008 |
| WO | WO-2008/099075 | A1 | 8/2008 |
| WO | WO-2008/128179 | A1 | 10/2008 |
| WO | WO-2008/150848 | A1 | 12/2008 |
| WO | WO-2009/056693 | A1 | 5/2009 |
| WO | WO-2009/071553 | A1 | 6/2009 |
| WO | WO-2009/106980 | A2 | 9/2009 |
| WO | WO-2009/114575 | A1 | 9/2009 |
| WO | WO-2009134726 | A1 | 11/2009 |
| WO | WO-2010/020675 | A1 | 2/2010 |
| WO | WO-2012/006419 | A2 | 1/2012 |
| WO | WO-2012/038980 | A2 | 3/2012 |
| WO | WO-2012/080729 | A2 | 6/2012 |
| WO | WO-2012/093101 | A1 | 7/2012 |
| WO | WO-2012/112687 | A1 | 8/2012 |
| WO | WO-2012/112708 | A1 | 8/2012 |
| WO | WO-2012/128868 | A1 | 9/2012 |
| WO | WO-2013/109991 | A1 | 7/2013 |
| WO | WO-2013/165193 | A1 | 11/2013 |
| WO | WO-2014/002057 | A1 | 1/2014 |
| WO | WO-2014/031125 | A1 | 2/2014 |
| WO | WO-2014081697 | A2 | 5/2014 |
| WO | WO-2015/040169 | A1 | 3/2015 |
| WO | WO-2015/067450 | A1 | 5/2015 |
| WO | WO-2015/070234 | A2 | 5/2015 |
| WO | WO-2015/070237 | A1 | 5/2015 |
| WO | WO-2016/005340 | A1 | 1/2016 |
| WO | WO-2016/100823 | A1 | 6/2016 |
| WO | WO-2016/107603 | A1 | 7/2016 |
| WO | WO-2016/123146 | A1 | 8/2016 |
| WO | WO-2016/151144 | A1 | 9/2016 |
| WO | WO-2016/195776 | A1 | 12/2016 |
| WO | WO-2016/196393 | A2 | 12/2016 |
| WO | WO-2016/197027 | A1 | 12/2016 |
| WO | WO-2017/035351 | A1 | 3/2017 |
| WO | WO-2017/098328 | A2 | 6/2017 |
| WO | WO-2017/161028 | A1 | 9/2017 |
| WO | WO-2018/065387 | A1 | 4/2018 |
| WO | WO-2018/086605 | A1 | 5/2018 |
| WO | WO-2018/160891 | A1 | 9/2018 |
| WO | WO-2018/226976 | A1 | 12/2018 |
| WO | WO-2018/229543 | A2 | 12/2018 |
| WO | WO-2019/008507 | A1 | 1/2019 |
| WO | WO-2019/079783 | A1 | 4/2019 |
| WO | WO-2019/123482 | A1 | 6/2019 |
| WO | WO-2019/195720 | A1 | 10/2019 |
| WO | WO-2019/227102 | A1 | 11/2019 |
| WO | WO-2020/041301 | A1 | 2/2020 |
| WO | WO-2020/051532 | A2 | 3/2020 |
| WO | WO-2020/069024 | A1 | 4/2020 |
| WO | WO-2021/202977 | A1 | 10/2021 |

OTHER PUBLICATIONS

Nilsson et al., "Compounds binding to the S2—S3 pockets of thrombin", *Journal of medicinal chemistry* 52.9: 2708-2715 (2009).
Partial European Search Report for EP Application No. 21781014.2 dated Mar. 11, 2024.
Stauffer et al., "9-hydroxyazafluorenes and their use in thrombin inhibitors", *Journal of medicinal chemistry* 48.7: 2282-2293 (2005).
CAS RN 1315662-90-8 Registry: Entered STN: Aug. 10, 2011; 2-Pyrrolidinecarboxamide, 1-[2-(2-amino-5,7-dimethyl[1,2,4]triazolo[1,5-a]pyrimidin-6-yl)acetyl]-N-(4-methoxyphenyl)-(CA Index Name).
International Search Report and Written Opinion for International Application No. PCT/US21/25547 mailed Aug. 9, 2021.
Invitation to Pay Additional Fees for International Application No. PCT/US21/25547 mailed Jun. 11, 2021.
PubChem SID: 379307159 (7 pages) (Jan. 24, 2019).
Zelek et al., "Compendium of current complement therapeutics," Molecular Immunology, 114: 341-352 (2019).
Shaabani et al., "Automated and accelerated synthesis of indole derivatives on a nano-scale." Green Chemistry 21.2 (2019): 225-232.
Brady et al., "Discovery and development of the novel potent orally active thrombin inhibitor N-(9-hydroxy-9-fluorenecarboxy) prolyl

(56) References Cited

OTHER PUBLICATIONS trans-4-aminocyclohexylmethyl amide (L-372,460): coapplication of structure-based design and rapid multiple analogue synthesis on solid support." Journal of Medicinal Chemistry 41(3) (1998): 401-406.
CAS RN, 1309078-61-2, Entered STN: Jun. 13, 2011.
CAS RN, 1331951-25-7, Entered STN: Sep. 13, 2011.
Lee et al., "Development of small-molecule Cryptochrome stabilizer derivatives as modulators of the circadian clock." ChemMedChem 10(9) (2015): 1489-1497.
Lee et al., "Development of small-molecule Cryptochrome stabilizer derivatives as modulators of the circadian clock." ChemMedChem 10(9) (2015): 26 pages (Supporting Information).
Database Registry CAS, Accession No. RN 1276833-91-0, Entered STN: Apr. 8, 2011.
Database Registry CAS, Accession No. RN 1277027-26-5, Entered STN: Apr. 8, 2011.
Database Registry CAS, Accession No. RN 1277035-51-4, Entered STN: Apr. 8, 2011.
Database Registry CAS, Accession No. RN 1277065-65-2, Entered STN: Apr. 8, 2011.
Database Registry CAS, Accession No. RN 1315960-90-7, Entered STN: Aug. 11, 2011.
Database Registry CAS, Accession No. RN 1315988-51-2, Entered STN: Aug. 11, 2011.
Database Registry CAS, Accession No. RN 1348652-40-3, Entered STN: Dec. 4, 2011.
Database Registry CAS, Accession No. RN 1349237-82-6, Entered STN: Dec. 5, 2011.
Database Registry CAS, Accession No. RN 1798894-59-3, Entered STN: Jul. 12, 2015.
Database Registry CAS, Accession No. RN 2174039-78-0, Entered STN: Feb. 15, 2018.
Database Registry CAS, Accession No. RN 2174574-92-4, Entered STN: Feb. 16, 2018.
CAS RN 1801857-12-4, Entered STN: Aug. 12, 2015.
CAS RN 247264-14-8, Entered STN: Nov. 18, 1999.

* cited by examiner

PYRROLOPYRIMIDINE AMINES AS COMPLEMENT INHIBITORS

RELATED APPLICATIONS

This application is a U.S. National Stage Application of International Application No. PCT/US2021/025547, filed Apr. 2, 2021; which claims the benefit of priority to U.S. Provisional Patent Application Ser. No. 63/004,799, filed Apr. 3, 2020.

BACKGROUND OF THE INVENTION

The complement system is a branch of an organism's immune system that enhances the ability of antibodies and phagocytic cells to destroy and remove foreign particles (e.g., pathogens) from the organism. The complement system comprises a set of plasma proteins that act together to attack extracellular forms of pathogens and induce a series of inflammatory responses to help fight infection. Complement activation can occur through several pathways. For example, complement activation can occur spontaneously in response to certain pathogens or by antibody binding to a pathogen. When complement proteins are activated a cascade is triggered by which one complement protein induces the activation of the next protein in the sequence. The activation of a small number of complement proteins at the start of the pathway is hugely amplified by each successive enzymatic reaction, resulting in the rapid generation of a disproportionately large complement response. (Marrides, S. *Pharmacological Reviews* 1998, Vol. 50, pages 59-88). In healthy organisms there are regulatory mechanisms to prevent uncontrolled complement activation.

When activated, complement proteins can bind to a pathogen, opsonizing them for engulfment by phagocytes bearing receptors for complement. Then, small fragments of some complement proteins act as chemoattractants to recruit more phagocytes to the site of complement activation, and also to activate these phagocytes. Next, the complement proteins create holes or pores in the invading organisms, leading to their destruction. While complement plays an important role in protecting the body from foreign organisms, it can also destroy healthy cells and tissue. The inappropriate activation of complement is implicated in a long list of disease pathologies (Morgan, B. *Eur J Clin Invest* 1994, Vol. 24, pages 219-228) affecting the immune, renal, cardiovascular, and neurological systems. Accordingly, there exists a need to develop further complement inhibitors, which have therapeutic potential in the treatment of numerous disorders.

SUMMARY OF THE INVENTION

In certain aspects, the invention provides compounds having the structure of formula (I), and pharmaceutically acceptable salts thereof:

(I)

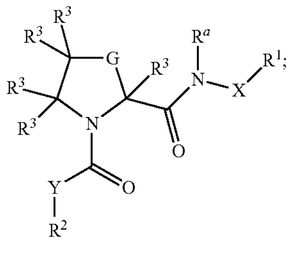

wherein, independently for each occurrence:

X is a bond or $C(R^X)_2$;

Y is a bond, $C(R^Y)_2$, or —$N(R^b)$—;

G is S or $C(R^3)_2$;

$R^a$ and $R^b$ are each independently H or $(C_1\text{-}C_6)$alkyl;

$R^1$ represents optionally substituted aryl, heteroaryl, alkyl, cycloalkyl, alkenyl, or cycloalkenyl;

$R^2$ represents optionally substituted bicyclic or tricyclic heteroaryl;

$R^3$ is independently for each occurrence H, halogen, —CN, —$NH_2$, —$CH_2NH_2$, $(C_1\text{-}C_6)$alkoxy or $(C_1\text{-}C_6)$ alkyl; or two vicinal occurrences of $R^3$ taken together with the carbon atoms to which they are bonded form an optionally substituted fused $(C_3\text{-}C_2)$cycloalkyl or $(C_6)$aryl; or two geminal occurrences of $R^3$ taken together with the carbon atom to which they are bonded form an optionally substituted spiro $(C_3\text{-}C_7)$cycloalkyl; or two hominal occurrences of $R^3$ taken together with the carbon atoms to which they are bonded form an optionally substituted bridged $(C_3\text{-}C_7)$cycloalkyl;

$R^X$ is independently for each occurrence H, $(C_1\text{-}C_6)$alkyl, or $(C_3\text{-}C_7)$cycloalkyl;

$R^Y$ is independently for each occurrence H, $(C_1\text{-}C_6)$alkyl, or $(C_3\text{-}C_7)$cycloalkyl; or an occurrence of $R^Y$ and a substituent on $R^2$ taken together with the intervening atoms form a ring;

optional substituents on $R^1$ or $R^2$ each independently represent halogen, —CN, —$NO_2$, —$OR^{13}$, —$NR^{13}R^{14}$, —$C(O)R^{13}$, —$C(O)OR^{13}$, —$C(O)NR^{13}R^{14}$, —$OC(O)R^{13}$, —$NR^{13}C(O)R^{14}$, —$OC(O)NR^{13}R^{14}$, —$OC(O)OR^{13}$, —$NR^{13}C(O)OR^{14}$, —$NR^{13}C(O)NR^{13}R^{14}$, —$OS(O)_p(R^{13})$, —$SR^{13}$, —$NR^{13}S(O)_p(R^{14})$, or optionally substituted alkyl, alkenyl, alkynyl, haloalkyl, hydroxyalkyl, alkoxyalkyl, cycloalkoxyalkyl, aryloxyalkyl, aralkyl, heteroaralkyl, heteroaryl, aryl, aryloxy, cycloalkyl, (cycloalkyl)alkyl, heterocycloalkyl, or (heterocycloalkyl)alkyl;

or wherein two substituents on $R^1$ or two substituents on $R^2$, taken together with the intervening atoms, form a ring;

$R^{13}$ and $R^{14}$, independently for each occurrence, represent H or optionally substituted alkyl, haloalkyl, alkenyl, alkynyl, aryl, or heteroaryl; and p is 0, 1, or 2.

In certain aspects, the invention provides a pharmaceutical composition, comprising a compound of the invention, or a pharmaceutically acceptable salt thereof; and a pharmaceutically acceptable carrier.

In certain aspects, the invention provides methods of treating a disease or condition characterized by aberrant complement system activity, comprising administering to a subject in need thereof a therapeutically effective amount of a compound the invention, or a pharmaceutically acceptable salt thereof. In certain embodiments, the disease or condition characterized by aberrant complement system activity is an immunological disorder. In certain embodiments, the disease or condition characterized by aberrant complement system activity is a disease of the central nervous system. In certain embodiments, the disease or condition characterized by aberrant complement system activity is a neurodegenerative disease or neurological disease. In certain embodiments, the disease or condition characterized by aberrant complement system activity is a renal disease. In certain embodiments, the disease or condition characterized by aberrant complement system activity is a cardiovascular disease. In certain embodiments, the disease or condition characterized by aberrant complement system activity is a cardiometabolic disease. In certain embodiments, the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, and catastrophic antiphospholipid syndrome. In certain other aspects, the disease or condition characterized by aberrant complement system activity is selected from the group consisting of adult respiratory distress syndrome, myocardial infarct, lung inflammation, sepsis, cardiopulmonary bypass, burns, asthma, restenosis, multiple organ dysfunction, Guillain-Barre syndrome, hemorrhagic shock, glomerulonephritis, systemic lupus erythematosus, rheumatoid arthritis, infertility, Alzheimer's disease, multiple sclerosis, platelet storage, and hemodialysis. In certain other aspects, the disease or condition characterized by aberrant complement system activity is selected from the group consisting of antineutrophil cytoplasmic antibody (ANCA)-associated vasculitis (AAV), warm autoimmune hemolytic anemia, IgA nephropathy, C3 glomerulonephritis, and focal segmental glomerulosclerosis. In further aspects, the disease or condition characterized by aberrant complement system activity is a hematological disorder. In further aspects, the disease or condition characterized by aberrant complement system activity is an ocular disorder or an eye disorder. In still further aspects, the disease or condition characterized by aberrant complement system activity is macular degeneration, age-related macular degeneration (AMD), wet AMD, geographic atrophy, macular edema, diabetic macular edema, choroidal neovascularization (CNV), uveitis, Behcet's uveitis, proliferative diabetic retinopathy, non-proliferative diabetic retinopathy, glaucoma, hypertensive retinopathy, a corneal neovascularization disease, post-corneal transplant rejection, a corneal dystrophic disease, an autoimmune dry eye disease, Stevens-Johnson syndrome, Sjogren's syndrome, an environmental dry eye disease, Fuchs' endothelial dystrophy, retinal vein occlusion, or post-operative inflammation. In certain other aspects, the disease or condition characterized by aberrant complement system activity is selected from the group consisting of obesity, insulin resistance, diabetes, dyslipidemia, nephropathy, neuropathy, angioedema, e.g., hereditary angioedema or acquired angioedema, thrombotic microangiopathy, Parkinson's disease, schizophrenia, periodontitis, Crohn's disease, C3 glomerulopathy, membranous nephropathy, osteoarthritis, bullous pemphigoid, psoriasis, hidradenitis suppurativa, of ischemia/reperfusion injury, acute kidney injury, and organ transplantation, e.g., kidney transplant, systemic inflammatory response syndrome, septic shock, trauma, cancer, antibody-mediated rejection, Berger's disease, delayed graft function, granulomatosis with polyangiitis, graft versus host disease, hematopoietic stem cell transplant-related thrombotic microangiopathy, immune complex-mediated membranoproliferative glomerulonephritis, immune-mediated necrotizing myopathy, idiopathic polypoidal choroidal vasculopathy, microscopic polyangiitis, pyoderma gangrenosum, and Stargardt Disease 1.

DETAILED DESCRIPTION

Inhibitors of the complement system are useful in therapeutic methods and compositions suitable for use in treating disorders of the immune, renal, cardiovascular, and neurological systems. Provided herein are compounds of formula (I) and pharmaceutically acceptable salts thereof that are useful in treating or preventing a disease or condition characterized by aberrant activity of the complement system.

Definitions

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium, and alternatively oxygen, nitrogen or sulfur.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ alkyl group. In certain embodiments, the term "alkyl" refers to a $C_1$-$C_6$ alkyl group, for example a $C_1$-$C_6$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" means mono- or bicyclic or bridged saturated carbocyclic rings, each having from 3 to 12 carbon atoms. Certain cycloalkyls have from 5-12 carbon atoms in their ring structure, and may have 6-10 carbons in the ring structure. Preferably, cycloalkyl is ($C_3$-$C_7$)cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form $-(CH_2)_w-$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "(cycloalkyl)alkyl" as used herein refers to an alkyl group substituted with one or more cycloalkyl groups. An example of cycloalkylalkyl is cyclohexylmethyl group.

The term "heterocycloalkyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this invention, the following are examples of heterocyclic rings; aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2-azobicyclo[3.1.0]hexane. A heterocycloalkyl group is optionally substituted by one or more substituents as described below.

The term "(heterocycloalkyl)alkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, arylalkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

 and 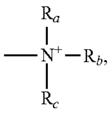, wherein $R_a$, $R_b$, and $R_c$ each independently represent a hydrogen, an alkyl, an alkenyl, $—(CH_2)_x—R_d$, or $R_a$ and $R_b$, taken together with the N atom to which they are attached complete a heterocycle having from 4 to 8 atoms in the ring structure. $R_d$ represents an aryl, a heteroaryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or $—(CH_2)_x—R_d$. In certain embodiments, $R_a$ and $R_b$ are each independently selected from hydrogen, alkyl, alkenyl, alkynyl, aryl, heteroaryl, cycloalkyl, cycloalkenyl, heterocycloalkyl, heterocycloalkenyl, (cycloalkyl)alkyl, (heterocycloalkyl)alkyl, arylalkyl, heteroarylalkyl, alkoxyalkyl, or haloalkyl, any of which may be further substituted (e.g., by halogen, alkyl, alkoxy, hydroxy, and so forth). In certain embodiments, the term "amino" refers to $—NH_2$.

In certain embodiments, the term "alkylamino" refers to —NH(alkyl).

In certain embodiments, the term "dialkylamino" refers to $—N(alkyl)_2$.

The term "amido", as used herein, means —NHC(═O)—, wherein the amido group is bound to the parent molecular moiety through the nitrogen. Examples of amido include alkylamido such as $CH_3C(═O)N(H)—$ and $CH_3CH_2C(═O)N(H)—$.

The term "acyl" is a term of art and as used herein refers to any group or radical of the form RCO— where R is any organic group, e.g., alkyl, aryl, heteroaryl, arylalkyl, and heteroarylalkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group, i.e., $—CH_2NH_2$.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

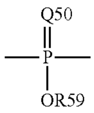

wherein Q50 represents S or O, and $R^{59}$ represents hydrogen, a lower alkyl or an aryl; for example, —P(O)(OMe)- or $—P(O)(OH)_2$. When used to substitute, e.g., an alkyl, the phosphoryl group of the phosphorylalkyl may be represented by the general formulas:

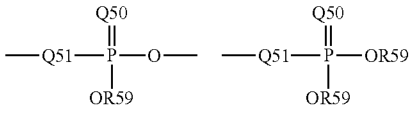

wherein Q50 and $R^{59}$, each independently, are defined above, and Q51 represents O, S or N; for example, —O—P(O)(OH)OMe or —NH—P(O)$(OH)_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)$NMe_2$.

The term "azide" or "azido", as used herein, means an —$N_3$ group.

The term "carbonyl" as used herein refers to —C(═O)—.

The term "thiocarbonyl" as used herein refers to —C(═S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—. The term "(alkylthio)alkyl" refers to an alkyl group substituted by an alkylthio group.

The term "carboxy", as used herein, means a —$CO_2H$ group.

The term "aryl" is a term of art and as used herein refers to includes monocyclic, bicyclic and polycyclic aromatic hydrocarbon groups, for example, benzene, naphthalene, anthracene, and pyrene. Typically, an aryl group contains from 6-10 carbon ring atoms (i.e., ($C_6$-$C_{10}$)aryl). The aromatic ring may be substituted at one or more ring positions with one or more substituents, such as halogen, azide, alkyl, arylalkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as triflurom-ethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group.

The term "heteroaryl" is a term of art and as used herein refers to a monocyclic, bicyclic, and polycyclic aromatic group having 3 to 12 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, arylalkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more atoms are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. Such heteroaryl groups may be connected to the rest of the molecule through either the aromatic group having one or more heteroatoms in the ring structure or the other cyclic group. For example, heteroaryl includes indole, which comprises a benzene ring and a pyrrole ring that are fused together. An indole substituent may be attached to a parent structure through either the benzene ring or through the pyrrole ring of the indole.

The term "aralkyl" or "arylalkyl" is a term of art and as used herein refers to an alkyl group substituted with an aryl group, wherein the moiety is appended to the parent molecule through the alkyl group.

The term "heteroaralkyl" or "heteroarylalkyl" is a term of art and as used herein refers to an alkyl group substituted with a heteroaryl group, appended to the parent molecular moiety through the alkyl group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" refers to an alkyl group substituted by an alkoxy group.

The term "alkoxycarbonyl" means an alkoxy group, as defined herein, appended to the parent molecular moiety through a carbonyl group, represented by —C(═O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein.

Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein.

Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2$═CH—$CH_2$—O—) and vinyloxy (i.e., $CH_2$═CH—O—).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "cyano" is a term of art and as used herein refers to —CN.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3Si$—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

In certain embodiments, the optional substituents contemplated in this invention include halogen, azide, alkyl, alkenyl, alkynyl, aryl, arylalkyl, heteroaryl, heteroarylalkyl, cycloalkyl, (cycloalkyl)alkyl, heterocyclyl, (heterocyclyl)alkyl, hydroxyl, alkoxyl, amino, aminoalkyl, nitro, sulfhydryl, imino, amido, phosphonate, phosphinate, carbonyl, carboxyl, silyl, ether (e.g., -alkylene-O(alkyl)), alkylthio, sulfonyl, sulfonamido, ketone (e.g., —CO(alkyl)), aldehyde (—C(O)H), ester (e.g., —COO(alkyl)), haloalkyl, hydroxyalkyl, alkoxyalkyl, haloalkoxy, haloalkoxyalkyl, and cyano.

As used herein, the term "optionally substituted" or "substituted or unsubstituted" when it precedes a list of chemical moieties means that the list of chemical moieties that follow are each substituted or unsubstituted. For example, "substituted or unsubstituted aryl, heteroaryl, and cycloalkyl" or "optionally substituted aryl, heteroaryl, and cycloalkyl" means substituted or unsubstituted aryl, substituted or unsubstituted heteroaryl, and substituted or unsubstituted cycloalkyl.

The term "vicinal" describes the positional relationship between two substituents, moieties, or functional groups each of which is bonded to one of two adjacent carbon atoms that are bonded to each other (i.e., the two substituents, moieties, or functional groups are in a 1,2-relationship). The methyl groups in 3,4-dimethylheptane are vicinal.

The term "geminal" describes the positional relationship between two substituents, moieties, or functional groups bonded to the same carbon atom (i.e., the two substituents, moieties, or functional groups are in a 1,1-relationship). The methyl groups in 3,3-dimethylheptane are geminal.

The term "hominal" describes the positional relationship between two substituents, moieties, or functional groups each of which is bonded to one of two carbon atoms that themselves are each bonded to a single carbon atom (i.e., the two substituents, moieties, or functional groups are in a 1,3-relationship). The methyl groups in 3,5-dimethylheptane are hominal.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.;

Wuts, P. G. M. *Protective Groups in Organic Synthesis*, 2nd ed.; Wiley; New York, 1991). Protected forms of the inventive compounds are included within the scope of this invention.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985). McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

The term "prodrug" as used herein refers to a compound that can be metabolized in vivo to provide a compound of formula I. Thus prodrugs include compounds that can be prepared by modifying one or more functional groups in a compound of formula I to provide a corresponding compound that can be metabolized in vivo to provide a compound of formula I. Such modifications are known in the art. For example, one or more hydroxyl groups or amine groups in a compound of formula I can be acylated with alkyl-C(═)— groups or with residues from amino acids to provide a prodrug.

Prodrug forms of a compound bearing various nitrogen-containing functional groups (amino, hydroxyamino, amide, etc.) may include the following types of derivatives, where each $R_p$ group individually may be hydrogen, substituted or unsubstituted alkyl, aryl, alkenyl, alkynyl, heterocycle, alkylaryl, arylalkyl, aralkenyl, aralkynyl, cycloalkyl or cycloalkenyl, (a) Carboxamides, represented as $—NHC(O)R_p$
(b) Carbamates, represented as $—NHC(O)OR_p$
(c) (Acyloxy)alkyl Carbamates, represented as $NHC(O)OROC(O)R_p$
(d) Enamines, represented as $—NHCR(═CHCO_2R_p)$ or $—NHCR(═CHCONR_pR_p)$
(e) Schiff Bases, represented as $—N═CR_pR_p$
(f) Mannich Bases (from carboximide compounds), represented as $RCONHCH_2NR_pR_p$ Preparations of such prodrug derivatives are discussed in Various literature sources (examples are: Alexander et al., J. Med. Chem. 1988, 31, 318. Aligas-Martin et al., PCT WO0041531, p. 30)

Prodrug forms of carboxyl-bearing compounds include esters ($—CO_2R_m$), where the $R_m$ group corresponds to any alcohol whose release in the body through enzymatic or hydrolytic processes would be at pharmaceutically acceptable levels. Another prodrug derived from a carboxylic acid form of the disclosure may be a quaternary salt type of structure described by Bodor et al., J. Med. Chem. 1980, 23, 469.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In one embodiment, a subject is a human.

Compounds

The present invention provides compounds having the structure of Formula (I), and pharmaceutically acceptable salts thereof:

(I)

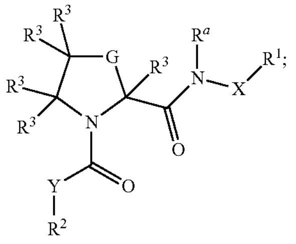

wherein, independently for each occurrence:

X is a bond or $C(R^X)_2$;

Y is a bond, $C(R^Y)_2$, or $—N(R^b)—$;

G is S or $C(R^3)_2$;

$R^a$ and $R^b$ are each independently H or $(C_1-C_6)$alkyl;

$R^1$ represents optionally substituted aryl, heteroaryl, alkyl, cycloalkyl, alkenyl, or cycloalkenyl;

$R^2$ represents optionally substituted bicyclic or tricyclic heteroaryl;

$R^3$ is independently for each occurrence H, halogen, —CN, —$NH_2$, —$CH_2NH_2$, ($C_1$-$C_6$)alkoxy or ($C_1$-$C_6$) alkyl; or two vicinal occurrences of $R^3$ taken together with the carbon atoms to which they are bonded form an optionally substituted fused ($C_3$-$C_7$)cycloalkyl or ($C_6$)aryl; or two geminal occurrences of $R^3$ taken together with the carbon atom to which they are bonded form an optionally substituted spiro ($C_3$-$C_7$)cycloalkyl; or two hominal occurrences of $R^3$ taken together with the carbon atoms to which they are bonded form an optionally substituted bridged ($C_3$-$C_7$)cycloalkyl;

$R^X$ is independently for each occurrence H, ($C_1$-$C_6$)alkyl, or ($C_3$-$C_7$)cycloalkyl;

$R^Y$ is independently for each occurrence H, ($C_1$-$C_6$)alkyl, or ($C_3$-$C_7$)cycloalkyl; or an occurrence of $R^Y$ and a substituent on $R^2$ taken together with the intervening atoms form a ring;

optional substituents on $R^1$ or $R^2$ each independently represent halogen, —CN, —$NO_2$, —$OR^{13}$, —$NR_{13}R^{14}$, —C(O)$R^{13}$, —C(O)$OR^{13}$, —C(O)$NR^{13}R^{14}$, —OC(O)$R^{13}$, —$NR^{13}$C(O)$R^{14}$, —OC(O)$NR^{13}R^{14}$, —OC(O)$OR^{13}$, —$NR^{13}$C(O)$OR^{14}$, —$NR^{13}$C(O)$NR^{13}R^{14}$, —$OS(O)_p(R^{13})$, —$SR^{13}$, —$NR^{13}S(O)_p(R^{14})$, or optionally substituted alkyl, alkenyl, alkynyl, haloalkyl, hydroxyalkyl, alkoxyalkyl, cycloalkoxyalkyl, aryloxyalkyl, aralkyl, heteroaralkyl, heteroaryl, aryl, aryloxy, cycloalkyl. (cycloalkyl)alkyl, heterocycloalkyl, or (heterocycloalkyl)alkyl;

or wherein two substituents on $R^1$ or two substituents on $R^2$, taken together with the intervening atoms, form a ring;

$R^{13}$ and $R^{14}$, independently for each occurrence, represent H or optionally substituted alkyl, haloalkyl, alkenyl, alkynyl, aryl, or heteroaryl; and p is 0, 1, or 2.

In certain embodiments, Y represents $C(R^Y)_2$, preferably $CH_2$.

In certain embodiments, X represents a bond. Alternatively. X may represent $CH_2$.

In certain embodiments, $R^1$ represents optionally substituted aryl or heteroaryl. In some embodiments, $R^1$ is optionally substituted heteroaryl. Exemplary embodiments of $R^1$ include optionally substituted phenyl (e.g., 3-halophenyl, or 2,3-dihalophenyl), ($C_3$—$C_6$)cycloalkyl, alkenyl, pyridinyl (e.g., 6-halopyridin-2-yl), or pyrazinyl (e.g., 6-halopyrazin-2-yl).

In certain embodiments, $R^1$ is mono-, di-, or tri-substituted.

In certain embodiments, $R^1$ represents optionally substituted pyridinyl, preferably optionally substituted 2-pyridinyl. For example, $R^1$ may represent

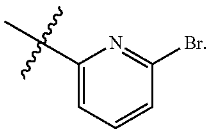

In other embodiments $R^1$ represents optionally substituted phenyl. For example, $R^1$ may represent

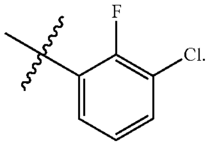 [SMILES: *c1cccc(Cl)c1F]

In certain embodiments, $R^2$ represents

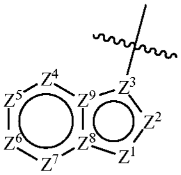
,
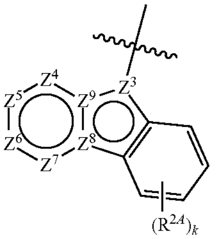
,
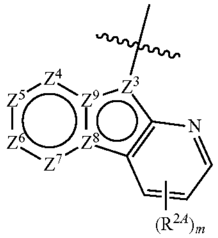
,
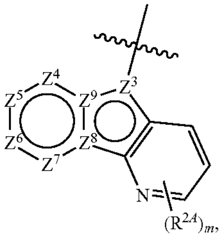

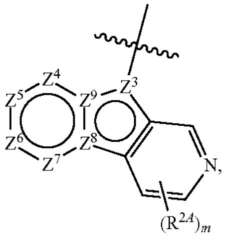

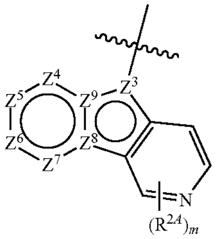
,

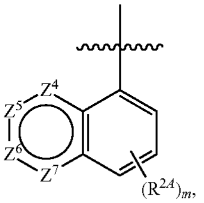
or
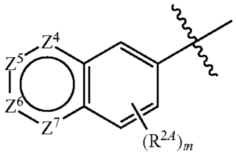
;

$Z^1$ represents N or $CR^{1Z}$;
$Z^2$ represents N or $CR^{2Z}$;
$Z^3$ represents N or C;
$Z^4$ represents N or $CR^{4Z}$;
$Z^5$ represents N or $CR^{5Z}$;
$Z^6$ represents N or $CR^{6Z}$;
$Z^7$ represents N or $CR^{7Z}$;
$Z^8$ represents C;
$Z^9$ represents N or C;
k is an integer from 1-4;
m is an integer from 1-3; and
each occurrence of $R^{1Z}$, $R^{2Z}$, $R^{4Z}$, $R^{5Z}$, $R^{6Z}$, $R^{7Z}$, $R^{2A}$ independently represents H, halogen, —CN, —$NO_2$, —$OR^{13}$, —$NR^{13}R^{14}$, —C(O)$R^{13}$, —C(O)$OR^{13}$, —C(O)$NR^{13}R^{14}$, —OC(O)$R^{13}$, —$NR^{13}$C(O)$R^{14}$, —OC(O)$NR^{13}R^{14}$, —OC(O)$OR^{13}$, —$NR^{13}$C(O)$OR^{14}$, —$NR^{13}$—C(O)$NR^{13}R^{14}$, —$OS(O)_p(R^{13})$, —$SR^{13}$—, —$NR^{13}S(O)_p(R^{14})$, or optionally substituted alkyl, alkenyl, alkynyl, haloalkyl, hydroxyalkyl, alkoxyalkyl, cycloalkoxyalkyl, aryloxyalkyl, arakyl, heteroaralkyl, heteroaryl, aryl, aryloxy, cycloalkyl, (cycloalkyl)alkyl, heterocycloalkyl, or (heterocycloalkyl)alkyl; or wherein an occurrence of $R^{6Z}$ and an occurrence of $R^{7Z}$ taken together with the intervening atoms form a ring; or wherein an occurrence of $R^Y$ and an occurrence of $R^{2Z}$ taken together with the intervening atoms form a ring.

In certain embodiments, $Z^2$, $Z^3$, $Z^4$, and $Z^6$ represent N.

In certain embodiments, $Z^3$, $Z^4$, and $Z^6$ represent N.

In certain embodiments, $Z^9$, $Z^4$, and $Z^6$ represent N.

In certain embodiments, $Z^3$ and $Z^4$ represent N.

In certain embodiments, $Z^1$, $Z^3$, $Z^4$, and $Z^6$ represent N.

In certain embodiments, $R^2$ represents

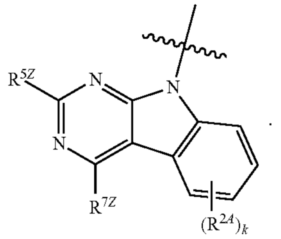

For example, $R^2$ may represent

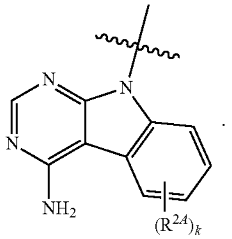

In some embodiments, k is 2.

In certain embodiments, $R^2$ represents

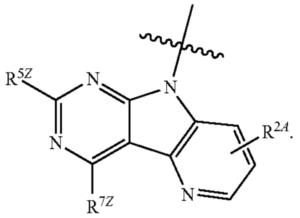

In certain embodiments, $R^2$ represents

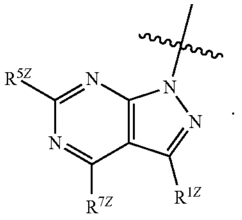

In certain embodiments, $R^2$ represents

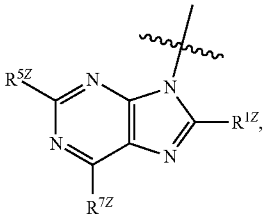

for example

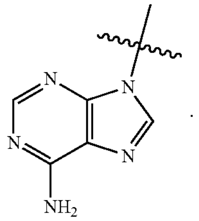 [SMILES: *n1cnc2c(N)ncnc21]

In certain embodiments, $R^2$ represents

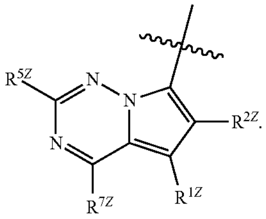

In certain embodiments, $R^2$ represents

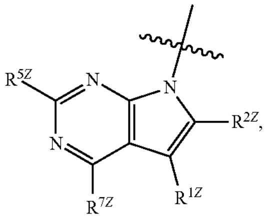

for example

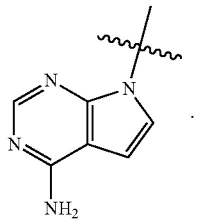

In certain embodiments, $R^{7Z}$ represents —$NR^{13}R^{14}$, for example —$NH_2$.

In certain embodiments, $R^{6Z}$ represents —$C(O)R^{13}$—, —$C(O)OR^{13}$, —$C(O)NR^{13}R^{14}$, or hydroxyalkyl.

In certain embodiments, $R^{5Z}$ represents alkyl, halo, or —$NR^{13}R^{14}$.

In certain embodiments, $R^{1Z}$ represents —CN, halo, haloalkyl, optionally substituted aryl, optionally substituted heteroaryl, optionally substituted alkyl, —$C(O)R^{13}$, —$SR^{13}$, —$NR^{13}R^{14}$, —$OR^{13}$, —$C(O)OR^{13}$, —$C(O)NR^{13}R^{14}$, or —$NR^{13}C(O)R^{14}$.

In certain embodiments, each occurrence of $R^{2A}$ independently represents —CN, —$NO_2$, halo, haloalkyl, optionally substituted aryl, optionally substituted heteroaryl, optionally substituted alkyl, optionally substituted alkenyl, optionally substituted hydroxyalkyl, —$C(O)R^{13}$, —$C(O)OR^{13}$, —$NR^{13}C(O)OR^{14}$. —$SR^{13}$, —$NR^{13}R^{14}$, —$OR^{13}$, —$C(O)NR^{13}R^{14}$, or —$NR^{13}C(O)R^{14}$.

In certain embodiments, G is $C(R^3)_2$.

In certain embodiments, the compound of the invention has the structure of formula (Ia):

(Ia)

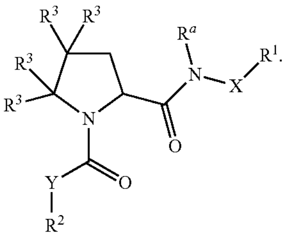

In certain embodiments, two vicinal occurrences of $R^3$ taken together with the carbon atoms to which they are bonded form an optionally substituted fused $C_3$-cycloalkyl.

In certain embodiments, at least one occurrence of $R^3$ is halo, preferably fluoro.

In certain embodiments, at least one occurrence of $R^3$ is methyl.

In certain embodiments, two vicinal occurrences of $R^3$ taken together with the carbon atoms to which they are bonded form an optionally substituted fused $C_3$-cycloalkyl and another occurrence of $R^3$ is methyl.

In certain embodiments, the compound of formula (I) is selected from the following table of compounds, and pharmaceutically acceptable salts thereof:

| # | Structure | # | Structure |
|---|---|---|---|
| 75d | 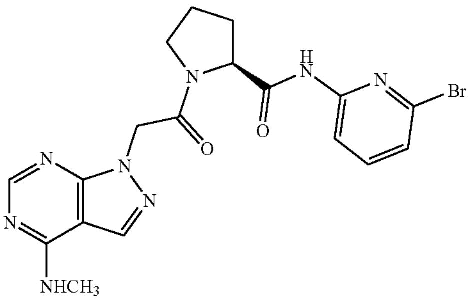 [SMILES: CNc1ncnc2c1cnn2CC(=O)N1CCC[C@H]1C(=O)Nc1cccc(Br)n1] | 24a | 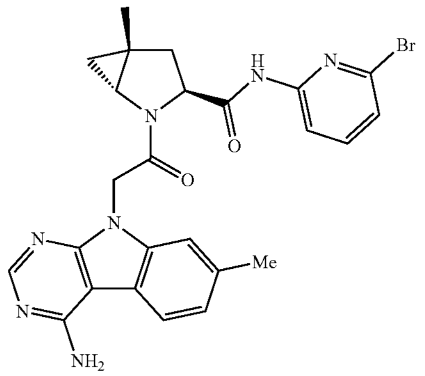 [SMILES: Cc1ccc2c3c(N)ncnc3n(CC(=O)N3[C@H](C(=O)Nc4cccc(Br)n4)C[C@@]4(C)C[C@@H]34)c2c1] |
| 76b | 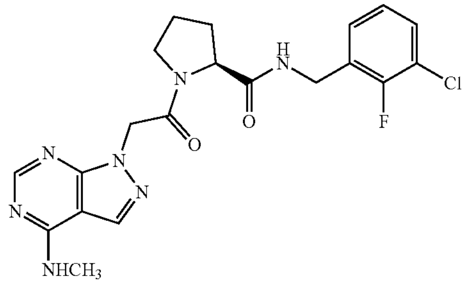 [SMILES: CNc1ncnc2c1cnn2CC(=O)N1CCC[C@H]1C(=O)NCc1cccc(Cl)c1F] | 50f | 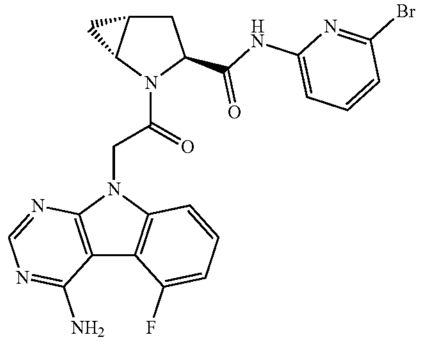 [SMILES: Nc1ncnc2c1c1c(F)cccc1n2CC(=O)N1[C@@H]2C[C@@H]2C[C@H]1C(=O)Nc1cccc(Br)n1] |

-continued
| # | Structure | # | Structure |
|---|---|---|---|
| 77b | 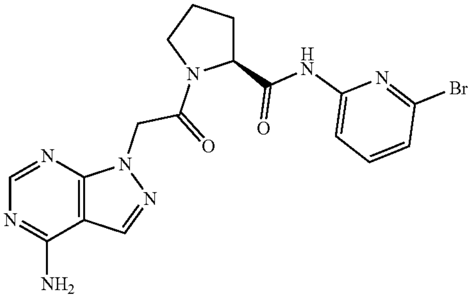 [SMILES: Nc1ncnc2c1cnn2CC(=O)N1CCC[C@H]1C(=O)Nc1cccc(Br)n1] | 157a | 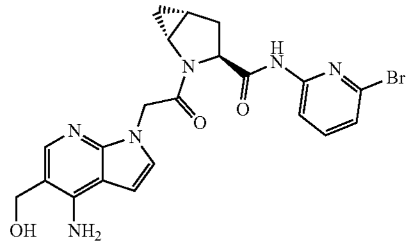 [SMILES: Nc1c(CO)cnc2c1ccn2CC(=O)N1[C@@H]2C[C@@H]2C[C@H]1C(=O)Nc1cccc(Br)n1] |
| 78a | 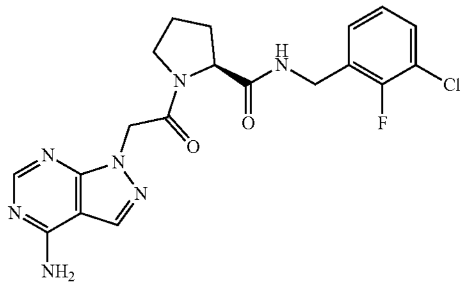 [SMILES: Nc1ncnc2c1cnn2CC(=O)N1CCC[C@H]1C(=O)NCc1cccc(Cl)c1F] | 158e | 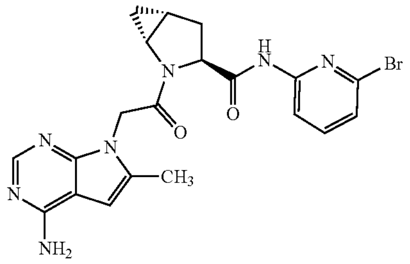 [SMILES: Cc1cc2c(N)ncnc2n1CC(=O)N1[C@@H]2C[C@@H]2C[C@H]1C(=O)Nc1cccc(Br)n1] |
| 79a | 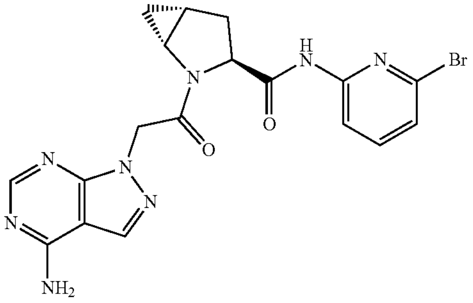 | 32f | 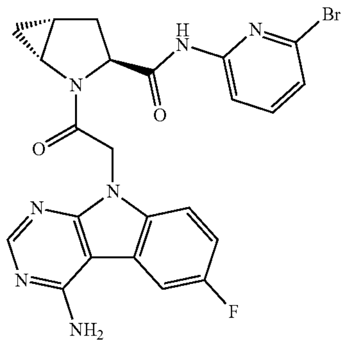 [SMILES: Nc1ncnc2c1c1cc(F)ccc1n2CC(=O)N1[C@@H]2C[C@@H]2C[C@H]1C(=O)Nc1cccc(Br)n1] |
| 80a | 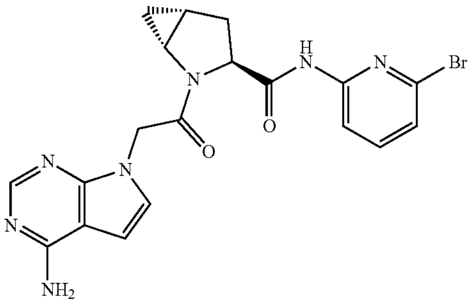 [SMILES: Nc1ncnc2c1ccn2CC(=O)N1[C@@H]2C[C@@H]2C[C@H]1C(=O)Nc1cccc(Br)n1] | 43a | 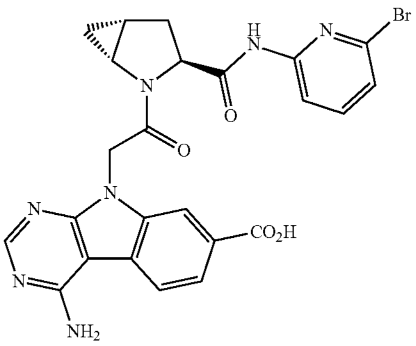 [SMILES: Nc1ncnc2c1c1ccc(C(=O)O)cc1n2CC(=O)N1[C@@H]2C[C@@H]2C[C@H]1C(=O)Nc1cccc(Br)n1] |

-continued
| # | Structure | # | Structure |
|---|---|---|---|
| 81a | 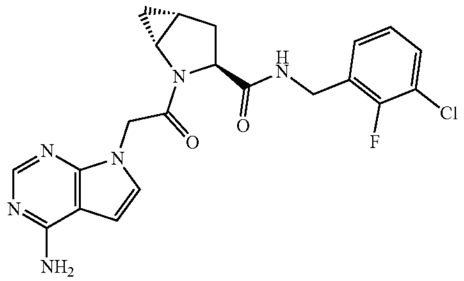 [SMILES: Nc1ncnc2c1ccn2CC(=O)N1[C@@H]2C[C@@H]2C[C@H]1C(=O)NCc1cccc(Cl)c1F] | 35f | 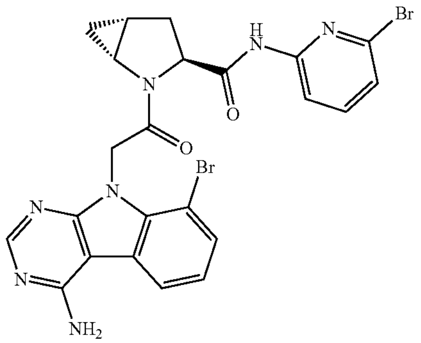 [SMILES: Nc1ncnc2c1c1cccc(Br)c1n2CC(=O)N1[C@@H]2C[C@@H]2C[C@H]1C(=O)Nc1cccc(Br)n1] |
| 82a | 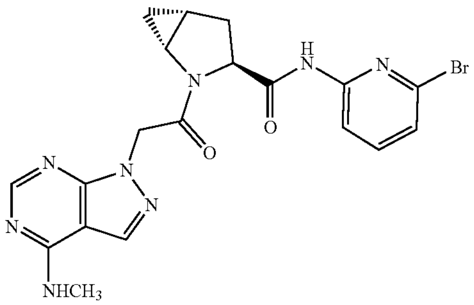 [SMILES: CNc1ncnc2c1cnn2CC(=O)N1[C@@H]2C[C@@H]2C[C@H]1C(=O)Nc1cccc(Br)n1] | 30f | 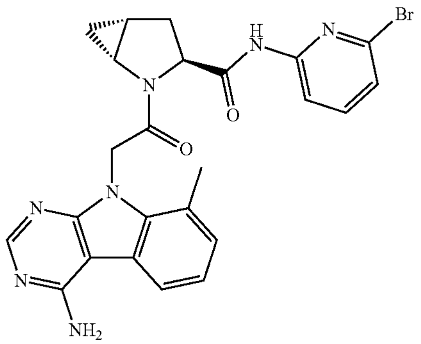 [SMILES: Cc1cccc2c3c(N)ncnc3n(CC(=O)N3[C@@H]4C[C@@H]4C[C@H]3C(=O)Nc3cccc(Br)n3)c12] |
| 83d | 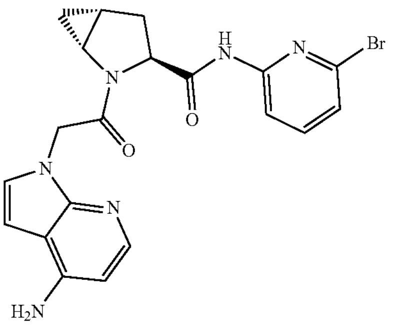 [SMILES: Nc1ccnc2c1ccn2CC(=O)N1[C@@H]2C[C@@H]2C[C@H]1C(=O)Nc1cccc(Br)n1] | 47g | 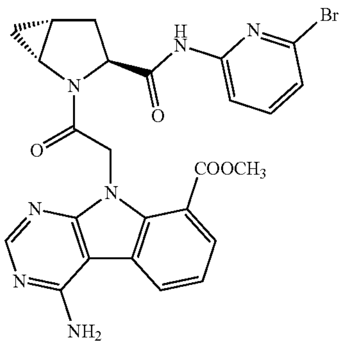 [SMILES: COC(=O)c1cccc2c3c(N)ncnc3n(CC(=O)N3[C@@H]4C[C@@H]4C[C@H]3C(=O)Nc3cccc(Br)n3)c12] |
| 84a | 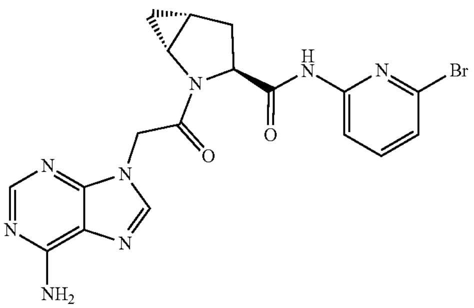 [SMILES: Nc1ncnc2c1ncn2CC(=O)N1[C@@H]2C[C@@H]2C[C@H]1C(=O)Nc1cccc(Br)n1] | 48d | 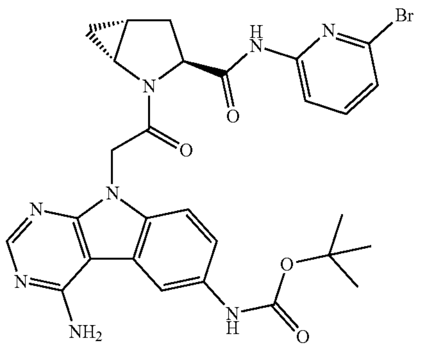 [SMILES: CC(C)(C)OC(=O)Nc1ccc2c(c1)c1c(N)ncnc1n2CC(=O)N1[C@@H]2C[C@@H]2C[C@H]1C(=O)Nc1cccc(Br)n1] |

-continued
| # | Structure | # | Structure |
|---|---|---|---|
| 85b | 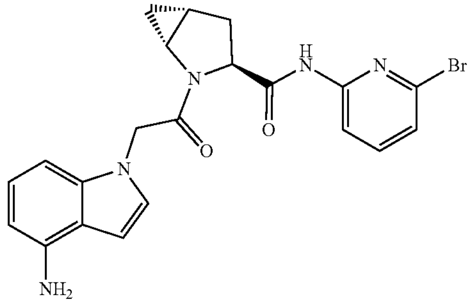 [SMILES: Nc1cccc2c1ccn2CC(=O)N1[C@@H]2C[C@@H]2C[C@H]1C(=O)Nc1cccc(Br)n1] | 38e | 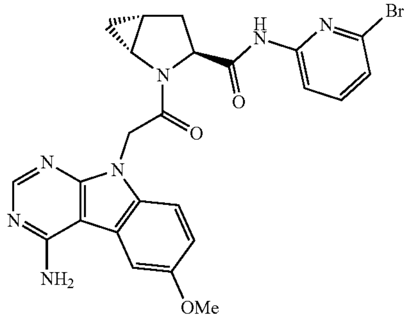 [SMILES: COc1ccc2c(c1)c1c(N)ncnc1n2CC(=O)N1[C@@H]2C[C@@H]2C[C@H]1C(=O)Nc1cccc(Br)n1] |
| 86b | 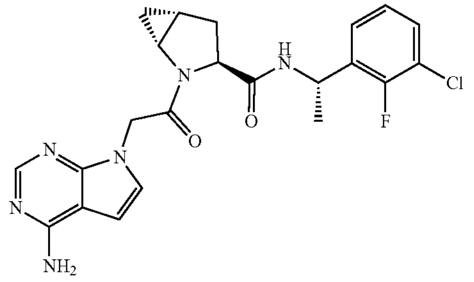 [SMILES: C[C@H](NC(=O)[C@@H]1C[C@H]2C[C@H]2N1C(=O)Cn1ccc2c(N)ncnc21)c1cccc(Cl)c1F] | 51g | 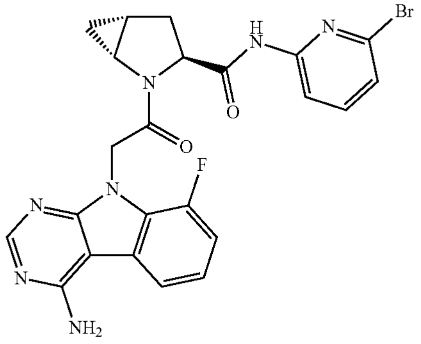 [SMILES: Nc1ncnc2c1c1cccc(F)c1n2CC(=O)N1[C@@H]2C[C@@H]2C[C@H]1C(=O)Nc1cccc(Br)n1] |
| 87f | 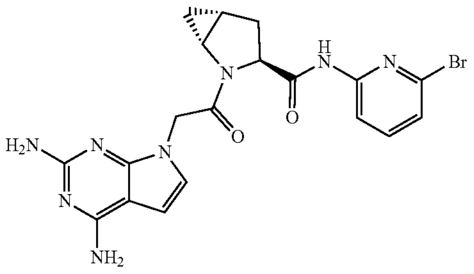 [SMILES: Nc1nc(N)c2ccn(CC(=O)N3[C@@H]4C[C@@H]4C[C@H]3C(=O)Nc3cccc(Br)n3)c2n1] | 52f | 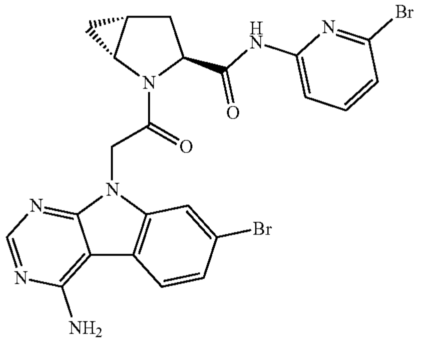 [SMILES: Nc1ncnc2c1c1ccc(Br)cc1n2CC(=O)N1[C@@H]2C[C@@H]2C[C@H]1C(=O)Nc1cccc(Br)n1] |
| 88f | 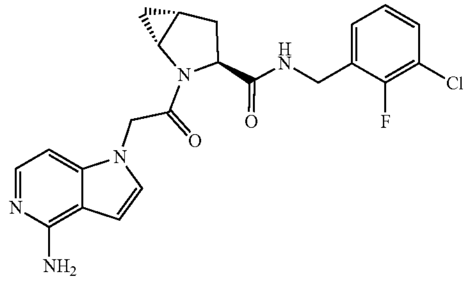 [SMILES: Nc1nccc2c1ccn2CC(=O)N1[C@@H]2C[C@@H]2C[C@H]1C(=O)NCc1cccc(Cl)c1F] | 54g | 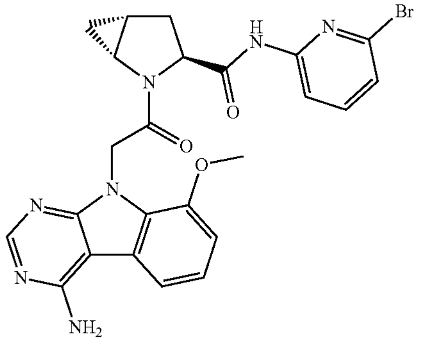 [SMILES: COc1cccc2c3c(N)ncnc3n(CC(=O)N3[C@@H]4C[C@@H]4C[C@H]3C(=O)Nc3cccc(Br)n3)c12] |

-continued
| # | Structure | # | Structure |
|---|---|---|---|
| 89b | 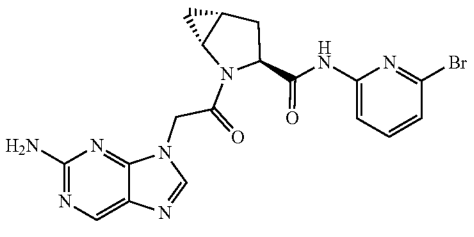 [SMILES: Nc1ncc2ncn(CC(=O)N3[C@@H]4C[C@@H]4C[C@H]3C(=O)Nc3cccc(Br)n3)c2n1] | 44a | 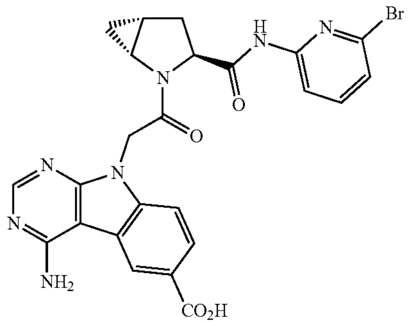 [SMILES: Nc1ncnc2c1c1cc(C(=O)O)ccc1n2CC(=O)N1[C@@H]2C[C@@H]2C[C@H]1C(=O)Nc1cccc(Br)n1] |
| 90d | 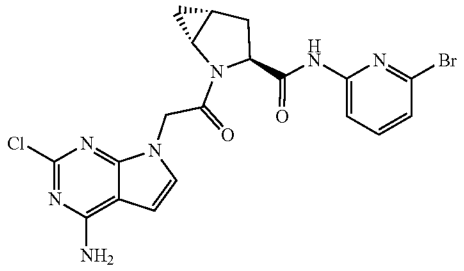 [SMILES: Nc1nc(Cl)nc2c1ccn2CC(=O)N1[C@@H]2C[C@@H]2C[C@H]1C(=O)Nc1cccc(Br)n1] | 29f | 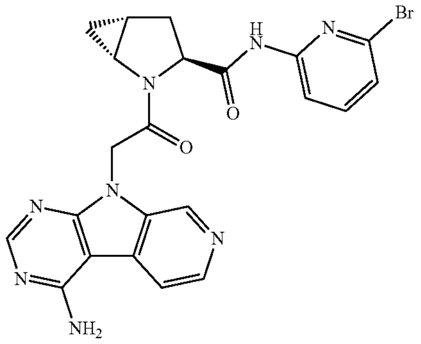 [SMILES: Nc1ncnc2c1c1ccncc1n2CC(=O)N1[C@@H]2C[C@@H]2C[C@H]1C(=O)Nc1cccc(Br)n1] |
| 91a | 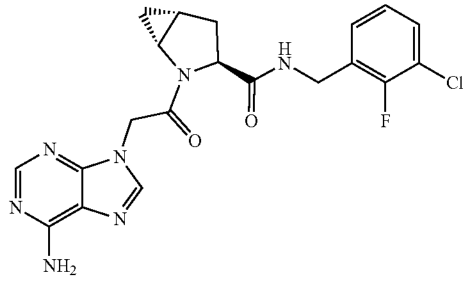 [SMILES: Nc1ncnc2c1ncn2CC(=O)N1[C@@H]2C[C@@H]2C[C@H]1C(=O)NCc1cccc(Cl)c1F] | 22c and 22d | 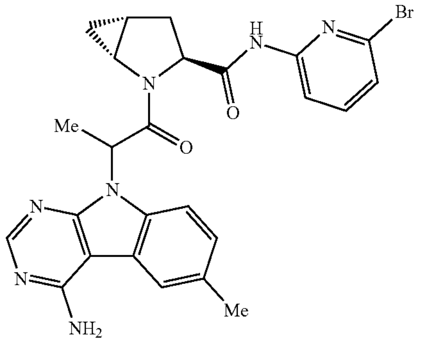<br>(+) and (-) isomer |
| 92b | 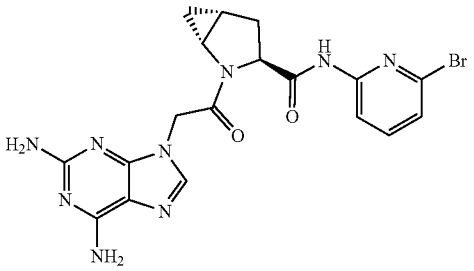 | 33e | 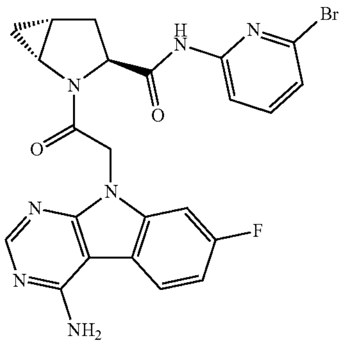 [SMILES: Nc1ncnc2c1c1ccc(F)cc1n2CC(=O)N1[C@@H]2C[C@@H]2C[C@H]1C(=O)Nc1cccc(Br)n1] |

-continued
| # | Structure | # | Structure |
|---|---|---|---|
| 93a | 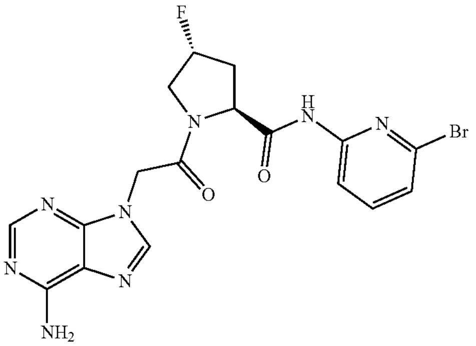 [SMILES: Nc1ncnc2c1ncn2CC(=O)N1C[C@H](F)C[C@H]1C(=O)Nc1cccc(Br)n1] | 49c | 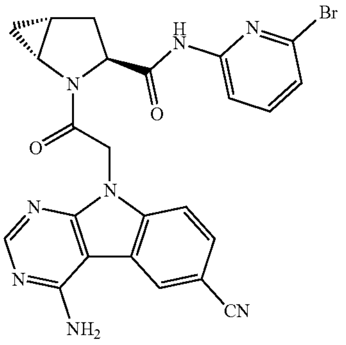 [SMILES: N#Cc1ccc2c(c1)c1c(N)ncnc1n2CC(=O)N1[C@@H]2C[C@@H]2C[C@H]1C(=O)Nc1cccc(Br)n1] |
| 94b | 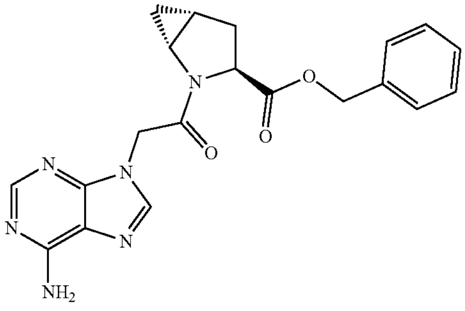 [SMILES: Nc1ncnc2c1ncn2CC(=O)N1[C@@H]2C[C@@H]2C[C@H]1C(=O)OCc1ccccc1] | 58c | 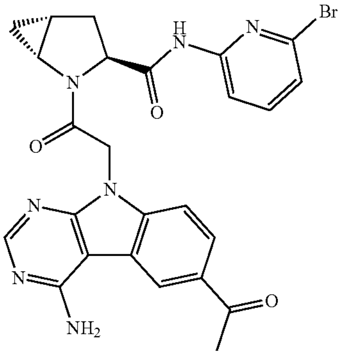 [SMILES: CC(=O)c1ccc2c(c1)c1c(N)ncnc1n2CC(=O)N1[C@@H]2C[C@@H]2C[C@H]1C(=O)Nc1cccc(Br)n1] |
| 95c | 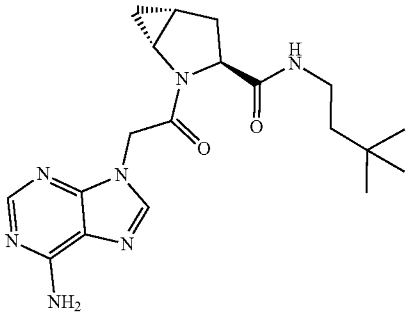 [SMILES: CC(C)(C)CCNC(=O)[C@@H]1C[C@H]2C[C@H]2N1C(=O)Cn1cnc2c(N)ncnc21] | 59c | 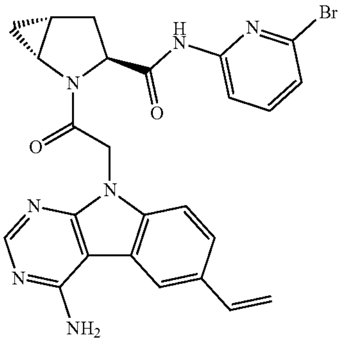 [SMILES: C=Cc1ccc2c(c1)c1c(N)ncnc1n2CC(=O)N1[C@@H]2C[C@@H]2C[C@H]1C(=O)Nc1cccc(Br)n1] |
| 96e | 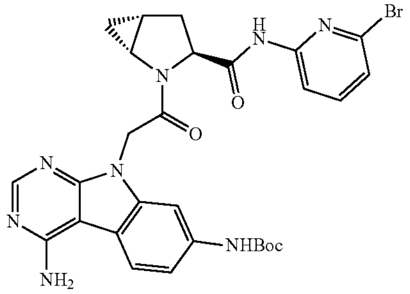 [SMILES: CC(C)(C)OC(=O)Nc1ccc2c3c(N)ncnc3n(CC(=O)N3[C@@H]4C[C@@H]4C[C@H]3C(=O)Nc3cccc(Br)n3)c2c1] | 17f | 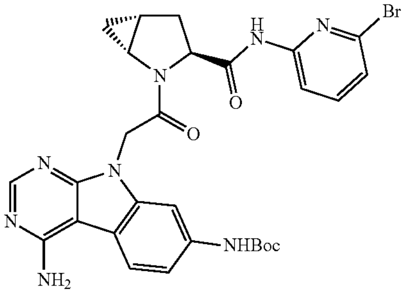 [SMILES: CC(C)(C)OC(=O)Nc1ccc2c3c(N)ncnc3n(CC(=O)N3[C@@H]4C[C@@H]4C[C@H]3C(=O)Nc3cccc(Br)n3)c2c1] |

-continued
| # | Structure | # | Structure |
| --- | --- | --- | --- |
| 97b | 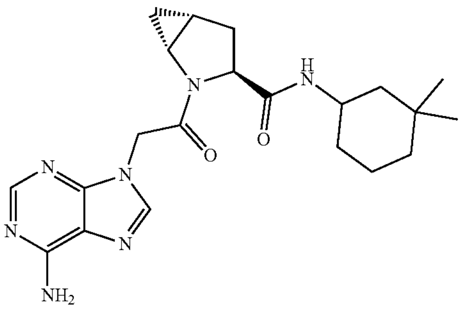 [SMILES: CC1(C)CCCC(NC(=O)[C@@H]2C[C@H]3C[C@H]3N2C(=O)Cn2cnc3c(N)ncnc32)C1] | 18a | 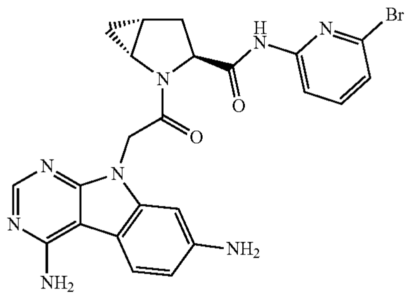 [SMILES: Nc1ccc2c3c(N)ncnc3n(CC(=O)N3[C@@H]4C[C@@H]4C[C@H]3C(=O)Nc3cccc(Br)n3)c2c1] |
| 98b | 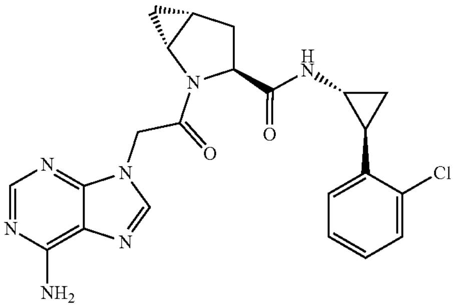 [SMILES: Nc1ncnc2c1ncn2CC(=O)N1[C@@H]2C[C@@H]2C[C@H]1C(=O)N[C@@H]1C[C@H]1c1ccccc1Cl] | 31f | 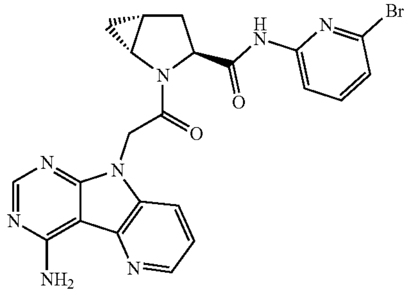 [SMILES: Nc1ncnc2c1c1ncccc1n2CC(=O)N1[C@@H]2C[C@@H]2C[C@H]1C(=O)Nc1cccc(Br)n1] |
| 99b | 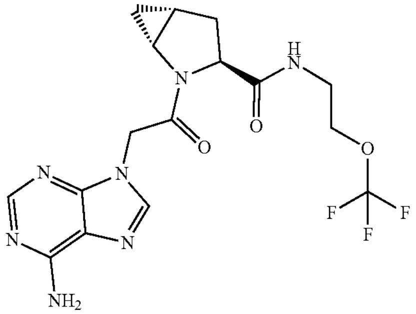 [SMILES: Nc1ncnc2c1ncn2CC(=O)N1[C@@H]2C[C@@H]2C[C@H]1C(=O)NCCOC(F)(F)F] | 60c | 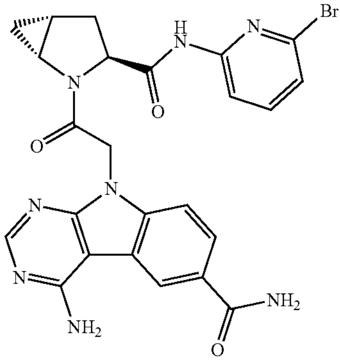 [SMILES: NC(=O)c1ccc2c(c1)c1c(N)ncnc1n2CC(=O)N1[C@@H]2C[C@@H]2C[C@H]1C(=O)Nc1cccc(Br)n1] |
| 100b | 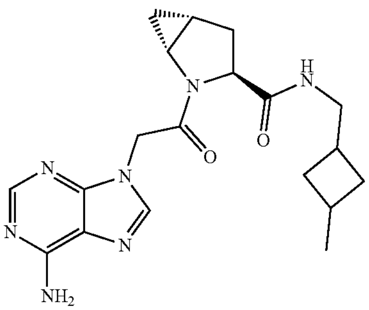 [SMILES: CC1CC(CNC(=O)[C@@H]2C[C@H]3C[C@H]3N2C(=O)Cn2cnc3c(N)ncnc32)C1] | 61a | 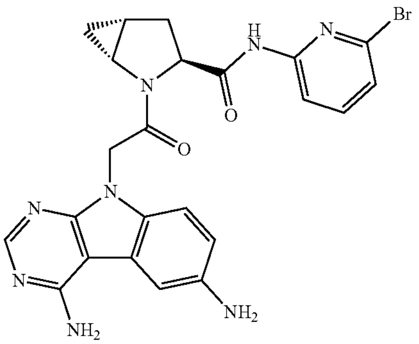 |

-continued
| # | Structure | # | Structure |
|---|---|---|---|
| 101b | 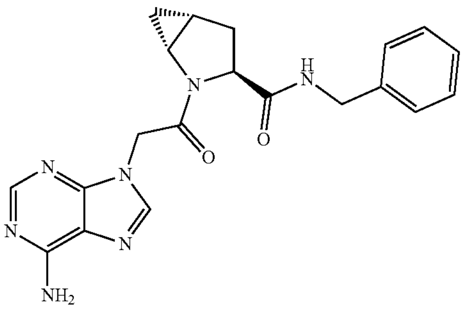 [SMILES: Nc1ncnc2c1ncn2CC(=O)N1[C@@H]2C[C@@H]2C[C@H]1C(=O)NCc1ccccc1] | 129f | 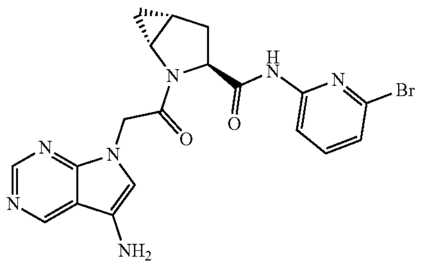 [SMILES: Nc1cn(CC(=O)N2[C@@H]3C[C@@H]3C[C@H]2C(=O)Nc2cccc(Br)n2)c2ncncc12] |
| 102b | 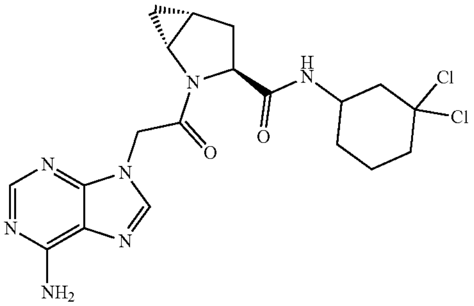 [SMILES: Nc1ncnc2c1ncn2CC(=O)N1[C@@H]2C[C@@H]2C[C@H]1C(=O)NC1CCCC(Cl)(Cl)C1] | 46g | 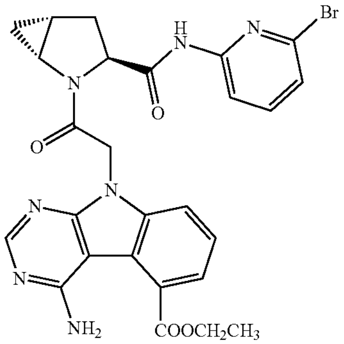 |
| 103b | 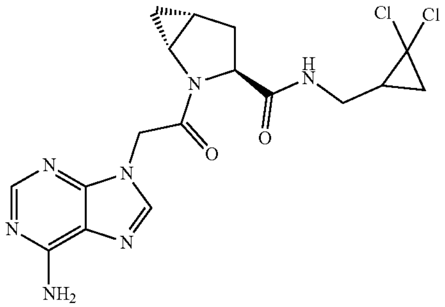 [SMILES: Nc1ncnc2c1ncn2CC(=O)N1[C@@H]2C[C@@H]2C[C@H]1C(=O)NCC1CC1(Cl)Cl] | 62c | 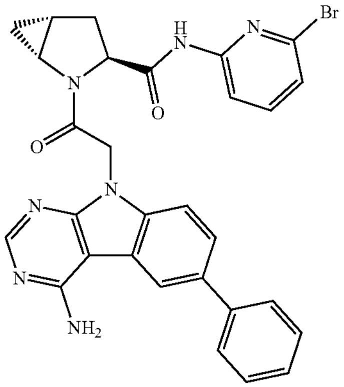 [SMILES: Nc1ncnc2c1c1cc(-c3ccccc3)ccc1n2CC(=O)N1[C@@H]2C[C@@H]2C[C@H]1C(=O)Nc1cccc(Br)n1] |
| 104a | 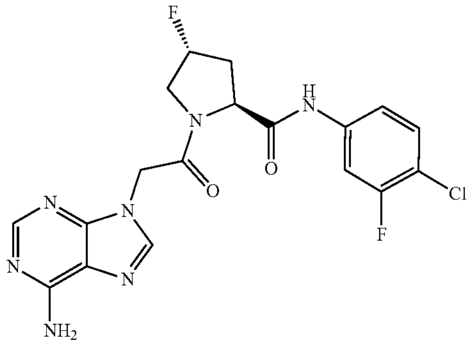 [SMILES: Nc1ncnc2c1ncn2CC(=O)N1C[C@H](F)C[C@H]1C(=O)Nc1ccc(Cl)c(F)c1] | 63d | 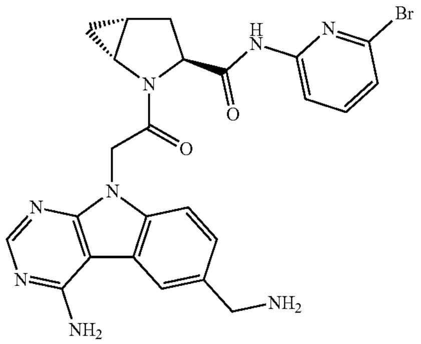 [SMILES: NCc1ccc2c(c1)c1c(N)ncnc1n2CC(=O)N1[C@@H]2C[C@@H]2C[C@H]1C(=O)Nc1cccc(Br)n1] |

-continued
| # | Structure | # | Structure |
|---|---|---|---|
| 105b | 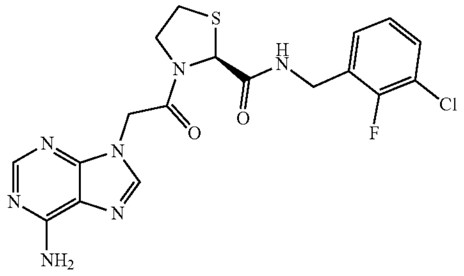 [SMILES: Nc1ncnc2c1ncn2CC(=O)N1CCS[C@H]1C(=O)NCc1cccc(Cl)c1F] | 53d | 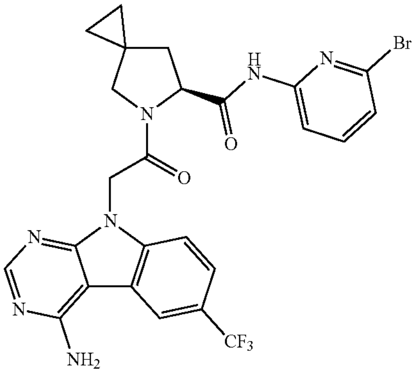 [SMILES: Nc1ncnc2c1c1cc(C(F)(F)F)ccc1n2CC(=O)N1CC2(CC2)C[C@H]1C(=O)Nc1cccc(Br)n1] |
| 111b | 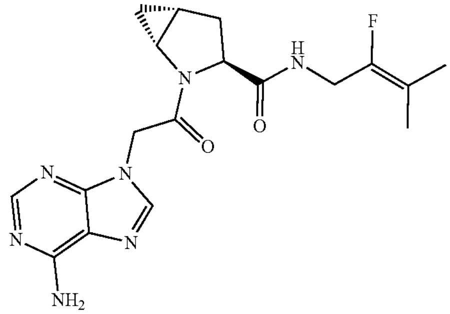 [SMILES: CC(C)=C(F)CNC(=O)[C@@H]1C[C@H]2C[C@H]2N1C(=O)Cn1cnc2c(N)ncnc21] | 55a | 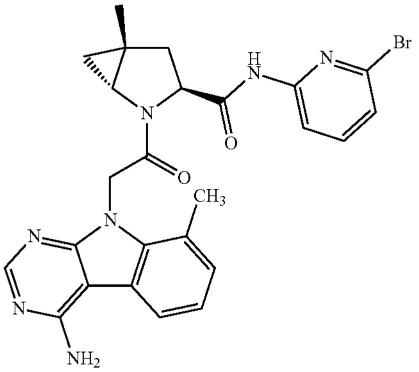 [SMILES: Cc1cccc2c3c(N)ncnc3n(CC(=O)N3[C@H](C(=O)Nc4cccc(Br)n4)C[C@@]4(C)C[C@@H]34)c12] |
| 107b | 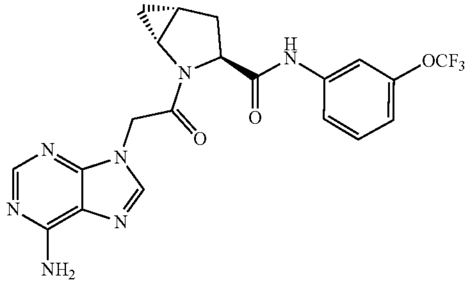 [SMILES: Nc1ncnc2c1ncn2CC(=O)N1[C@@H]2C[C@@H]2C[C@H]1C(=O)Nc1cccc(OC(F)(F)F)c1] | 56g | 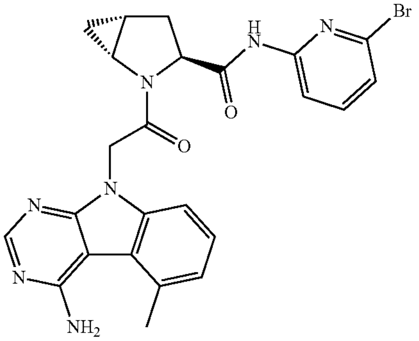 [SMILES: Cc1cccc2c1c1c(N)ncnc1n2CC(=O)N1[C@@H]2C[C@@H]2C[C@H]1C(=O)Nc1cccc(Br)n1] |
| 108b | 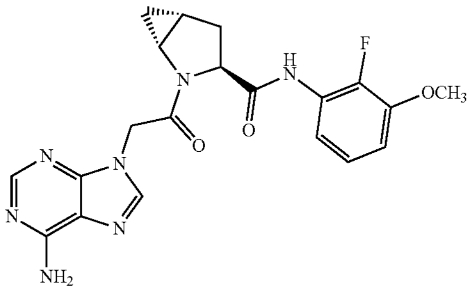 [SMILES: COc1cccc(NC(=O)[C@@H]2C[C@H]3C[C@H]3N2C(=O)Cn2cnc3c(N)ncnc32)c1F] | 57g | 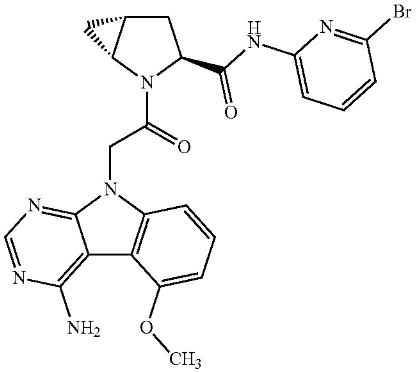 [SMILES: COc1cccc2c1c1c(N)ncnc1n2CC(=O)N1[C@@H]2C[C@@H]2C[C@H]1C(=O)Nc1cccc(Br)n1] |

-continued
| # | Structure | # | Structure |
|---|---|---|---|
| 109e | 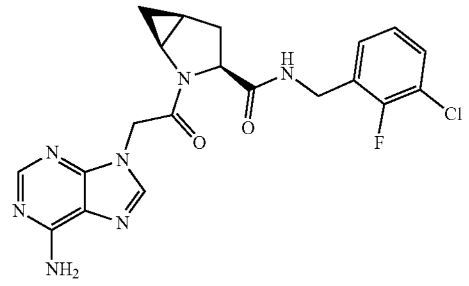 [SMILES: Nc1ncnc2c1ncn2CC(=O)N1[C@H](C(=O)NCc2cccc(Cl)c2F)C[C@@H]2C[C@@H]21] | 159a | 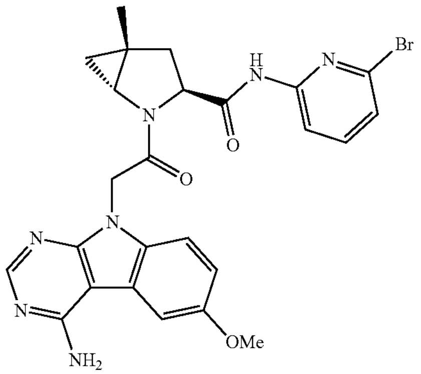 [SMILES: COc1ccc2c(c1)c1c(N)ncnc1n2CC(=O)N1[C@H](C(=O)Nc2cccc(Br)n2)C[C@@]2(C)C[C@@H]12] |
| 110d | 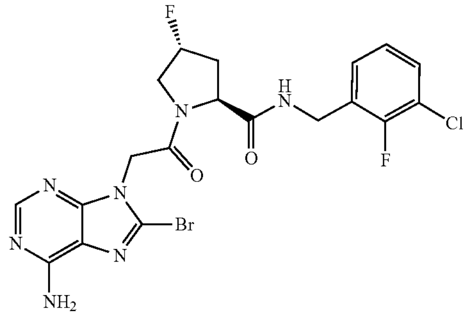 [SMILES: Nc1ncnc2c1nc(Br)n2CC(=O)N1C[C@H](F)C[C@H]1C(=O)NCc1cccc(Cl)c1F] | 160a | 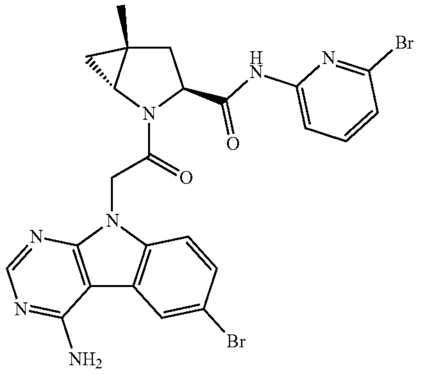 [SMILES: C[C@@]12C[C@@H](C(=O)Nc3cccc(Br)n3)N(C(=O)Cn3c4ccc(Br)cc4c4c(N)ncnc43)[C@@H]1C2] |
| 106b | 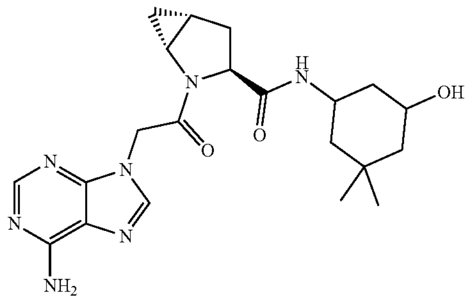 [SMILES: CC1(C)CC(O)CC(NC(=O)[C@@H]2C[C@H]3C[C@H]3N2C(=O)Cn2cnc3c(N)ncnc32)C1] | 171b | 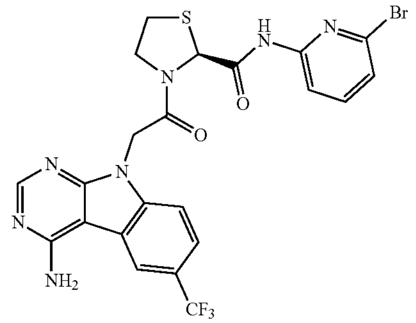 [SMILES: Nc1ncnc2c1c1cc(C(F)(F)F)ccc1n2CC(=O)N1CCS[C@H]1C(=O)Nc1cccc(Br)n1] |
| 112b | 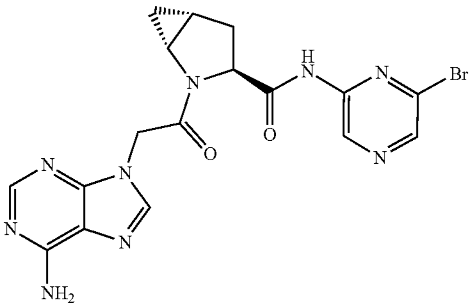 [SMILES: Nc1ncnc2c1ncn2CC(=O)N1[C@@H]2C[C@@H]2C[C@H]1C(=O)Nc1cncc(Br)n1] | 172a | 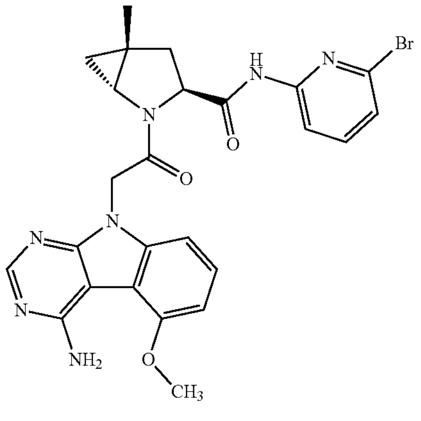 [SMILES: COc1cccc2c1c1c(N)ncnc1n2CC(=O)N1[C@H](C(=O)Nc2cccc(Br)n2)C[C@@]2(C)C[C@@H]12] |

-continued
| # | Structure | # | Structure |
|---|---|---|---|
| 119a | 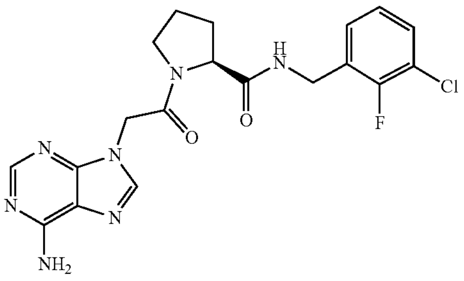 [SMILES: Nc1ncnc2c1ncn2CC(=O)N1CCC[C@H]1C(=O)NCc1cccc(Cl)c1F] | 173a | 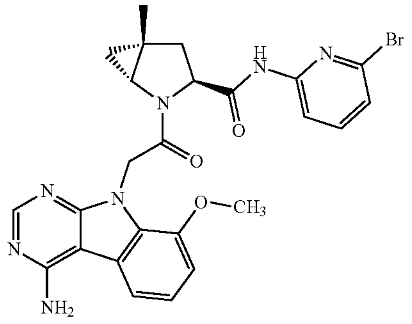 [SMILES: COc1cccc2c3c(N)ncnc3n(CC(=O)N3[C@H](C(=O)Nc4cccc(Br)n4)C[C@@]4(C)C[C@@H]34)c12] |
| 120c | 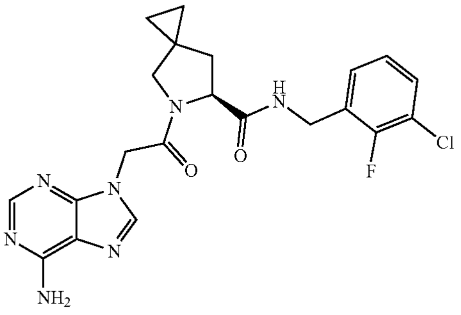 [SMILES: Nc1ncnc2c1ncn2CC(=O)N1CC2(CC2)C[C@H]1C(=O)NCc1cccc(Cl)c1F] | 161a | 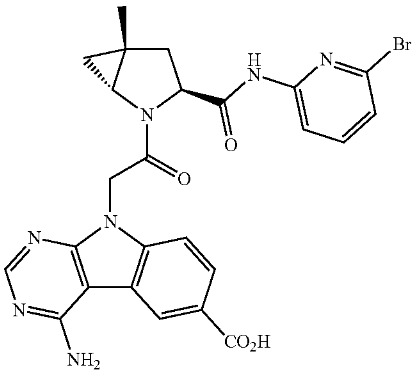 |
| 121d | 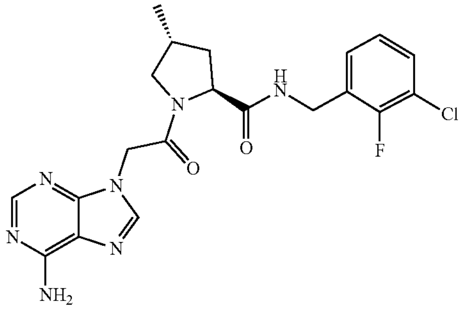 [SMILES: C[C@@H]1C[C@@H](C(=O)NCc2cccc(Cl)c2F)N(C(=O)Cn2cnc3c(N)ncnc32)C1] | 174g | 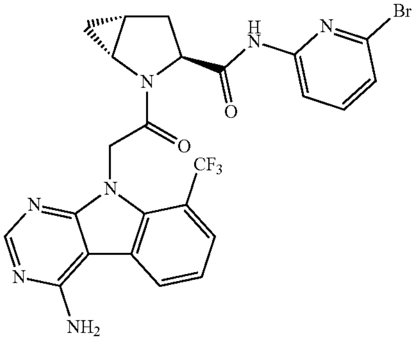 [SMILES: Nc1ncnc2c1c1cccc(C(F)(F)F)c1n2CC(=O)N1[C@@H]2C[C@@H]2C[C@H]1C(=O)Nc1cccc(Br)n1] |
| 122c | 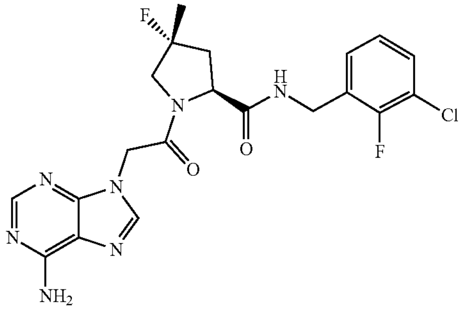 [SMILES: C[C@@]1(F)C[C@@H](C(=O)NCc2cccc(Cl)c2F)N(C(=O)Cn2cnc3c(N)ncnc32)C1] | 175a | 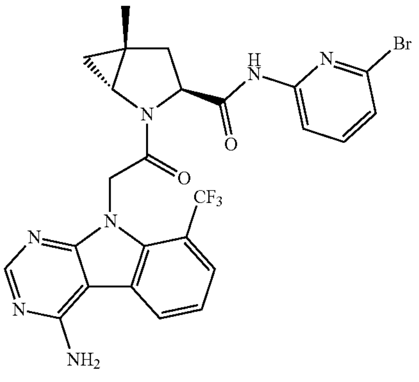 [SMILES: C[C@@]12C[C@@H](C(=O)Nc3cccc(Br)n3)N(C(=O)Cn3c4ncnc(N)c4c4cccc(C(F)(F)F)c43)[C@@H]1C2] |

-continued
| # | Structure | # | Structure |
| --- | --- | --- | --- |
| 123g | 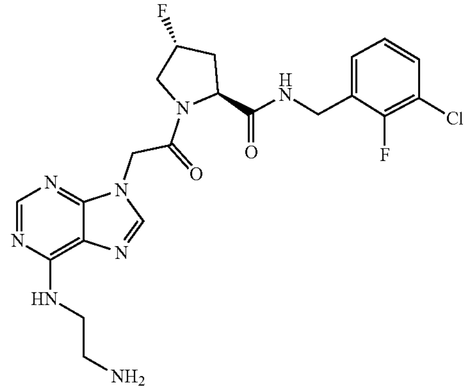 [SMILES: NCCNc1ncnc2c1ncn2CC(=O)N1C[C@H](F)C[C@H]1C(=O)NCc1cccc(Cl)c1F] | 176a | 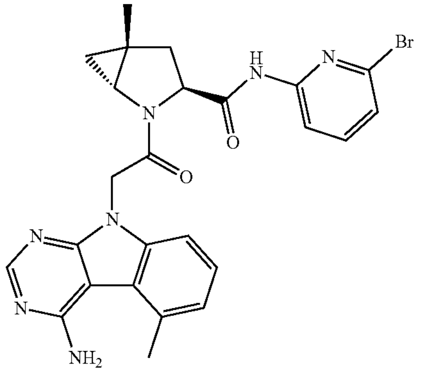 [SMILES: Cc1cccc2c1c1c(N)ncnc1n2CC(=O)N1[C@H](C(=O)Nc2cccc(Br)n2)C[C@@]2(C)C[C@@H]12] |
| 118a | 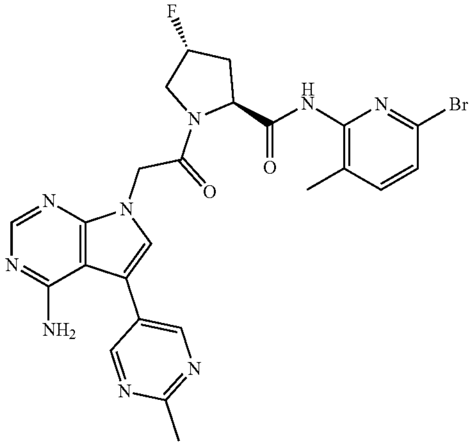 [SMILES: Cc1ncc(-c2cn(CC(=O)N3C[C@H](F)C[C@H]3C(=O)Nc3nc(Br)ccc3C)c3ncnc(N)c23)cn1] | 169f | 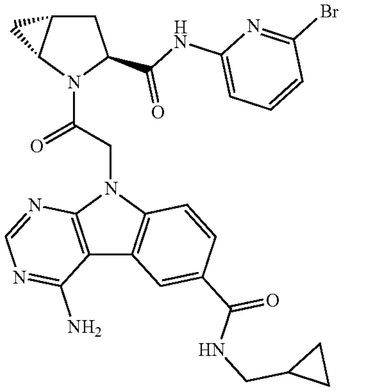 [SMILES: Nc1ncnc2c1c1cc(C(=O)NCC3CC3)ccc1n2CC(=O)N1[C@@H]2C[C@@H]2C[C@H]1C(=O)Nc1cccc(Br)n1] |
| 117d | 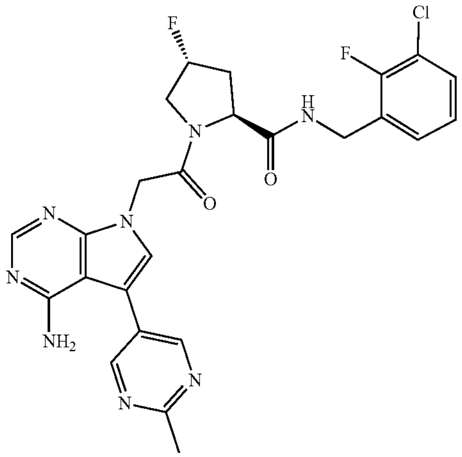 [SMILES: Cc1ncc(-c2cn(CC(=O)N3C[C@H](F)C[C@H]3C(=O)NCc3cccc(Cl)c3F)c3ncnc(N)c23)cn1] | 177d | 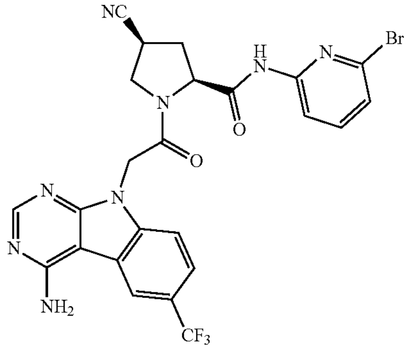 [SMILES: N#C[C@H]1C[C@@H](C(=O)Nc2cccc(Br)n2)N(C(=O)Cn2c3ccc(C(F)(F)F)cc3c3c(N)ncnc32)C1] |

-continued
| # | Structure | # | Structure |
|---|---|---|---|
| 116b | 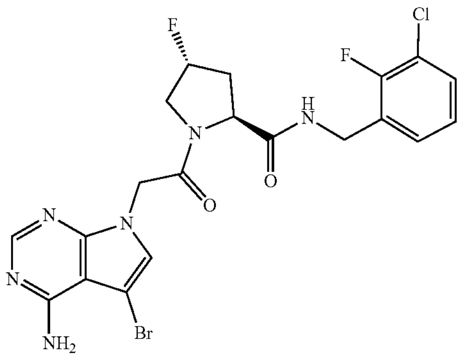 [SMILES: Nc1ncnc2c1c(Br)cn2CC(=O)N1C[C@H](F)C[C@H]1C(=O)NCc1cccc(Cl)c1F] | 178d | 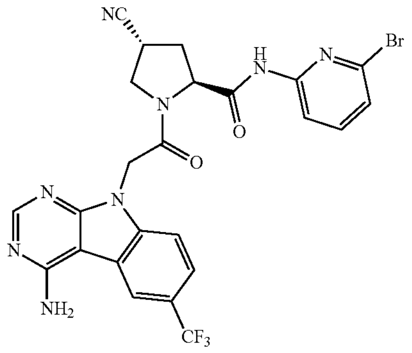 [SMILES: N#C[C@@H]1C[C@@H](C(=O)Nc2cccc(Br)n2)N(C(=O)Cn2c3ccc(C(F)(F)F)cc3c3c(N)ncnc32)C1] |
| 115e | 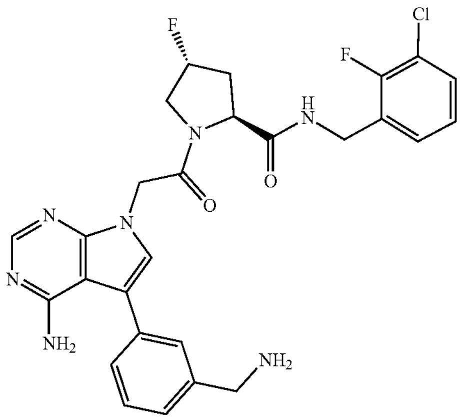 [SMILES: NCc1cccc(-c2cn(CC(=O)N3C[C@H](F)C[C@H]3C(=O)NCc3cccc(Cl)c3F)c3ncnc(N)c23)c1] | 162g | 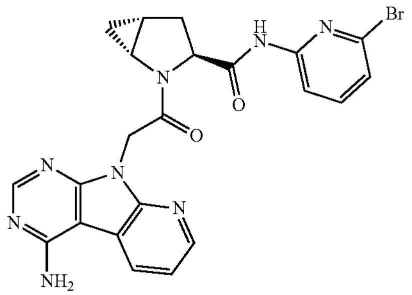 [SMILES: Nc1ncnc2c1c1cccnc1n2CC(=O)N1[C@@H]2C[C@@H]2C[C@H]1C(=O)Nc1cccc(Br)n1] |
| 114f | 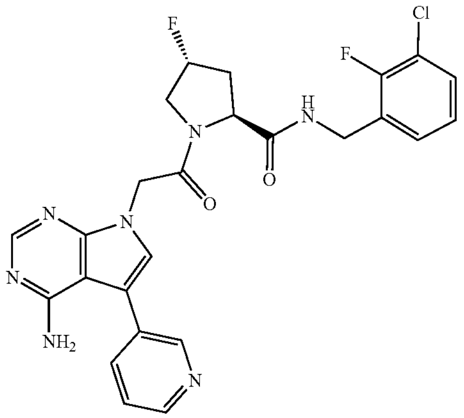 [SMILES: Nc1ncnc2c1c(-c1cccnc1)cn2CC(=O)N1C[C@H](F)C[C@H]1C(=O)NCc1cccc(Cl)c1F] | 163g | 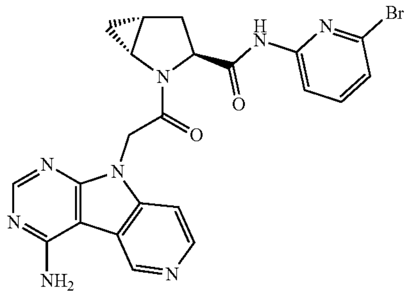 [SMILES: Nc1ncnc2c1c1cnccc1n2CC(=O)N1[C@@H]2C[C@@H]2C[C@H]1C(=O)Nc1cccc(Br)n1] |
| 113a | 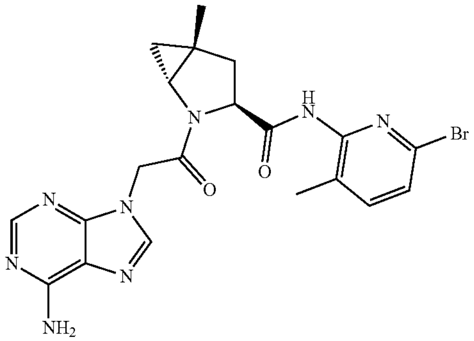 [SMILES: Cc1ccc(Br)nc1NC(=O)[C@@H]1C[C@@]2(C)C[C@H]2N1C(=O)Cn1cnc2c(N)ncnc21] | 164a | 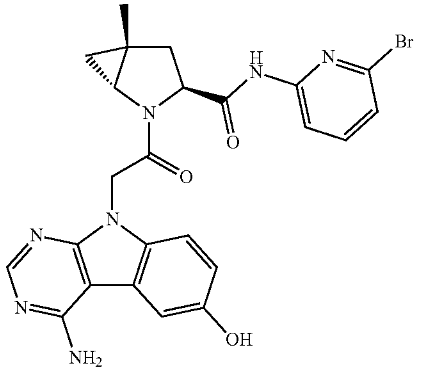 [SMILES: C[C@@]12C[C@@H](C(=O)Nc3cccc(Br)n3)N(C(=O)Cn3c4ccc(O)cc4c4c(N)ncnc43)[C@@H]1C2] |

-continued
| # | Structure | # | Structure |
|---|---|---|---|
| 66b | 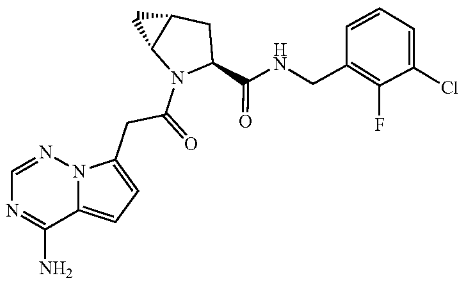 [SMILES: Nc1ncnn2c(CC(=O)N3[C@@H]4C[C@@H]4C[C@H]3C(=O)NCc3cccc(Cl)c3F)ccc12] | 165a | 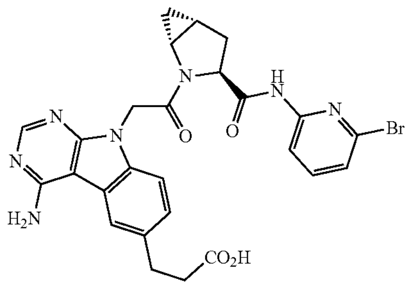 [SMILES: Nc1ncnc2c1c1cc(CCC(=O)O)ccc1n2CC(=O)N1[C@@H]2C[C@@H]2C[C@H]1C(=O)Nc1cccc(Br)n1] |
| 124b | 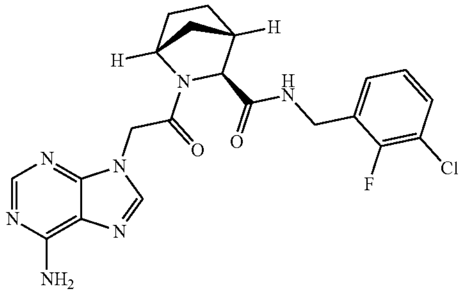 [SMILES: Nc1ncnc2c1ncn2CC(=O)N1[C@@H]2CC[C@@H](C2)[C@H]1C(=O)NCc1cccc(Cl)c1F] | 170c | 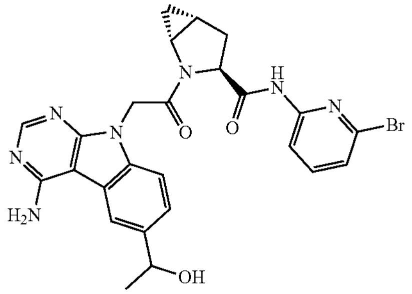 [SMILES: CC(O)c1ccc2c(c1)c1c(N)ncnc1n2CC(=O)N1[C@@H]2C[C@@H]2C[C@H]1C(=O)Nc1cccc(Br)n1] |
| 68a | 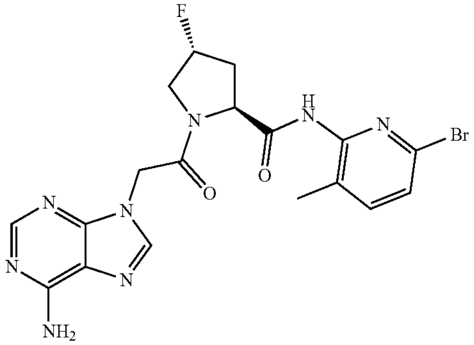 [SMILES: Cc1ccc(Br)nc1NC(=O)[C@@H]1C[C@@H](F)CN1C(=O)Cn1cnc2c(N)ncnc21] | 179d | 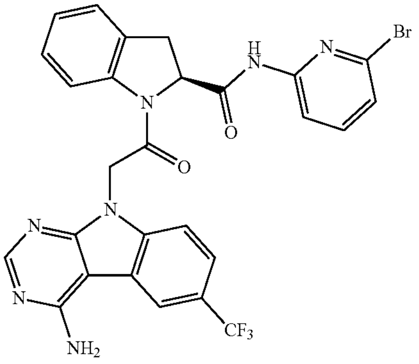 [SMILES: Nc1ncnc2c1c1cc(C(F)(F)F)ccc1n2CC(=O)N1c2ccccc2C[C@H]1C(=O)Nc1cccc(Br)n1] |
| 67c | 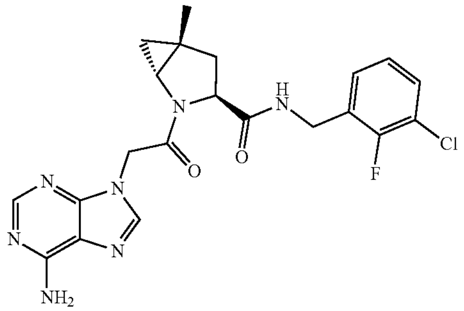 [SMILES: C[C@@]12C[C@@H](C(=O)NCc3cccc(Cl)c3F)N(C(=O)Cn3cnc4c(N)ncnc43)[C@@H]1C2] | 180e | 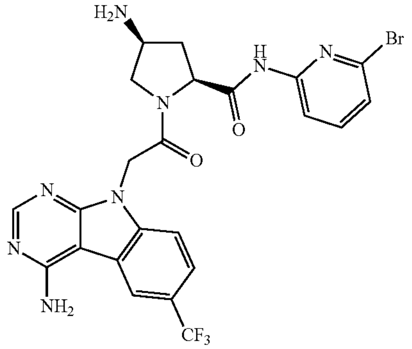 [SMILES: Nc1ncnc2c1c1cc(C(F)(F)F)ccc1n2CC(=O)N1C[C@@H](N)C[C@H]1C(=O)Nc1cccc(Br)n1] |

-continued
| # | Structure | # | Structure |
|---|---|---|---|
| 65a | 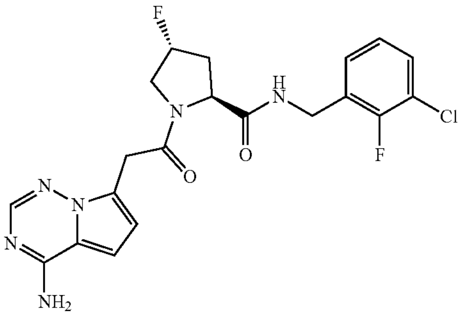 [SMILES: Nc1ncnn2c(CC(=O)N3C[C@H](F)C[C@H]3C(=O)NCc3cccc(Cl)c3F)ccc12] | 166a | 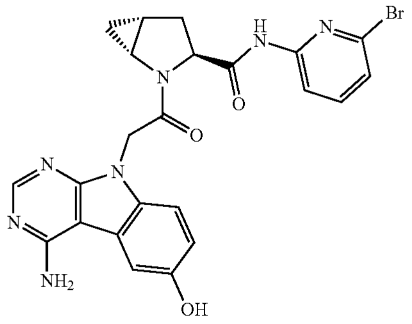 [SMILES: Nc1ncnc2c1c1cc(O)ccc1n2CC(=O)N1[C@@H]2C[C@@H]2C[C@H]1C(=O)Nc1cccc(Br)n1] |
| 64a | 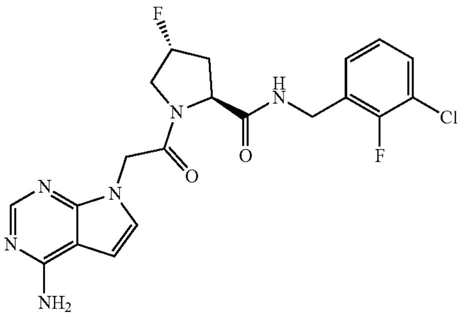 [SMILES: Nc1ncnc2c1ccn2CC(=O)N1C[C@H](F)C[C@H]1C(=O)NCc1cccc(Cl)c1F] | 167a | 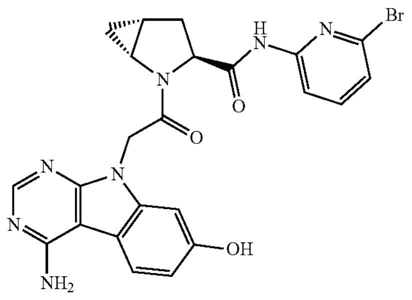 [SMILES: Nc1ncnc2c1c1ccc(O)cc1n2CC(=O)N1[C@@H]2C[C@@H]2C[C@H]1C(=O)Nc1cccc(Br)n1] |
| 130e | 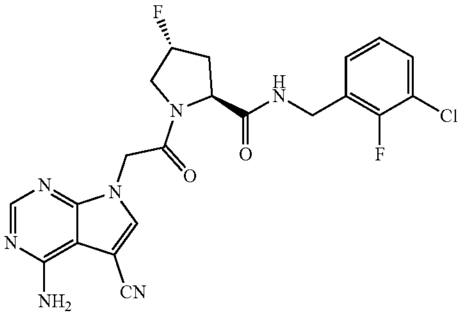 [SMILES: N#Cc1cn(CC(=O)N2C[C@H](F)C[C@H]2C(=O)NCc2cccc(Cl)c2F)c2ncnc(N)c12] | 168g | 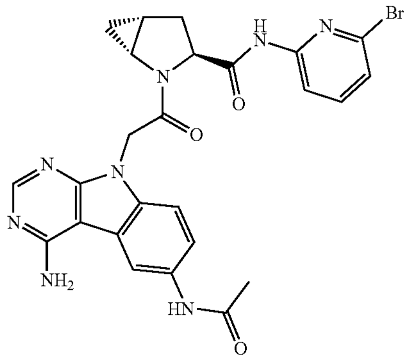 [SMILES: CC(=O)Nc1ccc2c(c1)c1c(N)ncnc1n2CC(=O)N1[C@@H]2C[C@@H]2C[C@H]1C(=O)Nc1cccc(Br)n1] |
| 131e | 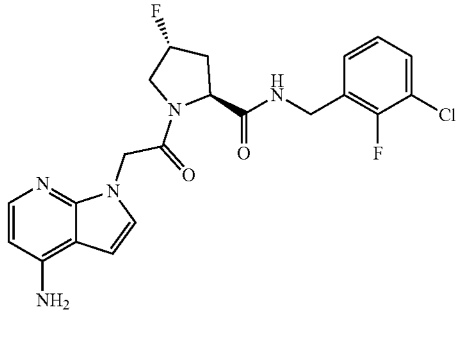 [SMILES: Nc1ccnc2c1ccn2CC(=O)N1C[C@H](F)C[C@H]1C(=O)NCc1cccc(Cl)c1F] | 187c | 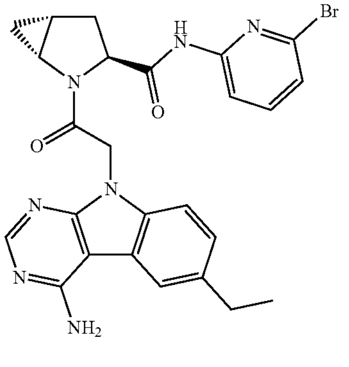 [SMILES: CCc1ccc2c(c1)c1c(N)ncnc1n2CC(=O)N1[C@@H]2C[C@@H]2C[C@H]1C(=O)Nc1cccc(Br)n1] |

-continued
| # | Structure | # | Structure |
|---|---|---|---|
| 132d | 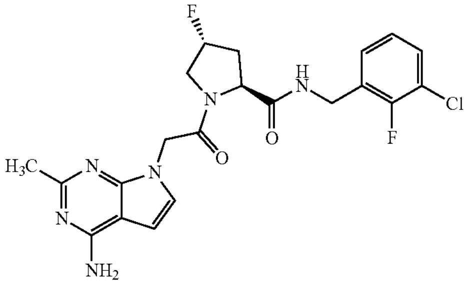 [SMILES: Cc1nc(N)c2ccn(CC(=O)N3C[C@H](F)C[C@H]3C(=O)NCc3cccc(Cl)c3F)c2n1] | 188g | 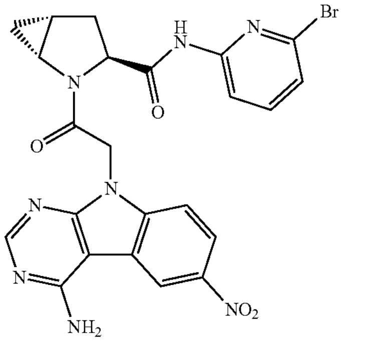 [SMILES: Nc1ncnc2c1c1cc([N+](=O)[O-])ccc1n2CC(=O)N1[C@@H]2C[C@@H]2C[C@H]1C(=O)Nc1cccc(Br)n1] |
| 133b | 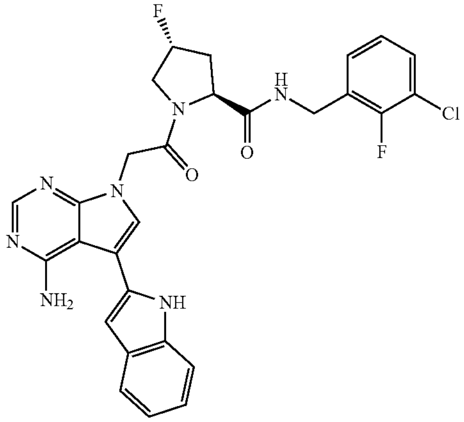 [SMILES: Nc1ncnc2c1c(-c1cc3ccccc3[nH]1)cn2CC(=O)N1C[C@H](F)C[C@H]1C(=O)NCc1cccc(Cl)c1F] | 195e | 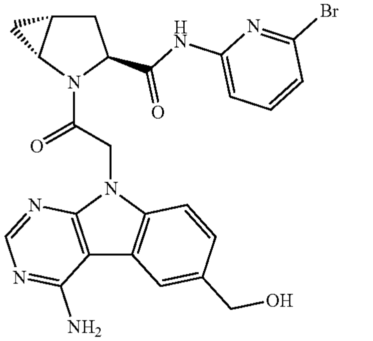 [SMILES: Nc1ncnc2c1c1cc(CO)ccc1n2CC(=O)N1[C@@H]2C[C@@H]2C[C@H]1C(=O)Nc1cccc(Br)n1] |
| 20a | 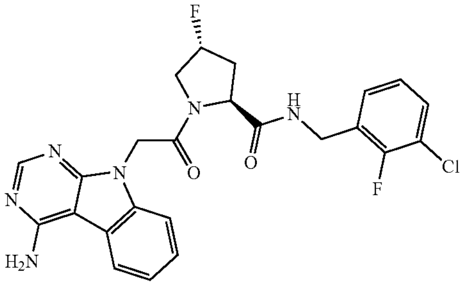 [SMILES: Nc1ncnc2c1c1ccccc1n2CC(=O)N1C[C@H](F)C[C@H]1C(=O)NCc1cccc(Cl)c1F] | 198a | 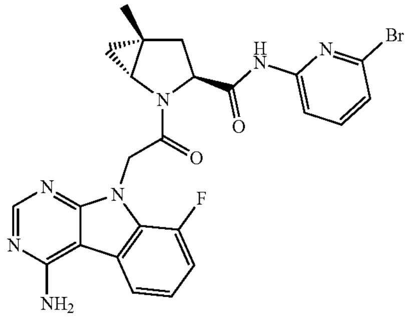 [SMILES: C[C@@]12C[C@@H](C(=O)Nc3cccc(Br)n3)N(C(=O)Cn3c4ncnc(N)c4c4cccc(F)c43)[C@@H]1C2] |
| 134b | 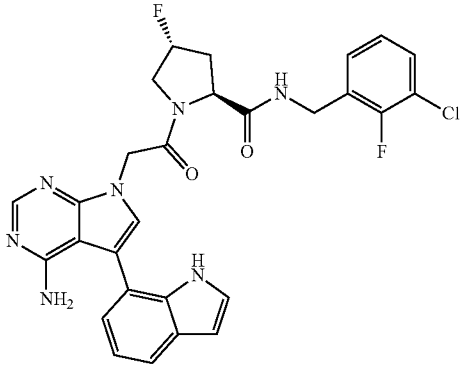 [SMILES: Nc1ncnc2c1c(-c1cccc3cc[nH]c13)cn2CC(=O)N1C[C@H](F)C[C@H]1C(=O)NCc1cccc(Cl)c1F] | 199a | 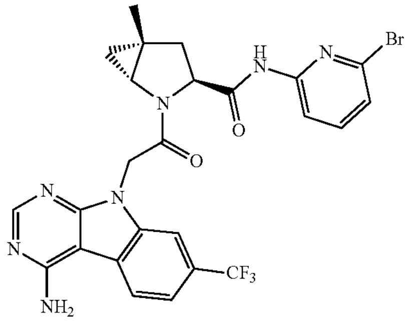 [SMILES: C[C@@]12C[C@@H](C(=O)Nc3cccc(Br)n3)N(C(=O)Cn3c4cc(C(F)(F)F)ccc4c4c(N)ncnc43)[C@@H]1C2] |

-continued
| # | Structure | # | Structure |
|---|---|---|---|
| 135a | 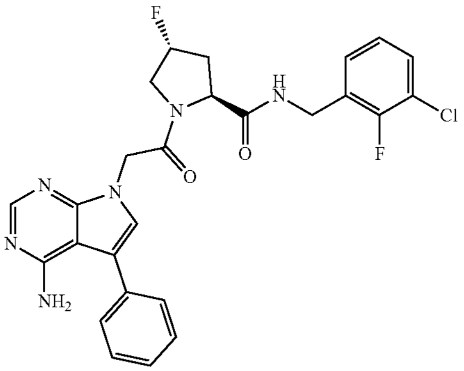 [SMILES: Nc1ncnc2c1c(-c1ccccc1)cn2CC(=O)N1C[C@H](F)C[C@H]1C(=O)NCc1cccc(Cl)c1F] | 200a | 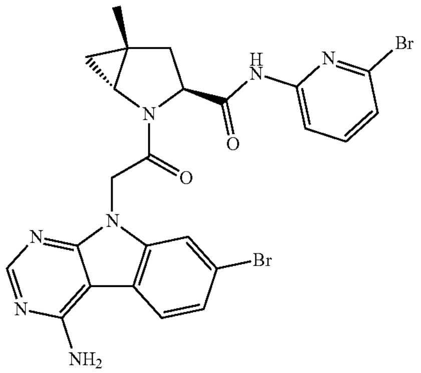 [SMILES: C[C@@]12C[C@@H](C(=O)Nc3cccc(Br)n3)N(C(=O)Cn3c4cc(Br)ccc4c4c(N)ncnc43)[C@@H]1C2] |
| 136a | 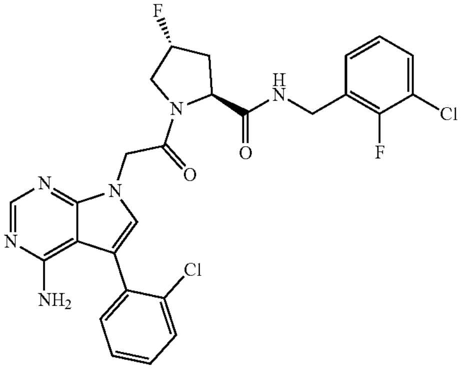 [SMILES: Nc1ncnc2c1c(-c1ccccc1Cl)cn2CC(=O)N1C[C@H](F)C[C@H]1C(=O)NCc1cccc(Cl)c1F] | 194a | 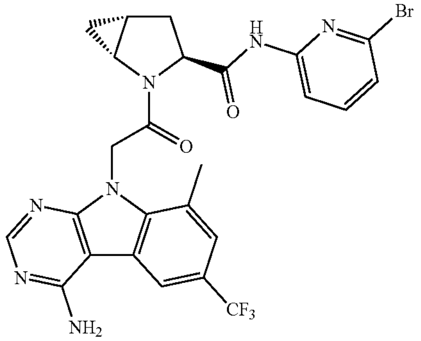 [SMILES: Cc1cc(C(F)(F)F)cc2c3c(N)ncnc3n(CC(=O)N3[C@@H]4C[C@@H]4C[C@H]3C(=O)Nc3cccc(Br)n3)c12] |
| 137b | 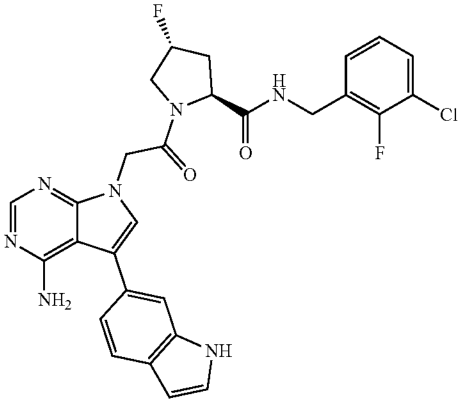 [SMILES: Nc1ncnc2c1c(-c1ccc3cc[nH]c3c1)cn2CC(=O)N1C[C@H](F)C[C@H]1C(=O)NCc1cccc(Cl)c1F] | 201e | 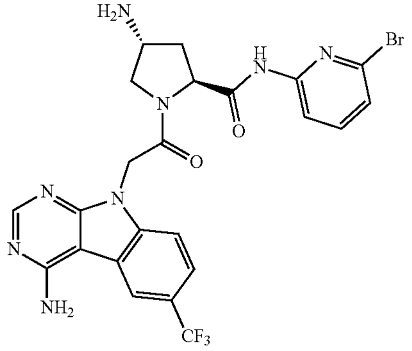 [SMILES: Nc1ncnc2c1c1cc(C(F)(F)F)ccc1n2CC(=O)N1C[C@H](N)C[C@H]1C(=O)Nc1cccc(Br)n1] |
| 140a | 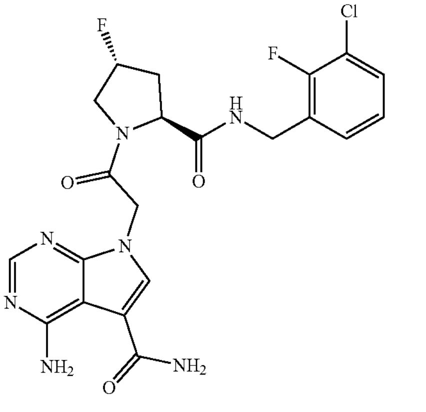 [SMILES: NC(=O)c1cn(CC(=O)N2C[C@H](F)C[C@H]2C(=O)NCc2cccc(Cl)c2F)c2ncnc(N)c12] | 211e | 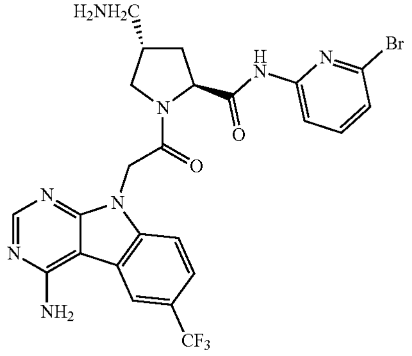 |

-continued
| # | Structure | # | Structure |
| --- | --- | --- | --- |
| 141a | 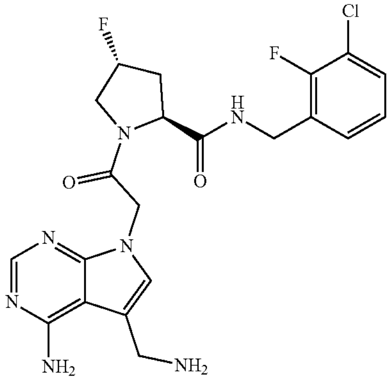 [SMILES: NCc1cn(CC(=O)N2C[C@H](F)C[C@H]2C(=O)NCc2cccc(Cl)c2F)c2ncnc(N)c12] | 212e | 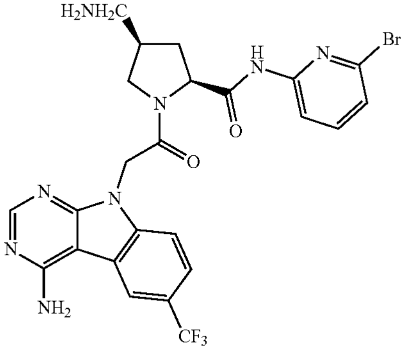 |
| 138d | 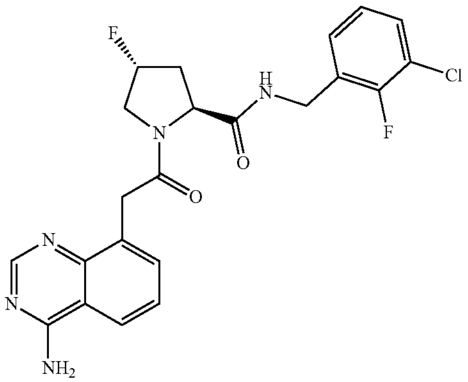 [SMILES: Nc1ncnc2c(CC(=O)N3C[C@H](F)C[C@H]3C(=O)NCc3cccc(Cl)c3F)cccc12] | 181a | 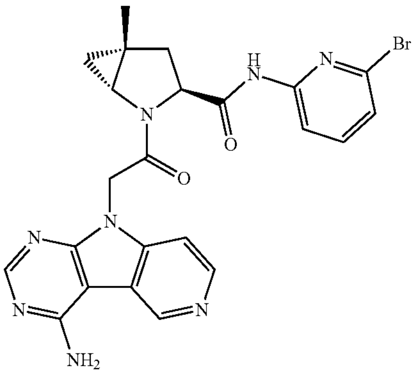 [SMILES: C[C@@]12C[C@@H](C(=O)Nc3cccc(Br)n3)N(C(=O)Cn3c4ccncc4c4c(N)ncnc43)[C@@H]1C2] |
| 139b | 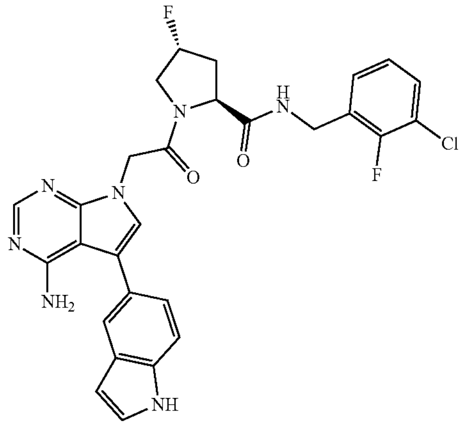 [SMILES: Nc1ncnc2c1c(-c1ccc3[nH]ccc3c1)cn2CC(=O)N1C[C@H](F)C[C@H]1C(=O)NCc1cccc(Cl)c1F] | 182a | 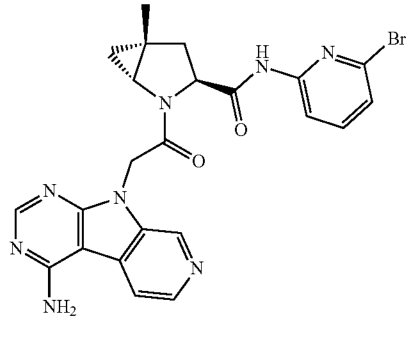 [SMILES: C[C@@]12C[C@@H](C(=O)Nc3cccc(Br)n3)N(C(=O)Cn3c4cnccc4c4c(N)ncnc43)[C@@H]1C2] |
| 125d | 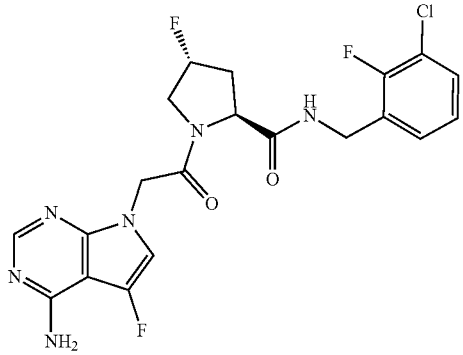 [SMILES: Nc1ncnc2c1c(F)cn2CC(=O)N1C[C@H](F)C[C@H]1C(=O)NCc1cccc(Cl)c1F] | 183a | 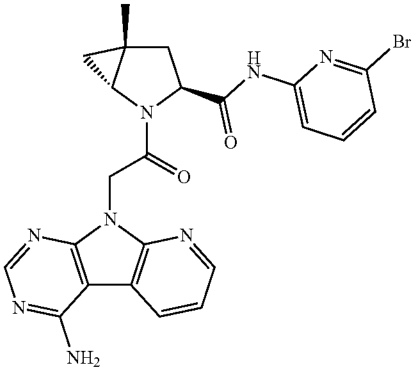 [SMILES: C[C@@]12C[C@@H](C(=O)Nc3cccc(Br)n3)N(C(=O)Cn3c4ncccc4c4c(N)ncnc43)[C@@H]1C2] |

-continued
| # | Structure | # | Structure |
| --- | --- | --- | --- |
| 126f | 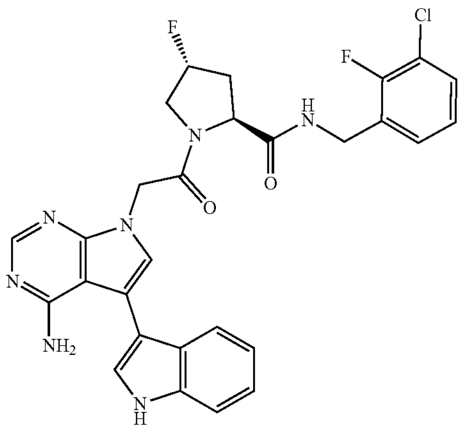 [SMILES: Nc1ncnc2c1c(-c1c[nH]c3ccccc13)cn2CC(=O)N1C[C@H](F)C[C@H]1C(=O)NCc1cccc(Cl)c1F] | 207b | 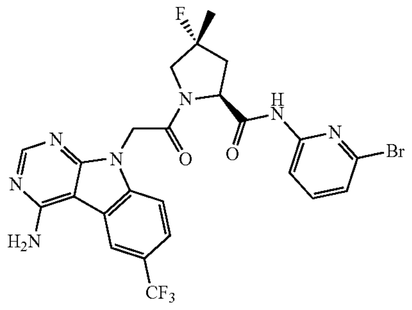 [SMILES: C[C@@]1(F)C[C@@H](C(=O)Nc2cccc(Br)n2)N(C(=O)Cn2c3ccc(C(F)(F)F)cc3c3c(N)ncnc32)C1] |
| 142d | 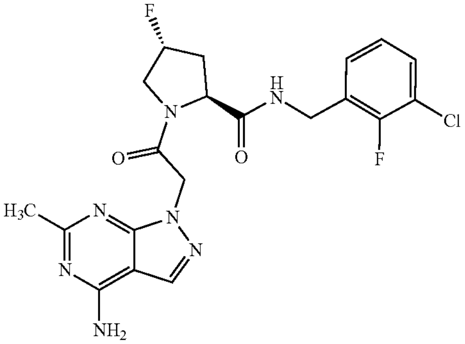 [SMILES: Cc1nc(N)c2cnn(CC(=O)N3C[C@H](F)C[C@H]3C(=O)NCc3cccc(Cl)c3F)c2n1] | 208d | 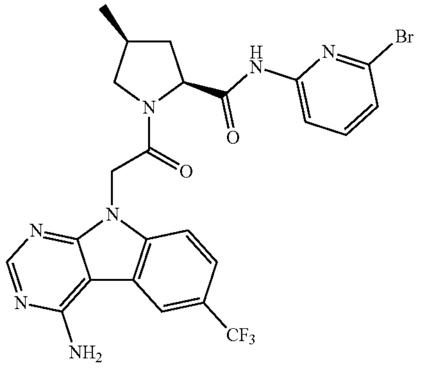 [SMILES: C[C@H]1C[C@@H](C(=O)Nc2cccc(Br)n2)N(C(=O)Cn2c3ccc(C(F)(F)F)cc3c3c(N)ncnc32)C1] |
| 143d | 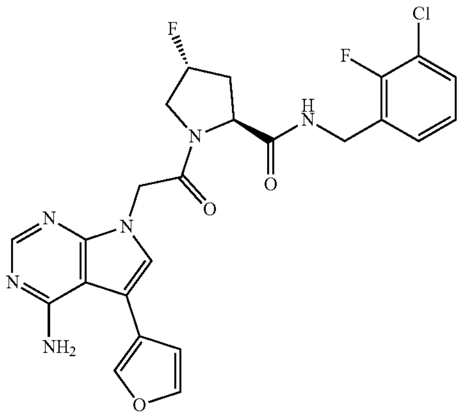 [SMILES: Nc1ncnc2c1c(-c1ccoc1)cn2CC(=O)N1C[C@H](F)C[C@H]1C(=O)NCc1cccc(Cl)c1F] | 203a | 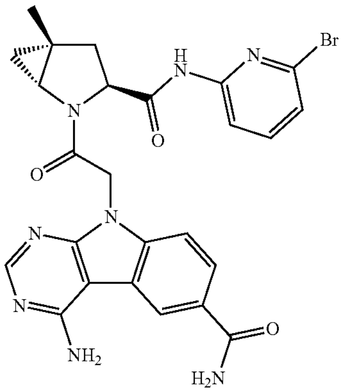 [SMILES: C[C@@]12C[C@@H](C(=O)Nc3cccc(Br)n3)N(C(=O)Cn3c4ccc(C(N)=O)cc4c4c(N)ncnc43)[C@@H]1C2] |

-continued
| # | Structure | # | Structure |
|---|---|---|---|
| 144g | 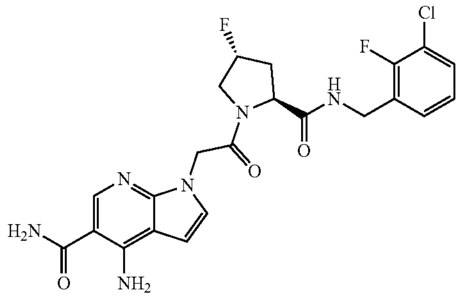 [SMILES: NC(=O)c1cnc2c(ccn2CC(=O)N2C[C@H](F)C[C@H]2C(=O)NCc2cccc(Cl)c2F)c1N] | 204a | 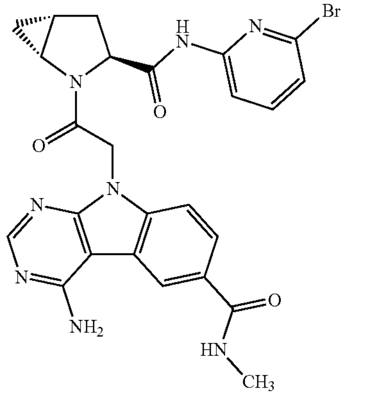 [SMILES: CNC(=O)c1ccc2c(c1)c1c(N)ncnc1n2CC(=O)N1[C@@H]2C[C@@H]2C[C@H]1C(=O)Nc1cccc(Br)n1] |
| 145a | 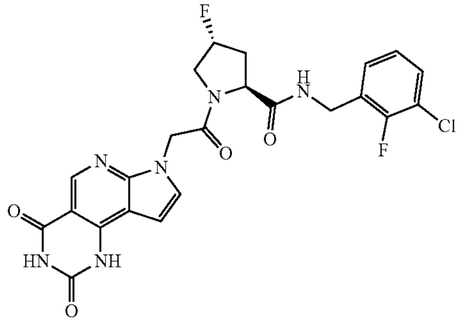 [SMILES: O=C(NCc1cccc(Cl)c1F)[C@@H]1C[C@@H](F)CN1C(=O)Cn1ccc2c3[nH]c(=O)[nH]c(=O)c3cnc21] | 184g | 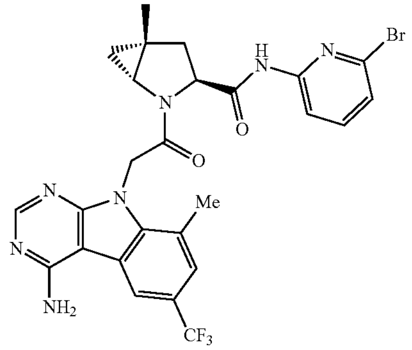 [SMILES: Cc1cc(C(F)(F)F)cc2c3c(N)ncnc3n(CC(=O)N3[C@H](C(=O)Nc4cccc(Br)n4)C[C@@]4(C)C[C@@H]34)c12] |
| 235a | 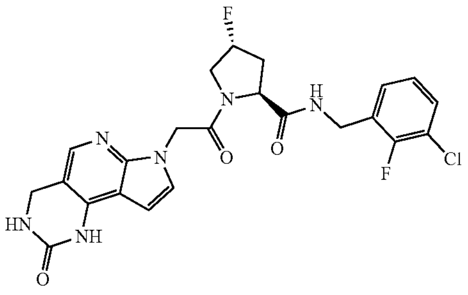 [SMILES: O=C1NCc2cnc3c(ccn3CC(=O)N3C[C@H](F)C[C@H]3C(=O)NCc3cccc(Cl)c3F)c2N1] | 185a | 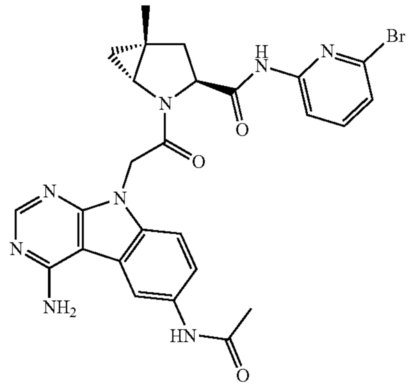 [SMILES: CC(=O)Nc1ccc2c(c1)c1c(N)ncnc1n2CC(=O)N1[C@H](C(=O)Nc2cccc(Br)n2)C[C@@]2(C)C[C@@H]12] |
| 146a | 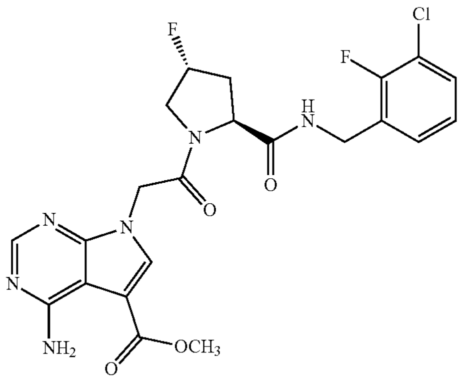 [SMILES: COC(=O)c1cn(CC(=O)N2C[C@H](F)C[C@H]2C(=O)NCc2cccc(Cl)c2F)c2ncnc(N)c12] | 186a | 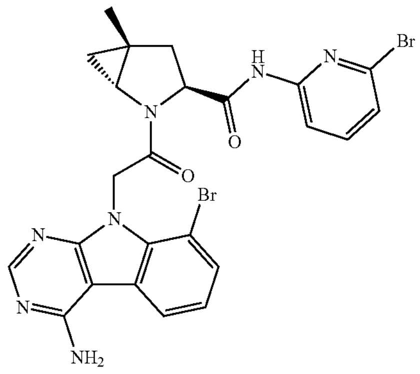 [SMILES: C[C@@]12C[C@@H](C(=O)Nc3cccc(Br)n3)N(C(=O)Cn3c4ncnc(N)c4c4cccc(Br)c43)[C@@H]1C2] |

-continued
| # | Structure | # | Structure |
| --- | --- | --- | --- |
| 147a | 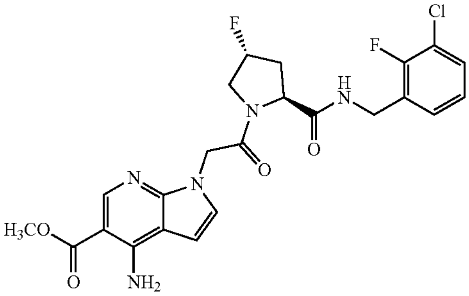 [SMILES: COC(=O)c1cnc2c(ccn2CC(=O)N2C[C@H](F)C[C@H]2C(=O)NCc2cccc(Cl)c2F)c1N] | 206c | 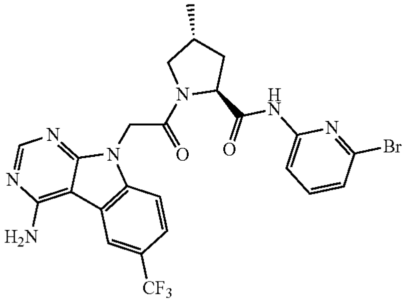 [SMILES: C[C@@H]1C[C@@H](C(=O)Nc2cccc(Br)n2)N(C(=O)Cn2c3ccc(C(F)(F)F)cc3c3c(N)ncnc32)C1] |
| 148d | 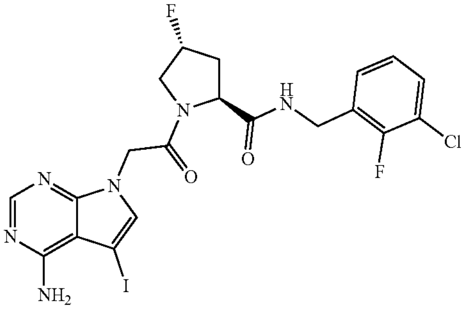 [SMILES: Nc1ncnc2c1c(I)cn2CC(=O)N1C[C@H](F)C[C@H]1C(=O)NCc1cccc(Cl)c1F] | 209b | 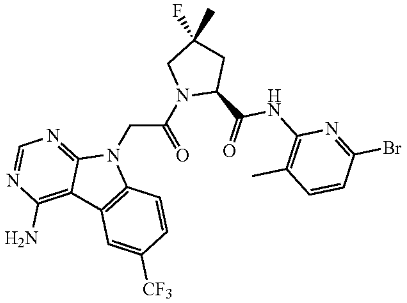 [SMILES: Cc1ccc(Br)nc1NC(=O)[C@@H]1C[C@@](C)(F)CN1C(=O)Cn1c2ccc(C(F)(F)F)cc2c2c(N)ncnc21] |
| 19a | 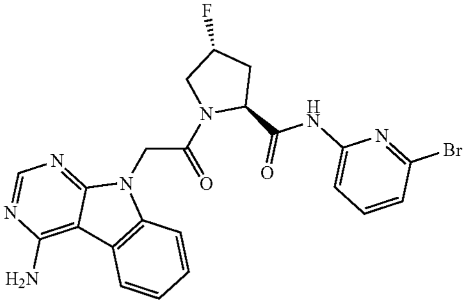 [SMILES: Nc1ncnc2c1c1ccccc1n2CC(=O)N1C[C@H](F)C[C@H]1C(=O)Nc1cccc(Br)n1] | 210d | 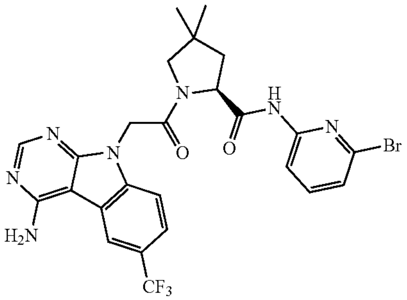 |
| 3b | 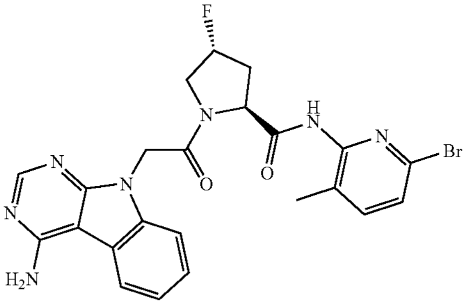 [SMILES: Cc1ccc(Br)nc1NC(=O)[C@@H]1C[C@@H](F)CN1C(=O)Cn1c2ccccc2c2c(N)ncnc21] | 189g | 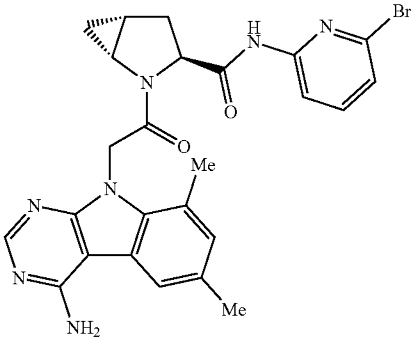 |

-continued
| # | Structure | # | Structure |
|---|---|---|---|
| 149b | 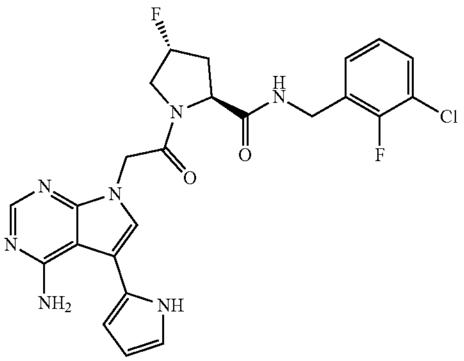 [SMILES: Nc1ncnc2c1c(-c1ccc[nH]1)cn2CC(=O)N1C[C@H](F)C[C@H]1C(=O)NCc1cccc(Cl)c1F] | 193a | 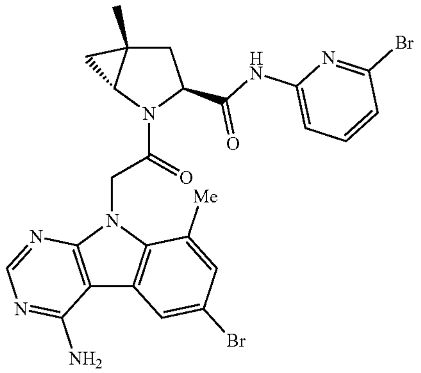 [SMILES: Cc1cc(Br)cc2c3c(N)ncnc3n(CC(=O)N3[C@H](C(=O)Nc4cccc(Br)n4)C[C@@]4(C)C[C@@H]34)c12] |
| 4b | 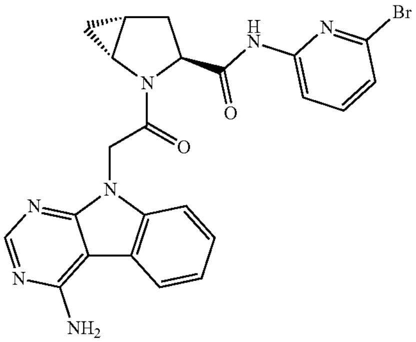 [SMILES: Nc1ncnc2c1c1ccccc1n2CC(=O)N1[C@@H]2C[C@@H]2C[C@H]1C(=O)Nc1cccc(Br)n1] | 190a | 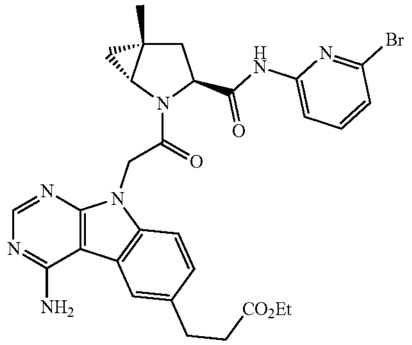 [SMILES: CCOC(=O)CCc1ccc2c(c1)c1c(N)ncnc1n2CC(=O)N1[C@H](C(=O)Nc2cccc(Br)n2)C[C@@]2(C)C[C@@H]12] |
| 5e | 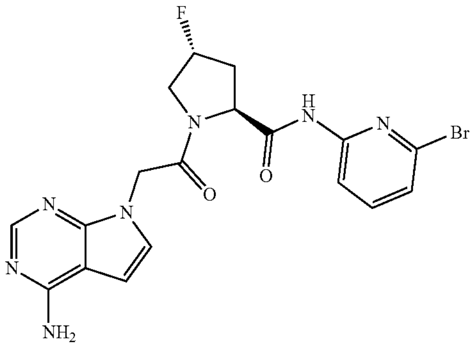 [SMILES: Nc1ncnc2c1ccn2CC(=O)N1C[C@H](F)C[C@H]1C(=O)Nc1cccc(Br)n1] | 191a | 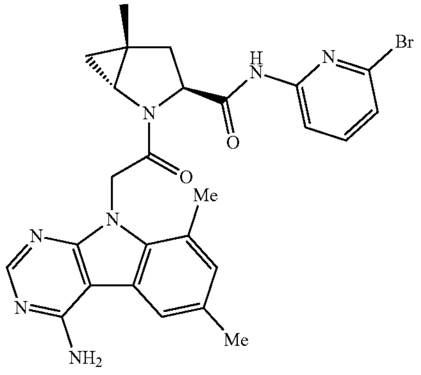 |
| 150d | 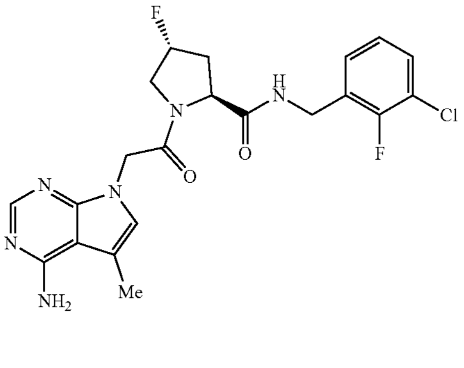 [SMILES: Cc1cn(CC(=O)N2C[C@H](F)C[C@H]2C(=O)NCc2cccc(Cl)c2F)c2ncnc(N)c12] | 192g | 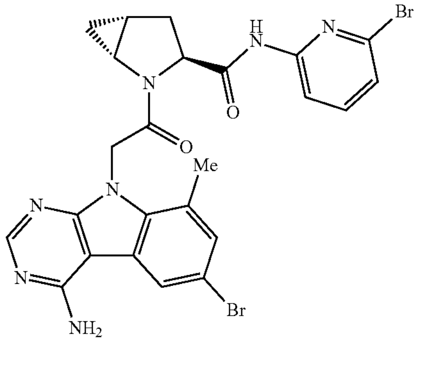 |

-continued
| # | Structure | # | Structure |
|---|---|---|---|
| 69a | 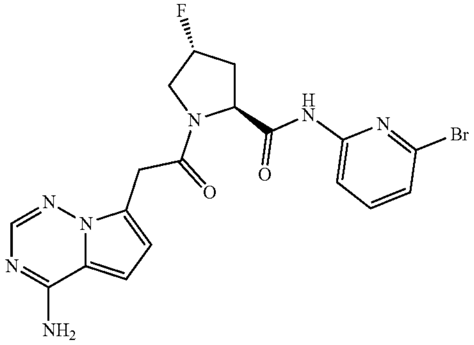 [SMILES: Nc1ncnn2c(CC(=O)N3C[C@H](F)C[C@H]3C(=O)Nc3cccc(Br)n3)ccc12] | 196d | 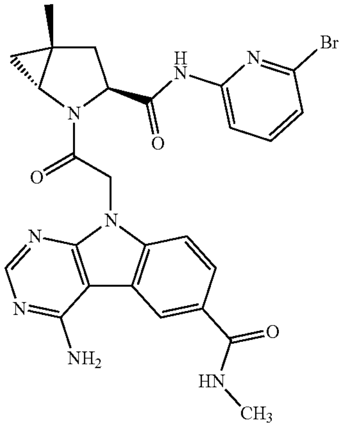 [SMILES: CNC(=O)c1ccc2c(c1)c1c(N)ncnc1n2CC(=O)N1[C@H](C(=O)Nc2cccc(Br)n2)C[C@@]2(C)C[C@@H]12] |
| 70a | 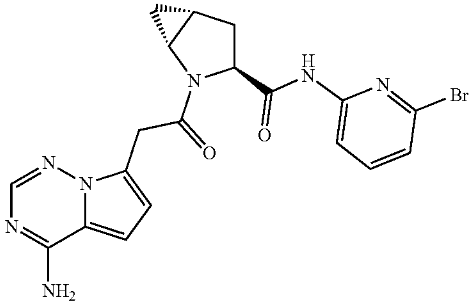 [SMILES: Nc1ncnn2c(CC(=O)N3[C@@H]4C[C@@H]4C[C@H]3C(=O)Nc3cccc(Br)n3)ccc12] | 197c | 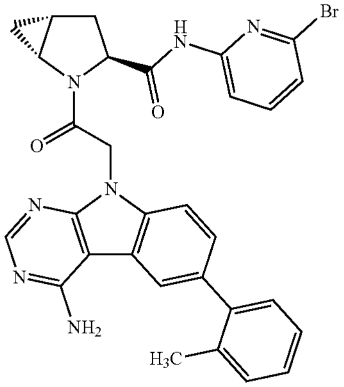 [SMILES: Cc1ccccc1-c1ccc2c(c1)c1c(N)ncnc1n2CC(=O)N1[C@@H]2C[C@@H]2C[C@H]1C(=O)Nc1cccc(Br)n1] |
| 2d | 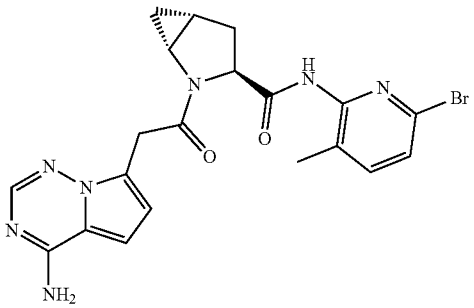 [SMILES: Cc1ccc(Br)nc1NC(=O)[C@@H]1C[C@H]2C[C@H]2N1C(=O)Cc1ccc2c(N)ncnn12] | 214b | 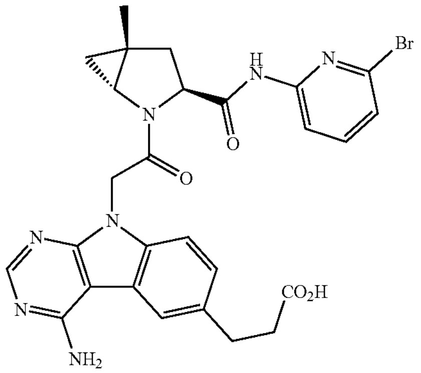 [SMILES: C[C@@]12C[C@@H](C(=O)Nc3cccc(Br)n3)N(C(=O)Cn3c4ccc(CCC(=O)O)cc4c4c(N)ncnc43)[C@@H]1C2] |
| 71a | 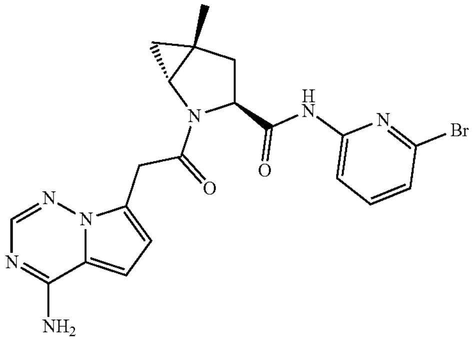 [SMILES: C[C@@]12C[C@@H](C(=O)Nc3cccc(Br)n3)N(C(=O)Cc3ccc4c(N)ncnn34)[C@@H]1C2] | 213d | 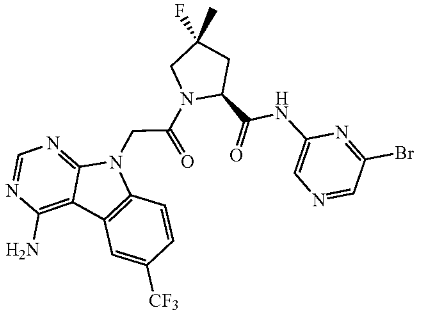 [SMILES: C[C@@]1(F)C[C@@H](C(=O)Nc2cncc(Br)n2)N(C(=O)Cn2c3ccc(C(F)(F)F)cc3c3c(N)ncnc32)C1] |

-continued
| # | Structure | # | Structure |
| --- | --- | --- | --- |
| 72a | 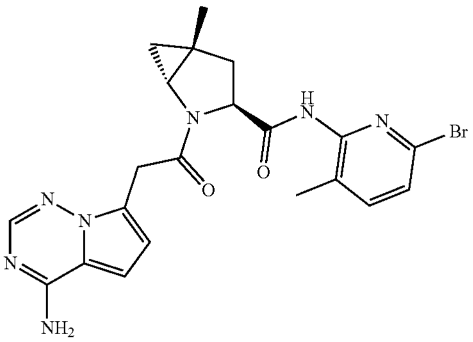 [SMILES: Cc1ccc(Br)nc1NC(=O)[C@@H]1C[C@@]2(C)C[C@H]2N1C(=O)Cc1ccc2c(N)ncnn12] | 215g | 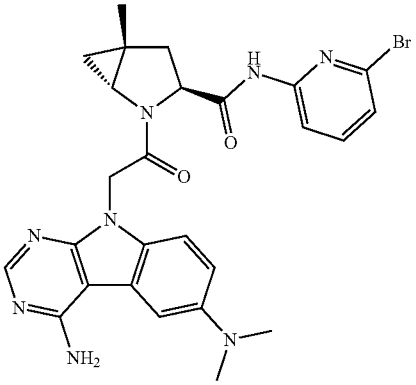 [SMILES: CN(C)c1ccc2c(c1)c1c(N)ncnc1n2CC(=O)N1[C@H](C(=O)Nc2cccc(Br)n2)C[C@@]2(C)C[C@@H]12] |
| 9a | 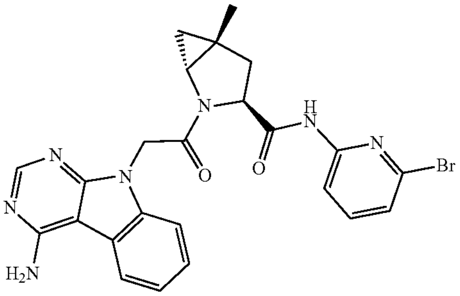 [SMILES: C[C@@]12C[C@@H](C(=O)Nc3cccc(Br)n3)N(C(=O)Cn3c4ccccc4c4c(N)ncnc43)[C@@H]1C2] | 216g | 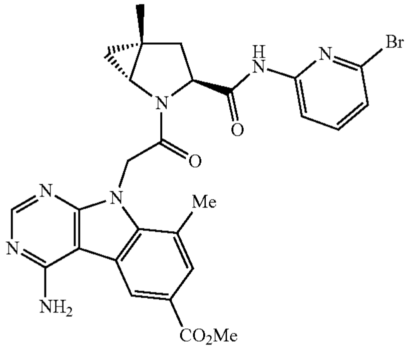 [SMILES: COC(=O)c1cc(C)c2c(c1)c1c(N)ncnc1n2CC(=O)N1[C@H](C(=O)Nc2cccc(Br)n2)C[C@@]2(C)C[C@@H]12] |
| 151a | 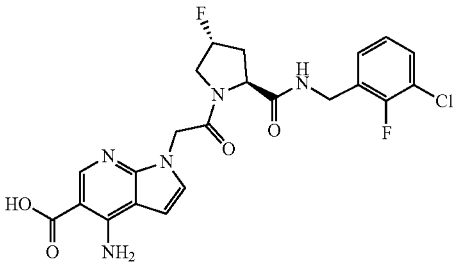 [SMILES: Nc1c(C(=O)O)cnc2c1ccn2CC(=O)N1C[C@H](F)C[C@H]1C(=O)NCc1cccc(Cl)c1F] | 217a | 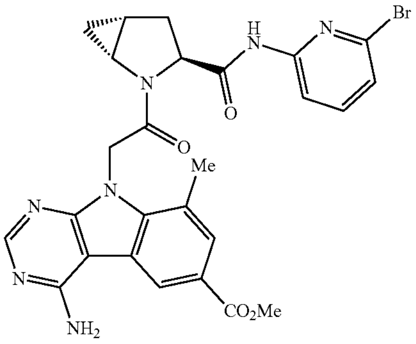 [SMILES: COC(=O)c1cc(C)c2c(c1)c1c(N)ncnc1n2CC(=O)N1[C@@H]2C[C@@H]2C[C@H]1C(=O)Nc1cccc(Br)n1] |
| 152d | 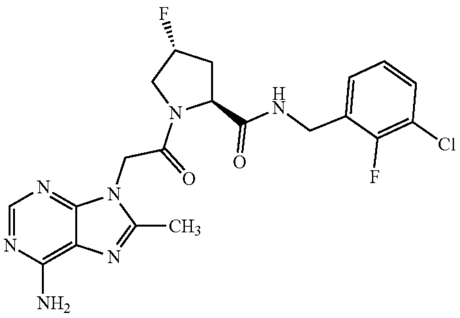 [SMILES: Cc1nc2c(N)ncnc2n1CC(=O)N1C[C@H](F)C[C@H]1C(=O)NCc1cccc(Cl)c1F] | 220a | 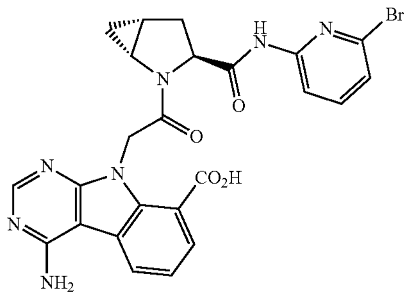 [SMILES: Nc1ncnc2c1c1cccc(C(=O)O)c1n2CC(=O)N1[C@@H]2C[C@@H]2C[C@H]1C(=O)Nc1cccc(Br)n1] |

-continued
| # | Structure | # | Structure |
|---|---|---|---|
| 1e | 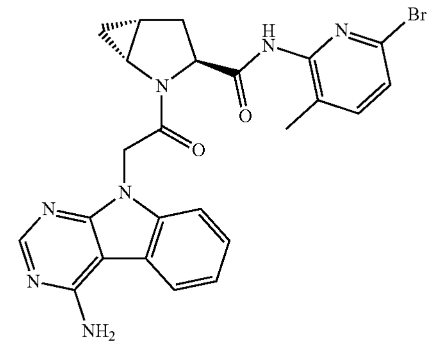 [SMILES: Cc1ccc(Br)nc1NC(=O)[C@@H]1C[C@H]2C[C@H]2N1C(=O)Cn1c2ccccc2c2c(N)ncnc21] | 202a | 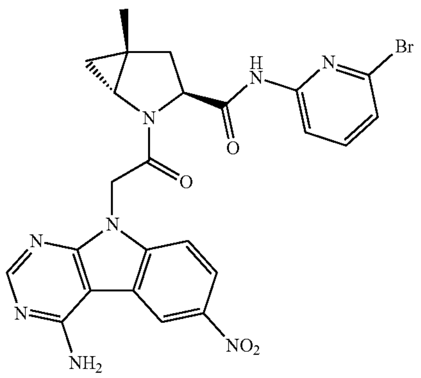 |
| 6e | 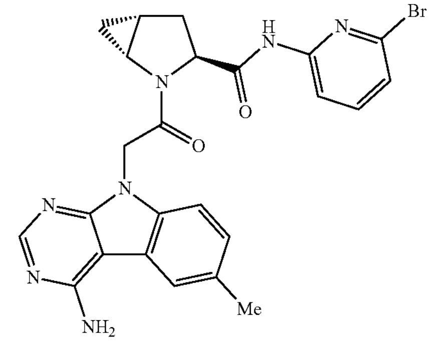 | 205c | 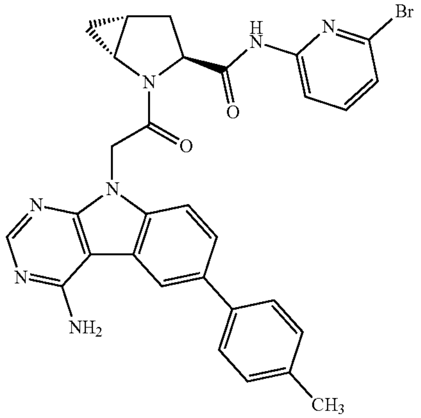 [SMILES: Cc1ccc(-c2ccc3c(c2)c2c(N)ncnc2n3CC(=O)N2[C@@H]3C[C@@H]3C[C@H]2C(=O)Nc2cccc(Br)n2)cc1] |
| 7b | 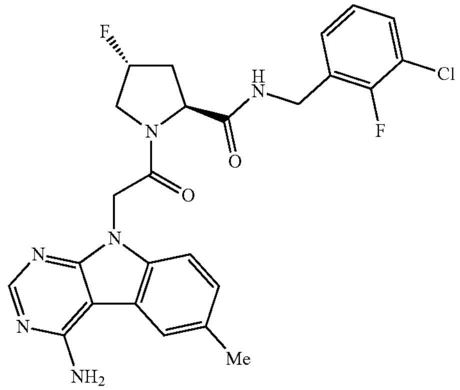 [SMILES: Cc1ccc2c(c1)c1c(N)ncnc1n2CC(=O)N1C[C@H](F)C[C@H]1C(=O)NCc1cccc(Cl)c1F] | 222a | 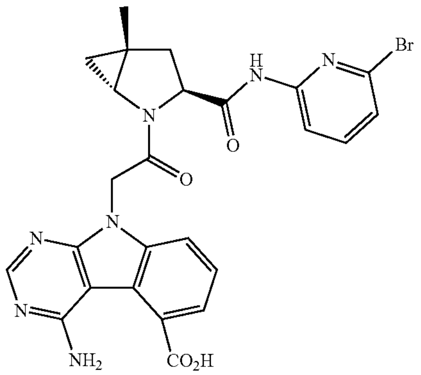 [SMILES: C[C@@]12C[C@@H](C(=O)Nc3cccc(Br)n3)N(C(=O)Cn3c4cccc(C(=O)O)c4c4c(N)ncnc43)[C@@H]1C2] |
| 21a | 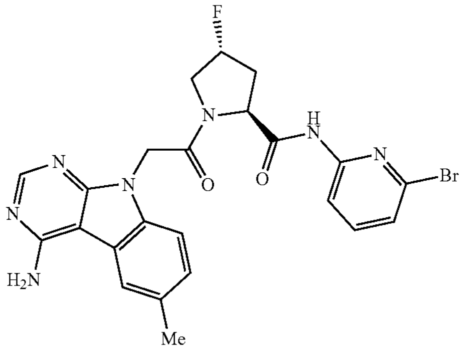 [SMILES: Cc1ccc2c(c1)c1c(N)ncnc1n2CC(=O)N1C[C@H](F)C[C@H]1C(=O)Nc1cccc(Br)n1] | 236f | 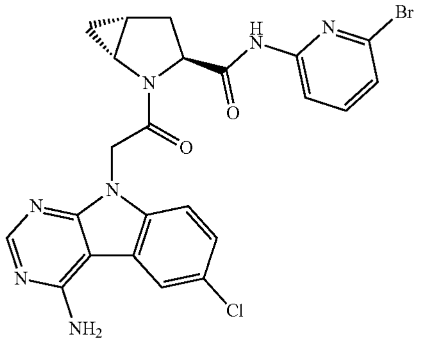 [SMILES: Nc1ncnc2c1c1cc(Cl)ccc1n2CC(=O)N1[C@@H]2C[C@@H]2C[C@H]1C(=O)Nc1cccc(Br)n1] |

-continued
| # | Structure | # | Structure |
|---|---|---|---|
| 73a | 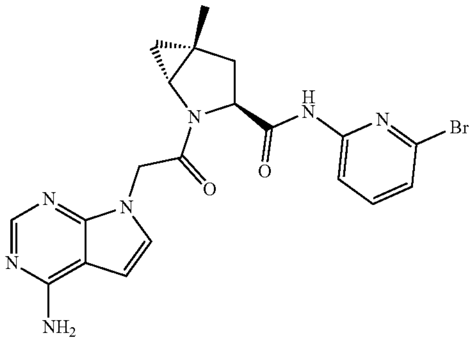 [SMILES: C[C@@]12C[C@@H](C(=O)Nc3cccc(Br)n3)N(C(=O)Cn3ccc4c(N)ncnc43)[C@@H]1C2] | 237a | 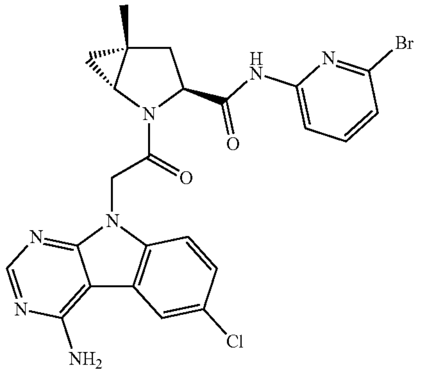 [SMILES: C[C@@]12C[C@@H](C(=O)Nc3cccc(Br)n3)N(C(=O)Cn3c4ccc(Cl)cc4c4c(N)ncnc43)[C@@H]1C2] |
| 74a | 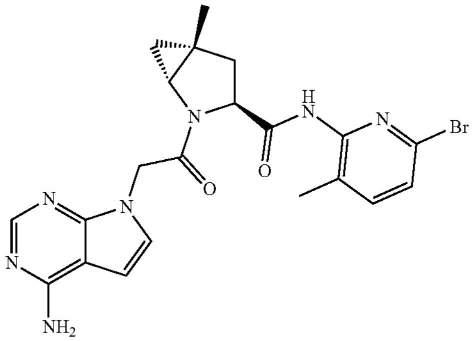 [SMILES: Cc1ccc(Br)nc1NC(=O)[C@@H]1C[C@@]2(C)C[C@H]2N1C(=O)Cn1ccc2c(N)ncnc21] | 238g | 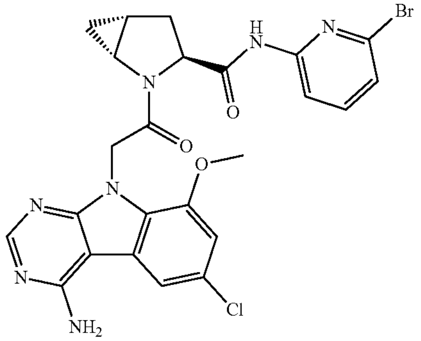 |
| 153a | 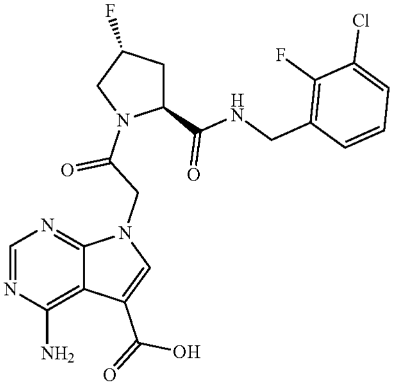 [SMILES: Nc1ncnc2c1c(C(=O)O)cn2CC(=O)N1C[C@H](F)C[C@H]1C(=O)NCc1cccc(Cl)c1F] | 239a | 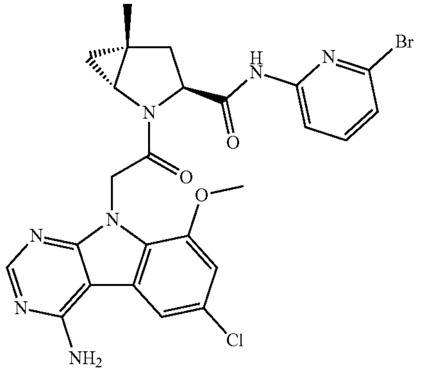 [SMILES: COc1cc(Cl)cc2c3c(N)ncnc3n(CC(=O)N3[C@H](C(=O)Nc4cccc(Br)n4)C[C@@]4(C)C[C@@H]34)c12] |
| 27a | 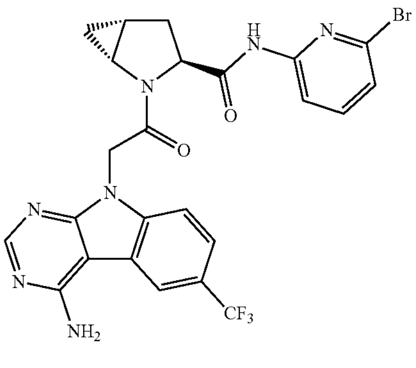 | 296a | 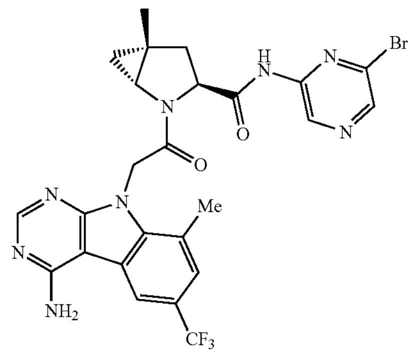 [SMILES: Cc1cc(C(F)(F)F)cc2c3c(N)ncnc3n(CC(=O)N3[C@H](C(=O)Nc4cncc(Br)n4)C[C@@]4(C)C[C@@H]34)c12] |

-continued
| # | Structure | # | Structure |
|---|---|---|---|
| 25a | 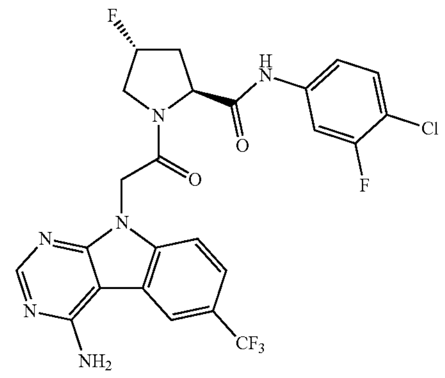 [SMILES: Nc1ncnc2c1c1cc(C(F)(F)F)ccc1n2CC(=O)N1C[C@H](F)C[C@H]1C(=O)Nc1ccc(Cl)c(F)c1] | 240g | 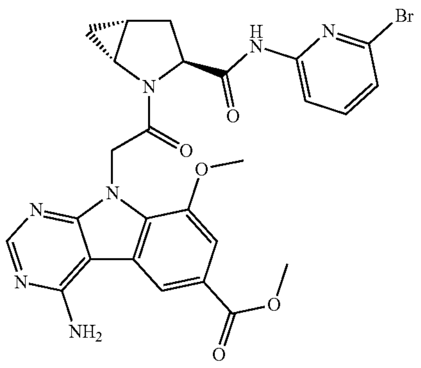 [SMILES: COC(=O)c1cc(OC)c2c(c1)c1c(N)ncnc1n2CC(=O)N1[C@@H]2C[C@@H]2C[C@H]1C(=O)Nc1cccc(Br)n1] |
| 26a | 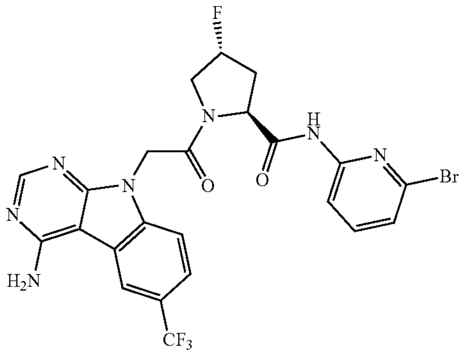 [SMILES: Nc1ncnc2c1c1cc(C(F)(F)F)ccc1n2CC(=O)N1C[C@H](F)C[C@H]1C(=O)Nc1cccc(Br)n1] | 241g | 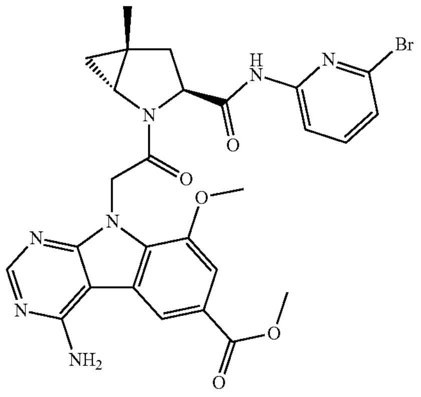 [SMILES: COC(=O)c1cc(OC)c2c(c1)c1c(N)ncnc1n2CC(=O)N1[C@H](C(=O)Nc2cccc(Br)n2)C[C@@]2(C)C[C@@H]12] |
| 8b | 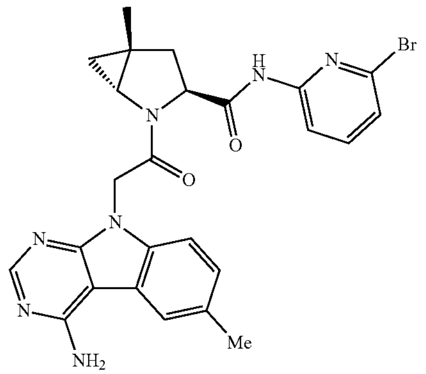 | 242a | 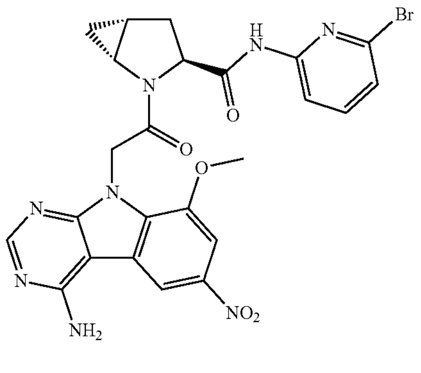 [SMILES: COc1cc([N+](=O)[O-])cc2c3c(N)ncnc3n(CC(=O)N3[C@@H]4C[C@@H]4C[C@H]3C(=O)Nc3cccc(Br)n3)c12] |
| 28a | 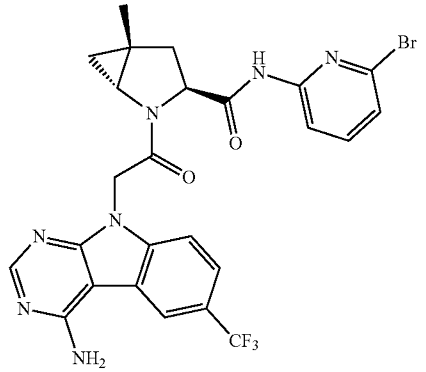 [SMILES: C[C@@]12C[C@@H](C(=O)Nc3cccc(Br)n3)N(C(=O)Cn3c4ccc(C(F)(F)F)cc4c4c(N)ncnc43)[C@@H]1C2] | 243a | 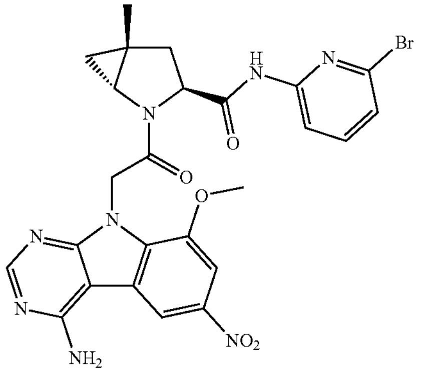 |

-continued
| # | Structure | # | Structure |
|---|---|---|---|
| 10b | 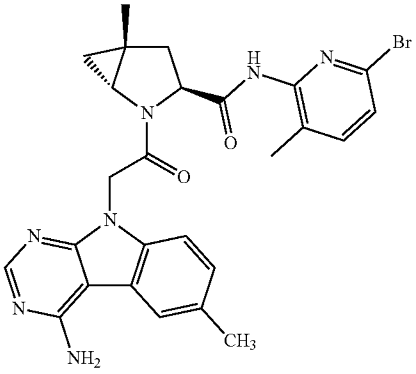 [SMILES: Cc1ccc2c(c1)c1c(N)ncnc1n2CC(=O)N1[C@H](C(=O)Nc2nc(Br)ccc2C)C[C@@]2(C)C[C@@H]12] | 244d | 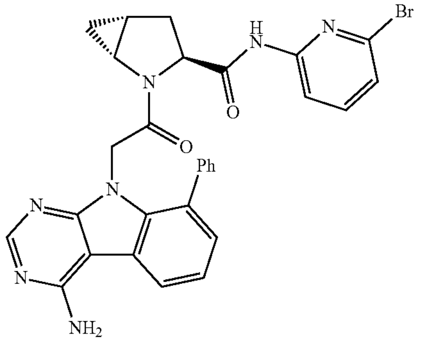 |
| 11f | 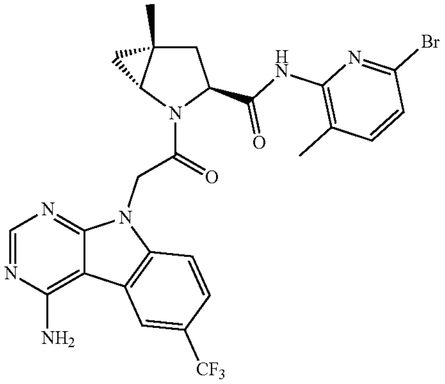 [SMILES: Cc1ccc(Br)nc1NC(=O)[C@@H]1C[C@@]2(C)C[C@H]2N1C(=O)Cn1c2ccc(C(F)(F)F)cc2c2c(N)ncnc21] | 245a | 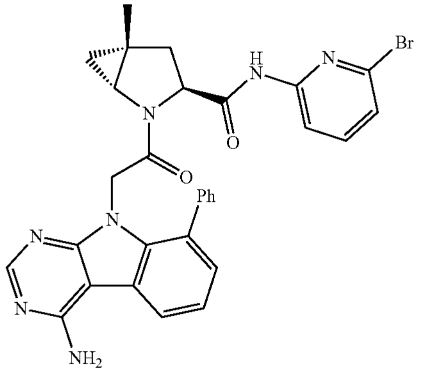 |
| 12a | 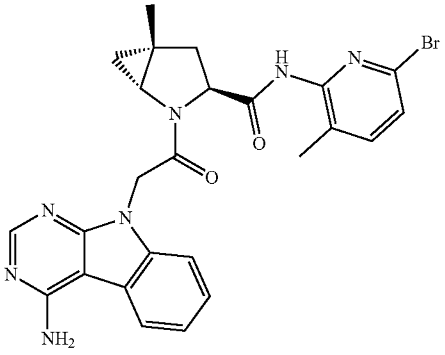 [SMILES: Cc1ccc(Br)nc1NC(=O)[C@@H]1C[C@@]2(C)C[C@H]2N1C(=O)Cn1c2ccccc2c2c(N)ncnc21] | 42a | 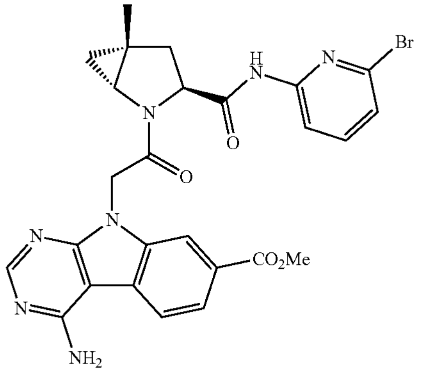 [SMILES: COC(=O)c1ccc2c3c(N)ncnc3n(CC(=O)N3[C@H](C(=O)Nc4cccc(Br)n4)C[C@@]4(C)C[C@@H]34)c2c1] |
| 127d | 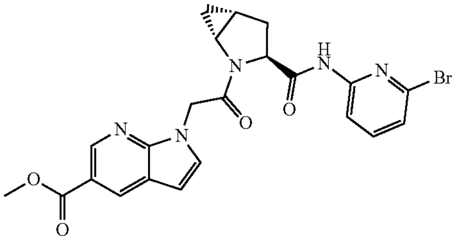 [SMILES: COC(=O)c1cnc2c(ccn2CC(=O)N2[C@@H]3C[C@@H]3C[C@H]2C(=O)Nc2cccc(Br)n2)c1] | 16e | 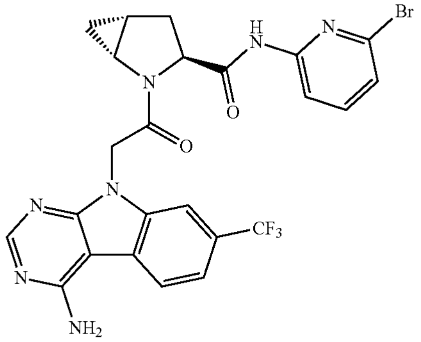 |

-continued
| # | Structure | # | Structure |
|---|---|---|---|
| 128a | 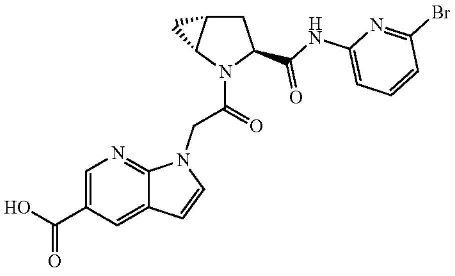 [SMILES: O=C(O)c1cnc2c(ccn2CC(=O)N2[C@@H]3C[C@@H]3C[C@H]2C(=O)Nc2cccc(Br)n2)c1] | 36e | 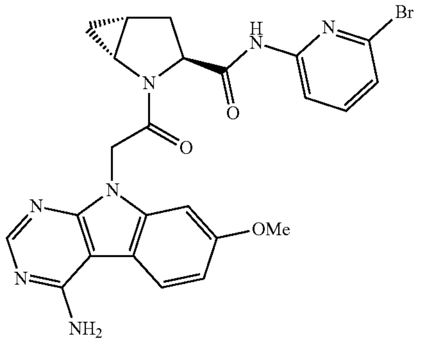 [SMILES: COc1ccc2c3c(N)ncnc3n(CC(=O)N3[C@@H]4C[C@@H]4C[C@H]3C(=O)Nc3cccc(Br)n3)c2c1] |
| 154e | 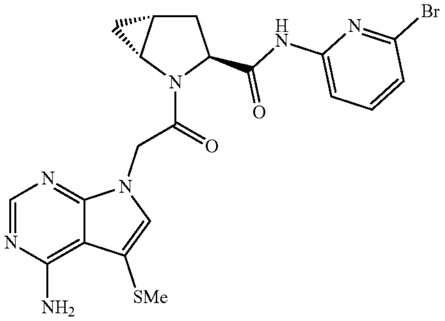 [SMILES: CSc1cn(CC(=O)N2[C@@H]3C[C@@H]3C[C@H]2C(=O)Nc2cccc(Br)n2)c2ncnc(N)c12] | 39f | 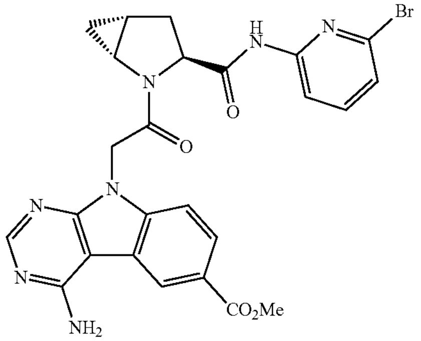 [SMILES: COC(=O)c1ccc2c(c1)c1c(N)ncnc1n2CC(=O)N1[C@@H]2C[C@@H]2C[C@H]1C(=O)Nc1cccc(Br)n1] |
| 34e | 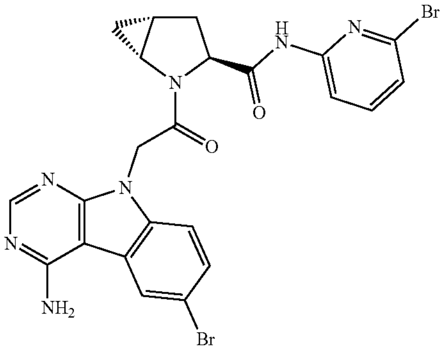 [SMILES: Nc1ncnc2c1c1cc(Br)ccc1n2CC(=O)N1[C@@H]2C[C@@H]2C[C@H]1C(=O)Nc1cccc(Br)n1] | 23f | 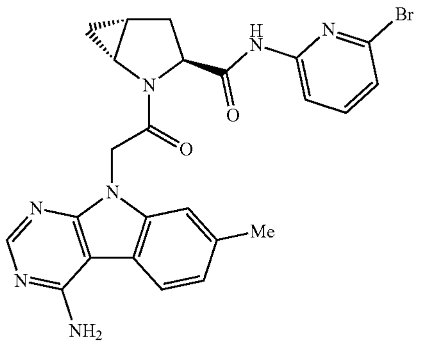 [SMILES: Cc1ccc2c3c(N)ncnc3n(CC(=O)N3[C@@H]4C[C@@H]4C[C@H]3C(=O)Nc3cccc(Br)n3)c2c1] |
| 13b | 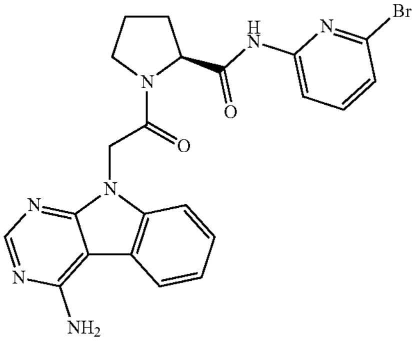 [SMILES: Nc1ncnc2c1c1ccccc1n2CC(=O)N1CCC[C@H]1C(=O)Nc1cccc(Br)n1] | 40a | 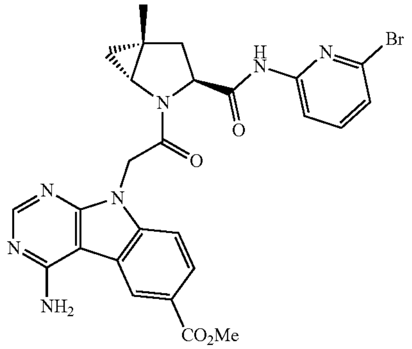 [SMILES: COC(=O)c1ccc2c(c1)c1c(N)ncnc1n2CC(=O)N1[C@H](C(=O)Nc2cccc(Br)n2)C[C@@]2(C)C[C@@H]12] |

-continued
| # | Structure | # | Structure |
|---|---|---|---|
| 14a | 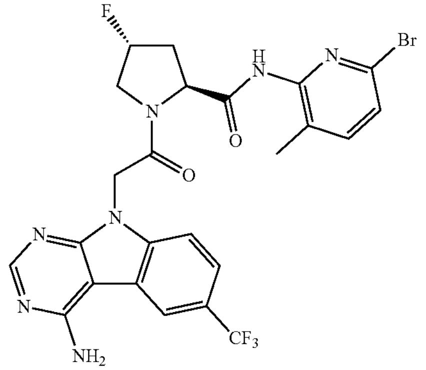 [SMILES: Cc1ccc(Br)nc1NC(=O)[C@@H]1C[C@@H](F)CN1C(=O)Cn1c2ccc(C(F)(F)F)cc2c2c(N)ncnc21] | 156e | 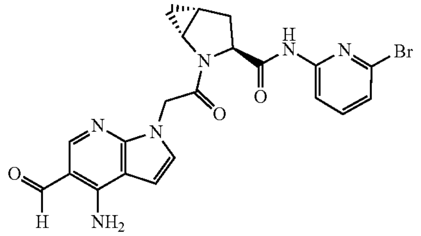 [SMILES: Nc1c(C=O)cnc2c1ccn2CC(=O)N1[C@@H]2C[C@@H]2C[C@H]1C(=O)Nc1cccc(Br)n1] |
| 15a | 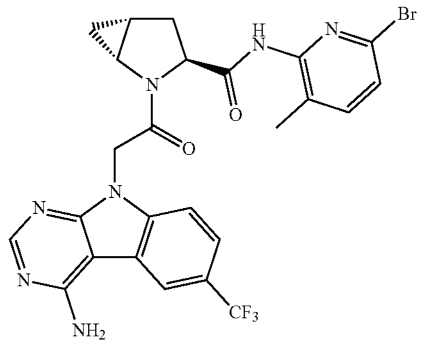 [SMILES: Cc1ccc(Br)nc1NC(=O)[C@@H]1C[C@H]2C[C@H]2N1C(=O)Cn1c2ccc(C(F)(F)F)cc2c2c(N)ncnc21] | 45d | 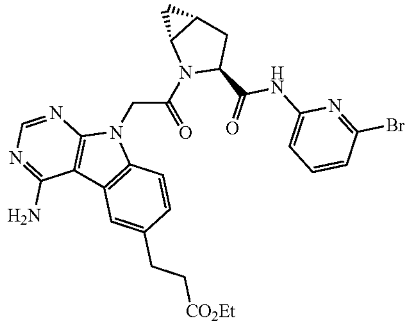 [SMILES: CCOC(=O)CCc1ccc2c(c1)c1c(N)ncnc1n2CC(=O)N1[C@@H]2C[C@@H]2C[C@H]1C(=O)Nc1cccc(Br)n1] |
| 155f | 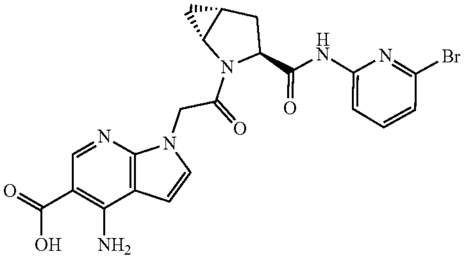 [SMILES: Nc1c(C(=O)O)cnc2c1ccn2CC(=O)N1[C@@H]2C[C@@H]2C[C@H]1C(=O)Nc1cccc(Br)n1] | 41f | 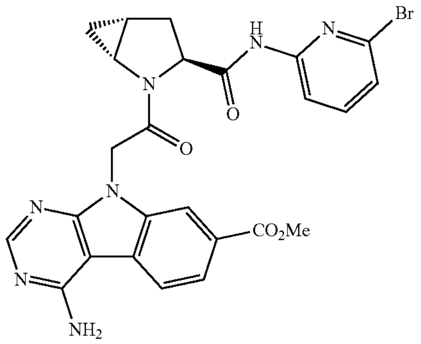 |
| 37a | 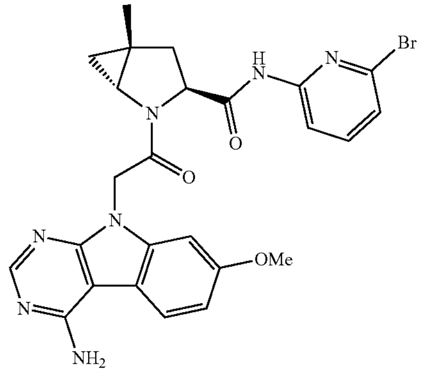 [SMILES: COc1ccc2c3c(N)ncnc3n(CC(=O)N3[C@H](C(=O)Nc4cccc(Br)n4)C[C@@]4(C)C[C@@H]34)c2c1] | 221c | 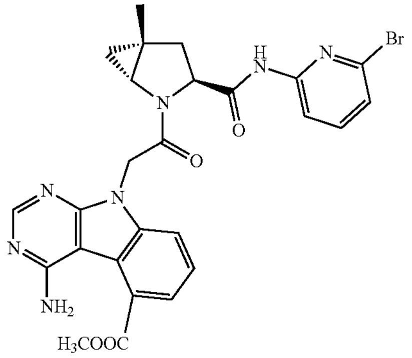 |

-continued
| # | Structure | # | Structure |
|---|---|---|---|
| 218a | 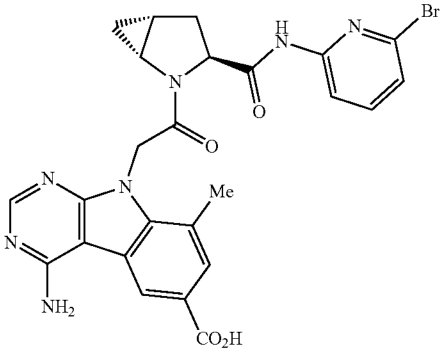 [SMILES: Cc1cc(C(=O)O)cc2c3c(N)ncnc3n(CC(=O)N3[C@@H]4C[C@@H]4C[C@H]3C(=O)Nc3cccc(Br)n3)c12] | 250b | 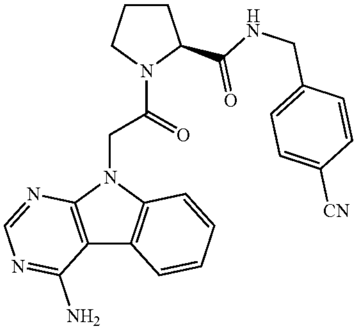 [SMILES: N#Cc1ccc(CNC(=O)[C@@H]2CCCN2C(=O)Cn2c3ccccc3c3c(N)ncnc32)cc1] |
| 223a | 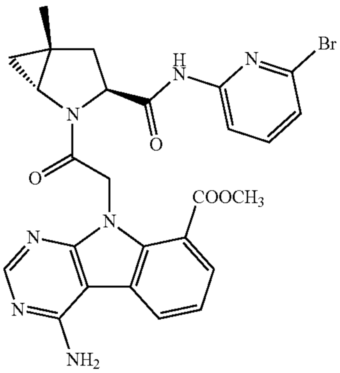 [SMILES: COC(=O)c1cccc2c3c(N)ncnc3n(CC(=O)N3[C@H](C(=O)Nc4cccc(Br)n4)C[C@@]4(C)C[C@@H]34)c12] | 270a | 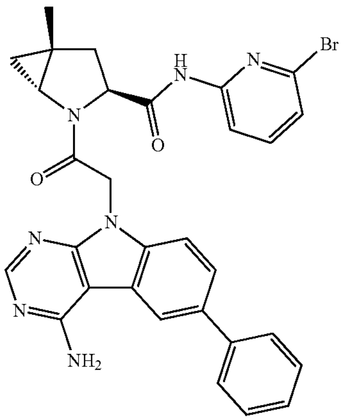 [SMILES: C[C@@]12C[C@@H](C(=O)Nc3cccc(Br)n3)N(C(=O)Cn3c4ccc(-c5ccccc5)cc4c4c(N)ncnc43)[C@@H]1C2] |
| 224b | 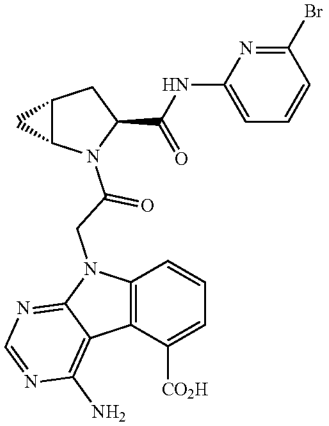 [SMILES: Nc1ncnc2c1c1c(C(=O)O)cccc1n2CC(=O)N1[C@@H]2C[C@@H]2C[C@H]1C(=O)Nc1cccc(Br)n1] | 271c | 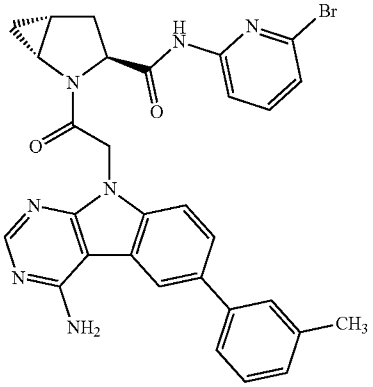 [SMILES: Cc1cccc(-c2ccc3c(c2)c2c(N)ncnc2n3CC(=O)N2[C@@H]3C[C@@H]3C[C@H]2C(=O)Nc2cccc(Br)n2)c1] |
| 225e | 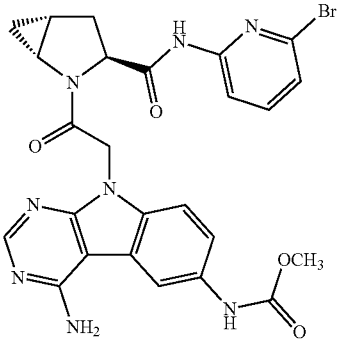 [SMILES: COC(=O)Nc1ccc2c(c1)c1c(N)ncnc1n2CC(=O)N1[C@@H]2C[C@@H]2C[C@H]1C(=O)Nc1cccc(Br)n1] | 249a | 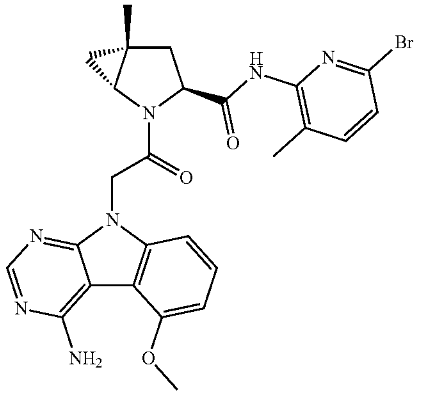 [SMILES: COc1cccc2c1c1c(N)ncnc1n2CC(=O)N1[C@H](C(=O)Nc2nc(Br)ccc2C)C[C@@]2(C)C[C@@H]12] |

-continued
| # | Structure | # | Structure |
|---|---|---|---|
| 226c | 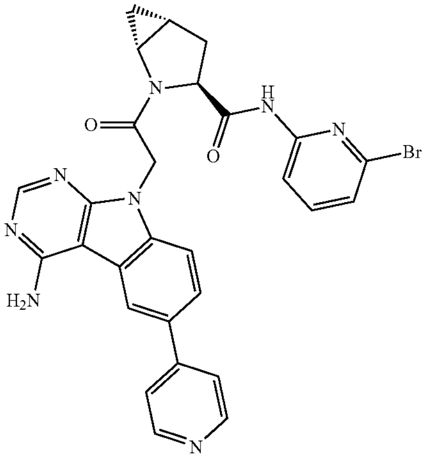 [SMILES: Nc1ncnc2c1c1cc(-c3ccncc3)ccc1n2CC(=O)N1[C@@H]2C[C@@H]2C[C@H]1C(=O)Nc1cccc(Br)n1] | 252a | 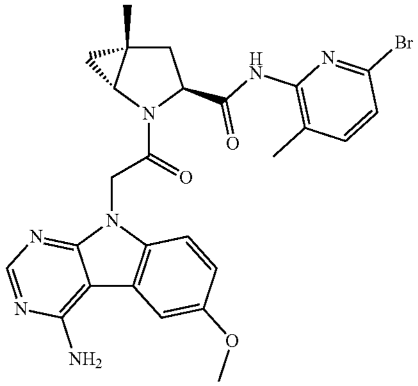 [SMILES: COc1ccc2c(c1)c1c(N)ncnc1n2CC(=O)N1[C@H](C(=O)Nc2nc(Br)ccc2C)C[C@@]2(C)C[C@@H]12] |
| 219a | 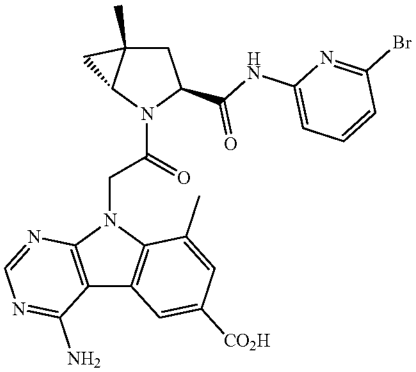 [SMILES: Cc1cc(C(=O)O)cc2c3c(N)ncnc3n(CC(=O)N3[C@H](C(=O)Nc4cccc(Br)n4)C[C@@]4(C)C[C@@H]34)c12] | 253a | 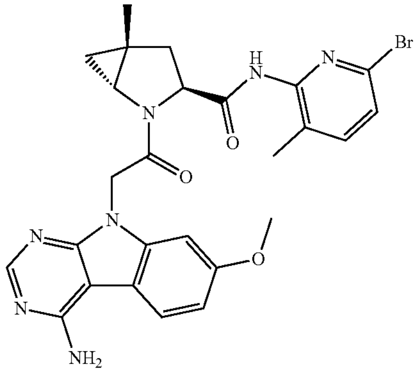 [SMILES: COc1ccc2c3c(N)ncnc3n(CC(=O)N3[C@H](C(=O)Nc4nc(Br)ccc4C)C[C@@]4(C)C[C@@H]34)c2c1] |
| 227c | 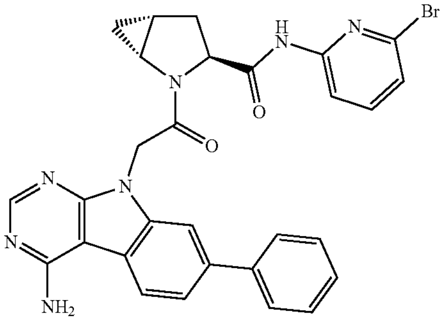 [SMILES: Nc1ncnc2c1c1ccc(-c3ccccc3)cc1n2CC(=O)N1[C@@H]2C[C@@H]2C[C@H]1C(=O)Nc1cccc(Br)n1] | 254a | 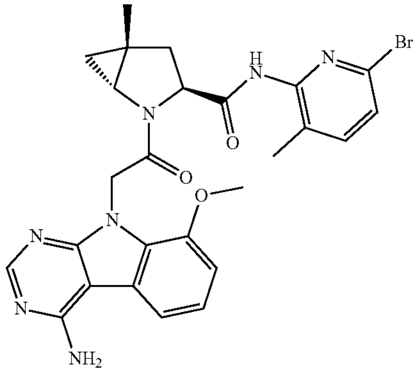 [SMILES: COc1cccc2c3c(N)ncnc3n(CC(=O)N3[C@H](C(=O)Nc4nc(Br)ccc4C)C[C@@]4(C)C[C@@H]34)c12] |

-continued
| # | Structure | # | Structure |
|---|---|---|---|
| 228a | 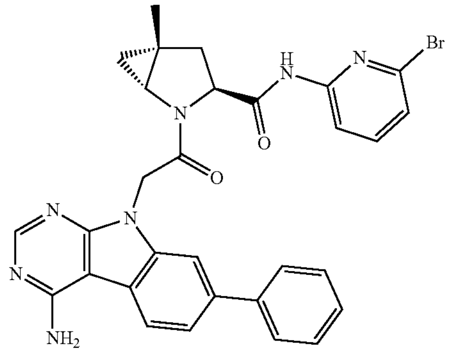 [SMILES: C[C@@]12C[C@@H](C(=O)Nc3cccc(Br)n3)N(C(=O)Cn3c4cc(-c5ccccc5)ccc4c4c(N)ncnc43)[C@@H]1C2] | 263c | 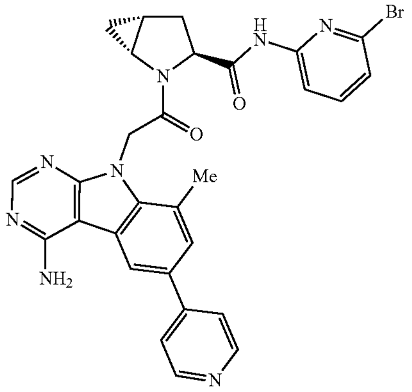 [SMILES: Cc1cc(-c2ccncc2)cc2c3c(N)ncnc3n(CC(=O)N3[C@@H]4C[C@@H]4C[C@H]3C(=O)Nc3cccc(Br)n3)c12] |
| 251f | 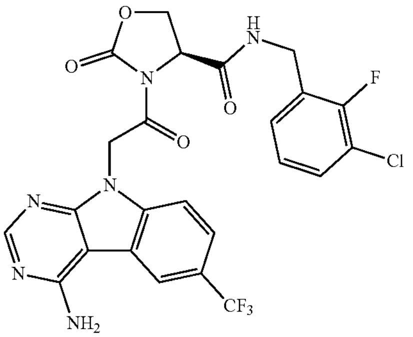 [SMILES: Nc1ncnc2c1c1cc(C(F)(F)F)ccc1n2CC(=O)N1C(=O)OC[C@H]1C(=O)NCc1cccc(Cl)c1F] | 272c | 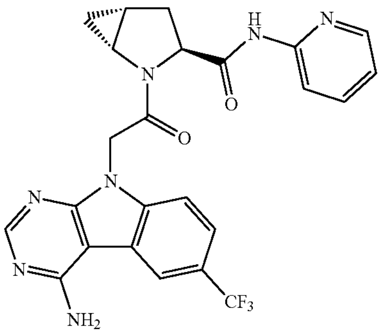 [SMILES: Nc1ncnc2c1c1cc(C(F)(F)F)ccc1n2CC(=O)N1[C@@H]2C[C@@H]2C[C@H]1C(=O)Nc1ccccn1] |
| 233h | 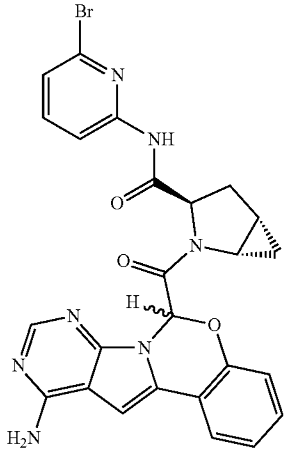 [SMILES: Nc1ncnc2c1cc1n2C(C(=O)N2[C@@H](C(=O)Nc3cccc(Br)n3)C[C@@H]3C[C@@H]32)Oc2ccccc2-1] | 255c | 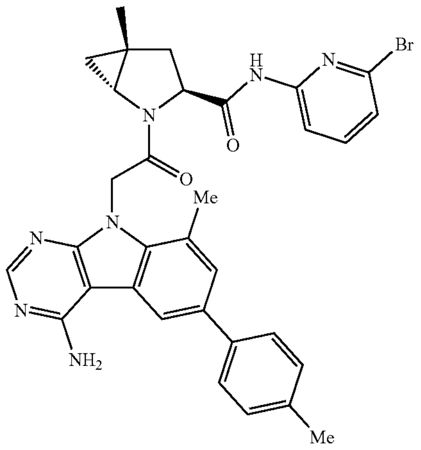 [SMILES: Cc1ccc(-c2cc(C)c3c(c2)c2c(N)ncnc2n3CC(=O)N2[C@H](C(=O)Nc3cccc(Br)n3)C[C@@]3(C)C[C@@H]23)cc1] |
| 229c | 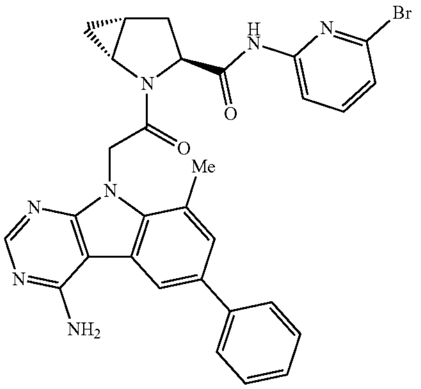 [SMILES: Cc1cc(-c2ccccc2)cc2c3c(N)ncnc3n(CC(=O)N3[C@@H]4C[C@@H]4C[C@H]3C(=O)Nc3cccc(Br)n3)c12] | 256a | 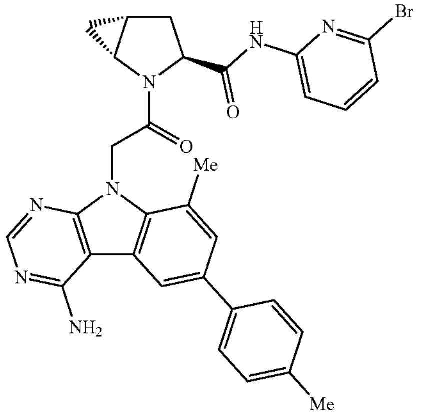 [SMILES: Cc1ccc(-c2cc(C)c3c(c2)c2c(N)ncnc2n3CC(=O)N2[C@@H]3C[C@@H]3C[C@H]2C(=O)Nc2cccc(Br)n2)cc1] |

-continued
| # | Structure | # | Structure |
|---|---|---|---|
| 230a | 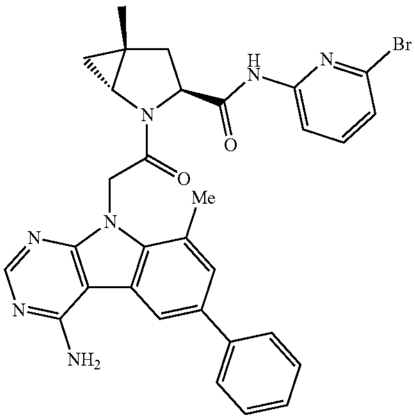 [SMILES: Cc1cc(-c2ccccc2)cc2c3c(N)ncnc3n(CC(=O)N3[C@H](C(=O)Nc4cccc(Br)n4)C[C@@]4(C)C[C@@H]34)c12] | 273c | 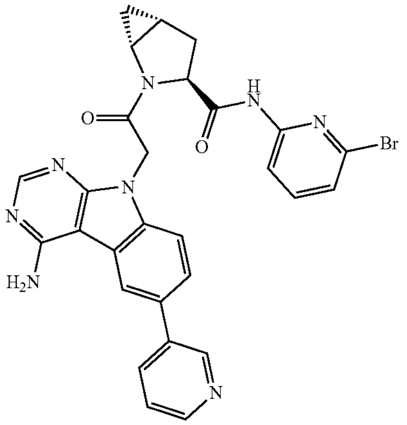 [SMILES: Nc1ncnc2c1c1cc(-c3cccnc3)ccc1n2CC(=O)N1[C@@H]2C[C@@H]2C[C@H]1C(=O)Nc1cccc(Br)n1] |
| 231g | 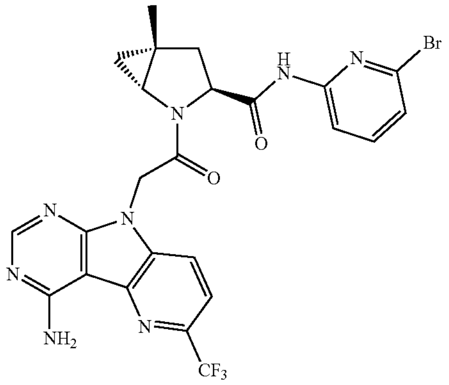 [SMILES: C[C@@]12C[C@@H](C(=O)Nc3cccc(Br)n3)N(C(=O)Cn3c4ccc(C(F)(F)F)nc4c4c(N)ncnc43)[C@@H]1C2] | 257g | 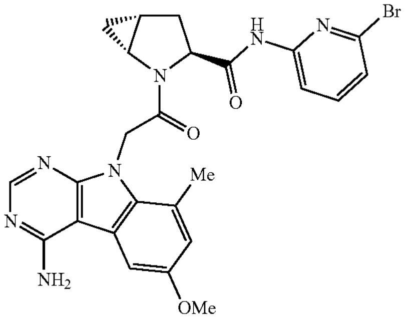 [SMILES: COc1cc(C)c2c(c1)c1c(N)ncnc1n2CC(=O)N1[C@@H]2C[C@@H]2C[C@H]1C(=O)Nc1cccc(Br)n1] |
| 246b | 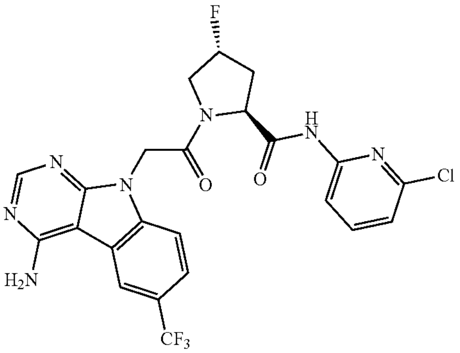 | 258a | 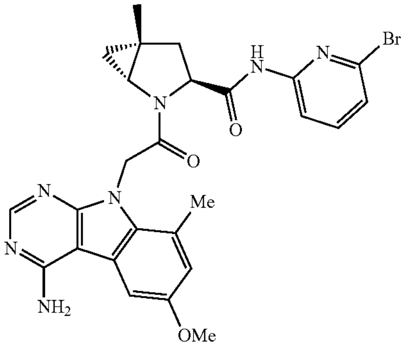 [SMILES: COc1cc(C)c2c(c1)c1c(N)ncnc1n2CC(=O)N1[C@H](C(=O)Nc2cccc(Br)n2)C[C@@]2(C)C[C@@H]12] |
| 247d | 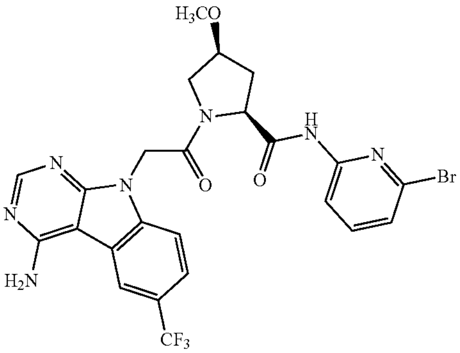 [SMILES: CO[C@H]1C[C@@H](C(=O)Nc2cccc(Br)n2)N(C(=O)Cn2c3ccc(C(F)(F)F)cc3c3c(N)ncnc32)C1] | 259d | 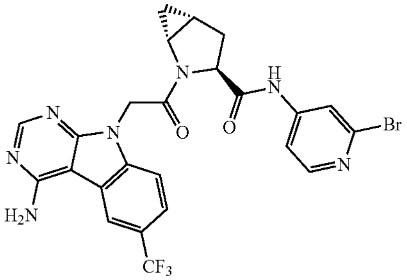 |

-continued
| # | Structure | # | Structure |
|---|---|---|---|
| 248d | 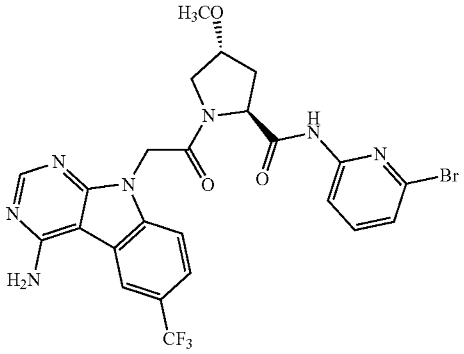 [SMILES: CO[C@@H]1C[C@@H](C(=O)Nc2cccc(Br)n2)N(C(=O)Cn2c3ccc(C(F)(F)F)cc3c3c(N)ncnc32)C1] | 260a | 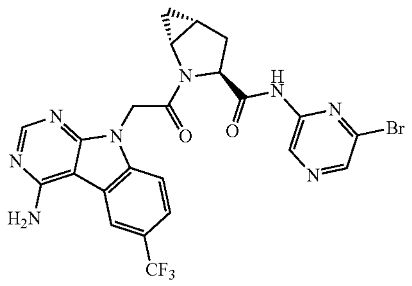 [SMILES: Nc1ncnc2c1c1cc(C(F)(F)F)ccc1n2CC(=O)N1[C@@H]2C[C@@H]2C[C@H]1C(=O)Nc1cncc(Br)n1] |
| 232a | 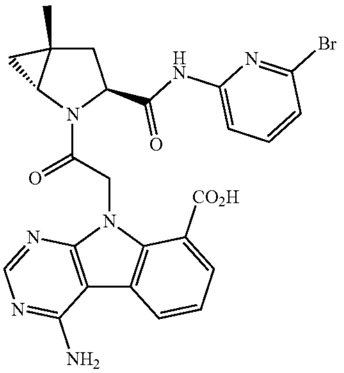 [SMILES: C[C@@]12C[C@@H](C(=O)Nc3cccc(Br)n3)N(C(=O)Cn3c4ncnc(N)c4c4cccc(C(=O)O)c43)[C@@H]1C2] | 261d | 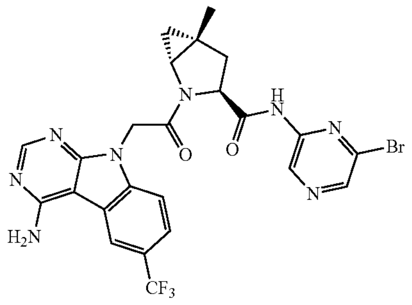 [SMILES: C[C@@]12C[C@@H](C(=O)Nc3cncc(Br)n3)N(C(=O)Cn3c4ccc(C(F)(F)F)cc4c4c(N)ncnc43)[C@@H]1C2] |
| 234a | 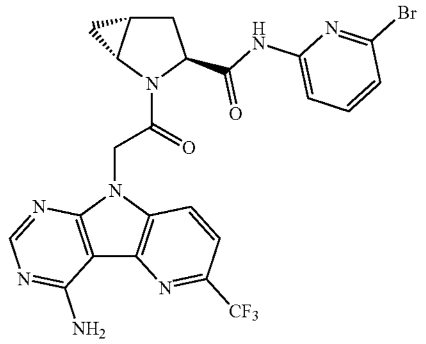 | 262a | 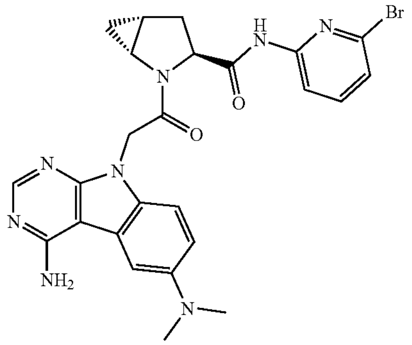 [SMILES: CN(C)c1ccc2c(c1)c1c(N)ncnc1n2CC(=O)N1[C@@H]2C[C@@H]2C[C@H]1C(=O)Nc1cccc(Br)n1] |
| 267c | 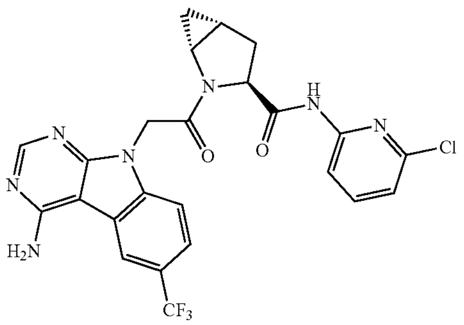 [SMILES: Nc1ncnc2c1c1cc(C(F)(F)F)ccc1n2CC(=O)N1[C@@H]2C[C@@H]2C[C@H]1C(=O)Nc1cccc(Cl)n1] | 264a | 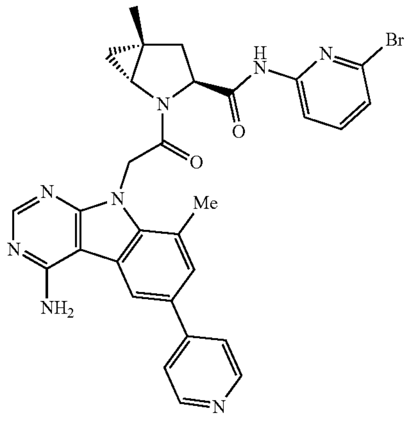 [SMILES: Cc1cc(-c2ccncc2)cc2c3c(N)ncnc3n(CC(=O)N3[C@H](C(=O)Nc4cccc(Br)n4)C[C@@]4(C)C[C@@H]34)c12] |

-continued
| # | Structure | # | Structure |
|---|---|---|---|
| 268b | 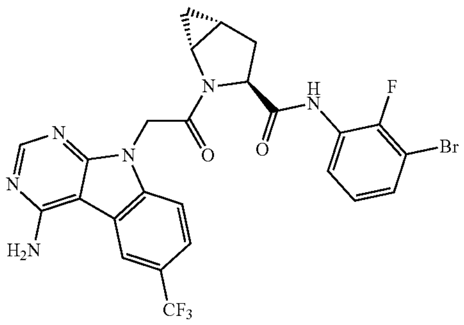 [SMILES: Nc1ncnc2c1c1cc(C(F)(F)F)ccc1n2CC(=O)N1[C@@H]2C[C@@H]2C[C@H]1C(=O)Nc1cccc(Br)c1F] | 265a | 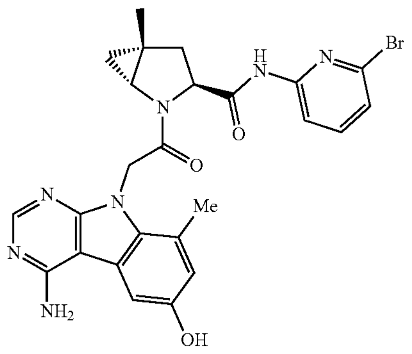 [SMILES: Cc1cc(O)cc2c3c(N)ncnc3n(CC(=O)N3[C@H](C(=O)Nc4cccc(Br)n4)C[C@@]4(C)C[C@@H]34)c12] |
| 269c | 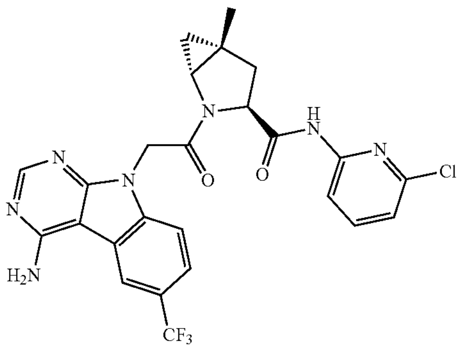 [SMILES: C[C@@]12C[C@@H](C(=O)Nc3cccc(Cl)n3)N(C(=O)Cn3c4ccc(C(F)(F)F)cc4c4c(N)ncnc43)[C@@H]1C2] | 266b | 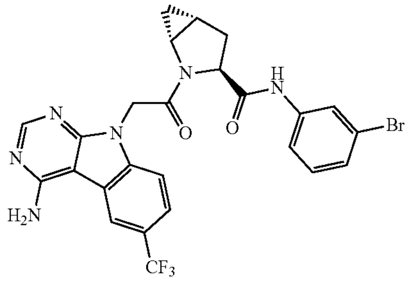 [SMILES: Nc1ncnc2c1c1cc(C(F)(F)F)ccc1n2CC(=O)N1[C@@H]2C[C@@H]2C[C@H]1C(=O)Nc1cccc(Br)c1] |
| 274g | 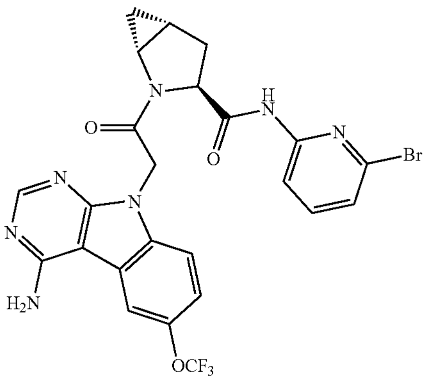 [SMILES: Nc1ncnc2c1c1cc(OC(F)(F)F)ccc1n2CC(=O)N1[C@@H]2C[C@@H]2C[C@H]1C(=O)Nc1cccc(Br)n1] | 275c | 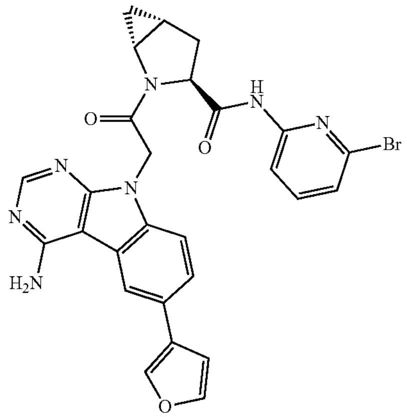 [SMILES: Nc1ncnc2c1c1cc(-c3ccoc3)ccc1n2CC(=O)N1[C@@H]2C[C@@H]2C[C@H]1C(=O)Nc1cccc(Br)n1] |
| 276g | 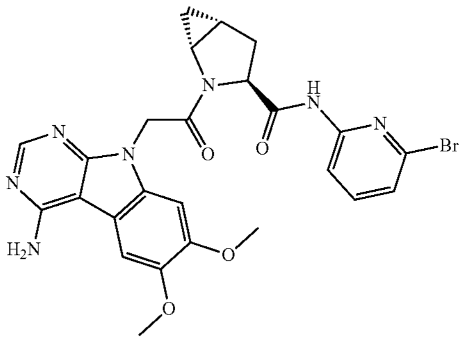 [SMILES: COc1cc2c3c(N)ncnc3n(CC(=O)N3[C@@H]4C[C@@H]4C[C@H]3C(=O)Nc3cccc(Br)n3)c2cc1OC] | 284a | 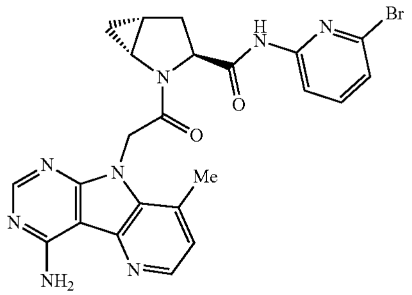 [SMILES: Cc1ccnc2c3c(N)ncnc3n(CC(=O)N3[C@@H]4C[C@@H]4C[C@H]3C(=O)Nc3cccc(Br)n3)c12] |

-continued
| # | Structure | # | Structure |
|---|---|---|---|
| 277a | 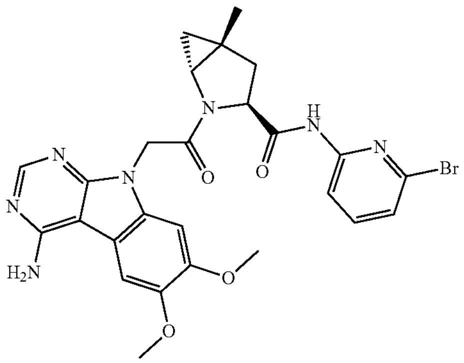 [SMILES: COc1cc2c3c(N)ncnc3n(CC(=O)N3[C@H](C(=O)Nc4cccc(Br)n4)C[C@@]4(C)C[C@@H]34)c2cc1OC] | 285g | 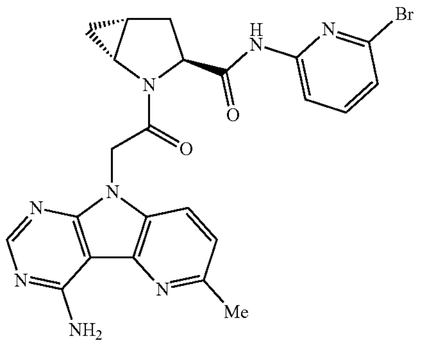 [SMILES: Cc1ccc2c(n1)c1c(N)ncnc1n2CC(=O)N1[C@@H]2C[C@@H]2C[C@H]1C(=O)Nc1cccc(Br)n1] |
| 278g | 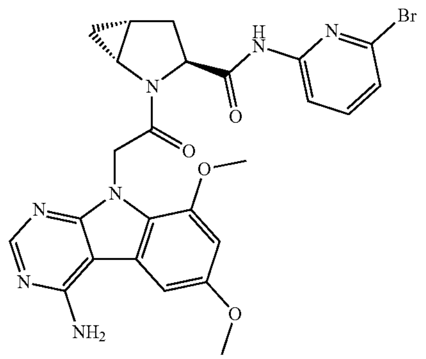 [SMILES: COc1cc(OC)c2c(c1)c1c(N)ncnc1n2CC(=O)N1[C@@H]2C[C@@H]2C[C@H]1C(=O)Nc1cccc(Br)n1] | 286a | 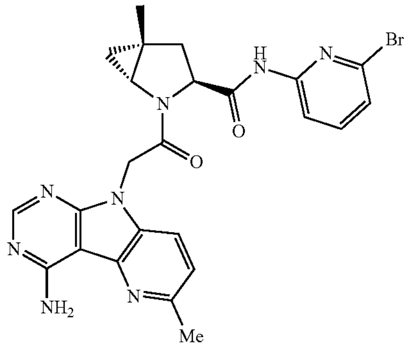 [SMILES: Cc1ccc2c(n1)c1c(N)ncnc1n2CC(=O)N1[C@H](C(=O)Nc2cccc(Br)n2)C[C@@]2(C)C[C@@H]12] |
| 279a | 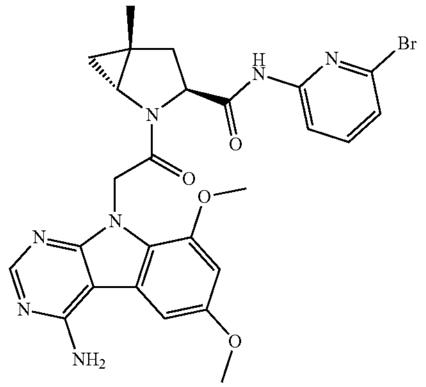 [SMILES: COc1cc(OC)c2c(c1)c1c(N)ncnc1n2CC(=O)N1[C@H](C(=O)Nc2cccc(Br)n2)C[C@@]2(C)C[C@@H]12] | 287a | 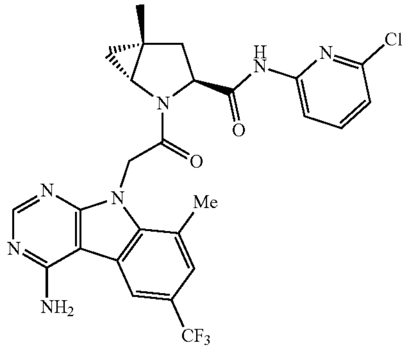 [SMILES: Cc1cc(C(F)(F)F)cc2c3c(N)ncnc3n(CC(=O)N3[C@H](C(=O)Nc4cccc(Cl)n4)C[C@@]4(C)C[C@@H]34)c12] |
| 280g | 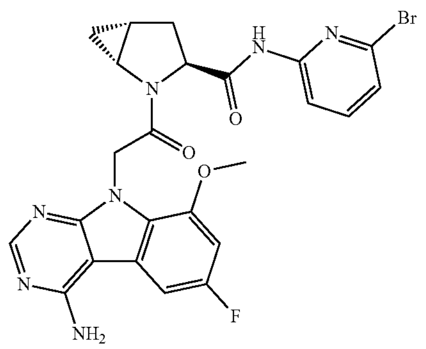 [SMILES: COc1cc(F)cc2c3c(N)ncnc3n(CC(=O)N3[C@@H]4C[C@@H]4C[C@H]3C(=O)Nc3cccc(Br)n3)c12] | 288c | 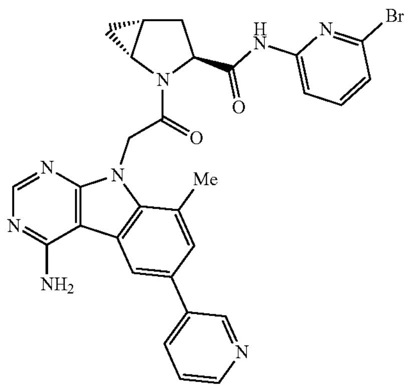 [SMILES: Cc1cc(-c2cccnc2)cc2c3c(N)ncnc3n(CC(=O)N3[C@@H]4C[C@@H]4C[C@H]3C(=O)Nc3cccc(Br)n3)c12] |

-continued
| # | Structure | # | Structure |
|---|---|---|---|
| 281a | 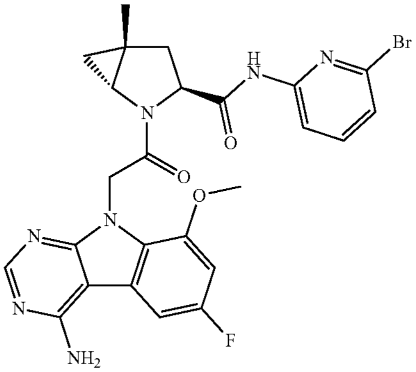 | 289a | 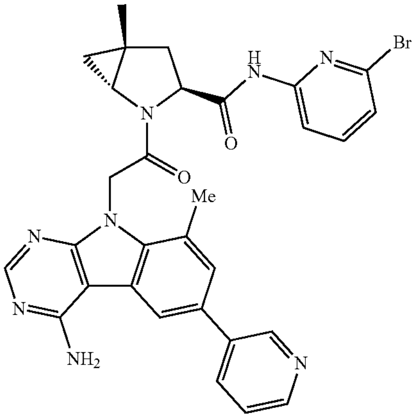 [SMILES: Cc1cc(-c2cccnc2)cc2c3c(N)ncnc3n(CC(=O)N3[C@H](C(=O)Nc4cccc(Br)n4)C[C@@]4(C)C[C@@H]34)c12] |
| 282a | 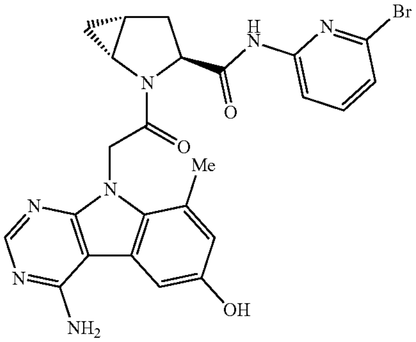 | 290g | 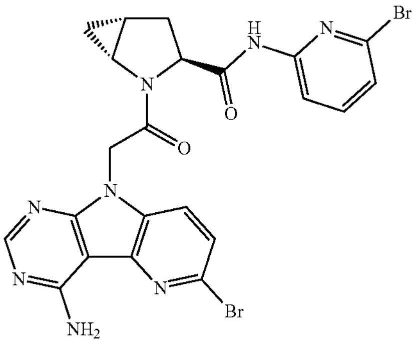 [SMILES: Nc1ncnc2c1c1nc(Br)ccc1n2CC(=O)N1[C@@H]2C[C@@H]2C[C@H]1C(=O)Nc1cccc(Br)n1] |
| 283g | 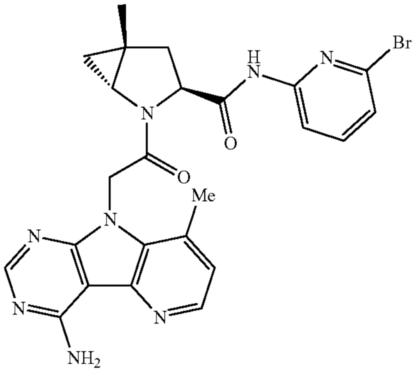 [SMILES: Cc1ccnc2c3c(N)ncnc3n(CC(=O)N3[C@H](C(=O)Nc4cccc(Br)n4)C[C@@]4(C)C[C@@H]34)c12] | 291a | 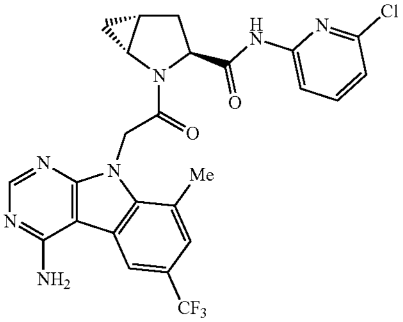 [SMILES: Cc1cc(C(F)(F)F)cc2c3c(N)ncnc3n(CC(=O)N3[C@@H]4C[C@@H]4C[C@H]3C(=O)Nc3cccc(Cl)n3)c12] |
| 292a | 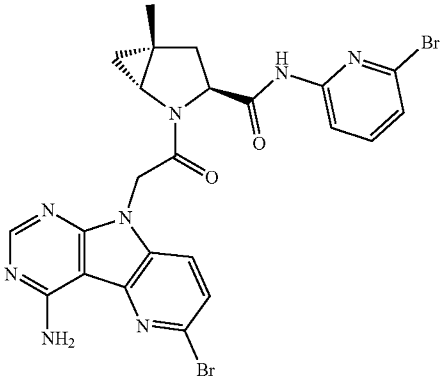 [SMILES: C[C@@]12C[C@@H](C(=O)Nc3cccc(Br)n3)N(C(=O)Cn3c4ccc(Br)nc4c4c(N)ncnc43)[C@@H]1C2] | 293a and 293b | 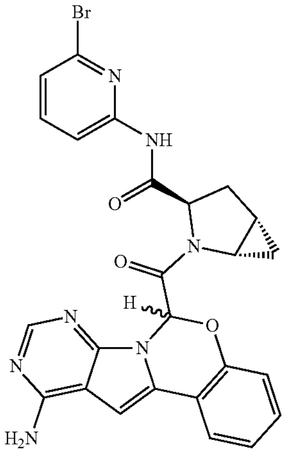 [SMILES: Nc1ncnc2c1cc1n2C(C(=O)N2[C@@H](C(=O)Nc3cccc(Br)n3)C[C@@H]3C[C@@H]32)Oc2ccccc2-1] |

-continued
| # | Structure | # | Structure |
|---|---|---|---|
| 294c | 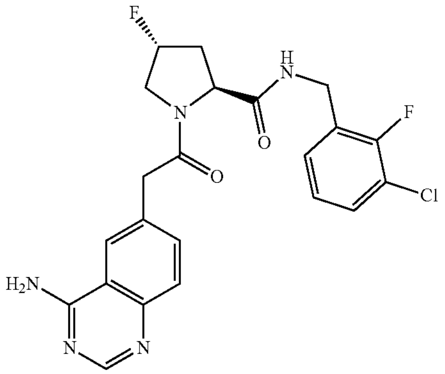 [SMILES: Nc1ncnc2ccc(CC(=O)N3C[C@H](F)C[C@H]3C(=O)NCc3cccc(Cl)c3F)cc12] | 295a | 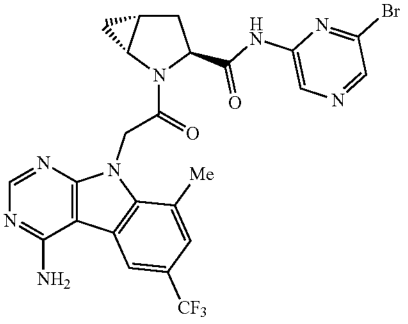 [SMILES: Cc1cc(C(F)(F)F)cc2c3c(N)ncnc3n(CC(=O)N3[C@@H]4C[C@@H]4C[C@H]3C(=O)Nc3cncc(Br)n3)c12] |
| 297d | 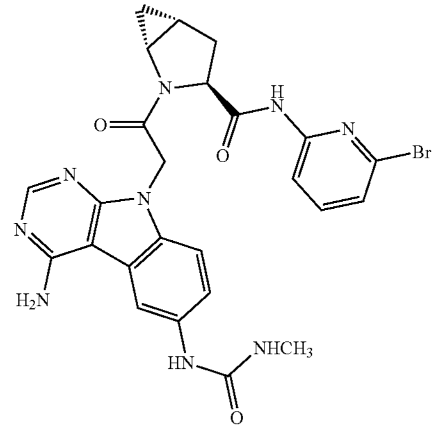 [SMILES: CNC(=O)Nc1ccc2c(c1)c1c(N)ncnc1n2CC(=O)N1[C@@H]2C[C@@H]2C[C@H]1C(=O)Nc1cccc(Br)n1] | 298c | 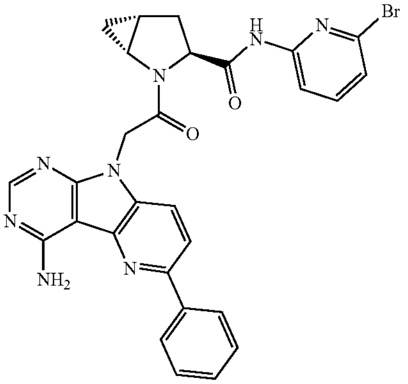 [SMILES: Nc1ncnc2c1c1nc(-c3ccccc3)ccc1n2CC(=O)N1[C@@H]2C[C@@H]2C[C@H]1C(=O)Nc1cccc(Br)n1] |
| 299a | 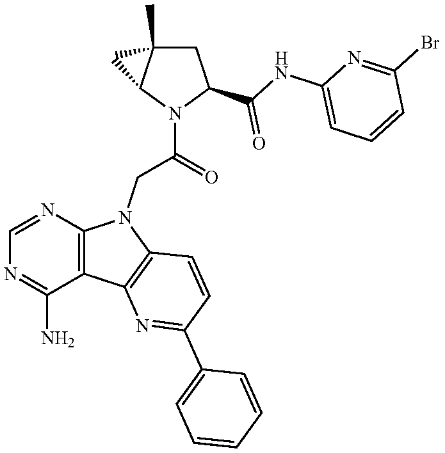 [SMILES: C[C@@]12C[C@@H](C(=O)Nc3cccc(Br)n3)N(C(=O)Cn3c4ccc(-c5ccccc5)nc4c4c(N)ncnc43)[C@@H]1C2] | 300a | 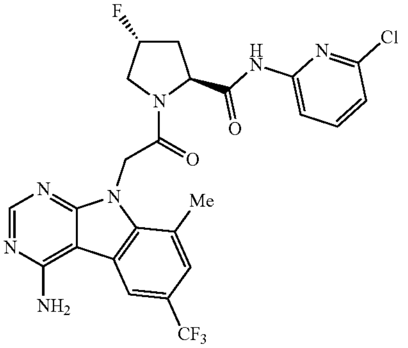 [SMILES: Cc1cc(C(F)(F)F)cc2c3c(N)ncnc3n(CC(=O)N3C[C@H](F)C[C@H]3C(=O)Nc3cccc(Br)n3)c12] |

-continued
| # | Structure | # | Structure |
|---|---|---|---|
| 301a | 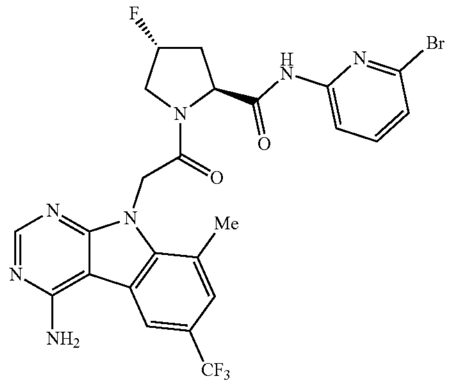 | 302a | 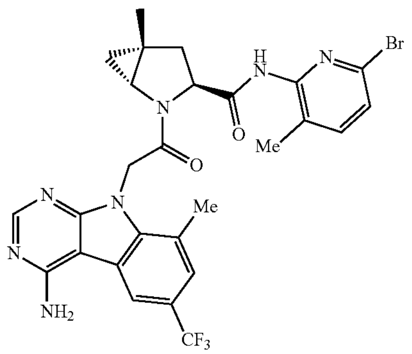 [SMILES: Cc1ccc(Br)nc1NC(=O)[C@@H]1C[C@@]2(C)C[C@H]2N1C(=O)Cn1c2ncnc(N)c2c2cc(C(F)(F)F)cc(C)c21] |
| 303a | 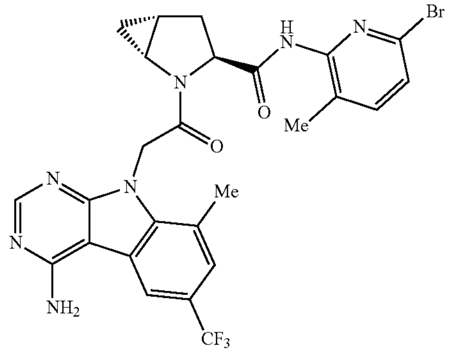 [SMILES: Cc1ccc(Br)nc1NC(=O)[C@@H]1C[C@H]2C[C@H]2N1C(=O)Cn1c2ncnc(N)c2c2cc(C(F)(F)F)cc(C)c21] | 307c | 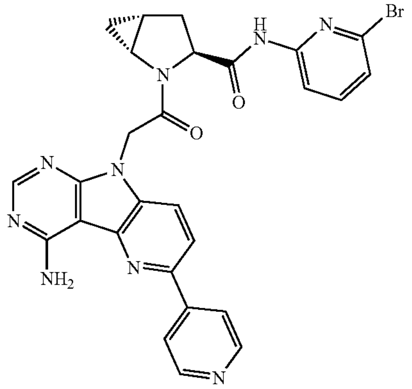 [SMILES: Nc1ncnc2c1c1nc(-c3ccncc3)ccc1n2CC(=O)N1[C@@H]2C[C@@H]2C[C@H]1C(=O)Nc1cccc(Br)n1] |
| 304a | 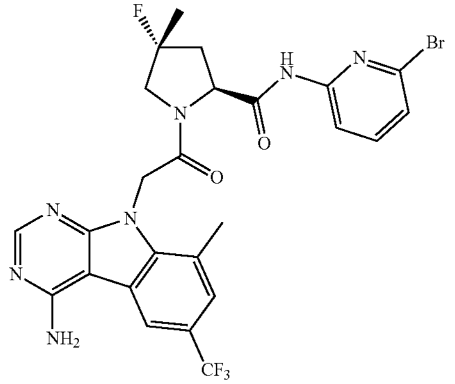 [SMILES: Cc1cc(C(F)(F)F)cc2c3c(N)ncnc3n(CC(=O)N3C[C@](C)(F)C[C@H]3C(=O)Nc3cccc(Br)n3)c12] | 305a | 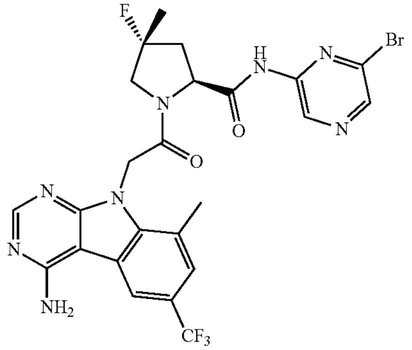 [SMILES: Cc1cc(C(F)(F)F)cc2c3c(N)ncnc3n(CC(=O)N3C[C@](C)(F)C[C@H]3C(=O)Nc3cncc(Br)n3)c12] |
| 308c | 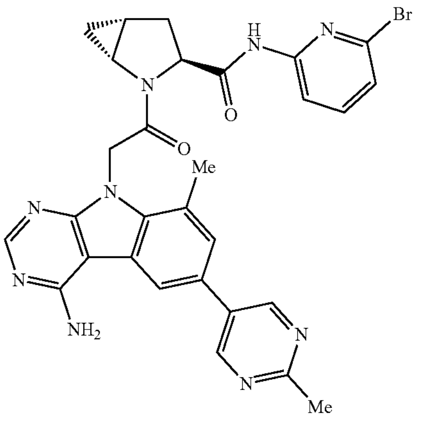 [SMILES: Cc1ncc(-c2cc(C)c3c(c2)c2c(N)ncnc2n3CC(=O)N2[C@@H]3C[C@@H]3C[C@H]2C(=O)Nc2cccc(Br)n2)cn1] | 309a | 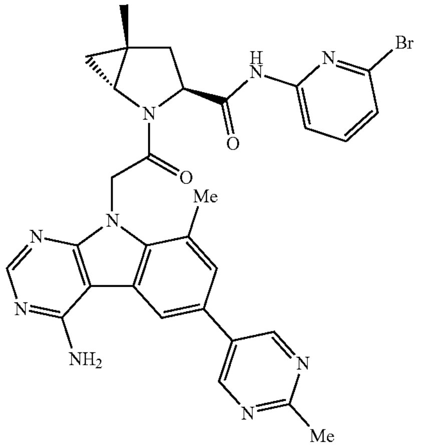 [SMILES: Cc1ncc(-c2cc(C)c3c(c2)c2c(N)ncnc2n3CC(=O)N2[C@H](C(=O)Nc3cccc(Br)n3)C[C@@]3(C)C[C@@H]23)cn1] |

-continued
| # | Structure | # | Structure |
|---|---|---|---|
| 310a | 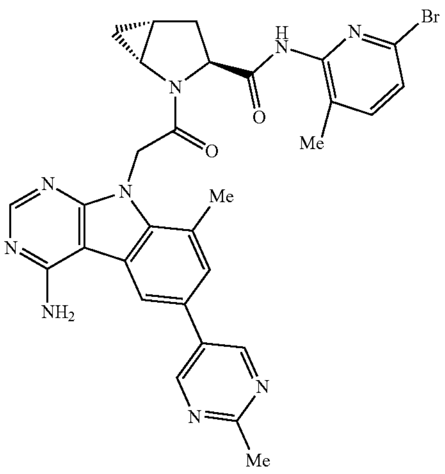 [SMILES: Cc1ncc(-c2cc(C)c3c(c2)c2c(N)ncnc2n3CC(=O)N2[C@@H]3C[C@@H]3C[C@H]2C(=O)Nc2nc(Br)ccc2C)cn1] | 311a | 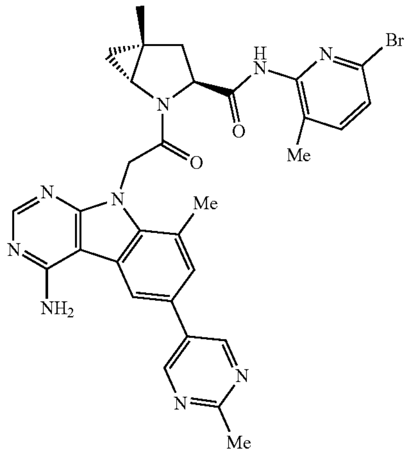 [SMILES: Cc1ncc(-c2cc(C)c3c(c2)c2c(N)ncnc2n3CC(=O)N2[C@H](C(=O)Nc3nc(Br)ccc3C)C[C@@]3(C)C[C@@H]23)cn1] |
| 317c | 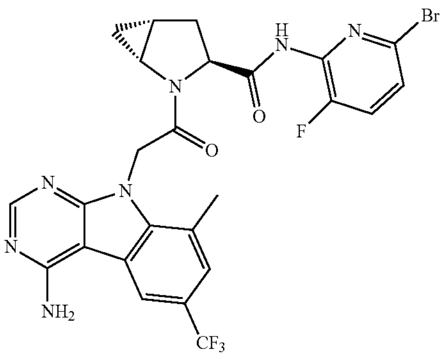 [SMILES: Cc1cc(C(F)(F)F)cc2c3c(N)ncnc3n(CC(=O)N3[C@@H]4C[C@@H]4C[C@H]3C(=O)Nc3nc(Br)ccc3F)c12] | 318c | 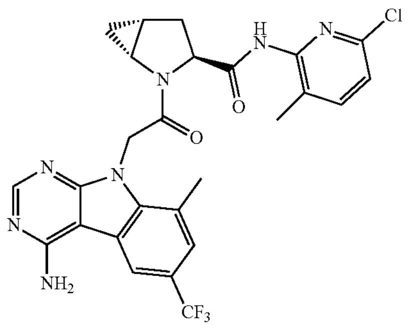 [SMILES: Cc1ccc(Cl)nc1NC(=O)[C@@H]1C[C@H]2C[C@H]2N1C(=O)Cn1c2ncnc(N)c2c2cc(C(F)(F)F)cc(C)c21] |
| 319c | 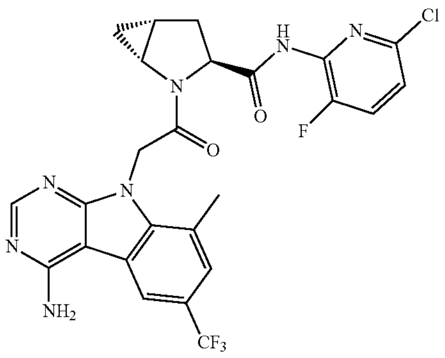 | 320c | 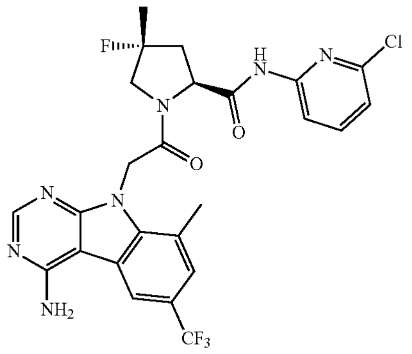 [SMILES: Cc1cc(C(F)(F)F)cc2c3c(N)ncnc3n(CC(=O)N3C[C@](C)(F)C[C@H]3C(=O)Nc3cccc(Cl)n3)c12] |
| 321d | 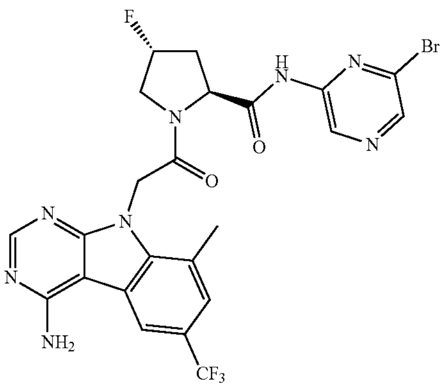 [SMILES: Cc1cc(C(F)(F)F)cc2c3c(N)ncnc3n(CC(=O)N3C[C@H](F)C[C@H]3C(=O)Nc3cncc(Br)n3)c12] | 322c | 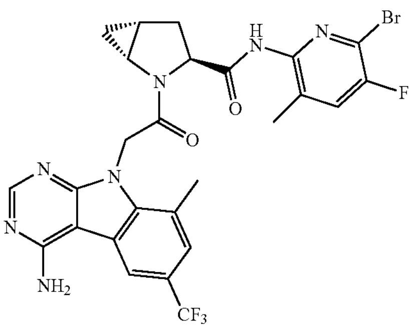 [SMILES: Cc1cc(F)c(Br)nc1NC(=O)[C@@H]1C[C@H]2C[C@H]2N1C(=O)Cn1c2ncnc(N)c2c2cc(C(F)(F)F)cc(C)c21] |

-continued
| # | Structure | # | Structure |
|---|---|---|---|
| 334a | 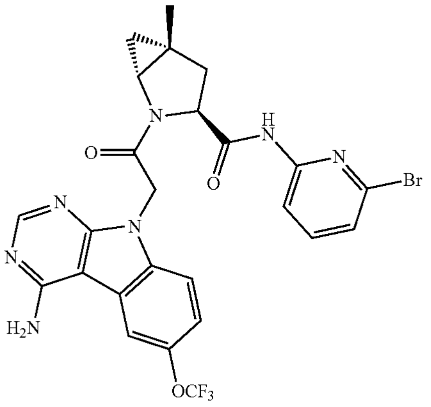 [SMILES: C[C@@]12C[C@@H](C(=O)Nc3cccc(Br)n3)N(C(=O)Cn3c4ccc(OC(F)(F)F)cc4c4c(N)ncnc43)[C@@H]1C2] | 335c | 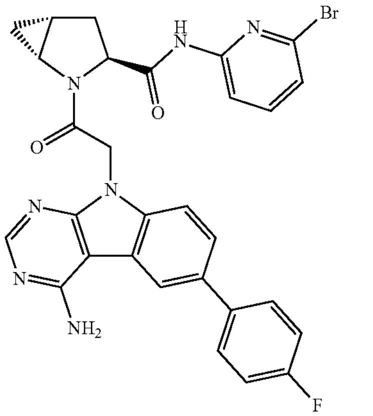 [SMILES: Nc1ncnc2c1c1cc(-c3ccc(F)cc3)ccc1n2CC(=O)N1[C@@H]2C[C@@H]2C[C@H]1C(=O)Nc1cccc(Br)n1] |
| 313b | 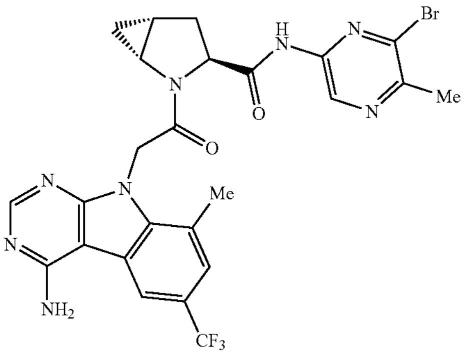 [SMILES: Cc1ncc(NC(=O)[C@@H]2C[C@H]3C[C@H]3N2C(=O)Cn2c3ncnc(N)c3c3cc(C(F)(F)F)cc(C)c32)nc1Br] | 314a | 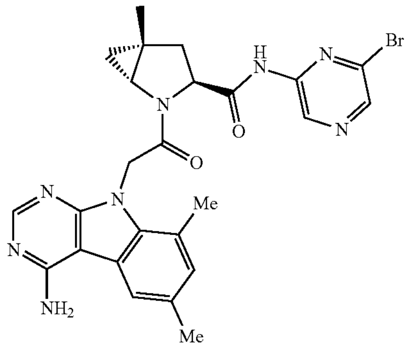 [SMILES: Cc1cc(C)c2c(c1)c1c(N)ncnc1n2CC(=O)N1[C@H](C(=O)Nc2cncc(Br)n2)C[C@@]2(C)C[C@@H]12] |
| 312a | 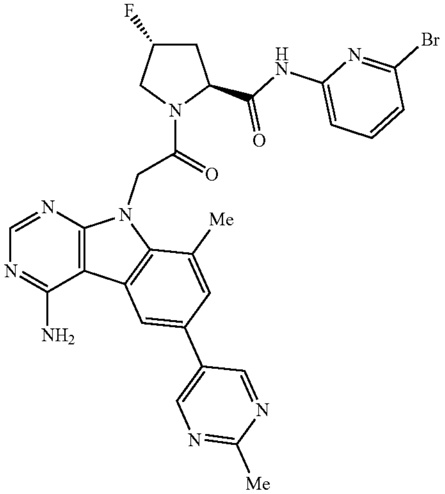 [SMILES: Cc1ncc(-c2cc(C)c3c(c2)c2c(N)ncnc2n3CC(=O)N2C[C@H](F)C[C@H]2C(=O)Nc2cccc(Br)n2)cn1] | 323a | 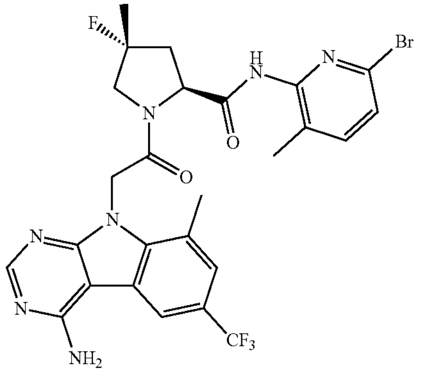 [SMILES: Cc1ccc(Br)nc1NC(=O)[C@@H]1C[C@@](C)(F)CN1C(=O)Cn1c2ncnc(N)c2c2cc(C(F)(F)F)cc(C)c21] |

-continued
| # | Structure | # | Structure |
|---|---|---|---|
| 324a | 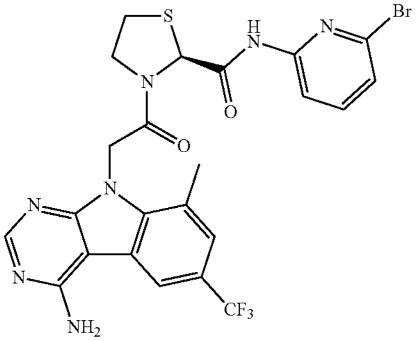 [SMILES: Cc1cc(C(F)(F)F)cc2c3c(N)ncnc3n(CC(=O)N3CCS[C@H]3C(=O)Nc3cccc(Br)n3)c12] | 306a | 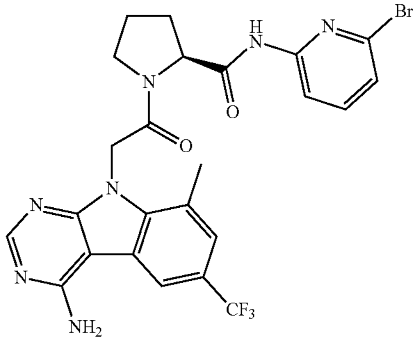 [SMILES: Cc1cc(C(F)(F)F)cc2c3c(N)ncnc3n(CC(=O)N3CCC[C@H]3C(=O)Nc3cccc(Br)n3)c12] |
| 325c | 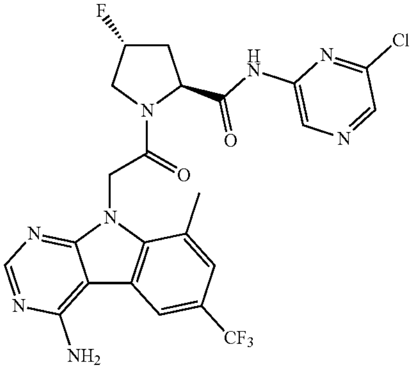 [SMILES: Cc1cc(C(F)(F)F)cc2c3c(N)ncnc3n(CC(=O)N3C[C@H](F)C[C@H]3C(=O)Nc3cncc(Cl)n3)c12] | 326c | 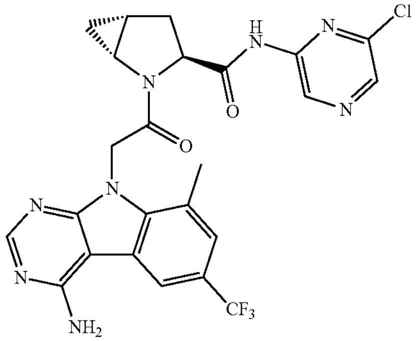 [SMILES: Cc1cc(C(F)(F)F)cc2c3c(N)ncnc3n(CC(=O)N3[C@@H]4C[C@@H]4C[C@H]3C(=O)Nc3cncc(Cl)n3)c12] |
| 327c | 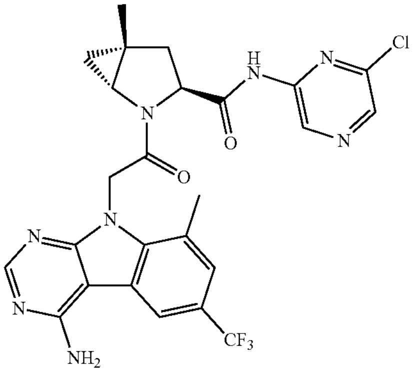 [SMILES: Cc1cc(C(F)(F)F)cc2c3c(N)ncnc3n(CC(=O)N3[C@H](C(=O)Nc4cncc(Cl)n4)C[C@@]4(C)C[C@@H]34)c12] | 328f | 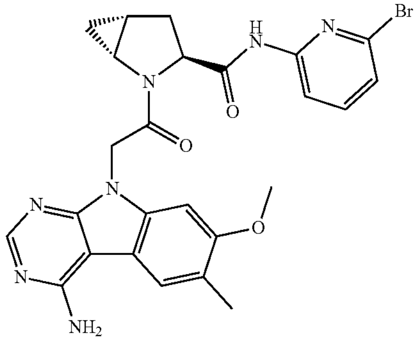 [SMILES: COc1cc2c(cc1C)c1c(N)ncnc1n2CC(=O)N1[C@@H]2C[C@@H]2C[C@H]1C(=O)Nc1cccc(Br)n1] |
| 329a | 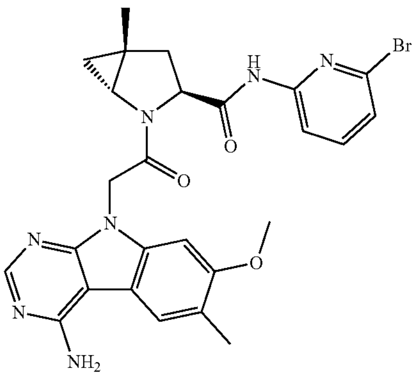 [SMILES: COc1cc2c(cc1C)c1c(N)ncnc1n2CC(=O)N1[C@H](C(=O)Nc2cccc(Br)n2)C[C@@]2(C)C[C@@H]12] | 330f | 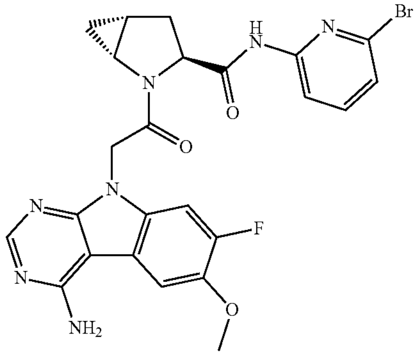 [SMILES: COc1cc2c3c(N)ncnc3n(CC(=O)N3[C@@H]4C[C@@H]4C[C@H]3C(=O)Nc3cccc(Br)n3)c2cc1F] |

-continued
| # | Structure | # | Structure |
|---|---|---|---|
| 331a | 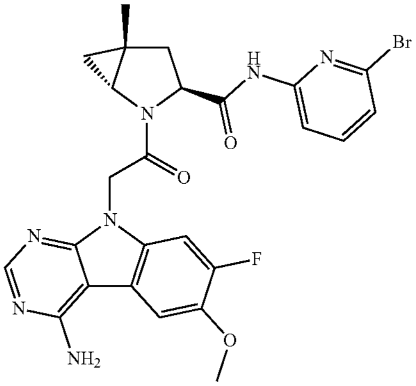 [SMILES: COc1cc2c3c(N)ncnc3n(CC(=O)N3[C@H](C(=O)Nc4cccc(Br)n4)C[C@@]4(C)C[C@@H]34)c2cc1F] | 336c | 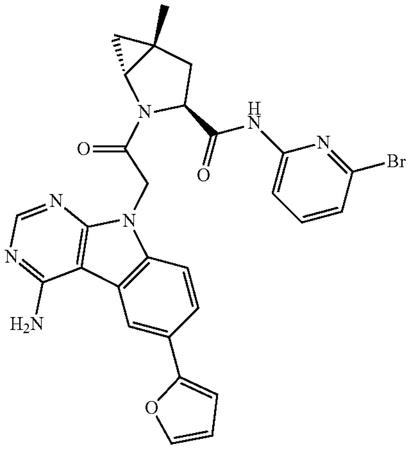 [SMILES: C[C@@]12C[C@@H](C(=O)Nc3cccc(Br)n3)N(C(=O)Cn3c4ccc(-c5ccco5)cc4c4c(N)ncnc43)[C@@H]1C2] |
| 337a | 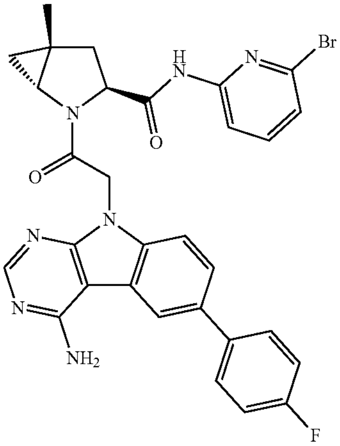 [SMILES: C[C@@]12C[C@@H](C(=O)Nc3cccc(Br)n3)N(C(=O)Cn3c4ccc(-c5ccc(F)cc5)cc4c4c(N)ncnc43)[C@@H]1C2] | 315a | 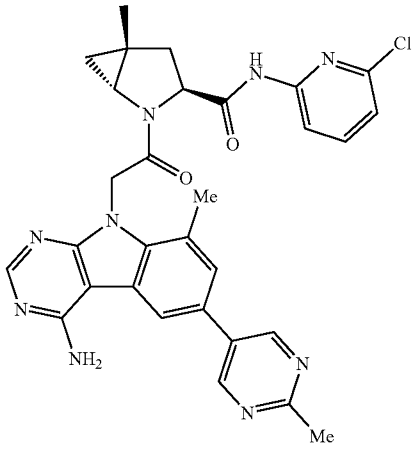 [SMILES: Cc1ncc(-c2cc(C)c3c(c2)c2c(N)ncnc2n3CC(=O)N2[C@H](C(=O)Nc3cccc(Cl)n3)C[C@@]3(C)C[C@@H]23)cn1] |
| 316a | 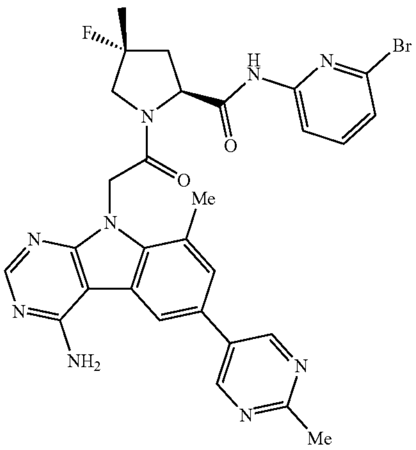 [SMILES: Cc1ncc(-c2cc(C)c3c(c2)c2c(N)ncnc2n3CC(=O)N2C[C@](C)(F)C[C@H]2C(=O)Nc2cccc(Br)n2)cn1] | 343a | 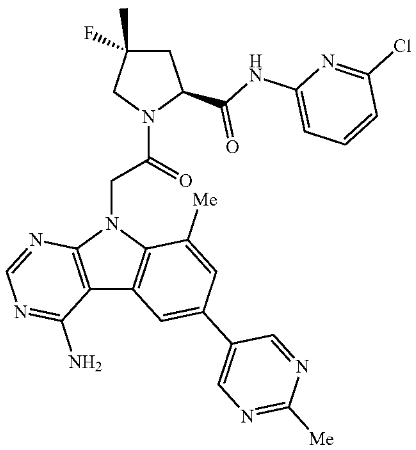 [SMILES: Cc1ncc(-c2cc(C)c3c(c2)c2c(N)ncnc2n3CC(=O)N2C[C@](C)(F)C[C@H]2C(=O)Nc2cccc(Cl)n2)cn1] |

-continued
| # | Structure | # | Structure |
|---|---|---|---|
| 344c | 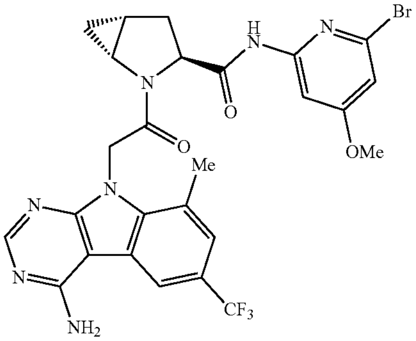 [SMILES: COc1cc(Br)nc(NC(=O)[C@@H]2C[C@H]3C[C@H]3N2C(=O)Cn2c3ncnc(N)c3c3cc(C(F)(F)F)cc(C)c32)c1] | 345c | 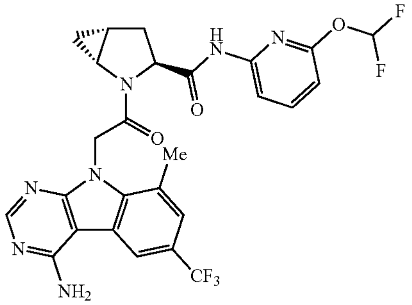 [SMILES: Cc1cc(C(F)(F)F)cc2c3c(N)ncnc3n(CC(=O)N3[C@@H]4C[C@@H]4C[C@H]3C(=O)Nc3cccc(OC(F)F)n3)c12] |
| 346g | 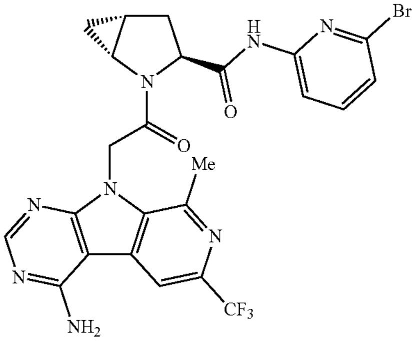 [SMILES: Cc1nc(C(F)(F)F)cc2c3c(N)ncnc3n(CC(=O)N3[C@@H]4C[C@@H]4C[C@H]3C(=O)Nc3cccc(Br)n3)c12] | 347a | 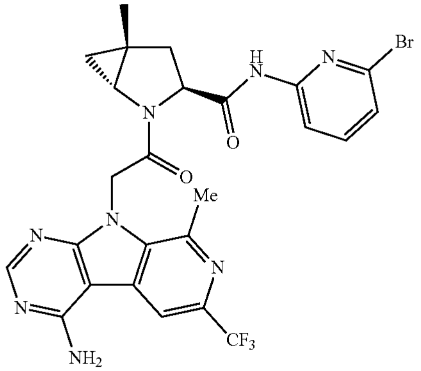 [SMILES: Cc1nc(C(F)(F)F)cc2c3c(N)ncnc3n(CC(=O)N3[C@H](C(=O)Nc4cccc(Br)n4)C[C@@]4(C)C[C@@H]34)c12] |
| 338e | 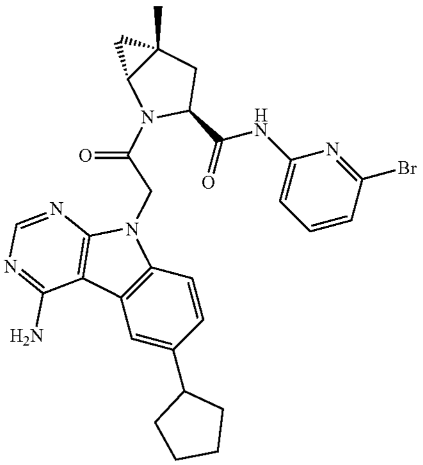 [SMILES: C[C@@]12C[C@@H](C(=O)Nc3cccc(Br)n3)N(C(=O)Cn3c4ccc(C5CCCC5)cc4c4c(N)ncnc43)[C@@H]1C2] | 339g | 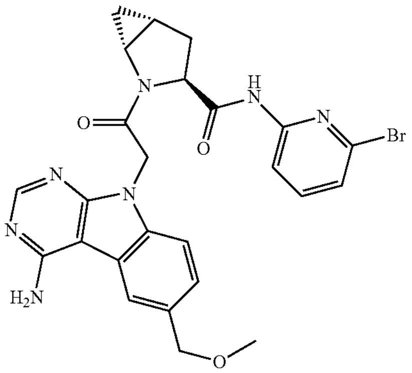 [SMILES: COCc1ccc2c(c1)c1c(N)ncnc1n2CC(=O)N1[C@@H]2C[C@@H]2C[C@H]1C(=O)Nc1cccc(Br)n1] |
| 348c | 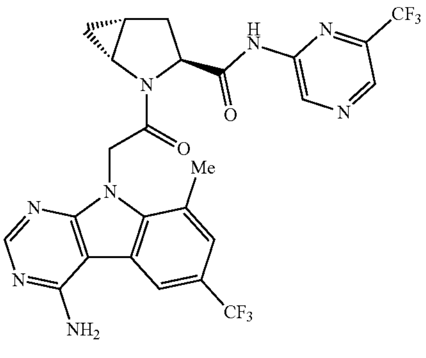 [SMILES: Cc1cc(C(F)(F)F)cc2c3c(N)ncnc3n(CC(=O)N3[C@@H]4C[C@@H]4C[C@H]3C(=O)Nc3cncc(C(F)(F)F)n3)c12] | 349c | 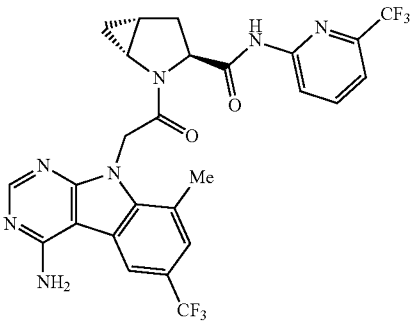 [SMILES: Cc1cc(C(F)(F)F)cc2c3c(N)ncnc3n(CC(=O)N3[C@@H]4C[C@@H]4C[C@H]3C(=O)Nc3cccc(C(F)(F)F)n3)c12] |

-continued
| # | Structure | # | Structure |
|---|---|---|---|
| 350a | 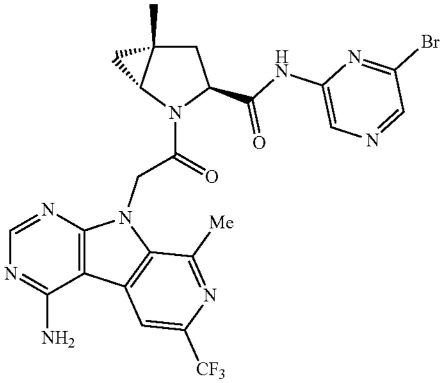 [SMILES: Cc1nc(C(F)(F)F)cc2c3c(N)ncnc3n(CC(=O)N3[C@H](C(=O)Nc4cncc(Br)n4)C[C@@]4(C)C[C@@H]34)c12] | 351a | 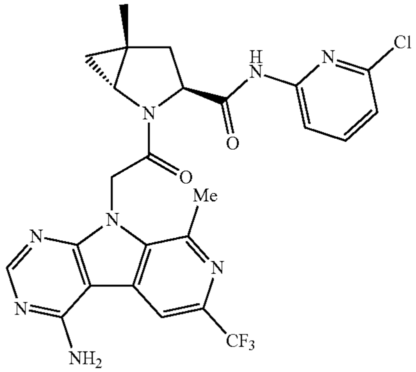 [SMILES: Cc1nc(C(F)(F)F)cc2c3c(N)ncnc3n(CC(=O)N3[C@H](C(=O)Nc4cccc(Cl)n4)C[C@@]4(C)C[C@@H]34)c12] |
| 332c | 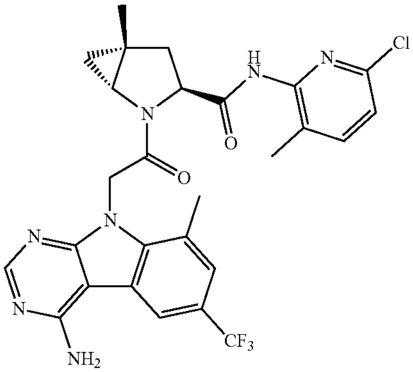 [SMILES: Cc1ccc(Cl)nc1NC(=O)[C@@H]1C[C@@]2(C)C[C@H]2N1C(=O)Cn1c2ncnc(N)c2c2cc(C(F)(F)F)cc(C)c21] | 333c | 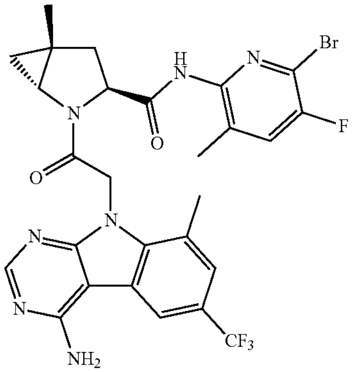 [SMILES: Cc1cc(F)c(Br)nc1NC(=O)[C@@H]1C[C@@]2(C)C[C@H]2N1C(=O)Cn1c2ncnc(N)c2c2cc(C(F)(F)F)cc(C)c21] |
| 365c | 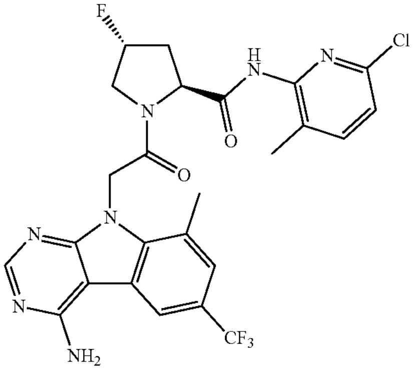 [SMILES: Cc1ccc(Cl)nc1NC(=O)[C@@H]1C[C@@H](F)CN1C(=O)Cn1c2ncnc(N)c2c2cc(C(F)(F)F)cc(C)c21] | 366c | 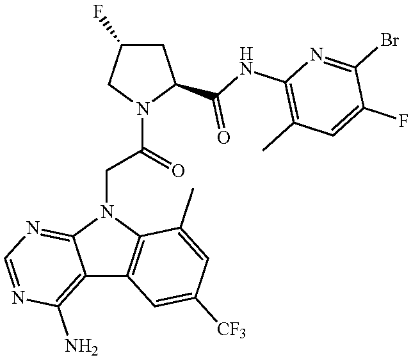 [SMILES: Cc1cc(F)c(Br)nc1NC(=O)[C@@H]1C[C@@H](F)CN1C(=O)Cn1c2ncnc(N)c2c2cc(C(F)(F)F)cc(C)c21] |
| 352c | 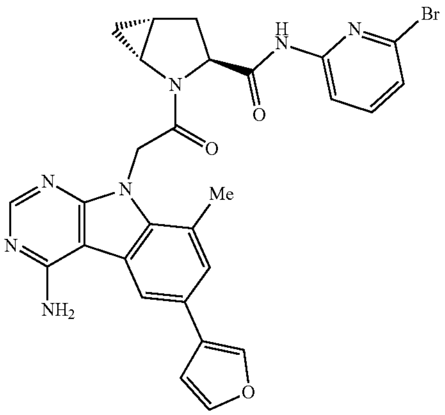 [SMILES: Cc1cc(-c2ccoc2)cc2c3c(N)ncnc3n(CC(=O)N3[C@@H]4C[C@@H]4C[C@H]3C(=O)Nc3cccc(Br)n3)c12] | 353a | 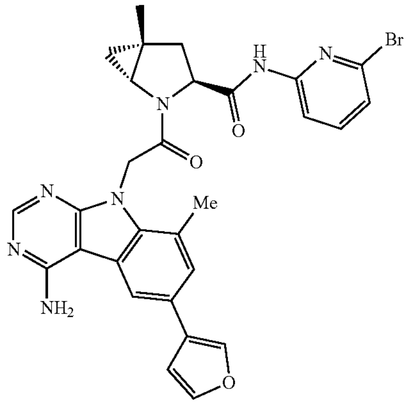 [SMILES: Cc1cc(-c2ccoc2)cc2c3c(N)ncnc3n(CC(=O)N3[C@H](C(=O)Nc4cccc(Br)n4)C[C@@]4(C)C[C@@H]34)c12] |

-continued
| # | Structure | # | Structure |
| --- | --- | --- | --- |
| 354c | 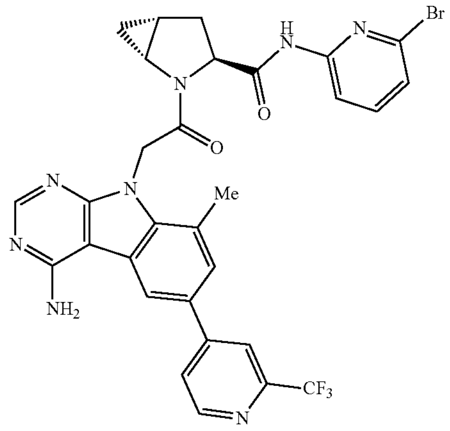 [SMILES: Cc1cc(-c2ccnc(C(F)(F)F)c2)cc2c3c(N)ncnc3n(CC(=O)N3[C@@H]4C[C@@H]4C[C@H]3C(=O)Nc3cccc(Br)n3)c12] | 355a | 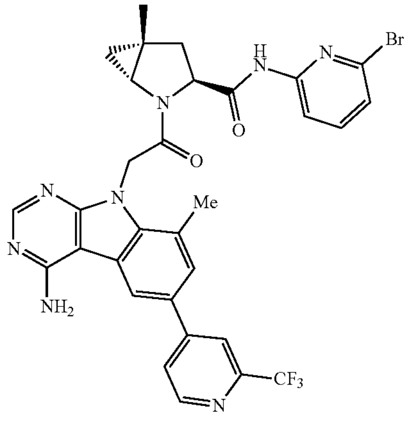 [SMILES: Cc1cc(-c2ccnc(C(F)(F)F)c2)cc2c3c(N)ncnc3n(CC(=O)N3[C@H](C(=O)Nc4cccc(Br)n4)C[C@@]4(C)C[C@@H]34)c12] |
| 340a | 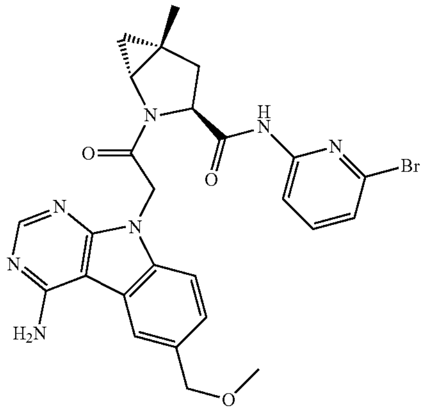 [SMILES: COCc1ccc2c(c1)c1c(N)ncnc1n2CC(=O)N1[C@H](C(=O)Nc2cccc(Br)n2)C[C@@]2(C)C[C@@H]12] | 341c | 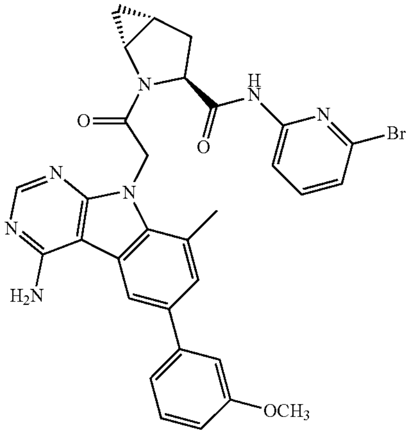 [SMILES: COc1cccc(-c2cc(C)c3c(c2)c2c(N)ncnc2n3CC(=O)N2[C@@H]3C[C@@H]3C[C@H]2C(=O)Nc2cccc(Br)n2)c1] |
| 342a | 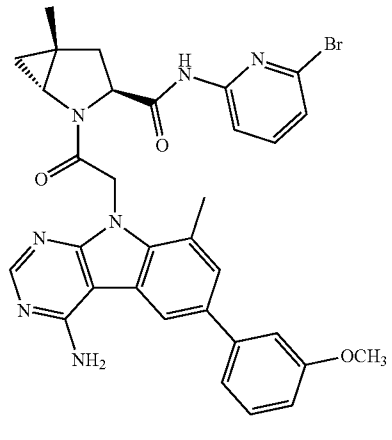 [SMILES: COc1cccc(-c2cc(C)c3c(c2)c2c(N)ncnc2n3CC(=O)N2[C@H](C(=O)Nc3cccc(Br)n3)C[C@@]3(C)C[C@@H]23)c1] | 356c | 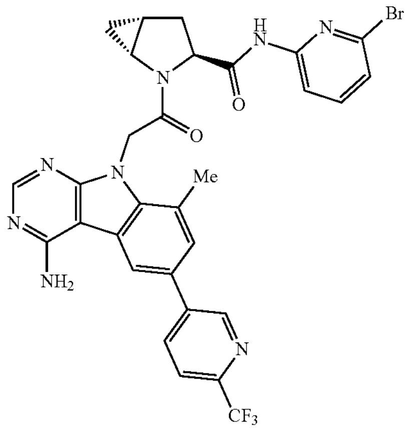 [SMILES: Cc1cc(-c2ccc(C(F)(F)F)nc2)cc2c3c(N)ncnc3n(CC(=O)N3[C@@H]4C[C@@H]4C[C@H]3C(=O)Nc3cccc(Br)n3)c12] |

-continued
| # | Structure | # | Structure |
|---|---|---|---|
| 357a | 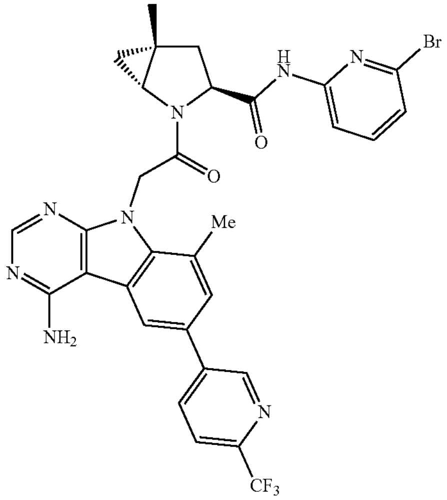 [SMILES: Cc1cc(-c2ccc(C(F)(F)F)nc2)cc2c3c(N)ncnc3n(CC(=O)N3[C@H](C(=O)Nc4cccc(Br)n4)C[C@@]4(C)C[C@@H]34)c12] | 358c | 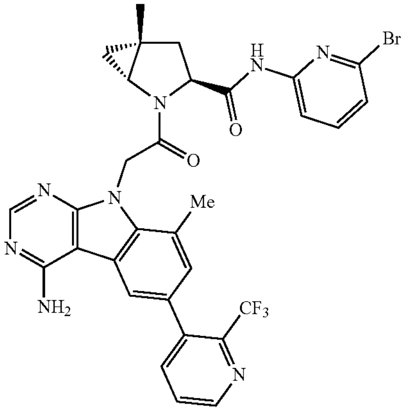 [SMILES: Cc1cc(-c2cccnc2C(F)(F)F)cc2c3c(N)ncnc3n(CC(=O)N3[C@H](C(=O)Nc4cccc(Br)n4)C[C@@]4(C)C[C@@H]34)c12] |
| 359c | 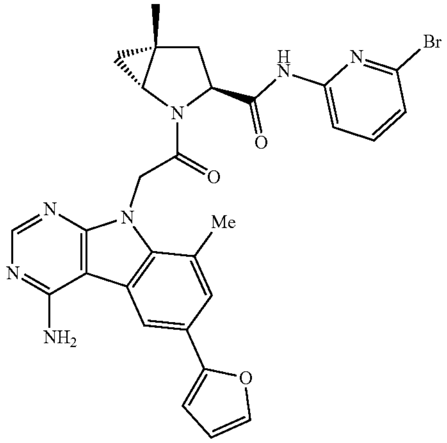 [SMILES: Cc1cc(-c2ccco2)cc2c3c(N)ncnc3n(CC(=O)N3[C@H](C(=O)Nc4cccc(Br)n4)C[C@@]4(C)C[C@@H]34)c12] | 360c | 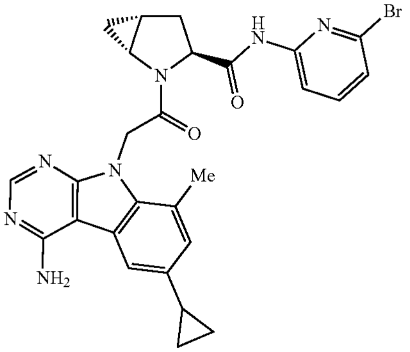 [SMILES: Cc1cc(C2CC2)cc2c3c(N)ncnc3n(CC(=O)N3[C@@H]4C[C@@H]4C[C@H]3C(=O)Nc3cccc(Br)n3)c12] |
| 361a | 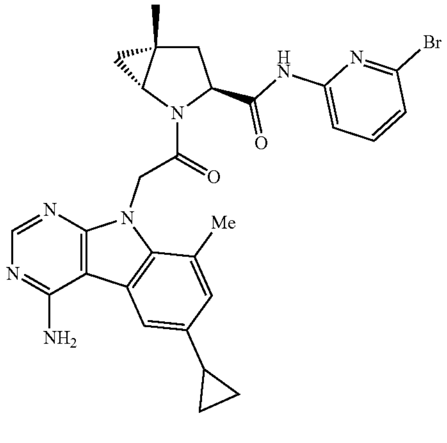 [SMILES: Cc1cc(C2CC2)cc2c3c(N)ncnc3n(CC(=O)N3[C@H](C(=O)Nc4cccc(Br)n4)C[C@@]4(C)C[C@@H]34)c12] | 367g | 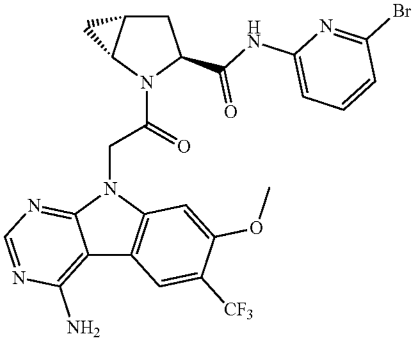 |

-continued
| # | Structure | # | Structure |
|---|---|---|---|
| 368a | 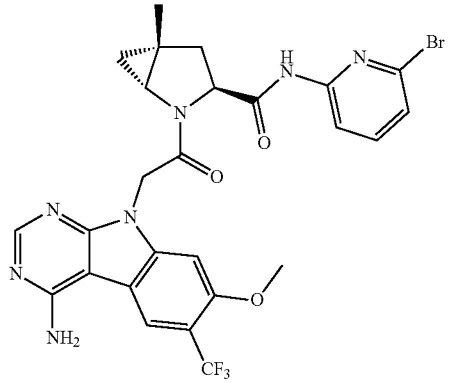 [SMILES: COc1cc2c(cc1C(F)(F)F)c1c(N)ncnc1n2CC(=O)N1[C@H](C(=O)Nc2cccc(Br)n2)C[C@@]2(C)C[C@@H]12] | 369g | 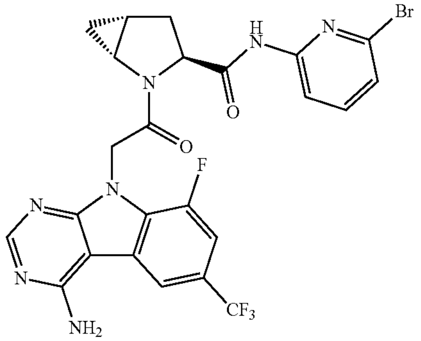 |
| 362f | 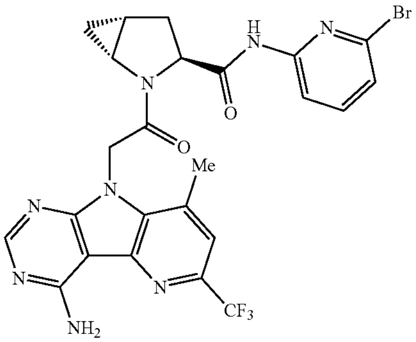 [SMILES: Cc1cc(C(F)(F)F)nc2c3c(N)ncnc3n(CC(=O)N3[C@@H]4C[C@@H]4C[C@H]3C(=O)Nc3cccc(Br)n3)c12] | 363a | 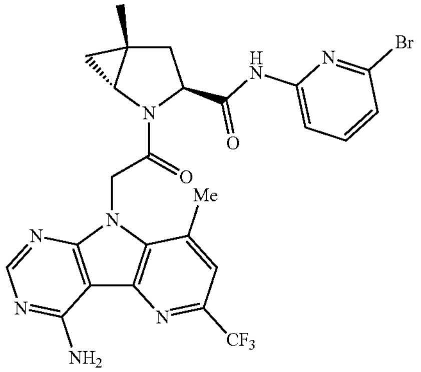 [SMILES: Cc1cc(C(F)(F)F)nc2c3c(N)ncnc3n(CC(=O)N3[C@H](C(=O)Nc4cccc(Br)n4)C[C@@]4(C)C[C@@H]34)c12] |
| 364e | 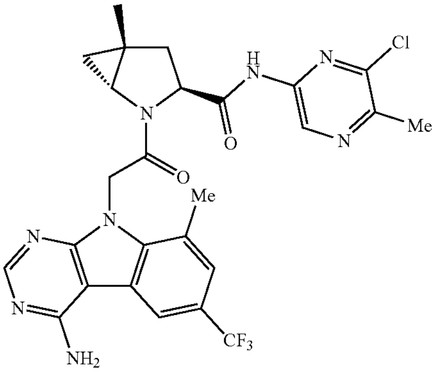 [SMILES: Cc1ncc(NC(=O)[C@@H]2C[C@@]3(C)C[C@H]3N2C(=O)Cn2c3ncnc(N)c3c3cc(C(F)(F)F)cc(C)c32)nc1Cl] | 364d | 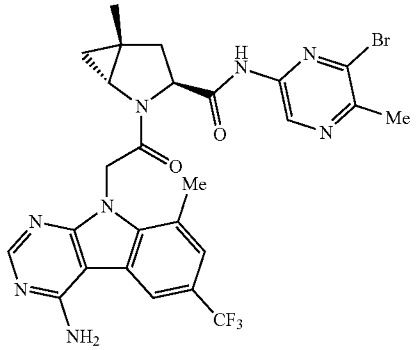 |
| 381g | 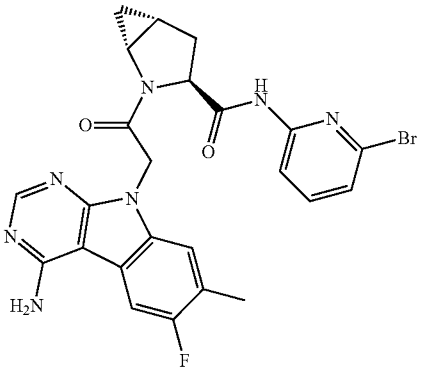 [SMILES: Cc1cc2c(cc1F)c1c(N)ncnc1n2CC(=O)N1[C@@H]2C[C@@H]2C[C@H]1C(=O)Nc1cccc(Br)n1] | 382a | 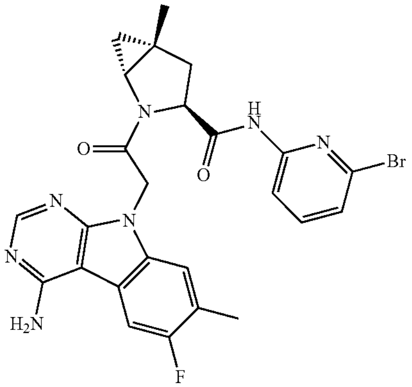 [SMILES: Cc1cc2c(cc1F)c1c(N)ncnc1n2CC(=O)N1[C@H](C(=O)Nc2cccc(Br)n2)C[C@@]2(C)C[C@@H]12] |

-continued
| # | Structure | # | Structure |
|---|---|---|---|
| 385a | 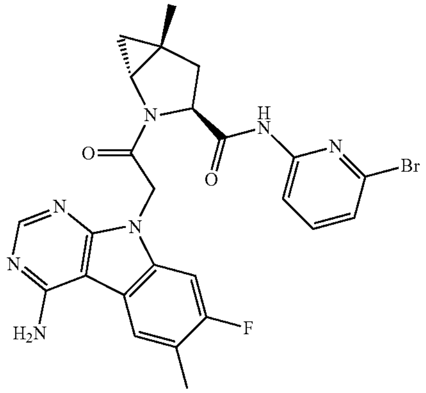 [SMILES: Cc1cc2c3c(N)ncnc3n(CC(=O)N3[C@H](C(=O)Nc4cccc(Br)n4)C[C@@]4(C)C[C@@H]34)c2cc1F] | 384g | 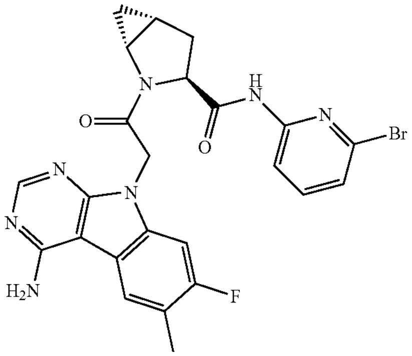 [SMILES: Cc1cc2c3c(N)ncnc3n(CC(=O)N3[C@@H]4C[C@@H]4C[C@H]3C(=O)Nc3cccc(Br)n3)c2cc1F] |
| 386g | 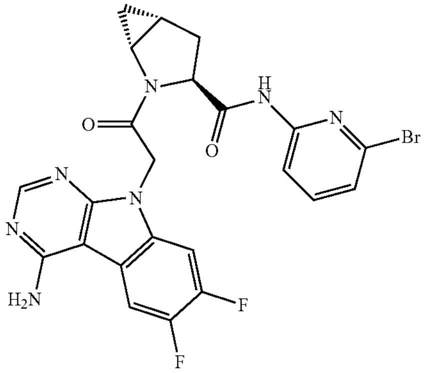 [SMILES: Nc1ncnc2c1c1cc(F)c(F)cc1n2CC(=O)N1[C@@H]2C[C@@H]2C[C@H]1C(=O)Nc1cccc(Br)n1] | 387a | 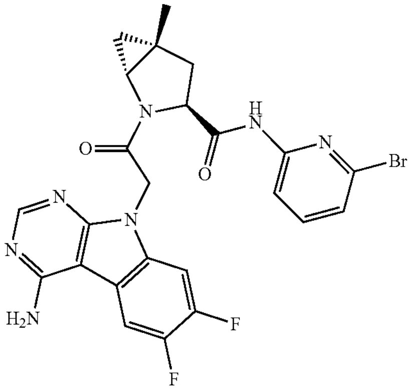 [SMILES: C[C@@]12C[C@@H](C(=O)Nc3cccc(Br)n3)N(C(=O)Cn3c4cc(F)c(F)cc4c4c(N)ncnc43)[C@@H]1C2] |
| 383g | 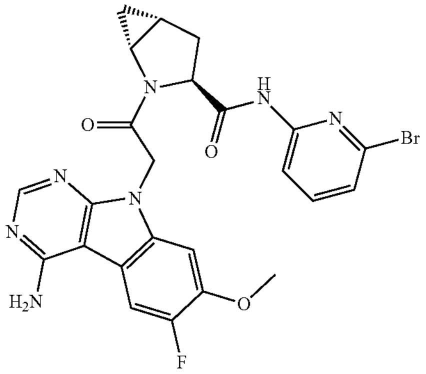 [SMILES: COc1cc2c(cc1F)c1c(N)ncnc1n2CC(=O)N1[C@@H]2C[C@@H]2C[C@H]1C(=O)Nc1cccc(Br)n1] | 388a | 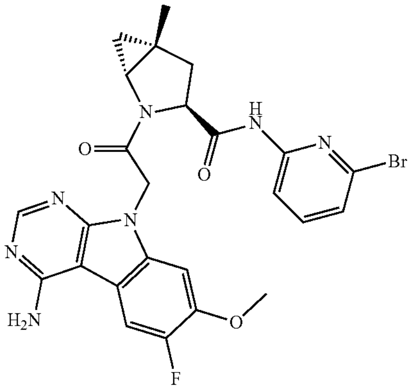 [SMILES: COc1cc2c(cc1F)c1c(N)ncnc1n2CC(=O)N1[C@H](C(=O)Nc2cccc(Br)n2)C[C@@]2(C)C[C@@H]12] |
| 389g | 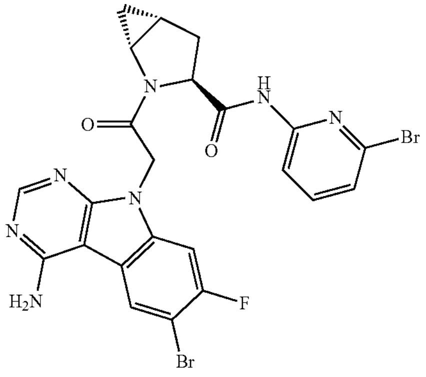 [SMILES: Nc1ncnc2c1c1cc(Br)c(F)cc1n2CC(=O)N1[C@@H]2C[C@@H]2C[C@H]1C(=O)Nc1cccc(Br)n1] | 390a | 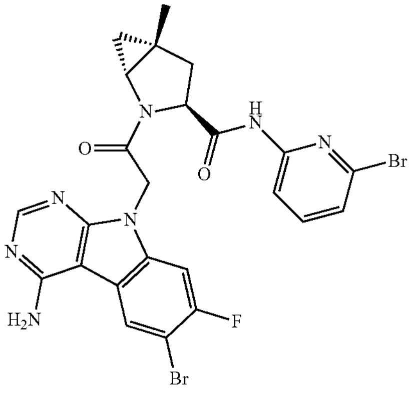 |

-continued
| # | Structure | # | Structure |
|---|---|---|---|
| 376g | 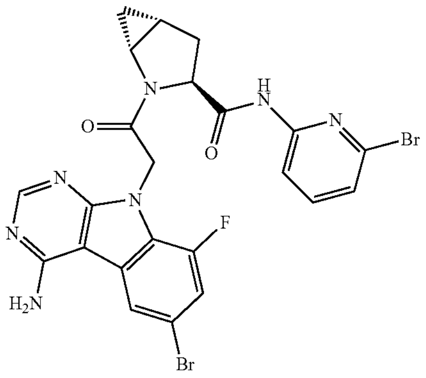 [SMILES: Nc1ncnc2c1c1cc(Br)cc(F)c1n2CC(=O)N1[C@@H]2C[C@@H]2C[C@H]1C(=O)Nc1cccc(Br)n1] | 377a | 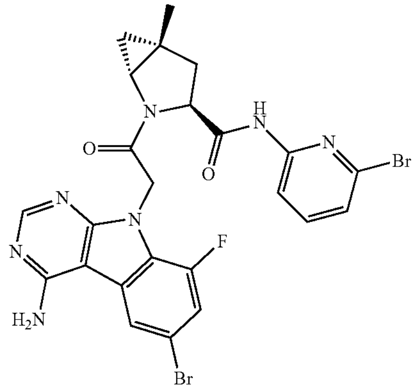 [SMILES: C[C@@]12C[C@@H](C(=O)Nc3cccc(Br)n3)N(C(=O)Cn3c4ncnc(N)c4c4cc(Br)cc(F)c43)[C@@H]1C2] |
| 379h | 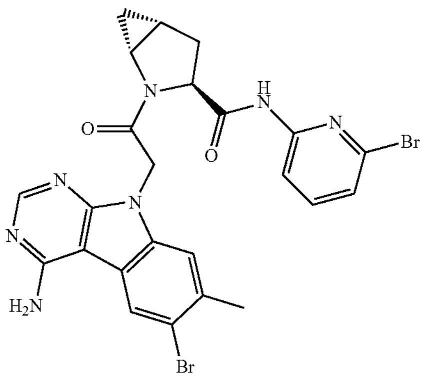 [SMILES: Cc1cc2c(cc1Br)c1c(N)ncnc1n2CC(=O)N1[C@@H]2C[C@@H]2C[C@H]1C(=O)Nc1cccc(Br)n1] | 380a | 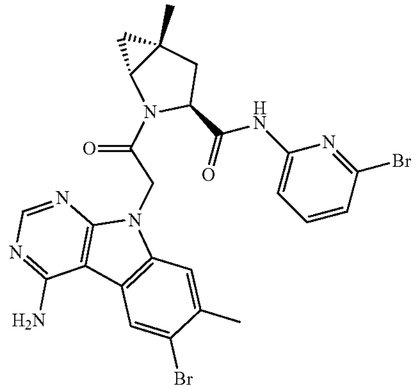 [SMILES: Cc1cc2c(cc1Br)c1c(N)ncnc1n2CC(=O)N1[C@H](C(=O)Nc2cccc(Br)n2)C[C@@]2(C)C[C@@H]12] |
| 374g | 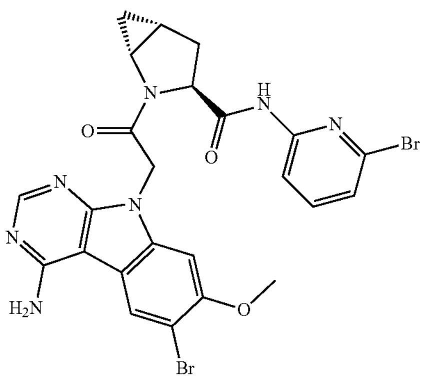 [SMILES: COc1cc2c(cc1Br)c1c(N)ncnc1n2CC(=O)N1[C@@H]2C[C@@H]2C[C@H]1C(=O)Nc1cccc(Br)n1] | 375a | 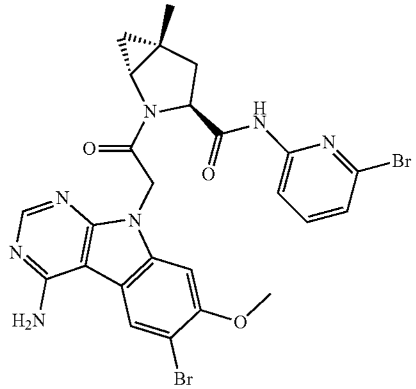 [SMILES: COc1cc2c(cc1Br)c1c(N)ncnc1n2CC(=O)N1[C@H](C(=O)Nc2cccc(Br)n2)C[C@@]2(C)C[C@@H]12] |
| 391g | 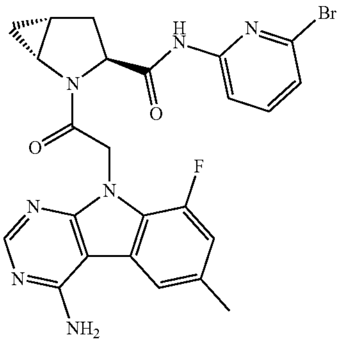 [SMILES: Cc1cc(F)c2c(c1)c1c(N)ncnc1n2CC(=O)N1[C@@H]2C[C@@H]2C[C@H]1C(=O)Nc1cccc(Br)n1] | 392a | 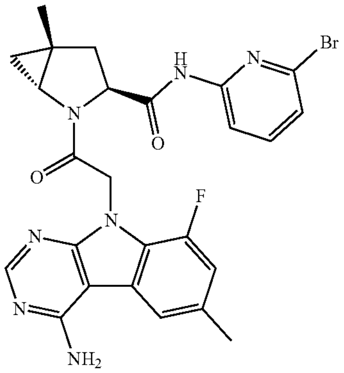 [SMILES: Cc1cc(F)c2c(c1)c1c(N)ncnc1n2CC(=O)N1[C@H](C(=O)Nc2cccc(Br)n2)C[C@@]2(C)C[C@@H]12] |

-continued

| # | Structure | # | Structure |
|---|---|---|---|
| 370a | 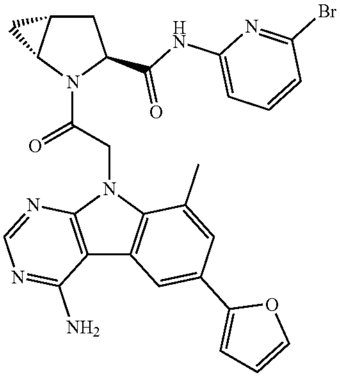 [SMILES: Cc1cc(-c2ccco2)cc2c3c(N)ncnc3n(CC(=O)N3[C@@H]4C[C@@H]4C[C@H]3C(=O)Nc3cccc(Br)n3)c12] | 378c | 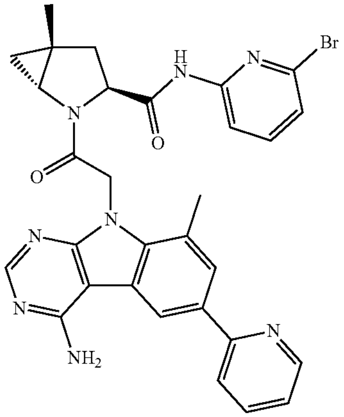 [SMILES: Cc1cc(-c2ccccn2)cc2c3c(N)ncnc3n(CC(=O)N3[C@H](C(=O)Nc4cccc(Br)n4)C[C@@]4(C)C[C@@H]34)c12] |
| 371c | 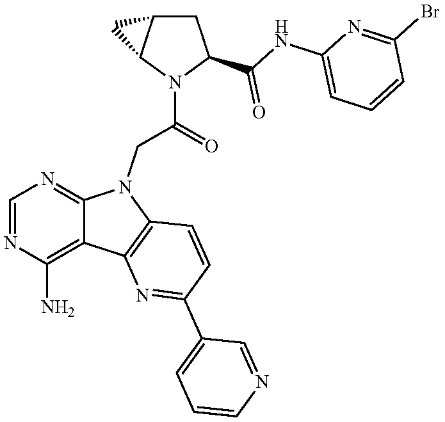 [SMILES: Nc1ncnc2c1c1nc(-c3cccnc3)ccc1n2CC(=O)N1[C@@H]2C[C@@H]2C[C@H]1C(=O)Nc1cccc(Br)n1] | 372a | 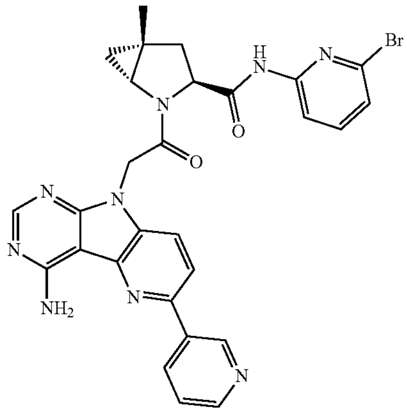 [SMILES: C[C@@]12C[C@@H](C(=O)Nc3cccc(Br)n3)N(C(=O)Cn3c4ccc(-c5cccnc5)nc4c4c(N)ncnc43)[C@@H]1C2] |
| 373a | 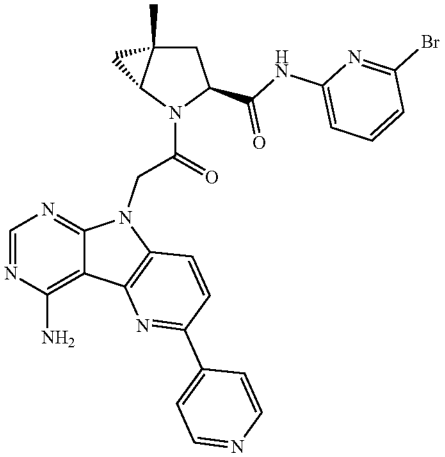 [SMILES: C[C@@]12C[C@@H](C(=O)Nc3cccc(Br)n3)N(C(=O)Cn3c4ccc(-c5ccncc5)nc4c4c(N)ncnc43)[C@@H]1C2] | | |

Pharmaceutical Compositions

The invention provides pharmaceutical compositions, each comprising one or more compounds of the invention, or pharmaceutically acceptable salts thereof, and a pharmaceutically acceptable carrier. In certain embodiments, the pharmaceutical composition comprises a compound of the invention, or a pharmaceutically acceptable salt thereof, and a pharmaceutically acceptable carrier. In certain embodiments, the pharmaceutical composition comprises a plurality of compounds of the invention, which may include pharmaceutically acceptable salts thereof, and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of a disease or condition characterized by aberrant complement system activity.

Pharmaceutical compositions of the invention can be prepared by combining one or more compounds of the invention with a pharmaceutically acceptable carrier and, optionally, one or more additional pharmaceutically active agents.

Methods of Use

The present invention provides compounds, and pharmaceutically acceptable salts thereof, that are useful for treating or preventing a disease or condition characterized by aberrant complement system activity.

In certain aspects, the invention provides a compound of the invention, or a pharmaceutically acceptable salt thereof, for use as a medicament.

In certain aspects, the invention provides methods of treating or preventing a disease or condition characterized by aberrant complement system activity. The method includes the step of administering to a subject in need thereof a therapeutically effective amount of a compound of the invention, or a pharmaceutically acceptable salt thereof, thereby treating or preventing the disease or condition characterized by aberrant complement system activity. By reducing complement system activity in the subject, the disease or condition characterized by aberrant complement system activity is treated.

Alternatively, in certain aspects, the invention provides a compound of the invention, or a pharmaceutically acceptable salt thereof, for treatment of a disease or condition characterized by aberrant complement system activity.

Alternatively, in certain aspects, the invention provides the use of a compound of the invention, or a pharmaceutically acceptable salt thereof, for the manufacture of a medicament for use in treatment of a disease or condition characterized by aberrant complement system activity.

As used herein, a "disease or condition characterized by aberrant complement system activity" refers to any disease or condition in which it is desirable to reduce complement system activity. For example, it may be desirable to reduce complement system activity in the setting of inappropriate activation or hyperactivation of the complement system.

In certain embodiments, the disease or condition characterized by aberrant complement system activity is an immunological disorder.

In certain embodiments, the disease or condition characterized by aberrant complement system activity is a disease of the central nervous system.

In certain embodiments, the disease or condition characterized by aberrant complement system activity is a neurodegenerative disease or neurological disease.

In certain embodiments, the disease or condition characterized by aberrant complement system activity is a renal disease.

In certain embodiments, the disease or condition characterized by aberrant complement system activity is a cardiovascular disease.

In certain embodiments, the disease or condition characterized by aberrant complement system activity is a cardiometabolic disease.

In certain embodiments, the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, and catastrophic antiphospholipid syndrome.

In certain embodiments, the disease or condition is paroxysmal nocturnal hemoglobinuria.

In certain embodiments, the disease or condition is atypical hemolytic uremic syndrome.

In certain embodiments, the disease or condition is organ transplant rejection.

In certain embodiments, the disease or condition is myasthenia gravis.

In certain embodiments, the disease or condition is neuromyelitis optica.

In certain embodiments, the disease or condition is membranoproliferative glomerulonephritis.

In certain embodiments, the disease or condition is dense-deposit disease.

In certain embodiments, the disease or condition is cold agglutinin disease.

In certain embodiments, the disease or condition is catastrophic antiphospholipid syndrome.

In other embodiments, the disease or condition characterized by aberrant complement system activity is adult respiratory distress syndrome, myocardial infarct, lung inflammation, hyperacute rejection (transplantation rejection), sepsis, cardiopulmonary bypass, burns, asthma, restenosis, multiple organ dysfunction syndrome, Guillain-Barré syndrome, hemorrhagic shock, paroxysmal nocturnal hemoglobinuria, glomerulonephritis, systemic lupus erythematosus, rheumatoid arthritis, infertility, Alzheimer's disease, organ rejection (transplantation), myasthenia gravis, multiple sclerosis, platelet storage, or hemodialysis.

In other embodiments, the disease or condition characterized by aberrant complement system activity is selected from the group consisting of antineutrophil cytoplasmic antibody (ANCA)-associated vasculitis (AAV), warm autoimmune hemolytic anemia, IgA nephropathy, C3 glomerulonephritis, and focal segmental glomerulosclerosis.

In certain embodiments, the disease or condition characterized by aberrant complement system activity is a hematological disorder.

In other embodiments, the disease or condition characterized by aberrant complement system activity is an ocular disorder or an eye disorder.

In certain embodiments, the disease or condition characterized by aberrant complement system activity is macular degeneration, age-related macular degeneration (AMD), wet AMD, geographic atrophy, macular edema, diabetic macular edema, choroidal neovascularization (CNV), uveitis, Behcet's uveitis, proliferative diabetic retinopathy, non-proliferative diabetic retinopathy, glaucoma, hypertensive retinopathy, a corneal neovascularization disease, post-corneal transplant rejection, a corneal dystrophic disease, an autoimmune dry eye disease. Stevens-Johnson syndrome, Sjogren's syndrome, an environmental dry eye disease, Fuchs' endothelial dystrophy, retinal vein occlusion, or post-operative inflammation.

In certain embodiments, the disease or condition characterized by aberrant complement system activity is angioedema, e.g., hereditary angioedema or acquired angioedema.

In certain embodiments, the disease or condition characterized by aberrant complement system activity is obesity, insulin resistance, diabetes, dyslipidemia, nephropathy, or neuropathy.

In certain embodiments, the disease or condition characterized by aberrant complement system activity is selected from the group consisting of antineutrophil cytoplasmic antibody (ANCA)-associated vasculitis (AAV), paroxysmal nocturnal hemoglobinuria, and thrombotic microangiopathy.

In certain embodiments, the disease or condition characterized by aberrant complement system activity is selected from the group consisting of Alzheimer's disease, multiple sclerosis, neuromyelitis optica, generalized myasthenia gravis. Guillain-Barre syndrome, Parkinson's disease, and schizophrenia.

In certain embodiments, the disease or condition characterized by aberrant complement system activity is periodontitis.

In certain embodiments, the disease or condition characterized by aberrant complement system activity is Crohn's disease.

In certain embodiments, the disease or condition characterized by aberrant complement system activity is selected from the group consisting of asthma, chronic obstructive pulmonary disease, and acute respiratory distress syndrome.

In certain embodiments, the disease or condition characterized by aberrant complement system activity is atherosclerosis.

In certain embodiments, the disease or condition characterized by aberrant complement system activity is selected from the group consisting of age-related macular degeneration (AMD), uveitis, glaucoma, and wet AMD.

In certain embodiments, the disease or condition characterized by aberrant complement system activity is myocardial infarction.

In certain embodiments, the disease or condition characterized by aberrant complement system activity is selected from the group consisting of atypical hemolytic uremic syndrome, C3 glomerulopathy, lupus nephritis, IgA nephropathy, and membranous nephropathy.

In certain embodiments, the disease or condition characterized by aberrant complement system activity is selected from the group consisting of rheumatoid arthritis, osteoarthritis, bullous pemphigoid, psoriasis, hidradenitis suppurativa, and burns.

In certain embodiments, the disease or condition characterized by aberrant complement system activity is hemodialysis.

In certain embodiments, the disease or condition characterized by aberrant complement system activity is selected from the group consisting of ischemia/reperfusion injury, acute kidney injury, and organ transplantation, e.g., kidney transplant.

In certain embodiments, the disease or condition characterized by aberrant complement system activity is selected from the group consisting of systemic inflammatory response syndrome, sepsis, septic shock, trauma, systemic lupus erythematosus, hereditary angioedema, and cancer.

In certain embodiments, the disease or condition characterized by aberrant complement system activity is selected from the group consisting of antibody-mediated rejection, antiphospholipid syndrome, Berger's disease, C3 glomerulonephritis, cold agglutinin disease, cardiopulmonary bypass, dense-deposit disease, delayed graft function, geographic atrophy, granulomatosis with polyangiitis, graft versus host disease, hematopoietic stem cell transplant-related thrombotic microangiopathy, immune complex-mediated membranoproliferative glomerulonephritis, immune-mediated necrotizing myopathy, idiopathic polypoidal choroidal vasculopathy, microscopic polyangiitis, pyoderma gangrenosum, Stargardt Disease 1, and warm type autoimmune hemolytic anemia.

Formulations, Routes of Administration, and Dosing

The compounds of the invention, and pharmaceutically acceptable salts thereof, can be formulated as pharmaceutical compositions and administered to a mammalian host, such as a human patient, in a variety of forms adapted to the chosen route of administration, e.g., orally or parenterally, by intravenous, intraperitoneal, intramuscular, topical, or subcutaneous routes. Additional routes of administration are also contemplated by the invention.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known in the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the compounds of the invention can be determined, at least initially, by comparing their in vitro activity and in vivo activity in animal models. Methods for the extrapolation of effective dosages in mice, and other animals, to humans are known in the art; for example, see U.S. Pat. No. 4,938,949 (incorporated herein by reference).

The amount of the compound, or pharmaceutically acceptable salt thereof, required for use in treatment will vary not only with the particular compound or salt selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram of body weight per day, from about of 10 to about 60 mg/kg of body weight per day, or from about 15 to about 50 mg/kg of body weight per day.

Compounds of the invention, or pharmaceutically acceptable salts thereof, can be conveniently formulated in unit dosage form; for example, containing 5 to 1000 mg, 10 to 750 mg, or 50 to 500 mg of active ingredient per unit dosage form. In one embodiment, the invention provides a composition comprising a compound of the invention, or pharmaceutically acceptable salts thereof, formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations.

Compounds of the invention, or pharmaceutically acceptable salts thereof, can also be administered in combination with other therapeutic agents, for example, other agents that are useful for treating or preventing ischemia, blood loss, or reperfusion injury. In certain embodiments, compounds of the invention, and pharmaceutically acceptable salts thereof, can also be administered in combination with one or more other therapeutic agents that are useful for treating or preventing an ocular disorder or eye disorder.

Other delivery systems can include time-release, delayed release, or sustained release delivery systems such as are well-known in the art. Such systems can avoid repeated administrations of the active compound, increasing convenience to the subject and the physician. Many types of release delivery systems are available and known to those of ordinary skill in the art. Use of a long-term sustained release implant may be desirable. Long-term release, as used herein, means that the delivery system or is implant constructed and arranged to deliver therapeutic levels of the active ingredient for at least 30 days, and preferably 60 days.

In certain embodiments, a compound of the invention is formulated for intraocular administration, for example direct injection or insertion within or in association with an intraocular medical device. In certain embodiments, a compound of the invention is formulated as an ophthalmic solution. In certain embodiments, a compound of the invention can be administered via ocular delivery, for example, by local ocular administration, including topical, intravitreal, periocular, transscleral, retrobulbar, juxtascleral, suprachoroidal, or sub-tenon administration. A compound of the invention can be administered via ocular delivery either alone or in combination with one or more additional therapeutic agents.

The compounds of the invention may be formulated for depositing into a medical device, which may include any of a variety of conventional grafts, stents, including stent grafts, catheters, balloons, baskets, or other device that can be deployed or permanently implanted within a body lumen. As a particular example, it would be desirable to have devices and methods which can deliver compounds of the invention to the region of a body which has been treated by interventional technique.

In exemplary embodiment, a compound of the invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No.

4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz), U.S. Pat. No. 5,419,760 (Narciso, Jr.), U.S. Pat. No. 5,429,634 (Narciso, Jr.), and in International Patent Application Nos. WO 91/12779 (Medtronic, Inc.) and WO 90/13332 (Cedars-Sanai Medical Center), for example.

The term "deposited" means that the compound is coated, adsorbed, placed, or otherwise incorporated into the device by methods known in the art. For example, the compound may be embedded and released from within ("matrix type") or surrounded by and released through ("reservoir type") polymer materials that coat or span the medical device. In the latter example, the compound may be entrapped within the polymer materials or coupled to the polymer materials using one or more the techniques for generating such materials known in the art. In other formulations, the compound may be linked to the surface of the medical device without the need for a coating, for example by means of detachable bonds, and release with time or can be removed by active mechanical or chemical processes. In other formulations, the compound may be in a permanently immobilized form that presents the compound at the implantation site.

In certain embodiments, the compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but frequently a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D, L-lactide) (PLA), poly (L-lactide) (PLLA), poly(glycolic acid-co-trimethylene carbonate) (PGA/PTMC), polyethylene oxide (PEO), polvdioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable polymers known in the art. Also, biostable polymers with a relatively low chronic tissue response such as polyurethanes, silicones, and polyesters could be used, and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In certain embodiments of the invention, the compound of the invention is coupled to a polymer or semipermeable polymer matrix that is formed as a stent or stent-graft device.

Typically, polymers are applied to the surface of an implantable device by spin coating, dipping, or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In certain embodiments of the invention, the compound is formulated for release from the polymer coating into the environment in which the medical device is placed. Preferably, the compound is released in a controlled manner over an extended time frame (e.g., months) using at least one of several well-known techniques involving polymer carriers or layers to control elution. Some of these techniques are described in U.S. Patent Application 2004/0243225A1, the entire disclosure of which is incorporated herein in its entirety.

Moreover, as described for example in U.S. Pat. No. 6,770,729, which is incorporated herein in its entirety, the reagents and reaction conditions of the polymer compositions can be manipulated so that the release of the compound from the polymer coating can be controlled. For example, the diffusion coefficient of the one or more polymer coatings can be modulated to control the release of the compound from the polymer coating. In a variation on this theme, the diffusion coefficient of the one or more polymer coatings can be controlled to modulate the ability of an analyte that is present in the environment in which the medical device is placed (e.g., an analyte that facilitates the breakdown or hydrolysis of some portion of the polymer) to access one or more components within the polymer composition (and for example, thereby modulate the release of the compound from the polymer coating). Yet another embodiment of the invention includes a device having a plurality of polymer coatings, each having a plurality of diffusion coefficients. In such embodiments of the invention, the release of the compound from the polymer coating can be modulated by the plurality of polymer coatings.

In yet another embodiment of the invention, the release of the compound from the polymer coating is controlled by modulating one or more of the properties of the polymer composition, such as the presence of one or more endogenous or exogenous compounds, or alternatively, the pH of the polymer composition. For example, certain polymer compositions can be designed to release a compound in response to a decrease in the pH of the polymer composition.

Kits

The invention also provides a kit, comprising a compound of the invention, or a pharmaceutically acceptable salt thereof, at least one other therapeutic agent, packaging material, and instructions for administering the compound of the invention or the pharmaceutically acceptable salt thereof and the other therapeutic agent or agents to a mammal to treat or prevent a disease or condition characterized by aberrant complement activity. In one embodiment, the mammal is a human.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXAMPLES

Having now described the present invention in detail, the same will be more clearly understood by reference to the following examples, which are included herewith for purposes of illustration only and are not intended to be limiting of the invention.

Scheme 1

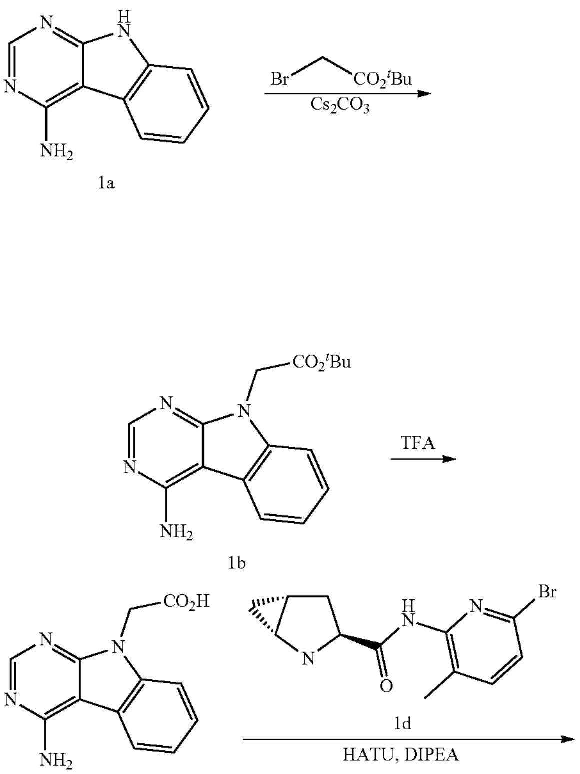

1a
1b
1c
1d

-continued

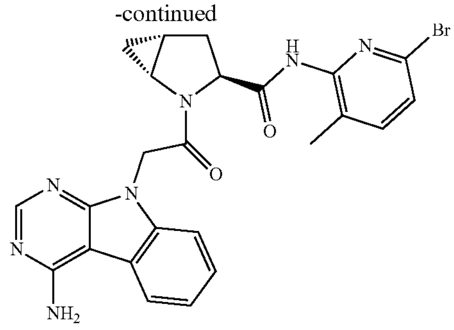

1e

Preparation of (1R,3S,5R)-2-(2-(4-amino-9H-pyrimido[4,5-b]indol-9-yl)acetyl)-N-(6-bromo-3-methylpyridin-2-yl)-2-azabicyclo[3.1.0]hexane-3-carboxamide (1e)

Step-1: Preparation of tert-butyl 2-(4-amino-9H-pyrimido[4,5-b]indol-9-yl)acetate (1b)

A mixture of 9H-pyrimido[4,5-b]indol-4-amine (1a) (0.50 g, 2.71 mmol; CAS #400754-64-5), tert-butyl 2-bromoacetate (0.582 g, 2.99 mmol) and $Cs_2CO_1$ (1.061 g, 3.26 mmol) in DMF (20 mL) was stirred at RT for 3 h, diluted with $H_2O$ (30 mL) and extracted with EtOAc (30 mL×3). The combined organics were washed with $H_2O$ (30 mL×4), brine (30 mL), dried, filtered and concentrated under vacuum and purified by flash column chromatography [silica gel (24 g), eluting with MeOH in DCM from 0-3%] to provide tert-butyl 2-(4-amino-9H-pyrimido[4,5-b]indol-9-yl)acetate (1b) (0.64 g, 79% yield) as a yellow solid; $^1$H NMR (300 MHz, DMSO-$d_6$) δ 8.35 (d, J=7.8 Hz, 1H), 8.29 (s, 1H), 7.55 (d, J=8.1 Hz, 1H), 7.41 (dd, J=8.3, 7.1 Hz, 1H), 7.35-7.18 (m, 3H), 5.12 (s, 2H), 1.41 (s, 9H).

Step-2: Preparation of 2-(4-amino-9H-pyrimido[4,5-b]indol-9-yl)acetic acid (1c)

A mixture of tert-butyl 2-(4-amino-9H-pyrimido[4,5-b]indol-9-yl)acetate (1b) (0.63 g, 2.112 mmol) and 2,2,2-trifluoroacetic acid (12.12 mL, 31.7 mmol) in DCM (20 mL) was stirred at RT for 16 h and concentrated in vacuum to dryness to afford 2-(4-amino-9H-pyrimido[4,5-b]indol-9-yl)acetic acid (1c) (0.74 g, 99%) TFA salt as an orange slid; $^1$H NMR (300 MHz, DMSO-$d_6$) δ 8.55 (s, 1H), 8.49 (d, J=7.8 Hz, 1H), 8.43-8.20 (m, 2H), 7.77 (d, J=8.2 Hz, 1H), 7.58-7.48 (m, 1H), 7.42 (t, J=7.6 Hz, 1H), 5.26 (s, 2H); $^{19}$F NMR (282 MHz, DMSO-$d_6$) δ-74.71.

Step-3: Preparation of (1R,3S,5R)-2-(2-(4-amino-9H-pyrimido[4,5-b]indol-9-yl)acetyl)-N-(6-bromo-3-methylpyridin-2-yl)-2-azabicyclo[3.1.0]hexane-3-carboxamide (1e)

To a solution of 2-(4-amino-9H-pyrimido[4,5-b]indol-9-yl)acetic acid (1c) (50.7 mg, 0.142 mmol) TFA salt, (1R, 3S,5R)—N-(6-bromo-3-methylpyridin-2-yl)-2-azabicyclo[3.1.0]hexane-3-carboxamide (1d) HCl salt [(43 mg, 0.129 mmol); prepared according to the procedure reported by Wiles, Jason A. et al., PCT Int. Appl. (2017), WO 2017035353 A1 20170302; incorporated by reference] and HATU (59.0 mg, 0.155 mmol) in DMF (5 mL) was added dropwise DIPEA (84 mg, 0.646 mmol) and stirred at RT for 16 h. The reaction mixture was diluted with $H_2O$ (30 mL) and extracted with EtOAc (20 mL×2). The combined organics were washed with 0.5 M NaOH (25 mL). $H_2O$ (25 mL×3), brine (25 mL), dried, filtered and concentrated in vacuum to dryness. The residue obtained was purified by flash column chromatography [silica gel (12 g), eluting with MeOH in DCM from 0-5%] to provide product as a pale oil, which was dissolved in MeOH (5 mL) and purified by reverse phase column chromatography [C18 column (100 g), eluting with ACN in water (containing 0.1% HCl) from 0-60%] to provide (1R,3S,5R)-2-(2-(4-amino-9H-pyrimido[4,5-b]indol-9-yl)acetyl)-N-(6-bromo-3-methylpyridin-2-yl)-2-azabicyclo[3.1.0]hexane-3-carboxamide (1e) (48 mg, 71% yield) HCl salt as a white solid. $^1H$ NMR (300 MHz, DMSO-$d_6$) δ 10.28 (s, 1H, $D_2O$ exchangeable), 8.83-8.59 (m, 3H, 2H $D_2O$ exchangeable), 8.54 (d, J=7.9 Hz, 1H), 7.71 (d, J=8.2 Hz, 1H), 7.62 (d, J=7.9 Hz, 1H), 7.56 (t, J=7.8 Hz, 1H), 7.45 (m, 2H), 5.75 (d, J=17.5 Hz, 1H), 5.47 (d, J=17.3 Hz, 1H), 4.39 (dd, J=9.1, 5.1 Hz, 1H), 3.93-3.86 (m, 1H), 2.41 (m, 1H), 2.27 (m, 1H), 1.99 (s, 4H), 1.11 (m, 1H), 0.82 (m, 1H); MS (ES+); 520.0 (M+1); (ES−): 518.0 (M−1); Analysis calculated for $C_{24}H_{22}BrN_7O_2 \cdot 1.1HCl \cdot 2.5H_2O$: C, 47.60; H, 4.68; Cl, 6.44; N, 16.19. Found: C, 47.57; H, 4.60; Cl, 6.33; N, 16.19.

Scheme 2

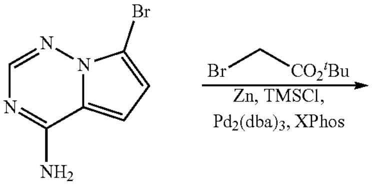

2a

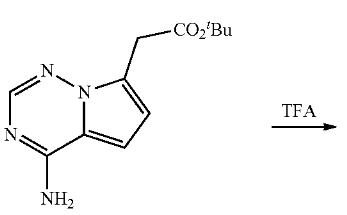

2b

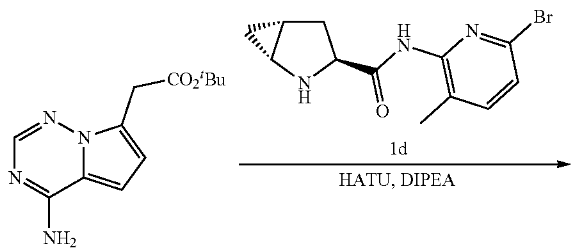

1d

2c

-continued

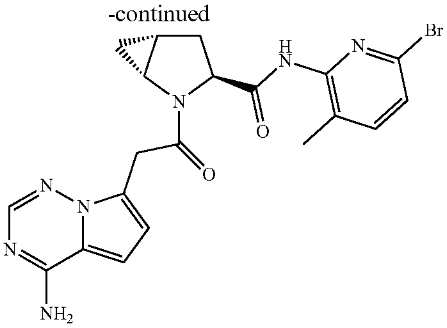

2d

Preparation of (1R,3S,5R)-2-(2-(4-aminopyrrolo[2,1-f][1,2,4]triazin-7-yl)acetyl)-N-(6-bromo-3-methylpyridin-2-yl)-2-azabicyclo[3.1.0]hexane-3-carboxamide (2d)

Step-1: Preparation of tert-butyl 2-(4-aminopyrrolo[2,1-f][1,2,4]triazin-7-yl)acetate (2b)

To a suspension of zinc (1.842 g, 28.2 mmol) (Note: Zinc dust was activated using aqueous 0.1 M HCl, followed by washing thoroughly with $H_2O$, EtOH and $Et_2O$, and drying at 100° C. under vacuum before use) and TMSCl (0.179 mL, 1.408 mmol) in THF (5 mL) at 50° C. was added dropwise tert-butyl 2-bromoacetate (2.75 g, 14.08 mmol) in THF (5 mL) under an argon atmosphere. The mixture was heated at 50° C. for 30 min cooled to RT and was added via syringe to a suspension of 7-bromopyrrolo[1,2-f][1,2,4]triazin-4-amine (2a) (1.00 g, 4.69 mmol; CAS #937046-98-5), $Pd_2(dba)_3$ (0.215 g, 0.235 mmol) and XPhos (0.224 g, 0.469 mmol) in THF (10 mL) at RT under an argon atmosphere and heated at 60° C. under argon for 16 h. The reaction mixture was cooled to RT diluted with EtOAc (30 mL), added solid $NH_4Cl$ (2 g) stirred at RT for 15-min and filtered to remove insoluble solids. The insoluble residue was washed with EtOAc (20 mL) and the filtrate was washed with saturated $NH_4Cl$ (30 mL), $H_2O$ (30 mL), brine (30 mL), dried, filtered and concentrated in vacuum. The obtained residue was purified by flash column chromatography [$SiO_2$ gel (24 g), eluting with EtOAc in hexane from 0-50%] to provide tert-butyl 2-(4-aminopyrrolo[2,1-f][1,2,4]triazin-7-yl)acetate (2b) (0.65 g, 56% yield) as a yellow solid, $^1H$ NMR (300 MHz, DMSO-$d_6$) δ 7.82 (s, 1H), 7.66 (s, 2H), 6.83 (d, J=4.3 Hz, 1H), 6.52 (d, J=4.3 Hz, 1H), 3.84 (s, 2H), 1.40 (s, 9H); MS (ES+): 249 (M+1), (ES−): 247 (M−1).

Step-2: Preparation of 2-(4-aminopyrrolo[2,1-f][1,2,4]triazin-7-yl)acetic acid (2c)

Compound 2c was prepared according to the procedure reported in step-4 of scheme-1, from tert-butyl 2-(4-aminopyrrolo[2,1-f][1,2,4]triazin-7-yl)acetate (2b) (0.65 g, 2.62 mmol) using TFA (4.01 mL, 52 mmol) in DCM (20 mL) and stirring at RT for 16 h. The reaction mixture was concentrated in vacuum to afford 2-(4-aminopyrrolo[2,1-f][1,2,4]triazin-7-yl)acetic acid (2c) (1.05 g) TFA salt as an orange solid; $^1H$ NMR (300 MHz, DMSO-$d_6$) δ 9.67 (dd, J=5.7, 2.9 Hz, 1H), 9.11 (s, 1H), 8.18 (s, 1H), 7.37 (d, J=4.6 Hz, 1H), 6.80 (d, J=4.5 Hz, 1H), 3.96 (s, 2H). $^{19}F$ NMR (282 MHz, DMSO-$d_6$) δ−74.71; MS (ES+): 193 (M+1), (ES−): 191 (M−1).

Step-3: Preparation of (1R,3S,5R)-2-(2-(4-aminopyrrolo[2,1-f][1,2,4]triazin-7-yl)acetyl)-N-(6-bromo-3-methylpyridin-2-yl)-2-azabicyclo[3.1.0]hexane-3-carboxamide (2d)

Compound 2d was prepared according to the procedure reported in step-3 of scheme-1 from TFA salt of 2-(4-aminopyrrolo[2,1-f][1,2,4]triazin-7-yl)acetic acid (2c) (54.7 mg, 0.179 mmol) in DMF (5 mL) using HCl salt of (1R,3S,5R)—N-(6-bromo-3-methylpyridin-2-yl)-2-azabicyclo[3.1.0]hexane-3-carboxamide (1d) (54 mg, 0.162 mmol), HATU (74.1 mg, 0.195 mmol), DIPEA (105 mg, 0.812 mmol) and stirring at RT for 16 h. This gave after workup and purification by flash column chromatography [silica gel (12 g) eluting with MeOH in DCM from 0-5%] followed by purification using reverse phase column chromatography [C18 column (100 g), eluting with ACN in water (containing 0.1% HCl) from 0-60%] (1R,3S,5R)-2-(2-(4-aminopyrrolo[2,1-f][1,2,4]triazin-7-yl)acetyl)-N-(6-bromo-3-methylpyridin-2-yl)-2-azabicyclo[3.1.0]hexane-3-carboxamide (2d) (20 mg, 26% yield) as a white solid; $^1H$ NMR (300 MHz, DMSO-$d_6$) δ 10.25 (s, 1H, $D_2O$ exchangeable), 10.01 (s, 1H, $D_2O$ exchangeable), 9.21 (s, 1H, $D_2O$ exchangeable), 8.20 (s, 1H), 7.64 (d, J=8.0 Hz, 11H), 7.52 (d, J=4.6 Hz, 1H), 7.45 (d, J=7.9 Hz, 1H), 6.84 (d, J=4.6 Hz, 1H), 4.38 (dd, J=9.1, 5.2 Hz, 1H), 4.31 (d, J=17.0 Hz, 1H), 4.17 (d, J=17.0 Hz, 1H), 3.68-3.66 (m, 1H), 2.36 (m, 1H), 2.24 (m, 1H), 2.07 (s, 3H), 1.92-1.77 (m, 1H), 0.96 (m, 1H), 0.62 (m, 1H); MS (ES+): 470.0 (M+1), (ES−): 468.0 (M−1).

Preparation of (2S,4R)-1-(2-(4-amino-9H-pyrimido[4,5-b]indol-9-yl)acetyl)-N-(6-bromo-3-methylpyridin-2-yl)-4-fluoropyrrolidine-2-carboxamide (3b)

Compound 3b was prepared according to the procedure reported in step-3 of scheme-1, from TFA salt of 2-(4-amino-9H-pyrimido[4,5-b]indol-9-yl)acetic acid (1c) (150 mg, 0.421 mmol) in DMF (5 mL) using HCl salt of (2S,4R)—N-(6-bromo-3-methylpyridin-2-yl)-4-fluoropyrrolidine-2-carboxamide (3a) [(143 mg, 0.421 mmol); prepared according to the procedure reported by Wiles, Jason A. et al., PCT Int. Appl. (2017). WO 2017035355 A1 20170302; incorporated by reference], HATU (192 mg, 0.505 mmol) DIPEA (272 mg, 2.105 mmol) and stirring at RT for 16 h. This gave after workup and purification by reverse-phase column chromatography [C18 column (100 g), eluting with ACN in water (containing 0.1% HCl) from 0-60%] (2S,4R)-1-(2-(4-amino-9H-pyrimido[4,5-b]indol-9-yl)acetyl)-N-(6-bromo-3-methylpyridin-2-yl)-4-fluoropyrrolidine-2-carboxamide (3b) (123 mg, 56% yield) HCl salt as a white solid; 1H NMR (300 MHz, DMSO-$d_6$) δ (a mixture of two rotamers) 10.92 (s) and 10.48 (s) (2s, 1H, $D_2O$ exchangeable), 8.73 (s, 3H, $D_2O$ exchangeable), 8.62 (s, 1H), 8.53 (d, J=7.8 Hz, 1H), 7.70 (d, J=8.0 Hz, 1H), 7.67-7.49 (m, 2H), 7.43 (t, J=7.9 Hz, 2H), 5.67 (d, J=4.0 Hz, 1H), 5.63-5.45 (m, 1H), 5.37 (d, J=17.3 Hz, 1H), 4.57 (t, J=9.4, 7.6 Hz, 1H), 4.48-4.23 (m, 1H), 4.20-3.95 (m, 1H), 2.79-2.49 (m, 4H), 2.32-2.05 (m, 1H); $^{19}F$ NMR (282 MHz, DMSO-$d_6$) δ-176.05-176.37; MS (ES+): 526.0 (M+1), 524.0 (M−1); Analysis calculated for $C_{23}H_{21}BrFN_7O_2$·HCl $2.75H_2O$: C, 45.11; H, 4.53; Cl, 5.79; N, 16.01. Found: C, 45.12; H, 4.29; Cl, 5.71; N, 15.84.

Scheme 3

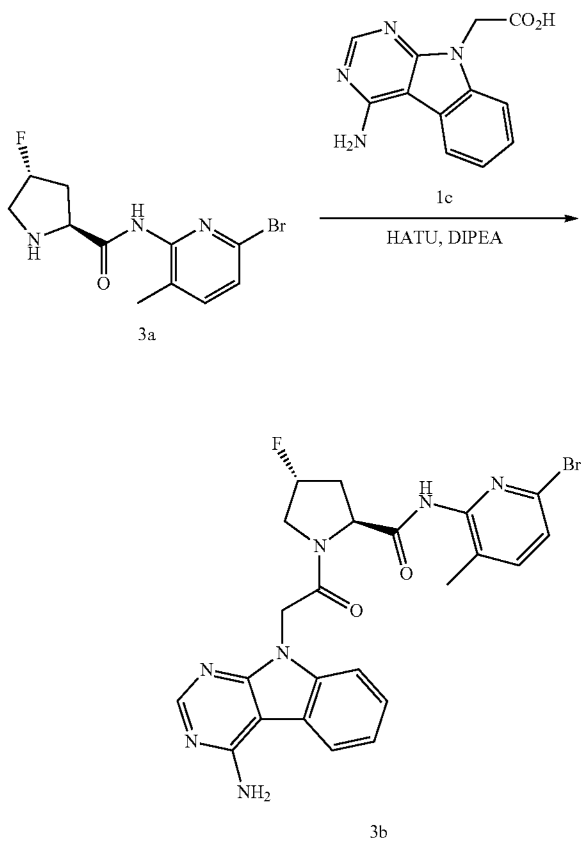

Scheme 4

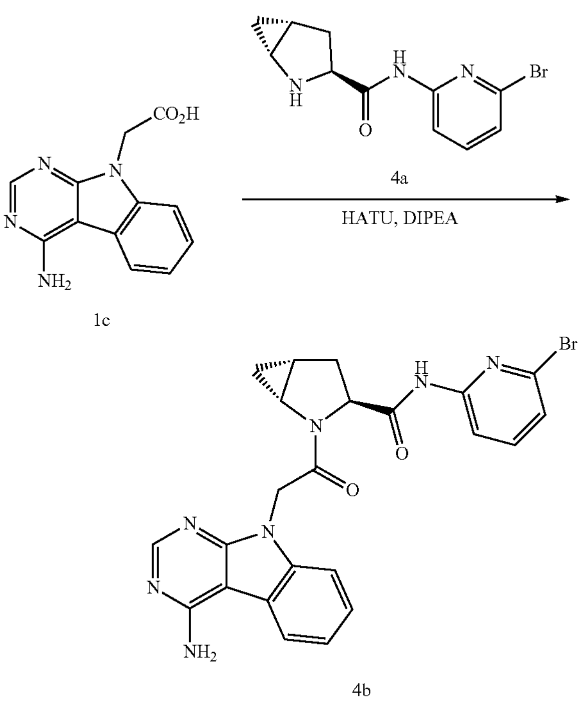

Preparation of (1R,3S,5R)-2-(2-(4-amino-9H-pyrimido[4,5-b]indol-9-yl)acetyl)-N-(6-bromopyridin-2-yl)-2-azabicyclo[3.1.0]hexane-3-carboxamide (4b)

Compound 4b was prepared according to the procedure reported in step-3 of scheme-1, from TFA salt of 2-(4-amino- 9H-pyrimido[4,5-b]indol-9-yl)acetic acid (1c) (150 mg, 0.421 mmol) in DMF (5 mL) using HCl salt of (1R,3S,5R)—N-(6-bromopyridin-2-yl)-2-azabicyclo[3.1.0]hexane-3-carboxamide (4a) [(134 mg, 0.421 mmol); prepared according to the procedure reported by Altmann, Eva et al., PCT Int. Appl. (2012), WO 2012093101 A1 20120712; incorporated by reference], HATU (192 mg, 0.505 mmol), DIPEA (272 mg, 2.105 mmol) and stirring at RT for 16 h. This gave after workup and purification by flash column chromatography [silica gel (12 g), eluting with MeOH in DCM from 0-5%] followed by purification using reverse phase column chromatography [C18 column (100 g), eluting with ACN in water (containing 0.1% HCl) from 0-60%] (1R,3S,5R)-2-(2-(4-amino-9H-pyrimido[4,5-b]indol-9-yl)acetyl)-N-(6-bromopyridin-2-yl)-2-azabicyclo[3.1.0]hexane-3-carboxamide (4b) (110 mg, 52% yield) HCl salt as a white solid. $^1$H NMR (300 MHz, DMSO-$d_6$) δ 10.77 (s, 1H, $D_2O$ exchangeable), 8.63 (m, 3H, 2H $D_2O$ exchangeable), 8.53 (d, J=7.9 Hz, 1H), 8.01 (d, J=8.1 Hz, 1H), 7.76-7.66 (m, 2H), 7.58 (t, J=7.5 Hz, 1H), 7.44 (t, J=7.5 Hz, 1H), 7.32 (d, J=7.7 Hz, 1H), 5.78 (d, J=17.4 Hz, 1H), 5.44 (d, J=17.3 Hz, 1H), 4.43 (dd, J=9.0, 5.5 Hz, 1H), 3.93 (m, 1H), 2.44-2.16 (m, 2H), 2.01-1.86 (m, 1H), 1.08 (m, 1H), 0.78 (m, 1H); MS (ES+) 506.0 (M+1); (ES−): 504.0 (M−1); Analysis calculated for: $C_{23}H_{20}BrN_7O_2 \cdot HCl$, $2.25H_2O$: C, 47.36; H, 4.41; Cl, 6.08; N, 16.81. Found: C, 47.25; H, 4.18; Cl, 6.02; N, 16.70.

Scheme 5

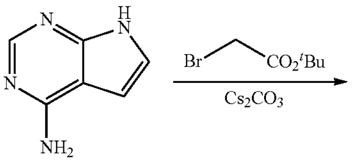

5a

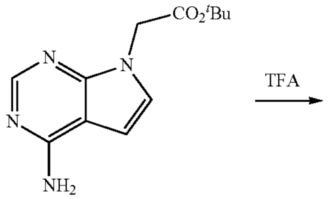

5b

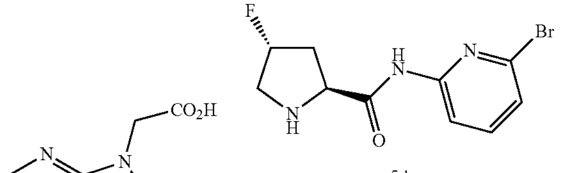

5d

5c

-continued

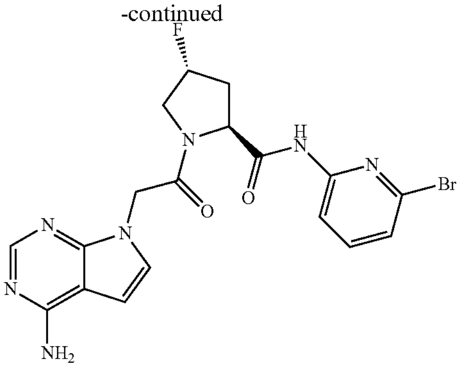

5e

Preparation of (2S,4R)-1-(2-(4-amino-7H-pyrrolo[2,3-d]pyrimidin-7-yl)acetyl)-N-(6-bromopyridin-2-yl)-4-fluoropyrrolidine-2-carboxamide (5e)

Step-3: Preparation of tert-butyl 2-(4-amino-7H-pyrrolo[2,3-d]pyrimidin-7-yl)acetate (5b)

Compound 5b was prepared according to the procedure reported in step-1 of scheme-1, from 7H-pyrrolo[2,3-d]pyrimidin-4-amine (5a) (1.0 g, 7.45 mmol; CAS #1500-85-2) in DMF (20 mL) using tert-butyl 2-bromoacetate (1.600 g, 8.20 mmol), $Cs_2CO_3$ (2.91 g, 8.95 mmol) and stirring at RT for 3 h. This gave after workup and purification by flash column chromatography. [silica (24 g), eluting with 0-3% MeOH in DCM] tert-butyl 2-(4-amino-7H-pyrrolo[2,3-d]pyrimidin-7-yl)acetate (5b) (0.62 g, 34% yield) as a yellow solid; $^1$H NMR (300 MHz, DMSO-$d_6$) δ 8.04 (s, 1H), 7.12 (d, J=3.5 Hz, 1H), 6.99 (s, 2H), 6.54 (d, J=3.5 Hz, 1H), 4.86 (s, 2H), 1.41 (s, 9H); MS (ES+): 249 (M+1).

Step-4: Preparation of 2-(4-amino-7H-pyrrolo[2,3-d]pyrimidin-7-yl)acetic acid (5c)

Compound 5c was prepared according to the procedure reported in step-2 of scheme-1, from tert-butyl 2-(4-amino-7H-pyrrolo[2,3-d]pyrimidin-7-yl)acetate (5b) (0.62 g, 2.497 mmol) using TFA (19.11 mL, 49.9 mmol) in DCM (20 mL) and stirring at RT for 16 h. This gave after workup 2-(4-amino-7H-pyrrolo[2,3-d]pyrimidin-7-yl)acetic acid (5c) (1.42 g) TFA salt as an orange solid: $^1$H NMR (300 MHz, DMSO-$d_6$) δ 9.00 (s, 2H), 8.39 (s, 1H), 7.50 (d, J=3.5 Hz, 1H), 6.93 (d, J=3.5 Hz, 1H), 5.05 (s, 2H); MS (ES+): 193 (M+1); (ES−): 191 (M−1).

Step-5: Preparation of (2S,4R)-1-(2-(4-amino-7H-pyrrolo[2,3-d]pyrimidin-7-yl)acetyl)-N-(6-bromopyridin-2-yl)-4-fluoropyrrolidine-2-carboxamide (5e)

Compound 5e was prepared according to the procedure reported in step-3 of scheme-1, from TFA salt of 2-(4-amino-7H-pyrrolo[2,3-d]pyrimidin-7-yl)acetic acid (5c) (137 mg, 0.448 mmol) in DMF (5 mL) using TFA salt of (2S,4R)—N-(6-bromopyridin-2-yl)-4-fluoropyrrolidine-2-carboxamide (5d) [(150 mg, 0.373 mmol); prepared according to the procedure reported by Wiles, Jason A. et al., PCT Int. Appl. (2017), WO 2017035348 A1 20170302; incorporated by reference], HATU (170 mg, 0.448 mmol), DIPEA (241 mg, 1.865 mmol) and stirring at RT for 16 h. This gave after workup and purification by flash column chromatography [silica gel (12 g), eluting with 0-5% MeOH in DCM] followed by purification using reverse phase column chromatography [C18 column (100 g), eluting with ACN in water (containing 0.1% HCl) from 0-60%] (2S,4R)-1-(2-(4-amino-7H-pyrrolo[2,3-d]pyrimidin-7-yl)acetyl)-N-(6-bromopyridin-2-yl)-4-fluoropyrrolidine-2-carboxamide (5e) (84 mg, 49% yield) as a white solid: $^1H$ NMR (300 MHz, DMSO-$d_6$) δ (a mixture of two rotamers) 11.36 (s) and 11.03 (s) (2s, 1H, $D_2O$ exchangeable), 9.22 (s, 2H, $D_2O$ exchangeable), 8.36 (s, 1H), 8.01 (d, J=8.2 Hz, 1H), 7.71 (t, J=8.0 Hz, 1H), 7.40 (d, J=3.5 Hz, 1H), 7.33 (d, J=7.7 Hz, 1H), 6.93 (d, J=3.5 Hz, 1H), 5.66-5.39 (m, 1H), 5.33 (d, J=17.1 Hz, 1H), 5.18 (d, J=17.1 Hz, 1H), 4.65 (t, J=8.5 Hz, 1H), 4.26-4.06 (m, 1H), 3.89 (ddd, J=38.2, 12.2, 3.0 Hz, 1H), 2.63-2.43 (m, 11H), 2.25-1.95 (m, 11H); $^{19}F$ NMR (282 MHz, DMSO-$d_6$) δ-175.70, −175.96; MS (ES+): 462.0 (M+1), 460.0 (M−1); Analysis calculated for $C_{18}H_{17}BrFN_7O_2{\cdot}HCl{\cdot}2H_2O$: C, 40.43; H, 4.15; Cl, 6.63; N, 18.33. Found: C, 40.19; H, 3.86; Cl, 6.98; N, 17.96.

Scheme 6

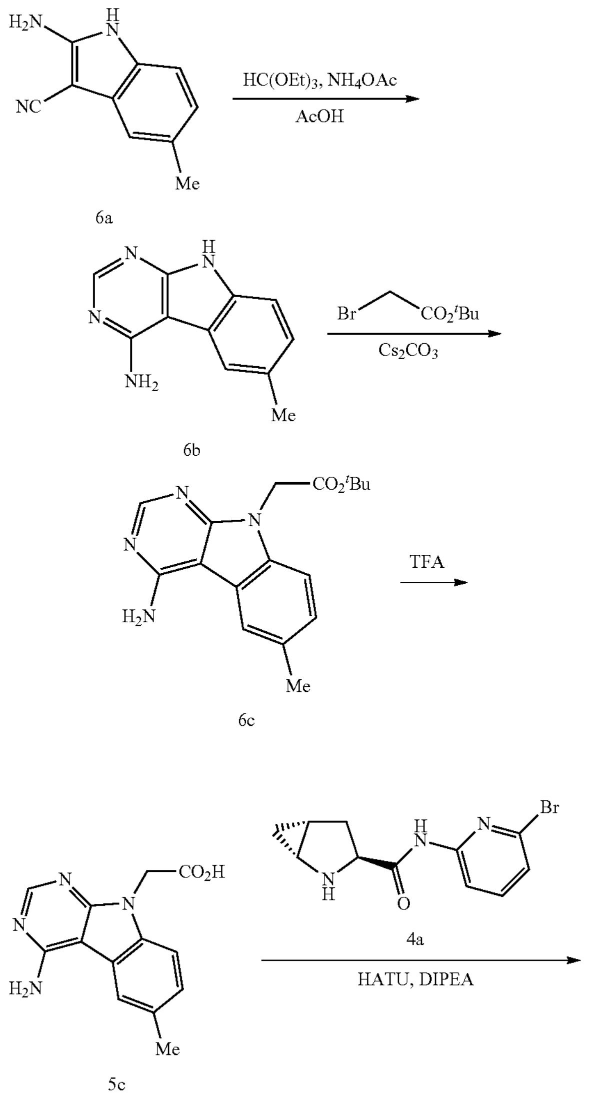

-continued

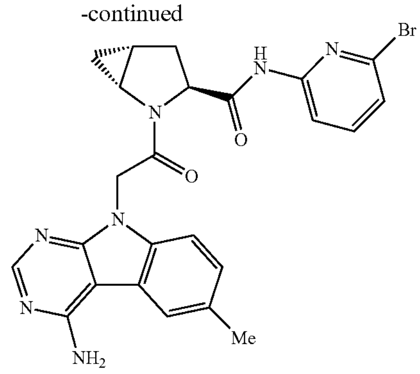

6e

Preparation of (1R,3S,5R)-2-(2-(4-amino-6-methyl-9H-pyrimido[4,5-b]indol-9-yl)acetyl)-N-(6-bromopyridin-2-yl)-2-azabicyclo[3.1.0]hexane-3-carboxamide (6e)

Step-1: Preparation of 6-methyl-9H-pyrimido[4,5-b]indol-4-amine (6b) To a solution of triethyl orthoformate (47.7 mL, 450 mmol), AcOH (6.43 mL, 112 mmol) was added 2-amino-5-methyl-1H-indole-3-carbonitrile (6a) (3.85 g, 22.49 mmol) and $NH_4OAc$ (8.67 g, 112 mmol) in a 350-mL pressure vessel and heated at 100° C. under pressure for 16 h. The reaction mixture was diluted with $H_2O$ (20 mL) and stirred for 15 min. The mixture was then filtered and the solid was washed $H_2O$ and air dried to provide 6-methyl-9H-pyrimido[4,5-b]indol-4-amine (6b) (3.60 g, 81%) as a pale-yellow solid; $^1H$ NMR (300 MHz, DMSO-$d_6$) δ 11.67 (s, 1H), 8.22 (s, 1H), 8.12 (s, 1H), 7.32 (d, J=8.2 Hz, 1H), 7.17 (dd, J=8.3, 1.5 Hz, 1H), 7.07 (s, 2H), 2.45 (s, 3H); MS (ES+): 1.99 (M+1), (ES−): 197 (M−1).

Step-2: Preparation of tert-butyl 2-(4-amino-6-methyl-9H-pyrimido[4,5-b]indol-9-yl)acetate (6c)

Compound 6c was prepared according to the procedure reported in step-1 of scheme-1, from 6-methyl-9H-pyrimido[4,5-b]indol-4-amine (6b) (2.00 g, 10.09 mmol; CAS #1242140-67-5) in DMF (20 mL) using tert-butyl 2-bromoacetate (2.362 g, 12.11 mmol), $Cs_2CO_3$ (6.57 g, 20.18 mmol) and stirring at RT for 16 h. This gave after workup and purification by flash column chromatography [silica gel (20 g), eluting with MeOH in DCM from 0-3%] tert-butyl 2-(4-amino-6-methyl-9H-pyrimido[4,5-b]indol-9-yl)acetate (6c) (2.57 g, 82% yield) as a pale yellow solid; $^1H$ NMR (300 MHz, DMSO-$d_6$) δ 8.26 (s, 1H), 8.18 (s, 1H), 7.42 (d, J=8.3 Hz, 1H), 7.29-7.15 (m, 3H), 5.08 (s, 2H), 2.47 (s, 3H), 1.40 (s, 9H); MS (ES+): 313 (M+1), (ES−): 311 (M−1).

Step-3: Preparation of 2-(4-amino-6-methyl-9H-pyrimido[4,5-b]indol-9-yl)acetic acid (6d)

Compound 6d was prepared according to the procedure reported in step-2 of scheme-1, from tert-butyl 2-(4-amino-6-methyl-9H-pyrimido[4,5-b]indol-9-yl)acetate (6c) (0.220 g, 0.704 mmol) using TFA (8.03 mg, 7.04) in DCM (10 mL) and stirring at RT for 16 h. This gave after workup 2-(4-amino-6-methyl-9H-pyrimido[4,5-b]indol-9-yl)acetic acid (6d) (300 mg) TFA salt as a purple solid; $^1H$ NMR (300 MHz, DMSO-$d_6$) δ 8.54 (d, J=1.1 Hz, 1H), 8.48-8.26 (m, 3H), 7.67 (d, J=8.4 Hz, 1H), 7.38 (d, J=8.6 Hz, 1H), 5.24 (s, 2H); $^{19}$F NMR (282 MHz, DMSO-$d_6$) δ−74.24; MS (ES+): 257 (M+1), (ES−): 255 (M−1).

Step-4: Preparation of (1R,3S,5R)-2-(2-(4-amino-6-methyl-9H-pyrimido[4,5-b]indol-9-yl)acetyl)-N-(6-bromopyridin-2-yl)-2-azabicyclo[3.1.0]hexane-3-carboxamide (6e)

Compound 6e was prepared according to the procedure reported in step-3 of scheme-1, from TFA salt of 2-(4-amino-6-methyl-9H-pyrimido[4,5-b]indol-9-yl)acetic acid (6d) (50 mg, 0.135 mmol) in DMF (5 mL) using HCl salt of (1R, 3S,5R)—N-(6-bromopyridin-2-yl)-2-azabicyclo[3.1.0]hexane-3-carboxamide (4a) (43 mg, 0.135 mmol), HATU (61.6 mg, 0.162 mmol), DIPEA (87 mg, 0.675 mmol) and stirring at RT for 16 h. This gave after workup and purification by flash column chromatography [silica gel (12 g), eluting with 0-5% MeOH in DCM] followed by purification using reverse phase column chromatography [C18 column (100 g), eluting with ACN in water (containing 0.1% HCl) from 0-60%] (1R,3S,5R)-2-(2-(4-amino-6-methyl-9H-pyrimido[4,5-b]indol-9-yl)acetyl)-N-(6-bromopyridin-2-yl)-2-azabicyclo[3.1.0]hexane-3-carboxamide (6e) (48 mg, 68% yield) HCl salt as a white solid; $^1$H NMR (300 MHz, DMSO-$d_6$) δ 10.76 (s, 1H, $D_2O$ exchangeable), 8.88 (s, 2H, $D_2O$ exchangeable), 8.68 (s, 1H), 8.40 (s, 1H), 8.01 (d, J=8.1 Hz, 1H), 7.71 (t, J=8.0 Hz, 1H), 7.63 (d, J=8.4 Hz, 1H), 7.42 (dd, J=8.3, 1.6 Hz, 1H), 7.32 (d, J=7.7 Hz, 1H), 5.76 (d, J=17.3 Hz, 1H), 5.41 (d, J=17.1 Hz, 1H), 4.42 (dd, J=9.0, 5.5 Hz, 1H), 3.92 (m, 1H), 2.34 (m, 1H), 2.21 (m, 1H), 1.92 (m, 1H), 1.07 (m, 1H), 0.77 (m, 1H); MS (ES+): 520.0 (M+1); (ES−): 518.0 (M−1); Analysis calculated for $C_{24}H_{22}BrN_7O_2·1.25HCl·2.75H_2O$: C, 46.83; H, 4.71; Cl, 7.20; N, 15.93. Found: C, 46.68; H, 4.62; Cl, 7.26; N, 15.75.

Scheme 7

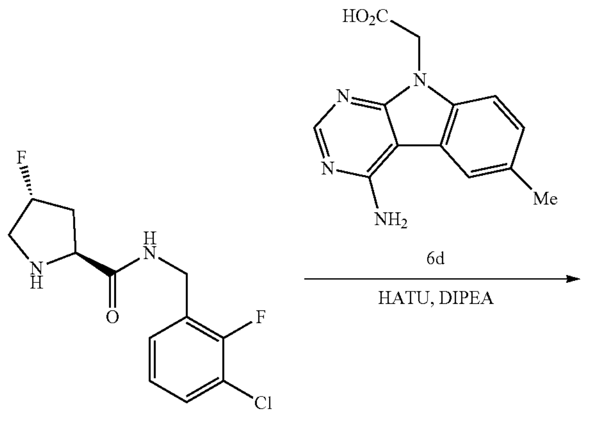

7a

-continued

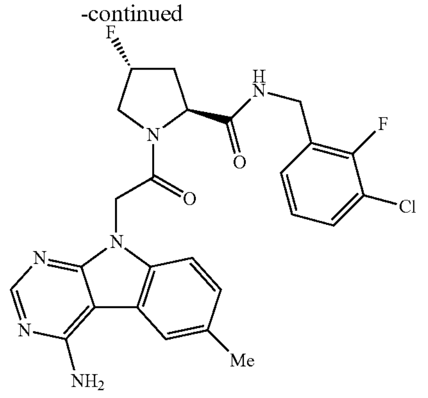

7b

Preparation of (2S,4R)-1-(2-(4-amino-6-methyl-9H-pyrimido[4,5-b]indol-9-yl)acetyl)-N-(3-chloro-2-fluorobenzyl)-4-fluoropyrrolidine-2-carboxamide (7b)

Compound 7b was prepared according to the procedure reported in step-3 of scheme-1, from TFA salt of 2-(4-amino-6-methyl-9H-pyrimido[4,5-b]indol-9-yl)acetic acid (6d) (50 mg, 0.135 mmol) in DMF (5 mL) using TFA salt of (2S,4R)—N-(3-chloro-2-fluorobenzyl)-4-fluoropyrrolidine-2-carboxamide (7a) [(52.5 mg, 0.135 mmol); prepared according to the procedure reported in Wiles, Jason A. et al., PCT Int. Appl. (2017), WO 2017035349 A1 20170302; incorporated by reference], HATU (61.6 mg, 0.162 mmol) DIPEA (0.118 mL, 0.675 mmol) and stirring at RT for 16 h. This gave after workup and purification by flash column chromatography [silica gel (12 g), eluting with MeOH in DCM from 0-5%] followed by purification using reverse phase column chromatography [C18 column (100 g), eluting with ACN in water (containing 0.1% HCl) from 0-60%] (2S,4R)-1-(2-(4-amino-6-methyl-9H-pyrimido[4,5-b]indol-9-yl)acetyl)-N-(3-chloro-2-fluorobenzyl)-4-fluoropyrrolidine-2-carboxamide (7b) (30 mg, 43% yield) HCl salt as a white solid; $^1$H NMR (300 MHz, DMSO-$d_6$) δ (a mixture of two rotamers) 9.12 (s) and 8.73-8.47 (m)(s and m, 4H, 2H exchangeable), 8.37 (s, 1H), 7.60 (d, J=8.4 Hz, 1H), 7.46-7.35 (m, 1H), 7.35-7.25 (m, 1H), 7.14 (td, J=8.8, 8.4, 3.0 Hz, 1H), 6.86 (t, J=7.9 Hz, 1H), 5.65-5.49 (m, 11H), 5.46-5.37 (m, 1H), 5.32 (d, J=17.3 Hz, 1H), 4.51-4.13 (m, 4H), 4.00 (ddd, J=37.1, 12.7, 3.1 Hz, 1H), 2.45 (s, 4H), 2.25-1.90 (m, 1H); $^{19}$F NMR (282 MHz, DMSO-$d_6$) δ−121.26, −121.77, −176.26, −176.48; MS (ES+): 513.0 (M+1), 511.0 (M−1); Analysis calculated for $C_{25}H_{23}ClF_2N(O_2·HCl·2H_2O$: C, 51.29; H, 4.82; Cl, 12.11; N, 14.36. Found: C, 51.22; H, 4.90; Cl, 12.01; N, 14.43.

Scheme 8

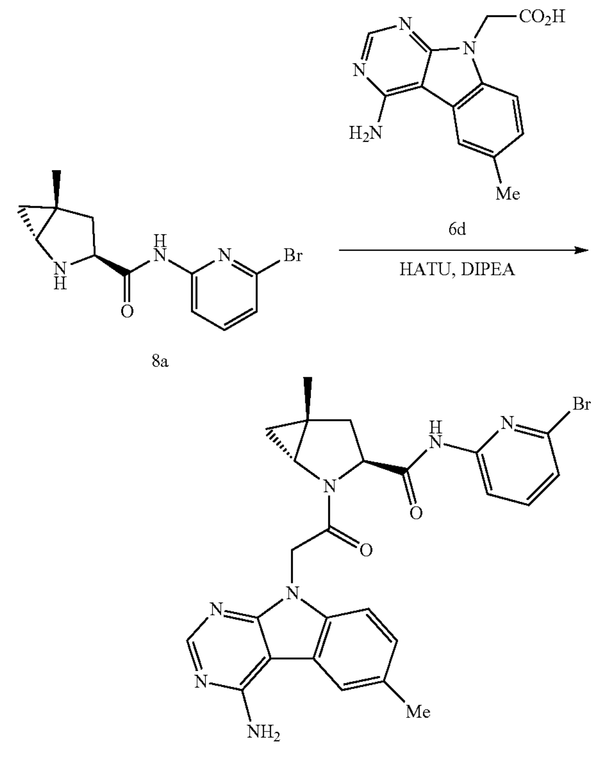

8a

8b

Scheme 9

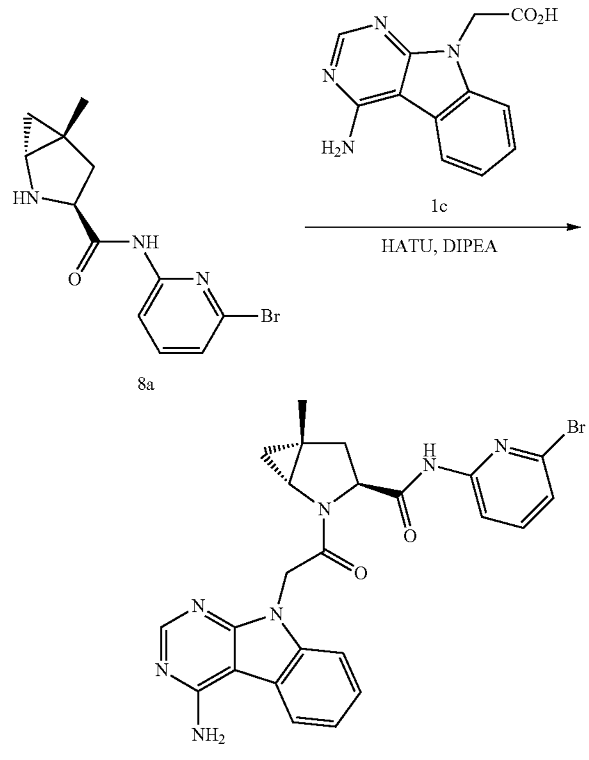

8a

9a

Preparation of (1R,3S,5R)-2-(2-(4-amino-6-methyl-9H-pyrimido[4,5-b]indol-9-yl)acetyl)-N-(6-bromopyridin-2-yl)-5-methyl-2-azabicyclo[3.1.0]hexane-3-carboxamide (8b)

Compound 8b was prepared according to the procedure reported in step-3 of scheme-1, from TFA salt of 2-(4-amino-6-methyl-9H-pyrimido[4,5-b]indol-9-yl)acetic acid (6d) (50 mg, 0.135 mmol) in DMF (5 mL) using HCl salt of (1R,3S,5R)—N-(6-bromopyridin-2-yl)-5-methyl-2-azabicyclo[3.1.0]hexane-3-carboxamide (8a) [(44.9 mg, 0.135 mmol); prepared according to the procedure reported by Wiles, Jason A. et al., PCT Int. Appl. (2017), WO 2017035353 A120170302], HATU (61.6 mg, 0.162 mmol), DIPEA (87 mg, 0.675 mmol) and stirring at RT for 16 h. This gave after workup and purification by flash column chromatography [silica gel (12 g), eluting with 0-5% MeOH in DCM] followed by purification using reverse phase column chromatography [C18 column (100 g), eluting with ACN in water (containing 0.1% HCl) from 0-60%] (1R,3S,5R)-2-(2-(4-amino-6-methyl-9H-pyrimido[4,5-b]indol-9-yl)acetyl)-N-(6-bromopyridin-2-yl)-5-methyl-2-azabicyclo[3.1.0]hexane-3-carboxamide (8b) (40 mg, 55% yield) HCl salt as a white solid; $^1$H NMR (300 MHz, DMSO-$d_6$) δ 10.76 (s, 1H, $D_2O$ exchangeable), 8.57 (s, 1H), 8.47 (s, 2H, $D_2O$ exchangeable), 8.33 (s, 1H), 8.01 (d, J=8.2 Hz, 1H), 7.70 (t, J=8.0 Hz, 1H), 7.57 (d, J=8.4 Hz, 1H), 7.37 (d, J=8.4 Hz, 1H), 7.31 (d, J=7.7 Hz, 1H), 5.68 (d, J=17.3 Hz, 1H), 5.34 (d, J=17.2 Hz, 1H), 4.36 (dd, J=9.0, 5.9 Hz, 1H), 3.71-3.66 (m, 1H), 2.59-2.39 (m, 4H), 1.97 (dd, J=13.2, 5.8 Hz, 1H), 1.30 (s, 3H), 1.05-0.96 (m, 1H), 0.96-0.88 (m, 1H); MS (ES+) 534.0 (M+1), 532.0 (M−1).

Preparation of (1R,3S,5R)-2-(2-(4-amino-9H-pyrimido[4,5-b]indol-9-yl)acetyl)-N-(6-bromopyridin-2-yl)-5-methyl-2-azabicyclo[3.1.0]hexane-3-carboxamide (9a)

Compound 9a was prepared according to the procedure reported in step-3 of scheme-1, from TFA salt of 2-(4-amino-9H-pyrimido[4,5-b]indol-9-yl)acetic acid (1c) (50 mg, 0.14 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (46.7 mg, 0.14 mmol), HATU (80 mg, 0.211 mmol), DIPEA (0.122 mL, 0.702 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-9H-pyrimido[4,5-b]indol-9-yl)acetyl)-N-(6-bromopyridin-2-yl)-5-methyl-2-azabicyclo[3.1.0]hexane-3-carboxamide (9a) (49 mg, 67% yield) HCl salt as a white solid; $^1$H NMR (300 MHz, DMSO-$d_6$) δ 10.78 (s, 1H, $D_2O$ exchangeable), 8.77 (s, 2H, $D_2O$ exchangeable), 8.66 (s, 1H), 8.54 (d, J=7.9 Hz, 1H), 8.01 (d, J=8.2 Hz, 1H), 7.75-7.67 (m, 2H), 7.61-7.55 (m, 1H), 7.45 (t, J=7.5 Hz, 1H), 7.32 (d, J=7.7 Hz, 1H), 5.75 (d, J=17.4 Hz, 1H), 5.39 (d, J=17.3 Hz, 1H), 4.38 (dd, J=9.1, 5.9 Hz, 1H), 3.71 (dd, J=5.5, 2.4 Hz, 1H), 2.49-2.41 (m, 1H), 1.99 (dd, J=13.3, 5.9 Hz, 1H), 1.31 (s, 3H), 1.02 (t, J=5.4 Hz, 1H), 0.94 (dd, J=5.4, 2.4 Hz, 1H); MS (ES+): 520.0 (M+1), 542.0 (M+Na); (ES−): 518.0 (M−1); Analysis calculated for $C_{24}H_{22}BrN_7O_2 \cdot 1.75\ (H_2O)$, 1.25 (HCl); C, 48.25; H, 4.51; Cl, 7.42; N, 16.41. Found: C, 48.06; H, 4.27; Cl, 7.28; N, 16.27.

Scheme 10

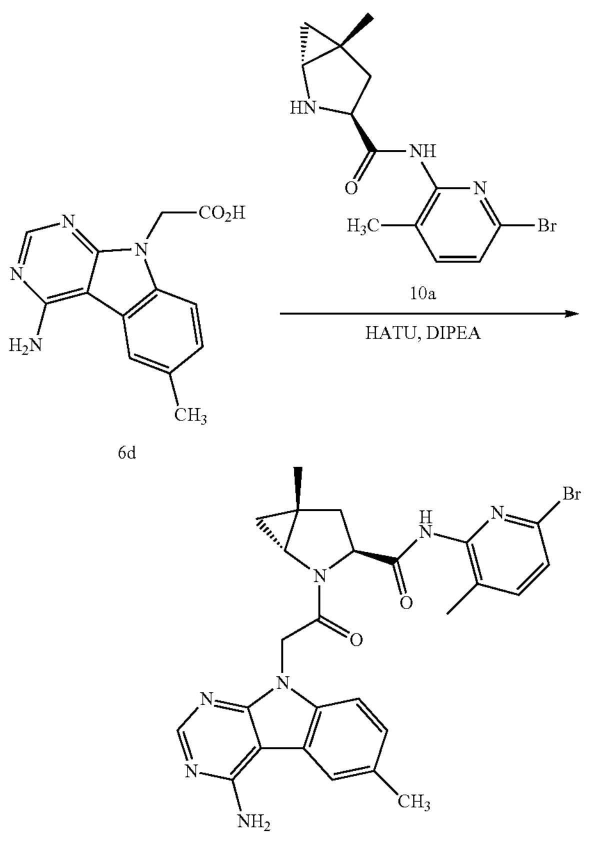

6d

10a

10b

Preparation of (1R,3S,5R)-2-(2-(4-amino-6-methyl-9H-pyrimido[4,5-b]indol-9-yl)acetyl)-N-(6-bromo-3-methylpyridin-2-yl)-5-methyl-2-azabicyclo[3.1.0]hexane-3-carboxamide (10b)

Compound 10b was prepared according to the procedure reported in step-3 of scheme-1, from TFA salt of 2-(4-amino-6-methyl-9H-pyrimido[4,5-b]indol-9-yl)acetic acid (6d) (50 mg, 0.135 mmol) in DMF (2 mL) using HCl salt of (1R,3S,5R)—N-(6-bromo-3-methylpyridin-2-yl)-5-methyl-2-azabicyclo[3.1.0]hexane-3-carboxamide (10a) [(46.7 mg, 0.14 mmol); prepared according to the procedure reported by Wiles, Jason A. et al., PCT Int. Appl. (2018), WO 2018160889 A1 20180907; incorporated by reference], HATU (80 mg, 0.211 mmol), DIPEA (0.122 mL, 0.702 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-methyl-9H-pyrimido[4,5-b]indol-9-yl)acetyl)-N-(6-bromo-3-methylpyridin-2-yl)-5-methyl-2-azabicyclo[3.1.0]hexane-3-carboxamide (10b) (49 mg, 67% yield) HCl salt as a white solid; $^1H$ NMR (300 MHz, DMSO-$d_6$) δ 10.29 (s, 1H, $D_2O$ exchangeable), 8.72-8.51 (m, 3H, 2H $D_2O$ exchangeable), 8.37 (s, 1H), 7.71-7.53 (m, 2H), 7.45 (d, J=7.9 Hz, 1H), 7.38 (d, J=8.5 Hz, 1H), 5.67 (d, J=17.4 Hz, 1H), 5.38 (d, J=17.3 Hz, 1H), 4.36 (dd, J=9.2, 5.2 Hz, 1H), 3.66 (dd, J=5.6, 2.4 Hz, 1H), 2.61-2.52 (m, 4H), 2.05 (d, J=5.4 Hz, 1H), 2.01 (s, 3H), 1.33 (s, 3H), 1.14-0.91 (m, 2H); MS (ES+): 548.0 (M+1), 569.9 (M+Na); (ES−): 546.0 (M−1); Analysis calculated for $C_{26}H_{26}BrN_7O_2·3H_2O·1.15HCl$: C, 48.46; H, 5.19; Cl, 6.33; N, 15.21. Found: C, 48.64; H, 5.03; Cl, 6.07; N, 15.02.

Scheme 11

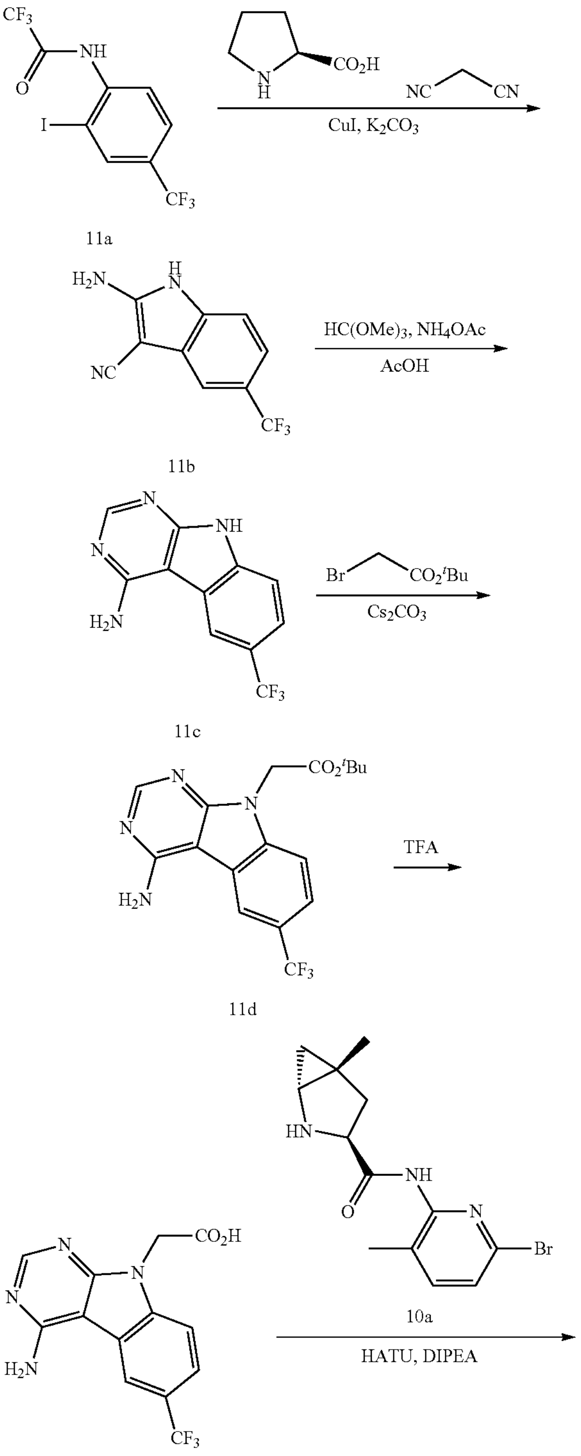

11a

11b

11c

11d

10a

11e

-continued

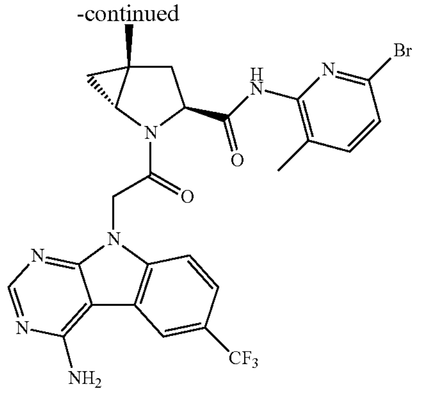

11f

Preparation of (1R,3S,5R)-2-(2-(4-amino-6-(trifluoromethyl)-9H-pyrimido[4,5-b]indol-9-yl)acetyl)-N-(6-bromo-3-methylpyridin-2-yl)-5-methyl-2-azabicyclo[3.1.0]hexane-3-carboxamide (11f)

Step-1: Preparation of 2-amino-5-(trifluoromethyl)-1H-indole-3-carbonitrile (11b)

A mixture of 2,2,2-trifluoro-N-(2-iodo-4-(trifluoromethyl)phenyl)acetamide (11a) (4.00 g, 10.44 mmol), malononitrile (0.828 g, 12.53 mmol), L-proline (0.240 g, 2.089 mmol), CuI (0.199 g, 1.044 mmol), and $K_2CO_3$ (2.89 g, 20.89 mmol) were suspended in a 1:1 mixture of DMSO (20 mL) and $H_2O$ (20 mL) and stirred at 60° C. for 16 h under an argon atmosphere. The reaction mixture was diluted with saturated $NH_4Cl$ (30 mL) and extracted with EtOAc (30 mL×3). The combined organics were washed with $H_2O$ (30 mL×4), brine (30 mL), dried, filtered and concentrated in vacuum. The residue obtained was purified by flash column chromatography [$SiO_2$ gel (40 g), eluting with EtOAc in hexane from 0-50%] to provide 2-amino-5-(trifluoromethyl)-1H-indole-3-carbonitrile (11b) (1.24 g, 53% yield) as an orange solid; $^1$H NMR (300 MHz, DMSO-$d_6$) δ 11.14 (s, 1H), 7.37 (d, J=1.7 Hz, 1H), 7.30 (d, J=8.3 Hz, 1H), 7.22 (dd, J=8.4, 1.8 Hz, 1H), 7.12 (s, 2H). $^{19}$F NMR (282 MHz, DMSO-$d_6$) δ−58.93; MS (ES+): 226 (M+1); (ES−): 224 (M−1).

Step-2: Preparation of 6-(trifluoromethyl)-9H-pyrimido[4,5-b]indol-4-amine (11c)

Compound 11c was prepared according to the procedure reported in step-1 of scheme-6, from 2-amino-5-(trifluoromethyl)-1H-indole-3-carbonitrile (11b) (1.24 g, 5.51 mmol) using trimethyl orthoformate (18.12 mL, 165 mmol), AcOH (1.575 mL, 27.5 mmol) and $NH_4OAc$ (2.122 g, 27.5 mmol). This gave after workup and purification [$SiO_2$ gel (24 g), eluting with MeOH in DCM from 0-5%] 6-(trifluoromethyl)-9H-pyrimido[4,5-b]indol-4-amine (11c) (1.13 g, 4.48 mmol) as a pale yellow solid; $^1$H NMR (300 MHz, DMSO-$d_6$) δ 12.25 (s, 1H), 8.78 (s, 1H), 8.31 (s, 1H), 7.66 (dd, J=8.4, 1.7 Hz, 1H), 7.60 (d, J=8.5 Hz, 1H), 7.46 (s, 2H). $^{19}$F NMR (282 MHz, DMSO-$d_6$) δ−58.13; MS (ES+): 253 (M+1); (ES−): 251 (M−1).

Step-3: Preparation of tert-butyl 2-(4-amino-6-(trifluoromethyl)-9H-pyrimido[4,5-b]indol-9-yl)acetate (11d)

Compound 11d was prepared according to the procedure reported in step-1 of scheme-1, from 6-(trifluoromethyl)-9H-pyrimido[4,5-b]indol-4-amine (11c) (0.75 g, 2.97 mmol) in DMF (20 mL) using tert-butyl 2-bromoacetate (0.580 g, 2.97 mmol), $Cs_2CO_3$ (1.163 g, 3.57 mmol) and stirring at RT for 16 h. This gave after workup and purification by flash column chromatography [silica gel (24 g), eluting with MeOH in DCM from 0-3%] tert-butyl 2-(4-amino-6-(trifluoromethyl)-9H-pyrimido[4,5-b]indol-9-yl)acetate (11d) (0.89 g, 82% yield) as a pale orange solid; $^1$H NMR (300 MHz, DMSO-$d_6$) δ 8.83 (s, 1H), 8.36 (s, 1H), 7.84-7.70 (m, 2H), 7.60 (s, 2H), 5.21 (s, 2H), 1.41 (s, 9H).

Step-4: Preparation of 2-(4-amino-6-(trifluoromethyl)-9H-pyrimido[4,5-b]indol-9-yl)acetic acid (11e)

Compound 11e was prepared according to the procedure reported in step-2 of scheme-1, from tert-butyl 2-(4-amino-6-(trifluoromethyl)-9H-pyrimido[4,5-b]indol-9-yl)acetate (11d) (0.89 g, 2.429 mmol) using TFA (4.43 g, 38.9 mmol) in DCM (7 mL) and stirring at RT for 16 h. This gave after workup 2-(4-amino-6-(trifluoromethyl)-9H-pyrimido[4,5-b]indol-9-yl)acetic acid (11e) (1.26 g) TFA salt as an orange solid; 1H NMR (300 MHz, DMSO-$d_6$) δ 8.96 (s, 1H), 8.57 (s, 1H), 8.43 (s, 2H), 7.96 (d, J=8.6 Hz, 1H), 7.84 (dd, J=8.6, 1.7 Hz, 1H), 5.31 (s, 2H). $^{19}$F NMR (282 MHz, DMSO-$d_6$) δ−58.51, −74.65; MS (ES+): 311 (M+1); (ES−): 309 (M−1).

Step-5: Preparation of (1R,3S,5R)-2-(2-(4-amino-6-(trifluoromethyl)-9H-pyrimido[4,5-b]indol-9-yl)acetyl)-N-(6-bromo-3-methylpyridin-2-yl)-5-methyl-2-azabicyclo[3.1.0]hexane-3-carboxamide (11f)

Compound 11f was prepared according to the procedure reported in step-3 of scheme-1, from TFA salt of 2-(4-amino-6-(trifluoromethyl)-9H-pyrimido[4,5-b]indol-9-yl)acetic acid (11e) (50 mg, 0.118 mmol) in DMF (2 mL) using HCl salt of (1R,3S,5R)—N-(6-bromo-3-methylpyridin-2-yl)-5-methyl-2-azabicyclo[3.1.0]hexane-3-carboxamide (10a) (40.9 mg, 0.118 mmol), HATU (67.2 mg, 0.177 mmol), DIPEA (76 mg, 0.589 mmol) and stirring at RT for 16 h. This gave after workup and purification by flash column chromatography [silica gel (24 g), eluting with MeOH in DCM from 0-5%] followed by purification using reverse phase column chromatography [C18 column (50 g), eluting with ACN in water (containing 0.1% HCl) from 0-100%] (1R,3S,5R)-2-(2-(4-amino-6-(trifluoromethyl)-9H-pyrimido[4,5-b]indol-9-yl)acetyl)-N-(6-bromo-3-methylpyridin-2-yl)-5-methyl-2-azabicyclo[3.1.0]hexane-3-carboxamide (11f) (55 mg, 77% yield) HCl salt as a white solid; $^1$H NMR (300 MHz, DMSO-$d_6$) δ 10.29 (s, 1H, $D_2O$ exchangeable), 8.99 (s, 1H), 8.59 (m, 3H, 2H $D_2O$ exchangeable), 7.84 (d, J=2.1 Hz, 2H), 7.62 (d, J=8.0 Hz, 1H), 7.45 (d, J=7.9 Hz, 1H), 5.73 (d, J=17.4 Hz, 1H), 5.45 (d, J=17.3 Hz, 1H), 4.36 (dd, J=9.2, 5.2 Hz, 1H), 3.67 (dd, J=5.4, 2.5 Hz, 1H), 2.60-2.54 (m, 1H), 2.09-2.02 (m, 1H), 2.00 (s, 3H), 1.34 (s, 3H), 1.06 (t, J=5.3 Hz, 1H), 0.99 (dd, J=5.4, 2.4 Hz, 1H); $^{19}$F NMR (282 MHz, DMSO-$d_6$) δ−58.51; MS (ES+): 602.0 (M+1), 623.9 (M+Na); (ES−): 600.0 (M−1). Analysis calculated for $C_{26}H_{23}BrF_3N_7O_2 \cdot 2.5H_2O \cdot 1HCl$: C, 45.66; H, 4.27; Cl, 5.18; N, 14.34. Found: C, 45.66; H, 4.02; Cl, 5.29; N, 14.26.

Scheme 12

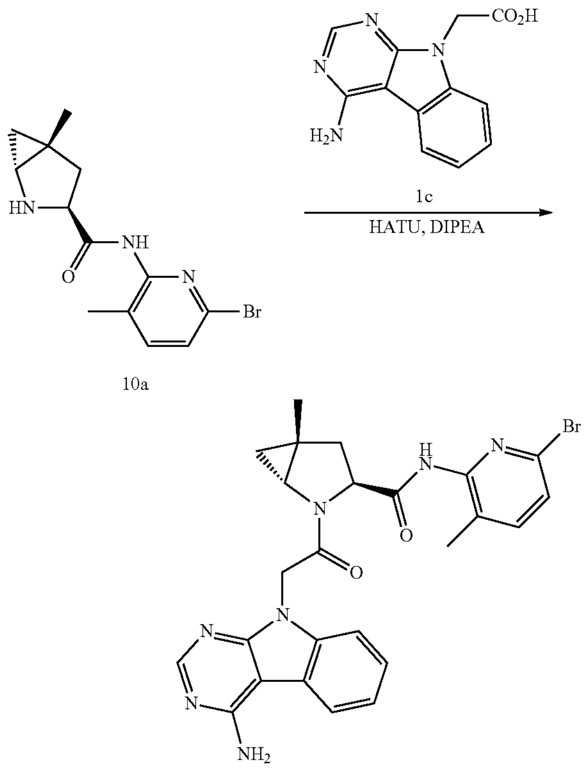

1c

10a

12a

Scheme 13

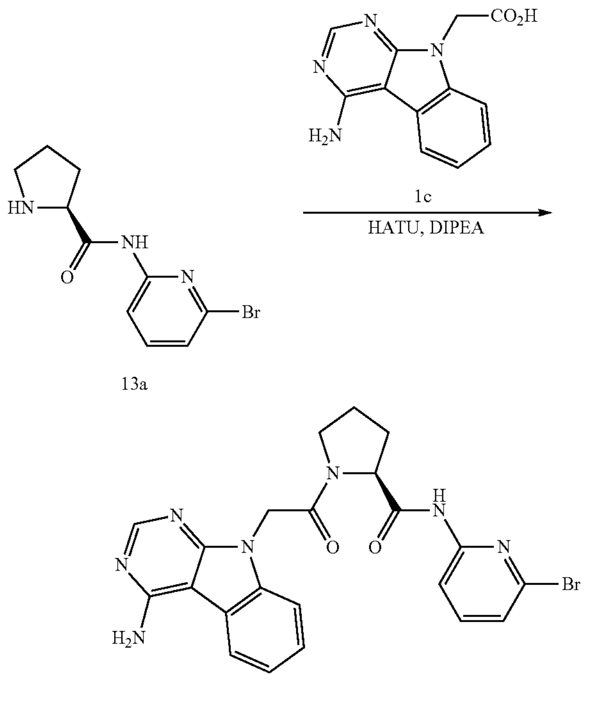

1c

13a

13b

Preparation of (1R,3S,5R)-2-(2-(4-amino-9H-pyrimido[4,5-b]indol-9-yl)acetyl)-N-(6-bromo-3-methylpyridin-2-yl)-5-methyl-2-azabicyclo[3.1.0]hexane-3-carboxamide (12a)

Compound 12a was prepared according to the procedure reported in step-3 of scheme-1, from TFA salt of 2-(4-amino-9H-pyrimido[4,5-b]indol-9-yl)acetic acid (1c) (50 mg, 0.14 mmol) in DMF (2 mL) using HCl salt of (1R,3S,5R)—N-(6-bromo-3-methylpyridin-2-yl)-5-methyl-2-azabicyclo [3.1.0]hexane-3-carboxamide (10a) (48.7 mg, 0.14 mmol), HATU (80 mg, 0.211 mmol), DIPEA (0.122 mL, 0.702 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-60%](1R,3S,5R)-2-(2-(4-amino-9H-pyrimido[4,5-b]indol-9-yl)acetyl)-N-(6-bromo-3-methylpyridin-2-yl)-5-methyl-2-azabicyclo[3.1.0]hexane-3-carboxamide (12a) (47 mg, 63% yield) as a white solid; $^{1}$H NMR (300 MHz, DMSO-$d_6$) δ 10.31 (s, 1H, $D_2O$ exchangeable), 8.77 (s, 2H, $D_2O$ exchangeable), 8.66 (s, 1H), 8.55 (d, J=7.9 Hz, 1H), 7.71 (d, J=8.2 Hz, 1H), 7.62 (d, J=8.0 Hz, 1H), 7.56 (t, J=7.7 Hz, 1H), 7.45 (dd, J=7.9, 6.0 Hz, 2H), 5.72 (d, J=17.3 Hz, 1H), 5.42 (d, J=17.3 Hz, 1H), 4.37 (dd, J=9.2, 5.3 Hz, 1H), 3.68 (dd, J=5.6, 2.4 Hz, 1H), 2.61-2.52 (m, 1H), 2.09-2.01 (m, 1H), 2.00 (s, 3H), 1.34 (s, 3H), 1.06 (t, J=5.4 Hz, 1H), 0.99 (dd, J=5.3, 2.4 Hz, 1H). MS (ES+): 534.0 (M+1), 556.0 (M+Na); (ES−): 532.0 (M−1); Analysis calculated for $C_{25}H_{24}BrN_7O_2 \cdot 2.5H_2O \cdot 1.1HCl$: C, 48.47; H, 4.90; Cl, 6.29; N, 15.83. Found: C, 48.70; H, 4.84; Cl, 6.26; N, 15.63.

Preparation of (S)-1-(2-(4-amino-9H-pyrimido[4,5-b]indol-9-yl)acetyl)-N-(6-bromopyridin-2-yl)pyrrolidine-2-carboxamide (13b)

Compound 13b was prepared according to the procedure reported in step-3 of scheme-1, from TFA salt of 2-(4-amino-9H-pyrimido[4,5-b]indol-9-yl)acetic acid (1c) (50 mg, 0.14 mmol) in DMF (2 mL) using TFA salt of(S)—N-(6-bromopyridin-2-yl)pyrrolidine-2-carboxamide (13a) [(53.9 mg, 0.140 mmol); Wiles, Jason A. et al., PCT Int. Appl. (2017), WO 2017035353 A1 20170302], HATU (80 mg, 0.211 mmol). DIPEA (0.122 mL, 0.702 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-60%] (S)-1-(2-(4-amino-9H-pyrimido[4,5-b]indol-9-yl)acetyl)-N-(6-bromopyridin-2-yl)pyrrolidine-2-carboxamide (13b) (42 mg, 61% yield) HCl salt as a white solid; $^{1}$H NMR (300 MHz, DMSO-$d_6$) δ 11.23 and 10.80 (2s, 1H $D_2O$ exchangeable), 8.63-8.50 (m, 3H, 2H $D_2O$ exchangeable), 8.45 (d, J=7.9 Hz, 1H), 8.11 and 7.93 (2d, J=8.1 Hz, 1H), 7.64 (q, J=8.2 Hz, 2H), 7.55-7.44 (m, 1H), 7.40-7.31 (m, 1H), 7.24 (d, J=7.7 Hz, 1H), 5.45-5.28 (m, 2H), 4.46 (dd, J=8.3, 4.3 Hz, 1H), 3.80 (tt, J=9.7, 5.3 Hz, 2H), 2.23-1.76 (m, 4H); MS (ES+): 494.0 (M+1); (ES−): 492.0 (M−1); Analysis calculated for $C_{22}H_{20}BrN_7O_2 \cdot 2.75H_2O \cdot 1 HCl$: C, 45.53; H, 4.60; Cl, 6.11; N, 16.89. Found: C, 45.78; H, 4.22; Cl, 6.37; N, 16.65.

Scheme 14

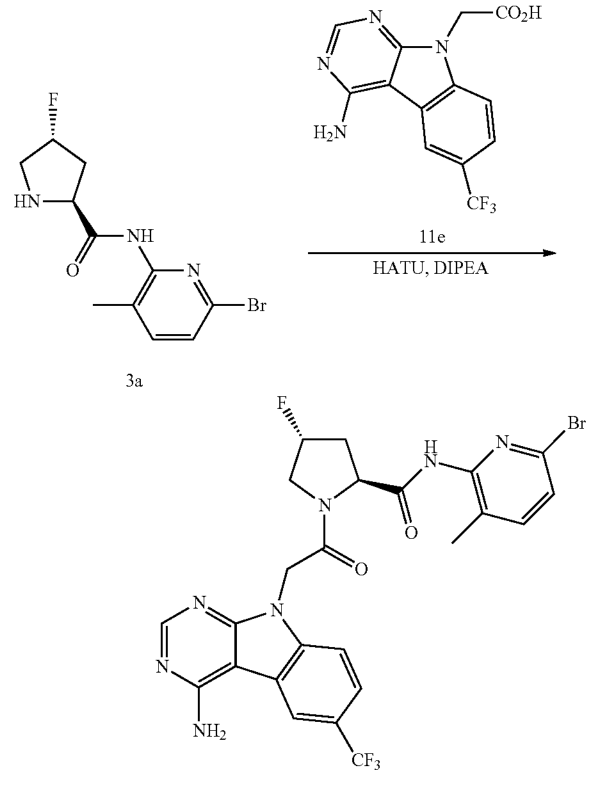

3a

14a

Preparation of (2S,4R)-1-(2-(4-amino-6-(trifluoromethyl)-9H-pyrimido[4,5-b]indol-9-yl)acetyl)-N-(6-bromo-3-methylpyridin-2-yl)-4-fluoropyrrolidine-2-carboxamide (14a)

Compound 14a was prepared according to the procedure reported in step-3 of scheme-1, from TFA salt of 2-(4-amino-6-(trifluoromethyl)-9H-pyrimido[4,5-b]indol-9-yl)acetic acid (11e) (50 mg, 0.118 mmol) in DMF (2 mL) using HCl salt of (2S,4R)—N-(6-bromo-3-methylpyridin-2-yl)-4-fluoropyrrolidine-2-carboxamide (3a) (39.9 mg, 0.118 mmol), HATU (67.2 mg, 0.177 mmol), DIPEA (0.103 mL, 0.589 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-60%] (2S,4R)-1-(2-(4-amino-6-(trifluoromethyl)-9H-pyrimido[4,5-b]indol-9-yl)acetyl)-N-(6-bromo-3-methylpyridin-2-yl)-4-fluoropyrrolidine-2-carboxamide (14a) (40 mg, 57% yield) HCl salt as a white solid; $^1$H NMR (300 MHz, DMSO-$d_6$) δ (a mixture of two rotamers) 10.89 and 10.46 (2s, 1H, $D_2O$ exchangeable), 8.96 (s, 1H), 8.55 (s, 1H), 8.44 (s, 2H, $D_2O$ exchangeable), 7.90-7.69 (m, 2H), 7.59 (d, J=8.0 Hz, 1H), 7.42 (d, J=8.0 Hz, 1H), 5.76-5.33 (m, 3H), 4.57 (t, J=8.6 Hz, 1H), 4.33 (dd, J=21.8, 12.7 Hz, 1H), 4.18-3.95 (m, 1H), 2.73 (s, 1H), 2.30-2.11 (m, 1H), 1.93 (s, 3H); $^{19}$F NMR (282 MHz, DMSO-$d_6$) δ−58.47, −58.75, −176.20; MS (ES+): 594.0 (M+1); (ES−): 592.0 (M−1); Analysis calculated for $C_{24}H_{20}BrF_4N_7O_2 \cdot 1.75H_2O \cdot 1HCl$: C, 43.52; H, 3.73; Cl, 5.35; N, 14.80. Found: C, 43.54; H, 3.24; Cl, 4.96; N, 14.54.

Scheme 15

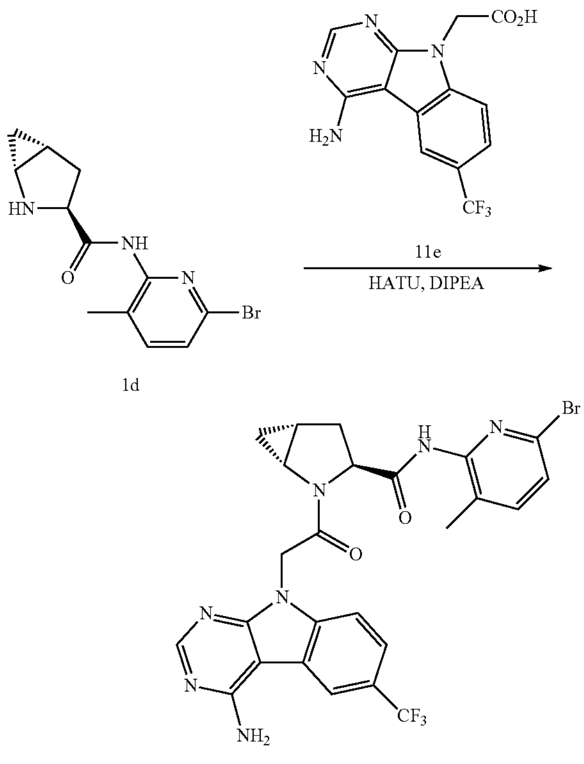

1d

15a

Preparation of (1R,3S,5R)-2-(2-(4-amino-6-(trifluoromethyl)-9H-pyrimido[4,5-b]indol-9-yl)acetyl)-N-(6-bromo-3-methylpyridin-2-yl)-2-azabicyclo[3.1.0]hexane-3-carboxamide (15a)

Compound 15a was prepared according to the procedure reported in step-3 of scheme-1, from TFA salt of 2-(4-amino-6-(trifluoromethyl)-9H-pyrimido[4,5-b]indol-9-yl)acetic acid (11e) (50 mg, 0.118 mmol) in DMF (2 mL) using HCl salt of (1R,3S,5R)—N-(6-bromo-3-methylpyridin-2-yl)-2-azabicyclo[3.1.0]hexane-3-carboxamide (I d) (39.2 mg, 0.118 mmol), HATU (67.2 mg, 0.177 mmol), DIPEA (0.103 mL, 0.589 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-(trifluoromethyl)-9H-pyrimido[4,5-b]indol-9-yl)acetyl)-N-(6-bromo-3-methylpyridin-2-yl)-2-azabicyclo[3.1.0]hexane-3-carboxamide (15a) (47 mg, 68% yield) HCl salt as a white solid; $^1$H NMR (300 MHz, DMSO-$d_6$) δ 10.27 (s, 1H, $D_2O$ exchangeable), 9.00 (s, 1H), 8.70-8.54 (m, 3H, 2H $D_2O$ exchangeable), 7.93-7.80 (m, 2H), 7.62 (d, J=8.0 Hz, 1H), 7.45 (d, J=7.9 Hz, 1H), 5.78 (d, J=17.4 Hz, 1H), 5.51 (d, J=17.3 Hz, 1H), 4.38 (dd, J=9.2, 5.1 Hz, 1H), 3.90 (td, J=6.3, 5.4, 2.3 Hz, 1H), 2.46-2.18 (m, 2H), 2.03-1.86 (m, 4H), 1.11 (dt, J=9.4, 5.3 Hz, 1H), 0.83 (dt, J=7.1, 3.4 Hz, 1H); $^{19}$F NMR (282 MHz, DMSO-$d_6$)

δ−58.52; MS (ES+): 587.9 (M+1); (ES−): 586.0 (M−1); Analysis calculated for $C_{25}H_{21}BrF_3N_7O_2 \cdot HCl \cdot 1.75H_2O$: C, 45.75; H, 3.92; Cl, 5.40; N, 14.94. Found: C, 45.96; H, 3.65; Cl, 4.95; N, 14.71.

Scheme 16

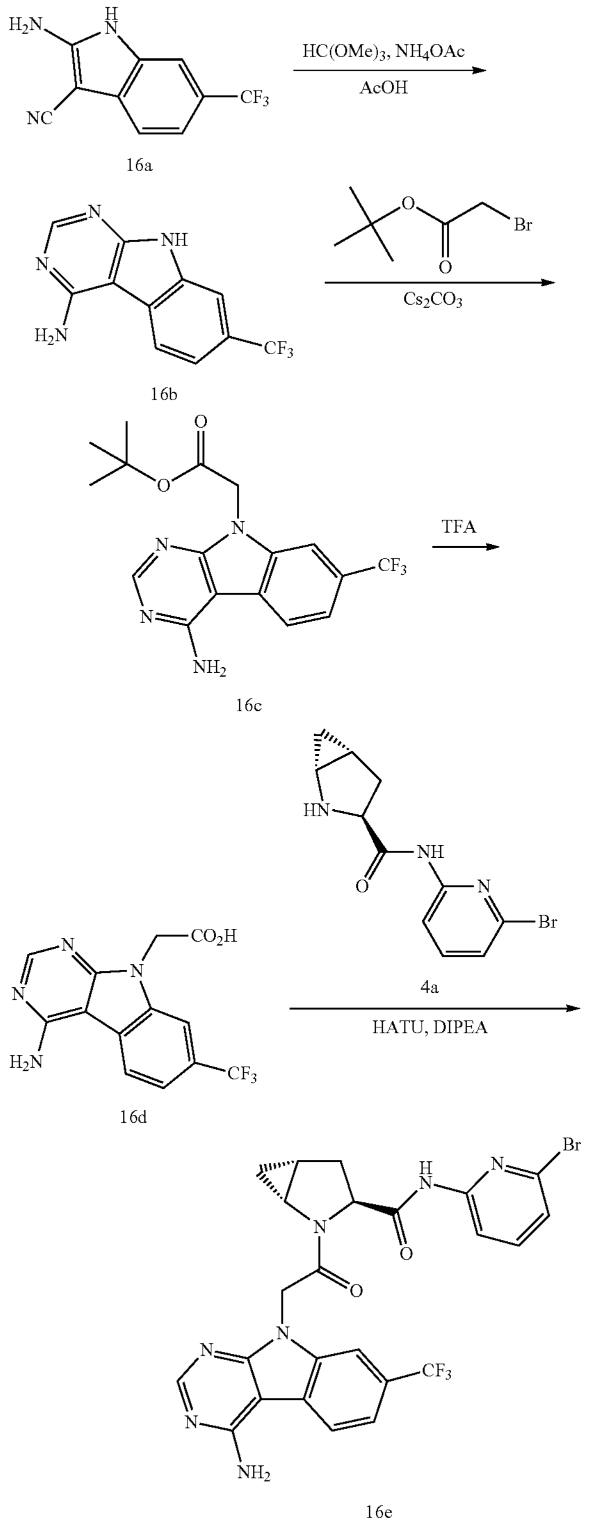

Preparation of (1R,3S,5R)-2-(2-(4-amino-7-(trifluoromethyl)-9H-pyrimido[4,5-b]indol-9-yl)acetyl)-N-(6-bromopyridin-2-yl)-2-azabicyclo[3.1.0]hexane-3-carboxamide (16e)

Step-1: Preparation of 7-(trifluoromethyl)-9H-pyrimido[4,5-b]indol-4-amine (16b)

Compound 16b was prepared according to the procedure reported in step-1 of scheme-6, from 2-amino-6-(trifluoromethyl)-1H-indole-3-carbonitrile (16a) (1.95 g, 8.66 mmol; CAS #1242140-69-7) using trimethyl orthoformate (18.95 mL, 173 mmol), AcOH (2.476 mL, 43.3 mmol) and $NH_4OAc$ (3.34 g, 43.3 mmol). This gave after workup 7-(trifluoromethyl)-9H-pyrimido[4,5-b]indol-4-amine (16b) (2.08 g, 77% yield) acetic acid salt as a pale yellow solid; $^1H$ NMR (300 MHz, DMSO-$d_6$) δ 12.20 (s, 1H), 11.98 (s, 1H), 8.52 (d, J=8.3 Hz, 1H), 8.31 (s, 1H), 7.76-7.65 (m, 1H), 7.58-7.47 (m, 1H), 7.43 (s, 2H), 1.91 (s, 3H); MS (ES+): 253.10 (M+1).

Step-2: Preparation of tert-butyl 2-(4-amino-7-(trifluoromethyl)-9H-pyrimido[4,5-b]indol-9-yl)acetate (16c)

Compound 16c was prepared according to the procedure reported in step-1 of scheme-1, from 7-(trifluoromethyl)-9H-pyrimido[4,5-b]indol-4-amine (16b) (2 g, 7.93 mmol) in DMF (50 mL) using $Cs_2CO_3$ (3.10 g, 9.52 mmol). This gave after workup and purification by flash column chromatography [silica gel (40 g), eluting with EtOAc in Hexane from 0-100%] tert-butyl 2-(4-amino-7-(trifluoromethyl)-9H-pyrimido[4,5-b]indol-9-yl)acetate (16c) (0.93 g, 32% yield) as a pale yellow solid; $^1H$ NMR (300 MHz, DMSO-$d_6$) δ 8.57 (d, J=8.2 Hz, 1H), 8.36 (s, 1H), 8.06 (d, J=1.5 Hz, 1H), 7.65-7.51 (m, 3H), 5.25 (s, 2H), 1.40 (s, 9H); MS (ES+): 367.10 (M+1).

Step-3: Preparation of 2-(4-amino-7-(trifluoromethyl)-9H-pyrimido[4,5-b]indol-9-yl)acetic acid (16d)

Compound 16d was prepared according to the procedure reported in step-2 of scheme-1, from tert-butyl 2-(4-amino-7-(trifluoromethyl)-9H-pyrimido[4,5-b]indol-9-yl)acetate (16c) (0.92 g, 2.51 mmol) using TFA (14.41 mL, 37.7 mmol; 20% TFA in DCM) and stirring at RT for 16 h. This gave after workup 2-(4-amino-7-(trifluoromethyl)-9H-pyrimido[4,5-b]indol-9-yl)acetic acid (16d) (0.9 g, 84% yield) TFA salt as a white solid; $^1H$ NMR (300 MHz, DMSO-$d_6$) δ 8.64 (d, J=8.3 Hz, 1H), 8.47 (s, 1H), 8.21 (s, 1H), 8.02 (s, 2H), 7.67 (d, J=8.3 Hz, 1H), 5.31 (s, 2H); MS (ES+): 311.00 (M+1).

Step-4: Preparation of (1R,3S,5R)-2-(2-(4-amino-7-(trifluoromethyl)-9H-pyrimido[4,5-b]indol-9-yl)acetyl)-N-(6-bromopyridin-2-yl)-2-azabicyclo[3.1.0]hexane-3-carboxamide (16e)

Compound 16e was prepared according to the procedure reported in step-3 of scheme-1, from TFA salt of 2-(4-amino-7-(trifluoromethyl)-9H-pyrimido[4,5-b]indol-9-yl)acetic acid (16d) (75 mg, 0.177 mmol) in DMF (2 mL) using HCl salt of (1R,3S,5R)—N-(6-bromopyridin-2-yl)-2-azabicyclo[3.1.0]hexane-3-carboxamide (4a) (70.0 mg, 0.177 mmol), HATU (101 mg, 0.265 mmol), DIPEA (0.154 mL, 0.884 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-7-(trifluoromethyl)-9H-pyrimido[4,5-b]indol-9-yl)acetyl)-N-(6-bromopyridin-2-yl)-2-azabicyclo[3.1.0]hexane-3-carboxamide (16e) (62 mg, 61% yield) HCl salt as a white solid; $^1H$ NMR (300 MHz, DMSO-$d_6$) δ 10.76 (s, 1H, $D_2O$ exchangeable), 8.73 (d, J=8.1 Hz, 3H, 2H $D_2O$ exchangeable), 8.65 (s, 1H), 8.17 (s, 1H), 8.00 (d, J=8.1 Hz, 1H), 7.77-7.61 (m, 2H), 7.30 (d, J=7.7 Hz, 1H), 5.87 (d, J=17.4 Hz, 1H), 5.51 (d, J=17.3 Hz, 1H), 4.42 (dd, J=9.0, 5.5 Hz, 1H), 3.91 (ddd, J=7.4, 5.4, 2.3 Hz, 1H), 2.41-2.13 (m, 2H), 1.92 (t, J=6.4 Hz, 1H), 1.09 (dt, J=8.7, 5.5 Hz, 1H), 0.77 (td, J=5.2, 2.3 Hz, 1H); $^{19}F$ NMR (282 MHz, DMSO-$d_6$) δ-59.33; MS (ES+): 574.0 (M+1); (ES-): 572.0 (M-1); Analysis calculated for $C_{24}H_{19}BrF_3N_7O_2 \cdot 1.5H_2O \cdot 1HCl$: C, 45.19; H, 3.63; Cl, 5.56; N, 15.37. Found: C, 45.06; H, 3.61; Cl, 5.38; N, 15.36.

Scheme 17

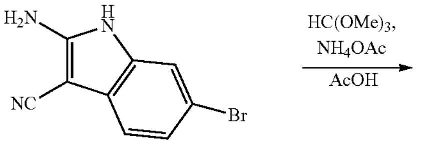

17a

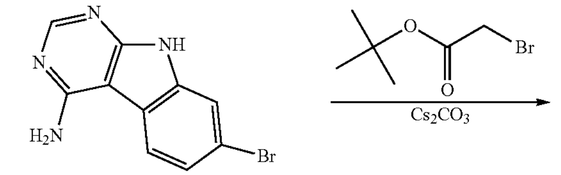

17b

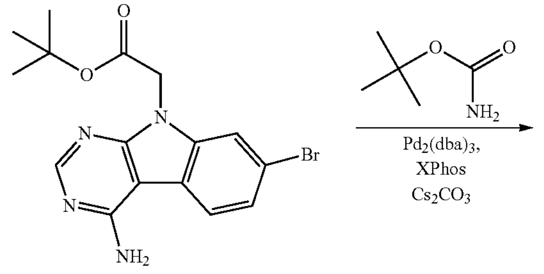

17c

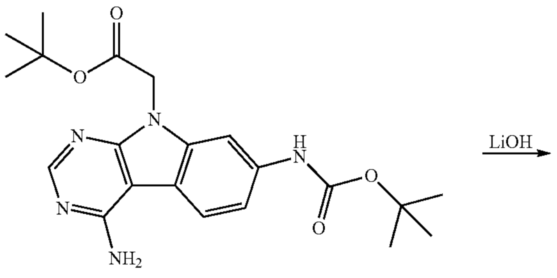

17d

-continued

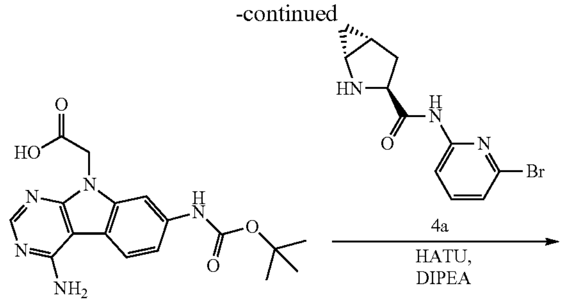

17e

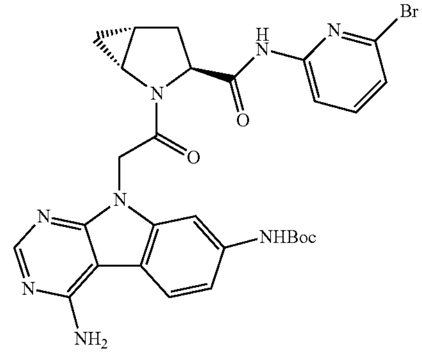

17f

Preparation of tert-butyl (4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-7-yl)carbamate (17f)

Step-1: Preparation of 7-bromo-9H-pyrimido[4,5-b]indol-4-amine (17b)

Compound 17b was prepared according to the procedure reported in step-1 of scheme-6, from 2-amino-6-bromo-1H-indole-3-carbonitrile (17a) (2 g, 8.47 mmol; CAS #1427028-36-1) using trimethyl orthoformate (18.54 mL, 169 mmol), AcOH (2.423 mL, 42.4 mmol) and $NH_4OAc$ (3.27 g, 42.4 mmol). This gave after workup 7-bromo-9H-pyrimido[4,5-b]indol-4-amine (17b) (2.29 g, 84% yield) as a pale yellow solid; 1H NMR (300 MHz, DMSO-$d_6$) δ 11.97 (s, 2H), 8.27 (t, J=4.2 Hz, 2H), 7.58 (d, J=1.8 Hz, 1H), 7.36 (dd, J=8.4, 1.8 Hz, 1H), 7.26 (s, 2H), 1.92 (s, 3H).

Step-2: Preparation of tert-butyl 2-(4-amino-7-bromo-9H-pyrimido[4,5-b]indol-9-yl)acetate (17c)

Compound 17c was prepared according to the procedure reported in step-2 of scheme-16, from 7-bromo-9H-pyrimido[4,5-b]indol-4-amine (17b) (2.2 g, 6.81 mmol) in DMF (75 mL) using tert-butyl 2-bromoacetate (1.056 mL, 7.15 mmol), $Cs_2CO_3$ (4.88 g, 14.98 mmol) and stirring at RT for 15 h. Additional tert-butyl 2-bromoacetate (1.006 mL, 6.81 mmol) and $K_2CO_3$ (0.941 g, 6.81 mmol) were needed for completion of reaction. This gave after workup and purification by flash column chromatography [silica gel (40 g), eluting with EtOAc in hexane from 0-100%] tert-butyl 2-(4-amino-7-bromo-9H-pyrimido[4,5-b]indol-9-yl)acetate (17c) (1.25 g, 49%, yield) as a pale yellow solid; $^1H$ NMR (300 MHz, DMSO-$d_6$) δ 8.31 (t, J=4.2 Hz, 2H), 7.91 (d, J=1.7 Hz, 1H), 7.46-7.36 (m, 3H), 5.14 (s, 2H), 1.41 (s, 9H).

Step-3: Preparation of tert-butyl 2-(4-amino-7-((tert-butoxycarbonyl)amino)-9H-pyrimido[4,5-b]indol-9-yl)acetate (17d)

To a degassed solution of tert-butyl 2-(4-amino-7-bromo-9H-pyrimido[4,5-b]indol-9-yl)acetate (17c) (200 mg, 0.530 mmol) in toluene (10 mL) was added XPhos (50.5 mg, 0.106 mmol), t-butyl carbamate (93 mg, 0.795 mmol), $Pd_2(dba)_3$ (48.5 mg, 0.053 mmol) and cesium carbonate (173 mg, 0.530 mmol), filled with nitrogen and heated at 90° C. for 16 h. The reaction mixture was diluted with ethyl acetate (100 mL), washed with water (50 mL), brine (50 mL), dried and concentrated in vacuum. The obtained residue was purified by flash column chromatography [silica gel (24 g), eluting with DMA-80 in DCM from 0-50%] to give tert-butyl 2-(4-amino-7-(tert-butoxycarbonylamino)-9H-pyrimido[4,5-b]indol-9-yl)acetate (17d) (92 mg, 42% yield) as a yellow solid; MS (ES+): 414.20 (M+1).

Step-4: Preparation of 2-(4-amino-7-((tert-butoxycarbonyl)amino)-9H-pyrimido[4,5-b]indol-9-yl)acetic acid (17e)

To a stirred solution of tert-butyl 2-(4-amino-7-(tert-butoxycarbonylamino)-9H-pyrimido[4,5-b]indol-9-yl)acetate (17d) (90 mg, 0.218 mmol) in THF/MeOH (4 mL; ratio 1:1) was added lithium hydroxide hydrate (1.088 mL, 1.088 mmol) and stirred at RT for 15 h. The reaction mixture was concentrated in vacuo, diluted with water (1 mL), acidified to pH 5-7 using 1M HCl and concentrated to dryness to afford 2-(4-amino-7-((tert-butoxycarbonyl)amino)-9H-pyrimido[4,5-b]indol-9-yl)acetic acid (17e) (67 mg, 86% yield): $^1$H NMR (300 MHz, DMSO-$d_6$) δ 9.71 (s, 1H), 8.63-8.45 (m, 4H), 8.38 (d, J=8.6 Hz, 1H), 7.95 (s, 1H), 7.36 (dd, J=8.7, 1.8 Hz, 1H), 5.19 (s, 2H), 1.51 (s, 9H); MS (ES+): 358.10 (M+1); (ES−): 356.10 (M−1).

Step-5: Preparation of tert-butyl (4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-7-yl)carbamate (17f)

Compound 17f was prepared according to the procedure reported in step-3 of scheme-1, from TFA salt of 2-(4-amino-7-((tert-butoxycarbonyl)amino)-9H-pyrimido[4,5-b]indol-9-yl)acetic acid (17e) (60 mg, 0.168 mmol) in DMF (1 mL) using TFA salt of (1R,3S,5R)—N-(6-bromopyridin-2-yl)-2-azabicyclo[3.1.0]hexane-3-carboxamide (4a) (66.5 mg, 0.168 mmol), HATU (96 mg, 0.252 mmol) DIPEA (0.146 mL, 0.839 mmol) and stirring at RT for 16 h. This gave after workup and purification by flash column chromatography [silica gel (12 g), eluting with DMA-80 in DCM from 0-100%] tert-butyl 4-amino-9-(2-((1R,3S,5R)-3-(6-bromopyridin-2-ylcarbamoyl)-2-azabicyclo[3.1.0]hexan-2-yl)-2-oxoethyl)-9H-pyrimido[4,5-b]indol-7-ylcarbamate (17f) (48 mg, 46% yield), 10 mg of this compound was purified by reverse phase column chromatography [C18 column (50 g), eluting with ACN in water (containing 0.1% HCl) from 0-100%] to yield tert-butyl 4-amino-9-(2-((1R,3S,5R)-3-(6-bromopyridin-2-ylcarbamoyl)-2-azabicyclo[3.1.0]hexan-2-yl)-2-oxoethyl)-9H-pyrimido[4,5-b]indol-7-ylcarbamate (17f) (6 mg) HCl salt as a white solid; 1H NMR (300 MHz, MeOD-$d_4$) δ 8.46 (s, 1H), 8.19 (d, J=8.7 Hz, 1H), 8.05 (d, J=8.2 Hz, 1H), 8.00 (d, J=1.8 Hz, 1H), 7.60 (t, J=8.0 Hz, 1H), 7.35 (dd, J=8.7, 1.9 Hz, 1H), 7.24 (dd, J=7.8, 0.7 Hz, 1H), 5.74 (d, J=17.2 Hz, 1H), 5.53 (d, J=17.1 Hz, 1H), 4.56 (t, J=7.1 Hz, 1H), 3.89 (ddd, J=7.4, 5.4, 2.4 Hz, 1H), 2.46 (dd, J=7.9, 3.6 Hz, 2H), 2.04 (d, J=6.4 Hz, 1H), 1.56 (s, 9H), 1.24 (dt, J=8.6, 5.5 Hz, 1H), 1.00 (dt, J=7.6, 3.7 Hz, 1H). MS (ES+): 621.2 (M+1); (ES−): 619.1 (M−1).

Scheme 18

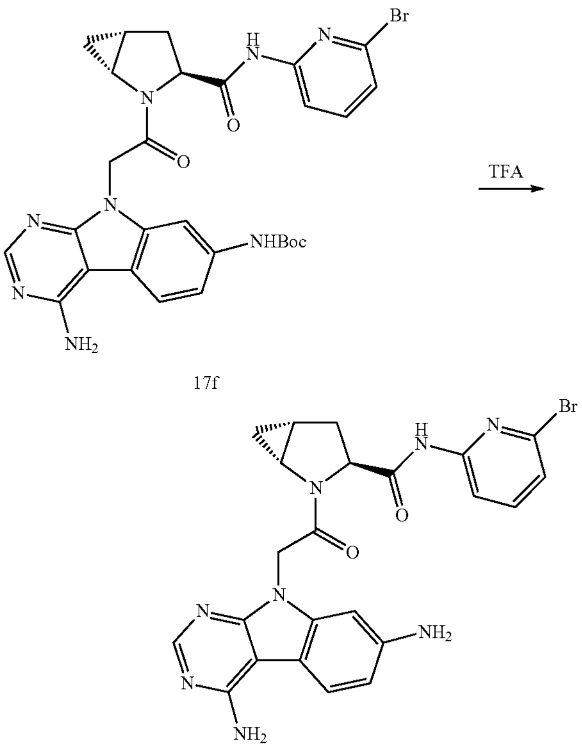

17f

18a

Preparation of (1R,3S,5R)—N-(6-bromopyridin-2-yl)-2-(2-(4,7-diamino-9H-pyrimido[4,5-b]indol-9-yl)acetyl)-2-azabicyclo[3.1.0]hexane-3-carboxamide (18a)

Compound 18a was prepared according to the procedure reported in step-3 of scheme-1, from tert-butyl (4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-7-yl)carbamate (17f) (35 mg, 0.056 mmol) in DCM (1 mL) using 2,2,2-trifluoroacetic acid (0.087 mL, 1.126 mmol) and stirring at RT for 16 h. This gave after workup and purification twice by reverse phase column chromatography [C18 column (50 g), eluting with ACN in water (containing 0.1% HCl) from 0-100%] (1R,3S,5R)—N-(6-bromopyridin-2-yl)-2-(2-(4,7-diamino-9H-pyrimido[4,5-b]indol-9-yl)acetyl)-2-azabicyclo[3.1.0]hexane-3-carboxamide (17 mg, 58% yield) (18a) HCl salt as a white solid. $^1$H NMR (300 MHz, DMSO-$d_6$) δ 10.74 (s, 1H, $D_2O$ exchangeable), 8.45 (s, 1H), 8.29 (s, 2H, $D_2O$ exchangeable), 8.18 (d, J=8.6 Hz, 1H), 7.95 (d, J=8.2 Hz, 1H), 7.64 (t, J=7.9 Hz, 1H), 7.25 (d, J=7.7 Hz, 1H), 6.81 (d, J=7.0 Hz, 2H), 5.58 (d, J=17.4 Hz, 1H), 5.22 (d, J=17.4 Hz, 1H), 4.36 (dd, J=9.0, 5.4 Hz, 1H), 3.89-3.76 (m, 1H), 2.34-2.06 (m, 2H), 1.85 (d, J=7.7 Hz, 1H), 1.10-0.92 (m, 1H), 0.68 (d, J=5.9 Hz, 1H). MS (ES+): 521.1 (M+1); (ES−): 519.1 (M−1).

Scheme 19

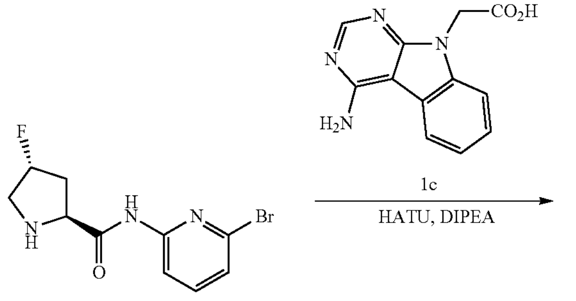

5d

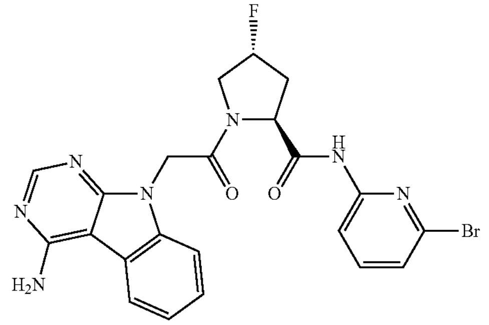

19a

Preparation of (2S,4R)-1-(2-(4-amino-9H-pyrimido[4,5-b]indol-9-yl)acetyl)-N-(6-bromopyridin-2-yl)-4-fluoropyrrolidine-2-carboxamide (19a)

Compound 19a was prepared according to the procedure reported in step-3 of scheme-1, from TFA salt of 2-(4-amino-9H-pyrimido[4,5-b]indol-9-yl)acetic acid (1c) (150 mg, 0.421 mmol) in DMF (5 mL) using TFA salt of (2S,4R)—N-(6-bromopyridin-2-yl)-4-fluoropyrrolidine-2-carboxamide (5d) (169 mg, 0.421 mmol), HATU (192 mg, 0.505 mmol), DIPEA (272 mg, 2.105 mmol) and stirring at RT for 16 h. This gave after workup and purification by flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (2S,4R)-1-(2-(4-amino-9H-pyrimido[4,5-b]indol-9-yl)acetyl)-N-(6-bromopyridin-2-yl)-4-fluoropyrrolidine-2-carboxamide (19a) (62 mg, 61% yield) HCl salt as a white solid; 1H NMR (300 MHz, DMSO-$d_6$) δ (a mixture of two rotamers) 11.37 (s) and 10.98 (s) (2s, 1H, $D_2O$ exchangeable), 8.80-8.56 (m, 3H, 2H $D_2O$ exchangeable), 8.51 (d, J=7.9 Hz, 1H), 7.98 (d, J=8.1 Hz, 1H), 7.75-7.63 (m, 2H), 7.55 (t, J=7.7 Hz, 1H), 7.50-7.37 (m, 1H), 7.31 (d, J=7.7 Hz, 1H), 5.64 (d, J=3.5 Hz, 1H), 5.60-5.45 (m, 1H), 5.40 (d, J=17.3 Hz, 1H), 4.71-4.57 (m, 1H), 4.43-4.21 (m, 1H), 4.18-3.96 (m, 1H), 2.74-2.50 (m, 1H), 2.29-2.02 (m, 1H); $^{19}F$ NMR (282 MHz, DMSO-$d_6$) δ−175.73, −176.14; MS (ES+): 512.0 (M+1), (ES−): 510.0 (M−1); Analysis calculated for $C_{22}H_{19}BrFN_7O_2 \cdot HCl \cdot 2.5H_2O$: C, 44.50; H, 4.24; Cl, 5.97; N, 16.51. Found: C, 44.36; H, 4.10; Cl, 5.76; N, 16.25.

Scheme 20

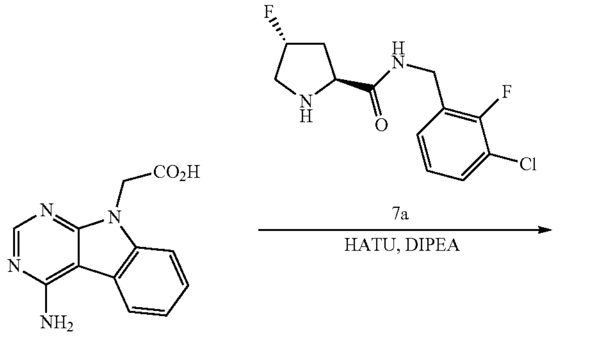

1c

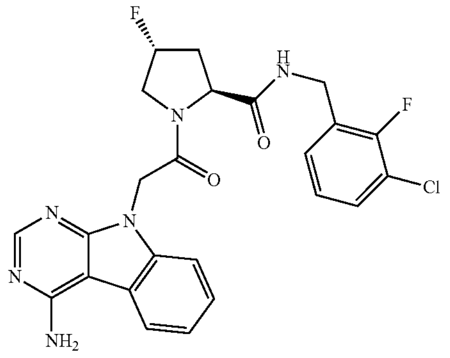

20a

Preparation of (2S,4R)-1-(2-(4-amino-9H-pyrimido[4,5-b]indol-9-yl)acetyl)-N-(3-chloro-2-fluorobenzyl)-4-fluoropyrrolidine-2-carboxamide (20a)

Compound 20a was prepared according to the procedure reported in step-3 of scheme-1, from TFA salt of 2-(4-amino-9H-pyrimido[4,5-b]indol-9-yl)acetic acid (1c) (200 mg, 0.561 mmol) in DMF (10 mL) using TFA salt of (2S,4R)—N-(3-chloro-2-fluorobenzyl)-4-fluoropyrrolidine-2-carboxamide (7a) (218 mg, 0.561 mmol), HATU (256 mg, 0.674 mmol), DIPEA (0.490 mL, 2.81 mmol) and stirring at RT for 16 h. This gave after workup and purification by flash column chromatography [silica gel (12 g), eluting with MeOH in DCM from 0-3%] followed by purification using reverse-phase column chromatography [C-18 column, 100 g, eluting with 0.1% aqueous HCl in $H_2O$ and MeCN from 0-100%] (2S,4R)-1-(2-(4-amino-9H-pyrimido[4,5-b]indol-9-yl)acetyl)-N-(3-chloro-2-fluorobenzyl)-4-fluoropyrrolidine-2-carboxamide (20a) (121 mg, 43% yield) HCl salt as a white solid; $^1H$ NMR (300 MHz. DMSO-$d_6$) (a mixture of two rotamers) δ 9.15 (t, J=5.8 Hz) and 8.79-8.64 (m, 3H, $D_2O$ exchangeable), 8.61 (d, J=3.0 Hz, 1H), 8.59-8.50 (m, 1H), 7.74 (d, J=8.1 Hz, 1H), 7.58-7.34 (m, 4H), 7.21-7.11 (m, 1H), 6.92-6.79 (m, 1H), 5.72-5.53 (m, 1H), 5.54-4.76 (m, 2H), 4.56-4.14 (m, 4H), 4.14-3.92 (m, 1H), 2.62-2.40 (m, 1H), 2.22-1.95 (m, 1H); $^{19}F$ NMR (282 MHz, DMSO-$d_6$) δ−121.24, −121.76, −176.25, −176.47; MS (ES+): 499/501 (M+1).

Scheme 21

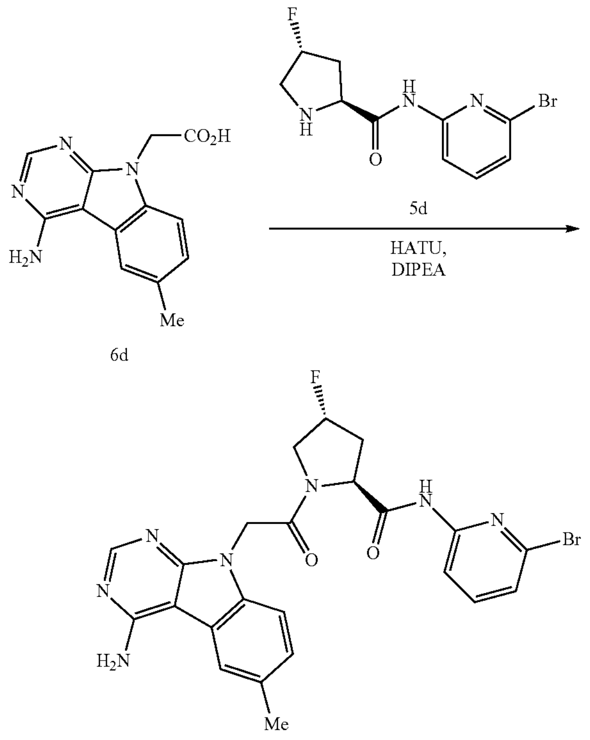

6d, 5d, 21a

Scheme 22

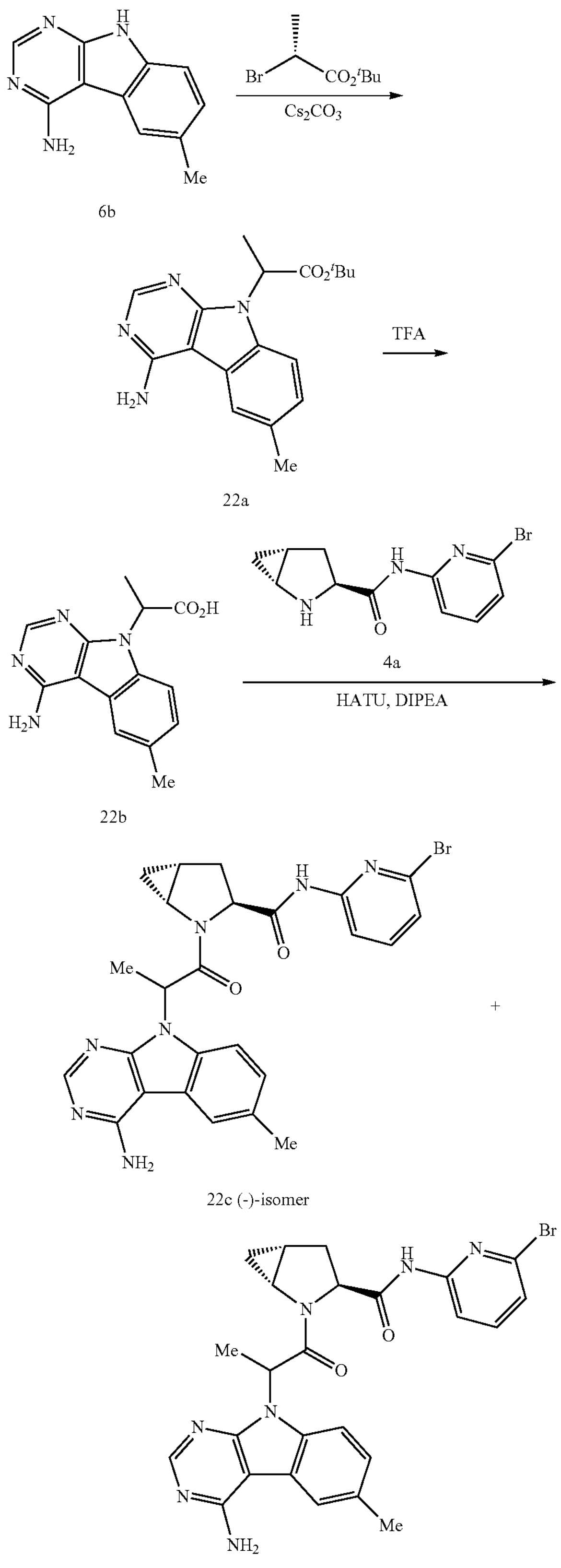

6b, 22a, 22b, 4a 22c (-)-isomer

+

22d (+)-isomer

Preparation of (2S,4R)-1-(2-(4-amino-6-methyl-9H-pyrimido[4,5-b]indol-9-yl)acetyl)-N-(6-bromopyridin-2-yl)-4-fluoropyrrolidine-2-carboxamide (21a)

Compound 21a was prepared according to the procedure reported in step-3 of scheme-1, from TFA salt of 2-(4-amino-6-methyl-9H-pyrimido[4,5-b]indol-9-yl)acetic acid (6d) (50 mg, 0.135 mmol) in DMF (5 mL) using TFA salt of (2S,4R)—N-(6-bromopyridin-2-yl)-4-fluoropyrrolidine-2-carboxamide (5d) (54.3 mg, 0.135 mmol), HATU (61.6 mg, 0.162 mmol), DIPEA (87 mg, 0.675 mmol) and stirring at RT for 16 h. This gave after workup and purification by flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (2S,4R)-1-(2-(4-amino-6-methyl-9H-pyrimido[4,5-b]indol-9-yl)acetyl)-N-(6-bromopyridin-2-yl)-4-fluoropyrrolidine-2-carboxamide (21a) (35 mg, 49% yield) HCl salt as a white solid; $^1$H NMR (300 MHz, DMSO-d$_6$) δ (a mixture of rotamers) 11.35 (s) and 10.97 (s, 1H, D$_2$O exchangeable), 8.76-8.52 (m, 3H, 2H D$_2$O exchangeable), 8.35 (s, 1H), 7.98 (d, J=8.2 Hz, 1H), 7.69 (t, J=7.9 Hz, 1H), 7.60 (d, J=8.4 Hz, 1H), 7.38 (d, J=8.5 Hz, 1H), 7.31 (d, J=7.7 Hz, 1H), 5.71-5.25 (m, 3H), 4.62 (t, J=8.5 Hz, 1H), 4.37-4.23 (m, 1H), 4.16-3.96 (m, 1H), 2.66-2.43 (m, 4H), 2.30-1.95 (m, 1H); $^{19}$F NMR (282 MHz, DMSO-d$_6$) δ−175.73, −176.15; MS (ES+): 526.0 (M+1), (ES−): 524.0 (M−1); Analysis calculated for $C_{23}H_2BrFN_7O_2 \cdot 1.1HCl \cdot 2.25H_2O$: C, 45.51; H, 4.42; Cl, 6.42; N, 16.15. Found: C, 45.21; H, 4.47; Cl, 6.40; N, 15.88.

Preparation of (1R,3S,5R)-2-((−)-2-(4-amino-6-methyl-9H-pyrimido[4,5-b]indol-9-yl)propanoyl)-N-(6-bromopyridin-2-yl)-2-azabicyclo[3.1.0]hexane-3-carboxamide (22c) and (1R,3S,5R)-2-((+)-2-(4-amino-6-methyl-9H-pyrimido[4,5-b]indol-9-yl)propanoyl)-N-(6-bromopyridin-2-yl)-2-azabicyclo[3.1.0]hexane-3-carboxamide (22d)

Step-1: Preparation of tert-butyl 2-(4-amino-6-methyl-9H-pyrimido[4,5-b]indol-9-yl)propanoate (22a)

Compound 22a was prepared according to the procedure reported in step-1 of scheme-1, from 6-methyl-9H-pyrimido[4,5-b]indol-4-amine (6b) (200 mg, 1.009 mmol) in DMF (10 mL) using (R)-tert-butyl 2-bromopropanoate (253 mg, 1.211 mmol; CAS #54631-38-8), $Cs_2CO_3$ (657 mg, 2.018 mmol) and stirring at RT for 16 h. This gave after workup and purification by flash column chromatography [silica gel (12 g), eluting with MeOH in DCM from 0-3%] a mixture of two enantiomers of tert-butyl 2-(4-amino-6-methyl-9H-pyrimido[4,5-b]indol-9-yl)propanoate (22a) (250 mg, 76% yield) as a pale yellow solid; 1H NMR (300 MHz, DMSO-$d_6$) δ 8.26 (d, J=6.0 Hz, 1H), 8.23-8.15 (m, 1H), 7.40 (dd, J=7.4, 3.1 Hz, 1H), 7.30-7.07 (m, 3H), 5.81-5.63 (m, 1H), 2.46 (s, 3H), 1.66 (d, J=7.1 Hz, 3H), 1.30 (d, J=5.7 Hz, 9H); MS (ES+): 327 (M+1).

Step-2: Preparation of 2-(4-amino-6-methyl-9H-pyrimido[4,5-b]indol-9-yl)propanoic acid (22b)

Compound 22b was prepared according to the procedure reported in step-2 of scheme-1, from tert-butyl 2-(4-amino-6-methyl-9H-pyrimido[4,5-b]indol-9-yl)propanoate (22a) (250 mg, 0.766 mmol) in DCM (20 mL) using TFA (0.879 mL, 11.49 mmol) and stirring at RT for 16 h. This gave after workup a mixture of two enantiomers of 2-(4-amino-6-methyl-9H-pyrimido[4,5-b]indol-9-yl)propanoic acid (22b) (304 mg) TFA salt as a white solid; 1H NMR (300 MHz, DMSO-$d_6$) δ 8.55 (s, 1H), 8.49-8.36 (m, 2H), 8.36 (s, 1H), 7.62 (d, J=8.5 Hz, 1H), 7.37 (dd, J=8.6, 1.6 Hz, 1H), 5.86 (q, J=7.1 Hz, 1H), 1.75 (d, J=7.2 Hz, 3H); $^{19}F$ NMR (282 MHz, DMSO-$d_6$) δ−74.15; MS (ES+): 271 (M+1), (ES−): 269 (M−1).

Step-3: Preparation of (1R,3S,5R)-2-((−)-2-(4-amino-6-methyl-9H-pyrimido[4,5-b]indol-9-yl)propanoyl)-N-(6-bromopyridin-2-yl)-2-azabicyclo[3.1.0]hexane-3-carboxamide (22c) and (1R,3S,5R)-2-((+)-2-(4-amino-6-methyl-9H-pyrimido[4,5-b]indol-9-yl)propanoyl)-N-(6-bromopyridin-2-yl)-2-azabicyclo[3.1.0]hexane-3-carboxamide (22d)

Compounds 22c and 22d were prepared according to the procedure reported in step-3 of scheme-1, from TFA salt of 2-(4-amino-6-methyl-9H-pyrimido[4,5-b]indol-9-yl)propanoic acid (22b) (50 mg, 0.130 mmol) in DMF (5 mL) using HCl salt of (1R,3S,5R)—N-(6-bromopyridin-2-yl)-2-azabicyclo[3.1.0]hexane-3-carboxamide (4a) (41.5 mg, 0.130 mmol), HATU (59.4 mg, 0.156 mmol), DIPEA (84 mg, 0.651 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%].

1. (1R,3S,5R)-2-((−)-2-(4-amino-6-methyl-9H-pyrimido[4,5-b]indol-9-yl)propanoyl)-N-(6-bromopyridin-2-yl)-2-azabicyclo[3.1.0]hexane-3-carboxamide (22c) (17 mgs, 25%) HCl salt as a white solid; 1H NMR (300 MHz, DMSO-$d_6$) δ 10.80 (s, 1H, $D_2O$ exchangeable), 8.64 (s, 1H), 8.62-8.50 (m, 2H, $D_2O$ exchangeable), 8.40 (s, 1H), 8.08 (d, J=8.1 Hz, 1H), 7.76 (t, J=7.9 Hz, 1H), 7.56 (d, J=8.5 Hz, 1H), 7.37 (dd, J=7.9, 2.6 Hz, 2H), 6.28 (q, J=6.8 Hz, 1H), 4.27 (t, J=7.2 Hz, 1H), 3.27-3.24 (m, 1H), 2.04-1.95 (m, 2H), 1.61 (m, 3H), 1.57-1.47 (m, 1H), −0.36 (m, 1H), −1.03 (m, 1H); MS (ES+): 534/536 (M+1), (ES−): 532/534 (M−1); Chiral HPLC: AD-H column 80/20 [(0.1% DEA in n-Hexane in 0.1% DEA in ethanol)] 1.0 mL/min UV detection 245 nm, 30 mins run time (Temp 40° C.). $R_t$=10.54 (peak-1 (22c), 98.0742%); $R_t$=19.473 (peak-2; (22d) 1.388%) 97.4084% ee; Optical rotation $[\alpha]_D$=−224 (c=0, 1, MeOH)
2. (1R,3S,5R)-2-((+)-2-(4-amino-6-methyl-9H-pyrimido[4,5-b]indol-9-yl)propanoyl)-N-(6-bromopyridin-2-yl)-2-azabicyclo[3.1.0]hexane-3-carboxamide (22d) (22 mgs, 32%) HCl salt as a white solid; $^{1}H$ NMR (300 MHz, DMSO-$d_6$) δ 10.64 (s, 1H, $D_2O$ exchangeable), 8.62 (s, 1H), 8.59-8.46 (m, 2H, $D_2O$ exchangeable), 8.36 (s, 1H), 7.92 (d, J=8.2 Hz, 1H), 7.72 (d, J=7.9 Hz, 1H), 7.66 (d, J=8.3 Hz, 1H), 7.34 (d, J=7.7 Hz, 1H), 7.29 (d, J=8.6 Hz, 11H), 6.22 (q, J=7.0 Hz, 1H), 4.53 (dd, J=9.1, 5.6 Hz, 1H), 3.06-2.% (m, 1H), 2.30-2.17 (m, 1H), 2.07 (m, 1H), 1.68 (m, 4H), 0.88 (m, 1H), 0.77 (m, 1H); MS (ES+): 534/536 (M+1), (ES−): 532/534 (M−1); Chiral HPLC: AD-H column 80/20 [(0.1% DEA in n-Hexane in 0.1% DEA in ethanol)] 1.0 mL/min UV detection 245 nm, 30 mins run time (Temp 40° C.); $R_t$=10.54 (peak-1 (22c) 0%); $R_t$=19.427 (peak-2; (22d) 100%)>99.99% ee; Optical rotation $[\alpha]_D$=+92.632 (c=0.095, MeOH).

Scheme 23

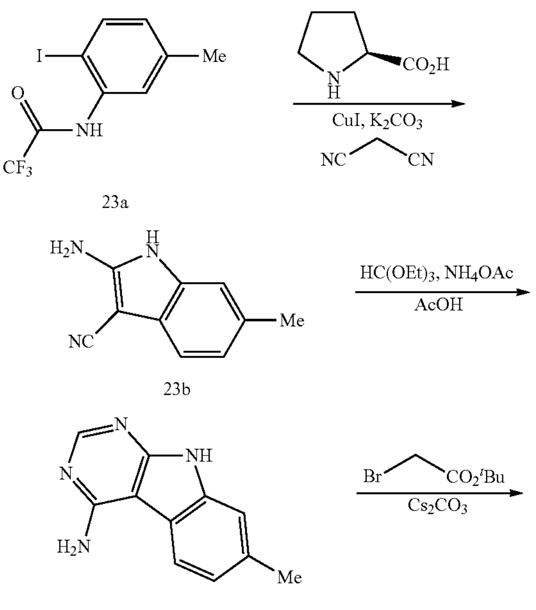

23a

23b

23c

-continued

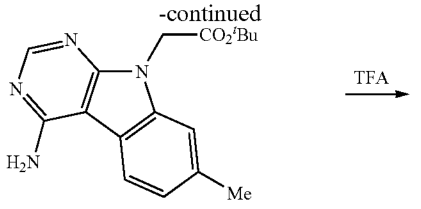

23d

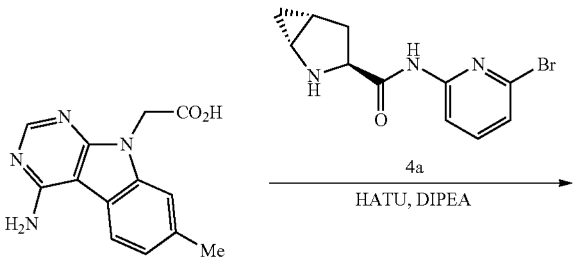

23e

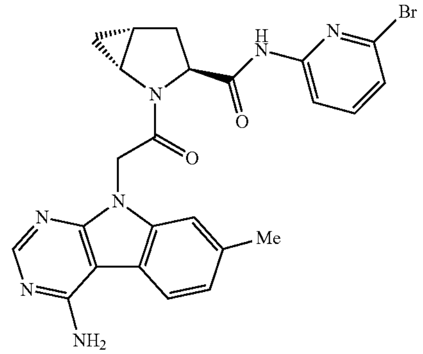

23f

Preparation of (1R,3S,5R)-2-(2-(4-amino-7-methyl-9H-pyrimido[4,5-b]indol-9-yl)acetyl)-N-(6-bromopyridin-2-yl)-2-azabicyclo[3.1.0]hexane-3-carboxamide (23f)

Step-1: Preparation of 2-amino-6-methyl-1H-indole-3-carbonitrile (23b)

Compound 23b was prepared according to the procedure reported in step-1 of scheme-11, from 2,2,2-trifluoro-N-(2-iodo-5-methylphenyl)acetamide (23a) (7.03 g, 21.36 mmol) in DMSO (20 mL) using malononitrile (1.694 g, 26.6 mmol), L-proline (0.492 g, 4.27 mmol), CuI (0.407 g, 2.136 mmol), $K_2CO_3$ (5.91 g, 42.7 mmol) and heating at 60° C. for 16 h under an argon atmosphere. This gave after workup and purification [$SiO_2$ gel (40 g), eluting with EtOAc in hexane from 0-40%] 2-amino-6-methyl-1H-indole-3-carbonitrile (23b) (2.65 g, 73% yield) as an brown solid; 1H NMR (300 MHz, DMSO-$d_6$) δ 10.58 (s, 1H), 7.00 (d, J=7.8 Hz, 1H), 6.93 (s, 1H), 6.78 (dd, J=8.3, 1.5 Hz, 1H), 6.63 (s, 2H), 2.31 (s, 3H); MS (ES+): 172 (M+1); (ES−): 170 (M−1).

Step-2: Preparation of 7-methyl-9H-pyrimido[4,5-b]indol-4-amine (23c)

Compound 23c was prepared according to the procedure reported in step-1 of scheme-6, from 2-amino-6-methyl-1H-indole-3-carbonitrile (23b) (2.65 g, 15.48 mmol) using triethyl orthoformate (51.5 mL, 310 mmol), AcOH (4.43 mL, 77 mmol) and $NH_4OAc$ (5.97 g, 77 mmol). This gave after workup and purification [$SiO_2$ gel (24 g), eluting with MeOH in DCM from 0-5%] 7-methyl-9H-pyrimido[4,5-b]indol-4-amine (23c) (1.45 g) as a brown yellow solid; $^1H$ NMR (300 MHz, DMSO-$d_6$) δ 11.70 (s, 1H), 8.21 (s, 1H), 8.16 (d, J=7.9 Hz, 1H), 7.23 (s, 1H), 7.15-6.96 (m, 3H), 2.45 (s, 3H); MS (ES+); 199 (M+1); (ES−): 197 (M−1).

Step-3: Preparation of tert-butyl 2-(4-amino-7-methyl-9H-pyrimido[4,5-b]indol-9-yl)acetate (23d)

Compound 23d was prepared according to the procedure reported in step-1 of scheme-1, from 7-methyl-9H-pyrimido[4,5-b]indol-4-amine (23c) (1.45 g, 7.31 mmol) in DMF (25 mL) using tert-butyl 2-bromoacetate (1.427 g, 7.31 mmol) $Cs_2CO_3$ (2.86 g, 8.78 mmol) and stirring at RT for 16 h. This gave after workup and purification by flash column chromatography [silica gel (24 g), eluting with MeOH in DCM from 0-3%] tert-butyl 2-(4-amino-7-methyl-9H-pyrimido[4,5-b]indol-9-yl)acetate (23d) (0.84 g, 37% yield) as a pale yellow solid: $^1H$ NMR (300 MHz, DMSO-$d_6$) δ 8.26 (s, 1H), 8.22 (d, J=8.0 Hz, 1H), 7.36 (s, 1H), 7.19 (s, 2H), 7.14-7.06 (m, 1H), 5.07 (s, 2H), 2.48 (s, 3H), 1.41 (s, 9H); MS (ES+): 313 (M+1).

Step-4: Preparation of 2-(4-amino-7-methyl-9H-pyrimido[4,5-b]indol-9-yl)acetic acid (23e)

Compound 23e was prepared according to the procedure reported in step-2 of scheme-1, from tert-butyl 2-(4-amino-7-methyl-9H-pyrimido[4,5-b]indol-9-yl)acetate (23d) (0.84 g, 2.69 mmol) using TFA (6.13 g, 53.8 mmol) in DCM (20 mL) and stirring at RT for 16 h. This gave after workup 2-(4-amino-7-methyl-9H-pyrimido[4,5-b]indol-9-yl)acetic acid (23e) (1.01 g) TFA salt as a yellow solid; $^1H$ NMR (300 MHz, DMSO-$d_6$) δ 8.51 (s, 1H), 8.36 (d, J=8.0 Hz, 1H), 8.24 (s, 2H), 7.59 (s, 1H), 7.26 (d, 1H), 5.21 (s, 2H), 2.49 (s, 3H); $^{19}F$ NMR (282 MHz, DMSO-$d_6$) δ−74.09; MS (ES+): 257 (M+1), (ES−): 255 (M−1).

Step-5: Preparation of (1R,3S,5R)-2-(2-(4-amino-7-methyl-9H-pyrimido[4,5-b]indol-9-yl)acetyl)-N-(6-bromopyridin-2-yl)-2-azabicyclo[3.1.0]hexane-3-carboxamide (23f)

Compound 23f was prepared according to the procedure reported in step-3 of scheme-1, from TFA salt of 2-(4-amino-7-methyl-9H-pyrimido[4,5-b]indol-9-yl)acetic acid (23e) (50 mg, 0.135 mmol) in DMF (5 mL) using HCl salt of (1R,3S,5R)—N-(6-bromopyridin-2-yl)-2-azabicyclo[3.1.0]hexane-3-carboxamide (4a) (43.0 mg, 0.135 mmol), HATU (61.6 mg, 0.162 mmol), DIPEA (87 mg, 0.675 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-7-methyl-9H-pyrimido[4,5-b]indol-9-yl)acetyl)-N-(6-bromopyridin-2-yl)-2-azabicyclo[3.1.0]hexane-3-carboxamide (23) (44 mg, 63% yield) HCl salt as a white solid; $^1H$ NMR (300 MHz, DMSO-$d_6$) δ 10.76 (s, 1H, $D_2O$ exchangeable), 8.57 (s, 1H), 8.44 (s, 2H, $D_2O$ exchangeable), 8.37 (d, J=8.1 Hz, 1H), 8.01 (d, J=8.2 Hz, 1H), 7.70 (t, J=8.0 Hz, 1H), 7.51 (s, 1H), 7.32 (d, J=7.7 Hz, 1H), 7.29-7.23 (m, 1H), 5.71 (d, J=17.3 Hz, 1H), 5.38 (d, J=17.3 Hz, 1H), 4.42 (dd, J=9.1, 5.6

Hz, 1H), 3.96-3.87 (m, 1H), 2.49 (s, 3H), 2.40-2.27 (m, 1H), 2.27-2.11 (m, 1H), 2.00-1.85 (m, 1H), 1.12-1.02 (m, 1H), 0.82-0.73 (m, 1H); MS (ES+): 520.0 (M+1), 518.0 (M−1); Analysis calculated for $C_{24}H_{22}BrN_7O_2 \cdot 1.2HCl \cdot 2.5H_2O$: C, 47.32; H, 4.67; Cl, 6.98; N, 16.10. Found: C, 47.10; H, 4.59; Cl, 6.75; N, 15.97.

Scheme 24

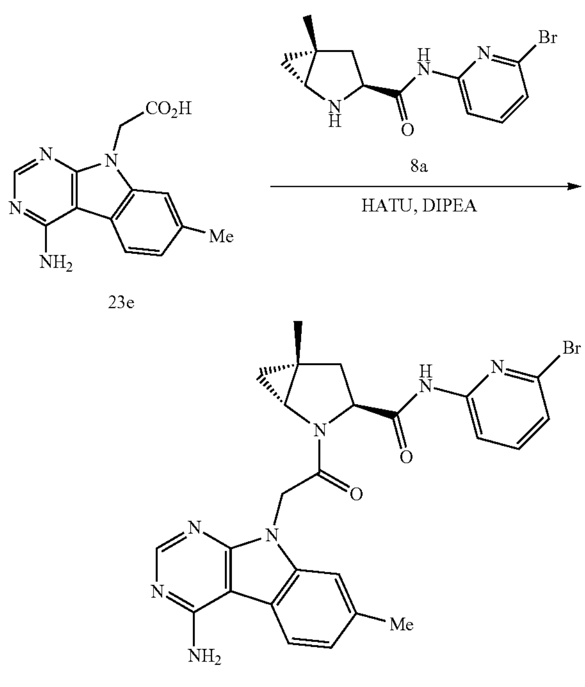

23e, 8a, 24a

Preparation of (1R,3S,5R)-2-(2-(4-amino-7-methyl-9H-pyrimido[4,5-b]indol-9-yl)acetyl)-N-(6-bromopyridin-2-yl)-5-methyl-2-azabicyclo[3.1.0]hexane-3-carboxamide (24a)

Compound 24a was prepared according to the procedure reported in step-3 of scheme-1, from TFA salt of 2-(4-amino-7-methyl-9H-pyrimido[4,5-b]indol-9-yl)acetic acid (23e) (50 mg, 0.135 mmol) in DMF (5 mL) using HCl salt of (1R,3S,5R)—N-(6-bromopyridin-2-yl)-5-methyl-2-azabicyclo[3.1.0]hexane-3-carboxamide (8a) (44.9 mg, 0.135 mmol), HATU (61.6 mg, 0.162 mmol), DIPEA (87 mg, 0.675 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-7-methyl-9H-pyrimido[4,5-b]indol-9-yl)acetyl)-N-(6-bromopyridin-2-yl)-5-methyl-2-azabicyclo[3.1.0]hexane-3-carboxamide (24a) (36 mg, 50% yield) HCl salt as a white solid; 1H NMR (300 MHz, DMSO-$d_6$) δ 10.77 (s, 1H, $D_2O$ exchangeable), 8.61 (s, 3H, 2H $D_2O$ exchangeable), 8.39 (d, J=8.1 Hz, 1H), 8.01 (d, J=8.2 Hz, 1H), 7.70 (t, J=8.0 Hz, 1H), 7.52 (s, 1H), 7.31 (d, J=7.7 Hz, 1H), 7.26 (d, J=8.9 Hz, 1H), 5.68 (d, J=17.3 Hz, 1H), 5.34 (d, J=17.3 Hz, 1H), 4.37 (dd, J=9.1, 5.9 Hz, 1H), 3.69 (dd, J=5.5, 2.4 Hz, 1H), 2.55-2.41 (m, 4H), 1.98 (dd, J=13.2, 5.9 Hz, 1H), 1.31 (s, 3H), 1.08-0.97 (m, 1H), 0.97-0.89 (m, 1H); MS (ES+) 534.0 (M+1), 532.0 (M−1); Analysis calculated for $C_{25}H_{24}BrN_7O_2 \cdot HCl \cdot 2.25H_2O$: C, 49.11; H, 4.86; Cl, 5.80; N, 16.04. Found: C, 48.98; H, 4.79; Cl, 6.02; N, 15.90.

Scheme 25

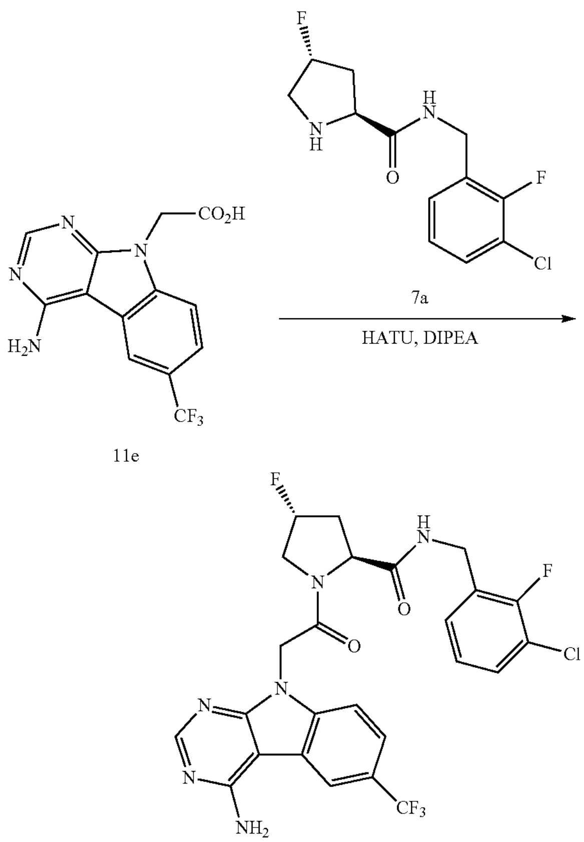

7a, 11e, 25a

Preparation of (2S,4R)-1-(2-(4-amino-6-(trifluoromethyl)-9H-pyrimido[4,5-b]indol-9-yl)acetyl)-N-(3-chloro-2-fluorobenzyl)-4-fluoropyrrolidine-2-carboxamide (25a)

Compound 25a was prepared according to the procedure reported in step-3 of scheme-1, from TFA salt of 2-(4-amino-6-(trifluoromethyl)-9H-pyrimido[4,5-b]indol-9-yl)acetic acid (11e) (50 mg, 0.118 mmol) in DMF (10 mL) using TFA salt of (2S,4R)—N-(3-chloro-2-fluorobenzyl)-4-fluoropyrrolidine-2-carboxamide (7a) (45.8 mg, 0.118 mmol), HATU (53.8 mg, 0.141 mmol), DIPEA (0.103 mL, 0.589 mmol) and stirring at RT for 16 h. This gave after workup and purification by flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (2S,4R)-1-(2-(4-amino-6-(trifluoromethyl)-9H-pyrimido[4,5-b]indol-9-yl)acetyl)-N-(3-chloro-2-fluorobenzyl)-4-fluoropyrrolidine-2-carboxamide (25a) (28 mg, 42% yield) HCl salt as a white solid; $^1$H NMR (300 MHz, DMSO-$d_6$) δ (a mixture of two rotamers) 8.98 (d, J=3.6 Hz, 1H), 8.71-8.52 (m, 4H, 2H $D_2O$ exchangeable), 7.88 (d, J=8.6 Hz, 1H), 7.75 (dd, J=8.7, 1.7 Hz, 1H), 7.45-7.31 (m, 1H), 7.17-7.08 (m, 1H), 6.80 (t, J=7.9 Hz, 1H), 5.64 (d, J=17.4 Hz, 1H), 5.43 (d, J=4.0 Hz, 1H), 4.54-4.26 (m, 3H), 4.23 (d, J=5.8 Hz, 1H), 4.19-4.05 (m, 1H), 3.96 (dd, J=12.3, 2.9 Hz, 1H), 2.62-2.41 (m, 1H), 2.23-1.91 (m, 1H); $^{19}F$ NMR (282 MHz, DMSO) δ−58.53, −121.26, −121.72, −176.26, −176.42; MS (ES+): 567.0 (M+1), (ES−): 565.0 (M−1).

Scheme 26

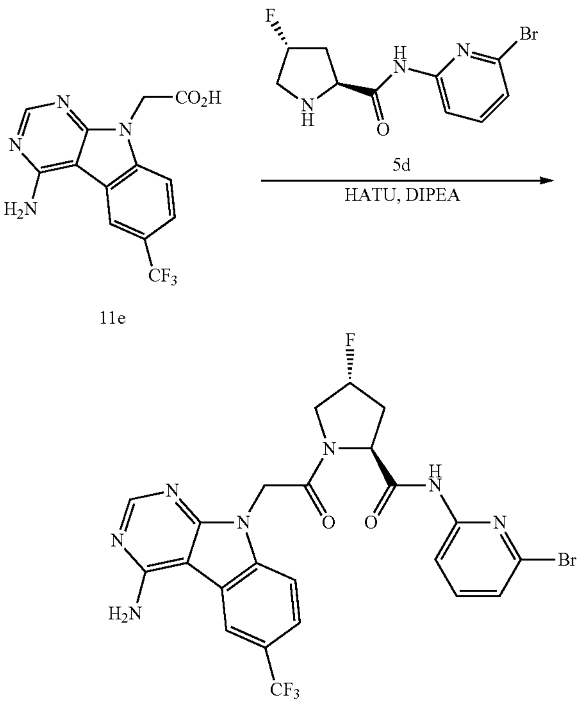

11e

26a

Preparation of (2S,4R)-1-(2-(4-amino-6-(trifluoromethyl)-9H-pyrimido[4,5-b]indol-9-yl)acetyl)-N-(6-bromopyridin-2-yl)-4-fluoropyrrolidine-2-carboxamide (26a)

Compound 26a was prepared according to the procedure reported in step-3 of scheme-1, from TFA salt of 2-(4-amino-6-(trifluoromethyl)-9H-pyrimido[4,5-b]indol-9-yl)acetic acid (11e) (50 mg, 0.118 mmol) in DMF (5 mL) using TFA salt of (2S,4R)—N-(6-bromopyridin-2-yl)-4-fluoropyrrolidine-2-carboxamide (5d) (47.4 mg, 0.118 mmol), HATU (53.8 mg, 0.141 mmol), DIPEA (76 mg, 0.589 mmol) and stirring at RT for 16 h. This gave after workup and purification by flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (2S,4R)-1-(2-(4-amino-6-(trifluoromethyl)-9H-pyrimido[4,5-b]indol-9-yl)acetyl)-N-(6-bromopyridin-2-yl)-4-fluoropyrrolidine-2-carboxamide (26a) (33 mg, 48% yield) HCl salt as a white solid; $^1H$ NMR (300 MHz, DMSO-$d_6$) δ 10.97 (s, 1H, $D_2O$ exchangeable), 8.95 (s, 1H), 8.64-8.38 (m, 3H, 2H $D_2O$ exchangeable), 7.98 (d, J=8.2 Hz, 1H), 7.84 (dd, J=8.4, 5.0 Hz, 2H), 7.68 (t, J=8.0 Hz, 1H), 7.31 (d, J=7.7 Hz, 1H), 5.71-5.57 (m, 1H), 5.51-5.39 (m, 1H), 4.62 (dd, J=9.7, 7.5 Hz, 1H), 4.32 (dd, J=22.1, 12.6 Hz, 1H), 4.18-4.08 (m, 1H), 4.01 (dd, J=12.8, 3.0 Hz, 1H), 2.68-2.33 (m, 1H), 2.30-1.97 (m, 1H); $^{19}F$ NMR (282 MHz, DMSO-$d_6$) δ−58.51, −175.70; MS (ES+): 580.0 (M+1), (ES−): 578.0 (M−1); Analysis calculated for $C_{23}H_{18}BrF_4N_7O_2 \cdot HCl \cdot 2.5H_2O$: C, 41.74; H, 3.66; Cl, 5.36; N, 14.81. Found: C, 41.66; H, 3.49; Cl, 5.10; N, 14.74.

Scheme 27

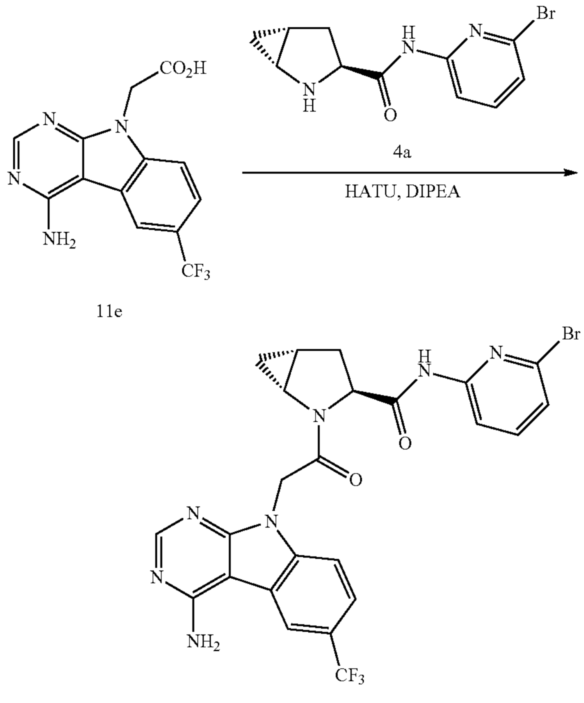

11e

27a

Preparation of (1R,3S,5R)-2-(2-(4-amino-6-(trifluoromethyl)-9H-pyrimido[4,5-b]indol-9-yl)acetyl)-N-(6-bromopyridin-2-yl)-2-azabicyclo[3.1.0]hexane-3-carboxamide (27a)

Compound 27a was prepared according to the procedure reported in step-3 of scheme-1, from TFA salt of 2-(4-amino-6-(trifluoromethyl)-9H-pyrimido[4,5-b]indol-9-yl)acetic acid (11e) (50 mg, 0.118 mmol) in DMF (10 mL) using HCl salt of (1R,3S,5R)—N-(6-bromopyridin-2-yl)-2-azabicyclo[3.1.0]hexane-3-carboxamide (4a) (37.5 mg, 0.118 mmol), HATU (53.8 mg, 0.141 mmol), DIPEA (76 mg, 0.589 mmol) and stirring at RT for 16 h. This gave after workup and purification by flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (1R,3S,5R)-2-(2-(4-amino-6-(trifluoromethyl)-9H-pyrimido[4,5-b]indol-9-yl)acetyl)-N-(6-bromopyridin-2-yl)-2-azabicyclo[3.1.0]hexane-3-carboxamide (27a) (42 mg, 62% yield) HCl salt as a white solid; $^1H$ NMR (300 MHz, DMSO-$d_6$) δ 10.75 (s, 1H, $D_2O$ exchangeable), 8.96 (s, 1H), 8.59 (s, 1H), 8.52 (s, 2H, $D_2O$ exchangeable), 8.00 (d, J=8.2 Hz, 1H), 7.85 (s, 2H), 7.70 (t, J=8.0 Hz, 11H), 7.31 (d, J=7.7 Hz, 1H), 5.80 (d, J=17.4 Hz, 1H), 5.46 (d, J=17.3 Hz, 1H), 4.41 (dd, J=9.1, 5.5 Hz, 1H), 3.95-3.88 (m, 1H), 2.40-2.28 (m, 1H), 2.28-2.13 (m, 1H), 1.99-1.82 (m, 1H), 1.14-1.00 (m, 1H), 0.81-0.74 (m, 1H); $^{19}F$ NMR (282 MHz, DMSO-$d_6$) δ−58.47; MS (ES+): 574.0 (M+1); (ES−): 572.0 (M−1): Analysis calculated for $C_{24}H_{19}BrF_3N_7O_2$·HCl·$2H_2O$: C, 44.56; H, 3.74; Br, 12.35; Cl, 5.48; N, 15.16. Found: C, 44.27; H, 3.69; Cl, 5.59; N, 14.75.

Scheme 28

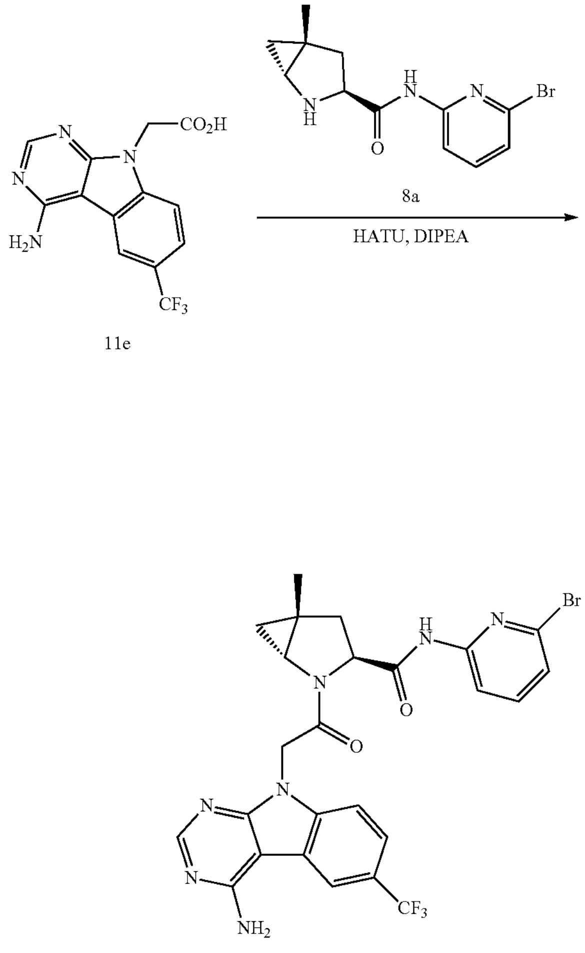

11e

8a

28a

Preparation of (1R,3S,5R)-2-(2-(4-amino-6-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (28a)

Compound 28a was prepared according to the procedure reported in step-3 of scheme-1, from TFA salt of 2-(4-amino-6-(trifluoromethyl)-9H-pyrimido[4,5-b]indol-9-yl)acetic acid (11e) (50 mg, 0.118 mmol) in DMF (5 mL) using HCl salt of (1R,3S,5R)—N-(6-bromopyridin-2-yl)-5-methyl-2-azabicyclo[3.1.0]hexane-3-carboxamide (8a) (39.2 mg, 0.118 mmol), HATU (53.8 mg, 0.141 mmol), DIPEA (76 mg, 0.589 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (28a) (50 mg, 72% yield) HCl salt as a white solid; $^1H$ NMR (300 MHz, DMSO-$d_6$) δ 10.76 (s, 1H, $D_2O$ exchangeable), 8.96 (s, 1H), 8.71-8.43 (m, 3H, 2H $D_2O$ exchangeable), 8.01 (d, J=8.2 Hz, 1H), 7.91-7.80 (m, 2H), 7.69 (t, J=8.0 Hz, 1H), 7.31 (d, J=7.7 Hz, 1H), 5.76 (d, J=17.4 Hz, 1H), 5.41 (d, J=17.3 Hz, 1H), 4.36 (dd, J=9.1, 6.0 Hz, 11H), 3.69 (dd, J=5.5, 2.4 Hz, 1H), 2.52-2.39 (m, 1H), 1.98 (dd, J=13.2, 5.9 Hz, 1H), 1.31 (s, 3H), 1.07-0.98 (m, 1H), 0.98-0.87 (m, 1H); $^{19}F$ NMR (282 MHz, DMSO-$d_6$) δ−58.53; MS (ES+): 588.0 (M+1), (ES−): 586.0 (M−1); Analysis calculated for $C_{25}H_{21}BrF_3N_7O_2$·1.1HCl·$1.75H_2O$: C, 45.49; H, 3.91; Cl, 5.91; N, 14.86. Found: C, 45.32; H, 3.90; Cl, 5.87; N, 14.62.

Scheme 29

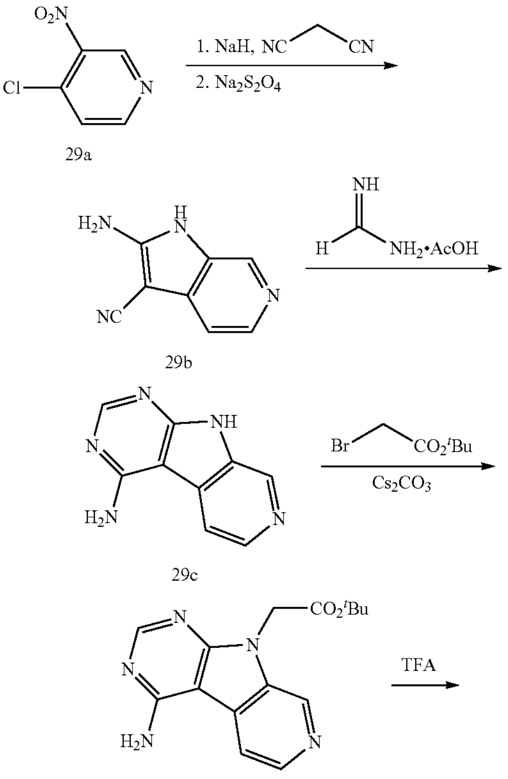

29a

29b

29c

29d

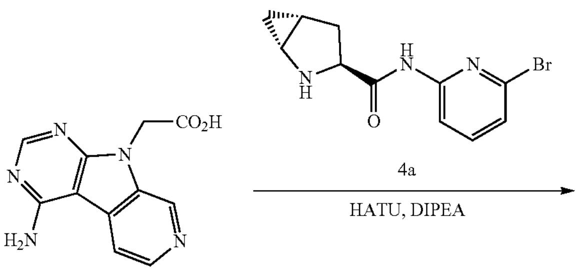

4a

29e

-continued

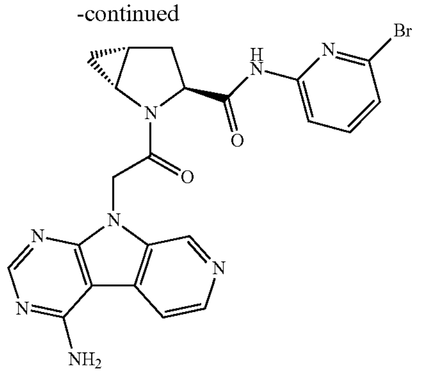

29f

Preparation of (1R,3S,5R)-2-(2-(4-amino-9H-pyrido[4',3':4,5]pyrrolo[2,3-d]pyrimidin-9-yl)acetyl)-N-(6-bromopyridin-2-yl)-2-azabicyclo[3.1.0]hexane-3-carboxamide (29f)

Step-1: Preparation of 2-amino-1H-pyrrolo[2,3-c]pyridine-3-carbonitrile (29b)

To NaH (2.55 g, 63.7 mmol) cooled to 0° C. was added portion-wise a solution of malononitrile (4.21 g, 63.7 mmol) in THF (40 mL). The resulting cloudy mixture was stirred at 0° C. for 1 h, followed by slow addition of 4-chloro-3-nitropyridine (29a) (5.00 g, 31.5 mmol) in THF (10 mL). The mixture was then heated at 60° C. under argon for 3 h. The cooled mixture was quenched with $H_2O$ (30 mL) and extracted with EtOAc (50 mL×5). The combined organic extract was washed with $H_2O$ (50 mL×2), brine (50 mL), dried over anhydrous $Na_2SO_4$, filtered and concentrated to provide 2-(3-nitropyridin-4-yl)malononitrile (8.77 g) as an orange-red solid, which was used as such in the next reaction; MS (ES+) 189 (M+1). (ES−) 187 (M−1). To 2-(3-nitropyridin-4-yl)malononitrile (4.40 g, 23.39 mmol) suspended in DMF (20 mL) at rt was added a solution $NaHCO_3$ (9.82 g, 117 mmol) in $H_2O$ (20 mL) followed by solid $Na_2S_2O_4$ (12.22 g, 70.2 mmol). The resulting mixture was stirred at rt for 16 h and filtered. The filtrate was extracted with EtOAc (50 mL×4). The combined organic extract was washed with $H_2O$ (30 mL×4) brine (30 mL), dried, filtered and concentrated in vacuum. The residue obtained was purified by flash column chromatography ($SiO_2$, 40 g, eluting with 0-20% DMA-80 in DCM) to provide 2-amino-1H-pyrrolo[2,3-c]pyridine-3-carbonitrile (29b) (0.673 g, 18% yield) as a beige solid. $^1H$ NMR (300 MHz, DMSO-$d_6$) δ 8.30 (s, 1H), 8.03 (d, J=5.3 Hz, 1H), 7.27 (s, 2H), 7.14 (d, J=5.3 Hz, 1H); MS (ES+): 159 (M+1), (ES−): 157 (M−1).

Step-2: Preparation of 9H-pyrido[4',3':4,5]pyrrolo[2,3-d]pyrimidin-4-amine (29c)

To a suspension of 2-amino-1H-pyrrolo[2,3-c]pyridine-3-carbonitrile (29b) (0.46 g, 2.91 mmol) in EtOH (10 mL) in a pressure vessel was added formamidine acetate (2.422 g, 23.27 mmol). The cloudy pale-yellow mixture was heated at 80° C. for 16 h, during which the cloudy mixture turned to a clear solution, and then a precipitate formed. The resulting cloudy pale-yellow mixture was hot-filtered. The filtered cake was washed thoroughly with boiling EtOH to provide the product 9H-pyrido[4',3':4,5]pyrrolo[2,3-d]pyrimidin-4-amine (29c) (0.35 g, 65.0% yield) as a pale-yellow solid. $^1H$ NMR (300 MHz, DMSO-$d_6$) δ 12.15 (s, 1H), 8.78 (s, 1H), 8.38 (d, J=5.3 Hz, 1H), 8.34 (s, 1H), 8.31 (d, J=5.4 Hz, 1H), 7.49 (s, 2H); MS (ES+): 186 (M+1), (ES−): 184 (M−1).

Step-3: Preparation of tert-butyl 2-(4-amino-9H-pyrido[4',3':4,5]pyrrolo[2,3-d]pyrimidin-9-yl)acetate (29d)

Compound 29d was prepared according to the procedure reported in step-1 of scheme-1, from 9H-pyrido[4',3':4,5]pyrrolo[2,3-d]pyrimidin-4-amine (29c) (0.35 g, 1.890 mmol) in DMF (25 mL) using tert-butyl 2-bromoacetate (0.369 g, 1.890 mmol), $Cs_2CO_3$ (1.232 g, 3.78 mmol) and stirring at RT for 16 h. This gave after workup and purification by flash column chromatography [silica gel (24 g), eluting with MeOH in DCM from 0-7%] tert-butyl 2-(4-amino-9H-pyrido[4',3':4,5]pyrrolo[2,3-d]pyrimidin-9-yl)acetate (29d) (0.27 g, 48% yield) as a pale yellow solid; $^1H$ NMR (300 MHz, DMSO-$d_6$) δ 8.94 (s, 1H), 8.45 (d, J=5.3 Hz, 1H), 8.39 (s, 1H), 8.38-8.34 (m, 1H), 7.66 (s, 2H), 5.22 (s, 2H), 1.41 (s, 9H); MS (ES+): 300 (M+1), (ES−1): 298 (M−1).

Step-4: Preparation of 2-(4-amino-9H-pyrido[4',3':4,5]pyrrolo[2,3-d]pyrimidin-9-yl)acetic acid (29e)

Compound 29e was prepared according to the procedure reported in step-2 of scheme-1, from tert-butyl 2-(4-amino-9H-pyrido[4',3':4,5]pyrrolo[2,3-d]pyrimidin-9-yl)acetate (29d) (270 mg, 0.902 mmol) in DCM (10 mL) using TFA (1029 mg, 9.02 mmol) and stirring at RT for 16 h. This gave after workup 2-(4-amino-9H-pyrido[4',3':4,5]pyrrolo[2,3-d]pyrimidin-9-yl)acetic acid (29e) (0.53 g) TFA salt as a white solid; $^1H$ NMR (300 MHz, DMSO-$d_6$) δ 9.51 (s, 1H), 8.96 (d, J=6.2 Hz, 1H), 8.78 (d, J=6.2 Hz, 1H), 8.56 (s, 1H), 5.35 (s, 2H); $^{19}F$ NMR (282 MHz, DMSO-$d_6$) δ−74.66. MS (ES+): 244 (M+1), (ES−): 242 (M−1).

Step-5: Preparation of (1R,3S,5R)-2-(2-(4-amino-9H-pyrido[4',3':4,5]pyrrolo[2,3-d]pyrimidin-9-yl)acetyl)-N-(6-bromopyridin-2-yl)-2-azabicyclo[3.1.0]hexane-3-carboxamide (29f)

Compound 29f was prepared according to the procedure reported in step-3 of scheme-1, from TFA salt of 2-(4-amino-9H-pyrido[4',3':4,5]pyrrolo[2,3-d]pyrimidin-9-yl)acetic acid (29e) (50 mg, 0.140 mmol) in DMF (5 mL) using HCl salt of (1R,3S,5R)—N-(6-bromopyridin-2-yl)-2-azabicyclo[3.1.0]hexane-3-carboxamide (4a) (70.0 mg, 0.177 mmol), HATU (63.9 mg, 0.168 mmol), DIPEA (90 mg, 0.7 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%](1R,3S,5R)-2-(2-(4-amino-9H-pyrido[4',3':4,5]pyrrolo[2,3-d]pyrimidin-9-yl)acetyl)-N-(6-bromopyridin-2-yl)-2-azabicyclo[3.1.0]hexane-3-carboxamide (29f) (57 mg, 80% yield) HCl salt as a white solid: $^1H$ NMR (300 MHz, DMSO-$d_6$) δ 10.80 (s, 1H), 9.53 (s, 1H), 9.13 (d, J=6.3 Hz, 1H), 8.94 (s, 2H), 8.80 (d, J=6.3 Hz, 11H), 8.69 (s, 1H), 8.00 (d, J=8.1 Hz, 1H), 7.70 (t, J=7.9 Hz, 1H), 7.31 (d, J=7.7 Hz, 1H), 5.96 (d, J=17.4 Hz, 1H), 5.53 (d, J=17.3 Hz, 1H), 4.47-4.44 (m, 1H), 3.91-3.86 (m, 1H), 2.40-2.29 (m, 11H), 2.29-2.13 (m, 1H), 2.00-1.85 (m, 1H), 1.16-1.00 (m, 1H), 0.98-0.80 (m, 1H); MS (ES+): 507/509 (M+1), (ES−): 505/507 (M−1).

Scheme 30

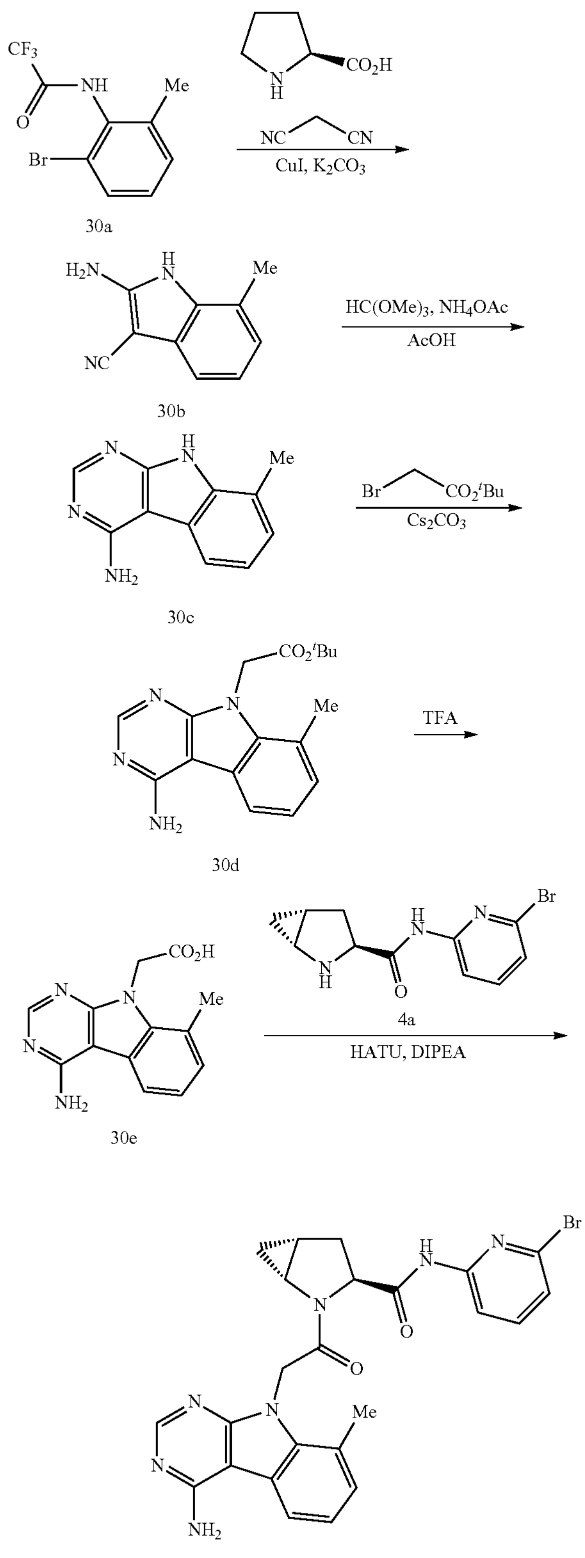

30a, 30b, 30c, 30d, 4a, 30e, 30f

Preparation of (1R,3S,5R)-2-(2-(4-amino-8-methyl-9H-pyrimido[4,5-b]indol-9-yl)acetyl)-N-(6-bromopyridin-2-yl)-2-azabicyclo[3.1.0]hexane-3-carboxamide (30f)

Step-1: Preparation of 2-amino-7-methyl-1H-indole-3-carbonitrile (30b)

Compound 30b was prepared according to the procedure reported in step-1 of scheme-11, from N-(2-bromo-6-methylphenyl)-2,2,2-trifluoroacetamide (30a) (7.45 g, 26.4 mmol; CAS #2007409-96-1) in DMSO (20 mL) using malononitrile (2.094 g, 31.7 mmol), L-proline (0.608 g, 5.28 mmol), CuI (0.503 g, 2.64 mmol), a solution of $K_2CO_3$ (7.30 g, 52.80 mmol) in water (20 mL) and heating at 60° C. for 16 h under an argon atmosphere. This gave after workup and purification [$SiO_2$ gel (40 g), eluting with EtOAc in hexane from 0-40%] 2-amino-7-methyl-1H-indole-3-carbonitrile (30b) (2.35 g, 52% yield) as a brown solid; $^1$H NMR (300 MHz, DMSO-$d_6$) δ 10.73 (s, 1H), 6.97 (d, J=7.6 Hz, 1H), 6.88 (t, J=7.5 Hz, 1H), 6.73 (d, J=7.3 Hz, 1H), 6.49 (s, 2H), 2.33 (s, 3H); MS (ES+): 172 (M+1); (ES−): 170 (M−1).

Step-2: Preparation of 8-methyl-9H-pyrimido[4,5-b]indol-4-amine (30c)

Compound 30c was prepared according to the procedure reported in step-1 of scheme-6, from 2-amino-7-methyl-1H-indole-3-carbonitrile (30b) (4.28 g, 25 mmol) using trimethyl orthoformate (26.5 g, 250 mmol). AcOH (4.50 g, 75 mmol) and $NH_4OAc$ (5.78 g, 75 mmol). This gave after workup 8-methyl-9H-pyrimido[4,5-b]indol-4-amine (30c) (4.24 g, 86% yield) as a pale-yellow solid; 1H NMR (300 MHz, DMSO-$d_6$) δ 11.81 (s, 1H), 8.26 (s, 1H), 8.10 (dd, J=7.4, 1.8 Hz, 1H), 7.21-7.02 (m, 4H), 2.54 (s, 3H). MS (ES+): 199 (M+1).

Step-3: Preparation of tert-butyl 2-(4-amino-8-methyl-9H-pyrimido[4,5-b]indol-9-yl)acetate (30d)

Compound 30d was prepared according to the procedure reported in step-1 of scheme-1, from 8-methyl-9H-pyrimido [4,5-b]indol-4-amine (30c) (3.07 g, 15.49 mmol) in DMF (20 mL) using tert-butyl 2-bromoacetate (3.02 g, 15.49 mmol) $Cs_2CO_3$ (6.06 g, 18.59 mmol) and stirring at RT for 16 h. This gave after workup and purification by flash column chromatography [silica gel (24 g), eluting with MeOH in DCM from 0-3%] tert-butyl 2-(4-amino-8-methyl-9H-pyrimido[4,5-b]indol-9-yl)acetate (30d) (3.52 g, 73% yield) as a pale yellow solid: $^1$H NMR (300 MHz, DMSO-$d_6$) δ 8.29 (s, 1H), 8.19 (dd, J=5.8, 3.4 Hz, 1H), 7.26 (s, 2H), 7.17 (d, J=2.6 Hz, 1H), 7.15 (s, 1H), 5.34 (s, 2H), 2.64 (s, 3H), 1.43 (s, 9H); MS (ES+): 313 (M+1); (ES−): 311 (M−1).

Step-4: Preparation of 2-(4-amino-8-methyl-9H-pyrimido[4,5-b]indol-9-yl)acetic acid (30e)

Compound 30e was prepared according to the procedure reported in step-2 of scheme-1, from tert-butyl 2-(4-amino-8-methyl-9H-pyrimido[4,5-b]indol-9-yl)acetate (30d) (0.12 g, 0.384 mmol) using TFA (438 mg, 3.84 mmol) in DCM (5 mL) and stirring at RT for 16 h. This gave after workup 2-(4-amino-8-methyl-9H-pyrimido[4,5-b]indol-9-yl)acetic acid (30e) (0.190 g) TFA salt as a yellow solid; $^1$H NMR (300 MHz, DMSO-$d_6$) δ 8.87-8.66 (m, 2H), 8.64 (s, 1H), 8.36 (dd, J=5.8, 3.4 Hz, 1H), 7.40-7.25 (m, 2H), 5.47 (s, 2H), 2.70 (s, 3H); $^{19}F$ NMR (282 MHz, DMSO-$d_6$) δ−74.60; MS (ES+): 257 (M+1), (ES−): 255 (M−1).

Step-5: Preparation of (1R,3S,5R)-2-(2-(4-amino-8-methyl-9H-pyrimido[4,5-b]indol-9-yl)acetyl)-N-(6-bromopyridin-2-yl)-2-azabicyclo[3.1.0]hexane-3-carboxamide (30f)

Compound 30f was prepared according to the procedure reported in step-3 of scheme-1, from TFA salt of 2-(4-amino-8-methyl-9H-pyrimido[4,5-b]indol-9-yl)acetic acid (30e) (50 mg, 0.135 mmol) in DMF (5 mL) using HCl salt of (1R,3S,5R)—N-(6-bromopyridin-2-yl)-2-azabicyclo[3.1.0]hexane-3-carboxamide (4a) (43.0 mg, 0.135 mmol), HATU (61.6 mg, 0.162 mmol) DIPEA (87 mg, 0.675 mmol) and stirring at RT for 16 h. This gave after workup and purification by flash column chromatography [silica gel (12 g), eluting with MeOH in DCM from 0-4%] followed by purification using reverse phase column chromatography [C18 column (100 g), eluting with ACN in water (containing 0.1% HCl) from 0-100%](1R,3S,5R)-2-(2-(4-amino-8-methyl-9H-pyrimido[4,5-b]indol-9-yl)acetyl)-N-(6-bromopyridin-2-yl)-2-azabicyclo[3.1.0]hexane-3-carboxamide (30f) (44 mg, 63% yield) HCl salt as a white solid; $^1H$ NMR (300 MHz, DMSO-$d_6$) δ 10.82 (s, 1H, $D_2O$ exchangeable), 8.82-8.54 (m, 3H, 2H $D_2O$ exchangeable), 8.42-8.28 (m, 1H), 8.00 (d, J=8.2 Hz, 1H), 7.70 (t, J=8.0 Hz, 1H), 7.38-7.24 (m, 3H), 5.93 (d, J=18.0 Hz, 1H), 5.65 (d, J=17.9 Hz, 1H), 4.42 (dd, J=9.0, 5.7 Hz, 1H), 3.96-3.90 (m, 1H), 2.71 (s, 3H), 2.43-2.28 (m, 1H), 2.25-2.12 (m, 1H), 1.99-1.83 (m, 1H), 1.14-0.99 (m, 1H), 0.74-0.59 (m, 1H); MS (ES+): 520.0 (M+1), (ES−): 518.0 (M−1); Analysis calculated for $C_{24}H_{22}BrN_7O_2 \cdot 1.1HCl \cdot 2.5H_2O$: C, 47.60; H, 4.68; Cl, 6.44; N, 16.19. Found: C, 47.64; H, 4.48; Cl, 6.39; N, 16.14.

Scheme 31

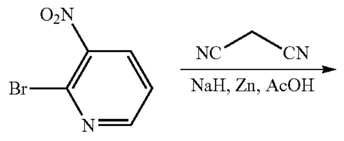

31a

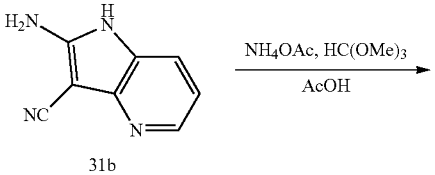

31b

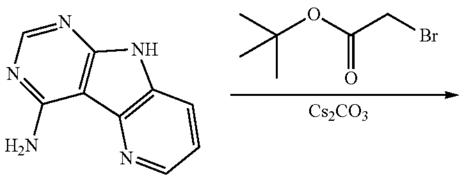

31c

-continued

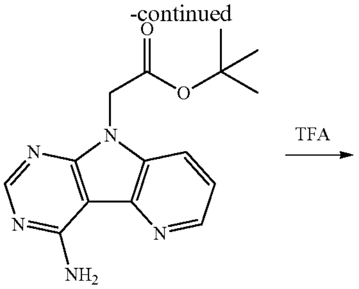

31d

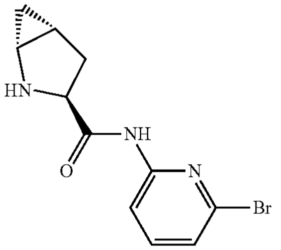

4a

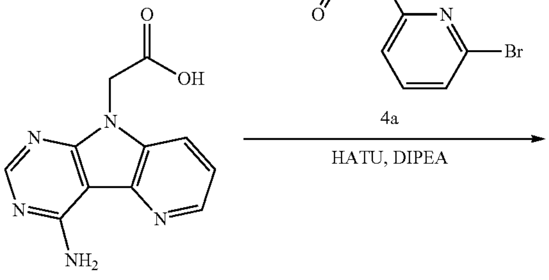

31e

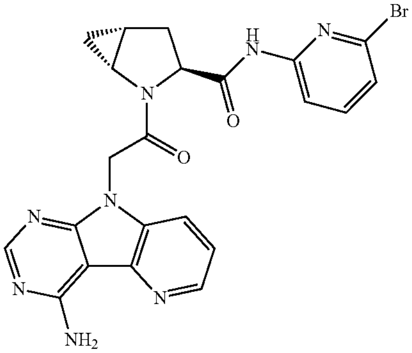

31f

Preparation of (1R,3S,5R)-2-(2-(4-amino-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (31f)

Step-1: Preparation of 2-amino-1H-pyrrolo[3,2-b]pyridine-3-carbonitrile (31b)

NaH (1.990 g, 49.8 mmol) was added portion-wise to a cold solution of malononitrile (3.29 g, 49.8 mmol) in THF (40 mL) at 0° C. The resulting cloudy mixture was stirred at 0° C. for 1 h, followed by slow addition of 2-bromo-3-nitropyridine (31a) (5.00 g, 24.63 mmol) in THF (10 mL). The mixture was then heated at 60° C. under argon for 3 h. The cooled mixture was quenched with $H_2O$ (30 mL) and extracted with EtOAc (50 mL×5). The combined organic extract was washed with $H_2O$ (50 mL×2), brine (50 mL), dried, filtered and concentrated to provide 2-(3-nitropyridin-2-yl)malononitrile (8.62 g) as an orange-red solid, which was used as such in the next reaction; MS (ES+): 189 (M+1), (ES−): 187 (M−1). A suspension of 2-(3-nitropyridin-2-yl) malononitrile (4.315 g, 22.93 mmol) zinc (7.50 g, 115 mmol) in acetic acid (27.5 g, 459 mmol) was heated at 60° C. for 2 h and filtered hot. The filtered cake was washed thoroughly with boiling EtOH. The filtrate was concentrated to dryness. The concentrate was suspended in $H_2O$ (50 mL), neutralized with 3 M aqueous NaOH until pH 7, and then extracted with EtOAc (50 mL×3). The combined extract was washed with $H_2O$ (30 mL×2), brine (30 mL), dried, filtered and concentrated in vacuum. The residue obtained was purified by flash column chromatography ($SiO_2$, 40 g, eluting with 0-20% DMA-80 in DCM) to provide 2-amino-1H-pyrrolo[3,2-b]pyridine-3-carbonitrile (31b) (320 mg, 9% yield) as beige solid; $^1$H NMR (300 MHz, DMSO-$d_6$) δ 10.82 (s, 1H), 8.04 (dd, J=5.0, 1.4 Hz, 1H), 7.36 (dd, J=7.8, 1.4 Hz, 1H), 7.16 (s, 2H), 6.86 (dd, J=7.8, 4.9 Hz, 1H); MS (ES+): 159 (M+1), (ES−): 157 (M−1).

Step-2: Preparation of 9H-pyrido[2',3':4,5]pyrrolo[2,3-d]pyrimidin-4-amine (31c)

Compound 31c was prepared according to the procedure reported in step-1 of scheme-6, from 2-amino-1H-pyrrolo[3,2-b]pyridine-3-carbonitrile (31b) (0.31 g, 1.960 mmol) using trimethyl orthoformate (4.16 g, 39.2 mmol), AcOH (0.589 g, 9.80 mmol) and $NH_4OAc$ (0.755 g, 9.80 mmol). This gave after workup and purification [silica gel (12 g), eluting with DMA-80 in DCM from 0-30%] 9H-pyrido[2',3':4,5]pyrrolo[2,3-d]pyrimidin-4-amine (31c) (100 mg, 28% yield) as a pale-yellow solid; $^1$H NMR (300 MHz, DMSO-$d_6$) δ 12.02 (d, J=2.0 Hz, 1H), 8.49 (dd, J=4.8, 1.4 Hz, 1H), 8.34 (s, 1H), 7.83 (dd, J=8.1, 1.4 Hz, 1H), 7.37 (dd, J=8.2, 4.8 Hz, 1H); MS (ES+): 186 (M+1), (ES−): 184 (M−1).

Step-3: Preparation of tert-butyl 2-(4-amino-9H-pyrido[2',3':4,5]pyrrolo[2,3-d]pyrimidin-9-yl)acetate (31d)

Compound 31d was prepared according to the procedure reported in step-2 of scheme-16, 9H-pyrido[2',3':4,5]pyrrolo[2,3-d]pyrimidin-4-amine (31c) (80 mg, 0.432 mmol) in DMF (2.5 mL) using tert-butyl 2-bromoacetate (0.077 mL, 0.518 mmol), $Cs_2CO_3$ (282 mg, 0.864 mmol) and stirring at RT for 1.5 h under nitrogen atmosphere and quenching by adding water. The solid separated was filtered and dried to give tert-butyl 2-(4-amino-9H-pyrido[2',3':4,5]pyrrolo[2,3-d]pyrimidin-9-yl)acetate (31d) (109 mg, 84% yield) as a pale yellow solid; $^1$H NMR (300 MHz, DMSO-$d_6$) δ 8.54 (dd, J=4.9, 1.3 Hz, 1H), 8.39 (s, 1H), 8.04 (dd, J=8.3, 1.3 Hz, 11H), 7.43 (dd, J=8.2, 4.8 Hz, 1H), 5.17 (s, 2H), 1.40 (s, 9H); MS (ES+): 300.1 (M+1).

Step-4: Preparation of 2-(4-amino-9H-pyrido[2',3':4,5]pyrrolo[2,3-d]pyrimidin-9-yl)acetic acid (31e)

Compound 31e was prepared according to the procedure reported in step-2 of scheme-1, from tert-butyl 2-(4-amino-9H-pyrido[2',3':4,5]pyrrolo[2,3-d]pyrimidin-9-yl)acetate (31d) (80 mg, 0.267 mmol) using 20% TFA in DCM (1534 μL, 4.01 mmol) and stirring at RT for 16 h. This gave after workup 2-(4-amino-9H-pyrido[2',3':4,5]pyrrolo[2,3-d]pyrimidin-9-yl)acetic acid (31e) (64 mg, 98% yield) TFA salt as a yellow solid; 1H NMR (300 MHz, DMSO-$d_6$) δ 8.65 (dd, J=4.9, 1.3 Hz, 1H), 8.55 (s, 1H), 8.25 (d, J=8.3 Hz, 1H), 7.56 (dd, J=8.3, 4.9 Hz, 1H), 5.28 (s, 2H); MS (ES+): 244.10 (M+1).

Step-5: Preparation of (1R,3S,5R)-2-(2-(4-amino-9H-pyrido[2',3':4.5]pyrrolo[2,3-d]pyrimidin-9-yl)acetyl)-N-(6-bromopyridin-2-yl)-2-azabicyclo[3.1.0]hexane-3-carboxamide (31f)

Compound 31f was prepared according to the procedure reported in step-3 of scheme-1, from TFA salt of 2-(4-amino-9H-pyrido[2',3':4,5]pyrrolo[2,3-d]pyrimidin-9-yl)acetic acid (31e) (60 mg, 0.247 mmol) in DMF (2 mL) using TFA salt of (1R,3S,5R)—N-(6-bromopyridin-2-yl)-2-azabicyclo[3.1.0]hexane-3-carboxamide (4a) (98.0 mg, 0.247 mmol). HATU (141 mg, 0.370 mmol), DIPEA (0.215 mL, 1.233 mmol) and stirring at RT for 1 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (31f) (79 mg, 63% yield) HCl salt as a white solid; $^1$H NMR (300 MHz, DMSO-$d_6$) δ 10.77 (s, 1H, $D_2O$ exchangeable), 8.97 (s, 1H, $D_2O$ exchangeable), 8.75-8.64 (m, 2H), 8.31 (d, J=8.4 Hz, 1H), 8.00 (d, J=8.2 Hz, 1H), 7.75-7.61 (m, 2H), 7.31 (d, J=7.7 Hz, 1H), 5.84 (d, J=17.4 Hz, 1H), 5.47 (d, J=17.3 Hz, 1H), 4.45-4.37 (m, 1H), 3.89 (ddd, J=7.5, 5.4, 2.4 Hz, 1H), 2.40-2.13 (m, 2H), 1.99-1.82 (m, 1H), 1.07 (dt, J=8.7, 5.4 Hz, 1H), 0.80 (td, J=5.2, 2.3 Hz, 1H); MS (ES+): 507.1 (M+1); (ES−): 505.0 (M−1); Analysis calculated for $C_{22}H_{19}BrNSO_2$ 1.75$H_2O$·1.2HCl: C, 45.35; H, 4.10; Cl, 7.30; N, 19.23. Found: C, 45.38; H, 4.02; Cl, 7.16; N, 18.95.

Scheme 32

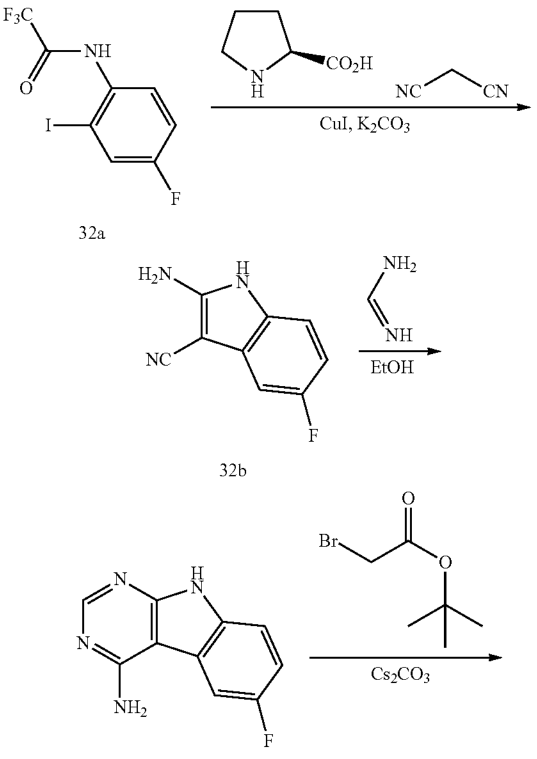

32a

32b

32c

-continued

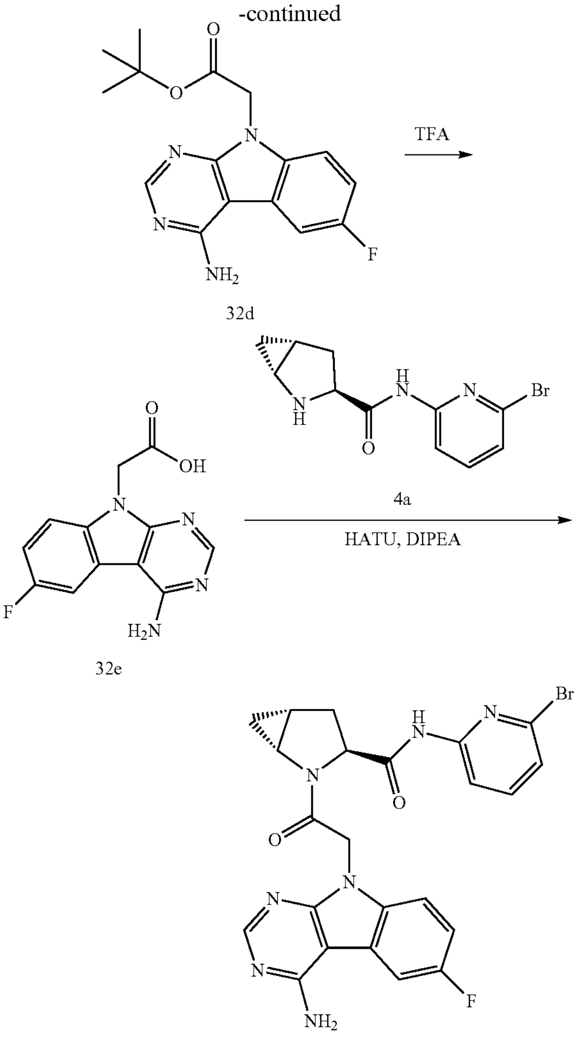

32d

4a

32e

32f

Preparation of (1R,3S,5R)-2-(2-(4-amino-6-fluoro-9H-pyrimido[4,5-b]indol-9-yl)acetyl)-N-(6-bromopyridin-2-yl)-2-azabicyclo[3.1.0]hexane-3-carboxamide (32f)

Step-1: Preparation of 2-amino-5-fluoro-1H-indole-3-carbonitrile (32b)

Compound 32b was prepared according to the procedure reported in step-1 of scheme-1, from 2,2,2-trifluoro-N-(4-fluoro-2-iodophenyl)acetamide (32a) (7.03 g, 21.1 mmol; CAS #784183-55-7) in DMSO (30 mL) using malononitrile (1.673 g, 25.3 mmol), L-proline (0.486 g, 4.22 mmol), CuI (0.402 g, 2.110 mmol), $K_2CO_3$ (5.83 g, 42.2 mmol) and heating at 60° C. for 15 h under an argon atmosphere. This gave after workup and purification [$SiO_2$ gel (80 g), eluting with EtOAc in hexane from 0-50%] 2-amino-5-fluoro-1H-indole-3-carbonitrile (32b) (2.657 g, 72% yield) as a brown solid; MS (ES+): 176.05 (M+1).

Step-2: Preparation of 6-fluoro-9H-pyrimido[4,5-b]indol-4-amine (32c)

Compound 32c was prepared according to the procedure reported in step-2 of scheme-29, from 2-amino-5-fluoro-1H-indole-3-carbonitrile (32b) (1.2 g, 6.85 mmol) in ethanol (30 mL) using formamidine acetate (5.76 g, 54.8 mmol) and refluxing for 40 h. This gave after workup 6-fluoro-9H-pyrimido[4,5-b]indol-4-amine (32c) as a brown solid (2.706 g) which was used as such in the next step; MS (ES+): 203.00 (M+1).

Step-3: Preparation of tert-butyl 2-(4-amino-6-fluoro-9H-pyrimido[4,5-b]indol-9H)acetate (32d)

Compound 32d was prepared according to the procedure reported in step-1 of scheme-1, from 6-fluoro-9H-pyrimido[4,5-b]indol-4-amine (32c) (346 mg, 1.71 mmol) in DMF (10 mL) using tert-butyl 2-bromoacetate (0.252 mL, 1.71 mmol), cesium carbonate (1.337 g) and stirring at RT for 47 h. This gave after workup and purification by flash column chromatography [silica gel (40 g), eluting with hexanes/10% methanol in ethyl acetate (1:0 to 1:1)] tert-butyl 2-(4-amino-6-fluoro-9H-pyrimido[4,5-b]indol-9-yl)acetate (32d) (160 mg, 30% yield) as a light yellow solid; 1H NMR (300 MHz, DMSO-$d_6$) δ 8.32-8.22 (m, 2H), 7.57 (dd, J=8.9, 4.5 Hz, 1H), 7.38 (s, 2H), 7.26 (td, J=9.2, 2.5 Hz, 1H), 5.12 (s, 2H), 1.39 (s, 9H); $^{19}$F NMR (282 MHz, DMSO-$d_6$) 5-122.42; MS (ES+): 317.10 (M+1).

Step-4: Preparation of 2-(4-amino-6-fluoro-9H-pyrimido[4,5-b]indol-9-yl)acetic acid (32e)

Compound 32e was prepared according to the procedure reported in step-2 of scheme-1, from tert-butyl 2-(4-amino-6-fluoro-9H-pyrimido[4,5-b]indol-9-yl)acetate (32d) (140 mg, 0.443 mmol) in DCM (10 mL) using TFA. The reaction mixture was concentrated to dryness to afford 2-(4-amino-6-fluoro-9H-pyrimido[4,5-b]indol-9-yl)acetic acid (32e) which used as such for the next step; MS (ES+): 261.10 (M+1); (ES−): 259.00 (M−1).

Step-5: Preparation of (1R,3S,5R)-2-(2-(4-amino-6-fluoro-9H-pyrimido[4,5-b]indol-9-yl)acetyl)-N-(6-bromopyridin-2-yl)-2-azabicyclo[3.1.0]hexane-3-carboxamide (32f)

Compound 32f was prepared according to the procedure reported in step-3 of scheme-1, from TFA salt of 2-(4-amino-6-fluoro-9H-pyrimido[4,5-b]indol-9-yl)acetic acid (32e) (0.443 mmol, from above step-4) in DMF (15 mL) using HCl salt of (1R,3S,5R)—N-(6-bromopyridin-2-yl)-2-azabicyclo[3.1.0]hexane-3-carboxamide (4a) (141.0 mg, 0.443 mmol), HATU (337 mg, 0.886 mmol) DIPEA (0.386 mL, 2.215 mmol) and stirring at RT for 16 h. This gave after workup and purification by flash column chromatography [silica gel (12 g), eluting with MeOH in DCM from 0-5%] followed by treating of product obtained with acetonitrile (2 mL) and 50 mM aq. HCl (8 mL) and lyophilization (1R,3S,5R)-2-(2-(4-amino-6-fluoro-9H-pyrimido[4,5-b]indol-9-yl)acetyl)-N-(6-bromopyridin-2-yl)-2-azabicyclo[3.1.0]hexane-3-carboxamide (32f) (53 mg, 23% yield) HCl salt as a light brown solid; $^1$H NMR (300 MHz, DMSO-$d_6$) δ 10.76 (s, 1H, $D_2O$ exchangeable), 8.73 (s, 2H, $D_2O$ exchangeable), 8.63 (s, 1H), 8.47 (dd, J=9.8, 2.5 Hz, 1H), 8.00 (d, J=8.1 Hz, 1H), 7.79-7.65 (m, 2H), 7.45 (td, J=9.2, 2.5 Hz, 1H), 7.32 (d, J=7.7 Hz, 1H), 5.78 (d, J=17.4 Hz, 1H), 5.43 (d, J=17.3 Hz, 1H), 4.41 (dd, J=9.0, 5.5 Hz, 1H), 4.02-3.82 (m, 1H), 2.41-2.12 (m, 2H), 1.99-1.79 (m, 1H), 1.16-0.97 (m, 1H), 0.82-0.71 (m, 1H); $^{19}$F NMR (282 MHz, DMSO-$d_6$) δ−119.89; MS (ES+): 524.10 & 526.10 (M+1); MS (ES−): 522.00 & 524.00 (M−1); Analysis calculated for $C_{23}H_{19}BrFN_7O_2 \cdot 1.2HCl \cdot 2.75H_2O$: C, 44.73; H, 4.19; N, 15.87; Cl, 6.89. Found: C, 44.84; H, 4.13; N, 15.51; Cl, 6.81.

Scheme 33

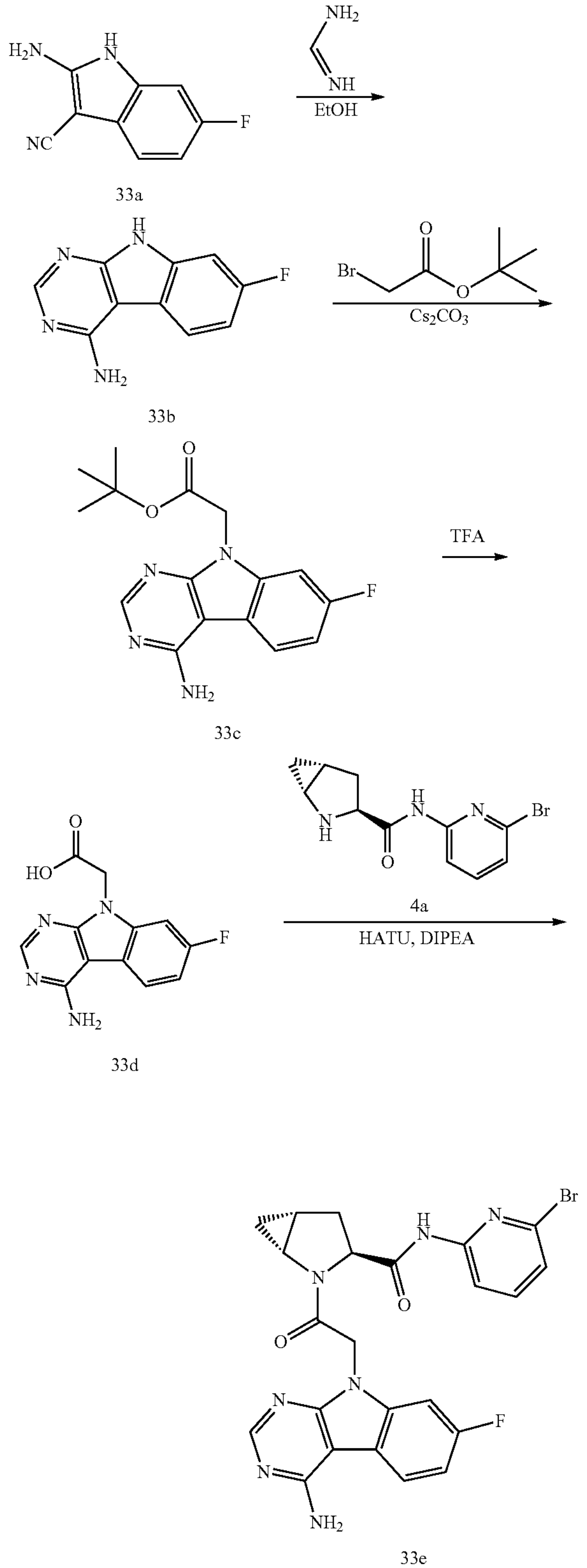

33e

Preparation of (1R,3S,5R)-2-(2-(4-amino-7-fluoro-9H-pyrimido[4,5-b]indol-9-yl)acetyl)-N-(6-bromopyridin-2-yl)-2-azabicyclo[3.1.0]hexane-3-carboxamide (33e)

Step-1: Preparation of 7-fluoro-9H-pyrimido[4,5-b]indol-4-amine (33b)

Compound 33b was prepared according to the procedure reported in step-2 of scheme-29, from 2-amino-6-fluoro-1H-indole-3-carbonitrile (33a) (1.2 g, 6.85 mmol; CAS #378236-80-7) in ethanol (30 mL) using formamidine acetate (5.76 g, 54.8 mmol) and refluxing for 20 h. This gave after workup 7-fluoro-9H-pyrimido[4,5-b]indol-4-amine (33b) as a brown solid (2.62 g) which was used as such in the next step; $^1$H NMR (300 MHz, DMSO-$d_6$) δ 8.29 (dd, J=8.7, 5.4 Hz, 1H), 8.23 (s, 1H), 7.78 (s, 1H), 7.22 (dd, J=9.7, 2.4 Hz, 1H), 7.10-7.01 (m, 1H); $^{19}$F NMR (282 MHz, DMSO-$d_6$) δ−116.72; MS (ES+): 203.10 (M+1).

Step-2: Preparation of tert-butyl 2-(4-amino-7-fluoro-9H-pyrimido[4,5-b]indol-9-yl)acetate (33c)

Compound 33c was prepared according to the procedure reported in step-1 of scheme-1, from 7-fluoro-9H-pyrimido[4,5-b]indol-4-amine (33b) (346 mg, 1.71 mmol) in DMF (10 mL) using tert-butyl 2-bromoacetate (0.252 mL, 1.71 mmol), cesium carbonate (1.337 g) and stirring at RT for 46 h. This gave after workup and purification by flash column chromatography [silica gel (40 g), eluting with hexanes/10% methanol in ethyl acetate (1:0 to 1:1)] tert-butyl 2-(4-amino-7-fluoro-9H-pyrimido[4,5-b]indol-9-yl)acetate (33c) (151 mg, 28% yield) as a light yellow solid; 1H NMR (300 MHz, DMSO-$d_6$) δ 8.35 (dd, J=8.7, 5.4 Hz, 1H), 8.28 (s, 1H), 7.53 (dd, J=10.2, 2.4 Hz, 1H), 7.31 (s, 2H), 7.17-7.04 (m, 1H), 5.11 (s, 2H), 1.40 (s, 9H); $^{19}$F NMR (282 MHz, DMSO-$d_6$) δ−116.10; MS (ES+): 317.20 (M+1).

Step-3: Preparation of 2-(4-amino-7-fluoro-9H-pyrimido[4,5-b]indol-9-yl)acetic acid (33d)

Compound 33d was prepared according to the procedure reported in step-2 of scheme-1, from tert-butyl 2-(4-amino-7-fluoro-9H-pyrimido[4,5-b]indol-9-yl)acetate (33c) (145 mg, 0.458 mmol) in DCM (10 mL) using TFA. This gave after workup 2-(4-amino-7-fluoro-9H-pyrimido[4,5-b]indol-9-yl)acetic acid (33d) which was used as such in next step; MS (ES+): 261.10 (M+1); (ES−): 259.00 (M−1).

Step-4: Preparation of (1R,3S,5R)-2-(2-(4-amino-7-fluoro-9H-pyrimido[4,5-b]indol-9-yl)acetyl)-N-(6-bromopyridin-2-yl)-2-azabicyclo[3.1.0]hexane-3-carboxamide (33e)

Compound 33e was prepared according to the procedure reported in step-3 of scheme-1, from TFA salt of 2-(4-amino-7-fluoro-9H-pyrimido[4,5-b]indol-9-yl)acetic acid (33d) (119 mg, 0.458 mmol) in DMF (15 mL) using HCl salt of (1R,3S,5R)—N-(6-bromopyridin-2-yl)-2-azabicyclo[3.1.0]hexane-3-carboxamide (4a) (146.0 mg, 0.458 mmol), HATU (348 mg, 0.916 mmol), DIPEA (0.399 mL, 2.29 mmol) and stirring at RT for 16 h. This gave after workup and purification by reverse phase column chromatography [C18 column (100 g), eluting with ACN in water (containing 0.1% HCl) from 0-100%] followed by purification using flash column chromatography [silica gel (12 g), eluting with MeOH in DCM from 0-5%], dissolving the product in acetonitrile (3 mL) and 0.1% aq. HCl (20 mL) followed by lyophilization (1R,3S,5R)-2-(2-(4-amino-7-fluoro-9H-pyrimido[4,5-b]indol-9-yl)acetyl)-N-(6-bromopyridin-2-yl)-2-azabicyclo[3.1.0]hexane-3-carboxamide (33e) (31 mg, 13% yield) HCl salt as a white solid; $^1$H NMR (300 MHz, DMSO-$d_6$) δ 10.77 (s, 1H, $D_2O$ exchangeable), 8.76-8.66 (m, 3H, $D_2O$ exchangeable), 8.63 (s, 1H), 8.56 (dd, J=8.8, 5.2 Hz, 1H), 8.00 (d, J=8.2 Hz, 1H), 7.75-7.63 (m, 2H), 7.37-7.25 (m, 2H), 5.76 (d, J=17.4 Hz, 11H), 5.40 (d, J=17.3 Hz, 1H), 4.42 (dd, J=9.1, 5.5 Hz, 1H), 3.95-3.84 (m, 1H), 2.42-2.12 (m, 2H), 2.02-1.76 (m, 1H), 1.12-0.99 (m, 1H), 0.89-0.75 (m, 1H); $^{19}$F NMR (282 MHz, DMSO-$d_6$) δ-113.65; MS (ES+): 524.10 & 526.10 (M+1); MS (ES−): 522.10 & 524.00 (M−1); Analysis calculated for $C_{21}H_{19}BrFN_7O_2$·1.1HCl·2.0$H_2O$: C, 46.00; H, 4.05; Cl, 6.49; N, 16.33. Found: C, 46.28; H, 4.10; Cl, 6.44; N, 15.96.

Scheme 34

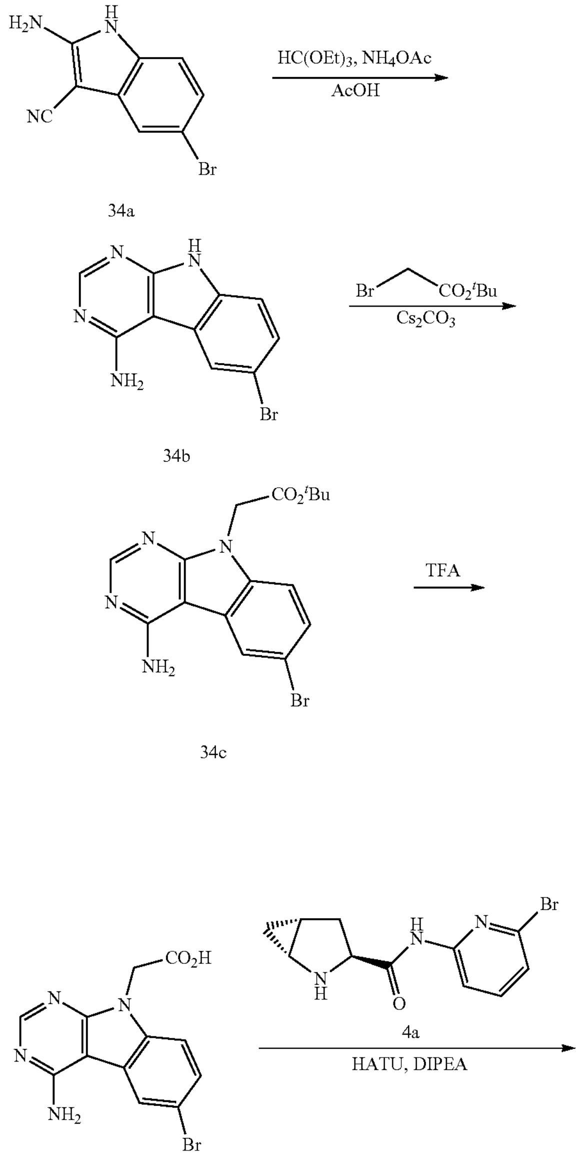

34a

34b

34c

34d

4a

-continued

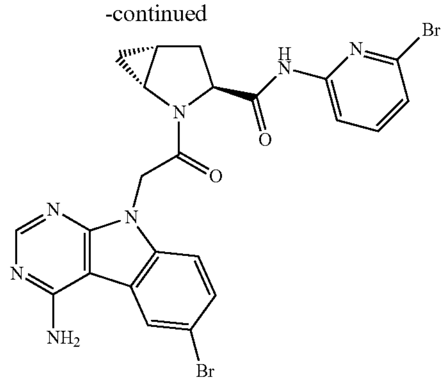

34e

Preparation of (1R,3S,5R)-2-(2-(4-amino-6-bromo-9H-pyrimido[4,5-b]indol-9-yl)acetyl)-N-(6-bromopyridin-2-yl)-2-azabicyclo[3.1.0]hexane-3-carboxamide (34e)

Step-1: Preparation of 6-bromo-9H-pyrimido[4,5-b]indol-4-amine (34b)

Compound 34b was prepared according to the procedure reported in step-1 of scheme-6, from 2-amino-5-bromo-1H-indole-3-carbonitrile (34a) (2.20 g, 9.32 mmol; CAS #1242140-64-2) using triethyl orthoformate (31.0 mL, 186 mmol), AcOH (2.66 mL, 46.6 mmol) and $NH_4OAc$ (3.59 g, 46.6 mmol). This gave after work up 6-bromo-9H-pyrimido[4,5-b]indol-4-amine (34b) (1.58 g, 64% yield) as a pale yellow solid; $^1$H NMR (300 MHz, DMSO-$d_6$) δ 11.99 (s, 1H), 8.58 (d, J=1.9 Hz, 1H), 8.26 (s, 1H), 7.48 (dd, J=8.6, 1.8 Hz, 1H), 7.39 (d, J=8.6 Hz, 1H), 7.30 (s, 2H); MS (ES+): 263/265 (M+1).

Step-2: Preparation of tert-butyl 2-(4-amino-6-bromo-9H-pyrimido[4,5-b]indol-9-yl)acetate (34c)

Compound 34c was prepared according to the procedure reported in step-1 of scheme-1, from 6-bromo-9H-pyrimido[4,5-b]indol-4-amine (34b) (1.58 g, 6.01 mmol) in DMF (20 mL) using tert-butyl 2-bromoacetate (1.171 g, 6.01 mmol), $Cs_2CO_3$ (2.348 g, 7.21 mmol) and stirring at RT for 16 h. This gave after workup and purification by flash column chromatography [silica gel (24 g), eluting with MeOH in DCM from 0-3%] tert-butyl 2-(4-amino-6-bromo-9H-pyrimido[4,5-b]indol-9-yl)acetate (34c) (2.265 g, 72% yield) as a pale orange solid; $^1$H NMR (300 MHz, DMSO-$d_6$) δ 8.64 (s, 1H), 8.31 (s, 1H), 7.56 (s, 2H), 7.44 (s, 2H), 5.13 (s, 2H), 1.40 (s, 9H); MS (ES+): 377/379 (M+1), (ES−): 375/377 (M−1).

Step-3: Preparation of 2-(4-amino-6-bromo-9H-pyrimido[4,5-b]indol-9-yl)acetic acid (34d)

Compound 34d was prepared according to the procedure reported in step-2 of scheme-1, from tert-butyl 2-(4-amino-6-bromo-9H-pyrimido[4,5-b]indol-9-yl)acetate (34c) (0.300 g, 0.795 mmol) in DCM (10 mL) using TFA (0.907 g, 7.95 mmol) and stirring at RT for 16 h. This gave after workup 2-(4-amino-6-bromo-9H-pyrimido[4,5-b]indol-9-yl)acetic acid (34d) (0.387 g) TFA salt as a yellow solid; $^1$H NMR (300 MHz, DMSO-$d_6$) δ 8.79 (s, 1H), 8.70-8.44 (m, 3H), 7.77 (d, J=8.8 Hz, 1H), 7.69 (dd, J=8.7, 1.8 Hz, 1H), 5.26 (s, 2H); MS (ES+): 321/323 (M+1), (ES−): 319/321 (M−1).

Step-4: Preparation of (1R,3S,5R)-2-(2-(4-amino-6-bromo-9H-pyrimido[4,5-b]indol-9-yl)acetyl)-N-(6-bromopyridin-2-yl)-2-azabicyclo[3.1.0]hexane-3-carboxamide (34e)

Compound 34e was prepared according to the procedure reported in step-3 of scheme-1, from TFA salt of 2-(4-amino-6-bromo-9H-pyrimido[4,5-b]indol-9-yl)acetic acid (34d) (50 mg, 0.115 mmol) in DMF (5 mL) using HCl salt of (1R,3S,5R)—N-(6-bromopyridin-2-yl)-2-azabicyclo[3.1.0]hexane-3-carboxamide (4a) (36.6 mg, 0.115 mmol), HATU (52.4 mg, 0.138 mmol) DIPEA (74.3 mg, 0.575 mmol) and stirring at RT for 16 h. This gave after workup and purification by flash column chromatography [silica gel (12 g), eluting with MeOH in DCM from 0-5%] followed by purification using reverse phase column chromatography [C18 column (100 g), eluting with ACN in water (containing 0.1% HCl) from 0-100%](1R,3S,5R)-2-(2-(4-amino-6-bromo-9H-pyrimido[4,5-b]indol-9-yl)acetyl)-N-(6-bromopyridin-2-yl)-2-azabicyclo[3.1.0]hexane-3-carboxamide (34e) (26 mg, 39% yield) HCl salt as a white solid; 1H NMR (300 MHz, DMSO-$d_6$) δ 10.75 (s, 1H, $D_2O$ exchangeable), 8.76 (d, J=3.1 Hz, 1H), 8.54 (d, J=5.2 Hz, 1H), 8.38 (s, 2H, $D_2O$ exchangeable), 8.00 (d, J=8.1 Hz, 1H), 7.75-7.58 (m, 3H), 7.32 (d, J=7.7 Hz, 1H), 5.73 (dd, J=17.7, 1.8 Hz, 1H), 5.39 (d, J=17.4 Hz, 1H), 4.40 (dd, J=9.2, 5.5 Hz, 1H), 3.94-3.86 (m, 1H), 2.38-2.26 (m, 1H), 2.26-2.15 (m, 1H), 1.96-1.84 (m, 1H), 1.13-0.97 (m, 1H), 0.81-0.72 (m, 1H); MS (ES+) 584.0 (M+1); (ES−): 582.0 (M−1); Analysis calculated for $C_{23}H_{19}Br_2N_7O_2\cdot HCl\cdot 2.25H_2O$: C, 41.71; H, 3.73; Cl, 5.35; N, 14.81. Found: C, 41.55; H, 3.58; Cl, 5.49; N, 14.65.

Scheme 35

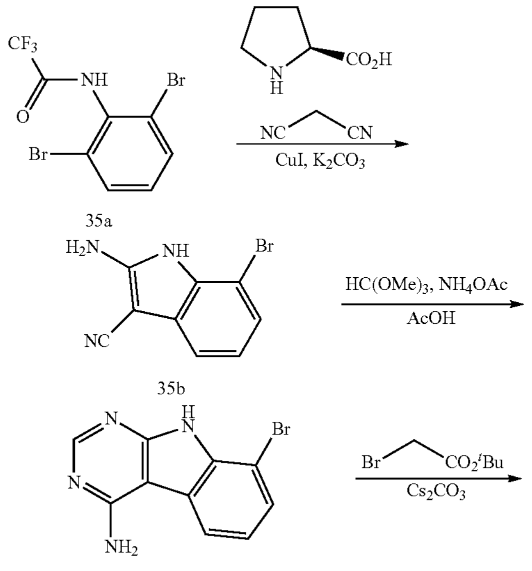

35a
35b
35c

-continued

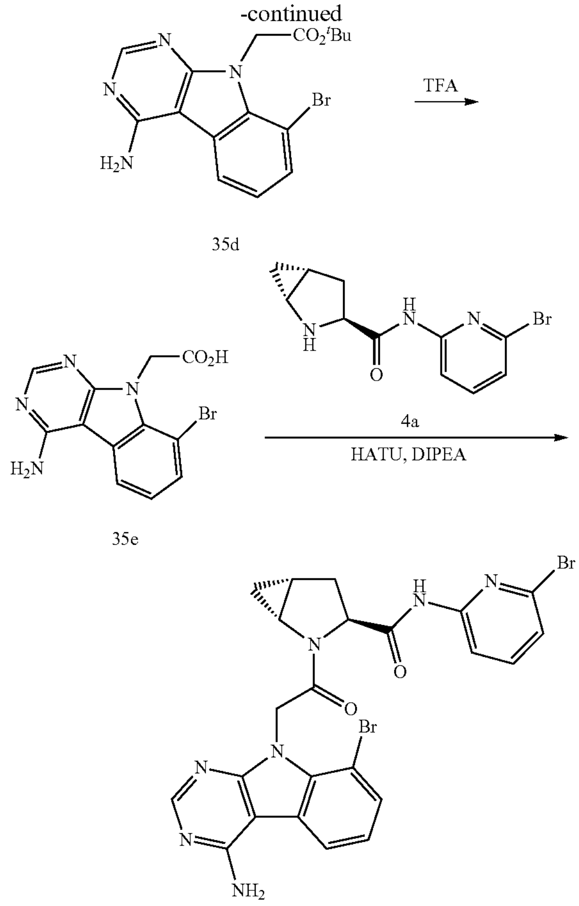

35d
35e
4a
35f

Preparation of (1R,3S,5R)-2-(2-(4-amino-8-bromo-9H-pyrimido[4,5-b]indol-9-yl)acetyl)-N-(6-bromopyridin-2-yl)-2-azabicyclo[3.1.0]hexane-3-carboxamide (35f)

Step-1: Preparation of 2-amino-7-bromo-1H-indole-3-carbonitrile (35b)

Compound 35b was prepared according to the procedure reported in step-1 of scheme-11, from N-(2,6-dibromophenyl)-2,2,2-trifluoroacetamide (35a) (7.79 g, 22.45 mmol; CAS #340034-49-3) in DMSO (20 mL) using malononitrile (1.780 g, 26.9 mmol), L-proline (0.517 g, 4.49 mmol), CuI (0.428 g, 2.245 mmol), $K_2CO_3$ (6.21 g, 44.9 mmol) and heating at 60° C. for 16 h under an argon atmosphere. This gave after workup and purification [$SiO_2$ gel (40 g), eluting with EtOAc in hexane from 0-40%] 2-amino-7-bromo-1H-indole-3-carbonitrile (35b) (4.18 g, 18% yield) as a pale orange solid; $^1$H NMR (300 MHz, DMSO-$d_6$) δ 10.91 (s, 1H), 7.15 (dd, J=7.7, 1.0 Hz, 1H), 7.11 (dd, J=7.9, 0.9 Hz, 1H), 6.93 (t, J=7.8 Hz, 1H), 6.69 (s, 2H); MS (ES+): 236; (ES−): 234 (M−1).

Step-2: Preparation of 8-bromo-9H-pyrimido[4,5-b]indol-4-amine (35c)

Compound 35c was prepared according to the procedure reported in step-1 of scheme-6, from 2-amino-7-bromo-1H- indole-3-carbonitrile (35b) (4.18 g, 17.71 mmol) using trimethyl orthoformate (37.6 mg, 354 mmol), AcOH (5.06 mL, 89 mmol) and $NH_4OAc$ (6.82 g, 89 mmol). This gave after workup 8-bromo-9H-pyrimido[4,5-b]indol-4-amine (35c) as a pale-yellow solid residue was used as such for the next step; $^1H$ NMR (300 MHz, DMSO-$d_6$) δ 11.97 (s, 1H), 8.32 (d, J=7.9 Hz, 2H), 7.56 (d, J=7.8 Hz, 1H), 7.30 (s, 2H), 7.17 (t, J=7.8 Hz, 1H).

Step-3: Preparation of tert-butyl 2-(4-amino-8-bromo-9H-pyrimido[4,5-b]indol-9-yl)acetate (35d)

Compound 35d was prepared according to the procedure reported in step-1 of scheme-1, from 8-bromo-9H-pyrimido[4,5-b]indol-4-amine (35c) (4.11 g, 15.62 mmol) in DMF (20 mL) using tert-butyl 2-bromoacetate (3.05 g, 15.62 mmol) $Cs_2CO_3$ (6.62 g, 20.31 mmol) and stirring at RT for 16 h. This gave after workup and purification by flash column chromatography [silica gel (24 g), eluting with MeOH in DCM from 0-3%] tert-butyl 2-(4-amino-8-bromo-9H-pyrimido[4,5-b]indol-9-yl)acetate (35d) (4.11 g, 88% yield) as a pale orange solid $^1H$ NMR (300 MHz, DMSO-$d_6$) δ 8.39 (d, J=7.8 Hz, 1H), 8.34 (s, 1H), 7.59 (d, J=7.8 Hz, 1H), 7.48 (s, 2H), 7.21 (t, J=7.8 Hz, 1H), 5.44 (s, 2H), 1.43 (s, 9H).

Step-4: Preparation of 2-(4-amino-8-bromo-9H-pyrimido[4,5-b]indol-9-yl)acetic acid (35e)

Compound 35e was prepared according to the procedure reported in step-2 of scheme-1, from tert-butyl 2-(4-amino-8-bromo-9H-pyrimido[4,5-b]indol-9-yl)acetate (35d) (0.250 g, 0.663 mmol) using TFA (1.511 g, 13.25 mmol) in DCM (20 mL) and stirring at RT for 16 h. This gave after workup 2-(4-amino-8-bromo-9H-pyrimido[4,5-b]indol-9-yl)acetic acid (35e) (0.356 g) TFA salt as a yellow solid; $^1H$ NMR (300 MHz, DMSO-$d_6$) δ 8.57 (s, 1H), 8.51 (d, J=7.9 Hz, 1H), 8.49-8.24 (m, 2H), 7.72 (d, J=7.8 Hz, 1H), 7.32 (t. J=7.9 Hz, 1H), 5.54 (s, 2H).

Step-5: Preparation of (1R,3S,5R)-2-(2-(4-amino-8-bromo-9H-pyrimido[4,5-b]indol-9-yl)acetyl)-N-(6-bromopyridin-2-yl)-2-azabicyclo[3.1.0]hexane-3-carboxamide (35f)

Compound 35f was prepared according to the procedure reported in step-3 of scheme-1, from TFA salt of 2-(4-amino-8-bromo-9H-pyrimido[4,5-b]indol-9-yl)acetic acid (35e) (50 mg, 0.115 mmol) in DMF (5 mL) using HCl salt of (1R,3S,5R)—N-(6-bromopyridin-2-yl)-2-azabicyclo[3.1.0]hexane-3-carboxamide (4a) (36.6 mg, 0.115 mmol), HATU (52.4 mg, 0.138 mmol), DIPEA (74.3 mg, 0.575 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-8-bromo-9H-pyrimido[4,5-b]indol-9-yl)acetyl)-N-(6-bromopyridin-2-yl)-2-azabicyclo[3.1.0]hexane-3-carboxamide (35f) (38 mg, 57% yield) HCl salt as a white solid: $^1H$ NMR (300 MHz, DMSO-$d_6$) δ 10.76 (s, 1H, $D_2O$ exchangeable), 8.59 (s, 1H), 8.55-8.32 (m, 3H, 2H $D_2O$ exchangeable), 8.00 (d, J=8.2 Hz, 1H), 7.70 (t, J=7.4 Hz, 2H), 7.30 (dt, J=7.9, 4.0 Hz, 2H), 5.98 (d, J=17.7 Hz, 1H), 5.84-5.72 (m, 1H), 4.41 (dd, J=9.0, 5.7 Hz, 1H), 3.91-3.87 (m, 1H), 2.40-2.25 (m, 1H), 2.25-2.15 (m, 1H), 2.00-1.84 (m, 1H), 1.12-0.99 (m, 1H), 0.81-0.69 (m, 1H); MS (ES+): 584.0 (M+1), (ES−): 582.0 (M−1); Analysis calculated for $C_{23}H_{18}Br_2N_7O_2 \cdot HCl \cdot 2H_2O$: C, 42.00; H, 3.68; Cl, 5.39; N, 14.91. Found: C, 41.98; H, 3.61; Cl, 5.08; N, 14.77.

Scheme 36

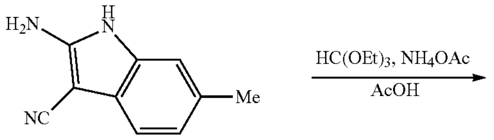

36a

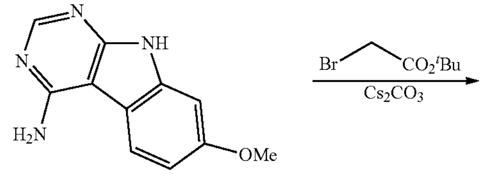

36c

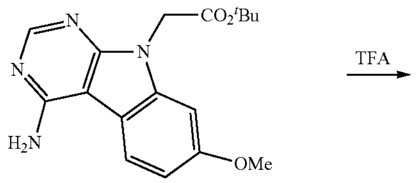

36c

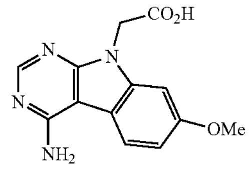

36d

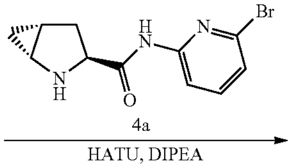

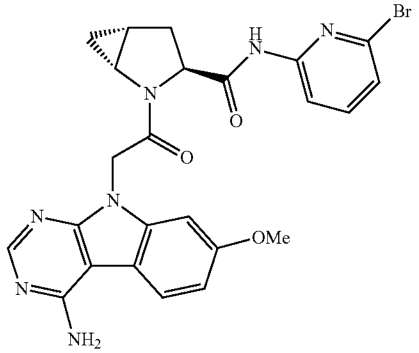

36e

Preparation of (1R,3S,5R)-2-(2-(4-amino-7-methoxy-9H-pyrimido[4,5-b]indol-9-yl)acetyl)-N-(6-bromopyridin-2-yl)-2-azabicyclo[3.1.0]hexane-3-carboxamide (36e)

Step-1: Preparation of 7-methoxy-9H-pyrimido[4,5-b]indol-4-amine (36b)

Compound 36b was prepared according to the procedure reported in step-1 of scheme-6, from 2-amino-6-methoxy-1H-indole-3-carbonitrile (36a) (2.50 g, 13.35 mmol; CAS #1016680-93-5) using triethyl orthoformate (44.4 mL, 267 mmol), AcOH (3.82 mL, 66.8 mmol) and $NH_4OAc$ (5.15 g, 66.8 mmol). This gave after work up 7-methoxy-9H-pyrimido[4,5-b]indol-4-amine (36b) (0.89 g, 31% yield) as a brown yellow solid; $^1H$ NMR (300 MHz, DMSO-$d_6$) δ 11.70 (s, 1H), 8.17 (d, J=9.9 Hz, 2H) 7.01 (s, 2H), 6.93 (d, J=2.3 Hz, 1H), 6.82 (dd, 1H), 3.83 (s, 3H).

Step-2: Preparation of tert-butyl 2-(4-amino-7-methoxy-9H-pyrimido[4,5-b]indol-9-yl)acetate (36c)

Compound 36c was prepared according to the procedure reported in step-1 of scheme-1, from 7-methoxy-9H-pyrimido[4,5-b]indol-4-amine (36b) (0.89 g, 4.15 mmol) in DMF (20 mL) using tert-butyl 2-bromoacetate (0.81 g, 4.15 mmol) and $CS_2CO_3$ (1.624 g, 4.99 mmol) and stirring at RT for 16 h. This gave after workup and purification by flash column chromatography [silica gel (24 g), eluting with MeOH in DCM from 0-3%] tert-butyl 2-(4-amino-7-methoxy-9H-pyrimido[4,5-b]indol-9-yl)acetate (36c) (0.83 g, 61% yield) as a pale yellow solid; $^1H$ NMR (300 MHz, DMSO-$d_6$) δ 8.22 (d, J=7.5 Hz, 2H), 7.22-7.07 (m, 3H), 6.89 (dd, J=8.6, 2.3 Hz, 1H), 5.10 (s, 2H), 3.85 (s, 3H), 1.41 (s, 9H).

Step-3: Preparation of 2-(4-amino-7-methoxy-9H-pyrimido[4,5-b]indol-9-yl)acetic acid (36d)

Compound 36d was prepared according to the procedure reported in step-2 of scheme-1, from tert-butyl 2-(4-amino-7-methoxy-9H-pyrimido[4,5-b]indol-9-yl)acetate (36c) (0.83 g, 2.53 mmol) in DMF (20 mL) using TFA (5.76 g, 50.6 mmol) and stirring at RT for 16 h. The reaction mixture was concentrated in vacuum to afford 2-(4-amino-7-methoxy-9H-pyrimido[4,5-b]indol-9-yl)acetic acid (36d) (1.18 g) TFA salt as a yellow solid; 1H NMR (300 MHz, DMSO-$d_6$) δ 8.61 (s, 2H), 8.59 (s, 1H), 8.41 (d, J=8.8 Hz, 1H), 7.46 (d, J=2.3 Hz, 1H), 7.07 (dd, J=8.8, 2.2 Hz, 1H), 5.28 (s, 2H), 3.89 (s, 3H).

Step-4: Preparation of (1R,3S,5R)-2-(2-(4-amino-7-methoxy-9H-pyrimido[4,5-b]indol-9-yl)acetyl)-N-(6-bromopyridin-2-yl)-2-azabicyclo[3.1.0]hexane-3-carboxamide (36e)

Compound 36e was prepared according to the procedure reported in step-3 of scheme-1, from TFA salt of 2-(4-amino-7-methoxy-9H-pyrimido[4,5-b]indol-9-yl)acetic acid (36d) (50 mg, 0.129 mmol) in DMF (5 mL) using HCl salt of (1R,3S,5R)—N-(6-bromopyridin-2-yl)-2-azabicyclo[3.1.0]hexane-3-carboxamide (4a) (41.2 mg, 0.129 mmol), HATU (59.1 mg, 0.155 mmol), DIPEA (84 mg, 0.647 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-7-methoxy-9H-pyrimido[4,5-b]indol-9-yl)acetyl)-N-(6-bromopyridin-2-yl)-2-azabicyclo[3.1.0]hexane-3-carboxamide (36e) (52 mg, 75% yield) HCl salt as a white solid; $^1H$ NMR (300 MHz, DMSO-$d_4$) δ 10.67 (s, 1H, $D_2O$ exchangeable), 8.48 (s, 1H), 8.35 (dd, J=12.4, 6.2 Hz, 3H, 2H $D_2O$ exchangeable), 7.94 (d, J=8.2 Hz, 1H), 7.64 (t, J=8.0 Hz, 1H), 7.25 (d, J=7.7 Hz, 1H), 7.19 (d, J=2.2 Hz, 1H), 6.97 (dd, J=8.7, 2.2 Hz, 1H), 5.64 (d, J=17.3 Hz, 1H), 5.35 (d, J=17.2 Hz, 1H), 4.40-4.29 (m, 1H), 3.88-3.80 (m, 4H), 2.34-2.23 (m, 1H), 2.23-2.10 (m, 1H), 1.92-1.80 (m, 1H), 1.06-0.95 (m, 1H), 0.74-0.64 (m, 1H); MS (ES+): 536.0 (M+1), (ES−): 534.0 (M−1); Analysis calculated for $C_{24}H_{22}BrN_7O_3 \cdot 1.2HCl \cdot 2.25H_2O$: C, 46.44; H, 4.50; Cl, 6.85; N, 15.80. Found: C, 46.47; H, 4.50; Cl, 6.46; N, 15.867.

Scheme 37

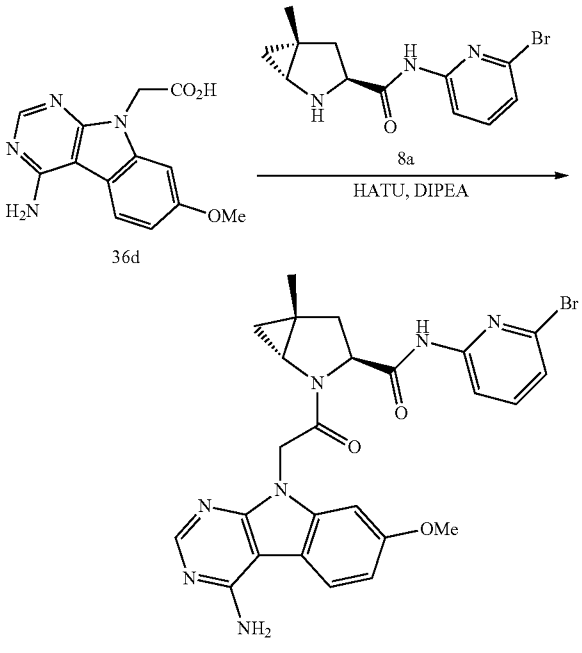

36d

8a

37a

Preparation of (1R,3S,5R)-2-(2-(4-amino-7-methoxy-9H-pyrimido[4,5-b]indol-9-yl)acetyl)-N-(6-bromopyridin-2-yl)-5-methyl-2-azabicyclo[3.1.0]hexane-3-carboxamide (37a)

Compound 37a was prepared according to the procedure reported in step-3 of scheme-1, from TFA salt of 2-(4-amino-7-methoxy-9H-pyrimido[4,5-b]indol-9-yl)acetic acid (36d) (100 mg, 0.259 mmol) in DMF (5 mL) using HCl salt of (1R,3S,5R)—N-(6-bromopyridin-2-yl)-5-methyl-2-azabicyclo[3.1.0]hexane-3-carboxamide (8a) (86 mg, 0.259 mmol), HATU (118 mg, 0.311 mmol), DIPEA (167 mg, 1.294 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-7-methoxy-9H-pyrimido[4,5-b]indol-9-yl)acetyl)-N-(6-bromopyridin-2-yl)-5-methyl-2-azabicyclo[3.1.0]hexane-3-carboxamide (37a) (85 mg, 60% yield) HCl salt as a white solid; $^1$H NMR (300 MHz, DMSO-$d_6$) δ 10.73 (s, 1H, $D_2O$ exchangeable), 8.55 (s, 1H), 8.46 (s, 2H, $D_2O$ exchangeable), 8.39 (d, J=8.8 Hz, 1H), 8.01 (d, J=8.2 Hz, 1H), 7.70 (t, J=8.0 Hz, 1H), 7.32 (d, J=7.7 Hz, 1H), 7.26 (d, J=2.3 Hz, 1H), 7.04 (dd, J=8.7, 2.3 Hz, 1H), 5.67 (d, J=17.3 Hz, 1H), 5.37 (d, J=17.3 Hz, 1H), 4.37 (dd, J=9.2, 5.9 Hz, 1H), 3.87 (s, 3H), 3.69 (dd, J=5.5, 2.3 Hz, 1H), 2.54-2.47 (m, 1H), 1.99 (dd, J=13.2, 5.9 Hz, 1H), 1.31 (s, 3H), 1.07-0.97 (m, 1H), 0.96-0.83 (m, 1H); MS (ES+): 550.0 (M+1); (ES−): 548.0 (M−1).

Scheme 38

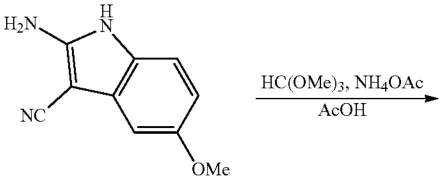

38a

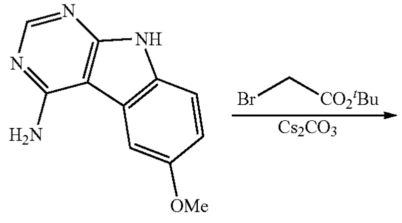

38b

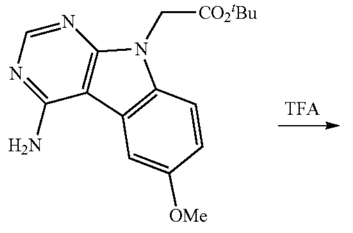

38c

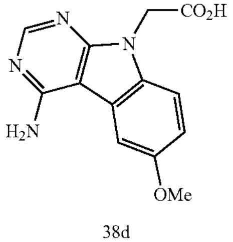

38d

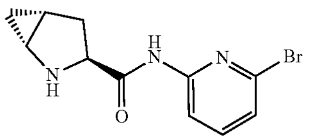

4a

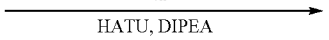

-continued

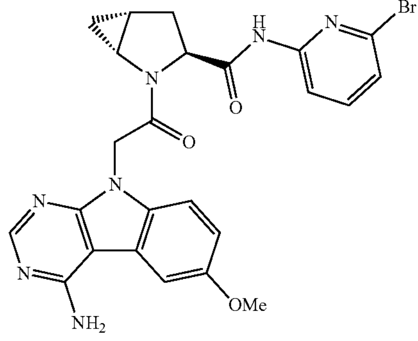

38e

Preparation of (1R,3S,5R)-2-(2-(4-amino-6-methoxy-9H-pyrimido[4,5-b]indol-9-yl)acetyl)-N-(6-bromopyridin-2-yl)-2-azabicyclo[3.1.0]hexane-3-carboxamide (38e)

Step-1: Preparation of 6-methoxy-9H-pyrimido[4,5-b]indol-4-amine (38b)

Compound 38b was prepared according to the procedure reported in step-1 of scheme-6, from 2-amino-5-methoxy-1H-indole-3-carbonitrile (38a) (3.10 g, 16.56 mmol; CAS #1304143-87-0) using trimethyl orthoformate (35.1 g, 331 mmol), AcOH (4.74 mL, 83 mmol) and $NH_4OAc$ (6.38 g, 83 mmol). This gave after work up 6-methoxy-9H-pyrimido[4,5-b]indol-4-amine (38b) (2.78 g, 78% yield) as a pale yellow solid; $^1$H NMR (300 MHz, DMSO-$d_6$) δ 11.62 (s, 1H), 8.20 (s, 1H), 7.85 (d, J=2.4 Hz, 1H), 7.32 (d, J=8.7 Hz, 1H), 7.17 (s, 2H), 6.96 (dd, J=8.7, 2.4 Hz, 1H), 3.85 (s, 3H). MS (ES+): 215 (M+1). (ES−): 213 (M−1).

Step-2: Preparation of tert-butyl 2-(4-amino-6-methoxy-9H-pyrimido[4,5-b]indol-9-yl)acetate (38c)

Compound 38c was prepared according to the procedure reported in step-1 of scheme-1, from 6-methoxy-9H-pyrimido[4,5-b]indol-4-amine (38b) (0.59 g, 2.75 mmol) in DMF (25 mL) using tert-butyl 2-bromoacetate (0.537 g, 2.75 mmol) $Cs_2CO_3$ (1.077 g, 3.30 mmol) and stirring at RT for 16 h. This gave after workup and purification by flash column chromatography [silica gel (24 g), eluting with MeOH in DCM from 0-3%] tert-butyl 2-(4-amino-6-methoxy-9H-pyrimido[4,5-b]indol-9-yl)acetate (38c) (0.56 g, 62% yield) as a pale yellow solid; $^1$H NMR (300 MHz, DMSO-$d_6$) δ 8.25 (s, 1H), 7.91 (d, J=2.4 Hz, 1H), 7.45 (d, J=8.8 Hz, 1H), 7.31 (s, 2H), 7.02 (dd, J=8.8, 2.4 Hz, 1H), 5.07 (s, 2H), 3.87 (s, 3H), 1.40 (s, 9H); MS (ES+): 329 (M+1), (ES−): 327 (M−1).

Step-3: Preparation of 2-(4-amino-6-methoxy-9H-pyrimido[4,5-b]indol-9-yl)acetic acid (38d)

Compound 38d was prepared according to the procedure reported in step-2 of scheme-1, from tert-butyl 2-(4-amino-6-methoxy-9H-pyrimido[4,5-b]indol-9-yl)acetate (38c) (0.56 g, 1.705 mmol) in DCM (20 mL) using TFA (1.945 g, 17.05 mmol) and stirring at RT for 16 h. This gave after workup 2-(4-amino-6-methoxy-9H-pyrimido[4,5-b]indol-9-yl)acetic acid (38d) (0.68 g) TFA salt as a yellow solid; $^1$H NMR (300 MHz, DMSO-$d_6$) δ 8.69-8.44 (m, 3H), 8.05 (d, J=2.4 Hz, 1H), 7.70 (d, J=9.0 Hz, 1H), 7.17 (dd, J=8.9, 2.4 Hz, 1H), 5.23 (s, 2H), 3.89 (s, 3H). $^{19}F$ NMR (282 MHz, DMSO-$d_6$) δ-74.16; MS (ES+): 273 (M+1), (ES-): 271 (M-1).

Step-4: Preparation of (1R,3S,5R)-2-(2-(4-amino-6-methoxy-9H-pyrimido[4,5-b]indol-9-yl)acetyl)-N-(6-bromopyridin-2-yl)-2-azabicyclo[3.1.0]hexane-3-carboxamide (38e)

Compound 38e was prepared according to the procedure reported in step-3 of scheme-1, from TFA salt of 2-(4-amino-6-methoxy-9H-pyrimido[4,5-b]indol-9-yl)acetic acid (38d) (50 mg, 0.129 mmol) in DMF (5 mL) using HCl salt of (1R,3S,5R)—N-(6-bromopyridin-2-yl)-2-azabicyclo[3.1.0]hexane-3-carboxamide (4a) (41.2 mg, 0.0.129 mmol), HATU (59.1 mg, 0.155 mmol), DIPEA (84 mg, 0.647 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-methoxy-9H-pyrimido[4,5-b]indol-9-yl)acetyl)-N-(6-bromopyridin-2-yl)-2-azabicyclo[3.1.0]hexane-3-carboxamide (38e) (41 mg, 59% yield) HCl salt as a white solid; $^1H$ NMR (300 MHz, DMSO-$d_6$) δ 10.75 (s, 1H), 8.81 (s, 2H), 8.60 (s, 1H), 8.07 (s, 1H), 7.99 (d, J=8.1 Hz, 1H), 7.69 (t, J=8.0 Hz, 1H), 7.61 (d, J=9.0 Hz, 1H), 7.31 (d, J=7.7 Hz, 1H), 7.18 (d, J=8.9 Hz, 1H), 5.71 (d, J=17.3 Hz, 1H), 5.39 (d, J=17.2 Hz, 1H), 4.40 (dd, J=9.0, 5.5 Hz, 1H), 3.90-3.86 (m, 4H), 2.40-2.27 (m, 1H), 2.27-2.13 (m, 1H), 1.98-1.83 (m, 1H), 1.12-1.00 (m, 1H), 0.84-0.70 (m, 1H); MS (ES+): 536/538 (M+1), (ES-): 534/536 (M-1); Analysis calculated for $C_{24}H_{22}BrN_7O_3 \cdot HCl \cdot 2.75H_2O$: C, 46.31; H, 4.62; Cl, 5.70; N, 15.75. Found: C, 46.48; H, 4.40; Cl, 5.45; N, 15.18.

Scheme 39

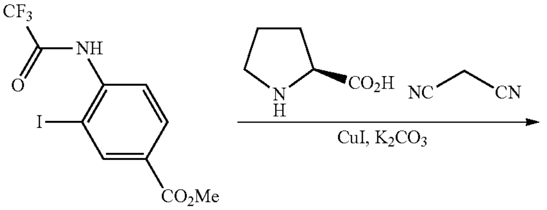

39a

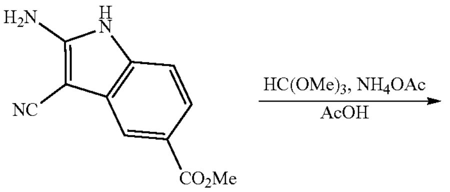

39b

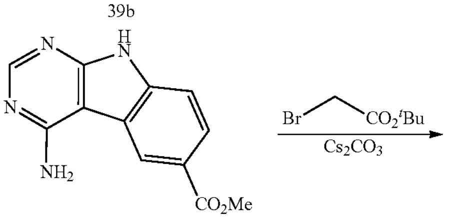

39c

-continued

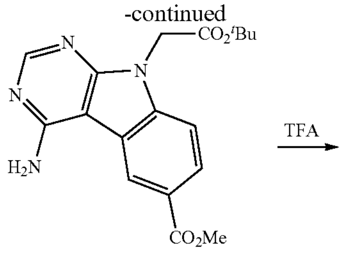

39d

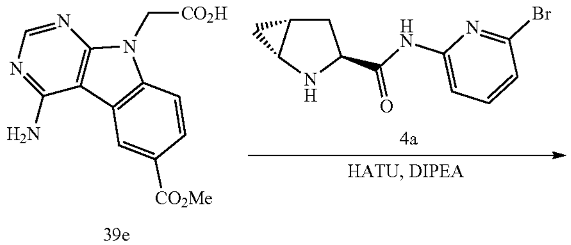

39e

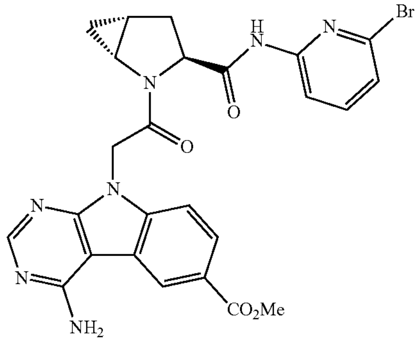

39f

Preparation of methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-6-carboxylate (39)

Step-1: Preparation of methyl 2-amino-3-cyano-1H-indole-5-carboxylate (39b)

Compound 39b was prepared according to the procedure reported in step-1 of scheme-11, from methyl 3-iodo-4-(2,2,2-trifluoroacetamido)benzoate (39a) (6.61 g, 17.72 mmol; CAS #848485-43-8) in DMSO (20 mL) using malononitrile (1.405 g, 21.26 mmol), L-proline (0.408 g, 3.54 mmol), CuI (0.337 g, 1.772 mmol), $K_2CO_3$ (4.90 g, 35.4 mmol) and heating at 60° C. for 16 h under an argon atmosphere. This gave after workup and purification [$SiO_2$ gel (40 g), eluting with EtOAc in hexane from 0-40%] methyl 2-amino-3-cyano-1H-indole-5-carboxylate (39b) (2.94 g, 77% yield) as a brown solid: 1H NMR (300 MHz, DMSO-$d_6$) δ 11.12 (s, 1H), 7.73 (d, J=1.6 Hz, 1H), 7.58 (dd, J=8.2, 1.7 Hz, 1H), 7.22 (d, J=8.3 Hz, 1H), 7.06 (s, 2H), 3.83 (s, 3H); MS (ES+): 216, (ES-): 214 (M-1).

Step-2: Preparation of methyl 4-amino-9H-pyrimido[4,5-b]indole-6-carboxylate (39c)

Compound 39c was prepared according to the procedure reported in step-1 of scheme-6, from methyl 2-amino-3-cyano-1H-indole-5-carboxylate (39b) (2.94 g, 13.66 mmol)

using trimethyl orthoformate (29.0 g, 273 mmol), AcOH (3.91 mL, 68.3 mmol) and $NH_4OAc$ (5.27 g, 68.3 mmol). The pale-yellow solid residue obtained after workup was used as such for the next step; $^1H$ NMR (300 MHz, DMSO-$d_6$) δ 12.25 (s, 1H), 8.95 (s, 1H), 8.30 (s, 1H), 7.99 (dd, J=8.5, 1.6 Hz, 1H), 7.52 (d, J=8.5 Hz, 1H), 7.42 (s, 2H), 3.89 (s, 3H).

Step-3: Preparation of methyl 4-amino-9-(2-(tert-butoxy)-2-oxoethyl)-9H-pyrimido[4,5-b]indole-6-carboxylate (39d)

Compound 39d was prepared according to the procedure reported in step-1 of scheme-1, from methyl 4-amino-9H-pyrimido[4,5-b]indole-6-carboxylate (39c) (2.68 g, 11.06 mmol) in DMF (20 mL) using tert-butyl 2-bromoacetate (2.158 g, 11.06 mmol), $Cs_2CO_3$ (4.33 g, 13.28 mmol) and stirring at RT for 16 h. This gave after workup and purification by flash column chromatography [silica gel (24 g), eluting with MeOH in DCM from 0-3%] methyl 4-amino-9-(2-(tert-butoxy)-2-oxoethyl)-9H-pyrimido[4,5-b]indole-6-carboxylate (39d) (2.50 g, 63% yield) as a pale orange solid; $^1H$ NMR (300 MHz, DMSO-$d_6$) δ 9.00 (d, J=1.6 Hz, 1H), 8.34 (s, 1H), 8.04 (dd, J=8.6, 1.6 Hz, 1H), 7.69 (d, J=8.6 Hz, 1H), 7.54 (s, 2H), 5.18 (s, 2H), 3.91 (s, 3H), 1.40 (s, 9H).

Step-4: Preparation of 2-(4-amino-6-(methoxycarbonyl)-9H-pyrimido[4,5-b]indol-9-yl)acetic acid (39e)

Compound 39e was prepared according to the procedure reported in step-2 of scheme-1, from methyl 4-amino-9-(2-(tert-butoxy)-2-oxoethyl)-9H-pyrimido[4,5-b]indole-6-carboxylate (39d) (2.50 g, 7.02 mmol) using TFA (16 g, 140 mmol) in DCM (20 mL) and stirring at RT for 16 h. This gave after workup 2-(4-amino-6-(methoxycarbonyl)-9H-pyrimido[4,5-b]indol-9-yl)acetic acid (39e) (3.70 g) TFA salt as a yellow solid; $^1H$ NMR (300 MHz, DMSO-$d_6$) δ 9.16 (d, J=1.6 Hz, 1H), 8.65 (s, 2H), 8.60 (s, 1H), 8.13 (dd, J=8.6, 1.6 Hz, 1H), 7.89 (d, J=8.7 Hz, 1H), 5.31 (s, 2H), 3.93 (s, 3H); $^{19}F$ NMR (282 MHz, DMSO-$d_6$) δ−74.65.

Step-5: Preparation of methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-6-carboxylate (39f)

Compound 39f was prepared according to the procedure reported in step-3 of scheme-1, from TFA salt of 2-(4-amino-6-(methoxycarbonyl)-9H-pyrimido[4,5-b]indol-9-yl)acetic acid (39e) (50 mg, 0.121 mmol) in DMF (5 mL) using HCl salt of (1R,3S,5R)—N-(6-bromopyridin-2-yl)-2-azabicyclo[3.1.0]hexane-3-carboxamide (4a) (38.5 mg, 0.121 mmol), HATU (55.1 mg, 0.145 mmol), DIPEA (78 mg, 0.603 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-6-carboxylate (39f) (53 mg, 78% yield) HCl salt as a white solid: $^1H$ NMR (300 MHz, DMSO-$d_6$) δ 10.76 (s, 1H, $D_2O$ exchangeable), 9.13 (s, 1H), 8.59 (s, 1H), 8.54 (s, 2H, $D_2O$ exchangeable), 8.12 (dd, J=8.7, 1.6 Hz, 1H), 8.00 (d, J=8.1 Hz, 1H), 7.77 (d, J=8.8 Hz, 1H), 7.70 (t, J=8.0 Hz, 1H), 7.31 (d, J=7.7 Hz, 1H), 5.79 (d, J=17.4 Hz, 1H), 5.44 (d, J=17.4 Hz, 1H), 4.41 (dd, J=8.9, 5.5 Hz, 1H), 3.92 (s, 4H), 2.38-2.28 (m, 1H), 2.28-2.14 (m, 1H), 1.99-1.84 (m, 1H), 1.14-0.97 (m, 1H), 0.84-0.74 (m, 1H); MS (ES+): 564.0 (M+1), (ES−): 562.0 (M−1): Analysis calculated for $C_{25}H_{22}BrN_7O_4 \cdot HCl \cdot 2.75H_2O$: C, 46.17; H, 4.42; Cl, 5.45; N, 15.08. Found: C, 46.19; H, 4.27; Cl, 5.68; N, 14.87.

Scheme 40

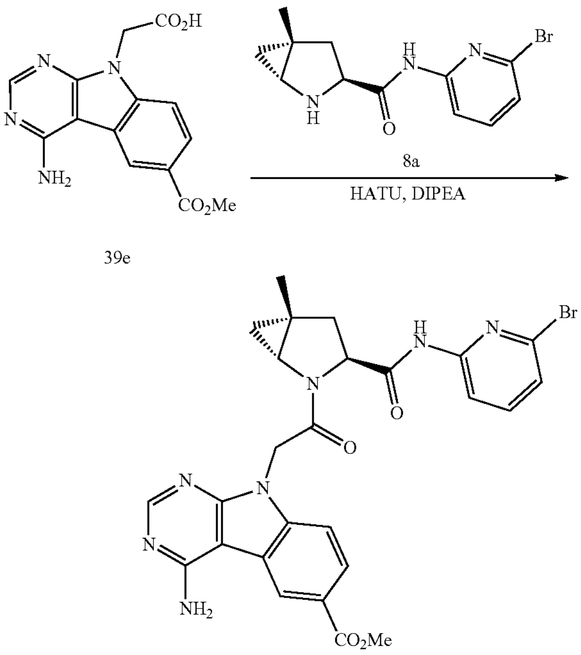

39e

8a

40a

Preparation of methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-6-carboxylate (40a)

Compound 40a was prepared according to the procedure reported in step-3 of scheme-1, from TFA salt of 2-(4-amino-6-(methoxycarbonyl)-9H-pyrimido[4,5-b]indol-9-yl)acetic acid (39e) (100 mg, 0.241 mmol) in DMF (5 mL) using HCl salt of (1R,3S,5R)—N-(6-bromopyridin-2-yl)-5-methyl-2-azabicyclo[3.1.0]hexane-3-carboxamide (8a) (80 mg, 0.241 mmol), HATU (110 mg, 0.290 mmol), DIPEA (156 mg, 1.207 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-6-carboxylate (40a) (53 mg, 78% yield) HCl salt as a white solid; 1H NMR (300 MHz, DMSO-$d_6$) δ 10.77 (s, 1H, $D_2O$ exchangeable), 9.14 (s, 1H), 8.79-8.52 (m, 3H, 2H $D_2O$ exchangeable), 8.13 (dd, J=8.7, 1.6 Hz, 1H), 8.00 (d, J=8.2 Hz, 1H), 7.78 (d, J=8.7 Hz, 1H), 7.69 (t, J=8.0 Hz, 1H), 7.31 (d, J=7.7 Hz, 1H), 5.75 (d, J=17.3 Hz, 1H), 5.39 (d, J=17.3 Hz, 1H), 4.37 (dd, J=9.0, 5.9 Hz, 1H), 3.92 (s, 3H), 3.69 (dd, J=5.7, 2.4 Hz, 1H), 2.56-2.42 (m, 1H), 1.98 (dd, J=13.2, 5.9 Hz, 1H), 1.31 (s, 3H), 1.05-0.97 (m, 1H), 0.97-0.90 (m, 1H); MS (ES+): 578.0 (M+1), (ES−): 576.0 (M−1); Analysis calculated for $C_{26}H_{24}BrN_7O_4 \cdot HCl \cdot 2.25H_2O$: C, 47.65; H, 4.54; Cl, 5.41; N, 14.96. Found: C, 47.54; H, 4.50; Cl, 5.29; N, 14.92.

Scheme 41

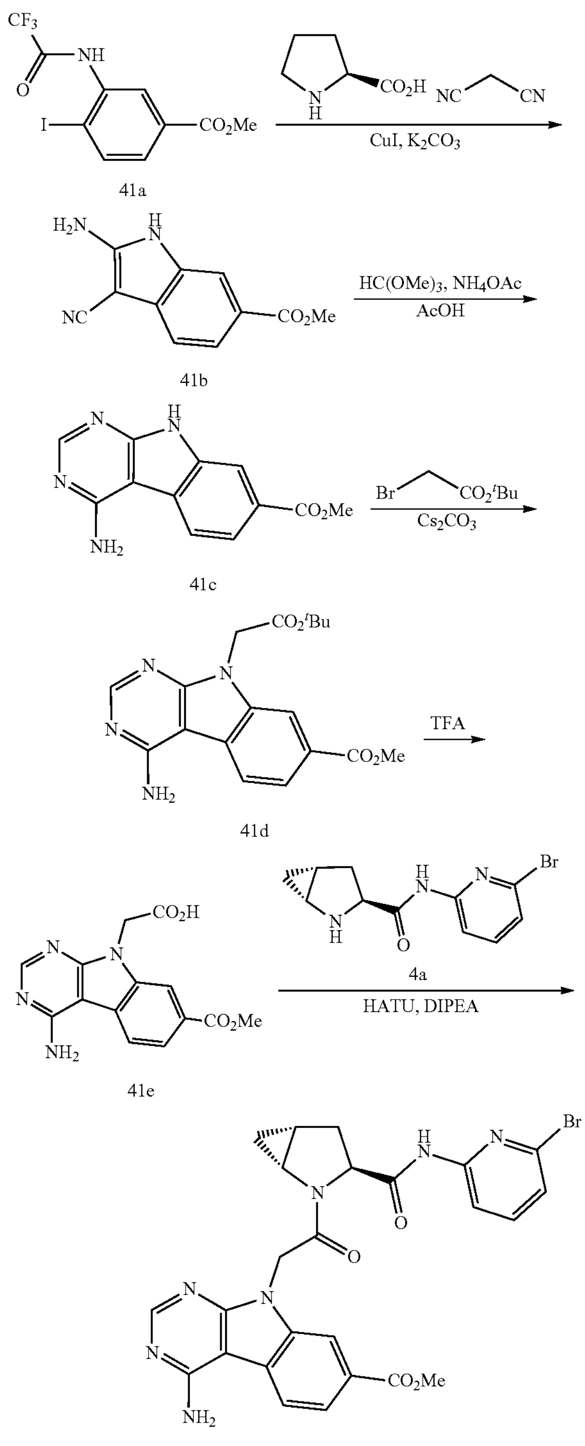

41a

41b

41c

41d

41e

41f

Preparation of methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-7-carboxylate (41f)

Step-1: Preparation of methyl 2-amino-3-cyano-1H-indole-6-carboxylate (41b)

Compound 41b was prepared according to the procedure reported in step-1 of scheme-11, from methyl 4-iodo-3-(2,2,2-trifluoroacetamido)benzoate (41a) (6.73 g, 18.04 mmol; CAS #494799-11-0) in DMSO (20 mL) and using malononitrile (1.430 g, 21.65 mmol), L-proline (0.415 g, 3.61 mmol), CuI (0.344 g, 1.804 mmol), $K_2CO_3$ (4.99 g, 36.1 mmol) and heating at 60° C. for 16 h under an argon atmosphere. This gave after workup and purification [$SiO_2$ gel (40 g), eluting with EtOAc in hexane from 0-50%] methyl 2-amino-3-cyano-1H-indole-6-carboxylate (41b) (1.32 g, 34% yield) as a brown solid; $^1H$ NMR (300 MHz, DMSO-$d_6$) δ 10.96 (s, 1H), 7.74 (d, J=1.5 Hz, 1H), 7.63 (dd, J=8.2, 1.5 Hz, 1H), 7.26-7.12 (m, 3H), 3.81 (s, 3H); MS (ES+): 216 (M+1), (ES−): 214 (M−1).

Step-2: Preparation of methyl 4-amino-9H-pyrimido[4,5-b]indole-7-carboxylate (41c)

Compound 41c was prepared according to the procedure reported in step-1 of scheme-6, from methyl 2-amino-3-cyano-1H-indole-6-carboxylate (41b) (1.32 g, 6.13 mmol) using trimethyl orthoformate (13.02 g, 123 mmol), AcOH (1.754 mL, 30.7 mmol) and $NH_4OAc$ (2.364 g, 30.7 mmol). This gave after workup methyl 4-amino-9H-pyrimido[4,5-b]indole-7-carboxylate (41c) (0.83 g, 56% yield) as a pale-yellow solid. $^1H$ NMR (300 MHz, DMSO-$d_6$) δ 12.14 (s, 1H), 8.43 (d, J=8.3 Hz, 1H), 8.30 (s, 1H), 8.03 (d, J=1.4 Hz, 1H), 7.82 (dd, J=8.3, 1.5 Hz, 1H), 7.41 (s, 2H), 3.90 (s, 3H); MS (ES+): 243 (M+1), (ES−): 241 (M−1).

Step-3: Preparation of methyl 4-amino-9-(2-(tert-butoxy)-2-oxoethyl)-9H-pyrimido[4,5-b]indole-7-carboxylate (41d)

Compound 41d was prepared according to the procedure reported in step-1 of scheme-1, from methyl 4-amino-9H-pyrimido[4,5-b]indole-7-carboxylate (41c) (0.83 g, 3.43 mmol) in DMF (20 mL) using tert-butyl 2-bromoacetate (0.668 g, 3.43 mmol), $Cs_2CO_3$ (1.340 g, 4.11 mmol) and stirring at RT for 16 h. This gave after workup and purification by flash column chromatography [silica gel (24 g), eluting with MeOH in DCM from 0-3%] methyl 4-amino-9-(2-(tert-butoxy)-2-oxoethyl)-9H-pyrimido[4,5-b]indole-7-carboxylate (41d) (0.67 g, 55% yield) as a pale orange solid; $^1H$ NMR (300 MHz, DMSO-$d_6$) δ 8.48 (d, J=8.3 Hz, 1H), 8.35 (s, 1H), 8.18 (d, J=1.5 Hz, 1H), 7.89 (dd, J=8.2, 1.4 Hz, 1H), 7.54 (s, 2H), 5.23 (s, 2H), 3.91 (s, 3H), 1.41 (s, 9H); MS (ES+): 357 (M+1), (ES−): 355 (M−1).

Step-4: Preparation of 2-(4-amino-7-(methoxycarbonyl)-9H-pyrimido[4,5-b]indol-9-yl)acetic acid (41e)

Compound 41e was prepared according to the procedure reported in step-2 of scheme-1, from methyl 4-amino-9-(2-(tert-butoxy)-2-oxoethyl)-9H-pyrimido[4,5-b]indole-7-carboxylate (41d) (0.67 g, 1.880 mmol) using TFA (4.29 g, 37.6 mmol) in DCM (20 mL) and stirring at RT for 16 h. This gave after workup 2-(4-amino-7-(methoxycarbonyl)-9H-pyrimido[4,5-b]indol-9-yl)acetic acid (41e) (3.70 g) TFA salt as a yellow solid. $^1$H NMR (300 MHz, DMSO-$d_6$) δ 8.71-8.47 (m, 4H), 8.36 (d, J=1.4 Hz, 1H), 7.99 (dd, J=8.3, 1.4 Hz, 1H), 5.36 (s, 2H), 3.93 (s, 3H); MS (ES+): 301 (M+1), (ES−): 299 (M−1).

Step-5: Preparation of methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-7-carboxylate (41f)

Compound 41f was prepared according to the procedure reported in step-3 of scheme-1, from TFA salt of 2-(4-amino-7-(methoxycarbonyl)-9H-pyrimido[4,5-b]indol-9-yl)acetic acid (41e) (50 mg, 0.121 mmol) in DMF (5 mL) using HCl salt of (1R,3S,5R)—N-(6-bromopyridin-2-yl)-2-azabicyclo[3.1.0]hexane-3-carboxamide (4a) (38.5 mg, 0.121 mmol), HATU (55.1 mg, 0.145 mmol), DIPEA (78 mg, 0.603 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-7-carboxylate (41f) (48 mg, 71% yield) HCl salt as a white solid; $^1$H NMR (300 MHz, DMSO-$d_6$) δ 10.77 (s, 1H, $D_2O$ exchangeable), 8.59 (d, J=8.5 Hz, 1H), 8.57 (s, 1H), 8.45 (s, 2H, $D_2O$ exchangeable), 8.28 (s, 1H), 8.05-7.92 (m, 2H), 7.70 (t, J=8.0 Hz, 1H), 7.31 (d, J=7.7 Hz, 1H), 5.86 (d, J=17.4 Hz, 1H), 5.49 (d, J=17.3 Hz, 1H), 4.42 (dd, J=9.1, 5.6 Hz, 1H), 3.92 (s, 4H), 2.39-2.29 (m, 1H), 2.29-2.16 (m, 1H), 2.01-1.87 (m, 1H), 1.15-1.03 (m, 1H), 0.76-0.69 (m, 1H); MS (ES+): 564/566 (M+1), (ES−): 562/564 (M−1); Analysis calculated for $C_{25}H_{22}BrN_7O_4 \cdot 1.1 \cdot HCl \cdot 2.75 \cdot H_2O$: C, 45.91; H, 4.41; Cl, 5.96; N, 14.99. Found: C, 45.90; H, 4.21; Cl, 5.98; N, 14.69.

Preparation of methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-7-carboxylate (42a)

Compound 42a was prepared according to the procedure reported in step-3 of scheme-1, from TFA salt of 2-(4-amino-7-(methoxycarbonyl)-9H-pyrimido[4,5-b]indol-9-yl)acetic acid (41e) (100 mg, 0.241 mmol) in DMF (5 mL) using HCl salt of (1R,3S,5R)—N-(6-bromopyridin-2-yl)-5-methyl-2-azabicyclo[3.1.0]hexane-3-carboxamide (8a) (80 mg, 0.241 mmol), HATU (110 mg, 0.290 mmol), DIPEA (156 mg, 1.207 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-7-carboxylate (42a) (82 mg, 59% yield) HCl salt as a white solid, 1H NMR (300 MHz, DMSO-$d_6$) δ 10.77 (s, 1H, $D_2O$ exchangeable), 8.70-8.41 (m, 4H, 2H $D_2O$ exchangeable), 8.29 (d, J=1.4 Hz, 1H), 8.06-7.92 (m, 2H), 7.69 (t, J=7.9 Hz, 1H), 7.31 (d, J=7.7 Hz, 1H), 5.83 (d, J=17.4 Hz, 1H), 5.43 (d, J=17.3 Hz, 1H), 4.38 (dd, J=9.0, 5.9 Hz, 1H), 3.92 (s, 3H), 3.73-3.70 (m, 1H), 2.54-2.44 (m, 1H), 1.99 (m, 1H), 1.32 (s, 3H), 1.09-1.01 (m, 1H), 0.93-0.85 (m, 1H); MS (ES+): 578/580 (M+1), (ES−): 576/578 (M−1); Analysis calculated for $C_{26}H_{24}BrN_7O_4 \cdot HCl \cdot 2.5 \cdot H_2O$: C, 47.32; H, 4.58; Cl, 5.37; N, 14.86. Found: C, 47.48; H, 4.28; Cl, 5.23; N, 14.68.

Scheme 42

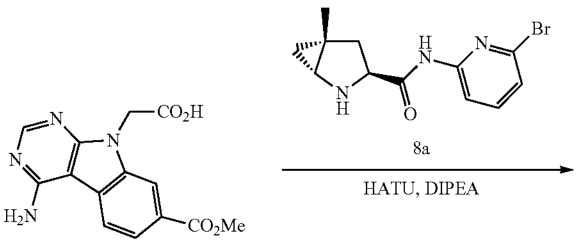

41e

Scheme 43

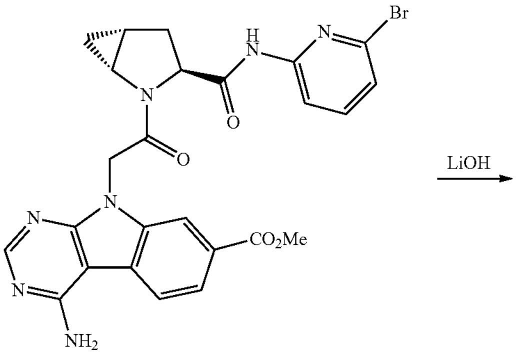

41f

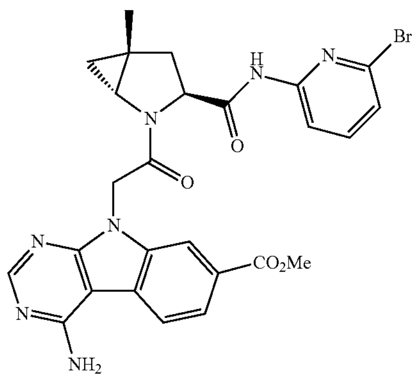

42a

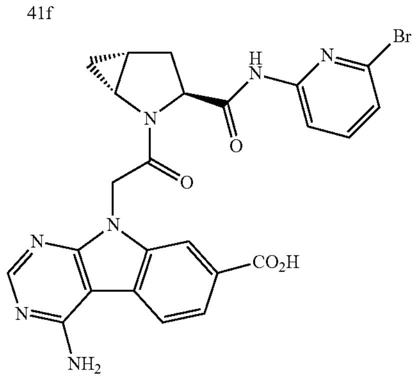

43a

Preparation of 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-7-carboxylic acid (43a)

Compound 43a was prepared according to the procedure reported in step-4 of scheme-17, from methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-7-carboxylate (41f) (78 mg, 0.138 mmol) in THF (1 mL) and water (2 mL) using 2M aqueous lithium hydroxide hydrate (0.138 mL, 0.276 mmol) and stirring at RT for 16 h. This gave after workup and purification by reverse phase column chromatography [C18 column (100 g), eluting with ACN in water (containing 0.1% HCl) from 0-100%] 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-7-carboxylic acid (43a) (34 mg, 45% yield) HCl salt as a white solid: $^1H$ NMR (300 MHz, DMSO-$d_6$) δ (a mixture of two rotamers) 10.85 (s) and 10.77 (s) (2s, 1H, $D_2O$ exchangeable), 8.93 (s, 2H, $D_2O$ exchangeable), 8.69 (d, J=4.9 Hz, 1H), 8.63 (d, J=8.3 Hz, 1H), 8.31 (s, 1H), 7.99 (d, J=7.9 Hz, 2H), 7.67 (q, J=7.7 Hz, 1H), 7.29 (dd, J=7.7, 4.7 Hz, 1H), 5.87 (dd, J=17.4, 11.5 Hz, 1H), 5.50 (dd, J=17.3, 7.3 Hz, 1H), 4.42 (dd, J=9.0, 5.5 Hz, 1H), 3.95-3.92 (m, 1H), 2.39-2.28 (m, 1H), 2.26-2.14 (m, 1H), 2.01-1.86 (m, 1H), 1.28-1.17 (m) and 1.16-1.04 (m) (2 m, 1H), 1.02-0.83 (m) and 0.79-0.67 (m) (2 m, 1H); MS (ES+): 550/552 (M+1), (ES−): 548/550 (M−1); Analysis calculated for $C_{24}H_{20}BrN_7O_4 \cdot 1.1HCl \cdot 3H_2O$: C, 44.72; H, 4.24; Cl, 6.05; N, 15.21. Found: C, 44.67; H, 4.12; Cl, 6.07; N, 15.23.

Scheme 44

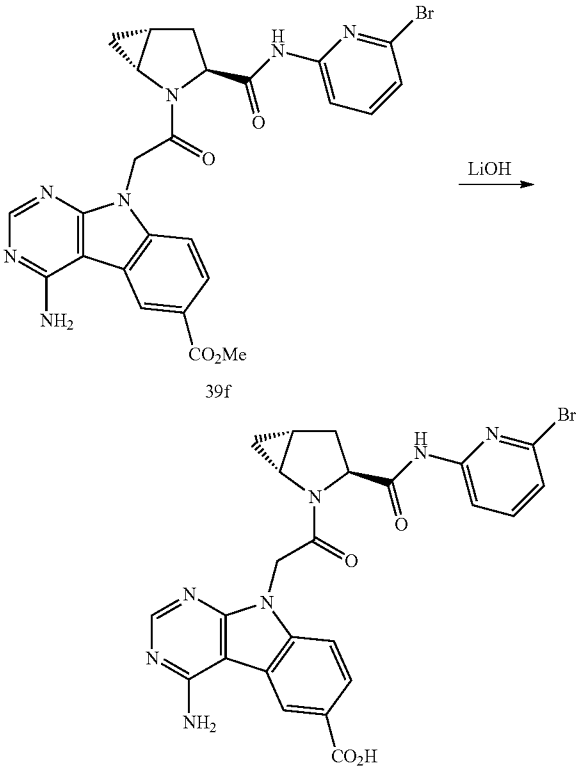

39f

44a

Preparation of 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-6-carboxylic acid (44a)

Compound 44a was prepared according to the procedure reported in step-4 of scheme-17, from TFA salt of methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-6-carboxylate (39f) (156 mg, 0.276 mmol) in in THF (2 mL) and water (4 mL) using 2M aqueous lithium hydroxide hydrate (0.553 mL, 0.553 mmol) and stirring at RT for 16 h. This gave after workup and purification by reverse phase column chromatography [C18 column (50 g), eluting with ACN in water (containing 0.1% HCl) from 0-100%) 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-6-carboxylic acid (44a) (31 mg, 20% yield) HCl salt as a white solid; $^1H$ NMR (300 MHz, DMSO-$d_6$) (a mixture of two rotamers) δ 12.98 (s, 1H, $D_2O$ exchangeable), 10.86 and 10.77 (2s, 1H, $D_2O$ exchangeable), 9.11 (s, 1H), 8.60 and 8.58 (2s, 1H), 8.48 (s, 2H, $D_2O$ exchangeable), 8.11 (dt, J=8.6, 2.1 Hz, 1H), 8.01 and 7.96 (2d, J=8.3 Hz, 1H), 7.78-7.62 (m, 2H), 7.38-7.22 (m, 1H), 5.79 (d, J=17.3 Hz, 1H), 5.44 (d, J=17.4 Hz, 1H), 4.42 (dd, J=9.1, 5.5 Hz, 1H), 3.91 (m, 1H), 2.40-2.12 (m, 2H), 1.93 (m, 1H), 1.30-0.53 (m, 2H). MS (ES+): 550.1 (M+1); (ES−): 548.0 (M−1); Analysis calculated for $C_{24}H_{20}BrN_7O_4$ $2.25H_2O \cdot 0.95HCl$: C, 46.08; H, 4.10; Cl, 5.38; N, 15.67. Found: C, 46.42; H, 4.03; Cl, 4.94; N, 15.29.

Scheme 45

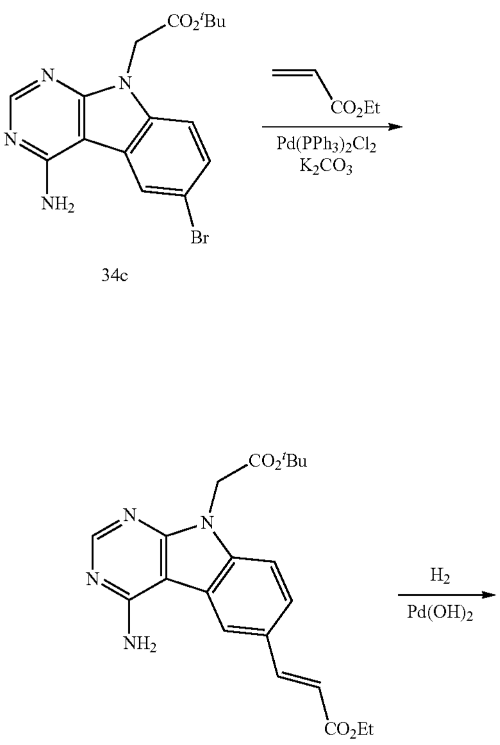

34c

45a

-continued

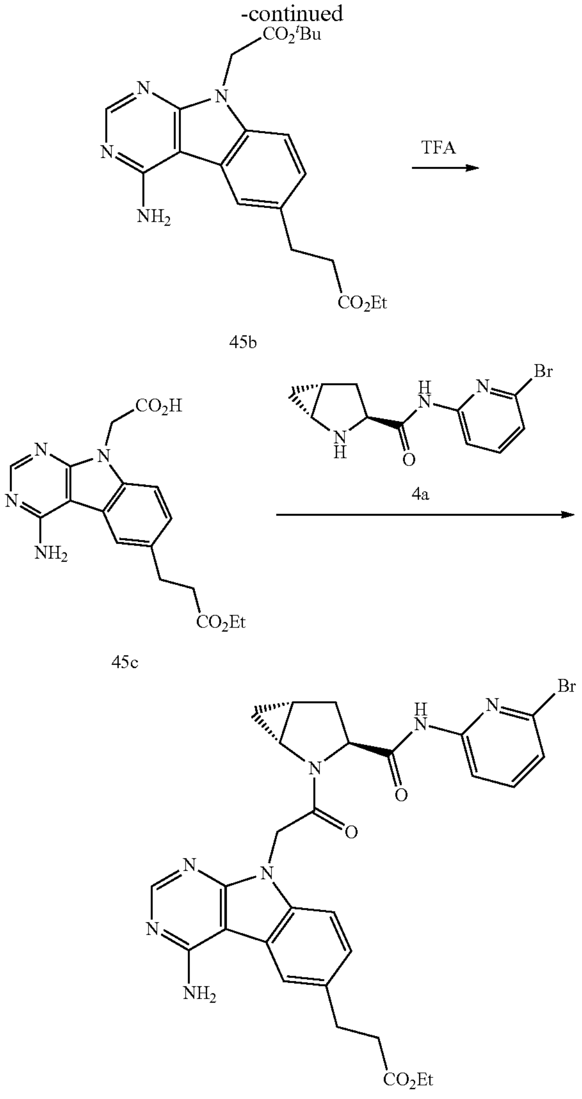

45b

4a

45c

45d

Preparation of ethyl 3-(4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)propanoate (45d)

Step-1: Preparation of (E)-ethyl 3-(4-amino-9-(2-(tert-butoxy)-2-oxoethyl)-9H-pyrimido[4,5-b]indol-6-yl)acrylate (45a)

A mixture of tert-butyl 2-(4-amino-6-bromo-9H-pyrimido[4,5-b]indol-9-yl)acetate (34c) (200 mg, 0.53 mmol), ethyl acrylate (80 mg, 0.795 mmol), $Pd(PPh_3)_2Cl_2$ (37.2 mg, 0.053 mmol), and $K_2CO_1$ (220 mg, 1.591 mmol) were suspended in DMF (4 mL) in a sealed scintillation vial. The vial was flushed with nitrogen and the yellow mixture then heated at 100° C. for 16 h. The resulting black mixture was filtered. The filtrate was diluted with $H_2O$ (25 mL) and extracted with EtOAc (25 mL×3). The combined extract was washed with $H_2O$ (25 mL×4), brine (25 mL), dried, filtered and concentrated in vacuum. The residue obtained was purified by flash column chromatography (silica gel, 24 g, eluting with 0-60% EtOAc in hexane) to provide (E)-ethyl 3-(4-amino-9-(2-(tert-butoxy)-2-oxoethyl)-9H-pyrimido[4,5-b]indol-6-yl)acrylate (45a) (102 mg, 49% yield) as a pale-yellow solid. $^1H$ NMR (300 MHz, DMSO-$d_6$) δ 8.78 (s, 1H), 8.32 (s, 1H), 7.79 (d, J=15.9 Hz, 1H), 7.73 (d, J=8.5 Hz, 1H), 7.61 (d, J=8.5 Hz, 1H), 7.48 (s, 2H), 6.86 (d, J=15.9 Hz, 1H), 5.15 (s, 2H), 4.22 (q, J=7.1 Hz, 2H), 1.41 (s, 9H), 1.29 (t, J=7.1 Hz, 3H); MS (ES+): 397 (M+1), (ES−): 395 (M−1).

Step-2: Preparation of ethyl 3-(4-amino-9-(2-(tert-butoxy)-2-oxoethyl)-9H-pyrimido[4,5-b]indol-6-yl)propanoate (45b)

To a solution of (E)-ethyl 3-(4-amino-9-(2-(tert-butoxy)-2-oxoethyl)-9H-pyrimido[4,5-b]indol-6-yl)acrylate (45a) (100 mg, 0.252 mmol) in THF/ethanol (15 mL, 1:2), was added palladium hydroxide on carbon (7 mg) and heated under a hydrogen atmosphere for 16 h at 100° C. The reaction mixture was cooled to room temperature filtered through Celite, washed with ethyl acetate and concentrated in vacuum to dryness. The residue obtained was purified by flash column chromatography [silica gel (12 g), eluting with MeOH in DCM 0-3%] to afford ethyl 3-(4-amino-9-(2-(tert-butoxy)-2-oxoethyl)-9H-pyrimido[4,5-b]indol-6-yl)propanoate (45b) (80 mg, 80% yield) as a white semisolid; $^1H$ NMR (300 MHz, DMSO-$d_6$) δ 8.25 (d, J=9.1 Hz, 2H), 7.44 (d, J=8.3 Hz, 1H), 7.36-7.14 (m, 3H), 5.08 (s, 2H), 4.06 (q, J=7.1 Hz, 2H), 3.01 (t, J=7.8 Hz, 2H), 2.75 (t, J=7.8 Hz, 2H), 1.40 (s, 9H), 1.17 (t, J=7.2 Hz, 3H); MS (ES+): 399 (M+1).

Step-3: Preparation of 2-(4-amino-6-(3-ethoxy-3-oxopropyl)-9H-pyrimido[4,5-b]indol-9-yl)acetic acid (45c)

Compound 45c was prepared according to the procedure reported in step-2 of scheme-1, from ethyl 3-(4-amino-9-(2-(tert-butoxy)-2-oxoethyl)-9H-pyrimido[4,5-b]indol-6-yl)propanoate (45b) (78 mg, 0.196 mmol) in DCM (5 mL) using TFA (223 mg, 1.96 mmol) and stirring at RT for 16 h. This gave after workup 2-(4-amino-6-(3-ethoxy-3-oxopropyl)-9H-pyrimido[4,5-b]indol-9-yl)acetic acid (45c) TFA salt as a pale yellow solid; 1H NMR (300 MHz, DMSO-$d_6$) δ 8.55 (s, 1H), 8.41 (d, J=10.5 Hz, 2H), 7.68 (d, J=8.4 Hz, 1H), 7.43 (d, J=8.4 Hz, 1H), 5.24 (s, 2H), 4.06 (q, J=7.1 Hz, 3H), 3.04 (t, J=7.7 Hz, 2H), 2.76 (t, J=7.8 Hz, 2H), 1.17 (t, J=7.1 Hz, 3H); $^{19}F$ NMR (282 MHz, DMSO-$d_6$) δ−74.25; MS (ES+): 343 (M+1), (ES−): 341 (M−1).

Step-4: Preparation of ethyl 3-(4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)propanoate (45d)

Compound 45d was prepared according to the procedure reported in step-3 of scheme-1, from TFA salt of 2-(4-amino-6-(3-ethoxy-3-oxopropyl)-9H-pyrimido[4,5-b]indol-9-yl)acetic acid (45c) (96 mg, 0.21 mmol) in DMF (5 mL) using HCl salt of (1R,3S,5R)—N-(6-bromopyridin-2-yl)-2-azabicyclo[3.1.0]hexane-3-carboxamide (4a) (67.0 mg, 0.210 mmol), HATU (96 mg, 0.252 mmol), DIPEA (136 mg, 1.05 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] ethyl 3-(4-amino-9-(2-((1R,3S,5R)-3-((6-bromopyridin-2-yl)carbamoyl)-2-azabicyclo

[3.1.0]hexan-2-yl)-2-oxoethyl)-9H-pyrimido[4,5-b]indol-6-yl)propanoate (45d) (44 mg, 35% yield) HCl salt as a white solid; $^1H$ NMR (300 MHz, DMSO-$d_6$) δ 10.75 (s, 1H, $D_2O$ exchangeable), 8.58 (s, 1H), 8.53 (s, 2H, $D_2O$ exchangeable), 8.39 (s, 1H), 8.00 (d, J=8.1 Hz, 1H), 7.70 (t, J=8.0 Hz, 1H), 7.59 (d, J=8.4 Hz, 1H), 7.43 (dd, J=8.3, 1.7 Hz, 1H), 7.32 (d, J=7.7 Hz, 1H), 5.73 (d, J=17.3 Hz, 1H), 5.39 (d, J=17.3 Hz, 1H), 4.41 (dd, J=9.0, 5.5 Hz, 1H), 4.05 (q, J=7.1 Hz, 2H), 3.96-3.86 (m, 1H), 3.03 (t, J=7.7 Hz, 2H), 2.74 (t, J=7.8 Hz, 2H), 2.39-2.26 (m, 1H), 2.26-2.13 (m, 1H), 1.98-1.84 (m, 1H), 1.16 (t, J=7.1 Hz, 3H), 1.10-1.01 (m, 1H), 0.81-0.72 (m, 1H); MS (ES+): 606/608 (M+1), (ES−): 604/606 (M−1); Analysis calculated for $C_2SH_2SBrN_7O_4 \cdot 1.25 HCl \cdot 1.75 H_2O$: C, 49.20; H, 4.83; Cl, 6.48; N, 14.34. Found: C, 49.16; H, 4.63; Cl, 6.68; N, 14.22.

Scheme 46

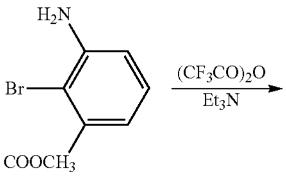

46a

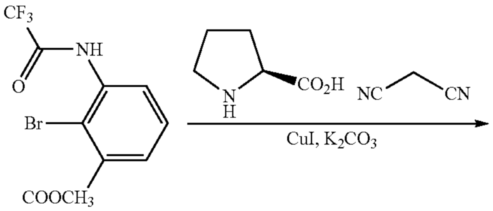

46b

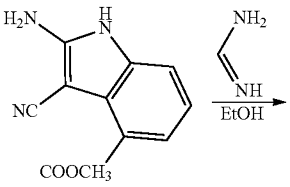

46c

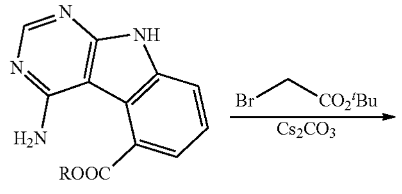

46d
(R = Me, Et moxture)

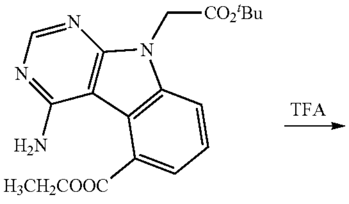

46e

-continued

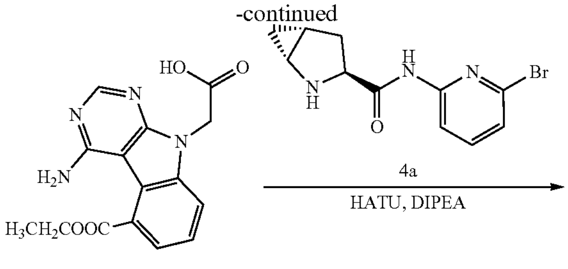

46f

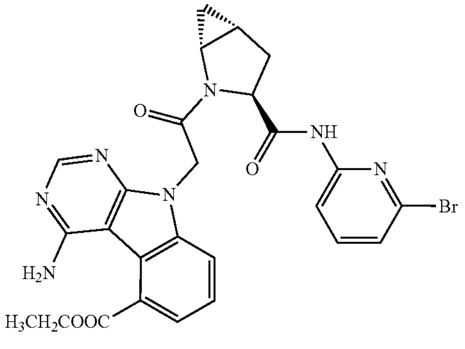

46g

Preparation of ethyl 4-amino-9-(2-((1R,3S,5R)-3-((6-bromopyridin-2-yl)carbamoyl)-2-azabicyclo [3.1.0]hexan-2-yl)-2-oxoethyl)-9H-pyrimido[4,5-b] indole-5-carboxylate (46 g)

Step-1: Preparation of methyl 2-bromo-3-(2,2,2-trifluoroacetamido)benzoate (46b)

To a solution of methyl 3-amino-2-bromobenzoate (46a) (4.5 g, 19.56 mmol; CAS #106896-48-4) and triethylamine (6.82 mL, 48.9 mmol) in DCM (30 mL) was added trifluoracetic anhydride (4.08 mL, 29.3 mmol) dropwise and stirred at RT for 15 h. The reaction mixture was diluted with dichloromethane (75 mL), washed with water (50 mL), dried, filtered and concentrated in vacuum to afford methyl 2-bromo-3-(2,2,2-trifluoroacetamido)benzoate (46b) as a yellow gum (8.17 g) and was used as such for next step; MS (ES+): 325.90 (M+1); (ES−): 323.90 (M−1).

Step-2: Preparation of methyl 2-amino-3-cyano-1H-indole-4-carboxylate (46c)

Compound 46c was prepared according to the procedure reported in step-1 of scheme-11, from methyl 2-bromo-3-(2,2,2-trifluoroacetamido)benzoate (46b) (1594 g, 4.89 mmol) in DMSO (8 mL) using malononitrile (388 mg, 5.87 mmol), L-proline (0.113 g, 0.978 mmol), CuI (93 mg, 0.489 mmol), $K_2CO_3$ (1.352 g, 9.78 mmol) in water (8 mL) and heating at 60° C. for 13 h under an argon atmosphere. This gave after workup and purification [$SiO_2$ gel (24 g), eluting with EtOAc in hexane from 0-66%] methyl 2-amino-3-cyano-1H-indole-4-carboxylate (46c) (115 mg, 11% yield) as a brown solid; (ES−): 214.00 (M−1).

Step-3: Preparation of methyl/ethyl 4-amino-9H-pyrimido[4,5-b]indole-5-carboxylate (46d)

Compound 46d was prepared according to the procedure reported in step-2 of scheme-29, from methyl 2-amino-3- cyano-1H-indole-4-carboxylate (46c) (105 mg, 0.488 mmol) in ethanol (10 mL) using formamidine acetate (513 mg, 4.88 mmol) and heating at 100° C. in a microwave. The reaction mixture was filtered, washed with ethanol, and dried under vacuum. The residue was purified by flash column chromatography [$SiO_2$ gel (24 g), eluting with EtOAc in hexane from 0-100% and then using hexanes/10% methanol in ethyl acetate (1:1)] a mixture of methyl/ethyl 4-amino-9H-pyrimido[4,5-b]indole-5-carboxylate (46d) (66 mg) as a brown solid, which was used as such for the next step; MS (ES+): 243.10, 257.10 (M+1).

Step-4: Preparation of methyl/ethyl 4-amino-9-(2-(tert-butoxy)-2-oxoethyl)-9H-pyrimido[4,5-b]indole-5-carboxylate (46e)

Compound 46e was prepared according to the procedure reported in step-1 of scheme-1, from a mixture of methyl/ethyl 4-amino-9H-pyrimido[4,5-b]indole-5-carboxylate (46d) (65 mg) in DMF (5 mL) using tert-butyl 2-bromoacetate (0.048 mL, 0.322 mmol), $Cs_2CO_3$ (219 mg, 0.671 mmol) and stirring at RT for 14 h. This gave after workup and purification by flash column chromatography [$SiO_2$ gel (24 g), eluting with 10% methanol in ethyl acetate in hexanes from 0-100%] methyl 4-amino-9-(2-(tert-butoxy)-2-oxoethyl)-9H-pyrimido[4,5-b]indole-5-carboxylate (7 mg, 7%); MS (ES+): 357.10 (M+1); ethyl 4-amino-9-(2-(tert-butoxy)-2-oxoethyl)-9H-pyrimido[4,5-b]indole-5-carboxylate (46e) (16 mg, 9% yield) as a white solid; MS (ES+): 371.20 (M+1); (ES−): 369.00 (M−1).

Step-5: Preparation of 2-(4-amino-5-(ethoxycarbonyl)-9H-pyrimido[4,5-b]indol-9-yl)acetic acid (46f)

Compound 46f was prepared according to the procedure reported in step-2 of scheme-1, from ethyl 4-amino-9-(2-(tert-butoxy)-2-oxoethyl)-9H-pyrimido[4,5-b]indole-5-carboxylate (46e) (16 mg, 0.043 mmol) using TFA (0.20 mL, 2.59 mmol) in DCM (5 mL) and stirring at RT for 17 h. This gave after workup 2-(4-amino-5-(ethoxycarbonyl)-9H-pyrimido[4,5-b]indol-9-yl)acetic acid (46f) which was used as such in next step-6 without further purification; MS (ES+): 315.10 (M+1).

Step-6: Preparation of ethyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-5-carboxylate (46 g)

Compound 46g was prepared according to the procedure reported in step-3 of scheme-1, from 2-(4-amino-5-(ethoxycarbonyl)-9H-pyrimido[4,5-b]indol-9-yl)acetic acid (46f) (13.51 mg, 0.043 mmol) in DMF (7 mL) using HCl salt of (1R,3S,5R)—N-(6-bromopyridin-2-yl)-2-azabicyclo[3.1.0]hexane-3-carboxamide (4a) (54.8 mg, 0.172 mmol), HATU (65.4 mg, 0.172 mmol) DIPEA (0.045 mL, 0.258 mmol) and stirring at RT for 19 h. This gave after workup and purification by flash column chromatography [silica gel (12 g), eluting with hexanes/10% MeOH in EtOAc from 0-100%] followed by conversion to HCl salt by dissolving product in acetonitrile (1.5 mL) and 0.1% aq. HCl (6 mL) and lyophilization ethyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-5-carboxylate (46 g) (6.5 mg, 26% yield) HCl salt as a white solid; $^1H$ NMR (300 MHz, DMSO-$d_6$) δ 10.76 (s, 1H), 8.57 (s, 1H), 8.14-7.93 (m, 4H), 7.77-7.60 (m, 3H), 7.32 (d, J=7.8 Hz, 1H), 5.82 (d, J=17.4 Hz, 1H), 5.49 (d, J=17.3 Hz, 1H), 4.55-4.33 (m, 3H), 3.98-3.88 (m, 1H), 2.43-2.12 (m, 2H), 2.01-1.85 (m, 1H), 1.40 (t, J=7.1 Hz, 3H), 1.15-1.02 (m, 1H), 0.84-0.73 (m, 1H); MS (ES+): 578.10 & 580.10 (M+1).

Scheme 47

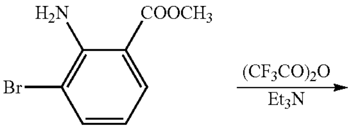

47a

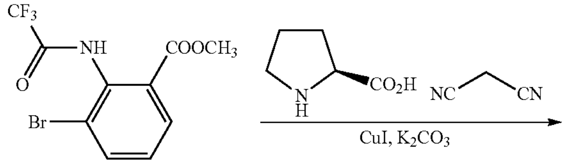

47b

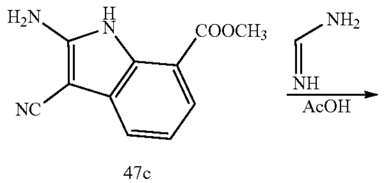

47c

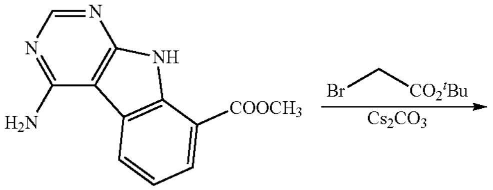

47d

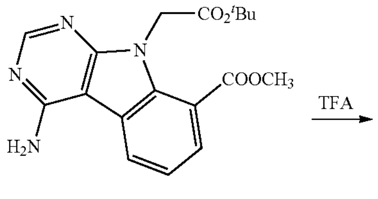

47e

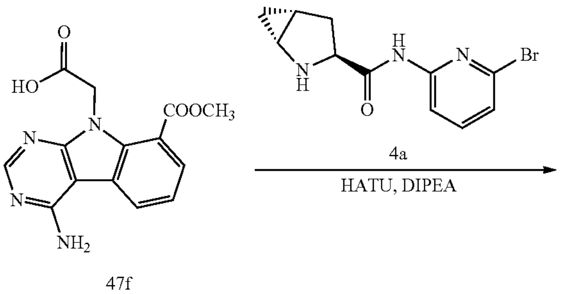

47f

-continued

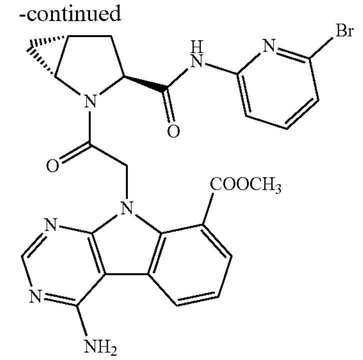

47g

Preparation of methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-8-carboxylate (47 g)

Step-1: Preparation of methyl 3-bromo-2-(2,2,2-trifluoroacetamido)benzoate (47b)

Compound 47b was prepared according to the procedure reported in step-1 of scheme-46, from methyl 2-amino-3-bromobenzoate (47a) (5 g, 21.73 mmol; CAS #104670-74-8) in DCM (30 mL) using triethylamine (7.57 mL, 54.3 mmol), trifluoroacetic acid anhydride (4.53 mL, 32.6 mmol) and stirring at RT for 43 h. This gave after workup and purification by flash column chromatography [$SiO_2$ gel (120 g), EtOAc in hexane from 0-14%] methyl 3-bromo-2-(2,2,2-trifluoroacetamido)benzoate (47b) as a yellow solid (5.27 g, 74% yield) and was used as such for next step: $^1$H NMR (300 MHz, DMSO-$d_6$) δ 11.40 (s, 1H), 8.03 (dd, J=8.1, 1.4 Hz, 1H), 7.91 (dd, J=7.8, 1.4 Hz, 1H), 7.48 (t, J=7.9 Hz, 1H), 3.80 (s, 3H); $^{19}$F NMR (282 MHz, DMSO-$d_6$) δ−74.44; MS (ES−): 323.90 & 325.90 (M−1).

Step-2: Preparation of methyl 2-amino-3-cyano-1H-indole-7-carboxylate (47c)

Compound 47c was prepared according to the procedure reported in step-1 of scheme-11, from methyl 3-bromo-2-(2,2,2-trifluoroacetamido)benzoate (47b) (2 g, 6.13 mmol) in DMSO (12 mL), using malononitrile (0.486 g, 7.36 mmol), L-proline (0.141 g, 1.227 mmol), CuI (0.117 g, 0.613 mmol), a solution of $K_2CO_3$ (1.695 g, 12.27 mmol) in water (12 mL) and heating at 60° C. for 13 h under an argon atmosphere. This gave after workup and purification by flash column chromatography [$SiO_2$ gel (24 g), eluting with EtOAc in hexane from 0-33%] methyl 2-amino-3-cyano-1H-indole-7-carboxylate (47c) (305 mg, 23% yield) as a brown solid: $^1$H NMR (300 MHz, DMSO-$d_6$) δ 10.75 (s, 1H), 7.51 (dd, J=7.8, 1.1 Hz, 1H), 7.41 (d, J=7.6 Hz, 1H), 7.09 (t, J=7.7 Hz, 1H), 6.93 (s, 2H), 3.91 (s, 3H); MS (ES+): 216).

Step-3: Preparation of methyl 4-amino-9H-pyrimido[4,5-b]indole-8-carboxylate (47d)

Compound 47d was prepared according to the procedure reported in step-2 of scheme-29, from methyl 2-amino-3-cyano-1H-indole-7-carboxylate (47c) (300 mg, 1.394 mmol) in ethanol (10 mL) using formamidine acetate (1466 mg, 13.94 mmol) and heating at reflux for 45 h. This gave after workup a grey solid residue (268 mg) which was used as such for the next step; 1H NMR (300 MHz, DMSO-$d_6$) δ 8.59 (dd, J=7.8, 1.2 Hz, 1H), 8.34 (s, 1H), 7.97 (dd, J=7.8, 1.1 Hz, 1H), 7.41-7.28 (m, 3H), 3.97 (s, 3H); MS (ES+): 243.10.

Step-4: Preparation of methyl 4-amino-9-(2-(tert-butoxy)-2-oxoethyl)-9H-pyrimido[4,5-b]indole-8-carboxylate (47e)

Compound 47e was prepared according to the procedure reported in step-1 of scheme-1, from methyl 4-amino-9H-pyrimido[4,5-b]indole-8-carboxylate (47d) (240 mg, 0.991 mmol) in DMF (6 mL) using tert-butyl 2-bromoacetate (0.176 mL, 1.189 mmol), $Cs_2CO_3$ (807 mg, 2.477 mmol) and stirring overnight at RT. This gave after workup and purification by flash column chromatography [$SiO_2$ gel (24 g), eluting with 10% methanol in ethyl acetate in hexanes from 0-100%] methyl 4-amino-9-(2-(tert-butoxy)-2-oxoethyl)-9H-pyrimido[4,5-b]indole-8-carboxylate (47e) (353 mg, 25% yield) as an off white solid; $^1$H NMR (300 MHz, DMSO-$d_6$) δ 8.61 (dd, J=7.9, 1.2 Hz, 1H), 8.36 (s, 1H), 7.84-7.79 (m, 1H), 7.49 (s, 2H), 7.37 (t, J=7.8 Hz, 1H), 5.35 (s, 2H), 3.90 (s, 3H), 1.36 (s, 9H); MS (ES+): 357.15.

Step-5: Preparation of 2-(4-amino-8-(methoxycarbonyl)-9H-pyrimido[4,5-b]indol-9-yl)acetic acid (47f)

Compound 47f was prepared according to the procedure reported in step-2 of scheme-1, from methyl 4-amino-9-(2-(tert-butoxy)-2-oxoethyl)-9H-pyrimido[4,5-b]indole-8-carboxylate (47e) (80 mg, 0.224 mmol) using TFA in DCM (10 mL) and stirring at RT. This gave after workup 2-(4-amino-8-(methoxycarbonyl)-9H-pyrimido[4,5-b]indol-9-yl)acetic acid (47f) which was used as such in next step-6 without purification; MS (ES+): 301.10 (M+1).

Step-6: Preparation of methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-8-carboxylate (47 g)

Compound 47g was prepared according to the procedure reported in step-3 of scheme-1, from 2-(4-amino-8-(methoxycarbonyl)-9H-pyrimido[4,5-b]indol-9-yl)acetic acid (47f) (67.3 mg, 0.224 mmol) in DMF (10 mL) using HCl salt of (1R,3S,5R)—N-(6-bromopyridin-2-yl)-2-azabicyclo[3.1.0]hexane-3-carboxamide (4a) (71.4 mg, 0.224 mmol), HATU (170 mg, 0.448 mmol), DIPEA (0.195 mL, 1.12 mmol) and stirring at RT for 18 h. This gave after workup and purification by flash column chromatography [silica gel (12 g), eluting with MeOH in DCM from 0-5%] followed by conversion to HCl salt by dissolving product in acetonitrile (2 mL) and 0.1% aq. HCl (8 mL) and lyophilization methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-8-carboxylate (47 g)(38 mg, 30% yield) HCl salt as a white solid; $^1$H NMR (300 MHz, DMSO-$d_6$) δ 10.72 (s, 1H, $D_2O$ exchangeable), 8.65 (d, J=7.7 Hz, 1H), 8.51 (s, 1H), 8.17-7.91 (m, 3H, 2H $D_2O$ exchangeable), 7.82 (d, J=7.7 Hz, 1H), 7.69 (t, J=7.9 Hz, 1H), 7.41 (t, J=7.7 Hz, 1H), 7.30 (d, J=7.7 Hz, 1H), 5.95 (d, J=17.5 Hz, 1H), 5.64 (d, J=17.3 Hz, 1H), 4.39-4.27 (m, 1H), 3.92 (s, 3H), 3.87-3.72 (m, 1H), 2.37-2.09 (m, 2H), 1.97-

1.78 (m, 1H), 1.16-0.99 (m, 1H), 0.83-0.65 (m, 1H); MS (ES+): 564.10 & 566.10 (M+1); MS (ES−): 562.10 & 564.10 (M−1).

Scheme 48

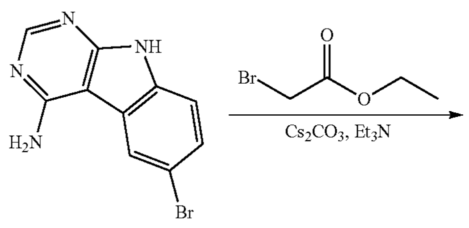

34b

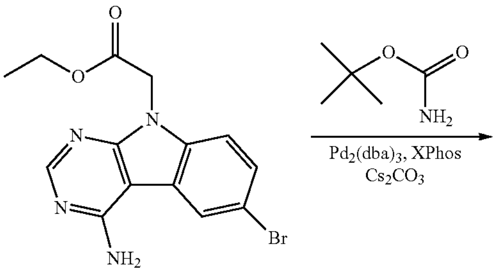

48a

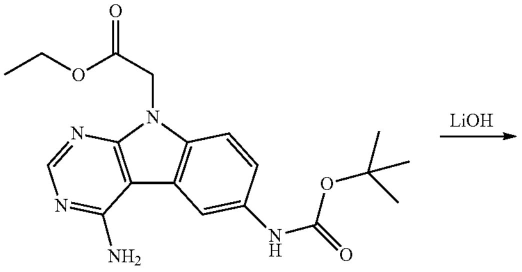

48b

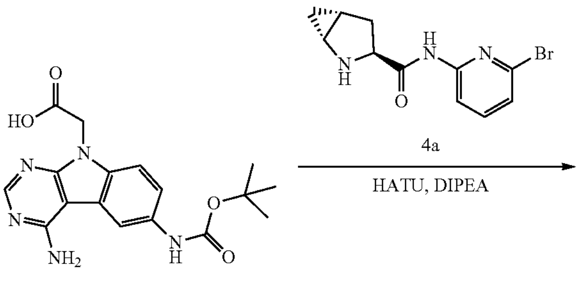

4a

48c

-continued

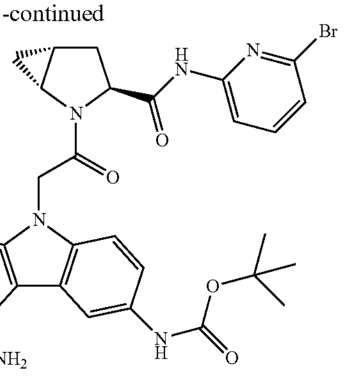

48d

Preparation of tert-butyl (4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)carbamate (48d)

Step-1: Preparation of ethyl 2-(4-amino-6-bromo-9H-pyrimido[4,5-b]indol-9-yl)acetate (48a)

Compound 48a was prepared according to the procedure reported in step-2 of scheme-16, from 6-bromo-9H-pyrimido[4,5-b]indol-4-amine (34b) (540 mg, 2.053 mmol) in DMF (10 mL) using ethyl 2-bromoacetate (0.228 mL, 2.053 mmol), $Cs_2CO_3$ (802 mg, 2.463 mmol), triethylamine (1.716 mL, 12.32 mmol) and stirring at RT for 27 h. This gave after workup 2-(4-amino-6-bromo-9H-pyrimido[4,5-b]indol-9-yl)acetate (48a) (166 mg) as a light yellow solid; $^1H$ NMR (300 MHz, DMSO-$d_6$) δ 8.63 (d, J=1.8 Hz, 1H), 8.29 (s, 1H), 7.60 (d, J=8.7 Hz, 1H), 7.54 (dd, J=8.7, 1.8 Hz, 1H), 7.45 (s, 2H), 5.23 (s, 2H), 4.13 (q, J=7.1 Hz, 2H), 1.19 (t, J=7.0 Hz, 3H); MS (ES+): 349.00 & 350.90 (M+1).

Step-2: Preparation of ethyl 2-(4-amino-6-((tert-butoxycarbonyl)amino)-9H-pyrimido[4,5-b]indol-9-yl)acetate (48b)

Compound 48b was prepared according to the procedure reported in step-3 of scheme-17, from ethyl 2-(4-amino-6-bromo-9H-pyrimido[4,5-b]indol-9-yl)acetate (48a) (150 mg, 0.430 mmol) in toluene (8 mL) using XPhos, t-butyl carbamate, $Pd_2(dba)_3$, $Cs_2CO_3$ (140 mg, 0.43 mmol) and heating at 90° C. for 20 h. This gave after work up and purification ethyl 2-(4-amino-6-((tert-butoxycarbonyl)amino)-9H-pyrimido[4,5-b]indol-9-yl)acetate (48b) (10 mg, 6% yield); MS (ES+): 386.20 (M+1).

Step-3: Preparation of 2-(4-amino-6-((tert-butoxycarbonyl)amino)-9H-pyrimido[4,5-b]indol-9-yl)acetic acid (48c)

Compound 48c was prepared according to the procedure reported in step-4 of scheme-17, from ethyl 2-(4-amino-6-((tert-butoxycarbonyl)amino)-9H-pyrimido[4,5-b]indol-9-yl)acetate (48b) (10 mg, 0.026 mmol) in THF (2 mL) and MeOH (2 mL) using lithium hydroxide hydrate (6.67 mg, 0.156 mmol) and stirring at RT for 18 h. This gave after work up 2-(4-amino-6-((tert-butoxycarbonyl)amino)-9H-pyrimido[4,5-b]indol-9-yl)acetic acid (48c) which was used as such in next step-4; MS (ES+): 358.20 (M+1); (ES−): 356.10 (M−1).

Step-4: Preparation of tert-butyl (4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)carbamate (48d)

Compound 48d was prepared according to the procedure reported in step-3 of scheme-1, from 2-(4-amino-6-((tert-butoxycarbonyl)amino)-9H-pyrimido[4,5-b]indol-9-yl)acetic acid (48c) (from above step-3, 0.026 mmol) in DMF (6 mL) using HCl salt of (1R,3S,5R)—N-(6-bromopyridin-2-yl)-2-azabicyclo[3.1.0]hexane-3-carboxamide (4a) (71 mg, 0.224 mmol), HATU (40 mg, 0.104 mmol), DIPEA (0.027 mL, 0.156 mmol) and stirring at RT for 14 h. This gave after workup and purification by flash column chromatography [silica gel (4 g), eluting with MeOH in DCM from 0-5%] followed by conversion to HCl salt in acetonitrile (1 mL) using 0.1% aq. HCl (5 mL) and lyophilization tert-butyl (4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)carbamate (48d) (6 mg, 37% yield) HCl salt as a white solid; $^1H$ NMR (300 MHz, DMSO-$d_6$) δ 10.76 (s, 1H, $D_2O$ exchangeable), 9.26 (s, 1H, $D_2O$ exchangeable), 8.54 (s, 1H), 8.38 (s, 1H), 8.29 (s, 2H, $D_2O$ exchangeable), 8.01 (d, J=8.1 Hz, 1H), 7.70 (t, J=8.0 Hz, 1H), 7.56 (d, J=8.8 Hz, 1H), 7.40 (d, J=8.1 Hz, 1H), 7.32 (d, J=7.7 Hz, 1H), 5.70 (d, J=17.3 Hz, 1H), 5.37 (d, J=17.2 Hz, 1H), 4.41 (dd, J=9.1, 5.5 Hz, 1H), 3.96-3.85 (m, 1H), 2.44-2.07 (m, 2H), 1.98-1.81 (m, 1H), 1.49 (s, 9H), 1.13-0.98 (m, 1H), 0.85-0.62 (m, 1H); MS (ES+): 621.20 & 623.20 (M+1); MS (ES−): 619.10 & 621.10 (M−1).

Scheme 49

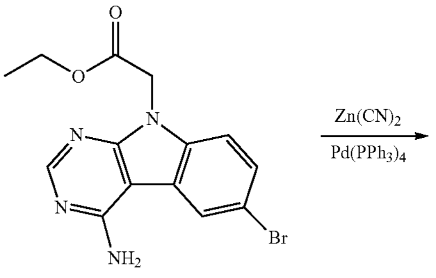

48a

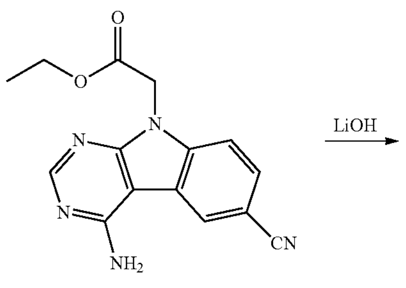

49a

-continued

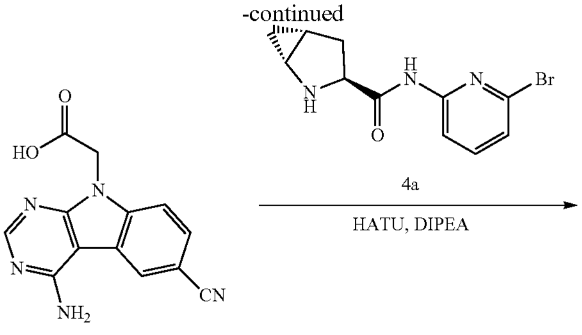

49b

4a

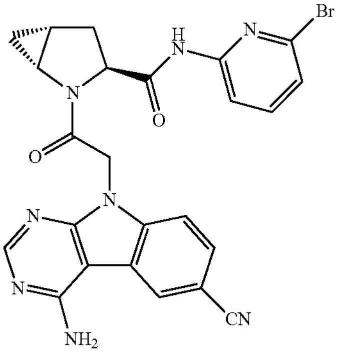

49c

Preparation of (1R,3S,5R)-2-(2-(4-amino-6-cyano-9H-pyrimido[4,5-b]indol-9-yl)acetyl)-N-(6-bromopyridin-2-yl)-2-azabicyclo[3.1.0]hexane-3-carboxamide (49c)

Step-1: Preparation of ethyl 2-(4-amino-6-cyano-9H-pyrimido[4,5-b]indol-9-yl)acetate (49a)

To a mixture of ethyl 2-(4-amino-6-bromo-9H-pyrimido[4,5-b]indol-9-yl)acetate (48a) (300 mg, 0.859 mmol) and dicyanozinc (303 mg, 2.58 mmol) in DMF (8 mL) was added $Pd(PPh_3)_4$ (149 mg, 0.129 mmol), degassed, filled with nitrogen, and heated at 100° C. for 13 h. The reaction mixture was diluted with ethyl acetate (120 mL), washed with water (2×60 mL), brine (60 mL), dried, filtered, concentrated in vacuum and triturated with ethyl acetate (20 mL). The solid obtained was collected by filtration and dried in vacuum to afford ethyl 2-(4-amino-6-cyano-9H-pyrimido[4,5-b]indol-9-yl)acetate (49a) (160 mg, 63% yield) as a white solid; 1H NMR (300 MHz, DMSO-$d_6$) δ 8.94-8.93 (m, 1H), 8.36 (s, 1H), 7.86-7.80 (m, 2H), 7.59 (s, 2H), 5.31 (s, 2H), 4.14 (q, J=7.1 Hz, 2H), 1.20 (t, J=7.2 Hz, 3H); MS (ES+): 296.10 (M+1); (ES−): 294.10 (M−1)

Step-2: Preparation of 2-(4-amino-6-cyano-9H-pyrimido[4,5-b]indol-9-yl)acetic acid (49b)

Compound 49b was prepared according to the procedure reported in step-4 of scheme-17, from ethyl 2-(4-amino-6-cyano-9H-pyrimido[4,5-b]indol-9-yl)acetate (49a) (80 mg, 0.271 mmol) in THF (3 mL) and MeOH (3 mL) using a solution of lithium hydroxide hydrate (69.6 mg, 1.625 mmol) in water (3 mL) and stirring at RT for 15 h. This gave after workup 2-(4-amino-6-cyano-9H-pyrimido[4,5-b]indol-9-yl)acetic acid (49b) (72 mg, 100% yield) which was used as such in next step-3 without further purification; MS (ES+): 268.10 (M+1).

Step-3: Preparation of (1R,3S,5R)-2-(2-(4-amino-6-cyano-9H-pyrimido[4,5-b]indol-9-yl)acetyl)-N-(6-bromopyridin-2-yl)-2-azabicyclo[3.1.0]hexane-3-carboxamide (49c)

Compound 49c was prepared according to the procedure reported in step-3 of scheme-1, from 2-(4-amino-6-cyano-9H-pyrimido[4,5-b]indol-9-yl)acetic acid (49b) (0.072 g, 0.271 mmol) in DMF (10 mL) using HCl salt of (1R,3S,5R)—N-(6-bromopyridin-2-yl)-2-azabicyclo[3.1.0]hexane-3-carboxamide (4a) (0.104 g, 0.325 mmol), HATU (0.206 g, 0.542 mmol), DIPEA (175 mg, 1.355 mmol) and stirring at RT for 22 h. This gave after workup and purification by flash column chromatography [silica gel (12 g), 10% MeOH in EtOAc in hexane from 0-100%] followed by conversion to HCl salt in acetonitrile (5 mL) using 0.1% aq. HCl (30 mL) and lyophilization (1R,3S,5R)-2-(2-(4-amino-6-cyano-9H-pyrimido[4,5-b]indol-9-yl)acetyl)-N-(6-bromopyridin-2-yl)-2-azabicyclo[3.1.0]hexane-3-carboxamide (49c) (54 mg, 38% yield) HCl salt as a white solid; $^1$H NMR (300 MHz, DMSO-$d_6$) δ 10.76 (s, 1H, $D_2O$ exchangeable), 9.09 (d, J=1.5 Hz, 1H), 8.74-8.54 (m, 3H, 2H $D_2O$ exchangeable), 8.00 (d, J=8.2 Hz, 1H), 7.94 (dd, J=8.6, 1.4 Hz, 1H), 7.87 (d, J=8.6 Hz, 1H), 7.70 (t, J=8.0 Hz, 1H), 7.31 (d, J=7.7 Hz, 1H), 5.81 (d, J=17.4 Hz, 1H), 5.45 (d, J=17.3 Hz, 11H), 4.42 (dd, J=9.0, 5.5 Hz, 1H), 3.95-3.84 (m, 1H), 2.42-2.08 (m, 2H), 1.98-1.83 (m, 1H), 1.16-0.98 (m, 1H), 0.90-0.67 (m, 1H); MS (ES+): 531.10 & 533.10 (M+1); MS (ES−): 529.00 & 531.10 (M−1); Analysis calculated for $C_{24}H_{19}BrN_8O_2 0.85HCl \cdot 2.0H_2O$: C, 48.17; H, 4.02; Cl, 5.04; N, 18.73. Found: C, 48.54; H, 4.17; Cl, 5.36; N, 18.40.

Scheme 50

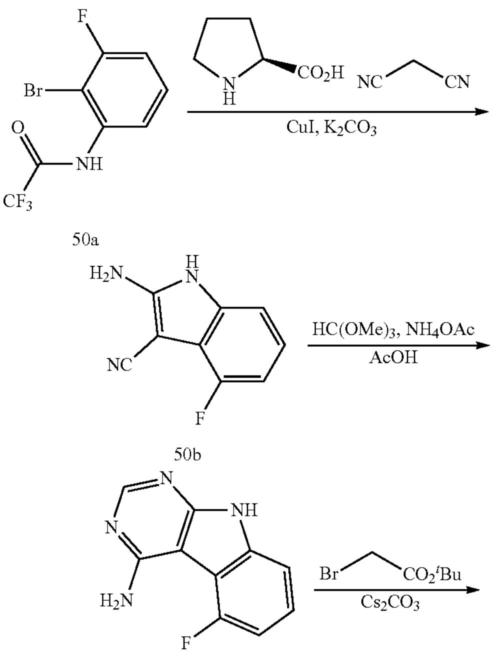

50a

50b

50c

-continued

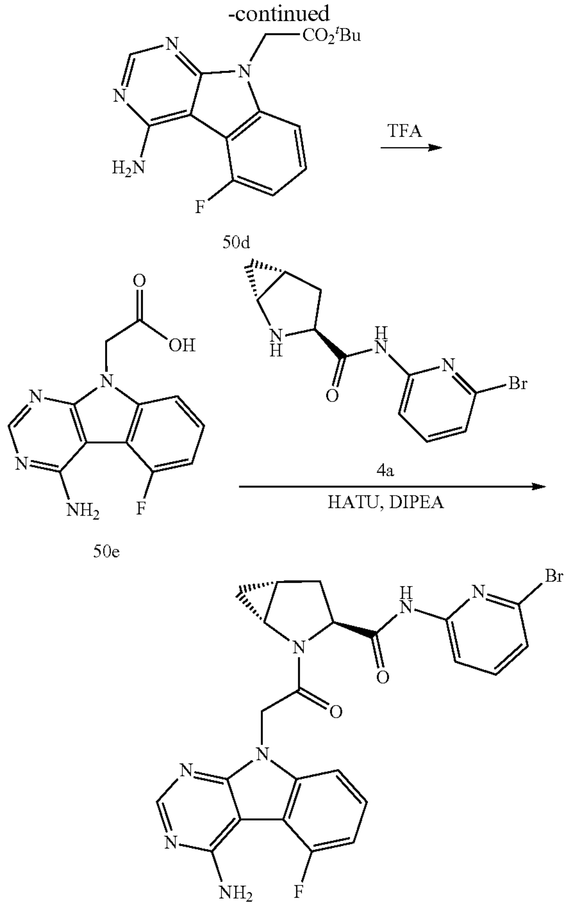

50d

4a

50e

50f

Preparation of (1R,3S,5R)-2-(2-(4-amino-5-fluoro-9H-pyrimido[4,5-b]indol-9-yl)acetyl)-N-(6-bromopyridin-2-yl)-2-azabicyclo[3.1.0]hexane-3-carboxamide (50f)

Step-1: Preparation of 2-amino-4-fluoro-1H-indole-3-carbonitrile (50b)

Compound 50b was prepared according to the procedure reported in step-1 of scheme-11, from N-(2-bromo-3-fluorophenyl)-2,2,2-trifluoroacetamide (50a) (5 g, 17.48 mmol; CAS #118313-91-0) in DMSO (20 mL) using malononitrile (1.386 g, 20.98 mmol), L-proline (0.403 g, 3.50 mmol). CuI (0.333 g, 1.748 mmol), $K_2CO_3$ (4.83 g, 35.0 mmol) and heating at 60° C. for 16 h under an argon atmosphere. This gave after workup and purification by flash column chromatography [$SiO_2$ gel (40 g), eluting with EtOAc in hexane from 0-50%] 2-amino-4-fluoro-1H-indole-3-carbonitrile (50b) (0.3 g, 10% yield) as an brown solid: $^1$H NMR (300 MHz, DMSO-$d_6$) δ 10.97 (s, 1H), 6.98 (d, J=7.8 Hz, 1H), 6.91-6.83 (m, 3H), 6.75 (ddd, J=10.8, 8.1, 1.0 Hz, 1H); MS (ES+): 176.0 (M+1), (ES−): 174.0 (M−1).

Step-2: Preparation of 5-fluoro-9H-pyrimido[4,5-b]indol-4-amine (50c)

Compound 50c was prepared according to the procedure reported in step-1 of scheme-6, from 2-amino-4-fluoro-1H- indole-3-carbonitrile (50b) (0.3 g, 1.713 mmol) using trimethyl orthoformate (3.64 g, 34.3 mmol), AcOH (0.490 mL, 8.56 mmol) and $NH_4OAc$ (0.660 g, 8.56 mmol). This gave after workup and purification by reverse phase column chromatography [C18 column (30 g), eluting with ACN in water (containing 0.1% HCl) from 0-100%] 5-fluoro-9H-pyrimido[4,5-b]indol-4-amine (50c) (83 mg, 24% yield) as a brown yellow solid; 1H NMR (300 MHz, DMSO-$d_6$) δ 13.18 (s, 1H), 8.60 (s, 1H), 7.61-7.38 (m, 2H), 7.23 (dd, J=11.3, 7.8 Hz, 1H); MS (ES+): 203.04 (M+1).

Step-3: Preparation of tert-butyl 2-(4-amino-5-fluoro-9H-pyrimido[4,5-b]indol-9-yl)acetate (50d)

Compound 50d was prepared according to the procedure reported in step-2 of scheme-16, from HCl salt of 5-fluoro-9H-pyrimido[4,5-b]indol-4-amine (50c) (80 mg, 0.335 mmol) in DMF (2.5 mL) using tert-butyl 2-bromoacetate (65.4 mg, 0.335 mmol) $Cs_2CO_3$ (218 mg, 0.670 mmol) and stirring at RT for 1.5 h. The solid separated was collected by filtration, dried to give tert-butyl 2-(4-amino-5-fluoro-9H-pyrimido[4,5-b]indol-9-yl)acetate (50d) (83 mg, 78% yield) as a pale yellow solid: 1H NMR (300 MHz, DMSO-$d_6$) δ 8.36 (s, 1H), 7.54-7.40 (m, 2H), 7.14 (ddd, J=11.5, 7.2, 1.7 Hz, 1H), 5.16 (s, 2H), 1.41 (s, 9H); MS (ES+): 317.10 (M+1).

Step-4: Preparation of 2-(4-amino-5-fluoro-9H-pyrimido[4,5-b]indol-9-yl)acetic acid (50e)

Compound 50e was prepared according to the procedure reported in step-2 of scheme-1, from tert-butyl 2-(4-amino-5-fluoro-9H-pyrimido[4,5-b]indol-9-yl)acetate (50d) (80 mg, 0.253 mmol) using 20% TFA in DCM (1452 μl, 3.79 mmol) and stirring at RT for 16 h. This gave after workup 2-(4-amino-5-fluoro-9H-pyrimido[4,5-b]indol-9-yl)acetic acid (50e) (85 mg, 90% yield) TFA salt as a yellow solid; $^1$H NMR (300 MHz, DMSO-$d_6$) δ 8.46 (s, 1H), 7.58 (d, J=8.2 Hz, 1H), 7.49 (td, J=8.1, 5.5 Hz, 1H), 7.20 (dd, J=11.3, 8.0 Hz, 1H), 5.22 (s, 2H); MS (ES+): 261.00 (M+1).

Step-5: Preparation of (1R,3S,5R)-2-(2-(4-amino-5-fluoro-9H-pyrimido[4,5-b]indol-9-yl)acetyl)-N-(6-bromopyridin-2-yl)-2-azabicyclo[3.1.0]hexane-3-carboxamide (501)

Compound 50f was prepared according to the procedure reported in step-3 of scheme-1, from TFA salt of 2-(4-amino-5-fluoro-9H-pyrimido[4,5-b]indol-9-yl)acetic acid (50e) (50 mg, 0.134 mmol) in DMF (1.5 mL) using TFA salt of (1R,3S,5R)—N-(6-bromopyridin-2-yl)-2-azabicyclo[3.1.0]hexane-3-carboxamide (4a) (52.9 mg, 0.134 mmol), HATU (76 mg, 0.200 mmol), DIPEA (0.116 mL, 0.668 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%](1R,3S,5R)-2-(2-(4-amino-5-fluoro-9H-pyrimido[4,5-b]indol-9-yl)acetyl)-N-(6-bromopyridin-2-yl)-2-azabicyclo[3.1.0]hexane-3-carboxamide (50) (53 mg, 76% yield) HCl salt as a white solid; $^1$H NMR (300 MHz, DMSO-$d_6$) δ 10.77 (s, 1H, $D_2O$ exchangeable), 8.68 (s, 1H), 8.01 (d, J=8.1 Hz, 1H), 7.71 (t, J=8.0 Hz, 1H), 7.62-7.49 (m, 2H), 7.35-7.20 (m, 2H), 5.79 (d, J=17.4 Hz, 1H), 5.44 (d, J=17.3 Hz, 1H), 4.43 (dd, J=9.1, 5.5 Hz, 1H), 3.91 (ddd, J=7.4, 5.4, 2.3 Hz, 1H), 2.40-2.14 (m, 2H), 1.92 (dq, J=13.3, 6.5, 6.0 Hz, 1H), 1.08 (dt, J=8.7, 5.4 Hz, 1H), 0.79 (td, J=5.2, 2.4 Hz, 1H); $^{19}$F NMR (282 MHz, DMSO-$d_6$) δ−113.23; MS (ES+): 524.0 (M+1); 546.0 (M+Na); (ES−): 522.0 (M−1); Analysis calculated for $C_{23}H_{19}BrFN_7O_2 \cdot 1.75H_2O \cdot 1HCl$: C, 46.64; H, 4.00; Cl, 5.99; N, 16.55. Found: C, 46.50; H, 3.71; Cl, 5.73, N, 16.29.

Scheme 51

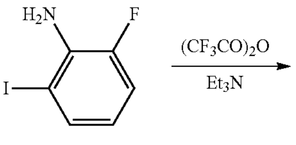

51a

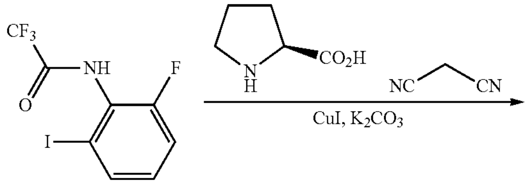

51b

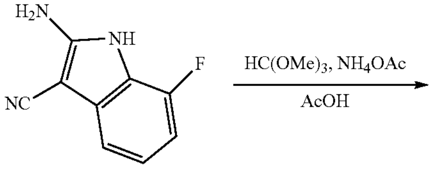

51c

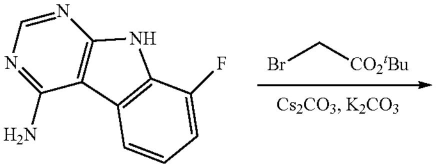

51d

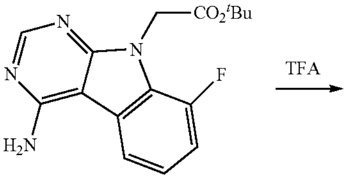

51e

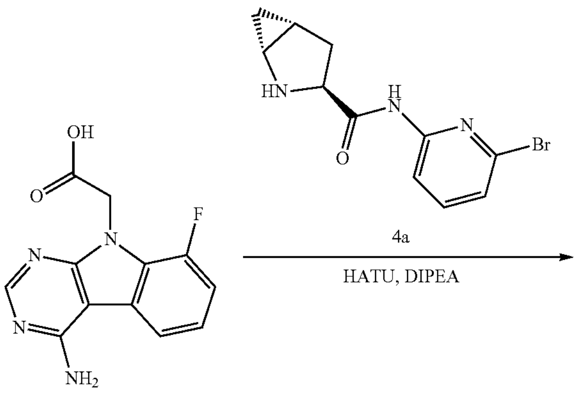

4a

51f

-continued

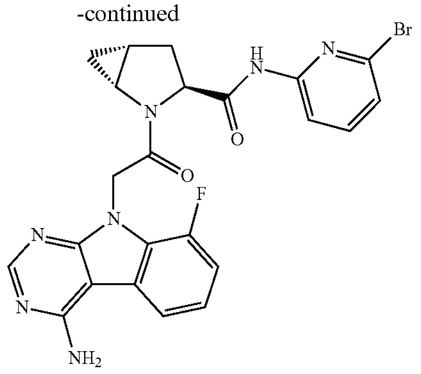

51g

Preparation of (1R,3S,5R)-2-(2-(4-amino-8-fluoro-9H-pyrimido[4,5-b]indol-9-yl)acetyl)-N-(6-bromopyridin-2-yl)-2-azabicyclo[3.1.0]hexane-3-carboxamide (51 g)

Step-1: Preparation of 2,2,2-trifluoro-N-(2-fluoro-6-iodophenyl)acetamide (51b)

Compound 51b was prepared according to the procedure reported in step-1 of scheme-46, from 2-fluoro-6-iodoaniline (51a) (5 g, 21.10 mmol; CAS #886762-73-8) in DCM (50 mL) using triethylamine (5 mL, 35.9 mmol), trifluoroacetic acid anhydride (4.40 mL, 6.65 mmol) and stirring at RT for 16 h. This gave after workup 2,2,2-trifluoro-N-(2-fluoro-6-iodophenyl)acetamide (51b) (6.5 g, 93% yield) as a yellow solid, which was used as such for the next step: $^1H$ NMR (300 MHz, DMSO-$d_6$) δ 11.42 (s, 1H), 7.81 (dt, J=8.0, 1.2 Hz, 1H), 7.43 (ddd, J=9.6, 8.4, 1.3 Hz, 1H), 7.26 (td, J=8.2, 5.6 Hz, 1H), MS (ES−): 331.80 (M−1).

Step-2: Preparation of 2-amino-7-fluoro-1H-indole-3-carbonitrile (51c)

Compound 51c was prepared according to the procedure reported in step-1 of scheme-11, from 2,2,2-trifluoro-N-(2-fluoro-6-iodophenyl)acetamide (51b) (6.4 g, 19.22 mmol) in DMSO (20 mL) using malononitrile (1.452 mL, 23.06 mmol), L-proline (0.443 g, 3.84 mmol), CuI (0.366 g, 1.922 mmol), $K_2CO_3$ (5.31 g, 38.4 mmol) and heating at 60° C. for 16 h under an argon atmosphere. This gave after workup and purification [$SiO_2$ gel (40 g), eluting with EtOAc in hexane from 0-50%] 2-amino-7-fluoro-1H-indole-3-carbonitrile (51c) (1.535 g, 46% yield) as a yellow solid, $^1H$ NMR (300 MHz, DMSO-$d_6$) δ 11.33 (s, 1H), 7.03-6.88 (m, 2H), 6.88-6.66 (m, 3H); MS (ES+): 176.0 (M+1), (ES−): 174.0 (M−1).

Step-3: Preparation of 8-fluoro-9H-pyrimido[4,5-b]indol-4-amine (51d)

Compound 51d was prepared according to the procedure reported in step-1 of scheme-6, from 2-amino-7-fluoro-1H-indole-3-carbonitrile (51c) (1.5 g, 8.56 mmol) using trimethyl orthoformate (18.74 mL, 171 mmol), AcOH (2.449 mL, 42.8 mmol) and $NH_4OAc$ (3.30 g, 42.8 mmol). This gave after workup 8-fluoro-9H-pyrimido[4,5-b]indol-4-amine (51d) (1.54 g, 69% yield) as a pale yellow solid; 1H NMR (300 MHz, DMSO-$d_6$) δ 12.33 (s, 1H), 11.98 (s, 1H), 8.29 (s, 1H), 8.18-8.03 (m, 1H), 7.27 (s, 2H), 7.26-7.16 (m, 2H), 1.92 (s, 3H); MS (ES+): 203.10 (M+1).

Step-4: Preparation of tert-butyl 2-(4-amino-8-fluoro-9H-pyrimido[4,5-b]indol-9-yl)acetate (51e)

Compound 51e was prepared according to the procedure reported in step-2 of scheme-16, from AcOH salt of 8-fluoro-9H-pyrimido[4,5-b]indol-4-amine (51d) (1.5 g, 5.72 mmol) in DMF (35 mL) using tert-butyl 2-bromoacetate (1.171 g, 6.01 mmol), $Cs_2CO_3$ (4.10 g, 12.58 mmol) stirring at RT for 15 h. followed by the addition of $K_2CO_3$ (0.791 g, 5.72 mmol), tert-butyl 2-bromoacetate (0.845 mL, 5.72 mmol) and stirring for additional 3 h. This gave after workup tert-butyl 2-(4-amino-8-fluoro-9H-pyrimido[4,5-b]indol-9-yl)acetate (51e) (1.15 g, 64% yield) as a pale yellow solid: $^1H$ NMR (300 MHz, DMSO-$d_6$) δ 8.34 (s, 1H), 8.22-8.16 (m, 1H), 7.45 (s, 2H), 7.28-7.21 (m, 2H), 5.17 (d, J=2.0 Hz, 2H), 1.42 (s, 9H); MS (ES+): 317.14 (M+1).

Step-5: Preparation of 2-(4-amino-8-fluoro-9H-pyrimido[4,5-b]indol-9-yl)acetic acid (51f)

Compound 51f was prepared according to the procedure reported in step-2 of scheme-1, from tert-butyl 2-(4-amino-8-fluoro-9H-pyrimido[4,5-b]indol-9-yl)acetate (51e) (0.9 g, 2.85 mmol) using 20% TFA in DCM (16.33 mL, 42.7 mmol)) and stirring at RT for 16 h. This gave after workup 2-(4-amino-8-fluoro-9H-pyrimido[4,5-b]indol-9-yl)acetic acid (51f) (0.92 g, 86% yield) TFA salt as a white solid; 1H NMR (300 MHz, DMSO-$d_6$) δ 8.49 (s, 1H), 8.32-8.23 (m, 1H), 8.07 (s, 2H), 7.40-7.27 (m, 2H), 5.25 (d, J=1.9 Hz, 2H); MS (ES+): 261.10 (M+1).

Step-6: Preparation of (1R,3S,5R)-2-(2-(4-amino-8-fluoro-9H-pyrimido[4,5-b]indol-9-yl)acetyl)-N-(6-bromopyridin-2-yl)-2-azabicyclo[3.1.0]hexane-3-carboxamide (51 g)

Compound 51g was prepared according to the procedure reported in step-3 of scheme-1, from TFA salt of 2-(4-amino-8-fluoro-9H-pyrimido[4,5-b]indol-9-yl)acetic acid (51f) (75 mg, 0.200 mmol) in DMF (2 mL) using TFA salt of (1R,3S,5R)—N-(6-bromopyridin-2-yl)-2-azabicyclo[3.1.0]hexane-3-carboxamide (4a) (79 mg, 0.200 mmol), HATU (114 mg, 0.301 mmol), DIPEA (0.175 mL, 1.002 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%](1R,3S,5R)-2-(2-(4-amino-8-fluoro-9H-pyrimido[4,5-b]indol-9-yl)acetyl)-N-(6-bromopyridin-2-yl)-2-azabicyclo[3.1.0]hexane-3-carboxamide (51 g) (81 mg, 77% yield) HCl salt as a white solid: 1H NMR (300 MHz, DMSO-$d_6$) δ 10.78 (s, 1H, $D_2O$ exchangeable), 8.60 (s, 1H), 8.45 (s, 2H, $D_2O$ exchangeable), 8.32 (dd, J=5.8, 3.0 Hz, 1H), 8.02 (d, J=8.2 Hz, 1H), 7.71 (t, J=8.0 Hz, 1H), 7.41-7.26 (m, 3H), 5.81 (d, J=17.5 Hz, 1H), 5.57-5.38 (m, 1H), 4.44 (dd, J=9.0, 5.6 Hz, 1H), 3.98-3.80 (m, 1H), 2.40-2.13 (m, 2H), 2.01-1.83 (m, 1H), 1.10 (dt, J=9.3, 5.4 Hz, 1H), 0.64 (q, J=3.8, 2.9 Hz, 1H). $^{19}F$ NMR (282 MHz, DMSO-$d_6$) δ−134.64. MS (ES+): 524.1 (M+1); (ES−): 522.1 (M−1); Analysis calculated for $C_{23}H_{19}BrFN_7O_2 \cdot 2H_2O \cdot 0.9HCl$: C, 46.57H, 4.06; Cl, 5.38; N, 16.53. Found: C, 46.54; H, 3.90; Cl, 5.43; N, 16.32.

Scheme 52

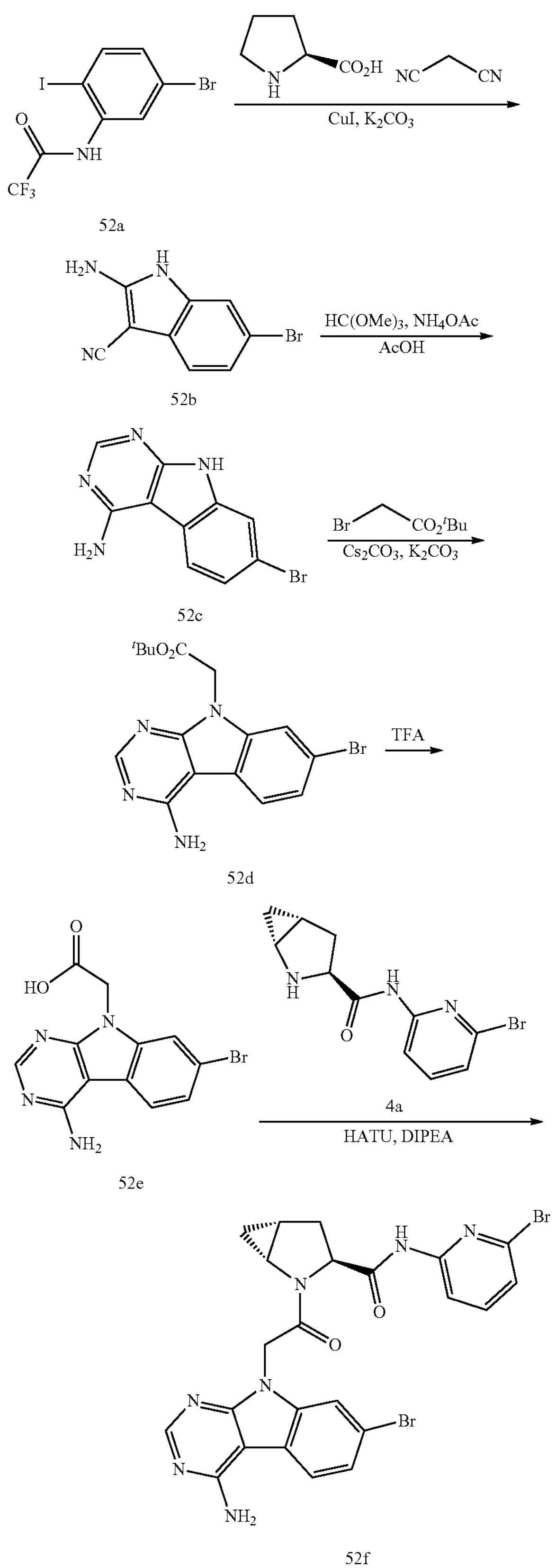

52a 52b 52c 52d 52e 4a 52f

Preparation of (1R,3S,5R)-2-(2-(4-amino-7-bromo-9H-pyrimido[4,5-b]indol-9-yl)acetyl)-N-(6-bromopyridin-2-yl)-2-azabicyclo[3.1.0]hexane-3-carboxamide (52f)

Step-1: Preparation of 2-amino-6-bromo-1H-indole-3-carbonitrile (52b)

Compound 52b was prepared according to the procedure reported in step-1 of scheme-11, from N-(5-bromo-2-iodophenyl)-2,2,2-trifluoroacetamide (52a) (6.4 g, 16.25 mmol; CAS #1870674-39-7) in DMSO (20 mL) using malononitrile (1.228 mL, 19.50 mmol), L-proline (0.374 g, 3.25 mmol), CuI (0.309 g, 1.625 mmol), $K_2CO_3$ (4.49 g, 32.5 mmol) and heating at 60° C. for 16 h under an argon atmosphere. This gave after workup and purification [$SiO_2$ gel (40 g), eluting with EtOAc in hexane from 0-50%] 2-amino-6-bromo-1H-indole-3-carbonitrile (52b) (2.06 g, 54% yield) as a yellow solid; $^1H$ NMR (300 MHz, DMSO-$d_6$) δ 10.80 (s, 1H), 7.29 (d, J=1.6 Hz, 1H), 7.17-7.00 (m, 2H), 6.95 (s, 2H); MS (ES+): 236.0 (M+1), (ES−): 233.9 (M−1).

Step-2: Preparation of 7-bromo-9H-pyrimido[4,5-b]indol-4-amine (52c)

Compound 52c was prepared according to the procedure reported in step-1 of scheme-6, from 2-amino-6-bromo-1H-indole-3-carbonitrile (52b) (2 g, 8.47 mmol) using trimethyl orthoformate (17.98 g, 169 mmol), AcOH (2.54 g, 42.4 mmol) and $NH_4OAc$ (3.27 g, 42.4 mmol). This gave after workup 7-bromo-9H-pyrimido[4,5-b]indol-4-amine (52c) (2.29 g, 84% yield) as a pale yellow solid; $^1H$ NMR (300 MHz, DMSO-$d_6$) δ 11.97 (s, 2H), 8.27 (t, J=4.2 Hz, 2H), 7.58 (d, J=1.8 Hz, 1H), 7.36 (dd, J=8.4, 1.8 Hz, 1H), 7.26 (s, 2H), 1.92 (s, 3H).

Step-3: Preparation of tert-butyl 2-(4-amino-7-bromo-9H-pyrimido[4,5-b]indol-9-yl)acetate (52d)

Compound 52d was prepared according to the procedure reported in step-2 of scheme-16, from AcOH salt of 7-bromo-9H-pyrimido[4,5-b]indol-4-amine (52c) (2.2 g, 6.81 mmol) in DMF (75 mL) using tert-butyl 2-bromoacetate (1.056 g, 7.15 mmol), $Cs_2CO_3$ (4.88 g, 14.98 mmol) stirring at RT for 15 h, followed by the addition of $K_2CO_3$ (0.941 g, 6.81 mmol), tert-butyl 2-bromoacetate (1.006 mL, 6.81 mmol) and stirring for 3 h at RT. This gave after workup tert-butyl 2-(4-amino-7-bromo-9H-pyrimido[4,5-b]indol-9-yl)acetate (52d) (1.25 g, 49% yield) as a pale yellow solid: $^1H$ NMR (300 MHz, DMSO-$d_6$) δ 8.31 (t. J=4.2 Hz, 2H), 7.91 (d, J=1.7 Hz, 1H), 7.46-7.36 (m, 3H), 5.14 (s, 2H), 1.41 (s, 9H).

Step-4: Preparation of 2-(4-amino-7-bromo-9H-pyrimido[4,5-b]indol-9-yl)acetic acid (52e)

Compound 52e was prepared according to the procedure reported in step-2 of scheme-1, from tert-butyl 2-(4-amino-7-bromo-9H-pyrimido[4,5-b]indol-9-yl)acetate (52d) (0.3 g, 0.795 mmol) using 20% TFA in DCM (4.56 mL, 11.93 mmol) and stirring at RT for 16 h. This gave after workup 2-(4-amino-7-bromo-9H-pyrimido[4,5-b]indol-9-yl)acetic acid (52e) (0.31 g, 90% yield) TFA salt as a white solid; 1H NMR (300 MHz, DMSO-$d_6$) δ 8.49 (s, 1H), 8.41 (d, J=8.4

Hz, 1H), 8.08 (d, J=1.7 Hz, 1H), 7.54 (dd, J=8.4, 1.7 Hz, 1H), 5.23 (s, 2H); MS (ES+): 321.00 (M+1).

Step-5: Preparation of (1R,3S,5R)-2-(2-(4-amino-7-bromo-9H-pyrimido[4,5-b]indol-9-yl)acetyl)-N-(6-bromopyridin-2-yl)-2-azabicyclo[3.1.0]hexane-3-carboxamide (52f)

Compound 52f was prepared according to the procedure reported in step-3 of scheme-1, from TFA salt of 2-(4-amino-7-bromo-9H-pyrimido[4,5-b]indol-9-yl)acetic acid (52e) (75 mg, 0.172 mmol) in DMF (2 mL) using TFA salt of (1R,3S,5R)—N-(6-bromopyridin-2-yl)-2-azabicyclo[3.1.0]hexane-3-carboxamide (4a) (68.3 mg, 0.172 mmol), HATU (98 mg, 0.259 mmol), DIPEA (0.150 mL, 0.862 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%](1R,3S,5R)-2-(2-(4-amino-7-bromo-9H-pyrimido[4,5-b]indol-9-yl)acetyl)-N-(6-bromopyridin-2-yl)-2-azabicyclo[3.1.0]hexane-3-carboxamide (52f) (79 mg, 78% yield) HCl salt as a white solid; $^1$H NMR (300 MHz, DMSO-$d_6$) δ 10.79 (s, 1H, $D_2O$ exchangeable), 8.70 (s, 2H, $D_2O$ exchangeable), 8.64 (s, 1H), 8.49 (d, J=8.5 Hz, 1H), 8.08-7.97 (m, 2H), 7.71 (t, J=8.0 Hz, 1H), 7.60 (dd, J=8.5, 1.7 Hz, 1H), 7.32 (d, J=7.7 Hz, 1H), 5.79 (d, J=17.4 Hz, 1H), 5.42 (d, J=17.3 Hz, 1H), 4.43 (dd, J=9.0, 5.5 Hz, 1H), 3.90 (ddd, J=7.6, 5.4, 2.4 Hz, 1H), 2.39-2.10 (m, 2H), 2.01-1.83 (m, 1H), 1.08 (dt, J=8.8, 5.5 Hz, 1H), 0.79 (td, J=5.2, 2.4 Hz, 1H). MS (ES+): 586.0 (M+1); (ES−): 584.0 (M−1); Analysis calculated for $C_3H_{19}Br_2N_7O_2 \cdot 2H_2O \cdot 1HCl$: C, 42.00; H, 3.68; Cl, 5.39; N, 14.91. Found: C, 42.08; H, 3.55; Cl, 5.18; N, 14.77.

Scheme 53

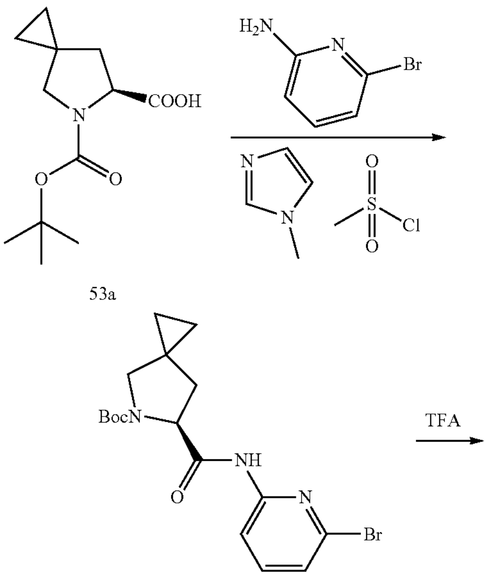

53a

53b

-continued

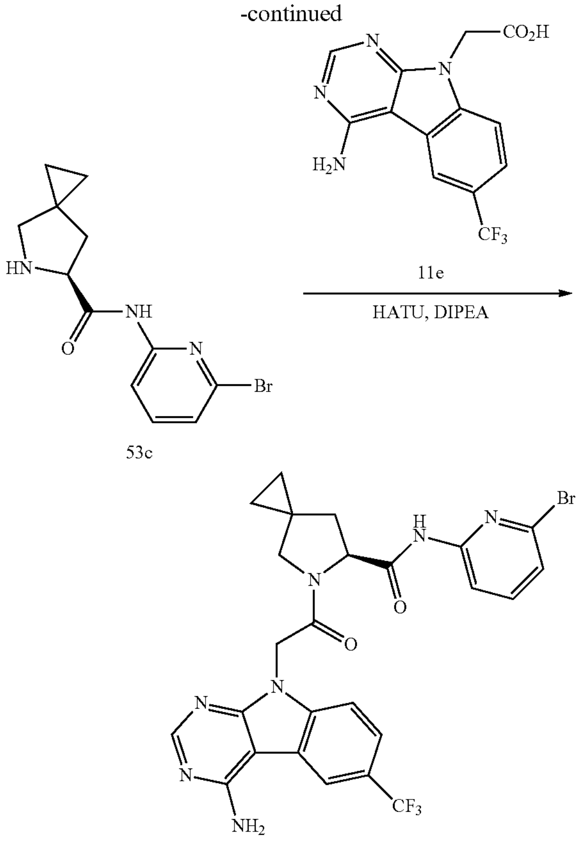

53c

53d

Preparation of (S)-5-(2-(4-amino-6-(trifluoromethyl)-9H-pyrimido[4,5-b]indol-9-yl)acetyl)-N-(6-bromopyridin-2-yl)-5-azaspiro[2.4]heptane-6-carboxamide (53d)

Step-1: Preparation of(S)-tert-butyl 6-((6-bromopyridin-2-yl)carbamoyl)-5-azaspiro[2.4]heptane-5-carboxylate (53b)

To a stirred solution of (S)-5-(tert-butoxycarbonyl)-5-azaspiro[2.4]heptane-6-carboxylic acid (53a) (0.5 g, 2.072 mmol) in DCM (15 mL) was added 1-methyl-1H-imidazole (0.413 mL, 5.18 mmol) at 0-5° C. under a nitrogen atmosphere. The reaction mixture was stirred for 10 min at 0-5° C., added methanesulfonyl chloride (0.192 mL, 2.487 mmol) followed by stirring at 0-5° C. for 1 h. To this mixture was added 6-bromopyridin-2-amine (0.359 g, 2.072 mmol) and stirred for 18 h at RT. Water (30 mL) was added to the reaction mixture, layers were separated, and aqueous layer was extracted with DCM (3×30 mL). The combined organics were washed with 1N HCl (30 mL), Sat, aqueous $NaHCO_3$ (30 mL), brine (30 mL), dried, filtered and concentrated in vacuum to afford (S)-tert-butyl 6-((6-bromopyridin-2-yl)carbamoyl)-5-azaspiro[2.4]heptane-5-carboxylate (53b) (0.8 g, 97% yield); $^1$H NMR (300 MHz, DMSO-$d_6$) δ 10.90 (d, J=18.6 Hz, 1H), 8.11 (dd, J=13.0, 8.1 Hz, 1H), 7.75 (q, J=7.8 Hz, 1H), 7.35 (d, J=7.7 Hz, 1H), 4.57-4.39 (m, 1H), 3.32-3.16 (m, 2H), 2.15 (ddd, J=27.3, 12.8, 8.3 Hz, 1H), 1.83 (ddd, J=35.1, 12.6, 5.2 Hz, 1H), 1.33 (d, J=36.8 Hz, 9H), 0.68-0.41 (m, 4H); MS (ES+): 396.00 (M+1).

Step-2: Preparation of (S)—N-(6-bromopyridin-2-yl)-5-azaspiro[2.4]heptane-6-carboxamide (53c)

Compound 53c was prepared according to the procedure reported in step-2 of scheme-1, from (S)-tert-butyl 6-((6-bromopyridin-2-yl)carbamoyl)-5-azaspiro[2.4]heptane-5-carboxylate (53b) (0.8 g, 2.019 mmol) using TFA (0.778 mL, 10.09 mmol) in DCM (7 mL) and stirring overnight at RT. This gave after workup (S)—N-(6-bromopyridin-2-yl)-5-azaspiro[2.4]heptane-6-carboxamide (53c) (0.55 g, 92% yield) TFA salt; $^1H$ NMR (300 MHz, DMSO-$d_6$) δ 11.43 (s, 1H), 9.71 (s, 1H), 8.90 (s, 1H), 8.08 (d, J=8.2 Hz, 1H), 7.83 (t, J=7.9 Hz, 1H), 7.45 (d, J=7.7 Hz, 1H), 4.63-4.47 (m, 1H), 3.20 (d, J=5.2 Hz, 2H), 2.33 (dd, J=13.1, 8.6 Hz, 1H), 2.03 (dd, J=13.1, 7.0 Hz, 1H), 0.76-0.46 (m, 4H); MS (ES+): 295.93 (M+1).

Step-3: Preparation of (S)-5-(2-(4-amino-6-(trifluoromethyl)-9H-pyrimido[4,5-b]indol-9-yl)acetyl)-N-(6-bromopyridin-2-yl)-5-azaspiro[2.4]heptane-6-carboxamide (53d)

Compound 53d was prepared according to the procedure reported in step-3 of scheme-1, from TFA salt of (S)—N-(6-bromopyridin-2-yl)-5-azaspiro[2.4]heptane-6-carboxamide (53c) (72.5 mg, 0.177 mmol) in DMF (2 mL) using TFA salt of 2-(4-amino-6-(trifluoromethyl)-9H-pyrimido[4,5-b]indol-9-yl)acetic acid (11e) (75 mg, 0.177 mmol), HATU (101 mg, 0.265 mmol), DIPEA (0.154 mL, 0.884 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (S)-5-(2-(4-amino-6-(trifluoromethyl)-9H-pyrimido[4,5-b]indol-9-yl)acetyl)-N-(6-bromopyridin-2-yl)-5-azaspiro[2.4]heptane-6-carboxamide (53d)) (89 mg, 86% yield) HCl salt as a white solid: $^1H$ NMR (300 MHz, DMSO-$d_6$) (a mixture of two rotamers) δ 11.25 and 10.82 (2s, 1H, $D_2O$ exchangeable), 8.96 (s, 1H), 8.59 and 8.57 (2s, 1H), 8.52 (s, 2H, $D_2O$ exchangeable), 8.19 and 8.02 (2d, J=8.2 Hz, 1H), 7.94-7.78 (m, 2H), 7.70 (t, J=8.0 Hz, 1H), 7.41 and 7.32 (2d, J=7.7 Hz, 1H), 5.45 (d, J=2.4 Hz, 2H), 4.65 (dd, J=8.5, 5.0 Hz, 1H), 3.90-3.74 (m, 2H), 2.25 (dd, J=12.7, 8.4 Hz, 1H), 1.89 (dd, J=12.6, 4.9 Hz, 1H), 0.81-0.49 (m, 4H). $^{19}F$ NMR (282 MHz, DMSO-$d_6$) δ-58.70. MS (ES+): 588.1 (M+1); (ES−): 586.1 (M−1); Analysis calculated for $C_{25}H_{21}BrF_3N_7O_2$ $1.5H_2O \cdot 1.1$ HCl: C, 45.81; H, 3.86; Cl, 5.95; N, 14.96. Found: C, 45.85; H, 3.73; Cl, 5.91; N, 14.70.

Scheme 54

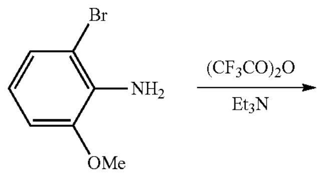

54a

-continued

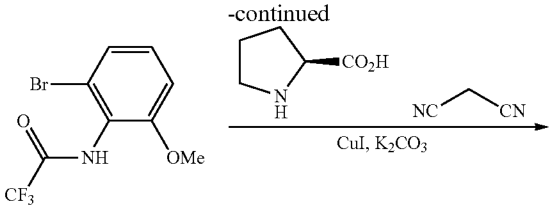

54b

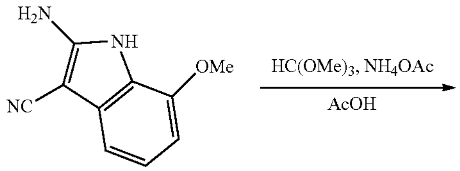

54c

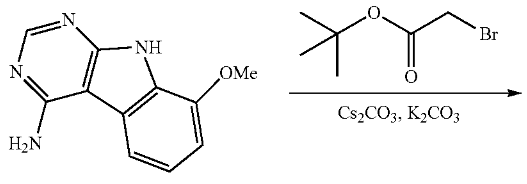

54d

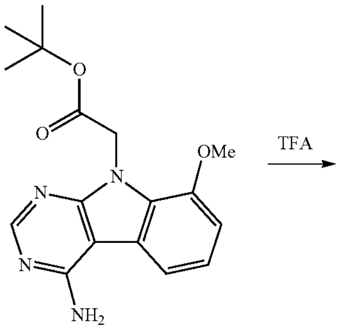

54e

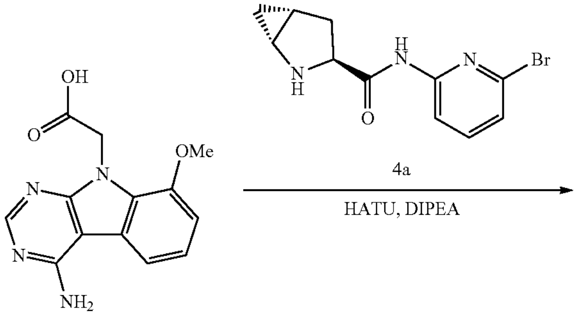

54f

-continued

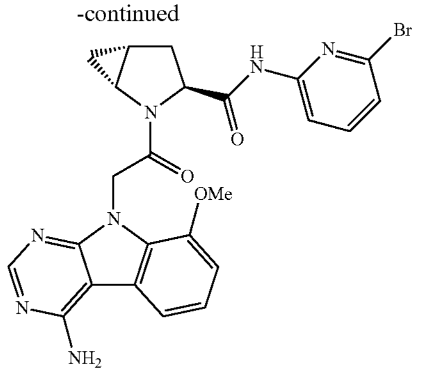

54g

Preparation of (1R,3S,5R)-2-(2-(4-amino-8-methoxy-9H-pyrimido[4,5-b]indol-9-yl)acetyl)-N-(6-bromopyridin-2-yl)-2-azabicyclo[3.1.0]hexane-3-carboxamide (54 g)

Step-1: Preparation of N-(2-bromo-6-methoxyphenyl)-2,2,2-trifluoroacetamide (54b)

Compound 54b was prepared according to the procedure reported in step-1 of scheme-46, from 2-bromo-6-methoxyaniline (54a) (5 g, 24.75 mmol; CAS #5473-01-8) in DCM (50 mL) using triethylamine (5.86 mL, 42.1 mmol), trifluoroacetic acid anhydride (5.16 mL, 37.1 mmol) and stirring at RT for 16 h. This gave after workup N-(2-bromo-6-methoxyphenyl)-2,2,2-trifluoroacetamide (54b) (7.35 g, 100% yield) as a pale yellow solid and was used as such for next step; 1H NMR (300 MHz, DMSO-$d_6$) δ 11.03 (s, 1H), 7.40-7.26 (m, 2H), 7.18 (dd, J=7.1, 2.5 Hz, 1H), 3.82 (s, 3H); MS (ES−): 295.9 (M−1).

Step-2: Preparation of 2-amino-7-methoxy-1H-indole-3-carbonitrile (54c)

Compound 54c was prepared according to the procedure reported in step-1 of scheme-11, from N-(2-bromo-6-methoxyphenyl)-2,2,2-trifluoroacetamide (54b) (7.2 g, 24.16 mmol) in DMSO (20 mL) and using malononitrile (1.826 mL, 29.0 mmol), L-proline (0.556 g, 4.83 mmol), CuI (0.460 g, 2.416 mmol). $K_2CO_3$ (6.68 g, 48.3 mmol) and stirring at 60° C. for 16 h under an argon atmosphere. This gave after workup and purification [$SiO_2$ gel (40 g), eluting with EtOAc in hexane from 0-50%] 2-amino-7-methoxy-1H-indole-3-carbonitrile (54c) (2.308 g, 51% yield) as a yellow solid; $^1$H NMR (300 MHz, DMSO-$d_6$) δ 10.81 (s, 1H), 6.92 (t, J=7.9 Hz, 1H), 6.77 (d, J=7.7 Hz, 1H), 6.59 (d, J=7.9 Hz, 1H), 6.37 (s, 2H), 3.86 (s, 3H); MS (ES+): 188.1 (M+1); (ES−): 186.0 (M−1).

Step-3: Preparation of 8-methoxy-9H-pyrimido[4,5-b]indol-4-amine (54d)

Compound 54d was prepared according to the procedure reported in step-1 of scheme-6, from 2-amino-7-methoxy-1H-indole-3-carbonitrile (54c) (2.3 g, 12.29 mmol) using trimethyl orthoformate (26.1 g, 246 mmol), AcOH (3.51 mL, 61.4 mmol) and $NH_4OAc$ (4.74 g, 61.4 mmol). This gave after workup 8-methoxy-9H-pyrimido[4,5-b]indol-4-amine (54d) (2.7 g, 80% yield) AcOH salt as a pale yellow solid $^1$H NMR (300 MHz, DMSO-$d_6$) δ 11.99 (s, 1H), 11.91 (s, 1H), 8.23 (s, 1H), 7.88 (d, J=7.8 Hz, 1H), 7.15 (t, J=7.9 Hz, 1H), 7.08 (s, 2H), 6.98 (d, J=7.9 Hz, 1H), 3.95 (s, 3H), 1.91 (s, 3H).

Step-4: Preparation of tert-butyl 2-(4-amino-8-methoxy-9H-pyrimido[4,5-b]indol-9-yl)acetate (54e)

Compound 54e was prepared according to the procedure reported in step-2 of scheme-16, from AcOH salt of 8-methoxy-9H-pyrimido[4,5-b]indol-4-amine (54d) (2.6 g, 9.48 mmol) in DMF (75 mL) using tert-butyl 2-bromoacetate (1.471 mL, 9.95 mmol), $Cs_2CO_3$ (6.80 g, 20.86 mmol), stirring at RT for 15 h, followed by the addition of tert-butyl 2-bromoacetate (1.401 mL, 9.48 mmol), $K_2CO_3$ (1.31 g, 9.48 mmol) and stirring for 3 h. The solid separated was filtered and dried to give tert-butyl 2-(4-amino-8-methoxy-9H-pyrimido[4,5-b]indol-9-yl)acetate (54e) (1.87 g, 60% yield) as a pale yellow solid; 1H NMR (300 MHz, DMSO-$d_6$) δ 8.28 (s, 1H), 7.94 (d, J=7.8 Hz, 11H), 7.26 (s, 2H), 7.20 (t, J=7.9 Hz, 1H), 7.01 (d, J=8.0 Hz, 1H), 5.19 (s, 2H), 3.89 (s, 3H), 1.42 (s, 9H).

Step-5: Preparation of 2-(4-amino-8-methoxy-9H-pyrimido[4,5-b]indol-9-yl)acetic acid (54f)

Compound 54f was prepared according to the procedure reported in step-2 of scheme-1, from tert-butyl 2-(4-amino-8-methoxy-9H-pyrimido[4,5-b]indol-9-yl)acetate (54e) (0.9 g, 2.74 mmol) using 20% TFA in DCM (15.73 mL, 41.1 mmol)) and stirring at RT for 16 h. his gave after workup afford 2-(4-amino-8-methoxy-9H-pyrimido[4,5-b]indol-9-yl)acetic acid (54f) (0.46 g, 43% yield) TFA salt as a white solid; $^1$H NMR (300 MHz, DMSO-$d_6$) δ 8.51 (s, 1H), 8.20 (s, 2H), 8.05 (d, J=7.9 Hz, 1H), 7.32 (t, J=8.0 Hz, 1H), 7.13 (d, J=8.0 Hz, 1H), 5.32 (s, 2H), 3.92 (s, 3H).

Step-6: Preparation of (1R,3S,5R)-2-(2-(4-amino-8-methoxy-9H-pyrimido[4,5-b]indol-9-yl)acetyl)-N-(6-bromopyridin-2-yl)-2-azabicyclo[3.1.0]hexane-3-carboxamide (54 g)

Compound 54g was prepared according to the procedure reported in step-3 of scheme-1, from TFA salt of 2-(4-amino-8-methoxy-9H-pyrimido[4,5-b]indol-9-yl)acetic acid (54f) (75 mg, 0.194 mmol) in DMF (2 mL) using TFA salt of (1R,3S,5R)—N-(6-bromopyridin-2-yl)-2-azabicyclo[3.1.0]hexane-3-carboxamide (4a) (77 mg, 0.194 mmol), HATU (111 mg, 0.291 mmol), DIPEA (0.169 mL, 0.971 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-8-methoxy-9H-pyrimido[4,5-b]indol-9-yl)acetyl)-N-(6-bromopyridin-2-yl)-2-azabicyclo[3.1.0]hexane-3-carboxamide (54 g) (85 mg, 82% yield) as a white solid: $^1$H NMR (300 MHz, DMSO-$d_6$) δ 10.74 (s, 1H, $D_2O$ exchangeable), 8.60 (s, 1H), 8.57 (s, 2H, $D_2O$ exchangeable), 8.08 (d, J=7.9 Hz, 1H), 8.02 (d, J=8.2 Hz, 1H), 7.71 (t, J=8.0 Hz, 1H), 7.40-7.24 (m, 2H), 7.15 (d, J=8.0 Hz, 1H), 5.81 (d, J=17.0 Hz, 1H), 5.59 (d, J=16.9 Hz, 1H), 4.43 (dd, J=8.9, 5.6 Hz, 1H), 3.94 (s, 3H), 3.85 (td, J=6.3, 5.3, 2.3 Hz, 1H), 2.42-2.14 (m, 2H), 2.06-1.88 (m, 1H), 1.12 (dt, J=10.0, 5.5 Hz, 1H), 0.67 (td, J=5.3, 2.4 Hz, 1H). MS (ES+): 536.1 (M+1); (ES−): 534.1 (M−1); Analysis calculated for $C_{24}H_{22}BrN_7O_3{\cdot}2H_2O{\cdot}1HCl$: C, 47.34; H, 4.47; Cl, 5.82; N, 16.10. Found: C, 47.34; H, 4.40; Cl, 5.48; N, 15.94.

Scheme 55

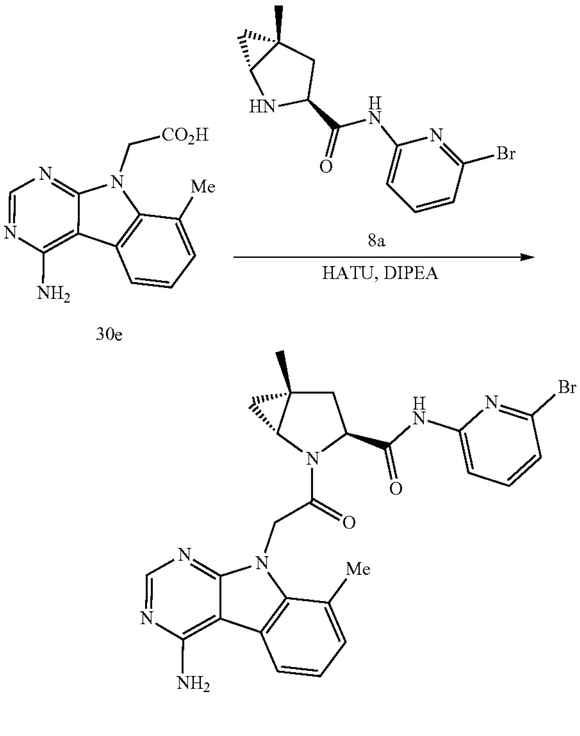

8a

30e

55a

Preparation of (1R,3S,5R)-2-(2-(4-amino-8-methyl-9H-pyrimido[4,5-b]indol-9-yl)acetyl)-N-(6-bromopyridin-2-yl)-5-methyl-2-azabicyclo[3.1.0]hexane-3-carboxamide (55a)

Compound 55a was prepared according to the procedure reported in step-3 of scheme-1, from TFA salt of 2-(4-amino-8-methyl-9H-pyrimido[4,5-b]indol-9-yl)acetic acid (30e) (50 mg, 0.135 mmol) in DMF (2 mL) using HCl salt of (1R,3S,5R)—N-(6-bromopyridin-2-yl)-5-methyl-2-azabicyclo[3.1.0]hexane-3-carboxamide (8a) (44.9 mg, 0.135 mmol), HATU (77 mg, 0.203 mmol), DIPEA (0.118 mL, 0.675 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-8-methyl-9H-pyrimido[4,5-b]indol-9-yl)acetyl)-N-(6-bromopyridin-2-yl)-5-methyl-2-azabicyclo[3.1.0]hexane-3-carboxamide (55a) (47 mg, 65% yield) HCl salt as a white solid; $^1H$ NMR (300 MHz, DMSO-$d_6$) δ 10.75 (s, 1H, $D_2O$ exchangeable), 8.51 (s, 1H), 8.35 (s, 2H, $D_2O$ exchangeable), 8.24 (dd, J=6.2, 3.0 Hz, 1H), 7.94 (d, J=8.2 Hz, 1H), 7.64 (t, J=8.0 Hz, 1H), 7.27-7.14 (m, 3H), 5.81 (d, J=18.0 Hz, 1H), 5.54 (d, J=17.9 Hz, 1H), 4.31 (dd, J=9.0, 6.1 Hz, 1H), 3.63 (dd, J=5.6, 2.3 Hz, 1H), 2.62 (s, 3H), 2.48-2.45 (m, 1H), 1.91 (dd, J=13.1, 6.1 Hz, 1H), 1.24 (s, 3H), 0.95 (t. J=5.4 Hz, 1H), 0.77 (dd, J=5.4, 2.4 Hz, 1H); MS (ES+): 534.1 (M+1); (ES−): 532.1 (M−1); Analysis calculated for $C_{25}H_{24}BrN_7O_2$ $1.5H_2O{\cdot}0.9HCl$: C, 50.53; H, 4.73; Cl, 5.37; N, 16.50. Found: C, 50.38; H, 4.74; Cl, 5.68; N, 16.43.

Scheme 56

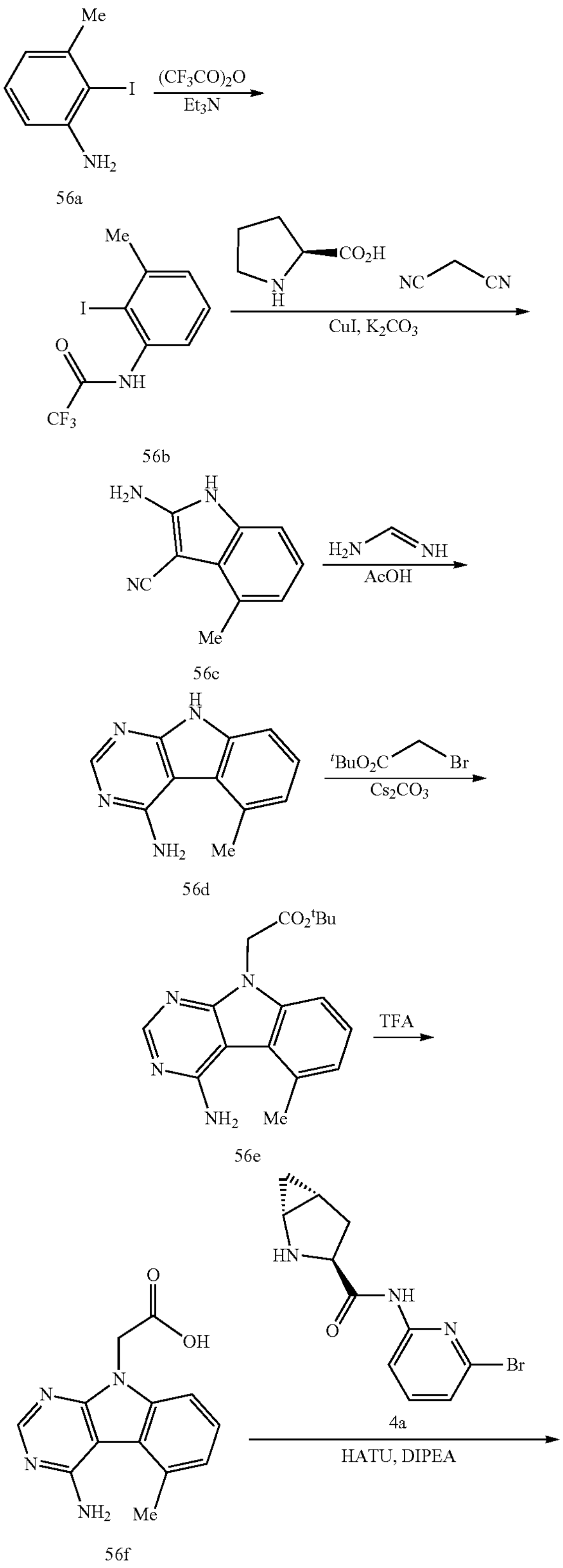

56a

56b

56c

56d

56e

4a

56f

-continued

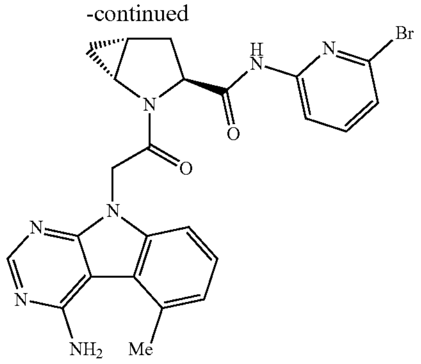

56g

Preparation of (1R,3S,5R)-2-(2-(4-amino-5-methyl-9H-pyrimido[4,5-b]indol-9-yl)acetyl)-N-(6-bromopyridin-2-yl)-2-azabicyclo[3.1.0]hexane-3-carboxamide (56 g)

Step-1: Preparation of 2,2,2-trifluoro-N-(2-iodo-3-methylphenyl)acetamide (56b)

Compound 56b was prepared according to the procedure reported in step-1 of scheme-46, from 2-iodo-3-methylaniline (56a) (5 g, 21.45 mmol; CAS #89938-16-9) in DCM (75 mL) using triethylamine (5.08 mL, 36.5 mmol), trifluoroacetic acid anhydride (4.47 mL, 32.2 mmol) and stirring at RT for 16 h. This gave after workup 2,2,2-trifluoro-N-(2-iodo-3-methylphenyl)acetamide (56b) (6.9 g, 21% yield) as a pale yellow solid and was used as such for the next step; $^1$H NMR (300 MHz, DMSO-$d_6$) δ 11.26 (s, 1H), 7.43-7.24 (m, 2H), 7.17 (dd, J=6.1, 3.3 Hz, 1H), 2.47 (s, 3H); MS (ES−): 327.90 (M−1).

Step-2: Preparation of 2-amino-4-methyl-1H-indole-3-carbonitrile (56c)

Compound 56c was prepared according to the procedure reported in step-1 of scheme-11, from 2,2,2-trifluoro-N-(2-iodo-3-methylphenyl)acetamide (56b) (4.9 g, 14.89 mmol) in DMSO (15 mL) using malononitrile (1.125 mL, 17.87 mmol), L-proline (0.343 g, 2.98 mmol), CuI (0.284 g, 1.489 mmol) $K_2CO_3$ (4.12 g, 29.8 mmol) and heating at 60° C. for 16 h under an argon atmosphere. This gave after workup and purification [$SiO_2$ gel (80 g), eluting with EtOAc in hexane from 0-50%] 2-amino-4-methyl-1H-indole-3-carbonitrile (56c) (0.81 g, 32% yield) as a brown solid $^1$H NMR (300 MHz, DMSO-$d_6$) δ 10.67 (s, 1H), 6.96 (d, J=7.8 Hz, 1H), 6.79 (t, J=7.6 Hz, 1H), 6.70 (dt, J=7.3, 1.0 Hz, 1H), 6.62 (s, 2H), 2.48 (s, 3H); MS (ES−): 170.10 (M−1).

Step-3: Preparation of 5-methyl-9H-pyrimido[4,5-b]indol-4-amine (56d)

Compound 56d was prepared according to the procedure reported in step-2 of scheme-29, from 2-amino-4-methyl-1H-indole-3-carbonitrile (56c) (0.8 g, 4.67 mmol) in ethanol (30 mL) using formamidine acetate (3.93 g, 37.4 mmol) and refluxing for 22 h. This gave after workup and purification by reverse-phase column chromatography [C18 column (275 g), eluting with ACN in water (containing 0.1% HCl) from 0-100%] to afford 5-methyl-9H-pyrimido[4,5-b]indol-4-amine (56d) (114 mg, 12% yield) HCl salt as a pale yellow solid; $^1$H NMR (300 MHz, DMSO-$d_6$) δ 13.15 (s, 1H), 8.65 (s, 1H), 8.03 (s, 2H), 7.49-7.32 (m, 2H), 7.22-7.05 (m, 1H), 2.94 (s, 3H); MS (ES+): 199.10 (M+1).

Step-4: Preparation of tert-butyl 2-(4-amino-5-methyl-9H-pyrimido[4,5-b]indol-9-yl)acetate (56e)

Compound 56e was prepared according to the procedure reported in step-2 of scheme-16, from HCl salt of 5-methyl-9H-pyrimido[4,5-b]indol-4-amine (56d) (110 mg, 0.469 mmol) in DMF (3 mL) using tert-butyl 2-bromoacetate (0.076 mL, 0.516 mmol) $Cs_2CO_3$ (336 mg, 1.031 mmol) and stirring at RT for 1.5 h. This gave after workup tert-butyl 2-(4-amino-5-methyl-9H-pyrimido[4,5-b]indol-9-yl)acetate (56e) (130 mg, 89% yield) as a pale yellow solid; $^1$H NMR (300 MHz, DMSO-$d_6$) δ 8.27 (s, 1H), 7.42-7.24 (m, 2H), 7.04 (d, J=7.1 Hz, 1H), 6.79 (s, 2H), 5.11 (s, 211), 2.96 (s, 3H), 1.41 (s, 9H); MS (ES+): 313.20 (M+1).

Step-5: Preparation of 2-(4-amino-5-methyl-9H-pyrimido[4,5-b]indol-9-yl)acetic acid (56f)

Compound 56f was prepared according to the procedure reported in step-2 of scheme-1, from tert-butyl 2-(4-amino-5-methyl-9H-pyrimido[4,5-b]indol-9-yl)acetate (56e) (100 mg, 0.320 mmol) using 20% TFA in DCM (1837 μL, 4.80 mmol)) and stirring at RT for 16 h. This gave after workup 2-(4-amino-5-methyl-9H-pyrimido[4,5-b]indol-9-yl)acetic acid (56f) (115 mg, 97% yield) TFA salt as a white solid; MS (ES+): 257.10 (M+1).

Step-6: Preparation of (1R,3S,5R)-2-(2-(4-amino-5-methyl-9H-pyrimido[4,5-b]indol-9-yl)acetyl)-N-(6-bromopyridin-2-yl)-2-azabicyclo[3.1.0]hexane-3-carboxamide (56 g)

Compound 56g was prepared according to the procedure reported in step-3 of scheme-1, from TFA salt of 2-(4-amino-5-methyl-9H-pyrimido[4,5-b]indol-9-yl)acetic acid (56f) (50 mg, 0.135 mmol) in DMF (1.5 mL) using TFA salt of (1R,3S,5R)—N-(6-bromopyridin-2-yl)-2-azabicyclo[3.1.0]hexane-3-carboxamide (4a) (53.5 mg, 0.135 mmol), HATU (77 mg, 0.203 mmol), DIPEA (0.118 mL, 0.675 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%](1R,3S,5R)-2-(2-(4-amino-5-methyl-9H-pyrimido[4,5-b]indol-9-yl)acetyl)-N-(6-bromopyridin-2-yl)-2-azabicyclo[3.1.0]hexane-3-carboxamide (56 g) (34 mg, 48% yield) HCl salt as a white solid: 1H NMR (300 MHz, DMSO-$d_6$) δ 10.76 (s, 1H, $D_2O$ exchangeable), 8.60 (s, 1H), 8.01 (d, J=8.2 Hz, 1H), 7.79-7.65 (m, 3H, 2H $D_2O$ exchangeable), 7.52-7.37 (m, 2H), 7.32 (d, J=7.7 Hz, 1H), 7.17 (d, J=7.0 Hz, 1H), 5.74 (d, J=17.3 Hz, 1H), 5.41 (d, J=17.3 Hz, 1H), 4.42 (dd, J=9.1, 5.4 Hz, 1H), 3.94-3.86 (m, 1H), 2.96 (s, 3H), 2.36-2.13 (m, 2H), 1.99-1.84 (m, 1H), 1.07 (dt, J=9.3, 5.3 Hz, 1H), 0.78 (dt, J=5.5, 2.7 Hz, 1H). MS (ES+): 520.1 (M+1); 542.1 (M+Na); (ES−): 518.0 (M−1).

Scheme 57

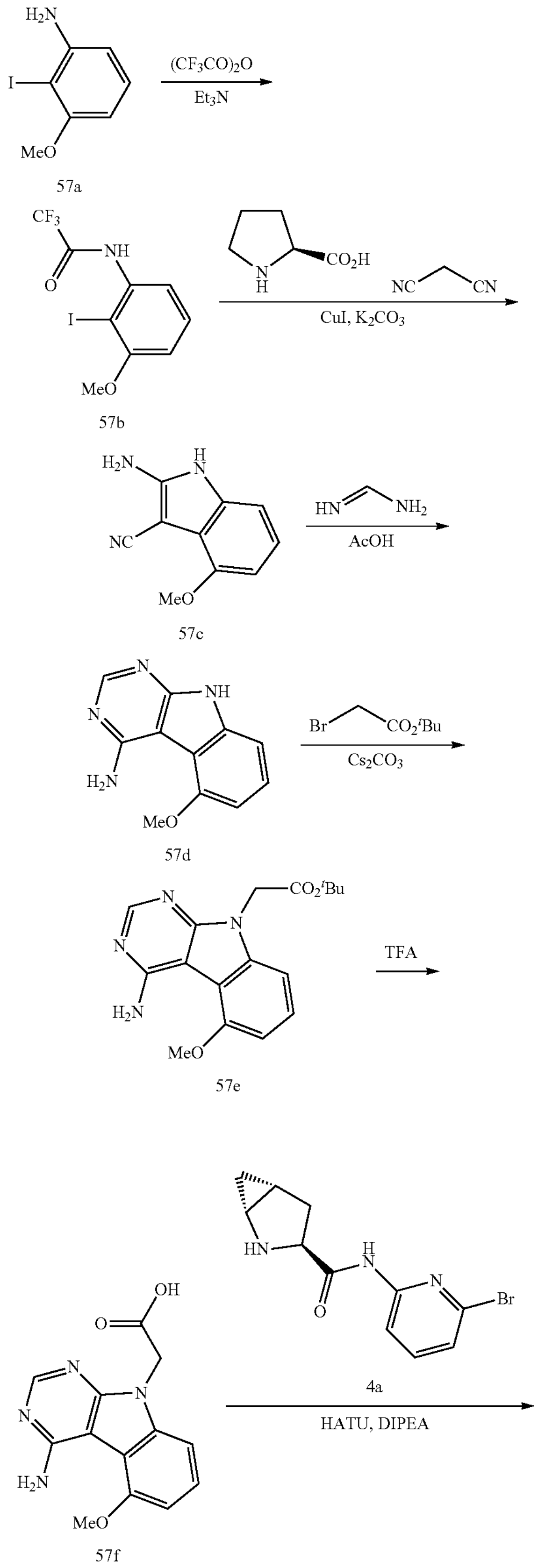

-continued

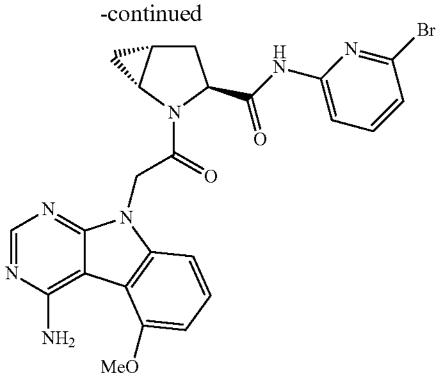

57g

Preparation of (1R,3S,5R)-2-(2-(4-amino-5-methoxy-9H-pyrimido[4,5-b]indol-9-yl)acetyl)-N-(6-bromopyridin-2-yl)-2-azabicyclo[3.1.0]hexane-3-carboxamide (57 g)

Step-1: Preparation of 2,2,2-trifluoro-N-(2-iodo-3-methoxyphenyl)acetamide (57b)

Compound 57b was prepared according to the procedure reported in step-1 of scheme-46, from 2-iodo-3-methoxyaniline (57a) (5 g, 20.08 mmol; CAS #98991-094) in DCM (75 mL) using triethylamine (4.76 mL, 34.1 mmol), trifluoroacetic acid anhydride (4.19 mL, 30.1 mmol) and stirring at RT for 16 h. This gave after workup 2,2,2-trifluoro-N-(2-iodo-3-methoxyphenyl)acetamide (57b) (6.8 g, 98% yield) as a dark oil and was used as such for next step; MS (ES−): 343.90 (M−1).

Step-2: Preparation of 2-amino-4-methoxy-1H-indole-3-carbonitrile (57c)

Compound 57c was prepared according to the procedure reported in step-1 of scheme-11, from 2,2,2-trifluoro-N-(2-iodo-3-methoxyphenyl)acetamide (57b) (5.1 g, 14.78 mmol) in DMSO (15 mL) using malononitrile (1.117 mL, 17.74 mmol), L-proline (0.340 g, 2.96 mmol), CuI (0.281 g, 1.478 mmol), $K_2CO_3$ (4.12 g, 29.8 mmol) and heating at 60° C. for 16 h under an argon atmosphere. This gave after workup and purification by flash column chromatography [$SiO_2$ gel (80 g), eluting with EtOAc in hexane from 0-50%] 2-amino-4-methoxy-1H-indole-3-carbonitrile (57c) (1.35 g, 49% yield) as a gray solid; $^1$H NMR (300 MHz, DMSO-$d_6$) δ 10.54 (s, 1H), 7.00 (d, J=8.4 Hz, 1H), 6.75 (d, J=2.3 Hz, 1H), 6.63-6.56 (m, 3H), 3.71 (s, 3H); MS (ES+): 188.10 (M+1); (ES−): 186.10 (M−1).

Step-3: Preparation of 5-methoxy-9H-pyrimido[4,5-b]indol-4-amine (57d)

Compound 57d was prepared according to the procedure reported in step-2 of scheme-29, 2-amino-4-methoxy-1H-indole-3-carbonitrile (57c) (1.3 g, 6.94 mmol) in ethanol (45 mL) using formamidine acetate (5.84 g, 55.6 mmol) and refluxing for 22 h. This gave after workup and purification by reverse phase column chromatography [C18 column (275 g), eluting with ACN in water (containing 0.1% HCl) from 0-100%] 5-methoxy-9H-pyrimido[4,5-b]indol-4-amine (57d) (0.9 g, 61% yield) HCl salt as a pale yellow solid; $^1$H NMR (300 MHz, DMSO-$d_6$) δ 12.97 (s, 1H), 8.60 (s, 2H), 8.55 (s, 1H), 8.40 (d, J=8.7 Hz, 1H), 7.09 (d, J=2.3 Hz, 1H), 7.03 (dd, J=8.7, 2.4 Hz, 1H), 3.87 (s, 3H); MS (ES+): 215.10 (M+1);

Step-4: Preparation of tert-butyl 2-(4-amino-5-methoxy-9H-pyrimido[4,5-b]indol-9-yl)acetate (57e)

Compound 57e was prepared according to the procedure reported in step-2 of scheme-16, from HCl salt of 5-methoxy-9H-pyrimido[4,5-b]indol-4-amine (57d) (810 mg, 3.23 mmol) in DMF (20 mL) using tert-butyl 2-bromoacetate (0.525 mL, 3.55 mmol), $Cs_2CO_3$ (2316 mg, 7.11 mmol) and stirring at RT for 1.5 h. This gave after workup tert-butyl 2-(4-amino-5-methoxy-9H-pyrimido[4,5-b]indol-9-yl)acetate (57e) (990 mg, 93% yield) as a pale yellow solid; $^1$H NMR (300 MHz, DMSO-$d_6$) δ 8.31-8.07 (m, 2H), 7.18-7.10 (m, 3H), 6.88 (dd, J=8.6, 2.3 Hz, 1H), 5.10 (s, 2H), 3.84 (s, 3H), 1.41 (s, 9H); MS (ES+): 329.20 (M+1).

Step-5: Preparation of 2-(4-amino-5-methoxy-9H-pyrimido[4,5-b]indol-9-yl)acetic acid (57f)

Compound 57f was prepared according to the procedure reported in step-2 of scheme-1, from tert-butyl 2-(4-amino-5-methoxy-9H-pyrimido[4,5-b]indol-9-yl)acetate (57e) (200 mg, 0.609 mmol) using 20% TFA in DCM (3496 μL, 9.14 mmol)) and stirring at RT for 16 h. This gave after workup 2-(4-amino-5-methoxy-9H-pyrimido[4,5-b]indol-9-yl)acetic acid (57f) (225 mg, 96% yield) TFA salt as a white solid; $^1$H NMR (300 MHz, DMSO-$d_6$) δ 8.53 (s, 1H), 8.45-8.34 (m, 2H), 7.44 (d, J=2.2 Hz, 1H), 7.05 (dd, J=8.7, 2.2 Hz, 1H), 5.26 (s, 2H), 3.88 (s, 3H); MS (ES+): 273.10 (M+1).

Step-6: Preparation of (1R,3S,5R)-2-(2-(4-amino-5-methoxy-9H-pyrimido[4,5-b]indol-9-yl)acetyl)-N-(6-bromopyridin-2-yl)-2-azabicyclo[3.1.0]hexane-3-carboxamide (57 g)

Compound 57g was prepared according to the procedure reported in step-3 of scheme-1, from TFA salt of 2-(4-amino-5-methoxy-9H-pyrimido[4,5-b]indol-9-yl)acetic acid (57f) (50 mg, 0.129 mmol) in DMF (1.5 mL) using TFA salt of (1R,3S,5R)—N-(6-bromopyridin-2-yl)-2-azabicyclo[3.1.0]hexane-3-carboxamide (4a) (51.3 mg, 0.129 mmol), HATU (73.8 mg, 0.194 mmol), DIPEA (0.113 mL, 0.647 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-5-methoxy-9H-pyrimido[4,5-b]indol-9-yl)acetyl)-N-(6-bromopyridin-2-yl)-2-azabicyclo[3.1.0]hexane-3-carboxamide (57 g) (35 mg, 50% yield) HCl salt as a white solid; $^1$H NMR (300 MHz, DMSO-$d_6$) δ 10.74 (s, 1H, $D_2O$ exchangeable), 8.53 (s, 1H), 8.42-8.19 (m, 3H, 2H $D_2O$ exchangeable), 8.02 (d, J=8.2 Hz, 1H), 7.71 (t, J=8.0 Hz, 1H), 7.33 (d, J=7.7 Hz, 1H), 7.25 (d, J=2.3 Hz, 1H), 7.04 (dd, J=8.7, 2.2 Hz, 1H), 5.71 (d, J=17.2 Hz, 1H), 5.42 (d, J=17.2 Hz, 1H), 4.42 (dd, J=9.0, 5.6 Hz, 1H), 3.97-3.86 (m, 4H), 2.28 (m, 2H), 1.99-1.86 (m, 1H), 1.08 (m, 1H), 0.81-0.70 (m, 1H). MS (ES+): 536.1 (M+1); 558.1 (M+Na); (ES−): 534.1 (M−1); Analysis calculated for $C_{24}H_{22}BrN_7O_3$ $1.5H_2O{\cdot}1HCl$: C, 48.05; H, 4.37; Cl, 5.91; N, 16.34. Found: C, 48.01; H, 4.33; Cl, 5.97; N, 16.16.

Scheme 58

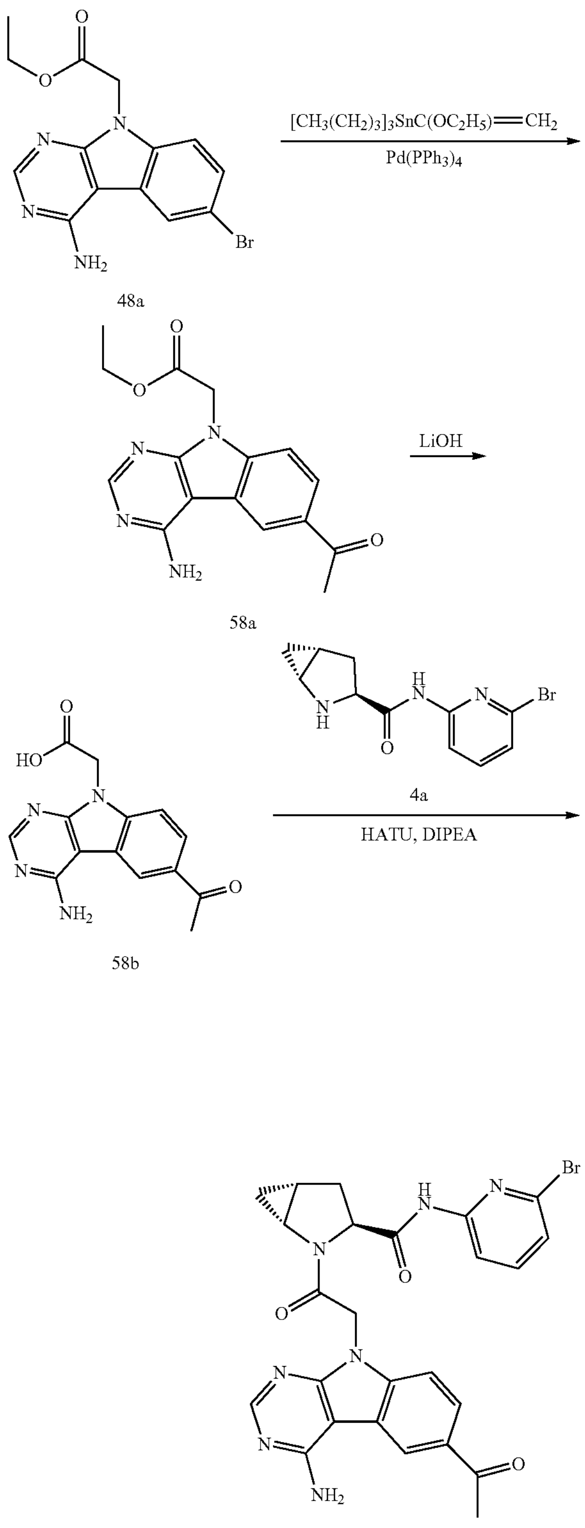

48a

58a

4a

58b

58c

Preparation of (1R,3S,5R)-2-(2-(6-acetyl-4-amino-9H-pyrimido[4,5-b]indol-9-yl)acetyl)-N-(6-bromopyridin-2-yl)-2-azabicyclo[3.1.0]hexane-3-carboxamide (58c)

Step-1: Preparation of ethyl 2-(6-acetyl-4-amino-9H-pyrimido[4,5-b]indol-9-yl)acetate (58a)

To a suspension of ethyl 2-(4-amino-6-bromo-9H-pyrimido[4,5-b]indol-9-yl)acetate (48a) (200 mg, 0.573 mmol) in toluene (8 mL) was added tributyl(1-ethoxyvinyl)stannane (0.279 mL, 0.802 mmol) and the mixture was degassed and filled with nitrogen followed by addition of $Pd(PPh_3)_4$ (132 mg, 0.115 mmol) and heating for 14 h at 120° C. Reaction mixture was cooled to RT, diluted with ethyl acetate (150 mL), treated with 1N HCl (30 mL), water (30 mL) followed by stirring at RT for 15 min. The mixture was treated with 2 M $K_2CO_3$, extracted, and separated. The organic layer was washed with brine (60 mL), dried, filtered and concentrated in vacuum. The residue obtained was purified by flash column chromatograph [silica gel (24 g), eluting with methanol in DCM (0-5%)] to afford ethyl 2-(6-acetyl-4-amino-9H-pyrimido[4,5-b]indol-9-yl)acetate (58a) (20 mg, 11% yield) as a white solid; 1H NMR (300 MHz, DMSO-$d_6$) δ 8, 96 (d, J=1.6 Hz, 1H), 8.34 (s, 1H), 8.01 (dd, J=8.6, 1.6 Hz, 1H), 7.72 (d, J=8.7 Hz, 1H), 7.60 (s, 2H), 5.29 (s, 2H), 4.14 (q, J=7.1 Hz, 2H), 2.71 (s, 3H), 1.20 (t, J=7.1 Hz, 3H); MS (ES+): 313.10 (M+1).

Step-2: Preparation of 2-(6-acetyl-4-amino-9H-pyrimido[4,5-b]indol-9-yl)acetic acid (58b)

Compound 58b was prepared according to the procedure reported in step-4 of scheme-17, from ethyl 2-(6-acetyl-4-amino-9H-pyrimido[4,5-b]indol-9-yl)acetate (58a) (18 mg, 0.058 mmol) in THF (3 mL) and methanol (3 mL) using a solution of lithium hydroxide hydrate (14.81 mg, 0.346 mmol) in water (3 mL) and stirring at RT for 14 h. This gave after workup 2-(6-acetyl-4-amino-9H-pyrimido[4,5-b]indol-9-yl)acetic acid (58b) (17 mg, 100%) which was used as such in next step-3 without further purification; MS (ES+): 285.10 (M+1), (ES−): 283.0 (M−1)

Step-3: Preparation of (1R,3S,5R)-2-(2-(6-acetyl-4-amino-9H-pyrimido[4,5-b]indol-9-yl)acetyl)-N-(6-bromopyridin-2-yl)-2-azabicyclo[3.1.0]hexane-3-carboxamide (58c)

Compound 58c was prepared according to the procedure reported in step-3 of scheme-1, from 2-(6-acetyl-4-amino-9H-pyrimido[4,5-b]indol-9-yl)acetic acid (58b) (17 mg, 0.058 mmol) in DMF (8 mL) using HCl salt of (1R,3S,5R)—N-(6-bromopyridin-2-yl)-2-azabicyclo[3.1.0]hexane-3-carboxamide (4a) (74 mg, 0.232 mmol), HATU (88 mg, 0.232 mmol), DIPEA (0.061 mL, 0.348 mmol) and stirring at RT for 20 h. This gave after workup and purification by flash column chromatography [silica gel (12 g), eluting with MeOH in DCM from 0-5%] followed by conversion of product obtained to HCl salt by dissolving in acetonitrile (2 mL) and 0.1% aq. HCl (15 mL) and lyophilization (1R,3S,5R)-2-(2-(6-acetyl-4-amino-9H-pyrimido[4,5-b]indol-9-yl)acetyl)-N-(6-bromopyridin-2-yl)-2-azabicyclo[3.1.0]hexane-3-carboxamide (58c) (27 mg, 85% yield) HCl salt as an off-white solid; $^1H$ NMR (300 MHz, DMSO-$d_6$) δ 10.76 (s, 1H, $D_2O$ exchangeable), 9.09 (d, J=1.6 Hz, 1H), 8.73-8.50 (m, 3H, 2H $D_2O$ exchangeable), 8.11 (dd, J=8.7, 1.6 Hz, 1H), 8.00 (d, J=8.2 Hz, 1H), 7.77 (d, J=8.7 Hz, 1H), 7.70 (t, J=8.0 Hz, 1H), 7.31 (d, J=7.7 Hz, 1H), 5.79 (d, J=17.3 Hz, 1H), 5.45 (d, J=17.3 Hz, 1H), 4.41 (dd, J=9.0, 5.6 Hz, 1H), 4.00-3.84 (m, 1H), 2.72 (s, 3H), 2.39-2.12 (m, 2H), 1.99-1.82 (m, 1H), 1.14-1.01 (m, 1H), 0.89-0.71 (m, 1H); MS (ES+): 548.10 & 550.10 (M+1); MS (ES−): 546.00 & 548.10 (M−1).

Scheme 59

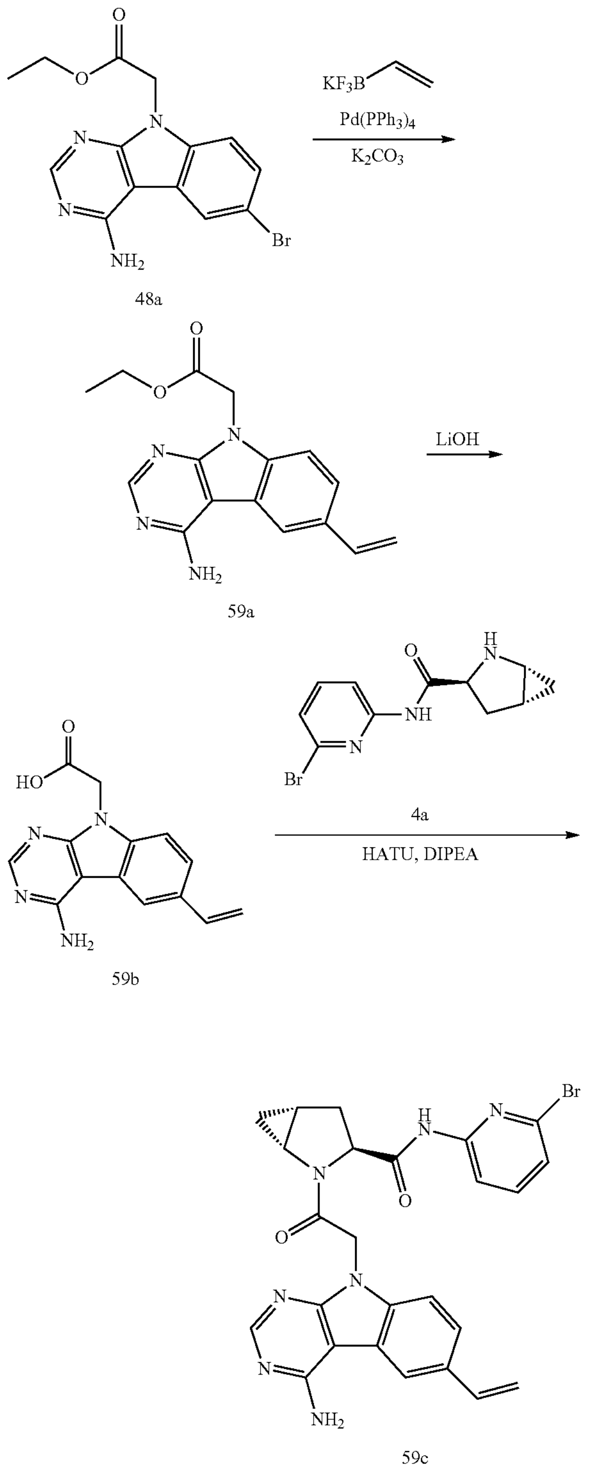

48a

59a

59b

59c

Preparation of (1R,3S,5R)-2-(2-(4-amino-6-vinyl-9H-pyrimido[4,5-b]indol-9-yl)acetyl)-N-(6-bromopyridin-2-yl)-2-azabicyclo[3.1.0]hexane-3-carboxamide (59c)

Step-1: Preparation of ethyl 2-(4-amino-6-vinyl-9H-pyrimido[4,5-b]indol-9-yl)acetate (59a)

To a degassed solution of ethyl 2-(4-amino-6-bromo-9H-pyrimido[4,5-b]indol-9-yl)acetate (48a) (200 mg, 0.573 mmol) in dioxane (8 mL) was added potassium vinyltrifluoroborate (153 mg, 1.146 mmol), $Pd(PPhs)_4$ (132 mg, 0.115 mmol), a solution of $K_2CO_3$ (158 mg, 1.146 mmol) in water (2.3 mL) and heated at 80° C. for 20 h under nitrogen. The reaction mixture was diluted with ethyl acetate (100 mL), washed with water (50 mL), brine (50 mL), dried, filtered and concentrated in vacuum. The residue obtained was purified by flash column chromatography [silica gel (25 g) eluting with 10% methanol in ethyl acetate in hexanes from 0-50%] to afford ethyl 2-(4-amino-6-vinyl-9H-pyrimido[4,5-b]indol-9-yl)acetate (59a) (82 mg, 48% yield) as a light yellow solid; $^1H$ NMR (300 MHz, DMSO-$d_6$) δ 8.49 (s, 1H), 8.28 (s, 1H), 7.56 (d, J=8.5 Hz, 1H), 7.50 (dd, J=8.8, 1.5 Hz, 1H), 7.38 (s, 2H), 6.84 (dd, J=17.7, 11.0 Hz, 1H), 6.03-5.95 (m, 1H), 5.29-5.16 (m, 3H), 4.14 (q, J=7.1 Hz, 2H), 1.20 (t, J=7.1 Hz, 3H); MS (ES+): 297.10 (M+1).

Step-2: Preparation of 2-(4-amino-6-vinyl-9H-pyrimido[4,5-b]indol-9-yl)acetic acid (59b)

Compound 59b was prepared according to the procedure reported in step-4 of scheme-17, from ethyl 2-(4-amino-6-vinyl-9H-pyrimido[4,5-b]indol-9-yl)acetate (59a) (80 mg, 0.270 mmol) in THF (3 mL) and methanol (3 mL) using a solution of lithium hydroxide hydrate (69.4 mg, 1.620 mmol) in water (3 mL) and stirring at RT for 20 h. This gave after workup 2-(4-amino-6-vinyl-9H-pyrimido[4,5-b]indol-9-yl)acetic acid (59b) (72 mg, 100%) which was used as such in next step-3 without further purification; MS (ES+): 269.10 (M+1), (ES−): 267.0 (M−1).

Step-3: Preparation of (1R,3S,5R)-2-(2-(4-amino-6-vinyl-9H-pyrimido[4,5-b]indol-9-yl)acetyl)-N-(6-bromopyridin-2-yl)-2-azabicyclo[3.1.0]hexane-3-carboxamide (59c)

Compound 59c was prepared according to the procedure reported in step-3 of scheme-1, from 2-(4-amino-6-vinyl-9H-pyrimido[4,5-b]indol-9-yl)acetic acid (59b) (72 mg, 0.27 mmol) in DMF (12 mL) using HCl salt of (1R,3S,5R)—N-(6-bromopyridin-2-yl)-2-azabicyclo[3.1.0]hexane-3-carboxamide (4a) (172 mg, 0.540 mmol), HATU (308 mg, 0.810 mmol) DIPEA (0.235 mL, 1.350 mmol) and stirring at RT for 20 h. This gave after workup and purification by flash column chromatography [silica gel (24 g), eluting with MeOH in DCM from 0-5%] followed by conversion of product obtained to HCl salt by dissolving in acetonitrile (5 mL) and 0.1% aq. HCl (30 mL) and lyophilization (1R,3S,5R)-2-(2-(4-amino-6-vinyl-9H-pyrimido[4,5-b]indol-9-yl)acetyl)-N-(6-bromopyridin-2-yl)-2-azabicyclo[3.1.0]hexane-3-carboxamide (59c) (54 mg, 38% yield) HCl salt as a light brown solid; $^1H$ NMR (300 MHz, DMSO-$d_6$) δ 10.76 (s, 1H, $D_2O$ exchangeable), 8.60 (s, 1H), 8.54 (s, 1H), 8.36 (s, 2H, $D_2O$ exchangeable), 8.01 (d, J=8.2 Hz, 1H), 7.70 (t, J=8.0 Hz, 1H), 7.63 (s, 2H), 7.32 (d, J=7.7 Hz, 1H), 6.86 (dd, J=17.8, 10.8 Hz, 1H), 6.01 (d, J=17.7 Hz, 1H), 5.72 (d, J=17.5 Hz, 1H), 5.39 (d, J=17.1 Hz, 1H), 5.29 (d, J=11.0 Hz, 1H), 4.47-4.36 (m, 1H), 3.96-3.85 (m, 1H), 2.43-2.13 (m, 2H), 2.00-1.83 (m, 1H), 1.14-0.99 (m, 1H), 0.85-0.67 (m, 1H); MS (ES+): 532.10 & 534.10 (M+1); MS (ES−): 530.05 & 532.10 (M−1); Analysis calculated for $C_{25}H_{22}BrN_7O_2 \cdot 1.0HCl \cdot 2.25H_2O$: C, 49.27; H, 4.55; Cl, 5.82; N, 16.09. Found: C, 49.02; H, 4.49; Cl, 5.61; N, 16.04.

Scheme 60

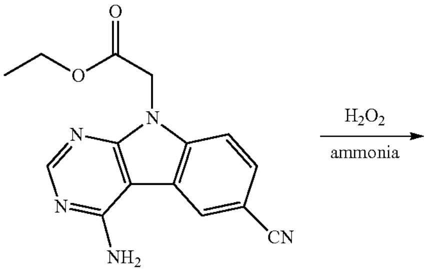

49a

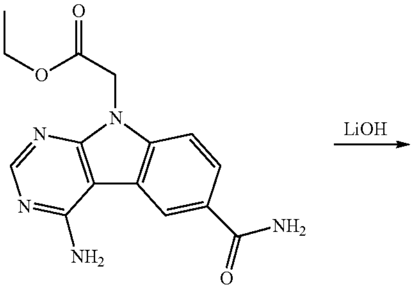

60a

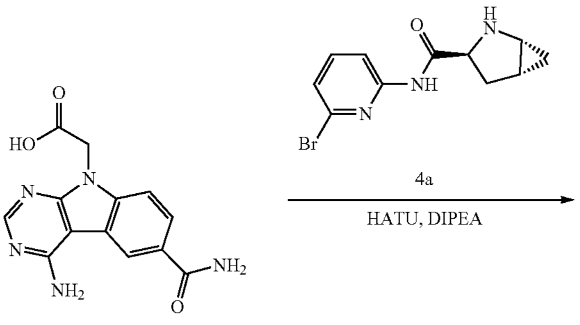

4a

60b

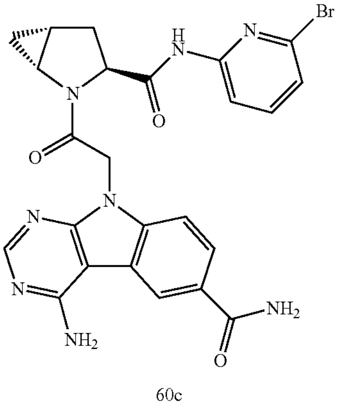

60c

Preparation of 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-6-carboxamide (60c)

Step-1: Preparation of ethyl 2-(4-amino-6-carbamoyl-9H-pyrimido[4,5-b]indol-9-yl)acetate (60a)

A suspension of ethyl 2-(4-amino-6-cyano-9H-pyrimido[4,5-b]indol-9-yl)acetate (49a) (70 mg, 0.237 mmol) in ethanol (6 mL) was treated with cone. $NH_4OH$ (2.25 mL) followed by hydrogen peroxide (0.084 mL, 0.948 mmol) and stirred at RT for 48 h. The solid obtained was collected by filtration, washed with ethanol and dried to obtain ethyl 2-(4-amino-6-carbamoyl-9H-pyrimido[4,5-b]indol-9-yl)acetate (60a) (40 mg, 54%) as a white solid residue which was used as such for next step; MS (ES+): 314.10 (M+1).

Step-2: Preparation of 2-(4-amino-6-carbamoyl-9H-pyrimido[4,5-b]indol-9-yl)acetic acid (60b)

Compound 60b was prepared according to the procedure reported in step-4 of scheme-17, from ethyl 2-(4-amino-6-carbamoyl-9H-pyrimido[4,5-b]indol-9-yl)acetate (60a) (38 mg, 0.121 mmol) in THF (2 mL) and methanol (2 mL) using a solution of lithium hydroxide hydrate (31.2 mg, 0.728 mmol) in water (2 mL) and stirring at RT for 68 h. This gave after workup 2-(4-amino-6-carbamoyl-9H-pyrimido[4,5-b]indol-9-yl)acetic acid (60b) (35 mg, 100%) which was used as such in next step-3 without further purification; MS (ES+): 286.10 (M+1), (ES−): 284.0 (M−1).

Step-3: Preparation of 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-6-carboxamide (60c)

Compound 60c was prepared according to the procedure reported in step-3 of scheme-1, from 2-(4-amino-6-carbamoyl-9H-pyrimido[4,5-b]indol-9-yl)acetic acid (60b) (34.5 mg, 0.121 mmol) in DMF (8 mL) using HCl salt of (1R,3S,5R)—N-(6-bromopyridin-2-yl)-2-azabicyclo[3.1.0]hexane-3-carboxamide (4a) (77 mg, 0.242 mmol), HATU (92 mg, 0.242 mmol) DIPEA (0.105 mL, 0.605 mmol) and stirring at RT for 19 h. This gave after workup and purification by flash column chromatography [silica gel (4 g), eluting with MeOH in DCM from 0-10%] followed by purification by reverse phase column chromatography [C18 column, eluting with ACN in water (containing 0.1% HCl) from 0-100%] of 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-6-carboxamide (60c) (12 mg, 18% yield) HCl salt as a white solid; $^1$H NMR (300 MHz, DMSO-$d_6$) δ 10.76 (s, 1H), 9.03 (s, 1H), 8.57 (s, 11H), 8.36 (s, 2H, $D_2O$ exchangeable), 8.08-7.97 (m, 2H), 7.89 (s, 1H, $D_2O$ exchangeable), 7.78-7.63 (m, 2H), 7.47 (s, 1H, $D_2O$ exchangeable), 7.31 (d, J=7.7 Hz, 1H), 5.76 (d, J=17.3 Hz, 1H), 5.42 (d, J=17.4 Hz, 1H), 4.42 (dd, J=9.2, 5.5 Hz, 1H), 3.95-3.86 (m, 1H), 2.41-2.10 (m, 2H), 2.01-1.74 (m, 1H), 1.18-0.98 (m, 1H), 0.87-0.69 (m, 1H); MS (ES+): 549.10 & 551.10 (M+1); MS (ES−): 547.05 & 549.10 (M−1).

Scheme 61

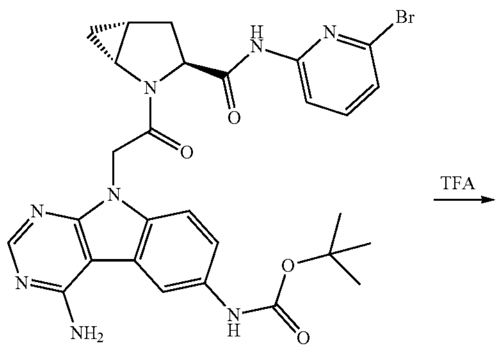

48d

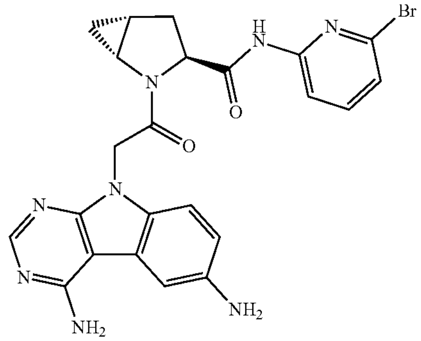

61a

Preparation of (1R,3S,5R)—N-(6-bromopyridin-2-yl)-2-(2-(4,6-diamino-9H-pyrimido[4,5-b]indol-9-yl)acetyl)-2-azabicyclo[3.1.0]hexane-3-carboxamide (61a)

Compound 61a was prepared according to the procedure reported in step-2 of scheme-1, from tert-butyl (4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)carbamate (48d) (6 mg, 9.65 μmol) in DCM (5 mL) using TFA. This gave after workup and purification by reverse phase column chromatography [C18 column, eluting with ACN in water (containing 0.1% HCl) from 0-100%] (1R,3S,5R)—N-(6-bromopyridin-2-yl)-2-(2-(4,6-diamino-9H-pyrimido[4,5-b]indol-9-yl)acetyl)-2-azabicyclo[3.1.0]hexane-3-carboxamide (61a) (3.9 mg, 77% yield) HCl salt as a white solid; $^1$H NMR (300 MHz, DMSO-$d_6$) δ 10.76 (s, 1H), 8.47 (s, 1H), 8.28 (s, 1H), 8.09 (s, 2H), 8.01 (d, J=8.2 Hz, 1H), 7.70 (t. J=8.1 Hz, 1H), 7.64 (d, J=8.8 Hz, 1H), 7.46-7.35 (m, 1H), 7.32 (d, J=7.6 Hz, 1H), 5.69 (d, J=17.4 Hz, 1H), 5.37 (d, J=17.4 Hz, 1H), 4.48-4.34 (m, 1H), 3.97-3.83 (m, 1H), 2.39-2.09 (m, 2H), 2.05-1.73 (m, 1H), 1.17-0.99 (m, 1H), 0.84-0.67 (m, 1H); MS (ES+); 521.10 & 523.10 (M+1).

Scheme 62

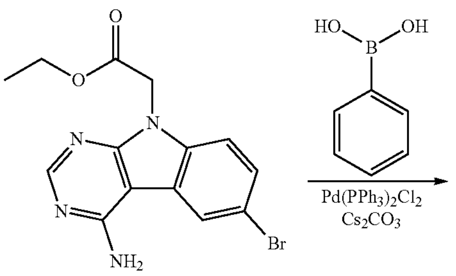

48a

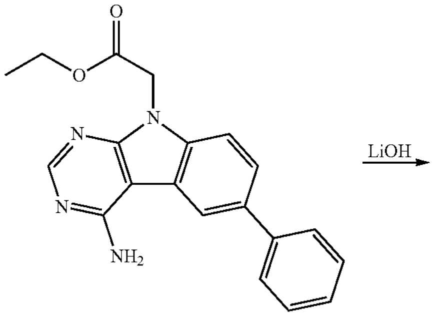

62a

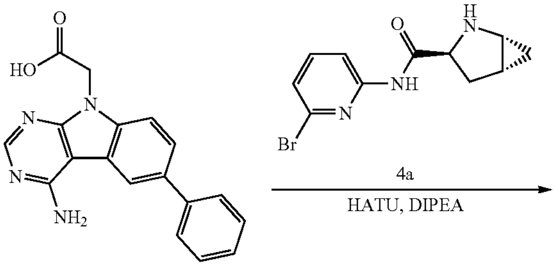

4a

62b

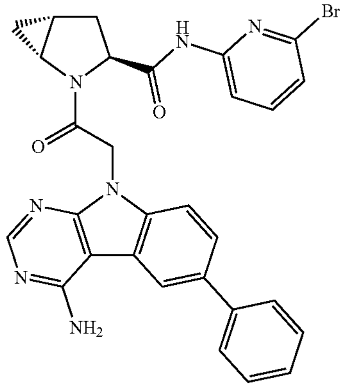

62c

Preparation of (1R,3S,5R)-2-(2-(4-amino-6-phenyl-9H-pyrimido[4,5-b]indol-9-yl)acetyl)-N-(6-bromopyridin-2-yl)-2-azabicyclo[3.1.0]hexane-3-carboxamide (62c)

Step-1: Preparation of ethyl 2-(4-amino-6-phenyl-9H-pyrimido[4,5-b]indol-9-yl)acetate (62a)

A degassed solution of ethyl 2-(4-amino-6-bromo-9H-pyrimido[4,5-b]indol-9-yl)acetate (48a) (150 mg, 0.43 mmol) and phenylboronic acid (79 mg, 0.644 mmol) in dioxane (15 mL) was treated with cesium carbonate (210 mg, 0.644 mmol) in water (1.8 mL), $Pd(PPh_3)_2Cl_2$ (60.3 mg, 0.086 mmol) and heated at 100° C. for 14 h under nitrogen. The reaction mixture was diluted with ethyl acetate/methanol (2:1, 75 mL), filtered, washed with ethyl acetate/methanol (2:1), and the filtrate was concentrated in vacuum. The residue obtained was purified by flash column chromatography [$SiO_2$ gel (25 g), eluting with MeOH in DCM from 5-40%] to afford ethyl 2-(4-amino-6-phenyl-9H-pyrimido[4,5-b]indol-9-yl)acetate (62a) (86 mg, 58% yield) as an off-white solid; MS (ES+): 347.15.

Step-2: Preparation of 2-(4-amino-6-phenyl-9H-pyrimido[4,5-b]indol-9-yl)acetic acid (62b)

Compound 62b was prepared according to the procedure reported in step-4 of scheme-17, from ethyl 2-(4-amino-6-phenyl-9H-pyrimido[4,5-b]indol-9-yl)acetate (62a) (80 mg, 0.231 mmol) in THF (2 mL) and methanol (2 mL) using a solution of lithium hydroxide hydrate (59.3 mg, 1.386 mmol) in water (2 mL) and stirring at RT for 19 h. This gave after workup 2-(4-amino-6-phenyl-9H-pyrimido[4,5-b]indol-9-yl)acetic acid (62b) (59 mg, 80%) which was used as such in next step-3 without further purification; MS (ES+): 319.10 (M+1).

Step-3: Preparation of (1R,3S,5R)-2-(2-(4-amino-6-phenyl-9H-pyrimido[4,5-b]indol-9-yl)acetyl)-N-(6-bromopyridin-2-yl)-2-azabicyclo[3.1.0]hexane-3-carboxamide (62c)

Compound 62c was prepared according to the procedure reported in step-3 of scheme-1, from 2-(4-amino-6-phenyl-9H-pyrimido[4,5-b]indol-9-yl)acetic acid (62b) (59 mg, 0.185 mmol) in DMF (8 mL) using HCl salt of (1R,3S,5R)—N-(6-bromopyridin-2-yl)-2-azabicyclo[3.1.0]hexane-3-carboxamide (4a) (89 mg, 0.278 mmol), HATU (141 mg, 0.371 mmol) DIPEA (0.097 mL, 0.556 mmol) and stirring at RT for 21 h. This gave after workup and purification by flash column chromatography [silica gel (12 g), eluting with hexanes/10% MeOH in EtOAc in hexanes from 0-100%] followed by conversion of product obtained to HCl salt by dissolving in acetonitrile (2 mL) and 0.1% aq. HCl (15 mL) and lyophilization (1R,3S,5R)-2-(2-(4-amino-6-phenyl-9H-pyrimido[4,5-b]indol-9-yl)acetyl)-N-(6-bromopyridin-2-yl)-2-azabicyclo[3.1.0]hexane-3-carboxamide (62c) (51.5 mg, 48% yield) HCl salt as a white solid; $^1H$ NMR (300 MHz, DMSO-$d_6$) δ 10.77 (s, 1H, $D_2O$ exchangeable), 8.77 (s, 1H), 8.56 (s, 1H), 8.43 (s, 2H, $D_2O$ exchangeable), 8.01 (d, J=8.1 Hz, 1H), 7.90-7.80 (m, 3H), 7.79-7.66 (m, 2H), 7.55-7.47 (m, 2H), 7.42-7.36 (m, 1H), 7.32 (d, J=7.7 Hz, 1H), 5.77 (d, J=17.3 Hz, 1H), 5.44 (d, J=17.3 Hz, 1H), 4.42 (dd, J=9.0, 5.5 Hz, 1H), 3.99-3.86 (m, 1H), 2.42-2.15 (m, 2H), 2.00-1.79 (m, 1H), 1.16-0.99 (m, 1H), 0.85-0.70 (m, 1H); MS (ES+): 582.10 & 584.20 (M+1); MS (ES−): 580.10 & 582.10 (M−1); Analysis calculated for $C_{29}H_{24}BrN_7O_2 \cdot 1.0HCl \cdot 1.5H_2O$: C, 53.92H, 4.37; N, 15.18; Cl, 5.49. Found: C, 54.10; H, 4.48; N, 14.92; Cl, 5.28.

Scheme 63

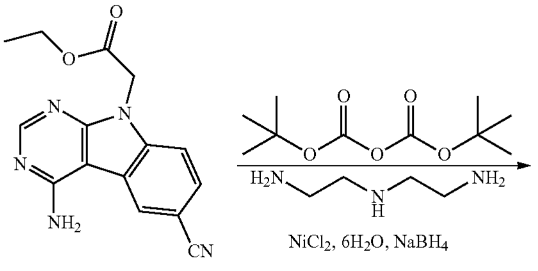

49a

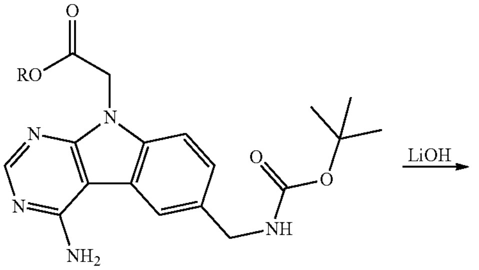

R = Et, Me

63a + 63b

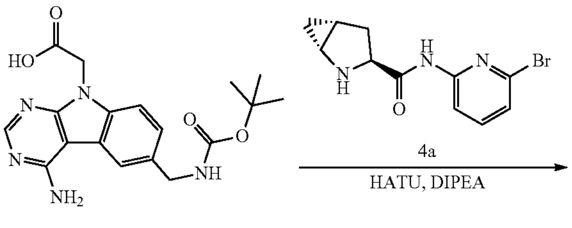

4a

63b

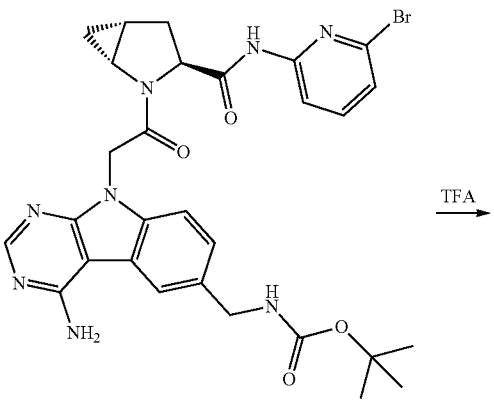

63c

-continued

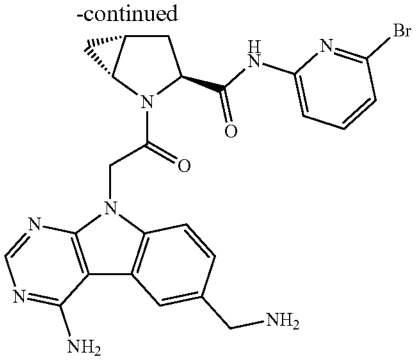

63d

Preparation of (1R,3S,5R)-2-(2-(4-amino-6-(aminomethyl)-9H-pyrimido[4,5-b]indol-9-yl)acetyl)-N-(6-bromopyridin-2-yl)-2-azabicyclo[3.1.0]hexane-3-carboxamide (63d)

Step-1: Preparation of ethyl/methyl 2-(4-amino-6-((tert-butoxycarbonylamino)methyl)-9H-pyrimido[4,5-b]indol-9-yl)acetate (63a)

To a solution of ethyl 2-(4-amino-6-cyano-9H-pyrimido[4,5-b]indol-9-yl)acetate (49a) (100 mg, 0.339 mmol) in MeOH (8 mL) cooled with ice/water and was added di-tert-butyl dicarbonate (299 mg, 1.355 mmol), nickel(II) chloride hexahydrate (40.2 mg, 0.169 mmol) followed by sodium borohydride (78 mg, 2.032 mmol) slowly over a period of 5 min and was stirred at RT for 1 h. The reaction mixture was treated with $N_1$-(2-aminoethyl)ethane-1,2-diamine (0.148 mL, 1.355 mmol) and stirred for 30 min at RT and concentrated to dryness. The residue obtained was purified by flash column chromatography [silica gel (25 g), with 10% methanol in ethyl acetate in hexanes/from 0-100%, followed by methanol in dichloromethane from 0-33% and DMA80] to afford a mixture of ethyl/methyl 2-(4-amino-6-((tert-butoxycarbonylamino)methyl)-9H-pyrimido[4,5-b]indol-9-yl)acetate (63a) (7 mg, 5%) as a colorless gum; MS (ES+): 400.20 (M+1); 386.20 (M+1) and 2-(4-amino-6-(((tert-butoxycarbonyl)amino)methyl)-9H-pyrimido[4,5-b]indol-9-yl)acetic acid (63b) (15 mg, 12%) as a colorless gum; MS (ES+): 372.20 (M+1), (ES−): 370.15 (M−1).

Step-2: Preparation of 2-(4-amino-6-(((tert-butoxycarbonyl)amino)methyl)-9H-pyrimido[4,5-b]indol-9-yl)acetic acid (63b)

Compound 63b was prepared according to the procedure reported in step-4 of scheme-17, from a mixture of ethyl/methyl 2-(4-amino-6-((tert-butoxycarbonylamino)methyl)-9H-pyrimido[4,5-b]indol-9-yl)acetate (63a) (7 mg, 0.018 mmol) in THF (2 mL) and methanol (2 mL) using a solution of lithium hydroxide hydrate (6 mg, 0.140 mmol) in water (2 mL) and stirring at RT for 19 h. This gave after workup 2-(4-amino-6-(((tert-butoxycarbonyl)amino)methyl)-9H-pyrimido[4,5-b]indol-9-yl)acetic acid (63b) which was used as such in next step-3 without further purification; MS (ES+): 372.20 (M+1), (ES−): 370.10 (M−1).

Step-3: Preparation of tert-butyl ((4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)methyl)carbamate (63c)

Compound 63c was prepared according to the procedure reported in step-3 of scheme-1, from 2-(4-amino-6-(((tert-butoxycarbonyl)amino)methyl)-9H-pyrimido[4,5-b]indol-9-yl)acetic acid (63b) (21 mg, 0.057 mmol) in DMF (8 mL) using HCl salt of (1R,3S,5R)—N-(6-bromopyridin-2-yl)-2-azabicyclo[3.1.0]hexane-3-carboxamide (4a) (55 mg, 0.171 mmol), HATU (65 mg, 0.171 mmol), DIPEA (0.05 mL, 0.285 mmol) and stirring at RT for 19 h. This gave after workup and purification by flash column chromatography [silica gel (12 g), 10% MeOH in EtOAc in hexane from 0-100%] tert-butyl ((4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)methyl)carbamate (63c) (8 mg) as an off-white solid; MS (ES+): 635.20 & 637.20 (M+1), (ES−): 633.10 & 635.10 (M−1).

Step-4: Preparation of (1R,3S,5R)-2-(2-(4-amino-6-(aminomethyl)-9H-pyrimido[4,5-b]indol-9-yl)acetyl)-N-(6-bromopyridin-2-yl)-2-azabicyclo[3.1.0]hexane-3-carboxamide (63d)

Compound 63d was prepared according to the procedure reported in step-2 of scheme-1, from tert-butyl ((4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)methyl)carbamate (63c) (8 mg, 0.013 mmol) in DCM (5 mL) using TFA (0.097 mL, 1.259 mmol) and stirring at RT for 21 h. This gave after workup and purification by reverse phase column chromatography [C18 column, eluting with ACN in water (containing 0.1% HCl) from 0-100%](1R,3S,5R)-2-(2-(4-amino-6-(aminomethyl)-9H-pyrimido[4,5-b]indol-9-yl)acetyl)-N-(6-bromopyridin-2-yl)-2-azabicyclo[3.1.0]hexane-3-carboxamide (63d) (1.6 mg, 24% yield) HCl salt as a white solid; $^1$H NMR (300 MHz, Methanol-$d_4$) δ 8.56 (s, 1H), 8.51 (d, J=1.5 Hz, 1H), 8.05 (d, J=8.2 Hz, 1H), 7.86 (d, J=8.5 Hz, 1H), 7.72 (dd, J=8.6, 1.7 Hz, 1H), 7.61 (t, J=8.0 Hz, 1H), 7.26 (dd, J=7.7, 0.7 Hz, 1H), 5.84-5.61 (m, 2H), 4.58-4.45 (m, 1H), 4.33 (s, 2H), 3.98-3.88 (m, 1H), 2.57-2.30 (m, 2H), 2.13-1.95 (m, 1H), 1.29-1.14 (m, 1H), 0.95-0.81 (m, 1H); MS (ES+): 535.10 & 537.10 (M+1).

Scheme 64

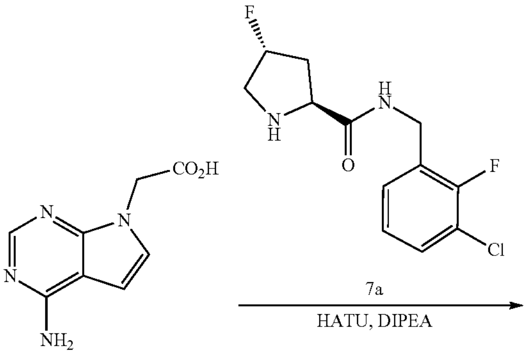

5c

-continued

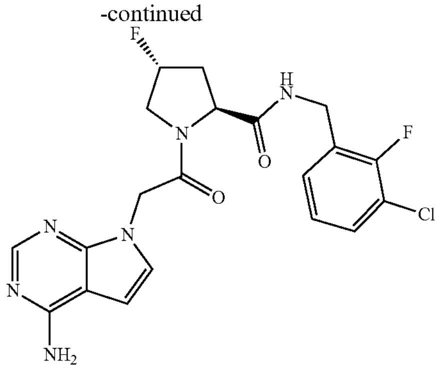

64a

Preparation of (2S,4R)-1-(2-(4-amino-7H-pyrrolo[2,3-d]pyrimidin-7-yl)acetyl)-N-(3-chloro-2-fluorobenzyl)-4-fluoropyrrolidine-2-carboxamide (64a)

Compound 64a was prepared according to the procedure reported in step-3 of scheme-1, from TFA salt of 2-(4-amino-7H-pyrrolo[2,3-d]pyrimidin-7-yl)acetic acid (5c) (158 mg, 0.515 mmol) in DMF (5 mL) using TFA salt of (2S,4R)—N-(3-chloro-2-fluorobenzyl)-4-fluoropyrrolidine-2-carboxamide (7a) (200 mg, 0.515 mmol), HATU (235 mg, 0.617 mmol) DIPEA (0.449 mL, 2.57 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (2S,4R)-1-(2-(4-amino-7H-pyrrolo[2,3-d]pyrimidin-7-yl)acetyl)-N-(3-chloro-2-fluorobenzyl)-4-fluoropyrrolidine-2-carboxamide (64a) (115 mg, 50% yield) HCl salt as a white solid; $^1$H NMR (300 MHz, DMSO-$d_6$) (a mixture of two rotamers) δ 9.28 (bs, 1H, $D_2O$ exchangeable), 9.14 and 8.70 (2t, J=5.9 Hz, 1H), 8.54 (bs, 1H, $D_2O$ exchangeable), 8.35 and 8.34 (2s, 1H), 7.55-7.34 (m, 2H), 7.21 (dt, J=22.4, 7.6 Hz, 1H), 7.07 (t, J=7.9 Hz, 1H), 6.95 (dd, J=6.0, 3.4 Hz, 11H), 5.62-4.55 (m, 3H), 4.39 (td, J=16.7, 6.9 Hz, 2H), 4.24 (dd, J=15.9, 5.7 Hz, 1H), 4.16-3.99 (m, 1H), 3.87 (ddd, J=37.7, 12.3, 3.0 Hz, 1H), 2.62-2.38 (m, 1H), 2.22-1.92 (m, 1H); $^{19}$F NMR (282 MHz, DMSO-$d_6$) δ−121.32, −121.65, −176.12, −176.32; MS (ES+): 449/451 (M+1).

Scheme 65

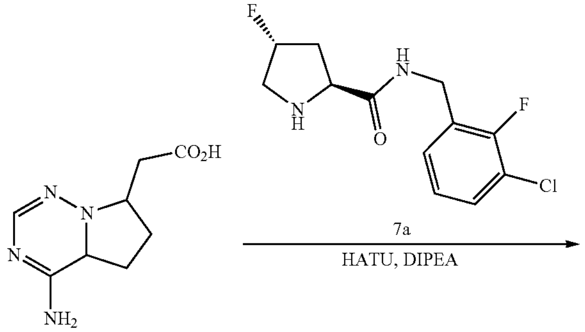

2c

-continued

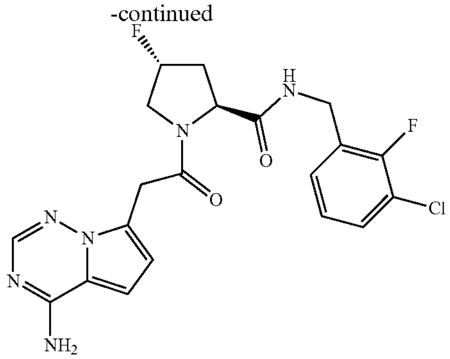

65a

-continued

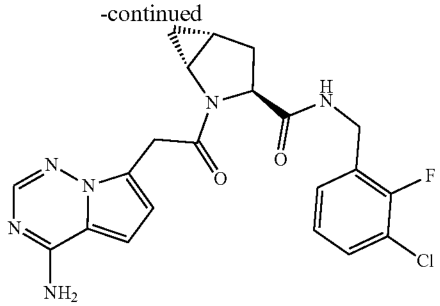

66b

Preparation of (2S,4R)-1-(2-(4-aminopyrrolo[2,1-f][1,2,4]triazin-7-yl)acetyl)-N-(3-chloro-2-fluorobenzyl)-4-fluoropyrrolidine-2-carboxamide (65a)

Compound 65a was prepared according to the procedure reported in step-3 of scheme-1, from TFA salt of 2-(4-aminopyrrolo[2,1-][1,2,4]triazin-7-yl)acetic acid (2c) (150 mg, 0.49 mmol) in DMF (5 mL) using TFA salt of (2S,4R)—N-(3-chloro-2-fluorobenzyl)-4-fluoropyrrolidine-2-carboxamide (7a) (190 mg, 0.490 mmol), HATU ((224 mg, 0.588 mmol) DIPEA (0.428 mL, 2.449 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (2S,4R)-1-(2-(4-aminopyrrolo[2,1-f][1,2,4]triazin-7-yl)acetyl)-N-(3-chloro-2-fluorobenzyl)-4-fluoropyrrolidine-2-carboxamide (65a) (104 mg, 47.3% yield) HCl salt as a white solid; $^1H$ NMR (300 MHz, DMSO-$d_6$) (a mixture of two rotamers) δ 9.81 (bs, 1H, $D_2O$ exchangeable), 9.21-8.91 (m, 1H, $D_2O$ exchangeable), 8.65 (t, J=5.9 Hz, 1H), 8.14 and 8.12 (2s, 1H), 7.54-7.38 (m, 2H), 7.38-7.26 (m, 1H), 7.14 (dt, J=15.6, 7.9 Hz, 1H), 6.78 and 6.66 (2d, J=4.5 Hz, 1H), 5.56-5.20 (m, 1H), 4.51-4.22 (m, 3H), 4.18-3.34 (m, 4H), 2.63-2.38 (m, 1H), 2.19-1.88 (m, 1H); $^{19}F$ NMR (282 MHz, DMSO-$d_6$) δ−121.27, −121.68, −176.19, −176.45; MS (ES+) 449/451 (M+1); Analysis calculated for $C_{20}H_{19}ClF_2N_6O_2 \cdot HCl \cdot 1.75H_2O$: C, 46.48; H, 4.58; Cl, 13.72; N, 16.26 Found: C, 46.64; H, 4.31; Cl, 13.61; N, 15.94.

Scheme 66

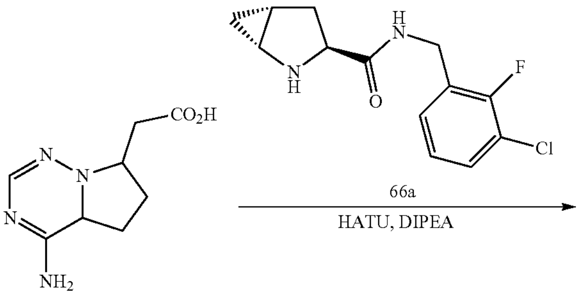

2c

Preparation of (1R,3S,5R)-2-(2-(4-aminopyrrolo[2,1-f][1,2,4]triazin-7-yl)acetyl)-N-(3-chloro-2-fluorobenzyl)-2-azabicyclo[3.1.0]hexane-3-carboxamide (66b)

Compound 66b was prepared according to the procedure reported in step-3 of scheme-1, from TFA salt of 2-(4-aminopyrrolo[2,1-f][1,2,4]triazin-7-yl)acetic acid (2c) (100 mg, 0.327 mmol) in DMF (5 mL) using TFA salt of (1R,3S,5R)—N-(3-chloro-2-fluorobenzyl)-2-azabicyclo[3.1.0]hexane-3-carboxamide (66a) (125 mg, 0.327 mmol; prepared according to the procedure reported by Wiles, Jason A. et al. PCT Int. Appl. (2017), WO 2017035349 A1 20170302), HATU (149 mg, 0.392 mmol) DIPEA (0.285 mL, 1.633 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%](1R,3S,5R)-2-(2-(4-aminopyrrolo[2,1-f][1,2,4]triazin-7-yl)acetyl)-N-(3-chloro-2-fluorobenzyl)-2-azabicyclo[3.1.0]hexane-3-carboxamide (66b) (59 mg, 40.8% yield) HCl salt as a white solid; $^1H$ NMR (300 MHz, DMSO-$d_6$) (a mixture of two rotamers) δ 9.93 (s, 1H, $D_2O$ exchangeable), 9.14 (s, 1H, $D_2O$ exchangeable), 8.46 (t, J=5.9 Hz, 1H $D_2O$ exchangeable), 8.17 (s, 1H), 7.55-7.41 (m, 2H), 7.25 (t, 1H), 7.14 (t, J=7.8 Hz, 1H), 6.82 (d, J=4.6 Hz, 1H), 4.42-4.12 (m, 5H), 3.67-3.55 (m, 1H), 2.31-2.05 (m, 2H), 1.90-1.70 (m, 1H), 1.04-0.86 (m, 1H), 0.70-0.53 (m, 1H); $^{19}F$ NMR (282 MHz, DMSO-$d_6$) δ −121.74; MS (ES+): 443/445 (M+1); Analysis calculated for $C_{21}H_{20}ClFN_6O_2 \cdot HCl \cdot 2.5H_2O$: C, 48.10; H, 5.00; Cl, 13.52; N, 16.03. Found: C, 48.08; H, 4.82; Cl, 13.96; N, 15.88.

Scheme 67

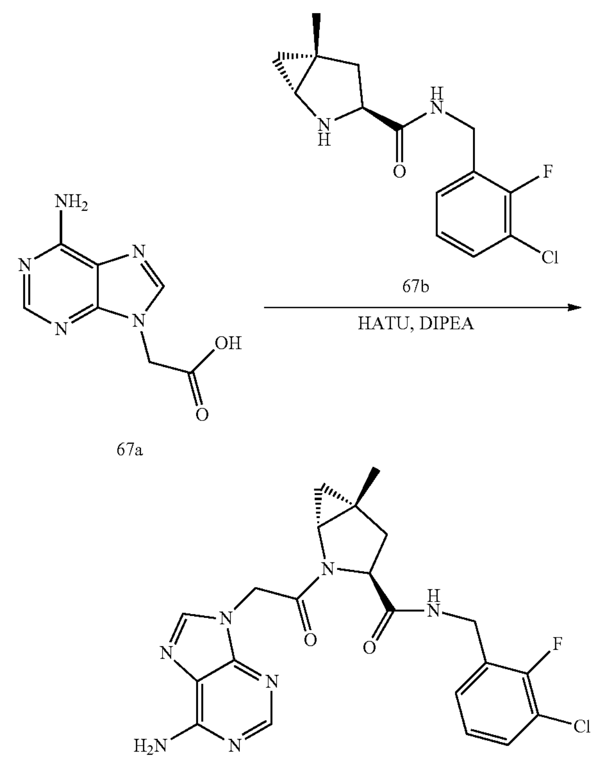

Scheme 68

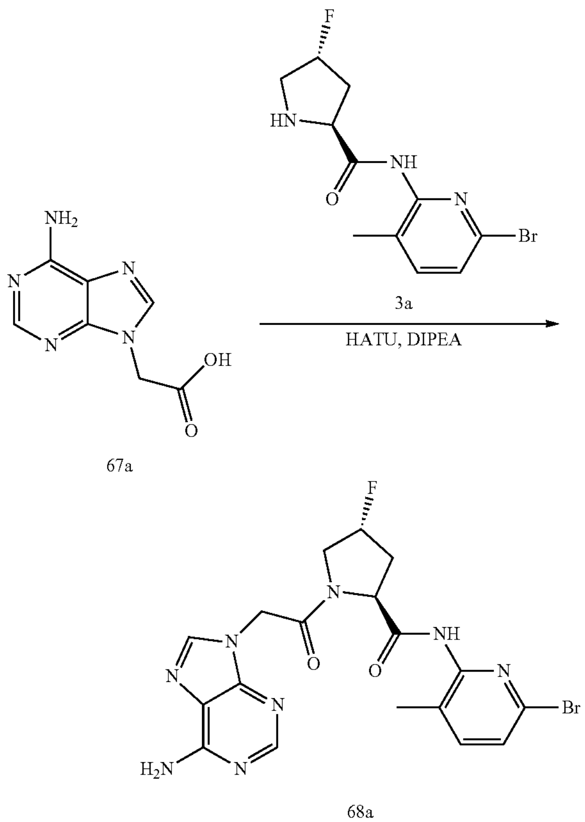

Preparation of (1R,3S,5R)-2-(2-(6-amino-9H-purin-9-yl)acetyl)-N-(3-chloro-2-fluorobenzyl)-5-methyl-2-azabicyclo[3.1.0]hexane-3-carboxamide (67c)

Compound 67c was prepared according to the procedure reported in step-3 of scheme-1, from 2-(6-amino-9H-purin-9-yl)acetic acid (67a) (65 mg, 0.337 mmol) in DMF (1.5 mL) and DMSO (0.5 mL) using (1R,3S,5R)—N-(3-chloro-2-fluorobenzyl)-5-methyl-2-azabicyclo[3.1.0]hexane-3-carboxamide (67b) (114 mg, 0.404 mmol), HATU (96 mg, 0.252 mmol), DIPEA (0.293 mL, 1.683 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%](1R,3S,5R)-2-(2-(6-amino-9H-purin-9-yl)acetyl)-N-(3-chloro-2-fluorobenzyl)-5-methyl-2-azabicyclo[3.1.0]hexane-3-carboxamide (67c) (92 mg, 60% yield) HCl salt as a white solid; $^{1}H$ NMR (300 MHz, DMSO-$d_6$) δ 8.52 (t, J=5.9 Hz, 1H, $D_2O$ exchangeable), 8.39 (s, 1H), 8.33 (s, 1H), 7.47 (td, J=7.6, 1.7 Hz, 1H), 7.28-7.19 (m, 1H), 7.13 (t, J=7.9 Hz, 1H), 5.46 (d, J=17.1 Hz, 1H), 5.20 (d, J=17.0 Hz, 1H), 4.33 (d, J=5.8 Hz, 2H), 4.24 (dd, J=9.2, 4.7 Hz, 1H), 3.46 (dd, J=5.5, 2.4 Hz, 1H), 2.40 (dd, J=13.2, 9.2 Hz, 1H), 1.91 (dd, J=13.2, 4.7 Hz, 1H), 1.25 (s, 3H), 1.00 (t, J=5.3 Hz, 1H), 0.89 (dd, J=5.3, 2.4 Hz, 1H); $^{19}F$ NMR (282 MHz, DMSO-$d_6$) δ-121.57. MS (ES+): 458.1 (M+1), 480.1 (M+Na); (ES−): 456.7 (M−1), 492.5 (M+Cl); Analysis calculated for $C_{21}H_{21}ClFN_7O_2 \cdot HCl \cdot 1.75H_2O$: C, 47.96; H, 4.89; Cl, 13.48; N, 18.64. Found: C, 47.91; H, 4.55; Cl, 13.17; N, 18.43.

Preparation of (2S,4R)-1-(2-(6-amino-9H-purin-9-yl)acetyl)-N-(6-bromo-3-methylpyridin-2-yl)-4-fluoropyrrolidine-2-carboxamide (68a)

Compound 68a was prepared according to the procedure reported in step-3 of scheme-1, from 2-(6-amino-9H-purin-9-yl)acetic acid (67a) (65 mg, 0.337 mmol) in DMF (1.5 mL) and DMSO (0.5 mL) using (2S,4R)—N-(6-bromo-3-methylpyridin-2-yl)-4-fluoropyrrolidine-2-carboxamide (3a) (102 mg, 0.337 mmol), HATU (192 mg, 0.505 mmol), DIPEA (0.293 mL, 1.683 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (2S,4R)-1-(2-(6-amino-9H-purin-9-yl)acetyl)-N-(6-bromo-3-methylpyridin-2-yl)-4-fluoropyrrolidine-2-carboxamide (68a) (45 mg, 28% yield) HCl salt as a white solid; $^{1}H$ NMR (300 MHz, DMSO-$d_6$) δ (a mixture of two rotamers) 10.92 (s) and 10.52 (s) (2s, 1H) ($D_2O$ exchangeable), 9.50 (s, 1H) ($D_2O$ exchangeable), 8.76 (s, 1H) ($D_2O$ exchangeable), 8.46 (m, J=3.0 Hz, 1H), 8.39 (s, 1H), 7.71 (d, J=8.0 Hz) and 7.61 (d, J=8.0 Hz) (2d, 1H), 7.52 (d, J=7.9 Hz) and 7.43 (d, J=7.9 Hz) (2d, 1H), 5.71-5.17 (m, 3H), 4.60 (t, J=8.5 Hz, 1H), 4.29-3.81 (m, 2H), 2.74-2.52 (m, 1H), 2.30-2.04 (m, 1H), 2.02 (s, 3H); $^{19}F$ NMR (282 MHz, DMSO-$d_6$) δ-175.88; MS (ES+): 477.1 (M+1), 499.1 (M+Na); (ES−): 475.6 (M−1); Analysis calculated for $C_{18}H_{18}BrFN_8O_2 \cdot 1.2HCl \cdot 2.5H_2O$: C, 38.19; H, 4.31; Cl, 7.52; N, 19.79. Found: C: 38.33; H, 3.98; Cl, 7.31; N, 19.64.

Scheme 69

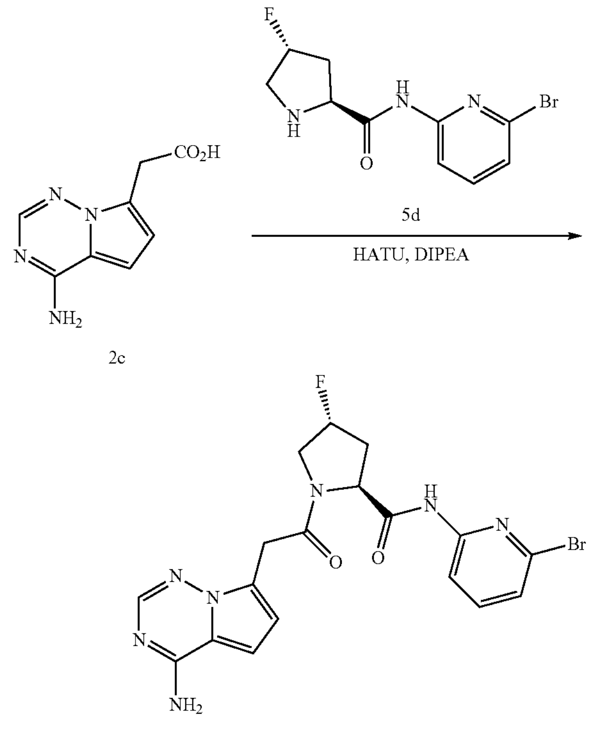

2c 5d 69a

Preparation of (2S,4R)-1-(2-(4-aminopyrrolo[2,1-f][1,2,4]triazin-7-yl)acetyl)-N-(6-bromopyridin-2-yl)-4-fluoropyrrolidine-2-carboxamide (69a)

Compound 69a was prepared according to the procedure reported in step-3 of scheme-1, from TFA salt of 2-(4-aminopyrrolo[2,1-f][1,2,4]triazin-7-yl)acetic acid (2c) (75 mg, 0.245 mmol) in DMF (5 mL) using TFA salt of (2S,4R)—N-(6-bromopyridin-2-yl)-4-fluoropyrrolidine-2-carboxamide (5d) (98 mg, 0.294 mmol), HATU (112 mg, 0.294 mmol) and DIPEA (158 mg, 1.225 mmol) and stirring at RT for 16 h. This gave after workup and purification by flash column chromatography [silica gel (12 g), MeOH in DCM from 0-5%] followed by purification using reverse phase column chromatography [C18 column (100 g), eluting with ACN in water (containing 0.1% HCl) from 0-60%] (2S,4R)-1-(2-(4-aminopyrrolo[2,1-f][1,2,4]triazin-7-yl)acetyl)-N-(6-bromopyridin-2-yl)-4-fluoropyrrolidine-2-carboxamide (69a) (40 mg, 35% yield) as a white solid; 1H NMR (300 MHz, DMSO-$d_6$) δ (a mixture of rotamers) 11.28 (s) and 10.99 (s) (2s, 1H, $D_2O$ exchangeable), 9.86 (s, 1H, $D_2O$ exchangeable), 9.09 (s, 1H, $D_2O$ exchangeable), 8.16 (s, 1H), 8.11-7.99 (m, 1H), 7.81-7.70 (m, 1H), 7.51-7.39 (m, 1H), 7.35 (d, J=8.2 Hz, 1H), 6.75 (dd, J=12.6, 4.6 Hz, 1H), 5.45 (dt, J=52.6, 2.9 Hz, 1H), 4.64 (t, J=8.5 Hz, 1H), 4.18-3.97 (m, 2H), 3.90 (dd. J=12.5, 3.1 Hz, 1H), 3.81-3.73 (m, 1H), 2.61-2.40 (m, 1H), 2.30-1.95 (m, 1H); $^{19}F$ NMR (282 MHz, DMSO-$d_6$) δ−175.77, −176.09; MS ES+): 462.0 (M+1); (ES−): 460.0 (M−1).

Scheme 70

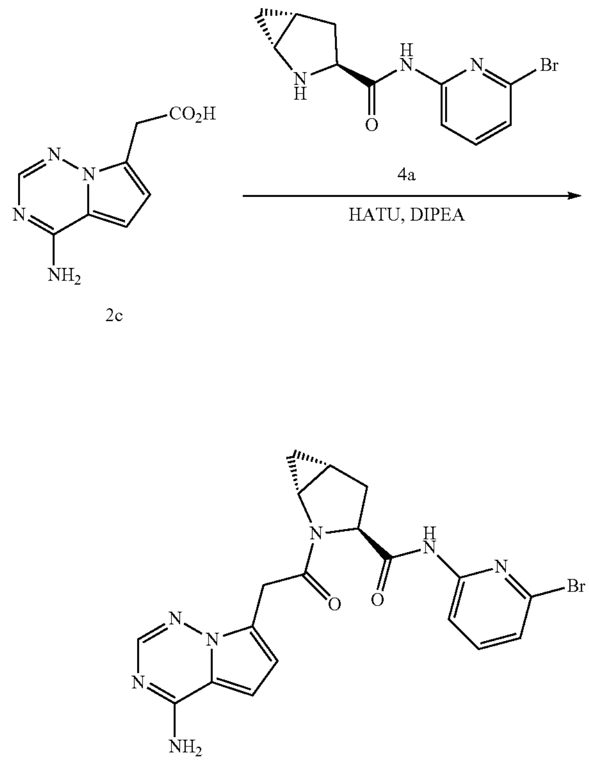

2c 4a 70a

Preparation of (1R,3S,5R)-2-(2-(4-aminopyrrolo[2,1-f][1,2,4]triazin-7-yl)acetyl)-N-(6-bromopyridin-2-yl)-2-azabicyclo[3.1.0]hexane-3-carboxamide (70a)

Compound 70a was prepared according to the procedure reported in step-3 of scheme-1, from TFA salt of 2-(4-aminopyrrolo[2,1-f][1,2,4]triazin-7-yl)acetic acid (2c) (75 mg, 0.245 mmol) in DMF (5 mL) using HCl salt of (1R,3S,5R)—N-(6-bromopyridin-2-yl)-2-azabicyclo[3.1.0]hexane-3-carboxamide (4a) (78 mg, 0.245 mmol), HATU (112 mg, 0.294 mmol), DIPEA (158 mg, 1.225 mmol) and stirring at RT for 16 h. This gave after workup and purification by flash column chromatography [silica gel (12 g), eluting with MeOH in DCM from 0-5%] followed by purification using reverse phase column chromatography [C18 column (100 g), eluting with ACN in water (containing 0.1% HCl) from 0-60%](1R,3S,5R)-2-(2-(4-aminopyrrolo[2,1-f][1,2,4]triazin-7-yl)acetyl)-N-(6-bromopyridin-2-yl)-2-azabicyclo[3.1.0]hexane-3-carboxamide (70a) (64 mg, 57% yield) HCl salt as a white solid; $^1H$ NMR (300 MHz, DMSO-$d_6$) δ 10.75 (s, 1H, $D_2O$ exchangeable), 9.91 (s, 1H, $D_2O$ exchangeable), 9.13 (s, 1H, $D_2O$ exchangeable), 8.19 (s, 1H), 8.05 (d, J=8.1 Hz, 1H), 7.73 (t, J=8.0 Hz, 1H), 7.48 (d, J=4.6 Hz, 1H), 7.34 (d, J=7.7 Hz, 1H), 6.82 (d, J=4.6 Hz, 1H), 4.43 (dd, J=9.0, 5.5 Hz, 1H), 4.31 (d, J=16.9 Hz, 1H), 4.15 (d, J=16.9 Hz, 1H), 3.71-3.66 (m, 1H), 2.39-2.12 (m, 2H), 1.89-1.72 (m, 1H), 1.02-0.90 (m, 1H), 0.66-0.52 (m, 1H); MS (ES+): 456.0 (M+1); (ES−): 454.0 (M−1); Analysis calculated for $C_{19}H_{18}BrN_7O_2 \cdot 1.25HCl \cdot 2.25H_2O$: C, 42.07; H, 4.41. Cl, 8.17; N, 18.08. Found: C, 42.33; H, 4.10; Cl, 7.92; N, 17.95.

Scheme 71

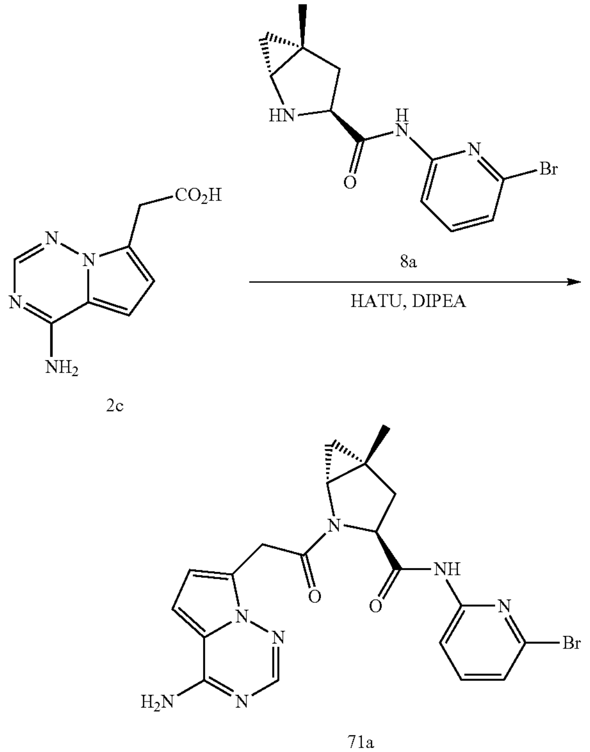

2c
71a

Scheme 72

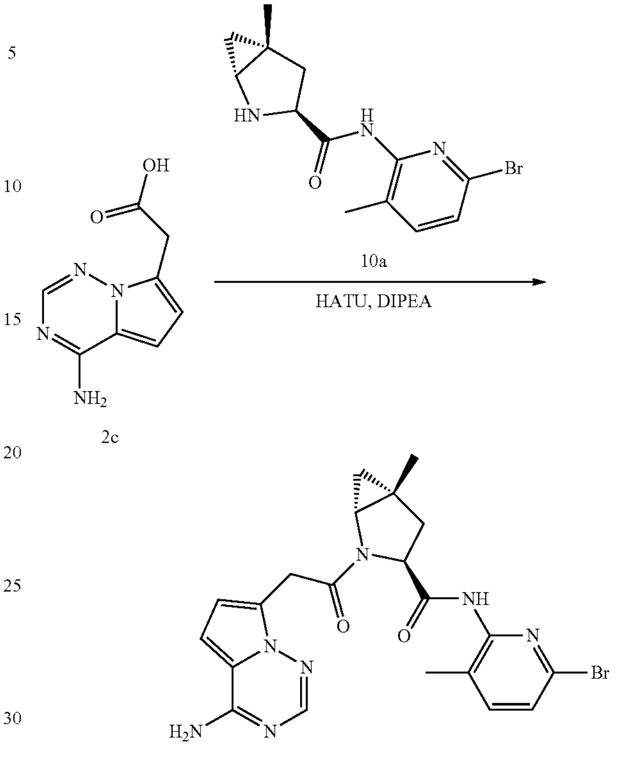

2c
72a

Preparation of (1R,3S,5R)-2-(2-(4-aminopyrrolo[2,1-f][1,2,4]triazin-7-yl)acetyl)-N-(6-bromopyridin-2-yl)-5-methyl-2-azabicyclo[3.1.0]hexane-3-carboxamide (71a)

Compound 71a was prepared according to the procedure reported in step-3 of scheme-1, from TFA salt of 2-(4-aminopyrrolo[2,1-f][1,2,4]triazin-7-yl)acetic acid (2c) (75 mg, 0.245 mmol) in DMF (2 mL) and using HCl salt of (1R,3S,5R)—N-(6-bromopyridin-2-yl)-5-methyl-2-azabicyclo[3.1.0]hexane-3-carboxamide (8a) (81 mg, 0.245 mmol), HATU (140 mg, 0.367 mmol), DIPEA (0.213 mL, 1.225 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%](1R,3S,5R)-2-(2-(4-aminopyrrolo[2,1-f][1,2,4]triazin-7-yl)acetyl)-N-(6-bromopyridin-2-yl)-5-methyl-2-azabicyclo[3.1.0]hexane-3-carboxamide (71a) (59 mg, 51% yield) HCl salt as a white solid; $^{1}$H NMR (300 MHz, DMSO-$d_6$) δ 10.75 (s, 1H, $D_2O$ exchangeable), 9.98 (s, 1H, $D_2O$ exchangeable), 9.18 (s, 1H, $D_2O$ exchangeable), 8.19 (s, 1H), 8.05 (d, J=8.2 Hz, 1H), 7.73 (t, J=8.0 Hz, 1H), 7.50 (d, J=4.6 Hz, 1H), 7.34 (d, J=7.7 Hz, 1H), 6.81 (d, J=4.6 Hz, 1H), 4.39 (dd, J=9.1, 5.7 Hz, 1H), 4.28 (d, J=17.0 Hz, 1H), 4.10 (d, J=16.9 Hz, 1H), 3.46 (dd, J=5.6, 2.3 Hz, 11H), 2.43 (dd, J=13.2, 9.1 Hz, 1H), 1.96 (dd, J=13.2, 5.7 Hz, 1H), 1.24 (s, 3H), 0.89 (t, J=5.4 Hz, 1H), 0.75 (dd, J=5.4, 2.3 Hz, 1H); MS (ES+): 469.9 (M+1); (ES−): 468.0 (M−1): Analysis calculated for $C_{20}H_{20}BrN_7O_2 \cdot 1.5H_2O \cdot 1.15HCl$: C, 44.54; H, 4.51; Cl, 7.56; N, 18.18. Found: C, 44.79; H, 4.29; Cl, 7.53; N, 18.23.

Preparation of (1R,3S,5R)-2-(2-(4-aminopyrrolo[2,1-f][,2,4]triazin-7-yl)acetyl)-N-(6-bromo-3-methylpyridin-2-yl)-5-methyl-2-azabicyclo[3.1.0]hexane-3-carboxamide (72a)

Compound 72a was prepared according to the procedure reported in step-3 of scheme-1, from TFA salt of 2-(4-aminopyrrolo[2,1-f][1,2,4]triazin-7-yl)acetic acid (2c) (75 mg, 0.245 mmol) in DMF (2 mL) and using HCl salt of (1R,3S,5R)—N-(6-bromo-3-methylpyridin-2-yl)-5-methyl-2-azabicyclo[3.1.0]hexane-3-carboxamide (10a) (85 mg, 0.245 mmol), HATU (140 mg, 0.367 mmol), DIPEA (0.213 mL, 1.225 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-aminopyrrolo[2,1-f][1,2,4]triazin-7-yl)acetyl)-N-(6-bromo-3-methylpyridin-2-yl)-5-methyl-2-azabicyclo[3.1.0] hexane-3-carboxamide (72a) (68 mg, 57.3% yield) HCl salt as a white solid; $^{1}$H NMR (300 MHz, DMSO-$d_6$) δ 10.29 (s, 1H, $D_2O$ exchangeable), 10.19 (s, 1H, $D_2O$ exchangeable), 9.33 (s, 1H, $D_2O$ exchangeable), 8.21 (s, 1H), 7.64 (d, J=8.0 Hz, 1H), 7.57 (d, J=4.6 Hz, 1H), 7.45 (d, J=7.9 Hz, 1H), 6.83 (d, J=4.6 Hz, 1H), 4.37 (dd, J=9.2, 5.2 Hz, 1H), 4.27 (d, J=17.0 Hz, 1H), 4.13 (d, J=17.0 Hz, 1H), 3.44 (dd, J=5.6, 2.4 Hz, 1H), 2.49-2.45 (m, 1H), 2.08 (s, 3H), 2.00 (dd, J=13.3, 5.2 Hz, 1H), 1.26 (s, 3H), 0.91 (t, J=5.4 Hz, 1H), 0.79 (dd, J=5.3, 2.4 Hz, 1H); MS (ES+): 484.0 (M+1); (ES−): 482.0 (M−1); Analysis calculated for $C_{21}H_{22}BrN_7O_2{\cdot}3.5H_2O{\cdot}1.5HCl$: C, 41.89; H, 5.11; N, 16.28. Found: C, 42.02; H, 5.02; N, 15.97.

Scheme 73

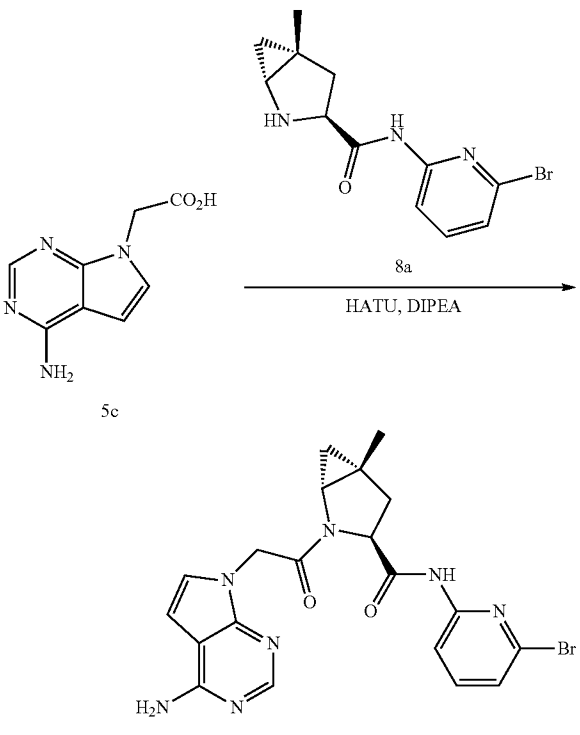

5c 8a 73a

Preparation of (1R,3S,5R)-2-(2-(4-amino-7H-pyrrolo[2,3-d]pyrimidin-7-yl)acetyl)-N-(6-bromopyridin-2-yl)-5-methyl-2-azabicyclo[3.1.0]hexane-3-carboxamide (73a)

Compound 73a was prepared according to the procedure reported in step-3 of scheme-1, from TFA salt of 2-(4-amino-7H-pyrrolo[2,3-d]pyrimidin-7-yl)acetic acid (5c) (75 mg, 0.245 mmol) in DMF (2 mL) and using HCl salt of (1R,3S,5R)—N-(6-bromopyridin-2-yl)-5-methyl-2-azabicyclo[3.1.0]hexane-3-carboxamide (8a) (81 mg, 0.245 mmol), HATU (140 mg, 0.367 mmol), DIPEA (0.213 mL, 1.225 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%](1R,3S,5R)-2-(2-(4-amino-7H-pyrrolo[2,3-d]pyrimidin-7-yl)acetyl)-N-(6-bromopyridin-2-yl)-5-methyl-2-azabicyclo[3.1.0]hexane-3-carboxamide (73a) (72 mg, 63% yield) HCl salt as a white solid; $^1$H NMR (300 MHz, DMSO-$d_6$) δ 10.81 (s, 1H, $D_2O$ exchangeable), 9.33 (s, 1H, $D_2O$ exchangeable), 8.54 (s, 1H, $D_2O$ exchangeable), 8.38 (s, 1H), 8.04 (d, J=8.2 Hz, 1H), 7.73 (t, J=8.0 Hz, 1H), 7.44 (d, J=3.6 Hz, 1H), 7.34 (d, J=7.7 Hz, 1H), 6.95 (d, J=3.6 Hz, 1H), 5.49 (d, J=17.1 Hz, 1H), 5.19 (d, J=17.0 Hz, 1H), 4.40 (dd, J=9.1, 5.8 Hz, 1H), 3.54 (dd, J=5.6, 2.3 Hz, 1H), 2.46-2.36 (m, 1H), 1.97 (dd, J=13.2, 5.8 Hz, 1H), 1.28 (s, 3H), 0.97 (t, J=5.5 Hz, 1H), 0.84 (dd, J=5.4, 2.4 Hz, 1H); MS (ES+): 470.0 (M+1); (ES−): 468.0 (M−1); Analysis calculated for $C_{20}H_{20}BrN_7O_2{\cdot}1.75H_2O{\cdot}1.1HCl$: C, 44.32; H, 4.58; Cl, 7.20; N, 18.09. Found: C, 43.99; H, 4.67; Cl, 6.95; N, 17.78.

Scheme 74

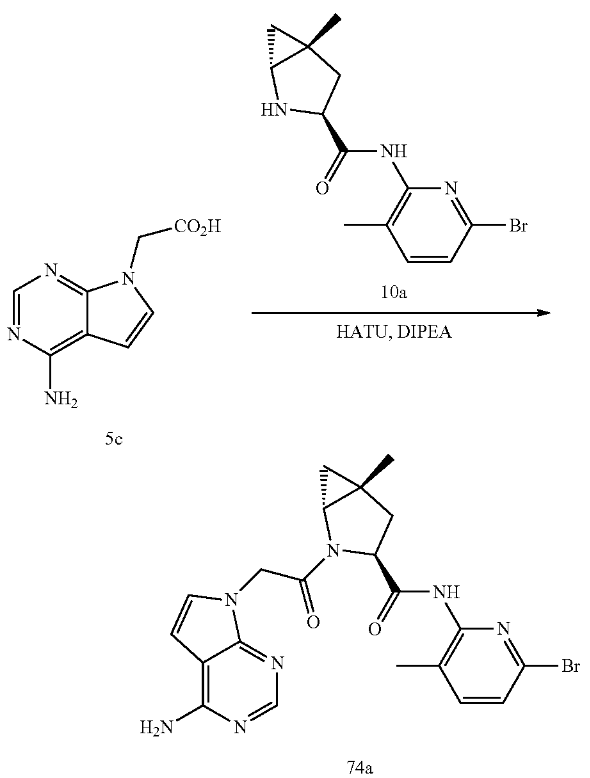

10a 5c 74a

Preparation of (1R,3S,5R)-2-(2-(4-amino-7H-pyrrolo[2,3-d]pyrimidin-7-yl)acetyl)-N-(6-bromo-3-methylpyridin-2-yl)-5-methyl-2-azabicyclo[3.1.0]hexane-3-carboxamide (74a)

Compound 74a was prepared according to the procedure reported in step-3 of scheme-1, from TFA salt of 2-(4-amino-7H-pyrrolo[2,3-d]pyrimidin-7-yl)acetic acid (5c) (75 mg, 0.245 mmol) in DMF (2 mL) and using HCl salt of (1R,3S,5R)—N-(6-bromo-3-methylpyridin-2-yl)-5-methyl-2-azabicyclo[3.1.0]hexane-3-carboxamide (10a) (85 mg, 0.245 mmol), HATU (140 mg, 0.367 mmol), DIPEA (0.213 mL, 1.225 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-7H-pyrrolo[2,3-d]pyrimidin-7-yl)acetyl)-N-(6-bromo-3-methylpyridin-2-yl)-5-methyl-2-azabicyclo[3.1.0]hexane-3-carboxamide (74a) (63 mg, 53% yield) HCl salt as a white solid; $^1$H NMR (300 MHz, DMSO-$d_6$) δ 10.32 (s, 1H, $D_2O$ exchangeable), 9.41 (s, 1H, $D_2O$ exchangeable), 8.58 (s, 1H, $D_2O$ exchangeable), 8.38 (s, 1H), 7.64 (d, J=8.0 Hz, 1H), 7.49-7.38 (m, 2H), 6.99 (d, J=3.5 Hz, 1H), 5.47 (d, J=17.0 Hz, 1H), 5.20 (d, J=16.9 Hz, 1H), 4.38 (dd, J=9.2, 5.1 Hz, 1H), 3.55-3.47 (m, 1H), 2.50-2.44 (m, 1H), 2.06 (s, 3H), 2.04-1.96 (m, 1H), 1.30 (s, 3H), 1.00 (t, J=5.4 Hz, 1H), 0.90 (dd, J=5.3, 2.4 Hz, 1H); MS (ES+): 484.0 (M+1); (ES−): 482.0 (M−1); Analysis calculated for $C_{21}H_{22}BrN_7O_2 \cdot 2.5H_2O \cdot 1.55HCl \cdot 0.25DMSO$: C, 42.78; H, 5.01; Cl, 8.81; N, 16.24. Found: C, 42.52; H, 5.00; Cl, 8.87; N, 15.99.

Scheme 75

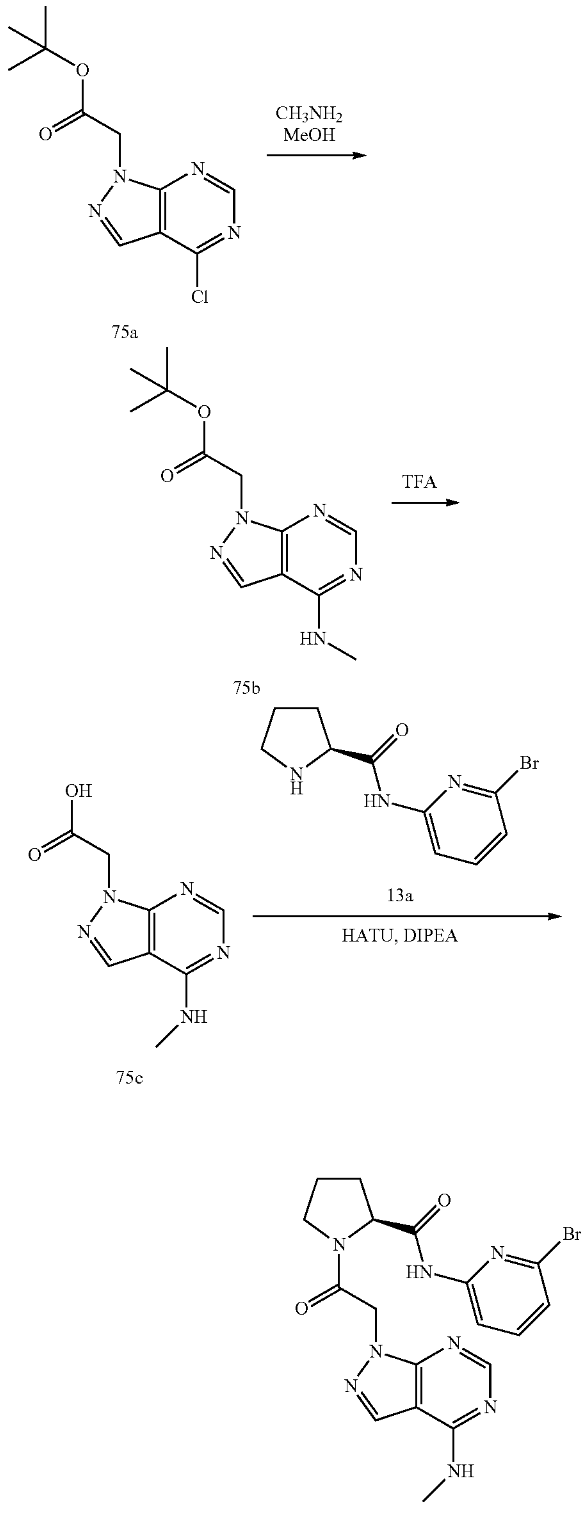

75a

75b

13a

75c

75d

Preparation of (S)—N-(6-bromopyridin-2-yl)-1-(2-(4-(methylamino)-1H-pyrazolo[3,4-d]pyrimidin-1-yl)acetyl)pyrrolidine-2-carboxamide (75d)

Step-1: Preparation of tert-butyl 2-(4-(methylamino)-1H-pyrazolo[3,4-d]pyrimidin-1-yl)acetate (75b)

To a solution of tert-butyl 2-(4-chloro-1H-pyrazolo[3,4-d]pyrimidin-1-yl)acetate (75a) (0.3 g, 1.116 mmol; prepared according to the procedure reported by Kotian, Pravin L. et al. From PCT Int Appl., 2017136395, 10 Aug. 2017) in THF (4 mL) was added methanamine in methanol (2.79 mL, 5.58 mmol) and stirred at RT for 2 h. The reaction mixture was concentrated and purified by flash column chromatography [silica gel (12 g), eluting with MeOH/EtOAc (9:1) in hexanes from 0 to 100%] to afford tert-butyl 2-(4-(methylamino)-1H-pyrazolo[3,4-d]pyrimidin-1-yl)acetate (75b); MS (ES+): 264.4 (M+1), (ES−): 262.3 (M−1).

Step-2: Preparation of 2-(4-(methylamino)-1H-pyrazolo[3,4-d]pyrimidin-1-yl)acetic acid (75c)

Compound 75c was prepared according to the procedure reported in step-2 of scheme-1, from tert-butyl 2-(4-(methylamino)-1H-pyrazolo[3,4-di]pyrimidin-1-yl)acetate (75b) using TFA (1.720 mL, 22.33 mmol) in DCM (4 mL) and stirring at RT for 4 days. The reaction mixture was concentrated in vacuum and was suspended in toluene (10 mL) and evaporated. This gave after workup 2-(4-(methylamino)-1H-pyrazolo[3,4-d]pyrimidin-1-yl)acetic acid (75c) (0.23 g, 99% yield) as white solid; $^1H$ NMR (300 MHz, DMSO-$d_6$) δ 9.43 (s, 1H), 8.40 (s, 1H), 8.25 (s, 1H), 5.16 (s, 2H), 3.06 (d, J=4.8 Hz, 3H); MS (ES+): 208.3 (M+1).

Step-3: Preparation of (S)—N-(6-bromopyridin-2-yl)-1-(2-(4-(methylamino)-1H-pyrazolo[3,4-d]pyrimidin-1-yl)acetyl)pyrrolidine-2-carboxamide (75d)

Compound 75d was prepared according to the procedure reported in step-3 of scheme-1, from 2-(4-(methylamino)-1H-pyrazolo[3,4-d]pyrimidin-1-yl)acetic acid (75c) (0.08 g, 0.386 mmol) in DMF (3 mL) and using (S)—N-(6-bromopyridin-2-yl)pyrrolidine-2-carboxamide (13a) (0.104 g, 0.386 mmol), HATU (0.161 g, 0.425 mmol), DIPEA (0.101 mL, 0.579 mmol) and stirring at RT for 16 h. This gave after workup and purification by flash column chromatography [silica gel (12 g), eluting with CMA-80 in chloroform from 0-40%] (S)—N-(6-bromopyridin-2-yl)-1-(2-(4-(methylamino)-1H-pyrazolo[3,4-d]pyrimidin-1-yl)acetyl)pyrrolidine-2-carboxamide (75d) (60 mg, 34% yield) as a white solid; 1H NMR (300 MHz, DMSO-$d_6$) δ 10.88 (s, 1H), 8.24 (s, 2H), 8.10-7.97 (m, 2H), 7.71 (t, J=7.9 Hz, 1H), 7.32 (d, J=7.6 Hz, 1H), 5.24 (s, 2H), 4.52 (dd, J=8.5, 4.1 Hz, 1H), 3.80-3.61 (m, 2H), 2.98 (d, J=4.5 Hz, 3H), 2.24-2.08 (m, 1H), 2.08-1.76 (m, 3H); MS (ES+): 459.4, (M+1); (ES−): 457.4, (M−1).

Scheme 76

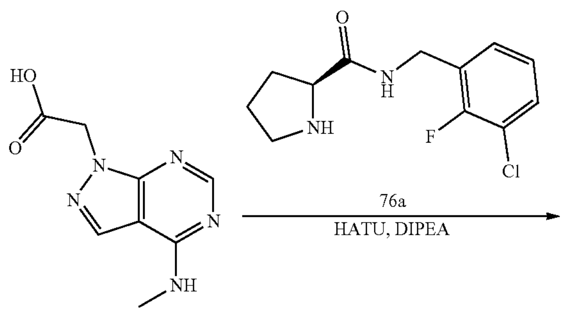

75c

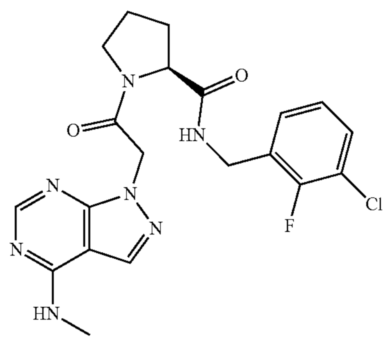

76b

Preparation of (S)—N-(3-chloro-2-fluorobenzyl)-1-(2-(4-(methylamino)-1H-pyrazolo[3,4-d]pyrimidin-1-yl)acetyl)pyrrolidine-2-carboxamide (76b)

Compound 76b was prepared according to the procedure reported in step-3 of scheme-1, from 2-(4-(methylamino)-1H-pyrazolo[3,4-d]pyrimidin-1-yl)acetic acid (75c) (0.08 g, 0.386 mmol) in DMF (3 mL) using TFA salt of (S)—N-(3-chloro-2-fluorobenzyl)pyrrolidine-2-carboxamide (76a) (0.143 g, 0.386 mmol; prepared according to the procedure reported by Kotian, Pravin L. et al., PCT Int. Appl. (2019). WO 2019195720 A1 20191010), HATU (0.161 g, 0.425 mmol), DIPEA (0.202 mL, 1.158 mmol) and stirring at RT for 16 h. This gave after workup and purification by flash column chromatography [silica gel (12 g), eluting with CMA-80 in chloroform from 0-40%] (S)—N-(3-chloro-2-fluorobenzyl)-1-(2-(4-(methylamino)-1H-pyrazolo[3,4-d]pyrimidin-1-yl)acetyl)pyrrolidine-2-carboxamide (76b) (59 mg, 34% yield) as a white solid; 1H NMR (300 MHz, DMSO-$d_6$) δ 8.46 (t, J=5.9 Hz, 1H), 8.32-8.19 (m, 2H), 8.06 (s, 1H), 7.45 (t, J=7.5 Hz, 1H), 7.20 (t, J=7.7 Hz, 1H), 7.08 (t, J=7.9 Hz, 1H), 5.22 (s, 2H), 4.46-4.20 (m, 3H), 3.80-3.57 (m, 2H), 2.99 (d, J=4.6 Hz, 3H), 2.17-1.70 (m, 4H); $^{19}$F NMR (282 MHz, DMSO-$d_6$) δ−121.60; MS (ES+): 446.5 (M+1).

Scheme 77

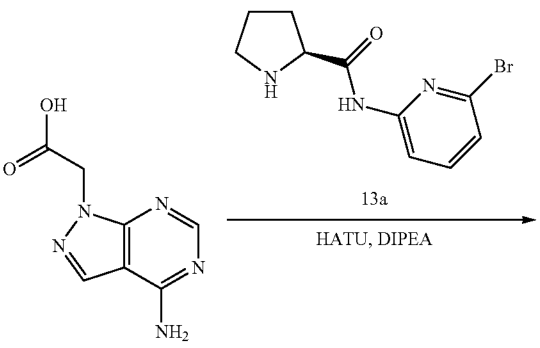

77a

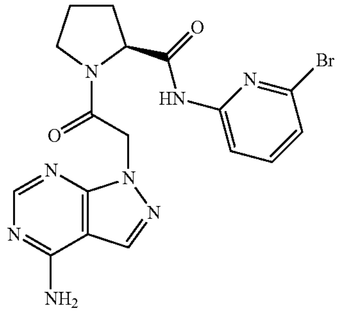

77d

Preparation of (S)-1-(2-(4-amino-1H-pyrazolo[3,4-d]pyrimidin-1-yl)acetyl)-N-(6-bromopyridin-2-yl)pyrrolidine-2-carboxamide (77b)

Compound 77b was prepared according to the procedure reported in step-3 of scheme-1, from 2-(4-amino-1H-pyrazolo[3,4-d]pyrimidin-1-yl)acetic acid (77a) (0.05 g, 0.259 mmol; prepared according to the procedure reported by Kotian, Pravin L. et al., PCT Int. Appl. (2017), WO 2017136395 A1 20170810; incorporated by reference) in DMF (3 mL) using (S)—N-(6-bromopyridin-2-yl)pyrrolidine-2-carboxamide (13a) (0.070 g, 0.259 mmol), HATU (0.108 g, 0.285 mmol), DIPEA (0.054 mL, 0.311 mmol) and stirring at RT for 16 h. This gave after workup and purification by flash column chromatography [silica gel (12 g), eluting with CMA-80 in chloroform from 0-40%] (S)-1-(2-(4-amino-1H-pyrazolo[3,4-d]pyrimidin-1-yl)acetyl)-N-(6-bromopyridin-2-yl)pyrrolidine-2-carboxamide (77b) (43 mg, 37% yield) as a white solid: $^{1}$H NMR (300 MHz, DMSO-$d_6$) δ 10.89 (s, 1H), 8.14 (s, 1H), 8.06 (s, 1H), 8.03 (d, J=8.2 Hz, 1H), 7.71 (t, J=7.9 Hz, 1H), 7.32 (d, J=7.6 Hz, 1H), 5.23 (s, 2H), 4.56-4.45 (m, 1H), 3.79-3.66 (m, 2H), 2.24-2.08 (m, 1H), 2.06-1.80 (m, 3H); MS (ES+): 445.4 (M+1).

Scheme 78

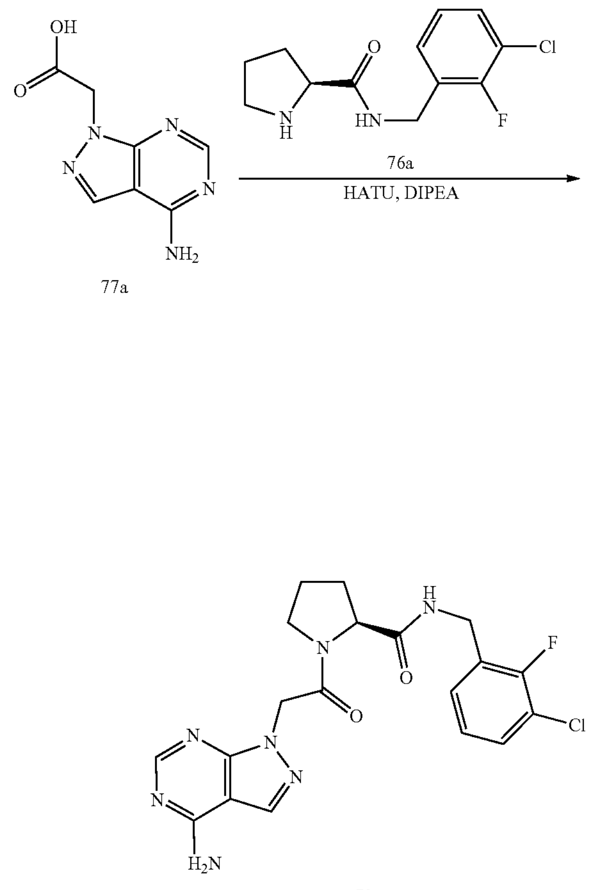

77a

78a

Scheme 79

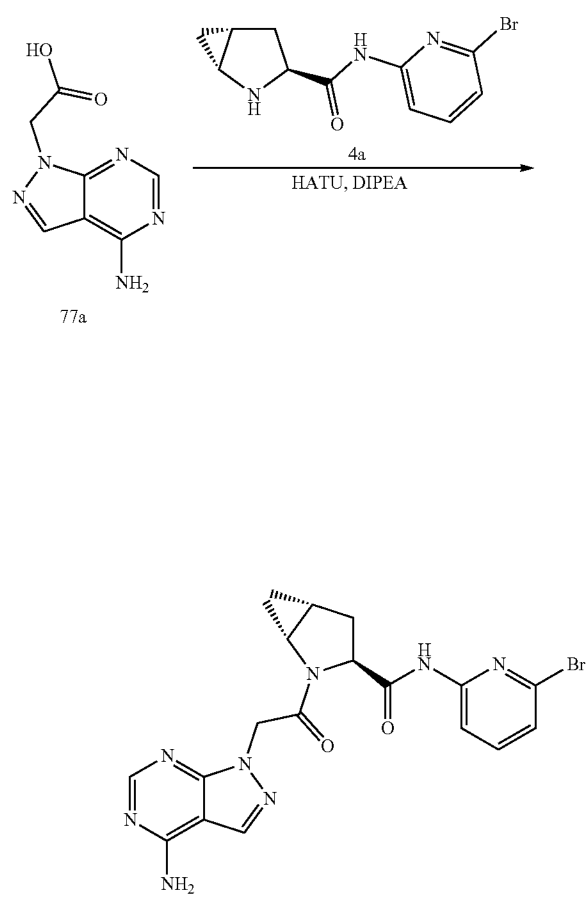

77a

79a

Preparation of(S)-1-(2-(4-amino-1H-pyrazolo[3,4-d]pyrimidin-1-yl)acetyl)-N-(3-chloro-2-fluorobenzyl)pyrrolidine-2-carboxamide (78a)

Compound 78a was prepared according to the procedure reported in step-3 of scheme-1, from 2-(4-amino-1H-pyrazolo[3,4-d]pyrimidin-1-yl)acetic acid (77a) (0.05 g, 0.259 mmol) in DMF (3 mL) using (S)—N-(3-chloro-2-fluorobenzyl)pyrrolidine-2-carboxamide (76a) (0.0% g, 0.259 mmol), HATU (0.108 g, 0.285 mmol) and DIPEA (0.136 mL, 0.777 mmol) and stirring at RT for 16 h. This gave after workup and purification by flash column chromatography [silica gel (12 g), CMA-80 in chloroform from 0-40%] (S)-1-(2-(4-amino-1H-pyrazolo[3,4-d]pyrimidin-1-yl)acetyl)-N-(3-chloro-2-fluorobenzyl)pyrrolidine-2-carboxamide (78a) (43 mg, 37% yield) as a white solid; The free based was converted to HCl salt by dissolving in acetonitrile and 0.1% aq. HCl followed by lyophilization to afford (S)-1-(2-(4-amino-1H-pyrazolo[3,4-d]pyrimidin-1-yl)acetyl)-N-(3-chloro-2-fluorobenzyl)pyrrolidine-2-carboxamide (78a) HCl salt as a white solid; $^{1}H$ NMR (300 MHz, DMSO-$d_6$) δ 8.46 (t, J=5.9 Hz, 1H), 8.13 (s, 1H), 8.09 (s, 1H), 7.45 (t, J=7.6 Hz, 1H), 7.20 (t, J=8.0 Hz, 1H), 7.08 (t, J=7.9 Hz, 1H), 5.22 (s, 2H), 4.47-4.21 (m, 3H), 3.80-3.55 (m, 2H), 2.17-1.72 (m, 4H); 19F NMR (282 MHz, DMSO-$d_6$) δ−121.60; MS (ES+): 432.5 (M+1), MS (ES−): 466.4 (M+Cl).

Preparation of (1R,3S,5R)-2-(2-(4-amino-1H-pyrazolo[3,4-d]pyrimidin-1-yl)acetyl)-N-(6-bromopyridin-2-yl)-2-azabicyclo[3.1.0]hexane-3-carboxamide (79a)

Compound 79a was prepared according to the procedure reported in step-3 of scheme-1, from 2-(4-amino-1H-pyrazolo[3,4-d]pyrimidin-1-yl)acetic acid (77a) (279 mg, 0.909 mmol) in DMF (15 mL) using (1R,3S,5R)—N-(6-bromopyridin-2-yl)-2-azabicyclo[3.1.0]hexane-3-carboxamide (4a) (300 mg, 0.757 mmol), HATU (432 mg, 1.136 mmol), DIPEA (0.660 mL, 3.79 mmol) and stirring at RT for 16 h. This gave after workup and purification by reverse phase column chromatography [C18 column (50 g), eluting with ACN in water (containing 0.1% HCl) from 0-50%] (1R,3S,5R)-2-(2-(4-amino-1H-pyrazolo[3,4-d]pyrimidin-1-yl)acetyl)-N-(6-bromopyridin-2-yl)-2-azabicyclo[3.1.0]hexane-3-carboxamide (79a) (202 mg, 58% yield) HCl salt as a white solid; $^{1}H$ NMR (300 MHz, DMSO-$d_6$) δ 10.79 (s, 1H), 10.00 (s, 1H), 9.00 (s, 1H), 8.49 (s, 1H), 8.47 (s, 1H), 8.02 (d, J=8.1 Hz, 1H), 7.72 (t, J=8.0 Hz, 1H), 7.33 (dd, J=7.7, 0.7 Hz, 1H), 5.78-5.27 (m, 2H), 4.41 (dd, J=9.0, 5.5 Hz, 1H), 3.86-3.76 (m, 1H), 2.38-2.11 (m, 2H), 1.95-1.80 (m, 1H), 1.05-0.92 (m, 1H), 0.70-0.60 (m, 1H); MS (ES+): 457.00 (M+1); (ES−): 455.00 (M−1).

Scheme 80

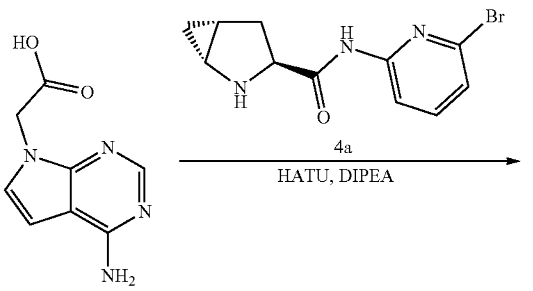

5c

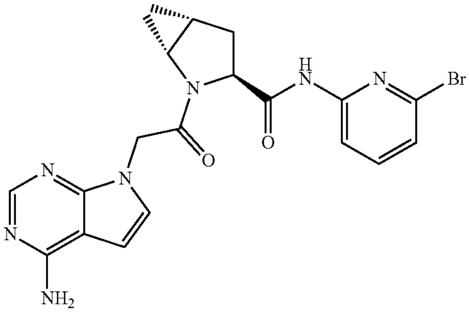

80a

Preparation of (1R,3S,5R)-2-(2-(4-amino-7H-pyrrolo[2,3-d]pyrimidin-7-yl)acetyl)-N-(6-bromopyridin-2-yl)-2-azabicyclo[3.1.0]hexane-3-carboxamide (80a)

Compound 80a was prepared according to the procedure reported in step-3 of scheme-1, from 2-(4-amino-7H-pyrrolo[2,3-d]pyrimidin-7-yl)acetic acid (5c) (0.06 g, 0.312 mmol) in DMF (2 mL) using (1R,3S,5R)—N-(6-bromopyridin-2-yl)-2-azabicyclo[3.1.0]hexane-3-carboxamide (4a) (0.118 g, 0.312 mmol), HATU (0.142 g, 0.375 mmol), DIPEA (0.164 mL, 0.937 mmol) and stirring at RT for 16 h. This gave after workup and purification by flash column chromatography [silica gel (12 g), eluting with MeOH:EtOAc (9:1) in hexanes 0 to 100%] (1R,3S,5R)-2-(2-(4-amino-7H-pyrrolo[2,3-d]pyrimidin-7-yl)acetyl)-N-(6-bromopyridin-2-yl)-2-azabicyclo[3.1.0]hexane-3-carboxamide (80a) (50 mg, 35% yield) as a white solid; 1H NMR (300 MHz, DMSO-$d_6$) δ 10.78 (s, 1H), 8.07-8.00 (m, 2H), 7.72 (t, J=8.0 Hz, 1H), 7.33 (d, J=7.7 Hz, 1H), 7.08 (d, J=3.5 Hz, 1H), 6.99 (brs, 2H), 6.52 (d, J=3.5 Hz, 1H), 5.38-5.05 (m, 2H), 4.47-4.38 (m, 1H), 3.77-3.68 (m, 1H), 2.34-2.11 (m, 2H), 1.94-1.79 (m, 1H), 1.06-0.95 (m, 1H), 0.69-0.61 (m, 1H); MS (ES+) 456.2 (M+1), MS (ES−) 454.3, (M−1); Analysis calculated for $C_{19}H_{18}BrN_7O_2 \cdot H_2O$: C, 48.11; H, 4.25; N, 20.67. Found: C, 47.86; H, 4.22; N, 20.27.

Scheme 81

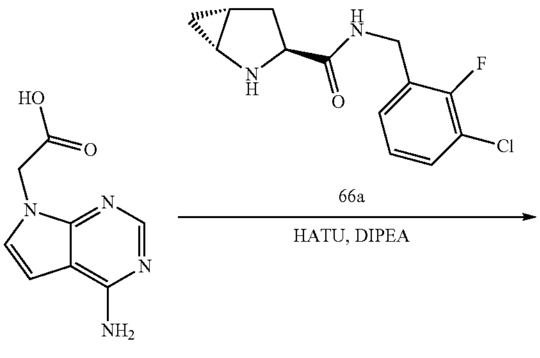

5c

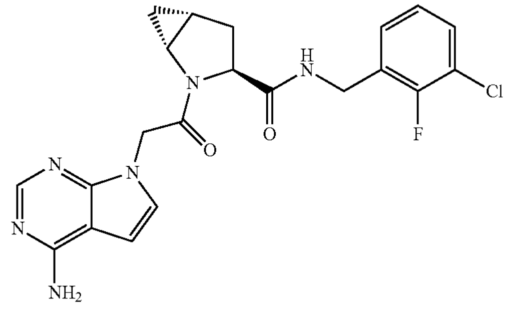

81a

Preparation of (1R,3S,5R)-2-(2-(4-amino-7H-pyrrolo[2,3-d]pyrimidin-7-yl)acetyl)-N-(3-chloro-2-fluorobenzyl)-2-azabicyclo[3.1.0]hexane-3-carboxamide (81a)

Compound 81a was prepared according to the procedure reported in step-3 of scheme-1, from 2-(4-amino-7H-pyrrolo[2,3-d]pyrimidin-7-yl)acetic acid (5c) (0.075 g, 0.392 mmol) in DMF (3 mL) using TFA salt of (1R,3S,5R)—N-(3-chloro-2-fluorobenzyl)-2-azabicyclo[3.1.0]hexane-3-carboxamide (66a) (0.15 g, 0.392 mmol), HATU (0.179 g, 0.470 mmol), DIPEA (0.205 mL, 1.176 mmol) and stirring at RT for 16 h. This gave after workup and purification by flash column chromatography [silica gel (12 g), eluting with DMA-80 in DCM from 0 to 50%) (1R,3S,5R)-2-(2-(4-amino-7H-pyrrolo[2,3-d]pyrimidin-7-yl)acetyl)-N-(3-chloro-2-fluorobenzyl)-2-azabicyclo[3.1.0]hexane-3-carboxamide (81a) (65 mg, 37% yield) as a white solid; $^1H$ NMR (300 MHz, DMSO-$d_6$) δ 8.47 (t, J=5.9 Hz, 1H), 8.08 (s, 1H), 7.50-7.41 (m, 1H), 7.29 (s, 2H), 7.25-7.17 (m, 1H), 7.16-7.07 (m, 2H), 6.61 (d, J=3.5 Hz, 1H), 5.30 (d, J=17.1 Hz, 1H), 5.15 (d, J=17.1 Hz, 1H), 4.33 (dd, J=11.4, 6.0 Hz, 1H), 4.25 (q, J=4.5 Hz, 1H), 3.69-3.58 (m, 1H), 2.30-2.18 (m, 1H), 2.18-2.06 (m, 1H), 1.90-1.76 (m, 1H), 1.06-0.96 (m, 1H), 0.73-0.63 (m, 1H); $^{19}F$ NMR (282 MHz, DMSO-$d_6$) δ−121.78; MS (ES+) 443.2 (M+1); MS (ES−): 477.2 (M+Ci); Analysis Calculated for $C_{21}H_{20}ClFN_6O_2 \cdot 1.25H_2O$: C, 54.20; H, 4.87; N, 18.06. Found: C, 54.13; H, 4.90; N, 17.69.

Scheme 82

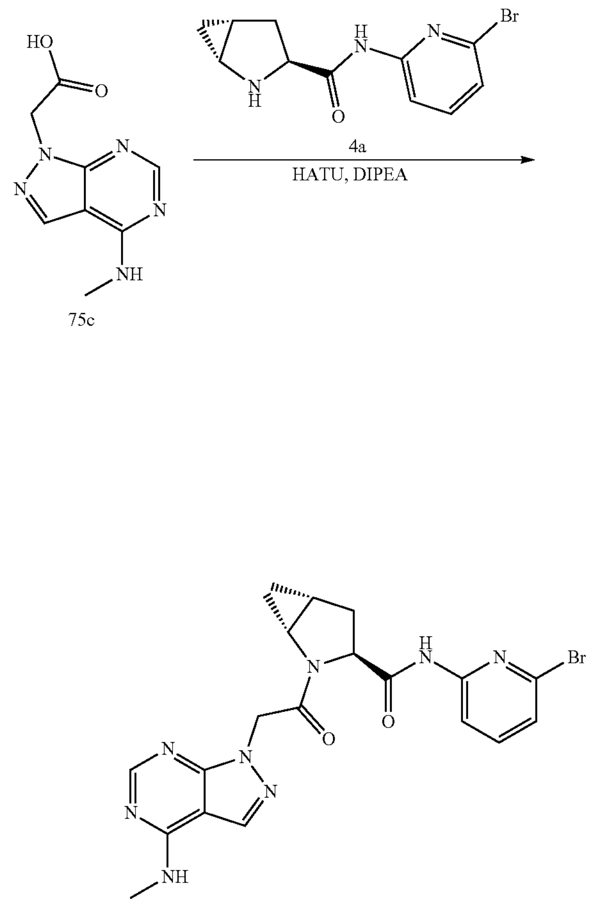

75c

82a

Preparation of (1R,3S,5R)—N-(6-bromopyridin-2-yl)-2-(2-(4-(methylamino)-1H-pyrazolo[3,4-d]pyrimidin-1-yl)acetyl)-2-azabicyclo[3.1.0]hexane-3-carboxamide (82a)

Compound 82a was prepared according to the procedure reported in step-3 of scheme-1, from 2-(4-(methylamino)-1H-pyrazolo[3,4-di]pyrimidin-1-yl)acetic acid (75c) (0.06 g, 0.290 mmol) in DMF (2 mL) using (1R,3S,5R)—N-(6-bromopyridin-2-yl)-2-azabicyclo[3.1.0]hexane-3-carboxamide (4a) (0.110 g, 0.290 mmol), HATU (0.143 g, 0.376 mmol), DIPEA (0.152 mL, 0.869 mmol) and stirring at RT for 16 h. This gave after workup and purification by flash column chromatography [silica gel (12 g), eluting with DMA-80 in DCM from 0 to 80%] (1R,3S,5R)—N-(6-bromopyridin-2-yl)-2-(2-(4-(methylamino)-1H-pyrazolo[3,4-d]pyrimidin-1-yl)acetyl)-2-azabicyclo[3.1.0]hexane-3-carboxamide (82a) (75 mg, 55% yield) as a white solid; 1H NMR (300 MHz, DMSO-$d_6$) δ 10.78 (s, 1H), 8.63 (brs, 1H), 8.29 (s, 1H), 8.13 (s, 1H), 8.03 (d, J=8.2 Hz, 1H), 7.72 (t, J=8.0 Hz, 1H), 7.33 (d, J=7.7 Hz, 1H), 5.64-5.16 (m, 2H), 4.40 (dd, J=9.1, 5.5 Hz, 1H), 3.83-3.75 (m, 1H), 3.00 (d, J=4.5 Hz, 3H), 2.35-2.11 (m, 2H), 1.94-1.78 (m, 1H), 1.02-0.92 (m, 1H), 0.67-0.55 (m, 1H); MS (ES+): 471.3, 473.3 (M+1), 493.2, 495.2 (M+Na).

Scheme 83

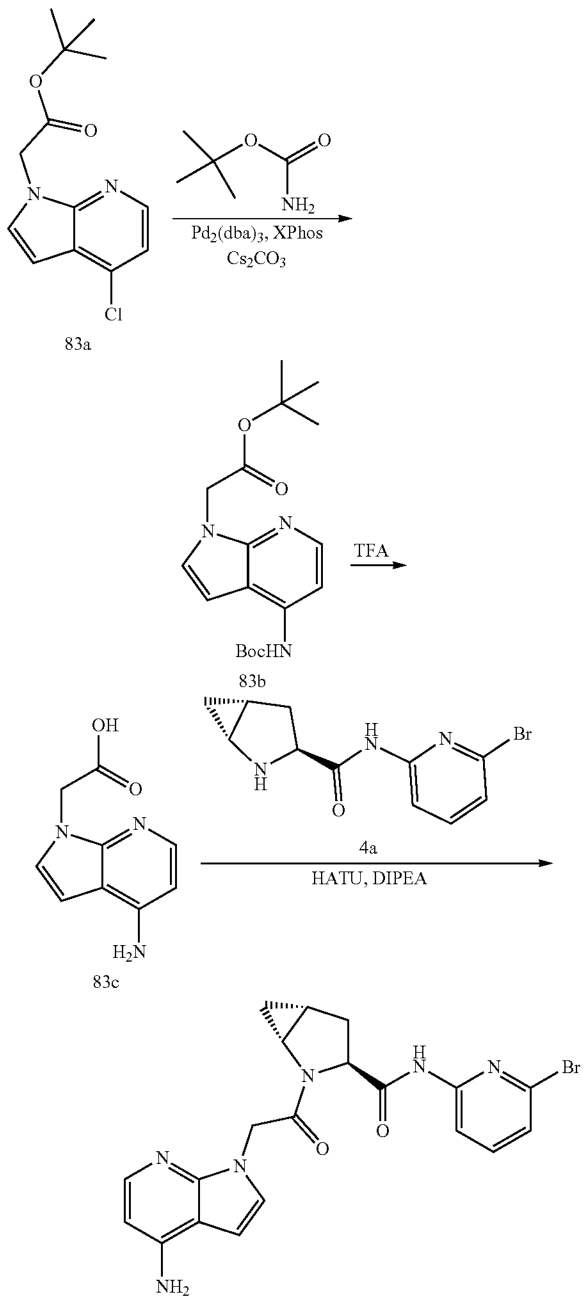

83a

83b

83c

83d

Preparation of (1R,3S,5R)-2-(2-(4-amino-1H-pyrrolo[2,3-b]pyridin-1-yl)acetyl)-N-(6-bromopyridin-2-yl)-2-azabicyclo[3.1.0]hexane-3-carboxamide (83d)

Step-1: Preparation of tert-butyl 2-(4-((tert-butoxycarbonyl)amino)-1H-pyrrolo[2,3-b]pyridin-1-yl) acetate (83b)

Compound 83b was prepared according to the procedure reported in step-3 of scheme-17, from tert-butyl 2-(4-chloro-1H-pyrrolo[2,3-b]pyridin-1-yl)acetate (83a) (1.5 g, 5.62 mmol; CAS #2243596-23-6; prepared according to the procedure reported in Kotian, P. L. et al., PCT Int. Appl. (2017), WO 2017136395 A1 20170810) in toluene (40 mL) using XPhos (0.268 g, 0.562 mmol), t-butyl carbamate (0.988 g, 8.44 mmol), $Pd_2(dba)_3$ (0.257 g, 0.281 mmol), cesium carbonate (1.832 g, 5.62 mmol) and heating at 90° C. for 20 h. This gave after work up and purification tert-butyl 2-(4-((tert-butoxycarbonyl)amino)-1H-pyrrolo[2,3-b]pyridin-1-yl)acetate (83b) (1.4 g, 72% yield); $^1H$ NMR (300 MHz, DMSO-$d_6$) δ 9.73 (s, 1H), 8.05 (d, J=5.5 Hz, 1H), 7.61 (d, J=5.5 Hz, 1H), 7.32 (d, J=3.6 Hz, 1H), 6.90 (d, J=3.6 Hz, 1H), 4.94 (s, 2H), 1.52 (s, 9H), 1.40 (s, 9H); MS (ES+): 348.3 (M+1); (ES−): 346.3 (M−1).

Step-2: Preparation of 2-(4-amino-1H-pyrrolo[2,3-b]pyridin-1-yl)acetic acid (83c)

Compound 83c was prepared according to the procedure reported in step-2 of scheme-1, from tert-butyl 2-(4-((ter-butoxycarbonyl)amino)-1H-pyrrolo[2,3-b]pyridin-1-yl)acetate (83b) (0.65 g, 2.159 mmol) using TFA (0.166 mL, 2.159 mmol) in DCM (10 mL) and stirring at RT for 16 h. This gave afterwork up 2-(4-amino-1H-pyrrolo[2,3-b]pyridin-1-yl)acetic acid (83c) (1.05 g) TFA salt as a light-orange solid; MS (ES+): 192.1 (M+1).

Step-3: Preparation of (1R,3S,5R)-2-(2-(4-amino-1H-pyrrolo[2,3-b]pyridin-1-yl)acetyl)-N-(6-bromopyridin-2-yl)-2-azabicyclo[3.1.0]hexane-3-carboxamide (83d)

Compound 83d was prepared according to the procedure reported in step-3 of scheme-1, from 2-(4-amino-1H-pyrrolo[2,3-b]pyridin-1-yl)acetic acid (83c) (0.09 g, 0.314 mmol) in DMF (2 mL) using HCl salt of (1R,3S,5R)—N-(6-bromopyridin-2-yl)-2-azabicyclo[3.1.0]hexane-3-carboxamide (4a) (0.1 g, 0.314 mmol), HATU (0.143 g, 0.377 mmol), DIPEA (0.274 mL, 1.569 mmol) and stirring at RT for 16 h. This gave after workup and purification by flash column chromatography [silica gel (4 g), eluting with DMA-80 in DCM from 0 to 80%] (1R,3S,5R)-2-(2-(4-amino-1H-pyrrolo[2,3-b]pyridin-1-yl)acetyl)-N-(6-bromopyridin-2-yl)-2-azabicyclo[3.1.0]hexane-3-carboxamide (83d) (25 mg, 17% yield) as a white solid; $^1H$ NMR (300 MHz, DMSO-$d_6$) δ 10.76 (s, 1H), 8.04 (d, J=8.2 Hz, 1H), 7.76-7.67 (m, 2H), 7.32 (d, J=7.7 Hz, 1H), 7.05 (d, J=3.5 Hz, 1H), 6.49 (d, J=3.5 Hz, 1H), 6.24-6.11 (m, 3H), 5.30 (d, J=17.0 Hz, 1H), 5.11 (d, J=16.9 Hz, 1H), 4.42 (dd, J=9.0, 5.5 Hz, 1H), 3.76-3.68 (m, 1H), 2.33-2.10 (m, 2H), 1.91-1.78 (m, 1H), 1.04-0.94 (m, 1H), 0.68-0.60 (m, 1H); MS (ES+): 455.2, 457.2 (M+1), 477.2, 479.2 (M+Na), MS (ES−): 453.2, 455.3 (M−1); Analysis calculated for $C_{20}H_{19}BrN_6O_2 \cdot H_2O$; C, 50.75; H, 4.47; N, 17.76. Found C, 50.70; H, 4.53; N, 17.46.

Scheme 84

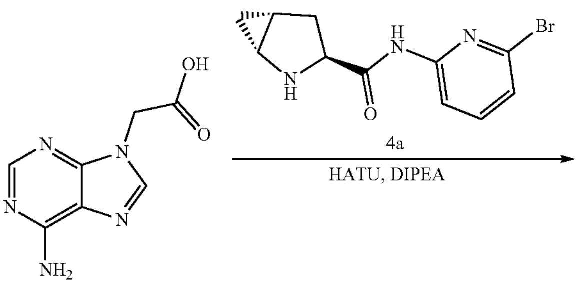

67a

-continued

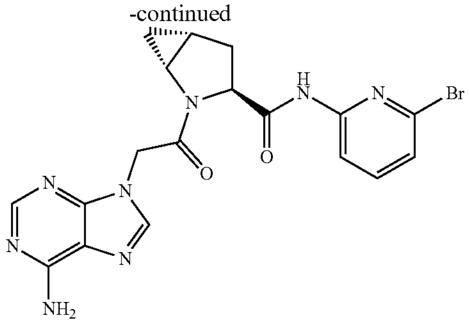

84a

Preparation of (1R,3S,5R)-2-(2-(6-amino-9H-purin-9-yl)acetyl)-N-(6-bromopyridin-2-yl)-2-azabicyclo[3.1.0]hexane-3-carboxamide (84a)

Compound 84a was prepared according to the procedure reported in step-3 of scheme-1, from 2-(6-amino-9H-purin-9-yl)acetic acid (67a) (0.05 g, 0.259 mmol) in DMF (1 mL) using HCl salt of (1R,3S,5R)—N-(6-bromopyridin-2-yl)-2-azabicyclo[3.1.0]hexane-3-carboxamide (4a) (0.082 g, 0.259 mmol), HATU (0.118 g, 0.311 mmol), DIPEA (0.181 mL, 1.035 mmol) and stirring at RT for 2 days. This gave after workup and purification by flash column chromatography [silica gel (4 g), eluting with DMA-80 in DCM from 0 to 80%] (1R,3S,5R)-2-(2-(6-amino-9H-purin-9-yl)acetyl)-N-(6-bromopyridin-2-yl)-2-azabicyclo[3.1.0]hexane-3-carboxamide (84a) (31 mg, 26% yield) as a white solid; $^1H$ NMR (300 MHz, DMSO-$d_6$) δ 10.82 (s, 1H), 8.12 (s, 1H), 8.07 (s, 1H), 8.03 (d, J=8.2 Hz, 1H), 7.72 (t, J=8.0 Hz, 1H), 7.33 (d, J=7.7 Hz, 1H), 7.24 (s, 2H), 5.42 (d, J=17.2 Hz, 1H), 5.15 (d, J=17.1 Hz, 1H), 4.45 (dd, J=9.0, 5.4 Hz, 1H), 3.80-3.71 (m, 1H), 2.36-2.12 (m, 2H), 1.95-1.82 (m, 1H), 1.09-0.98 (m, 1H), 0.72-0.65 (m, 11H); MS (ES+): 457.2 (M+1), 479.2, 481.2 (M+Na).

Scheme 85

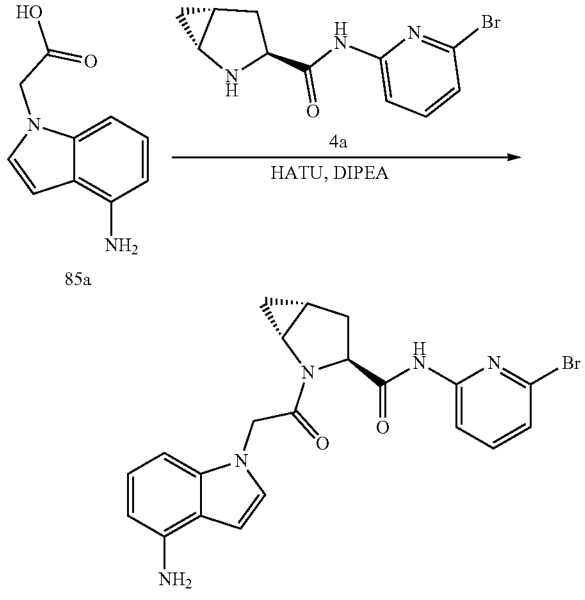

85a

85b

Preparation of (1R,3S,5R)-2-(2-(4-amino-1H-indol-1-yl)acetyl)-N-(6-bromopyridin-2-yl)-2-azabicyclo[3.1.0]hexane-3-carboxamide (85b)

Compound 85b was prepared according to the procedure reported in step-3 of scheme-1, from 2-(4-amino-1H-indol-1-yl)acetic acid (85a) (0.08 g, 0.279 mmol) in DMF (2 mL) using HCl salt of (1R,3S,5R)—N-(6-bromopyridin-2-yl)-2-azabicyclo[3.1.0]hexane-3-carboxamide (4a) (0.089 g, 0.279 mmol), HATU (0.127 g, 0.334 mmol), DIPEA (0.243 mL, 1.393 mmol) and stirring at RT for 16 h. This gave after workup and purification by flash column chromatography [silica gel (4 g), eluting with DMA-80 in DCM from 0 to 40%] to afford (1R,3S,5R)-2-(2-(4-amino-1H-indol-1-yl)acetyl)-N-(6-bromopyridin-2-yl)-2-azabicyclo[3.1.0]hexane-3-carboxamide (85b) (18 mg, 14% yield) as a white solid; $^1H$ NMR (300 MHz, DMSO-$d_6$) δ 10.77 (s, 1H), 8.03 (d, J=8.2 Hz, 1H), 7.71 (t, J=8.0 Hz, 1H), 7.35-7.29 (m, 1H), 7.05 (d, J=3.2 Hz, 1H), 6.79 (t, J=7.8 Hz, 1H), 6.56-6.46 (m, 2H), 6.15 (d, J=7.4 Hz, 1H), 5.24 (d, J=17.1 Hz, 1H), 5.18 (s, 2H), 5.03 (d, J=17.1 Hz, 1H), 4.42 (dd, J=9.0, 5.5 Hz, 1H), 3.80-3.71 (m, 1H), 2.33-2.10 (m, 2H), 1.92-1.76 (m, 1H), 1.01-0.92 (m, 1H), 0.69-0.58 (m, 1H); MS (ES+): 454.2, 456.2 (M+1), MS (ES−): 452.2, 454.2 (M−1).

Scheme 86

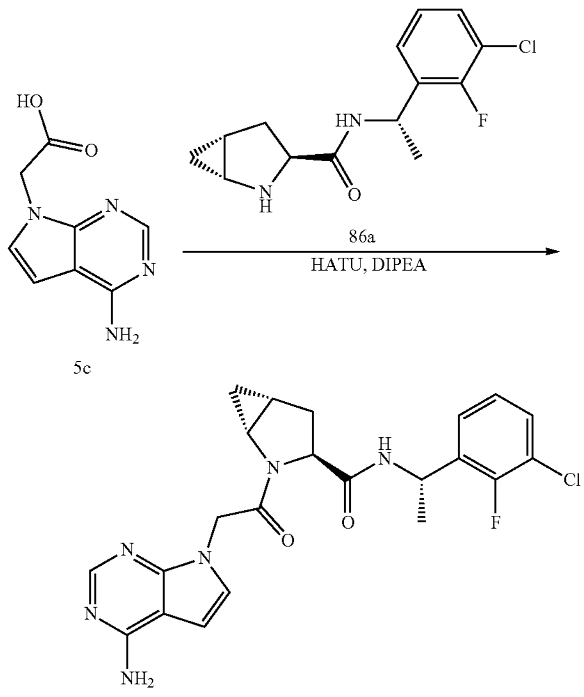

5c

86a

86b

Preparation of (1R,3S,5R)-2-(2-(4-amino-7H-pyrrolo[2,3-d]pyrimidin-7-yl)acetyl)-N—((S)-1-(3-chloro-2-fluorophenyl)ethyl)-2-azabicyclo[3.1.0]hexane-3-carboxamide (86b)

Compound 86b was prepared according to the procedure reported in step-3 of scheme-1, from 2-(4-amino-7H-pyrrolo[2,3-d]pyrimidin-7-yl)acetic acid (5c) (0.05 g, 0.260 mmol) in DMF (2 mL) using HCl salt of (1R,3S,5R)—N—((S)-1-(3-chloro-2-fluorophenyl)ethyl)-2-azabicyclo[3.1.0]hexane-3-carboxamide (86a) (0.083 g, 0.260 mmol; prepared according to the procedure reported by Altmann, E. et al., PCT Int. Appl. (2012), WO 2012093101 A1 20120712; incorporated by reference), HATU (0.119 g, 0.312 mmol), DIPEA (0.182 mL, 1.041 mmol) and stirring at RT for 2 days. This gave after workup and purification by flash column chromatography [silica gel (4 g), eluting with DMA-80 in DCM from 0 to 80%] (1R,3S,5R)-2-(2-(4-amino-7H-pyrrolo[2,3-d]pyrimidin-7-yl)acetyl)-N—((S)-1-(3-chloro-2-fluorophenyl)ethyl)-2-azabicyclo[3.1.0]hexane-3-carboxamide (86b) (0.033 g, 28% yield) as a white solid; $^1H$ NMR (300 MHz, DMSO-$d_6$) δ 8.35 (d, J=7.7 Hz, 1H), 8.05 (s, 1H), 7.48-7.39 (m, 1H), 7.35-7.27 (m, 1H), 7.20-7.04 (m, 5H), 6.56 (d, J=3.6 Hz, 1H), 5.35-4.96 (m, 3H), 4.26 (dd, J=8.8, 4.9 Hz, 1H), 3.67-3.57 (m, 1H), 2.28-2.03 (m, 2H), 1.88-1.74 (m, 1H), 1.35-1.26 (m, 3H), 1.05-0.94 (m, 1H), 0.70-0.60 (m, 1H); $^{19}F$ NMR (282 MHz, DMSO-$d_6$) δ−122.65; MS (ES+): 479.3, 481.2 (M+Na); MS (ES−): 491.3, 493.3 (M+Cl); Analysis calculated for $C_{22}H_{22}ClFN_6O_2 \cdot 1.5H_2O$; C, 54.60; H, 5.21; N, 17.37. Found C, 54.97; H, 5.19; N, 17.39.

Scheme 87

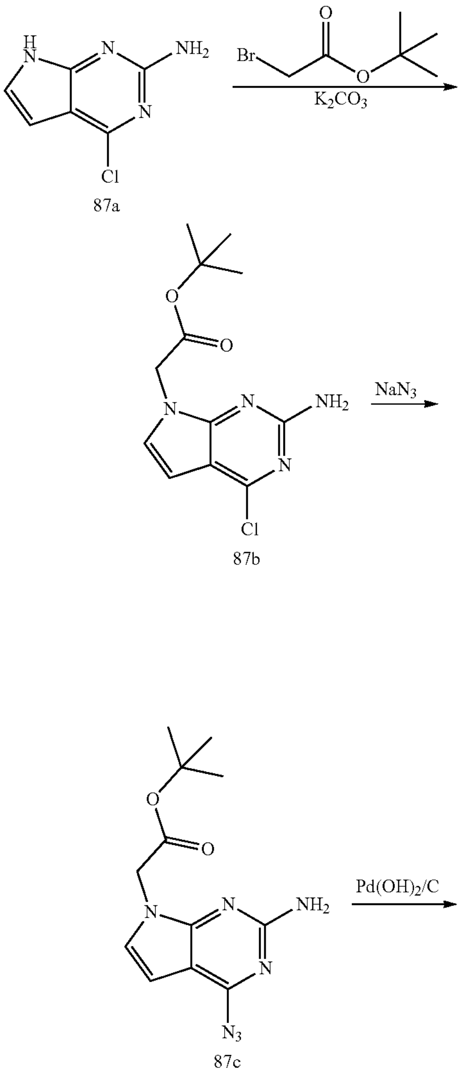

87a

87b

87c

-continued

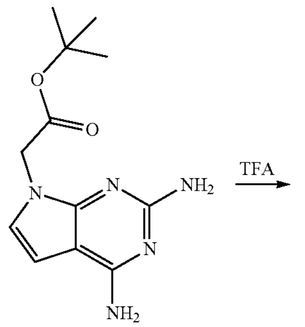

87d

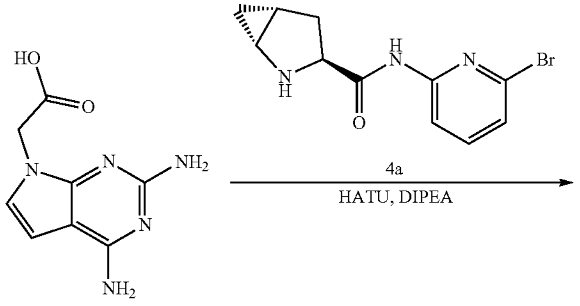

87e

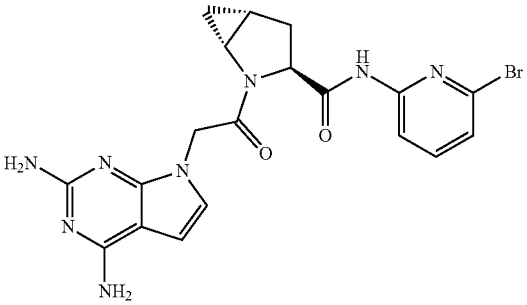

87f

Preparation of (1R,3S,5R)—N-(6-bromopyridin-2-yl)-2-(2-(2,4-diamino-7H-pyrrolo[2,3-d]pyrimidin-7-yl)acetyl)-2-azabicyclo[3.1.0]hexane-3-carboxamide (87f)

Step-1: Preparation of tert-butyl 2-(2-amino-4-chloro-7H-pyrrolo[2,3-d]pyrimidin-7-yl)acetate (87b)

Compound 87b was prepared according to the procedure reported in step-1 of scheme-1, from 4-chloro-7H-pyrrolo[2,3-d]pyrimidin-2-amine (87a) (6 g, 35.6 mmol; CAS #651035-58-4) in acetonitrile (400 mL) using tert-butyl 2-bromoacetate (5.78 mL, 39.1 mmol), $K_2CO_3$ (9.84 g, 71.2 mmol) and heating at 65° C. for 48 h. This gave after workup and purification by flash column chromatography [silica gel (120 g), eluting with EtOAc/MeOH (9:1) in Hexane from 0-100%] tert-butyl 2-(2-amino-4-chloro-7H-pyrrolo[2,3-d]pyrimidin-7-yl)acetate (87b) (1.51 g, 15% yield) as an off-white solid; $^1H$ NMR (300 MHz, DMSO-$d_6$) δ 7.14 (d, J=3.7 Hz, 1H), 6.71 (s, 2H), 6.31 (d, J=3.7 Hz, 1H), 4.78 (s, 2H), 1.41 (s, 9H).

Step-2: Preparation of tert-butyl 2-(2-amino-4-azido-7H-pyrrolo[2,3-d]pyrimidin-7-yl)acetate (87c)

To a solution of tert-butyl 2-(2-amino-4-chloro-7H-pyrrolo[2,3-d]pyrimidin-7-yl)acetate (87b) (1.5 g, 5.31 mmol) in DMF (20 mL) was added sodium azide (1.725 g, 26.5 mmol) and heated at 80° C. for 10 h. The reaction was cooled to 25° C., extracted with chloroform (3×50 mL) and the combined organics were dried, filtered and evaporated to dryness. The residue obtained was purified by flash column chromatography [silica gel (40 g), eluting with methanol in DCM from 0-100%] to afford tert-butyl 2-(2-amino-4-azido-7H-pyrrolo[2,3-d]pyrimidin-7-yl)acetate (87c) (0.556 g, 36% yield) as an off-white solid; $^1H$ NMR (300 MHz, DMSO-$d_6$) δ 8.18 (s, 2H), 7.20 (d, J=3.5 Hz, 1H), 6.76 (d, J=3.5 Hz, 1H), 4.93 (s, 2H), 1.42 (s, 9H); MS (ES+): 290.3 (M+1); MS (ES−): 288.3 (M−1).

Step-3: Preparation of tert-butyl 2-(2,4-diamino-7H-pyrrolo[2,3-d]pyrimidin-7-yl)acetate (87d)

To a solution of tert-butyl 2-(2-amino-4-azido-7H-pyrrolo[2,3-d]pyrimidin-7-yl)acetate (87c) (0.528 g, 1.825 mmol) in methanol (20 mL) was added palladium hydroxide on carbon (0.064 g, 0.091 mmol) and heated with stirring at 22° C. for 10 h. The reaction was cooled to 25° C., and extracted with chloroform (3×50 mL). The combined organics were dried, filtered, and evaporated to dryness. The residue obtained was purified by flash column chromatography [silica gel (24 g), eluting with methanol in DCM from 0-100%] to furnish tert-butyl 2-(2,4-diamino-7H-pyrrolo[2,3-d]pyrimidin-7-yl)acetate (87d) (0.362 g, 75% yield) as an off-white solid; MS (ES+): 264.3 (M+1); MS (ES−): 262.3 (M−1).

Step-4: Preparation of 2-(2,4-diamino-7H-pyrrolo[2,3-d]pyrimidin-7-yl)acetic acid (87e)

Compound 87e was prepared according to the procedure reported in step-2 of scheme-1, from tert-butyl 2-(2,4-diamino-7H-pyrrolo[2,3-d]pyrimidin-7-yl)acetate (87d) (0.351 g, 1.333 mmol) using TFA (1.027 mL, 13.33 mmol) in DCM (10 mL) and stirring at RT for 12 h. This gave after workup 2-(2,4-diamino-7H-pyrrolo[2,3-d]pyrimidin-7-yl) acetic acid (87e) (0.428 g, 100% yield) TFA salt as a yellow solid; MS (ES+): 208.2 (M+1).

Step-5 Preparation of (1R,3S,5R)—N-(6-bromopyridin-2-yl)-2-(2-(2,4-diamino-7H-pyrrolo[2,3-d]pyrimidin-7-yl)acetyl)-2-azabicyclo[3.1.0]hexane-3-carboxamide (87f)

Compound 87f was prepared according to the procedure reported in step-3 of scheme-1, from (1R,3S,5R)—N-(6-bromopyridin-2-yl)-2-azabicyclo[3.1.0]hexane-3-carboxamide trifluoro acetate (4a) (0.259 g, 0.654 mmol) in DMF (10 mL) using TFA salt of 2-(2,4-diamino-7H-pyrrolo[2,3-d]pyrimidin-7-yl)acetic acid (87e) (0.21 g, 0.654 mmol), HATU (0.373 g, 0.981 mmol), DIPEA (0.911 mL, 5.23 mmol) and stirring at RT for 16 h. This gave after workup and purification by flash column chromatography [silica gel 25 g] (1R,3S,5R)—N-(6-bromopyridin-2-yl)-2-(2-(2,4-diamino-7H-pyrrolo[2,3-d]pyrimidin-7-yl)acetyl)-2-azabicyclo[3.1.0]hexane-3-carboxamide (87f) (0.023 g, 8% yield) as a white solid; $^1H$ NMR (300 MHz, DMSO-$d_6$) δ 11.92 (s, 1H), 10.83 (s, 1H), 8.37 (s, 1H), 8.03 (d, J=8.2 Hz, 1H), 7.73 (t, J=8.0 Hz, 1H), 7.34 (d, J=7.7 Hz, 1H), 7.23 (s, 2H), 6.96

(d, J=3.7 Hz, 1H), 6.60 (d, J=3.7 Hz, 1H), 5.23 (d, J=17.0 Hz, 1H), 4.96 (d, J=17.0 Hz, 1H), 4.42 (dd, J=9.0, 5.5 Hz, 1H), 3.75-3.61 (m, 1H), 2.36-2.11 (m, 2H), 1.94-1.79 (m, 1H), 1.08-0.94 (m, 1H), 0.77-0.60 (m, 1H).

Scheme 88

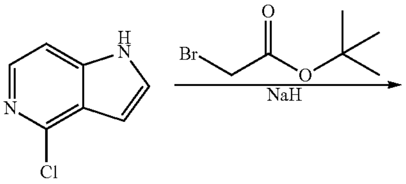

88a

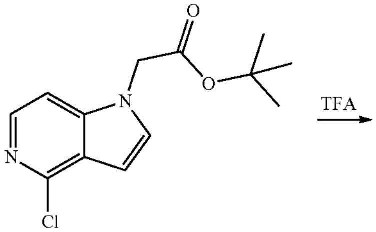

88b

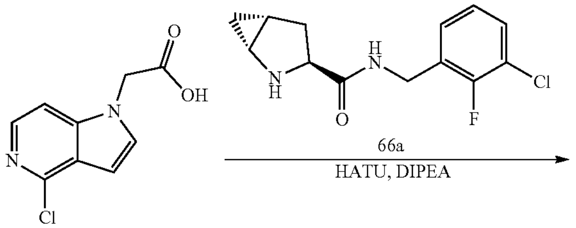

88c

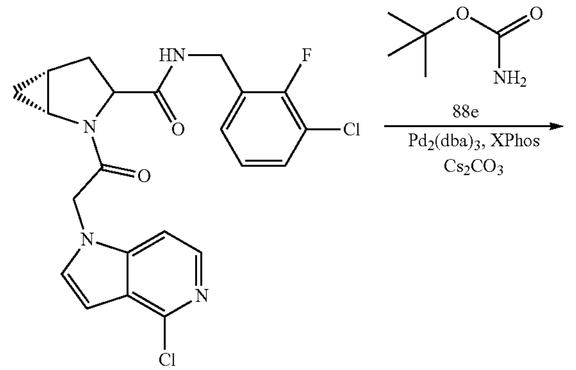

88d

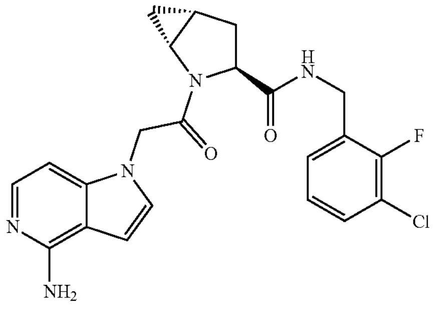

88f

Preparation of (1R,3S,5R)-2-(2-(4-amino-1H-pyrrolo[3,2-c]pyridin-1-yl)acetyl)-N-(3-chloro-2-fluorobenzyl)-2-azabicyclo[3.1.0]hexane-3-carboxamide (88f)

Step-1: Preparation of tert-butyl 2-(4-chloro-1H-pyrrolo[3,2-c]pyridin-1-yl)acetate (88b)

To a solution of 4-chloro-1H-pyrrolo[3,2-c]pyridine (88a) (0.3 g, 1.966 mmol; CAS #60290-21-3) in DMF (10 mL) was added sodium hydride (0.079 g, 1.966 mmol) in portions at 0° C. under an argon atmosphere. After stirring for 15 min was added tert-butyl bromoacetate (0.436 mL, 2.95 mmol) drop wise and stirred at RT for 2 h. Reaction mixture was poured into sat. $NH_4Cl$ solution and extracted with EtOAc (2×60 mL). The combined organics were washed with brine, dried, filtered and concentrated in vacuum. The residue obtained was purified by flash column chromatography [silica gel (40 g), eluting with EtOAc in hexane as eluents from 0 to 50%] to afford tert-butyl 2-(4-chloro-1H-pyrrolo[3,2-c]pyridin-1-yl)acetate (88b) (0.45 g, 86% yield) as a white solid; $^1H$ NMR (300 MHz, DMSO-$d_6$) δ 8.01 (d, J=5.8 Hz, 1H), 7.55 (d, J=3.3 Hz, 1H), 7.52 (dd, J=5.7, 0.9 Hz, 1H), 6.59 (dd, J=3.3, 0.9 Hz, 1H), 5.13 (s, 2H), 1.41 (s, 9H).

Step-2: Preparation of 2-(4-chloro-1H-pyrrolo[3,2-c]pyridin-1-yl)acetic acid (88c)

Compound 88c was prepared according to the procedure reported in step-2 of scheme-1, from tert-butyl 2-(4-chloro-1H-pyrrolo[3,2-c]pyridin-1-yl)acetate (88b) (0.45 g, 1.687 mmol) using TFA (1.30 mL, 16.87 mmol) in DCM (10 mL) and stirring at RT for 16 h. This gave after workup 2-(4-chloro-1H-pyrrolo[3,2-c]pyridin-1-yl)acetic acid (88c) (0.34 g, 66% yield) TFA salt as an off-white solid; $^1H$ NMR (300 MHz, DMSO-$d_6$) δ 8.01 (d, J=5.8 Hz, 1H), 7.60-7.52 (m, 2H), 6.59 (dd, J=3.2, 0.9 Hz, 1H), 5.13 (s, 2H).

Step-3: Preparation of (1R,3S,5R)-2-(2-(4-chloro-1H-pyrrolo[3,2-c]pyridin-1-yl)acetyl)-N-(3-chloro-2-fluorobenzyl)-2-azabicyclo[3.1.0]hexane-3-carboxamide (88d)

Compound 88d was prepared according to the procedure reported in step-3 of scheme-1, from TFA salt of 2-(4-chloro-1H-pyrrolo[3,2-c]pyridin-1-yl)acetic acid (88c) (0.13 g, 0.423 mmol) in DMF (3 mL) using HCl salt of (1R,3S,5R)—N-(3-chloro-2-fluorobenzyl)-2-azabicyclo[3.1.0]hexane-3-carboxamide (66a) (0.129 g, 0.423 mmol), HATU (0.193 g, 0.507 mmol), DIPEA (0.328 g, 2.54 mmol) and stirring at RT for 16 h. This gave after workup and purification by flash column chromatography [silica gel (4 g), eluting with MeOH:EtOAc (9:1) in hexanes from 0-80%] (1R,3S,5R)-2-(2-(4-chloro-1H-pyrrolo[3,2-c]pyridin-1-yl)acetyl)-N-(3-chloro-2-fluorobenzyl)-2-azabicyclo[3.1.0]hexane-3-carboxamide (88d) (0.16 g, 82% yield) as a white solid; $^1H$ NMR (300 MHz, DMSO-$d_6$) δ 8.48 (t, J=6.0 Hz, 1H), 7.95 (dd, J=5.7, 1.2 Hz, 1H), 7.53 (d, J=3.3 Hz, 1H), 7.51-7.41 (m, 2H), 7.18 (t, J=7.3 Hz, 1H), 7.05 (t, J=7.8 Hz, 1H), 6.58 (dd, J=3.2, 1.0 Hz, 1H), 5.47 (d, J=17.4 Hz, 11H), 5.27 (d, J=17.3 Hz, 1H), 4.46-4.35 (m, 1H), 4.33-4.20 (m, 2H), 3.71-3.63 (m, 1H), 2.32-2.08 (m, 2H), 1.94-1.79 (m, 1H), 1.07-0.97 (m, 1H), 0.82-0.71 (m, 1H); MS (ES+): 461.2 (M+1).

Step-4: Preparation of (1R,3S,5R)-2-(2-(4-amino-1H-pyrrolo[3,2-c]pyridin-1-yl)acetyl)-N-(3-chloro-2-fluorobenzyl)-2-azabicyclo[3.1.0]hexane-3-carboxaamide (88f)

Compound 88f was prepared according to the procedure reported in step-3 of scheme-17, from (1R,3S,5R)-2-(2-(4-chloro-1H-pyrrolo[3,2-c]pyridin-1-yl)acetyl)-N-(3-chloro-2-fluorobenzyl)-2-azabicyclo[3.1.0]hexane-3-carboxamide (88d) (0.15 g, 0.325 mmol) in dioxane (5 mL) using XPhos (0.016 g, 0.033 mmol), tert-butyl carbamate (88e) (0.076 g, 0650 mmol), $Pd_2(dba)_3$ (0.015 g, 0.016 mmol), cesium carbonate (0.106 g, 0.325 mmol) and heating at 90° C. for 20 h. This gave after work up and purification [silica gel (12 g), eluting with DMA-80 in DCM from 0-100%] (1R,3S,5R)-2-(2-(4-amino-1H-pyrrolo[3,2-c]pyridin-1-yl)acetyl)-N-(3-chloro-2-fluorobenzyl)-2-azabicyclo[3.1.0]hexane-3-carboxamide (88f) (0.01 g, 7% yield) as a white solid: $^1H$ NMR (300 MHz, DMSO-$d_6$) δ 8.52-8.41 (m, 1H), 7.57-7.40 (m, 2H), 7.27-7.15 (m, 1H), 7.14-7.02 (m, 2H), 6.70-6.57 (m, 2H), 6.19 (s, 2H), 5.25 (d, J=17.3 Hz, 1H), 5.08 (d, J=17.4 Hz, 1H), 4.48-4.18 (m, 3H), 3.70-3.61 (m, 1H), 2.32-2.06 (m, 2H), 1.92-1.77 (m, 1H), 1.06-0.94 (m, 1H), 0.76-0.64 (m, 1H); 19F NMR (282 MHz, DMSO-$d_6$) δ-121.81; MS (ES+) 442.3, 444.3 (M+1), MS (ES−) 476.3, 478.3 (M+Cl).

Scheme 89

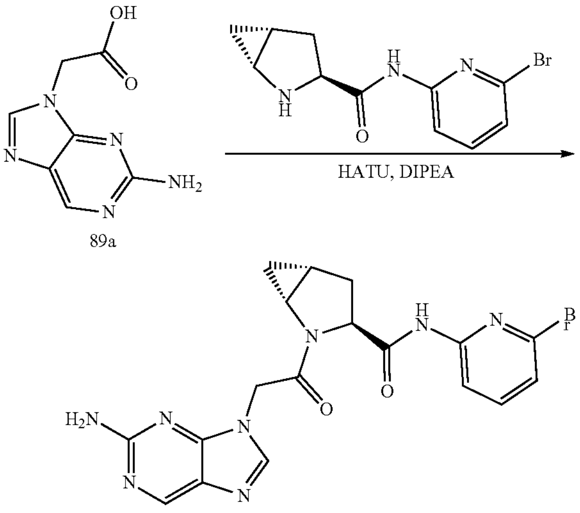

89a

89b

Preparation of (1R,3S,5R)-2-(2-(2-amino-9H-purin-9-yl)acetyl)-N-(6-bromopyridin-2-yl)-2-azabicyclo[3.1.0]hexane-3-carboxamide (89b)

Compound 89b was prepared according to the procedure reported in step-3 of scheme-1, from 2-(2-amino-9H-purin-9-yl)acetic acid (89a) (0.04 g, 0.207 mmol; CAS #933477-63-5) in DMF (1 mL) using HCl salt of (1R,3S,5R)—N-(6-bromopyridin-2-yl)-2-azabicyclo[3.1.0]hexane-3-carboxamide (4a) (0.066 g, 0.207 mmol), HATU (0.094 g, 0.248 mmol), DIPEA (0.145 mL, 0.828 mmol) and stirring at RT for 16 h. This gave after workup and purification by flash column chromatography [silica gel (4 g), eluting with DMA-80 in DCM from 0-100%] (1R,3S,5R)-2-(2-(2-amino-9H-purin-9-yl)acetyl)-N-(6-bromopyridin-2-yl)-2-azabicyclo[3.1.0]hexane-3-carboxamide (89b) (62 mg, 66% yield) as a white solid: $^1H$ NMR (300 MHz, DMSO-$d_6$) δ 10.85 (s, 1H), 8.58 (s, 1H), 8.07-7.97 (m, 2H), 7.72 (t, J=8.0 Hz, 1H), 7.35-7.31 (m, 1H), 6.61 (s, 2H), 5.32 (d, J=17.3 Hz, 1H), 5.06 (d, J=17.3 Hz, 1H), 4.44 (dd, J=9.0, 5.4 Hz, 1H), 3.76-3.68 (m, 1H), 2.37-2.11 (m, 2H), 1.95-1.81 (m, 1H), 1.10-0.96 (m, 1H), 0.74-0.63 (m, 11H); MS (ES+): 457.2, 459.2 (M+1), 479.2, 481.2 (M+Na), MS (ES−): 455.3 (M−1); Analysis calculated for $C_{18}H_{17}BrN_8O_2 \cdot H_2O$; C, 45.49; H, 4.03; N, 23.58. Found C, 44.88; H, 4.12; N, 22.82.

Scheme 90

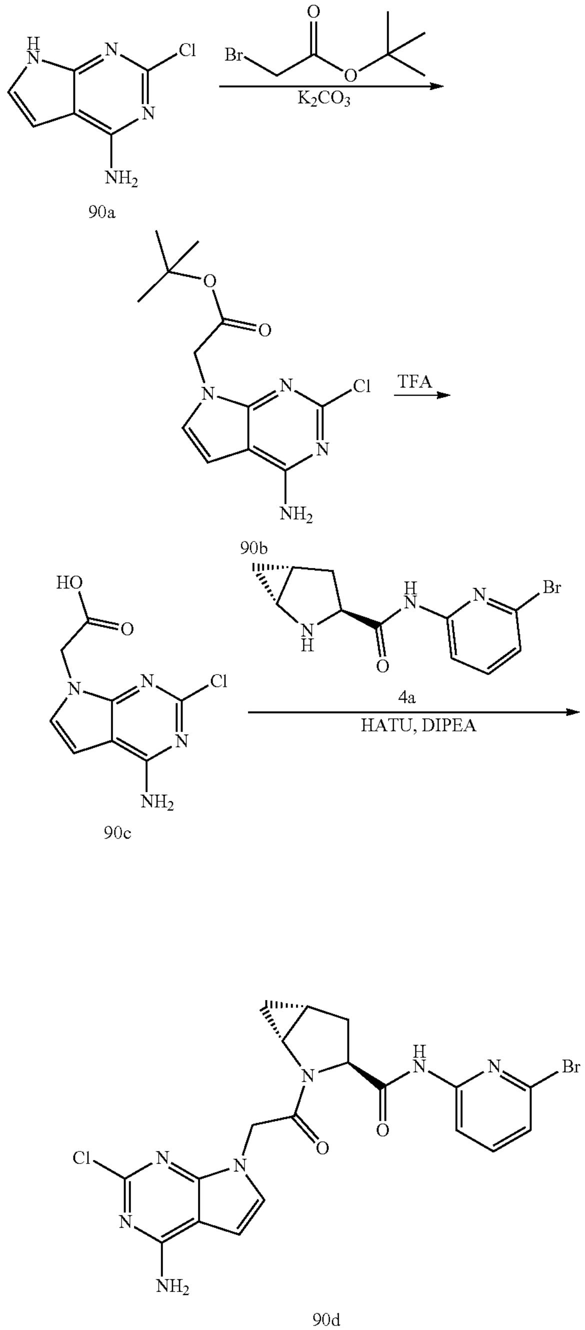

90a

90b

90c

90d

Preparation of (1R,3S,5R)-2-(2-(4-amino-2-chloro-7H-pyrrolo[2,3-d]pyrimidin-7-yl)acetyl)-N-(6-bromopyridin-2-yl)-2-azabicyclo[3.1.0]hexane-3-carboxamide (90d)

Step-1: Preparation of tert-butyl 2-(4-amino-2-chloro-7H-pyrrolo[2,3-d]pyrimidin-7-yl)acetate (90b)

Compound 90b was prepared according to the procedure reported in step-1 of scheme-1, from 2-chloro-7H-pyrrolo[2,3-d]pyrimidin-4-amine (90a) (1 g, 5.93 mmol; CAS #1192711-88-8) in acetonitrile (50 mL) using tert-butyl 2-bromoacetate (0.963 mL, 6.52 mmol) and $K_2CO_3$ (1.640 g, 11.86 mmol) and heating at 65° C. for 14 h. This gave after workup and purification by flash column chromatography [silica gel (40 g), eluting with EtOAc in Hexane from 0-100%] tert-butyl 2-(4-amino-2-chloro-7H-pyrrolo[2,3-d]pyrimidin-7-yl)acetate (90b) (1.102 g, 66% yield) as a white solid: 1H NMR (300 MHz, DMSO-$d_6$) δ 7.52 (s, 2H), 7.12 (d, J=3.5 Hz, 1H), 6.55 (d, J=3.5 Hz, 1H), 4.83 (s, 2H), 1.41 (s, 9H); MS (ES+): 283.2 (M+1); (ES−): 281.3 (M−1).

Step-2: Preparation of 2-(4-amino-2-chloro-7H-pyrrolo[2,3-d]pyrimidin-7-yl)acetic acid (90c)

Compound 90c was prepared according to the procedure reported in step-2 of scheme-1, from tert-butyl 2-(4-amino-2-chloro-7H-pyrrolo[2,3-d]pyrimidin-7-yl)acetate (90b) (0.251 g, 0.888 mmol) using TFA (0.684 mL, 8.88 mmol) in DCM (10 mL) and stirring at RT for 12 h. This gave after workup 2-(4-amino-2-chloro-7H-pyrrolo[2,3-d]pyrimidin-7-yl)acetic acid (90c) (0.302 g, 100% yield) TFA salt as a yellow solid; MS (ES+): 227.1 (M+1).

Step-3: Preparation of (1R,3S,5R)-2-(2-(4-amino-2-chloro-7H-pyrrolo[2,3-d]pyrimidin-7-yl)acetyl)-N-(6-bromopyridin-2-yl)-2-azabicyclo[3.1.0]hexane-3-carboxamide (90d)

Compound 90d was prepared according to the procedure reported in step-3 of scheme-1, from TFA salt of 2-(4-amino-2-chloro-7H-pyrrolo[2,3-d]pyrimidin-7-yl)acetic acid (90c) (0.175 g, 0.514 mmol) in DMF (10 mL) using TFA salt of (1R,3S,5R)—N-(6-bromopyridin-2-yl)-2-azabicyclo[3.1.0]hexane-3-carboxamide (4a) (0.204 g, 0.514 mmol), HATU (293 mg, 0.771 mmol), DIPEA (0.716 mL, 4.11 mmol) and stirring at RT for 16 h. This gave after workup and purification by flash column chromatography [silica gel (25 g), eluting with EtOAc in MeOH (9:1) from 0-100%] (1R,3S,5R)-2-(2-(4-amino-2-chloro-7H-pyrrolo[2,3-d]pyrimidin-7-yl)acetyl)-N-(6-bromopyridin-2-yl)-2-azabicyclo[3.1.0]hexane-3-carboxamide (90d) (132 mg, 52% yield) as a white solid: $^1H$ NMR (300 MHz, DMSO-$d_6$) δ 10.81 (s, 1H, $D_2O$ exchangeable), 8.04 (d, J=8.2 Hz, 1H), 7.72 (t, J=8.0 Hz, 1H), 7.48 (s, 2H, $D_2O$ exchangeable), 7.33 (dd, J=7.8, 0.7 Hz, 1H), 7.08 (d, J=3.5 Hz, 1H), 6.53 (d, J=3.5 Hz, 1H), 5.31 (d, J=17.1 Hz, 1H), 5.03 (d, J=17.1 Hz, 1H), 4.43 (dd, J=9.0, 5.5 Hz, 1H), 3.82-3.68 (m, 1H), 2.36-2.11 (m, 2H), 1.93-1.75 (m, 1H), 1.07-0.94 (m, 11H), 0.74-0.62 (m, 1H); Analysis calculated for $C_{19}H_{17}BrClN_7O_2{\cdot}H_2O$: C, 44.86; H, 3.76; N, 19.27. Found: C, 44.79; H, 3.67; N, 19.12.

Scheme 91

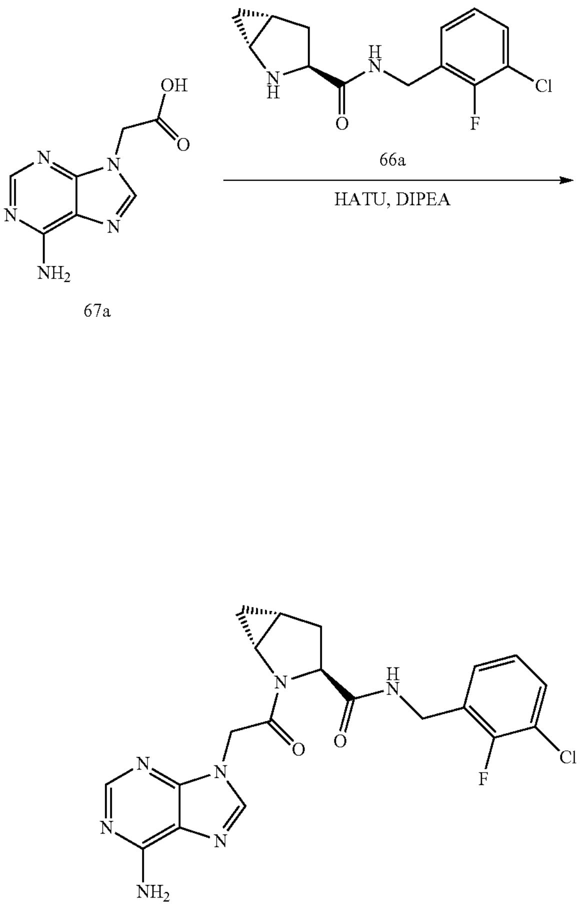

67a

66a

91a

Preparation of (1R,3S,5R)-2-(2-(6-amino-9H-purin-9-yl)acetyl)-N-(3-chloro-2-fluorobenzyl)-2-azabicyclo[3.1.0]hexane-3-carboxamide (91a)

Compound 91a was prepared according to the procedure reported in step-3 of scheme-1, from TFA salt of 2-(6-amino-9H-purin-9-yl)acetic acid (67a) (0.188 g, 0.612 mmol) in DMF (15 mL) using HCl salt of (1R,3S,5R)—N-(3-chloro-2-fluorobenzyl)-2-azabicyclo[3.1.0]hexane-3-carboxamide (66a) (0.224 g, 0.734 mmol), HATU (349 mg, 0.918 mmol), DIPEA (0.533 mL, 3.06 mmol) and stirring at RT for 16 h. This gave after workup and purification by flash column chromatography [silica gel (12 g), eluting with MeOH in DCM from 0-15%](1R,3S,5R)-2-(2-(6-amino-9H-purin-9-yl)acetyl)-N-(3-chloro-2-fluorobenzyl)-2-azabicyclo[3.1.0]hexane-3-carboxamide (91a) (101 mg, 37% yield) as a white solid; $^1H$ NMR (300 MHz, DMSO-$d_6$) δ 8.47 (t, J=6.0 Hz, 1H), 8.11 (s, 1H), 8.04 (s, 1H), 7.51-7.40 (m, 1H), 7.27-7.16 (m, 3H), 7.10 (t, J=7.9 Hz, 1H), 5.44-5.10 (m, 2H), 4.48-4.19 (m, 3H), 3.77-3.59 (m, 1H), 2.34-2.05 (m, 2H), 1.94-1.76 (m, 1H), 1.13-0.96 (m, 1H), 0.77-0.65 (m, 1H); $^{19}F$ NMR (282 MHz, DMSO-$d_6$) δ−121.75; MS ($ES^+$); 444.10 (M+1); MS (ES−): 442.10 (M−1).

Scheme 92

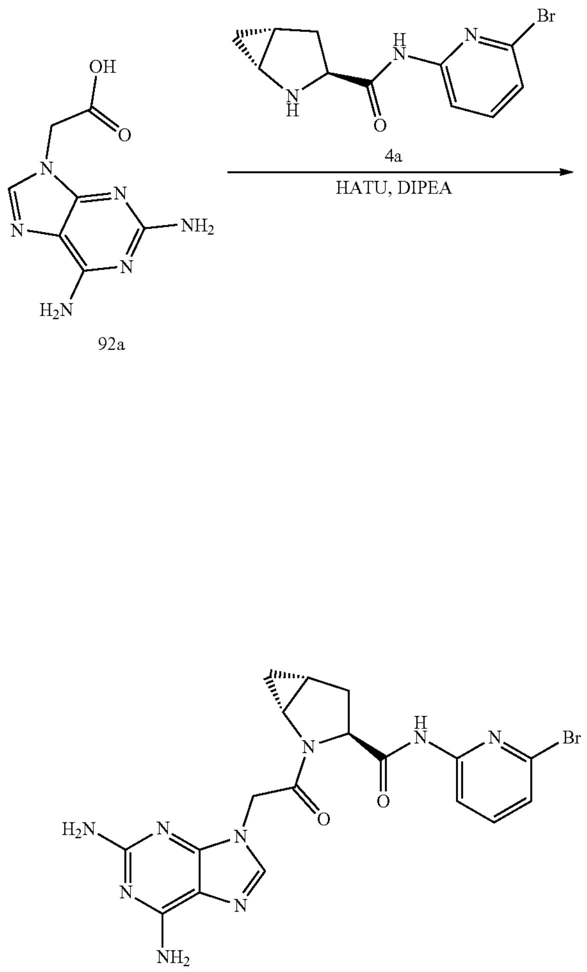

92a

4a

Preparation of (1R,3S,5R)—N-(6-bromopyridin-2-yl)-2-(2-(2,6-diamino-9H-purin-9-yl)acetyl)-2-azabicyclo[3.1.0]hexane-3-carboxamide (92b)

Compound 92b was prepared according to the procedure reported in step-3 of scheme-1, from 2-(2,6-diamino-9H-purin-9-yl)acetic acid (92a) (0.1 g, 0.328 mmol) in DMF (1 mL) and using HCl salt of (1R,3S,5R)—N-(6-bromopyridin-2-yl)-2-azabicyclo[3.1.0]hexane-3-carboxamide (4a) (0.104 g, 0.328 mmol), HATU (0.150 g, 0.393 mmol), DIPEA (0.343 mL, 1.966 mmol) and stirring at RT for 16 h. This gave after workup and purification by flash column chromatography [silica gel (4 g), eluting with DMA-80 in DCM from 0-100%] (1R,3S,5R)—N-(6-bromopyridin-2-yl)-2-(2-(2,6-diamino-9H-purin-9-yl)acetyl)-2-azabicyclo[3.1.0]hexane-3-carboxamide (92b) (0.06 g, 39% yield) as a white solid: $^1$H NMR (300 MHz, DMSO-$d_6$) δ 10.84 (s, 1H), 8.04 (d, J=8.2 Hz, 1H), 7.72 (t, J=8.0 Hz, 1H), 7.63 (s, 1H), 7.33 (d, J=7.7 Hz, 1H), 6.69 (brs, 2H), 5.81 (brs, 2H), 5.19 (d, J=17.3 Hz, 1H), 4.94 (d, J=17.3 Hz, 1H), 4.44 (dd, J=9.1, 5.6 Hz, 1H), 3.75-3.64 (m, 1H), 2.34-2.10 (m, 2H), 1.94-1.79 (m, 1H), 1.07-0.96 (m, 1H), 0.72-0.60 (m, 1H); MS (ES+): 494.2, 496.2 (M+Na); MS (ES−): 470.3, 472.3 (M−1).

Scheme 93

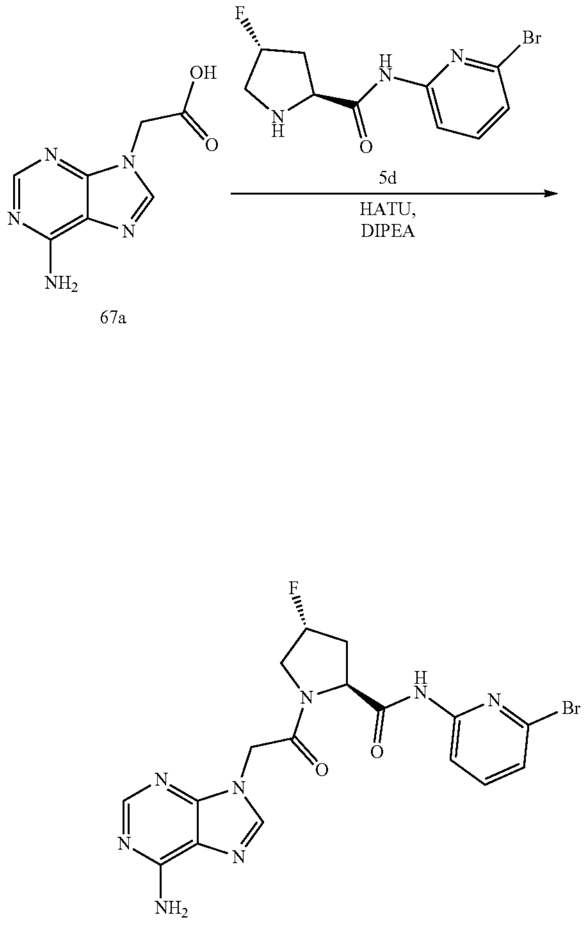

67a

5d

93a

Preparation of (2S,4R)-1-(2-(6-amino-9H-purin-9-yl)acetyl)-N-(6-bromopyridin-2-yl)-4-fluoropyrrolidine-2-carboxamide (93a)

Compound 93a was prepared according to the procedure reported in step-3 of scheme-1, from TFA salt of 2-(6-amino-9H-purin-9-yl)acetic acid (67a) (0.466 mmol, 190 mg) in DMF (15 mL) and using TFA salt of (2S,4R)—N-(6-bromopyridin-2-yl)-4-fluoropyrrolidine-2-carboxamide (5d) (0.559 mmol, 250 mg), HATU (266 mg, 0.698 mmol), DIPEA (0.405 mL, 2.328 mmol) and stirring at RT for 16 h. This gave after workup and purification by flash column chromatography [silica gel (24 g), eluting with DMA-80 in DCM from 0-25%](2S,4R)-1-(2-(6-amino-9H-purin-9-yl)acetyl)-N-(6-bromopyridin-2-yl)-4-fluoropyrrolidine-2-carboxamide (93a) (129 mg, 60% yield) as a white solid; $^1$H NMR (300 MHz, DMSO-$d_6$) δ 11.04 (s, 1H), 8.11 (s, 1H), 8.07-7.99 (m, 2H), 7.71 (t, J=8.0 Hz, 1H), 7.36-7.29 (m, 1H), 7.21 (s, 2H), 5.65-5.36 (m, 1H), 5.32-5.00 (m, 2H), 4.66 (t, J=8.5 Hz, 1H), 4.29-3.74 (m, 2H), 2.67-1.95 (m, 2H); $^{19}$F NMR (282 MHz, DMSO-$d_6$) δ−175.72; MS (ES+): 463.00 & 465.00 (M+1); MS (ES−): 461.00 & 463.00 (M−1); Analysis calculated for $C_{17}H_{16}BrFN_8O_2 \cdot 2.0H_2O$: C, 40.89; H, 4.04; N, 22.44. Found: C, 41.06; H, 4.05; N, 22.30.

Scheme 94

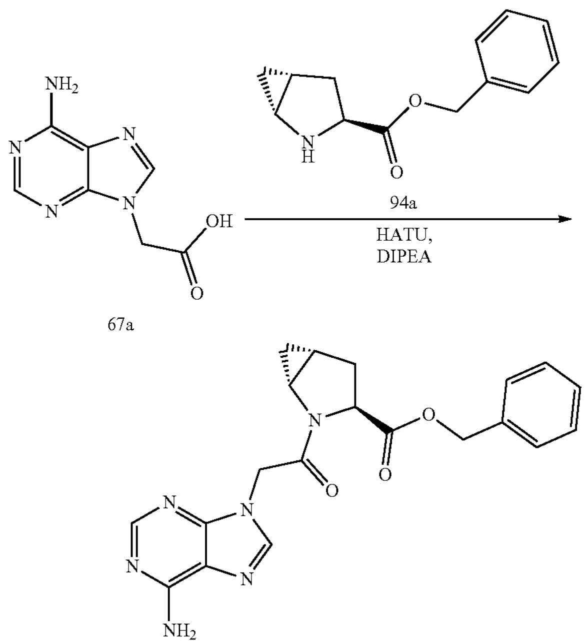

67a

94a

94b

Preparation of (1R,3S,5R)-benzyl 2-(2-(6-amino-9H-purin-9-yl)acetyl)-2-azabicyclo[3.1.0]hexane-3-carboxylate (94b)

Compound 94b was prepared according to the procedure reported in step-3 of scheme-1, from 2-(6-amino-9H-purin-9-yl)acetic acid (67a) (2.127 g, 11.01 mmol) in DMF (30 mL) and using TFA salt of (1R,3S,5R)-benzyl 2-azabicyclo [3.1.0]hexane-3-carboxylate (94a) (4.56 g, 13.76 mmol; CAS #1386459-65-9), HATU (6.28 g 16.52 mmol). DIPEA (7.67 mL, 44.0 mmol) and stirring at RT for 16 h. This gave after workup and purification by flash column chromatography [silica gel (40 g), DMA-80 in DCM from 0-50%] (1R,3S,5R)-benzyl 2-(2-(6-amino-9H-purin-9-yl)acetyl)-2-azabicyclo[3.1.0]hexane-3-carboxylate (94b) (2.83 g, 65.5% yield) as a yellow solid; $^1$H NMR (300 MHz, DMSO-$d_6$) δ 8.13 (s, 1H), 8.06 (s, 1H), 7.41-7.24 (m, 7H), 5.43 (d, J=17.2 Hz, 1H), 5.20-5.03 (m, 3H), 4.33 (dd, J=9.3, 5.6 Hz, 1H), 3.77 (ddd, J=7.1, 5.5, 2.4 Hz, 1H), 2.42-2.28 (m, 1H), 2.23-2.09 (m, 1H), 1.94-1.83 (m, 1H), 1.07-0.94 (m, 1H), 0.81-0.71 (m, 1H); MS (ES+): 393.1 (M+1); Analysis calculated for $C_{20}H_{20}N_6O_3 \cdot 2H_2O \cdot 1.75HCl$: C, 48.80; H, 5.27; N, 17.07. Found: C, 48.78; H, 5.17; N, 17.01.

Scheme 95

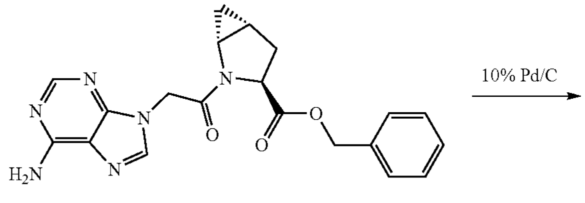

94b

-continued

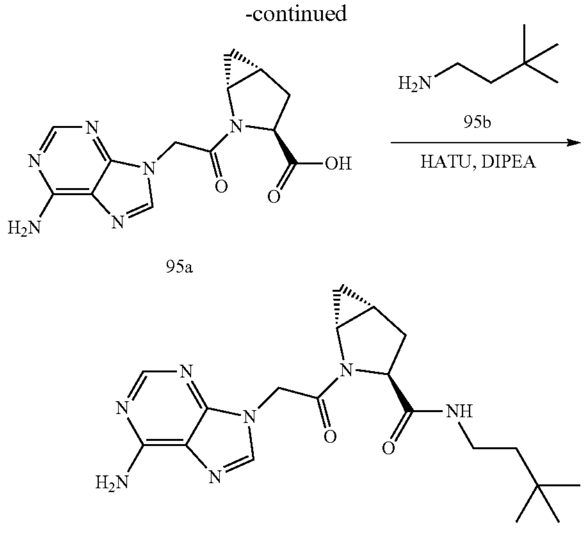

95b

95a

95c

Preparation of (1R,3S,5R)-2-(2-(6-amino-9H-purin-9-yl)acetyl)-N-(3,3-dimethylbutyl)-2-azabicyclo [3.1.0]hexane-3-carboxamide (95c)

Step-1: Preparation of (1R,3S,5R)-2-(2-(6-amino-9H-purin-9-yl)acetyl)-2-azabicyclo[3.1.0]hexane-3-carboxylic acid (95a)

To a solution of (1R,3S,5R)-benzyl 2-(2-(6-amino-9H-purin-9-yl)acetyl)-2-azabicyclo[3.1.0]hexane-3-carboxylate (94b) (300 mg, 0.765 mmol) in MeOH (20 mL) was added 10% Pd/C (100 mg, 0.093 mmol). The reaction mixture was shaken for 5 hours under a hydrogen atmosphere (50-55 psi), filtered through a pad of Celite and the pad was washed with methanol. The filtrate was concentrated in vacuum and residue obtained was purified by reverse-phase column chromatography [C-18 column (50 g), eluting with ACN in water (containing 0.1% HCl) from 0-100%] to afford (1R,3S,5R)-2-(2-(6-amino-9H-purin-9-yl)acetyl)-2-azabicyclo [3.1.0]hexane-3-carboxylic acid (95a) (145 mg, 63% yield) HCl salt as a white solid; $^1$H NMR (300 MHz, DMSO-$d_6$) δ 9.62 (s, 1H), 8.88 (s, 1H), 8.52 (s, 1H), 8.46 (s, 1H), 5.57 (d, J=17.2 Hz, 1H), 5.28 (d, J=17.1 Hz, 1H), 4.20 (dd, J=9.2, 5.2 Hz, 1H), 3.72 (td, J=6.2, 5.2, 2.3 Hz, 1H), 2.38-2.25 (m, 1H), 2.19 (dq, J=13.0, 6.4, 5.8 Hz, 1H), 1.28 (dd, J=9.8, 6.5 Hz, 1H), 1.09-0.91 (m, 1H), 0.73 (td, J=5.1, 2.5 Hz, 1H). MS (ES+): 303.1 (M+1), (ES−): 301.1 (M−1).

Step-2: Preparation of (1R,3S,5R)-2-(2-(6-amino-9H-purin-9-yl)acetyl)-N-(3,3-dimethylbutyl)-2-azabicyclo[3.1.0]hexane-3-carboxamide (95c)

Compound 95c was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) 135 mg, 0.447 mmol) in DMF (1.5 mL) using HCl salt of 3,3-dimethylbutan-1-amine (95b) (4.56 g, 13.76 mmol; CAS #30654-98-8), HATU (255 mg, 0.670 mmol), DIPEA (0.311 mL, 1.786 mmol) and stirring at RT for 16 h. This gave after workup and purification by reverse phase column chromatography [C18 column (100 g), eluting with ACN in water (containing 0.1% HCl) from 0-100%] followed by purification using flash column chromatography [silica gel (12 g), eluting with DMA-80 in DCM from 0-50%] (1R,3S,5R)-2-(2-(6-amino-9H-purin-9-yl) acetyl)-N-(3,3-dimethylbutyl)-2-azabicyclo[3.1.0]hexane-3-carboxamide (95c) (25 mg, 15% yield) as a white solid; $^1$H NMR (300 MHz, DMSO-$d_6$) δ 8.12 (s, 1H), 8.05 (s, 1H), 7.75 (t. J=5.7 Hz, 1H), 7.22 (s, 2H), 5.35 (d, J=17.1 Hz, 1H), 5.13 (d. J=17.0 Hz, 1H), 4.18 (dd, J=8.3, 5.0 Hz, 1H), 3.65-3.59 (m, 1H), 3.10-2.96 (m, 2H), 2.24-2.08 (m, 2H), 1.81 (s, 1H), 1.33-1.22 (m, 2H), 1.10-0.97 (m, 11H), 0.87 (s, 9H), 0.73-0.63 (m, 1H); MS (ES+): 386.2 (M+1); Analysis calculated for $C_{19}H_{27}N_7O_2 \cdot 1.25H_2O$: C, 55.93; H, 7.29; N, 24.03. Found: C, 56.04; H, 7.35; N, 23.94.

Scheme 96

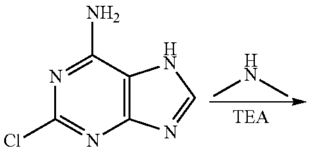

96a

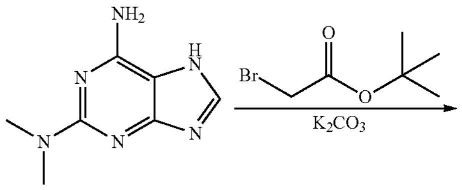

96b

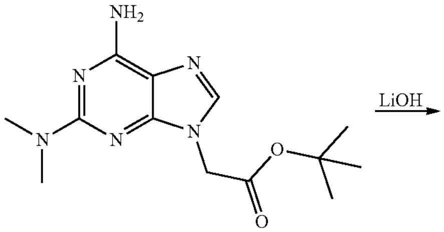

96c

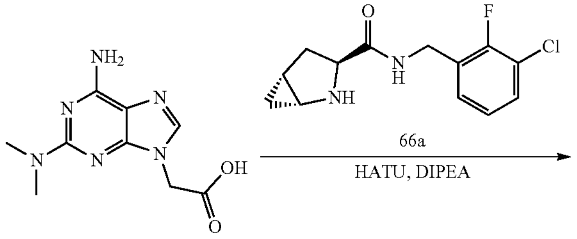

96d

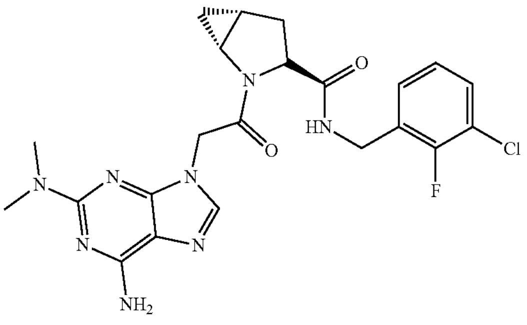

96e

Preparation of (1R,3S,5R)-2-(2-(6-amino-2-(dimethylamino)-9H-purin-9-yl)acetyl)-N-(3-chloro-2-fluorobenzyl)-2-azabicyclo[3.1.0]hexane-3-carboxamide (96e)

Step-1: Preparation of N2,N2-dimethyl-7H-purine-2,6-diamine (% b)

To a stirred suspension of 2-chloro-7H-purin-6-amine (% a) (1 g, 5.90 mmol; CAS #1839-18-5) in isopropanol (10 mL) was added triethylamine (1.644 mL, 11.79 mmol) and dimethylamine (0.717 mL, 7.08 mmol) and heated in a microwave at 150° C. for 1.5 h. The solid separated was collected by filtration to afford N2,N2-dimethyl-7H-purine-2,6-diamine (96b) (750 mg, 71.4% yield) as a white solid; $^1$H NMR (300 MHz, DMSO-$d_6$) δ 12.19 (s, 1H), 7.67 (s, 1H), 6.65 (s, 2H), 3.05 (s, 6H); MS (ES+): 179.10 (M+1).

Step-2: Preparation of tert-butyl 2-(6-amino-2-(dimethylamino)-9H-purin-9-yl)acetate (96c)

Compound 96c was prepared according to the procedure reported in step-1 of scheme-1, from N2,N2-dimethyl-7H-purine-2,6-diamine (96b) (500 mg, 2.81 mmol) in N,N-dimethylformamide (5 mL) using tert-butyl 2-bromoacetate (0.498 mL, 3.37 mmol), $K_2CO_3$ (582 mg, 4.21 mmol) and stirring at RT for 10 h. This gave after workup and purification by flash column chromatography [silica gel (25 g), eluting with EtOAc/MeOH (9:1) in Hexane from 0-100%] tert-butyl 2-(6-amino-2-(dimethylamino)-9H-purin-9-yl)acetate (96c) (620 mg, 76% yield) as a bright yellow solid; $^1$H NMR (300 MHz, DMSO-$d_6$) δ 7.68 (s, 1H), 6.74 (s, 2H), 4.75 (s, 2H), 3.04 (s, 6H), 1.42 (s, 9H); MS (ES+): 293.20 (M+1).

Step-3: Preparation of 2-(6-amino-2-(dimethylamino)-9H-purin-9-yl)acetic acid (96d)

Compound 96d was prepared according to the procedure reported in step-4 of scheme-17, from tert-butyl 2-(6-amino-2-(dimethylamino)-9H-purin-9-yl)acetate (% c) (600 mg, 2.052 mmol) in THF (5 mL), methanol (5.0 mL), water (5 mL) using lithium hydroxide (147 mg, 6.16 mmol) and stirring overnight at RT. This gave after workup 2-(6-amino-2-(dimethylamino)-9H-purin-9-yl)acetic acid (96d) (352 mg, 73% yield) as a yellow solid; $^1$H NMR (300 MHz, DMSO-$d_6$) δ 7.70 (s, 1H), 6.75 (s, 2H), 4.77 (s, 2H), 3.05 (s, 6H).

Step-4: Preparation of (1R,3S,5R)-2-(2-(6-amino-2-(dimethylamino)-9H-purin-9-yl)acetyl)-N-(3-chloro-2-fluorobenzyl)-2-azabicyclo[3.1.0]hexane-3-carboxamide (96e)

Compound 96e was prepared according to the procedure reported in step-3 of scheme-1, from 2-(6-amino-2-(dimethylamino)-9H-purin-9-yl)acetic acid (96d) (150 mg, 0.635 mmol) in DMF (3 mL) using HCl salt of (1R,3S,5R)—N-(3-chloro-2-fluorobenzyl)-2-azabicyclo[3.1.0]hexane-3-carboxamide (66a) (242 mg, 0.794 mmol), HATU (362 mg, 0.952 mmol), DIPEA (0.442 mL, 2.54 mmol) and stirring at RT for 16 h. This gave after workup and purification by flash column chromatography [silica gel (12 g), eluting with EtOAc/MeOH (9:1) in dioxane from 0-100%] followed by purification using reverse phase column chromatography [C18 column (50 g), eluting with ACN in water (containing 0.1% HCl) from 0-100%] to afford (1R,3S,5R)-2-(2-(6- amino-2-(dimethylamino)-9H-purin-9-yl)acetyl)-N-(3-chloro-2-fluorobenzyl)-2-azabicyclo[3.1.0]hexane-3-carboxamide (96e) (240 mg, 78% yield) HCl salt as a white solid; $^1$H NMR (300 MHz, DMSO-$d_6$+$D_2O$) δ 8.57 (t, J=6.0 Hz, 1H), 8.16 (d, J=6.1 Hz, 1H), 7.45 (t, J=7.6 Hz, 1H), 7.21 (t, J=7.3 Hz, 1H), 7.10 (t, J=7.9 Hz, 1H), 5.29 (dd, J=17.1, 3.1 Hz, 1H), 5.15 (d, J=17.0 Hz, 1H), 4.33 (t, J=6.9 Hz, 2H), 4.28-4.19 (m, 1H), 3.13 (s, 6H), 2.28 (dd, J=13.5, 9.2 Hz, 1H), 2.14 (dt, J=12.9, 6.0 Hz, 1H), 1.88 (p, J=7.1 Hz, 2H), 1.07 (dt, J=9.5, 5.4 Hz, 1H), 0.68 (d, J=6.0 Hz, 11H); $^{19}$F NMR (282 MHz, DMSO-$d_6$) δ-121.73; MS (ES+): 487.2 (M+1); (ES−): 485.10 (M−1).

Scheme 97

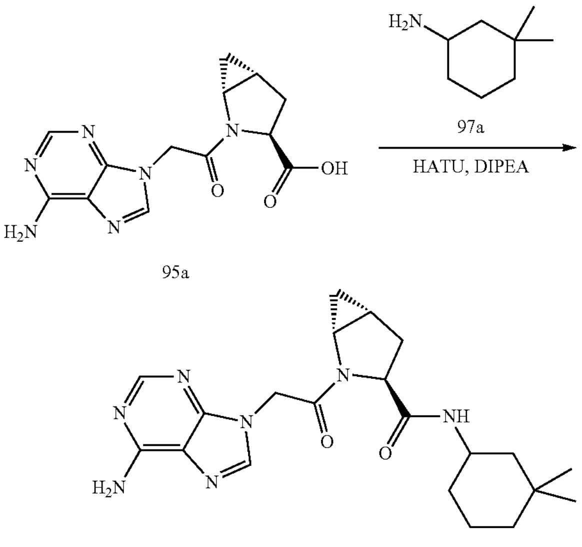

Preparation of (1R,3S,5R)-2-(2-(6-amino-9H-purin-9-yl)acetyl)-N-(3,3-dimethylcyclohexyl)-2-azabicyclo[3.1.0]hexane-3-carboxamide (97b)

Compound 97b was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) 150 mg, 0.496 mmol) in DMF (1.5 mL) using 3,3-dimethylcyclohexanamine (97a) (63.1 mg, 0.496 mmol; CAS #226549-07-1), HATU (283 mg, 0.744 mmol) DIPEA (0.346 mL, 1.985 mmol) and stirring at RT for 2 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(6-amino-9H-purin-9-yl)acetyl)-N-(3,3-dimethylcyclohexyl)-2-azabicyclo[3.1.0]hexane-3-carboxamide (97b) (20 mg, 10% yield) HCl salt as a white solid; $^1$H NMR (300 MHz, DMSO-$d_6$) δ 8.49 (s, 1H), 8.43 (s, 1H), 7.58 (d, J=8.0 Hz, 1H), 5.54 (d, J=17.1 Hz, 1H), 5.24 (d, J=17.1 Hz, 1H), 4.14 (dd, J=8.9, 4.9 Hz, 1H), 3.70-3.65 (m, 2H), 2.28-2.00 (m, 2H), 1.95-1.77 (m, 1H), 1.77-1.60 (m, 1H), 1.60-1.16 (m, 4H), 1.11-0.91 (m, 4H), 0.87 (s, 6H), 0.74-0.56 (m, 1H); MS (ES+): 412.2 (M+1).

Scheme 98

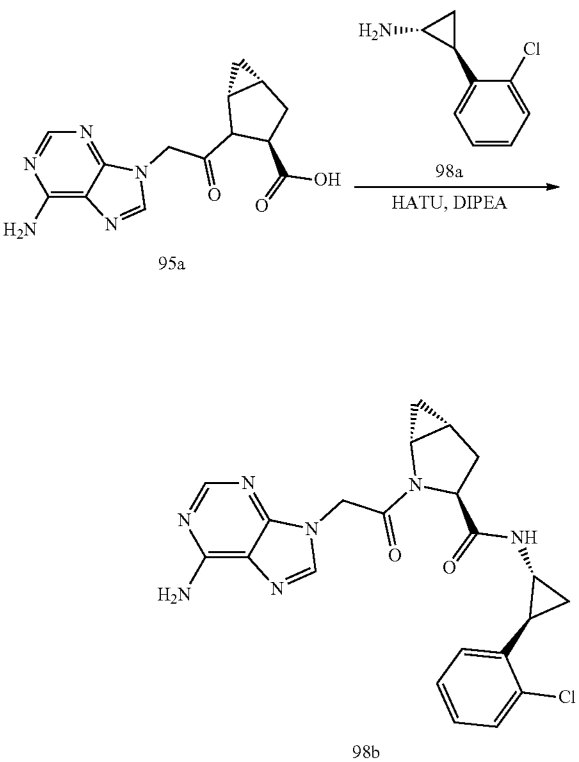

Preparation of (1R,3S,5R)-2-(2-(6-amino-9H-purin-9-yl)acetyl)-N-((1R,2S)-2-(2-chlorophenyl)cyclopropyl)-2-azabicyclo[3.1.0]hexane-3-carboxamide (98b)

Compound 98b was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) (150 mg, 0.496 mmol) in DMF (1.5 mL) using (1R,2S)-2-(2-chlorophenyl)cyclopropanamine (98a) (83 mg, 0.496 mmol; CAS #1820575-68-5), HATU (283 mg, 0.744 mmol), DIPEA (0.346 mL, 1.985 mmol) and stirring at RT for 2 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(6-amino-9H-purin-9-yl)acetyl)-N-((1R,2S)-2-(2-chlorophenyl)cyclopropyl)-2-azabicyclo[3.1.0]hexane-3-carboxamide (98b) (39 mg, 17% yield) HCl salt as a white solid; $^1$H NMR (300 MHz, DMSO-$d_6$) δ 8.50-8.33 (m, 2H), 8.23 (d, J=4.8 Hz, 1H), 7.40 (dt, J=7.4, 1.8 Hz, 1H), 7.31-7.14 (m, 2H), 7.08 (dd, J=7.4, 2.1 Hz, 1H), 5.54 (d, J=17.1 Hz, 1H), 5.25 (d, J=17.0 Hz, 1H), 4.22-4.11 (m, 1H), 3.75-3.64 (m, 1H), 3.01-2.88 (m, 1H), 2.29-2.07 (m, 3H), 1.89-1.83 (m, 1H), 1.30-1.17 (m, 1H), 1.17-1.04 (m, 1H), 1.08-0.97 (m, 1H), 0.72-0.65 (m, 1H); MS (ES+) 452.1 (M+1); Analysis calculated for $C_{22}H_{22}ClN_7O_2 \cdot HCl \cdot 3H_2O$: C, 48.71; H, 5.39; Cl, 13.07; N, 18.08. Found: C, 48.61; H, 5.22; Cl, 13.33; N, 18.00.

Scheme 99

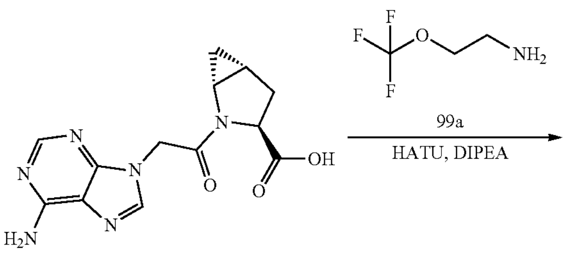

95a

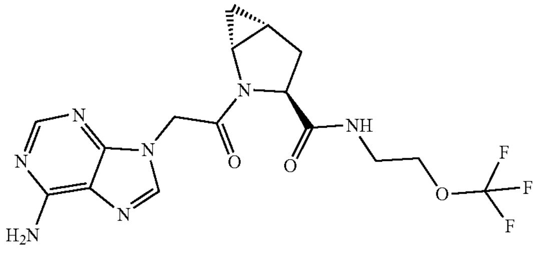

99b

Preparation of (1R,3S,5R)-2-(2-(6-amino-9H-purin-9-yl)acetyl)-N-(2-(trifluoromethoxy)ethyl)-2-azabicyclo[3.1.0]hexane-3-carboxamide (99b)

Compound 99b was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) (150 mg, 0.496 mmol) in DMF (1.5 mL) using 2-(trifluoromethoxy)ethanamine (99a) (64.1 mg, 0.496 mmol; CAS #886050-51-7), HATU (283 mg, 0.744 mmol), DIPEA (0.346 mL, 1.985 mmol) and stirring at RT for 2 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(6-amino-9H-purin-9-yl)acetyl)-N-(2-(trifluoromethoxy)ethyl)-2-azabicyclo[3.1.0]hexane-3-carboxamide (99b) (17 mg, 8% yield) as a white solid; $^{1}$H NMR (300 MHz, DMSO-do) δ 9.55 (s, 11H), 8.86 (s, 1H), 8.51 (s, 1H), 8.45 (s, 1H), 8.26 (t, J=5.7 Hz, 1H), 5.57 (d, J=17.1 Hz, 1H), 5.25 (d, J=17.0 Hz, 1H), 4.22 (dd, J=9.0, 4.6 Hz, 1H), 4.04 (t, J=5.4 Hz, 2H), 3.69-3.64 (m, 1H), 3.39-3.16 (m, 2H), 2.30-2.01 (m, 2H), 1.89-1.74 (m, 1H), 1.11-0.94 (m, 1H), 0.78-0.61 (m, 1H), $^{19}$F NMR (282 MHz, DMSO-$d_6$) δ−58.83; MS (ES+): 414.1 (M+1).

Scheme 100

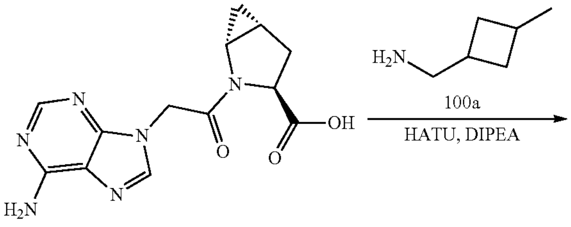

95a

-continued

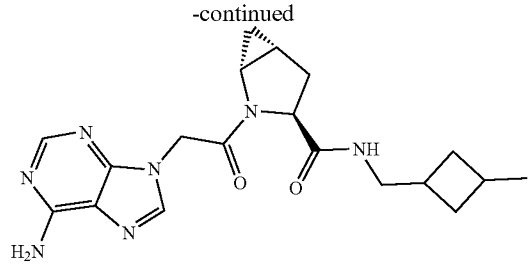

100b

Preparation of (1R,3S,5R)-2-(2-(6-amino-9H-purin-9-yl)acetyl)-N-((3-methylcyclobutyl)methyl)-2-azabicyclo[3.1.0]hexane-3-carboxamide (100b)

Compound 100b was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) (150 mg, 0.496 mmol) in DMF (1.5 mL) using (3-methylcyclobutyl)methanamine (100a) (98 mg, 0.992 mmol; CAS #144595146-1), HATU (283 mg, 0.744 mmol), DIPEA (0.346 mL, 1.985 mmol) and stirring at RT for 3 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(6-amino-9H-purin-9-yl)acetyl)-N-((3-methylcyclobutyl)methyl)-2-azabicyclo[3.1.0]hexane-3-carboxamide (100b) (19 mg, 10% yield) HCl salt as a white solid; 1H NMR (300 MHz, DMSO-$d_6$) δ 9.61 (s, 1H), 8.87 (s, 1H), 8.52 (s, 1H), 8.45 (s, 1H), 7.95-7.76 (m, 1H), 5.57 (dd, J=17.2, 1.3 Hz, 1H), 5.26 (dd, J=17.0, 1.5 Hz, 1H), 4.30-4.14 (m, 1H), 3.78-3.60 (m, 1H), 3.26-2.86 (m, 2H), 2.44-1.90 (m, 3H), 1.93-1.70 (m, 2H), 1.62-1.42 (m, 2H), 1.39-0.82 (m, 6H), 0.78-0.61 (m, 1H); MS (ES+): 384.2 (M+1).

Scheme 101

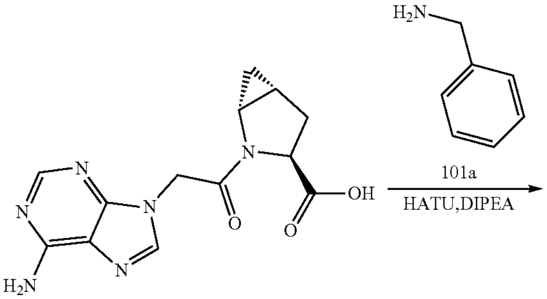

95a

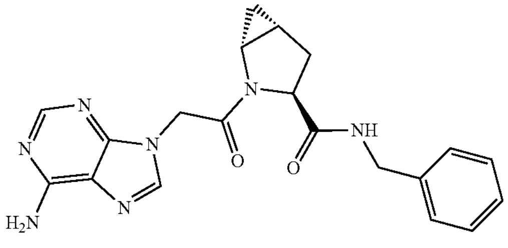

101b

Preparation of (1R,3S,5R)-2-(2-(6-amino-9H-purin-9-yl)acetyl)-N-benzyl-2-azabicyclo[3.1.0]hexane-3-carboxamide (101b)

Compound 101b was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) (150 mg, 0.496 mmol) in DMF (1.5 mL) using phenylmethanamine (101a) (80 mg, 0.744 mmol, CAS #100-46-9), HATU (283 mg, 0.744 mmol), DIPEA (0.346 mL, 1.985 mmol) and stirring at RT for 2 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(6-amino-9H-purin-9-yl)acetyl)-N-benzyl-2-azabicyclo[3.1.0]hexane-3-carboxamide (101b) (51 mg, 26% yield) HCl salt as a white solid; $^1$H NMR (300 MHz, DMSO-$d_6$) δ 9.38 (s, 1H), 8.73 (s, 1H), 8.52-8.44 (m, 2H), 8.43 (s, 1H), 7.36-7.17 (m, 5H), 5.55 (d, J=17.1 Hz, 1H), 5.27 (d, J=17.1 Hz, 1H), 4.35-4.19 (m, 3H), 3.73-3.67 (m, 1H), 2.33-2.10 (m, 2H), 1.93-1.84 (m, 1H), 1.13-1.01 (m, 1H), 0.77-0.67 (m, 1H); MS (ES+): 392.2 (M+1).

Scheme 102

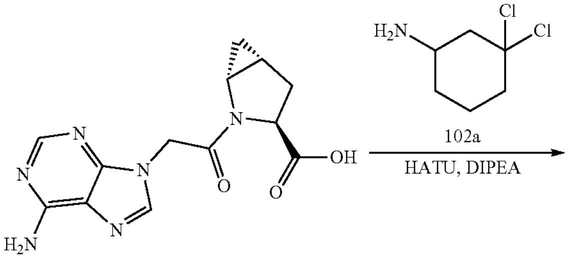

95a

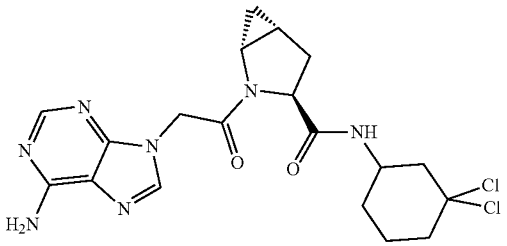

102b

Preparation of (1R,3S,5R)-2-(2-(6-amino-9H-purin-9-yl)acetyl)-N-(3,3-dichlorocyclohexyl)-2-azabicyclo[3.1.0]hexane-3-carboxamide (102b)

Compound 102b was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) (90 mg, 0.298 mmol) in DMF (1 mL) using 3,3-dichlorocyclohexanamine (102a) (50 mg, 0.298 mmol; CAS #226549-07-1), HATU (170 mg, 0.446 mmol), DIPEA (0.207 mL, 1.190 mmol) and stirring at RT for 2 h. This gave after workup and purification twice by reverse phase column chromatography [C18 column (50 g), eluting with ACN in water (containing 0.1% HCl) from 0-100%] followed by purification twice using flash column chromatography [silica gel (12 g), DMA80 in DCM from 0-100%] (1R,3S,5R)-2-(2-(6-amino-9H-purin-9-yl)acetyl)-N-(3,3-dichlorocyclohexyl)-2-azabicyclo[3.1.0]hexane-3-carboxamide (102b) (10 mg, 7% yield) as a white solid; $^1$H NMR (300 MHz, DMSO-$d_6$) δ 8.15 (s, 1H), 8.08 (d, J=3.6 Hz, 1H), 7.80 (dd, J=8.1, 2.1 Hz, 1H), 7.33 (s, 2H), 5.36 (dd, J=17.1, 1.5 Hz, 1H), 5.14 (d, J=17.1 Hz, 1H), 4.13 (dd, J=8.8, 5.2 Hz, 1H), 3.93-3.77 (m, 1H), 3.71-3.60 (m, 1H), 2.45-2.34 (m, 1H), 2.27-2.00 (m, 4H), 1.94-1.50 (m, 5H), 1.34-1.13 (m, 1H), 1.08-0.95 (m, 1H), 0.71-0.62 (m, 1H); MS (ES+): 452.1 (M+1).

Scheme 103

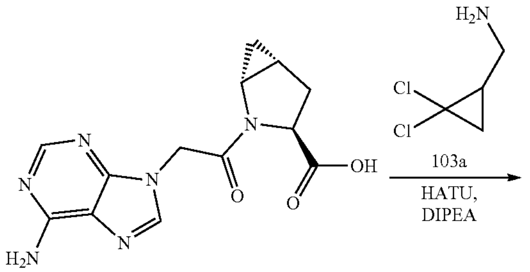

95a

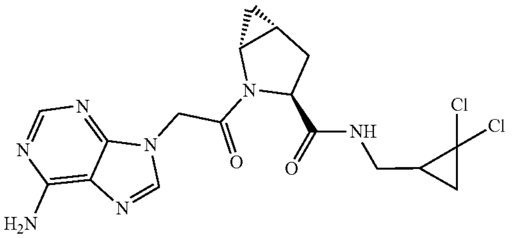

103b

Preparation of (1R,3S,5R)-2-(2-(6-amino-9H-purin-9-yl)acetyl)-N-((2,2-dichlorocyclopropyl)methyl)-2-azabicyclo[3.1.0]hexane-3-carboxamide (103b)

Compound 103b was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) (120 mg, 0.397 mmol) in DMF (1 mL) using (2,2-dichlorocyclopropyl)methanamine (103a) (55.6 mg, 0.397 mmol; CAS #226549-07-1), HATU (226 mg, 0.595 mmol), DIPEA (0.207 mL, 1.191 mmol) and stirring at RT for 16 h. This gave after workup and purification by flash column chromatography [silica gel (12 g), using DMA-80 in DCM from 0 to 100%] followed by purification using reverse phase column chromatography [C18 column (50 g), eluting with ACN in water (containing 0.1% HCl) from 0-100%] (1R,3S,5R)-2-(2-(6-amino-9H-purin-9-yl)acetyl)-N-((2,2-dichlorocyclopropyl)methyl)-2-azabicyclo[3.1.0]hexane-3-carboxamide (103b) (67 mg, 40% yield) HCl salt as a white solid; $^1$H NMR (300 MHz, DMSO-$d_6$) δ 8.39 (s, 1H), 8.33 (s, 1H), 8.20-8.10 (m, 1H), 5.49 (d, J=17.1 Hz, 1H), 5.23 (d, J=17.0 Hz, 1H), 4.28-4.19 (m, 1H), 3.72-3.63 (m, 1H), 3.30-3.11 (m, 2H), 2.30-2.02 (m, 2H), 1.93-1.75 (m, 2H), 1.68 (ddd, J=10.8, 7.2, 3.6 Hz, 1H), 1.34 (t, J=7.5 Hz, 1H), 1.05 (dt, J=9.6, 5.3 Hz, 1H), 0.74-0.62 (m, 1H); MS (ES+) 424.1 (M+1).

Scheme 104

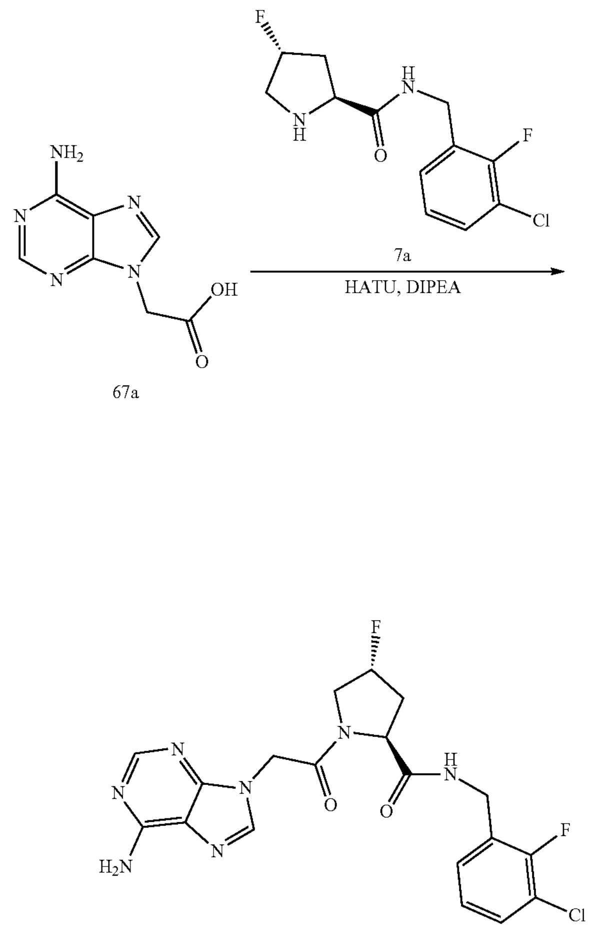

67a 7a

104a

Scheme 105

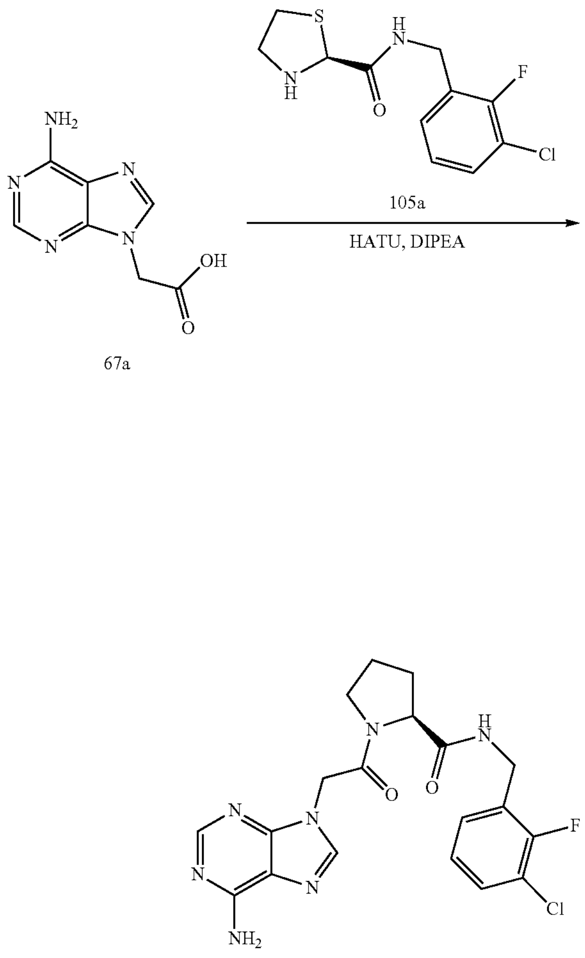

67a 105a

105b

Preparation of (2S,4R)-1-(2-(6-amino-9H-purin-9-yl)acetyl)-N-(3-chloro-2-fluorobenzyl)-4-fluoropyrrolidine-2-carboxamide (104a)

Compound 104a was prepared according to the procedure reported in step-3 of scheme-1, from 2-(6-amino-9H-purin-9-yl)acetic acid (67a) (100 mg, 0.518 mmol) in DMF (2 mL) using (2S,4R)—N-(3-chloro-2-fluorobenzyl)-4-fluoropyrrolidine-2-carboxamide (7a) (142 mg, 0.518 mmol), HATU (295 mg, 0.777 mmol), DIPEA (0.271 mL, 1.553 mmol) and stirring at RT for 16 h. This gave after workup and purification by reverse phase column chromatography [C18 column (30 g), eluting with ACN in water (containing 0.1% HCl) from 0-100%] (2S,4R)-1-(2-(6-amino-9H-purin-9-yl)acetyl)-N-(3-chloro-2-fluorobenzyl)-4-fluoropyrrolidine-2-carboxamide (104a) (57 mg, 24% yield) HCl salt as a white solid; $^1$H NMR (300 MHz, DMSO-$d_6$) δ 8.64 (t, J=5.9 Hz, 1H), 8.40-8.33 (m, 1H), 8.33-8.25 (m, 1H), 7.52-7.34 (m, 1H), 7.29-7.14 (m, 1H), 7.06 (td, J=7.9, 1.1 Hz, 1H), 5.63-5.06 (m, 3H), 4.92-3.72 (m, 5H), 2.21-1.86 (m, 1H); MS (ES+) 450.1 (M+1); Analysis calculated for $C_{19}H_{18}ClF_2N_7O_2 \cdot 2.5H_2O \cdot HCl$: C, 42.95; H, 4.55; Cl, 13.34; N, 18.45. Found: C, 42.80; H, 4.26; Cl, 13.15; N, 18.25.

Preparation of (S)-3-(2-(6-amino-9H-purin-9-yl)acetyl)-N-(3-chloro-2-fluorobenzyl)thiazolidine-2-carboxamide (105b)

Compound 105b was prepared according to the procedure reported in step-3 of scheme-1, from 2-(6-amino-9H-purin-9-yl)acetic acid (67a) (100 mg, 0.518 mmol) in DMF (2 mL) using (S)—N-(3-chloro-2-fluorobenzyl)thiazolidine-2-carboxamide (105a) [142 mg, 0.518 mmol; prepared according to the procedure reported by Altmann, Eva et al., PCT Int. Appl. (2012), WO 2012093101 A1 20120712], HATU (295 mg, 0.777 mmol), DIPEA (0.271 mL, 1.553 mmol) and stirring at RT for 16 h. The solid obtained was collected by filtration washed with water, ethyl acetate and dried to yield (S)-3-(2-(6-amino-9H-purin-9-yl)acetyl)-N-(3-chloro-2-fluorobenzyl)thiazolidine-2-carboxamide (105b) (75 mg, 32% yield) as a white solid; $^1$H NMR (300 MHz, DMSO-$d_6$) δ 8.62 (t, J=5.9 Hz, 1H), 8.15-8.09 (m, 1H), 8.02 (s, 1H), 7.46 (td, J=7.6, 1.8 Hz, 1H), 7.32-7.19 (m, 3H), 7.12 (td, J=7.8, 1.0 Hz, 1H), 5.44 (s, 1H), 5.32-5.11 (m, 2H), 4.52-3.74 (m, 4H), 3.40-3.09 (m, 2H); MS (ES+): 450.1 (M+1); (ES−): 448.1 (M−1).

Scheme 106

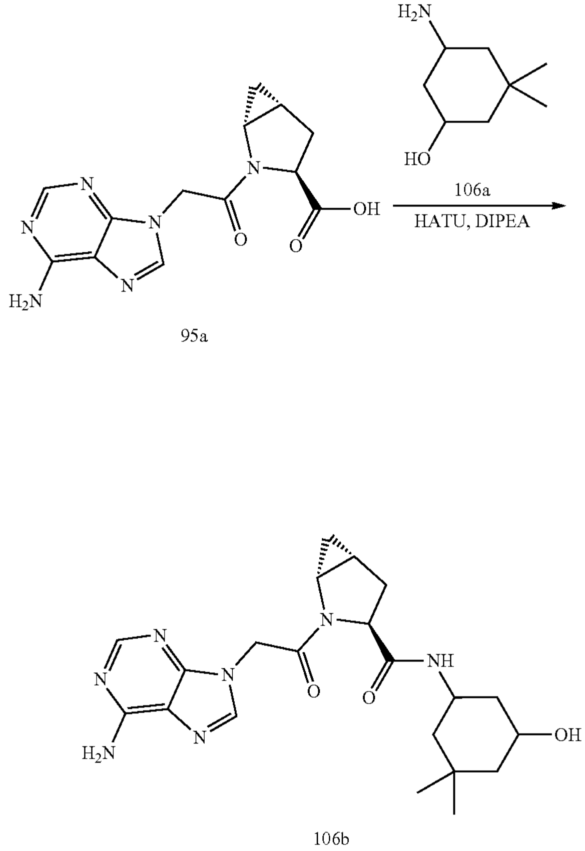

95a

106b

Preparation of (1R,3S,5R)-2-(2-(6-amino-9H-purin-9-yl)acetyl)-N-(5-hydroxy-3,3-dimethylcyclohexyl)-2-azabicyclo[3.1.0]hexane-3-carboxamide (106b)

Compound 106b was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) (120 mg, 0.397 mmol) in DMF (1 mL) using racemic-(1R,5S)-5-amino-3,3-dimethylcyclohexan-ol (106a) (56.9 mg, 0.397 mmol); CAS #1529781-98-3), HATU (189 mg, 0.496 mmol), DIPEA (0.207 mL, 1.191 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (150 g), eluting with ACN in water (containing 0.1% HCl) from 0-100%] (1R,3S,5R)-2-(2-(6-amino-9H-purin-9-yl)acetyl)-N-(5-hydroxy-3,3-dimethylcyclohexyl)-2-azabicyclo[3.1.0]hexane-3-carboxamide (106b) (40 mg, 24% yield) (racemic mixture) HCl salt as a white solid; $^{1}H$ NMR (300 MHz, DMSO-$d_6$) δ 8.47 (s, 1H), 8.42 (s, 1H), 7.65-7.54 (m, 1H), 5.53 (d, J=17.1 Hz, 1H), 5.24 (d, J=17.0 Hz, 1H), 4.21-4.07 (m, 1H), 3.89-3.22 (m, 3H), 2.24-1.99 (m, 2H), 1.94-1.76 (m, 2H), 1.60-1.42 (m, 1H), 1.42-1.27 (m, 1H), 1.08-0.89 (m, 4H), 0.89 (s, 3H), 0.85 (s, 3H), 0.73-0.57 (m, 1H); Analysis calculated for $C_{21}H_{29}N_7O_3 \cdot 1.5H_2O \cdot 2.75HCl$: C, 45.46; H, 6.31; Cl, 17.57; N, 17.67. found; C, 45.75; H, 6.68; Cl, 17.63; N, 17.68.

Scheme 107

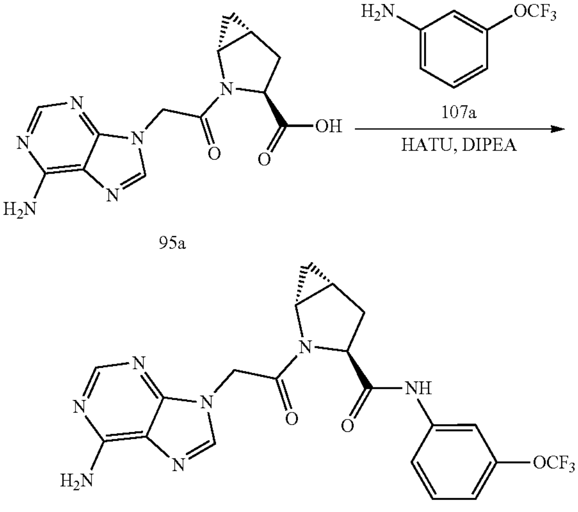

95a

107b

Preparation of (1R,3S,5R)-2-(2-(6-amino-9H-purin-9-yl)acetyl)-N-(3-(trifluoromethoxy)phenyl)-2-azabicyclo[3.1.0]hexane-3-carboxamide (107b)

Compound 107b was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) (120 mg, 0.397 mmol) in DMF (1 mL) using 3-(trifluoromethoxy)aniline (107a) (55.6 mg, 0.397 mmol; CAS #1535-73-5), HATU (226 mg, 0.595 mmol), DIPEA (0.207 mL, 1.191 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (150 g), eluting with ACN in water (containing 0.1% HCl) from 0-100%] (1R,3S,5R)-2-(2-(6-amino-9H-purin-9-yl)acetyl)-N-(3-(trifluoromethoxy)phenyl)-2-azabicyclo[3.1.0]hexane-3-carboxamide (107b) (97 mg, 53% yield) HCl salt as a white solid; 1H NMR (300 MHz, DMSO-$d_6$) δ 10.20 (s, 1H), 8.12 (s, 1H), 8.06 (s, 1H), 7.77-7.74 (m, 1H), 7.54-7.36 (m, 2H), 7.19 (s, 2H), 7.06-7.00 (m, 1H), 5.41 (d, J=17.2 Hz, 1H), 5.18 (d, J=17.1 Hz, 1H), 4.33 (dd, J=8.8, 5.6 Hz, 1H), 3.76 (ddd, J=7.2, 5.4, 2.4 Hz, 1H), 2.39-2.16 (m, 2H), 2.00-1.80 (m, 1H), 1.05 (dt, J=8.7, 5.4 Hz, 1H), 0.74 (td, J=5.1, 2.4 Hz, 1H); $^{19}F$ NMR (282 MHz, DMSO-$d_6$) δ-56.65; MS (ES+): 462.1 (M+1).

Scheme 108

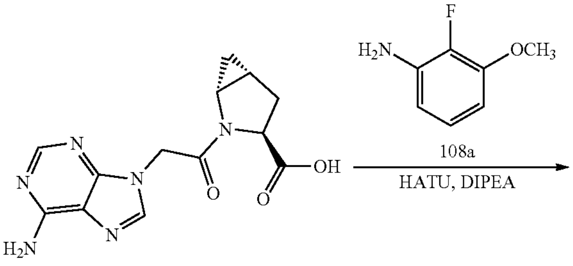

95a

-continued

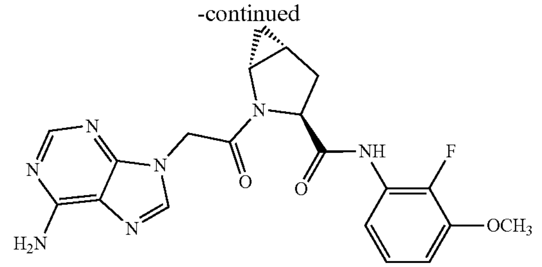

108b

Preparation of (1R,3S,5R)-2-(2-(6-amino-9H-purin-9-yl)acetyl)-N-(2-fluoro-3-methoxyphenyl)-2-azabicyclo[3.1.0]hexane-3-carboxamide (108b)

Compound 108b was prepared according to the procedure reported in step-3 of scheme-1, from (1R,3S,5R)-2-(2-(6-amino-9H-purin-9-yl)acetyl)-2-azabicyclo[3.1.0]hexane-3-carboxylic acid (95a) (120 mg, 0.397 mmol) in DMF (1 mL) using 2-fluoro-3-methoxyaniline (108a) (67.2 mg, 0.476 mmol; CAS #801282-00-8), HATU (226 mg, 0.595 mmol), DIPEA (0.207 mL, 1.191 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (150 g), eluting with ACN in water (containing 0.1% HCl) from 0-100%](1R,3S,5R)-2-(2-(6-amino-9H-purin-9-yl)acetyl)-N-(2-fluoro-3-methoxyphenyl)-2-azabicyclo[3.1.0]hexane-3-carboxamide (108b) (65 mg, 39% yield) HCl salt as a white solid; $^{1}H$ NMR (300 MHz, DMSO-$d_6$) δ 9.69 (s, 1H), 8.48 (s, 1H), 8.44 (s, 1H), 7.40-7.33 (m, 1H), 7.05 (td, J=8.3, 1.8 Hz, 1H), 6.93 (td, J=8.2, 1.6 Hz, 1H), 5.58 (d, J=17.2 Hz, 1H), 5.29 (d, J=17.1 Hz, 1H), 4.52 (dd, J=8.5, 5.5 Hz, 1H), 3.82 (s, 3H), 3.80-3.65 (m, 1H), 2.37-2.16 (m, 2H), 1.97-1.84 (m, 1H), 1.07 (dt, J=9.2, 5.3 Hz, 1H), 0.72 (td, J=5.1, 2.4 Hz, 1H); $^{19}F$ NMR (282 MHz, DMSO-$d_6$) δ-147.09 (t, J=7.3 Hz); MS (ES+): 426.1 (M+1).

Scheme 109

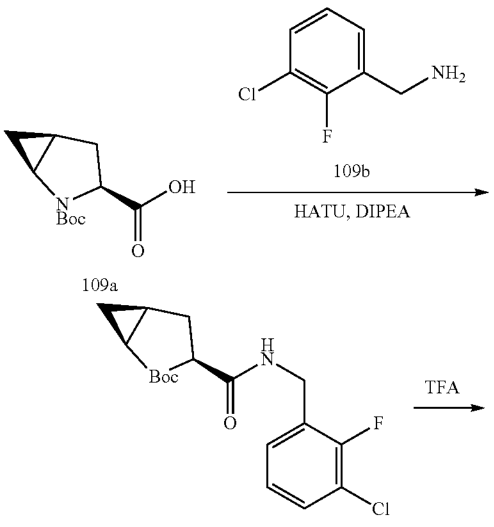

-continued

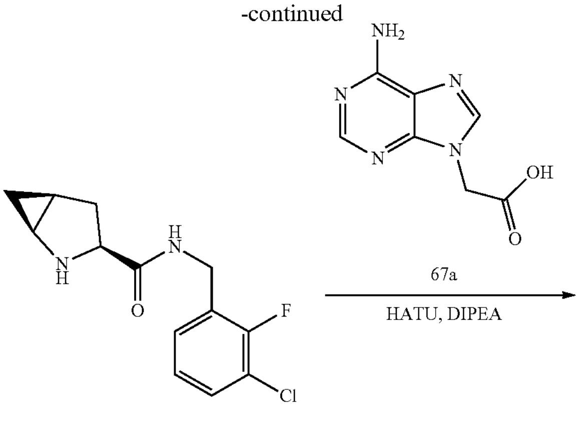

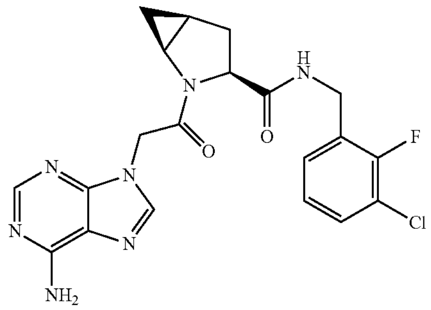

109e

Preparation of (1S,3S,5S)-2-(2-(6-amino-9H-purin-9-yl)acetyl)-N-(3-chloro-2-fluorobenzyl)-2-azabicyclo[3.1.0]hexane-3-carboxamide (109e)

Step-1: Preparation of tert-butyl (1S,3S,5S)-3-((3-chloro-2-fluorobenzyl)carbamoyl)-2-azabicyclo[3.1.0]hexane-2-carboxylate (109c)

Compound 109c was prepared according to the procedure reported in step-3 of scheme-1, from (1S,3S,5S)-2-(tert-butoxycarbonyl)-2-azabicyclo[3.1.0]hexane-3-carboxylic acid (109a) (0.5 g, 2.2 mmol; CAS #197142-36-2) using (3-chloro-2-fluorophenyl)methanamine (109b) (0.386 g, 2.420 mmol; CAS #72235-55-3), (HATU) (1.255 g, 3.30 mmol), DIPEA (1.150 mL, 6.60 mmol) in DMF (5 mL) and stirring at RT for 16 h. This gave after workup and purification by flash column chromatography [silica gel (40 g), eluting with MeOH in DCM 0-10%] tert-butyl (1S,3S,5S)-3-((3-chloro-2-fluorobenzyl)carbamoyl)-2-azabicyclo[3.1.0]hexane-2-carboxylate (109c) (0.8 g, 99% yield) as a pale-yellow gel; MS (ES+): 391.1 (M+Na).

Step-2: Preparation of (1S,3S,5S)—N-(3-chloro-2-fluorobenzyl)-2-azabicyclo[3.1.0]hexane-3-carboxamide (109d)

Compound 109d was prepared according to the procedure reported in step-2 of scheme-1, from tert-butyl (1S,3S,5S)-3-((3-chloro-2-fluorobenzyl)carbamoyl)-2-azabicyclo[3.1.0]hexane-2-carboxylate (109c) (0.75 g, 2.033 mmol) using TFA (0.627 mL, 8.13 mmol) in DCM (6 mL) and stirring overnight at room temperature. This gave after workup and purification by reverse phase column chromatography [C18 (140 g), eluting with ACN in water (containing 0.1% HCl) from 0 to 100%] (1S,3S,5S)—N-(3-chloro-2-fluorobenzyl)-2-azabicyclo[3.1.0]hexane-3-carboxamide (109d); $^1$H NMR (300 MHz, DMSO-$d_6$) δ 10.33 (s, 1H), 9.11 (t, J=5.7 Hz, 1H), 8.79 (d, J=9.1 Hz, 1H), 7.52 (ddd, J=7.9, 7.1, 1.8 Hz, 1H), 7.33 (ddd, J=7.8, 6.7, 1.8 Hz, 1H), 7.22 (td, J=7.8, 1.1 Hz, 1H), 4.54 (s, 1H), 4.39 (d, J=5.6 Hz, 2H), 3.29 (s, 1H), 2.55 (s, 1H), 2.10 (dd, J=13.7, 3.1 Hz, 1H), 1.75 (dq. J=9.0, 5.4 Hz, 1H), 0.90-0.76 (m, 1H), 0.65 (ddd, J=7.1, 5.0, 2.6 Hz, 1H); $^{19}$F NMR (282 MHz, DMSO-$d_6$) δ−121.11; MS (ES+): 269.1 (M+1).

Step-3: Preparation of (1S,3S,5S)-2-(2-(6-amino-9H-purin-9-yl)acetyl)-N-(3-chloro-2-fluorobenzyl)-2-azabicyclo[3.1.0]hexane-3-carboxamide (109e)

Compound 109e was prepared according to the procedure reported in step-3 of scheme-1, from (1S,3S,5S)—N-(3-chloro-2-fluorobenzyl)-2-azabicyclo[3.1.0]hexane-3-carboxamide (109d) (139 mg, 0.518 mmol) in DMF (2 mL) using 2-(6-amino-9H-purin-9-yl)acetic acid (100 mg, 0.518 mmol) (67a), HATU (295 mg, 0.777 mmol), DIPEA (0.271 mL, 1.553 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (150 g), eluting with ACN in water (containing 0.1% HCl) from 0-100%] (1S,3S,5S)-2-(2-(6-amino-9H-purin-9-yl)acetyl)-N-(3-chloro-2-fluorobenzyl)-2-azabicyclo[3.1.0]hexane-3-carboxamide (109e) (71 mg, 31% yield) as a white solid; $^1$H NMR (300 MHz, DMSO-$d_6$) δ 8.49 (t, J=5.8 Hz, 11H), 8.42 (s, 1H), 8.35 (s, 1H), 7.52-7.37 (m, 1H), 7.29-7.18 (m, 1H), 7.10 (td, J=7.9, 1.0 Hz, 1H), 5.52 (d, J=17.0 Hz, 1H), 5.27 (d, J=17.0 Hz, 1H), 4.67 (dd, J=11.2, 3.4 Hz, 1H), 4.49-4.10 (m, 2H), 3.86-3.69 (m, 1H), 2.63-2.51 (m, 1H), 1.89-1.67 (m, 2H), 1.16 (td, J=5.1, 2.4 Hz, 1H), 0.89-0.78 (m, 1H); $^{19}$F NMR (282 MHz, DMSO-$d_6$) δ−121.60; MS (ES+): 444.1 (M+1).

Scheme 110

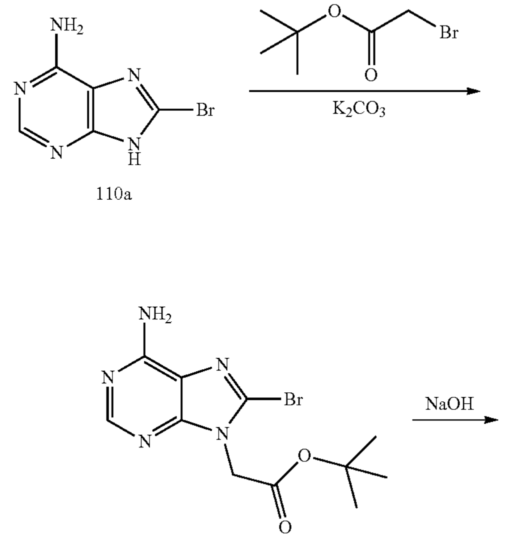

110a

110b

-continued

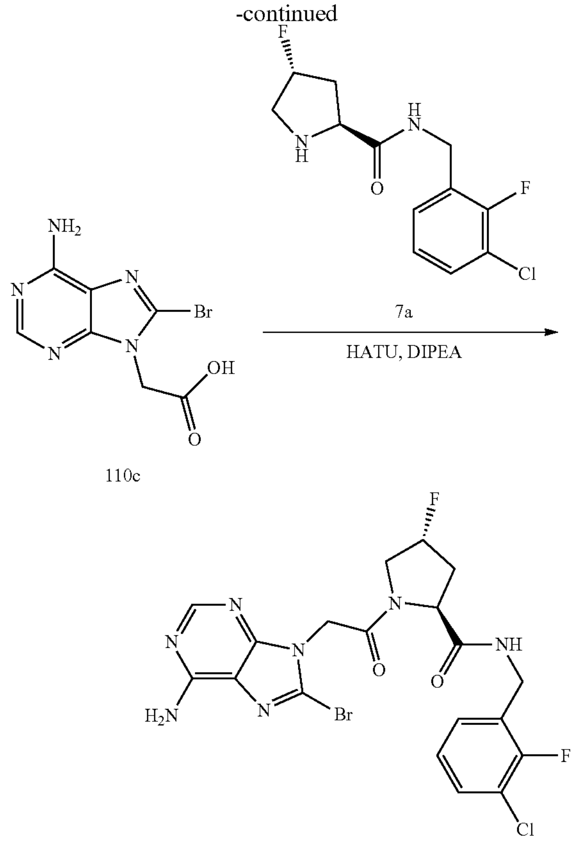

110c

110d

Preparation of (2S,4R)-1-(2-(6-amino-8-bromo-9H-purin-9-yl)acetyl)-N-(3-chloro-2-fluorobenzyl)-4-fluoropyrrolidine-2-carboxamide (110d)

Step-1: Preparation of tert-butyl 2-(6-amino-8-bromo-9H-purin-9-yl)acetate (110b)

Compound 110b was prepared according to the procedure reported in step-1 of scheme-1, from 8-bromo-9H-purin-6-amine (110a) (I g, 4.67 mmol; CAS #6974-78-3) in DMF (10 mL) using tert-butyl 2-bromoacetate and $K_2CO_3$ (0.775 g, 5.61 mmol). This gave after workup and recrystallization with ethyl acetate tert-butyl 2-(6-amino-8-bromo-9H-purin-9-yl)acetate (110b) (550 mg, 36% yield); $^1$H NMR (300 MHz, DMSO-$d_6$) δ 8.33 (s, 1H), 8.31 (s, 1H), 8.15 (s, 1H), 5.04 (s, 2H), 1.43 (s, 9H).

Step-2: Preparation of 2-(6-amino-8-bromo-9H-purin-9-yl)acetic acid (110c)

Compound 110c was prepared according to the procedure reported in step-4 of scheme-17, from tert-butyl 2-(6-amino-8-bromo-9H-purin-9-yl)acetate (110b) (0.5 g, 1.524 mmol) in THF (1.676 mL) and MeOH (1.676 mL) using 2N sodium hydroxide (0.838 mL, 1.676 mmol) and stirring at RT for 45 min. This gave after workup 2-(6-amino-8-bromo-9H-purin-9-yl)acetic acid (110c) (346 mg, 83% yield); $^1$H NMR (300 MHz, DMSO-$d_6$) δ 8.31 (s, 1H), 5.04 (s, 2H).

Step-3: Preparation of (2S,4R)-1-(2-(6-amino-8-bromo-9H-purin-9-yl)acetyl)-N-(3-chloro-2-fluorobenzyl)-4-fluoropyrrolidine-2-carboxamide (110d)

Compound 110d was prepared according to the procedure reported in step-3 of scheme-1, from 2-(6-amino-8-bromo-9H-purin-9-yl)acetic acid (110c) (141 mg, 0.518 mmol) in DMF (2 mL) using (2S,4R)—N-(3-chloro-2-fluorobenzyl)-4-fluoropyrrolidine-2-carboxamide (7a) (142 mg. 0.518 mmol), HATU (296 mg, 0.777 mmol). DIPEA (0.271 mL, 1.555 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (150 g), eluting with ACN in water (containing 0.1% HCl) from 0-100%] (2S,4R)-1-(2-(6-amino-8-bromo-9H-purin-9-yl)acetyl)-N-(3-chloro-2-fluorobenzyl)-4-fluoropyrrolidine-2-carboxamide (110d) (123 mg, 45% yield) as a white solid; $^1$H NMR (300 MHz, DMSO-$d_6$) δ 8.63 (t, J=5.9 Hz, 1H), 8.38 (s, 2H), 8.29 (s, 1H), 7.52-7.32 (m, 1H), 7.28-7.13 (m, 1H), 7.07-7.00 (m, 1H), 5.64-5.12 (m, 3H), 4.94-3.75 (m, 5H), 2.57-1.93 (m, 2H); $^{19}$F NMR (282 MHz, DMSO-$d_6$) δ−121.69, −173.83−−179.95; MS (ES+): 528.0 (M+1).

Scheme 111

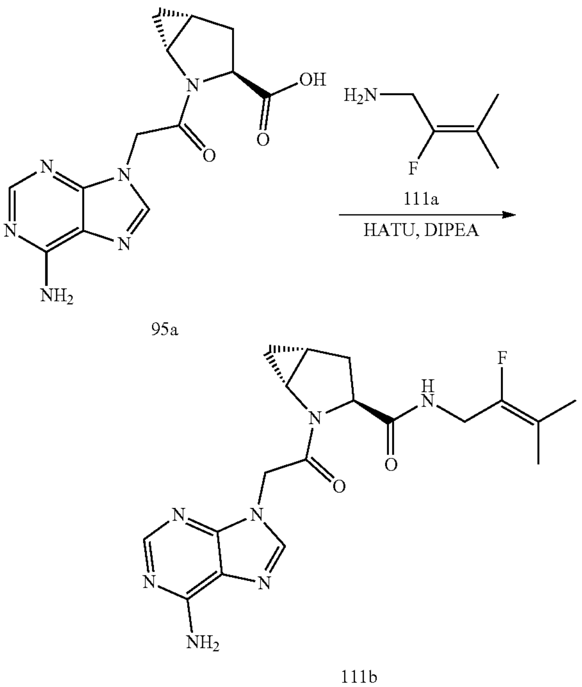

95a

111a

111b

Preparation of (1R,3S,5R)-2-(2-(6-amino-9H-purin-9-yl)acetyl)-N-(2-fluoro-3-methylbut-2-en-1-yl)-2-azabicyclo[3.1.0]hexane-3-carboxamide (111b)

Compound 111b was prepared according to the procedure reported in step-3 of scheme-1, from 2-fluoro-3-methylbut-2-en-1-amine (111a) (61.4 mg, 0.595 mmol; prepared according to the procedure reported by Flohr. Stefanie et al; in PCT Int. Appl., 2014002052, 3 Jan. 2014) in DMF (1 mL) using (1R,3S,5R)-2-(2-(6-amino-9H-purin-9-yl)acetyl)-2-azabicyclo[3.1.0]hexane-3-carboxylic acid (95a) (120 mg, 0.397 mmol), HATU (226 mg, 0.595 mmol), DIPEA (0.277 mL, 1.588 mmol) and stirring at RT for 16 h. This gave after workup and purification by reverse phase column chromatography [C18 column (150 g), eluting with ACN in water (containing 0.1% HCl) from 0-100%] (1R,3S,5R)-2-(2-(6-amino-9H-purin-9-yl)acetyl)-N-(2-fluoro-3-methylbut-2-en-1-yl)-2-azabicyclo[3.1.0]hexane-3-carboxamide (111b) (35 mg, 23% yield) HCl salt as a white solid; $^1$H NMR (300 MHz, DMSO-$d_6$) δ 8.49 (s, 1H), 8.42 (s, 1H), 8.17 (t, J=5.6 Hz, 1H), 5.53 (d, J=17.1 Hz, 11H), 5.25 (d, J=17.1 Hz, 1H), 4.23 (dd, J=9.0, 4.6 Hz, 1H), 3.86 (dt, J=21.9, 5.6 Hz, 2H), 3.70-3.58 (m, 1H), 2.32-2.01 (m, 2H), 1.92-1.78 (m, 1H), 1.63 (d, J=2.9 Hz, 3H), 1.57 (d, J=3.3 Hz, 3H), 1.13-0.97 (m, 1H), 0.75-0.61 (m, 1H); $^{19}$F NMR (282 MHz, DMSO-$d_6$) δ−68.80; MS (ES+): 388.2 (M+1); (ES−): 386.2 (M−1).

Scheme 112

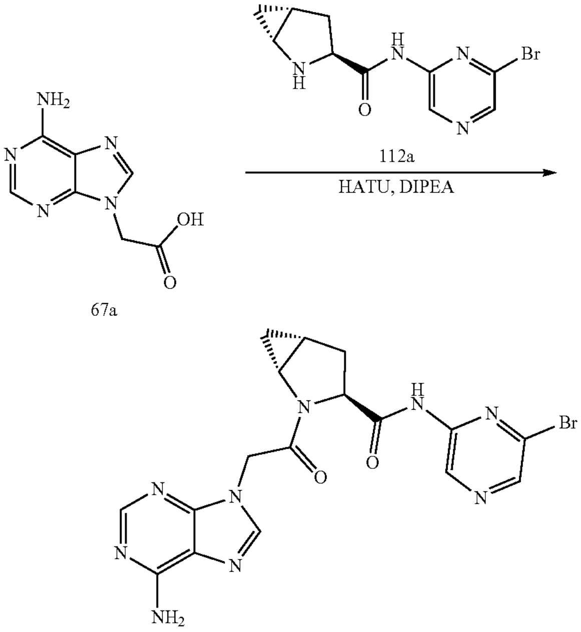

112a

67a

112b

Preparation of (1R,3S,5R)-2-(2-(6-amino-9H-purin-9-yl)acetyl)-N-(6-bromopyrazin-2-yl)-2-azabicyclo[3.1.0]hexane-3-carboxamide (112b)

Compound 112b was prepared according to the procedure reported in step-3 of scheme-1, from 2-(6-amino-9H-purin-9-yl)acetic acid (67a) (47.8 mg, 0.247 mmol) in DMF (2 mL) using (1R,3S,5R)—N-(6-bromopyrazin-2-yl)-2-azabicyclo[3.1.0]hexane-3-carboxamide (112a) [70 mg, 0.247 mmol; prepared according to the procedure reported by Wiles, Jason A et al., PCT Int. Appl. (2017), WO 2017035355 A1 20170302], HATU (141 mg, 0.371 mmol), DIPEA (0.172 mL, 0.989 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (150 g), eluting with ACN in water (containing 0.1% HCl) from 0-100%] (1R,3S,5R)-2-(2-(6-amino-9H-purin-9-yl)acetyl)-N-(6-bromopyrazin-2-yl)-2-azabicyclo[3.1.0]hexane-3-carboxamide (112b) (14 mg, 12% yield) HCl salt as a white solid; $^1$H NMR (300 MHz, DMSO-$d_6$) δ 11.17 (s, 1H), 9.26 (d, J=0.6 Hz, 1H), 8.55 (d, J=0.6 Hz, 1H), 8.41 (s, 1H), 8.36 (s, 1H), 5.57 (d, J=17.2 Hz, 1H), 5.27 (d, J=17.1 Hz, 1H), 4.48 (dd, J=8.9, 5.5 Hz, 1H), 3.86-3.70 (m, 1H), 2.39-2.15 (m, 2H), 1.97-1.81 (m, 1H), 1.14-0.94 (m, 1H), 0.73 (td, J=5.1, 2.4 Hz, 1H); MS (ES+): 458.0, 460.0 (M+1).

Scheme 113

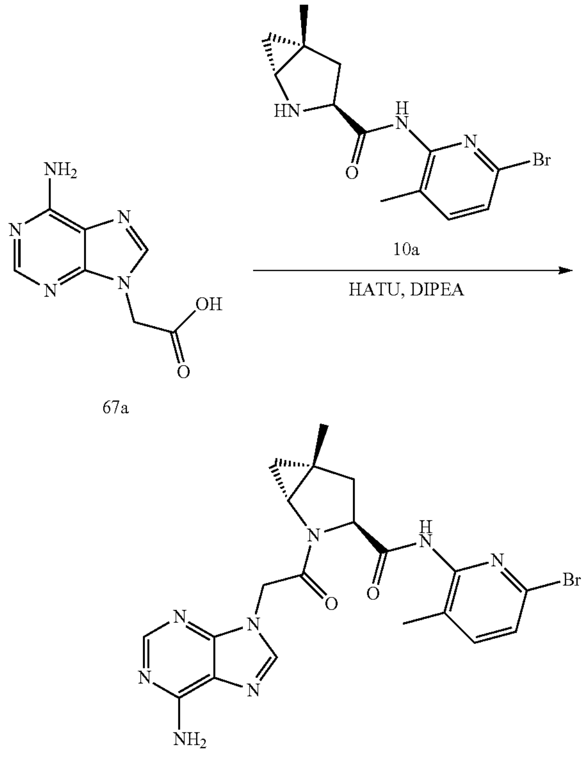

10a

67a

113a

Preparation of (1R,3S,5R)-2-(2-(6-amino-9H-purin-9-yl)acetyl)-N-(6-bromo-3-methylpyridin-2-yl)-5-methyl-2-azabicyclo[3.1.0]hexane-3-carboxamide (113a)

Compound 113a was prepared according to the procedure reported in step-3 of scheme-1, from 2-(6-amino-9H-purin-9-yl)acetic acid (67a) (65 mg, 0.337 mmol) in DMF (1.5 mL) using (1R,3S,5R)—N-(6-bromo-3-methylpyridin-2-yl)-5-methyl-2-azabicyclo[3.1.0]hexane-3-carboxamide (10a) 1115 mg, 0.370 mmol), HATU (192 mg, 0.505 mmol), DIPEA (0.234 mL, 1.346 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] (1R,3S,5R)-2-(2-(6-amino-9H-purin-9-yl)acetyl)-N-(6-bromo-3-methylpyridin-2-yl)-5-methyl-2-azabicyclo[3.1.0]hexane-3-carboxamide (113a) (39 mg, 24% yield) HCl salt as a white solid; $^1$H NMR (300 MHz, DMSO-$d_6$) δ 10.35 (s, 1H, $D_2O$ exchangeable), 9.63 (s, 1H, $D_2O$ exchangeable), 8.88 (s, 1H, $D_2O$ exchangeable), 8.51 (s, 1H), 8.45 (s, 1H), 7.64 (d, J=8.0 Hz, 1H), 7.45 (d, J=7.9 Hz, 1H), 5.55 (d, J=17.1 Hz, 1H), 5.25 (d, J=17.1 Hz, 1H), 4.41

(dd, J=9.2, 5.1 Hz, 1H), 3.54 (dd, J=5.5, 2.4 Hz, 1H), 2.57-2.53 (m, 1H), 2.06 (s, 3H), 2.01 (d, J=5.1 Hz, 1H), 1.30 (s, 3H), 1.02 (t, J=5.4 Hz, 1H), 0.92 (dd, J=5.2, 2.4 Hz, 1H); MS (ES+): 485.1 (M+1), 507.0 (M+Na); (ES−): 483.0 (M−1); Calculated for $C_{20}H_{21}BrNSO_2 \cdot 1.25$ (HCl)·2.75 ($H_2O$); C, 41.38; H, 4.82; Cl, 7.63; N, 19.30 found: C, 41.65; H, 4.62; Cl, 7.61; N, 19.04.

Scheme 114

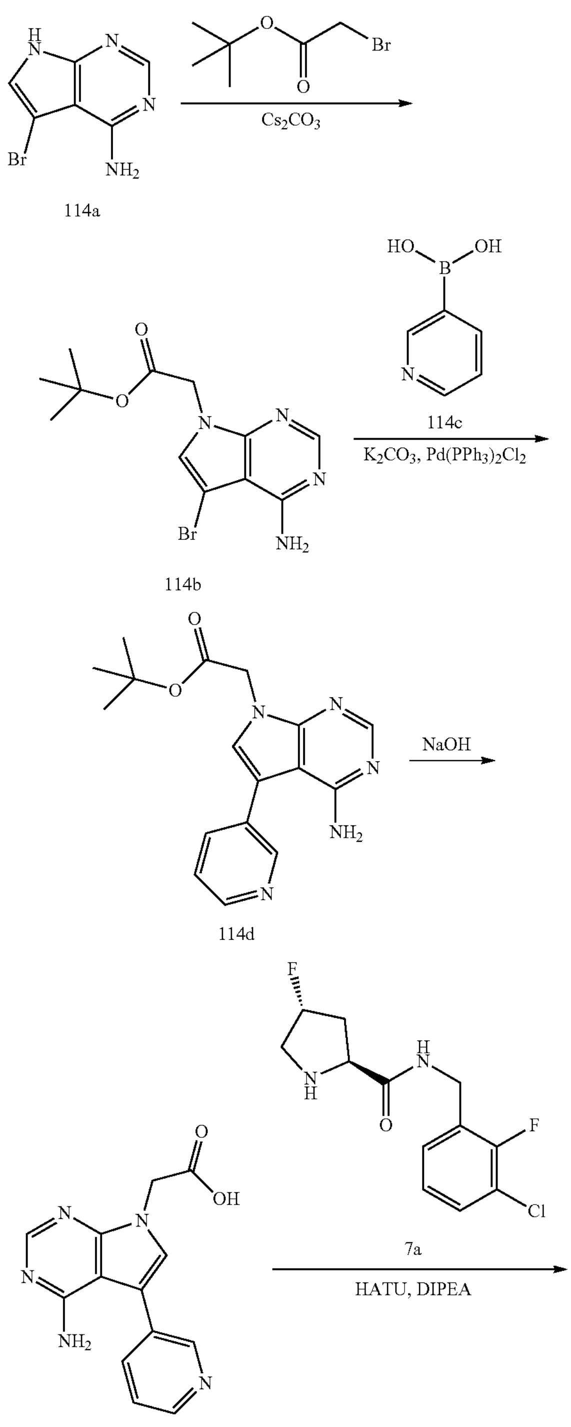

114a

114c

114b

114d

7a

114e

-continued

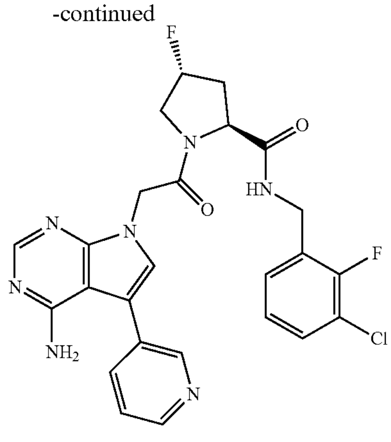

114f

Preparation of (2S,4R)-1-(2-(4-amino-5-(pyridin-3-yl)-7H-pyrrolo[2,3-d]pyrimidin-7-yl)acetyl)-N-(3-chloro-2-fluorobenzyl)-4-fluoropyrrolidine-2-carboxamide (114f)

Step-1: Preparation of tert-butyl 2-(4-amino-5-bromo-7H-pyrrolo[2,3-d]pyrimidin-7-yl)acetate (114b)

Compound 114b was prepared according to the procedure reported in step-1 of scheme-1, from 5-bromo-7H-pyrrolo[2,3-d]pyrimidin-4-amine (114a) (2 g, 9.39 mmol) in DMF (50 mL) using tert-butyl 2-bromoacetate (1.387 mL, 9.39 mmol), $Cs_2CO_3$ (3.67 g, 11.27 mmol) and stirring at RT for 16 h. This gave after workup and purification by flash column chromatography [silica gel (40 g), eluting with EtOAc in Hexane from 0-50%] tert-butyl 2-(4-amino-5-bromo-7H-pyrrolo[2,3-d]pyrimidin-7-yl)acetate (114b) (2.68 g, 87% yield) as a light pink solid; MS (ES+): 327.00 (M+1).

Step-2: Preparation of tert-butyl 2-(4-amino-5-(pyridin-3-yl)-7H-pyrrolo[2,3-d]pyrimidin-7-yl)acetate (114d)

Compound 114d was prepared according to the procedure reported in step-1 of scheme-59, from tert-butyl 2-(4-amino-5-bromo-7H-pyrrolo[2,3-d]pyrimidin-7-yl)acetate (114b) in dioxane (10 mL) using pyridin-3-ylboronic acid (114c) (113 mg, 0.917 mmol; CAS #1692-25-7), bis(triphenylphosphine)palladium(II) chloride (97 mg, 0.138 mmol) a solution of potassium carbonate (380 mg, 2.75 mmol) in water (1.250 mL) and heating at 100° C. for 5 h. This gave after workup and purification by chromatography [silica gel (24 g), eluting with DMA-80 in DCM from 0-50%] tert-butyl 2-(4-amino-5-(pyridin-3-yl)-7H-pyrrolo[2,3-d]pyrimidin-7-yl) acetate (114d) (188 mg, 63% yield) as a yellow solid; $^1$H NMR (300 MHz, DMSO-$d_6$) δ 8.71-8.62 (m, 1H), 8.54 (dd, J=4.9, 1.6 Hz, 1H), 8.16 (s, 1H), 7.90-7.75 (m, 1H), 7.48 (dd, J=7.9, 4.8 Hz, 1H), 7.43 (s, 1H), 6.24 (s, 2H), 4.95 (s, 2H), 1.43 (s, 9H); MS (ES+): 326.1 (M+1).

Step-3: Preparation of 2-(4-amino-5-(pyridin-3-yl)-7H-pyrrolo[2,3-d]pyrimidin-7-yl)acetic acid (114e)

Compound 114e was prepared according to the procedure reported in step-4 of scheme-17, from tert-butyl 2-(4-amino-5-(pyridin-3-yl)-7H-pyrrolo[2,3-d]pyrimidin-7-yl)acetate (114d) in THF/MeOH (2 mL; ratio 1:1) using 2N sodium hydroxide (0.318 mL, 0.636 mmol) and stirring at RT for 2 h. This gave after workup 2-(4-amino-5-(pyridin-3-yl)-7H-pyrrolo[2,3-d]pyrimidin-7-yl)acetic acid (114e) (114 mg, 77% yield) as a yellow solid; 1H NMR (300 MHz, DMSO-$d_6$) δ 8.68 (dd, J=2.3, 0.9 Hz, 1H), 8.54 (dd, J=4.8, 1.6 Hz, 1H), 8.16 (s, 1H), 7.84 (dt, J=7.9, 1.9 Hz, 1H), 7.53-7.39 (m, 2H), 6.24 (s, 2H), 4.95 (s, 2H); MS (ES+): 270.10 (M+1).

Step-4: Preparation of (2S,4R)-1-(2-(4-amino-5-(pyridin-3-yl)-7H-pyrrolo[2,3-d]pyrimidin-7-yl) acetyl)-N-(3-chloro-2-fluorobenzyl)-4-fluoropyrrolidine-2-carboxamide (114f)

Compound 114f was prepared according to the procedure reported in step-3 of scheme-1, from 2-(4-amino-5-(pyridin-3-yl)-7H-pyrrolo[2,3-d]pyrimidin-7-yl)acetic acid (114e) (100 mg, 0.371 mmol) in DMF (5 mL) using (2S,4R)—N-(3-chloro-2-fluorobenzyl)-4-fluoropyrrolidine-2-carboxamide (7a) (122 mg, 0.446 mmol), HATU (212 mg, 0.557 mmol), DIPEA (0.259 mL, 1.486 mmol) and stirring at RT for 16 h. This gave after workup and purification by flash column chromatography [silica gel (24 g), using DMA80 in DCM from 0 to 100%] followed by purification using reverse phase column chromatography [C18 column (50 g), eluting with ACN in water (containing 0.1% HCl) from 0-100%] (2S,4R)-1-(2-(4-amino-5-(pyridin-3-yl)-7H-pyrrolo[2,3-d]pyrimidin-7-yl)acetyl)-N-(3-chloro-2-fluorobenzyl)-4-fluoropyrrolidine-2-carboxamide (114f) (111 mg, 57% yield) HCl salt as a white solid; $^1$H NMR (300 MHz, DMSO-$d_6$) (a mixture of two rotamers) δ 8.91 (s, J=2.1 Hz, 1H), 8.82 (d, J=5.6 Hz, 1H), 9.16 (t, J=5.7 Hz) and 8.69 (t, J=5.9 Hz) (2t, 1H) ($D_2O$ exchangeable), 8.57-8.18 (m, 2H), 7.98 (dd, J=8.1, 5.5 Hz, 1H), 7.77 (s, 1H), 7.46-7.29 (m, 1H), 7.21-7.06 (m, 1H), 6.96 (td, J=7.9, 1.1 Hz, 1H), 5.57-5.13 (m, 3H), 4.91-3.72 (m, 5H), 3.82-3.24 (s, 2H), 2.54-2.35 (m, 1H), 2.13-1.83 (m, 1H); $^{19}$F NMR (282 MHz, DMSO-$d_6$) δ−121.31, −121.62, −176.11; MS (ES+): 526.2 (M+1); (ES−): 524.1 (M−1), 560.1 (M+Cl); Analysis Calculated for $C_{25}H_{22}ClF_2N_7O_2 \cdot 2HCl \cdot 3.5H_2O$: C, 45.36; H, 4.72; N, 14.81. found: C, 45.43; H, 4.65; N, 14.67.

Scheme 115

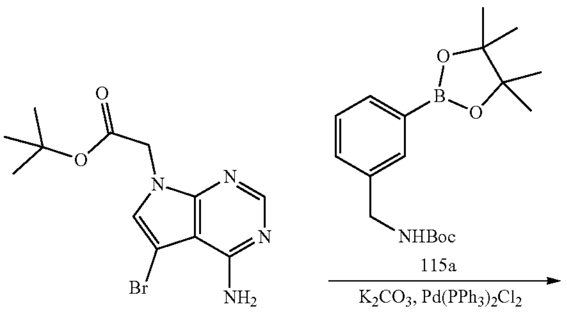

114b

-continued

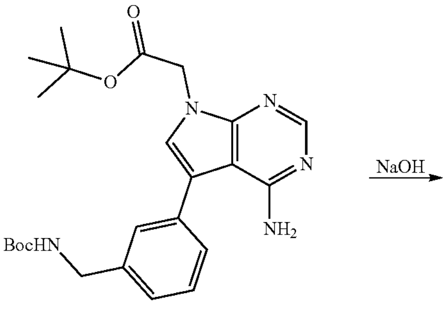

115b

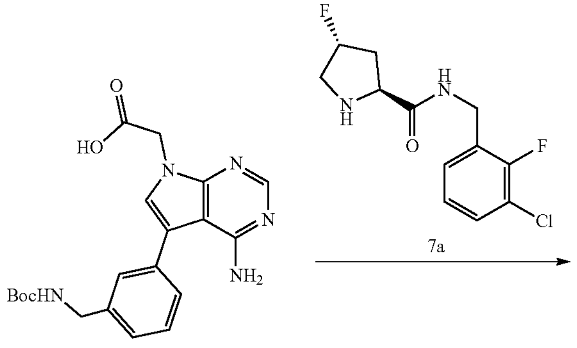

115c

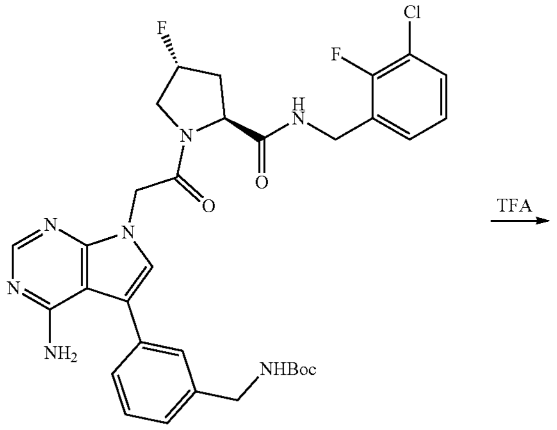

115d

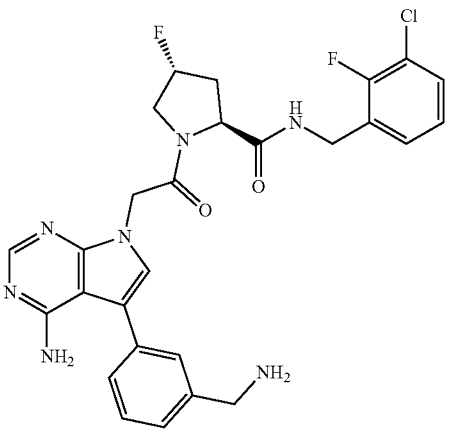

115e

Preparation of (2S,4R)-1-(2-(4-amino-5-(3-(aminomethyl)phenyl)-7H-pyrrolo[2,3-d]pyrimidin-7-yl)acetyl)-N-(3-chloro-2-fluorobenzyl)-4-fluoropyrrolidine-2-carboxamide (115e)

Step-1: Preparation of tert-butyl 2-(4-amino-5-(3-(((tert-butoxycarbonyl)amino)methyl)phenyl)-7H-pyrrolo[2,3-d]pyrimidin-7-yl)acetate (115b)

Compound 115b was prepared according to the procedure reported in step-1 of scheme-59, from tert-butyl 2-(4-amino-5-bromo-7H-pyrrolo[2,3-d]pyrimidin-7-yl)acetate (114b) (300 mg, 0.917 mmol) in dioxane (10 mL) using tert-butyl 3-(4,4,5,5-tetramethyl-1,3,2-dioxaborolan-2-yl)benzylcarbamate (115a) (306 mg, 0.917 mmol), bis(triphenylphosphine)palladium(I) chloride (97 mg, 0.138 mmol) a solution of potassium carbonate (380 mg, 2.75 mmol) in water (1.250 mL) and heating at 100° C. for 4 h. This gave after workup and purification by flash column chromatography [silica gel (24 g), eluting with DMA-80 in DCM from 0-50%] tert-butyl 2-(4-amino-5-(3-(((tert-butoxycarbonyl)amino)methyl)phenyl)-7H-pyrrolo[2,3-d]pyrimidin-7-yl)acetate (115b) (240 mg, 58% yield) as a clear gel; $^{1}$H NMR (300 MHz, DMSO-$d_6$) δ 8.14 (s, 1H), 7.43 (t, J=7.5 Hz, 2H), 7.37-7.19 (m, 4H), 6.12 (s, 2H), 4.94 (s, 2H), 4.19 (d, J=6.1 Hz, 2H), 1.43 (s, 9H), 1.39 (s, 9H); MS (ES+): 454.2 (M+1).

Step-2: Preparation of 2-(4-amino-5-(3-(((tert-butoxycarbonyl)amino)methyl)phenyl)-7H-pyrrolo[2,3-d]pyrimidin-7-yl)acetic acid (115c)

Compound 115c was prepared according to the procedure reported in step-4 of scheme-17, from tert-butyl 2-(4-amino-5-(3-(((tert-butoxycarbonyl)amino)methyl)phenyl)-7H-pyrrolo[2,3-d]pyrimidin-7-yl)acetate (115b) (230 mg, 0.507 mmol) in THF/MeOH (2 mL; ratio 1:1) using 2N sodium hydroxide (0.292 mL, 0.583 mmol) and stirring for 1.5 h at RT. This gave after workup 2-(4-amino-5-(3-(((tert-butoxycarbonyl)amino)methyl)phenyl)-7H-pyrrolo[2,3-d]pyrimidin-7-yl)acetic acid (115c) (137 mg, 68% yield) as a pink solid: $^{1}$H NMR (300 MHz, DMSO-$d_6$) 8.13 (s, 1H), 7.43 (t, J=7.6 Hz, 2H), 7.37-7.14 (m, 4H), 6.11 (s, 2H), 4.93 (s, 2H), 4.19 (d, J=6.1 Hz, 2H), 1.39 (s, 9H); MS (ES+): 398.20 (M+1).

Step-3: Preparation of tert-butyl 3-(4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidin-5-yl)benzylcarbamate (115d)

Compound 115d was prepared according to the procedure reported in step-3 of scheme-1, from 2-(4-amino-5-(3-(((tert-butoxycarbonyl)amino)methyl)phenyl)-7H-pyrrolo[2,3-d]pyrimidin-7-yl)acetic acid (115c) (100 mg, 0.252 mmol) in DMF (5 mL) using (2S,4R)—N-(3-chloro-2-fluorobenzyl)-4-fluoropyrrolidine-2-carboxamide (7a) (83 mg, 0.302 mmol), HATU (144 mg, 0.377 mmol), DIPEA (0.175 mL, 1.006 mmol) and stirring at RT for 16 h. This gave after workup and purification by flash column chromatography [silica gel (24 g), eluting with DMA-80 in DCM from 0 to 50%] tert-butyl 3-(4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidin-5-yl)benzylcarbamate (115d) (156 mg, 95% yield) as a white solid; MS (ES+): 654.3 (M+1).

Step-4: Preparation of (2S,4R)-1-(2-(4-amino-5-(3-(aminomethyl)phenyl)-7H-pyrrolo[2,3-d]pyrimidin-7-yl)acetyl)-N-(3-chloro-2-fluorobenzyl)-4-fluoropyrrolidine-2-carboxamide (115e)

Compound 115e was prepared according to the procedure reported in step-2 of scheme-1, from tert-butyl 3-(4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidin-5-yl)benzylcarbamate (115d) (150 mg, 0.229 mmol) in DCM (3 mL) using TFA (0.353 mL, 4.59 mmol) and stirring at RT for 70 min. This gave after workup and purification by reverse phase column chromatography [C18 column (50 g), eluting with ACN in water (containing 0.1% HCl) from 0-100%](2S,4R)-1-(2-(4-amino-5-(3-(aminomethyl)phenyl)-7H-pyrrolo[2,3-d]pyrimidin-7-yl)acetyl)-N-(3-chloro-2-fluorobenzyl)-4-fluoropyrrolidine-2-carboxamide (115e) (92 mg, 72% yield) HCl salt as a white solid; $^1$H NMR (300 MHz, DMSO-$d_6$) (a mixture of two rotamers) δ 9.19 (t, J=5.8 Hz) and 8.74 (t, J=5.9 Hz) (2t, 1H), 8.53-8.40 (m, 4H, 3H $D_2O$ exchangeable), 7.66-7.35 (m, 6H), 7.30-7.14 (m, 1H), 7.02 (t, J=7.9 Hz, 1H), 5.66-5.15 (m, 3H), 4.96-3.88 (m, 7H), 2.59-2.41 (m, 1H), 2.23-1.89 (m, 1H); $^{19}$F NMR (282 MHz, DMSO) δ−121.29, −121.63, −175.96; MS (ES+): 554.2 (M+1); (ES−): 552.2 (M−1), 588.1 (M+Cl); Analysis calculated for $C_{27}H_{26}ClF_2N_7O_2 \cdot 2HCl \cdot 3H_2O$: C, 47.62; H, 5.03; Cl, 15.62; N, 14.40. Found; C, 47.74; H, 4.94; Cl, 15.37; N, 14.30.

Scheme 116

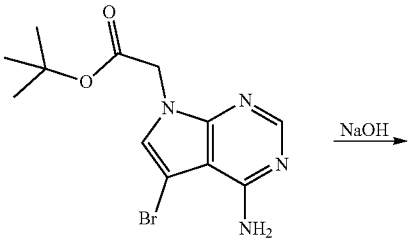

114b

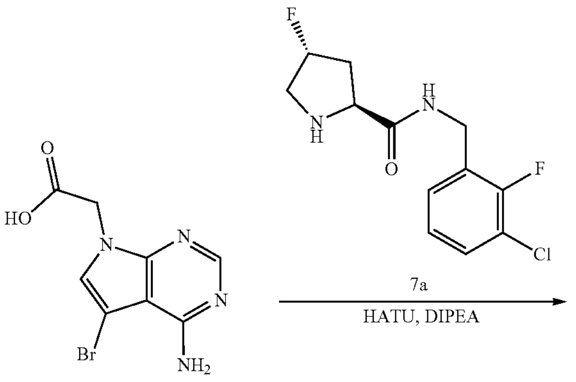

7a

116a

-continued

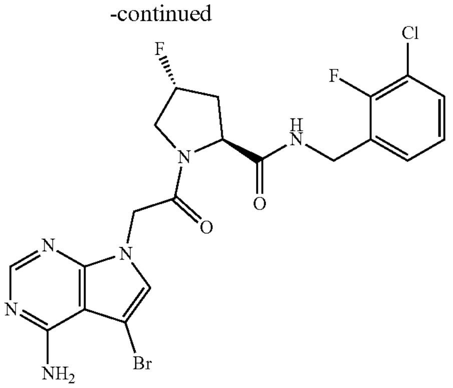

116b

Preparation of (2S,4R)-1-(2-(4-amino-5-bromo-7H-pyrrolo[2,3-d]pyrimidin-7-yl)acetyl)-N-(3-chloro-2-fluorobenzyl)-4-fluoropyrrolidine-2-carboxamide (116b)

Step-1: Preparation of 2-(4-amino-5-bromo-7H-pyrrolo[2,3-d]pyrimidin-7-yl)acetic acid (116a)

Compound 116a was prepared according to the procedure reported in step-4 of scheme-17, from tert-butyl 2-(4-amino-5-bromo-7H-pyrrolo[2,3-d]pyrimidin-7-yl)acetate (114b) (200 mg, 0.611 mmol) in THF/MeOH (2.4 mL; ratio 1:1) using 2N sodium hydroxide (0.367 mL, 0.734 mmol) and stirring for 1 h at RT. This gave after workup 2-(4-amino-5-bromo-7H-pyrrolo[2,3-d]pyrimidin-7-yl)acetic acid (116a) (138 mg, 83% yield) as a pale purple solid; $^1$H NMR (300 MHz, DMSO-$d_6$) δ 13.11 (s, 1H), 8.08 (s, 1H), 7.41 (s, 1H), 6.76 (s, 2H), 4.87 (s, 2H).

Step-2: Preparation of (2S,4R)-1-(2-(4-amino-5-bromo-7H-pyrrolo[2,3-d]pyrimidin-7-yl)acetyl)-N-(3-chloro-2-fluorobenzyl)-4-fluoropyrrolidine-2-carboxamide (116b)

Compound 116b was prepared according to the procedure reported in step-3 of scheme-1, from 2-(4-amino-5-bromo-7H-pyrrolo[2,3-d]pyrimidin-7-yl)acetic acid (116a) (50 mg, 0.184 mmol) in DMF (5 mL) using (2S,4R)—N-(3-chloro-2-fluorobenzyl)-4-fluoropyrrolidine-2-carboxamide (7a) (51 mg, 0.184 mmol), HATU (105 mg, 0.277 mmol), DIPEA (0.129 mL, 0.738 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] (2S,4R)-1-(2-(4-amino-5-bromo-7H-pyrrolo[2,3-d]pyrimidin-7-yl)acetyl)-N-(3-chloro-2-fluorobenzyl)-4-fluoropyrrolidine-2-carboxamide (116b)(29 mg, 30% yield) HCl salt as a white solid; $^1$H NMR (300 MHz, DMSO-$d_6$) (a mixture of two rotamers) δ 9.04 (t, J=5.7 Hz) and 8.63 (t, J=5.8 Hz) (2t, 1H), 8.28 (s) and 8.26 (s) (2s, 1H), 7.83 (s, 3H, $D_2O$ exchangeable), 7.53 (s, 1H), 7.49-7.34 (m, 1H), 7.29-7.13 (m, 1H), 7.08 (td, J=7.9, 1.1 Hz, 1H), 5.47 (d, J=52.8 Hz, 1H), 5.31-5.02 (m, 2H), 4.84-3.73 (m, 5H), 2.43 (m, 1H), 2.19-1.85 (m, 1H); $^{19}$F NMR (282 MHz, DMSO-$d_6$) δ−121.32, −121.62, −176.08. MS (ES+): 527.0 (M+1); (ES−): 525.0 (M−1); Analysis calculated for $C_{20}H_{18}BrClF_2N_6O\cdot HCl\cdot 1.5H_2O$: C, 40.63; H, 3.75; N, 14.21. Found: C, 40.70; H, 3.54; N, 13.95.

Scheme 117

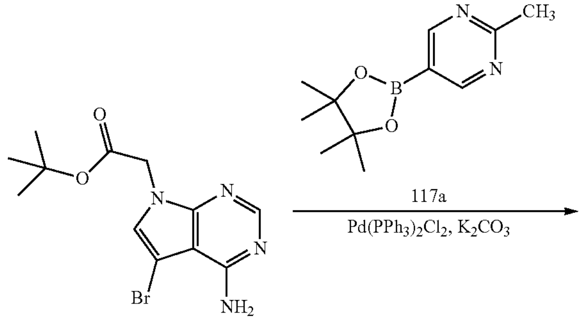

114b

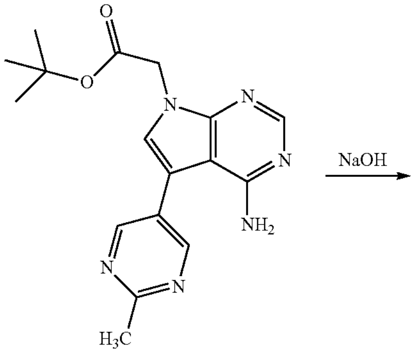

117b

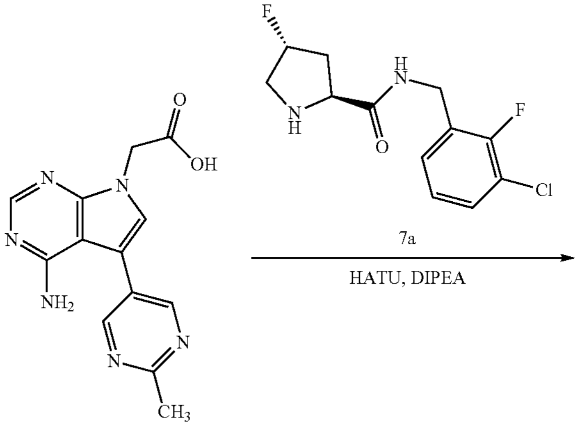

117c

-continued

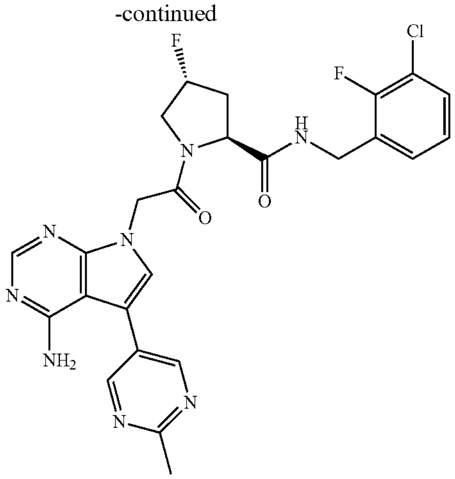

117d

Preparation of (2S,4R)-1-(2-(4-amino-5-(2-methylpyrimidin-5-yl)-7H-pyrrolo[2,3-d]pyrimidin-7-yl)acetyl)-N-(3-chloro-2-fluorobenzyl)-4-fluoropyrrolidine-2-carboxamide (117d)

Step-1: Preparation of tert-butyl 2-(4-amino-5-(2-methylpyrimidin-5-yl)-7H-pyrrolo[2,3-d]pyrimidin-7-yl)acetate (117b)

Compound 117b was prepared according to the procedure reported in step-1 of scheme-59, from tert-butyl 2-(4-amino-5-bromo-7H-pyrrolo[2,3-d]pyrimidin-7-yl)acetate (114b) (1 g, 3.06 mmol) in dioxane (30 mL) using 2-methyl-5-(4,4,5,5-tetramethyl-1,3,2-dioxaborolan-2-yl)pyrimidine (117a) (673 mg, 3.06 mmol; CAS #1052686-67-5), bis(triphenylphosphine)palladium(II) chloride (322 mg, 0.458 mmol) a solution of potassium carbonate (1.267 g, 9.17 mmol) in water (3.75 mL) and heating at 100° C. for 3 h. This gave after workup and purification by flash column chromatography [silica gel (24 g), eluting with DMA-80 in DCM from 0-50%] tert-butyl 2-(4-amino-5-(2-methylpyrimidin-5-yl)-7H-pyrrolo[2,3-d]pyrimidin-7-yl)acetate (117b) (375 mg, 36% yield) as a white solid; $^1H$ NMR (300 MHz, DMSO-$d_6$) δ 8.72 (s, 2H), 8.16 (s, 1H), 7.47 (s, 1H), 6.43 (s, 2H), 4.95 (s, 2H), 2.66 (s, 3H), 1.43 (s, 9H); MS (ES+): 341.1 (M+1).

Step-2: Preparation of 2-(4-amino-5-(2-methylpyrimidin-5-yl)-7H-pyrrolo[2,3-d]pyrimidin-7-yl)acetic acid (117c)

Compound 117c was prepared according to the procedure reported in step-4 of scheme-17, from tert-butyl 2-(4-amino-5-(2-methylpyrimidin-5-yl)-7H-pyrrolo[2,3-d]pyrimidin-7-yl)acetate (117b) (350 mg, 1.028 mmol) in THF/MeOH (4 mL; ratio 1:1) using 2N sodium hydroxide (0.6 mL, 1.20 mmol) and stirring for 3 h at RT. This gave after workup 2-(4-amino-5-(2-methylpyrimidin-5-yl)-7H-pyrrolo[2,3-d]pyrimidin-7-yl)acetic acid (117c) (167 mg, 57% yield) as a white solid; $^1H$ NMR (300 MHz, DMSO-$d_6$) δ 8.72 (s, 2H), 8.16 (s, 1H), 7.48 (s, 1H), 6.43 (s, 2H), 4.96 (s, 2H), 2.66 (s, 3H); MS (ES+): 285.1 (M+1).

Step-3: Preparation of (2S,4R)-1-(2-(4-amino-5-(2-methylpyrimidin-5-yl)-7H-pyrrolo[2,3-d]pyrimidin-7-yl)acetyl)-N-(3-chloro-2-fluorobenzyl)-4-fluoropyrrolidine-2-carboxamide (117d)

Compound 117d was prepared according to the procedure reported in step-3 of scheme-1, from 2-(4-amino-5-(2-methylpyrimidin-5-yl)-7H-pyrrolo[2,3-d]pyrimidin-7-yl)acetic acid (117c) (50 mg, 0.176 mmol) in DMF (3 mL) using (2S,4R)—N-(3-chloro-2-fluorobenzyl)-4-fluoropyrrolidine-2-carboxamide (7a) (48.3 mg, 0.176 mmol), HATU (100 mg, 0.264 mmol), DIPEA (0.123 mL, 0.704 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] (2S,4R)-1-(2-(4-amino-5-(2-methylpyrimidin-5-yl)-7H-pyrrolo[2,3-d]pyrimidin-7-yl)acetyl)-N-(3-chloro-2-fluorobenzyl)-4-fluoropyrrolidine-2-carboxamide (117d) (67 mg, 70% yield) HCl salt as a white solid; $^1$H NMR (300 MHz, DMSO-$d_6$) δ 9.22 and 8.75 (2t, J=5.9 Hz, 1H, $D_2O$ exchangeable), 8.80 (s, 2H), 8.52 (s, 1H), 8.40 (s, 2H, $D_2O$ exchangeable), 7.73 and 7.72 (2s, 1H), 7.49-7.34 (m, 1H), 7.29-7.13 (m, 1H), 7.02 (td, J=7.9, 1.1 Hz, 1H), 5.63-4.68 (m, 3H), 4.52-3.76 (m, 5H), 2.72 (s, 3H), 2.60-2.19 (m, 1H), 2.18-1.93 (m, 1H). $^1$H NMR (300 MHz, DMSO-$d_6$/$D_2O$) δ 8.80 (s, 2H), 8.48 and 8.46 (2s, 1H), 7.70 and 7.68 (2s, 1H), 7.49-7.33 (m, 1H), 7.28-7.13 (m, 1H), 7.04 (td, J=7.9, 1.1 Hz, 1H), 5.63-5.15 (m, 3H), 4.52-3.84 (m, 5H), 2.73 (s, 3H), 2.52-2.25 (m, 1H), 2.23-1.90 (m, 1H); $^{19}$F NMR (282 MHz, DMSO) δ−121.30, −121.61, −176.09, MS (ES+): 541.2 (M+1); (ES−): 539.2 (M−1); Analysis calculated for $C_{25}H_{23}ClF_2N_8O_2 \cdot 1.65HCl \cdot 3.75H_2O$: C, 44.91; H, 4.85; Cl, 14.05; N, 16.76. Found: C, 45.01; H, 4.68; Cl, 14.10; N, 16.44.

Scheme 118

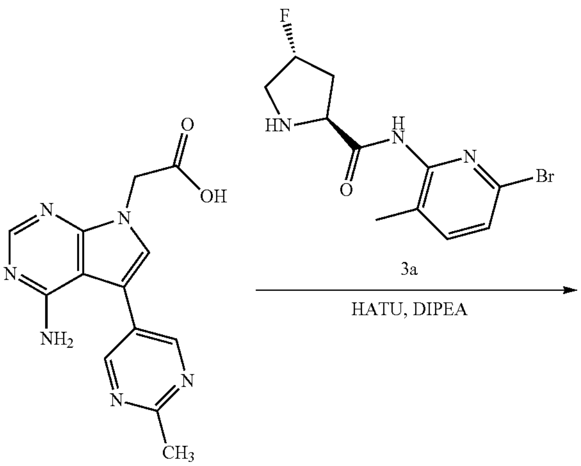

117c

3a

-continued

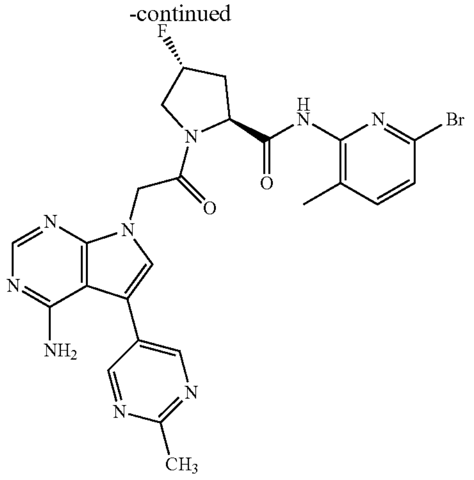

118a

Preparation of (2S,4R)-1-(2-(4-amino-5-(2-methylpyrimidin-5-yl)-7H-pyrrolo[2,3-d]pyrimidin-7-yl)acetyl)-N-(6-bromo-3-methylpyridin-2-yl)-4-fluoropyrrolidine-2-carboxamide (118a)

Compound 118a was prepared according to the procedure reported in step-3 of scheme-1, from 2-(4-amino-5-(2-methylpyrimidin-5-yl)-7H-pyrrolo[2,3-d]pyrimidin-7-yl)acetic acid (117c) (50 mg, 0.176 mmol) in DMF (3 mL) using (2S,4R)—N-(6-bromo-3-methylpyridin-2-yl)-4-fluoropyrrolidine-2-carboxamide (3a) (53 mg, 0.176 mmol), HATU (100 mg, 0.264 mmol) and DIPEA (0.123 mL, 0.704 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] (2S,4R)-1-(2-(4-amino-5-(2-methylpyrimidin-5-yl)-7H-pyrrolo[2,3-d]pyrimidin-7-yl)acetyl)-N-(6-bromo-3-methylpyridin-2-yl)-4-fluoropyrrolidine-2-carboxamide (118a) (37 mg, 37% yield) HCl salt as a pale yellow solid; $^1$H NMR (300 MHz, DMSO-$d_6$) δ 10.92 and 10.50 (2s, 1H, $D_2O$ exchangeable), 8.78 (s, 2H), 8.50 (s, 1H), 8.32 (s, 2H, $D_2O$ exchangeable), 7.78 and 7.71 (2s, 1H), 7.64-7.57 (m, 1H), 7.52 and 7.43 (2d, J=7.9 Hz, 11H), 5.65-5.21 (m, 3H), 4.61 (t, J=8.5 Hz, 1H), 4.21 (dd, J=21.7, 12.5 Hz, 1H), 3.94 (dd, J=38.0, 12.6 Hz, 1H), 2.70 (s, 3H), 2.67-2.60 (m, 1H), 2.34-2.06 (m, 1H), 2.03 (s, 3H); $^{19}$F NMR (282 MHz, DMSO-$d_6$) δ−176.04. MS (ES+): 568.1 (M+1); (ES−): 566.1 (M−1).

Scheme 119

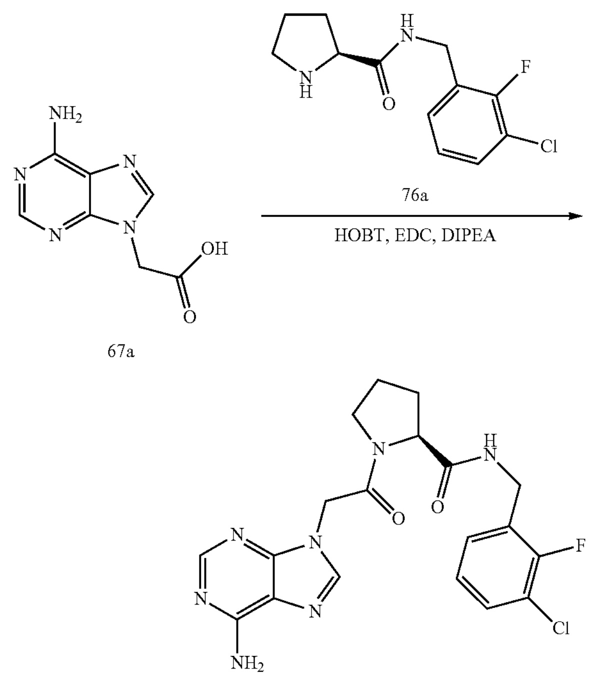

76a

67a

119a

Preparation of (S)-1-(2-(6-amino-9H-purin-9-yl) acetyl)-N-(3-chloro-2-fluorobenzyl)pyrrolidine-2-carboxamide (119a)

To a mixture of 2-(6-amino-9H-purin-9-yl)acetic acid (67a) (50 mg, 0.259 mmol) and (S)—N-(3-chloro-2-fluorobenzyl)pyrrolidine-2-carboxamide (76a) (66.4 mg, 0.259 mmol) in DMF (1 mL) was added 1H-benzo[d][1,2,3]triazol-1-ol (HOBT) (17.49 mg, 0.129 mmol), N1-((ethylimino)methylene)-N3,N3-dimethylpropane-1,3-diamine hydrochloride (EDC) (99 mg, 0.518 mmol), DIPEA (0.135 mL, 0.777 mmol) and stirred at RT for 16 h. This mixture was diluted with ethyl acetate (120 mL), washed with water (2×30 mL), brine (30 mL), dried, filtered and concentrated under vacuum. The residue obtained was purified by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] to afford (S)-1-(2-(6-amino-9H-purin-9-yl)acetyl)-N-(3-chloro-2-fluorobenzyl)pyrrolidine-2-carboxamide (119a) (9 mg, 8% yield) HCl salt as a white solid: $^1H$ NMR (300 MHz, DMSO-$d_6$) δ 8.49 (t, J=5.9 Hz, 1H), 8.36 (s, 1H), 8.25 (s, 1H), 7.53-7.32 (m, 1H), 7.26-7.15 (m, 1H), 7.09 (td, J=7.9, 1.0 Hz, 1H), 5.30-5.11 (m, 2H), 4.78-4.40 (m, 1H), 4.36-4.25 (m, 2H), 3.79-3.61 (m, 2H), 2.20-1.69 (m, 4H). $^{19}F$ NMR (282 MHz, DMSO-$d_6$) δ−121.70; MS (ES+): 432.1 (M+1); (ES−): 430.1 (M−1), 466.1 (M+Cl).

Scheme 120

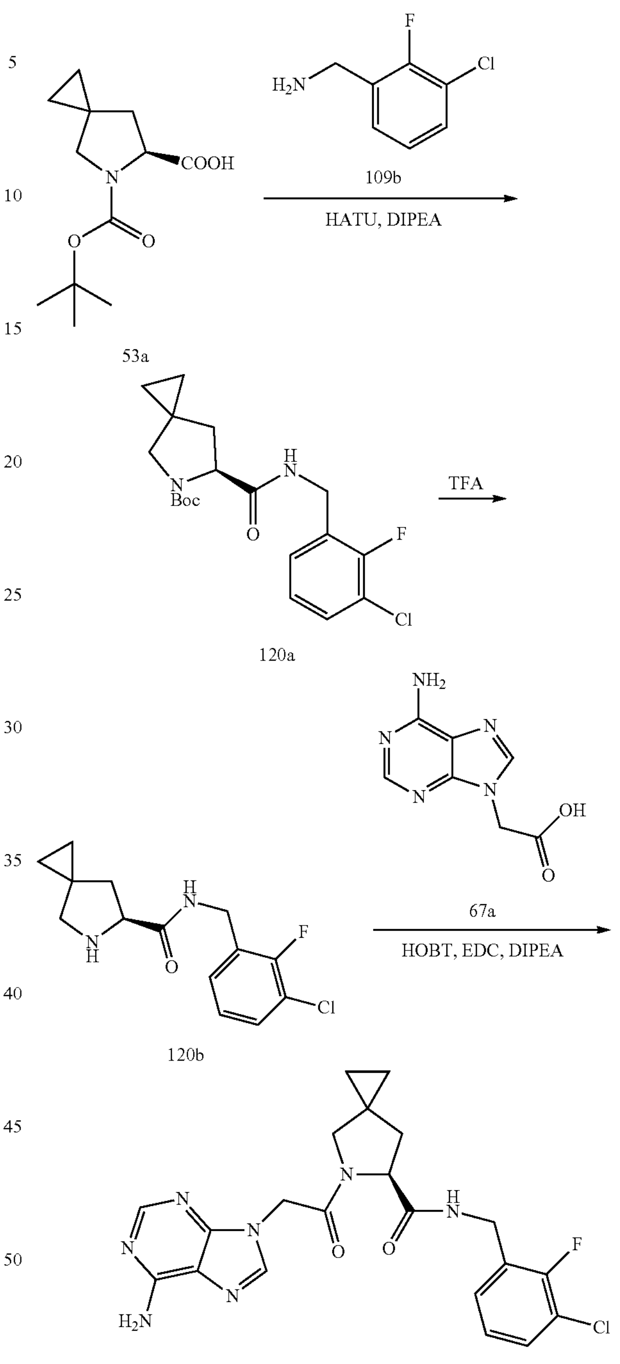

53a

109b

120a

67a

120b

120c

Preparation of(S)-5-(2-(6-amino-9H-purin-9-yl) acetyl)-N-(3-chloro-2-fluorobenzyl)-5-azaspiro[2.4]heptane-6-carboxamide (120c)

Step-1: Preparation of (S)-tert-butyl 6-((3-chloro-2-fluorobenzyl)carbamoyl)-5-azaspiro[2.4]heptane-5-carboxylate (120a)

Compound 120a was prepared according to the procedure reported in step-3 of scheme-1, from (S)-5-(tert-butoxycarbonyl)-5-azaspiro[2.4]heptane-6-carboxylic acid (53a) (0.5 g, 2.072 mmol) using (3-chloro-2-fluorophenyl)methanamine (109b) (0.331 mg, 2.072 mmol), (HATU) (1.182 g, 3.11 mmol), DIPEA (1.083 mL, 6.22 mmol) in DMF (5 mL) and stirring at RT for 16 h. This gave after workup and purification by flash column chromatography [silica gel (40 g), eluting with EtOAc/MeOH in Hexanes 0-100%] (S)-tert-butyl 6-((3-chloro-2-fluorobenzyl)carbamoyl)-5-azaspiro[2.4]heptane-5-carboxylate (120a) as a pale-yellow gel (0.758 g, 96% yield); MS (ES+): 405.1 (M+Na).

Step-2: Preparation of (S)—N-(3-chloro-2-fluorobenzyl)-5-azaspiro[2.4]heptane-6-carboxamide (120b)

Compound 120b was prepared according to the procedure reported in step-2 of scheme-1, from (S)-tert-butyl 6-((3-chloro-2-fluorobenzyl)carbamoyl)-5-azaspiro[2.4]heptane-5-carboxylate (120a) (0.758 g, 1.980 mmol) using TFA (0.763 mL, 9.90 mmol) in DCM (6 mL) and stirring overnight at room temperature. This gave after workup and purification by reverse phase column chromatography [C18 (30 g), eluting with ACN in water (containing 0.1% HCl) from 0 to 100%] (S)—N-(3-chloro-2-fluorobenzyl)-5-azaspiro[2.4]heptane-6-carboxamide (120b) (0.535 g, 9% yield); $^1$H NMR (300 MHz, DMSO-$d_6$) δ 9.09 (t, J=5.7 Hz, 1H), 8.78 (s, 1H), 7.53 (ddd, J=7.9, 7.2, 1.8 Hz, 1H), 7.34 (ddd, J=7.7, 6.7, 1.8 Hz, 1H), 7.22 (td, J=7.8, 1.1 Hz, 1H), 4.56-4.26 (m, 3H), 3.14 (s, 2H), 2.23 (dd, J=13.0, 8.3 Hz, 1H), 1.90 (dd, J=13.0, 7.3 Hz, 1H), 0.78-0.42 (m, 4H); $^{19}$F NMR (282 MHz, DMSO-$d_6$) δ−121.07; MS (ES+): 283.1 (M+Na).

Step-3: Preparation of (S)-5-(2-(6-amino-9H-purin-9-yl)acetyl)-N-(3-chloro-2-fluorobenzyl)-5-azaspiro[2.4]heptane-6-carboxamide (120c)

Compound 120c was prepared according to the procedure reported in scheme-119, from (S)—N-(3-chloro-2-fluorobenzyl)-5-azaspiro[2.4]heptane-6-carboxamide (120b) (73.2 mg, 0.259 mmol) in DMF (5 mL) using 2-(6-amino-9H-purin-9-yl)acetic acid (67a) (50 mg, 0.259 mmol), HOBT (17.49 mg, 0.129 mmol), EDC (99 mg, 0.518 mmol), DIPEA (0.180 mL, 1.035 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] (S)-5-(2-(6-amino-9H-purin-9-yl)acetyl)-N-(3-chloro-2-fluorobenzyl)-5-azaspiro[2.4]heptane-6-carboxamide (120c) (11 mg, 9% yield) HCl salt as a white solid; $^1$H NMR (300 MHz, DMSO-$d_6$) δ 8.94 and 8.64 (2t, J=6.0 Hz, 1H), 8.45 (s, 1H), 8.37 and 8.32 (2s, 1H), 7.57-7.35 (m, 1H), 7.31-7.15 (m, 1H), 7.10 (td, J=7.9, 1.1 Hz, 1H), 5.37-5.11 (m, 2H), 4.92-4.18 (m, 3H), 3.83-3.16 (m, 2H), 2.28 (dd, J=12.7, 8.7 Hz, 1H), 1.88-1.61 (m, 1H), 0.76-0.29 (m, 4H). $^{19}$F NMR (282 MHz, DMSO-$d_6$) δ-121.60; MS (ES+): 458.1 (M+1); (ES−): 456.1 (M−1), 492.1 (M+Cl).

Scheme 121

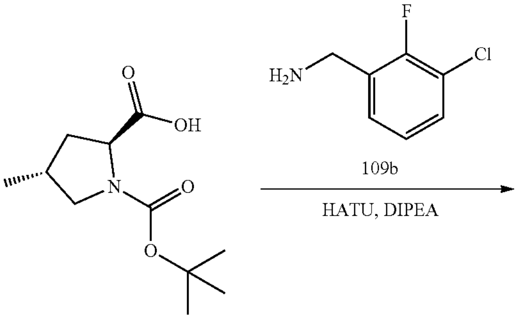

121a

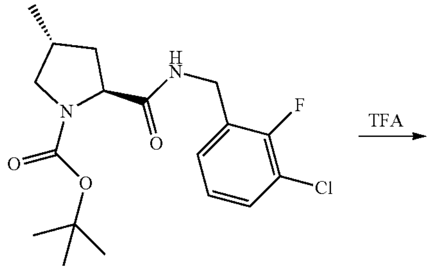

121b

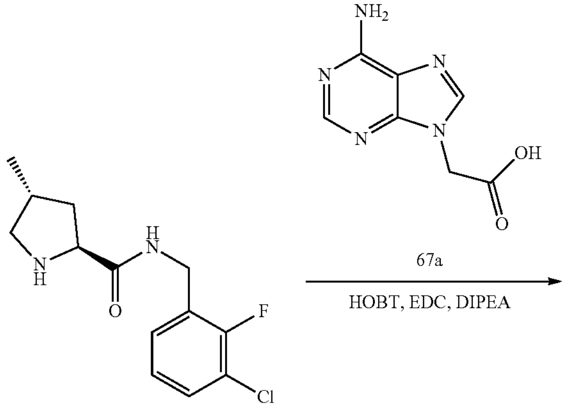

121c

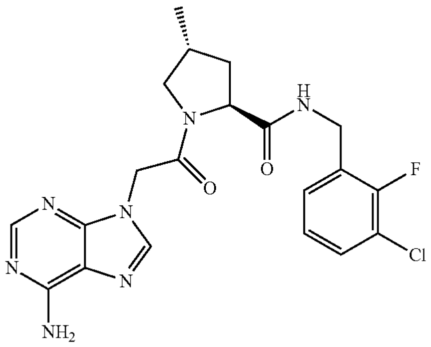

121d

Preparation of (2S,4R)-1-(2-(6-amino-9H-purin-9-yl)acetyl)-N-(3-chloro-2-fluorobenzyl)-4-methylpyrrolidine-2-carboxamide (121d)

Step-1: Preparation of (2S,4R)-tert-butyl 2-((3-chloro-2-fluorobenzyl)carbamoyl)-4-methylpyrrolidine-1-carboxylate (121b)

Compound 121b was prepared according to the procedure reported in step-1 of scheme-5, from (2S,4R)-1-(tert-butoxycarbonyl)-4-methylpyrrolidine-2-carboxylic acid (121a) (0.4 g, 1.745 mmol; CAS #364750-80-1) using (3-chloro-2-fluorophenyl)methanamine (109b) (0.658 mL, 5.23 mmol; CAS #72235-55-3), HATU (995 mg, 2.62 mmol), DIPEA (0.912 mL, 5.23 mmol) in DMF (5 mL) and stirring at RT for 16 h. This gave after workup and purification by flash column chromatography [silica gel (40 g), eluting with EtOAc/MeOH (ratio 9:1) in Hexanes from 0-100%] (2S,4R)-tert-butyl 2-((3-chloro-2-fluorobenzyl)carbamoyl)-4-methylpyrrolidine-1-carboxylate (121b) as a white solid (0.55 g, 85% yield); MS (ES+): 393.1 (M+Na).

Step-2: Preparation of (2S,4R)—N-(3-chloro-2-fluorobenzyl)-4-methylpyrrolidine-2-carboxamide (121c)

Compound 121c was prepared according to the procedure reported in step-2 of scheme-1, from (2S,4R)-tert-butyl 2-((3-chloro-2-fluorobenzyl)carbamoyl)-4-methylpyrrolidine-1-carboxylate (121b) (0.55 g, 1.483 mmol) using TFA (1.143 mL, 14.83 mmol) in DCM (6 mL) and stirring overnight at room temperature. This gave after workup and purification by reverse phase column chromatography [C18 (30 g), eluting with ACN in water (containing 0.1% HCl) from 0 to 100%] (2S,4R)—N-(3-chloro-2-fluorobenzyl)-4-methylpyrrolidine-2-carboxamide (121c) (0.34 g, 85% yield); $^{1}H$ NMR (300 MHz, DMSO-$d_4$) δ 9.92 (s, 1H), 9.15 (t, J=5.7 Hz, 1H), 8.56 (s, 1H), 7.52 (ddd, J=8.9, 7.2, 1.8 Hz, 1H), 7.39-7.29 (m, 1H), 7.22 (td, J=7.9, 1.1 Hz, 1H), 4.42 (d, J=5.7 Hz, 2H), 4.32 (s, 1H), 3.47-3.36 (m, 1H), 2.87-2.64 (m, 1H), 2.29 (h, J=7.2 Hz, 1H), 2.12-1.99 (m, 1H), 1.99-1.79 (m, 1H), 1.02 (d, J=6.7 Hz, 3H); $^{19}F$ NMR (282 MHz, DMSO-$d_6$) δ−121.13; MS (ES+): 271.1 (M+1).

Step-3: Preparation of (2S,4R)-1-(2-(6-amino-9H-purin-9-yl)acetyl)-N-(3-chloro-2-fluorobenzyl)-4-methylpyrrolidine-2-carboxamide (121d)

Compound 121d was prepared according to the procedure reported in scheme-119, from (2S,4R)—N-(3-chloro-2-fluorobenzyl)-4-methylpyrrolidine-2-carboxamide (121c) (70.1 mg, 0.259 mmol) in DMF (5 mL) using 2-(6-amino-9H-purin-9-yl)acetic acid (67a) (50 mg, 0.259 mmol) HOBT (17.49 mg, 0.129 mmol), EDC (99 mg, 0.518 mmol), DIPEA (0.180 mL, 1.035 mmol) and stirring at RT for 16 h. This gave after workup and purification by flash column chromatography [silica gel (12 g), eluting with DMA-80 in DCM from 0 to 100%] followed by purification using reverse phase column chromatography [C18 column (15 g), eluting with ACN in water (containing 0.1% HCl) from 0-100%] (2S,4R)-1-(2-(6-amino-9H-purin-9-yl)acetyl)-N-(3-chloro-2-fluorobenzyl)-4-methylpyrrolidine-2-carboxamide (121d) (11 mg, 9% yield) HCl salt as a white solid: $^{1}H$ NMR (300 MHz, DMSO-$d_6$) δ 8.89 and 8.52 (2t, J=5.9 Hz, 1H), 8.35 and 8.33 (2s, 1H), 8.25 and 8.22 (2s, 1H), 7.53-7.33 (m, 1H), 7.21 (td, J=7.2, 6.5, 1.9 Hz, 1H), 7.09 (td, J=7.9, 1.0 Hz, 1H), 5.20 (q, J=17.0 Hz, 2H), 4.79-4.16 (m, 3H), 3.92 (t, J=8.4 Hz, 1H), 3.73-3.56 (m, 1H), 3.22 (t, J=9.3 Hz, 1H), 2.04-1.91 (m, 1H), 1.86-1.68 (m, 1H), 1.07 and 1.01 (2d, J=6.4 Hz, 3H). $^{19}F$ NMR (282 MHz, DMSO-$d_6$) δ−121.70; MS (ES+): 446.1 (M+1), 468.1 (M+Na); (ES−): 444.1 (M−1), 480.1 (M+Cl).

Scheme 122

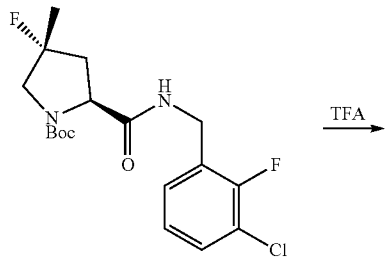

122a

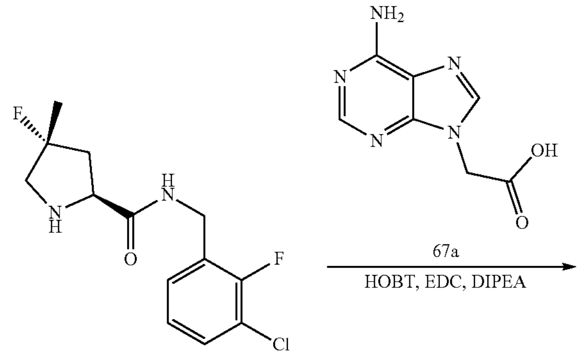

122b

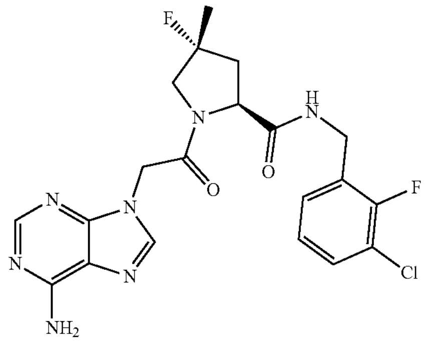

122c

Preparation of (2S,4R)-1-(2-(6-amino-9H-purin-9-yl)acetyl)-N-(3-chloro-2-fluorobenzyl)-4-fluoro-4-methylpyrrolidine-2-carboxamide (122c)

Step-1: Preparation of (2S,4R)—N-(3-chloro-2-fluorobenzyl)-4-fluoro-4-methylpyrrolidine-2-carboxamide (122b)

Compound 122b was prepared according to the procedure reported in step-2 of scheme-1, from (2S,4R)-tert-butyl 2-((3-chloro-2-fluorobenzyl)carbamoyl)-4-fluoro-4-methylpyrrolidine-1-carboxylate (122a) [(700 mg, 1.800 mmol); prepared according to the procedure reported by Altmann, Eva; et al., PCT Int. Appl. (2012), WO 2012093101 A1 20120712] using TFA (0.693 mL, 9.0 mmol) in DCM (7 mL) and stirring overnight at room temperature. This gave after workup and purification by flash column chromatography [C18 (30 g), eluting with ACN in water (containing 0.1% HCl) from 0 to 100%] (2S,4R)—N-(3-chloro-2-fluorobenzyl)-4-fluoro-4-methylpyrrolidine-2-carboxamide (122b) (449 mg, 86% yield); 1H NMR (300 MHz, DMSO-$d_6$) δ 9.23 (t, J=5.7 Hz, 1H), 7.53 (ddd, J=8.0, 7.2, 1.8 Hz, 1H), 7.35 (ddd, J=7.8, 6.7, 1.8 Hz, 1H), 7.23 (td, J=7.9, 1.1 Hz, 1H), 4.53-4.32 (m, 3H), 3.60-3.22 (m, 3H), 2.66 (td, J=14.3, 7.5 Hz, 1H), 2.20-1.92 (m, 1H), 1.54 (d, J=21.3 Hz, 3H); MS (ES+): 289.1 (M+1).

Step-2: Preparation of (2S,4R)-1-(2-(6-amino-9H-purin-9-yl)acetyl)-N-(3-chloro-2-fluorobenzyl)-4-fluoro-4-methylpyrrolidine-2-carboxamide (122c)

Compound 122c was prepared according to the procedure reported in scheme-119, from (2S,4R)—N-(3-chloro-2-fluorobenzyl)-4-fluoro-4-methylpyrrolidine-2-carboxamide (122b) (75 mg, 0.259 mmol) in DMF (5 mL) using 2-(6-amino-9H-purin-9-yl)acetic acid (67a) (50 mg, 0.259 mmol) HOBT (17.49 mg, 0.129 mmol), EDC (99 mg, 0.518 mmol), DIPEA (0.180 mL, 1.035 mmol) and stirring at RT for 16 h. This gave after workup and purification by flash column chromatography [silica gel (12 g), eluting with DMA-80 in DCM from 0 to 100%] followed by purification using reverse phase column chromatography [C18 column (15 g), eluting with ACN in water (containing 0.1% HCl) from 0-100%] (2S,4R)-1-(2-(6-amino-9H-purin-9-yl)acetyl)-N-(3-chloro-2-fluorobenzyl)-4-fluoro-4-methylpyrrolidine-2-carboxamide (122c) (11 mg, 9% yield) HCl salt as a white solid; 1H NMR (300 MHz, DMSO-$d_6$) δ 9.06 and 8.67 (2t, J=5.9 Hz, 1H), 8.37 (s, 1H), 8.31 (s, 1H), 7.57-7.37 (m, 1H), 7.25-7.13 (m, 1H), 7.07 (td, J=7.9, 1.1 Hz, 1H), 5.45-5.03 (m, 2H), 4.92-3.57 (m, 5H), 2.44 (m, 11H), 2.14-1.82 (m, 1H), 1.55 (d, J=21.1, 3H). $^{19}F$ NMR (282 MHz, DMSO-$d_6$) δ−121.65, −139.64; MS (ES+): 464.1 (M+1), 486.1 (M+Na); (ES−): 462.1 (M−1), 498.1 (M+Cl).

Scheme 123

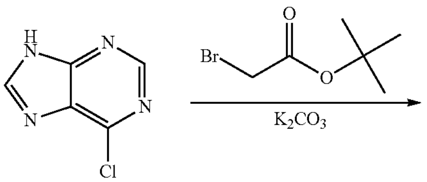

123a

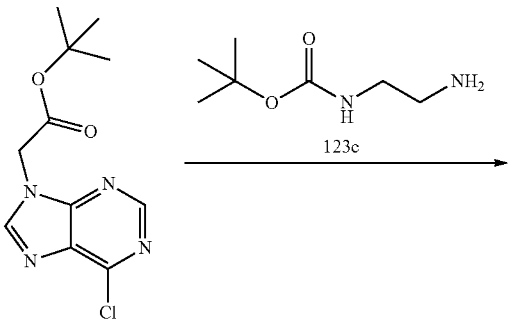

123c

123b

-continued

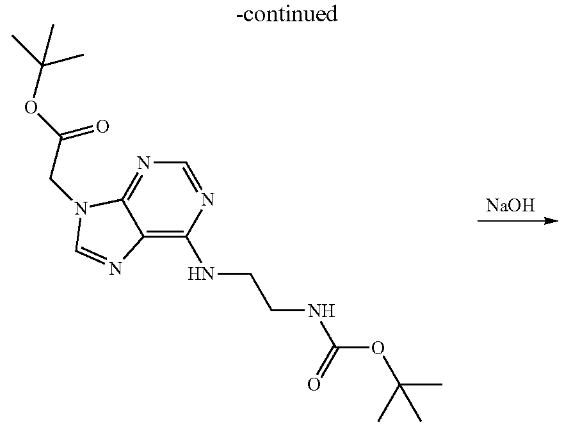

123d

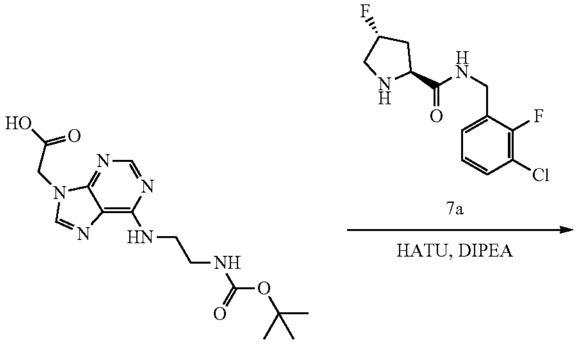

7a

123e

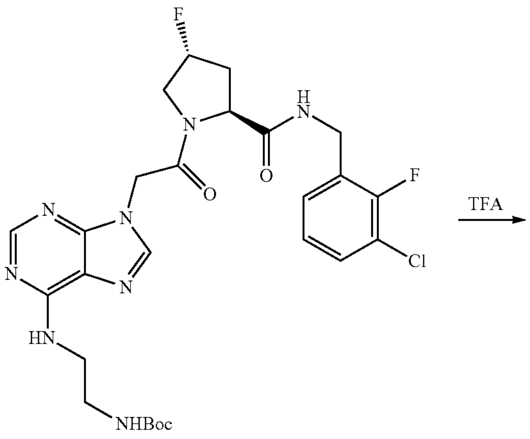

123f

-continued

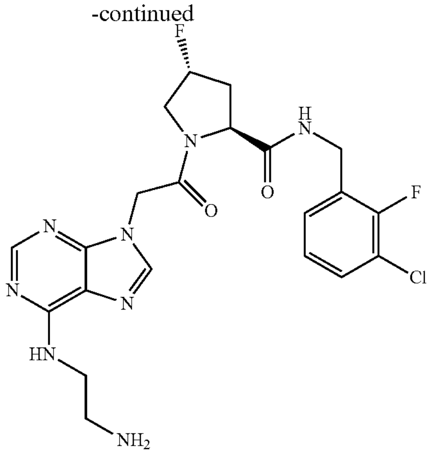

123g

Preparation of (2S,4R)-1-(2-(6-((2-aminoethyl) amino)-9H-purin-9-yl)acetyl)-N-(3-chloro-2-fluorobenzyl)-4-fluoropyrrolidine-2-carboxamide (123 g)

Step-1: Preparation of tert-butyl 2-(6-chloro-9H-purin-9-yl)acetate (123b)

Compound 123b was prepared according to the procedure reported in step-1 of scheme-1, from 6-chloro-9H-purine (123a) (8 g, 51.8 mmol; CAS #87-42-3) in acetonitrile (400 mL) using tert-butyl 2-bromoacetate (11.46 mL, 78 mmol), $K_2CO_3$ (14.31 g, 104 mmol) and beating at 65° C. for 48 h. This gave after workup and purification by flash column chromatography [silica gel (120 g), eluting with EtOAc in Hexane from 0-100%] tert-butyl 2-(6-chloro-9H-purin-9-yl) acetate (123b) (8.89 g, 64% yield) as an off-white solid; 1H NMR (300 MHz, DMSO-$d_6$) δ 8.81 (s, 1H), 8.68 (s, 1H), 5.16 (s, 2H), 1.42 (s, 9H); MS (ES+): 269.10 (M+1).

Step-2: Preparation of tert-butyl 2-(6-((2-((tert-butoxycarbonyl)amino)ethyl)amino)-9H-purin-9-yl) acetate (123d)

A mixture of tert-butyl 2-(6-chloro-9H-purin-9-yl)acetate (123b) (0.699 g, 2.6 mmol) and tert-butyl 2-aminoethylcarbamate (123c) (0.961 g, 6.0 mmol; CAS #57260-73-8) in EtOH (20 mL) was refluxed for 6 h. The solvent was evaporated under reduced pressure, and the product was purified by flash column chromatography [silica gel (40 g), eluting with DMA-80 in DCM from 0 to 100%] yielding tert-butyl 2-(6-((2-((tert-butoxycarbonyl)amino)ethyl) amino)-9H-purin-9-yl)acetate (123d) (1.02 g, 100% yield); $^1$H NMR (300 MHz, DMSO-$d_6$) δ 8.20 (s, 1H), 8.11 (s, 1H), 7.75 (s, 1H), 6.93 (s, 1H), 4.95 (s, 2H), 3.52 (s, 2H), 3.17 (q, J=6.1 Hz, 2H), 1.39 (d, J=16.4 Hz, 18H); MS (ES+): 393.20 (M+1).

Step-3: Preparation of 2-(6-((2-((tert-butoxycarbonyl)amino)ethyl)amino)-9H-purin-9-yl)acetic acid (123e)

To a stirred solution of tert-butyl 2-(6-((2-((tert-butoxycarbonyl)amino)ethyl)amino)-9H-purin-9-yl)acetate (123d) (1.02 g, 2.60 mmol) in THF (3.00 mL) and MeOH (3.00 mL) was added 2N sodium hydroxide (1.5 mL, 3.00 mmol) and stirred at room temperature for 45 min. This gave after workup 2-(6-(2-(tert-butoxycarbonylamino)ethylamino)-9H-purin-9-yl)acetic acid (123e) (735 mg, 84% yield); MS (ES+): 337.20 (M+1).

Step-4: Preparation of tert-butyl (2-((9-(2-((2S,4R)-2-((3-chloro-2-fluorobenzyl)carbamoyl)-4-fluoropyrrolidin-1-yl)-2-oxoethyl)-9H-purin-6-yl)amino) ethyl)carbamate (123f)

Compound 123f was prepared according to the procedure reported in step-3 of scheme-1, from 2-(6-((2-((tert-butoxycarbonyl)amino)ethyl)amino)-9H-purin-9-yl)acetic acid (123e) (100 mg, 0.297 mmol) in DMF (2 mL) using (2S, 4R)—N-(3-chloro-2-fluorobenzyl)-4-fluoropyrrolidine-2-carboxamide (7a) (82 mg, 0.297 mmol), HATU (170 mg, 0.446 mmol), DIPEA (0.207 mL, 1.189 mmol) and stirring at RT for 16 h. This gave after workup and purification by flash column chromatography [silica gel (24 g), eluting with DMA-80 in DCM from 0-100%] tert-butyl (2-((9-(2-((2S, 4R)-2-((3-chloro-2-fluorobenzyl)carbamoyl)-4-fluoropyrrolidin-1-yl)-2-oxoethyl)-9H-purin-6-yl)amino)ethyl)carbamate (123f) (102 mg, 58% yield) HCl salt as a white solid; MS (ES+): 593.2 (M+1).

Step-5: Preparation of (2S,4R)-1-(2-(6-((2-aminoethyl)amino)-9H-purin-9-yl)acetyl)-N-(3-chloro-2-fluorobenzyl)-4-fluoropyrrolidine-2-carboxamide (123 g)

Compound 123g was prepared according to the procedure reported in step-2 of scheme-1, from tert-butyl (2-((9-(2-((2S,4R)-2-((3-chloro-2-fluorobenzyl)carbamoyl)-4-fluoropyrrolidin-1-yl)-2-oxoethyl)-9H-purin-6-yl)amino)ethyl) carbamate (123f) (100 mg, 0.169 mmol) in DCM (2.5 mL) using TFA (0.260 mL, 3.37 mmol) and stirring at RT for 70 min. This gave after workup and purification by reverse phase column chromatography [C18 column (50 g), eluting with ACN in water (containing 0.1% HCl) from 0-100%] (2S,4R)-1-(2-(6-((2-aminoethyl)amino)-9H-purin-9-yl) acetyl)-N-(3-chloro-2-fluorobenzyl)-4-fluoropyrrolidine-2-carboxamide (123 g) (65 mg, 78% yield) HCl salt as a white solid; $^1$H NMR (300 MHz, DMSO-$d_6$) δ 9.26 and 8.82 (2t, J=5.9 Hz, 1H, $D_2O$ exchangeable), 8.38 (d, J=11.2 Hz, 2H, 1H $D_2O$ exchangeable), 8.20 (s, 3H, 2H $D_2O$ exchangeable), 7.53-7.35 (m, 1H), 7.35-7.13 (m, 1H), 7.05 (t, J=7.9 Hz, 1H), 5.67-5.10 (m, 3H), 4.95-3.94 (m, 5H), 3.87 (m, 2H), 3.13 (m, 2H), 2.62-2.53 (m, 1H), 2.18-1.80 (m, 1H). $^{19}$F NMR (282 MHz, DMSO-$d_6$) δ−121.70, −176.23; MS (ES+): 493.1 (M+1); (ES−): 491.2 (M−1), 527.1 (M+Cl). Analysis calculated for $C_{21}H_{23}ClF_2N_8O_2 \cdot 1.875HCl \cdot 2H_2O$: C, 42.23; H, 4.87; Cl, 17.06; N, 18.76. Found: C, 42.28; H, 4.81; Cl, 16.88; N, 18.54.

Scheme 124

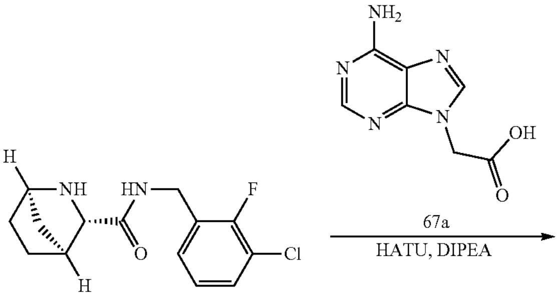

124a

-continued

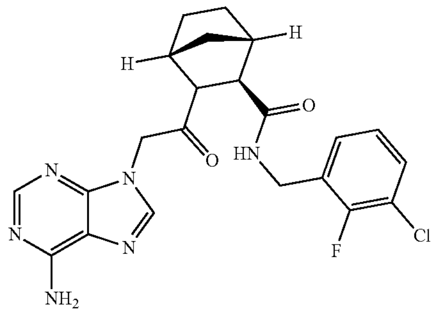

124b

Preparation of (1R,3S,4S)-2-(2-(6-amino-9H-purin-9-yl)acetyl)-N-(3-chloro-2-fluorobenzyl)-2-azabicyclo[2.2.1]heptane-3-carboxamide (124b)

Compound 124b was prepared according to the procedure reported in step-3 of scheme-1, from (1R,3S,4S)—N-(3-chloro-2-fluorobenzyl)-2-azabicyclo[2.2.1]heptane-3-carboxamide (124a) (143 mg, 0.505 mmol; prepared according to the procedure reported by McDonald, Andrew; Qian, Shawn in PCT Int. Appl. (2018), WO 2018229543 A2 20181220) in DMF (1.5 mL) using 2-(6-amino-9H-purin-9-yl)acetic acid (67a) (65 mg, 0.337 mmol), HATU (192 mg, 0.505 mmol), DIPEA (0.293 mL, 1.683 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] (1R,3S,4S)-2-(2-(6-amino-9H-purin-9-yl)acetyl)-N-(3-chloro-2-fluorobenzyl)-2-azabicyclo[2.2.1]heptane-3-carboxamide (124b) (73 mg, 47% yield) HCl salt as a white solid; 1H NMR (300 MHz, DMSO-$d_6$) (a mixture of two rotamers) δ 8.98 (t, J=5.8 Hz) and 8.56 (t, J=5.9 Hz) (2t, 1H, $D_2O$ exchangeable), 8.49 (s) and 8.47 (s) (2s, 1H), 8.43 (s) and 8.35 (s), (2s, 1H), 7.51-7.03 (m, 3H), 5.46 (d, J=17.0 Hz, 1H), 5.10 (d, J=16.9 Hz, 1H), 4.79-4.16 (m, 3H), 3.84 (s, 1H), 2.58 (s, 1H), 1.99 (d, J=9.8 Hz, 1H), 1.88-1.21 (m, 5H); $^{19}F$ NMR (282 MHz, DMSO-$d_6$) δ−121.38, −121.65. MS (ES+): 458.1 (M+1); (ES−): 456.7 (M−1); Analysis calculated for $C_{21}H_{21}ClFN_7O_2 \cdot HCl \cdot 2.25H_2O$: C, 47.16; H, 4.99; Cl, 13.26; N, 18.33. Found: C, 47.34; H, 4.76; Cl, 13.09; N, 18.16.

Scheme 125

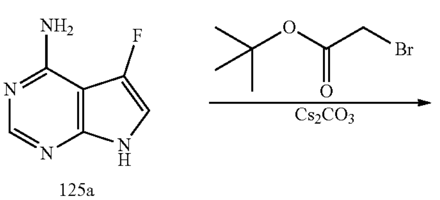

125a

-continued

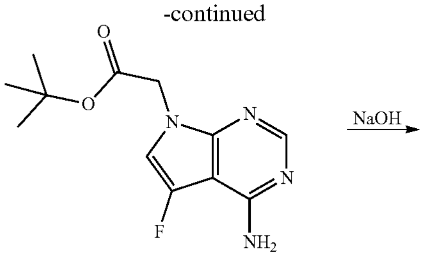

125b

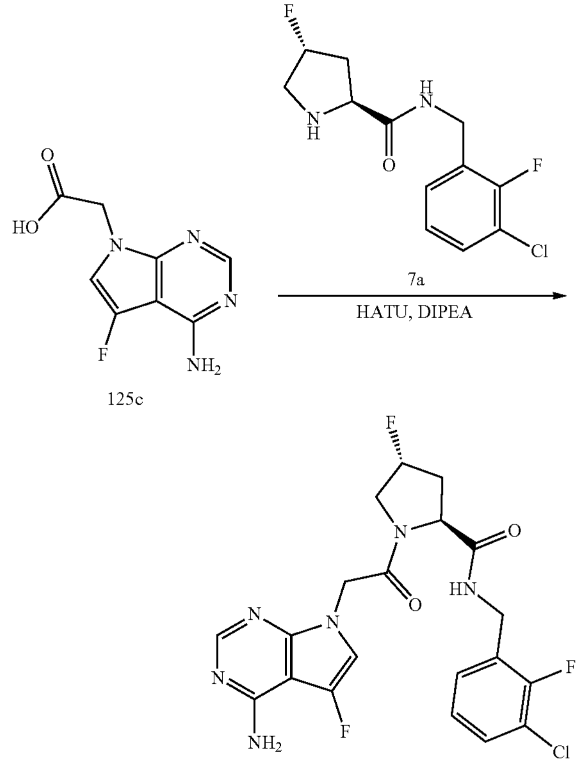

125c

125d

Preparation of (2S,4R)-1-(2-(4-amino-5-fluoro-7H-pyrrolo[2,3-d]pyrimidin-7-yl)acetyl)-N-(3-chloro-2-fluorobenzyl)-4-fluoropyrrolidine-2-carboxamide (125d)

Step-1: Preparation of tert-butyl 2-(4-amino-5-fluoro-7H-pyrrolo[2,3-d]pyrimidin-7-yl)acetate (125b)

Compound 125b was prepared according to the procedure reported in step-1 of scheme-1, from 5-fluoro-7H-pyrrolo[2,3-d]pyrimidin-4-amine (125a) (0.5 g, 3.29 mmol; CAS #1080467-52-2) in DMF (15 mL) using tert-butyl 2-bromoacetate (0.510 mL, 3.45 mmol), $Cs_2CO_3$ (1.285 g, 3.94 mmol) and stirring at RT for 1.5 h. This gave after workup ter-butyl 2-(4-amino-5-fluoro-7H-pyrrolo[2,3-d]pyrimidin-7-yl)acetate (125b) (0.75 g, 86% yield) as an off-white solid; $^1H$ NMR (300 MH-z, DMSO-$d_6$) δ 8.05 (s, 1H), 7.13 (d, J=2.3 Hz, 1H), 6.99 (s, 2H), 4.81 (s, 2H), 1.41 (s, 9H); $^{19}F$ NMR (282 MHz, DMSO-$d_4$) δ−168.96; MS (ES+): 267.10 (M+1).

Step-2: Preparation of 2-(4-amino-5-fluoro-7H-pyrrolo[2,3-d]pyrimidin-7-yl)acetic acid (125c)

Compound 125c was prepared according to the procedure reported in step-4 of scheme-17, from tert-butyl 2-(4-amino-5-fluoro-7H-pyrrolo[2,3-d]pyrimidin-7-yl)acetate (125b) (720 mg, 2.70 mmol) in THF/MeOH (10 mL; ratio 1:1) using 2N sodium hydroxide (1.487 mL, 2.97 mmol) and stirring the reaction mixture for 1.5 h at RT. This gave after workup 2-(4-amino-5-fluoro-7H-pyrrolo[2,3-d]pyrimidin-7-yl)acetic acid (125c) (515 mg, 91% yield) as a pale purple solid; $^1H$ NMR (300 MHz, DMSO-$d_6$) δ 8.05 (s, 1H), 7.14 (d, J=2.3 Hz, 1H), 6.99 (s, 2H), 4.83 (s, 2H); MS (ES+): 211.1 (M+1).

Step-3: Preparation of (2S,4R)-1-(2-(4-amino-5-fluoro-7H-pyrrolo[2,3-d]pyrimidin-7-yl)acetyl)-N-(3-chloro-2-fluorobenzyl)-4-fluoropyrrolidine-2-carboxamide (125d)

Compound 125d was prepared according to the procedure reported in step-3 of scheme-1, from 2-(4-amino-5-fluoro-7H-pyrrolo[2,3-d]pyrimidin-7-yl)acetic acid (125c) (50 mg, 0.238 mmol) in DMF (2 mL) using (2S,4R)—N-(3-chloro-2-fluorobenzyl)-4-fluoropyrrolidine-2-carboxamide (7a) HCl salt (74 mg, 0.238 mmol), HATU (113 mg, 0.297 mmol), DIPEA (0.166 mL, 0.952 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] (2S,4R)-1-(2-(4-amino-5-fluoro-7H-pyrrolo[2,3-d]pyrimidin-7-yl)acetyl)-N-(3-chloro-2-fluorobenzyl)-4-fluoropyrrolidine-2-carboxamide (125d) (59 mg, 53% yield) HCl salt as a white solid; $^1H$ NMR (300 MHz, DMSO-$d_6$) δ 9.19 (t, J=5.7 Hz) and 8.75 (t, J=5.9 Hz) (2t, 1H, $D_2O$ exchangeable), 8.87 (s, 2H, $D_2O$ exchangeable), 8.35 (s, 1H), 7.48-7.33 (m, 2H), 7.29-7.21 (m, 1H), 7.06 (td, J=7.9, 1.1 Hz, 1H), 5.59-5.36 (m, 1H), 5.29 (d, J=17.0 Hz, 1H), 5.12 (d, J=16.9 Hz, 1H), 4.48-3.76 (m, 5H), 2.50-2.38 (m, 1H), 2.22-1.90 (m, 1H); $^{19}F$ NMR (282 MHz, DMSO-$d_6$) δ−121.33, −121.64, −165.54, −176.28; MS (ES+): 467.0 (M+1); Calculated for $C_{20}H_{18}ClF_3N_6O_2\cdot(H_2O)\cdot(HCl)$; C, 46.08; H, 4.06; Cl, 13.60; N, 16.12. Found: C, 45.98; H, 3.98; Cl, 13.26; N, 15.77.

Scheme 126

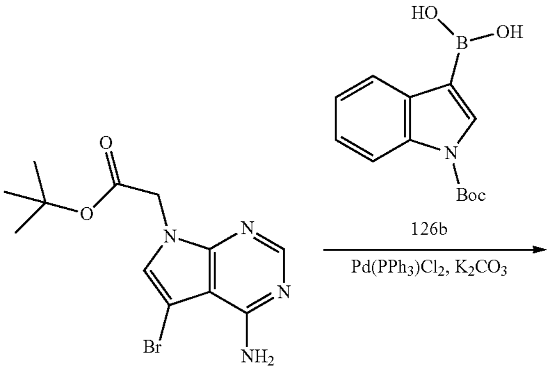

114b

-continued

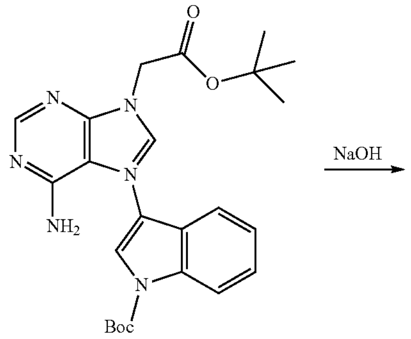

126c

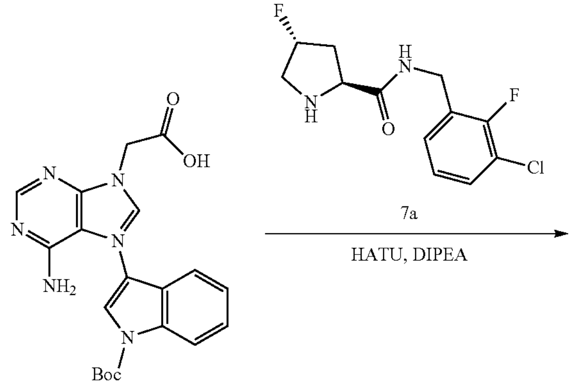

126d

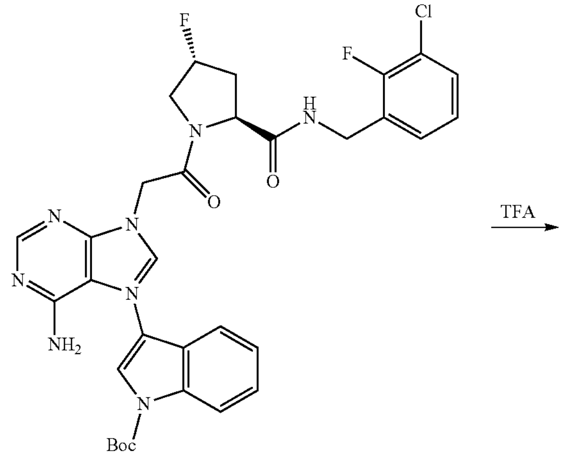

126e

-continued

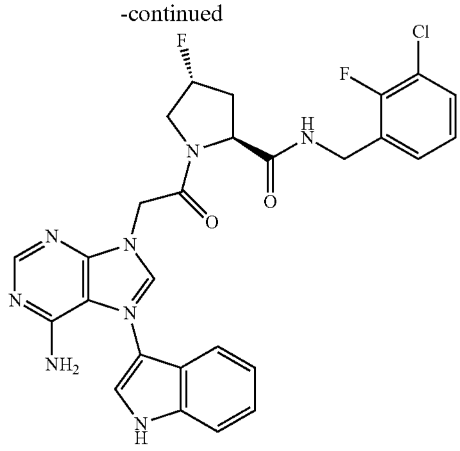

126f

Preparation of (2S,4R)-1-(2-(4-amino-5-(1H-indol-3-yl)-7H-pyrrolo[2,3-d]pyrimidin-7-yl)acetyl)-N-(3-chloro-2-fluorobenzyl)-4-fluoropyrrolidine-2-carboxamide (126f)

Step-1: Preparation of tert-butyl 3-(4-amino-7-(2-(tert-butoxy)-2-oxoethyl)-7H-pyrrolo[2,3-d]pyrimidin-5-yl)-1H-indole-1-carboxylate (126c)

Compound 126c was prepared according to the procedure reported in step-1 of scheme-59, from tert-butyl 2-(4-amino-5-bromo-7H-pyrrolo[2,3-d]pyrimidin-7-yl)acetate (114b) (290 mg, 0.886 mmol) in dioxane (8 mL) using (1-(tert-butoxycarbonyl)-1H-indol-3-yl)boronic acid (126b) (231 mg, 0.886 mmol), bis(triphenylphosphine)palladium(II) chloride (93 mg, 0.133 mmol) a solution of potassium carbonate (368 mg, 2.66 mmol) in water (1 mL) and heating at 100° C. for 4 h. This gave after workup and purification by flash column chromatography [silica gel (24 g), eluting with DMA-80 in DCM from 0-50%] tert-butyl 3-(4-amino-7-(2-(tert-butoxy)-2-oxoethyl)-7H-pyrrolo[2,3-d]pyrimidin-5-yl)-1H-indole-1-carboxylate (126c) (165 mg, 40% yield) as a yellow solid; MS (ES+): 464.2 (M+1).

Step-2: Preparation of 2-(4-amino-5-(1-(tert-butoxycarbonyl)-1H-indol-3-yl)-7H-pyrrolo[2,3-d]pyrimidin-7-yl)acetic acid (126d)

Compound 126d was prepared according to the procedure reported in step-4 of scheme-17, from tert-butyl 3-(4-amino-7-(2-(tert-butoxy)-2-oxoethyl)-7H-pyrrolo[2,3-d]pyrimidin-5-yl)-1H-indole-1-carboxylate (126c) (160 mg, 0.345 mmol) in THF/MeOH (1.26 mL; ratio 1:1) using 2N sodium hydroxide (0.190 mL, 0.380 mmol) and stirring for 1.5 h at RT. This gave after workup 2-(4-amino-5-(1-(tert-butoxycarbonyl)-1H-indol-3-yl)-7H-pyrrolo[2,3-d]pyrimidin-7-yl) acetic acid (126d) (97 mg, 69% yield) as a pale yellow solid; MS (ES+): 408.1 (M+1).

Step-3: Preparation of tert-butyl 3-(4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidin-5-yl)-1H-indole-1-carboxylate (126e)

Compound 126e was prepared according to the procedure reported in step-3 of scheme-1, from 2-(4-amino-5-(1-(tert-butoxycarbonyl)-1H-indol-3-yl)-7H-pyrrolo[2,3-d]pyrimidin-7-yl)acetic acid (126d) (60 mg, 0.147 mmol) in DMF (2 mL) using HCl salt of (2S,4R)—N-(3-chloro-2-fluorobenzyl)-4-fluoropyrrolidine-2-carboxamide (7a) (45.8 mg, 0.147 mmol), HATU (70 mg, 0.184 mmol), DIPEA (0.103 mL, 0.589 mmol) and stirring at RT for 16 h. This gave after workup and purification by flash column chromatography [silica gel (24 g), eluting with DMA-80 in DCM from 0-100%] tert-butyl 3-(4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidin-5-yl)-1H-indole-1-carboxylate (126e) (40 mg, 41% yield) as a white solid: MS (ES+): 664.2 (M+1).

Step-4: Preparation of (2S,4R)-1-(2-(4-amino-5-(1H-indol-3-yl)-7H-pyrrolo[2,3-d]pyrimidin-7-yl)acetyl)-N-(3-chloro-2-fluorobenzyl)-4-fluoropyrrolidine-2-carboxamide (126f)

Compound 126f was prepared according to the procedure reported in step-2 of scheme-1, from tert-butyl 3-(4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidin-5-yl)-1H-indole-1-carboxylate (126e) (39 mg, 0.059 mmol) in DCM (I mL) using TFA (0.090 mL, 1.175 mmol) and stirring at RT for 4 h. This gave after workup and purification by reverse phase column chromatography [C18 column (50 g) eluting with ACN in water (containing 0.1% HCl) from 0-100%] (2S,4R)-1-(2-(4-amino-5-(1H-indol-3-yl)-7H-pyrrolo[2,3-d]pyrimidin-7-yl)acetyl)-N-(3-chloro-2-fluorobenzyl)-4-fluoropyrrolidine-2-carboxamide (126f) (15 mg, 45% yield) HCl salt as a white solid; $^1$H NMR (300 MHz, DMSO-$d_6$) (a mixture of two rotamers) δ 11.45 (d, J=2.6 Hz, 1H), 9.08 (t, J=5.7 Hz) and 8.64 (t, J=5.9 Hz) (2t, 1H), 8.36 (d, J=4.2 Hz, 1H), 7.56-7.30 (m, 6H, 2H $D_2O$ exchangeable), 7.30-7.23 (m, 1H), 7.23-7.08 (m, 2H), 7.02 (q, J=7.2 Hz, 11H), 6.92 (t, J=7.9 Hz, 1H), 5.55-5.02 (m, 3H), 4.41-3.74 (m, 5H), 2.78-2.37 (m, 1H), 2.18-1.84 (m, 1H); $^{19}$F NMR (282 MHz, DMSO) δ−121.29, −121.68, −176.38; MS (ES+): 564.2 (M+1).

Scheme 127

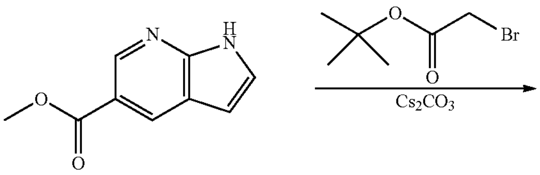

127a

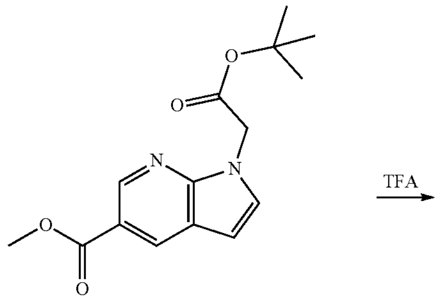

127b

-continued

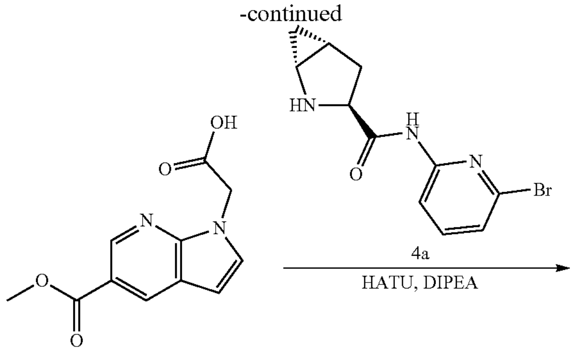

127c

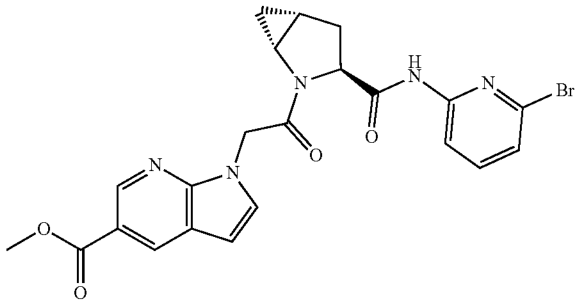

127d

Preparation of methyl 1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylate (127d)

Step-1: Preparation of methyl 1-(2-(tert-butoxy)-2-oxoethyl)-1H-pyrrolo[2,3-b]pyridine-5-carboxylate (127b)

Compound 127b was prepared according to the procedure reported in step-1 of scheme-1, from methyl 1H-pyrrolo[2,3-b]pyridine-5-carboxylate (127a) (0.5 g, 2.84 mmol; CAS #849067-96-5) in DMF (15 mL) using tert-butyl 2-bromoacetate (0.419 mL, 2.84 mmol), $Cs_2CO_3$ (1.110 g, 3.41 mmol) and stirring at RT for 1.5 h. This gave after workup methyl 1-(2-(tert-butoxy)-2-oxoethyl)-1H-pyrrolo[2,3-b]pyridine-5-carboxylate (127b) (746 mg, 91% yield) as an off-white solid: $^1H$ NMR (300 MHz, DMSO-$d_6$) δ 8.82 (d, J=2.0 Hz, 1H), 8.58 (d, J=2.0 Hz, 1H), 7.68 (d, J=3.6 Hz, 1H), 6.68 (d, J=3.6 Hz, 1H), 5.08 (s, 2H), 3.89 (s, 3H), 1.41 (s, 9H); MS (ES+): 235.00 (M+1).

Step-2: Preparation of 2-(5-(methoxycarbonyl)-1H-pyrrolo[2,3-b]pyridin-1-yl)acetic acid (127c)

Compound 127c was prepared according to the procedure reported in step-2 of scheme-1, from methyl 1-(2-(tert-butoxy)-2-oxoethyl)-1H-pyrrolo[2,3-b]pyridine-5-carboxylate (127b) (400 mg, 1.378 mmol) in DCM (8 mL) using TFA (1.582 mL, 20.67 mmol) and stirring at RT for 16 h. This gave after workup 2-(5-(methoxycarbonyl)-1H-pyrrolo[2,3-b]pyridin-1-yl)acetic acid (127c) (470 mg, 98% yield) TFA salt as a yellow solid; $^1H$ NMR (300 MHz, DMSO-$d_6$) δ 8.82 (d, J=2.0 Hz, 1H), 8.58 (d, J=2.0 Hz, 1H), 7.69 (d, J=3.6 Hz, 1H), 6.67 (d, J=3.6 Hz, 1H), 5.10 (s, 2H), 3.89 (s, 3H); MS (ES+): 235.10 (M+1).

Step-3: Preparation of methyl 1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylate (127d)

Compound 127d was prepared according to the procedure reported in step-3 of scheme-1, from TFA salt of 2-(5-(methoxycarbonyl)-1H-pyrrolo[2,3-b]pyridin-1-yl)acetic acid (127c) (75 mg, 0.215 mmol) in DMF (2 mL) using (1R,3S,5R)—N-(6-bromopyridin-2-yl)-2-azabicyclo[3.1.0]hexane-3-carboxamide (4a) HCl salt (68.6 mg, 0.215 mmol), HATU (123 mg, 0.323 mmol), DIPEA (0.188 mL, 1.077 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] methyl 1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylate (127d) (95 mg, 89% yield) as a white solid; $^1H$ NMR (300 MHz, DMSO-$d_6$) δ 10.78 (s, 1H, $D_2O$ exchangeable), 8.82 (d, J=2.0 Hz, 1H), 8.56 (d, J=2.0 Hz, 1H), 8.03 (d, J=8.2 Hz, 1H), 7.72 (t, J=8.0 Hz, 1H), 7.64 (d, J=3.6 Hz, 1H), 7.32 (d, J=7.7 Hz, 1H), 6.66 (d, J=3.6 Hz, 1H), 5.57 (d, J=17.1 Hz, 1H), 5.31 (d, J=17.0 Hz, 1H), 4.44 (dd, J=9.0, 5.5 Hz, 1H), 3.89 (s, 3H), 3.79 (ddd, J=7.4, 5.5, 2.3 Hz, 1H), 2.39-2.11 (m, 2H), 1.89 (tt, J=6.5, 3.7 Hz, 1H), 1.03 (dt, J=8.8, 5.4 Hz, 1H), 0.70 (td, J=5.2, 2.3 Hz, 1H); MS (ES+): 497.9 (M+1), 519.9 (M+Na); (ES−): 496.0 (M−1); Analysis calculated for $C_{22}H_{20}BrNSO_4 \cdot 1.75H_2O$: C, 49.87; H, 4.47; N, 13.22. Found: C, 49.80; H, 4.09; N, 13.01.

Scheme 128

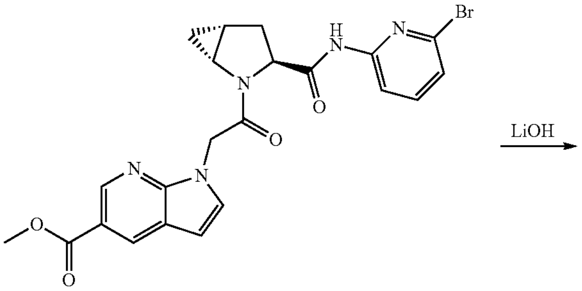

127d

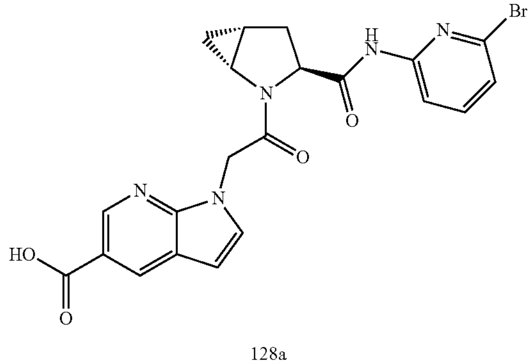

128a

Preparation of 1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylic acid (128a)

Compound 128a was prepared according to the procedure reported in step-4 of scheme-17, from methyl 1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylate (127d) (67 mg, 0.134 mmol) in THF (0.8 mL), acetonitrile (0.4 mL) and water (2 mL) using 1N aqueous lithium hydroxide monohydrate (0.403 mL, 0.403 mmol) and stirring at RT for 16 h. This gave after workup and purification by reverse phase column chromatography [C18 column (50 g), eluting with ACN in water (containing 0.1% HCl) from 0-100%] 1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylic acid (128a) (6 mg, 9% yield) HCl salt as a white solid. $^1$H NMR (300 MHz, Methanol-$d_4$) δ 8.96-8.84 (m, 2H), 8.02 (dd, J=12.4, 8.6 Hz, 1H), 7.62 (m, 2H), 7.25 (dt, J=7.5, 3.4 Hz, 1H), 6.86 (dt, J=5.9, 3.1 Hz, 1H), 5.76-5.36 (m, 2H), 4.53 (d, J=8.6 Hz, 1H), 3.77 (m, 1H), 2.43 (q, J=6.0, 4.2 Hz, 1H), 2.13-1.80 (m, 2H), 1.27-1.11 (m, 1H), 1.03-0.76 (m, 1H); MS (ES+): 483.9 (M+1), 505.9 (M+Na); (ES−): 481.9 (M−1).

Scheme 129

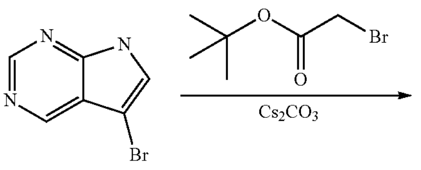

129a

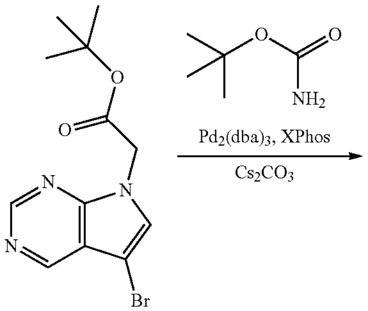

129b

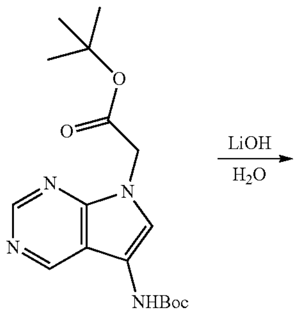

129c

-continued

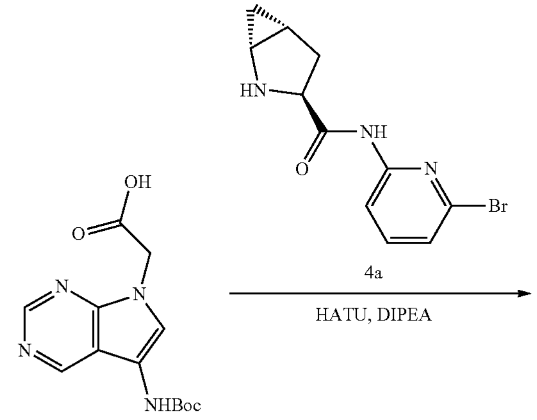

129d

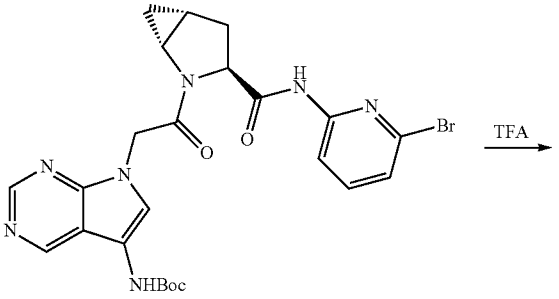

129e

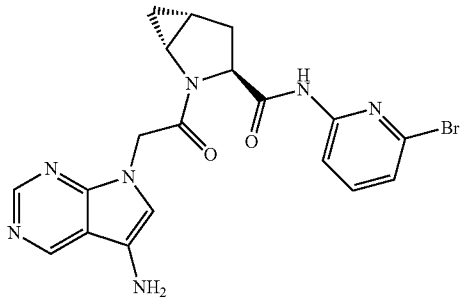

129f

Preparation of (1R,3S,5R)-2-(2-(5-amino-7H-pyrrolo[2,3-d]pyrimidin-7-yl)acetyl)-N-(6-bromopyridin-2-yl)-2-azabicyclo[3.1.0]hexane-3-carboxamide (129f)

Step-1: Preparation of tert-butyl 2-(5-bromo-7H-pyrrolo[2,3-d]pyrimidin-7-yl)acetate (129b)

Compound 129b was prepared according to the procedure reported in step-1 of scheme-1, from 5-bromo-7H-pyrrolo[2,3-d]pyrimidine (129a) (1 g, 5.05 mmol; CAS #175791-49-8) in DMF (25 mL) using tert-butyl 2-bromoacetate (0.784 mL, 5.30 mmol), $Cs_2CO_3$ (1.974 g, 6.06 mmol) and stirring at RT for 1.5 h. This gave after workup tert-butyl 2-(5-bromo-7H-pyrrolo[2,3-d]pyrimidin-7-yl)acetate (129b) (1.54 g, 98% yield) as a pale-yellow solid; $^1$H NMR (300 MHz, DMSO-$d_6$) δ 8.96 (s, 1H), 8.90 (s, 1H), 7.89 (s, 1H), 5.06 (s, 2H), 1.42 (s, 9H); MS (ES+): 312.00 (M+1).

Step-2: Preparation of tert-butyl 2-(5-((tert-butoxycarbonyl)amino)-7H-pyrrolo[2,3-d]pyrimidin-7-yl) acetate (129c)

Compound 129c was prepared according to the procedure reported in step-3 of scheme-17, from tert-butyl 2-(5-bromo-7H-pyrrolo[2,3-d]pyrimidin-7-yl)acetate (129b) (500 mg, 1.602 mmol) in toluene (30 mL) using XPhos (153 mg, 0.320 mmol), t-butyl carbamate (563 mg, 4.81 mmol), $Pd_2(dba)_3$ (147 mg, 0.160 mmol), cesium carbonate (522 mg, 1.602 mmol) and heating at 95° C. for 16 h. This gave after work up and purification tert-butyl 2-(5-((tert-butoxycarbonyl)amino)-7H-pyrrolo[2,3-d]pyrimidin-7-yl)acetate (129c) (29 mg, 5% yield); $^1$H NMR (300 MHz, DMSO-$d_6$) δ 9.89 (s, 1H), 9.30 (s, 1H), 8.88 (s, 1H), 7.80 (s, 1H), 5.05 (s, 2H), 1.52 (s, 9H), 1.42 (s, 9H); MS (ES+): 349.20 (M+1).

Step-3: Preparation of 2-(5-((tert-butoxycarbonyl) amino)-7H-pyrrolo[2,3-d]pyrimidin-7-yl)acetic acid (129d)

Compound 129d was prepared according to the procedure reported in step-4 of scheme-17, from tert-butyl 2-(5-((tert-butoxycarbonyl)amino)-7H-pyrrolo[2,3-d]pyrimidin-7-yl) acetate (129c) (80 mg, 0.23 mmol) in THF (2 mL) and MeOH (2 mL) using 1 N solution of aqueous lithium hydroxide hydrate (1.148 mL, 1.148 mmol) and stirring at RT for 15 h. This gave after workup 2-(5-((tert-butoxycarbonyl)amino)-7H-pyrrolo[2,3-d]pyrimidin-7-yl)acetic acid (129d) (62 mg, 92% yield); 1H NMR (300 MHz, DMSO-$d_6$) δ 9.89 (s, 1H), 9.30 (s, 1H), 8.87 (s, 1H), 7.80 (s, 1H), 5.06 (s, 2H), 1.52 (s, 9H); MS (ES+): 293.10 (M+1).

Step-4: Preparation of tert-butyl (7-(2-((1R,3S,5R)-3-((6-bromopyridin-2-yl)carbamoyl)-2-azabicyclo [3.1.0]hexan-2-yl)-2-oxoethyl)-7H-pyrrolo[2,3-d] pyrimidin-5-yl)carbamate (129e)

Compound 129e was prepared according to the procedure reported in step-3 of scheme-1, from 2-(5-((tert-butoxycarbonyl)amino)-7H-pyrrolo[2,3-d]pyrimidin-7-yl)acetic acid (129d) (50 mg, 0.171 mmol) in DMF (1 mL) using TFA salt of (1R,3S,5R)—N-(6-bromopyridin-2-yl)-2-azabicyclo [3.1.0]hexane-3-carboxamide (4a) (74.5 mg, 0.188 mmol), HATU (98 mg, 0.257 mmol), DIPEA (0.149 mL, 0.855 mmol) and stirring at RT for 4 h. This gave after workup and purification by flash column chromatography [silica gel (12 g), DMA-80 in DCM from 0-100%] tert-butyl (7-(2-((1R,3S,5R)-3-((6-bromopyridin-2-yl)carbamoyl)-2-azabicyclo [3.1.0]hexan-2-yl)-2-oxoethyl)-7H-pyrrolo[2,3-d]pyrimidin-5-yl)carbamate (129e) (85 mg, 89% yield) as a white solid; $^1$H NMR (300 MHz, DMSO-$d_6$) δ 10.77 (s, 1H), 9.77 (s, 1H), 9.19 (s, 1H), 8.73 (s, 1H), 8.04 (d, J=8.2 Hz, 1H), 7.72 (t, J=7.9 Hz, 1H), 7.64 (s, 1H), 7.33 (d, J=7.7 Hz, 1H), 5.47 (d, J=17.1 Hz, 1H), 5.20 (d, J=17.0 Hz, 1H), 4.47-4.33 (m, 1H), 3.75 (s, 1H), 2.34-2.11 (m, 2H), 1.89 (d, J=12.1 Hz, 1H), 1.51 (s, 9H), 1.03 (t, J=9.3 Hz, 1H), 0.72 (s, 1H); MS (ES+): 556.20 (M+1).

Step-5: Preparation of (1R,3S,5R)-2-(2-(5-amino-7H-pyrrolo[2,3-d]pyrimidin-7-yl)acetyl)-N-(6-bromopyridin-2-yl)-2-azabicyclo[3.1.0]hexane-3-carboxamide (129f)

Compound 129f was prepared according to the procedure reported in step-2 of scheme-1, from tert-butyl (7-(2-((1R,3S,5R)-3-((6-bromopyridin-2-yl)carbamoyl)-2-azabicyclo [3.1.0]hexan-2-yl)-2-oxoethyl)-7H-pyrrolo[2,3-d]pyrimidin-5-yl)carbamate (129e) (80 mg, 0.144 mmol) in DCM (0.8 mL) using TFA (0.222 mL, 2.88 mmol) and stirring at RT for 16 h. This gave after workup (1R,3S,5R)-2-(2-(5-amino-7H-pyrrolo[2,3-d]pyrimidin-7-yl)acetyl)-N-(6-bromopyridin-2-yl)-2-azabicyclo[3.1.0]hexane-3-carboxamide (129f) (59 mg, 90% yield) HCl salt as a yellow solid; 1H NMR (300 MHz, DMSO-$d_6$) δ 10.80 (s, 1H, $D_2O$ exchangeable), 9.34 (s, 1H), 9.04 (s, 1H), 8.03 (d, J=8.1 Hz, 1H), 7.77 (s, 1H), 7.72 (t, J=8.0 Hz, 1H), 7.34 (d, J=7.6 Hz, 1H), 5.65 (d, J=17.1 Hz, 1H), 5.34 (d, J=17.0 Hz, 1H), 4.45 (dd, J=9.0, 5.4 Hz, 1H), 3.78 (m, 1H), 2.26 (m, 2H), 1.90 (p, J=6.7 Hz, 1H), 1.04 (m, 1H), 0.73 (m, 1H). MS (ES+): 456.1 (M+1); (ES−): 454.1 (M−1); Analysis calculated for $C_{19}H_{18}BrN_7O_2$ $2.25H_2O \cdot 2.25HCl$: C, 39.42; H, 4.31; Cl, 13.78; N, 16.94. Found: C, 39.7; H, 4.28; Cl, 13.43; N, 16.71.

Scheme 130

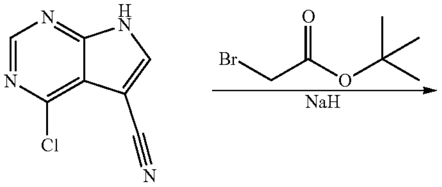

130a

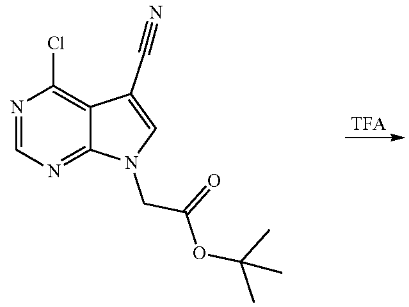

130b

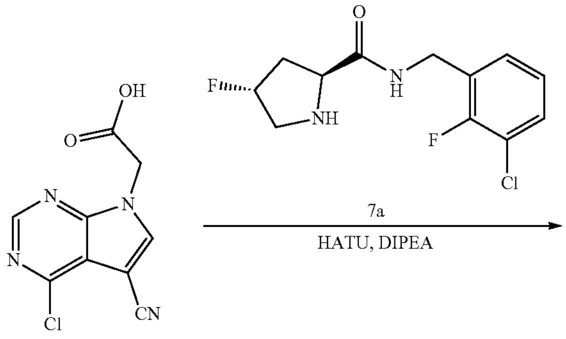

130c

-continued

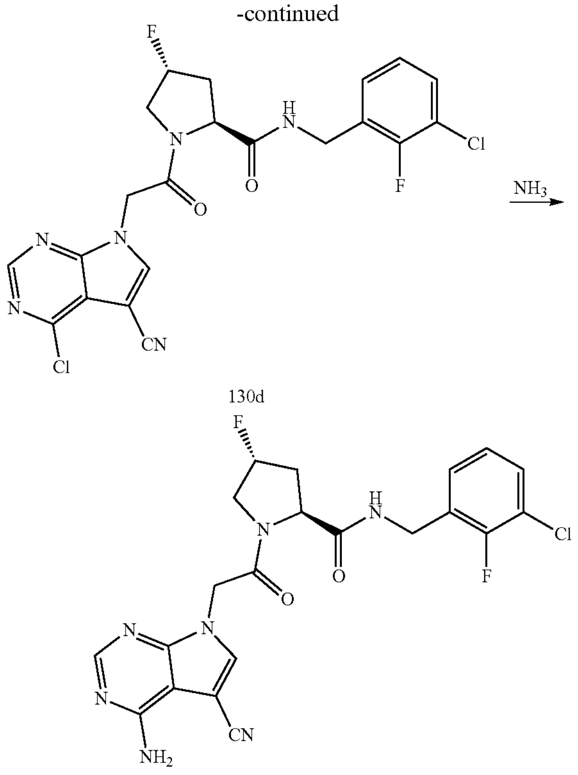

130d

130e

Preparation of (2S,4R)-1-(2-(4-amino-5-cyano-7H-pyrrolo[2,3-d]pyrimidin-7-yl)acetyl)-N-(3-chloro-2-fluorobenzyl)-4-fluoropyrrolidine-2-carboxamide (130e)

Step-1: Preparation of tert-butyl 2-(4-chloro-5-cyano-7H-pyrrolo[2,3-d]pyrimidin-7-yl)acetate (130b)

Compound 130b was prepared according to the procedure reported in step-1 of scheme-1, from 4-chloro-7H-pyrrolo[2,3-d]pyrimidine-5-carbonitrile (130a) (2 g, 11.20 mmol; CAS #24391-41-1) in DMF (50 mL) using sodium hydride (0.538 g, 13.44 mmol), tert-butyl 2-bromoacetate (1.986 mL, 13.44 mmol) and stirring at RT for 19 h. This gave after workup tert-butyl 2-(4-chloro-5-cyano-7H-pyrrolo[2,3-d]pyrimidin-7-yl)acetate (130b) (2.005 g, 61% yield) as a white solid; $^1$H NMR (300 MHz, DMSO-$d_6$) δ 8.86 (s, 1H), 8.71 (s, 1H), 5.17 (s, 2H), 1.41 (s, 9H); MS (ES+): 293.05 (M+1).

Step-2: Preparation of 2-(4-chloro-5-cyano-7H-pyrrolo[2,3-d]pyrimidin-7-yl)acetic acid (130c)

Compound 130c was prepared according to the procedure reported in step-2 of scheme-1, from tert-butyl 2-(4-chloro-5-cyano-7H-pyrrolo[2,3-d]pyrimidin-7-yl)acetate (130b) (1.98 g, 6.76 mmol) in DCM (60 mL) using TFA (5.21 mL, 67.6 mmol) and stirring at RT for 20 h. This gave after workup 2-(4-chloro-5-cyano-7H-pyrrolo[2,3-d]pyrimidin-7-yl)acetic acid (130c) (2.38 g) as an off-white solid which was used as such for next step.

Step-3: Preparation of (2S,4R)—N-(3-chloro-2-fluorobenzyl)-1-(2-(4-chloro-5-cyano-7H-pyrrolo[2,3-d]pyrimidin-7-yl)acetyl)-4-fluoropyrrolidine-2-carboxamide (130d)

Compound 130d was prepared according to the procedure reported in step-3 of scheme-1, from of 2-(4-chloro-5-cyano-7H-pyrrolo[2,3-d]pyrimidin-7-yl)acetic acid (130c) (516 mg, 2.182 mmol) in DMF (30 mL) using (2S,4R)—N-(3-chloro-2-fluorobenzyl)-4-fluoropyrrolidine-2-carboxamide (7a) (472 mg, 1.718 mmol), HATU (1307 mg, 3.44 mmol), DIPEA (1110 mg, 8.59 mmol) and stirring at RT for 21 h. This gave after workup and purification by flash column chromatography [silica gel, eluting with MeOH:EtOAc (1:9) in hexanes] (2S,4R)—N-(3-chloro-2-fluorobenzyl)-1-(2-(4-chloro-5-cyano-7H-pyrrolo[2,3-d]pyrimidin-7-yl)acetyl)-4-fluoropyrrolidine-2-carboxamide (130d) (155 mg, 18%) as a yellow solid; $^1$H NMR (300 MHz, DMSO-$d_6$) (a mixture of two rotamers) δ 9.03 (t) & 8.67-8.57 (m) (2H), 8.82 & 8.80 (2s, 1H), 7.54-7.32 (m, 1H), 7.26-7.12 (m, 1H), 7.09-6.97 (m, 1H), 5.68-5.18 (m, 3H), 4.97-3.71 (m, 5H), 2.61-2.35 (m, 1H), 2.21-1.92 (m, 1H) $^{19}$F NMR (282 MHz, DMSO-$d_6$) (a mixture of two rotamers) δ−121.32 & −121.57 (1F), −176.13 & −176.41 (1F) MS (ES+): 493.10 & 495.00 (M+1).

Step-4: Preparation of (2S,4R)-1-(2-(4-amino-5-cyano-7H-pyrrolo[2,3-d]pyrimidin-7-yl)acetyl)-N-(3-chloro-2-fluorobenzyl)-4-fluoropyrrolidine-2-carboxamide (130e)

To a solution of (2S,4R)—N-(3-chloro-2-fluorobenzyl)-1-(2-(4-chloro-5-cyano-7H-pyrrolo[2,3-d]pyrimidin-7-yl)acetyl)-4-fluoropyrrolidine-2-carboxamide (130d) (100 mg, 0.203 mmol) in dioxane (4 mL) was added ammonium hydroxide (3.84 mL, 56.8 mmol) and heated at 85° C. in a sealed tube for 14 h. The reaction mixture was concentrated to dryness and purified by flash column chromatography [silica gel, eluting with MeOH in DCM from 0-5%] to afford (2S,4R)-1-(2-(4-amino-5-cyano-7H-pyrrolo[2,3-d]pyrimidin-7-yl)acetyl)-N-(3-chloro-2-fluorobenzyl)-4-fluoropyrrolidine-2-carboxamide (130e) (37 mg, 39% yield) as a white solid. $^1$H NMR (300 MHz, DMSO-$d_6$) (a mixture of two rotamers) δ 9.02 & 8.60 (2t, J=5.9 Hz, 1H, $D_2O$ exchangeable), 8.18 & 8.17 (2s, 1H), 8.10 & 8.07 (2s, 1H), 7.53-7.33 (m, 1H), 7.27-7.13 (m, 1H), 7.10-7.01 (m, 1H), 6.86 (s, 2H, $D_2O$ exchangeable), 5.60-5.36 (m, 1H), 5.32-5.02 (m, 2H), 4.93-3.58 (m, 5H), 2.62-2.34 (m, 1H), 2.31-1.85 (m, 1H); $^{19}$F NMR (282 MHz, DMSO-$d_6$) (a mixture of two rotamers) δ−121.36 &−121.64, −176.12 & −176.39; MS (ES+): 474.10 (M+1); MS (ES−): 472.60 (M−1).

Scheme 131

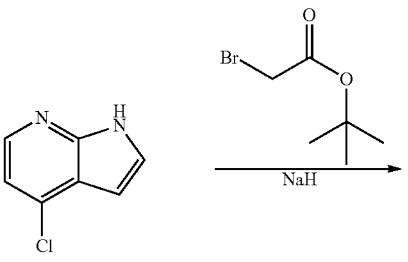

131a

-continued

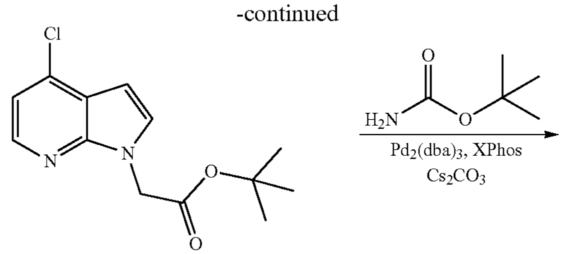

131b

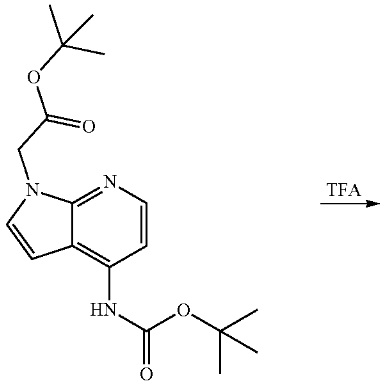

131c

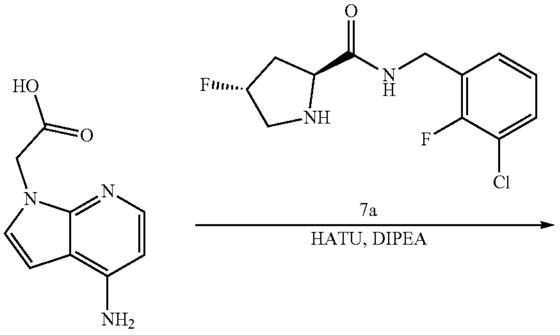

131d

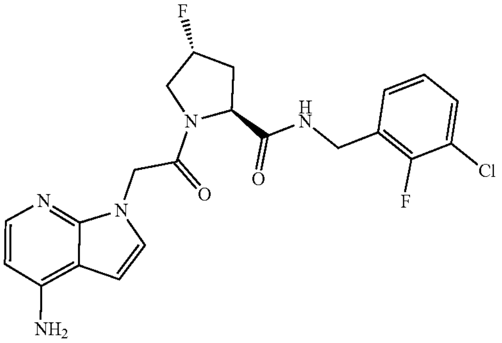

131e

Preparation of (2S,4R)-1-(2-(4-amino-1H-pyrrolo[2,3-b]pyridin-1-yl)acetyl)-N-(3-chloro-2-fluorobenzyl)-4-fluoropyrrolidine-2-carboxamide (131e)

Step-1: Preparation of tert-butyl 2-(4-chloro-1H-pyrrolo[2,3-b]pyridin-1-yl)acetate (131b)

Compound 131b was prepared according to the procedure reported in step-1 of scheme-1, from 4-chloro-1H-pyrrolo[2,3-b]pyridine (131a) (1 g, 6.55 mmol; CAS #55052-28-3) in DMF (25 mL) using sodium hydride (0.315 g, 7.86 mmol), tert-butyl 2-bromoacetate (1.162 mL, 7.86 mmol) and stirring at RT for 14 h. This gave after workup and purification by flash column chromatography [silica gel (40 g), eluting with EtOAc in hexane from 0 to 85%] tert-butyl 2-(4-chloro-1H-pyrrolo[2,3-b]pyridin-1-yl)acetate (131 b) (1.45 g, 83% yield) as a yellow solid: $^{1}H$ NMR (300 MHz, DMSO-$d_6$) δ 8.21 (d, J=5.2 Hz, 1H), 7.66 (d, J=3.6 Hz, 1H), 7.26 (d, J=5.2 Hz, 1H), 6.56 (d, J=3.6 Hz, 1H), 5.05 (s, 2H), 1.40 (s, 9H); MS (ES+): 267.10 & 269.10 (M+1).

Step-2: Preparation of tert-butyl 2-(4-((tert-butoxycarbonyl)amino)-1H-pyrrolo[2,3-b]pyridin-1-yl) acetate (131c)

Compound 131c was prepared according to the procedure reported in step-3 of scheme-17, from (tert-butyl 2-(4-chloro-1H-pyrrolo[2,3-b]pyridin-1-yl)acetate (131b) (1 g, 3.75 mmol) in toluene (30 mL) using XPhos (0.179 g, 0.375 mmol), t-butyl carbamate (0.659 g, 5.62 mmol), $Pd_2(dba)_3$ (0.172 g, 0.187 mmol), cesium carbonate (1.222 g, 3.75 mmol) and heating at 90° C. for 19 h. This gave after work up and purification by flash column chromatography [silica gel, EtOAc in Hexane from 0-14% then 33%] tert-butyl 2-(4-((tert-butoxycarbonyl)amino)-1H-pyrrolo[2,3-b]pyridin-1-yl)acetate (131c) (1.145 g, 88% yield) as a yellow gum; $^{1}H$ NMR (300 MHz, DMSO-$d_6$) δ 9.72 (s, 1H), 8.05 (d, J=5.5 Hz, 1H), 7.61 (d, J=5.5 Hz, 1H), 7.32 (d, J=3.6 Hz, 1H), 6.90 (d, J=3.6 Hz, 1H), 4.94 (s, 2H), 1.53 (s, 9H), 1.40 (s, 9H); MS (ES+): 348.20 (M+1).

Step-3: Preparation of 2-(4-amino-1H-pyrrolo[2,3-b]pyridin-1-yl)acetic acid (131d)

Compound 131d was prepared according to the procedure reported in step-2 of scheme-1, from tert-butyl 2-(4-((tert-butoxycarbonyl)amino)-1H-pyrrolo[2,3-b]pyridin-1-yl)acetate (131c) (1 g, 2.88 mmol) in DCM (30 mL) using TFA (1.711 mL, 23.03 mmol) and stirring at RT for 18 h. This gave after work up 2-(4-amino-1H-pyrrolo[2,3-b]pyridin-1-yl)acetic acid (131d) (1.62 g) as a yellow gum; MS (ES+): 192.10 (M+1).

Step-4: Preparation of (2S,4R)-1-(2-(4-amino-1H-pyrrolo[2,3-b]pyridin-1-yl)acetyl)-N-(3-chloro-2-fluorobenzyl)-4-fluoropyrrolidine-2-carboxamide (131e)

Compound 131e was prepared according to the procedure reported in step-3 of scheme-1, from 2-(4-amino-1H-pyrrolo[2,3-b]pyridin-1-yl)acetic acid (131d) (83 mg, 0.432 mmol) in DMF (10 mL) using (2S,4R)—N-(3-chloro-2-fluorobenzyl)-4-fluoropyrrolidine-2-carboxamide (7a) (148 mg, 0.540 mmol), HATU (329 mg, 0.864 mmol), DIPEA (0.376 mL, 2.160 mmol) and stirring at RT for 18 h. This gave after workup and purification using reverse phase column chromatography [C18 column (26 g), eluting with ACN in water (containing 0.1% HCl) from 0-100%] (2S,4R)-1-(2-(4-amino-1H-pyrrolo[2,3-b]pyridin-1-yl)acetyl)-N-(3-chloro-2-fluorobenzyl)-4-fluoropyrrolidine-2-carboxamide (131e) (23 mg, 12% yield) HCl salt as a light yellow solid; $^{1}H$ NMR (300 MHz, DMSO-$d_6$) (a mixture of two rotamers) δ 14.17-13.83 (m, 1H), 9.23-8.79 (m, 1H), 8.16 (s, 2H), 7.97-7.74 (m, 1H), 7.57-7.35 (m, 1H), 7.32-7.08 (m, 2H), 6.96-6.79 (m, 2H), 6.51-6.45 (m, 1H), 5.62-5.24 (m, 3H), 4.99-3.54 (m, 5H), 2.73-2.42 (m, 1H), 2.37-1.86 (m, 1H); $^{19}F$ NMR (282 MHz, DMSO-$d_6$) (a mixture of two rotamers)

δ−121.29 &−121.79, −175.81 & −175.96; MS (ES+): 448.10 (M+1); MS (ES−): 446.70 (M−1).

Scheme 132

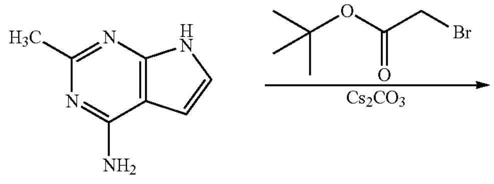

132a

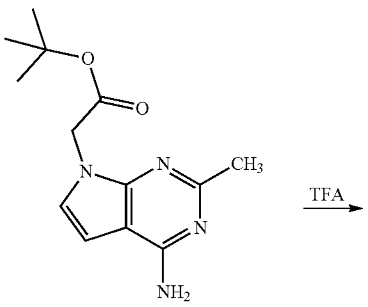

132b

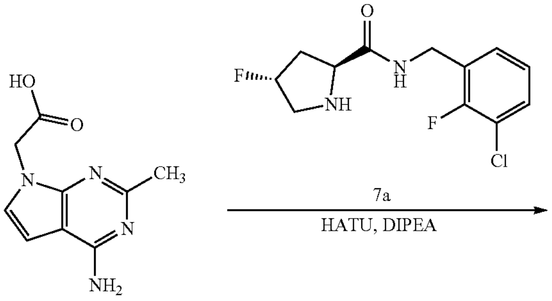

7a

132c

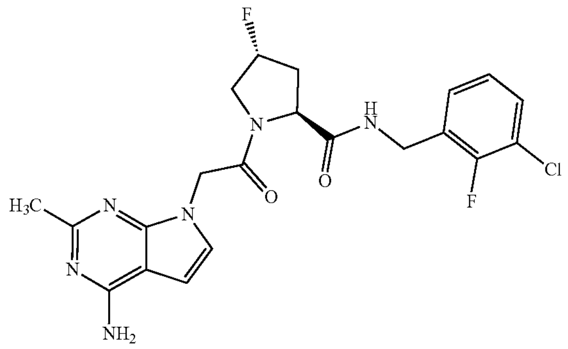

132d

Preparation of (2S,4R)-1-(2-(4-amino-2-methyl-7H-pyrrolo[2,3-d]pyrimidin-7-yl)acetyl)-N-(3-chloro-2-fluorobenzyl)-4-fluoropyrrolidine-2-carboxamide (132d)

Step-1: Preparation of tert-butyl 2-(4-amino-2-methyl-7H-pyrrolo[2,3-d]pyrimidin-7-yl)acetate (132b)

Compound 132b was prepared according to the procedure reported in step-1 of scheme-1, from 2-methyl-7H-pyrrolo[2,3-d]pyrimidin-4-amine (132a) (500 mg, 3.37 mmol) in DMF (15 mL) using tert-butyl 2-bromoacetate (0.498 mL, 3.37 mmol), $Cs_2CO$, (1.319 g 4.05 mmol) and stirring at RT for 18 h. This gave after workup and purification by flash column chromatography [silica gel, eluting with MeOH in DCM from 0-5%, then 10%] tert-butyl 2-(4-amino-2-methyl-7H-pyrrolo[2,3-d]pyrimidin-7-yl)acetate (132b) (700 mg, 79% yield) as off-white solid, $^1H$ NMR (300 MHz, DMSO-$d_6$) δ 7.01 (d, J=3.5 Hz, 1H), 6.87 (s, 2H), 6.46 (d, J=3.5 Hz, 1H), 4.80 (s, 2H), 2.33 (s, 3H), 1.41 (s, 9H); MS (ES+): 263.10 (M+1).

Step-2: Preparation of 2-(4-amino-2-methyl-7H-pyrrolo[2,3-d]pyrimidin-7-yl)acetic acid (132c)

Compound 132c was prepared according to the procedure reported in step-2 of scheme-1, from tert-butyl 2-(4-amino-2-methyl-7H-pyrrolo[2,3-d]pyrimidin-7-yl)acetate (132b) (670 mg, 2.55 mmol) using TFA. This gave after workup 2-(4-amino-2-methyl-7H-pyrrolo[2,3-d]pyrimidin-7-yl)acetic acid (132c) (875 mg) off white solid; MS (ES+): 207.05 (M+1).

Step-3: Preparation of (2S,4R)-1-(2-(4-amino-2-methyl-7H-pyrrolo[2,3-d]pyrimidin-7-yl)acetyl)-N-(3-chloro-2-fluorobenzyl)-4-fluoropyrrolidine-2-carboxamide (132d)

Compound 132d was prepared according to the procedure reported in step-3 of scheme-1, from 2-(4-amino-2-methyl-7H-pyrrolo[2,3-d]pyrimidin-7-yl)acetic acid (132c) (89 mg, 0.432 mmol) in DMF (10 mL) using (2S,4R)—N-(3-chloro-2-fluorobenzyl)-4-fluoropyrrolidine-2-carboxamide (7a) (148 mg, 0.540 mmol), HATU (329 mg, 0.864 mmol), DIPEA (0.376 mL, 2.160 mmol) and stirring at RT for 12 h. This gave after workup and purification using reverse phase column chromatography [C18 column (26 g), eluting with ACN in water (containing 0.1% HCl) from 0-100%] (2S,4R)-1-(2-(4-amino-2-methyl-7H-pyrrolo[2,3-d]pyrimidin-7-yl)acetyl)-N-(3-chloro-2-fluorobenzyl)-4-fluoropyrrolidine-2-carboxamide (132d) (34 mg, 17% yield) HCl salt as a white solid; $^1H$ NMR (300 MHz, DMSO-$d_6$) (a mixture of two rotamers) δ 13.94 (s, 1H, $D_2O$ exchangeable), 9.26 (s, 1H, $D_2O$ exchangeable), 9.15-8.61 (m, 1H, $D_2O$ exchangeable), 8.07 (s, 1H, $D_2O$ exchangeable), 7.51-7.35 (m, 1H), 7.33-7.20 (m, 2H), 7.16 & 7.06 (2t, J=7.9 Hz, 1H), 6.93-6.86 (m, 1H), 5.64-4.94 (m, 3H), 4.92-3.69 (m, 5H), 2.77-2.25 (m, 4H), 2.27-1.89 (m, 1H); $^{19}F$ NMR (282 MHz, DMSO-$d_6$) (a mixture of two rotamers) δ−121.33 & −121.66 (1F), −176.06 & −176.34 (1F); MS (ES+): 463.10 & 465.10 (M+1).

Scheme 133

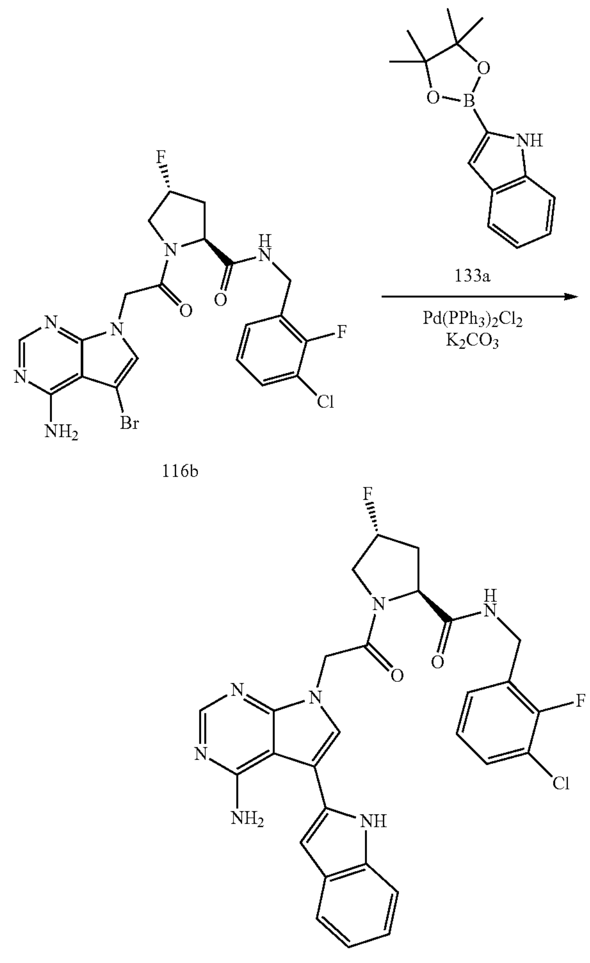

Preparation of (2S,4R)-1-(2-(4-amino-5-(I H-indol-2-yl)-7H-pyrrolo[2,3-d]pyrimidin-7-yl)acetyl)-N-(3-chloro-2-fluorobenzyl)-4-fluoropyrrolidine-2-carboxamide (133b)

Compound 133b was prepared according to the procedure reported in step-1 of scheme-59, from (2S,4R)-1-(2-(4-amino-5-bromo-7H-pyrrolo[2,3-d]pyrimidin-7-yl)acetyl)-N-(3-chloro-2-fluorobenzyl)-4-fluoropyrrolidine-2-carboxamide (116b) (200 mg, 0.379 mmol), 1H-Indole-2-boronic acid pinacol ester (133a) (92 mg, 0.379 mmol), $Pd(PPh_3)_2Cl_2$ (26.6 mg, 0.038 mmol) in dioxane (5 mL) using a 3.3 M aqueous $K_2CO_3$ (0.345 mL, 1.137 mmol) and heating at 100° C. for 16 h under argon. This gave after workup and purification by flash column chromatography ($SiO_2$, 12 g, eluting with 0-5% MeOH in DCM) followed by purification using reverse phase column chromatography [C18 column (100 g), eluting with ACN in water (containing 0.1% HCl) from 0-100%] (2S,4R)-1-(2-(4-amino-5-(1H-indol-2-yl)-7H-pyrrolo[2,3-d]pyrimidin-7-yl)acetyl)-N-(3-chloro-2-fluorobenzyl)-4-fluoropyrrolidine-2-carboxamide (133b) (37 mg, 17% yield) HCl salt as a pale-orange solid: $^1H$ NMR (300 MHz, DMSO-$d_6$) (mixture of two rotamers) δ 11.65-11.50 (m, 1H, $D_2O$ exchangeable), 8.69 (t, J=5.9 Hz, 1H), 8.45 (t, J=2.3 Hz, 1H), 7.89 (s, 2H, $D_2O$ exchangeable), 7.66 (dd, J=3.8, 1.2 Hz, 1H), 7.59 (d, J=7.8 Hz, 1H), 7.52-7.40 (m, 1H), 7.40-7.29 (m, 1H), 7.29-7.20 (m, 1H), 7.19-7.10 (m, 1H), 7.04 (dt, J=12.1, 7.7 Hz, 2H), 6.59 (d, J=2.0 Hz, 1H), 5.67-5.10 (m, 3H), 4.41 (m, 2H), 4.31-4.09 (m, 1H), 3.90 (m, 1H), 2.22-1.93 (m, 1H). $^{19}F$ NMR (282 MHz, DMSO-$d_6$) δ-121.30, −121.63, −176.11, −176.32; MS (ES+) 564/566 (M+1), (ES−) 560/562 (M−1); Analysis calculated for $C_{28}H_{24}ClF_2N_7O_2HCl\cdot 2.75H_2O$: C, 51.74; H, 4.73; Cl, 10.91; N, 15.08. Found: C, 51.74; H, 4.56; Cl, 10.98; N, 15.07.

Scheme 134

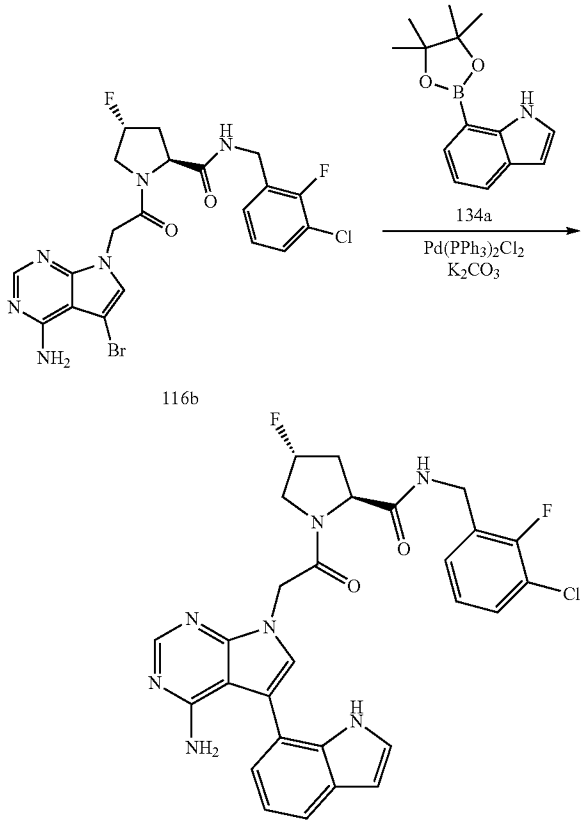

Preparation of (2S,4R)-1-(2-(4-amino-5-(1H-indol-7-yl)-7H-pyrrolo[2,3-d]pyrimidin-7-yl)acetyl)-N-(3-chloro-2-fluorobenzyl)-4-fluoropyrrolidine-2-carboxamide (134b)

Compound 134b was prepared according to the procedure reported in step-1 of scheme-59, from (2S,4R)-1-(2-(4-amino-5-bromo-7H-pyrrolo[2,3-d]pyrimidin-7-yl)acetyl)-N-(3-chloro-2-fluorobenzyl)-4-fluoropyrrolidine-2-carboxamide (116b) (200 mg, 0.379 mmol), 1H-Indole-7-boronic acid pinacol ester (134a) (92 mg, 0.379 mmol), $Pd(PPh_3)_2Cl_2$ (26.6 mg, 0.038 mmol) in dioxane (5 mL) using a 3.3 M aqueous $K_2CO_3$ (0.345 mL, 1.137 mmol) and heating at 100° C. for 16 h under argon. This gave after workup and purification by flash column chromatography ($SiO_2$, 12 g, eluting with 0-5% MeOH in DCM) followed by purification using reverse phase column chromatography

[C18 column (100 g), eluting with ACN in water (containing 0.1% HCl) from 0-100%] (2S,4R)-1-(2-(4-amino-5-(1H-indol-7-yl)-7H-pyrrolo[2,3-d]pyrimidin-7-yl)acetyl)-N-(3-chloro-2-fluorobenzyl)-4-fluoropyrrolidine-2-carboxamide (134b) (47 mg, 22% yield) HCl salt as a white solid; $^{1}$H NMR (300 MHz, DMSO-$d_6$) (mixture of two rotamers) δ 11.03 (q, J=4.1, 3.2 Hz, 1H, $D_2O$ exchangeable), 8.68 (t, J=5.9 Hz, 1H), 8.45 (d, J=3.7 Hz, 1H), 7.64 (dt, J=7.7, 1.7 Hz, 1H), 7.56 (d, J=6.4 Hz, 1H), 7.50-7.30 (m, 2H, $D_2O$ exchangeable), 7.30-7.20 (m, 1H), 7.15 (t, J=7.5 Hz, 1H), 7.11-7.06 (m, 1H), 7.01-6.92 (m, 1H), 6.57 (dd, J=3.1, 1.7 Hz, 1H), 5.62-5.13 (m, 3H), 4.52-4.31 (m, 2H), 4.29-4.11 (m, 2H), 3.88 (m, 1H), 2.21-1.92 (m, 1H), $^{19}$F NMR (282 MHz, DMSO-$d_6$) δ−121.29, −121.67, −176.13, −176.29; MS (ES+): 564/566 (M+1), (ES−): 560/562 (M−1); Analysis calculated for $C_{25}H_{24}ClF_2N_7O_2 \cdot 1.25HCl \cdot 2.5H_2O$: C, 51.37; H, 4.66; Cl, 12.19; N, 14.98. Found: C, 51.69; H, 4.49; Cl, 11.79; N, 14.99.

Scheme 135

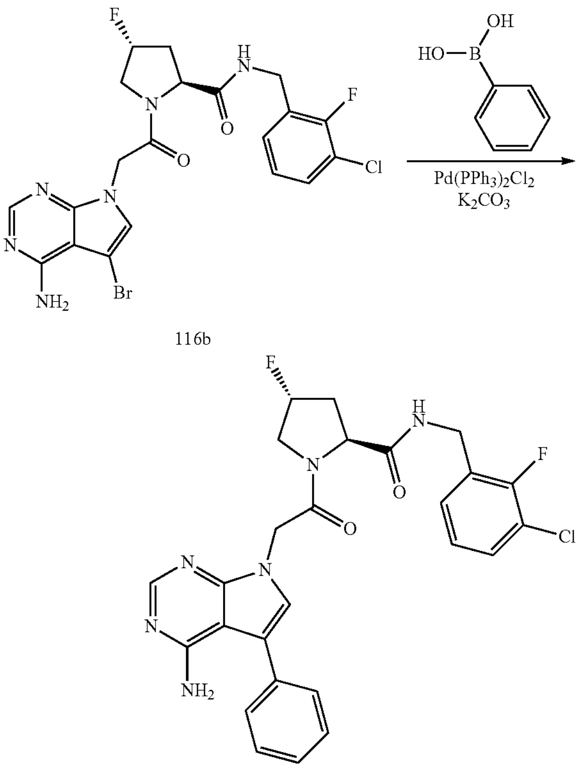

116b

135a

Preparation of (2S,4R)-1-(2-(4-amino-5-phenyl-7H-pyrrolo[2,3-d]pyrimidin-7-yl)acetyl)-N-(3-chloro-2-fluorobenzyl)-4-fluoropyrrolidine-2-carboxamide (135a)

Compound 135a was prepared according to the procedure reported in step-1 of scheme-59, from (2S,4R)-1-(2-(4-amino-5-bromo-7H-pyrrolo[2,3-d]pyrimidin-7-yl)acetyl)-N-(3-chloro-2-fluorobenzyl)-4-fluoropyrrolidine-2-carboxamide (116b) (200 mg, 0.379 mmol), phenylboronic acid (46.2 mg, 0.379 mmol), $Pd(PPh_3)_2Cl_2$ (26.6 mg, 0.038 mmol) in dioxane (5 mL) using a 3.3 M aqueous $K_2CO_3$ (0.345 mL, 1.137 mmol) and heating at 100° C. for 16 h under argon. This gave after workup and purification by flash column chromatography ($SiO_2$, 12 g, eluting with 0-5% MeOH in DCM) followed by purification using reverse phase column chromatography [C18 column (100 g), eluting with ACN in water (containing 0.1% HCl) from 0-100%](2S,4R)-1-(2-(4-amino-5-phenyl-7H-pyrrolo[2,3-d]pyrimidin-7-yl)acetyl)-N-(3-chloro-2-fluorobenzyl)-4-fluoropyrrolidine-2-carboxamide (135a) (53 mg, 27% yield) HCl salt as a white solid after lyophilization. $^{1}$H NMR (300 MHz, DMSO-$d_6$) (mixture of two rotamers) δ 8.69 (t, J=6.0 Hz, 1H), 8.45 (d, J=4.3 Hz, 1H), 7.97-7.34 (m, 9H), 7.22 (m, 1H), 7.00 (m, 1H), 5.58-5.16 (m, 3H), 4.51-4.09 (m, 5H), 4.02-3.77 (m, 1H), 2.21-1.92 (m, 1H). $^{19}$F NMR (282 MHz, DMSO-$d_6$) δ−121.29, −121.64, −176.12, −176.32; MS (ES+): 525/527 (M+1), (ES−): 521/523 (M−1); Analysis calculated for $C_{26}H_{23}ClF_2N_6O_2 \cdot HCl \cdot 2H_2O$: C, 52.27; H, 4.72; Cl, 11.87; N, 14.07. Found: C, 52.01; H, 4.69; Cl, 11.63; N, 13.99.

Scheme 136

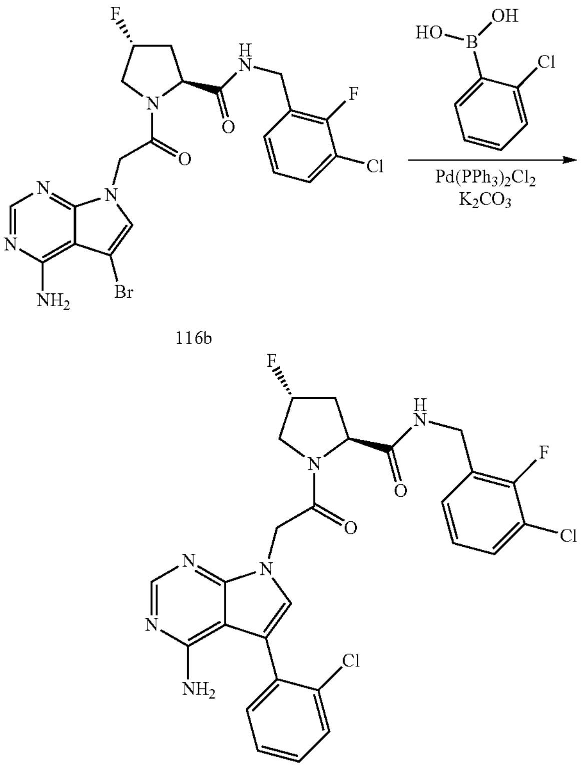

116b

136a

Preparation of (2S,4R)-1-(2-(4-amino-5-(2-chlorophenyl)-7H-pyrrolo[2,3-d]pyrimidin-7-yl)acetyl)-N-(3-chloro-2-fluorobenzyl)-4-fluoropyrrolidine-2-carboxamide (136a)

Compound 136a was prepared according to the procedure reported in step-1 of scheme-59, from (2S,4R)-1-(2-(4-amino-5-bromo-7H-pyrrolo[2,3-d]pyrimidin-7-yl)acetyl)-N-(3-chloro-2-fluorobenzyl)-4-fluoropyrrolidine-2-carboxamide (116b) (200 mg, 0.379 mmol), 2-chlorophenylboronic acid (59.3 mg, 0.379 mmol), $Pd(PPh_3)_2Cl_2$ (26.6 mg, 0.038 mmol) in dioxane (5 mL) using a 3.3 M aqueous $K_2CO_3$ (0.345 mL, 1.137 mmol) and heating at 100° C. for 16 h under argon. This gave after workup and purification by flash column chromatography ($SiO_2$, 12 g, eluting with 0-5% MeOH in DCM) followed by purification using reverse phase column chromatography [C18 column (100 g), eluting with 0-60% ACN in water (containing 0.1% HCl) from 0-100%] (2S,4R)-1-(2-(4-amino-5-(2-chlorophenyl)-7H-pyrrolo[2,3-d]pyrimidin-7-yl)acetyl)-N-(3-chloro-2-fluorobenzyl)-4-fluoropyrrolidine-2-carboxamide (136a) (43 mg, 20% yield) HCl salt as a white solid after lyophilization. $^1H$ NMR (300 MHz, DMSO-$d_6$) (mixture of two rotamers) δ 8.70 (t, J=5.9 Hz, 1H), 8.43 (d, J=4.3 Hz, 1H), 7.83-7.61 (m, 2H), 7.54-7.35 (m, 6H), 7.30-7.23 (m, 1H), 7.02 (t, J=7.9 Hz, 1H), 5.61-5.17 (m, 3H), 4.51-4.09 (m, 5H), 4.02-3.77 (m, 1H), 2.21-1.91 (m, 1H), $^{19}F$ NMR (282 MHz, DMSO-$d_6$) δ-121.28, −121.65, −176.10, −176.29; MS (ES+) 559/561 (M+1), (ES−) 555/557 (M−1); Analysis calculated for $C_{26}H_{22}C_{12}F_2N_6O_2 \cdot HCl \cdot 2H_2O$: C, 49.42; H, 4.31; Cl, 16.83; N, 13.30. Found: C, 49.20; H, 4.24; Cl, 16.72; N, 13.24.

Scheme 137

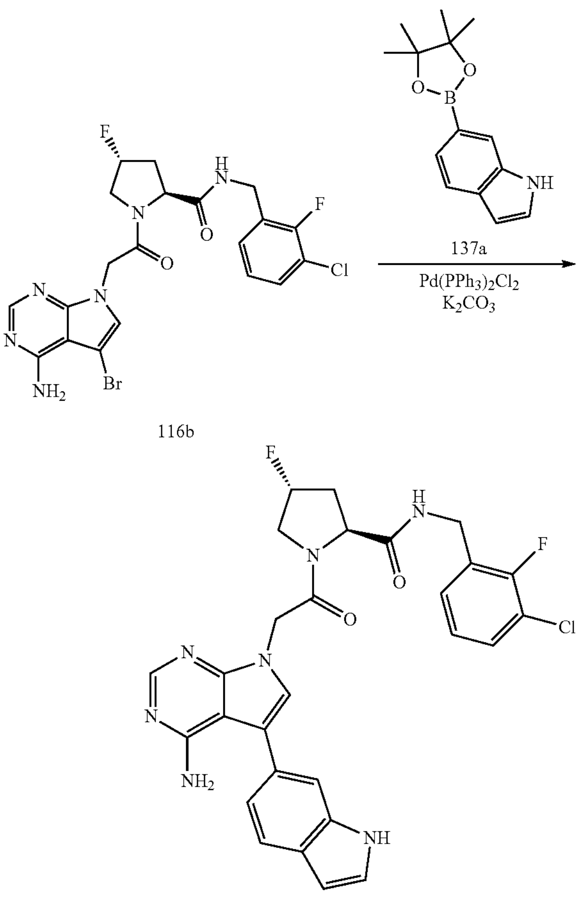

116b

137b

Preparation of (2S,4R)-1-(2-(4-amino-5-(1H-indol-6-yl)-7H-pyrrolo[2,3-d]pyrimidin-7-yl)acetyl)-N-(3-chloro-2-fluorobenzyl)-4-fluoropyrrolidine-2-carboxamide (137b)

Compound 137b was prepared according to the procedure reported in step-1 of scheme-59, from (2S,4R)-1-(2-(4-amino-5-bromo-7H-pyrrolo[2,3-d]pyrimidin-7-yl)acetyl)-N-(3-chloro-2-fluorobenzyl)-4-fluoropyrrolidine-2-carboxamide (116b) (200 mg, 0.379 mmol), indole-6-boronic acid pinacol ester (137a) (92 mg, 0.379 mmol), $Pd(PPh_3)_2Cl_2$ (26.6 mg, 0.038 mmol) in dioxane (5 mL) using a 3.3 M aqueous $K_2CO_3$ (0.345 mL, 1.137 mmol) and heating at 100° C. for 16 h under argon. This gave after workup and purification by flash column chromatography ($SiO_2$, 12 g. eluting with 0-5% MeOH in DCM) followed by purification using reverse phase column chromatography [C18 column (100 g), eluting with 0-60% ACN in water (containing 0.1% HCl) from 0-100%](2S,4R)-1-(2-(4-amino-5-(1H-indol-6-yl)-7H-pyrrolo[2,3-d]pyrimidin-7-yl)acetyl)-N-(3-chloro-2-fluorobenzyl)-4-fluoropyrrolidine-2-carboxamide (137b) (30 mg, 14% yield) HCl as a white solid; $^1H$ NMR (300 MHz, DMSO-$d_6$) (mixture of two rotamers) δ 11.30 (d, J=2.3 Hz, 1H, $D_2O$ exchangeable), 8.67 (t, J=5.9 Hz, 1H), 8.43 (d, J=4.0 Hz, 1H), 7.69 (d, J=8.1 Hz, 1H), 7.51-7.41 (m, 3H), 7.36 (m, 1H), 7.28-7.18 (m, 1H), 7.11 (m, 1H), 7.05-6.96 (m, 1H), 6.51 (t, J=2.5 Hz, 1H), 5.78-5.13 (m, 2H), 4.93-4.32 (m, 2H), 4.32-4.06 (m, 1H), 3.89 (m, 1H), 2.22-1.90 (m, 1H). $^{19}F$ NMR (282 MHz, DMSO-$d_6$) δ-121.28, −121.64, −176.09, −176.30; MS (ES+): 564/566 (M+1). (ES−): 560/562 (M−1); Analysis calculated for $C_{28}H_{24}ClF_2N_7O_2 \cdot HCl \cdot 2H_2O$: C, 52.10; H, 4.68; Cl, 10.98; N, 15.19. Found: C, 51.79; H, 4.31; Cl, 11.23; N, 15.29.

Scheme 138

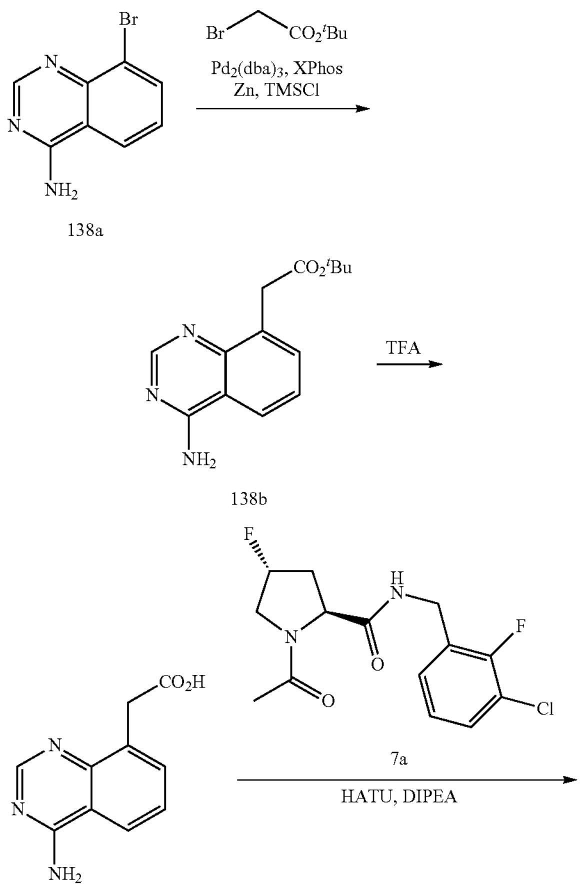

138a

138b

138c

-continued

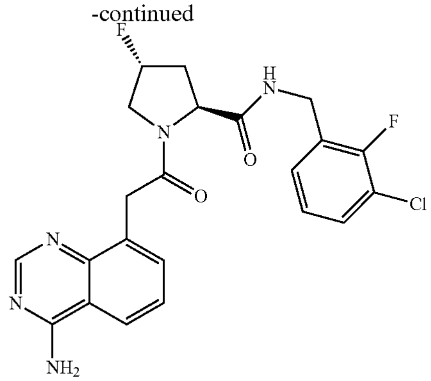

138d

Preparation of (2S,4R)-1-(2-(4-aminoquinazolin-8-yl)acetyl)-N-(3-chloro-2-fluorobenzyl)-4-fluoropyrrolidine-2-carboxamide (138d)

Step-1: Preparation of tert-butyl 2-(4-aminoquinazolin-8-yl)acetate (138b)

Compound 138b was prepared according to the procedure reported in step-1 of scheme-2, from 8-bromoquinazolin-4-amine (138a) (1.00 g, 4.46 mmol; CAS #1260657-19-9) using zinc (1.752 g, 26.8 mmol). TMSCl (0.283 mL, 2.232 mmol) in THF (5 mL), $Pd_2(dba)_3$ (0.409 g, 0.446 mmol), XPhos (0.426 g, 0.893 mmol) in THF (10 mL). This gave after work up and purification using flash column chromatography [silicagel (24 g), eluting with EtOAc in hexane from 0-50%] tert-butyl 2-(4-aminoquinazolin-8-yl)acetate (138b) (97 mg, 8.4%) as a yellow solid; $^1$H NMR (300 MHz, DMSO-$d_6$) δ 8.39 (s, 1H), 8.12 (dd, J=8.4, 1.4 Hz, 1H), 7.90-7.68 (m, 2H), 7.65 (dd, J=7.0, 1.2 Hz, 1H), 7.42 (dd, J=8.3, 7.1 Hz, 1H), 3.94 (s, 2H), 1.39 (s, 9H); MS (ES+): 260 (M+1).

Step-2: Preparation of 2-(4-aminoquinazolin-8-yl)acetic acid (138c)

Compound 138c was prepared according to the procedure reported in step-2 of scheme-1, from tert-butyl 2-(4-aminoquinazolin-8-yl)acetate (138b) (95 mg, 0.366 mmol) using TFA (2.103 mL, 5.50 mmol) in DCM (5 mL) and stirring at RT for 16 h. This gave after work up 2-(2-(4-aminoquinazolin-8-yl)acetic acid (138c) (106 mg, 91%) TFA salt as an orange solid; $^1$H NMR (300 MHz, DMSO-$d_6$) δ 9.88-9.57 (m, 2H), 8.76 (s, 1H), 8.36 (dd, J=8.4, 1.2 Hz, 1H), 7.97 (dd, J=7.4, 1.2 Hz, 1H), 7.73 (t, J=7.8 Hz, 1H), 4.07 (s, 2H). $^{19}$F NMR (282 MHz, DMSO-$d_6$) δ−74.37; LC-MS; t=0.56 min; MS (ES+): 204 (M+1).

Step-3: Preparation of (2S,4R)-1-(2-(4-aminoquinazolin-8-yl)acetyl)-N-(3-chloro-2-fluorobenzyl)-4-fluoropyrrolidine-2-carboxamide (138d)

Compound 138d was prepared according to the procedure reported in step-3 of scheme-1, from 2-(4-aminoquinazolin-8-yl)acetic acid (138c) (93 mg, 0.293 mmol) in DMF (5 mL) using (2S,4R)—N-(3-chloro-2-fluorobenzyl)-4-fluoropyrrolidine-2-carboxamide (7a) (114 mg, 0.293 mmol), HATU (134 mg, 0.352 mmol), DIPEA (0.490 mL, 2.81 mmol) and stirring at RT for 16 h. This gave after workup and purification by flash column chromatography ($SiO_2$, 12 g, eluting with 0-3% MeOH in DCM) followed by reverse phase column chromatography [C-18 column, 100 g, eluting with 0.1% aqueous HCl in $H_2O$ and MeCN from 0-100%](2S,4R)-1-(2-(4-aminoquinazolin-8-yl)acetyl)-N-(3-chloro-2-fluorobenzyl)-4-fluoropyrrolidine-2-carboxamide (138d) (22 mg, 16% yield) HCl salt as a pale-yellow solid; $^1$H NMR (300 MHz, DMSO-$d_6$) (mixture of two rotamers) δ 9.80 (s, 2H, $D_2O$ exchangeable), 8.82 (q, J=5.6, 4.1 Hz, 1H, $D_2O$ exchangeable), 8.52 (s, 1H), 8.39 (d, J=8.3 Hz, 1H), 7.91 (d, J=7.3 Hz, 1H), 7.72 (t, J=7.8 Hz, 1H), 7.40 (td, J=7.6, 1.6 Hz, 1H), 7.30-7.15 (m, 1H), 6.92 (t, J=8.2 Hz, 1H), 5.65-5.19 (m, 1H), 4.50-3.90 (m, 9H), 2.25-1.95 (m, 1H). $^{19}$F NMR (282 MHz, DMSO-$d_6$) δ−121.15, −121.69, −175.82; MS (ES+): 460/462 (M+1), (ES−): 457/459 (M−1).

Scheme 139

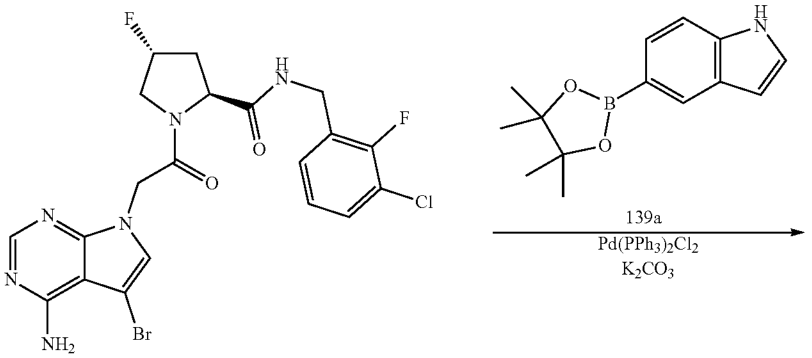

116b

-continued

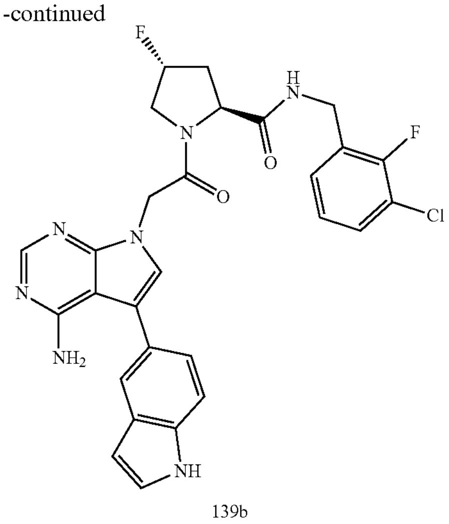

139b

Preparation of (2S,4R)-1-(2-(4-amino-5-(1H-indol-5-yl)-7H-pyrrolo[2,3-d]pyrimidin-7-yl)acetyl)-N-(3-chloro-2-fluorobenzyl)-4-fluoropyrrolidine-2-carboxamide (139b)

Compound 139b was prepared according to the procedure reported in step-1 of scheme-59, from (2S,4R)-1-(2-(4-amino-5-bromo-7H-pyrrolo[2,3-d]pyrimidin-7-yl)acetyl)-N-(3-chloro-2-fluorobenzyl)-4-fluoropyrrolidine-2-carboxamide (116b) (200 mg, 0.379 mmol), indole-5-boronic acid pinacol ester (139a) (92 mg, 0.379 mmol), $Pd(PPh_3)_2Cl_2$ (26.6 mg, 0.038 mmol) in dioxane (5 mL) using a 3.3 M aqueous $K_2CO_3$ (0.345 mL, 1.137 mmol) and heating at 100° C. for 16 h under argon. This gave after workup and purification by flash column chromatography ($SiO_2$, 12 g, eluting with 0-3% MeOH in DCM) followed by purification using reverse phase column chromatography [C18 column (100 g), eluting with ACN in water (containing 0.1% HCl) from 0-100%] (2S,4R)-1-(2-(4-amino-5-(1H-indol-5-yl)-7H-pyrrolo[2,3-d]pyrimidin-7-yl)acetyl)-N-(3-chloro-2-fluorobenzyl)-4-fluoropyrrolidine-2-carboxamide (139b) (73 mg, 34% yield) HCl salt as a white solid: $^1$H NMR (300 MHz, DMSO-$d_6$) (a mixture of two rotamers) δ 11.31 (d, J=2.6 Hz, 1H, $D_2O$ exchangeable), 8.67 (t, J=6.0 Hz, 1H), 8.42 (d, J=4.0 Hz, 1H), 7.63 (d, J=1.6 Hz, 1H), 7.54 (d, J=8.4 Hz, 1H), 7.44 (m, 3H), 7.37 (m, 1H), 7.29-7.22 (m, 1H), 7.19 (m, 2H), 7.02 (t, J=7.9 Hz, 1H), 6.51 (d, J=2.6 Hz, 1H), 5.64-5.10 (m, 4H), 4.41 (m, 3H), 4.20 (m, 2H), 4.03-3.78 (m, 1H), 2.22-1.93 (m, 1H). $^{19}$F NMR (282 MHz, DMSO-$d_6$) δ−121.29, −121.64, −176.11, −176.30; MS (ES+): 564/566 (M+1), (ES−): 560/562 (M−1); Analysis calculated for $C_{28}H_{24}ClF_2N_7O_2 \cdot HCl \cdot 2.25H_2O$: C, 52.47; H, 4.64; Cl, 11.06; N, 15.30 Found: C, 52.27; H, 4.40, Cl, 11.42; N, 15.41.

Scheme 140

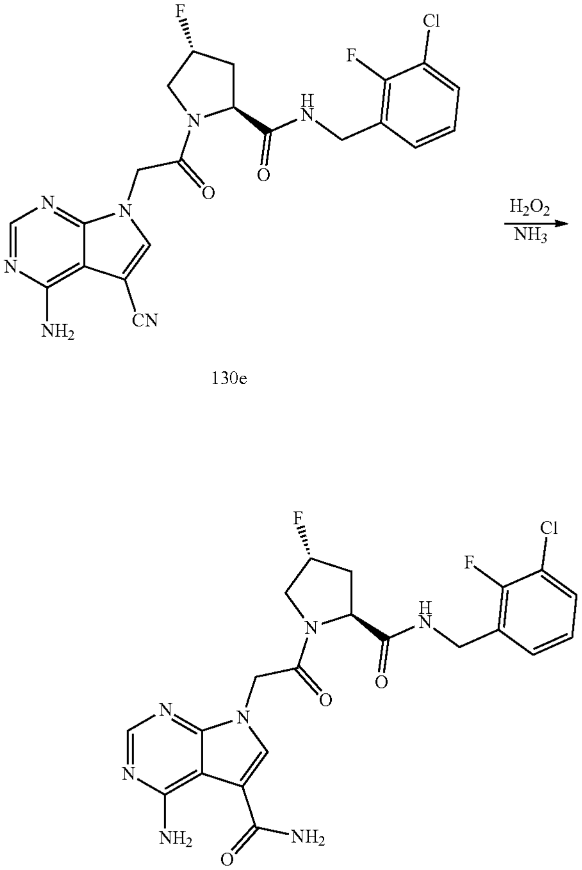

130e

140a

Preparation of 4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidine-5-carboxamide (140a)

Compound 140a was prepared according to the procedure reported in step-1 of scheme-60, from (2S,4R)-1-(2-(4-amino-5-cyano-7H-pyrrolo[2,3-d]pyrimidin-7-yl)acetyl)-N-(3-chloro-2-fluorobenzyl)-4-fluoropyrrolidine-2-carboxamide (130e) (150 mg, 0.317 mmol) in ethanol (8 mL) using conc. $NH_4OH$ (3 mL) and hydrogen peroxide (0.112 mL, 1.266 mmol) and stirring at RT for 5 h. This gave after workup and purification by reverse phase column chromatography [C18 column (26 g), eluting with ACN in water (containing 0.1% HCl) from 0-100%] 4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidine-5-carboxamide (140a) (134 mg, 86% yield) HCl salt as a white solid: 1H NMR (300 MHz, DMSO-$d_6$/$D_2O$) (a mixture of two rotamers) S 8.81-8.65 (m, 1H), 8.38 (d, J=4.6 Hz, 1H), 8.15 (s, 1H), 7.42 (q. J=10.2, 9.0 Hz, 1H), 7.21 (q, J=8.7, 8.1 Hz, 1H), 7.07 (t, J=7.9 Hz, 1H), 5.64-5.11 (m, 3H), 4.93-3.87 (m, 5H), 2.51 (s, 1H), 2.23-1.85 (m, 1H); $^{19}F$ NMR (282 MHz, DMSO-$d_6$) (a mixture of two rotamers) δ–121.33 & –121.61, –176.20 &-176.51; MS (ES+): 492.10, 494.10 (M+1): Analysis calculated for $C_{21}H_{20}ClF_2N_7O_3HCl \cdot 2H_2O$: C, 44.69; H, 4.46; N, 17.37; Cl, 12.56. Found: C, 44.49; H, 4.44; N, 17.34; Cl, 12.42.

Scheme 141

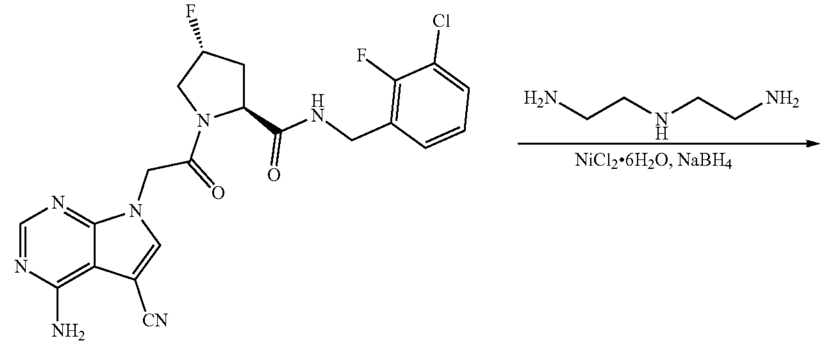

130e

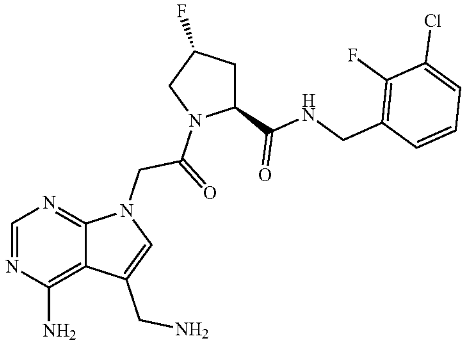

141a

Preparation of (2S,4R)-1-(2-(4-amino-5-(aminomethyl)-7H-pyrrolo[2,3-d]pyrimidin-7-yl)acetyl)-N-(3-chloro-2-fluorobenzyl)-4-fluoropyrrolidine-2-carboxamide (141a)

To a cooled solution of (2S,4R)-1-(2-(4-amino-5-cyano-7H-pyrrolo[2,3-d]pyrimidin-7-yl)acetyl)-N-(3-chloro-2-fluorobenzyl)-4-fluoropyrrolidine-2-carboxamide (130e) (300 mg, 0.633 mmol) in methanol (20 mL) was added nickel(II) chloride hexahydrate (37.6 mg, 0.158 mmol) followed by sodium borohydride (144 mg, 3.80 mmol) in several portions over a period of 10 min and stirred at RT for 1 h. To this mixture was added N1-(2-aminoethyl)ethane-1,2-diamine (0.137 mL, 1.266 mmol) and stirred at RT for 0.5 h and concentrated under vacuum. The residue was treated with ethyl acetate (120 mL), washed with water (60 mL) and the aqueous phase was extracted again with ethyl acetate (60 mL). The combined organics were washed with brine (75 mL), dried, filtered and concentrated in vacuum. The obtained residue was purified by reverse phase column chromatography [C18 column (26 g), eluting with ACN in water (containing 0.1% HCl) from 0-100%] to afford (2S,4R)-1-(2-(4-amino-5-(aminomethyl)-7H-pyrrolo[2,3-d]pyrimidin-7-yl)acetyl)-N-(3-chloro-2-fluorobenzyl)-4-fluoropyrrolidine-2-carboxamide (141a) (48 mg, 16% yield) HCl salt as a white solid; $^1$H NMR (300 MHz, DMSO-$d_6$) (a mixture of two rotamers) δ 9.18-8.53 (m, 3H, $D_2O$ exchangeable), 8.39-8.36 (m, 1H), 8.23 (s, 3H, $D_2O$ exchangeable), 7.52 & 7.51 (2s, 1H), 7.49-7.05 (m, 3H), 5.65-5.07 (m, 3H), 4.99-3.72 (m, 7H), 2.61-2.40 (m, 1H), 2.21-1.88 (m, 1H); $^{19}$F NMR (282 MHz, DMSO-$d_6$) (a mixture of two rotamers) δ−121.32 & −121.61, −176.11 & −176.32; MS (ES+): 478.10 & 480.10 (M+1); Analysis calculated for $C_{21}H_{22}ClF_2N_7O_2$ 1.85 HCl·1.75$H_2O$: C, 43.72; H, 4.78; N, 17.00; Cl, 17.52. Found: C, 43.89; H, 4.62; N, 16.93; Cl, 17.84.

Scheme 142

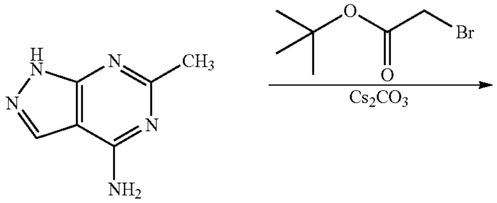

142a

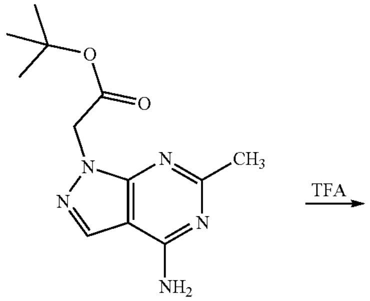

142b

-continued

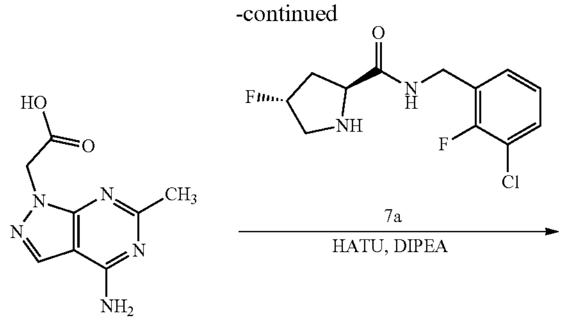

142c

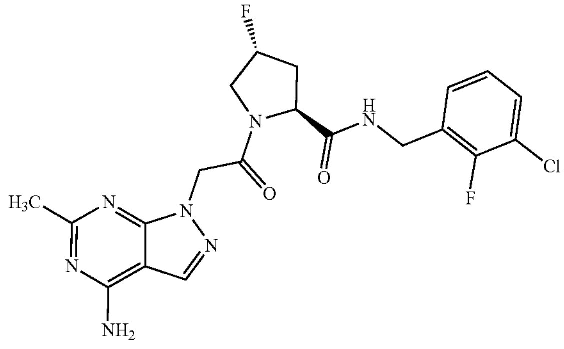

142d

Preparation of (2S,4R)-1-(2-(4-amino-6-methyl-1H-pyrazolo[3,4-d]pyrimidin-1-yl)acetyl)-N-(3-chloro-2-fluorobenzyl)-4-fluoropyrimidine-2-carboxamide (142d)

Step-1: Preparation of tert-butyl 2-(4-amino-6-methyl-1H-pyrazolo[3,4-d]pyrimidin-1-yl)acetate (142b)

Compound 142b was prepared according to the procedure reported in step-1 of scheme-1, from 6-methyl-1H-pyrazolo[3,4-d]pyrimidin-4-amine (142a) (500 mg, 3.35 mmol; CAS #5326-80-7) in DMF (15 mL) using tert-butyl 2-bromoacetate (0.495 mL, 3.35 mmol), $Cs_2CO_3$ (1.311 g, 4.02 mmol) and stirring at RT for 18 h. This gave after workup and purification by flash column chromatography [silica gel; eluting with MeOH in DCM from 0-5%] tert-butyl 2-(4-amino-6-methyl-1H-pyrazolo[3,4-d]pyrimidin-1-yl)acetate (142b) (360 mg, 41% yield) as a yellow solid; $^1$H NMR (300 MHz, DMSO-$d_6$) δ 8.03 (s, 1H), 7.62 (s, 2H), 4.97 (s, 2H), 2.37 (s, 3H), 1.40 (s, 9H); MS (ES+): 264.1 (M+1).

Step-2: Preparation of 2-(4-amino-6-methyl-1H-pyrazolo[3,4-d]pyrimidin-1-yl)acetic acid (142c)

Compound 142c was prepared according to the procedure reported in step-2 of scheme-1, from tert-butyl 2-(4-amino-6-methyl-1H-pyrazolo[3,4-d]pyrimidin-1-yl)acetate (142b) (335 mg, 1.272 mmol) using TFA in DCM (20 mL). This gave after workup 2-(4-amino-6-methyl-1H-pyrazolo[3,4-d]pyrimidin-1-yl)acetic acid (142c) (715 mg) and used as such for the next step; MS (ES+): 208.10 (M+1).

Step-3: Preparation of (2S,4R)-1-(2-(4-amino-6-methyl-1H-pyrazolo[3,4-d]pyrimidin-1-yl)acetyl)-N-(3-chloro-2-fluorobenzyl)-4-fluoropyrrolidine-2-carboxamide (142d)

Compound 142d was prepared according to the procedure reported in step-3 of scheme-1, from 2-(4-amino-6-methyl- 1H-pyrazolo[3,4-d]pyrimidin-1-yl)acetic acid (142c) (0.432 mmol) in DMF (10 mL) using (2S,4R)—N-(3-chloro-2-fluorobenzyl)-4-fluoropyrrolidine-2-carboxamide (7a) (0.540 mmol), HATU (0.329 g, 0.864 mmol), DIPEA (0.376 mL, 2.160 mmol) and stirring at RT for 20 h. This gave after workup and purification using reverse phase column chromatography [C18 column (26 g), eluting with ACN in water (containing 0.1% HCl) from 0-100%] (2S,4R)-1-(2-(4-amino-6-methyl-1H-pyrazolo[3,4-d]pyrimidin-1-yl)acetyl)-N-(3-chloro-2-fluorobenzyl)-4-fluoropyrrolidine-2-carboxamide (142d) (92 mg, 46% yield) HCl salt as a white solid; $^{1}$H NMR (300 MHz, DMSO-$d_6$) (a mixture of two rotamers) δ 10.00 (s, 1H, $D_2O$ exchangeable), 9.09 (t, J=5.9 Hz) & 8.73-8.57 (m) (2H, $D_2O$ exchangeable), 8.45 & 8.44 (2s, 1H), 7.52-7.41 (m, 1H), 7.40-7.19 (m, 1H), 7.16 & 7.06 (2t, J=7.9 Hz, 1H), 5.62-5.17 (m, 3H), 4.96-3.73 (m, 5H), 2.54 & 2.52 (2s, 3H), 2.60-2.40 (m, 1H), 2.19-1.90 (m, 1H); $^{19}$F NMR (282 MHz, DMSO-$d_6$) (a mixture of two rotamers) δ−121.30 & −121.65, −176.29 & −176.51; MS (ES+): 464.10 & 466.10 (M+1); Analysis calculated for $C_{20}H_{20}ClF_2N_7O_2 \cdot HCl \cdot 2.25H_2O$: C, 44.41; H, 4.75; Cl, 13.11; N, 18.13. Found: C, 44.52; H, 4.47; Cl, 12.80; N, 17.95.

Scheme 143

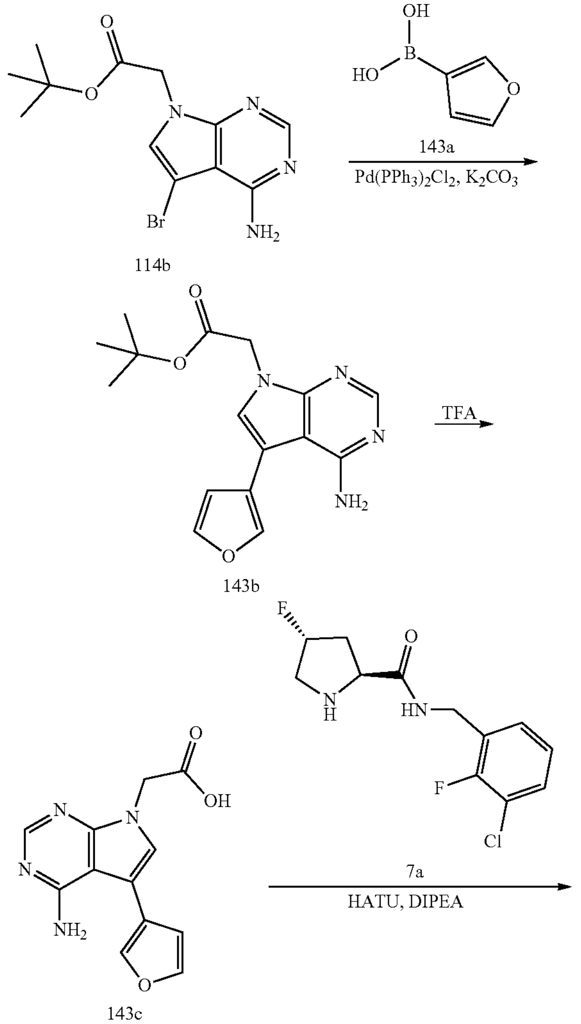

-continued

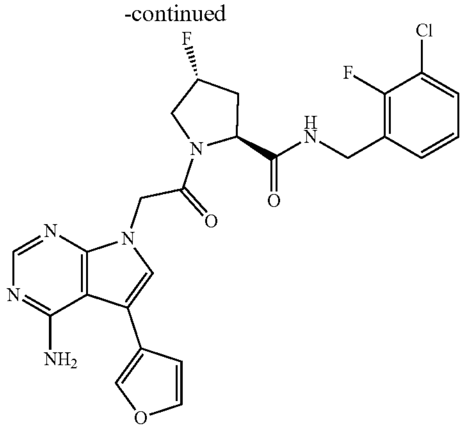

143d

Preparation of (2S,4R)-1-(2-(4-amino-5-(furan-3-yl)-7H-pyrrolo[2,3-d]pyrimidin-7-yl)acetyl)-N-(3-chloro-2-fluorobenzyl)-4-fluoropyrrolidine-2-carboxamide (143d)

Step-1: Preparation of tert-butyl 2-(4-amino-5-(furan-3-yl)-7H-pyrrolo[2,3-d]pyrimidin-7-yl)acetate (143b)

Compound 143b was prepared according to the procedure reported in step-1 of scheme-59, from tert-butyl 2-(4-amino-5-bromo-7H-pyrrolo[2,3-d]pyrimidin-7-yl)acetate (114b) (500 mg, 1.528 mmol) in dioxane (15 mL) using furan-3-ylboronic acid (143a) (171 mg, 1.528 mmol), bis(triphenylphosphine)palladium(II) chloride (161 mg, 0.229 mmol) a solution of potassium carbonate (634 mg, 4.58 mmol) in water (1.8 mL) and heating at 100° C. for 11 h. This gave after workup and purification by flash column chromatography [silica gel, eluting with EtOAc in hexane from 0-67% followed by 10% methanol in EtOAc (1:1)] tert-butyl 2-(4-amino-5-(furan-3-yl)-7H-pyrrolo[2,3-d]pyrimidin-7-yl)acetate (143b) (190 mg, 40% yield) as a yellow solid; $^{1}$H NMR (300 MHz, DMSO-$d_6$) δ 8.11 (s, 1H), 7.83 (s, 1H), 7.81-7.78 (m, 1H), 7.27 (s, 1H), 6.69 (dd, J=1.8, 0.9 Hz, 1H), 6.25 (s, 2H), 4.90 (s, 2H), 1.42 (s, 9H); MS (ES+): 315.10 (M+1).

Step-2: Preparation of 2-(4-amino-5-(furan-3-yl)-7H-pyrrolo[2,3-d]pyrimidin-7-yl)acetic acid (143c)

Compound 143c was prepared according to the procedure reported in step-2 of scheme-1, from tert-butyl 2-(4-amino-5-(furan-3-yl)-7H-pyrrolo[2,3-d]pyrimidin-7-yl)acetate (143b) (175 mg, 0.557 mmol) using TFA in DCM (10 mL). This gave after workup 2-(4-amino-5-(furan-3-yl)-7H-pyrrolo[2,3-d]pyrimidin-7-yl)acetic acid (143c) which was used as such for the next step; MS (ES+): 259.05 (M+1).

Step-3: Preparation of (2S,4R)-1-(2-(4-amino-5-(furan-3-yl)-7H-pyrrolo[2,3-d]pyrimidin-7-yl)acetyl)-N-(3-chloro-2-fluorobenzyl)-4-fluoropyrrolidine-2-carboxamide (143d)

Compound 143d was prepared according to the procedure reported in step-3 of scheme-1,2-(4-amino-5-(furan-3-yl)-7H-pyrrolo[2,3-d]pyrimidin-7-yl)acetic acid (143c) (0.557 mmol) in DMF (15 mL) using (2S,4R)—N-(3-chloro-2- fluorobenzyl)-4-fluoropyrrolidine-2-carboxamide (7a) (0.668 mmol), HATU (0.424 g 1.114 mmol), DIPEA (0.485 mL, 2.79 mmol) and stirring at RT for 13 h. This gave after workup and purification using flash column chromatography [silica column. DCM in MeOH from 0-5%] followed by purification using reverse phase column chromatography [C18 column (26 g), eluting with ACN in water (containing 0.1% HCl) from 0-100%] (2S,4R)-1-(2-(4-amino-5-(furan-3-yl)-7H-pyrrolo[2,3-d]pyrimidin-7-yl)acetyl)-N-(3-chloro-2-fluorobenzyl)-4-fluoropyrrolidine-2-carboxamide (143d) (30 mg, 10% for two steps) HCl salt as a white solid: $^1H$ NMR (300 MHz, DMSO-$d_6$) (a mixture of two rotamers) δ 9.11 & 8.68 (2t, J=5.9 Hz, 1H), 8.43 & 8.42 (2s, 1H), 7.91-7.89 (m, 1H), 7.88-7.83 (m, 1H), 7.51 &7.50 (2s, 1H), 7.49-6.97 (m, 3H), 6.72-6.69 (m, 1H), 5.63-5.08 (m, 3H), 4.93-3.70 (m, 5H), 2.67-2.30 (m, 1H), 2.23-1.89 (m, 1H); $^{19}F$ NMR (282 MHz, DMSO-$d_6$) (a mixture of two rotamers) δ−121.31 & −121.64, −176.12 &−176.34; MS (ES+): 515.10 & 517.10 (M+1); Analysis calculated for $C_{24}H_{21}ClF_2N_6O_3 \cdot HCl$, $1.75H_2O$: C, 49.45; H, 4.41; N, 14.42; Cl, 12.16. Found: C, 49.31; H, 4.13; N, 14.34; Cl, 11.94.

Scheme 144

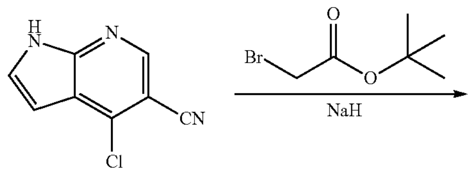

144a

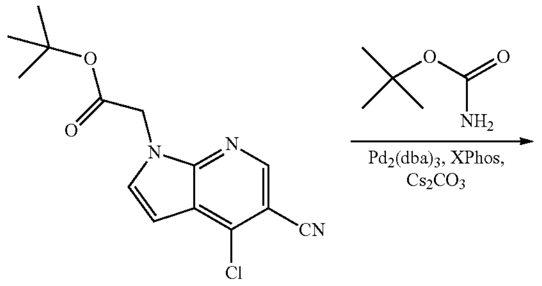

144b

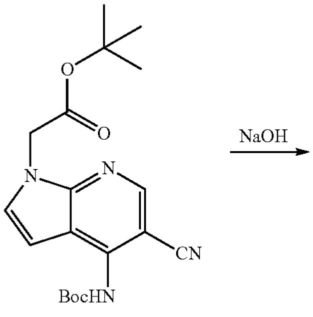

144c

-continued

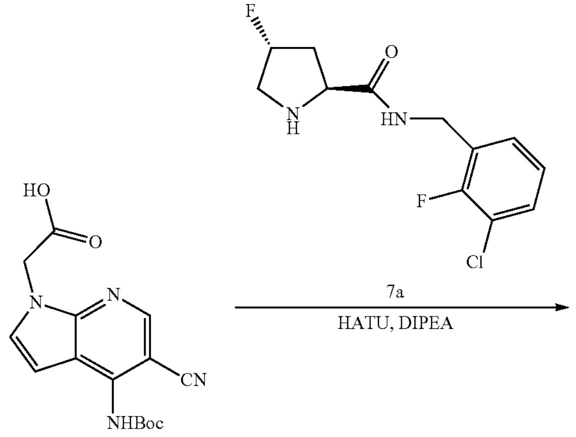

144d

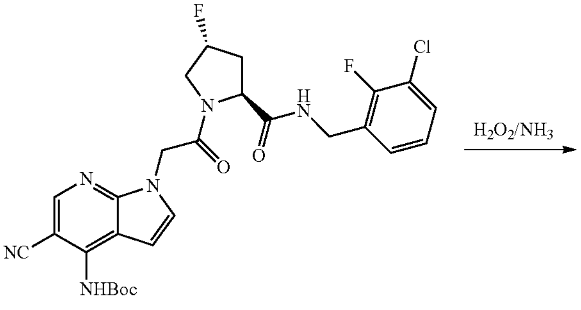

144e

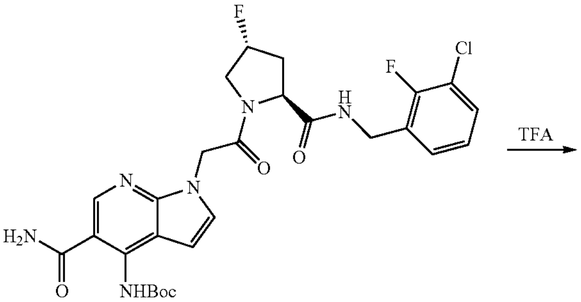

144f

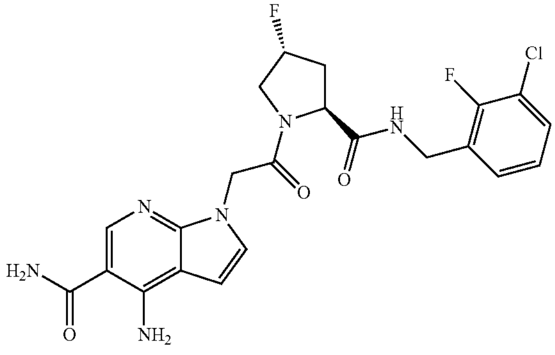

144g

Preparation of 4-amino-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridine-5-carboxamide (144 g)

Step-1: Preparation of tert-butyl 2-(4-chloro-5-cyano-1H-pyrrolo[2,3-b]pyridin-1-yl)acetate (144b)

Compound 144b was prepared according to the procedure reported in step-1 of scheme-88, from 4-chloro-1H-pyrrolo[2,3-b]pyridine-5-carbonitrile (144a) (950 mg, 5.35 mmol; CAS #920966-02-5) in DMF (25 mL) using sodium hydride (0.257 g 6.42 mmol), tert-butyl bromoacetate (0.949 mL, 6.42 mmol) and stirring at RT for 18 h. This gave after workup and purification by flash column chromatography [silica gel, EtOAc in hexane from 0-14%] tert-butyl 2-(4-chloro-5-cyano-1H-pyrrolo[2,3-b]pyridin-1-yl)acetate (144b) (970 mg, 62% yield) as a white solid; $^1$H NMR (300 MHz, DMSO-$d_6$) δ 8.73 (s, 1H), 7.88 (d, J=3.7 Hz, 1H), 6.78 (d, J=3.6 Hz, 1H), 5.12 (s, 2H), 1.40 (s, 9H). MS (ES+): 292.10 & 294.10 (M+1).

Step-2: Preparation of tert-butyl 2-(4-((tert-butoxycarbonyl)amino)-5-cyano-1H-pyrrolo[2,3-b]pyridin-1-yl)acetate (144c)

Compound 144c was prepared according to the procedure reported in step-3 of scheme-17, from tert-butyl 2-(4-chloro-5-cyano-1H-pyrrolo[2,3-b]pyridin-1-yl)acetate (144b) (950 mg, 3.26 mmol) in toluene (30 mL) using XPhos (155 mg, 0.326 mmol), t-butyl carbamate (572 mg, 4.88 mmol), $Pd_2(dba)_3$ (149 mg, 0.163 mmol), cesium carbonate (1061 mg, 3.26 mmol) and heating at 90° C. for 19 h. This gave after work up and purification by flash column chromatography [silica gel, EtOAc in hexane from 0-33%] tert-butyl 2-(4-((tert-butoxycarbonyl)amino)-5-cyano-1H-pyrrolo[2,3-b]pyridin-1-yl)acetate (144c) (1.13 g 93% yield); $^1$H NMR (300 MHz, DMSO-$d_6$) δ 10.19 (s, 1H), 8.51 (s, 1H), 7.61 (d, J=3.7 Hz, 1H), 6.68 (d, J=3.6 Hz, 1H), 5.04 (s, 2H), 1.51 (s, 9H), 1.40 (s, 9H); MS (ES+): 373.20 (M+1).

Step-3: Preparation of 2-(4-((tert-butoxycarbonyl)amino)-5-cyano-1H-pyrrolo[2,3-b]pyridin-1-yl)acetic acid (144d)

Compound 144d was prepared according to the procedure reported in step-4 of scheme-17, from tert-butyl 2-(4-((tert-butoxycarbonyl)amino)-5-cyano-1H-pyrrolo[2,3-b]pyridin-1-yl)acetate (144c) (1.1 g, 2.95 mmol) in THF (5 mL) and MeOH (5 mL) using 2M sodium hydroxide (1.698 mL, 3.40 mmol) and stirring at RT for 25 h. This gave after workup 2-(4-((tert-butoxycarbonyl)amino)-5-cyano-1H-pyrrolo[2,3-b]pyridin-1-yl)acetic acid (144d) (782 mg, 84% yield) as a light yellow solid; MS (ES+): 317.10 (M+1).

Step-4: Preparation of tert-butyl (1-(2-((2S,4R)-2-((3-chloro-2-fluorobenzyl)carbamoyl)-4-fluoropyrrolidin-1-yl)-2-oxoethyl)-5-cyano-1H-pyrrolo[2,3-b]pyridin-4-yl)carbamate (144e)

Compound 144e was prepared according to the procedure reported in step-3 of scheme-1, from 2-(4-((tert-butoxycarbonyl)amino)-5-cyano-1H-pyrrolo[2,3-b]pyridin-1-yl)acetic acid (144d) (600 mg, 1.897 mmol) in DMF (30 mL) using (2S,4R)—N-(3-chloro-2-fluorobenzyl)-4-fluoropyrrolidine-2-carboxamide (7a) (625 mg, 2.276 mmol), HATU (1442 mg, 3.79 mmol), DIPEA (1.652 mL, 9.48 mmol) and stirring at RT for 13 h. This gave after workup and purification by flash column chromatography [silica gel, eluting with MeOH in DCM from 0-5%] tert-butyl (1-(2-((2S,4R)-2-((3-chloro-2-fluorobenzyl)carbamoyl)-4-fluoropyrrolidin-1-yl)-2-oxoethyl)-5-cyano-1H-pyrrolo[2,3-b]pyridin-4-yl)carbamate (144e) (855 mg, 79% yield) as a white solid; $^1$H NMR (300 MHz, DMSO-$d_6$) (a mixture of two rotamers) δ 10.20 (s, 1H), 9.03 & 8.60 (2t, J=5.8 Hz, 1H), 8.473 & 8.467 (2s, 1H), 7.56-7.37 (m, 2H), 7.28-7.13 (m, 1H), 7.09-7.00 (m, 1H), 6.69 & 6.66 (2d, J=3.6 Hz, 1H), 5.68-5.05 (m, 3H), 4.91-3.66 (m, 5H), 2.61-2.04 (m, 2H), 1.52 (s, 9H); $^{19}$F NMR (282 MHz, DMSO-$d_6$) (a mixture of two rotamers) δ−121.32 & −121.71 (1F), −176.11 & −176.35 (1F); MS (ES+): 573.20 & 575.20 (M+1);

Step-5: Preparation of tert-butyl (5-carbamoyl-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridin-4-yl)carbamate (144f)

Compound 144f was prepared according to the procedure reported in step-1 of scheme-60, from tert-butyl (1-(2-((2S,4R)-2-((3-chloro-2-fluorobenzyl)carbamoyl)-4-fluoropyrrolidin-1-yl)-2-oxoethyl)-5-cyano-1H-pyrrolo[2,3-b]pyridin-4-yl)carbamate (144e) (150 mg, 0.262 mmol) in ethanol (8 mL) using conc. $NH_4OH$ (3 mL), hydrogen peroxide (0.093 mL, 1.047 mmol) and stirring for 5 h at RT. This gave after workup and purification by flash column chromatography [silica gel, eluting with MeOH in DCM from 0-5%] tert-butyl (5-carbamoyl-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridin-4-yl)carbamate (144f) (42 mg, 27% yield) as a white solid: $^1$H NMR (300 MHz, DMSO-$d_6$) (a mixture of two rotamers) δ 11.15 & 11.14 (2s, 1H), 9.02 & 8.60 (2t, 1H), 8.51 & 8.50 (2s, 1H), 8.23 (s, 1H), 7.62 (s, 1H), 7.53-7.37 (m, 1H), 7.34 & 7.31 (2d, J=3.6 Hz, 1H), 7.28-7.15 (m, 1H), 7.11-7.02 (m, 1H), 6.72 & 6.70 (2d, J=3.8 Hz, 1H), 5.60-5.36 (m, 1H), 5.34-5.03 (m, 2H), 4.93-3.65 (m, 5H), 2.63-1.77 (m, 2H), 1.50 (s, 9H); $^{19}$F NMR (282 MHz, DMSO-$d_6$) (a mixture of two rotamers) δ−121.36 & −121.74 (1F), −176.10 & −176.38 (1F); MS (ES+): 591.10 & 593.20 (M+1):

Step-6: Preparation of 4-amino-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridine-5-carboxamide (144 g)

Compound 144g was prepared according to the procedure reported in step-2 of scheme-1, from tert-butyl (5-carbamoyl-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridin-4-yl)carbamate (144f) (40 mg, 0.068 mmol) in DCM (10 mL) using TFA (0.101 mL, 1.354 mmol) and stirring at RT for 25 h. This gave after workup and purification by reverse phase column chromatography [C18 column (26 g), eluting with ACN in water (containing 0.1% HCl) from 0-100%] 4-amino-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridine-5-carboxamide (144 g) (21 mg, 63% yield) HCl salt as a white solid; $^1$H NMR (300 MHz, DMSO-$d_6$) (a mixture of two rotamers) δ 9.09 & 8.76 (2t, J=6.1 Hz, 1H, $D_2O$ exchangeable), 8.47 & 8.42 (2s, 1H), 8.16 (s, 1H, $D_2O$ exchangeable), 7.59 (s, 1H, $D_2O$ exchangeable), 7.53-7.33 (m, 1H), 7.30-6.85 (m, 4H), 5.62-5.56 & 5.45-5.39 (2m, 1H), 5.37 (s, 2H), 4.91-3.81 (m, 5H), 2.64-2.41 (m, 1H), 2.31-1.93 (m, 1H); $^{19}$F NMR (282 MHz, $DMSO-d_6$) (a mixture of two rotamers) δ−121.31 & −121.66 9, −175.78 & −175.96; MS (ES+): 491.10 & 493.10 (M+1).

Scheme 145

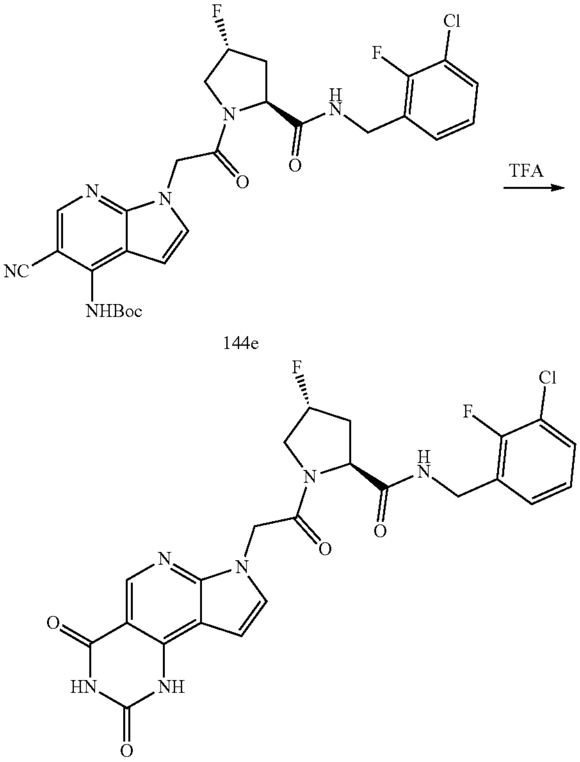

144e

145a

Preparation of (2S,4R)—N-(3-chloro-2-fluorobenzyl)-1-(2-(2,4dioxo-3,4dihydro-1H-pyrrolo[3',2':5,6]pyrido[4,3-d]pyrimidin-7 (2H)-yl)acetyl)-4-fluoropyrrolidine-2-carboxamide (145a)

Compound 145a was prepared according to the procedure reported in step-2 of scheme-1, from tert-butyl (1-(2-((2S,4R)-2-((3-chloro-2-fluorobenzyl)carbamoyl)-4-fluoropyrrolidin-1-yl)-2-oxoethyl)-5-cyano-1H-pyrrolo[2,3-b]pyridin-4-yl)carbamate (144e) (100 mg, 0.175 mmol) in DCM (10 mL) using TFA (0.104 mL, 1.396 mmol) and stirring at RT for 22 h. This gave after workup and purification by reverse phase column chromatography [C18 column (26 g), eluting with ACN in water (containing 0.1% HCl) from 0-100%] (2S,4R)—N-(3-chloro-2-fluorobenzyl)-1-(2-(2,4dioxo-3,4dihydro-1H-pyrrolo[3',2':5,6]pyrido[4,3-d]pyrimidin-7 (2H)-yl)acetyl)-4-fluoropyrrolidine-2-carboxamide (145a) (8 mg, 9% yield) as a white solid: 1H NMR (300 MHz, $DMSO-d_6$) (a mixture of two rotamers) δ 11.84 (s, 1H, $D_2O$ exchangeable), 11.35 (s, 1H, $D_2O$ exchangeable), 9.08-8.99 & 8.62-8.56 (2t, 1H, $D_2O$ exchangeable), 8.64 (s, 1H) 7.52-6.92 (m, 5H), 5.60-5.11 (m, 3H), 4.95-3.69 (m, 5H), 2.78-1.84 (m, 2H); $^{19}F$ NMR (282 MHz, $DMSO-d_6$) (a mixture of two rotamers) δ−121.32 &-121.71, −176.10 & −176.32; MS (ES+): 517.10 & 519.10 (M+1).

Scheme 146

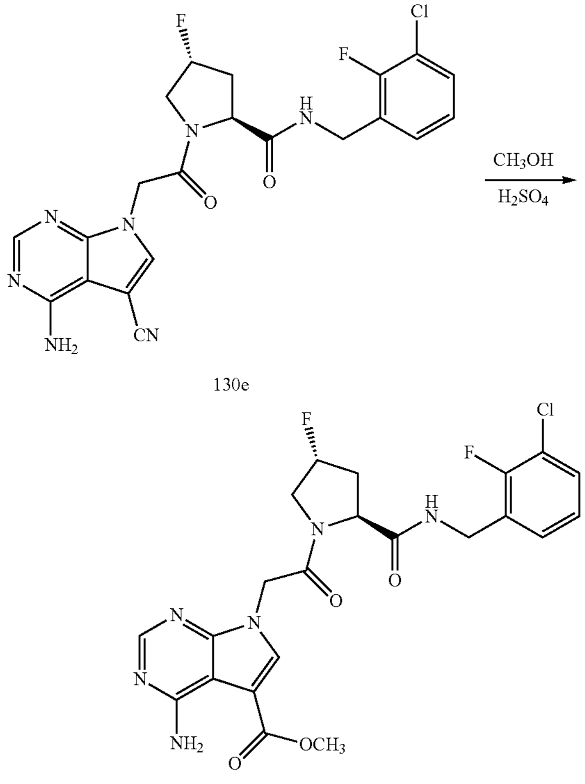

130e

146a

Preparation of methyl 4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidine-5-carboxylate (146a)

To a solution of (2S,4R)-1-(2-(4-amino-5-cyano-7H-pyrrolo[2,3-d]pyrimidin-7-yl)acetyl)-N-(3-chloro-2-fluorobenzyl)-4-fluoropyrrolidine-2-carboxamide (190 mg, 0.401 mmol) (130e) in methanol (10 mL) was added conc. sulfuric acid (0.214 mL, 4.01 mmol) and refluxed for 43 h. The reaction mixture was cooled to RT diluted with ethyl acetate (100 mL) and 0.5 M $K_2CO_3$ (40 mL). The organic layer was washed with brine (50 mL), dried, filtered and concentrated in vacuum. The residue obtained was purified using reverse-phase column chromatography [C18 column (26 g), eluting with ACN in water (containing 0.1% HCl) from 0-100%] to afford methyl 4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidine-5-carboxylate HCl salt (146a) (1.3 mg, 0.64% yield) HCl salt as a white solid. $^1H$ NMR (300 MHz, $DMSO-d_6$) (a mixture of two rotamers) δ 9.11-8.42 (m, 3H, $D_2O$ exchangeable), 8.39-8.35 (m, 1H), 8.17 & 8.16 (2s, 1H), 7.57-6.99 (m, 3H), 5.65-5.08 (m, 3H), 4.88-3.91 (m, 5H), 3.88 (s, 3H), 2.62-2.36 (m, 1H), 2.24-1.87 (m, 1H); $^{19}F$ NMR (282 MHz, $DMSO-d_6$) (a mixture of two rotamers) δ−121.64, −176.14; MS (ES+): 507.10 & 509.10 (M+1).

Scheme 147

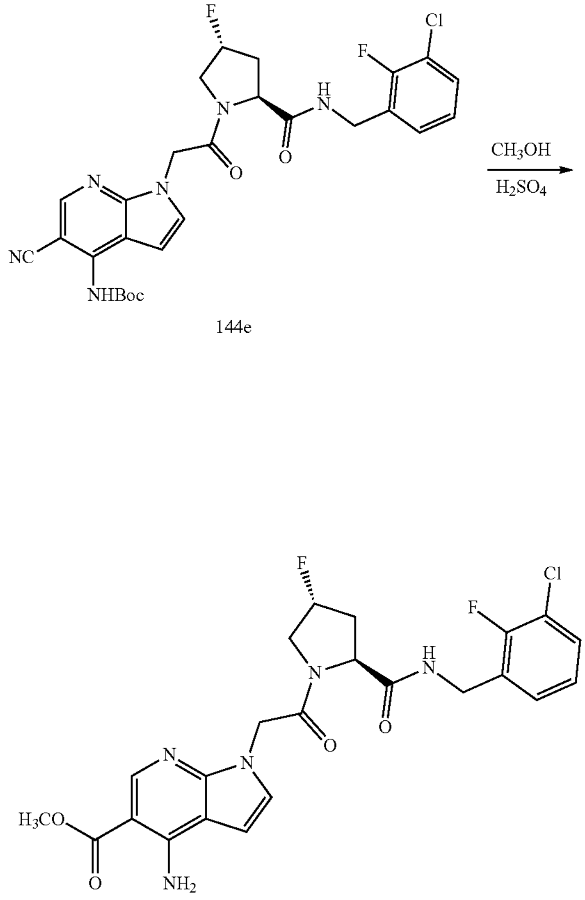

144e

147a

Preparation of methyl 4-amino-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridine-5-carboxylate (147a)

Compound 147a was prepared according to the procedure reported in scheme-146, from tert-butyl (1-(2-((2S,4R)-2-((3-chloro-2-fluorobenzyl)carbamoyl)-4-fluoropyrrolidin-1-yl)-2-oxoethyl)-5-cyano-1H-pyrrolo[2,3-b]pyridin-4-yl)carbamate (144e) (200 mg, 0.349 mmol) in methanol (10 mL) using conc. sulfuric acid (0.186 mL, 3.49 mmol) and refluxing for 14 h. This gave after work up and purification using reverse-phase column chromatography [C18 column (26 g), eluting with ACN in water (containing 0.1% HCl) from 0-100%] methyl 4-amino-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridine-5-carboxylate (147a) (2.3 mg, 1.3% yield) HCl salt as a white solid: 1H NMR (300 MHz, DMSO-$d_6$) (a mixture of two rotamers) δ 9.03 & 8.64 (2t, J=5.8 Hz, 1H, $D_2O$ exchangeable), 8.52 & 8.44 (2s, 1H), 7.56-6.83 (m, 5H), 5.63-5.07 (m, 3H), 4.93-3.71 (m, 8H), 2.68-2.37 (m, 1H), 2.32-1.90 (m, 1H); $^{19}F$ NMR (282 MHz, DMSO-$d_6$) (a mixture of two rotamers) δ−121.33 & −121.68, −175.91 & −176.15; MS (ES+): 506.10 & 508.15 (M+1).

Scheme 148

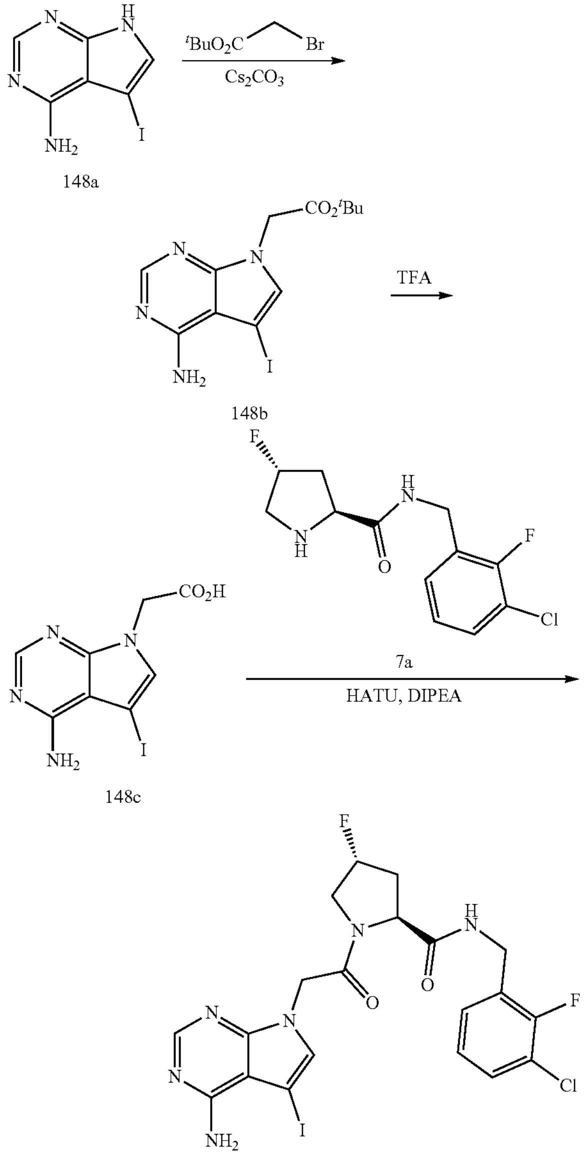

148a

148b

148c

148d

Preparation of (2S,4R)-1-(2-(4-amino-5-iodo-7H-pyrrolo[2,3-d]pyrimidin-7-yl)acetyl)-N-(3-chloro-2-fluorobenzyl)-4-fluoropyrrolidine-2-carboxamide (148d)

Step-1: Preparation of tert-butyl 2-(4-amino-5-iodo-7H-pyrrolo[2,3-d]pyrimidin-7-yl)acetate (148b)

Compound 148b was prepared according to the procedure reported in step-1 of scheme-1, from 5-iodo-7H-pyrrolo[2,3-d]pyrimidin-4-amine (148a) (5 g, 19.23 mmol; CAS #163622-50-2) in DMF (20 mL) using tert-butyl 2-bromoacetate (3.75 g, 19.23 mmol), $Cs_2CO_3$ (7.52 g, 23.07 mmol) and stirring at RT for 16 h. This gave after workup and purification by flash column chromatography [silica gel (24 g), eluting with MeOH in DCM from 0-3%] tert-butyl 2-(4-amino-5-iodo-7H-pyrrolo[2,3-d]pyrimidin-7-yl)acetate (148b) (5 g, 70% yield) as a pale orange solid; $^1$H NMR (300 MHz, DMSO-$d_6$) δ 8.09 (s, 1H), 7.43 (s, 1H), 6.86-6.41 (m, 2H), 4.87 (s, 2H), 1.41 (s, 9H). MS (ES+): 375 (M+1).

Step-2: Preparation of 2-(4-amino-5-iodo-7H-pyrrolo[2,3-d]pyrimidin-7-yl)acetic acid (148c)

Compound 148c was prepared according to the procedure reported in step-2 of scheme-1, from tert-butyl 2-(4-amino-5-iodo-7H-pyrrolo[2,3-d]pyrimidin-7-yl)acetate (148b) (2.50 g, 6.68 mmol) using TFA (38.3 mL, 100 mmol; 20% TFA in DCM) and stirring at RT for 16 h. This gave after workup 2-(4-amino-5-iodo-7H-pyrrolo[2,3-d]pyrimidin-7-yl)acetic acid (148c) (2.91 g) TFA salt as a purple solid: $^1$H NMR (300 MHz, DMSO-$d_6$) δ 8.32 (d, J=1.2 Hz, 1H), 7.66 (d, J=1.3 Hz, 1H), 4.97 (s, 2H). $^{19}$F NMR (282 MHz, DMSO-$d_6$) δ−74.24; MS (ES+): 319 (M+1).

Step-3: Preparation of (2S,4R)-1-(2-(4-amino-5-iodo-7H-pyrrolo[2,3-d]pyrimidin-7-yl)acetyl)-N-(3-chloro-2-fluorobenzyl)-4-fluoropyrrolidine-2-carboxamide (148d)

Compound 148d was prepared according to the procedure reported in step-3 of scheme-1, from TFA salt of 2-(4-amino-5-iodo-7H-pyrrolo[2,3-d]pyrimidin-7-yl)acetic acid (148c) (2.88 g, 6.67 mmol) in DCM (10 mL) using (2S,4R)—N-(3-chloro-2-fluorobenzyl)-4-fluoropyrrolidine-2-carboxamide (7a) (2.59 g, 6.67 mmol), HATU (3.04 g, 8.00 mmol), DIPEA (5.82 mL, 33.3 mmol) and stirring at RT for 16 h. This gave after workup and purification using reverse phase column chromatography [C18 column (100 g), eluting with ACN in water (containing 0.1% HCl) from 0-60%] (2S,4R)-1-(2-(4-amino-5-iodo-7H-pyrrolo[2,3-d]pyrimidin-7-yl)acetyl)-N-(3-chloro-2-fluorobenzyl)-4-fluoropyrrolidine-2-carboxamide (148d) (55 mg, 0.096 mmol) HCl salt as a white solid; 1H NMR (300 MHz, DMSO-$d_6$) δ (a mixture of two rotamers) 9.08 (t, J=5.9 Hz) and 8.67 (t, J=5.9 Hz) (2t, 1H), 8.36 (d, J=3.8 Hz, 1H), 8.01 (s, 2H, $D_2O$ exchangeable), 7.61 (d, J=5.6 Hz, 1H), 7.52-7.34 (m, 1H), 7.29-7.13 (m, 1H), 7.08 (t, J=8.1 Hz, 1H), 5.64-5.36 (m, 1H), 5.29 (d, J=17.1 Hz, 1H), 5.19-5.03 (m, 1H), 4.50-4.31 (m, 2H), 4.31-4.03 (m, 2H), 3.85 (ddd, J=38.4, 12.6, 3.1 Hz, 1H), 2.60-2.21 (m, 1H), 2.20-1.90 (m, 1H); $^{19}$F NMR (282 MHz, DMSO) δ−121.32, −121.62, −176.13, −176.34; MS (ES+): 575.0 (M+1); (ES−): 573.0 (M−1); Analysis calculated for $C_{20}H_{18}ClF_{21}N_6O_2 \cdot HCl \cdot 2H_2O$: C, 37.11; H, 3.58; Cl, 10.96; N, 12.98. Found: C, 37.13; H, 3.20; Cl, 10.93; N, 13.12.

Scheme 149

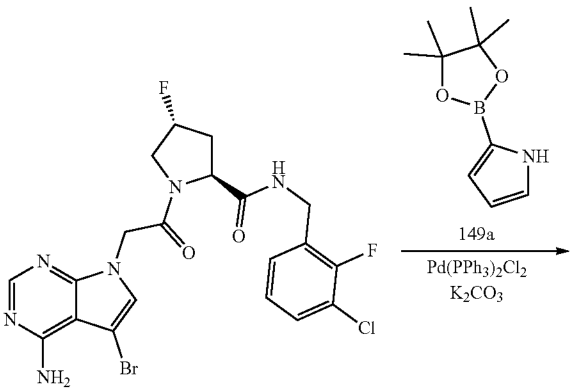

116b

-continued

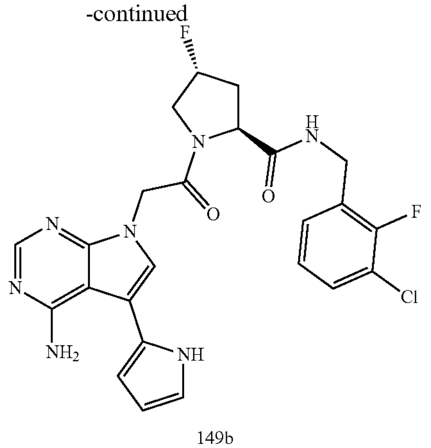

149b

Preparation of (2S,4R)-1-(2-(4-amino-5-(1H-pyrrol-2-yl)-7H-pyrrolo[2,3-d]pyrimidin-7-yl)acetyl)-N-(3-chloro-2-fluorobenzyl)-4-fluoropyrrolidine-2-carboxamide (149b)

Compound 149b was prepared according to the procedure reported in step-1 of scheme-62, from (2S,4R)-1-(2-(4-amino-5-bromo-7H-pyrrolo[2,3-d]pyrimidin-7-yl)acetyl)-N-(3-chloro-2-fluorobenzyl)-4-fluoropyrrolidine-2-carboxamide (116b) (200 mg, 0.379 mmol) in dioxane (5 mL) using 2-(4,4,5,5-tetramethyl-1,3,2-dioxaborolan-2-yl)-1H-pyrrole (149a) (110 mg, 0.568 mmol; CAS #476004-79-2), $Pd(PPh_3)_2Cl_2$ (26.6 mg, 0.038 mmol), 3.3 M aqueous $K_2CO_3$ (0.345 mL, 1.137 mmol) and heating at 100° C. for 16 h under argon. This gave after workup and purification using flash column chromatography [silica column (12 g), eluting with MeOH in DCM from 0-5%] followed by purification using reverse phase column chromatography [C18 column (100 g), eluting with ACN in water (containing 0.1% HCl) from 0-60%] (2S,4R)-1-(2-(4-amino-5-(1H-pyrrol-2-yl)-7H-pyrrolo[2,3-d]pyrimidin-7-yl)acetyl)-N-(3-chloro-2-fluorobenzyl)-4-fluoropyrrolidine-2-carboxamide (149b) (27 mg, 14% yield) HCl salt as a white solid; $^1$H NMR (300 MHz, DMSO-$d_6$) δ (a mixture of two rotamers) 11.31 (d, J=8.3 Hz, 1H, $D_2O$ exchangeable), 9.08 (t), 8.65 (t, J=5.8 Hz) (2t, 1H), 8.39 (d, J=3.6 Hz, 1H), 7.64 (s, 2H, $D_2O$ exchangeable), 7.50-7.34 (m, 2H), 7.29-7.13 (m, 1H), 7.02 (t, J=7.9 Hz, 1H), 6.91 (p, J=2.0 Hz, 1H), 6.22 (t, J=2.2 Hz, 2H), 5.66-5.04 (m, 3H), 4.56-4.07 (m, 4H), 4.01-3.72 (m, 1H), 2.62-2.37 (m, 1H), 2.21-1.89 (m, 1H); $^{19}$F NMR (282 MHz, DMSO-$d_6$) δ−121.31, −121.64, −176.11, −176.31; MS (ES+) 514.0 (M+1), 512.0 (M−1); Analysis calculated for: $C_{24}H_{22}ClF_2N_7O_2 \cdot HCl$, $2.50H_2O$: C, 48.41; H, 4.74; Cl, 11.91; N, 16.47. Found: C, 48.22; H, 4.49; Cl, 12.01; N, 16.36.

Scheme 150

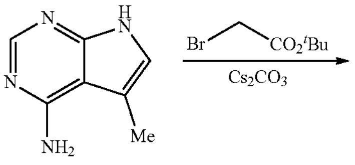

150a

-continued

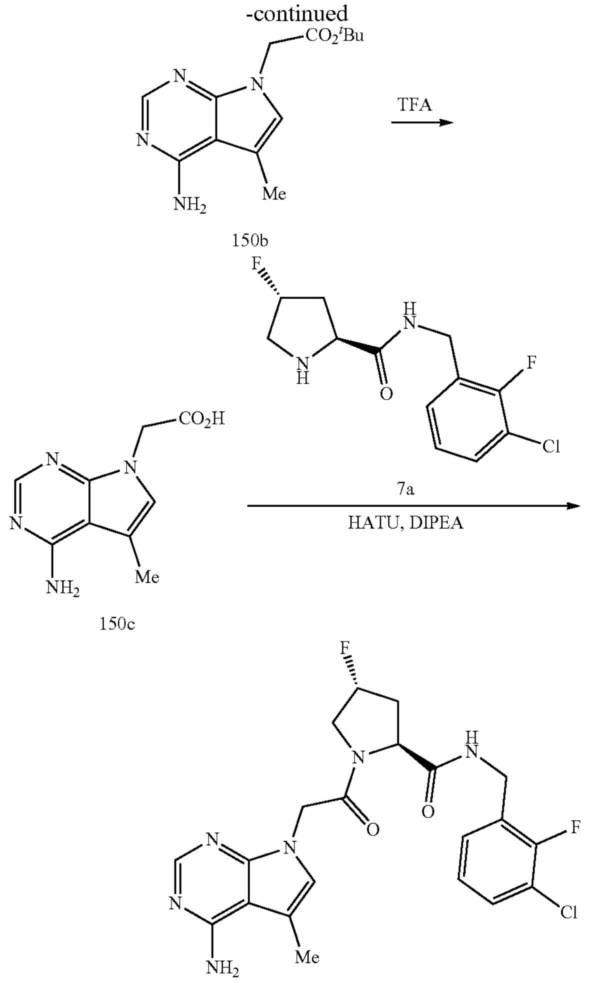

150b

7a

150c

150d

Preparation of (2S,4R)-1-(2-(4-amino-5-methyl-7H-pyrrolo[2,3-d]pyrimidin-7-yl)acetyl)-N-(3-chloro-2-fluorobenzyl)-4-fluoropyrrolidine-2-carboxamide (150d)

Step-1: Preparation of tert-butyl 2-(4-amino-5-methyl-7H-pyrrolo[2,3-d]pyrimidin-7-yl)acetate (150b)

Compound 150b was prepared according to the procedure reported in step-1 of scheme-1, from 5-methyl-7H-pyrrolo[2,3-d]pyrimidin-4-amine (150a) (0.5 g, 3.37 mmol; CAS #1501-10-6) in DMF (20 mL) using tert-butyl 2-bromoacetate (0.658 g, 3.37 mmol), $Cs_2CO_3$ (1.319 g, 4.05 mmol) and stirring at RT for 16 h. his gave after workup and purification by flash column chromatography [silica gel (24 g), eluting with MeOH in DCM from 0-3%] tert-butyl 2-(4-amino-5-methyl-7H-pyrrolo[2,3-d]pyrimidin-7-yl)acetate (150b) (0.30 g, 34% yield) as a pale orange solid; $^1H$ NMR (300 MHz, DMSO-$d_6$) δ 7.99 (s, 1H), 6.86 (d, J=1.3 Hz, 1H), 6.55 (s, 2H), 4.78 (s, 2H), 2.34 (s, 3H), 1.41 (s, 9H).

Step-2: Preparation of 2-(4-amino-5-methyl-7H-pyrrolo[2,3-d]pyrimidin-7-yl)acetic acid (150c)

Compound 150c was prepared according to the procedure reported in step-2 of scheme-1, from tert-butyl 2-(4-amino-5-methyl-7H-pyrrolo[2,3-d]pyrimidin-7-yl)acetate (150b) (300 mg, 1.144 mmol) using TFA (9781 mg, 17.16 mmol; 20% TFA in DCM) and stirring at RT for 16 h. This gave after workup TFA salt of 2-(4-amino-5-methyl-7H-pyrrolo[2,3-d]pyrimidin-7-yl)acetic acid (150c) (470 mg) as a pale-orange solid; $^1H$ NMR (300 MHz, DMSO-$d_6$) δ 8.68-8.38 (m, 2H), 8.35 (s, 1H), 7.26 (d, J=1.3 Hz, 1H), 4.98 (s, 2H), 2.41 (d, J=1.2 Hz, 3H).

Step-3: Preparation of (2S,4R)-1-(2-(4-amino-5-methyl-7H-pyrrolo[2,3-d]pyrimidin-7-yl)acetyl)-N-(3-chloro-2-fluorobenzyl)-4-fluoropyrrolidine-2-carboxamide (150d)

Compound 150d was prepared according to the procedure reported in step-3 of scheme-1, from TFA salt of 2-(4-amino-5-methyl-7H-pyrrolo[2,3-d]pyrimidin-7-yl)acetic acid (150c) (150 mg, 0.468 mmol) in DMF (5 mL) using TFA salt of (2S,4R)—N-(3-chloro-2-fluorobenzyl)-4-fluoropyrrolidine-2-carboxamide (7a) (182 mg, 0.468 mmol), HATU (214 mg, 0.562 mmol), DIPEA (0.409 mL, 2.342 mmol) and stirring at RT for 16 h. This gave after workup and purification by flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (2S,4R)-1-(2-(4-amino-5-methyl-7H-pyrrolo[2,3-d]pyrimidin-7-yl)acetyl)-N-(3-chloro-2-fluorobenzyl)-4-fluoropyrrolidine-2-carboxamide (150d) (83 mg, 38% yield) as a white solid: $^1H$ NMR (300 MHz, DMSO-$d_6$) δ (a mixture of two rotamers) 9.15 (t, J=5.8 Hz) and 8.71 (t, J=5.9 Hz) (2s, 1H), 8.47 (s, 2H, $D_2O$ exchangeable), 8.34 (d, J=3.2 Hz, 1H), 7.53-7.40 (m, 1H), 7.31-7.21 (m, 1H), 7.20-7.11 (m, 1H), 7.07 (t, J=7.9 Hz, 1H), 5.59-5.33 (m, 1H), 5.26 (d, J=17.0 Hz, 1H), 5.09 (d, J=17.1 Hz, 1H), 4.39 (ddd, J=21.1, 10.2, 5.7 Hz, 2H), 4.23 (dd, J=21.7, 5.8 Hz, 1H), 4.16-4.02 (m, 1H), 3.86 (ddd, J=37.2, 12.9, 3.3 Hz, 1H), 2.82-2.47 (m, 1H), 2.39 (s, 3H), 2.16-1.91 (m, 1H); $^{19}F$ NMR (282 MHz, DMSO-$d_6$) δ−121.32, −121.66, −176.15, −176.34; MS (ES+): 463.0 (M+1), (ES−): 461.0 (M−1); Analysis calculated for $C_{21}H_{21}ClF_2N_6O_2$·HCl·2.25$H_2O$: C, 46.72; H, 4.95; Cl, 13.13; N, 15.57. Found: C, 46.35; H, 4.56; Cl, 13.52; N, 15.40.

Scheme 151

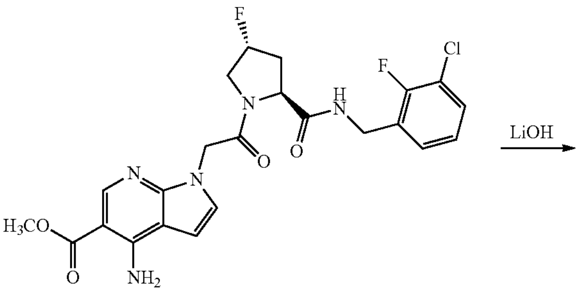

147a

-continued

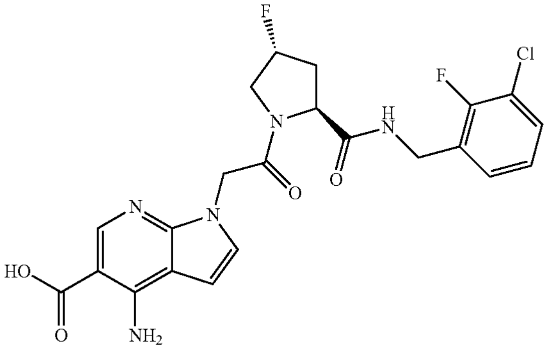

151a

Preparation of 4-amino-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridine-5-carboxylic acid (151a)

Compound 151a was prepared according to the procedure reported in step-4 of scheme-17, from methyl 4-amino-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridine-5-carboxylate (147a) (22 mg, 0.043 mmol) in THF (3 mL) and MeOH (3 mL) using a solution of lithium hydroxide (18.62 mg, 0.435 mmol) in water (3 mL) and stirring at RT for 19 h. Additional lithium hydroxide hydrate (25 mg, and 50 mg), 2N sodium hydroxide solution (0.4 mL and 0.6 mL) were added and stirred at RT overnight after each addition. This gave after workup and purification by reverse phase column chromatography [C18 column (26 g), eluting with ACN in water (containing 0.1% HCl) from 0-100%] 4-amino-1-(2-((2S,4R)-2-((3-chloro-2-fluorobenzyl)carbamoyl)-4-fluoropyrrolidin-1-yl)-2-oxoethyl)-1H-pyrrolo[2,3-b]pyridine-5-carboxylic acid (151a) (2.2 mg, 10% yield) HCl salt as a white solid; 1H NMR (300 MHz, DMSO-$d_6$) (a mixture of two rotamers) δ 8.64 (t, J=5.7 Hz, 1H, $D_2O$ exchangeable), 8.53 & 8.48 (2s, 1H), 7.55-6.92 (m, 5H), 5.62-5.14 (m, 3H), 4.97-3.70 (m, 5H), 2.68-2.38 (m, 1H), 2.27 (s, 1H); $^{19}F$ NMR (282 MHz, DMSO-$d_6$) (a mixture of two rotamers) δ−121.32 &−121.65 (1F), −175.81 & −176.07 (1F); MS (ES+): 492.00 & 494.00 (M+1); MS (ES−): 490.00 & 492.00 (M−1).

Scheme 152

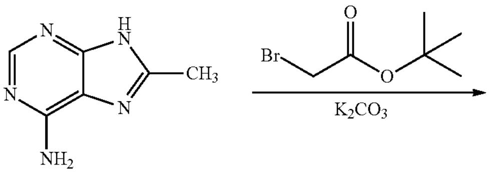

152a

-continued

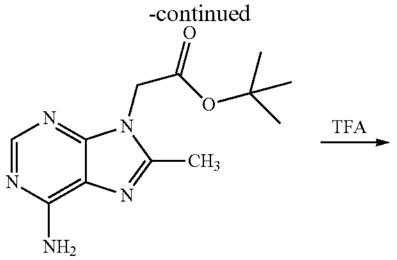

152b

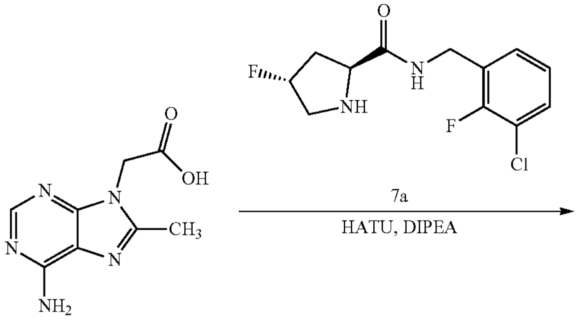

152c

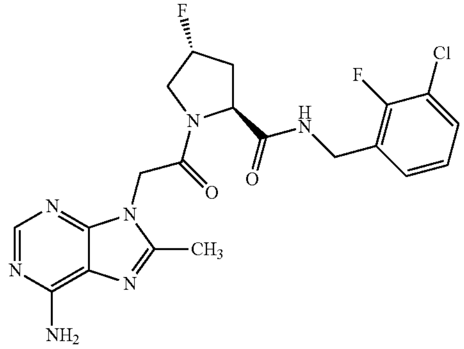

152d

Preparation of (2S,4R)-1-(2-(6-amino-8-methyl-9H-purin-9-yl)acetyl)-N-(3-chloro-2-fluorobenzyl)-4-fluoropyrrolidine-2-carboxamide (152d)

Step-1: Preparation of tert-butyl 2-(6-amino-8-methyl-9H-purin-9-yl)acetate (152b)

Compound 152b was prepared according to the procedure reported in step-1 of scheme-1, from 8-methyl-7H-purin-6-amine (152a) (500 mg, 3.35 mmol; CAS #22387-37-7) in DMF (15 mL) using tert-butyl 2-bromoacetate and $K_2CO_3$ (556 mg, 4.02 mmol). This gave after workup tert-butyl 2-(6-amino-8-methyl-9H-purin-9-yl)acetate (152b) (390 mg, 44% yield) as a yellow solid; 1H NMR (300 MHz, DMSO-$d_6$) δ 8.07 (s, 1H), 7.11 (s, 2H), 4.90 (s, 2H), 2.42 (s, 3H), 1.42 (s, 9H); MS (ES+): 264.10 (M+1).

Step-2: Preparation of 2-(6-amino-8-methyl-9H-purin-9-yl)acetic acid (152c)

Compound 152c was prepared according to the procedure reported in step-2 of scheme-1, from tert-butyl 2-(6-amino-8-methyl-9H-purin-9-yl)acetate (152b) (150 mg, 0.570 mmol) in DCM (10 mL) using TFA and stirred at RT. This gave after workup 2-(6-amino-8-methyl-9H-purin-9-yl)acetic acid (152c) which was used as such in the next step; MS (ES+): 208.10 (M+1).

Step-3: Preparation of (2S,4R)-1-(2-(6-amino-8-methyl-9H-purin-9-yl)acetyl)-N-(3-chloro-2-fluorobenzyl)-4-fluoropyrrolidine-2-carboxamide (152d)

Compound 152d was prepared according to the procedure reported in step-3 of scheme-1, from TFA salt of 2-(6-amino-8-methyl-9H-purin-9-yl)acetic acid (152c) (118 mg, 0.57 mmol) in DMF (10 mL) using TFA salt of (2S,4R)—N-(3-chloro-2-fluorobenzyl)-4-fluoropyrrolidine-2-carboxamide (7a) (188 mg, 0.684 mmol), HATU (433 mg, 1.140 mmol), DIPEA (0.496 mL, 2.85 mmol) and stirring at RT overnight. This gave after workup and purification by flash column chromatography [silica gel, eluting with DCM/methanol (1:0 to 19:1)] (2S,4R)-1-(2-(6-amino-8-methyl-9H-purin-9-yl)acetyl)-N-(3-chloro-2-fluorobenzyl)-4-fluoropyrrolidine-2-carboxamide (152d) (31 mg, 12% yield) as a white solid; $^1$H NMR (300 MHz, DMSO-$d_6$) (a mixture of two rotamers) δ 9.00 & 8.64 (2t, J=6.2 Hz, 1H), 8.22 & 8.20 (2s, 1H), 7.54-7.39 (m, 1H), 7.31-7.17 (m, 1H), 7.11-7.00 (m, 1H), 5.62-5.36 (m, 1H), 5.31 (d, J=17.5 Hz, 1H), 5.03 (d, J=17.6 Hz, 1H), 4.61-3.74 (m, 5H), 2.60-1.90 (m, 2H), 2.37 (s, 3H); $^{19}$F NMR (282 MHz, DMSO-$d_6$) δ-121.28, −175.82; MS (ES+): 464.0 (M+1).

Preparation of 4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidine-5-carboxylic acid (153a)

Compound 153a was prepared according to the procedure reported in step-4 of scheme-17, from methyl 4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidine-5-carboxylate (146a) (15 mg, 0.030 mmol) in THF (3 mL) and MeOH (3 mL) using a solution of lithium hydroxide (25.3 mg, 0.592 mmol) in water (3 mL) and stirring at RT overnight. This gave after workup and purification by reverse phase column chromatography [C18 column (26 g), eluting with ACN in water (containing 0.1% HCl) from 0-100%] 4-amino-7-(2-((2S,4R)-2-((3-chloro-2-fluorobenzyl)carbamoyl)-4-fluoropyrrolidin-1-yl)-2-oxoethyl)-7H-pyrrolo[2,3-d]pyrimidine-5-carboxylic acid (153a) (4.6 mg, 32%) HCl salt as a white solid; $^1$H NMR (300 MHz, DMSO-$d_6$) (a mixture of two rotamers) δ 9.08 & 8.65 (2t, J=5.9 Hz, 1H, $D_2O$ exchangeable), 8.49 (s, 2H, $D_2O$ exchangeable), 8.38 & 8.36 (2s, 1H), 8.11 & 8.10 (2s, H), 7.52-7.01 (m, 3H), 5.66-5.04 (m, 3H), 4.89-3.70 (m, 5H), 2.75-2.30 (m, 1H), 2.23-1.89 (m, 1H); $^{19}$F NMR (282 MHz, DMSO-$d_6$) (a mixture of two rotamers) δ-121.34 &-121.63 (1F), −176.12 & −176.34 (1F); MS (ES+): 493.00 & 495.00 (M+1); MS (ES−): 491.00 & 493.00 (M−1).

Scheme 153

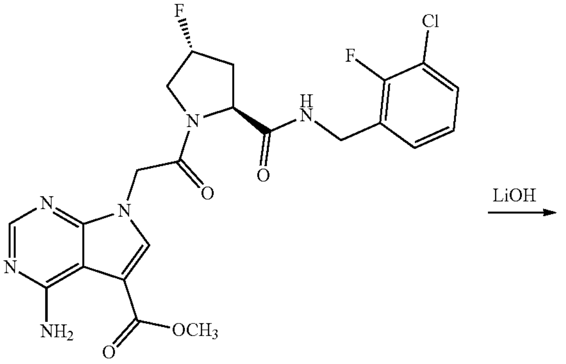

146a

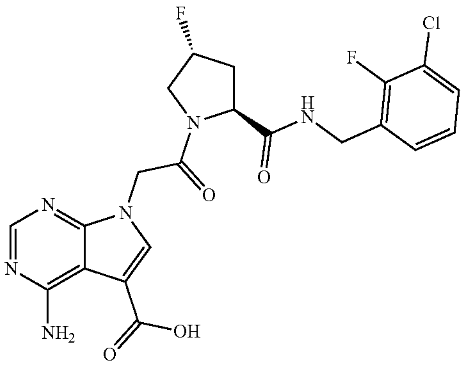

153a

Scheme 154

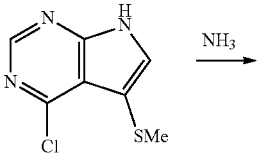

154a

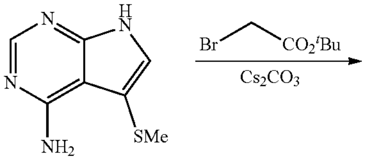

154b

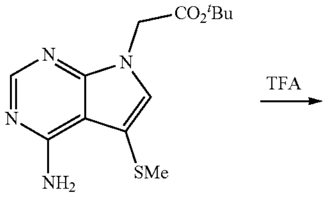

154c

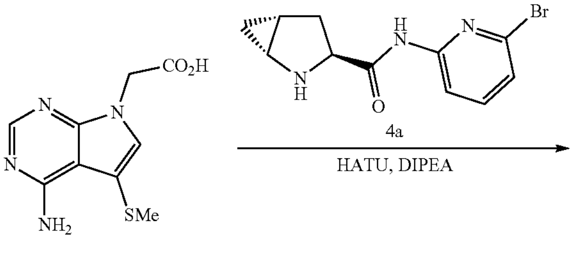

154d

-continued

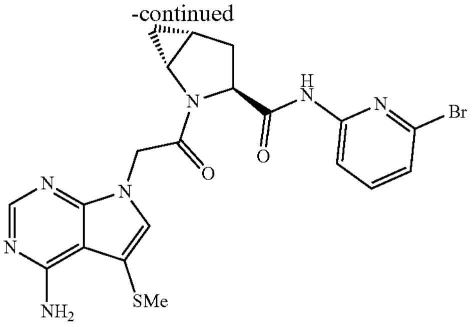

154e

Preparation of (1R,3S,5R)-2-(2-(4-amino-5-(methylthio)-7H-pyrrolo[2,3-d]pyrimidin-7-yl)acetyl)-N-(6-bromopyridin-2-yl)-2-azabicyclo[3.1.0]hexane-3-carboxamide (154e)

Step-1: Preparation of 5-(methylthio)-7H-pyrrolo[2,3-d]pyrimidin-4-amine (154b)

Compound 154b was prepared according to the procedure reported in step-4 of scheme-130, from 4-chloro-5-(methylthio)-7H-pyrrolo[2,3-d]pyrimidine (154a) (3.96 g, 19.83 mmol; CAS #144927-56-0)) in isopropanol (20 mL) using ammonium hydroxide (11.26 g, 198 mmol; 30 wt. % in water) in a sealed tube and heating at 100° C. for 16 h. This gave after workup and purification by flash column chromatography [$SiO_2$ (24 g), eluting with MeOH in DCM from 0-3%] 5-(methylthio)-7H-pyrrolo[2,3-d]pyrimidin-4-amine (154b) (1.94 g, 54.3% yield) as a yellow solid. $^1$H NMR (300 MHz, DMSO-$d_6$) δ 11.83 (s, 1H), 8.06 (s, 1H), 7.31 (s, 1H), 6.75 (s, 2H), 2.32 (s, 3H); MS (ES+): 181 (M+1).

Step-2: Preparation of tert-butyl 2-(4-amino-5-(methylthio)-7H-pyrrolo[2,3-d]pyrimidin-7-yl)acetate (154c)

Compound 154c was prepared according to the procedure reported in step-1 of scheme-1, from 5-(methylthio)-7H-pyrrolo[2,3-d]pyrimidin-4-amine (154b) (1.94 g, 10.76 mmol) in DMF (20 mL) using tert-butyl 2-bromoacetate (2.100 g, 10.76 mmol), $Cs_2CO_1$ (4.21 g, 12.92 mmol) and stirring at RT for 16 h. This gave after workup and purification by flash column chromatography [silica gel (24 g), eluting with MeOH in DCM from 0-3%] tert-butyl 2-(4-amino-5-(methylthio)-7H-pyrrolo[2,3-d]pyrimidin-7-yl)acetate (154c) (2.73 g, 86% yield) as a pale orange solid; $^1$H NMR (300 MHz, DMSO-$d_6$) δ 8.09 (s, 1H), 7.37 (s, 1H), 6.83 (s, 2H), 4.87 (s, 2H), 2.34 (d, J=1.0 Hz, 3H), 1.41 (s, 9H); MS (ES+) 295 (M+1).

Step-3: Preparation of 2-(4-amino-5-(methylthio)-7H-pyrrolo[2,3-d]pyrimidin-7-yl)acetic acid (154d)

Compound 154d was prepared according to the procedure reported in step-2 of scheme-1, from tert-butyl 2-(4-amino-5-(methylthio)-7H-pyrrolo[2,3-d]pyrimidin-7-yl)acetate (154c) (2.73 g, 9.27 mmol) in DCM (20 mL) using TFA (106 g, 185 mmol) and stirring at RT for 16 h. This gave after workup and purification by flash column chromatography [silica gel (24 g), eluting with MeOH in DCM from 0-3%] 2-(4-amino-5-(methylthio)-7H-pyrrolo[2,3-d]pyrimidin-7-yl)acetic acid (154d) (4.50 g) TFA salt as a pale-orange solid. $^1$H NMR (300 MHz, DMSO-$d_6$) δ 8.37 (s, 1H), 7.64 (s, 1H), 5.00 (s, 2H), 2.40 (s, 3H); $^{19}$F NMR (282 MHz, DMSO-$d_6$) δ −74.22; MS (ES+): 239 (M+1), (ES−): 237 (M−1).

Step-4: Preparation of (1R,3S,5R)-2-(2-(4-amino-5-(methylthio)-7H-pyrrolo[2,3-d]pyrimidin-7-yl)acetyl)-N-(6-bromopyridin-2-yl)-2-azabicyclo[3.1.0]hexane-3-carboxamide (154e)

Compound 154e was prepared according to the procedure reported in step-3 of scheme-1, from TFA salt of 2-(4-amino-5-(methylthio)-7H-pyrrolo[2,3-d]pyrimidin-7-yl)acetic acid (154d) (80 mg, 0.227 mmol) in DMF (5 mL) using (1R,3S,5R)—N-(6-bromopyridin-2-yl)-2-azabicyclo[3.1.0]hexane-3-carboxamide (4a) (72.3 mg, 0.227 mmol), HATU (104 mg, 0.273 mmol), DIPEA (147 mg, 1.135 mmol) and stirring at RT for 16 h. This gave after workup and purification by flash column chromatography [silica gel (12 g), using MeOH in DCM from 0 to 3%] followed by purification using reverse phase column chromatography [C18 column (100 g), eluting with ACN in water (containing 0.1% HCl) from 0-100%](1R,3S,5R)-2-(2-(4-amino-5-(methylthio)-7H-pyrrolo[2,3-d]pyrimidin-7-yl)acetyl)-N-(6-bromopyridin-2-yl)-2-azabicyclo[3.1.0]hexane-3-carboxamide (154e) (46 mg, 40% yield) HCl salt as a white solid: $^1$H NMR (300 MHz, DMSO-$d_6$) δ 10.80 (s, 1H, $D_2O$ exchangeable), 8.41 (s and bs, 3H, 2H $D_2O$ exchangeable), 8.02 (d, J=8.2 Hz, 1H), 7.72 (t, J=8.0 Hz, 1H), 7.63 (s, 1H), 7.33 (d, J=7.7 Hz, 1H), 5.50 (d, J=17.0 Hz, 1H), 5.20 (d, J=17.0 Hz, 1H), 4.43 (dd, J=9.0, 5.5 Hz, 1H), 3.74 (ddd, J=7.2, 5.3, 2.2 Hz, 1H), 2.39 (s, 3H), 2.30 (dd, J=13.6, 9.2 Hz, 1H), 2.19 (dt, J=12.9, 5.9 Hz, 1H), 1.95-1.81 (m, 1H), 1.06-0.95 (m, 1H), 0.73-0.62 (m, 1H); MS (ES+): 502.0 (M+1); (ES−): 500.0 (M−1); Analysis calculated for $C_{20}H_{20}BrN_7O_2S·1.1·HCl·2·H_2O$: C, 41.52; H, 4.37; Cl, 6.74; N, 16.95. Found: C, 41.36; H, 4.35; Cl, 6.99; N, 16.87.

Scheme 155

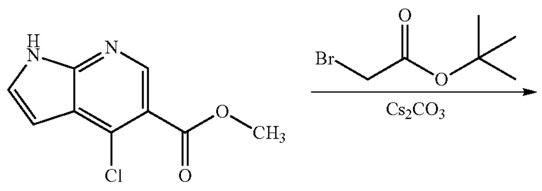

155a

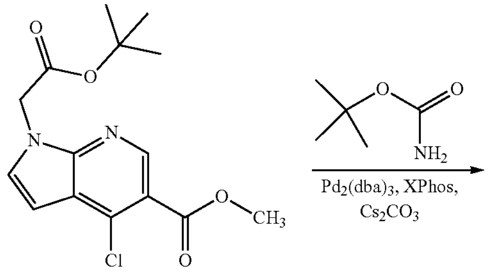

155b

-continued

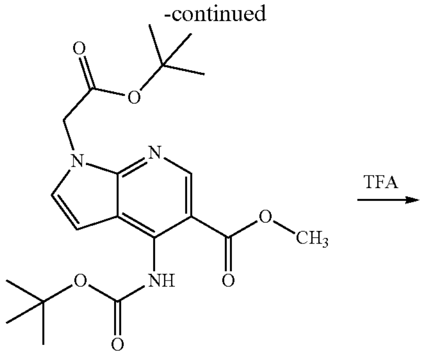

155c

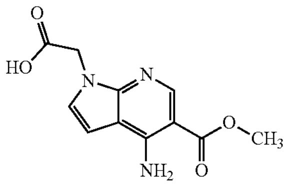

155d

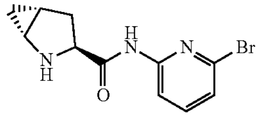

4a

HATU, DIPEA

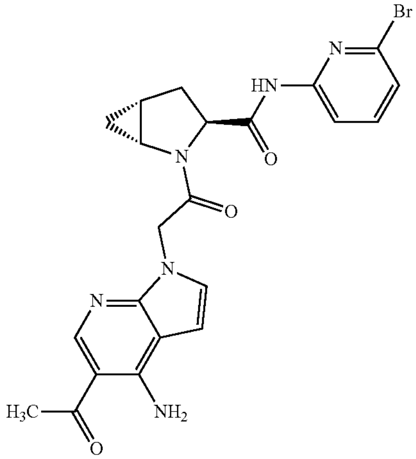

155e

LiOH

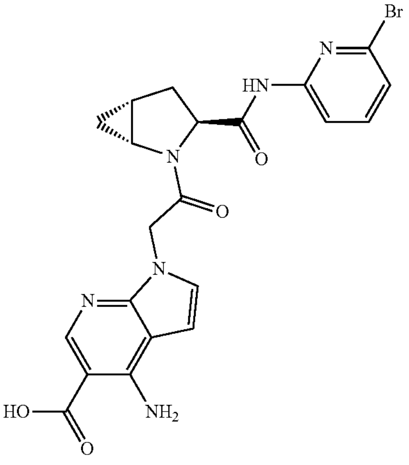

155f

Preparation of 4-amino-1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylic acid (155f)

Step-1: Preparation of methyl 1-(2-(tert-butoxy)-2-oxoethyl)-4-chloro-1H-pyrrolo[2,3-b]pyridine-5-carboxylate (155b)

Compound 155b was prepared according to the procedure reported in step-1 of scheme-1, from methyl 4-chloro-1H-pyrrolo[2,3-b]pyridine-5-carboxylate (155a) (450 mg, 2.137 mmol; CAS #951625-93-7) in DMF (10 mL) using tert-butyl 2-bromoacetate (0.379 mL, 2.56 mmol), $Cs_2CO_3$ (835 mg, 2.56 mmol) and stirring at RT for 20 h. This gave after workup and purification by flash column chromatography [silica gel, eluting with EtOAc in Hexane from 0-14%] methyl 1-(2-(tert-butoxy)-2-oxoethyl)-4-chloro-1H-pyrrolo[2,3-b]pyridine-5-carboxylate (155b) (605 mg, 87% yield) as a white solid; 1H NMR (300 MHz, DMSO-$d_6$) δ 8.73 (s, 1H), 7.77 (d, J=3.7 Hz, 1H), 6.71 (d, J=3.6 Hz, 1H), 5.09 (s, 2H), 3.89 (s, 3H), 1.40 (s, 9H); MS (ES+): 325.00 (M+1).

Step-2: Preparation of methyl 1-(2-(tert-butoxy)-2-oxoethyl)-4-((tert-butoxycarbonyl)amino)-1H-pyrrolo[2,3-b]pyridine-5-carboxylate (155c)

Compound 155c was prepared according to the procedure reported in step-3 of scheme-17, from methyl 1-(2-(tert-butoxy)-2-oxoethyl)-4-chloro-1H-pyrrolo[2,3-b]pyridine-5-carboxylate (155b) (560 mg, 1.724 mmol) in toluene (16 mL) using XPhos (82 mg, 0.172 mmol), t-butyl carbamate (303 mg, 2.59 mmol), $Pd_2(dba)_3$ (79 mg, 0.086 mmol), cesium carbonate (562 mg, 1.724 mmol) and heating at 90° C. for 16 h. This gave after work up and purification by flash column chromatography [silica gel, eluting with EtOAc in Hexane from 0-17%] methyl 1-(2-(tert-butoxy)-2-oxoethyl)-4-((tert-butoxycarbonyl)amino)-1H-pyrrolo[2,3-b]pyridine-5-carboxylate (155c) (628 mg, 90% yield); $^1$H NMR (300 MHz, DMSO-$d_6$) δ 10.19 (s, 1H), 8.56 (s, 1H), 7.48 (d, J=3.7 Hz, 1H), 6.78 (d, J=3.6 Hz, 1H), 5.01 (s, 2H), 3.81 (s, 3H), 1.49 (s, 9H), 1.40 (s, 9H); MS (ES+): 406.10 (M+1).

Step-3: Preparation of 2-(4-amino-5-(methoxycarbonyl)-1H-pyrrolo[2,3-b]pyridin-1-yl)acetic acid (155d)

Compound 155d was prepared according to the procedure reported in step-2 of scheme-1, from methyl 1-(2-(tert-butoxy)-2-oxoethyl)-4-((tert-butoxycarbonyl)amino)-1H-pyrrolo[2,3-b]pyridine-5-carboxylate (155c) (0.620 g, 1.529 mmol) using TFA. This gave after work up 2-(4-amino-5-(methoxycarbonyl)-1H-pyrrolo[2,3-b]pyridin-1-yl)acetic acid (155d) (840 mg) which was used as such for the next step; MS (ES+): 250.00 (M+1).

Step-4: Preparation of methyl 4-amino-1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylate (155e)

Compound 155e was prepared according to the procedure reported in step-3 of scheme-1, from 2-(4-amino-5-(methoxycarbonyl)-1H-pyrrolo[2,3-b]pyridin-1-yl)acetic acid (155d) (95 mg, 0.383 mmol) in DMF (10 mL) using HCl salt of (1R,3S,5R)—N-(6-bromopyridin-2-yl)-2-azabicyclo[3.1.0]hexane-3-carboxamide (4a) (122 mg, 0.383 mmol), HATU (291 mg, 0.766 mmol), DIPEA (0.334 mL, 1.915 mmol) and stirring at RT for 20 h. This gave after workup and purification by flash column chromatography [silica gel, MeOH in DCM from 0-5%]methyl 4-amino-1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylate (155e) (115 mg, 59% yield) as a yellow solid; $^1H$ NMR (300 MHz, DMSO-$d_6$) δ 10.76 (s, 1H), 8.49 (s, 1H), 8.03 (d, J=8.2 Hz, 1H), 7.71 (t, J=7.9 Hz, 1H), 7.59 (s, 2H), 7.32 (d, J=7.7 Hz, 1H), 7.14 (d, J=3.5 Hz, 1H), 6.75 (d, J=3.6 Hz, 1H), 5.38 (d, J=17.0 Hz, 1H), 5.15 (d, J=17.0 Hz, 1H), 4.42 (dd, J=9.0, 5.6 Hz, 1H), 3.80 (s, 3H), 3.77-3.66 (m, 1H), 2.36-2.07 (m, 2H), 1.94-1.68 (m, 1H), 1.08-0.91 (m, 1H), 0.76-0.50 (m, 1H); MS (ES+): 513.00 (M+1).

Step-5: Preparation of 4-amino-1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylic acid (155f)

Compound 155f was prepared according to the procedure reported in step-4 of scheme-17, from methyl 4-amino-1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylate (155e) (110 mg, 0.214 mmol) in THF (2 mL) and acetonitrile (2 mL) using a solution of lithium hydroxide hydrate (27.5 mg, 0.643 mmol) in water (2 mL) and stirring at RT for 20 h. This gave after workup and purification by reverse phase column chromatography [C18 column (26 g), eluting with ACN in water (containing 0.1% HCl) from 0-100%] 4-amino-1-(2-((1R,3S,5R)-3-((6-bromopyridin-2-yl)carbamoyl)-2-azabicyclo[3.1.0]hexan-2-yl)-2-oxoethyl)-1H-pyrrolo[2,3-b]pyridine-5-carboxylic acid (155f) (10 mg, 9% yield) HCl salt as a white solid; $^1H$ NMR (300 MHz, DMSO-$d_6$) (a mixture of two rotamers) δ 10.88 & 10.77 (2s, 1H, $D_2O$ exchangeable), 8.60 & 8.60 (2s, 1H), 8.07-7.93 (m, 1H), 7.78-7.65 (m, 1H), 7.42-7.21 (m, 2H), 7.05-6.93 (m, 1H), 5.75-5.15 (m, 2H), 4.92 & 4.43 (2dd, J=8.9, 5.7 Hz, 1H), 3.82-3.62 (m, 1H), 2.43-1.63 (m, 3H), 1.34-0.63 (m, 2H); MS (ES+): 498.90 & 500.90 (M+1); MS (ES−): 496.90 & 498.90 (M−1).

Scheme 156

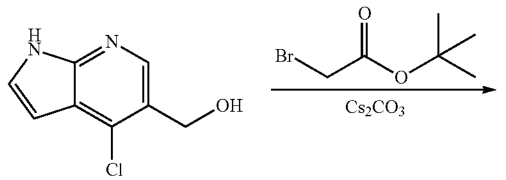

156a

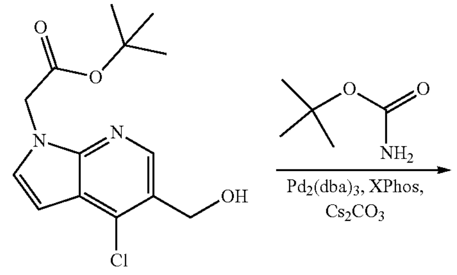

156b

-continued

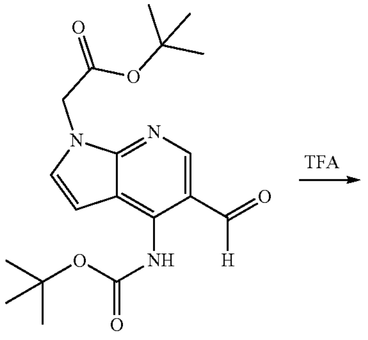

156c

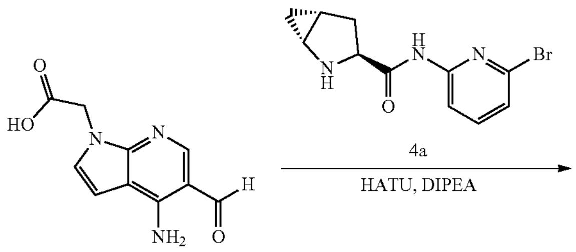

156d

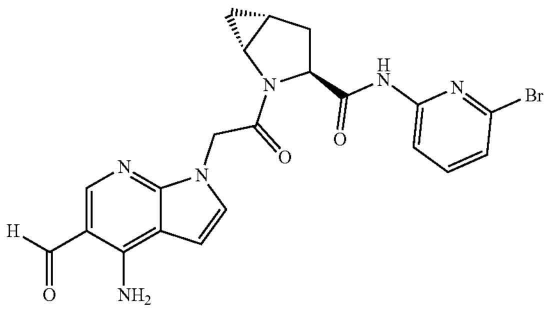

156e

Preparation of (1R,3S,5R)-2-(2-(4-amino-5-formyl-1H-pyrrolo[2,3-b]pyridin-1-yl)acetyl)-N-(6-bromopyridin-2-yl)-2-azabicyclo[3.1.0]hexane-3-carboxamide (156e)

Step-1: Preparation of tert-butyl 2-(4-chloro-5-(hydroxymethyl)-1H-pyrrolo[2,3-b]pyridin-1-yl)acetate (156b)

Compound 156b was prepared according to the procedure reported in step-1 of scheme-1, from (4-chloro-1H-pyrrolo[2,3-b]pyridin-5-yl)methanol (156a) (115 mg, 0.630 mmol; CAS #1015610-07-7) in DMF (6 mL) using tert-butyl 2-bromoacetate (0.112 mL, 0.756 mmol), $Cs_2CO_3$ (246 mg, 0.756 mmol) and stirring at RT for 13 h. This gave after workup and purification by flash column chromatography [silica gel, eluting with EtOAc in Hexane from 0-50%] tert-butyl 2-(4-chloro-5-(hydroxymethyl)-1H-pyrrolo[2,3-b]pyridin-1-yl)acetate (156b) (155 mg, 83% yield) as a white solid; $^1H$ NMR (300 MHz, DMSO-$d_6$) δ 8.30 (s, 1H), 7.63 (d, J=3.6 Hz, 1H), 6.53 (d, J=3.5 Hz, 1H), 5.30 (t, J=5.6 Hz, 1H), 5.03 (s, 2H), 4.69 (d, J=5.5 Hz, 2H), 1.40 (s, 9H); MS (ES+): 297.00 (M+1).

Step-2: Preparation of tert-butyl 2-(4-((tert-butoxycarbonyl)amino)-5-formyl-1H-pyrrolo[2,3-b]pyridin-1-yl)acetate (156c)

Compound 156c was prepared according to the procedure reported in step-3 of scheme-17, from tert-butyl 2-(4-chloro-5-(hydroxymethyl)-1H-pyrrolo[2,3-b]pyridin-1-yl)acetate (156b) (132 mg, 0.445 mmol) in toluene (10 mL) using XPhos (21.21 mg, 0.044 mmol), t-butyl carbamate (78 mg, 0.667 mmol), $Pd_2(dba)_3$ (20.37 mg, 0.022 mmol), cesium carbonate (145 mg, 0.445 mmol) and heating at 90° C. for 12 h. This gave after work up and purification by flash column chromatography [silica gel, eluting with EtOAc in Hexane from 0-20%] tert-butyl 2-(4-((tert-butoxycarbonyl) amino)-5-formyl-1H-pyrrolo[2,3-b]pyridin-1-yl)acetate (156c) (50 mg, 30% yield); $^1$H NMR (300 MHz, DMSO-$d_6$) δ 10.76 (s, 1H), 10.00 (s, 1H), 8.58 (s, 1H), 7.50 (d, J=3.7 Hz, 1H), 6.94 (d, J=3.7 Hz, 1H), 5.04 (s, 2H), 1.52 (s, 9H), 1.41 (s, 9H); MS (ES+): 376.10 (M+1).

Step-3: Preparation of 2-(4-amino-5-formyl-1H-pyrrolo[2,3-b]pyridin-1-yl)acetic acid (156d)

Compound 156d was prepared according to the procedure reported in step-2 of scheme-1, from tert-butyl 2-(4-((tert-butoxycarbonyl)amino)-5-formyl-1H-pyrrolo[2,3-b]pyridin-1-yl)acetate (156c) (45 mg, 0.12 mmol) in DCM (10 mL) using TFA. This gave after work up 2-(4-amino-5-formyl-1H-pyrrolo[2,3-b]pyridin-1-yl)acetic acid (156d), which was used as such for the next step; MS (ES+): 220.00 (M+1).

Step-4: Preparation of (1R,3S,5R)-2-(2-(4-amino-5-formyl-1H-pyrrolo[2,3-b]pyridin-1-yl)acetyl)-N-(6-bromopyridin-2-yl)-2-azabicyclo[3.1.0]hexane-3-carboxamide (156e)

Compound 156e was prepared according to the procedure reported in step-3 of scheme-1, from 2-(4-amino-5-formyl-1H-pyrrolo[2,3-b]pyridin-1-yl)acetic acid (156d) (0.12 mmol) in DMF (6 mL) using TFA salt of (1R,3S,5R)—N-(6-bromopyridin-2-yl)-2-azabicyclo[3.1.0]hexane-3-carboxamide (4a) (0.144 mmol), HATU (91 mg, 0.240 mmol), DIPEA (0.105 mL, 0.600 mmol) and stirring at RT for 14 h. This gave after workup and purification using flash column chromatography [silica gel (12 g), eluting with MeOH in DCM from 0-5%] (1R,3S,5R)-2-(2-(4-amino-5-formyl-1H-pyrrolo[2,3-b]pyridin-1-yl)acetyl)-N-(6-bromopyridin-2-yl)-2-azabicyclo[3.1.0]hexane-3-carboxamide (156e) (36 mg, 62% yield) as a light yellow solid; $^1$H NMR (300 MHz, DMSO-$d_6$) δ 10.76 (s, 1H, $D_2O$ exchangeable), 9.84 (s, 1H), 8.25 (s, 1H), 8.03 (d, J=8.2 Hz, 1H), 7.72 (t, J=7.9 Hz, 1H), 7.33 (d, J=7.7 Hz, 1H), 7.16 (d, J=3.6 Hz, 1H), 6.77 (d, J=3.6 Hz, 1H), 5.45-5.12 (m, 2H), 4.43 (dd, J=9.0, 5.5 Hz, 1H), 3.82-3.65 (m, 1H), 2.35-2.10 (m, 2H), 1.93-1.78 (m, 1H), 1.27-1.19 (m, 1H), 1.08-0.94 (m, 1H); MS (ES+): 482.900 & 485.00 (M+1); MS (ES−): 480.90 & 483.00 (M−1).

Scheme 157

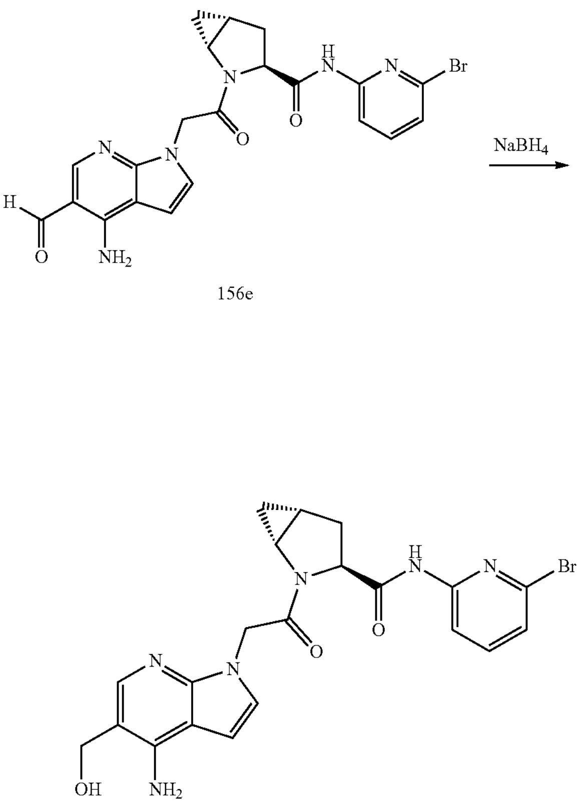

156e

157a

Preparation of (1R,3S,5R)-2-(2-(4-amino-5-(hydroxymethyl)-1H-pyrrolo[2,3-b]pyridin-1-yl)acetyl)-N-(6-bromopyridin-2-yl)-2-azabicyclo[3.1.0]hexane-3-carboxamide (157a)

To a solution of (1R,3S,5R)-2-(2-(4-amino-5-formyl-1H-pyrrolo[2,3-b]pyridin-1-yl)acetyl)-N-(6-bromopyridin-2-yl)-2-azabicyclo[3.1.0]hexane-3-carboxamide (156e) (23 mg, 0.048 mmol) in THF (4 mL) and MeOH (2 mL) was added sodium borohydride (5.51 mg, 0.143 mmol) stirred at RT for 19 h and diluted with ethyl acetate (100 mL), sat. $NH_4Cl$ (50 mL). The organic phase was washed with brine (50 mL), dried, filtered and concentrated in vacuum. The residue obtained was purified by flash column chromatography [silica gel (4 g), eluting with MeOH in DCM (0-5%)] to give (1R,3S,5R)-2-(2-(4-amino-5-(hydroxymethyl)-1H-pyrrolo[2,3-b]pyridin-1-yl)acetyl)-N-(6-bromopyridin-2-yl)-2-azabicyclo[3.1.0]hexane-3-carboxamide (157a) (12 mg, 52% yield) as a white solid; $^1$H NMR (300 MHz, DMSO-$d_6$) δ 10.74 (s, 1H, $D_2O$ exchangeable), 8.03 (d, J=8.2 Hz, 1H), 7.78-7.61 (m, 2H), 7.32 (d, J=7.7 Hz, 1H), 7.06 (d, J=3.5 Hz, 1H), 6.55 (d, J=3.6 Hz, 1H), 5.99 (s, 2H, D, 20 exchangeable), 5.29 (d, J=17.0 Hz, 1H), 5.10 (d, J=16.9 Hz, 1H), 4.82 (t, J=5.2 Hz, 1H), 4.48 (d, J=5.0 Hz, 2H), 4.42 (dd, J=9.0, 5.5 Hz, 1H), 3.76-3.68 (m, 1H), 2.36-2.08 (m, 2H), 1.92-1.72 (m, 1H), 1.05-0.92 (m, 1H), 0.70-0.56 (m, 1H); MS (ES+): 484.95 & 487.00 (M+1); MS (ES−): 482.95 & 484.95 (M−1).

Scheme 158

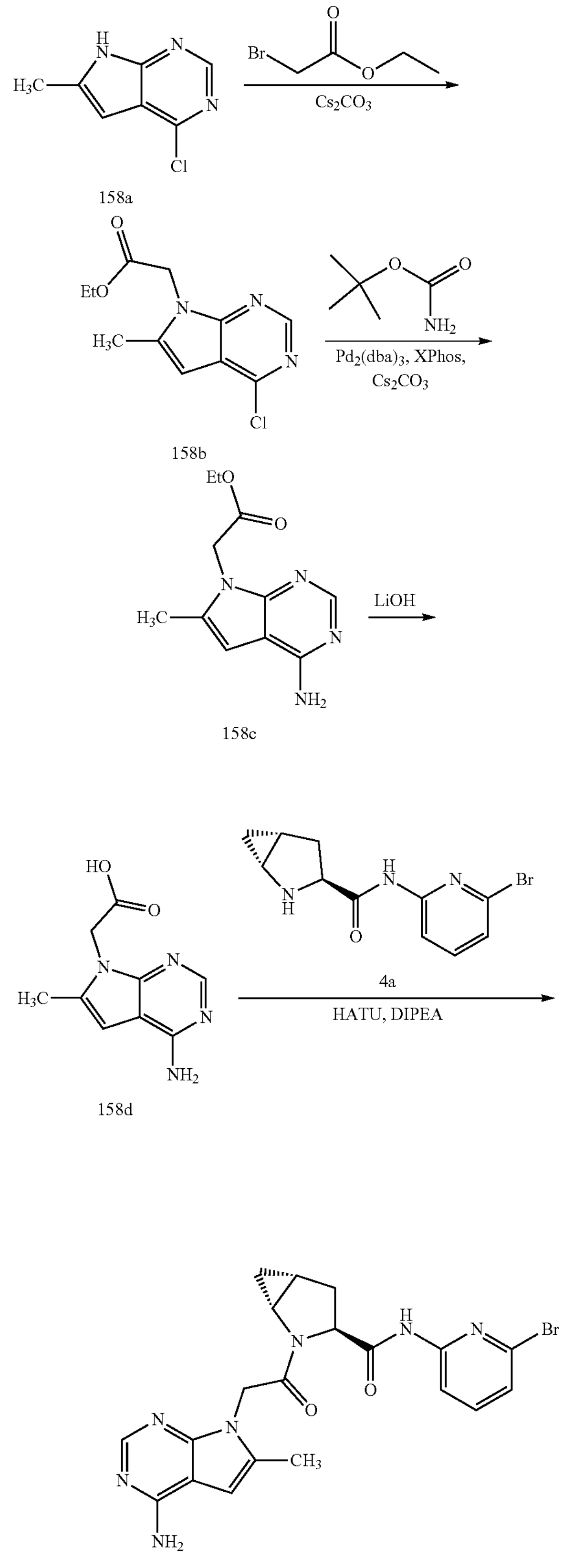

158a 158b 158c 158d 158e

Preparation of (1R,3S,5R)-2-(2-(4-amino-6-methyl-7H-pyrrolo[2,3-d]pyrimidin-7-yl)acetyl)-N-(6-bromopyridin-2-yl)-2-azabicyclo[3.1.0]hexane-3-carboxamide (158e)

Step-1: Preparation of ethyl 2-(4-chloro-6-methyl-7H-pyrrolo[2,3-d]pyrimidin-7-yl)acetate (158b)

Compound 158b was prepared according to the procedure reported in step-1 of scheme-1, from 4-chloro-6-methyl-7H-pyrrolo[2,3-d]pyrimidine (158a) (I g, 5.97 mmol; CAS #35808-68-5) in DMF (25 mL) using ethyl 2-bromoacetate (0.794 mL, 7.16 mmol), $Cs_2CO_3$ (2.33 g, 7.16 mmol) and stirring at 0° C. for 20 min. This gave after workup and purification by flash column chromatography [silica gel, eluting with EtOAc in Hexane from 0-25%] ethyl 2-(4-chloro-6-methyl-7H-pyrrolo[2,3-d]pyrimidin-7-yl)acetate (158b) (1.32 g, 87% yield) as a light yellow solid; $^1$H NMR (300 MHz, DMSO-$d_6$) δ 8.56 (s, 1H), 6.51-6.46 (m, 1H), 5.17 (s, 2H), 4.16 (q, J=7.1 Hz, 2H), 2.43 (d, J=1.1 Hz, 3H), 1.21 (t, J=7.1 Hz, 3H); MS (ES+): 254.00 (M+1).

Step-2: Preparation of ethyl 2-(4-amino-6-methyl-7H-pyrrolo[2,3-d]pyrimidin-7-yl)acetate (158c)

Compound 158c was prepared according to the procedure reported in step-3 of scheme-17, from ethyl 2-(4-chloro-6-methyl-7H-pyrrolo[2,3-d]pyrimidin-7-yl)acetate (158b) (500 mg, 1.971 mmol) in toluene (15 mL) using XPhos (94 mg, 0.197 mmol), t-butyl carbamate (346 mg, 2.96 mmol), $Pd_2(dba)_3$ (90 mg, 0.099 mmol), cesium carbonate (642 mg, 1.971 mmol) and heating at 90° C. for 13 h under nitrogen. This gave after work up and purification by flash column chromatography [silica gel, eluting with EtOAc in Hexane/10% MeOH from 0-50%] ethyl 2-(4-amino-6-methyl-7H-pyrrolo[2,3-d]pyrimidin-7-yl)acetate (158c) (110 mg, 24% yield); MS (ES+): 235.10 (M+1).

Step-3: Preparation of 2-(4-amino-6-methyl-7H-pyrrolo[2,3-d]pyrimidin-7-yl)acetic acid (158d)

Compound 158d was prepared according to the procedure reported in step-4 of scheme-17, from ethyl 2-(4-amino-6-methyl-7H-pyrrolo[2,3-d]pyrimidin-7-yl)acetate (158c) (100 mg, 0.427 mmol) in THF (3 mL) and MeOH (3 mL) using a solution of lithium hydroxide hydrate (110 mg, 2.56 mmol) in water (3 mL) and stirring at RT for 19 h. This gave after work up 2-(4-amino-6-methyl-7H-pyrrolo[2,3-d]pyrimidin-7-yl)acetic acid (158d) (88 mg, 100% yield) which was used as such for the next step; MS (ES+): 207.10 (M+1).

Step-4: Preparation of (1R,3S,5R)-2-(2-(4-amino-6-methyl-7H-pyrrolo[2,3-d]pyrimidin-7-yl)acetyl)-N-(6-bromopyridin-2-yl)-2-azabicyclo[3.1.0]hexane-3-carboxamide (158e)

Compound 158e was prepared according to the procedure reported in step-3 of scheme-1, from 2-(4-amino-6-methyl-7H-pyrrolo[2,3-d]pyrimidin-7-yl)acetic acid (158d) (0.427 mmol) in DMF (15 mL) using HCl salt of (1R,3S,5R)—N-(6-bromopyridin-2-yl)-2-azabicyclo[3.1.0]hexane-3-carboxamide (4a) (163 mg, 0.512 mmol), HATU (325 mg, 0.854 mmol), DIPEA (0.372 mL, 2.135 mmol) and stirring at RT for 23 h. This gave after workup and purification using flash column chromatography [silica gel (12 g), eluting with MeOH in DCM from 0-5%] followed by conversion of product obtained to HCl salt by dissolving in acetonitrile (2 mL) and 50 mM aq. HCl (8 mL) and lyophilization (1R,3S,5R)-2-(2-(4-amino-6-methyl-7H-pyrrolo[2,3-d]pyrimidin-7-yl)acetyl)-N-(6-bromopyridin-2-yl)-2-azabicyclo[3.1.0]hexane-3-carboxamide (158e) (50 mg, 25% yield) as an off white solid; $^1$H NMR (300 MHz, DMSO-$d_6$) δ 10.80 (s, 1H, $D_2O$ exchangeable), 8.33 (s, 1H), 8.02 (d, J=8.1 Hz, 1H), 7.72 (t, J=8.0 Hz, 1H), 7.33 (d, J=7.7 Hz, 1H), 6.68 (d, J=1.3 Hz, 1H), 5.47 (d, J=17.4 Hz, 1H), 5.20 (d, J=17.3 Hz, 1H), 4.43 (dd, J=9.1, 5.5 Hz, 1H), 3.83 (td, J=6.7, 6.2, 2.3 Hz, 1H), 2.42-2.12 (m, 5H), 1.95-1.77 (m, 1H), 1.12-0.93 (m, 1H), 0.78-0.59 (m, 1H); MS (ES+): 470.10 & 472.10 (M+1); MS (ES−): 468.10 & 470.10 (M−1); Analysis calculated for $C_{20}H_{20}BrN_7O_2\cdot1.2HCl\cdot2.5H_2O$: C, 42.96; H, 4.72; Cl, 7.61; N, 17.54. Found: C, 42.96; H, 4.48; Cl, 7.38; N, 17.36.

Scheme 159

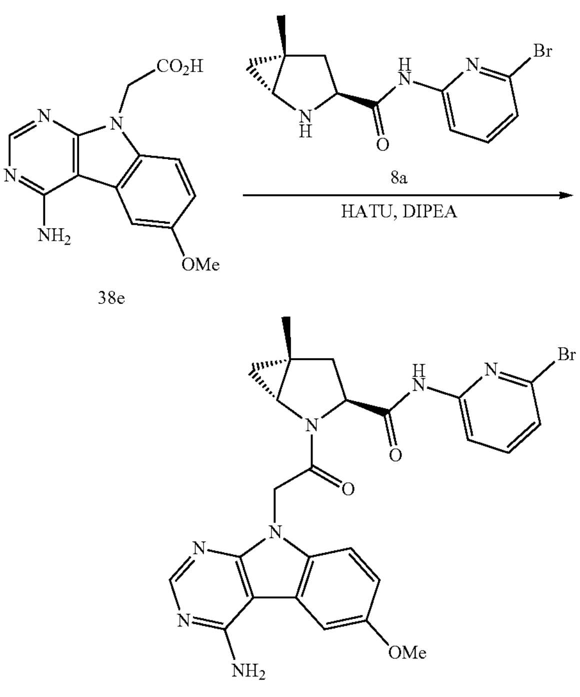

38e

159a

Preparation of (1R,3S,5R)-2-(2-(4-amino-6-methoxy-9H-pyrimido[4,5-b]indol-9-yl)acetyl)-N-(6-bromopyridin-2-yl)-5-methyl-2-azabicyclo[3.1.0]hexane-3-carboxamide (159a)

Compound 159a was prepared according to the procedure reported in step-3 of scheme-1, from TFA salt of 2-(4-amino-6-methoxy-9H-pyrimido[4,5-b]indol-9-yl)acetic acid (38e) (100 mg, 0.259 mmol) in DMF (5 mL) using HCl salt of (1R,3S,5R)—N-(6-bromopyridin-2-yl)-5-methyl-2-azabicyclo[3.1.0]hexane-3-carboxamide (8a) (95 mg, 0.285 mmol), HATU (148 mg, 0.388 mmol), DIPEA (167 mg, 1.294 mmol) and stirring at RT for 16 h. This gave after workup and purification using flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-methoxy-9H-pyrimido[4,5-b]indol-9-yl)acetyl)-N-(6-bromopyridin-2-yl)-5-methyl-2-azabicyclo[3.1.0]hexane-3-carboxamide (159a) (117 mg, 82% yield) HCl salt as a white solid; $^1$H NMR (300 MHz, DMSO-$d_6$) δ 10.77 (s, 1H, $D_2O$ exchangeable), 8.75 (s, 2H, $D_2O$ exchangeable), 8.60 (s, 1H), 8.08 (d, J=2.3 Hz, 1H), 8.01 (d, J=8.2 Hz, 1H), 7.70 (t, J=8.0 Hz, 1H), 7.62 (d, J=9.0 Hz, 1H), 7.32 (d, J=7.7 Hz, 1H), 7.19 (dd, J=9.1, 2.3 Hz, 1H), 5.69 (d, J=17.3 Hz, 1H), 5.35 (d, J=17.3 Hz, 1H), 4.37 (dd, J=9.1, 5.9 Hz, 1H), 3.88 (s, 3H), 3.71-3.66 (m, 1H), 2.44 (s, 1H), 1.98 (dd, J=13.3, 5.8 Hz, 1H), 1.31 (s, 3H), 1.07-0.98 (m, 1H), 0.98-0.83 (m, 1H); MS (ES+): 550 (M+1), (ES−): 548 (M−1); Analysis calculated for $C_{25}H_{24}BrN_7O_3\cdot HCl\cdot2.25H_2O$: C, 47.86; H, 4.74; Cl, 5.65; N, 15.63. Found: C, 47.64; H, 4.71; Cl, 5.77; N, 15.34.

Scheme 160

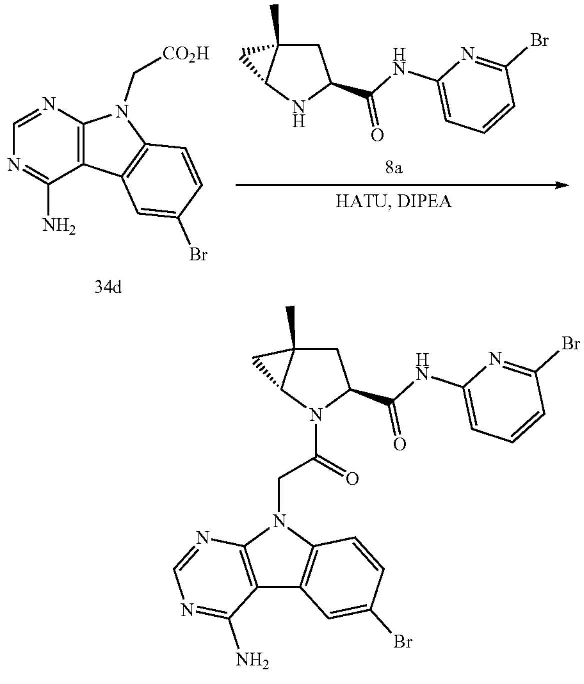

34d

160a

Preparation of (1R,3S,5R)-2-(2-(4-amino-6-bromo-9H-pyrimido[4,5-b]indol-9-yl)acetyl)-N-(6-bromopyridin-2-yl)-5-methyl-2-azabicyclo[3.1.0]hexane-3-carboxamide (160a)

Compound 160a was prepared according to the procedure reported in step-3 of scheme-1, from TFA salt of 2-(4-amino-6-bromo-9H-pyrimido[4,5-b]indol-9-yl)acetic acid (34d) (50 mg, 0.115 mmol) in DMF (5 mL) using HCl salt of (1R,3S,5R)—N-(6-bromopyridin-2-yl)-5-methyl-2-azabicyclo[3.1.0]hexane-3-carboxamide (8a) (42 mg, 0.126 mmol), HATU (65.5 mg, 0.172 mmol), DIPEA (74.3 mg, 0.575 mmol) and stirring at RT for 16 h. This gave after workup and purification using flash column chromatography [silica gel (12 g), MeOH in DCM from 0-3%] followed by purification using reverse phase column chromatography [C18 column (100 g), eluting with ACN in water (containing 0.1% HCl) from 0-100%] to afford (1R,3S,5R)-2-(2-(4-amino-6-bromo-9H-pyrimido[4,5-b]indol-9-yl)acetyl)-N-(6-bromopyridin-2-yl)-5-methyl-2-azabicyclo[3.1.0]hexane-3-carboxamide (160a) (42 mg, 61% yield) HCl salt as a white solid; $^1$H NMR (300 MHz, DMSO-$d_6$) δ 10.77 (s, 1H, $D_2O$ exchangeable), 8.96-8.69 (m, 3H, 2H $D_2O$ exchangeable), 8.65 (s, 1H), 8.01 (d, J=8.1 Hz, 1H), 7.77-7.64 (m, 3H), 7.32 (d, J=7.7 Hz, 1H), 5.73 (d, J=17.4 Hz, 1H), 5.37 (d, J=17.3 Hz, 1H), 4.37 (dd, J=9.1, 5.9 Hz, 1H), 3.69-3.65 (m, 1H), 2.45 (d, J=8.9 Hz, 1H), 1.98 (dd, J=13.3, 5.9 Hz, 1H), 1.31 (s, 3H), 1.01 (m, 1H), 0.93 (m, 1H); MS (ES+): 598 (M+1), (ES−): 596 (M−1); Analysis calculated for $C_{24}H_{21}Br_2N_7O_2 \cdot HCl \cdot 1.5 \cdot H_2O$: C, 43.49; H, 3.80; Cl, 5.35; N, 14.79. Found: C, 43.36; H, 3.76; Cl, 5.49; N, 14.69.

Scheme 161

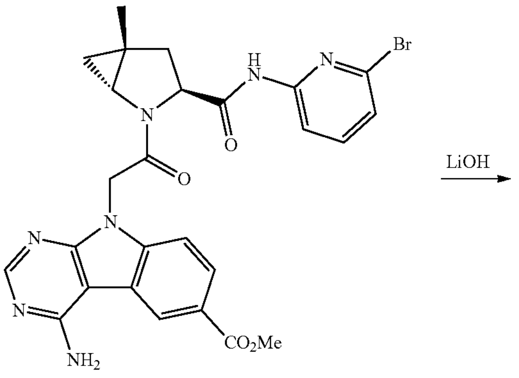

40a

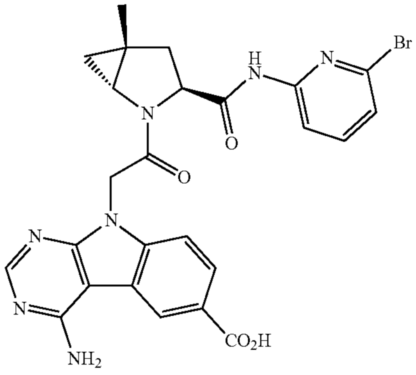

161a

Preparation of 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-6-carboxylic acid (161a)

Compound 161a was prepared according to the procedure reported in step-4 of scheme-17, from methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-6-carboxylate (40a) (107 mg, 0.185 mmol) in THF (3 mL) and using 2M aqueous lithium hydroxide hydrate (0.111 mL, 0.222 mmol) and stirring at RT for 16 h. This gave after workup and purification by reverse phase column chromatography [C18 column (100 g), eluting with ACN in water (containing 0.1% HCl) from 0-100%] 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-6-carboxylic acid (161a) (33 mg, 32% yield) HCl salt as a white solid; 1H NMR (300 MHz, DMSO-$d_6$) δ 10.77 (s, 1H, $D_2O$ exchangeable), 9.10 (s, 1H), 8.81-8.40 (m, 3H, 2H $D_2O$ exchangeable), 8.11 (dt, J=8.8, 2.0 Hz, 1H), 7.97 (dd, J=18.4, 8.2 Hz, 1H), 7.70 (ddd, J=16.5, 8.4, 3.9 Hz, 2H), 7.30 (dd, J=7.8, 5.2 Hz, 1H), 5.74 (d, J=17.8 Hz, 1H), 5.39 (dd, J=17.2, 3.4 Hz, 1H), 4.37 (dd, J=9.0, 5.9 Hz, 1H), 3.70-3.68 (m, 1H), 2.45-2.33 (m, 1H), 2.12-1.90 (m, 1H), 1.28 (s, 3H), 1.07-0.80 (m, 2H); MS (ES+) 564.0 (M+1); (ES−): 562.0 (M−1).

Scheme 162

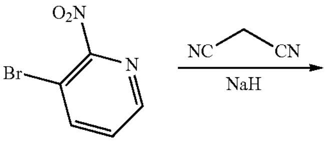

162a

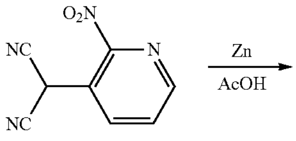

162b

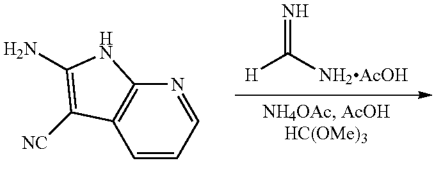

162c

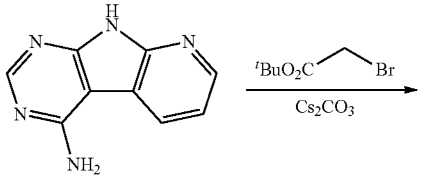

162d

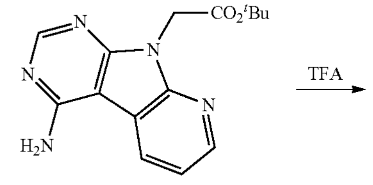

162e

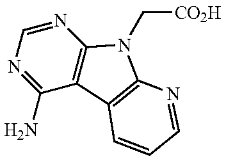

162f

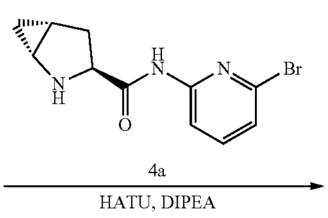

-continued

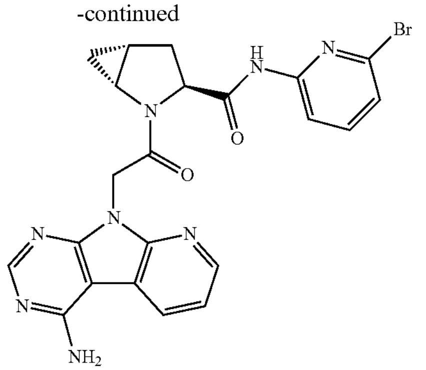

162g

Preparation of (1R,3S,5R)-2-(2-(4-amino-9H-pyrido[3',2':4.5]pyrrolo[2,3-d]pyrimidin-9-yl)acetyl)-N-(6-bromopyridin-2-yl)-2-azabicyclo[3.1.0]hexane-3-carboxamide (162 g)

Step-1: Preparation of 2-(2-nitropyridin-3-yl)malononitrile (162b)

NaH (1.958 g, 49.0 mmol) was added portion-wise to a cold solution of malononitrile (3.23 g, 49.0 mmol) in THF (50 mL) at 0° C., during which hydrogen gas liberated and a white precipitate formed. The resulting cloudy white mixture was stirred at 0° C. for 1 h, followed by addition of 3-bromo-2-nitropyridine (162a) (4.92 g, 24.24 mmol). The resulting deep red/black suspension was then heated at 60° C. under argon for 3 h. The cooled reaction was quenched with saturated $NH_4Cl$ (50 mL) and diluted with EtOAc (50 mL). After 30-min stirring at it, the two layers were separated. The aqueous layer was extracted with EtOAc (30 mL×3). The combined extract was concentrated to provide the crude product 2-(2-nitropyridin-3-yl)malononitrile (162b) (5.75 g) as a brown/black solid, which was used as such in the next reaction; MS (ES+): 159 (M+1), (ES−): 157 (M−1).

Step-2: Preparation of 2-amino-1H-pyrrolo[2,3-b]pyridine-3-carbonitrile (162c)

Crude 2-(2-nitropyridin-3-yl)malononitrile (162b) (5.75 g) from step-1 above was diluted in acetic acid (36.7 g, 611 mmol), followed by slow addition of zinc (10.00 g, 153 mmol) at rt. The mixture was stirred at 60° C. for 2 h and then filtered hot. The filtered cake was washed thoroughly with boiling EtOH. The filtrate was concentrated to dryness. The residue was suspended in $H_2O$ (50 mL), neutralized with 3 M aqueous NaOH until pH 7, and then extracted with EtOAc (50 mL×3). The combined extract was washed with $H_2O$ (30 mL×2), brine (30 mL), dried, filtered and concentrated in vacuum. The residue obtained was purified by flash column chromatography ($SiO_2$, 40 g, eluting with 0-20% DMA80 in DCM) to provide 2-amino-1H-pyrrolo[2,3-b]pyridine-3-carbonitrile (162c) (1.00 g, 21% yield) as a beige solid; $^1$H NMR (300 MHz, DMSO-$d_6$) δ 11.43 (s, 1H), 7.89 (dd, J=5.0, 1.5 Hz, 1H), 7.47 (dd, J=7.7, 1.5 Hz, 1H), 7.11-6.84 (m, 3H); MS (ES+): 159 (M+1), (ES−): 157 (M−1).

Step-3: Preparation of 9H-pyrido[3',2':4,5]pyrrolo[2,3-d]pyrimidin-4-amine (162d)

Compound 162d was prepared according to the procedure reported in step-2 of scheme-29, from 2-amino-1H-pyrrolo[2,3-b]pyridine-3-carbonitrile (162c) (1.00 g, 6.32 mmol) in ethanol (30 mL) using formamidine acetate (5.27 g, 50.6 mmol), $NH_4OAc$ (1.462 g, 18.97 mmol), glacial AcOH (1.139 g, 18.97 mmol). $HC(OMe)_3$ (6.71 g, 63.2 mmol) and heating at 80° C. for 5 days. The solid obtained was collected by filtration washed with boiling EtOH and air-dried to provide 9H-pyrido[3',2':4,5]pyrrolo[2,3-d]pyrimidin-4-amine (162d) (0.27 g, 23% yield) as a brown solid; $^1$H NMR (300 MHz, DMSO-$d_6$) δ 12.36 (s, 1H), 8.68 (dd, J=7.8, 1.6 Hz, 1H), 8.36 (dd, J=4.9, 1.5 Hz, 1H), 8.31 (s, 1H), 7.34 (s, 2H), 7.25 (dd, J=7.8, 4.9 Hz, 1H); MS (ES+): 186 (M+1), (ES−): 184 (M−1).

Step-4: Preparation of tert-butyl 2-(4-amino-9H-pyrido[3',2':4,5]pyrrolo[2,3-d]pyrimidin-9-yl)acetate (162e)

Compound 162e was prepared according to the procedure reported in step-1 of scheme-1, from 9H-pyrido[3',2':4,5]pyrrolo[2,3-d]pyrimidin-4-amine (162d) (0.27 g, 1.458 mmol) in DMF (10 mL) using tert-butyl 2-bromoacetate (0.341 g, 1.750 mmol) and $Cs_2CO_3$ (0.950 g, 2.92 mmol). This gave after workup and purification using flash column chromatography [$SiO_2$ gel (24 g), eluting with MeOH in DCM from 0-4%] tert-butyl 2-(4-amino-9H-pyrido[3',2':4.5]pyrrolo[2,3-d]pyrimidin-9-yl)acetate (162e) (0.27 g, 0.902 mmol, 62% yield) as a pale-yellow solid; $^1$H NMR (300 MHz, DMSO-$d_6$) δ 8.75 (dd, J=7.8, 1.5 Hz, 1H), 8.40 (dd, J=4.9, 1.5 Hz, 1H), 8.36 (s, 1H), 7.50 (s, 2H), 7.34 (dd, J=7.8, 4.9 Hz, 1H), 5.06 (s, 2H), 1.40 (s, 9H); MS (ES+): 300 (M+1), (ES−): 298 (M−1).

Step-5: Preparation of 2-(4-amino-9H-pyrido[3',2':4,5]pyrrolo[2,3-d]pyrimidin-9-yl)acetic acid (162f)

Compound 162f was prepared according to the procedure reported in step-2 of scheme-1, from tert-butyl 2-(4-amino-9H-pyrido[3',2':4,5]pyrrolo[2,3-d]pyrimidin-9-yl)acetate (162e) (0.27 g, 0.902 mmol) in DCM (10 mL) using TFA (1.029 g, 9.02 mmol) and stirring at RT for 16 h. This gave after workup TFA salt of 2-(4-amino-9H-pyrido[3',2':4,5]pyrrolo[2,3-d]pyrimidin-9-yl)acetic acid (162f) (311 mg, 97% yield) as a pale-yellow solid; $^1$H NMR (300 MHz, DMSO-$d_6$) δ 8.84 (dd, J=7.9, 1.5 Hz, 1H), 8.59-8.44 (m, 2H), 8.04 (s, 2H), 7.43 (dd, J=7.8, 4.9 Hz, 1H), 5.14 (s, 2H). $^{19}$F NMR (282 MHz, DMSO) δ−74.47; MS (ES+): 244 (M+1), (ES−): 242 (M−1).

Step-6: Preparation of (1R,3S,5R)-2-(2-(4-amino-9H-pyrido[3',2':4,5]pyrrolo[2,3-d]pyrimidin-9-yl)acetyl)-N-(6-bromopyridin-2-yl)-2-azabicyclo[3.1.0]hexane-3-carboxamide (162 g)

Compound 162g was prepared according to the procedure reported in step-3 of scheme-1, from TFA salt of 2-(4-amino-9H-pyrido[3',2':4,5]pyrrolo[2,3-d]pyrimidin-9-yl)acetic acid (162f) (75 mg, 0.210 mmol) in DMF (5 mL) using (1R,3S,5R)—N-(6-bromopyridin-2-yl)-2-azabicyclo[3.1.0]hexane-3-carboxamide (4a) (80 mg, 0.252 mmol), HATU (120 mg, 0.315 mmol), DIPEA (136 mg, 1.050 mmol) and stirring at RT for 16 h. This gave after workup and purification by flash column chromatography [silica gel (12 g), eluting with MeOH in DCM from 0-6%] followed by purification using reverse phase column chromatography [C18 column (100 g), eluting with ACN in water (containing 0.1% HCl) from 0-100%](1R,3S,5R)-2-(2-(4-amino-9H-pyrido[3',2':4,5]pyrrolo[2,3-d]pyrimidin-9-yl)acetyl)-N-(6- bromopyridin-2-yl)-2-azabicyclo[3.1.0]hexane-3-carboxamide (162 g) (75 mg, 70% yield) HCl salt as a white solid; $^1$H NMR (300 MHz, DMSO-$d_6$) δ 10.78 (s, 1H, $D_2O$ exchangeable), 9.29-8.91 (m, 3H, 2H $D_2O$ exchangeable), 8.74 (s, 1H), 8.59 (dd, J=4.8, 1.4 Hz, 1H), 8.01 (d, J=8.2 Hz, 1H), 7.71 (t, J=8.0 Hz, 1H), 7.53 (dd, J=7.9, 4.8 Hz, 1H), 7.32 (d, J=7.7 Hz, 1H), 5.78 (d, J=17.0 Hz, 1H), 5.41 (d, J=16.9 Hz, 1H), 4.42 (m, 1H), 4.03-3.84 (m, 1H), 2.39-2.27 (m, 1H), 2.27-2.18 (m, 1H), 1.99-1.86 (m, 1H), 1.11 (m, 1H), 0.70 (m, 1H); MS (ES+): 507/509 (M+1), 505/507 (M−1).

Scheme 163

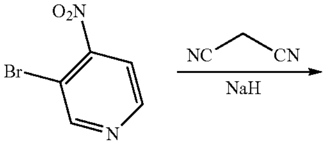

163a

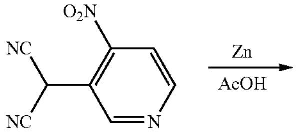

163b

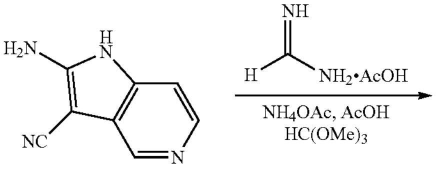

163c

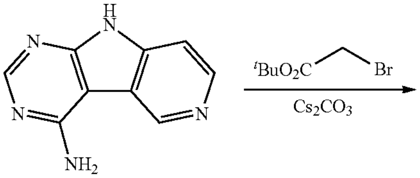

163d

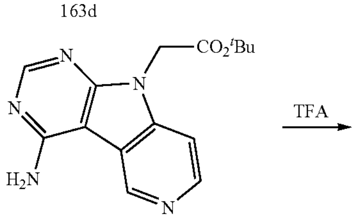

163e

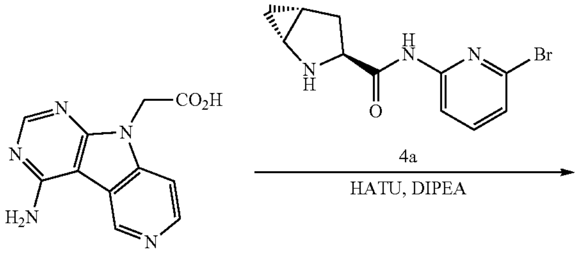

163f

-continued

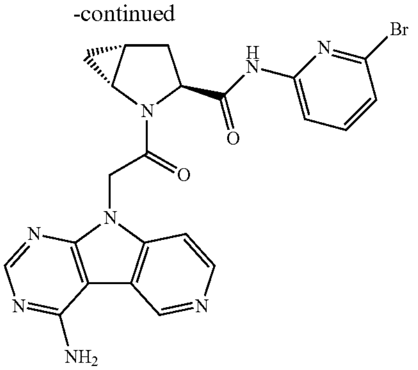

163g

Preparation of (1R,3S,5R)-2-(2-(4-amino-9H-pyrido[3',4':4,5]pyrrolo[2,3-d]pyrimidin-9-yl)acetyl)-N-(6-bromopyridin-2-yl)-2-azabicyclo[3.1.0]hexane-3-carboxamide (163 g)

Step-1: Preparation of 2-(4-nitropyridin-3-yl)malononitrile (163b)

Compound 163b was prepared according to the procedure reported in step-1 of scheme-162 from 3-bromo-4-nitropyridine (163a) (5.00 g, 24.63 mmol) using NaH (1.990 g, 49.8 mmol) malononitrile (3.29 g, 49.8 mmol) in THF (100 mL). This gave after workup 2-(4-nitropyridin-3-yl)malononitrile (163b) (5.27 g) as a brown/black solid, which was used as such in the next reaction; MS (ES+): 159 (M+1), (ES−): 157 (M−1).

Step-2: Preparation of 2-amino-1H-pyrrolo[3,2-c]pyridine-3-carbonitrile (163c)

Compound 163c was prepared according to the procedure reported in step-2 of scheme-162 from 2-(4-nitropyridin-3-yl)malononitrile (163b) (5.27 g, 28.0 mmol) in acetic acid (16.82 g, 280 mmol), using zinc (9.16 g, 140 mmol). This gave after workup and purification by flash column chromatography ($SiO_2$, 40 g, eluting with 0-20% DMA-80 in DCM) 2-amino-1H-pyrrolo[3,2-c]pyridine-3-carbonitrile (163c) (0.23 g, 1.454 mmol, 5.19% yield) as a beige solid; 1H NMR (300 MHz, DMSO-$d_6$) δ 11.30 (s, 1H), 8.34 (d, J=0.9 Hz, 1H), 8.04 (d, J=5.4 Hz, 1H), 7.33-7.01 (m, 3H). LC-MS: t=0.54 min, MS (ES+): 159 (M+1), (ES−): 157 (M−1).

Step-3: Preparation of 9H-pyrido[3',4':4,5]pyrrolo[2,3-d]pyrimidin-4-amine (163d)

Compound 163d was prepared according to the procedure reported in step-2 of scheme-29, from 2-amino-1H-pyrrolo[3,2-c]pyridine-3-carbonitrile (163c) (0.23 g, 1.454 mmol) in ethanol (20 mL) using formamidine acetate (1.211 g, 11.63 mmol), $NH_4OAc$ (0.336 g, 4.36 mmol), glacial AcOH (0.262 g, 4.36 mmol), $HC(OMe)_3$ (0.772 g, 7.27 mmol) and heating at 80° C. for 5 days. This gave after work up 9H-pyrido[3',4':4,5]pyrrolo[2,3-d]pyrimidin-4-amine (163d) (0.14 g, 52% yield) as a brown solid; $^1$H NMR (300 MHz, DMSO-$d_6$) δ 12.24 (s, 1H), 9.47 (d, J=1.0 Hz, 1H), 8.42 (d, J=5.6 Hz, 1H), 8.32 (s, 1H), 7.42 (dd, J=5.6, 1.0 Hz, 1H), 7.37 (s, 2H). MS (ES+): 186 (M+1); (ES−): 184 (M−1).

Step-4: Preparation of tert-butyl 2-(4-amino-9H-pyrido[3',4':4,5]pyrrolo[2,3-d]pyrimidin-9-yl)acetate (163e)

Compound 163e was prepared according to the procedure reported in step-1 of scheme-1, from 9H-pyrido[3',4':4,5]pyrrolo[2,3-d]pyrimidin-4-amine (163d) (0.14 g, 0.756 mmol) in DMF (10 mL) using tert-butyl 2-bromoacetate (0.177 g, 0.907 mmol) and $Cs_2CO_3$ (0.493 g, 1.512 mmol). This gave after workup and purification using flash column chromatography [$SiO_2$ gel (24 g), eluting with MeOH in DCM from 0-6%] tert-butyl 2-(4-amino-9H-pyrido[3',4':4.5]pyrrolo[2,3-d]pyrimidin-9-yl)acetate (163e) (0.11 g, 49% yield) as a pale-yellow solid; 1H NMR (300 MHz, DMSO-$d_6$) δ 9.51 (s, 1H), 8.49 (d, J=5.6 Hz, 1H), 8.37 (s, 1H), 7.64 (dd, J=5.7, 0.9 Hz, 1H), 7.52 (s, 2H), 5.16 (s, 2H), 1.40 (s, 9H).

Step-5: Preparation of 2-(4-amino-9H-pyrido[3',4':4,5]pyrrolo[2,3-d]pyrimidin-9-yl)acetic acid (163f)

Compound 163f was prepared according to the procedure reported in step-2 of scheme-1, from tert-butyl 2-(4-amino-9H-pyrido[3',4':4.5]pyrrolo[2,3-d]pyrimidin-9-yl)acetate (163e) (0.108 g, 0.361 mmol) in DCM (10 mL) using TFA (411 mg, 3.61 mmol) and stirring at RT for 16 h. This gave after work up TFA salt of 2-(4-amino-9H-pyrido[3',4':4,5]pyrrolo[2,3-d]pyrimidin-9-yl)acetic acid (163f) (202 mg) as a pale-yellow solid; $^1H$ NMR (300 MHz, DMSO-$d_6$) δ 9.87 (d, J=2.1 Hz, 1H), 8.85 (dd, J=6.9, 2.1 Hz, 1H), 8.55 (d, J=2.1 Hz, 1H), 8.37 (dd, J=6.7.2.1 Hz, 1H), 8.10 (s, 2H), 5.37 (d, J=2.0 Hz, 2H). $^{19}F$ NMR (282 MHz, DMSO-$d_6$) δ −74.58; MS (ES+): 244 (M+1), (ES−): 242 (M−1).

Step-6: Preparation of (1R,3S,5R)-2-(2-(4-amino-9H-pyrido[3',4':4.5]pyrrolo[2,3-d]pyrimidin-9-yl)acetyl)-N-(6-bromopyridin-2-yl)-2-azabicyclo[3.1.0]hexane-3-carboxamide (163 g)

Compound 163g was prepared according to the procedure reported in step-3 of scheme-1, from TFA salt 2-(4-amino-9H-pyrido[3',4':4,5]pyrrolo[2,3-d]pyrimidin-9-yl)acetic acid (163f) (75 mg, 0.210 mmol) in DMF (5 mL) using HCl salt of (1R,3S,5R)—N-(6-bromopyridin-2-yl)-2-azabicyclo[3.1.0]hexane-3-carboxamide (4a) (80 mg, 0.252 mmol), HATU (120 mg, 0.315 mmol), DIPEA (136 mg, 1.050 mmol) and stirring at RT for 16 h. This gave after workup and purification by flash column chromatography [silica gel (12 g), eluting with MeOH in DCM from 0-7%] followed by purification using reverse phase column chromatography [C18 column (100 g), eluting with ACN in water (containing 0.1% HCl) from 0-100%] (1R,3S,5R)-2-(2-(4-amino-9H-pyrido[3',4':4,5]pyrrolo[2,3-d]pyrimidin-9-yl)acetyl)-N-(6-bromopyridin-2-yl)-2-azabicyclo[3.1.0]hexane-3-carboxamide (163 g) (43 mg, 40% yield) HCl salt as a pale yellow solid; 1H NMR (300 MHz, DMSO-$d_6$) δ 10.78 (s, 1H, $D_2O$ exchangeable), 10.08 (s, 1H), 8.83 (d, J=6.6 Hz, 1H), 8.62 (s, 1H), 8.44 (s, 2H, $D_2O$ exchangeable)), 8.25 (d, J=6.7 Hz, 1H), 8.00 (d, J=8.1 Hz, 1H), 7.71 (t, J=8.0 Hz, 11H), 7.32 (d, J=7.7 Hz, 1H), 5.92 (d, J=17.4 Hz, 1H), 5.53 (d, J=17.4 Hz, 1H), 4.48-4.37 (m, 1H), 3.97-3.83 (m, 1H), 2.37-2.29 (m, 1H), 2.28-2.17 (m, 1H), 1.99-1.85 (m, 1H), 1.15-1.02 (m, 1H), 0.91-0.78 (m, 1H); MS (ES+): 507/509 (M+1); (ES−): 505/507 (M−1).

Scheme 164

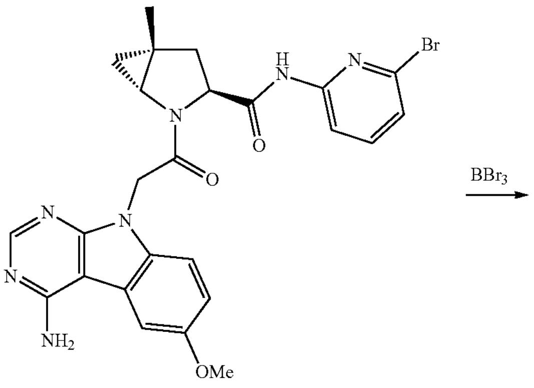

159a

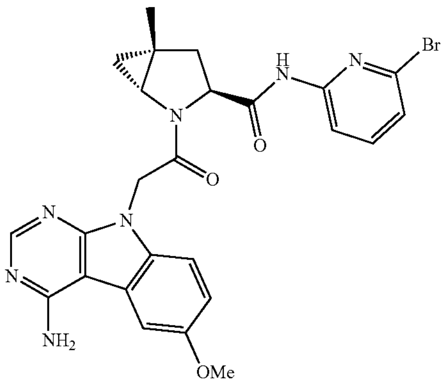

164a

Preparation of (1R,3S,5R)-2-(2-(4-amino-6-hydroxy-9H-pyrimido[4,5-b]indol-9-yl)acetyl)-N-(6-bromopyridin-2-yl)-5-methyl-2-azabicyclo[3.1.0]hexane-3-carboxamide (164a)

To a solution of (1R,3S,5R)-2-(2-(4-amino-6-methoxy-9H-pyrimido[4,5-b]indol-9-yl)acetyl)-N-(6-bromopyridin-2-yl)-5-methyl-2-azabicyclo[3.1.0]hexane-3-carboxamide (159a) (70 mg, 0.127 mmol) in DCM (5 mL) was added 1.0 M $BBr_3$ in DCM (0.636 mL, 0.636 mmol) drop wise at 0° C. under argon and stirred at RT for 16 h. The reaction mixture was quenched with $H_2O$ (2 mL) and concentrated in vacuum. The residue was purified by reverse-phase column chromatography [C18 column (100 g), eluting with ACN in water (containing 0.1% HCl) from 0-100%] to provide (1R,3S,5R)-2-(2-(4-amino-6-hydroxy-9H-pyrimido[4,5-b]indol-9-yl)acetyl)-N-(6-bromopyridin-2-yl)-5-methyl-2-azabicyclo[3.1.0]hexane-3-carboxamide (164a) (41 mg, 60% yield) HCl salt as a white solid: 1H NMR (300 MHz, DMSO-$d_6$) δ 10.77 (s, 1H, $D_2O$ exchangeable), 9.46 (s, 1H, $D_2O$ exchangeable), 8.54 (s, 1H), 8.46 (s, 2H, $D_2O$ exchangeable), 8.01 (d, J=8.2 Hz, 1H), 7.84 (d, J=2.2 Hz, 1H), 7.70 (t, J=7.9 Hz, 1H), 7.47 (d, J=8.8 Hz, 1H), 7.32 (d, J=7.7 Hz, 1H), 7.06 (dd, J=8.8, 2.3 Hz, 1H), 5.63 (d, J=17.3 Hz, 1H), 5.29 (d, J=17.3 Hz, 1H), 4.36 (m, 1H), 3.66 (dd, J=5.4, 2.3 Hz, 1H), 2.52-2.39 (m, 1H), 1.97 (dd, J=13.2, 5.9 Hz, 1H), 1.29 (s, 3H), 1.06-0.94 (m, 1H), 0.94-0.84 (m, 1H); MS (ES+): 536/538 (M+1), (ES−): 534/536 (M−1).

Scheme 165

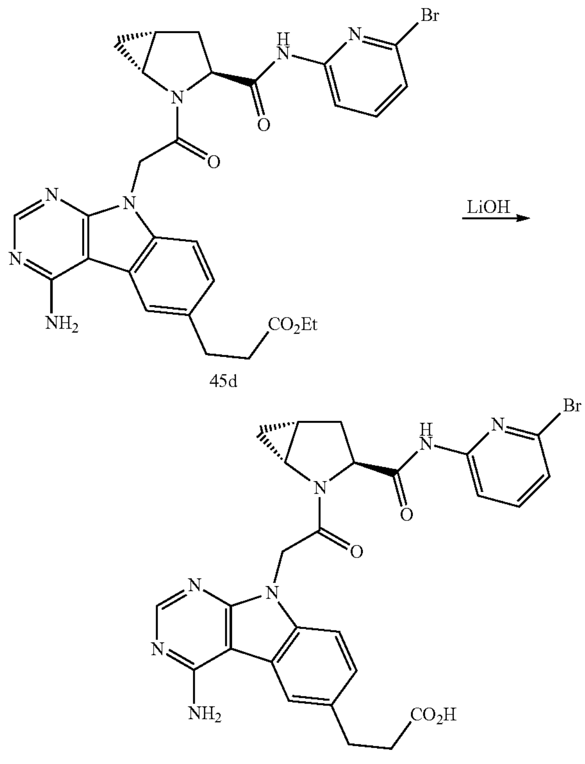

45d

165a

Preparation of 3-(4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)propanoic acid (165a)

Compounds 165a was prepared according to the procedure reported in step-4 of scheme-17, from ethyl 3-(4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)propanoate (45d) (78 mg, 0.129 mmol) in THF (3 mL) using 2M aqueous lithium hydroxide (0.077 mL, 0.154 mmol) and stirring at RT for 16 h. This gave after workup and purification by reverse phase column chromatography [C18 column (100 g), eluting with ACN in water (containing 0.1% HCl) from 0-100%] 3-(4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)propanoic acid (165a) (55 mg, 74% yield) HCl salt as a white solid; $^1$H NMR (300 MHz, DMSO-$d_6$) δ 10.77 (s, 1H, $D_2O$ exchangeable), 8.59 (d, J=4.5 Hz, 1H), 8.51 (d, J=9.2 Hz, 2H, $D_2O$ exchangeable), 8.43-8.34 (m, 1H), 7.98 (dd, J=16.3, 8.2 Hz, 1H), 7.70 (td, J=8.1, 6.0 Hz, 1H), 7.59 (dd, J=8.4, 2.2 Hz, 1H), 7.44 (d, J=8.7 Hz, 1H), 7.31 (dd, J=7.8, 5.4 Hz, 1H), 5.74 (d, J=17.3 Hz, 1H), 5.39 (dd, J=17.3, 3.0 Hz, 1H), 4.48-4.35 (m, 1H), 4.05-3.85 (m, 1H), 3.01 (t, J=7.8 Hz, 2H), 2.67 (dd, J=8.6, 6.9 Hz, 2H), 2.40-2.27 (m, 1H), 2.27-2.14 (m, 1H), 1.99-1.87 (m, 1H), 1.28-1.02 (m, 1H), 0.96-0.74 (m, 1H); MS (ES+): 578/580 (M+1), (ES−): 576/578 (M−1); Analysis calculated for $C_{26}H_{24}BrN_7O_4 \cdot HCl \cdot 2H_2O$: C, 47.98; H, 4.49; Cl, 5.45; N, 15.06. Found: C, 47.70; H, 4.29; Cl, 5.69; N, 14.77.

Scheme 166

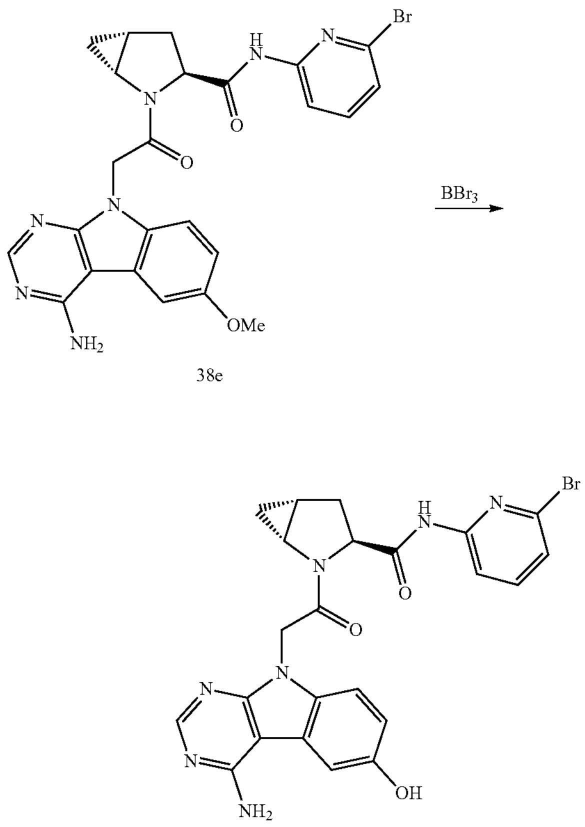

38e

166a

Preparation of (1R,3S,5R)-2-(2-(4-amino-6-hydroxy-9H-pyrimido[4,5-b]indol-9-yl)acetyl)-N-(6-bromopyridin-2-yl)-2-azabicyclo[3.1.0]hexane-3-carboxamide (166a)

Compound 166a was prepared according to the procedure reported in scheme-164, from (1R,3S,5R)-2-(2-(4-amino-6-methoxy-9H-pyrimido[4,5-b]indol-9-yl)acetyl)-N-(6-bromopyridin-2-yl)-2-azabicyclo[3.1.0]hexane-3-carboxamide (38e) (85 mg, 0.158 mmol) in DCM (5 mL) using a solution of 1.0 M $BBr_3$ in DCM (0.792 mL, 0.792 mmol) and stirring at RT for 30 min. This gave after work up and purification using reverse phase column chromatography [C18 column (100 g), eluting with ACN in water (containing 0.1% HCl) from 0-100%] (1R,3S,5R)-2-(2-(4-amino-6-hydroxy-9H-pyrimido[4,5-b]indol-9-yl)acetyl)-N-(6-bromopyridin-2-yl)-2-azabicyclo[3.1.0]hexane-3-carboxamide (166a) (30 mg, 36% yield) HCl salt as a white solid; $^1$H NMR (300 MHz, DMSO-$d_6$) δ 10.77 (s, 1H, $D_2O$ exchangeable), 9.91-9.13 (m, 1H, $D_2O$ exchangeable), 8.68 (s, 2H, $D_2O$ exchangeable), 8.60 (s, 1H), 8.01 (d, J=8.2 Hz, 1H), 7.87 (d, J=2.2 Hz, 1H), 7.71 (t, J=7.9 Hz, 1H), 7.52 (d, J=8.8 Hz, 1H), 7.32 (d, J=7.7 Hz, 1H), 7.11 (dd, J=8.8, 2.3 Hz, 1H), 5.70 (d, J=17.3 Hz, 1H), 5.36 (d, J=17.2 Hz, 1H), 4.42 (dd, J=9.1, 5.5 Hz, 1H), 3.89 (td, J=6.2, 5.4, 2.2 Hz, 1H), 2.39-2.26 (m, 1H), 2.26-2.14 (m, 1H), 1.98-1.84 (m, 1H), 1.12-0.98 (m, 1H), 0.83-0.69 (m, 1H); MS (ES+): 522/524 (M+1), 520/522 (M−1).

Scheme 167

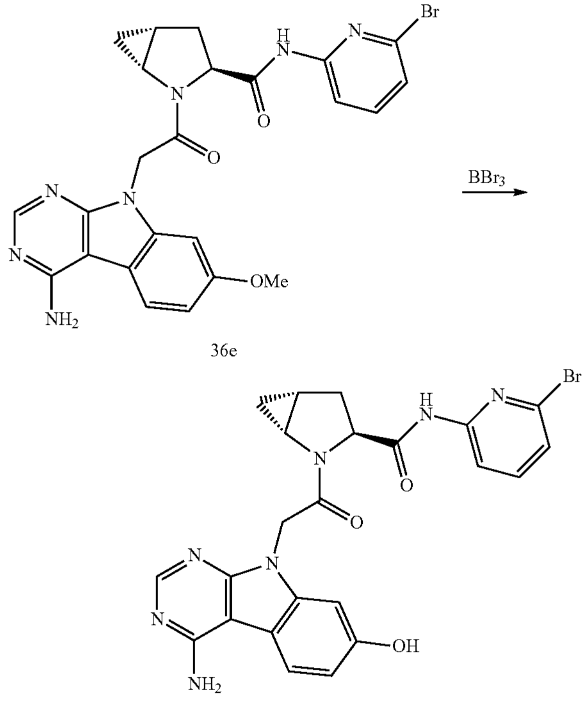

36e

167a

Preparation of (1R,3S,5R)-2-(2-(4-amino-7-hydroxy-9H-pyrimido[4,5-b]indol-9-yl)acetyl)-N-(6-bromopyridin-2-yl)-2-azabicyclo[3.1.0]hexane-3-carboxamide (167a)

Compound 167a was prepared according to the procedure reported in scheme-164, from (1R,3S,5R)-2-(2-(4-amino-7-methoxy-9H-pyrimido[4,5-b]indol-9-yl)acetyl)-N-(6-bromopyridin-2-yl)-2-azabicyclo[3.1.0]hexane-3-carboxamide (36e) (82 mg, 0.153 mmol) in DCM (5 mL) using a solution of 1.0 M $BBr_3$ in DCM (0.764 mL, 0.764 mmol) and stirring at RT for 16 h. This gave after work up and purification using reverse phase column chromatography [C18 column (100 g), eluting with ACN in water (containing 0.1% HCl) from 0-100%] (1R,3S,5R)-2-(2-(4-amino-7-hydroxy-9H-pyrimido[4,5-b]indol-9-yl)acetyl)-N-(6-bromopyridin-2-yl)-2-azabicyclo[3.1.0]hexane-3-carboxamide (167a) (30 mg, 38% yield) HCl salt as a white solid; $^1H$ NMR (300 MHz, DMSO-$d_6$) δ 10.79 (s, 1H, $D_2O$ exchangeable), 9.97 (s, 1H, $D_2O$ exchangeable), 8.53 (d, J=3.1 Hz, 1H), 8.37 (s, 2H, $D_2O$ exchangeable), 8.28 (d, J=8.5 Hz, 1H), 8.01 (d, J=8.1 Hz, 1H), 7.70 (t, J=8.0 Hz, 11H), 7.32 (d, J=7.7 Hz, 1H), 6.97 (d, J=2.0 Hz, 1H), 6.89 (dd, J=8.6, 2.1 Hz, 1H), 5.66 (d, J=17.3 Hz, 1H), 5.31 (d, J=17.4 Hz, 1H), 4.42 (dd, J=9.0, 5.5 Hz, 1H), 3.90 (td, J=6.9, 6.3, 2.5 Hz, 1H), 2.38-2.29 (m, 1H), 2.26-2.15 (m, 1H), 1.98-1.87 (m, 1H), 1.12-1.02 (m, 1H), 0.77-0.70 (m, 1H); MS (ES+): 522/524 (M+1), (ES−): 520/522 (M−1).

Scheme 168

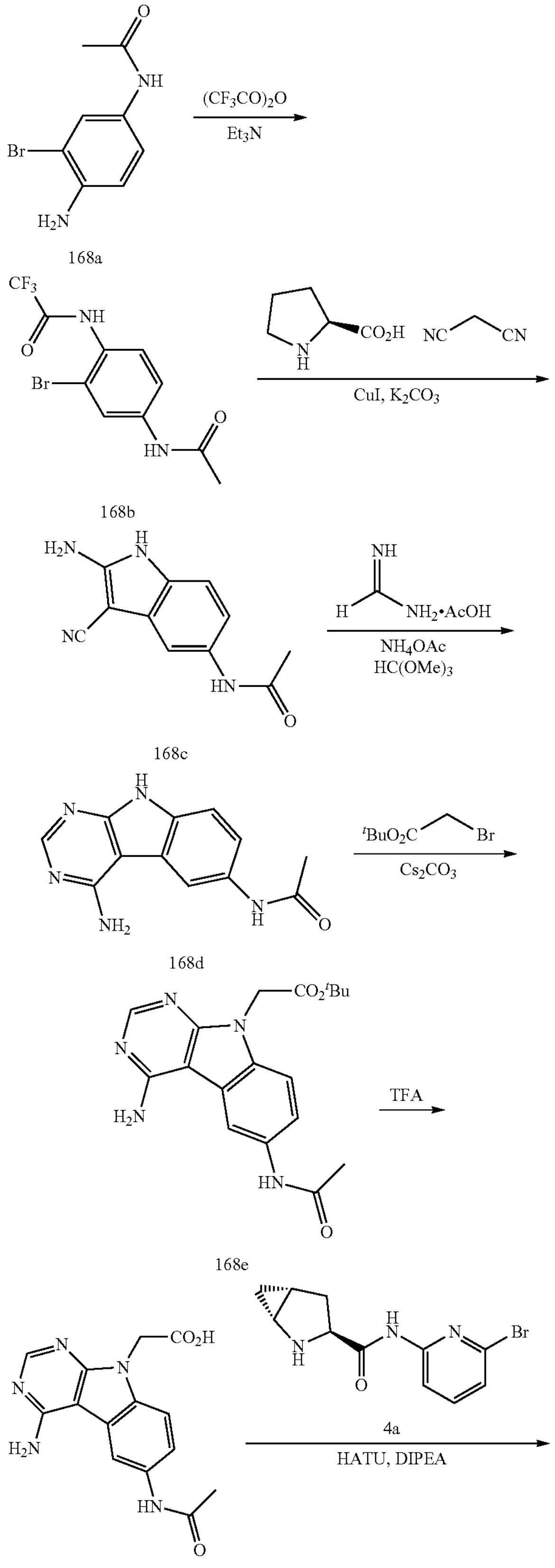

168a

168b

168c

168d

168e

168f

-continued

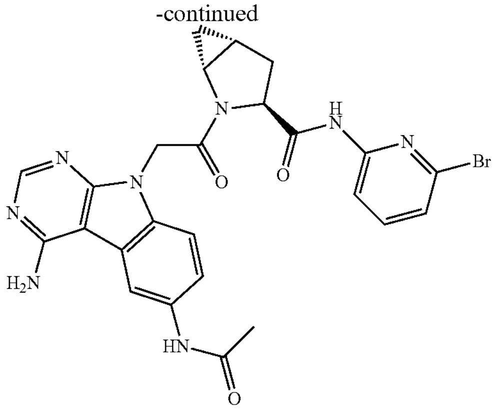

168g

Preparation of (1R,3S,5R)-2-(2-(6-acetamido-4-amino-9H-pyrimido[4,5-b]indol-9-yl)acetyl)-N-(6-bromopyridin-2-yl)-2-azabicyclo[3.1.0]hexane-3-carboxamide (168 g)

Step-1: Preparation of N-(4-acetamido-2-bromophenyl)-2,2,2-trifluoroacetamide (168b)

Compound 168b was prepared according to the procedure reported in step-1 of scheme-46, from N-(4-amino-3-bromophenyl)acetamide (168a) (0.88 g, 3.84 mmol; CAS #860745-87-5) in DCM (30 mL) using triethylamine (0.661 g, 6.53 mmol), trifluoroacetic acid anhydride (1.210 g, 5.76 mmol) and stirring at RT for 3 h. This gave after workup N-(4-acetamido-2-bromophenyl)-2,2,2-trifluoroacetamide (168b) (400 mg, 32% yield) as a yellow solid which was used as such for the next step: $^1$H NMR (300 MHz, DMSO-$d_6$) δ 11.18 (s, 1H), 10.25 (s, 1H), 8.09 (d, J=2.2 Hz, 1H), 7.55 (dd, J=8.6, 2.3 Hz, 1H), 7.37 (d, J=8.6 Hz, 1H), 2.07 (s, 3H). $^{19}$F NMR (282 MHz, DMSO) δ-74.07; MS (ES+): 325/327 (M+1); (ES−): 323/325 (M−1).

Step-2: Preparation of N-(2-amino-3-cyano-1H-indol-5-yl)acetamide (168c)

Compound 168c was prepared according to the procedure reported in step-1 of scheme-11, from N-(4-acetamido-2-bromophenyl)-2,2,2-trifluoroacetamide (168b) (400 mg, 1.230 mmol) in DMSO (10 mL) using malononitrile (203 mg, 3.08 mmol), L-proline (56.7 mg, 0.492 mmol). CuI (46.9 mg, 0.246 mmol), a solution of $K_2CO_3$ (340 mg, 2.461 mmol) in water (10 mL) and heating at 60° C. for 16 h under an argon atmosphere. This gave after workup and purification [$SiO_2$ gel (24 g), eluting with MeOH in DCM from 0-5%] N-(2-amino-3-cyano-1H-indol-5-yl)acetamide (168c) (120 mg, 46% yield) as a yellow solid; $^1$H NMR (300 MHz, DMSO-$d_6$) δ 10.58 (s, 1H), 9.72 (s, 1H), 7.52 (d, J=1.5 Hz, 1H), 7.01 (d, J=1.3 Hz, 2H), 6.72 (s, 2H), 2.01 (s, 3H). LC-MS: t=1.47 min; MS (ES+): 215 (M+1); (ES−): 213 (M−1).

Step-3: Preparation of N-(4-amino-9H-pyrimido[4,5-b]indol-6-yl)acetamide (168d)

Compound 168d was prepared according to the procedure reported in step-2 of scheme-29, from N-(2-amino-3-cyano-1H-indol-5-yl)acetamide (168c) (1.77 g, 8.26 mmol) in ethanol (30 mL) using formamidine acetate (6.88 g, 66.1 mmol), $NH_4OAc$ (1.911 g, 24.79 mmol), $HC(OMe)_3$ (8.77 g, 83 mmol) and heating at 80° C. for 16 h. This gave after work up N-(4-amino-9H-pyrimido[4,5-b]indol-6-yl)acetamide (168d) (1.48 g, 74% yield) as a tan solid; $^1$H NMR (300 MHz, DMSO-$d_6$) δ 11.76 (s, 1H), 9.81 (s, 1H), 8.22 (d, J=2.2 Hz, 2H), 7.46-7.31 (m, 2H), 7.09-6.90 (m, 2H), 2.06 (s, 3H); MS (ES+): 242 (M+1), (ES−): 240 (M−1).

Step-4: Preparation of tert-butyl 2-(6-acetamido-4-amino-9H-pyrimido[4,5-b]indol-9-yl)acetate (168e)

Compound 168e was prepared according to the procedure reported in step-1 of scheme-1, from N-(4-amino-9H-pyrimido[4,5-b]indol-6-yl)acetamide (168d) (0.74 g, 3.07 mmol) in DMF (10 mL) using tert-butyl 2-bromoacetate (0.718 g, 3.68 mmol) and $Cs_2CO_3$ (1.999 g, 6.13 mmol). This gave after workup and purification using flash column chromatography [$SiO_2$ gel (40 g), eluting with MeOH in DCM from 0-6%] tert-butyl 2-(6-acetamido-4-amino-9H-pyrimido[4,5-b]indol-9-yl)acetate (168e) (0.77 g, 71% yield) as a pale-yellow solid: $^1$H NMR (300 MHz, DMSO-$d_6$) δ 9.86 (s, 1H), 8.28 (s, 2H), 7.56-7.40 (m, 2H), 7.14 (s, 2H), 5.09 (s, 2H), 2.07 (s, 3H), 1.41 (s, 9H); MS (ES+): 356 (M+1), (ES−): 354 (M−1).

Step-5: Preparation of 2-(6-acetamido-4-amino-9H-pyrimido[4,5-b]indol-9-yl)acetic acid (168f)

Compound 168f was prepared according to the procedure reported in step-2 of scheme-1, from tert-butyl 2-(6-acetamido-4-amino-9H-pyrimido[4,5-b]indol-9-yl)acetate (168e) (0.77 g, 2.167 mmol) in DCM (15 mL) using TFA (2.470 g, 21.67 mmol) and stirring at RT for 16 h. This gave after work up TFA salt of 2-(6-acetamido-4-amino-9H-pyrimido[4,5-b]indol-9-yl)acetic acid (168f) (1.34 g) as a pale-yellow solid; $^1$H NMR (300 MHz, DMSO-$d_6$) δ 10.04 (s, 1H), 8.66 (s, 2H), 8.62 (s, 1H), 8.54 (d, J=1.9 Hz, 1H), 7.76 (d, J=8.8 Hz, 1H), 7.54 (dd, J=8.8, 1.9 Hz, 1H), 5.27 (s, 2H), 2.09 (s, 3H). $^{19}$F NMR (282 MHz, DMSO-$d_6$) δ−74.68; MS (ES+): 300 (M+1); (ES−): 298 (M−1).

Step-6: Preparation of (1R,3S,5R)-2-(2-(6-acetamido-4-amino-9H-pyrimido[4,5-b]indol-9-yl)acetyl)-N-(6-bromopyridin-2-yl)-2-azabicyclo[3.1.0]hexane-3-carboxamide (168 g)

Compound 168g was prepared according to the procedure reported in step-3 of scheme-1, from TFA salt of 2-(6-acetamido-4-amino-9H-pyrimido[4,5-b]indol-9-yl)acetic acid (1680) (200 mg, 0.484 mmol) in DMF (5 mL) using HCl salt of (1R,3S,5R)—N-(6-bromopyridin-2-yl)-2-azabicyclo[3.1.0]hexane-3-carboxamide (4a) (170 mg, 0.532 mmol), HATU (276 mg, 0.726 mmol), DIPEA (313 mg, 2.420 mmol) and stirring at RT for 16 h. This gave after workup and purification by flash column chromatography [silica gel (12 g), eluting with MeOH in DCM from 0 to 7%] followed by purification using reverse phase column chromatography [C18 column (100 g), eluting with ACN in water (containing 0.1% HCl) from 0-100%] (1R,3S,5R)-2-(2-(6-acetamido-4-amino-9H-pyrimido[4,5-b]indol-9-yl)acetyl)-N-(6-bromopyridin-2-yl)-2-azabicyclo[3.1.0]hexane-3-carboxamide (168 g) (70 mg, 26% yield) HCl salt as a white solid; $^1$H NMR (300 MHz, DMSO-$d_6$) δ 10.77 (s, 1H, $D_2O$ exchangeable), 10.09 (s, 1H, $D_2O$ exchangeable), 8.77 (s, 2H, $D_2O$ exchangeable), 8.66 (s, 1H), 8.52 (d, J=1.9 Hz, 1H), 8.00 (d, J=8.2 Hz, 1H), 7.75-7.60 (m, 2H), 7.55

(dd, J=8.8, 1.8 Hz, 1H), 7.31 (d, 1H), 5.76 (d, J=17.4 Hz, 1H), 5.40 (d, J=17.3 Hz, 1H), 4.42 (dd, J=9.0, 5.4 Hz, 1H), 3.94-3.86 (m, 1H), 2.40-2.26 (m, 1H), 2.26-2.15 (m, 1H), 2.08 (s, 3H), 1.97-1.85 (m, 1H), 1.12-0.98 (m, 1H), 0.83-0.72 (m, 1H); MS (ES+): 563/565 (M+1), (ES−): 561/563 (M−1); Analysis calculated for $C_{25}H_{23}BrN_8O_3 \cdot 1.75HCl \cdot 3H_2O$: C, 44.08; H, 4.55; N, 16.45. Found: C, 44.12; H, 4.67; N, 15.87.

Scheme 169

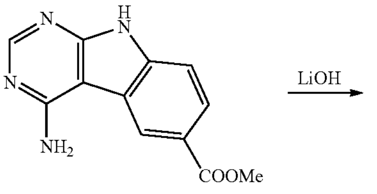

39c

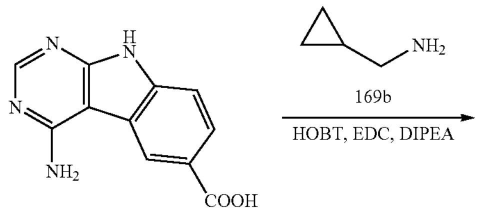

169a

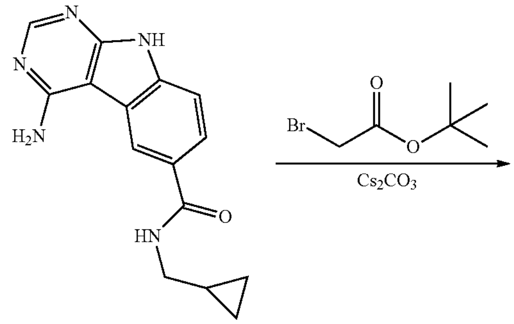

169c

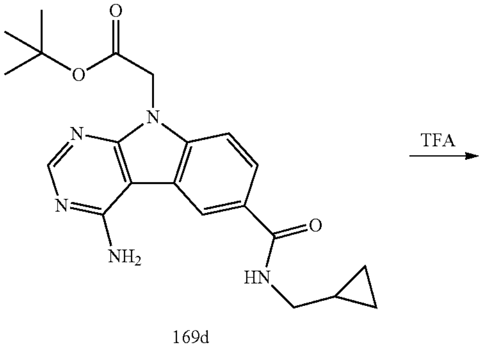

169d

-continued

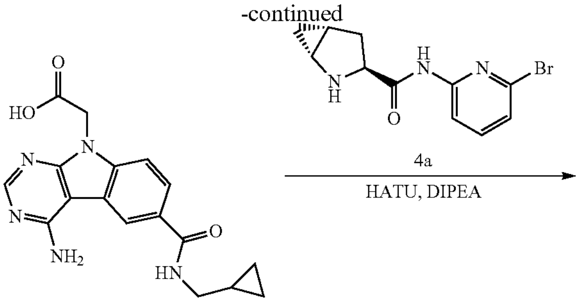

169e

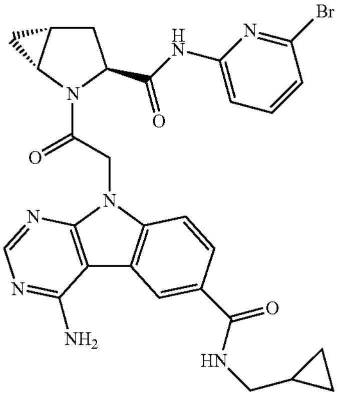

169f

Preparation of 4-amino-9-(2-((1R,3S,5R)-3-((6-bromopyridin-2-yl)carbamoyl)-2-azabicyclo[3.1.0]hexan-2-yl)-2-oxoethyl)-N-(cyclopropylmethyl)-9H-pyrimido[4,5-b]indole-6-carboxamide (169f)

Step-1: Preparation of 4-amino-9H-pyrimido[4,5-b]indole-6-carboxylic acid (169a)

Compound 169a was prepared according to the procedure reported in step-4 of scheme-17, from methyl 4-amino-9H-pyrimido[4,5-b]indole-6-carboxylate (39c) (400 mg, 1.651 mmol) in THF (5 mL) and MeOH (5 mL) using a solution of lithium hydroxide hydrate (424 mg, 9.91 mmol) in water (5 mL) and stirring at RT for 16 h. Additional lithium hydroxide hydrate (212 mg) in water (2 mL) and stirring for 6 h at RT was required for complete hydrolysis. This gave after work up 4-amino-9H-pyrimido[4,5-b]indole-6-carboxylic acid (169a) (305 mg, 81% yield) as a gray solid which was used as such for the next step; $^1$H NMR (300 MHz, DMSO-$d_6$) δ 12.16 (s, 1H), 8.90 (d, J=1.5 Hz, 1H), 8.27 (s, 1H), 7.97 (dd, J=8.5, 1.5 Hz, 1H), 7.48 (d, J=8.5 Hz, 1H), 7.32 (s, 2H); MS (ES+): 229.00 (M+1).

Step-2: Preparation of 4-amino-N-(cyclopropylmethyl)-9H-pyrimido[4,5-b]indole-6-carboxamide (169c)

Compound 169c was prepared according to the procedure reported in scheme-119, from 4-amino-9H-pyrimido[4,5-b]indole-6-carboxylic acid (169a) (100 mg, 0.438 mmol) in DMF (3 mL) using cyclopropylmethanamine (169b) (93 mg, 1.315 mmol), HOBT (29.6 mg, 0.219 mmol), EDC (168 mg, 0.876 mmol), DIPEA (0.153 mL, 0.876 mmol) and stirring at RT for 41 h. This gave after workup 4-amino-N-(cyclopropylmethyl)-9H-pyrimido[4,5-b]indole-6-carboxamide (169c) (12 mg, 10% yield) as a yellow solid which was used as such for the next step; MS (ES+): 282.10 (M+1).

Step-3: Preparation of tert-butyl 2-(4-amino-6-((cyclopropylmethyl)carbamoyl)-9H-pyrimido[4,5-b]indol-9-yl)acetate (169d)

Compound 169d was prepared according to the procedure reported in step-1 of scheme-1, from 4-amino-N-(cyclopropylmethyl)-9H-pyrimido[4,5-b]indole-6-carboxamide (169c) (12 mg, 0.043 mmol) in DMF (4 mL) using tert-butyl 2-bromoacetate (7.56 μL, 0.051 mmol), $Cs_2CO_3$ (34.7 mg, 0.107 mmol) and stirring at RT for 19 h. This gave after workup tert-butyl 2-(4-amino-6-((cyclopropylmethyl)carbamoyl)-9H-pyrimido[4,5-b]indol-9-yl)acetate (169d) (21 mg) as a yellow gum which was used as such for the next step; MS (ES+): 396.20 (M+1).

Step-4: Preparation of 2-(4-amino-6-((cyclopropylmethyl)carbamoyl)-9H-pyrimido[4,5-b]indol-9-yl) acetic acid (169e)

Compound 169e was prepared according to the procedure reported in step-2 of scheme-1, from tert-butyl 2-(4-amino-6-((cyclopropylmethyl)carbamoyl)-9H-pyrimido[4,5-b]indol-9-yl)acetate (169d) (0.017 g, 0.043 mmol) in DCM (5 mL) using TFA and stirring at RT. This gave after workup 2-(4-amino-6-((cyclopropylmethyl)carbamoyl)-9H-pyrimido[4,5-b]indol-9-yl)acetic acid (169e) (15 mg) and was used as such for the next step; MS (ES+): 340.20 (M+1).

Step-5: Preparation of 4-amino-9-(2-((1R,3S,5R)-3-((6-bromopyridin-2-yl)carbamoyl)-2-azabicyclo[3.1.0]hexan-2-yl)-2-oxoethyl)-N-(cyclopropylmethyl)-9H-pyrimido[4,5-b]indole-6-carboxamide (169f)

Compound 169f was prepared according to the procedure reported in step-3 of scheme-1, from TFA salt of 2-(4-amino-6-((cyclopropylmethyl)carbamoyl)-9H-pyrimido[4,5-b]indol-9-yl)acetic acid (169e) (14.59 mg, 0.043 mmol) in DMF (7 mL) using HCl salt of (1R,3S,5R)—N-(6-bromopyridin-2-yl)-2-azabicyclo[3.1.0]hexane-3-carboxamide (4a) (55 mg, 0.172 mmol), HATU (65 mg, 0.172 mmol), DIPEA (0.045 mL, 0.258 mmol) and stirring at RT for 18 h. This gave after workup and purification by flash column chromatography [silica gel (4 g), eluting with dichloromethane/methanol (1:0 to 19:1)] followed by conversion of product obtained to HCl salt by dissolving in acetonitrile (2 mL) and 0.1% aq. HCl (15 mL) and lyophilization 4-amino-9-(2-((1R,3S,5R)-3-((6-bromopyridin-2-yl)carbamoyl)-2-azabicyclo[3.1.0]hexan-2-yl)-2-oxoethyl)-N-(cyclopropylmethyl)-9H-pyrimido[4,5-b]indole-6-carboxamide (1690) (4 mg, 15% yield) HCl salt as a white solid; 1H NMR (300 MHz, DMSO-$d_6$) δ 10.76 (s, 1H), 8.97 (s, 1H), 8.58-8.44 (m, 2H), 8.06-7.97 (m, 2H), 7.75-7.64 (m, 2H), 7.31 (d, J=7.7 Hz, 1H), 5.74 (d, J=17.4 Hz, 1H), 5.41 (d, J=17.4 Hz, 1H), 4.48-4.35 (m, 1H), 3.95-3.86 (m, 1H), 3.31-3.10 (m, 2H), 2.41-2.12 (m, 2H), 1.97-1.83 (m, 1H), 1.30-1.01 (m, 2H), 0.84-0.70 (m, 1H), 0.54-0.39 (m, 2H), 0.36-0.21 (m, 2H); MS (ES+): 603.15 & 605.10 (M+1); MS (ES−): 601.10 & 603.10 (M−1).

Scheme 170

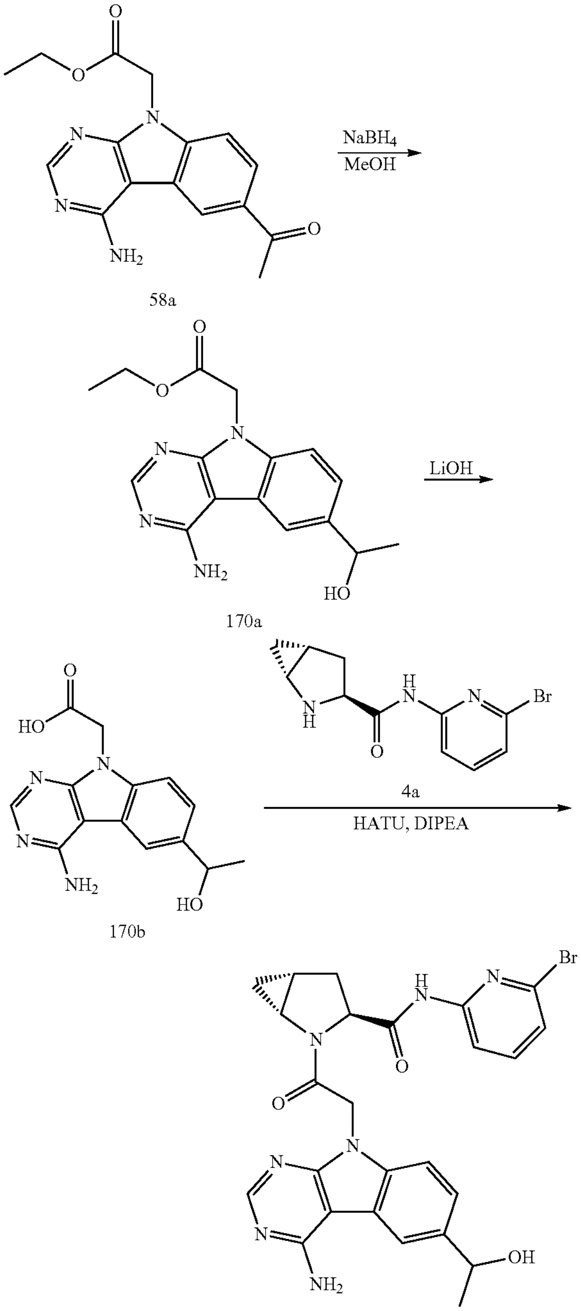

58a, 170a, 170b, 170c

Preparation of (1R,3S,5R)-2-(2-(4-amino-6-(1-hydroxyethyl)-9H-pyrimido[4,5-b]indol-9-yl)acetyl)-N-(6-bromopyridin-2-yl)-2-azabicyclo[3.1.0]hexane-3-carboxamide (170c)

Step-1: Preparation of ethyl 2-(4-amino-6-(1-hydroxyethyl)-9H-pyrimido[4,5-b]indol-9-yl)acetate (170a)

Compound 170a was prepared according to the procedure reported in scheme-157, from ethyl 2-(6-acetyl-4-amino- 9H-pyrimido[4,5-b]indol-9-yl)acetate (58a) (32 mg, 0.102 mmol) in THF (6 mL) and MeOH (3 mL) using sodium borohydride (11.87 mg, 0.307 mmol) and stirring at RT for 24 h. The residue obtained after work up was used as such for the next step; MS (ES+): 301.10 (M+1).

Step-2: Preparation of 2-(4-amino-6-(I-hydroxyethyl)-9H-pyrimido[4,5-b]indol-9-yl)acetic acid (170b)

Compound 170b was prepared according to the procedure reported in step-4 of scheme-17, from ethyl 2-(4-amino-6-(1-hydroxyethyl)-9H-pyrimido[4,5-b]indol-9-yl)acetate (170a) (0.032 mg, 0.102 mmol) in THF (3 mL) and MeOH (3 mL) using a solution of lithium hydroxide hydrate (0.026 g) and stirring at RT for 20 h. The obtained residue after work up was used as such for the next step; MS (ES+): 287.10 (M+1).

Step-3: Preparation of (1R,3S,5R)-2-(2-(4-amino-6-(1-hydroxyethyl)-9H-pyrimido[4,5-b]indol-9-yl)acetyl)-N-(6-bromopyridin-2-yl)-2-azabicyclo[3.1.0]hexane-3-carboxamide (170c)

Compound 170c was prepared according to the procedure reported in step-3 of scheme-1, from TFA salt of 2-(4-amino-6-(1-hydroxyethyl)-9H-pyrimido[4,5-b]indol-9-yl)acetic acid (170b) (29.2 mg, 0.102 mmol) in DMF (8 mL) using HCl salt of (1R,3S,5R)—N-(6-bromopyridin-2-yl)-2-azabicyclo[3.1.0]hexane-3-carboxamide (4a) (65 mg, 0.204 mmol), HATU (97 mg, 0.255 mmol), DIPEA (0.071 mL, 0.408 mmol) and stirring at RT for 20 h. This gave after workup and purification by flash column chromatography [silica gel (12 g), eluting with dichloromethane/methanol (1:0 to 19:1)] followed by conversion of product obtained to HCl salt by dissolving in acetonitrile (2 mL) and 0.1% aq. HCl (15 mL) and lyophilization(1R,3S,5R)-2-(2-(4-amino-6-(1-hydroxyethyl)-9H-pyrimido[4,5-b]indol-9-yl)acetyl)-N-(6-bromopyridin-2-yl)-2-azabicyclo[3.1.0]hexane-3-carboxamide (170c) (12 mg, 21% yield) HCl salt as a white solid; $^1$H NMR (300 MHz, DMSO-$d_6$) δ 10.76 (s, 1H), 8.62 (s, 2H), 8.61 (s, 1H), 8.45 (s, 1H), 8.00 (d, J=8.2 Hz, 1H), 7.70 (t, J=8.0 Hz, 1H), 7.67-7.55 (m, 2H), 7.31 (d, J=7.7 Hz, 1H), 5.75 (d, J=17.4 Hz, 1H), 5.41 (d, J=17.3 Hz, 1H), 4.91 (q, J=6.4 Hz, 1H), 4.40 (dd, J=9.1, 5.5 Hz, 1H), 3.99-3.86 (m, 1H), 2.43-2.10 (m, 2H), 2.01-1.78 (m, 1H), 1.43 (d, J=6.4 Hz, 3H), 1.14-0.99 (m, 1H), 0.82-0.69 (m, 1H); MS (ES+): 550.10 & 552.10 (M+1); MS (ES−): 548.00 & 550.10 (M−1).

Scheme 171

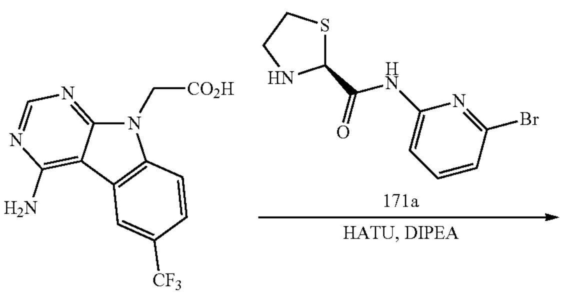

11e

-continued

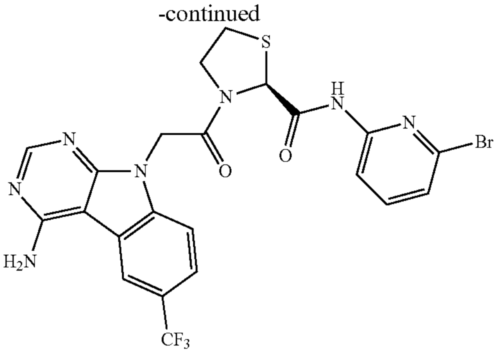

171b

Preparation of (S)-3-(2-(4-amino-6-(trifluoromethyl)-9H-pyrimido[4,5-b]indol-9-yl)acetyl)-N-(6-bromopyridin-2-yl)thiazolidine-2-carboxamide (171b)

Compound 171b was prepared according to the procedure reported in step-3 of scheme-1, from TFA salt of 2-(4-amino-6-(trifluoromethyl)-9H-pyrimido[4,5-b]indol-9-yl)acetic acid (11e) (75 mg, 0.177 mmol) in DMF (2 mL) using TFA salt of (S)—N-(6-bromopyridin-2-yl)thiazolidine-2-carboxamide (171a) (71.1 mg, 0.177 mmol; prepared according to the procedure reported by Yang, Chao-Yie in ACS Med. Chem. Lett. 2016, 7, 1092-1096), HATU (101 mg, 0.265 mmol), DIPEA (0.154 mL, 0.884 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] (S)-3-(2-(4-amino-6-(trifluoromethyl)-9H-pyrimido[4,5-b]indol-9-yl)acetyl)-N-(6-bromopyridin-2-yl)thiazolidine-2-carboxamide (171b) (61 mg, 60% yield) HCl salt as a white solid; $^1$H NMR (300 MHz, DMSO-$d_6$) (a mixture of two rotamers) δ 11.39 and 11.03 (2s, 1H, $D_2O$ exchangeable), 8.99 (s, 1H), 8.62 (m, 3H, 2H $D_2O$ exchangeable), 8.11 and 7.96 (2dd, J=8.4, 4.5 Hz, 2H), 7.87 (dd, J=8.8, 1.7 Hz, 1H), 7.73 (t, J=8.0 Hz, 1H), 7.42 and 7.34 (2d, J=7.7 Hz, 1H), 5.75-5.46 (m, 3H), 4.40 (dt, J=9.9, 4.8 Hz, 1H), 4.21-4.05 (m, 1H), 3.38 (dd, J=8.3, 5.4 Hz, 2H). $^{19}$F NMR (282 MHz, DMSO-$d_6$) δ−58.73. MS (ES+): 580.0 (M+1); (ES−): 578.0 (M−1); Analysis calculated for $C_2H_{17}BrF_3N_7O_2S$ $1.75H_2O{\cdot}HCl$: C, 40.75; H, 3.34; Cl, 5.47; N, 15.12. Found: C, 40.84; H, 3.18; Cl, 5.40; N, 14.93.

Scheme 172

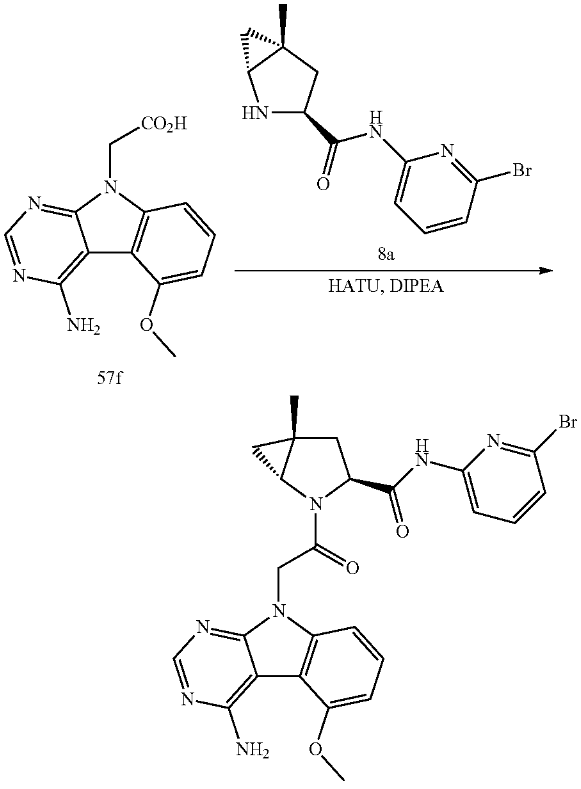

57f

172a

Preparation of (1R,3S,5R)-2-(2-(4-amino-5-methoxy-9H-pyrimido[4,5-b]indol-9-yl)acetyl)-N-(6-bromopyridin-2-yl)-5-methyl-2-azabicyclo[3.1.0]hexane-3-carboxamide (172a)

Compound 172a was prepared according to the procedure reported in step-3 of scheme-1, from TFA salt of 2-(4-amino-5-methoxy-9H-pyrimido[4,5-b]indol-9-yl)acetic acid (57f) (50 mg, 0.129 mmol) in DMF (2 mL) using HCl salt of (1R,3S,5R)—N-(6-bromopyridin-2-yl)-5-methyl-2-azabicyclo[3.1.0]hexane-3-carboxamide (8a) (43.1 mg, 0.129 mmol), HATU (73.8 mg, 0.194 mmol), DIPEA (0.113 mL, 0.647 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] (1R,3S,5R)-2-(2-(4-amino-5-methoxy-9H-pyrimido[4,5-b]indol-9-yl)acetyl)-N-(6-bromopyridin-2-yl)-5-methyl-2-azabicyclo[3.1.0]hexane-3-carboxamide (172a) (51 mg, 72% yield) HCl salt as a white solid; $^1H$ NMR (300 MHz, DMSO-$d_6$) δ 10.74 (s, 1H, $D_2O$ exchangeable), 8.65 (s, 2H, $D_2O$ exchangeable), 8.60 (s, 1H), 8.42 (d, J=8.8 Hz, 1H), 8.02 (d, J=8.1 Hz, 1H), 7.71 (t, J=8.0 Hz, 1H), 7.36-7.25 (m, 2H), 7.06 (dd, J=8.8, 2.3 Hz, 1H), 5.69 (d, J=17.3 Hz, 1H), 5.38 (d, J=17.3 Hz, 1H), 4.38 (dd, J=9.1, 6.0 Hz, 1H), 3.89 (s, 3H), 3.69 (dd, J=5.6, 2.4 Hz, 1H), 2.47 (d, J=9.0 Hz, 11H), 2.00 (dd, J=13.3, 6.0 Hz, 1H), 1.32 (s, 3H), 1.03 (t, J=5.4 Hz, 1H), 0.92 (dd, J=5.3, 2.4 Hz, 1H); MS (ES+): 550.1 (M+1), 572.1 (M+Na); (ES−): 548.1 (M−1); Analysis calculated for $C_{25}H_{24}BrN_7O_3 \cdot 1.2HCl \cdot 1.5H_2O$: C, 48.34; H, 4.58; Cl, 6.85; N, 15.78. Found: C, 48.20; H, 4.62; Cl, 6.50; N, 15.83.

Scheme 173

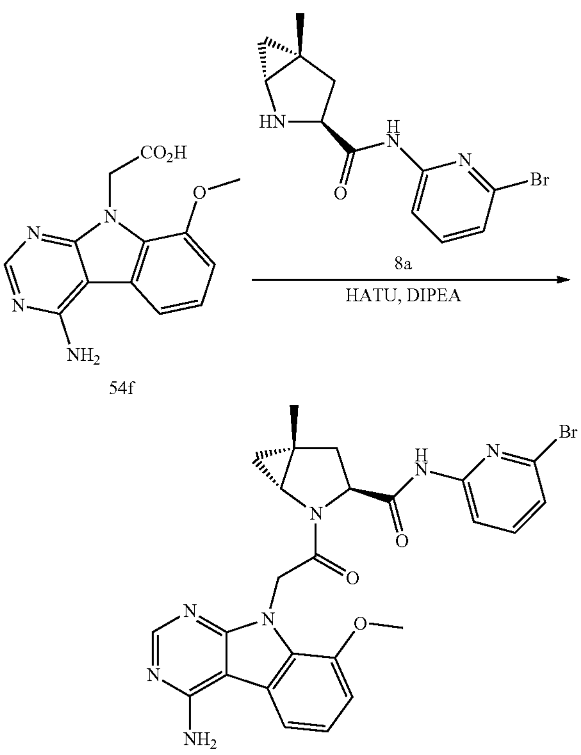

54f

173a

Preparation of (1R,3S,5R)-2-(2-(4-amino-8-methoxy-9H-pyrimido[4,5-b]indol-9-yl)acetyl)-N-(6-bromopyridin-2-yl)-5-methyl-2-azabicyclo[3.1.0]hexane-3-carboxamide (173a)

Compound 173a was prepared according to the procedure reported in step-3 of scheme-1, from TFA salt of 2-(4-amino-8-methoxy-9H-pyrimido[4,5-b]indol-9-yl)acetic acid (54f) (50 mg, 0.129 mmol) in DMF (2 mL) using HCl salt of (1R,3S,5R)—N-(6-bromopyridin-2-yl)-5-methyl-2-azabicyclo[3.1.0]hexane-3-carboxamide (8a) (43.1 mg, 0.129 mmol), HATU (73.8 mg, 0.194 mmol), DIPEA (0.113 mL, 0.647 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%] (1R,3S,5R)-2-(2-(4-amino-8-methoxy-9H-pyrimido[4,5-b]indol-9-yl)acetyl)-N-(6-bromopyridin-2-yl)-5-methyl-2-azabicyclo[3.1.0]hexane-3-carboxamide (173a) (47 mg, 66% yield) HCl salt as a white solid; $^1H$ NMR (300 MHz, DMSO-$d_6$) δ 10.73 (s, 1H, $D_2O$ exchangeable), 8.69-8.50 (m, 3H, 2H $D_2O$ exchangeable), 8.05 (dd, J=16.9, 8.1 Hz, 2H), 7.71 (t, J=8.0 Hz, 1H), 7.40-7.27 (m, 2H), 7.14 (d, J=8.1 Hz, 1H), 5.76 (d, J=17.0 Hz, 1H), 5.55 (d, J=16.9 Hz, 1H), 4.39 (dd, J=9.0, 5.9 Hz, 1H), 3.93 (s, 3H), 3.62 (dd, J=5.4, 2.3 Hz, 1H), 2.49-2.41 (m, 1H), 2.05-1.91 (m, 1H), 1.31 (s, 3H), 1.06 (t, J=5.4 Hz, 1H), 0.83 (dd, J=5.3, 2.3 Hz, 1H); MS (ES+): 550.1 (M+1), 572.1 (M+Na); (ES−): 548.1 (M−1);

Analysis calculated for $C_{25}H_{24}BrN_7O_3 \cdot HCl \cdot 2H_2O$: C, 48.20; H, 4.69; Cl, 5.69; N, 15.74. Found: C, 48.00; H, 4.59; Cl, 5.46; N, 15.60.

Scheme 174

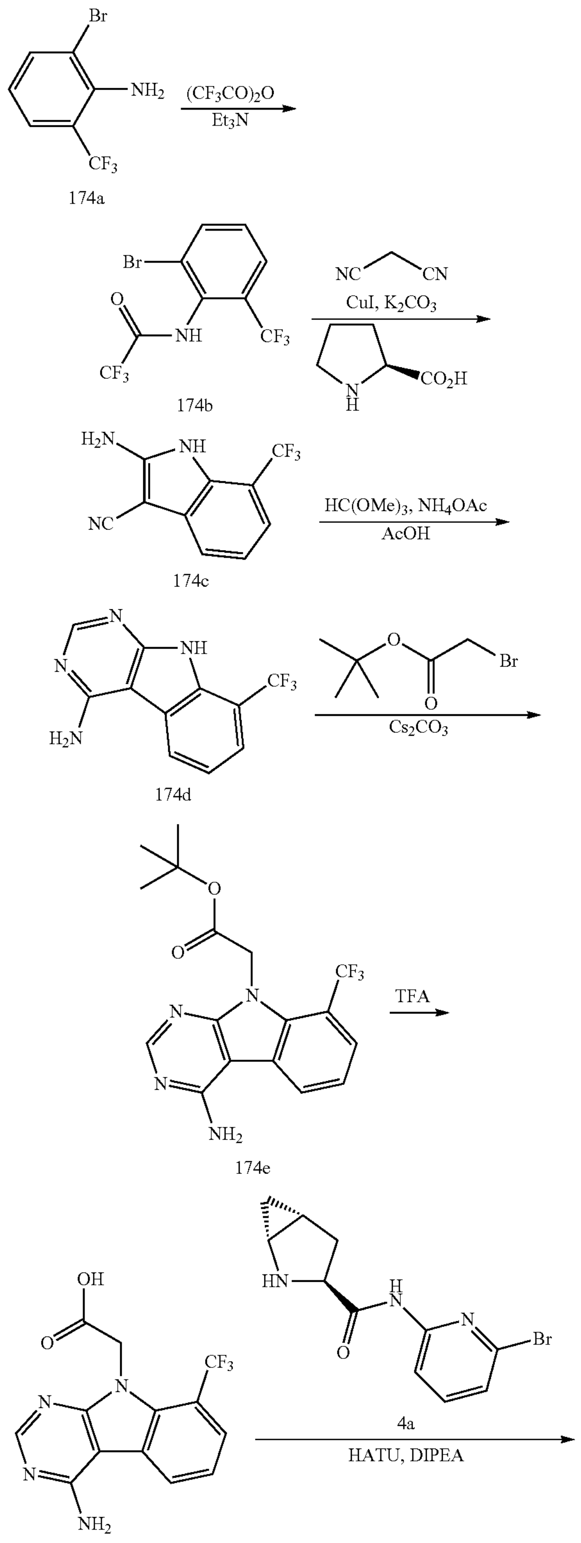

174a

174b

174c

174d

174e

174f

4a

-continued

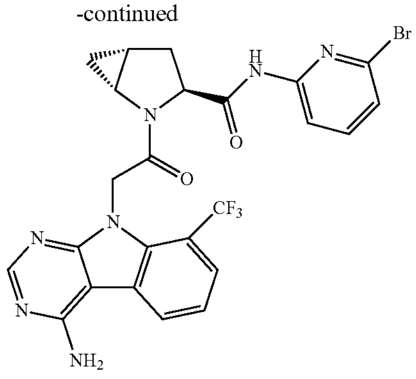

174g

Preparation of (1R,3S,5R)-2-(2-(4-amino-8-(trifluoromethyl)-9H-pyrimido[4,5-b]indol-9-yl)acetyl)-N-(6-bromopyridin-2-yl)-2-azabicyclo[3.1.0]hexane-3-carboxamide (174 g)

Step-1: Preparation of N-(2-bromo-6-(trifluoromethyl)phenyl)-2,2,2-trifluoroacetamide (174b)

Compound 174b was prepared according to the procedure reported in step-1 of scheme-46, from 2-bromo-6-(trifluoromethyl)aniline (174a) (5 g, 20.83 mmol; CAS #58458-13-2) in DCM (50 mL) using triethylamine (4.94 mL, 35.4 mmol) and trifluoroacetic acid anhydride (4.34 mL, 31.2 mmol) and stirring at RT for 16 h. This gave after workup N-(2-bromo-6-(trifluoromethyl)phenyl)-2,2,2-trifluoroacetamide (174b) as a pale yellow solid (7 g, 100% yield) which was used as such for next step; 1H NMR (300 MHz, DMSO-$d_6$) δ 11.72 (s, 1H), 8.16 (dd, J=8.2, 1.3 Hz, 1H), 7.91 (dd, J=8.0, 1.3 Hz, 1H), 7.61 (t, J=8.0 Hz, 11H); MS (ES−): 333.90 (M−1).

Step-2: Preparation of 2-amino-7-(trifluoromethyl)-1H-indole-3-carbonitrile (174c)

Compound 174c was prepared according to the procedure reported in step-1 of scheme-11, from N-(2-bromo-6-(trifluoromethyl)phenyl)-2,2,2-trifluoroacetamide (174b) (3 g, 8.93 mmol) in DMSO (9 mL) using malononitrile (0.675 mL, 10.71 mmol), L-proline (0.206 g, 1.786 mmol), CuI (0.170 g, 0.893 mmol), a solution of $K_2CO_3$ (2.468 g, 17.86 mmol) in water (9 mL) and heating at 60° C. for 16 h under an argon atmosphere. This gave after workup and purification [$SiO_2$ gel (80 g), eluting with EtOAc in hexane from 0-50%] 2-amino-7-(trifluoromethyl)-1H-indole-3-carbonitrile (174c) (650 mg, 32% yield) as a yellow solid; $^1$H NMR (300 MHz, DMSO-$d_6$) δ 11.04 (s, 1H), 7.43 (d, J=7.5 Hz, 1H), 7.29-7.09 (m, 2H), 6.79 (s, 2H); MS (ES−): 224.00 (M−1).

Step-3: Preparation of 8-(trifluoromethyl)-9H-pyrimido[4,5-b]indol-4-amine (174d)

Compound 174d was prepared according to the procedure reported in step-1 of scheme-6, from 2-amino-7-(trifluoromethyl)-1H-indole-3-carbonitrile (174c) (600 mg, 2.66 mmol) using trimethyl orthoformate (5830 μL, 53.3 mmol), AcOH (762 μL, 13.32 mmol), $NH_4OAc$ (1027 mg, 13.32 mmol) and heating at 100° C. for 16 h in a pressure vessel. This gave after workup acetic acid salt of 8-(trifluoromethyl)-

9H-pyrimido[4,5-b]indol-4-amine (174d) (478 mg, 58% yield) as a yellow solid; 1H NMR (300 MHz, DMSO-$d_6$) δ 12.30 (s, 1H), 11.98 (s, 1H), 8.61 (d, J=7.9 Hz, 1H), 8.35 (s, 1H), 7.67 (d, J=7.7 Hz, 1H), 7.50-7.29 (m, 3H), 1.91 (s, 3H); MS (ES+): 253.00 (M+1).

Step-4: Preparation of tert-butyl 2-(4-amino-8-(trifluoromethyl)-9H-pyrimido[4,5-b]indol-9-yl)acetate (174e)

Compound 174e was prepared according to the procedure reported in step-1 of scheme-1, from acetic acid salt of 8-(trifluoromethyl)-9H-pyrimido[4,5-b]indol-4-amine (174d) (450 mg, 1.441 mmol) in DMF (10 mL) using tert-butyl 2-bromoacetate (0.234 mL, 1.585 mmol), $Cs_2CO_3$ (1033 mg, 3.17 mmol) and stirring at RT for 15 h. This gave after work up and purification using flash column chromatography [$SiO_2$ gel (40 g), eluting with ethyl acetate in hexanes from 0-100%] tert-butyl 2-(4-amino-8-(trifluoromethyl)-9H-pyrimido[4,5-b]indol-9-yl)acetate (174e) (180 mg, 34% yield) as a pale yellow solid; $^1$H NMR (300 MHz, DMSO-$d_6$) δ 8.56-8.48 (m, 2H), 7.54 (d, J=7.6 Hz, 1H), 7.20 (t, J=7.7 Hz, 1H), 5.14 (s, 2H), 1.42 (s, 9H); MS (ES+): 367.10 (M+1).

Step-5: Preparation of 2-(4-amino-8-(trifluoromethyl)-9H-pyrimido[4,5-b]indol-9-yl)acetic acid (174f)

Compound 174f was prepared according to the procedure reported in step-2 of scheme-1, from tert-butyl 2-(4-amino-8-(trifluoromethyl)-9H-pyrimido[4,5-b]indol-9-yl)acetate (174e) (175 mg, 0.478 mmol) using 20% TFA in DCM (2742 μL, 7.17 mmol) and stirring at RT for 16 h. This gave after work up TFA salt of 2-(4-amino-8-(trifluoromethyl)-9H-pyrimido[4,5-b]indol-9-yl)acetic acid (174f) (198 mg, 98% yield) as a pale yellow solid; MS (ES+): 311.08 (M+1).

Step-6: Preparation of (1R,3S,5R)-2-(2-(4-amino-8-(trifluoromethyl)-9H-pyrimido[4,5-b]indol-9-yl)acetyl)-N-(6-bromopyridin-2-yl)-2-azabicyclo[3.1.0]hexane-3-carboxamide (174 g)

Compound 174g was prepared according to the procedure reported in step-3 of scheme-1, from TFA salt of 2-(4-amino-8-(trifluoromethyl)-9H-pyrimido[4,5-b]indol-9-yl)acetic acid (174f) (60 mg, 0.141 mmol) in DMF (1.5 mL) using TFA salt of (1R,3S,5R)—N-(6-bromopyridin-2-yl)-2-azabicyclo[3.1.0]hexane-3-carboxamide (4a) (56.0 mg, 0.141 mmol), HATU (81 mg, 0.212 mmol), DIPEA (0.123 mL, 0.707 mmol) and stirring at RT for 16 h. This gave after workup and purification by flash column chromatography [silica gel (12 g), eluting with DMA-80 in DCM from 0 to 100%] followed by purification using reverse phase column chromatography [C18 column (50 g), eluting with ACN in water (containing 0.1% HCl) from 0-100%] (1R,3S,5R)-2-(2-(4-amino-8-(trifluoromethyl)-9H-pyrimido[4,5-b]indol-9-yl)acetyl)-N-(6-bromopyridin-2-yl)-2-azabicyclo[3.1.0]hexane-3-carboxamide (174 g) (75 mg, 92% yield) HCl salt as a white solid; $^1$H NMR (300 MHz, DMSO-$d_6$/$D_2O$) δ 8.82-8.69 (m, 2H), 7.98 (d, J=8.1 Hz, 1H), 7.88 (d, J=7.7 Hz, 1H), 7.69 (t, J=8.0 Hz, 1H), 7.60 (t, J=7.8 Hz, 1H), 7.31 (d, J=7.7 Hz, 1H), 6.01 (d, J=17.2 Hz, 1H), 5.64 (d, J=17.2 Hz, 1H), 4.45 (dd, J=9.0, 5.7 Hz, 1H), 3.73 (ddd, J=7.4, 5.5, 2.3 Hz, 1H), 2.36 (dd, J=13.2, 9.5 Hz, 1H), 2.23 (dt, J=13.0, 6.2 Hz, 1H), 1.96 (tt, J=6.6, 3.5 Hz, 1H), 1.10 (dt, J=8.6, 5.5 Hz, 1H), 0.86 (td, J=5.3, 2.3 Hz, 1H); $^{19}$F NMR (282 MHz, DMSO-$d_6$) δ−59.64. MS (ES+): 574.00 & 576.1 (M+1); (ES−): 572.10 & 574.10 (M−1); Analysis calculated for $C_{24}H_{19}BrF_3N_7O_2$ $1.5H_2O·HCl$: C, 45.19; H, 3.63; Cl, 5.56; N, 15.37. Found: C, 44.94; H, 3.71; Cl, 5.32; N, 15.36.

Scheme 175

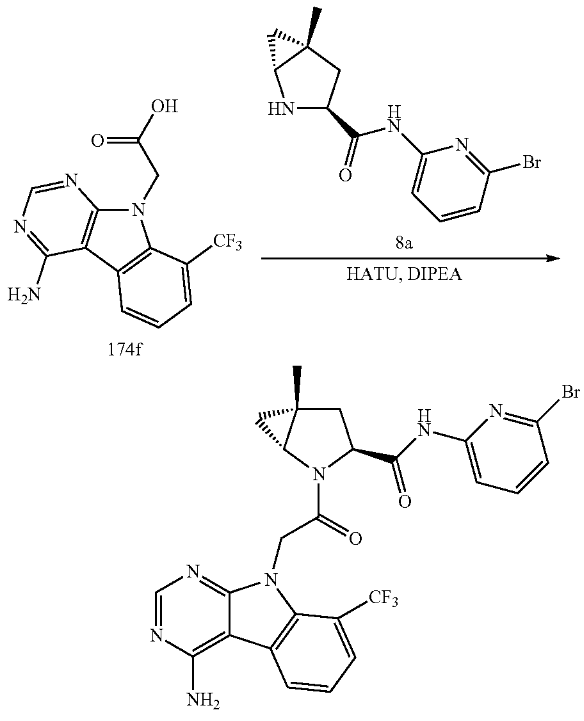

Preparation of (1R,3S,5R)-2-(2-(4-amino-8-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (175a)

Compound 175a was prepared according to the procedure reported in step-3 of scheme-1, from TFA salt of 2-(4-amino-8-(trifluoromethyl)-9H-pyrimido[4,5-b]indol-9-yl)acetic acid (174f) (60 mg, 0.141 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (47 mg, 0.141 mmol), HATU (81 mg, 0.212 mmol) DIPEA (0.123 mL, 0.707 mmol) and stirring at RT for 16 h. This gave after workup and purification by flash column chromatography [silica gel (12 g), using DMA-80 in DCM from 0 to 100%] followed by purification using reverse phase column chromatography [C18 column (50 g), eluting with ACN in water (containing 0.1% HCl) from 0-100%] (1R,3S,5R)-2-(2-(4-amino-8-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (175a) (47 mg, 57% yield) HCl salt as a white solid: 1H NMR (300 MHz, DMSO-d/$D_2O$) S 8.78-8.57 (m, 2H), 7.94 (d, J=8.2 Hz, 1H), 7.79 (d, J=7.7 Hz, 1H), 7.64 (t, J=8.0 Hz, 1H), 7.58-7.40 (m, 1H), 7.26 (d, J=7.7 Hz, 1H), 5.85 (d, J=17.2 Hz, 1H), 5.52 (d, J=17.0 Hz, 1H), 4.36 (dd, J=9.0, 6.1 Hz, 1H), 3.47-3.42 (m, 1H), 2.43-2.38 (m, 1H), 1.95 (dd, J=13.3, 6.0 Hz, 1H), 1.26 (s, 3H), 1.02-0.92 (m, 2H); $^{19}$F NMR (282 MHz, DMSO-$d_6$) δ−59.60; MS (ES+): 588.1 (M+1), 610.1

(M+Na); (ES−): 586.1 (M−1); Analysis calculated for $C_{25}H_{21}BrF_3N_7O_2$ $2H_2O{\cdot}HCl$: C, 45.44; H, 3.97; Cl, 5.36; N, 14.84. Found: C, 45.71; H, 3.97; Cl, 5.09; N, 14.63.

Scheme 176

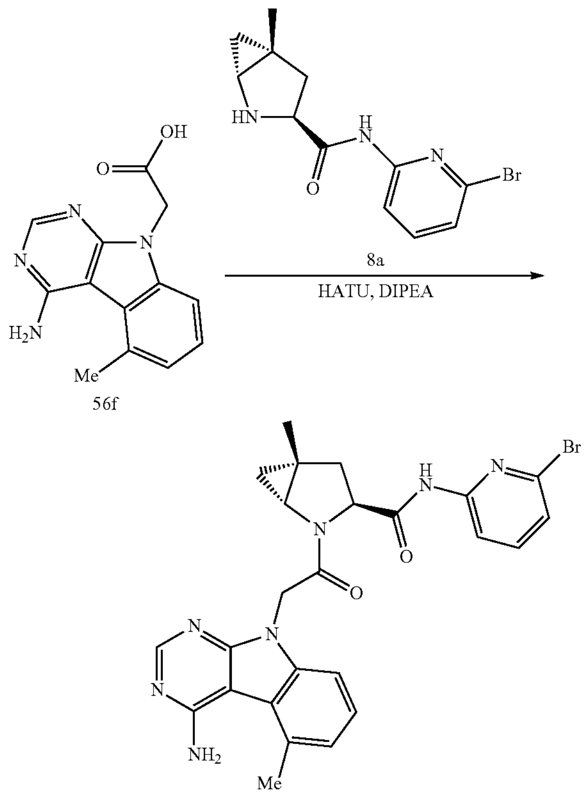

56f

176a

Preparation of (1R,3S,5R)-2-(2-(4-amino-5-methyl-9H-pyrimido[4,5-b]indol-9-yl)acetyl)-N-(6-bromopyridin-2-yl)-5-methyl-2-azabicyclo[3.1.0]hexane-3-carboxamide (176a)

Compound 176a was prepared according to the procedure reported in step-3 of scheme-1, from TFA salt of 2-(4-amino-5-methyl-9H-pyrimido[4,5-b]indol-9-yl)acetic acid (56f) (50 mg, 0.135 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (44.9 mg, 0.135 mmol), HATU (77 mg, 0.203 mmol), DIPEA (0.118 mL, 0.675 mmol) and stirring at RT for 4 h. This gave after workup and purification by flash column chromatography [silica gel (12 g), eluting DMA-80 in DCM from 0 to 100%] followed by purification using reverse phase column chromatography [C18 column (50 g), eluting with ACN in water (containing 0.1% HCl) from 0-100%] (1R,3S,5R)-2-(2-(4-amino-5-methyl-9H-pyrimido[4,5-b]indol-9-yl)acetyl)-N-(6-bromopyridin-2-yl)-5-methyl-2-azabicyclo[3.1.0]hexane-3-carboxamide (176a) (53 mg, 73% yield) HCl salt as a white solid; $^1$H NMR (300 MHz, DMSO-$d_6$) δ 10.77 (s, 1H, $D_2O$ exchangeable), 8.63 (s, 1H), 8.01 (d, J=8.1 Hz, 1H), 7.86 (s, 2H, $D_2O$ exchangeable), 7.70 (t, J=8.0 Hz, 1H), 7.46 (dt, J=15.3, 8.0 Hz, 2H), 7.32 (d, J=7.7 Hz, 1H), 7.18 (d, J=7.0 Hz, 1H), 5.71 (d, J=17.4 Hz, 1H), 5.37 (d, J=17.3 Hz, 1H), 4.37 (dd, J=9.1, 5.9 Hz, 1H), 3.70 (dd, J=5.5, 2.4 Hz, 1H), 2.96 (s, 3H), 2.49-2.41 (m, 1H), 1.98 (dd, J=13.2, 5.9 Hz, 1H), 1.31 (s, 3H), 1.02 (t, J=5.4 Hz, 1H), 0.93 (dd, J=5.4, 2.4 Hz, 1H). MS (ES+): 534.1 (M+1), 556.1 (M+Na); (ES−): 532.0 (M−1); Analysis calculated for $C_{25}H_{24}BrN_7O_2$ $1.25H_2O{\cdot}HCl$: C, 50.60; H, 4.67; Cl, 5.97; N, 16.52. Found: C, 50.63; H, 4.76; Cl, 5.73; N, 16.55.

Scheme 177

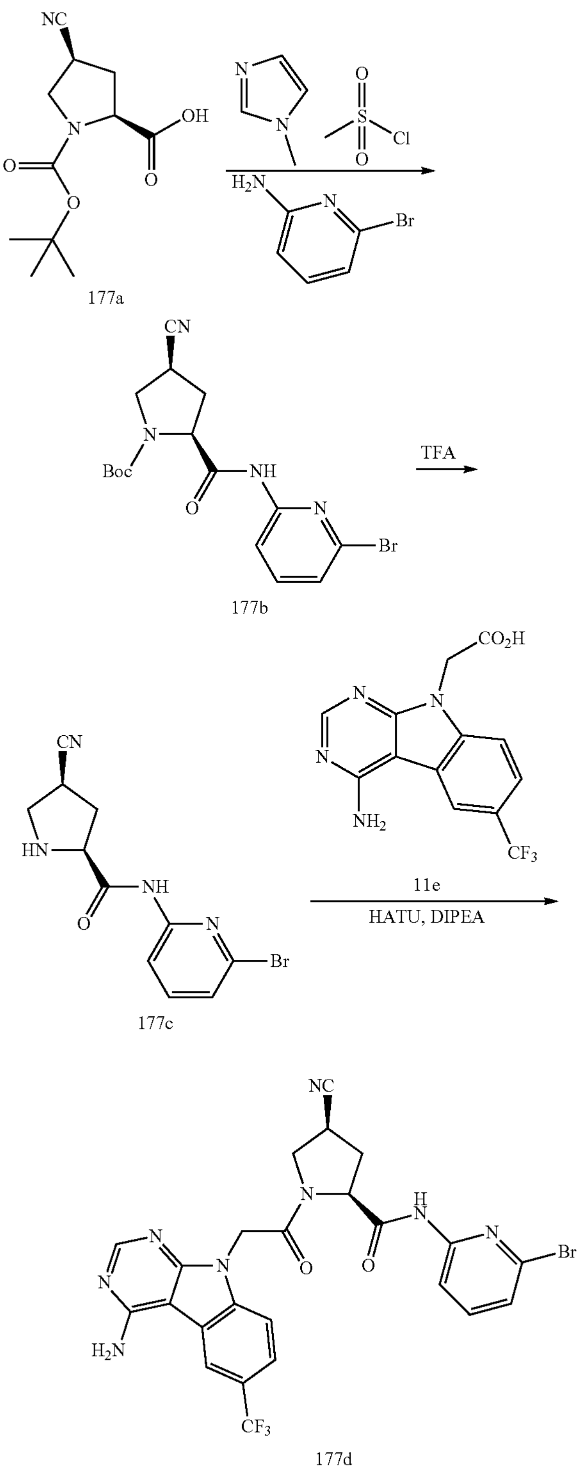

177a

177b

177c

177d

Preparation of (2S,4S)-1-(2-(4-amino-6-(trifluoromethyl)-9H-pyrimido[4,5-b]indol-9-yl)acetyl)-N-(6-bromopyridin-2-yl)-4-cyanopyrrolidine-2-carboxamide (177d)

Step-1: Preparation of (2S,4S)-tert-butyl 2-((6-bromopyridin-2-yl)carbamoyl)-4-cyanopyrrolidine-1-carboxylate (177b)

Compound 177b was prepared according to the procedure reported in step-1 of scheme-53, from (2S,4S)-1-(tert-butoxycarbonyl)-4-cyanopyrrolidine-2-carboxylic acid (177a) (0.5 g, 2.081 mmol; CAS #132622-71-0) in DCM (15 mL) using 1-methyl-1H-imidazole (0.415 mL, 5.20 mmol), methanesulfonyl chloride (0.193 mL, 2.497 mmol), 6-bromopyridin-2-amine (0.360 g, 2.081 mmol) and stirring at RT for 18 h. This gave after workup (2S,4S)-tert-butyl 2-((6-bromopyridin-2-yl)carbamoyl)-4-cyanopyrrolidine-1-carboxylate (177b) (0.5 g, 61% yield); $^1$H NMR (300 MHz, DMSO-$d_6$) δ 11.05 (d, J=14.5 Hz, 1H), 8.17-8.05 (m, 1H), 7.77 (q, J=7.7 Hz, 1H), 7.37 (d, J=7.7 Hz, 1H), 4.39 (q, J=7.9 Hz, 1H), 3.82 (d, J=13.5 Hz, 1H), 3.49 (d, J=6.0 Hz, 2H), 2.70 (dd, J=14.3, 7.6 Hz, 1H), 2.10 (dt, J=13.7, 8.0 Hz, 1H), 1.33 (d, J=43.3 Hz, 9H); MS (ES+): 395.10 (M+1).

Step-2: Preparation of (2S,4S)—N-(6-bromopyridin-2-yl)-4-cyanopyrrolidine-2-carboxamide (177c)

Compound 177c was prepared according to the procedure reported in step-2 of scheme-1, from (2S,4S)-tert-butyl 2-((6-bromopyridin-2-yl)carbamoyl)-4-cyanopyrrolidine-1-carboxylate (177b) (200 mg, 0.506 mmol) in DCM (2.5 mL) using TFA (404 mg, 3.54 mmol) and stirring overnight at RT. This gave after workup TFA salt of (2S,4S)—N-(6-bromopyridin-2-yl)-4-cyanopyrrolidine-2-carboxamide (177c) (0.2 g, 97% yield) as a clear gel; $^1$H NMR (300 MHz, DMSO-$d_6$) δ 11.52 (s, 1H), 8.06 (d, J=8.1 Hz, 1H), 7.83 (t, J=8.0 Hz, 1H), 7.46 (d, J=7.7 Hz, 1H), 4.48 (t, J=8.3 Hz, 1H), 3.67 (dt, J=12.9, 8.0 Hz, 2H), 3.55 (dd, J=9.9, 5.8 Hz, 1H), 2.87 (dt, J=13.6, 7.9 Hz, 1H), 2.32 (dt, J=14.3, 7.3 Hz, 1H); MS (ES+): 295.00 (M+1).

Step-3: Preparation of (2S,4S)-1-(2-(4-amino-6-(trifluoromethyl)-9H-pyrimido[4,5-b]indol-9-yl)acetyl)-N-(6-bromopyridin-2-yl)-4-cyanopyrrolidine-2-carboxamide (177d)

Compound 177d was prepared according to the procedure reported in step-3 of scheme-1, from TFA salt of (2S,4S)—N-(6-bromopyridin-2-yl)-4-cyanopyrrolidine-2-carboxamide (177c) (0.2 g, 0.489 mmol) in DMF (1.5 mL) using TFA salt of 2-(4-amino-6-(trifluoromethyl)-9H-pyrimido[4,5-b]indol-9-yl)acetic acid (11e) (0.207 g, 0.489 mmol), HATU (0.279 g, 0.733 mmol), DIPEA (0.426 mL, 2.444 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%](2S,4S)-1-(2-(4-amino-6-(trifluoromethyl)-9H-pyrimido[4,5-b]indol-9-yl)acetyl)-N-(6-bromopyridin-2-yl)-4-cyanopyrrolidine-2-carboxamide (177d) (173 mg, 60% yield) HCl salt as a white solid; $^1$H NMR (300 MHz, DMSO-$d_6$) (a mixture of two rotamers) δ 11.40 and 10.97 (2s, 1H, $D_2O$ exchangeable), 8.93 (s, 1H), 8.54 (s, 1H), 8.33 (s, 2H, $D_2O$ exchangeable), 8.17 and 8.01 (2d, J=8.2 Hz, 1H), 7.84 (d, J=4.7 Hz, 2H), 7.71 (t, J=7.9 Hz, 1H), 7.43 and 7.34 (2d, J=7.7 Hz, 1H), 5.77 and 5.50 (2s, 2H), 4.55 (t, J=7.5 Hz, 1H), 4.39 (dd, J=10.0, 7.8 Hz, 1H), 4.07 (dd, J=10.1, 7.8 Hz, 1H), 3.77-3.68 (m, 1H), 2.82-2.68 (m, 1H), 2.19 (dt, J=14.0, 7.6 Hz, 1H). $^{19}$F NMR (282 MHz, DMSO-$d_6$) δ−58.53. MS (ES+): 587.1 (M+1); (ES−): 585.0 (M−1); Analysis calculated for $C_{24}H_{18}BrF_3NSO_2$ $2H_2O{\cdot}HCl$: C, 43.69; H, 3.51; Cl, 5.37; N, 16.98. Found: C, 43.70; H, 3.49; Cl, 4.98; N, 16.62.

Scheme 178

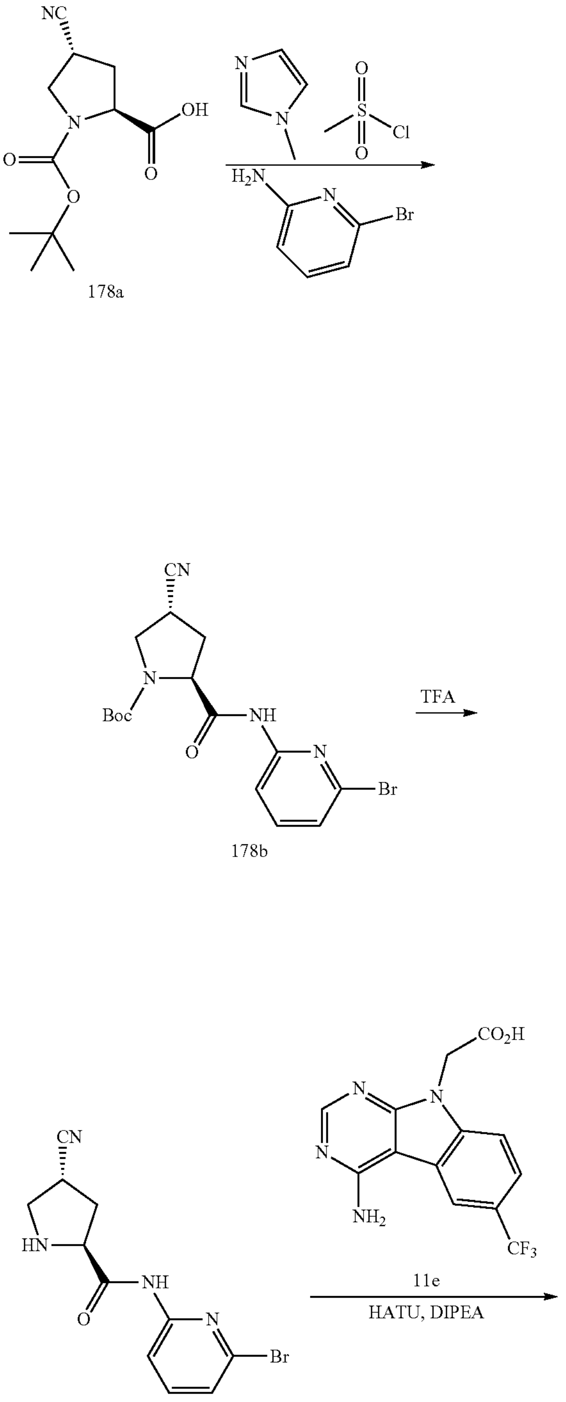

178a

178b

178c

-continued

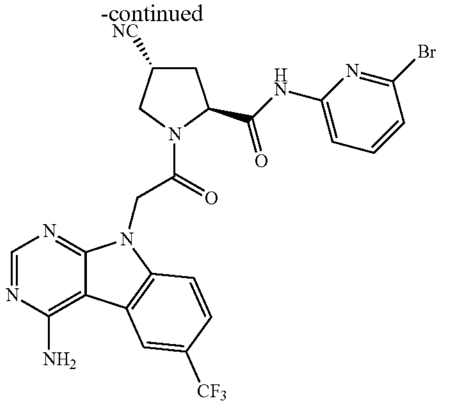

178d

Preparation of (2S,4R)-1-(2-(4-amino-6-(trifluoromethyl)-9H-pyrimido[4,5-b]indol-9-yl)acetyl)-N-(6-bromopyridin-2-yl)-4-cyanopyrrolidine-2-carboxamide (178d)

Step-1: Preparation of (2S,4R)-tert-butyl 2-((6-bromopyridin-2-yl)carbamoyl)-4-cyanopyrrolidine-1-carboxylate (178b)

Compound 178b was prepared according to the procedure reported in step-1 of scheme-53, from (2S,4R)-1-(tert-butoxycarbonyl)-4-cyanopyrrolidine-2-carboxylic acid (178a) (0.5 g, 2.081 mmol, CAS #273221-94-6) in DCM (15 mL) using 1-methyl-1H-imidazole (0.415 mL, 5.20 mmol), methanesulfonyl chloride (0.193 mL, 2.497 mmol), 6-bromopyridin-2-amine (0.360 g, 2.081 mmol) and stirring at RT for 18 h. This gave after workup (2S,4R)-tert-butyl 2-((6-bromopyridin-2-yl)carbamoyl)-4-cyanopyrrolidine-1-carboxylate (178b) (747 mg, 91% yield); $^1$H NMR (300 MHz, DMSO-$d_6$) δ 11.07 (d, J=17.6 Hz, 1H), 8.07 (dd, J=12.9, 8.1 Hz, 1H), 7.77 (q, J=8.0 Hz, 1H), 7.37 (d, J=7.7 Hz, 1H), 4.53 (ddd, J=13.0, 8.2, 4.9 Hz, 1H), 3.73 (dd, J=10.4, 7.1 Hz, 1H), 3.57 (dt, J=10.6, 5.7 Hz, 1H), 3.46 (tt, J=7.1, 4.2 Hz, 1H), 2.46 (d, J=8.2 Hz, 1H), 2.30 (dt, J=12.6, 6.1 Hz, 1H), 1.40 (s, 3H), 1.27 (s, 6H).

Step-2: Preparation of (2S,4R)—N-(6-bromopyridin-2-yl)-4-cyanopyrrolidine-2-carboxamide (178c)

Compound 178c was prepared according to the procedure reported in step-2 of scheme-1, from (2S,4R)-tert-butyl 2-((6-bromopyridin-2-yl)carbamoyl)-4-cyanopyrrolidine-1-carboxylate (178b) (0.2 g, 0.506 mmol) in DCM (2.5 mL) using TFA (0.273 mL, 3.54 mmol) and stirring overnight at RT. This gave after workup TFA salt of (2S,4R)—N-(6-bromopyridin-2-yl)-4-cyanopyrrolidine-2-carboxamide (178c) (0.2 g, 97% yield) as a clear gel; $^1$H NMR (300 MHz, DMSO-$d_6$) δ 11.50 (s, 1H), 8.04 (d, J=8.2 Hz, 1H), 7.82 (t, J=8.0 Hz, 1H), 7.45 (dd, J=7.8, 0.7 Hz, 1H), 4.62 (t, J=7.8 Hz, 1H), 3.76-3.51 (m, 3H), 2.68 (ddd, J=11.2, 8.0, 5.5 Hz, 1H), 2.49-2.40 (m, 1H); MS (ES+): 295.00 (M+1).

Step-3: Preparation of (2S,4R)-1-(2-(4-amino-6-(trifluoromethyl)-9H-pyrimido[4,5-b]indol-9-yl)acetyl)-N-(6-bromopyridin-2-yl)-4-cyanopyrrolidine-2-carboxamide (178d)

Compound 178d was prepared according to the procedure reported in step-3 of scheme-1, from TFA salt of (2S,4R)—N-(6-bromopyridin-2-yl)-4-cyanopyrrolidine-2-carboxamide (178c) (200 mg, 0.488 mmol) in DMF (5 mL) using TFA salt of 2-(4-amino-6-(trifluoromethyl)-9H-pyrimido[4,5-b]indol-9-yl)acetic acid (11e) (207 mg, 0.488 mmol), HATU (0.278 g, 0.732 mmol), DIPEA (0.425 mL, 2.440 mmol) and stirring at RT for 16 h. This gave after workup and purification by flash column chromatography [silica gel (24 g), eluting with DMA-80 in DCM from 0 to 100%] followed by purification using reverse phase column chromatography [C18 column (50 g), eluting with ACN in water (containing 0.1% HCl) from 0-100%](2S,4R)-1-(2-(4-amino-6-(trifluoromethyl)-9H-pyrimido[4,5-b]indol-9-yl)acetyl)-N-(6-bromopyridin-2-yl)-4-cyanopyrrolidine-2-carboxamide (178d) (177 mg, 62% yield) HCl salt as a white solid; $^1$H NMR (300 MHz, DMSO-$d_6$) (a mixture of two rotamers) S 11.38 and 11.00 (2s, 1H, $D_2O$ exchangeable), 8.95 (s, 1H), 8.56 and 8.52 (2s, 1H), 8.42 (s, 2H, $D_2O$ exchangeable), 8.16 and 7.99 (2d, J=8.2 Hz, 1H), 7.85 (d, J=2.2 Hz, 2H), 7.71 (t, J=8.0 Hz, 1H), 7.43 and 7.33 (2d, J=7.7 Hz, 1H), 5.53 (d, J=2.91 Hz, 2H), 4.68 (dd, J=8.4, 4.5 Hz, 1H), 4.31 (dd, J=10.0, 7.5 Hz, 1H), 4.19 (dd, J=10.0, 6.9 Hz, 1H), 3.70 (p, J=7.2 Hz, 1H), 2.59-2.52 (m, 1H), 2.46-2.36 (m, 1H); $^{19}$F NMR (282 MHz, DMSO-$d_6$) δ-58.55; MS (ES+): 587.1 (M+1); (ES−): 585.0 (M−1).

Scheme 179

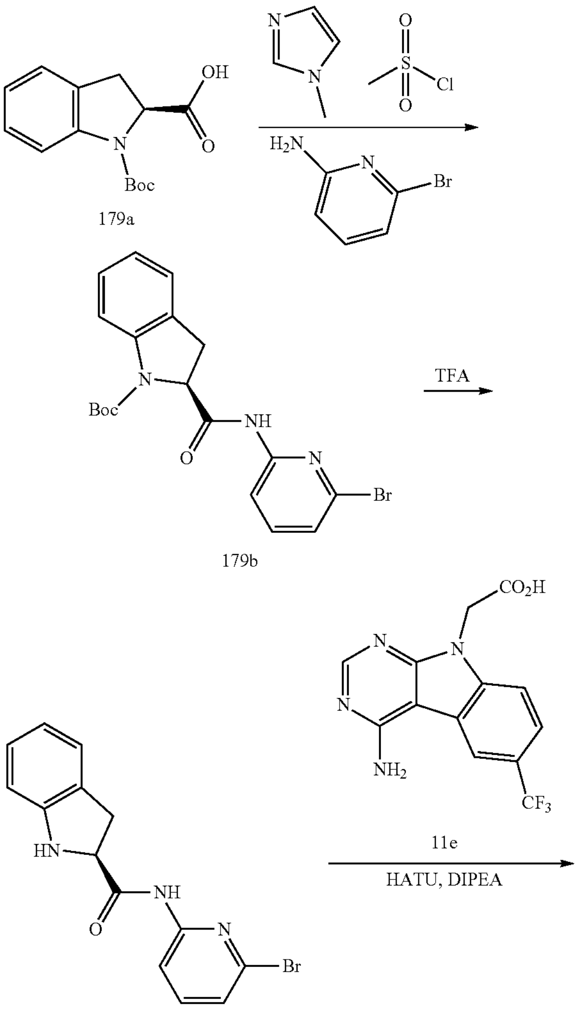

179c

-continued

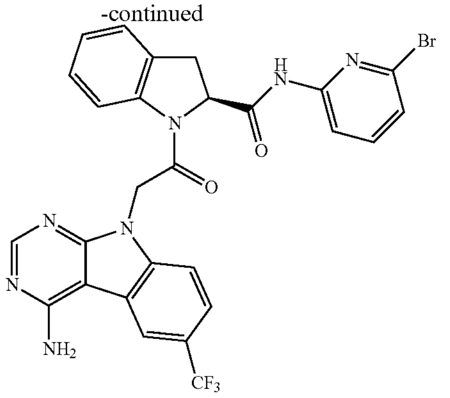

179d

Preparation of (S)-1-(2-(4-amino-6-(trifluoromethyl)-9H-pyrimido[4,5-b]indol-9-yl)acetyl)-N-(6-bromopyridin-2-yl)indoline-2-carboxamide (179d)

Step-1: Preparation of (S)-tert-butyl 2-((6-bromopyridin-2-yl)carbamoyl)indoline-1-carboxylate (179b)

Compound 179b was prepared according to the procedure reported in step-1 of scheme-53, from (S)-1-(tert-butoxycarbonyl)indoline-2-carboxylic acid (179a) (1 g, 3.80 mmol; CAS #144069-674)) in DCM (30 mL) using 1-methyl-1H-imidazole (0.780 mL, 9.50 mmol), methanesulfonyl chloride (0.353 mL, 4.56 mmol), 6-bromopyridin-2-amine (0.657 g, 3.80 mmol) and stirring at RT for 18 h. This gave after workup (S)-tert-butyl 2-((6-bromopyridin-2-yl)carbamoyl)indoline-1-carboxylate (179b) (1.49 g, 94% yield); $^1$H NMR (300 MHz, DMSO-$d_6$) δ 11.21 (s, 1H), 8.08 (d, J=8.3 Hz, 1H), 7.77 (t, J=8.3 Hz, 2H), 7.37 (d, J=7.7 Hz, 1H), 7.17 (d, J=7.4 Hz, 2H), 6.94 (t, J=7.4 Hz, 1H), 5.04 (dd, J=11.1, 4.6 Hz, 1H), 3.49 (dd, J=17.0, 11.2 Hz, 1H), 3.06 (d, J=17.0 Hz, 1H), 1.44 (d, J=53.8 Hz, 9H); MS (ES+): 418.10 (M+1).

Step-2: Preparation of (S)—N-(6-bromopyridin-2-yl)indoline-2-carboxamide (179c)

Compound 179c was prepared according to the procedure reported in step-2 of scheme-1, from (S)-tert-butyl 2-((6-bromopyridin-2-yl)carbamoyl)indoline-1-carboxylate (179b) (1 g, 2.391 mmol) in DCM (10 mL) using TFA (1.289 mL, 16.74 mmol) and stirring overnight at RT. This gave after work up and purification using reverse phase column chromatography [C18 column (50 g), eluting with ACN in water (containing 0.1% HCl) from 0-100%] (S)—N-(6-bromopyridin-2-yl)indoline-2-carboxamide (179c) (0.66 g, 78% yield) HCl salt as an off white solid; $^1$H NMR (300 MHz, DMSO-$d_6$) δ 10.59 (s, 1H), 8.10 (d, J=8.1 Hz, 1H), 7.76 (t, J=8.0 Hz, 1H), 7.37 (d, J=7.7 Hz, 1H), 7.06-6.92 (m, 2H), 6.68-6.56 (m, 2H), 4.51 (dd, J=10.5, 6.9 Hz, 1H), 3.35 (dd, J=16.2, 10.5 Hz, 1H), 3.11 (dd, J=16.2.6.8 Hz, 1H); MS (ES+): 318.00 (M+1).

Step-3: Preparation of (S)-1-(2-(4-amino-6-(trifluoromethyl)-9H-pyrimido[4,5-b]indol-9-yl)acetyl)-N-(6-bromopyridin-2-yl)indoline-2-carboxamide (179d)

Compound 179d was prepared according to the procedure reported in step-3 of scheme-1, from HCl salt of (S)—N-(6-bromopyridin-2-yl)indoline-2-carboxamide (179c) (83 mg, 0.234 mmol) in DMF (2 mL) using TFA salt of 2-(4-amino-6-(trifluoromethyl)-9H-pyrimido[4,5-b]indol-9-yl)acetic acid (11e) (99 mg, 0.234 mmol), HATU (133 mg, 0.351 mmol), DIPEA (0.204 mL, 1.170 mmol) and stirring at RT for 16 h. This gave after workup and purification by flash column chromatography [silica gel (24 g), eluting with DMA-80 in DCM from 0 to 50%] followed by purification using reverse phase column chromatography [C18 column (50 g), eluting with ACN in water (containing 0.1% HCl) from 0-100%] (S)-1-(2-(4-amino-6-(trifluoromethyl)-9H-pyrimido[4,5-b]indol-9-yl)acetyl)-N-(6-bromopyridin-2-yl) indoline-2-carboxamide (179d) (71 mg, 49% yield) HCl salt as a white solid; $^1$H NMR (300 MHz, DMSO-$d_6$) (a mixture of two rotamers) δ 11.58 and 11.08 (2s, 1H, $D_2O$ exchangeable), 8.98 (s, 1H), 8.55 (s, 1H), 8.45 (s, 3H, $D_2O$ exchangeable), 8.14 (d, J=8.2 Hz, 1H), 8.01-7.70 (m, 4H), 7.44-7.25 (m, 2H), 7.16 (t, J=7.6 Hz, 1H), 7.05 (t, J=7.4 Hz, 1H), 5.80-5.60 (m, 2H), 5.16 (d, J=17.1 Hz, 1H), 3.82 and 3.58 (2dd, J=17.1, 11.5 Hz, 1H), 3.38 and 3.13 (2d, J=17.1 Hz, 1H); $^{19}$F NMR (282 MHz, DMSO-$d_6$) δ−58.46; MS (ES+): 610.50 (M+1); (ES−): 608.50 (M−1).

Scheme 180

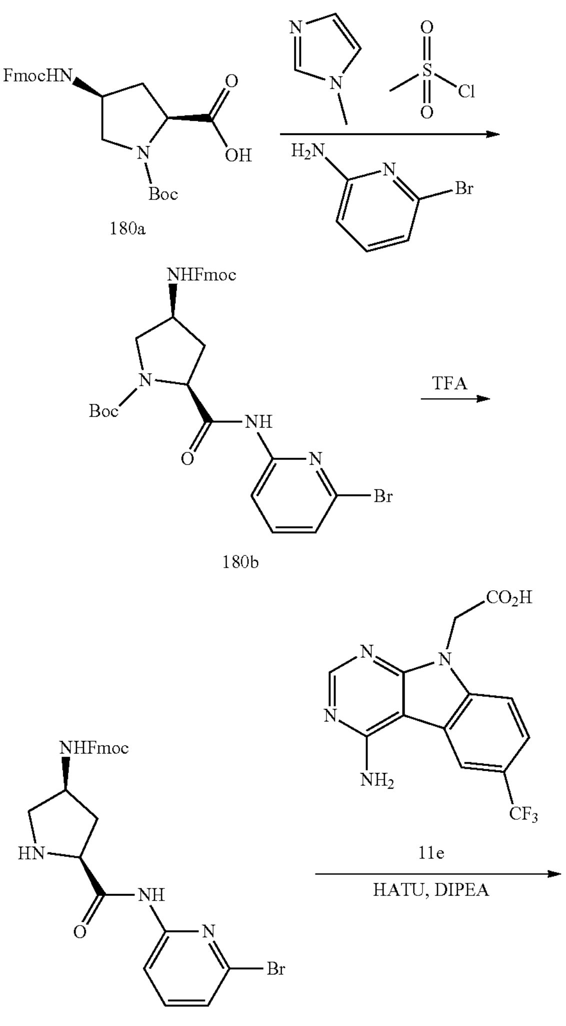

180a 180b 11e 180c

-continued

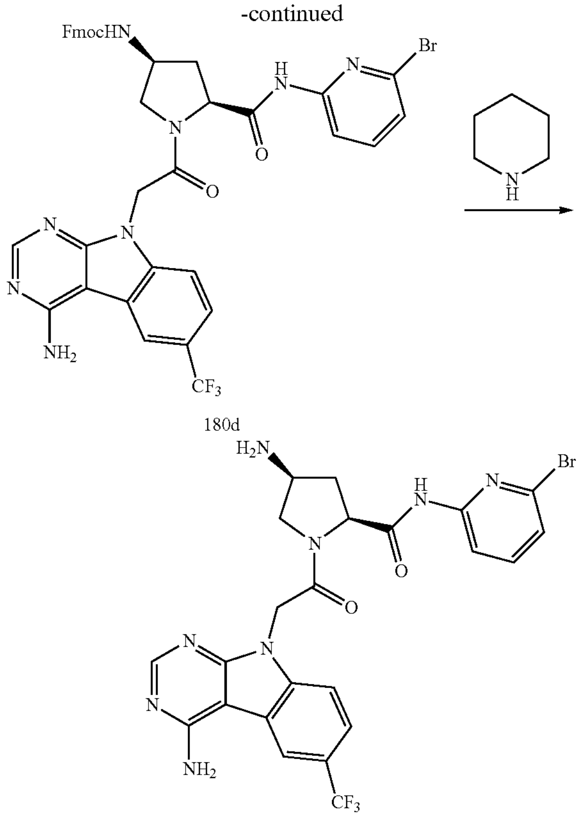

180d

180e

Preparation of (2S,4S)-4-amino-1-(2-(4-amino-6-(trifluoromethyl)-9H-pyrimido[4,5-b]indol-9-yl)acetyl)-N-(6-bromopyridin-2-yl)pyrrolidine-2-carboxamide (180e)

Step-1: Preparation of (2S,4S)-tert-butyl 4-((((9H-fluoren-9-yl)methoxy)carbonyl)amino)-2-((6-bromopyridin-2-yl)carbamoyl)pyrrolidine-1-carboxylate (180b)

Compound 180b was prepared according to the procedure reported in step-1 of scheme-53, from (2S,4S)-4-((((9H-fluoren-9-yl)methoxy)carbonyl)amino)-1-(tert-butoxycarbonyl)pyrrolidine-2-carboxylic acid (180a) (1 g, 2.210 mmol; CAS #174148-03-9) in DCM (30 mL) using 1-methyl-1H-imidazole (0.440 mL, 5.52 mmol), methanesulfonyl chloride (0.205 mL, 2.65 mmol), 6-bromopyridin-2-amine (0.382 g, 2.210 mmol) and stirring at RT for 18 h. This gave after workup (2S,4S)-tert-butyl 4-((((9H-fluoren-9-yl)methoxy)carbonyl)amino)-2-((6-bromopyridin-2-yl)carbamoyl)pyrrolidine-1-carboxylate (180b) (1.22 g, 91% yield); 1H NMR (300 MHz, DMSO-$d_6$) δ 10.98 (d, J=18.4 Hz, 1H), 8.22-8.06 (m, 1H), 7.89 (d, J=7.5 Hz, 2H), 7.78 (t, J=8.1 Hz, 1H), 7.67 (d, J=7.4 Hz, 2H), 7.56 (d, J=7.7 Hz, 1H), 7.36 (ddt, J=20.7, 12.9, 7.3 Hz, 5H), 4.40-4.27 (m, 3H), 4.21 (t, J=6.8 Hz, 1H), 4.02 (d, J=8.1 Hz, 1H), 3.82-3.56 (m, 1H), 3.14 (s, 1H), 2.51 (p, J=1.9 Hz, 1H), 1.78 (d, J=10.0 Hz, 11H), 1.39 (s, 3H), 1.25 (s, 6H); MS (ES+): 607.20 (M+1).

Step-2: Preparation of (9H-fluoren-9-yl)methyl ((3S,5S)-5-((6-bromopyridin-2-yl)carbamoyl)pyrrolidin-3-yl)carbamate (180c)

Compound 180c was prepared according to the procedure reported in step-2 of scheme-1, from (2S,4S)-tert-butyl 4-((((9H-fluoren-9-yl)methoxy)carbonyl)amino)-2-((6-bromopyridin-2-yl)carbamoyl)pyrrolidine-1-carboxylate (180b) (1 g, 1.646 mmol) in DCM (8 mL) using TFA (0.888 mL, 11.52 mmol) and stirring overnight at RT. This gave after work up and purification using reverse phase column chromatography [C18 column (50 g), eluting with ACN in water (containing 0.1% HCl) from 0-100%] (9H-fluoren-9-yl)methyl ((3S,5S)-5-((6-bromopyridin-2-yl)carbamoyl)pyrrolidin-3-yl)carbamate (180c) (0.62 g, 69% yield) HCl salt as a white solid; $^1$H NMR (300 MHz, DMSO-$d_6$) δ 11.45 (s, 1H), 9.71 (s, 1H), 8.87 (s, 1H), 8.07 (d, J=8.1 Hz, 1H), 7.93-7.79 (m, 3H), 7.67 (d, J=7.4 Hz, 2H), 7.58 (d, J=6.2 Hz, 1H), 7.48-7.29 (m, 5H), 4.48-4.31 (m, 3H), 4.19 (dt, J=19.5, 6.7 Hz, 2H), 3.40 (s, 1H), 3.16 (d, J=9.0 Hz, 1H), 2.77-2.63 (m, 1H), 1.92 (dt, J=15.1, 8.1 Hz, 1H); MS (ES+): 507.10 (M+1).

Step-3: Preparation of (9H-fluoren-9-yl)methyl ((3S,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)carbamate (180d)

Compound 180d was prepared according to the procedure reported in step-3 of scheme-1, from HCl salt of (9H-fluoren-9-yl)methyl ((3S,5S)-5-((6-bromopyridin-2-yl)carbamoyl)pyrrolidin-3-yl)carbamate (180c) (200 mg, 0.368 mmol) in DMF (3 mL) using TFA salt of 2-(4-amino-6-(trifluoromethyl)-9H-pyrimido[4,5-b]indol-9-yl)acetic acid (11e) (156 mg, 0.368 mmol), HATU (210 mg, 0.552 mmol), DIPEA (0.320 mL, 1.839 mmol) and stirring at RT for 16 h. This gave after workup and purification by flash column chromatography [silica gel (40 g), eluting with DMA-80 in DCM from 0-50%] (9H-fluoren-9-yl)methyl ((3S,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)carbamate (180d) (280 mg, 95% yield) as a white solid; MS (ES+): 799.38 (M+1).

Step-4: Preparation of (2S,4S)-4-amino-1-(2-(4-amino-6-(trifluoromethyl)-9H-pyrimido[4,5-b]indol-9-yl)acetyl)-N-(6-bromopyridin-2-yl)pyrrolidine-2-carboxamide (180e)

To a stirred solution of (9H-fluoren-9-yl)methyl ((3S,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)carbamate (180d) (150 mg, 0.188 mmol) in DMF (0.8 mL) was added piperidine (0.185 mL, 1.876 mmol) and stirred at RT for 1 h. The reaction mixture was concentrated and purified using reverse phase column chromatography [C18 column (50 g), eluting with ACN in water (containing 0.1% HCl) from 0-100%] yielding (2S,4S)-4-amino-1-(2-(4-amino-6-(trifluoromethyl)-9H-pyrimido[4,5-b]indol-9-yl)acetyl)-N-(6-bromopyridin-2-yl)pyrrolidine-2-carboxamide (180e) (27 mg, 25% yield) as a white solid; $^1$H NMR (300 MHz, DMSO-$d_6$) (a mixture of two rotamers) δ 11.51 and 11.12 (2s, 1H, $D_2O$ exchangeable), 8.94 (s, 1H), 8.53 (s, 1H), 8.45-8.29 and 8.27-8.17 (m, 4H, D, 20 exchangeable), 7.99 (d, J=8.2 Hz, 1H), 7.90-7.78 (m, 2H), 7.72 (t, J=8.0 Hz, 1H), 7.45 and 7.35 (d, J=7.7 Hz, 1H), 5.49 (s, 2H), 4.57 (t, J=7.5 Hz, 1H), 4.23 (dd, J=10.3, 6.1 Hz, 1H), 4.08-3.95 (m, 1H), 3.88 (dd, J=10.2, 6.2 Hz, 1H), 2.64 (dt, J=14.3, 7.4 Hz, 1H), 2.05 (dt, J=13.2, 6.5 Hz, 1H); $^{19}F$ NMR (282 MHz, DMSO-$d_6$) δ−58.43. MS (ES+): 576.5 (M+1); 598.5 (M+Na); (ES−): 574.6 (M−1); Analysis calculated for $C_{23}H_{20}BrF_3N_8O_2$ 2HCl $3.5H_2O$ 0.5DMSO: C, 38.31; H, 4.29; N, 14.89. Found: C, 38.58; H, 4.28; N, 14.59.

Scheme 181

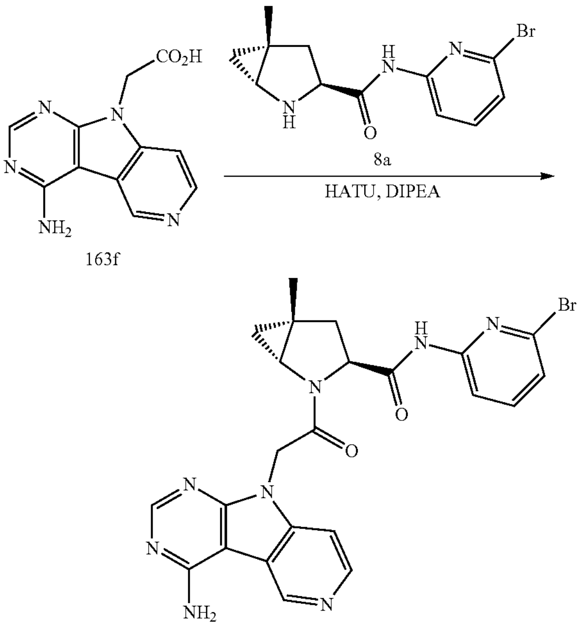

163f

8a

181a

Preparation of (1R,3S,5R)-2-(2-(4-amino-9H-pyrido[3',4':4,5]pyrrolo[2,3-d]pyrimidin-9-yl)acetyl)-N-(6-bromopyridin-2-yl)-5-methyl-2-azabicyclo[3.1.0]hexane-3-carboxamide (181a)

Compound 181a was prepared according to the procedure reported in step-3 of scheme-1, from TFA salt of 2-(4-amino-9H-pyrido[3',4':4,5]pyrrolo[2,3-d]pyrimidin-9-yl)acetic acid (1631) (96 mg, 0.269 mmol) in DMF (5 mL) using HCl salt of (1R,3S,5R)—N-(6-bromopyridin-2-yl)-5-methyl-2-azabicyclo[3.1.0]hexane-3-carboxamide (8a) (98 mg, 0.296 mmol), HATU (153 mg, 0.403 mmol), DIPEA (174 mg, 1.344 mmol) and stirring at RT for 16 h. This gave after workup and purification by flash column chromatography [silica gel (12 g), eluting with MeOH in DCM from 0 to 7%] followed by purification using reverse phase column chromatography [C18 column (100 g), eluting with ACN in water (containing 0.1% HCl) from 0-100%] (1R,3S,5R)-2-(2-(4-amino-9H-pyrido[3',4':4,5]pyrrolo[2,3-d]pyrimidin-9-yl)acetyl)-N-(6-bromopyridin-2-yl)-5-methyl-2-azabicyclo[3.1.0]hexane-3-carboxamide (181a) (62 mg, 44% yield) as a white solid; $^{1}H$ NMR (300 MHz, DMSO-$d_6$) δ 10.78 (s, 1H, $D_2O$ exchangeable), 10.06 (s, 1H), 8.83 (d, J=6.7 Hz, 1H), 8.60 (s, 1H), 8.42 (s, 2H, $D_2O$ exchangeable), 8.25 (d, J=6.7 Hz, 1H), 8.01 (d, J=8.2 Hz, 1H), 7.70 (t, J=8.0 Hz, 1H), 7.32 (d, J=7.7 Hz, 1H), 5.87 (d, J=17.3 Hz, 1H), 5.48 (d, J=17.2 Hz, 1H), 4.39 (dd, J=9.0, 5.8 Hz, 1H), 3.68 (dd, J=5.5, 2.4 Hz, 1H), 2.49-2.42 (m, 1H), 2.05-1.92 (m, 1H), 1.31 (s, 3H), 1.04 (t, J=5.5 Hz, 1H), 1.01-0.94 (m, 1H); MS (ES+): 521/523 (M+1), (ES−): 519/521 (M−1).

Scheme 182

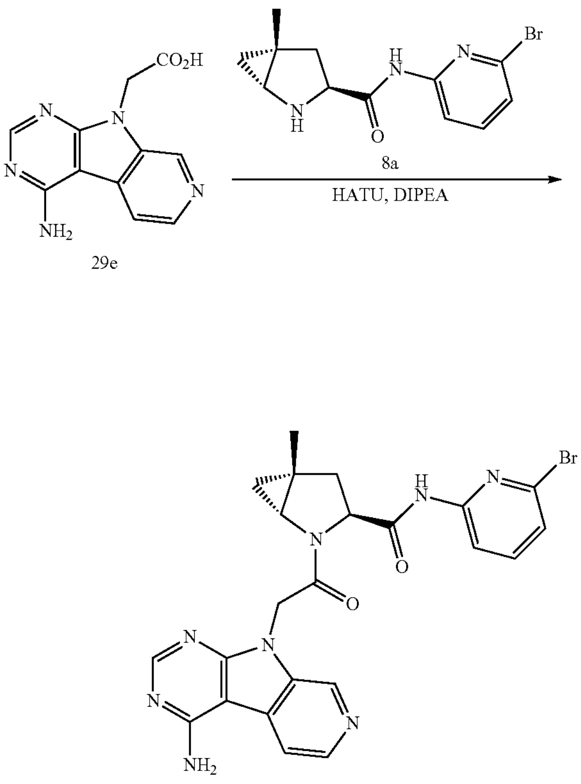

29e

8a

182a

Preparation of (1R,3S,5R)-2-(2-(4-amino-9H-pyrido[4',3':4,5]pyrrolo[2,3-d]pyrimidin-9-yl)acetyl)-N-(6-bromopyridin-2-yl)-5-methyl-2-azabicyclo[3.1.0]hexane-3-carboxamide (182a)

Compound 182a was prepared according to the procedure reported in step-3 of scheme-1, from TFA salt of 2-(4-amino-9H-pyrido[4',3':4,5]pyrrolo[2,3-d]pyrimidin-9-yl)acetic acid (29e) (100 mg, 0.280 mmol) in DMF (5 mL) using HCl salt of (1R,3S,5R)—N-(6-bromopyridin-2-yl)-5-methyl-2-azabicyclo[3.1.0]hexane-3-carboxamide (8a) (102 mg, 0.308 mmol), HATU (160 mg, 0.420 mmol), DIPEA (181 mg, 1.400 mmol) and stirring at RT for 16 h. This gave after workup and purification by flash column chromatography [silica gel (12 g), eluting with MeOH in DCM from 0 to 7%] followed by purification using reverse phase column chromatography [C18 column (100 g), eluting with ACN in water (containing 0.1% HCl) from 0-100%] (1R,3S,5R)-2-(2-(4-amino-9H-pyrido[4',3':4,5]pyrrolo[2,3-d]pyrimidin-9-yl)acetyl)-N-(6-bromopyridin-2-yl)-5-methyl-2-azabicyclo[3.1.0]hexane-3-carboxamide (182a) (87 mg, 60% yield) HCl salt as a white solid; $^{1}H$ NMR (300 MHz, DMSO-$d_6$) δ 10.80 (s, 1H, $D_2O$ exchangeable), 9.48 (s, 1H), 9.07 (d, J=6.3 Hz, 1H), 8.93-8.53 (m, 4H, 2H $D_2O$ exchangeable), 8.01 (d, J=8.2 Hz, 1H), 7.70 (t, J=8.0 Hz, 1H), 7.31 (d, J=7.7 Hz, 1H), 5.89 (d, J=17.4 Hz, 1H), 5.47 (d, J=17.2 Hz, 1H), 4.40 (dd, J=9.1, 5.9 Hz, 1H), 3.65 (dd, J=5.4, 2.6 Hz, 1H), 2.48-2.42 (m, 1H), 1.98 (dd, J=13.3, 5.7 Hz, 1H), 1.31 (s, 3H), 1.08-0.97 (m, 2H); MS (ES+): 521/523 (M+1), (ES−): 519/521 (M−1).

Scheme 183

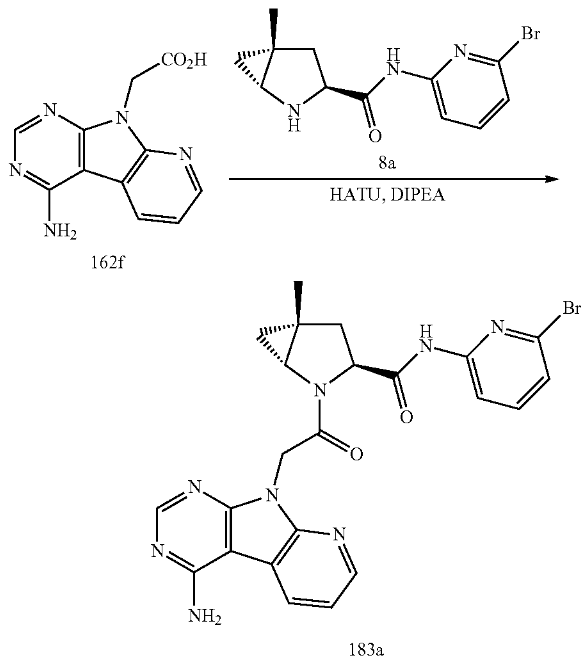

162f

8a

183a

Preparation of (1R,3S,5R)-2-(2-(4-amino-9H-pyrido[3',2':4,5]pyrrolo[2,3-d]pyrimidin-9-yl)acetyl)-N-(6-bromopyridin-2-yl)-5-methyl-2-azabicyclo[3.1.0]hexane-3-carboxamide (183a)

Compound 183a was prepared according to the procedure reported in step-3 of scheme-1, from TFA salt of 2-(4-amino-9H-pyrido[3',2':4,5]pyrrolo[2,3-d]pyrimidin-9-yl)acetic acid (162f) (100 mg, 0.280 mmol) in DMF (5 mL) using HCl salt of (1R,3S,5R)—N-(6-bromopyridin-2-yl)-5-methyl-2-azabicyclo[3.1.0]hexane-3-carboxamide (8a) (102 mg, 0.308 mmol), HATU (160 mg, 0.420 mmol), DIPEA (181 mg, 1.400 mmol) and stirring at RT for 16 h. This gave after workup and purification by flash column chromatography [silica gel (12 g), eluting with MeOH in DCM from 0 to 7%] followed by purification using reverse phase column chromatography [C18 column (100 g), eluting with ACN in water (containing 0.1% HCl) from 0-100%] (1R,3S,5R)-2-(2-(4-amino-9H-pyrido[3',2':4,5]pyrrolo[2,3-d]pyrimidin-9-yl)acetyl)-N-(6-bromopyridin-2-yl)-5-methyl-2-azabicyclo[3.1.0]hexane-3-carboxamide (183a) (110 mg, 75% yield) HCl salt as a white solid; $^1$H NMR (300 MHz, DMSO-$d_6$) δ 10.77 (s, 1H, $D_2O$ exchangeable), 8.97 (dd, J=7.9, 1.5 Hz, 1H), 8.74 (s, 2H, $D_2O$ exchangeable), 8.66 (s, 1H), 8.56 (dd, J=4.9, 1.5 Hz, 1H), 8.01 (d, J=8.2 Hz, 1H), 7.70 (t, J=8.0 Hz, 1H), 7.49 (dd, J=7.9, 4.9 Hz, 1H), 7.31 (d, J=7.7 Hz, 1H), 5.71 (d, J=17.0 Hz, 1H), 5.34 (d, J=16.9 Hz, 1H), 4.37 (dd, J=9.0, 5.9 Hz, 1H), 3.72 (dd, J=5.4, 2.3 Hz, 1H), 2.48-2.42 (m, 1H), 1.98 (dd, J=13.2.5.9 Hz, 1H), 1.31 (s, 3H), 1.05 (t, J=5.5 Hz, 1H), 0.86 (dd, J=5.4, 2.3 Hz, 1H); MS (ES+): 521/523 (M+1), (ES−): 519/521 (M−1); Analysis calculated for $C_3H_2BrNBO_2$·1.1HCl·1.5$H_2O$: C, 46.94; H, 4.30; Cl, 6.63; N, 19.04. Found: C, 46.81; H, 4.17; Cl, 6.66; N, 18.90.

Scheme 184

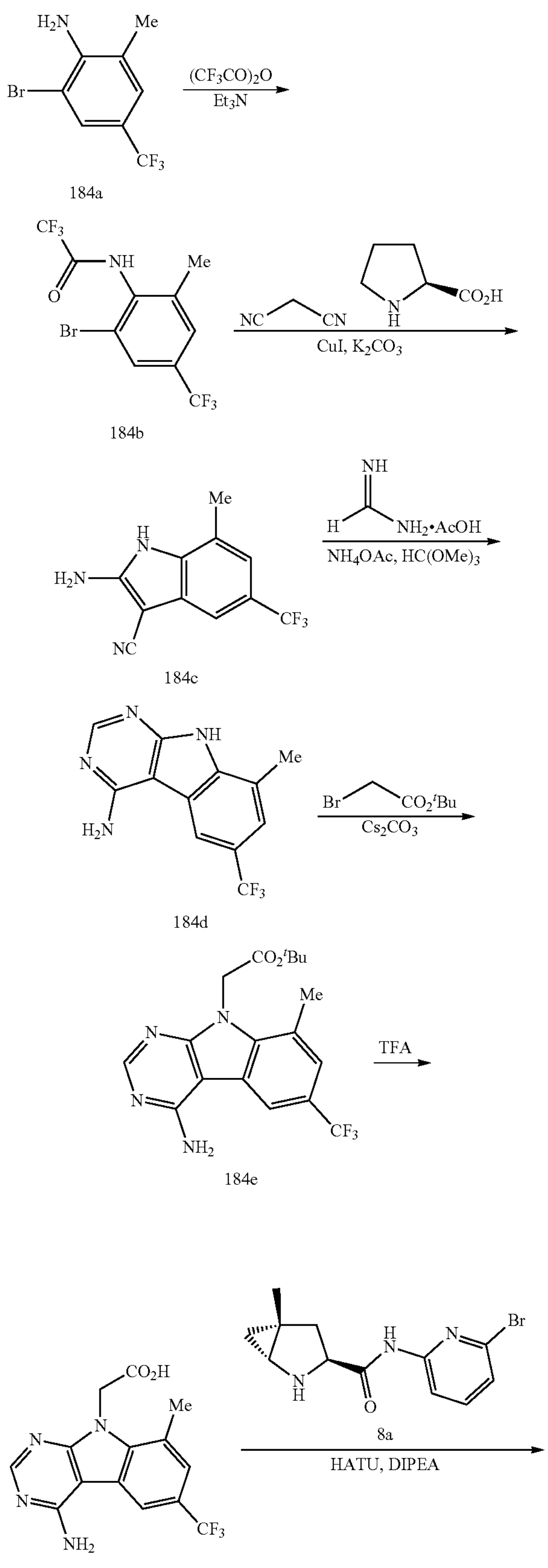

184a

184b

184c

184d

184e

8a

184f

-continued

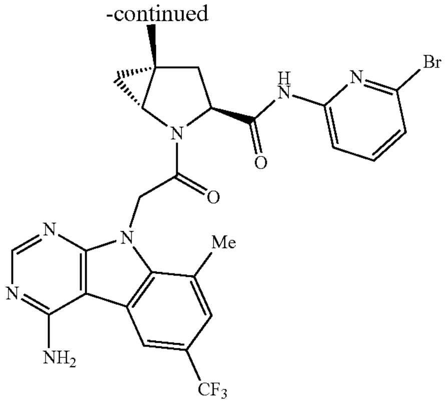

184g

Preparation of (1R,3S,5R)-2-(2-(4-amino-8-methyl-6-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (184 g)

Step-1: Preparation of N-(2-bromo-6-methyl-4-(trifluoromethyl)phenyl)-2,2,2-trifluoroacetamide (184b)

Compound 184b was prepared according to the procedure reported in step-1 of scheme-46, from 2-bromo-6-methyl-4-(trifluoromethyl)aniline (184a) (5.34 g, 21.02 mmol; CAS #1100212-65-4) in DCM (30 mL) using triethylamine (3.62 g, 35.7 mmol), trifluoroacetic acid anhydride (6.62 g, 31.5 mmol) and stirring at RT for 1 h. This gave after workup N-(2-bromo-6-methyl-4-(trifluoromethyl)phenyl)-2,2,2-trifluoroacetamide (184b) (7.50 g, 102% yield) as a pale-orange solid; $^1$H NMR (300 MHz, DMSO-$d_6$) δ 11.55 (s, 1H), 8.03 (d, J=2.0 Hz, 1H), 7.83 (d, J=2.0 Hz, 1H), 2.31 (s, 3H). $^{19}$F NMR (282 MHz, DMSO-$d_6$) δ−61.20, −74.06. MS (ES−): 348/350 (M−1).

Step-2: Preparation of 2-amino-7-methyl-5-(trifluoromethyl)-1H-indole-3-carbonitrile (184c)

Compound 184c was prepared according to the procedure reported in step-1 of scheme-11, from N-(2-bromo-6-methyl-4-(trifluoromethyl)phenyl)-2,2,2-trifluoroacetamide (184b) (7.50 g, 21.43 mmol) in DMSO (25 mL) using malononitrile (1.698 g, 25.7 mmol), L-proline (0.493 g, 4.29 mmol), CuI (0.408 g, 0.2.143 mmol), $K_2CO_3$ (5.92 g, 42.9 mmol) in water (25 mL) and heating at 60° C. for 16 h under an argon atmosphere. This gave after workup and purification [$SiO_2$ gel (80 g), eluting with EtOAc in hexane from 0-40%] to provide 2-amino-7-methyl-5-(trifluoromethyl)-1H-indole-3-carbonitrile (184c) (3.68 g, 72% yield) as a pale-green solid: $^1$H NMR (300 MHz, DMSO-$d_6$) δ 11.23 (s, 1H), 7.30-7.17 (m, 1H), 7.07 (d, J=1.8 Hz, 1H), 6.84 (s, 2H), 2.41 (s, 3H). $^{19}$F NMR (282 MHz, DMSO-$d_6$) δ−58.92; MS (ES+) 240 (M+1): (ES−): 238 (M−1).

Step-3: Preparation of 8-methyl-6-(trifluoromethyl)-9H-pyrimido[4,5-b]indol-4-amine (184d)

Compound 184d was prepared according to the procedure reported in step-2 of scheme-29, from 2-amino-7-methyl-5-(trifluoromethyl)-1H-indole-3-carbonitrile (184c) (3.68 g, 15.38 mmol) in ethanol (10 mL) using formamidine acetate (8.01 g, 77 mmol) and $NH_4OAc$ (3.56 g, 46.2 mmol) and heating at 90° C. for 16 h. This gave after work up 8-methyl-6-(trifluoromethyl)-9H-pyrimido[4,5-b]indol-4-amine (184d) (2.69 g, 66% yield) as a tan solid; $^1$H NMR (300 MHz, DMSO-$d_6$) δ 12.26 (s, 1H), 8.60 (s, 1H), 8.32 (s, 1H), 7.48 (d, J=1.6 Hz, 1H), 7.41 (s, 2H), 2.59 (s, 3H); $^{19}$F NMR (282 MHz, DMSO-$d_6$) δ−58.08; MS (ES+): 267 (M+1), (ES−): 265 (M−1).

Step-4: Preparation of tert-butyl 2-(4-amino-8-methyl-6-(trifluoromethyl)-9H-pyrimido[4,5-b]indol-9-yl)acetate (184e)

Compound 184e was prepared according to the procedure reported in step-1 of scheme-1, from 8-methyl-6-(trifluoromethyl)-9H-pyrimido[4,5-b]indol-4-amine (184d) (0.56 g, 2.104 mmol) in DMF (10 mL) using tert-butyl 2-bromoacetate (0.492 g, 2.52 mmol) $Cs_2CO_3$ (1.371 g, 4.21 mmol) and stirring at RT for 16 h. This gave after work up and purification [$SiO_2$ gel (24 g), eluting with methanol in DCM from 0-6%] tert-butyl 2-(4-amino-8-methyl-6-(trifluoromethyl)-9H-pyrimido[4,5-b]indol-9-yl)acetate (184e) (0.74 g, 92% yield) as a pale-yellow solid; MS (ES+): 381 (M+1), (ES−): 379 (M−1).

Step-5: Preparation of 2-(4-amino-8-methyl-6-(trifluoromethyl)-9H-pyrimido[4,5-b]indol-9-yl)acetic acid (184f)

Compound 184f was prepared according to the procedure reported in step-2 of scheme-1, from tert-butyl 2-(4-amino-8-methyl-6-(trifluoromethyl)-9H-pyrimido[4,5-b]indol-9-yl)acetate (184e) (0.74 g, 1.946 mmol) using TFA (2.218 g, 19.46 mmol) in DCM (15 mL) and stirring at RT for 16 h. This gave after work up TFA salt of 2-(4-amino-8-methyl-6-(trifluoromethyl)-9H-pyrimido[4,5-b]indol-9-yl)acetic acid (184f) (0.88 g, 103% yield) as a pale-yellow solid; MS (ES+): 325 (M+1), (ES−): 323 (M−1).

Step-6: Preparation of (1R,3S,5R)-2-(2-(4-amino-8-methyl-6-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (184 g)

Compound 184g was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (100 mg, 0.228 mmol) in DMF (5 mL) using HCl salt of (1R,3S,5R)—N-(6-bromopyridin-2-yl)-5-methyl-2-azabicyclo[3.1.0]hexane-3-carboxamide (8a) (83 mg, 0.251 mmol), HATU (130 mg, 0.342 mmol) DIPEA (147 mg, 1.14 mmol) and stirring at RT for 16 h. This gave after workup and purification by flash column chromatography [silica gel (12 g), eluting with MeOH in DCM from 0 to 2%] followed by purification using reverse phase column chromatography [C18 column (100 g), eluting with ACN in water (containing 0.1% HCl) from 0-100%] (1R,3S,5R)-2-(2-(4-amino-8-methyl-6-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (184 g) (76 mg, 55% yield) HCl salt as a white solid: $^1$H NMR (300 MHz, DMSO-$d_6$) δ 10.83 (s, 1H, $D_2O$ exchangeable), 8.79 (s, 1H), 8.72 (s, 2H, $D_2O$ exchangeable), 8.64 (s, 1H), 8.00 (d, J=8.2 Hz, 1H), 7.70 (t, J=8.0 Hz, 1H), 7.60 (s, 1H), 7.31 (d, J=7.7 Hz, 1H), 5.92 (d, J=18.0 Hz, 1H), 5.64 (d, J=17.9 Hz, 1H), 4.38 (dd, J=9.0, 6.1 Hz, 1H), 3.71 (dd, J=5.6, 2.4 Hz, 1H), 2.75 (s, 3H), 2.48-2.44 (m, 1H), 1.97 (dd, J=13.2, 6.0 Hz, 1H), 1.30 (s, 3H), 1.02 (t. J=5.4 Hz, 1H), 0.85 (dd, J=5.4, 2.4 Hz, 1H): $^{19}$F NMR (282 MHz, DMSO-$d_6$) δ−58.78; MS (ES+): 602/604 (M+1), (ES−): 600/602 (M−1).

Scheme 185

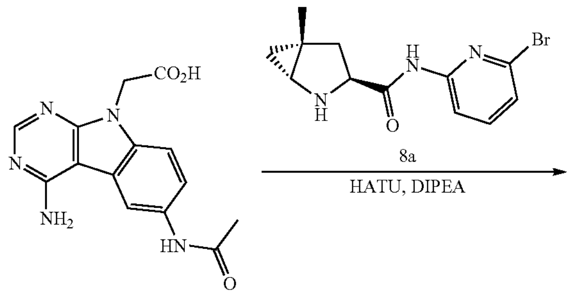

168f

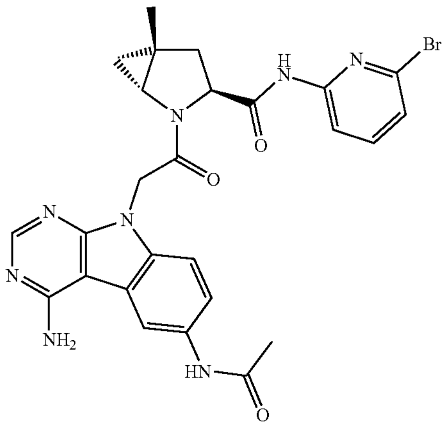

185a

Preparation of (1R,3S,5R)-2-(2-(6-acetamido-4-amino-9H-pyrimido[4,5-b]indol-9-yl)acetyl)-N-(6-bromopyridin-2-yl)-5-methyl-2-azabicyclo[3.1.0]hexane-3-carboxamide (185a)

Compound 185a was prepared according to the procedure reported in step-3 of scheme-1, from TFA salt of 2-(6-acetamido-4-amino-9H-pyrimido[4,5-b]indol-9-yl)acetic acid (168f) (75 mg, 0.181 mmol) in DMF (5 mL) using HCl salt of (1R,3S,5R)—N-(6-bromopyridin-2-yl)-5-methyl-2-azabicyclo[3.1.0]hexane-3-carboxamide (8a) (66.4 mg, 0.200 mmol), HATU (103 mg, 0.272 mmol) DIPEA (117 mg, 0.907 mmol) and stirring at RT for 16 h. This gave after workup and purification by flash column chromatography [silica gel (12 g), eluting with MeOH in DCM from 0 to 7%] followed by purification using reverse phase column chromatography [C18 column (100 g), eluting with ACN in water (containing 0.1% HCl) from 0-100%] (1R,3S,5R)-2-(2-(6-acetamido-4-amino-9H-pyrimido[4,5-b]indol-9-yl)acetyl)-N-(6-bromopyridin-2-yl)-5-methyl-2-azabicyclo[3.1.0]hexane-3-carboxamide (185a) (57 mg, 54% yield) HCl salt as a white solid; $^1$H NMR (300 MHz, DMSO-$d_6$) δ 10.78 (s, 11H, $D_2O$ exchangeable), 10.06 (s, 1H, $D_2O$ exchangeable), 8.82-8.52 (m, 3H, 2H $D_2O$ exchangeable), 8.49 (d, J=1.9 Hz, 1H), 8.01 (d, J=8.1 Hz, 1H), 7.70 (t, J=8.0 Hz, 1H), 7.62 (d, J=8.8 Hz, 11H), 7.53 (dd, J=8.8, 1.8 Hz, 11H), 7.31 (d, J=7.7 Hz, 1H), 5.70 (d, J=17.3 Hz, 1H), 5.34 (d, J=17.3 Hz, 11H), 4.37 (dd, J=9.1, 5.9 Hz, 1H), 3.68 (dd, J=5.5, 2.4 Hz, 1H), 2.47-2.41 (m, 1H), 2.08 (s, 3H), 1.97 (dd, J=13.3, 5.9 Hz, 1H), 1.30 (s, 3H), 1.00 (t, J=5.5 Hz, 1H), 0.93 (dd, J=5.4, 2.4 Hz, 1H); MS (ES+): 577/579 (M+1); (ES−): 575/577 (M−1).

Scheme 186

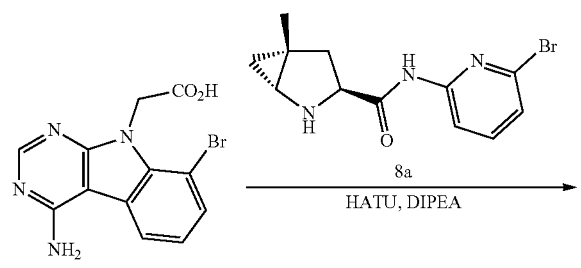

35e

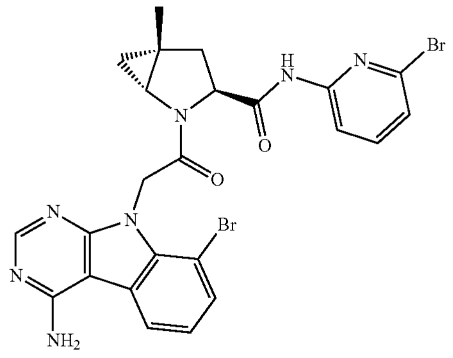

186a

Preparation of (1R,3S,5R)-2-(2-(4-amino-8-bromo-9H-pyrimido[4,5-b]indol-9-yl)acetyl)-N-(6-bromopyridin-2-yl)-5-methyl-2-azabicyclo[3.1.0]hexane-3-carboxamide (186a)

Compound 186a was prepared according to the procedure reported in step-3 of scheme-1, from TFA salt of 2-(4-amino-8-bromo-9H-pyrimido[4,5-b]indol-9-yl)acetic acid (35e) (75 mg, 0.172 mmol) in DMF (5 mL) using HCl salt of (1R,3S,5R)—N-(6-bromopyridin-2-yl)-5-methyl-2-azabicyclo[3.1.0]hexane-3-carboxamide (8a) (57.3 mg, 0.172 mmol), HATU (79 mg, 0.207 mmol), DIPEA (111 mg, 0.862 mmol) and stirring at RT for 16 h. This gave after workup and purification by flash column chromatography [silica gel (12 g), eluting with MeOH in DCM from 0 to 3%] followed by purification using reverse phase column chromatography [C18 column (100 g), eluting with ACN in water (containing 0.1% HCl) from 0-100%] (1R,3S,5R)-2-(2-(4-amino-8-bromo-9H-pyrimido[4,5-b]indol-9-yl)acetyl)-N-(6-bromopyridin-2-yl)-5-methyl-2-azabicyclo[3.1.0]hexane-3-carboxamide (186a) (69 mg, 67% yield) HCl salt as a white solid; $^1$H NMR (300 MHz, DMSO-$d_6$) δ 10.77 (s, 1H, $D_2O$ exchangeable), 8.57 (s, 1H), 8.49 (d, J=7.9 Hz, 1H), 8.37 (s, 2H, $D_2O$ exchangeable), 8.01 (d, J=8.2 Hz, 1H), 7.75-7.61 (m, 2H), 7.29 (t, J=8.0 Hz, 2H), 5.93 (d, J=17.7 Hz, 1H), 5.72 (d, J=17.6 Hz, 1H), 4.36 (dd, J=8.9, 6.1 Hz, 1H), 3.66 (dd, J=5.5, 2.4 Hz, 1H), 2.43 (d, J=6.6 Hz, 1H), 1.97 (dd, J=13.1, 5.9 Hz, 1H), 1.30 (s, 3H), 1.00 (t, J=5.5 Hz, 1H), 0.89 (dd, J=5.6, 2.3 Hz, 1H); MS (ES+): 598/600 (M+1), 596/598 (M−1).

Scheme 187

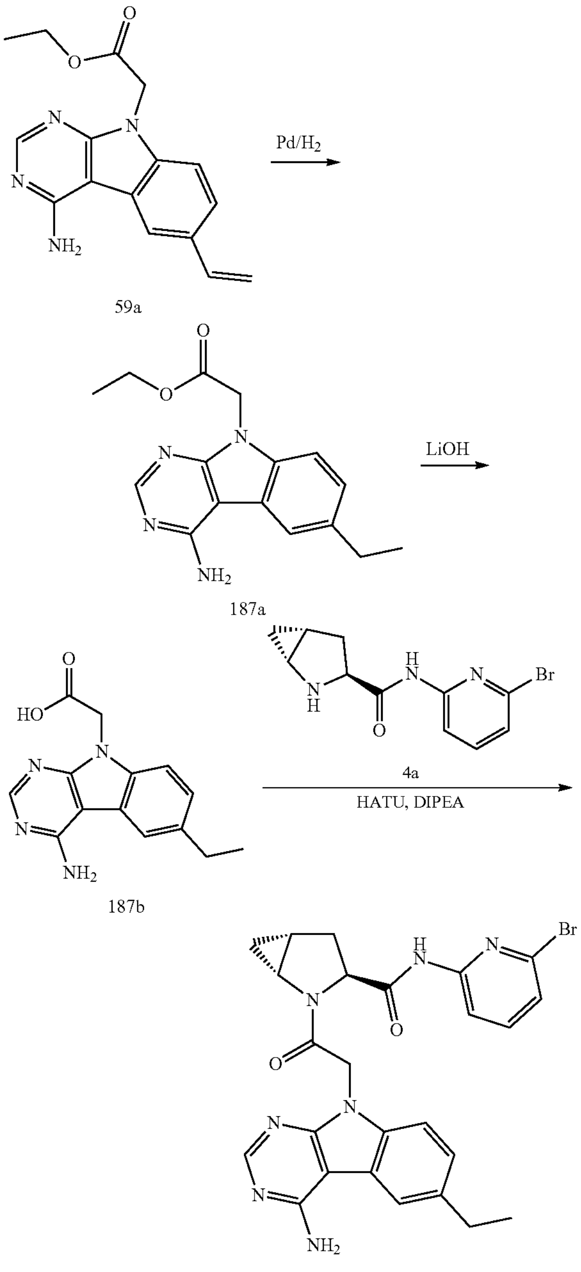

59a

187a

187b

187c

Preparation of (1R,3S,5R)-2-(2-(4-amino-6-ethyl-9H-pyrimido[4,5-b]indol-9-yl)acetyl)-N-(6-bromopyridin-2-yl)-2-azabicyclo[3.1.0]hexane-3-carboxamide (187c)

Step-1: Preparation of ethyl 2-(4-amino-6-ethyl-9H-pyrimido[4,5-b]indol-9-yl)acetate (187a)

A solution of ethyl 2-(4-amino-6-vinyl-9H-pyrimido[4,5-b]indol-9-yl)acetate (59a) (100 mg, 0.337 mmol) in ethyl acetate (5 mL) and ethanol (5.00 mL) was treated with palladium (53.9 mg, 0.051 mmol) and hydrogenated for 2 h. The reaction mixture was filtered, washed with ethyl acetate/ethanol. The filtrate was concentrated to afford ethyl 2-(4-amino-6-ethyl-9H-pyrimido[4,5-b]indol-9-yl)acetate (187a) which was used as such for next step; MS (ES+): 299.10 (M+1).

Step-2: Preparation of 2-(4-amino-6-ethyl-9H-pyrimido[4,5-b]indol-9-yl)acetic acid (187b)

Compound 187b was prepared according to the procedure reported in step-4 of scheme-17, from ethyl 2-(4-amino-6-ethyl-9H-pyrimido[4,5-b]indol-9-yl)acetate (187a) (67 mg, 0.225 mmol) in THF (3 mL) and MeOH (3 mL) using a solution of lithium hydroxide hydrate (57.7 mg, 1.347 mmol) in water (3 mL) and stirring at RT for 20 h. This gave after workup 2-(4-amino-6-ethyl-9H-pyrimido[4,5-b]indol-9-yl)acetic acid (187b) which used as such for the next step; MS (ES+): 271.10 (M+1).

Step-3: Preparation of (1R,3S,5R)-2-(2-(4-amino-6-ethyl-9H-pyrimido[4,5-b]indol-9-yl)acetyl)-N-(6-bromopyridin-2-yl)-2-azabicyclo[3.1.0]hexane-3-carboxamide (187c)

Compound 187c was prepared according to the procedure reported in step-3 of scheme-1, from 2-(4-amino-6-ethyl-9H-pyrimido[4,5-b]indol-9-yl)acetic acid (187b) (61 mg, 0.225 mmol) in DMF (10 mL) using HCl salt of (1R,3S,5R)—N-(6-bromopyridin-2-yl)-2-azabicyclo[3.1.0]hexane-3-carboxamide (4a) (108 mg, 0.338 mmol), HATU (171 mg, 0.450 mmol), DIPEA (0.157 mL, 0.900 mmol) and stirring at RT for 18 h. This gave after workup and purification by flash column chromatography [silica gel (12 g), eluting with dichloromethane/methanol (1:0 to 19:1)] followed by purification using reverse phase column chromatography [C18 column, eluting with ACN in water (containing 0.1% HCl) from 0-100%] (1R,3S,5R)-2-(2-(4-amino-6-ethyl-9H-pyrimido[4,5-b]indol-9-yl)acetyl)-N-(6-bromopyridin-2-yl)-2-azabicyclo[3.1.0]hexane-3-carboxamide (187c) (25 mg, 21% yield) HCl salt as a white solid; $^1H$ NMR (300 MHz, DMSO-$d_6$) δ 10.75 (s, 1H), 8.58 (s, 1H), 8.52 (s, 2H), 8.35 (s, 1H), 8.00 (d, J=8.2 Hz, 1H), 7.70 (t, J=8.0 Hz, 1H), 7.60 (d, J=8.4 Hz, 1H), 7.45-7.39 (m, 1H), 7.32 (d, J=7.7 Hz, 1H), 5.73 (d, J=17.3 Hz, 1H), 5.40 (d, J=17.3 Hz, 1H), 4.40 (dd, J=9.0, 5.5 Hz, 1H), 4.04-3.78 (m, 1H), 2.78 (q, J=7.6 Hz, 2H), 2.41-2.13 (m, 2H), 2.00-1.78 (m, 1H), 1.28 (t, J=7.5 Hz, 3H), 1.12-0.98 (m, 1H), 0.82-0.67 (m, 1H); MS (ES+): 534.10 & 536.10 (M+1); MS (ES−): 532.00 & 534.10 (M−1); Analysis calculated for $C_{25}H_{24}BrN_7O_2 \cdot HCl \cdot 2.25H_2O$: C, 49.11; H, 4.86; N, 16.04. Found: C, 49.18; H, 4.52; N, 15.67.

Scheme 188

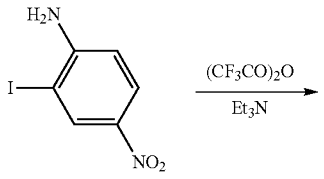

188a

-continued

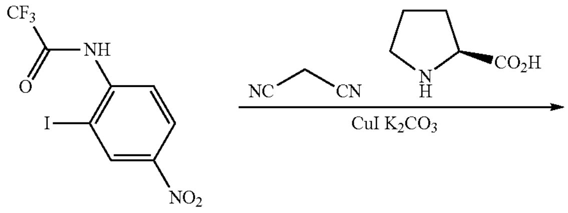

188b

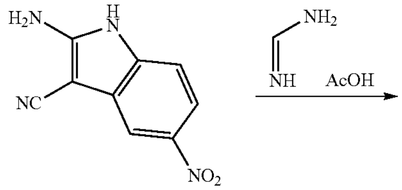

188c

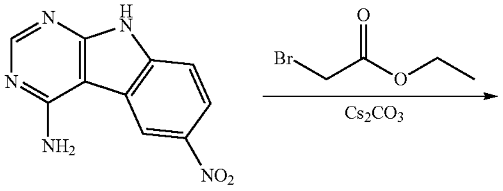

188d

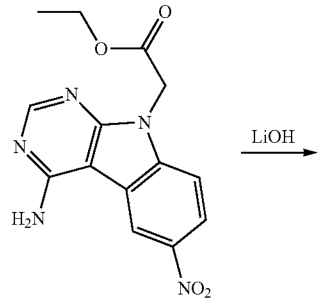

188e

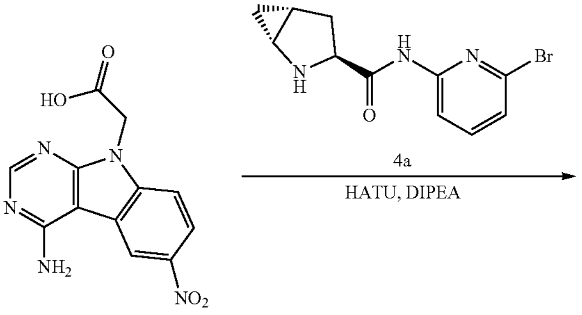

188f

-continued

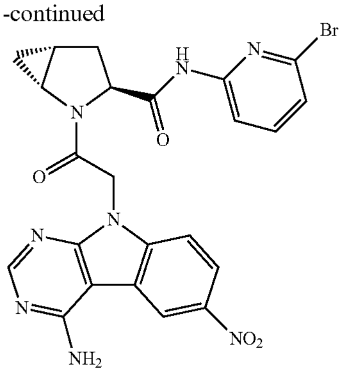

188g

Preparation of (1R,3S,5R)-2-(2-(4-amino-6-nitro-9H-pyrimido[4,5-b]indol-9-yl)acetyl)-N-(6-bromopyridin-2-yl)-2-azabicyclo[3.1.0]hexane-3-carboxamide (188 g)

Step-1: Preparation of 2,2,2-trifluoro-N-(2-iodo-4-nitrophenyl)acetamide (188b)

Compound 188b was prepared according to the procedure reported in step-1 of scheme-46, from 2-iodo-4-nitroaniline (188a) (5 g, 18.94 mmol; CAS #6293-83-0) in DCM (35 mL) using triethylamine (6.60 mL, 47.3 mmol), trifluoroacetic acid anhydride (3.95 mL, 28.4 mmol) and stirring at RT for 19 h. This gave after workup 2,2,2-trifluoro-N-(2-iodo-4-nitrophenyl)acetamide (188b) (8.986 g) as a brown gum which was used as such for the next step: (ES−): 358.90 (M−1).

Step-2: Preparation of 2-amino-5-nitro-1H-indole-3-carbonitrile (188c)

Compound 188c was prepared according to the procedure reported in step-1 of scheme-11, from 2,2,2-trifluoro-N-(2-iodo-4-nitrophenyl)acetamide (188b) (6.819 g, 18.94 mmol) in DMSO (25 mL) using malononitrile (1.501 g, 22.73 mmol), L-proline (0.436 g, 3.79 mmol), CuI (0.361 g, 1.894 mmol), a solution of $K_2CO_3$ (5.235 g, 37.9 mmol) in water (25 mL) and heating at 60° C. for 13 h under an argon atmosphere. This gave after workup and purification [$SiO_2$ gel (120 g), eluting with EtOAc in hexane from 0-67%] 2-amino-5-nitro-1H-indole-3-carbonitrile (188c) (531 mg, 14% yield) as a red solid; $^1H$ NMR (300 MHz, DMSO-$d_6$) δ 11.43 (s, 1H), 7.92 (d, J=2.3 Hz, 114), 7.85 (dd, J=8.7, 2.3 Hz, 1H), 7.34 (s, 2H), 7.28 (d, J=8.7 Hz, 1H); (ES+): 203.05 (M+1); (ES−): 201.00 (M−1).

Step-3: Preparation of 6-nitro-9H-pyrimido[4,5-b]indol-4-amine (188d)

Compound 188d was prepared according to the procedure reported in step-2 of scheme-29, from 2-amino-5-nitro-1H-indole-3-carbonitrile (188c) (520 mg, 2.57 mmol) in ethanol (12 mL) using formamidine acetate (2.164 g, 20.58 mmol) and refluxing for 44 h. This gave after work up 6-nitro-9H-pyrimido[4,5-b]indol-4-amine (188d) (497 mg, 84% yield) as a gray solid: $^1H$ NMR (300 MHz, DMSO-$d_6$) δ 12.54 (s, 1H), 9.34 (d, J=2.2 Hz, 1H), 8.33 (s, 11H), 8.26 (dd, J=8.9, 2.2 Hz, 1H), 7.62 (s, 2H), 7.58 (d, J=9.0 Hz, 1H); (ES+): 230.10 (M+1); (ES−): 228.05 (M−1).

Step-4: Preparation of ethyl 2-(4-amino-6-nitro-9H-pyrimido[4,5-b]indol-9-yl)acetate (188e)

Compound 188e was prepared according to the procedure reported in step-1 of scheme-1, from 6-nitro-9H-pyrimido[4,5-b]indol-4-amine (188d) (300 mg, 1.309 mmol) in DMF (15 mL) using ethyl 2-bromoacetate (0.160 mL, 1.440 mmol), $Cs_2CO_3$ (1.066 g, 3.27 mmol) and stirring at RT for 18 h. This gave after work up ethyl 2-(4-amino-6-nitro-9H-pyrimido[4,5-b]indol-9-yl)acetate (188e) (0.373 g, 90% yield) as a yellow solid; $^1H$ NMR (300 MHz, DMSO-$d_6$) δ 9.39 (d, J=2.2 Hz, 1H), 8.38 (s, 1H), 8.32 (dd, J=9.0, 2.2 Hz, 1H), 7.85 (d, J=9.1 Hz, 1H), 7.78 (s, 2H), 5.35 (s, 2H), 4.15 (q, J=7.1 Hz, 2H), 1.20 (t, J=7.1 Hz, 3H); (ES+): 316.15 (M+1); (ES−): 314.00 (M−1).

Step-5: Preparation of 2-(4-amino-6-nitro-9H-pyrimido[4,5-b]indol-9-yl)acetic acid (188f)

Compound 188f was prepared according to the procedure reported in step-4 of scheme-17, from ethyl 2-(4-amino-6-nitro-9H-pyrimido[4,5-b]indol-9-yl)acetate (188e) (0.100 g, 0.317 mmol) in THF (3 mL) and MeOH (3 mL) using a solution of lithium hydroxide hydrate (81 mg, 1.903 mmol) in water (3 mL) and stirring at RT for 22 h. This gave after work up 2-(4-amino-6-nitro-9H-pyrimido[4,5-b]indol-9-yl) acetic acid (188f) which was used as such for the next step; (ES+): 287.80 (M+1).

Step-6: Preparation of (1R,3S,5R)-2-(2-(4-amino-6-nitro-9H-pyrimido[4,5-b]indol-9-yl)acetyl)-N-(6-bromopyridin-2-yl)-2-azabicyclo[3.1.0]hexane-3-carboxamide (188 g)

Compound 188g was prepared according to the procedure reported in step-3 of scheme-1, from 2-(4-amino-6-nitro-9H-pyrimido[4,5-b]indol-9-yl)acetic acid (188f) (61 mg, 0.225 mmol) in DMF (12 mL) using HCl salt of (1R,3S,5R)—N-(6-bromopyridin-2-yl)-2-azabicyclo[3.1.0]hexane-3-carboxamide (4a) (151 mg, 0.476 mmol), HATU (241 mg, 0.634 mmol), DIPEA (0.276 mL, 1.585 mmol) and stirring at RT for 15 h. This gave after workup and purification by reverse phase column chromatography [C18 column, eluting with ACN in water (containing 0.1% HCl) from 0-100%] (1R,3S,5R)-2-(2-(4-amino-6-nitro-9H-pyrimido[4,5-b]indol-9-yl)acetyl)-N-(6-bromopyridin-2-yl)-2-azabicyclo[3.1.0]hexane-3-carboxamide (188 g) (50 mg, 29% yield) HCl salt as a white solid; $^1H$ NMR (300 MHz, DMSO-$d_6$) δ 10.76 (s, 1H), 9.52 (d, J=2.2 Hz, 1H), 8.73 (s, 3H), 8.64 (s, 1H), 8.41 (dd, J=9.1, 2.2 Hz, 1H), 8.00 (d, J=8.1 Hz, 1H), 7.88 (d, J=9.2 Hz, 1H), 7.70 (t, J=8.0 Hz, 1H), 7.31 (d, J=7.7 Hz, 1H), 5.84 (d, J=17.4 Hz, 1H), 5.48 (d, J=17.3 Hz, 1H), 4.42 (dd, J=9.0, 5.5 Hz, 1H), 3.97-3.86 (m, 1H), 2.44-2.12 (m, 2H), 1.99-1.79 (m, 1H), 1.17-0.96 (m, 1H), 0.88-0.67 (m, 1H); (ES+): 551.10 & 553.10 (M+1); (ES−): 549.00 & 551.00 (M−1): Analysis calculated for $C_{23}H_{19}BrN_8O_4 \cdot 0.85HCl \cdot 1.75H_2O$: C, 45.00; H, 3.83; N, 18.25; Cl, 4.91. Found: C, 45.22; H, 3.59; N, 17.88; Cl, 4.90.

Scheme 189

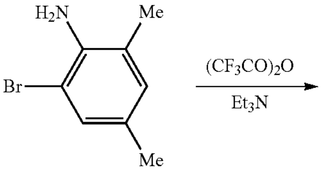

189a

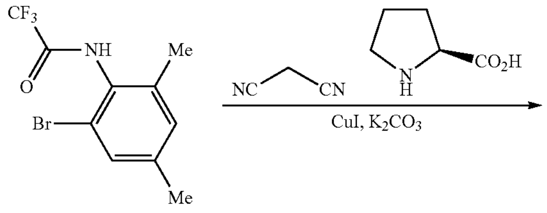

189b

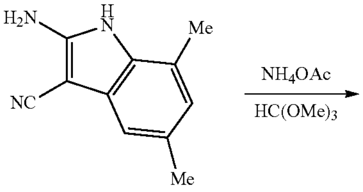

189c

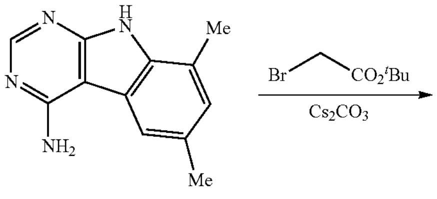

189d

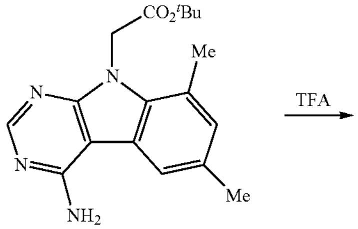

189e

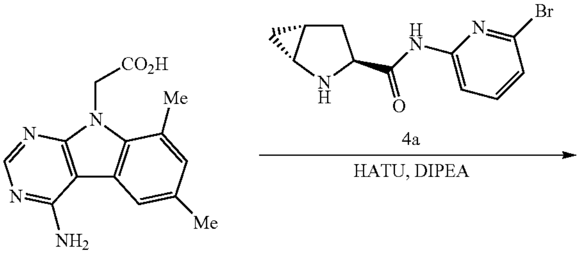

189f

-continued

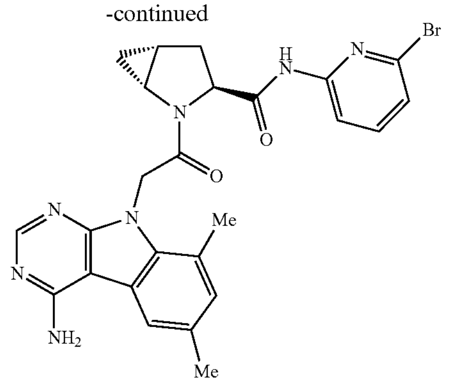

189g

Preparation of (1R,3S,5R)-2-(2-(4-amino-6,8-dimethyl-9H-pyrimido[4,5-b]indol-9-yl)acetyl)-N-(6-bromopyridin-2-yl)-2-azabicyclo[3.1.0]hexane-3-carboxamide (189 g)

Step-1: Preparation of N-(2-bromo-4,6-dimethylphenyl)-2,2,2-trifluoroacetamide (189b)

Compound 189b was prepared according to the procedure reported in step-1 of scheme-46, from 2-bromo-4,6-dimethylaniline (189a) (7 g, 35.0 mmol; CAS #41825-734) in DCM (30 mL) using triethylamine (6.02 g, 59.5 mmol), trifluoroacetic acid anhydride (11.02 g, 52.5 mmol) and stirring at RT for 1 h. This gave after workup N-(2-bromo-4,6-dimethylphenyl)-2,2,2-trifluoroacetamide (189b) (10.32 g, 100% yield) as a pale-yellow solid; $^1$H NMR (300 MHz, DMSO-$d_6$) δ 11.12 (s, 1H), 7.43 (s, 1H), 7.18 (s, 1H), 2.30 (s, 3H), 2.16 (s, 3H); $^{19}$F NMR (282 MHz, DMSO-$d_6$) δ−74.08; MS (ES+): 296/298 (M+1): (ES−): 294/296 (M−1).

Step-2: Preparation of 2-amino-5,7-dimethyl-1H-indole-3-carbonitrile (189c)

Compound 189c was prepared according to the procedure reported in step-1 of scheme-11, from N-(2-bromo-4,6-dimethylphenyl)-2,2,2-trifluoroacetamide (189b) (10.32 g, 34.9 mmol) in DMSO (30 mL), using malononitrile (2.76 g, 41.8 mmol), L-proline (0.803 g, 6.97 mmol), CuI (0.664 g, 3.49 mmol), and a solution of $K_2CO_3$ (9.63 g, 69.7 mmol) in water (30 mL) and heating at 60° C. for 16 h under an argon atmosphere. This gave after workup and purification [$SiO_2$ gel (40 g), eluting with EtOAc in hexane from 0-40%] 2-amino-5,7-dimethyl-1H-indole-3-carbonitrile (189c) (3.97 g, 62% yield) as a pale-orange solid: $^1$H NMR (300 MHz, DMSO-$d_6$) δ 10.60 (s, 1H), 6.77 (s, 1H), 6.54 (d, J=1.6 Hz, 1H), 6.43 (s, 2H), 2.28 (s, 3H), 2.27 (s, 3H); MS (ES+): 186 (M+1); (ES−): 184 (M−1).

Step-3: Preparation of 6,8-dimethyl-9H-pyrimido[4,5-b]indol-4-amine (189d)

Compound 189d was prepared according to the procedure reported in step-2 of scheme-29, from 2-amino-5,7-dimethyl-1H-indole-3-carbonitrile (189c) (3.97 g, 21.43 mmol) in ethanol (10 mL) using trimethoxymethane (11.37 g, 107 mmol), $NH_4OAc$ (4.96 g, 64.3 mmol) and heating at 90° C. for 16 h. This gave after work up 6,8-dimethyl-9H-pyrimido[4,5-b]indol-4-amine (189d) (4.07 g, 89% yield) as a pale-yellow solid: $^1$H NMR (300 MHz, DMSO-$d_6$) δ 11.68 (s, 1H), 8.22 (s, 1H), 7.93 (s, 1H), 7.03 (s, 2H), 6.98 (s, 1H), 2.47 (s, 3H), 2.42 (s, 3H); MS (ES+): 213 (M+1), (ES−): 211 (M−1).

Step-4: Preparation of tert-butyl 2-(4-amino-6,8-dimethyl-9H-pyrimido[4,5-b]indol-9-yl)acetate (189e)

Compound 189e was prepared according to the procedure reported in step-1 of scheme-1, from 6,8-dimethyl-9H-pyrimido[4,5-b]indol-4-amine (189d) (2.00 g, 9.42 mmol) in DMF (15 mL) using tert-butyl 2-bromoacetate (2.206 g, 11.31 mmol), $Cs_2CO_3$ (6.14 g, 18.85 mmol) and stirring at RT for 16 h. This gave after work up tert-butyl 2-(4-amino-6,8-dimethyl-9H-pyrimido[4,5-b]indol-9-yl)acetate (189e) (1.79 g, 58%) as a tan solid which was used as such for the next step; $^1$H NMR (300 MHz, DMSO-$d_6$) δ 8.26 (s, 1H), 8.02 (s, 1H), 7.19 (s, 2H), 6.98 (s, 1H), 5.29 (s, 2H), 2.59 (s, 3H), 2.41 (s, 3H), 1.42 (s, 9H); MS (ES+): 327 (M+1).

Step-5: Preparation of 2-(4-amino-6,8-dimethyl-9H-pyrimido[4,5-b]indol-9-yl)acetic acid (189f)

Compound 189f was prepared according to the procedure reported in step-2 of scheme-1, from tert-butyl 2-(4-amino-6,8-dimethyl-9H-pyrimido[4,5-b]indol-9-yl)acetate (189e) (300 mg, 0.919 mmol) using TFA (1048 mg, 9.19 mmol) in DCM (15 mL) and stirring at RT for 16 h. This gave after work up TFA salt of 2-(4-amino-6,8-dimethyl-9H-pyrimido[4,5-b]indol-9-yl)acetic acid (189f) (0.366 g, 104% yield) as a pale-yellow solid: $^1$H NMR (300 MHz, DMSO-$d_6$) δ 8.66 (s, 2H), 8.61 (s, 1H), 8.19 (s, 1H), 7.16 (s, 1H), 5.43 (s, 2H), 2.65 (s, 3H), 2.45 (s, 3H); $^{19}$F NMR (282 MHz, DMSO-$d_6$) δ−74.52; MS (ES+): 271 (M+1); (ES−): 269 (M−1).

Step-6: Preparation of (1R,3S,5R)-2-(2-(4-amino-6,8-dimethyl-9H-pyrimido[4,5-b]indol-9-yl)acetyl)-N-(6-bromopyridin-2-yl)-2-azabicyclo[3.1.0]hexane-3-carboxamide (189 g)

Compound 189g was prepared according to the procedure reported in step-3 of scheme-1, from TFA salt of 2-(4-amino-6,8-dimethyl-9H-pyrimido[4,5-b]indol-9-yl)acetic acid (189f) (75 mg, 0.195 mmol) in DMF (5 mL) using HCl salt of (1R,3S,5R)—N-(6-bromopyridin-2-yl)-2-azabicyclo[3.1.0]hexane-3-carboxamide (4a) (62.2 mg, 0.195 mmol), HATU (89 mg, 0.234 mmol), DIPEA (126 mg, 0.976 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%](1R,3S,5R)-2-(2-(4-amino-6,8-dimethyl-9H-pyrimido[4,5-b]indol-9-yl)acetyl)-N-(6-bromopyridin-2-yl)-2-azabicyclo[3.1.0]hexane-3-carboxamide (189 g) (75 mg, 72% yield) HCl salt as a white solid; $^1$H NMR (300 MHz, DMSO-$d_6$) δ 10.82 (s, 1H, $D_2O$ exchangeable), 8.68 (s, 2H, $D_2O$ exchangeable), 8.62 (s, 1H), 8.17 (s, 1H), 8.00 (d, J=8.2 Hz, 1H), 7.70 (t, J=8.0 Hz, 1H), 7.31 (d, J=7.7 Hz, 1H), 7.11 (s, 1H), 5.88 (d, J=17.9 Hz, 1H), 5.60 (d, J=17.8 Hz, 1H), 4.41 (dd, J=9.1, 5.7 Hz, 1H), 3.91 (ddd, J=7.3, 5.4, 2.4 Hz, 1H), 2.66 (s, 3H), 2.42 (s, 3H), 2.40-2.29 (m, 1H), 2.26-2.14 (m, 1H), 1.99-1.85 (m, 1H), 1.14-0.98 (m, 1H), 0.74-0.62 (m, 1H); MS (ES+): 534/536 (M+1), (ES−): 532/534 (M−1); Analysis calculated for $C_{25}H_{24}BrN_7O_2 \cdot HCl \cdot 1.75H_2O$: C, 49.85; H, 4.77; Cl, 5.89; N, 16.28. Found: C, 49.82; H, 4.65; Cl, 5.83; N, 16.03.

Scheme 190

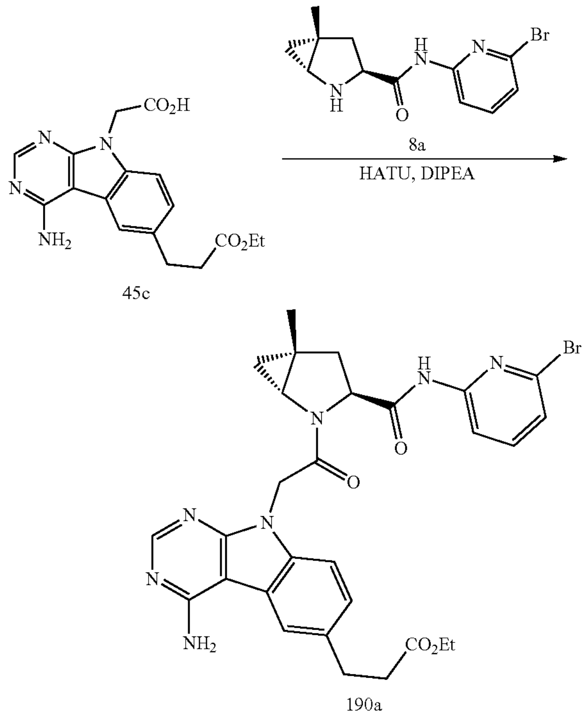

Preparation of ethyl 3-(4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indol-6-yl)propanoate (190a)

Compound 190a was prepared according to the procedure reported in step-3 of scheme-1, from TFA salt of 2-(4-amino-6-(3-ethoxy-3-oxopropyl)-9H-pyrimido[4,5-b]indol-9-yl) acetic acid (45c) (75 mg, 0.164 mmol) in DMF (5 mL) using HCl salt of (1R,3S,5R)—N-(6-bromopyridin-2-yl)-5-methyl-2-azabicyclo[3.1.0]hexane-3-carboxamide (8a) (65.6 mg, 0.197 mmol), HATU (94 mg, 0.247 mmol) DIPEA (106 mg, 0.822 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] ethyl 3-(4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indol-6-yl)propanoate (190a) (78 mg, 76% yield) HCl salt as a white solid; $^1H$ NMR (300 MHz, DMSO-$d_6$) δ 10.77 (s, 1H, $D_2O$ exchangeable), 8.80-8.54 (m, 3H, 2H $D_2O$ exchangeable), 8.46-8.36 (m, 1H), 8.01 (d, J=8.2 Hz, 1H), 7.70 (t, J=8.0 Hz, 1H), 7.61 (d, J=8.5 Hz, 1H), 7.45 (dd, J=8.5, 1.5 Hz, 1H), 7.32 (d, J=7.7 Hz, 1H), 5.70 (d, J=17.3 Hz, 1H), 5.35 (d, J=17.2 Hz, 1H), 4.37 (dd, J=9.0, 6.0 Hz, 1H), 4.05 (q, J=7.1 Hz, 2H), 3.69 (dd, J=5.6, 2.4 Hz, 1H), 3.03 (t, J=7.7 Hz, 2H), 2.75 (t, J=7.7 Hz, 2H), 2.49-2.40 (m, 1H), 2.05-1.92 (m, 1H), 1.31 (s, 3H), 1.16 (t, J=7.1 Hz, 3H), 1.01 (t, J=5.5 Hz, 1H), 0.97-0.88 (m, 1H);

MS (ES+): 620/622 (M+1), (ES−): 618/620 (M−1); Analysis calculated for $C_{29}H_{30}BrN_7O_4 \cdot HCl \cdot 1.5H_2O$: C, 50.92; H, 5.01; N, 14.33. Found: C, 50.82; H, 4.90; N, 14.05.

Scheme 191

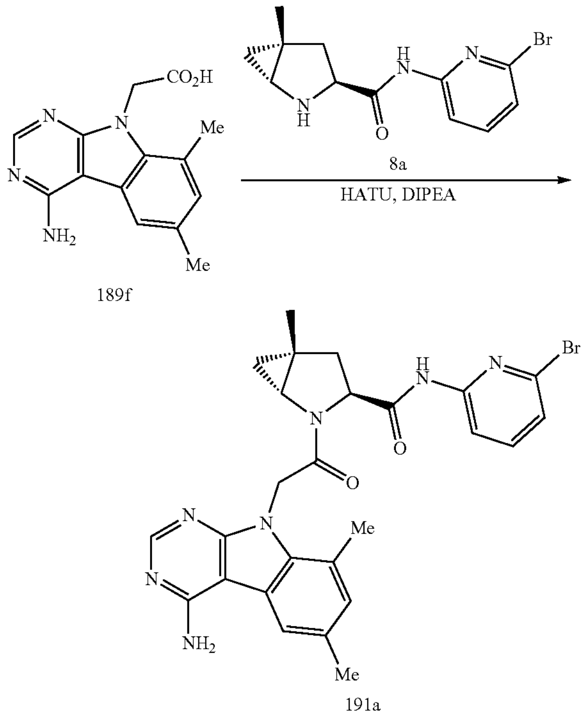

Preparation of (1R,3S,5R)-2-(2-(4-amino-6,8-dimethyl-9H-pyrimido[4,5-b]indol-9-yl)acetyl)-N-(6-bromopyridin-2-yl)-5-methyl-2-azabicyclo[3.1.0]hexane-3-carboxamide (191a)

Compound 191a was prepared according to the procedure reported in step-3 of scheme-1, from TFA salt of 2-(4-amino-6,8-dimethyl-9H-pyrimido[4,5-b]indol-9-yl)acetic acid (189f) (75 mg, 0.195 mmol) in DMF (5 mL) using HCl salt of (1R,3S,5R)—N-(6-bromopyridin-2-yl)-5-methyl-2-azabicyclo[3.1.0]hexane-3-carboxamide (8a) (64.9 mg, 0.195 mmol), HATU (89 mg, 0.234 mmol), DIPEA (126 mg, 0.976 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6,8-dimethyl-9H-pyrimido[4,5-b]indol-9-yl)acetyl)-N-(6-bromopyridin-2-yl)-5-methyl-2-azabicyclo[3.1.0]hexane-3-carboxamide (191a) (63 mg, 59% yield) HCl as a white solid; 1H NMR (300 MHz, DMSO-$d_6$) δ 10.80 (s, 1H, $D_2O$ exchangeable), 8.70 (s, 2H, $D_2O$ exchangeable), 8.61 (s, 1H), 8.16 (s, 1H), 8.00 (d, J=8.2 Hz, 1H), 7.70 (t, J=8.0 Hz, 1H), 7.30 (d, J=7.7 Hz, 1H), 7.11 (s, 1H), 5.82 (d, J=18.0 Hz, 1H), 5.55 (d, J=17.9 Hz, 1H), 4.37 (dd, J=9.0, 6.2 Hz, 1H), 3.69-3.67 (m, 1H), 2.63 (s, 3H), 2.48-2.33 (m, 4H), 1.97 (dd, J=13.2, 6.1 Hz, 1H), 1.30 (s, 3H), 1.01 (t, J=5.5 Hz, 1H), 0.83 (dd, J=5.4, 2.3 Hz, 1H); MS (ES+) 548/550 (M+1), 546/548 (M−1); Analysis calculated for $C_{26}H_{26}BrN_7O_2{\cdot}HCl{\cdot}2H_2O$: C, 50.29; H, 5.03; Cl, 5.71; N, 15.79. Found: C, 50.14; H, 4.95; Cl, 5.64; N, 15.56.

Scheme 192

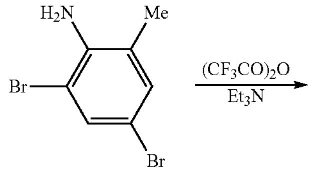

184a

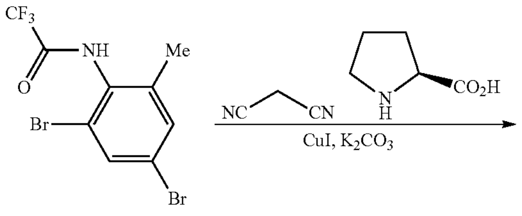

192b

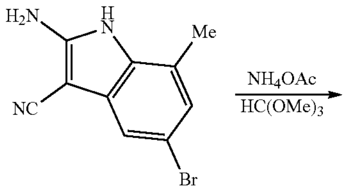

192c

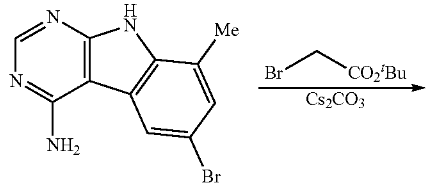

192d

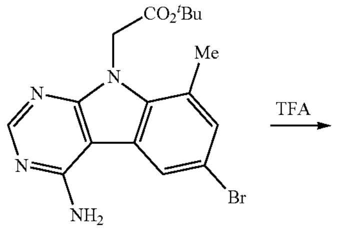

192e

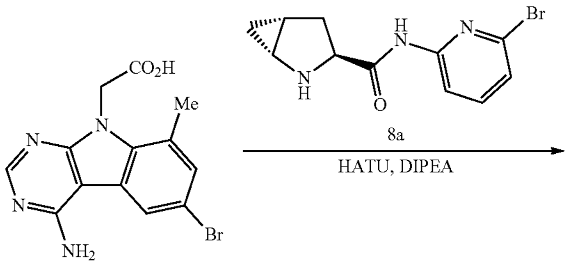

8a

192f

-continued

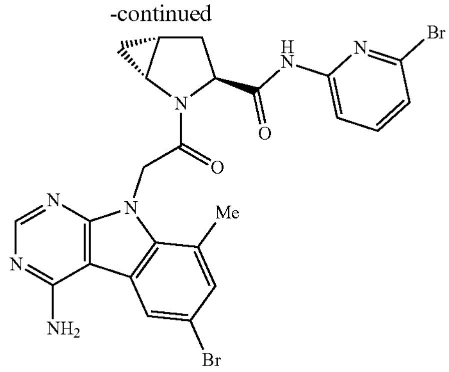

192g

Preparation of (1R,3S,5R)-2-(2-(4-amino-6-bromo-8-methyl-9H-pyrimido[4,5-b]indol-9-yl)acetyl)-N-(6-bromopyridin-2-yl)-2-azabicyclo[3.1.0]hexane-3-carboxamide (192 g)

Step-1: Preparation of N-(2,4-dibromo-6-methylphenyl)-2,2,2-trifluoroacetamide (192b)

Compound 192b was prepared according to the procedure reported in step-1 of scheme-46, from 2,4-dibromo-6-methylaniline (192a) (10 g, 37.7 mmol; CAS #30273-41-7) in DCM (30 mL) using triethylamine (6.49 g, 64.2 mmol), trifluoroacetic acid anhydride (11.89 g, 56.6 mmol) and stirring at RT for 1 h. This gave after workup N-(2,4-dibromo-6-methylphenyl)-2,2,2-trifluoroacetamide (192b) (13.29 g, 98% yield) as a purple solid: 1H NMR (300 MHz, DMSO-$d_6$) δ 11.30 (s, 1H), 7.88 (s, 1H), 7.66 (s, 1H), 2.21 (s, 3H); $^{19}$F NMR (282 MHz. DMSO-$d_6$) δ-74.09; MS (ES−): 358/360 (M−1).

Step-2: Preparation of 2-amino-5-bromo-7-methyl-1H-indole-3-carbonitrile (192c)

Compound 192c was prepared according to the procedure reported in step-1 of scheme-11, from N-(2,4-dibromo-6-methylphenyl)-2,2,2-trifluoroacetamide (192b) (13.29 g, 36.8 mmol) in DMSO (20 mL) using malononitrile (2.92 g, 44.2 mmol), L-proline (0.848 g, 7.36 mmol), CuI (0.701 g, 3.68 mmol), a solution of $K_2CO_3$ (10.18 g, 73.6 mmol) in water (30 mL) and heating at 60° C. for 16 h under an argon atmosphere. This gave after workup and purification [$SiO_2$ gel (40 g), eluting with MeOH in DCM from 0-6%] 2-amino-5-bromo-7-methyl-1H-indole-3-carbonitrile (192c) (5.54 g, 60% yield) as a deep green-black solid; $^1$H NMR (300 MHz, DMSO-$d_6$) δ 10.97 (s, 1H), 7.06 (d, J=1.9 Hz, 1H), 6.89 (d, J=1.9 Hz, 1H), 6.71 (s, 2H), 2.32 (s, 3H); MS (ES+): 250/252 (M+1); (ES−): 248/250 (M−1).

Step-3: Preparation of 6-bromo-8-methyl-9H-pyrimido[4,5-b]indol-4-amine (192d)

Compound 192d was prepared according to the procedure reported in step-2 of scheme-29, from 2-amino-5-bromo-7-methyl-1H-indole-3-carbonitrile (192c) (5.54 g, 22.15 mmol) in ethanol (10 mL) using trimethoxymethane (11.75 g, 111 mmol). $NH_4OAc$ (5.12 g, 66.5 mmol) and heating at 80° C. for 16 h. This gave after work up 6-bromo-8-methyl-9H-pyrimido[4,5-b]indol-4-amine (192d) (5.57 g, 91% yield) as a green solid: $^1$H NMR (300 MHz, DMSO-$d_6$) δ

12.01 (s, 1H), 8.40 (d, J=1.8 Hz, 1H), 8.27 (s, 1H), 7.33 (dd, J=1.9.0.9 Hz, 1H), 7.26 (s, 2H), 2.50 (d, J=2.2 Hz, 3H); MS (ES+): 277/279 (M+1), (ES−): 275/277 (M−1).

Step-4: Preparation of tert-butyl 2-(4-amino-6-bromo-8-methyl-9H-pyrimido[4,5-b]indol-9-yl)acetate (192e)

Compound 192e was prepared according to the procedure reported in step-1 of scheme-1, from 6-bromo-8-methyl-9H-pyrimido[4,5-b]indol-4-amine (192d) (2.00 g, 7.22 mmol) in DMF (15 mL) using tert-butyl 2-bromoacetate (1.689 g, 8.66 mmol), $Cs_2CO_3$ (4.70 g, 14.43 mmol) and stirring at RT for 16 h. This gave after work up and purification [$SiO_2$ gel (40 g), eluting with methanol in DCM from 0-4%] tert-butyl 2-(4-amino-6-bromo-8-methyl-9H-pyrimido[4,5-b]indol-9-yl)acetate (192e) (1.65 g, 58% yield) as a tan solid, $^1$H NMR (300 MHz, DMSO-$d_6$) δ 8.47 (d, J=1.9 Hz, 1H), 8.31 (s, 1H), 7.43 (s, 2H), 7.38-7.30 (m, 1H), 5.33 (s, 2H), 2.62 (s, 3H), 1.42 (s, 9H); MS (ES+): 391/393 (M+1), (ES−): 389/391 (M−1).

Step-5: Preparation of 2-(4-amino-6-bromo-8-methyl-9H-pyrimido[4,5-b]indol-9-yl)acetic acid (192f)

Compound 192f was prepared according to the procedure reported in step-2 of scheme-1, from tert-butyl 2-(4-amino-6-bromo-8-methyl-9H-pyrimido[4,5-b]indol-9-yl)acetate (192e) (300 mg, 0.767 mmol) using TFA (874 mg, 7.67 mmol) in DCM (15 mL) and stirring at RT for 16 h. This gave after work up TFA salt of 2-(4-amino-6-bromo-8-methyl-9H-pyrimido[4,5-b]indol-9-yl)acetic acid (192f) (0.357 g) as a pale-yellow solid; $^1$H NMR (300 MHz, DMSO-$d_6$) δ 8.62 (d, J=1.9 Hz, 1H), 8.55 (s, 1H), 8.45 (s, 2H), 7.48 (d, J=1.9 Hz, 1H), 5.42 (s, 2H), 2.67 (s, 3H); $^{19}$F NMR (282 MHz, DMSO-$d_6$) δ−74.55; MS (ES+): 335/337 (M+1); (ES−): 333/335 (M−1).

Step-6: Preparation of (1R,3S,5R)-2-(2-(4-amino-6-bromo-8-methyl-9H-pyrimido[4,5-b]indol-9-yl)acetyl)-N-(6-bromopyridin-2-yl)-2-azabicyclo[3.1.0]hexane-3-carboxamide (192 g)

Compound 192g was prepared according to the procedure reported in step-3 of scheme-1, from TFA salt of 2-(4-amino-6-bromo-8-methyl-9H-pyrimido[4,5-b]indol-9-yl)acetic acid (192f) (75 mg, 0.167 mmol) in DMF (5 mL) using HCl salt of (1R,3S,5R)—N-(6-bromopyridin-2-yl)-2-azabicyclo[3.1.0]hexane-3-carboxamide (4a) (53.2 mg, 0.167 mmol), HATU (76 mg, 0.200 mmol), DIPEA (108 mg, 0.835 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-bromo-8-methyl-9H-pyrimido[4,5-b]indol-9-yl)acetyl)-N-(6-bromopyridin-2-yl)-2-azabicyclo[3.1.0]hexane-3-carboxamide (192 g) (83 mg, 83% yield) HCl salt as a white solid; $^1$H NMR (300 MHz, DMSO-$d_6$) δ 10.83 (s, 1H, $D_2O$ exchangeable), 8.76 (s, 2H, $D_2O$ exchangeable), 8.68-8.56 (m, 2H), 8.00 (d, J=8.1 Hz, 1H), 7.71 (t, J=8.0 Hz, 1H), 7.48 (d, J=1.9 Hz, 1H), 7.31 (d, J=7.7 Hz, 1H), 5.90 (d, J=18.0 Hz, 1H), 5.63 (d, J=17.9 Hz, 1H), 4.42 (dd, J=9.0, 5.7 Hz, 1H), 3.91 (td, J=5.4, 3.0 Hz, 1H), 2.69 (s, 3H), 2.41-2.29 (m, 1H), 2.26-2.10 (m, 1H), 2.00-1.83 (m, 1H), 1.18-0.97 (m, 1H), 0.75-0.60 (m, 11H); MS (ES+): 598/600 (M+1); (ES−): 596/598 (M−1); Analysis calculated for $C_{24}H_{21}Br_2N_7O_2 \cdot 1.1HCl \cdot 1.75H_2O$: C, 42.96; H, 3.85; Cl, 5.81; N, 14.61. Found: C, 43.08; H, 3.70; Cl, 5.91; N, 14.34.

Scheme 193

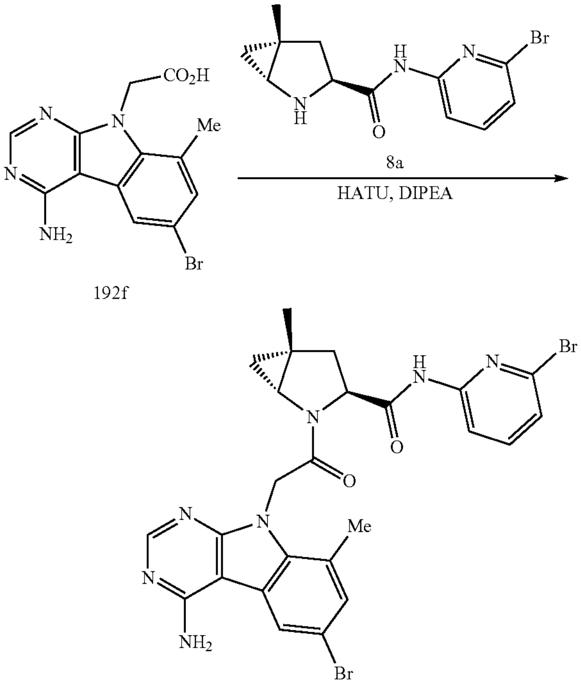

192f

8a

193a

Preparation of (1R,3S,5R)-2-(2-(4-amino-6-bromo-8-methyl-9H-pyrimido[4,5-b]indol-9-yl)acetyl)-N-(6-bromopyridin-2-yl)-5-methyl-2-azabicyclo[3.1.0]hexane-3-carboxamide (193a)

Compound 193a was prepared according to the procedure reported in step-3 of scheme-1, from TFA salt of 2-(4-amino-6-bromo-8-methyl-9H-pyrimido[4,5-b]indol-9-yl)acetic acid (192f) (75 mg, 0.167 mmol) in DMF (5 mL) using HCl salt of (1R,3S,5R)—N-(6-bromopyridin-2-yl)-5-methyl-2-azabicyclo[3.1.0]hexane-3-carboxamide (8a) (55.5 mg, 0.167 mmol), HATU (76 mg, 0.200 mmol), DIPEA (108 mg, 0.835 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-bromo-8-methyl-9H-pyrimido[4,5-b]indol-9-yl)acetyl)-N-(6-bromopyridin-2-yl)-5-methyl-2-azabicyclo[3.1.0]hexane-3-carboxamide (193a) (83 mg, 81% yield) HCl salt as a white solid: 1H NMR (300 MHz, DMSO-$d_6$) δ 10.82 (s, 1H, $D_2O$ exchangeable), 8.60 (d, J=1.9 Hz, 1H), 8.57 (s, 1H), 8.51 (s, 2H, $D_2O$ exchangeable), 8.01 (d, J=8.2 Hz, 1H), 7.71 (t, J=8.0 Hz, 1H), 7.45 (d, J=1.8 Hz, 1H), 7.31 (d, J=7.7 Hz, 1H), 5.84 (d, J=18.0 Hz, 1H), 5.58 (d, J=17.9 Hz, 1H), 4.37 (dd, J=9.0, 6.1 Hz, 1H), 3.70-3.66 (m, 1H), 2.67 (s, 3H), 2.48-2.40 (m, 1H), 1.97 (dd, J=13.2, 6.1 Hz, 1H), 1.30 (s, 3H), 1.01 (t, J=5.5 Hz, 1H), 0.83 (dd, J=5.4, 2.4 Hz, 1H); MS (ES+): 612/614 (M+1), (ES−): 610/612 (M−1), Analysis calculated for $C_{25}H_{23}Br_2N_7O_2\cdot HCl\cdot 1.75H_2O$: C, 44.07; H, 4.07; Cl, 5.20; N, 14.39. Found: C, 44.02; H, 3.91; Cl, 5.46; N, 14.13.

Scheme 194

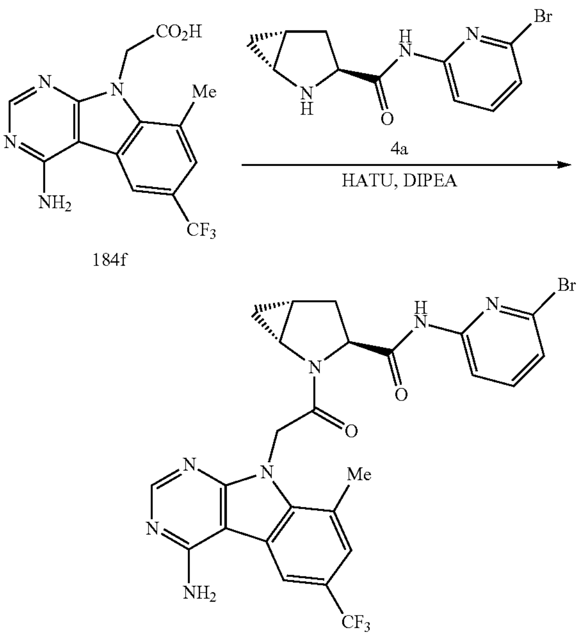

184f

194a

Preparation of (1R,3S,5R)-2-(2-(4-amino-8-methyl-6-(trifluoromethyl)-9H-pyrimido[4,5-b]indol-9-yl)acetyl)-N-(6-bromopyridin-2-yl)-2-azabicyclo[3.1.0]hexane-3-carboxamide (194a)

Compound 194a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (100 mg, 0.228 mmol) in DMF (5 mL) using HCl salt of (1R,3S,5R)—N-(6-bromopyridin-2-yl)-2-azabicyclo[3.1.0]hexane-3-carboxamide (4a) (80 mg, 0.251 mmol), HATU (130 mg, 0.342 mmol), DIPEA (147 mg, 1.141 mmol) and stirring at RT for 16 h. This gave after workup and purification by flash column chromatography [silica gel (12 g), eluting with MeOH in DCM from 0-2%] followed by purification using reverse phase column chromatography [C18 column (100 g), eluting with ACN in water (containing 0.1% HCl) from 0-100%] (1R,3S,5R)-2-(2-(4-amino-8-methyl-6-(trifluoromethyl)-9H-pyrimido[4,5-b]indol-9-yl)acetyl)-N-(6-bromopyridin-2-yl)-2-azabicyclo[3.1.0]hexane-3-carboxamide (194a) (33 mg, 25% yield) HCl salt as a white solid; $^1H$ NMR (300 MHz, DMSO-$d_6$) δ 10.83 (s, 1H, $D_2O$ exchangeable), 8.78 (s, 1H), 8.59 (s, 1H), 8.50 (s, 2H, $D_2O$ exchangeable), 8.01 (d, J=8.2 Hz, 1H), 7.71 (t, J=8.0 Hz, 1H), 7.64-7.57 (m, 1H), 7.32 (d, J=7.7 Hz, 1H), 5.96 (d, J=18.0 Hz, 1H), 5.69 (d, J=17.9 Hz, 1H), 4.43 (dd, J=9.1, 5.6 Hz, 1H), 3.97-3.92 (m, 1H), 2.78 (s, 3H), 2.40-2.30 (m, 1H), 2.30-2.15 (m, 1H), 2.00-1.86 (m, 1H), 1.15-1.04 (m, 1H), 0.74-0.64 (m, 1H); $^{19}F$ NMR (282 MHz, DMSO-$d_6$) δ−58.71; MS (ES+): 588/590 (M+1), (ES−): 586/588 (M−1).

Scheme 195

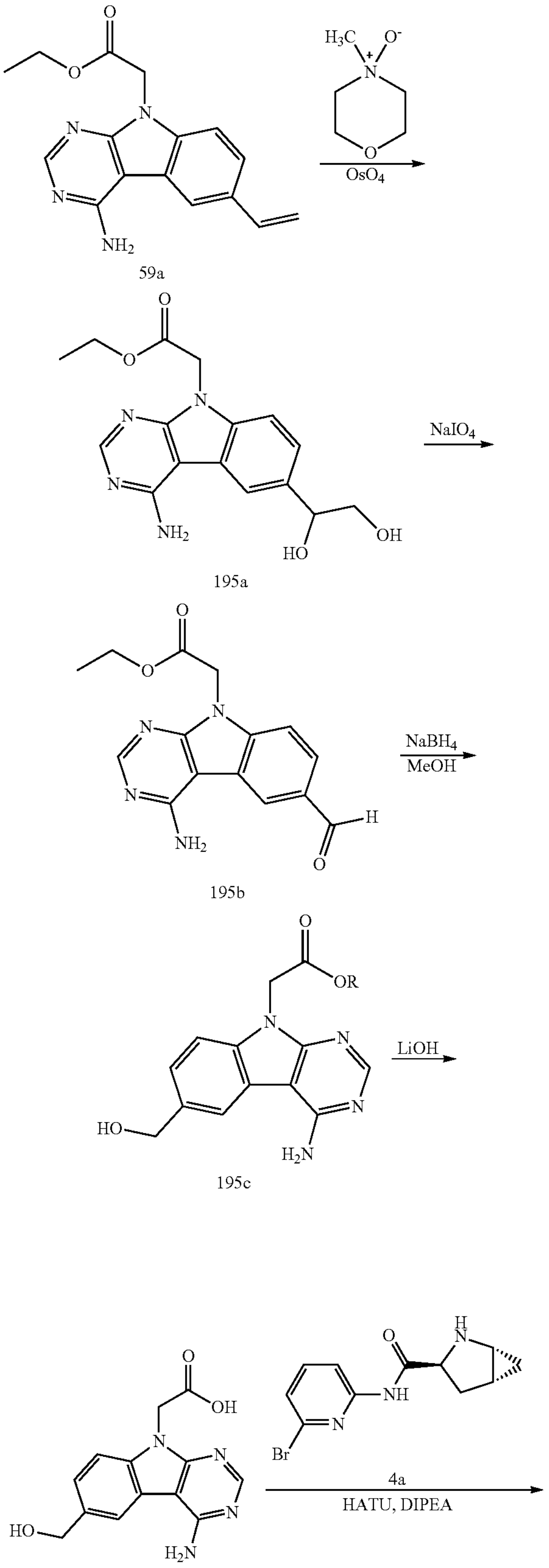

59a

195a

195b

195c

195d

-continued

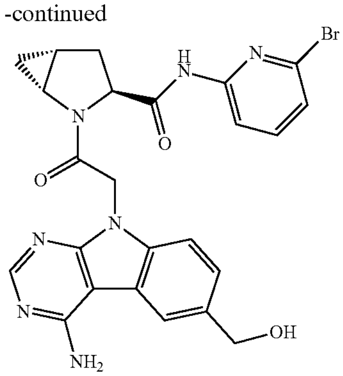

195e

R = Et, Me

Preparation of (1R,3S,5R)-2-(2-(4-amino-6-(hydroxymethyl)-9H-pyrimido[4,5-b]indol-9-yl)acetyl)-N-(6-bromopyridin-2-yl)-2-azabicyclo[3.1.0]hexane-3-carboxamide (195e) Step-1: Preparation of ethyl 2-(4-amino-6-(1,2-dihydroxyethyl)-9H-pyrimido[4,5-b]indol-9-yl)acetate (195a)

To a solution of ethyl 2-(4-amino-6-vinyl-9H-pyrimido[4,5-b]indol-9-yl)acetate (59a) (300 mg, 1.012 mmol) in acetonitrile (20 mL) and water (10 mL) was added 4-methylmorpholine 4-oxide (232 mg, 1.924 mmol) followed by osmium(VIII) oxide (4% in water) (0.619 mL, 0.101 mmol) and stirred at RT for 22 h. Reaction mixture was quenched with 1 M aqueous $Na_2S_2O_3$ solution (10 mL), diluted with water (50 mL), and extracted with ethyl acetate (100 mL, 2×75 mL). The combined organics were dried, filtered and concentrated in vacuum. The residue obtained was purified by flash column chromatography [silica gel (12 g), eluting with MeOH in DCM (from 0-10%)] to afford ethyl 2-(4-amino-6-(1,2-dihydroxyethyl)-9H-pyrimido[4,5-b]indol-9-yl)acetate (195a) (122 mg, 37%) as a yellow solid; $^1H$ NMR (300 MHz, DMSO-$d_6$) δ 8.29-8.24 (m, 2H), 7.51 (d, J=8.4 Hz, 1H), 7.44-7.38 (m, 1H), 7.25 (s, 2H), 5.27-5.15 (m, 3H), 4.75-4.64 (m, 2H), 4.13 (q, J=7.1 Hz, 2H), 3.55 (t, J=5.9 Hz, 2H), 1.20 (t, J=7.1 Hz, 3H); MS (ES+): 331.15 (M+1); (ES−): 329.10 (M−1).

Step-2: Preparation of ethyl 2-(4-amino-6-formyl-9H-pyrimido[4,5-b]indol-9-yl)acetate (195b)

To a solution of ethyl 2-(4-amino-6-(1,2-dihydroxyethyl)-9H-pyrimido[4,5-b]indol-9-yl)acetate (195a) (117 mg, 0.354 mmol) in diethyl ether (10 mL) and water (5 mL) was added sodium periodate (152 mg, 0.708 mmol) and stirred at RT for 1 h. The reaction mixture was diluted with ethyl acetate (100 mL), water (50 mL), 1 M aqueous $Na_2S_2O_3$ solution (1 mL) and filtered. The filtrate was separated washed with brine (50 mL), dried, filtered and concentrated in vacuum to afford ethyl 2-(4-amino-6-formyl-9H-pyrimido[4,5-b]indol-9-yl)acetate (195b) as an off-white solid (101 mg) which was used as such for next step; $^1H$ NMR (300 MHz, DMSO-$d_6$) δ 10.06 (s, 1H), 9.00 (d, J=1.5 Hz, 1H), 8.35 (s, 1H), 7.96 (dd, J=8.6, 1.5 Hz, 1H), 7.81 (d, J=8.5 Hz, 1H), 7.58 (s, 2H), 5.32 (s, 2H), 4.15 (q, J=7.1 Hz, 2H), 1.20 (t, J=7.1 Hz, 3H); MS (ES+): 299.10 (M+1).

Step-3: Preparation of methyl/ethyl 2-(4-amino-6-(hydroxymethyl)-9H-pyrimido[4,5-b]indol-9-yl)acetate (195c)

Compound 195c was prepared according to the procedure reported in scheme-157, from ethyl 2-(4-amino-6-formyl-9H-pyrimido[4,5-b]indol-9-yl)acetate (195b) (0.106 g, 0.354 mmol) in THF (10 mL) and MeOH (5 mL) using sodium borohydride (0.027 g, 0.708 mmol) and stirring at RT for 2 h. This gave after work up a mixture of methyl/ethyl 2-(4-amino-6-(hydroxymethyl)-9H-pyrimido[4,5-b]indol-9-yl)acetate (195c) as a white solid (90 mg) which was used as such for the next step; MS (ES+): 301.10 & 287.10 (M+1).

Step-4: Preparation of 2-(4-amino-6-(hydroxymethyl)-9H-pyrimido[4,5-b]indol-9-yl)acetic acid (195d)

Compound 195d was prepared according to the procedure reported in step-4 of scheme-17, from a mixture of methyl/ethyl 2-(4-amino-6-(hydroxymethyl)-9H-pyrimido[4,5-b]indol-9-yl)acetate (195c) (90 mg, 0.3 mmol) in THF (5 mL) and MeOH (5 mL) using a solution of lithium hydroxide hydrate (77 mg, 1.798 mmol) in water (5 mL) and stirring at RT for 20 h. This gave after work up 2-(4-amino-6-(hydroxymethyl)-9H-pyrimido[4,5-b]indol-9-yl)acetic acid (195d) which was used as such for the next step; MS (ES+): 272.80 (M+1).

Step-5: Preparation of (1R,3S,5R)-2-(2-(4-amino-6-(hydroxymethyl)-9H-pyrimido[4,5-b]indol-9-yl)acetyl)-N-(6-bromopyridin-2-yl)-2-azabicyclo[3.1.0]hexane-3-carboxamide (195e)

Compound 195e was prepared according to the procedure reported in step-3 of scheme-1, from 2-(4-amino-6-(hydroxymethyl)-9H-pyrimido[4,5-b]indol-9-yl)acetic acid (195d) (82 mg, 0.3 mmol) in DMF (12 mL) using HCl salt of (1R,3S,5R)—N-(6-bromopyridin-2-yl)-2-azabicyclo[3.1.0]hexane-3-carboxamide (4a) (143 mg, 0.450 mmol), HATU (228 mg, 0.600 mmol), DIPEA (0.261 mL, 1.500 mmol) and stirring at RT for 15 h. This gave after workup and purification using reverse phase column chromatography [C18 column, eluting with ACN in water (containing 0.1% HCl) from 0-100%] (1R,3S,5R)-2-(2-(4-amino-6-(hydroxymethyl)-9H-pyrimido[4,5-b]indol-9-yl)acetyl)-N-(6-bromopyridin-2-yl)-2-azabicyclo[3.1.0]hexane-3-carboxamide (195e) (33 mg, 21% yield) HCl salt as a white solid; $^1H$ NMR (300 MHz, DMSO-$d_6$) δ 10.76 (s, 1H), 8.58 (s, 1H), 8.52 (s, 3H), 8.44 (s, 1H), 8.00 (d, J=8.2 Hz, 1H), 7.70 (t, J=8.0 Hz, 1H), 7.65 (d, J=8.7 Hz, 1H), 7.58-7.51 (m, 1H), 7.31 (d, J=7.7 Hz, 1H), 5.75 (d, J=17.3 Hz, 1H), 5.41 (d, J=17.2 Hz, 1H), 4.66 (s, 2H), 4.41 (dd, J=9.1, 5.6 Hz, 1H), 3.96-3.86 (m, 1H), 2.41-2.13 (m, 2H), 2.01-1.79 (m, 1H), 1.14-0.99 (m, 1H), 0.87-0.59 (m, 1H); MS (ES+): 536.10 & 538.10 (M+1); MS (ES−): 534.10 & 536.10 (M−1); Analysis calculated for $C_{24}H_{22}BrN_7O_3 \cdot 1.0HCl \cdot 2.75H_2O$: C, 46.31; H, 4.62; N, 15.75. Found: C, 46.28; H, 4.29; N, 15.40.

Scheme 196

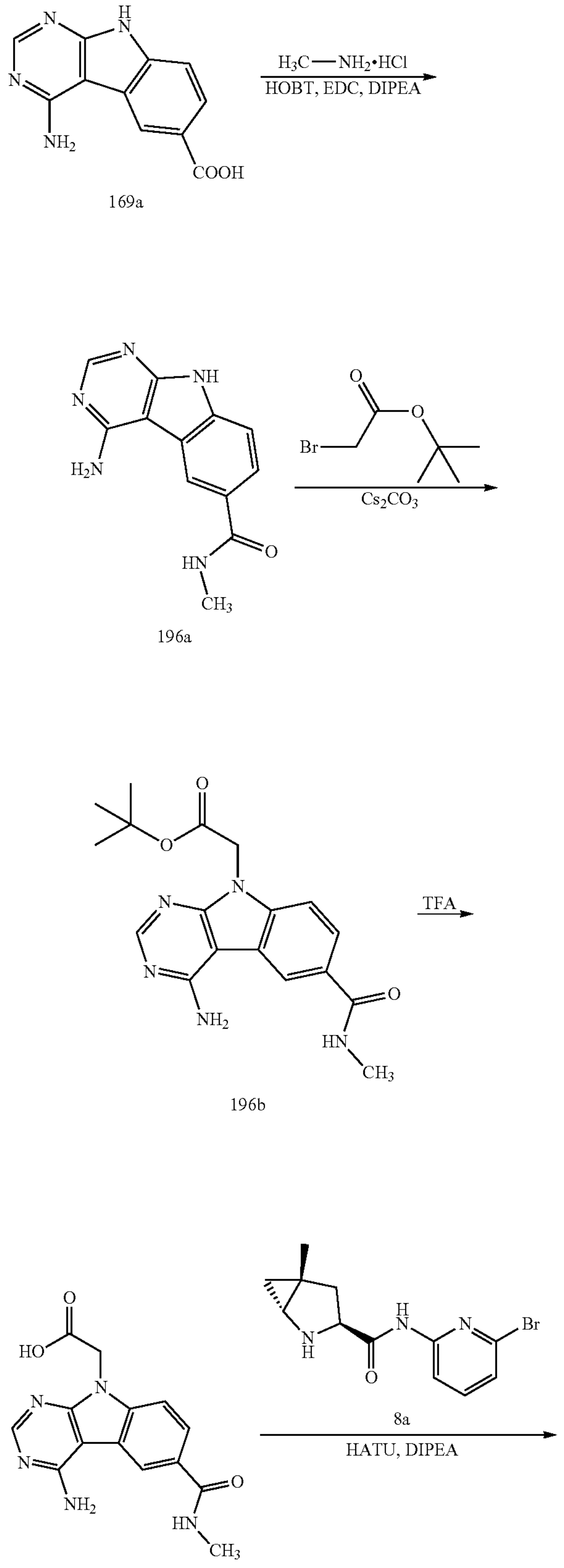

169a

196a

196b

8a

196c

-continued

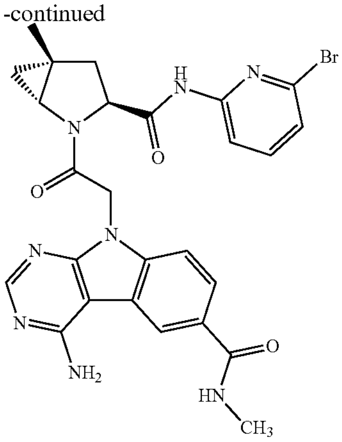

196d

Preparation of 4-amino-9-(2-((1R,3S,5R)-3-((6-bromopyridin-2-yl)carbamoyl)-5-methyl-2-azabicyclo[3.1.0]hexan-2-yl)-2-oxoethyl)-N-methyl-9H-pyrimido[4,5-b]indole-6-carboxamide (196d)

Step-1: Preparation of 4-amino-N-methyl-9H-pyrimido[4,5-b]indole-6-carboxamide (196a)

Compound 1% a was prepared according to the procedure reported in scheme-119, from 4-amino-9H-pyrimido[4,5-b]indole-6-carboxylic acid (169a) (200 mg, 0.876 mmol) in DMSO (12 mL) using methanamine hydrochloride (178 mg, 2.63 mmol; CAS #593-51-1), HOBT (59.2 mg, 0.438 mmol), EDC (336 mg, 1.753 mmol), DIPEA (0.458 mL, 2.63 mmol) and stirring at RT for 20 h. The residue obtained after work up of 4-amino-N-methyl-9H-pyrimido[4,5-b]indole-6-carboxamide (1% a) was used as such for the next step; MS (ES+): 241.90 (M+1); (ES−): 239.85 (M−1).

Step-2: Preparation of tert-butyl 2-(4-amino-6-(methylcarbamoyl)-9H-pyrimido[4,5-b]indol-9-yl)acetate (1% b)

Compound 1% b was prepared according to the procedure reported in step-1 of scheme-1, from 4-amino-N-methyl-9H-pyrimido[4,5-b]indole-6-carboxamide (1% a) (211 mg, 0.876 mmol) in DMF using tert-butyl 2-bromoacetate, $Cs_2CO_3$ and stirring at RT. This gave after workup tert-butyl 2-(4-amino-6-(methylcarbamoyl)-9H-pyrimido[4,5-b]indol-9-yl)acetate (196b) which was used as such in the next step; MS (ES+): 356.20 (M+1); (ES−): 354.10 (M−1).

Step-3: Preparation of 2-(4-amino-6-(methylcarbamoyl)-9H-pyrimido[4,5-b]indol-9-yl)acetic acid (1% c)

Compound 196c was prepared according to the procedure reported in step-2 of scheme-1, from tert-butyl 2-(4-amino-6-(methylcarbamoyl)-9H-pyrimido[4,5-b]indol-9-yl)acetate (196b) (311 mg, 0.876 mmol) in DCM (10 mL) using TFA and stirring at RT. This gave after workup 2-(4-amino-6-(methylcarbamoyl)-9H-pyrimido[4,5-b]indol-9-yl)acetic acid (196c) which was used as such in the next step; MS (ES+): 300.10 (M+1); (ES−): 298.05 (M−1).

Step-4: Preparation of 4-amino-9-(2-((1R,3S,5R)-3-((6-bromopyridin-2-yl)carbamoyl)-5-methyl-2-azabicyclo[3.1.0]hexan-2-yl)-2-oxoethyl)-N-methyl-9H-pyrimido[4,5-b]indole-6-carboxamide (196d)

Compound 1% d was prepared according to the procedure reported in step-3 of scheme-1, from 2-(4-amino-6-(methylcarbamoyl)-9H-pyrimido[4,5-b]indol-9-yl)acetic acid (1% c) (131 mg, 0.438 mmol) in DMF (12 mL) using HCl salt of (1R,3S,5R)—N-(6-bromopyridin-2-yl)-5-methyl-2-azabicyclo[3.1.0]hexane-3-carboxamide (8a) (146 mg, 0.438 mmol), HATU (333 mg, 0.876 mmol) DIPEA (0.381 mL, 2.190 mmol) and stirring at RT for 21 h. This gave after workup and purification by flash column chromatography [silica gel (25 g), eluting with MeOH in DCM from 0-10%] followed by purification using reverse phase column chromatography [C18 column eluting with ACN in water (containing 0.1% HCl) from 0-100%] 4-amino-9-(2-((1R,3S,5R)-3-((6-bromopyridin-2-yl)carbamoyl)-5-methyl-2-azabicyclo[3.1.0]hexan-2-yl)-2-oxoethyl)-N-methyl-9H-pyrimido[4,5-b]indole-6-carboxamide (196d) (19 mg, 7.5% yield) as a white solid; 1H NMR (300 MHz, DMSO-$d_6$) δ 10.77 (s, 1H), 9.05 (s, 1H), 8.58 (s, 1H), 8.51-8.35 (m, 4H), 8.05-7.96 (m, 2H), 7.76-7.65 (m, 2H), 7.31 (d, J=7.7 Hz, 1H), 5.73 (d, J=17.4 Hz, 1H), 5.37 (d, J=17.3 Hz, 1H), 4.37 (dd, J=9.1, 5.8 Hz, 1H), 3.72-3.64 (m, 1H), 2.86 (d, J=4.4 Hz, 3H), 2.58-2.38 (m, 1H), 1.98 (dd, J=13.2, 5.9 Hz, $1H_1$), 1.30 (s, 3H), 1.09-0.97 (m, 1H), 0.96-0.90 (m, 1H); MS (ES+): 577.15 & 579.20 (M+1); MS (ES−): 575.10 & 577.10 (M−1).

Scheme 197

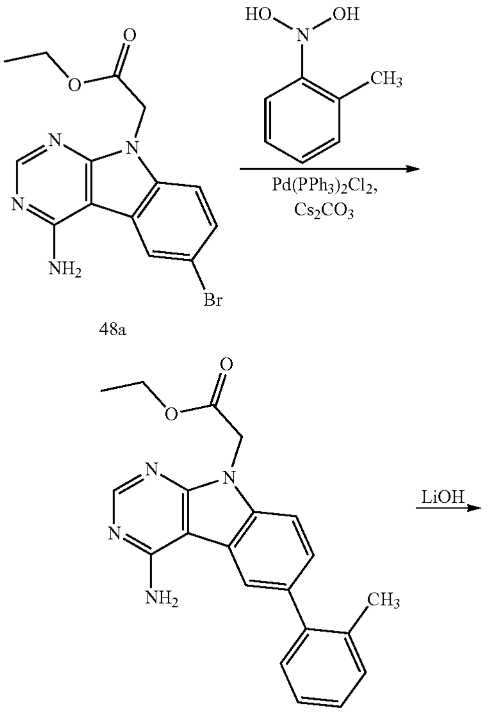

48a

197a

-continued

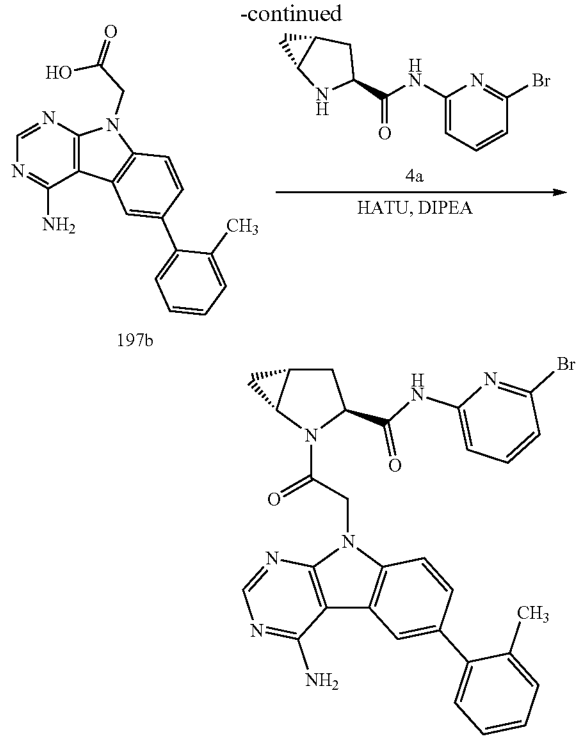

4a

197b

197c

Preparation of (1R,3S,5R)-2-(2-(4-amino-6-(o-tolyl)-9H-pyrimido[4,5-b]indol-9-yl)acetyl)-N-(6-bromopyridin-2-yl)-2-azabicyclo[3.1.0]hexane-3-carboxamide (197c)

Step-1: Preparation of ethyl 2-(4-amino-6-(o-tolyl)-9H-pyrimido[4,5-b]indol-9-yl)acetate (197a)

Compound 197a was prepared according to the procedure reported in step-1 of scheme-59, from ethyl 2-(4-amino-6-bromo-9H-pyrimido[4,5-b]indol-9-yl)acetate (48a) (150 mg, 0.430 mmol) in dioxane (15 mL) using o-tolylboronic acid (88 mg, 0.644 mmol; CAS #16419-60-6), bis(triphenylphosphine)palladium(II) chloride (60.3 mg, 0.086 mmol) a solution of cesium carbonate (210 mg, 0.644 mmol) in water (1.8 mL) and heating at 100° C. for 17 h. This gave after workup and purification by flash column chromatography [silica gel (12 g), eluting with MeOH in DCM from 0-5%] ethyl 2-(4-amino-6-(o-tolyl)-9H-pyrimido[4,5-b]indol-9-yl)acetate (197a) (70 mg, 45% yield) as an off-white solid; MS (ES+): 361.20 (M+1).

Step-2: Preparation of 2-(4-amino-6-(o-tolyl)-9H-pyrimido[4,5-b]indol-9-yl)acetic acid (197b)

Compound 197b was prepared according to the procedure reported in step-4 of scheme-17, from ethyl 2-(4-amino-6-(o-tolyl)-9H-pyrimido[4,5-b]indol-9-yl)acetate (197a) (64 mg, 0.178 mmol) in THF (3 mL) and methanol (3 mL) using a solution of lithium hydroxide hydrate (45.6 mg, 1.065 mmol) in water (3 mL) and stirring at RT for 14 h. This gave after workup 2-(4-amino-6-(o-tolyl)-9H-pyrimido[4,5-b]indol-9-yl)acetic acid (197b) which was used as such for the next step; MS (ES+): 333.15 (M+1).

Step-3: Preparation of (1R,3S,5R)-2-(2-(4-amino-6-(o-tolyl)-9H-pyrimido[4,5-b]indol-9-yl)acetyl)-N-(6-bromopyridin-2-yl)-2-azabicyclo[3.1.0]hexane-3-carboxamide (197c)

Compound 197c was prepared according to the procedure reported in step-3 of scheme-1, from 2-(4-amino-6-(o-tolyl)-9H-pyrimido[4,5-b]indol-9-yl)acetic acid (197b) (59.2 mg, 0.178 mmol) in DMF (8 mL) using HCl salt of (1R,3S,5R)—N-(6-bromopyridin-2-yl)-2-azabicyclo[3.1.0]hexane-3-carboxamide (4a) (85 mg, 0.267 mmol), HATU (169 mg, 0.445 mmol), DIPEA (0.186 mL, 1.068 mmol) and stirring at RT for 19 h. This gave after workup and purification by flash column chromatography [silica gel (25 g), MeOH in DCM from 0-10%] followed by purification using reverse phase column chromatography [C18 column, eluting with ACN in water (containing 0.1% HCl) from 0-100%] (1R,3S,5R)-2-(2-(4-amino-6-(o-tolyl)-9H-pyrimido[4,5-b]indol-9-yl)acetyl)-N-(6-bromopyridin-2-yl)-2-azabicyclo[3.1.0]hexane-3-carboxamide (197c) (23 mg, 22% yield) as a white solid; $^1$H NMR (300 MHz, DMSO-$d_6$) δ 10.79 (s, 1H), 8.61 (s, 1H), 8.52-8.50 (m, 2H), 8.02 (d, J=8.2 Hz, 1H), 7.78-7.66 (m, 2H), 7.52 (dd, J=8.4, 1.5 Hz, 1H), 7.38-7.26 (m, 6H), 5.81 (d, J=17.4 Hz, 1H), 5.45 (d, J=17.2 Hz, 11H), 4.44 (dd, J=9.1, 5.5 Hz, 1H), 4.01-3.84 (m, 1H), 2.46-2.14 (m, 5H), 2.02-1.83 (m, 1H), 1.17-1.03 (m, 1H), 0.89-0.72 (m, 1H); MS (ES+): 596.15 & 598.15; (ES−): 594.10 & 596.10 (M−1).

Scheme 198

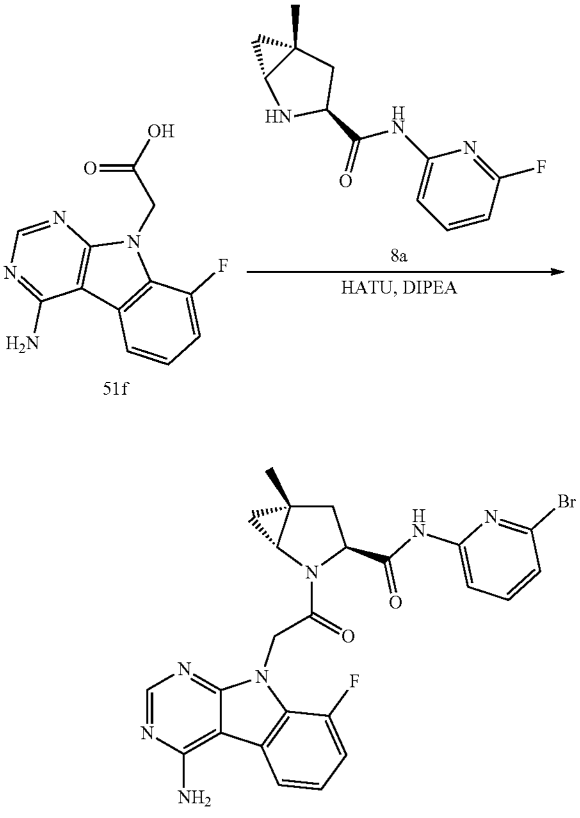

51f

198a

Preparation of (1R,3S,5R)-2-(2-(4-amino-8-fluoro-9H-pyrimido[4,5-b]indol-9-yl)acetyl)-N-(6-bromopyridin-2-yl)-5-methyl-2-azabicyclo[3.1.0]hexane-3-carboxamide (198a)

Compound 198a was prepared according to the procedure reported in step-3 of scheme-1, from TFA salt of 2-(4-amino-8-fluoro-9H-pyrimido[4,5-b]indol-9-yl)acetic acid (51f) (50 mg, 0.134 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (44.4 mg, 0.134 mmol), HATU (76 mg, 0.200 mmol), DIPEA (0.116 mL, 1.068 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-8-fluoro-9H-pyrimido[4,5-b]indol-9-yl)acetyl)-N-(6-bromopyridin-2-yl)-5-methyl-2-azabicyclo[3.1.0]hexane-3-carboxamide (198a) (48 mg, 67% yield) HCl salt as a white solid. $^1$H NMR (300 MHz, DMSO-$d_6$) δ 10.78 (s, 1H, $D_2O$ exchangeable), 8.58 (s, 1H), 8.40 (s, 2H, $D_2O$ exchangeable), 8.30 (dd, J=5.9, 3.0 Hz, 1H), 8.02 (d, J=8.1 Hz, 1H), 7.70 (t, J=8.0 Hz, 1H), 7.38-7.29 (m, 3H), 5.75 (d, J=17.5 Hz, 1H), 5.41 (d, J=17.5 Hz, 1H), 4.39 (dd, J=9.0, 6.0 Hz, 1H), 3.66 (dd, J=5.4, 2.3 Hz, 1H), 2.47-2.41 (m, 1H), 1.99 (dd, J=13.3, 5.9 Hz, 1H), 1.30 (s, 3H), 1.03 (t, J=5.4 Hz, 1H), 0.86-0.71 (m, 1H). $^{19}$F NMR (282 MHz, DMSO) δ−134.67. MS (ES+): 538.1 (M+1); (ES−): 536.1 (M−1); Analysis calculated for $C_{24}H_{20}BrFN_7O_2 \cdot 1.75H_2O \cdot HCl$: C, 47.54; H, 4.24; Cl, 5.85; N, 16.17. Found: C, 47.63; H, 4.20; Cl, 5.59; N, 15.97.

Scheme 199

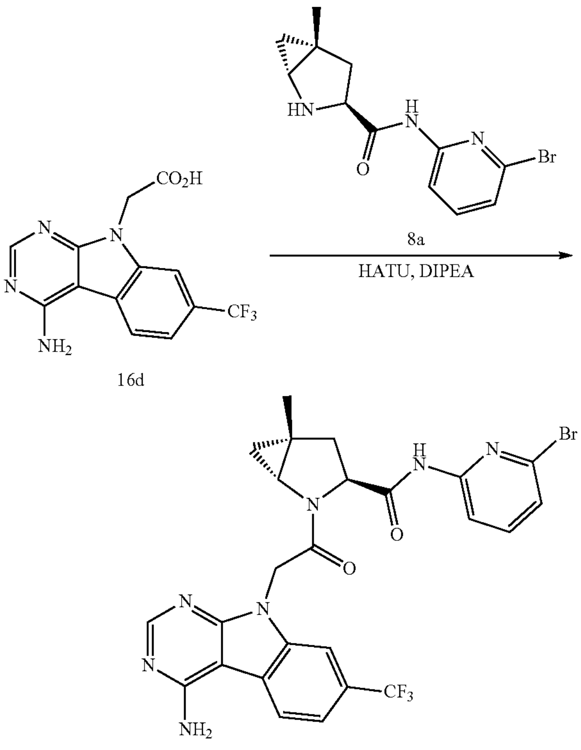

16d

199a

Preparation of (1R,3S,5R)-2-(2-(4-amino-7-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (199a)

Compound 199a was prepared according to the procedure reported in step-3 of scheme-1, from TFA salt of 2-(4-amino-7-(trifluoromethyl)-9H-pyrimido[4,5-b]indol-9-yl)acetic acid (16d) (50 mg, 0.118 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (39.2 mg, 0.118 mmol), HATU (67.2 mg, 0.177 mmol), DIPEA (0.103 mL, 0.589 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-7-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (199a) HCl salt (50 mg, 72% yield) HCl salt as a white solid; $^1$H NMR (300 MHz, DMSO-$d_6$) δ 10.77 (s, 1H, $D_2O$ exchangeable), 8.84-8.69 (m, 3H, 2H $D_2O$ exchangeable), 8.66 (s, 1H), 8.18 (s, 1H), 8.00 (d, J=8.1 Hz, 1H), 7.79-7.61 (m, 2H), 7.31 (d, J=7.6 Hz, 1H), 5.85 (d, J=17.4 Hz, 1H), 5.46 (d, J=17.3 Hz, 1H), 4.38 (dd, J=9.0, 5.9 Hz, 1H), 3.69 (dd, J=5.6, 2.4 Hz, 1H), 2.48-2.40 (m, 1H), 1.99 (dd, J=13.2, 5.9 Hz, 1H), 1.32 (s, 3H), 1.03 (t, J=5.4 Hz, 1H), 0.92 (dd, J=5.4, 2.4 Hz, 1H). $^{19}$F NMR (282 MHz, DMSO) δ-59.34. MS (ES+): 588.1 (M+1); (ES−): 586.1 (M−1); Analysis calculated for $C_{25}H_{21}BrF_3N_7O_2 \cdot 2H_2O \cdot HCl$: C, 45.44; H, 3.97; Cl, 5.36; N, 14.84. Found: C, 45.44; H, 3.85; Cl, 5.30; N, 14.74.

Preparation of (1R,3S,5R)-2-(2-(4-amino-7-bromo-9H-pyrimido[4,5-b]indol-9-yl)acetyl)-N-(6-bromopyridin-2-yl)-5-methyl-2-azabicyclo[3.1.0]hexane-3-carboxamide (200a)

Compound 200a was prepared according to the procedure reported in step-3 of scheme-1, from TFA salt of 2-(4-amino-7-bromo-9H-pyrimido[4,5-b]indol-9-yl)acetic acid (52e) (60 mg, 0.138 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (45.9 mg, 0.138 mmol), HATU (79 mg, 0.207 mmol), DIPEA (0.120 mL, 0.689 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-7-bromo-9H-pyrimido[4,5-b]indol-9-yl)acetyl)-N-(6-bromopyridin-2-yl)-5-methyl-2-azabicyclo[3.1.0]hexane-3-carboxamide (200a) (59 mg, 71% yield) HCl salt as a white solid; $^1$H NMR (300 MHz, DMSO-$d_6$) δ 10.78 (s, 1H, $D_2O$ exchangeable), 8.67-8.50 (m, 3H, 2H $D_2O$ exchangeable), 8.46 (d, J=8.5 Hz, 1H), 8.06-7.95 (m, 2H), 7.70 (t, J=8.0 Hz, 1H), 7.57 (dd, J=8.4, 1.7 Hz, 1H), 7.32 (d, J=7.7 Hz, 1H), 5.73 (d, J=17.4 Hz, 1H), 5.36 (d, J=17.3 Hz, 1H), 4.38 (dd, J=9.1, 6.0 Hz, 1H), 3.67 (dd, J=5.6, 2.4 Hz, 1H), 2.48-2.42 (m, 1H), 1.98 (dd, J=13.3, 5.9 Hz, 1H), 1.31 (s, 3H), 1.02 (t, J=5.6 Hz, 1H), 0.94 (dd, J=5.3, 2.4 Hz, 1H). MS (ES+): 598.0/600.1 (M+1): (ES−): 596/598.0 (M−1); Analysis calculated for $C_{24}H_{21}Br_2N_7O_2$ $2H_2O \cdot HCl$: C, 42.91; H, 3.90; Cl, 5.28; N, 14.60. Found: C, 43.02; H, 3.69; Cl, 5.09; N, 14.47.

Scheme 200

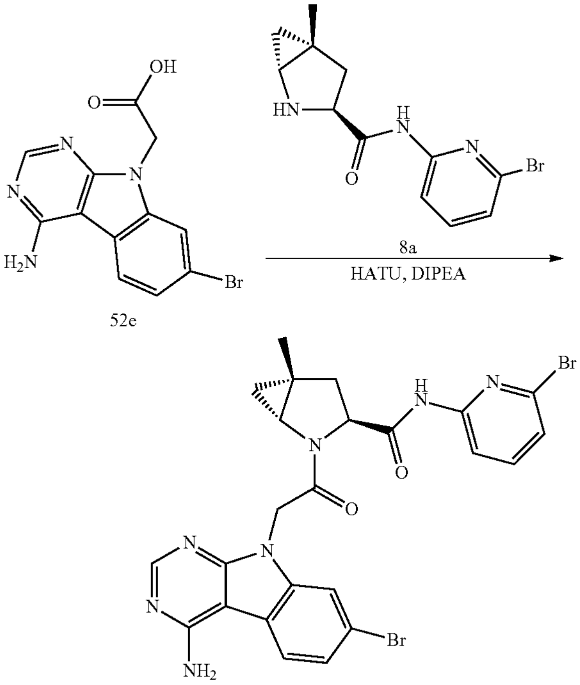

52e

200a

Scheme 201

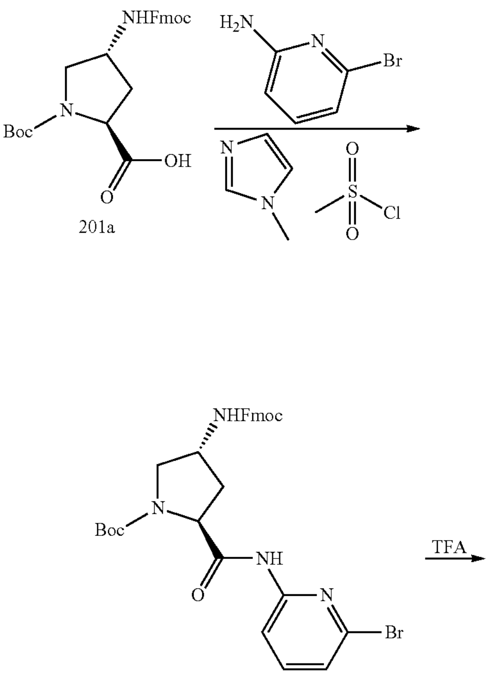

201a

201b

-continued

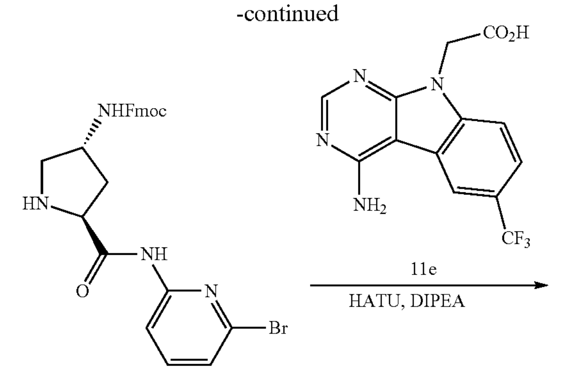

201c

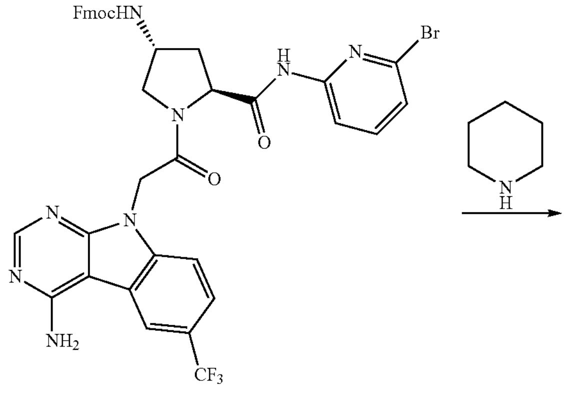

201d

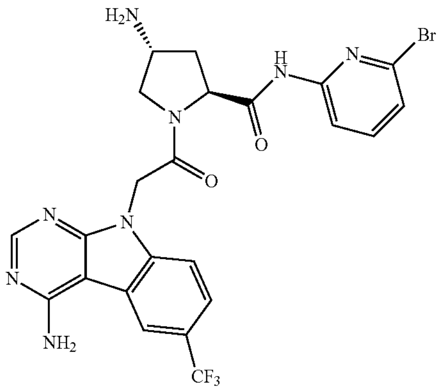

201e

Preparation of (2S,4R)-4-amino-1-(2-(4-amino-6-(trifluoromethyl)-9H-pyrimido[4,5-b]indol-9-yl)acetyl)-N-(6-bromopyridin-2-yl)pyrrolidine-2-carboxamide (201e)

Step-1: Preparation of (2S,4R)-tert-butyl 4-((((9H-fluoren-9-yl)methoxy)carbonyl)amino)-2-((6-bromopyridin-2-yl)carbamoyl)pyrrolidine-1-carboxylate (201b)

Compound 201b was prepared according to the procedure reported in step-1 of scheme-53, from (2S,4R)-4-((((9H-fluoren-9-yl)methoxy)carbonyl)amino)-1-(tert-butoxycarbonyl)pyrrolidine-2-carboxylic acid (201a) (1 g, 2.210 mmol; CAS #176486-63-8) in DCM (30 mL) using 1-methyl-1H-imidazole (0.440 mL, 5.52 mmol), methanesulfonyl chloride (0.205 mL, 2.65 mmol) and 6-bromopyridin-2-amine (0.382 g, 2.210 mmol) and stirring at RT for 18 h. This gave after workup (2S,4R)-tert-butyl 4-((((9H-fluoren-9-yl)methoxy)carbonyl)amino)-2-((6-bromopyridin-2-yl)carbamoyl)pyrrolidine-1-carboxylate (201b) (1.22 g, 91% yield); MS (ES+): 607.60 (M+1).

Step-2: Preparation of (9H-fluoren-9-yl)methyl ((3R,5S)-5-((6-bromopyridin-2-yl)carbamoyl)pyrrolidin-3-yl)carbamate (201c)

Compound 201c was prepared according to the procedure reported in step-2 of scheme-1, from (2S,4R)-tert-butyl 4-((((9H-fluoren-9-yl)methoxy)carbonyl)amino)-2-((6-bromopyridin-2-yl)carbamoyl)pyrrolidine-1-carboxylate (201b) (1.2 g, 1.975 mmol) in DCM (11 mL) using TFA (1.065 mL, 13.83 mmol) and stirring overnight at RT. This gave after workup and purification using reverse phase column chromatography [C18 column (50 g), eluting with ACN in water (containing 0.1% HCl) from 0-100%] HCl salt of (9H-fluoren-9-yl)methyl ((3R,5S)-5-((6-bromopyridin-2-yl)carbamoyl)pyrrolidin-3-yl)carbamate (201c) (720 mg, 67% yield); $^1$H NMR (300 MHz, DMSO-$d_6$) δ 11.47 (s, 1H), 10.15 (s, 1H), 8.94 (s, 1H), 8.06 (d, J=8.1 Hz, 1H), 7.99-7.62 (m, 6H), 7.39 (dt, J=25.2, 7.3 Hz, 5H), 4.63-4.51 (m, 1H), 4.46-4.31 (m, 2H), 4.31-4.14 (m, 2H), 3.52 (dd, J=11.7, 6.9 Hz, 1H), 3.14 (dd, J=12.1, 5.6 Hz, 1H), 2.36 (t, J=6.7 Hz, 1H), 2.23 (dt, J=13.9, 7.2 Hz, 1H); MS (ES+): 507.10 (M+1).

Step-3: Preparation of (9H-fluoren-9-yl)methyl ((3R,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)carbamate (201d)

Compound 201d was prepared according to the procedure reported in step-3 of scheme-1, from HCl salt of (9H-fluoren-9-yl)methyl ((3R,5S)-5-((6-bromopyridin-2-yl)carbamoyl)pyrrolidin-3-yl)carbamate (201c) (120 mg, 0.221 mmol) in DMF (3 mL) using TFA salt of 2-(4-amino-6-(trifluoromethyl)-9H-pyrimido[4,5-b]indol-9-yl)acetic acid (11e) (94 mg, 0.221 mmol), HATU (126 mg, 0.331 mmol), DIPEA (0.192 mL, 1.103 mmol) and stirring at RT for 16 h. This gave after workup and purification by flash column chromatography [silica gel (24 g), eluting with DMA-80 in DCM from 0-50%] (9H-fluoren-9-yl)methyl ((3R,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)carbamate (201d) (173 mg, 98% yield) as a white solid; $^1$H NMR (300 MHz, DMSO-$d_6$) δ 10.88 (s, 1H), 8.79 (s, 1H), 8.34 (s, 1H), 8.01 (d, J=8.2 Hz, 1H), 7.92 (d, J=7.4 Hz, 2H), 7.77-7.64 (m, 5H), 7.55 (s, 2H), 7.38 (ddd, J=27.2, 13.4, 7.5 Hz, 6H), 5.34 (s, 2H), 4.55 (s, 1H), 4.43 (d, J=6.7 Hz, 2H), 4.28 (d, J=6.7 Hz, 1H), 4.17 (d, J=9.2 Hz, 1H), 3.61 (s, 1H), 3.22-3.02 (m, OH), 2.24 (d, J=19.2 Hz, 1H), 2.09 (d, J=6.0 Hz, 1H); $^{19}$F NMR (282 MHz, DMSO-$d_6$) δ-58.18.

Step-4: Preparation of (2S,4R)-4-amino-1-(2-(4-amino-6-(trifluoromethyl)-9H-pyrimido[4,5-b]indol-9-yl)acetyl)-N-(6-bromopyridin-2-yl)pyrrolidine-2-carboxamide (201e)

Compound 201e was prepared according to the procedure reported in step-4 of scheme-180, from (9H-fluoren-9-yl) methyl ((3R,5S)-1-(2-(4-amino-6-(trifluoromethyl)-9H-pyrimido[4,5-b]indol-9-yl)acetyl)-5-((6-bromopyridin-2-yl) carbamoyl)pyrrolidin-3-yl)carbamate (201d) (170 mg, 0.213 mmol) in DMF (0.8 mL) using piperidine (0.210 mL, 2.126 mmol) and stirring at RT for 1 h. This gave after work up and purification using flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (2S,4R)-4-amino-1-(2-(4-amino-6-(trifluoromethyl)-9H-pyrimido[4,5-b]indol-9-yl)acetyl)-N-(6-bromopyridin-2-yl)pyrrolidine-2-carboxamide (201e) (59 mg, 48% yield) HCl salt as a white solid: $^1H$ NMR (300 MHz, DMSO-$d_6$) δ (a mixture of two rotamers) 11.50 and 11.04 (2s, 1H, $D_2O$ exchangeable), 9.02 (s, 1H), 8.91 (s, 2H, $D_2O$ exchangeable), 8.69 (m, 4H, 3H $D_2O$ exchangeable), 8.21-7.96 (m, 2H), 7.89-7.81 (m, 1H), 7.71 (t, J=8.0 Hz, 1H), 7.43 and 7.34 (2d, J=7.7 Hz, 1H), 5.63-5.49 (m, 2H), 4.70 (dd, J=8.5, 6.0 Hz, 1H), 4.21 (dd, J=11.2, 6.2 Hz, 1H), 4.13-3.97 (m, 2H), 2.48 (m, 1H), 2.27 (dt, J=13.1, 6.1 Hz, 1H), $^{19}F$ NMR (282 MHz, DMSO-$d_6$) δ-58.58. MS (ES+): 577.1 (M+1): (ES−): 575.1 (M−1): Analysis calculated for $C_{23}H_{20}BrF_3N_8O_2$ $1.25H_2O \cdot 1.9HCl \cdot 0.5DMSO$: C, 40.70; H, 3.90; Cl, 9.51; N, 15.82. Found: C, 40.41; H, 3.65; Cl, 9.32; N, 15.85.

Scheme 202

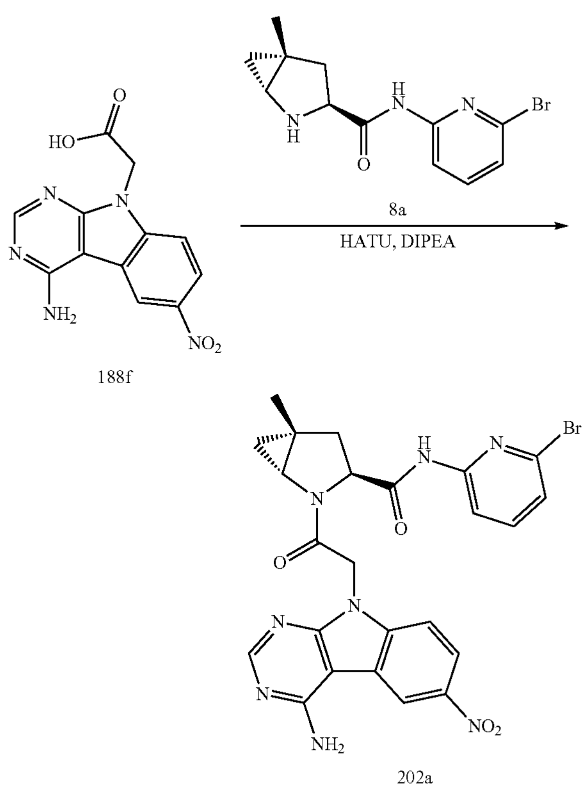

188f

202a

Preparation of (1R,3S,5R)-2-(2-(4-amino-6-nitro-9H-pyrimido[4,5-b]indol-9-yl)acetyl)-N-(6-bromopyridin-2-yl)-5-methyl-2-azabicyclo[3.1.0]hexane-3-carboxamide (202a)

Compound 202a was prepared according to the procedure reported in step-3 of scheme-1, from 2-(4-amino-6-nitro-9H-pyrimido[4,5-b]indol-9-yl)acetic acid (188f) (91 mg, 0.317 mmol) in DMF (12 mL) using HCl salt of (1R,3S,5R)—N-(6-bromopyridin-2-yl)-5-methyl-2-azabicyclo[3.1.0]hexane-3-carboxamide (8a) (105 mg, 0.317 mmol), HATU (241 mg, 0.634 mmol) and DIPEA (0.276 mL, 1.585 mmol) and stirring at RT for 13 h. This gave after workup and purification using reverse phase column chromatography [C18 column, eluting with ACN in water (containing 0.1% HCl) from 0-100%] (1R,3S,5R)-2-(2-(4-amino-6-nitro-9H-pyrimido[4,5-b]indol-9-yl)acetyl)-N-(6-bromopyridin-2-yl)-5-methyl-2-azabicyclo[3.1.0]hexane-3-carboxamide (202a) (42 mg, 23% yield) as a white solid: $^1H$ NMR (300 MHz, DMSO-$d_6$) δ 10.77 (s, 1H), 9.52 (d, J=2.2 Hz, 1H), 8.72 (s, 2H), 8.63 (s, 1H), 8.40 (dd, J=9.1, 2.2 Hz, 1H), 8.00 (d, J=8.2 Hz, 1H), 7.87 (d, J=9.1 Hz, 1H), 7.69 (t, J=8.0 Hz, 1H), 7.31 (d, J=7.7 Hz, 11H), 5.79 (d, J=17.4 Hz, 1H), 5.43 (d, J=17.3 Hz, 1H), 4.37 (dd, J=9.0, 6.0 Hz, 1H), 3.68 (dd, J=5.6, 2.4 Hz, 1H), 2.50-2.42 (m, 1H), 1.98 (dd, J=13.2, 5.9 Hz, 1H), 1.31 (s, 3H), 1.02 (t, J=5.4 Hz, 1H), 0.95 (dd, J=5.4, 2.4 Hz, 1H); MS (ES+): 565.10 & 567.10 (M+1); MS (ES−): 563.10 & 565.00 (M−1); Analysis calculated for $C_{24}H_{21}BrNSO_4 \cdot 0.85HCl \cdot 2.0H_2O$: C, 45.58; H, 4.12; N, 17.72; Cl, 4.77. Found: C, 45.65; H, 3.97; N, 17.42; Cl, 4.59.

Scheme 203

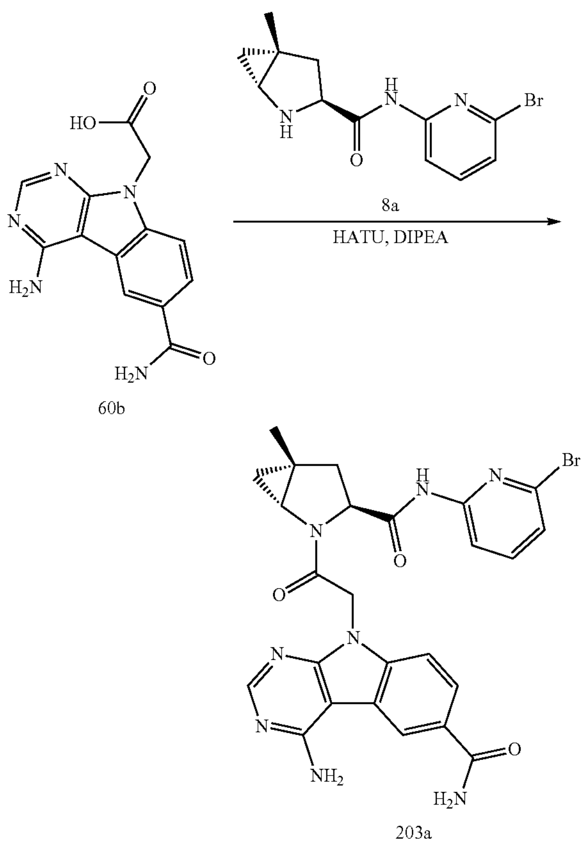

60b

203a

Preparation of 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-6-carboxamide (203a)

Compound 203a was prepared according to the procedure reported in step-3 of scheme-1, from 2-(4-amino-6-carbamoyl-9H-pyrimido[4,5-b]indol-9-yl)acetic acid (60b) (0.079 g, 0.278 mmol) in DMF (10 mL) using HCl salt of (1R,3S,5R)—N-(6-bromopyridin-2-yl)-5-methyl-2-azabicyclo

[3.1.0]hexane-3-carboxamide (8a) (111 mg, 0.334 mmol), HATU (211 mg, 0.556 mmol), DIPEA (0.242 mL, 1.39 mmol) and stirring at RT for 22 h. This gave after workup and purification using reverse phase column chromatography [C18 column, eluting with ACN in water (containing 0.1% HCl) from 0-100%] 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-6-carboxamide (203a) (42 mg, 27% yield) as a white solid; $^1$H NMR (300 MHz, DMSO-$d_6$) δ 10.77 (s, 1H), 9.14 (d, J=1.6 Hz, 1H), 8.66 (s, 3H), 8.62 (s, 1H), 8.07 (dd, J=8.7, 1.5 Hz, 1H), 8.01 (d, J=8.2 Hz, 1H), 7.96 (s, 1H), 7.76-7.64 (m, 2H), 7.48 (s, 1H), 7.31 (d, J=7.7 Hz, 1H), 5.75 (d, J=17.4 Hz, 1H), 5.38 (d, J=17.3 Hz, 1H), 4.38 (dd, J=9.1, 5.9 Hz, 1H), 3.77-3.63 (m, 1H), 2.53-2.38 (m, 1H), 1.98 (dd, J=13.1, 5.8 Hz, 1H), 1.30 (s, 3H), 1.07-0.97 (m, 1H), 0.96-0.89 (m, 1H); MS (ES+): 563.20 & 565.10 (M+1); MS (ES−): 561.10 & 563.10 (M−1); Analysis calculated for $C_{25}H_{23}BrN_8O_3\cdot1.0HCl\cdot2.75H_2O$: C, 46.24; H, 4.58; N, 17.25. Found: C, 46.38; H, 4.51; N, 16.99.

Scheme 204

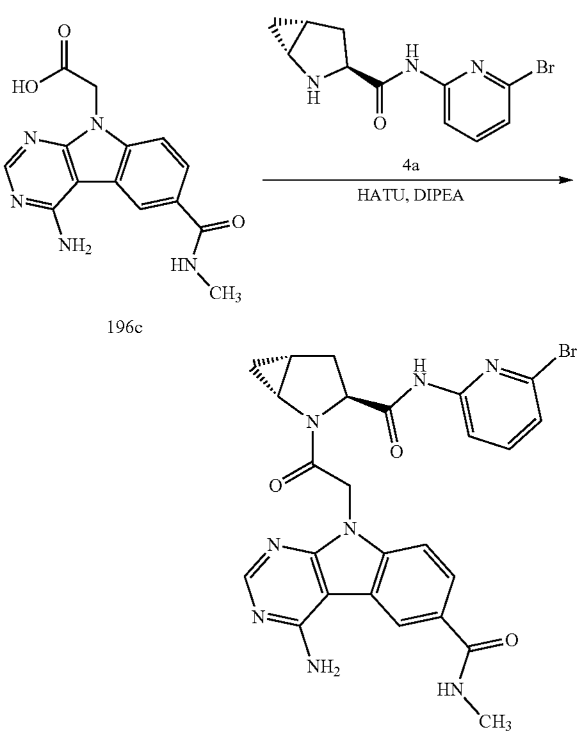

196c

204a

Preparation of 4-amino-9-(2-((1R,3S,5R)-3-((6-bromopyridin-2-yl)carbamoyl)-2-azabicyclo[3.1.0]hexan-2-yl)-2-oxoethyl)-N-methyl-9H-pyrimido[4,5-b]indole-6-carboxamide (204a)

Compound 204a was prepared according to the procedure reported in step-3 of scheme-1, from 2-(4-amino-6-(methylcarbamoyl)-9H-pyrimido[4,5-b]indol-9-yl)acetic acid (196c) (0.131 g, 0.438 mmol) in DMF (12 mL) using HCl salt of (1R,3S,5R)—N-(6-bromopyridin-2-yl)-2-azabicyclo[3.1.0]hexane-3-carboxamide (4a) (167 mg, 0.526 mmol), HATU (333 mg, 0.876 mmol), DIPEA (0.381 mL, 2.19 mmol) and stirring at RT for 21 h. This gave after workup and purification by flash column chromatography [silica gel (40 g), eluting with MeOH in DCM from 0-8% then 15%] followed by purification using reverse phase column chromatography [C18 column, eluting with ACN in water (containing 0.1% HCl) from 0-100%] 4-amino-9-(2-((1R,3S,5R)-3-((6-bromopyridin-2-yl)carbamoyl)-2-azabicyclo[3.1.0]hexan-2-yl)-2-oxoethyl)-N-methyl-9H-pyrimido[4,5-b]indole-6-carboxamide (204a) (12 mg, 5% yield) HCl salt as a white solid; $^1$H NMR (300 MHz, DMSO-$d_6$) δ 10.77 (s, 1H), 9.13 (s, 1H), 8.66 (s, 2H), 8.62 (s, 1H), 8.55-8.44 (m, 1H), 8.06-7.95 (m, 2H), 7.78-7.66 (m, 2H), 7.31 (d, J=7.7 Hz, 1H), 5.79 (d, J=17.3 Hz, 1H), 5.43 (d, J=17.3 Hz, 1H), 4.42 (dd, J=9.1, 5.4 Hz, 1H), 3.98-3.83 (m, 1H), 2.86 (d, J=4.4 Hz, 3H), 2.41-2.14 (m, 2H), 2.01-1.82 (m, 1H), 1.17-0.94 (m, 1H), 0.87-0.60 (m, 1H); MS (ES+): 563.15 & 565.10 (M+1), MS (ES−): 561.10 & 563.05 (M−1).

Scheme 205

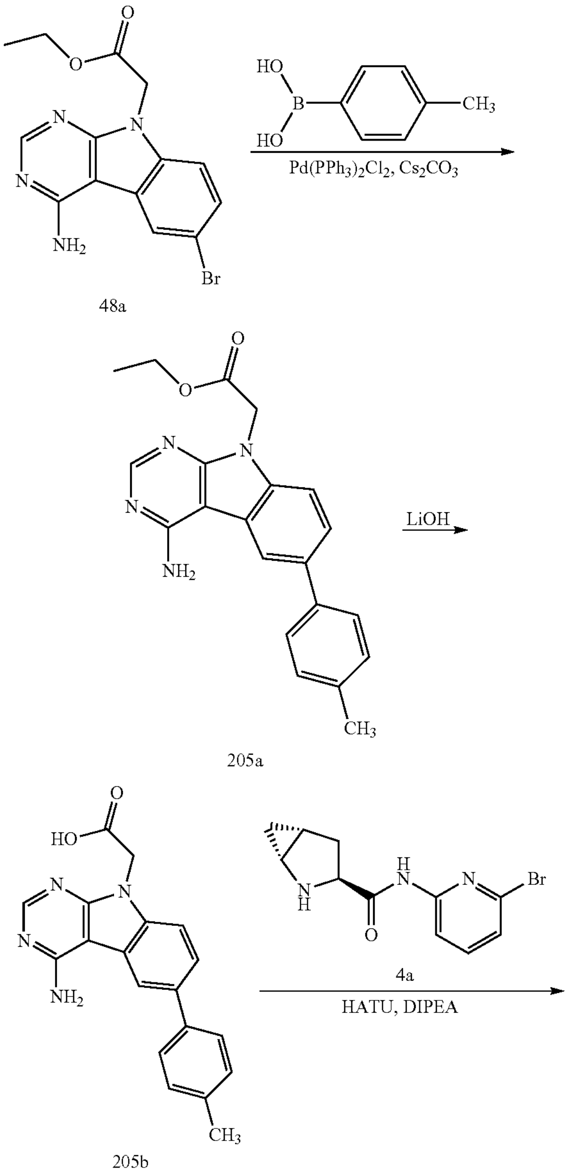

48a

205a

205b

-continued

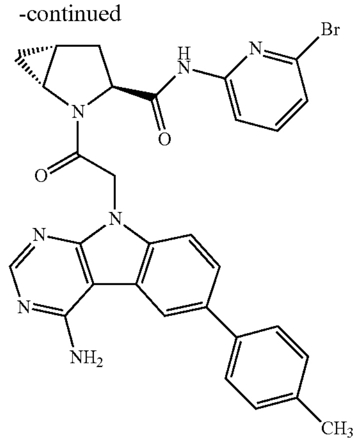

205c

Preparation of (1R,3S,5R)-2-(2-(4-amino-6-(p-tolyl)-9H-pyrimido[4,5-b]indol-9-yl)acetyl)-N-(6-bromopyridin-2-yl)-2-azabicyclo[3.1.0]hexane-3-carboxamide (205c)

Step-1: Preparation of ethyl 2-(4-amino-6-(p-tolyl)-9H-pyrimido[4,5-b]indol-9-yl)acetate (205a)

Compound 205a was prepared according to the procedure reported in step-1 of scheme-62, from ethyl 2-(4-amino-6-bromo-9H-pyrimido[4,5-b]indol-9-yl)acetate (48a) (200 mg, 0.573 mmol) in dioxane (18 mL) using p-tolylboronic acid (117 mg, 0.859 mmol; CAS #16419-60-6), bis(triphenylphosphine)palladium(II) chloride (80 mg, 0.115 mmol) a solution of cesium carbonate (280 mg, 0.859 mmol) in water (2.2 mL) and heating at 100° C. for 13 h. This gave after workup and purification by flash column chromatography [silica gel (25 g), eluting with MeOH in DCM from 0-5%] ethyl 2-(4-amino-6-(p-tolyl)-9H-pyrimido[4,5-b]indol-9-yl)acetate (205a) (52 mg, 25% yield) as an off-white solid; 1H NMR (300 MHz, DMSO-$d_6$) δ 8.62 (d, J=1.6 Hz, 1H), 8.29 (s, 1H), 7.76 (d, J=8.0 Hz, 2H), 7.71 (dd, J=8.6, 1.6 Hz, 1H), 7.65 (d, J=8.5 Hz, 1H), 7.44 (s, 2H), 7.29 (d, J=7.9 Hz, 2H), 5.26 (s, 2H), 4.15 (q, J=7.1 Hz, 2H), 2.36 (s, 3H), 1.21 (t, J=7.1 Hz, 3H); MS (ES+): 361.20 (M+1).

Step-2: Preparation of 2-(4-amino-6-(p-tolyl)-9H-pyrimido[4,5-b]indol-9-yl)acetic acid (205b)

Compound 205b was prepared according to the procedure reported in step-4 of scheme-17, from ethyl 2-(4-amino-6-(p-tolyl)-9H-pyrimido[4,5-b]indol-9-yl)acetate (205a) (50 mg, 0.139 mmol) in THF (3 mL) and methanol (3 mL) using a solution of lithium hydroxide hydrate (35.6 mg, 0.832 mmol) in water (3 mL) and stirring at RT for 18 h. This gave after workup 2-(4-amino-6-(p-tolyl)-9H-pyrimido[4,5-b]indol-9-yl)acetic acid (205b) which was used as such for the next step; MS (ES+): 333.10 (M+1).

Step-3: Preparation of (1R,3S,5R)-2-(2-(4-amino-6-(p-tolyl)-9H-pyrimido[4,5-b]indol-9-yl)acetyl)-N-(6-bromopyridin-2-yl)-2-azabicyclo[3.1.0]hexane-3-carboxamide (205c)

Compound 205c was prepared according to the procedure reported in step-3 of scheme-1, from 2-(4-amino-6-(p-tolyl)-9H-pyrimido[4,5-b]indol-9-yl)acetic acid (205b) (46 mg, 0.139 mmol) in DMF (8 mL) using HCl salt of (1R,3S,5R)—N-(6-bromopyridin-2-yl)-2-azabicyclo[3.1.0]hexane-3-carboxamide (4a) (66.4 mg, 0.209 mmol), HATU (106 mg, 0.278 mmol), DIPEA (0.121 mL, 0.695 mmol) and stirring at RT for 14 h. This gave after workup and purification by flash column chromatography [silica gel (12 g), eluting with MeOH in DCM from 0-5%] followed by purification using reverse phase column chromatography [C18 column, eluting with ACN in water (containing 0.1% HCl) from 0-100%] (1R,3S,5R)-2-(2-(4-amino-6-(p-tolyl)-9H-pyrimido[4,5-b]indol-9-yl)acetyl)-N-(6-bromopyridin-2-yl)-2-azabicyclo[3.1.0]hexane-3-carboxamide (205c) (42 mg, 51% yield) HCl salt as a white solid; $^1$H NMR (300 MHz, DMSO-$d_6$) δ 10.77 (s, 1H), 8.77 (d, J=1.6 Hz, 1H), 8.70 (s, 2H), 8.62 (s, 1H), 8.01 (d, J=8.2 Hz, 1H), 7.86 (dd, J=8.6, 1.6 Hz, 1H), 7.78-7.65 (m, 4H), 7.34-7.29 (m, 3H), 5.78 (d, J=17.3 Hz, 1H), 5.44 (d, J=17.3 Hz, 1H), 4.42 (dd, J=9.0, 5.5 Hz, 1H), 4.01-3.84 (m, 1H), 2.40-2.29 (m, 4H), 2.28-2.13 (m, 1H), 2.01-1.85 (m, 1H), 1.16-1.02 (m, 1H), 0.84-0.73 (m, 1H); MS (ES+): 596.20 & 598.10 (M+1). MS (ES−): 594.10 & 596.10 (M−1); Analysis calculated for $C_{30}H_{26}BrN_7O_2 \cdot HCl \cdot 2.25H_2O$: C, 53.50; H, 4.71; N, 14.56; Cl, 5.26. Found: C, 53.68; H, 4.56; N, 14.58; Cl, 5.07.

Scheme 206

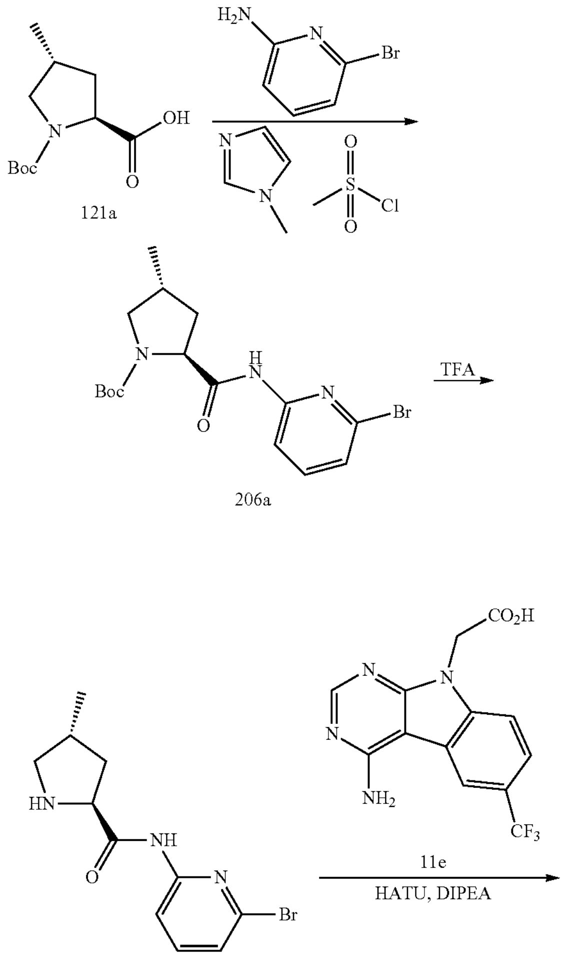

121a

206a

206b

-continued

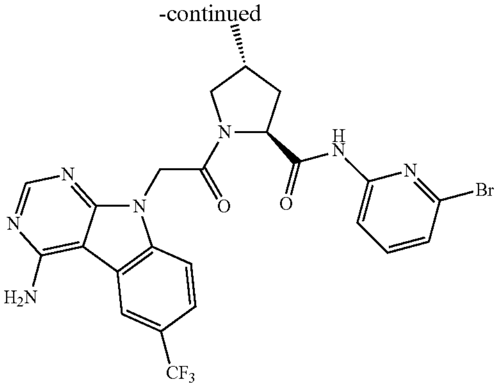

206c

Preparation of (2S,4R)-1-(2-(4-amino-6-(trifluoromethyl)-9H-pyrimido[4,5-b]indol-9-yl)acetyl)-N-(6-bromopyridin-2-yl)-4-methylpyrrolidine-2-carboxamide (206c)

Step-1: Preparation of (2S,4R)-tert-butyl 2-((6-bromopyridin-2-yl)carbamoyl)-4-methylpyrrolidine-1-carboxylate (206a)

Compound 206a was prepared according to the procedure reported in step-1 of scheme-53, from (2S,4R)-1-(tert-butoxycarbonyl)-4-methylpyrrolidine-2-carboxylic acid (121a) (0.5 g, 2.181 mmol) in DCM (15 mL) using 1-methyl-1H-imidazole (0.435 mL, 5.45 mmol), methanesulfonyl chloride (0.203 mL, 2.62 mmol), 6-bromopyridin-2-amine (0.377 g, 2.181 mmol) and stirring at RT for 18 h. This gave after workup (2S,4R)-tert-butyl 2-((6-bromopyridin-2-yl)carbamoyl)-4-methylpyrrolidine-1-carboxylate (206a) (656 mg, 78% yield); $^1$H NMR (300 MHz, DMSO-$d_6$) δ 10.90 (d, J=12.5 Hz, 1H), 8.07 (dd, J=11.8, 8.1 Hz, 1H), 7.74 (q, J=7.6 Hz, 1H), 7.34 (d, J=7.7 Hz, 1H), 4.50-4.30 (m, 1H), 3.58 (dt, J=10.0, 6.7 Hz, 1H), 2.91-2.79 (m, 1H), 2.33 (dt, J=15.6, 7.4 Hz, 1H), 1.97 (q, J=4.4 Hz, 1H), 1.89-1.72 (m, 1H), 1.32 (d, J=39.6 Hz, 9H), 0.96 (d, J=6.6 Hz, 3H); MS (ES+): 284.00 (M-Boc+1).

Step-2: Preparation of (2S,4R)—N-(6-bromopyridin-2-yl)-4-methylpyrrolidine-2-carboxamide (206b)

Compound 206b was prepared according to the procedure reported in step-2 of scheme-1, from (2S,4R)-tert-butyl 2-((6-bromopyridin-2-yl)carbamoyl)-4-methylpyrrolidine-1-carboxylate (206a) (650 mg, 1.692 mmol) in DCM (9 mL) using TFA (0.912 mL, 11.84 mmol) and stirring overnight at RT. This gave after workup and purification using reverse phase column chromatography [C18 column (50 g), eluting with ACN in water (containing 0.1% HCl) from 0-100%] HCl salt of (2S,4R)—N-(6-bromopyridin-2-yl)-4-methylpyrrolidine-2-carboxamide (206b) (541 mg, 100% yield) as a white solid; $^1$H NMR (300 MHz, DMSO-$d_6$) δ 11.44 (s, 11H), 9.63 (s, 1H), 8.68 (s, 1H), 8.05 (d, J=8.2 Hz, 1H), 7.82 (t, J=7.9 Hz, 1H), 7.44 (d, J=7.7 Hz, 1H), 4.49 (s, 1H), 3.45 (s, 1H), 2.80 (s, 1H), 2.32 (dd, J=14.9, 7.6 Hz, 1H), 2.19 (dt, J=12.5, 6.0 Hz, 1H), 1.98 (dt, J=13.1, 8.7 Hz, 1H), 1.03 (d, J=6.6 Hz, 3H).

Step-3: Preparation of (2S,4R)-1-(2-(4-amino-6-(trifluoromethyl)-9H-pyrimido[4,5-b]indol-9-yl)acetyl)-N-(6-bromopyridin-2-yl)-4-methylpyrrolidine-2-carboxamide (206c)

Compound 206c was prepared according to the procedure reported in step-3 of scheme-1, from HCl salt of (2S,4R)—N-(6-bromopyridin-2-yl)-4-methylpyrrolidine-2-carboxamide (206b) (50 mg, 0.156 mmol) in DMF (1.5 mL) using TFA salt of 2-(4-amino-6-(trifluoromethyl)-9H-pyrimido[4,5-b]indol-9-yl)acetic acid (11e) (66.2 mg, 0.156 mmol), HATU (89 mg, 0.234 mmol), DIPEA (0.136 mL, 0.780 mmol) and stirring at RT for 16 h. This gave after workup and purification by flash column chromatography [silica gel (24 g), eluting with DMA-80 in DCM from 0-50%] followed by purification using reverse phase column chromatography [C18 column (50 g), eluting with ACN in water (containing 0.1% HCl) from 0-100%] (2S,4R)-1-(2-(4-amino-6-(trifluoromethyl)-9H-pyrimido[4,5-b]indol-9-yl)acetyl)-N-(6-bromopyridin-2-yl)-4-methylpyrrolidine-2-carboxamide (206c) (41 mg, 46% yield) HCl salt as a white solid; $^1$H NMR (300 MHz, DMSO-$d_6$) (a mixture of two rotamers) δ 11.22 and 10.78 (2s, 1H, $D_2O$ exchangeable), 8.94 (s, 1H), 8.81 (s, 2H, $D_2O$ exchangeable), 8.61 and 8.58 (2s, 1H), 8.10 and 7.93 (2d, J=8.1 Hz, 1H), 7.89-7.72 (m, 2H), 7.63 (t, J=8.0 Hz, 1H), 7.33 and 7.24 (d, J=7.7 Hz, 1H), 5.43 (q, J=17.3 Hz, 2H), 4.60-4.43 (m, 1H), 4.03 (t, J=8.5 Hz, 1H), 3.34 (t, 1H), 2.54-2.46 (m, 1H), 2.00 (dd, J=13.2, 6.6 Hz, 1H), 1.88-1.70 (m, 1H), 1.04 and 0.96 (2d, J=6.5 Hz, 3H), $^{19}$F NMR (282 MHz, DMSO) δ −58.59. MS (ES+): 576.1 (M+1); (ES−): 574.1 (M−1); Analysis calculated for $C_{24}H_{21}BrF_3N_7O_2$ $1.5H_2O{\cdot}HCl$: C, 45.05; H, 3.94; Cl, 5.54; N, 15.32. Found: C, 45.09; H, 3.91; Cl, 5.42; N, 15.09.

Scheme 207

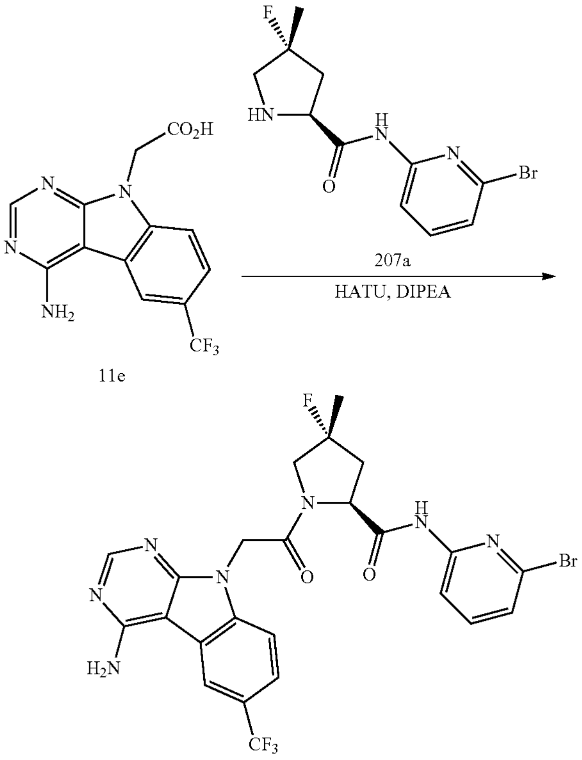

11e

207a

207b

Preparation of (2S,4R)-1-(2-(4-amino-6-(trifluoromethyl)-9H-pyrimido[4,5-b]indol-9-yl)acetyl)-N-(6-bromopyridin-2-yl)-4-fluoro-4-methylpyrrolidine-2-carboxamide (207b)

Compound 207b was prepared according to the procedure reported in step-3 of scheme-1, from TFA salt of 2-(4-amino-6-(trifluoromethyl)-9H-pyrimido[4,5-b]indol-9-yl)acetic acid (11e) (60 mg, 0.141 mmol) in DMF (1.2 mL) using TFA salt of (2S,4R)—N-(6-bromopyridin-2-yl)-4-fluoro-4-methylpyrrolidine-2-carboxamide (207a) (58.9 mg, 0.141 mmol; prepared according to the procedure reported in Wiles, Jason A. et al., PCT Int. Appl. (2017), WO 2017035353 A120170302), HATU (81 mg, 0.212 mmol), DIPEA (0.123 mL, 0.707 mmol) and stirring at RT for 16 h. This gave after workup and purification by flash column chromatography [silica gel (24 g), eluting with DMA-80 in DCM from 0-50%] followed by purification using reverse phase column chromatography [C18 column (50 g), eluting with ACN in water (containing 0.1% HCl) from 0-100%] (2S,4R)-1-(2-(4-amino-6-(trifluoromethyl)-9H-pyrimido[4,5-b]indol-9-yl)acetyl)-N-(6-bromopyridin-2-yl)-4-fluoro-4-methylpyrrolidine-2-carboxamide (207b) (55 mg, 65% yield) HCl salt as a white solid; $^1H$ NMR (300 MHz, DMSO-$d_6$) (a mixture of two rotamers) δ 11.35 and 10.96 (2s, 1H, $D_2O$ exchangeable), 8.95 (s, 1H), 8.57 (s, 1H), 8.47 (s, 2H, $D_2O$ exchangeable), 8.21 and 7.98 (2d, J=8.2 Hz, 1H), 7.84 (s, 2H), 7.68 (t, J=8.0 Hz, 1H), 7.43 and 7.31 (2d, J=7.7 Hz, 1H), 5.61 (d, J=17.4 Hz, 1H), 5.38 (d, J=17.3 Hz, 1H), 4.62 (t, J=8.6 Hz, 1H), 4.30 (dd, J=18.9, 12.0 Hz, 1H), 3.97 (dd, J=35.2, 11.9 Hz, 1H), 2.54 (m, 1H), 2.20-1.93 (m, 1H), 1.62 (d, J=21.0 Hz, 3H). $^{19}F$ NMR (282 MHz, DMSO-$d_6$) δ-58.50, −139.31. MS (ES+): 594.1 (M+1): (ES−): 592.0 (M−1): Analysis calculated for $C_{24}H_2OBrF_4N_7O_2$ $1.25H_2O{\cdot}HCl$: C, 44.12; H, 3.63; Cl, 5.43; N, 15.01. Found: C, 44.16; H, 3.67; Cl, 5.59; N, 14.84.

Scheme 208

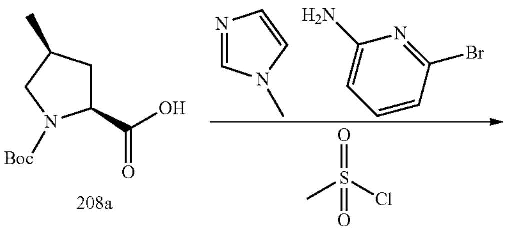

208a

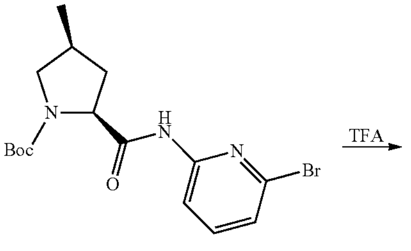

208b

-continued

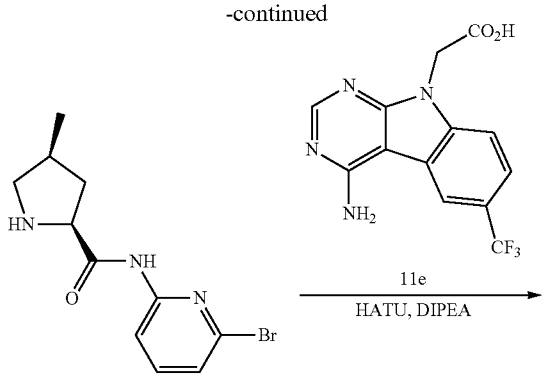

208c

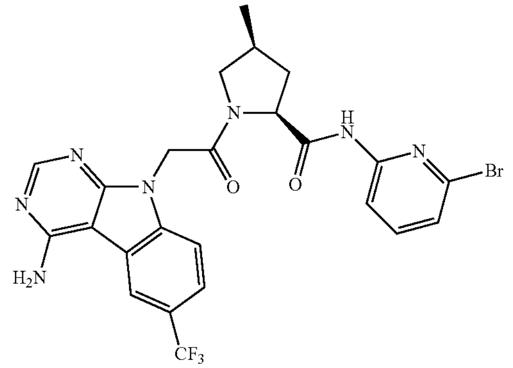

208b

Preparation of (2S,4S)-1-(2-(4-amino-6-(trifluoromethyl)-9H-pyrimido[4,5-b]indol-9-yl)acetyl)-N-(6-bromopyridin-2-yl)-4-methylpyrrolidine-2-carboxamide (208d)

Step-1: Preparation of (2S,4S)-tert-butyl 2-((6-bromopyridin-2-yl)carbamoyl)-4-methylpyrrolidine-1-carboxylate (208b)

Compound 208b was prepared according to the procedure reported in step-1 of scheme-53, from (2S,4S)-1-(tert-butoxycarbonyl)-4-methylpyrrolidine-2-carboxylic acid (208a) (0.45 g, 1.963 mmol; CAS #364750-81-2) in DCM (15 mL) using 1-methyl-1H-imidazole (0.391 mL, 4.91 mmol), methanesulfonyl chloride (0.182 mL, 2.355 mmol), 6-bromopyridin-2-amine (0.340 g, 1.963 mmol) and stirring at RT for 18 h. This gave after workup (2S,4S)-tert-butyl 2-((6-bromopyridin-2-yl)carbamoyl)-4-methylpyrrolidine-1-carboxylate (208b) (623 mg, 83% yield): $^1H$ NMR (300 MHz, DMSO-$d_6$) δ 10.92 (d, J=16.6 Hz, 1H), 8.10 (dd, J=14.1, 8.2 Hz, 1H), 7.76 (t, J=8.1 Hz, 1H), 7.34 (d, J=7.7 Hz, 1H), 4.32 (t, J=8.3 Hz, 1H), 3.70-3.49 (m, 1H), 2.93-2.79 (m, 1H), 2.40-2.10 (m, 2H), 1.30 (d, J=43.9 Hz, 10H), 1.00 (t, J=6.1 Hz, 3H); MS (ES+): 384.10 (M+1).

Step-2: Preparation of (2S,4S)—N-(6-bromopyridin-2-yl)-4-methylpyrrolidine-2-carboxamide (208c)

Compound 208c was prepared according to the procedure reported in step-2 of scheme-1, from (2S,4S)-tert-butyl 2-((6-bromopyridin-2-yl)carbamoyl)-4-methylpyrrolidine-1-carboxylate (208b) (610 mg, 1.587 mmol) in DCM (9 mL) using TFA (0.856 mL, 11.11 mmol) and stirring overnight at RT. This gave after workup TFA salt of (2S,4S)—N-(6- bromopyridin-2-yl)-4-methylpyrrolidine-2-carboxamide (208c) (621 mg, 98% yield); $^1$H NMR (300 MHz, DMSO-$d_6$) δ 11.41 (s, 1H), 9.31 (s, 1H), 8.75 (s, 1H), 8.07 (d, J=8.2 Hz, 1H), 7.82 (t, J=8.0 Hz, 1H), 7.44 (d, J=7.7 Hz, 1H), 4.51-4.27 (m, 1H), 3.54-3.26 (m, 1H), 2.91-2.64 (m, 1H), 2.59 (dd, J=13.2, 7.1 Hz, 1H), 2.38-2.14 (m, 1H), 1.53 (dt, J=12.6, 10.0 Hz, 1H), 1.04 (d, J=6.6 Hz, 3H); MS (ES+): 284.00 (M+1).

Step-3: Preparation of (2S,4S)-1-(2-(4-amino-6-(trifluoromethyl)-9H-pyrimido[4,5-b]indol-9-yl)acetyl)-N-(6-bromopyridin-2-yl)-4-methylpyrrolidine-2-carboxamide (208d)

Compound 208d was prepared according to the procedure reported in step-2 of scheme-1, from TFA salt of (2S,4S)—N-(6-bromopyridin-2-yl)-4-methylpyrrolidine-2-carboxamide (208c) (56.3 mg, 0.141 mmol) in DMF (1.2 mL) using TFA salt of 2-(4-amino-6-(trifluoromethyl)-9H-pyrimido[4,5-b]indol-9-yl)acetic acid (11e) (60 mg, 0.141 mmol) HATU (81 mg, 0.212 mmol), N-ethyl-N-isopropylpropan-2-amine (0.123 mL, 0.707 mmol) and stirring at RT for 16 h. This gave after workup and purification using flash column chromatography [silica gel (24 g), eluting with DMA-80 in DCM from 0-50%] followed by purification using reverse phase column chromatography [C18 column (50 g), eluting with ACN in water (containing 0.1% HCl) from 0-100%] (2S,4S)-1-(2-(4-amino-6-(trifluoromethyl)-9H-pyrimido[4,5-b]indol-9-yl)acetyl)-N-(6-bromopyridin-2-yl)-4-methylpyrrolidine-2-carboxamide (208d) (60 mg, 74% yield) HCl salt as a white solid; $^1$H NMR (300 MHz, DMSO-$d_6$) (a mixture of two rotamers) δ 11.31 and 10.86 (2s, 1H, $D_2O$ exchangeable), 8.97 (s, 1H), 8.61 (s, 3H, 2H $D_2O$ exchangeable), 8.20 and 7.99 (2d. J=8.2 Hz, 1H), 7.92-7.81 (m, 2H), 7.68 (t, J=8.0 Hz, 1H), 7.41 and 7.30 (2d, J=7.7 Hz, 1H), 5.55 (d, J=17.3 Hz, 1H), 5.38 (d, J=17.3 Hz, 1H), 4.44 (t, J=8.1 Hz, 1H), 4.14 (t, J=8.4 Hz, 1H), 3.34 (t, J=9.6 Hz, 1H), 2.54 (m, 1H), 2.42 (t, J=7.2 Hz, 1H), 1.49 (q, J=9.6 Hz, 1H), 1.13 and 1.02 (2d, J=6.6 Hz, 3H). $^{19}$F NMR (282 MHz, DMSO-$d_6$) δ−58.53. MS (ES+): 576.1 (M+1); (ES−): 574.0 (M−1); Analysis calculated for $C_{24}H_{21}BrF_3N_7O_2$ $1.5H_2O{\cdot}HCl$: C, 45.05; H, 3.94; Cl, 5.54; N, 15.32. Found: C, 45.08; H, 4.01; Cl, 5.43; N, 15.12.

Scheme 209

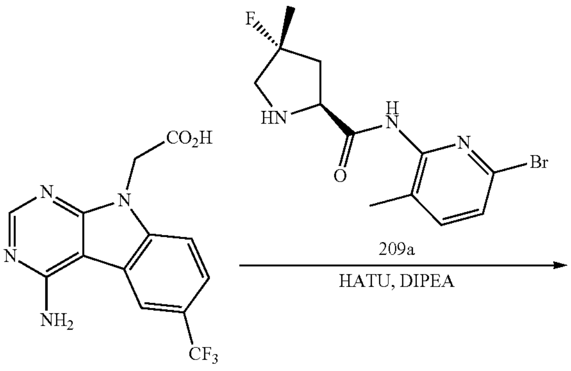

11e

-continued

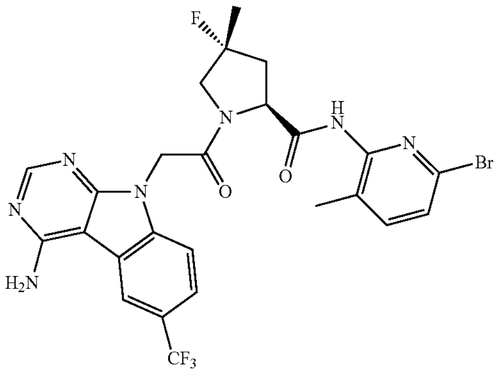

209b

Preparation of (2S,4R)-1-(2-(4-amino-6-(trifluoromethyl)-9H-pyrimido[4,5-b]indol-9-yl)acetyl)-N-(6-bromo-3-methylpyridin-2-yl)-4-fluoro-4-methylpyrrolidine-2-carboxamide (209b)

Compound 209b was prepared according to the procedure reported in step-3 of scheme-1, from TFA salt of 2-(4-amino-6-(trifluoromethyl)-9H-pyrimido[4,5-b]indol-9-yl)acetic acid (11e) (60 mg, 0.141 mmol) in DMF (1.2 mL) using HCl salt of (2S,4R)—N-(6-bromo-3-methylpyridin-2-yl)-4-fluoro-4-methylpyrrolidine-2-carboxamide (209a) (50 mg, 0.141 mmol; prepared according to the procedure reported in Wiles, Jason A. et al., PCT Int. Appl. (2018), WO 2018160889 A1 20180907), HATU (81 mg, 0.212 mmol) DIPEA (0.123 mL, 0.707 mmol) and stirring at RT for 16 h. This gave after workup and purification by flash column chromatography [silica gel (24 g), eluting with DMA-80 in DCM from 0-50%] followed by purification using reverse phase column chromatography [C18 column (50 g), eluting with ACN in water (containing 0.1% HCl) from 0-100%] (2S,4R)-1-(2-(4-amino-6-(trifluoromethyl)-9H-pyrimido[4,5-b]indol-9-yl)acetyl)-N-(6-bromo-3-methylpyridin-2-yl)-4-fluoro-4-methylpyrrolidine-2-carboxamide (209b) (33 mg, 38% yield) HCl salt as a white solid; $^1$H NMR (300 MHz, DMSO-$d_6$) (a mixture of two rotamers) δ 10.83 and 10.40 (2s, 1H, $D_2O$ exchangeable), 8.94 (s, 1H), 8.69 (s, 2H, $D_2O$ exchangeable), 8.56 (s, 1H), 7.76 (qd, J=10.7, 9.7, 6.2 Hz, 2H), 7.66 and 7.51 (d, J=8.0 Hz, 1H), 7.46 and 7.35 (2d, J=7.9 Hz, 1H), 5.58 (d, J=17.3 Hz, 1H), 5.31 (d, J=17.3 Hz, 1H), 4.51 (dd, J=9.8, 7.5 Hz, 1H), 4.24 (dd, J=18.9, 12.3 Hz, 1H), 3.89 (dd, J=35.1, 12.0 Hz, 1H), 2.56 (td, J=14.9, 7.6 Hz, 1H), 2.18-1.93 (m, 1H), 1.85 (s, 3H), 1.58 (d, J=21.1 Hz, 3H). $^{19}$F NMR (282 MHz, DMSO-$d_6$) δ-58.56, −139.44; MS (ES+): 608.1 (M+1), 630.1 (M+Na); (ES−): 606.1 (M−1); Analysis calculated for $C_{25}H_{22}BrF_4N_7O_2$ $1.25H_2O{\cdot}HCl$: C, 44.99; H, 3.85; N, 14.69. Found: C, 45.03; H, 3.79; N, 14.43.

Scheme 210

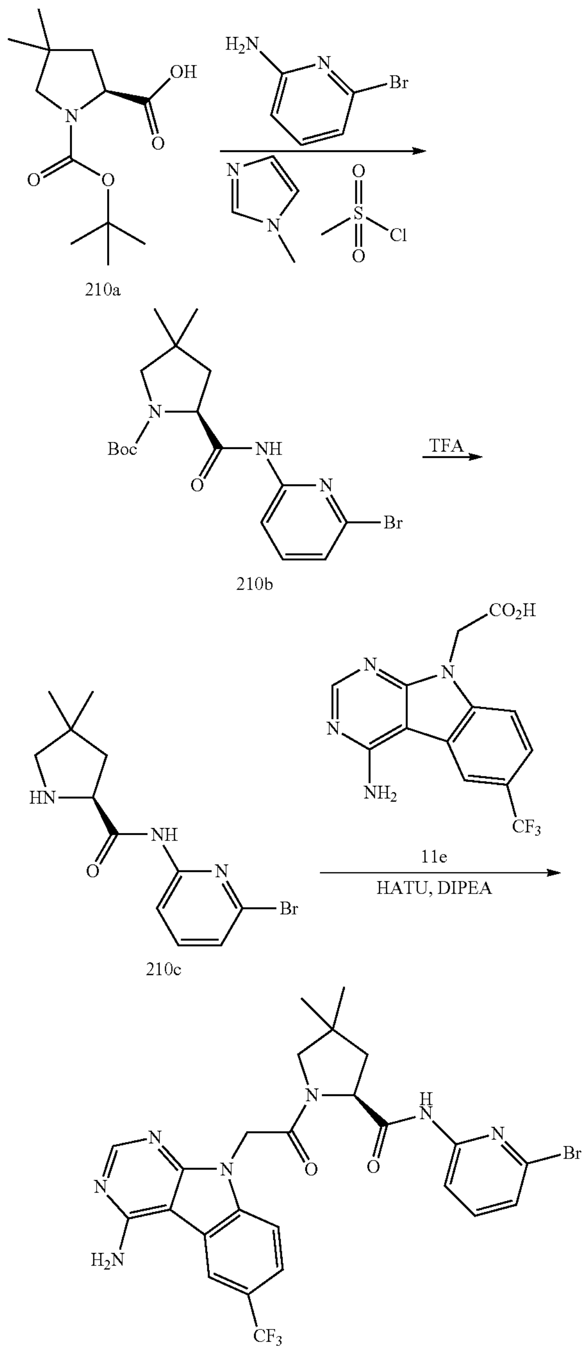

210a

210b

210c

210d

Preparation of (S)-1-(2-(4-amino-6-(trifluoromethyl)-9H-pyrimido[4,5-b]indol-9-yl)acetyl)-N-(6-bromopyridin-2-yl)-4,4-dimethylpyrrolidine-2-carboxamide (210d)

Step-1: Preparation of (S)-tert-butyl 2-((6-bromopyridin-2-yl)carbamoyl)-4,4-dimethylpyrrolidine-1-carboxylate (210b)

Compound 210b was prepared according to the procedure reported in step-1 of scheme-53, from (S)-1-(tert-butoxycarbonyl)-4,4-dimethylpyrrolidine-2-carboxylic acid (210a) (0.45 g, 1.850 mmol; CAS #87691-27-8) in DCM (15 mL) using 1-methyl-1H-imidazole (0.369 mL, 4.62 mmol), methanesulfonyl chloride (0.172 mL, 2.219 mmol), 6-bromopyridin-2-amine (0.320 g, 1.850 mmol) and stirring at RT for 18 h. This gave after workup (S)-tert-butyl 2-((6-bromopyridin-2-yl)carbamoyl)-4,4-dimethylpyrrolidine-1-carboxylate (210b) (570 mg, 77% yield); $^1$H NMR (300 MHz, DMSO-$d_6$) δ 10.89 (d, J=19.4 Hz, 1H), 8.10 (dd, J=14.6, 8.2 Hz, 1H), 7.75 (q, J=8.3 Hz, 1H), 7.34 (d, J=7.7 Hz, 1H), 4.53-4.32 (m, 1H), 3.22 (dd. J=10.2, 5.8 Hz, 1H), 3.09 (dd, J=10.2, 5.2 Hz, 1H), 2.01 (dt, J=12.5, 6.5 Hz, 1H), 1.70-1.55 (m, 1H), 1.31 (d, J=40.7 Hz, 9H), 1.07 (d, J=5.3 Hz, 3H), 1.00 (s, 3H); MS (ES+): 398.10 (M+1).

Step-2: Preparation of(S)—N-(6-bromopyridin-2-yl)-4,4-dimethylpyrrolidine-2-carboxamide (210c)

Compound 210c was prepared according to the procedure reported in step-2 of scheme-1, from (S)-tert-butyl 2-((6-bromopyridin-2-yl)carbamoyl)-4,4-dimethylpyrrolidine-1-carboxylate (210b) (570 mg, 1.431 mmol) in DCM (8 mL) using TFA (0.772 mL, 10.02 mmol) and stirring overnight at RT. This gave after workup and purification using reverse phase column chromatography [C18 column (50 g), eluting with ACN in water (containing 0.1% HCl) from 0-100%] to afford the HCl salt of (S)—N-(6-bromopyridin-2-yl)-4,4-dimethylpyrrolidine-2-carboxamide (210c) (375 mg, 78% yield); $^1$H NMR (300 MHz, DMSO-$d_6$) δ 11.44 (s, 1H), 10.24 (s, 1H), 8.81 (s, 1H), 8.06 (d, J=8.2 Hz, 1H), 7.83 (t, J=7.9 Hz, 1H), 7.44 (d, J=7.7 Hz, 1H), 4.52 (s, 1H), 3.04 (q, J=5.6, 5.1 Hz, 2H), 2.30 (dd, J=12.8, 8.3 Hz, 1H), 1.80 (dd, J=12.9, 9.4 Hz, 1H), 1.11 (d, J=2.5 Hz, 6H); MS (ES+): 298.10 (M+1).

Step-3: Preparation of (S)-1-(2-(4-amino-6-(trifluoromethyl)-9H-pyrimido[4,5-b]indol-9-yl)acetyl)-N-(6-bromopyridin-2-yl)-4,4-dimethylpyrrolidine-2-carboxamide (210d)

Compound 210d was prepared according to the procedure reported in step-3 of scheme-1, from HCl salt of (S)—N-(6-bromopyridin-2-yl)-4,4-dimethylpyrrolidine-2-carboxamide (210c) (47.3 mg, 0.141 mmol) in DMF (1.2 mL) using TFA salt of 2-(4-amino-6-(trifluoromethyl)-9H-pyrimido[4,5-b]indol-9-yl)acetic acid (11e) (60 mg, 0.141 mmol), HATU (81 mg, 0.212 mmol), DIPEA (0.123 mL, 0.707 mmol) and stirring at RT for 16 h. This gave after workup and purification by flash column chromatography [silica gel (24 g), eluting with DMA-80 in DCM from 0-50%] followed by purification using reverse phase column chromatography [C18 column (50 g), eluting with ACN in water (containing 0.1% HCl) from 0-100%] (S)-1-(2-(4-amino-6-(trifluoromethyl)-9H-pyrimido[4,5-b]indol-9-yl)acetyl)-N-(6-bromopyridin-2-yl)-4,4-dimethylpyrrolidine-2-carboxamide (210d) (34 mg, 41% yield) HCl salt as a white solid; $^1$H NMR (300 MHz, DMSO-$d_6$) (a mixture of two rotamers) δ 11.26 and 10.83 (2s, 1H, $D_2O$ exchangeable), 8.92 (s, 1H), 8.53 and 8.49 (2s, 1H), 8.26 (s, 2H, $D_2O$ exchangeable), 8.20 and 7.99 (2d, J=8.2 Hz, 1H), 7.81 (s, 2H), 7.68 (t, J=8.0 Hz, 1H), 7.41 and 7.31 (2d, J=7.7 Hz, 1H), 5.52 (d, J=17.3 Hz, 1H), 5.34 (d, J=17.3 Hz, 1H), 4.54 (t, J=8.3 Hz, 1H), 3.77 (d, J=9.8 Hz, 1H), 3.60 (d, J=9.9 Hz, 1H), 2.08 (dd, J=12.4, 7.9 Hz, 1H), 1.71 (dd, J=12.4, 9.0 Hz, 1H), 1.21 and 1.10 (2s, 3H), 1.14 and 1.08 (2s, 3H). F NMR (282 MHz, DMSO-$d_6$) δ–58.42. MS (ES+): 590.0 (M+1), 612.0 (M+Na); (ES−): 588.0 (M−1); Analysis calculated for $C_{25}H_{23}BrF_3N_7O_2$ $1.25H_2O{\cdot}HCl$: C, 46.24; H, 4.11; Cl, 5.46. N, 15.10. Found: C, 46.21; H, 4.05; Cl, 5.62; N, 14.78.

Scheme 211

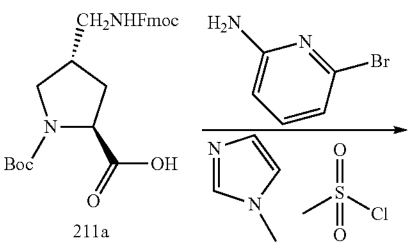

211a

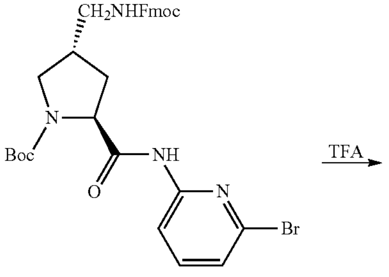

211b

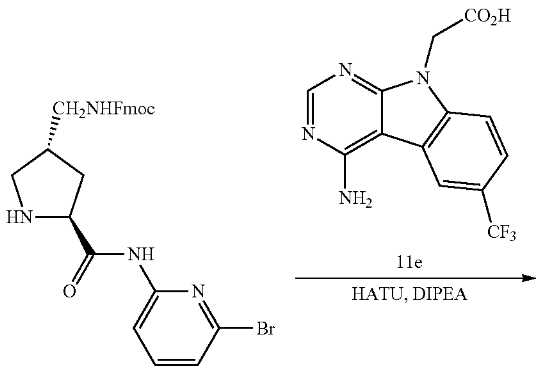

211c

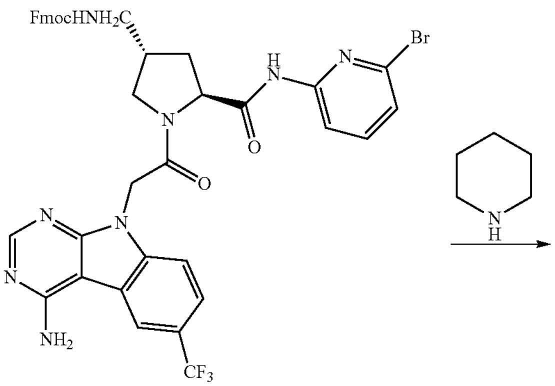

211d

-continued

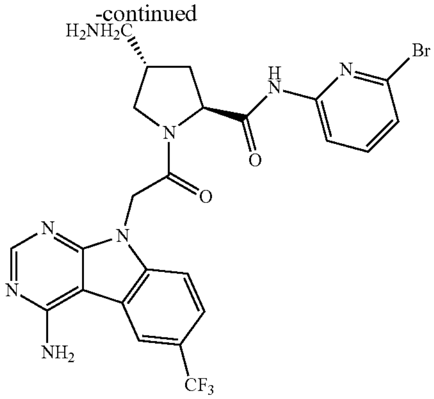

211e

Preparation of (2S,4S)-1-(2-(4-amino-6-(trifluoromethyl)-9H-pyrimido[4,5-b]indol-9-yl)acetyl)-4-(aminomethyl)-N-(6-bromopyridin-2-yl)pyrrolidine-2-carboxamide (211e)

Step-1: Preparation of (2S,4S)-tert-butyl 4-(((((9H-fluoren-9-yl)methoxy)carbonyl)amino)methyl)-2-((6-bromopyridin-2-yl)carbamoyl)pyrrolidine-1-carboxylate (211b)

Compound 211b was prepared according to the procedure reported in step-1 of scheme-53, from (2S,4S)-4-(((((9H-fluoren-9-yl)methoxy)carbonyl)amino)methyl)-1-(tert-butoxycarbonyl)pyrrolidine-2-carboxylic acid (211a) (0.25 g, 0.536 mmol; CAS #273221-98-0) in DCM (10 mL) using 1-methyl-1H-imidazole (0.107 mL, 1.340 mmol), methanesulfonyl chloride (0.050 mL, 0.643 mmol), 6-bromopyridin-2-amine (0.093 g, 0.536 mmol) and stirring at RT for 18 h. This gave after workup (2S,4S)-tert-butyl 4-(((((9H-fluoren-9-yl)methoxy)carbonyl)amino)methyl)-2-((6-bromopyridin-2-yl)carbamoyl)pyrrolidine-1-carboxylate (211b) (67 mg, 20% yield); MS (ES+): 621.20 (M+1).

Step-2: Preparation of (9H-fluoren-9-yl)methyl (((3R,5S)-5-((6-bromopyridin-2-yl)carbamoyl)pyrrolidin-3-yl)methyl)carbamate (211c)

Compound 211c was prepared according to the procedure reported in step-2 of scheme-1, from (2S,4S)-tert-butyl 4-(((((9H-fluoren-9-yl)methoxy)carbonyl)amino)methyl)-2-((6-bromopyridin-2-yl)carbamoyl)pyrrolidine-1-carboxylate (211b) (65 mg, 0.105 mmol) in DCM (I mL) using TFA (0.056 mL, 0.732 mmol) and stirring overnight at RT. This gave after workup TFA salt of (9H-fluoren-9-yl)methyl (((3R,5S)-5-((6-bromopyridin-2-yl)carbamoyl)pyrrolidin-3-yl)methyl)carbamate (211c) (60 mg, 90% yield); 1H NMR (300 MHz, DMSO-$d_6$) δ 11.44 (s, 1H), 9.38 (s, 1H), 8.75 (s, 1H), 8.06 (d, J=8.2 Hz, 1H), 7.87 (dd, J=15.0, 7.7 Hz, 3H), 7.67 (d, J=7.4 Hz, 2H), 7.51-7.26 (m, 6H), 4.47 (s, 1H), 4.36 (d, J=6.8 Hz, 2H), 4.22 (t, J=6.7 Hz, 1H), 3.42 (s, 1H), 3.02 (dt, J=33.5, 7.9 Hz, 3H), 2.41 (t, J=7.6 Hz, 1H), 2.10 (t, J=8.9 Hz, 2H).

Step-3: Preparation of (9H-fluoren-9-yl)methyl (((3S,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)methyl)carbamate (211d)

Compound 211d was prepared according to the procedure reported in step-3 of scheme-1, from TFA salt of (9H- fluoren-9-yl)methyl (((3R,5S)-5-((6-bromopyridin-2-yl)carbamoyl)pyrrolidin-3-yl)methyl)carbamate (211c) (55 mg, 0.087 mmol) in DMF (1 mL) using TFA salt of 2-(4-amino-6-(trifluoromethyl)-9H-pyrimido[4,5-b]indol-9-yl)acetic acid (11e) (36.7 mg, 0.087 mmol), HATU (49.4 mg, 0.130 mmol), DIPEA (0.075 mL, 0.433 mmol) and stirring at RT for 16 h. This gave after workup and purification by flash column chromatography [silica gel (24 g), eluting with DMA-80 in DCM from 0-50%] (9H-fluoren-9-yl)methyl (((3S,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)methyl)carbamate (211d) (70 mg, 99% yield) as a white solid; $^1$H NMR (300 MHz, DMSO-$d_6$) δ 10.87 (s, 1H), 8.80 (s, 11H), 8.33 (s, 1H), 8.02 (d, J=8.2 Hz, 1H), 7.88 (d, J=7.4 Hz, 2H), 7.74-7.66 (m, 5H), 7.55 (s, 3H), 7.44-7.26 (m, 5H), 5.34 (q, J=17.3 Hz, 2H), 4.57 (s, 1H), 4.39 (d, J=6.7 Hz, 2H), 4.25 (t, J=6.7 Hz, 1H), 4.00 (t, J=8.6 Hz, 1H), 3.71-3.44 (m, 1H), 3.21-3.04 (m, 3H), 1.98 (d, J=7.8 Hz, 2H), 1.22 (s, 1H); MS (ES+): 813.10 (M+1).

Step-4: Preparation of (2S,4S)-1-(2-(4-amino-6-(trifluoromethyl)-9H-pyrimido[4,5-b]indol-9-yl)acetyl)-4-(aminomethyl)-N-(6-bromopyridin-2-yl)pyrrolidine-2-carboxamide (211e)

Compound 211e was prepared according to the procedure reported in step-4 of scheme-180, from (9H-fluoren-9-yl)methyl (((3S,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)methyl)carbamate (211d) (60 mg, 0.074 mmol) in DMF (0.4 mL) using piperidine (0.073 mL, 0.737 mmol) and stirring at RT for 1 h. This gave after work up and purification using flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (2S,4S)-1-(2-(4-amino-6-(trifluoromethyl)-9H-pyrimido[4,5-b]indol-9-yl)acetyl)-4-(aminomethyl)-N-(6-bromopyridin-2-yl)pyrrolidine-2-carboxamide (211e) (21 mg, 48% yield) HCl salt as a white solid; $^1$H NMR (300 MHz, DMSO-$d_6$) (a mixture of two rotamers) δ 11.40 and 10.93 (2s, 1H, $D_2O$ exchangeable), 9.00 (s, 1H), 8.79 (s, 2H, $D_2O$ exchangeable), 8.66 and 8.62 (2s, 1H), 8.26 (s, 3H, $D_2O$ exchangeable), 8.02-7.78 (m, 3H), 7.71 (t, J=8.0 Hz, 1H), 7.42 and 7.33 (2d, J=7.6 Hz, 1H), 5.53 (s, 2H), 4.63 (d, J=8.3 Hz, 1H), 4.13 (dd, J=9.9, 7.2 Hz, 1H), 3.73 (t, J=8.8 Hz, 1H), 3.05-2.88 (m, 2H), 2.84-2.69 (m, 1H), 2.28-1.99 (m, 2H). $^{19}$F NMR (282 MHz, DMSO-$d_6$) δ-58.56. MS (ES+): 591.1 (M+1); (ES−): 589.1 (M−1).

Scheme 212

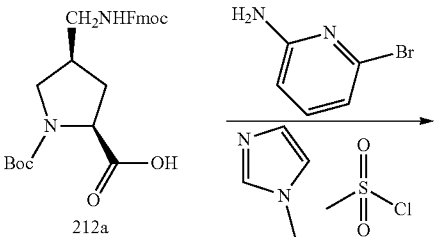

212a

-continued

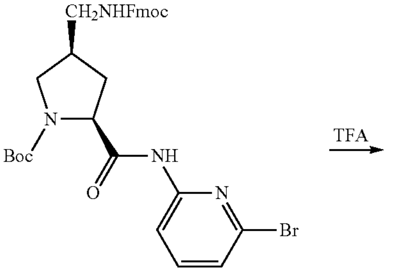

212b

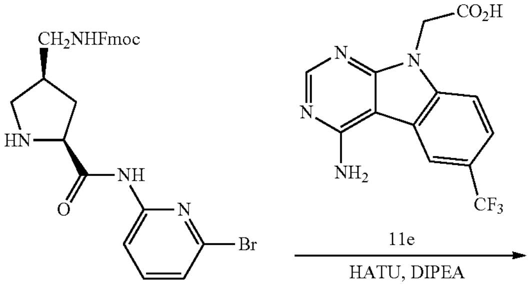

212c

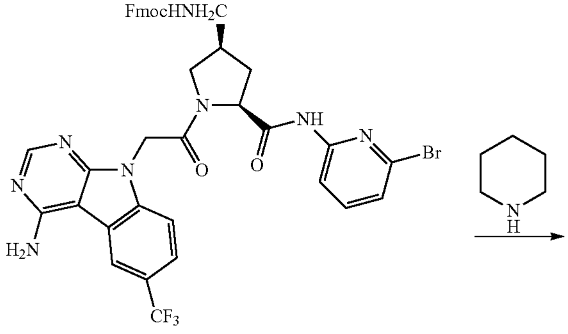

212d

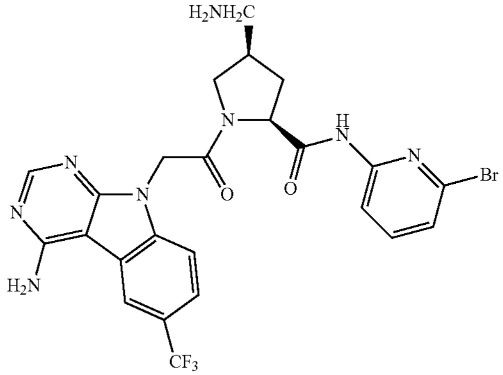

212e

Preparation of (2S,4R)-1-(2-(4-amino-6-(trifluoromethyl)-9H-pyrimido[4,5-b]indol-9-yl)acetyl)-4-(aminomethyl)-N-(6-bromopyridin-2-yl)pyrrolidine-2-carboxamide (212e)

Step-1: Preparation of (2S,4R)-tert-butyl 4-(((((9H-fluoren-9-yl)methoxy)carbonyl)amino)methyl)-2-((6-bromopyridin-2-yl)carbamoyl)pyrrolidine-1-carboxylate (212b)

Compound 212b was prepared according to the procedure reported in step-1 of scheme-53, from (2S,4R)-4-(((((9H- fluoren-9-yl)methoxy)carbonyl)amino)methyl)-1-(tert-butoxycarbonyl)pyrrolidine-2-carboxylic acid (212a) (0.25 g, 0.536 mmol; CAS #2173052-84-9) in DCM (10 mL) using 1-methyl-1H-imidazole (0.107 mL, 1.340 mmol), methanesulfonyl chloride (0.050 mL, 0.643 mmol), 6-bromopyridin-2-amine (0.093 g, 0.536 mmol) and stirring at RT for 18 h. This gave after workup (2S,4R)-tert-butyl 4-(((((9H-fluoren-9-yl)methoxy)carbonyl)amino)methyl)-2-((6-bromopyridin-2-yl)carbamoyl)pyrrolidine-1-carboxylate (212b) (231 mg, 69% yield); $^1$H NMR (300 MHz, DMSO-$d_6$) δ 10.93 (d, J=15.8 Hz, 1H), 8.11 (dd, J=14.0, 8.1 Hz, 1H), 7.89 (d, J=7.4 Hz, 2H), 7.81-7.60 (m, 3H), 7.52-7.39 (m, 2H), 7.39-7.27 (m, 4H), 4.26 (dd, J=27.9, 7.3 Hz, 4H), 3.52 (t, J=9.2 Hz, 1H), 3.05 (d, J=9.3 Hz, 3H), 2.28 (s, 2H), 1.57 (d, J=10.8 Hz, 1H), 1.31 (d, J=42.3 Hz, 9H).

Step-2: Preparation of (9H-fluoren-9-yl)methyl (((3S,5S)-5-((6-bromopyridin-2-yl)carbamoyl)pyrrolidin-3-yl)methyl)carbamate (212c)

Compound 212c was prepared according to the procedure reported in step-2 of scheme-1, from (2S,4R)-tert-butyl 4-(((((9H-fluoren-9-yl)methoxy)carbonyl)amino)methyl)-2-((6-bromopyridin-2-yl)carbamoyl)pyrrolidine-1-carboxylate (212b) (220 mg, 0.354 mmol) in DCM (2 mL) using TFA (0.191 mL, 2.478 mmol) and stirring overnight at RT. This gave after workup TFA salt of (9H-fluoren-9-yl)methyl (((3S,5S)-5-((6-bromopyridin-2-yl)carbamoyl)pyrrolidin-3-yl)methyl)carbamate (212c) (210 mg, 93% yield); $^1$H NMR (300 MHz, DMSO-$d_6$) δ 11.42 (s, 1H), 9.32 (s, 1H), 8.83 (s, 1H), 8.07 (d, J=8.2 Hz, 1H), 7.95-7.74 (m, 3H), 7.66 (d, J=7.4 Hz, 2H), 7.52-7.25 (m, 6H), 4.33 (d, J=6.9 Hz, 3H), 4.20 (t, J=6.7 Hz, 1H), 3.35 (s, 1H), 3.09 (t, J=6.0 Hz, 2H), 2.97 (s, 1H), 2.57-2.53 (m, 1H), 2.43 (s, 1H), 1.73-1.58 (m, 1H); MS (ES+): 521.10 (M+1).

Step-3: Preparation of (9H-fluoren-9-yl)methyl (((3R,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)methyl)carbamate (212d)

Compound 212d was prepared according to the procedure reported in step-3 of scheme-1, from TFA salt of (9H-fluoren-9-yl)methyl (((3S,5S)-5-((6-bromopyridin-2-yl)carbamoyl)pyrrolidin-3-yl)methyl)carbamate (212c) (200 mg, 0.315 mmol) in DMF (2 mL) using TFA salt of 2-(4-amino-6-(trifluoromethyl)-9H-pyrimido[4,5-b]indol-9-yl)acetic acid (11e) (134 mg, 0.315 mmol). HATU (180 mg, 0.472 mmol), DIPEA (0.274 mL, 1.574 mmol) and stirring at RT for 16 h. This gave after workup and purification by flash column chromatography [silica gel (24 g), eluting with DMA-80 in DCM from 0-50%] (9H-fluoren-9-yl)methyl (((3R,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)methyl)carbamate (212d) (248 mg, 97% yield) as a white solid; $^1$H NMR (300 MHz, DMSO-$d_6$) δ 10.86 (s, 1H), 8.79 (s, 1H), 8.34 (s, 1H), 8.01 (d, J=8.2 Hz, 1H), 7.90 (d, J=7.3 Hz, 2H), 7.74-7.63 (m, 5H), 7.55 (d, J=4.2 Hz, 3H), 7.43-7.29 (m, 5H), 5.41 (d, J=17.3 Hz, 1H), 5.25 (d, J=17.1 Hz, 1H), 4.44 (t, J=8.1 Hz, 1H), 4.37 (d, J=6.7 Hz, 2H), 4.24 (t, J=6.8 Hz, 1H), 4.05 (t, J=8.7 Hz, 1H), 3.50 (t, J=9.5 Hz, 1H), 3.15-3.06 (m, 3H), 2.33 (dt, J=16.9, 8.7 Hz, 1H), 1.62 (q, J=10.1 Hz, 1H).

Step-4: Preparation of (2S,4R)-1-(2-(4-amino-6-(trifluoromethyl)-9H-pyrimido[4,5-b]indol-9-yl)acetyl)-4-(aminomethyl)-N-(6-bromopyridin-2-yl)pyrrolidine-2-carboxamide (212e)

Compound 212e was prepared according to the procedure reported in step-4 of scheme-180, from (9H-fluoren-9-yl)methyl (((3R,5S)-1-(2-(4-amino-6-(trifluoromethyl)-9H-pyrimido[4,5-b]indol-9-yl)acetyl)-5-((6-bromopyridin-2-yl)carbamoyl)pyrrolidin-3-yl)methyl)carbamate (212d) (240 mg, 0.295 mmol) in DMF (1.2 mL) using piperidine (0.291 mL, 2.95 mmol) and stirring at RT for 1 h. This gave after work up and purification using flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (2S,4R)-1-(2-(4-amino-6-(trifluoromethyl)-9H-pyrimido[4,5-b]indol-9-yl)acetyl)-4-(aminomethyl)-N-(6-bromopyridin-2-yl)pyrrolidine-2-carboxamide (212e) (65 mg, 37% yield) HCl salt as a white solid; $^1$H NMR (300 MHz, DMSO-$d_6$) (a mixture of two rotamers) δ 11.42 and 10.95 (2s, 1H, $D_2O$ exchangeable), 9.07-8.93 (m, 3H, 2H $D_2O$ exchangeable), 8.71 and 8.68 (2s, 1H), 8.37 (s, 3H, $D_2O$ exchangeable), 7.98 (dd, J=8.5, 5.6 Hz, 2H), 7.89-7.81 (m, 1H), 7.69 (t, J=8.0 Hz, 1H), 7.42 and 7.31 (2d, J=7.7 Hz, 1H), 5.53 (s, 2H), 4.49 (t, J=7.8 Hz, 1H), 4.13 (dd, J=10.1, 7.0 Hz, 1H), 3.76 (dd, J=10.2, 7.4 Hz, 1H), 3.19-3.03 (m, 1H), 3.01-2.86 (m, 1H), 2.81-2.67 (m, 1H), 2.61-2.57 (m, 1H), 1.78 (dt, J=12.8, 7.7 Hz, 1H). F NMR (282 MHz, DMSO-$d_6$) δ−58.60. MS (ES+): 591.2 (M+1); (ES−): 589.1 (M−1); Analysis calculated for $C_{24}H_{22}BrF_3N_8O_2$ $2H_2O{\cdot}1.9HCl$: C, 41.38; H, 4.04; Cl, 9.67; N, 16.08. Found: C, 41.53; H, 3.96; Cl, 9.47; N, 15.72.

Scheme 213

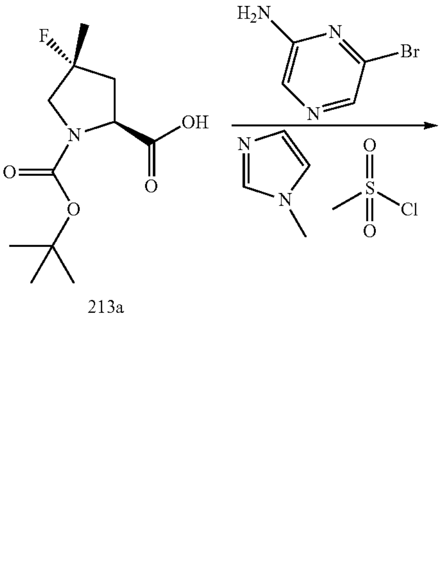

213a

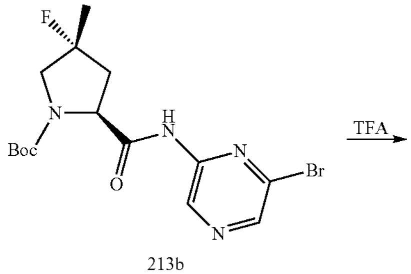

213b

-continued

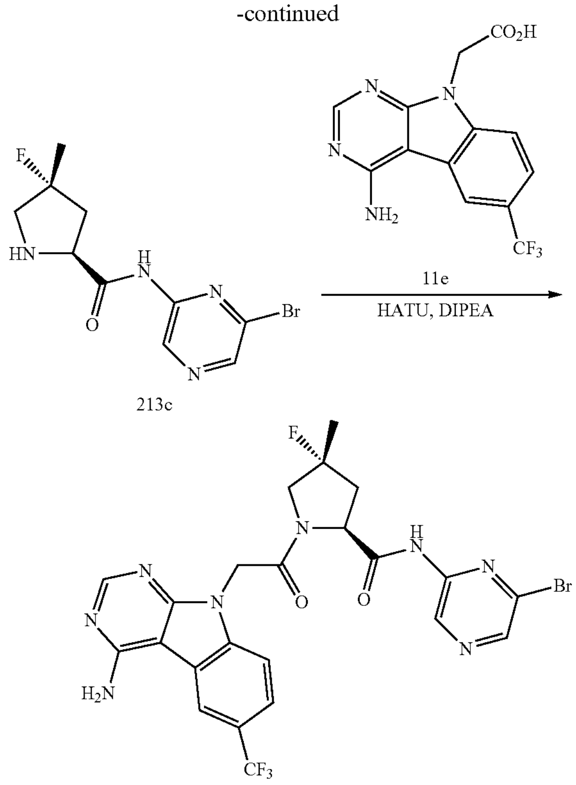

213c

213d

Preparation of (2S,4R)-1-(2-(4-amino-6-(trifluoromethyl)-9H-pyrimido[4,5-b]indol-9-yl)acetyl)-N-(6-bromopyrazin-2-yl)-4-fluoro-4-methylpyrrolidine-2-carboxamide (213d)

Step-1: Preparation of (2S,4R)-tert-butyl 2-((6-bromopyrazin-2-yl)carbamoyl)-4-fluoro-4-methylpyrrolidine-1-carboxylate (213b)

Compound 213b was prepared according to the procedure reported in step-1 of scheme-53, from (2S,4R)-1-(tert-butoxycarbonyl)-4-fluoro-4-methylpyrrolidine-2-carboxylic acid (213a) (0.5 g, 2.022 mmol: CAS #1386458-93-0) in DCM (15 mL) using 1-methyl-1H-imidazole (0.403 mL, 5.06 mmol), methanesulfonyl chloride (0.188 mL, 2.427 mmol), 6-bromopyrazin-2-amine (0.352 g, 2.022 mmol; CAS #54237-53-5) and stirring at RT for 18 h. This gave after workup (2S,4R)-tert-butyl 2-((6-bromopyrazin-2-yl)carbamoyl)-4-fluoro-4-methylpyrrolidine-1-carboxylate (213b) (0.5 g, 61% yield); MS (ES+): 403.10 (M+1).

Step-2: Preparation of (2S,4R)—N-(6-bromopyrazin-2-yl)-4-fluoro-4-methylpyrrolidine-2-carboxamide (213c)

Compound 213c was prepared according to the procedure reported in step-2 of scheme-1, from (2S,4R)-tert-butyl 2-((6-bromopyrazin-2-yl)carbamoyl)-4-fluoro-4-methylpyrrolidine-1-carboxylate (213b) (0.5 g, 1.240 mmol) in DCM (7 mL) using TFA (0.669 mL, 8.68 mmol) and stirring overnight at RT. This gave after workup and purification using reverse phase column chromatography [C18 column (50 g), eluting with ACN in water (containing 0.1% HCl) from 0-100%] (2S,4R)—N-(6-bromopyrazin-2-yl)-4-fluoro-4-methylpyrrolidine-2-carboxamide (213c) (176 mg, 47% yield); H NMR (300 MHz, DMSO-$d_6$) δ 11.76 (s, 1H), 9.60 (s, 1H), 9.30 (s, 1H), 8.68 (s, 1H), 4.66 (dd, J=10.8, 7.6 Hz, 1H), 3.66-3.51 (m, 1H), 3.41 (dd, J=35.2, 13.1 Hz, 1H), 2.77 (td, J=14.6, 7.5 Hz, 1H), 2.27 (ddd, J=37.3, 14.2, 10.9 Hz, 1H), 1.56 (d, J=21.4 Hz, 3H); MS (ES+): 303.00 (M+1).

Step-3: Preparation of (2S,4R)-1-(2-(4-amino-6-(trifluoromethyl)-9H-pyrimido[4,5-b]indol-9-yl)acetyl)-N-(6-bromopyrazin-2-yl)-4-fluoro-4-methylpyrrolidine-2-carboxamide (213d)

Compound 213d was prepared according to the procedure reported in step-3 of scheme-1, from HCl salt of (2S,4R)—N-(6-bromopyrazin-2-yl)-4-fluoro-4-methylpyrrolidine-2-carboxamide (213c) (48.0 mg, 0.141 mmol) in DMF (1.2 mL) using TFA salt of 2-(4-amino-6-(trifluoromethyl)-9H-pyrimido[4,5-b]indol-9-yl)acetic acid (11e) (60 mg, 0.141 mmol), HATU (81 mg, 0.212 mmol), DIPEA (0.123 mL, 0.707 mmol) and stirring at RT for 16 h. This gave after workup and purification by flash column chromatography [silica gel (24 g), eluting with DMA-80 in DCM from 0-50%] followed by purification using reverse phase column chromatography [C18 column (50 g), eluting with ACN in water (containing 0.1% HCl) from 0-100%] (2S,4R)-1-(2-(4-amino-6-(trifluoromethyl)-9H-pyrimido[4,5-b]indol-9-yl)acetyl)-N-(6-bromopyrazin-2-yl)-4-fluoro-4-methylpyrrolidine-2-carboxamide (213d) (35 mg, 42% yield) HCl salt as a white solid; $^1$H NMR (300 MHz, DMSO-$d_6$) (a mixture of two rotamers) δ 11.67 and 11.33 (2s, 1H, $D_2O$ exchangeable), 9.44 and 9.21 (2s, 1H), 8.99 (s, 1H), 8.73 (s, 2H, $D_2O$ exchangeable), 8.64 (s, 1H), 8.54 (s, 1H), 7.93-7.83 (m, 2H), 5.65 (d, J=17.4 Hz, 1H), 5.42 (d, J=17.4 Hz, 1H), 4.65 (dd, J=10.0, 7.3 Hz, 1H), 4.32 (dd, J=18.9, 12.0 Hz, 1H), 3.99 (dd, J=35.3, 11.9 Hz, 1H), 2.68-2.55 (m, 1H), 2.32-1.99 (m, 1H), 1.64 and 1.54 (2d, J=21.1 Hz, 3H). $^{19}F$ NMR (282 MHz, DMSO-$d_6$) δ−58.57, −139.00. MS (ES+): 595.1 (M+1): (ES−): 593.0 (M−1); Analysis calculated for $C_{23}H_{19}BrF_4N_8O_2$ $2.5H_2O{\cdot}HCl$: C, 40.81; H, 3.72; Cl, 5.24; N, 16.56. Found: C, 40.91; H, 3.67; Cl, 5.37; N, 16.25.

Scheme 214

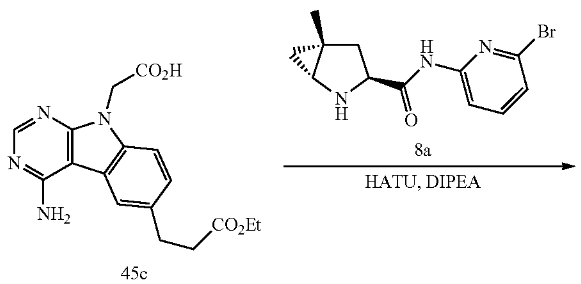

8a

45c

-continued

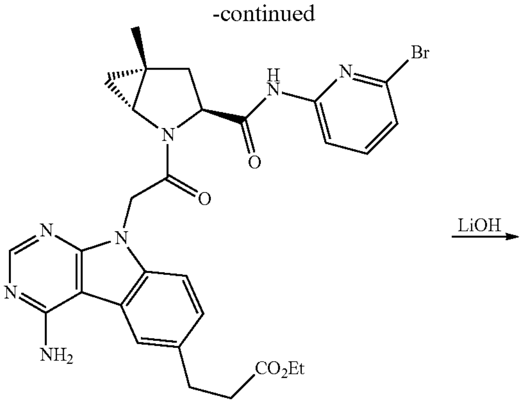

214a

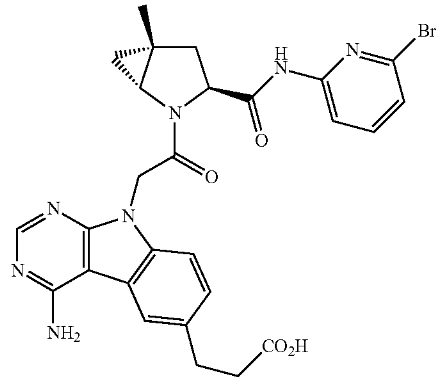

214b

Preparation of 3-(4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indol-6-yl)propanoic acid (214b)

Step-1: Preparation of ethyl 3-(4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indol-6-yl)propanoate (214a)

Compound 214a was prepared according to the procedure reported in step-3 of scheme-1, from TFA salt of 2-(4-amino-6-(3-ethoxy-3-oxopropyl)-9H-pyrimido[4,5-b]indol-9-yl) acetic acid (45c) (75 mg, 0.164 mmol) in DMF (5 mL) using HCl salt of (1R,3S,5R)—N-(6-bromopyridin-2-yl)-5-methyl-2-azabicyclo[3.1.0]hexane-3-carboxamide (8a) (65.6 mg, 0.197 mmol), HATU (94 mg, 0.247 mmol), DIPEA (106 mg, 0.822 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] ethyl 3-(4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indol-6-yl)propanoate (214a) (78 mg, 76% yield) as a white solid; $^1$H NMR (300 MHz, DMSO-$d_6$) δ 10.77 (s, 1H), 8.80-8.54 (m, 3H), 8.46-8.36 (m, 1H), 8.01 (d, J=8.2 Hz, 1H), 7.70 (t. J=8.0 Hz, 1H), 7.61 (d, J=8.5 Hz, 1H), 7.45 (dd, J=8.5, 1.5 Hz, 1H), 7.32 (d, J=7.7 Hz, 1H), 5.70 (d, J=17.3 Hz, 1H), 5.35 (d, J=17.2 Hz, 1H), 4.37 (dd, J=9.0, 6.0 Hz, 1H), 4.05 (q, J=7.1 Hz, 2H), 3.69 (dd, J=5.6, 2.4 Hz, 1H), 3.03 (t, J=7.7 Hz, 2H), 2.75 (t, J=7.7 Hz, 2H), 2.49-2.40 (m, 1H), 2.05-1.92 (m, 1H), 1.31 (s, 3H), 1.16 (t, J=7.1 Hz, 3H), 1.01 (t. J=5.5 Hz, 1H), 0.93 (dd, J=5.4, 2.4 Hz, 1H); MS (ES+): 620/622 (M+1), (ES−): 618/620 (M−1).

Step-2: Preparation of 3-(4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indol-6-yl)propanoic acid (214b)

Compound 214b was prepared according to the procedure reported in step-4 of scheme-17, from ethyl 3-(4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indol-6-yl)propanoate (214a) (50 mg, 0.081 mmol) in THF (2 mL) and water (1 mL) using 2M aqueous lithium hydroxide hydrate (0.040 mL, 0.081 mmol) and stirring at RT for 16 h. This gave after workup and purification by reverse phase column chromatography [C18 column (100 g), eluting with ACN in water (containing 0.1% HCl) from 0-100%] 3-(4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indol-6-yl)propanoic acid (214b) (33 mg, 69% yield) HCl salt as a white solid: $^1$H NMR (300 MHz, DMSO-$d_6$) (a mixture of two rotamers) δ 10.85 and 10.76 (2s, 1H, $D_2O$ exchangeable), 8.71 (s, 2H, $D_2O$ exchangeable), 8.63 and 8.62 (2s, 1H), 8.41 (s, 1H), 8.00 and 7.94 (2d, J=8.1 Hz, 1H), 7.69 (td, J=8.0, 4.5 Hz, 1H), 7.60 (dd, J=8.6, 2.5 Hz, 1H), 7.45 (d, J=8.5 Hz, 1H), 7.30 (dd, J=7.7, 4.9 Hz, 11H), 5.70 (d, J=17.3 Hz, 1H), 5.35 (d, J=17.3 Hz, 1H), 4.36 (dd, J=9.0, 5.9 Hz, 11H), 3.71-3.67 (m, 1H), 3.00 (t, J=7.8 Hz, 2H), 2.67 (t, J=7.8 Hz, 2H), 2.48-2.39 (m, 1H), 2.05-1.92 (m, 1H), 1.31 (s, 3H), 1.01 (t, J=5.5 Hz, 1H), 0.97-0.78 (m, 1H); MS (ES+): 592/594 (M+1), (ES−): 590/592 (M−1): Analysis calculated for $C_{27}H_{26}BrN_7O_4 \cdot 1.1HCl \cdot 2.75H_2O$: C, 47.54; H, 4.82; Cl, 5.72; N, 14.37. Found: C, 47.62; H, 4.56; Cl, 5.97; N, 14.24.

Scheme 215

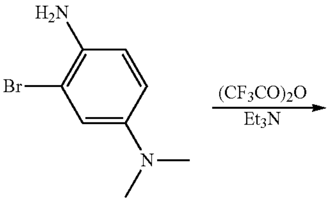

215a

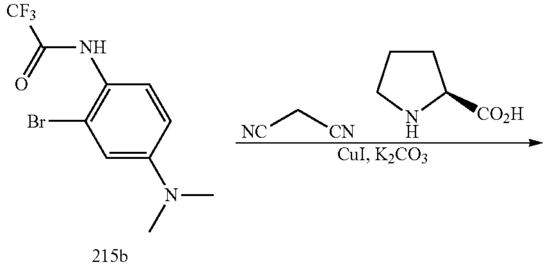

215b

-continued

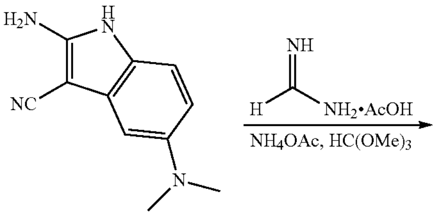

215c

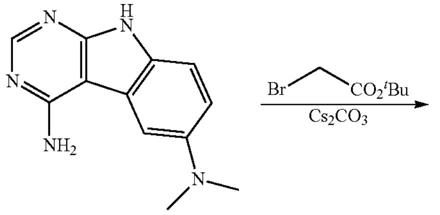

215d

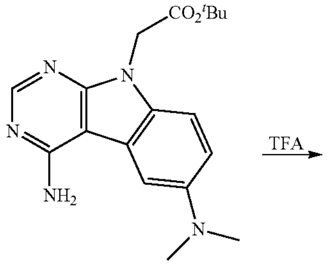

215e

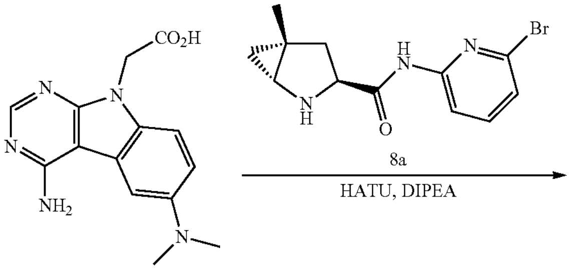

215f

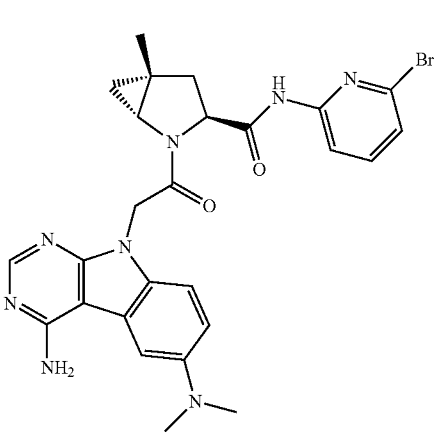

215g

Preparation of (1R,3S,5R)-2-(2-(4-amino-6-(dimethylamino)-9H-pyrimido[4,5-b]indol-9-yl)acetyl)-N-(6-bromopyridin-2-yl)-5-methyl-2-azabicyclo[3.1.0]hexane-3-carboxamide (215 g)

Step-1: Preparation of N-(2-bromo-4-(dimethylamino)phenyl)-2,2,2-trifluoroacetamide (215b)

Compound 215b was prepared according to the procedure reported in step-1 of scheme-46, from 3-bromo-N1,N1-dimethylbenzene-1,4-diamine (215a) (1.75 g, 8.14 mmol: CAS #107100-00-5) in DCM (25 mL) using triethylamine (1.40 g, 13.83 mmol) trifluoroacetic acid anhydride (2.56 g, 12.20 mmol) in DCM (5 mL) and stirring at RT for 1 h. This gave after workup N-(2-bromo-4-(dimethylamino)phenyl)-2,2,2-trifluoroacetamide (215b) as a black solid (2.59 g, 102% yield) which was used as such for the next step; $^1$H NMR (300 MHz, DMSO-$d_6$) δ 10.92 (s, 1H), 7.17 (d, J=8.8 Hz, 1H), 6.95 (d, J=2.8 Hz, 1H), 6.74 (dd, J=8.9, 2.8 Hz, 1H), 2.93 (s, 6H). $^{19}$F NMR (282 MHz, DMSO-$d_6$) δ −74.03; MS (ES+): 311/313 (M+1), (ES−): 309/311 (M−1).

Step-2: Preparation of 2-amino-5-(dimethylamino)-1H-indole-3-carbonitrile (215c)

Compound 215c was prepared according to the procedure reported in step-1 of scheme-11, from N-(2-bromo-4-(dimethylamino)phenyl)-2,2,2-trifluoroacetamide (215b) (2.59 g, 8.33 mmol) in DMSO (20 mL) using malononitrile (0.660 g, 9.99 mmol), L-proline (0.192 g, 1.665 mmol), CuI (159 mg, 0.833 mmol) a solution of $K_2CO_3$ (2.301 g, 16.65 mmol) in water (20 mL) and heating at 60° C. for 16 h under an argon atmosphere. This gave after workup and purification [$SiO_2$ gel (40 g), eluting with EtOAc in hexane from 0-60%] 2-amino-5-(dimethylamino)-1H-indole-3-carbonitrile (215c) (0.94 g, 56% yield) as a plum solid; $^1$H NMR (300 MHz, DMSO-$d_6$) δ 10.32 (s, 1H), 6.96 (d, J=8.5 Hz, 1H), 6.56 (s, 2H), 6.48 (d, J=2.3 Hz, 1H), 6.44 (dd, J=8.6, 2.4 Hz, 1H), 2.82 (s, 6H); MS (ES+): 201 (M+1), (ES−): 199 (M−1).

Step-3: Preparation of N6,N6-dimethyl-9H-pyrimido[4,5-b]indole-4,6-diamine (215d)

Compound 215d was prepared according to the procedure reported in step-2 of scheme-29, from 2-amino-5-(dimethylamino)-1H-indole-3-carbonitrile (215c) (0.94 g, 4.69 mmol) in ethanol (30 mL) using formamidine acetate (3.91 g, 37.6 mmol) and heating at 80° C. for 16 h. This gave after work up and purification by flash column chromatography [$SiO_2$ gel (24 g), eluting with CMA-80 in DCM from 0-20%] N6,N6-dimethyl-9H-pyrimido[4,5-b]indole-4,6-diamine (215d) (0.26 g, 24% yield) as a pale-green solid; $^1$H NMR (300 MHz, DMSO-$d_6$) δ 11.42 (s, 1H), 8.17 (s, 1H), 7.56 (d, J=2.4 Hz, 1H), 7.27 (d, J=8.8 Hz, 1H), 7.09 (s, 2H), 6.91 (dd, J=8.8, 2.4 Hz, 1H), 2.93 (s, 6H); MS (ES+): 228 (M+1), (ES−): 226 (M−1).

Step-4: Preparation of tert-butyl 2-(4-amino-6-(dimethylamino)-9H-pyrimido[4,5-b]indol-9-yl)acetate (215e)

Compound 215e was prepared according to the procedure reported in step-1 of scheme-1, from N6,N6-dimethyl-9H-pyrimido[4,5-b]indole-4,6-diamine (215d) (0.26 g, 1.144 mmol) in DMF (10 mL) using tert-butyl 2-bromoacetate (0.268 g, 1.373 mmol), $Cs_2CO_3$ (0.746 g, 2.288 mmol) and stirring at RT for 16 h. This gave after work up and purification using flash column chromatography [$SiO_2$ gel (40 g), methanol in DCM from 0-6%] tert-butyl 2-(4-amino-6-(dimethylamino)-9H-pyrimido[4,5-b]indol-9-yl)acetate (215e) (0.23 g, 59% yield) as a pale-yellow solid; $^1H$ NMR (300 MHz, DMSO-$d_6$) δ 8.21 (s, 1H), 7.61 (d, J=2.3 Hz, 1H), 7.36 (d, J=8.9 Hz, 1H), 7.23 (d, J=2.8 Hz, 2H), 6.94 (dd, J=9.0, 2.3 Hz, 1H), 5.02 (s, 2H), 2.95 (s, 6H), 1.40 (s, 9H); MS (ES+): 342 (M+1).

Step-5: Preparation of 2-(4-amino-6-(dimethylamino)-9H-pyrimido[4,5-b]indol-9-yl)acetic acid (215f)

Compound 215f was prepared according to the procedure reported in step-2 of scheme-1, from tert-butyl 2-(4-amino-6-(dimethylamino)-9H-pyrimido[4,5-b]indol-9-yl)acetate (215e) (230 mg, 0.674 mmol) using TFA (768 mg, 6.74 mmol) in DCM (10 mL) and stirring at RT for 16 h. This gave after work up TFA salt of 2-(4-amino-6-(dimethylamino)-9H-pyrimido[4,5-b]indol-9-yl)acetic acid (215f) (315 mg); $^1H$ NMR (300 MHz, DMSO-$d_6$) δ 8.54 (s, 3H), 8.02 (s, 1H), 7.71 (d, J=9.0 Hz, 1H), 7.27 (d, J=9.8 Hz, 1H), 5.22 (d, J=4.3 Hz, 2H), 3.09 (s, 6H). $^{19}F$ NMR (282 MHz, DMSO-$d_6$) δ-74.29; MS (ES+): 286 (M+1), (ES−): 284 (M−1).

Step-6: Preparation of (1R,3S,5R)-2-(2-(4-amino-6-(dimethylamino)-9H-pyrimido[4,5-b]indol-9-yl)acetyl)-N-(6-bromopyridin-2-yl)-5-methyl-2-azabicyclo[3.1.0]hexane-3-carboxamide (215 g)

Compound 215g was prepared according to the procedure reported in step-3 of scheme-1, from TFA salt of 2-(4-amino-6-(dimethylamino)-9H-pyrimido[4,5-b]indol-9-yl)acetic acid (215f) (75 mg, 0.188 mmol) in DMF (5 mL) using HCl salt of (1R,3S,5R)—N-(6-bromopyridin-2-yl)-5-methyl-2-azabicyclo[3.1.0]hexane-3-carboxamide (8a) (62.5 mg, 0.188 mmol), HATU (86 mg, 0.225 mmol), DIPEA (121 mg, 0.939 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-(dimethylamino)-9H-pyrimido[4,5-b]indol-9-yl)acetyl)-N-(6-bromopyridin-2-yl)-5-methyl-2-azabicyclo[3.1.0]hexane-3-carboxamide (215 g) (13 mg, 12% yield) HCl salt as a white solid; 1H NMR (300 MHz, DMSO-$d_6$/$D_2O$) δ 8.44 (s, 1H), 8.25 (s, 1H), 7.92 (d, J=8.2 Hz, 1H), 7.71-7.57 (m, 2H), 7.44 (dd, J=9.0, 2.3 Hz, 1H), 7.28 (d, J=7.7 Hz, 1H), 5.58 (d, J=17.5 Hz, 1H), 5.36 (d, J=17.4 Hz, 1H), 4.37-4.22 (m, 1H), 3.67-3.50 (m, 1H), 3.14 (s, 6H), 2.56-2.41 (m, 1H), 1.94 (dd, J=13.3, 6.1 Hz, 11H), 1.27 (s, 3H), 1.00 (t, J=5.5 Hz, 1H), 0.95-0.81 (m, 1H); MS (ES+): 563/565 (M+1), (ES−): 561/563 (M−1).

Scheme 216

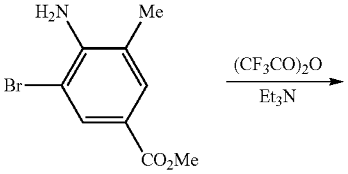

216a

-continued

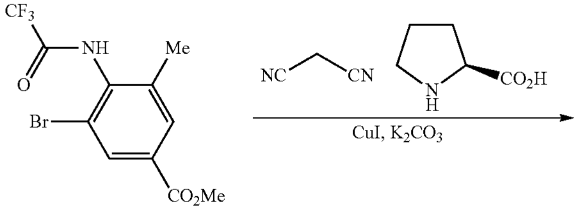

216b

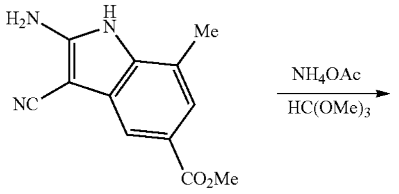

216c

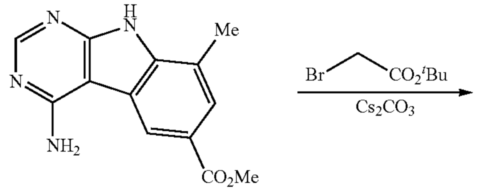

216d

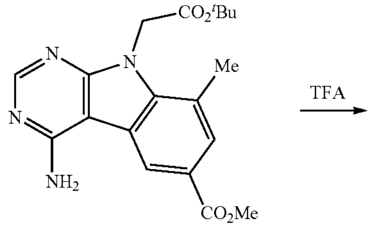

216e

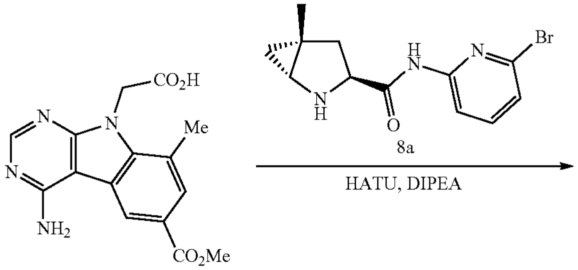

8a

216f

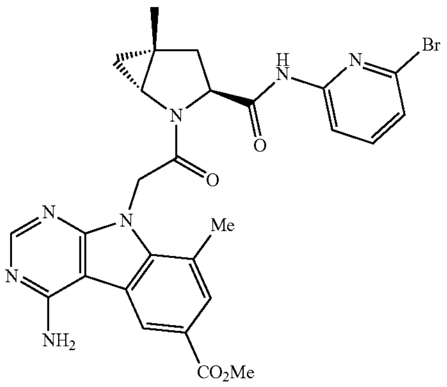

216g

Preparation of methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-8-methyl-9H-pyrimido[4,5-b]indole-6-carboxylate (216 g)

Step-1: Preparation of methyl 3-bromo-5-methyl-4-(2,2,2-trifluoroacetamido)benzoate (216b)

Compound 216b was prepared according to the procedure reported in step-1 of scheme-46, from methyl 4-amino-3-bromo-5-methylbenzoate (216a) (5.00 g, 20.48 mmol; CAS #900019-52-5) in DCM (25 mL) using triethylamine (3.52 g, 34.8 mmol) and trifluoroacetic acid anhydride (6.45 g, 30.7 mmol) in DCM (5 mL) and stirring at RT for 1 h. This gave after workup methyl 3-bromo-5-methyl-4-(2,2,2-trifluoroacetamido)benzoate (216b) (7.04 g) as a purple solid; $^1H$ NMR (300 MHz, DMSO-$d_6$) δ 11.49 (s, 1H), 8.08 (d, J=1.8 Hz, 1H), 7.96 (d, J=1.9 Hz, 1H), 3.88 (s, 3H), 2.29 (s, 3H). $^{19}F$ NMR (282 MHz, DMSO-$d_6$) δ−74.06; MS (ES−): 338/340 (M−1).

Step-2: Preparation of methyl 2-amino-3-cyano-7-methyl-1H-indole-5-carboxylate (216c)

Compound 216c was prepared according to the procedure reported in step-1 of scheme-11, from methyl 3-bromo-5-methyl-4-(2,2,2-trifluoroacetamido)benzoate (216b) (7.04 g, 20.70 mmol) in DMSO (30 mL) using malononitrile (1.641 g, 24.84 mmol), L-proline (0.477 g, 4.14 mmol), CuI (394 mg, 2.070 mmol), a solution of $K_2CO_3$ (5.72 g, 41.4 mmol) in water (30 mL) and heating at 60° C. for 16 h under an argon atmosphere. This gave after workup and purification [$SiO_2$ gel (40 g), eluting with EtOAc in hexane from 0-50%] methyl 2-amino-3-cyano-7-methyl-1H-indole-5-carboxylate (216c) (2.75 g, 58% yield) as an orange solid: $^1H$ NMR (300 MHz, DMSO-$d_6$) δ 11.18 (s, 1H), 7.60 (d, J=1.6 Hz, 1H), 7.41 (dd, J=1.6, 0.9 Hz, 1H), 6.79 (s, 2H), 3.82 (s, 3H), 2.39 (s, 3H). MS (ES+): 230 (M+1), (ES−): 228 (M−1).

Step-3: Preparation of methyl 4-amino-8-methyl-9H-pyrimido[4,5-b]indole-6-carboxylate (216d)

Compound 216d was prepared according to the procedure reported in step-2 of scheme-29, from methyl 2-amino-3-cyano-7-methyl-1H-indole-5-carboxylate (216c) (2.75 g, 12 mmol) using $NH_4OAc$ (2.77 g, 36.0 mmol), $HC(OMe)_3$ (12.73 g, 120 mmol) and heating at 90° C. for 16 h. This gave after work up methyl 4-amino-8-methyl-9H-pyrimido[4,5-b]indole-6-carboxylate (216d) (2.65 g, 86% yield) as a pale-yellow solid; $^1H$ NMR (300 MHz, DMSO-$d_6$) δ 12.22 (s, 1H), 8.78 (s, 1H), 8.30 (s, 1H), 7.80 (s, 1H), 7.34 (s, 2H), 3.88 (s, 3H), 2.57 (s, 3H); MS (ES+): 257 (M+1), (ES−): 255 (M−1).

Step-4: Preparation of methyl 4-amino-9-(2-(tert-butoxy)-2-oxoethyl)-8-methyl-9H-pyrimido[4,5-b]indole-6-carboxylate (216e)

Compound 216e was prepared according to the procedure reported in step-1 of scheme-1, from methyl 4-amino-8-methyl-9H-pyrimido[4,5-b]indole-6-carboxylate (216d) (2.00 g, 7.80 mmol) in DMF (15 mL) using tert-butyl 2-bromoacetate (1.827 g, 9.37 mmol), $Cs_2CO_3$ (5.09 g, 15.61 mmol) and stirring at RT for 16 h. This gave after work up methyl 4-amino-9-(2-(tert-butoxy)-2-oxoethyl)-8-methyl-9H-pyrimido[4,5-b]indole-6-carboxylate (216e) (2.25 g, 78% yield) as a beige solid; $^1H$ NMR (300 MHz, DMSO-$d_6$) δ 8.82 (d, J=1.6 Hz, 1H), 8.34 (s, 1H), 7.79 (s, 1H), 7.51 (s, 2H), 5.39 (s, 2H), 3.90 (s, 3H), 2.69 (s, 3H), 1.43 (s, 9H); MS (ES+): 371 (M+1), (ES−): 369 (M−1).

Step-5: Preparation of 2-(4-amino-6-(methoxycarbonyl)-8-methyl-9H-pyrimido[4,5-b]indol-9-yl)acetic acid (216f)

Compound 216f was prepared according to the procedure reported in step-2 of scheme-1, from methyl 4-amino-9-(2-(tert-butoxy)-2-oxoethyl)-8-methyl-9H-pyrimido[4,5-b]indole-6-carboxylate (216e) (1.10 g, 2.97 mmol) in DCM (15 mL) using TFA (3.39 g, 29.7 mmol) and stirring at RT for 16 h. This gave after work up TFA salt of 2-(4-amino-6-(methoxycarbonyl)-8-methyl-9H-pyrimido[4,5-b]indol-9-yl)acetic acid (216f) (1.65 g); $^1H$ NMR (300 MHz, DMSO-$d_6$) δ 8.96 (s, 1H), 8.75-8.62 (m, 2H), 8.60 (s, 1H), 7.89 (s, 1H), 5.48 (s, 2H), 3.92 (s, 3H), 2.74 (s, 3H); $^{19}F$ NMR (282 MHz, DMSO) δ−74.69; MS (ES+): 315 (M+1), (ES−): 313 (M−1).

Step-6: Preparation of methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-8-methyl-9H-pyrimido[4,5-b]indole-6-carboxylate (216 g)

Compound 216g was prepared according to the procedure reported in step-3 of scheme-1, from TFA salt of 2-(4-amino-6-(methoxycarbonyl)-8-methyl-9H-pyrimido[4,5-b]indol-9-yl)acetic acid (216f) (125 mg, 0.292 mmol) in DMF (5 mL) using HCl salt of (1R,3S,5R)—N-(6-bromopyridin-2-yl)-5-methyl-2-azabicyclo[3.1.0]hexane-3-carboxamide (8a) (97 mg, 0.292 mmol), HATU (133 mg, 0.350 mmol), DIPEA (189 mg, 1.459 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-8-methyl-9H-pyrimido[4,5-b]indole-6-carboxylate (216 g) (105 mg, 61% yield) HCl salt as a white solid; $^1H$ NMR (300 MHz, DMSO-$d_6$) δ 10.83 (s, 1H, $D_2O$ exchangeable), 8.94 (s, 1H), 8.85 (s, 2H, $D_2O$ exchangeable), 8.66 (s, 1H), 8.01 (d, J=8.1 Hz, 1H), 7.86 (s, 1H), 7.70 (t, J=8.0 Hz, 1H), 7.31 (d, J=7.7 Hz, 1H), 5.91 (d, J=18.0 Hz, 1H), 5.62 (d, J=17.9 Hz, 1H), 4.39 (dd, J=9.0, 6.1 Hz, 1H), 3.90 (s, 3H), 3.71 (dd, J=5.5, 2.3 Hz, 1H), 2.73 (s, 3H), 2.48-2.44 (m, 1H), 1.98 (dd, J=13.3, 6.0 Hz, 1H), 1.31 (s, 3H), 1.03 (t, J=5.5 Hz, 1H), 0.85 (dd, J=5.5, 2.4 Hz, 1H); MS (ES+): 592/594 (M+1), (ES−): 590/592 (M−1); Analysis calculated for $C_{27}H_{26}BrN_7O_4 \cdot 0.9HCl \cdot 2.5H_2O$: C, 48.38; H, 4.80; Cl, 4.76; N, 14.63. Found: C, 48.38; H, 4.71; Cl, 4.94; N, 14.34.

Scheme 217

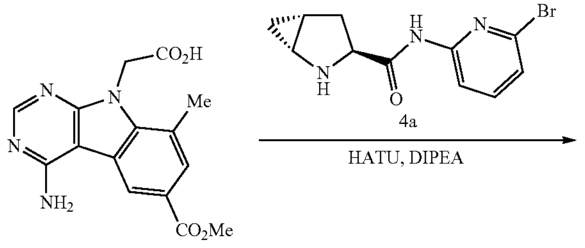

216f

-continued

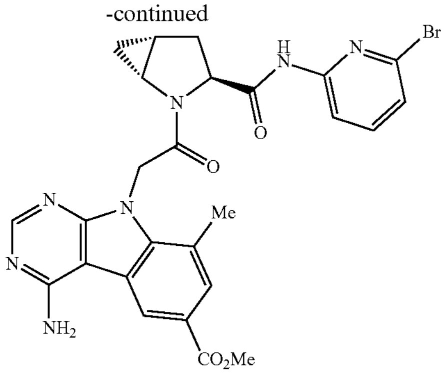

217a

Scheme 218

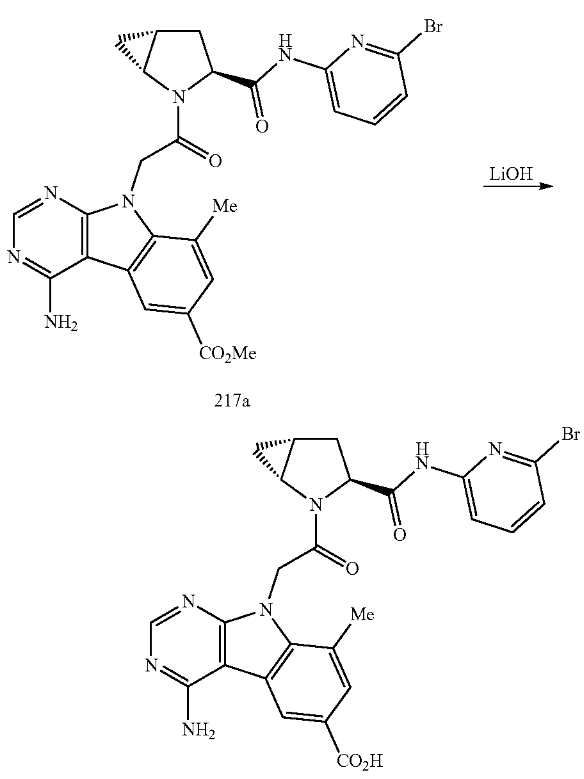

217a

218a

Preparation of methyl 4-amino-9-(2-((1R,3S,5R)-3-((6-bromopyridin-2-yl)carbamoyl)-2-azabicyclo[3.1.0]hexan-2-yl)-2-oxoethyl)-8-methyl-9H-pyrimido[4,5-b]indole-6-carboxylate (217a)

Compound 217a was prepared according to the procedure reported in step-3 of scheme-1, from TFA salt of 2-(4-amino-6-(methoxycarbonyl)-8-methyl-9H-pyrimido[4,5-b]indol-9-yl)acetic acid (216f) (125 mg, 0.292 mmol) in DMF (5 mL) using HCl salt of (1R,3S,5R)—N-(6-bromopyridin-2-yl)-2-azabicyclo[3.1.0]hexane-3-carboxamide (4a) (93 mg, 0.292 mmol), HATU (133 mg, 0.350 mmol), DIPEA (189 mg, 1.459 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] methyl 4-amino-9-(2-((1R,3S,5R)-3-((6-bromopyridin-2-yl)carbamoyl)-2-azabicyclo[3.1.0]hexan-2-yl)-2-oxoethyl)-8-methyl-9H-pyrimido[4,5-b]indole-6-carboxylate (217a) (110 mg, 65% yield) HCl salt as a white solid: 1H NMR (300 MHz, DMSO-$d_6$) δ 10.83 (s, 1H, $D_2O$ exchangeable), 8.94 (s, 1H), 8.79-8.43 (m, 3H, 2H $D_2O$ exchangeable), 8.00 (d, J=8.2 Hz, 1H), 7.86 (s, 1H), 7.71 (t, J=8.0 Hz, 1H), 7.31 (d, J=7.7 Hz, 1H), 5.95 (d, J=18.0 Hz, 1H), 5.67 (d, J=18.0 Hz, 1H), 4.42 (dd, J=9.1, 5.7 Hz, 1H), 3.96-3.89 (m, 4H), 2.75 (s, 3H), 2.43-2.29 (m, 1H), 2.29-2.11 (m, 1H), 2.01-1.87 (m, 1H), 1.18-1.04 (m, 1H), 0.77-0.63 (m, 1H); MS (ES+): 578/580 (M+1), (ES−): 576/578 (M−1); Analysis calculated for $C_{26}H_{24}BrN_7O_4 \cdot 0.9HCl \cdot 2.25H_2O$: C, 47.91; H, 4.55; Cl, 4.90; N, 15.04. Found: C, 47.86; H, 4.52. Cl, 4.67; N, 15.08.

Preparation of 4-amino-9-(2-((1R,3S,5R)-3-((6-bromopyridin-2-yl)carbamoyl)-2-azabicyclo[3.1.0]hexan-2-yl)-2-oxoethyl)-8-methyl-9H-pyrimido[4,5-b]indole-6-carboxylic acid (218a)

Compound 218a was prepared according to the procedure reported in step-4 of scheme-17, from methyl 4-amino-9-(2-((1R,3S,5R)-3-((6-bromopyridin-2-yl)carbamoyl)-2-azabicyclo[3.1.0]hexan-2-yl)-2-oxoethyl)-8-methyl-9H-pyrimido[4,5-b]indole-6-carboxylate (217a) (60 mg, 0.104 mmol) in THF (2 mL) and $H_2O$ (1 mL) using 2 M aqueous LiOH (0.052 mL, 0.104 mmol) and stirring for 16 h at RT. This gave after workup and purification by reverse phase column chromatography [C18 column (100 g), eluting with ACN in water (containing 0.1% HCl) from 0-100%] HCl salt of 4-amino-9-(2-((1R,3S,5R)-3-((6-bromopyridin-2-yl)carbamoyl)-2-azabicyclo[3.1.0]hexan-2-yl)-2-oxoethyl)-8-methyl-9H-pyrimido[4,5-b]indole-6-carboxylic acid (218a) (15 mg, 26% yield) as a white solid. $^1H$ NMR (300 MHz, DMSO-$d_6$) (mixture of two rotamers) δ 12.93 (bs, 1H, $D_2O$ exchangeable), 10.89 and 10.83 (s, 1H, $D_2O$ exchangeable), 8.91 (s, 1H), 8.60 (d, J=1.9 Hz, 1H), 8.53 (s, 2H, $D_2O$ exchangeable), 8.02 and 7.96 (d, J=8.1 Hz, 1H), 7.85 (s, 1H), 7.69 (q, J=8.0 Hz, 1H), 7.30 (dd, J=7.7, 5.0 Hz, 1H), 5.94 (dd, J=17.9, 2.4 Hz, 1H), 5.67 (d, J=17.9 Hz, 1H), 4.91 and 4.44 (dd, J=10.1, 4.7 Hz, 1H), 3.97-3.91 (m, 1H), 2.79 and 2.74 (s, 3H), 2.44-2.15 (m, 2H), 1.97-1.81 (m, 1H), 1.27-1.02 (m, 1H), 0.97 and 0.70 (m, 1H); MS (ES+): 564/566 (M+1), (ES−): 562/564 (M−1).

Scheme 219

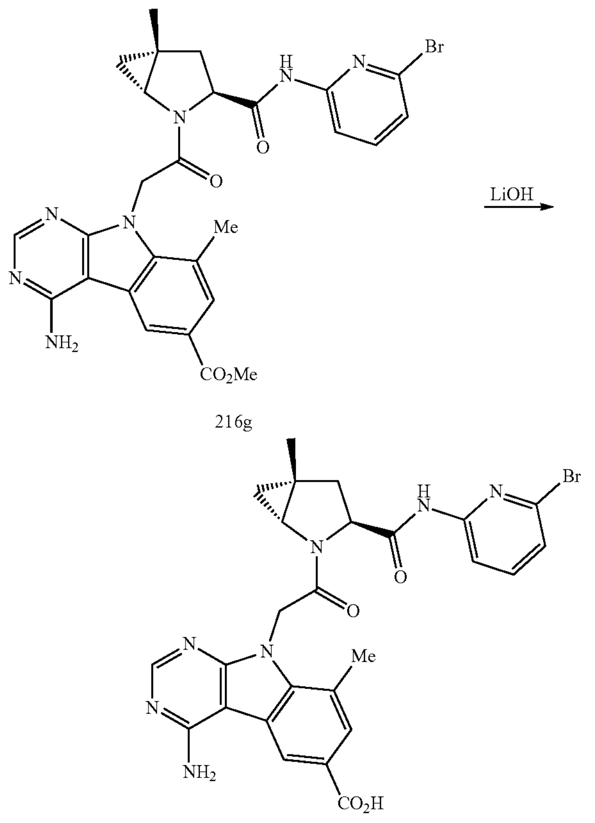

216g

219a

Scheme 220

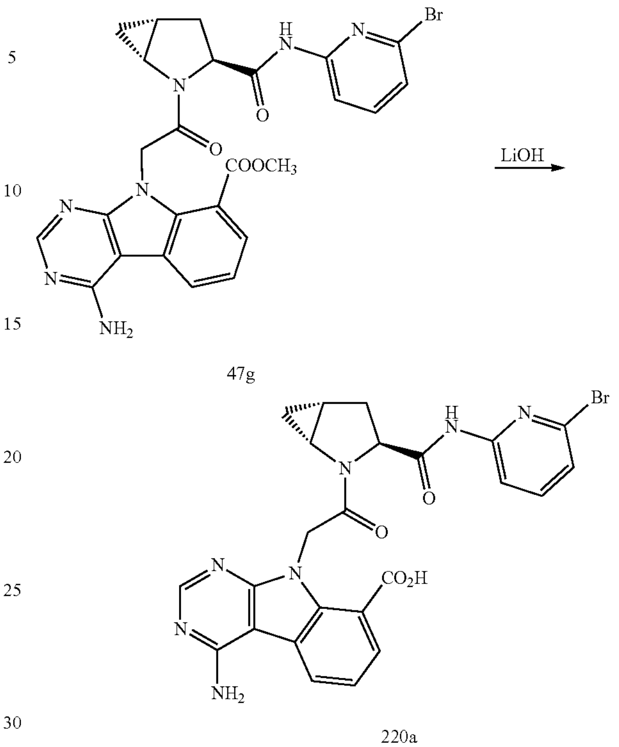

47g

220a

Preparation of 4-amino-9-(2-((1R,3S,5R)-3-((6-bromopyridin-2-yl)carbamoyl)-5-methyl-2-azabicyclo[3.1.0]hexan-2-yl)-2-oxoethyl)-8-methyl-9H-pyrimido[4,5-b]indole-6-carboxylic acid (219a)

Compound 219a was prepared according to the procedure reported in step-4 of scheme-17, from methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-8-methyl-9H-pyrimido[4,5-b]indole-6-carboxylate (216 g) (64 mg, 0.108 mmol) in THF (2 mL) and water (1 mL) using 2M aqueous lithium hydroxide hydrate (0.054 mL, 0.108 mmol) and stirring at RT for 16 h. This gave after workup and purification by reverse phase column chromatography [C18 column (100 g), eluting with ACN in water (containing 0.1% HCl) from 0-100%] 4-amino-9-(2-((1R,3S,5R)-3-((6-bromopyridin-2-yl)carbamoyl)-5-methyl-2-azabicyclo[3.1.0]hexan-2-yl)-2-oxoethyl)-8-methyl-9H-pyrimido[4,5-b]indole-6-carboxylic acid (219a) (23 mg, 37% yield) HCl salt as a white solid: 1H NMR (300 MHz, DMSO-$d_6$) (mixture of two rotamers) δ 12.97 (bs, 1H, $D_2O$ exchangeable), 10.89 and 10.82 (s, 1H, $D_2O$ exchangeable), 8.91 (s, 1H), 8.61 (d, J=2.5 Hz, 1H), 8.60 (s, 2H, $D_2O$ exchangeable), 8.02 and 7.95 (d, J=8.1 Hz, 1H), 7.85 (s, 1H), 7.69 (q, J=7.8 Hz, 1H), 7.30 (dd, J=7.7, 4.9 Hz, 1H), 5.90 (d, J=18.0 Hz, 1H), 5.62 (d, J=17.9 Hz, 1H), 4.91 and 4.41 (dd, J=10.0, 4.7 Hz, 1H), 3.71-3.68 (m, 1H), 2.77 and 2.73 (s, 3H), 2.53-2.33 (m, 1H), 2.13-1.93 (m, 1H), 1.31 (s, 3H), 1.07-0.98 (m, 1H), 0.91-0.81 (m, 1H); MS (ES+): 578/580 (M+1), (ES−): 576/578 (M−1).

Preparation of 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-8-carboxylic acid (220a)

Compound 220a was prepared according to the procedure reported in step-4 of scheme-17, from methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-8-carboxylate (47 g) (130 mg, 0.230 mmol) in THF (2 mL) and water (4 mL) using 1N aqueous lithium hydroxide hydrate (0.461 mL, 0.461 mmol) and stirring at RT for 16 h. This gave after workup and purification by reverse phase column chromatography [C18 column (50 g), eluting with ACN in water (containing 0.1% HCl) from 0-50%] 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-8-carboxylic acid (220a) (10 mg, 8% yield) HCl salt as a white solid; $^1H$ NMR (300 MHz, DMSO-$d_6$) δ 13.28 (s, 1H), 10.70 (s, 1H), 8.61 (d, J=7.8 Hz, 1H), 8.49 (s, 1H), 7.97 (d, J=8.2 Hz, 1H), 7.84 (d, J=7.5 Hz, 1H), 7.67 (t, J=8.0 Hz, 1H), 7.39 (t, J=7.8 Hz, 1H), 7.29 (d, J=7.7 Hz, 1H), 6.00 (d, J=17.4 Hz, 1H), 5.68 (d, J=17.3 Hz, 1H), 4.34 (dd, J=8.8, 5.7 Hz, 1H), 3.87-3.67 (m, 1H), 2.38-2.10 (m, 2H), 1.96-1.80 (m, 1H), 1.14-0.97 (m, 1H), 0.89-0.77 (m, 1H); MS (ES+): 552.10 (M+1); MS (ES+): 550.10 & 552.10 (M+1), MS (ES−): 548.10 & 550.00 (M−1).

Scheme 221

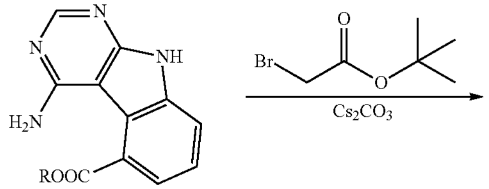

(R = Me, Et mixture)
46d

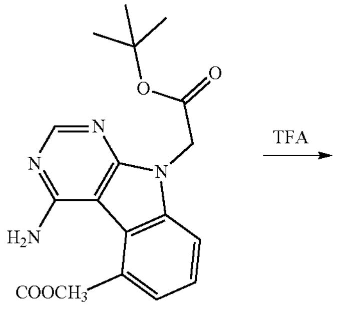

221a

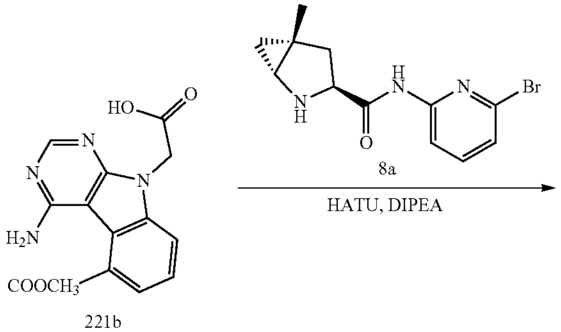

8a

221b

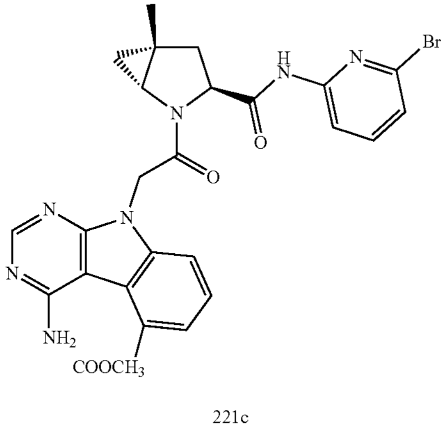

221c

Preparation of methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-5-carboxylate (221c)

Step-1: Preparation of methyl 4-amino-9-(2-(tert-butoxy)-2-oxoethyl)-9H-pyrimido[4,5-b]indole-5-carboxylate (221a)

Compound 221a was prepared according to the procedure reported in step-1 of scheme-1, from a mixture of methyl/ethyl 4-amino-9H-pyrimido[4,5-b]indole-5-carboxylate (46d) (230 mg) in DMF (15 mL) using tert-butyl 2-bromoacetate (0.168 mL, 1.139 mmol), $Cs_2CO_3$ (773 mg, 2.374 mmol) and stirring at RT for 14 h. This gave after work up and purification using flash column chromatography [$SiO_2$ gel (25 g), eluting with methanol/ethyl acetate (1:9) in hexanes from 0-50%] methyl 4-amino-9-(2-(tert-butoxy)-2-oxoethyl)-9H-pyrimido[4,5-b]indole-5-carboxylate (221a) (76 mg); $^1H$ NMR (300 MHz, DMSO-$d_6$) δ 8.33 (s, 1H), 7.92 (dd, J=8.2, 1.1 Hz, 1H), 7.83 (dd, J=7.8, 1.1 Hz, 1H), 7.56 (t, J=7.9 Hz, 1H), 7.25 (s, 2H), 5.23 (s, 2H), 4.01 (s, 3H), 1.40 (s, 9H); MS (ES+): 357.20 (M+1).

Step-2: Preparation of 2-(4-amino-5-(methoxycarbonyl)-9H-pyrimido[4,5-b]indol-9-yl)acetic acid (221b)

Compound 221b was prepared according to the procedure reported in step-2 of scheme-1, from methyl 4-amino-9-(2-(tert-butoxy)-2-oxoethyl)-9H-pyrimido[4,5-b]indole-5-carboxylate (221a) (75 mg, 0.21 mmol) in DCM (10 mL) using TFA (0.486 mL, 6.31 mmol) and stirring at RT for 17 h. This gave after work up 2-(4-amino-5-(methoxycarbonyl)-9H-pyrimido[4,5-b]indol-9-yl)acetic acid (221b) (99 mg) as TFA salt which was used as such for the next step; MS (ES+): 301.10 (M+1).

Step-3: Preparation of 2methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-5-carboxylate (221c)

Compound 221c was prepared according to the procedure reported in step-3 of scheme-1, from TFA salt of 2-(4-amino-5-(methoxycarbonyl)-9H-pyrimido[4,5-b]indol-9-yl)acetic acid (221b) (63 mg, 0.210 mmol) in DMF (10 mL) using HCl salt of (1R,3S,5R)—N-(6-bromopyridin-2-yl)-5-methyl-2-azabicyclo[3.1.0]hexane-3-carboxamide (8a) (84 mg, 0.252 mmol), HATU (160 mg, 0.420 mmol), DIPEA (0.183 mL, 1.05 mmol) and stirring at RT for 16 h. This gave after workup and purification by flash column chromatography [silica gel (12 g), eluting with MeOH/EtOAc (1:9) in hexanes from 0-60%] followed by purification using reverse phase column chromatography [C18 column (100 g), eluting with ACN in water (containing 0.1% HCl) from 0-100%] methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-5-carboxylate (221c) (52 mg, 43% yield) HCl salt as a white solid; $^1H$ NMR (300 MHz, DMSO-$d_6$) δ 10.77 (s, 1H), 8.64 (s, 1H), 8.34 (s, 2H), 8.04-7.97 (m, 3H), 7.73-7.64 (m, 2H), 7.31 (d, J=7.7 Hz, 1H), 5.81 (d, J=17.4 Hz, 1H), 5.46 (d, J=17.3 Hz, 1H), 4.37 (dd, J=9.1, 5.9 Hz, 1H), 4.00 (s, 3H), 3.70 (dd, J=5.5, 2.4 Hz, 1H), 2.54-2.39 (m, 1H), 1.98 (dd, J=13.2, 5.9 Hz, 1H), 1.31 (s, 3H), 1.02 (t, J=5.5 Hz, 1H), 0.96 (dd, J=5.3, 2.4 Hz, 1H); MS (ES+): 578.10 & 580.10 (M+1), MS (ES−): 576.10 & 578.10 (M−1): Analysis calculated for $C_{26}H_{24}BrN_7O_4 \cdot HCl \cdot 2H_2O$: C, 47.98; H, 4.49; Cl, 5.45; N, 15.06. Found: C, 48.24; H, 4.63; Cl, 5.30; N, 15.14.

Scheme 222

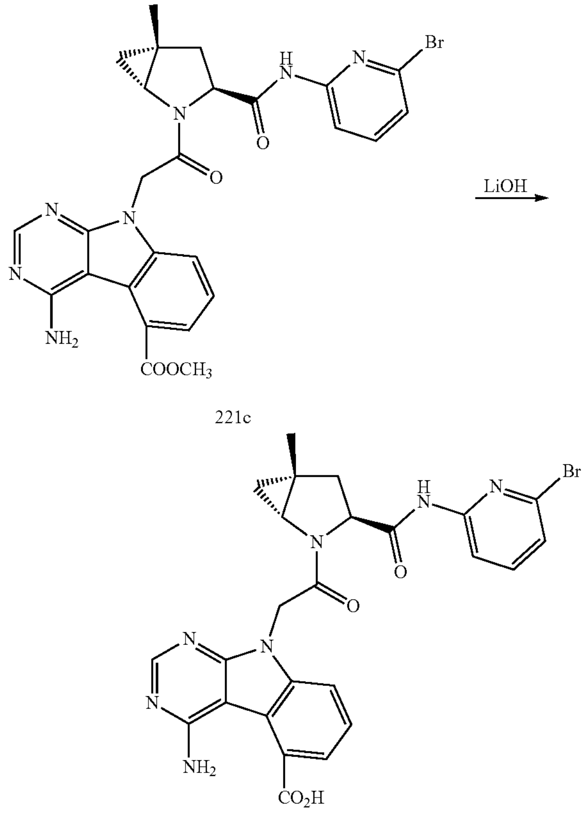

221c

222a

Scheme 223

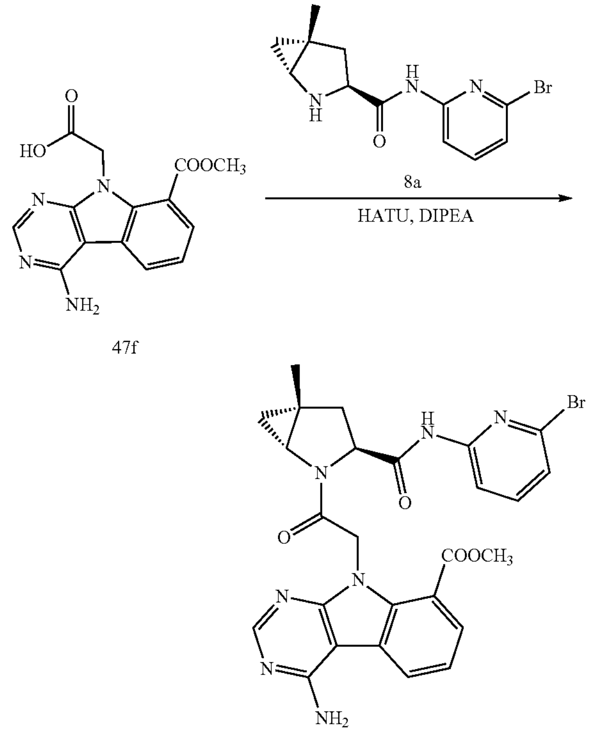

47f

8a

223a

Preparation of 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-5-carboxylic acid (222a)

Compound 222a was prepared according to the procedure reported in step-4 of scheme-17, from methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-5-carboxylate (221c) (100 mg, containing ethyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-5-carboxylate, ratio: 1:1) in THF (2 mL) and water (4 mL) using 1N aqueous lithium hydroxide hydrate (0.346 mL, 0, 346 mmol) and stirring at RT for 16 h. This gave after workup and purification by reverse phase column chromatography [C18 column (50 g), eluting with ACN in water (containing 0.1% HCl) from 0-50%] 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-5-carboxylic acid (222a) (6 mg, 6% yield) HCl salt as a white solid; $^1$H NMR (300 MHz, DMSO-$d_6$) δ 10.85 (s, 1H), 8.55 (s, 1H), 8.27 (s, 2H), 8.01-7.86 (m, 3H), 7.68 (t, J=8.0 Hz, 1H), 7.62 (t, J=7.9 Hz, 1H), 7.30 (d, J=7.6 Hz, 1H), 5.80-5.71 (m, 1H), 5.44 (d, J=17.0 Hz, 1H), 4.96-4.84 (m, 1H), 3.77-3.67 (m, 1H), 2.46-2.35 (m, 1H), 2.12-1.99 (m, 1H), 1.46-1.37 (m, 1H), 1.31 (s, 3H), 0.92-0.82 (m, 1H); MS (ES+): 564.10 & 566.10 (M+1), MS (ES−): 562.00 & 564.10 (M−1).

Preparation of methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-8-carboxylate (223a)

Compound 223a was prepared according to the procedure reported in step-3 of scheme-1, from TFA salt of 2-(4-amino-8-(methoxycarbonyl)-9H-pyrimido[4,5-b]indol-9-yl)acetic acid (47f) (152 mg, 0.505 mmol) in DMF (10 mL) using HCl salt of (1R,3S,5R)—N-(6-bromopyridin-2-yl)-5-methyl-2-azabicyclo[3.1.0]hexane-3-carboxamide (8a) (168 mg, 0.505 mmol), HATU (288 mg, 0.758 mmol), DIPEA (0.440 mL, 2.53 mmol) and stirring at RT for 19 h. This gave after workup and purification by flash column chromatography [silica gel (12 g), eluting with MeOH in DCM from 0-5%] followed by purification using reverse phase column chromatography [C18 column (50 g), eluting with ACN in water (containing 0.1% HCl) from 0-70%] methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-8-carboxylate (223a) (215 mg, 74% yield) HCl salt as a white solid; $^1$H NMR (300 MHz, DMSO-$d_6$) δ 10.74 (s, 1H), 8.73 (dd, J=7.9, 1.2 Hz, 1H), 8.64 (s, 1H), 8.58 (s, 3H), 7.99 (d, J=8.2 Hz, 1H), 7.87 (dd, J=7.7, 1.1 Hz, 1H), 7.69 (t, J=8.0 Hz, 1H), 7.47 (t, J=7.8 Hz, 1H), 7.30 (d, J=7.7 Hz, 1H), 5.93 (d, J=17.5 Hz, 1H), 5.62 (d, J=17.4 Hz, 1H), 4.31 (dd, J=9.0, 6.0 Hz, 1H), 3.92 (s, 3H), 3.59 (dd, J=5.3, 2.2 Hz, 1H), 2.51-2.35 (m, 1H), 1.96 (dd, J=13.2, 6.0 Hz, 1H), 1.30 (s, 3H), 1.04 (t, J=5.5 Hz, 1H), 0.90 (dd, J=5.5, 2.3 Hz, 1H); MS (ES+): 578.10 & 580.10 (M+1), MS (ES−): 576.10 & 578.10 (M−1); Analysis calculated for $C_{26}H_{24}BrN_7O_4{\cdot}0.95HCl{\cdot}2.25H_2O$: C, 47.78; H, 4.54; Cl, 5.15; N, 15.00. Found: C, 47.67; H, 4.37; Cl, 4.86; N, 14.71.

Scheme 224

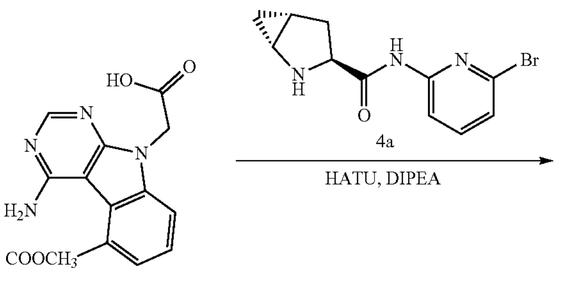

4a

221b

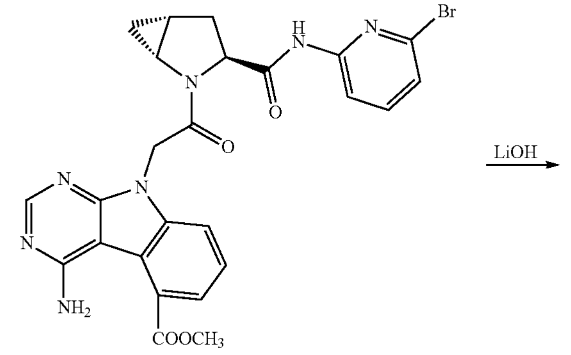

224a

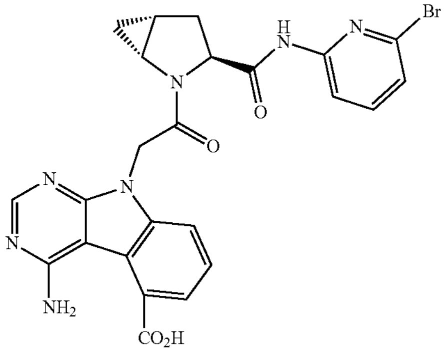

224b

Preparation of 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-5-carboxylic acid (224b)

Step-1: Preparation of methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-5-carboxylate (224a)

Compound 224a was prepared according to the procedure reported in step-3 of scheme-1, from TFA salt of 2-(4-amino-5-(methoxycarbonyl)-9H-pyrimido[4,5-b]indol-9-yl)acetic acid (221b) (61 mg, containing 2-(4-amino-5-(ethoxycarbonyl)-9H-pyrimido[4,5-b]indol-9-yl)acetic acid, ratio: 1:1) in DMF (10 mL) using HCl salt of (1R,3S,5R)—N-(6-bromopyridin-2-yl)-2-azabicyclo[3.1.0]hexane-3-carboxamide (4a) (77 mg, 0.242 mmol), HATU (154 mg, 0.404 mmol). DIPEA (0.176 mL, 1.010 mmol) and stirring at RT for 19 h. This gave after workup and purification by flash column chromatography [silica gel (12 g), eluting with MeOH/EtOAc (1:9) in hexanes from 0-60%] methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-5-carboxylate (224a) (115 mg, containing ethyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-5-carboxylate, ratio: 1:1) as a white solid; MS (ES+): 564.10 (M+1).

Step-2: Preparation of 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-5-carboxylic acid (224b)

Compound 224b was prepared according to the procedure reported in step-4 of scheme-17, from methyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-5-carboxylate (224a) (100 mg, containing ethyl 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-5-carboxylate, ratio: 1:1) in THF (2 mL) and water (4 mL) using 1N aqueous lithium hydroxide hydrate (0.354 mL, 0.354 mmol) and stirring at RT for 16 h. This gave after workup and purification by reverse phase column chromatography [C18 column (50 g), eluting with ACN in water (containing 0.1% HCl) from 0-50%] 4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indole-5-carboxylic acid (224b) (2 mg, 2% yield) HCl salt as a white solid; $^1$H NMR (300 MHz, DMSO-$d_6$) δ 10.85 (s, 1H), 8.56 (s, 1H), 8.28 (s, 2H), 8.00-7.88 (m, 3H), 7.74-7.57 (m, 2H), 7.31 (d, 1H), 5.80 (d, J=17.3 Hz, 1H), 5.48 (d, J=17.2 Hz, 1H), 4.90 (dd, J=11.5, 3.8 Hz, 1H), 4.03-3.88 (m, 1H), 2.69-2.52 (m, 1H), 2.02-1.72 (m, 2H), 1.33-1.15 (m, 1H), 1.03-0.86 (m, 1H); MS (ES+): 550.10 & 552.10 (M+1), MS (ES−): 548.10 & 550.00 (M−1).

Scheme 225

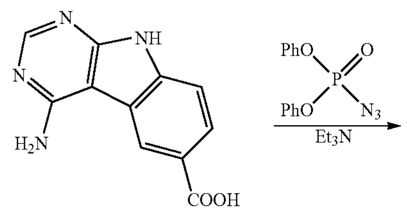

169a

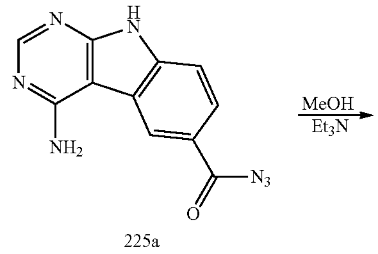

225a

-continued

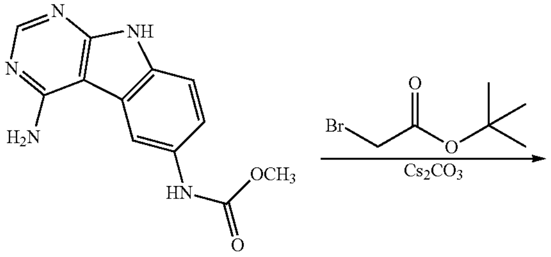

225b

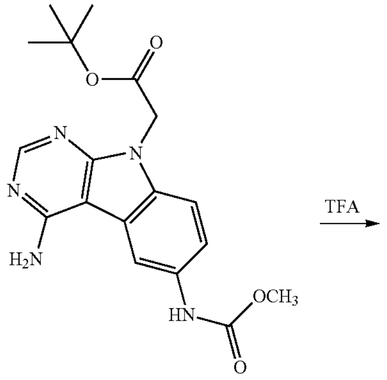

225c

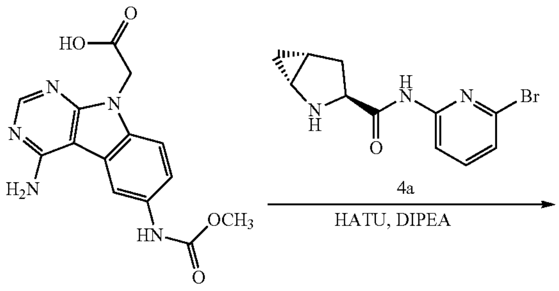

225d

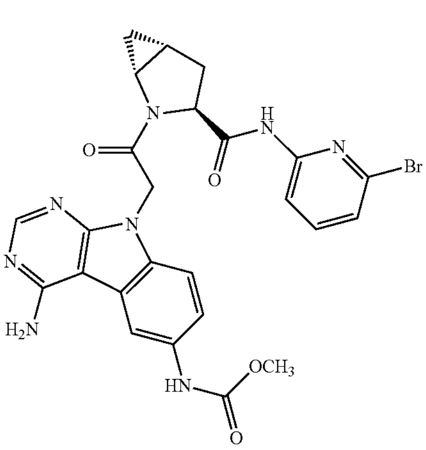

225e

Preparation of methyl (4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)carbamate (225e)

Step-1: Preparation of 4-amino-9H-pyrimido[4,5-b]indole-6-carbonyl azide (225a)

To a suspension of 4-amino-9H-pyrimido[4,5-b]indole-6-carboxylic acid (169a) (1 g, 4.38 mmol) in THF (25 mL) and DMF (25.00 mL) was added triethylamine (1.832 μL, 13.15 mmol) and stirred at RT for 15 min. The mixture was treated with diphenyl phosphorazidate (2.93 mL, 13.15 mmol; CAS #26386-88-9) and stirred at RT for 22 h. The reaction mixture was concentrated to dryness to afford 4-amino-9H-pyrimido[4,5-b]indole-6-carbonyl azide (225a) (4.29 g) which was used as such for the next step; MS (ES+): 254.10 (M+1).

Step-2: Preparation of methyl (4-amino-9H-pyrimido[4,5-b]indol-6-yl)carbamate (225b)

To a suspension of 4-amino-9H-pyrimido[4,5-b]indole-6-carbonyl azide (225a) (111 mg) in toluene (4 mL) was added methanol (6.03 mL, 149 mmol), triethylamine (0.366 mL, 2.63 mmol) and stirred at 15° C. for 4 h in a microwave. The reaction mixture was concentrated in vacuum and purified using flash column chromatography [silica gel (24 g), eluting with MeOH in DCM from 0-10%] to afford methyl (4-amino-9H-pyrimido[4,5-b]indol-6-yl)carbamate (225b) (96 mg) as a white solid; MS (ES+): 258.10 (M+1).

Step-3: Preparation of tert-butyl 2-(4-amino-6-((methoxycarbonyl)amino)-9H-pyrimido[4,5-b]indol-9-yl)acetate (225c)

Compound 225c was prepared according to the procedure reported in step-1 of scheme-1, from methyl (4-amino-9H-pyrimido[4,5-b]indol-6-yl)carbamate (225b) (90 mg, 0.350 mmol) in DMF (10 mL) using tert-butyl 2-bromoacetate (0.062 mL, 0.420 mmol) $Cs_2CO_3$ (285 mg, 0.875 mmol) and stirring at RT for 20 h. This gave after workup tert-butyl 2-(4-amino-6-((methoxycarbonyl)amino)-9H-pyrimido[4,5-b]indol-9-yl)acetate (225c) as a brown solid (75 mg) which was used as such for the next step; MS (ES+): 372.20 (M+1).

Step-4: Preparation of 2-(4-amino-6-((methoxycarbonyl)amino)-9H-pyrimido[4,5-b]indol-9-yl)acetic acid (225d)

Compound 225d was prepared according to the procedure reported in step-2 of scheme-1, from tert-butyl 2-(4-amino-6-((methoxycarbonyl)amino)-9H-pyrimido[4,5-b]indol-9-yl)acetate (225c) (75 mg) in DCM (10 mL) using TFA and stirring at RT. This gave after workup TFA salt of 2-(4-amino-6-((methoxycarbonyl)amino)-9H-pyrimido[4,5-b]indol-9-yl)acetic acid (225d) which was used as such for next step; MS (ES+): 316.10 (M+1).

Step-5: Preparation of methyl (4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)carbamate (225e)

Compound 225e was prepared according to the procedure reported in step-3 of scheme-1, from TFA salt of 2-(4-amino-6-((methoxycarbonyl)amino)-9H-pyrimido[4,5-b]indol-9- yl)acetic acid (225d) (64 mg, 0.202 mmol) in DMF (12 mL) using HCl salt of (1R,3S,5R)—N-(6-bromopyridin-2-yl)-2-azabicyclo[3.1.0]hexane-3-carboxamide (4a) (97 mg, 0.303 mmol), HATU (154 mg, 0.404 mmol), DIPEA (0.176 mL, 1.010 mmol) and stirring at RT for 20 h. This gave after workup and purification by flash column chromatography [silica gel (25 g), eluting with MeOH in DCM from 0-5%] followed by purification using reverse phase column chromatography [C18 column, eluting with ACN in water (containing 0.1% HCl) from 0-100%] methyl (4-amino-9-(2-((1R,3S,5R)-3-((6-bromopyridin-2-yl)carbamoyl)-2-azabicyclo[3.1.0]hexan-2-yl)-2-oxoethyl)-9H-pyrimido[4,5-b]indol-6-yl)carbamate (225e) (52 mg, 44% yield) HCl salt as a white solid; $^1$H NMR (300 MHz, DMSO-$d_6$) δ 10.77 (s, 1H), 9.61 (s, 1H), 8.67-8.59 (m, 3H), 8.43 (d, J=1.9 Hz, 1H), 8.00 (d, J=8.2 Hz, 1H), 7.70 (t, J=8.0 Hz, 1H), 7.63 (d, J=8.8 Hz, 1H), 7.46 (dd, J=8.8, 1.9 Hz, 1H), 7.32 (d, J=7.7 Hz, 1H), 5.74 (d, J=17.3 Hz, 1H), 5.40 (d, J=17.3 Hz, 1H), 4.42 (dd, J=9.1, 5.5 Hz, 1H), 3.99-3.78 (m, 1H), 3.69 (s, 3H), 2.43-2.09 (m, 2H), 2.02-1.79 (m, 1H), 1.14-0.96 (m, 1H), 0.85-0.68 (m, 1H); MS (ES+): 579.10 & 581.10 (M+1), MS (ES−): 577.00 & 579.10 (M−1); Analysis calculated for $C_{25}H_{23}BrNSO_4 \cdot 1.15HCl \cdot 2.25H_2O$: C, 45.37; H, 4.36; N: 16.93; Cl, 6.16. Found: C, 45.49; H, 4.22; N, 16.61; Cl: 5.98.

Scheme 226

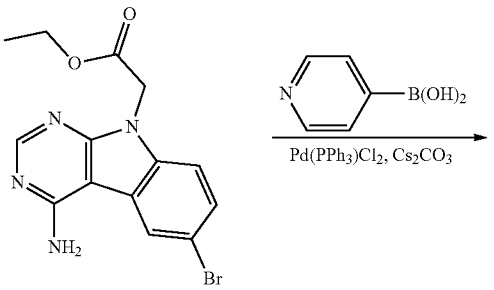

48a

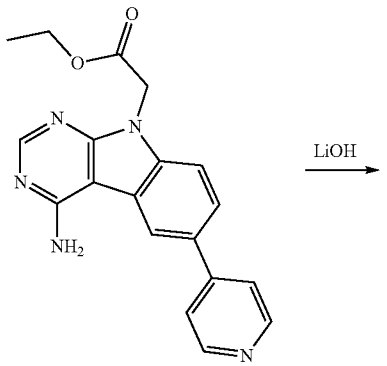

226a

-continued

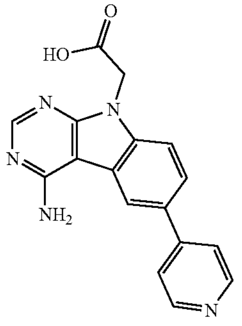

226b

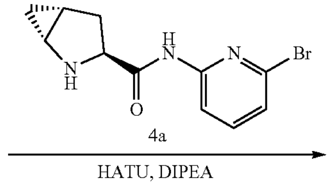

4a

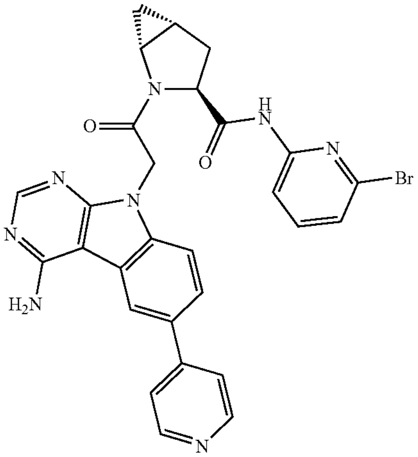

226c

Preparation of (1R,3S,5R)-2-(2-(4-amino-6-(pyridin-4-yl)-9H-pyrimido[4,5-b]indol-9-yl)acetyl)-N-(6-bromopyridin-2-yl)-2-azabicyclo[3.1.0]hexane-3-carboxamide (226c)

Step-1: Preparation of ethyl 2-(4-amino-6-(pyridin-4-yl)-9H-pyrimido[4,5-b]indol-9-yl)acetate (226a)

Compound 226a was prepared according to the procedure reported in step-1 of scheme-62, from ethyl 2-(4-amino-6-bromo-9H-pyrimido[4,5-b]indol-9-yl)acetate (48a) (200 mg, 0.573 mmol) in dioxane (18 mL) using pyridin-4-ylboronic acid (106 mg, 0.859 mmol), cesium carbonate (280 mg, 0.859 mmol) in water (2.2 mL), $Pd(PPh_3)_2Cl_2$ (80 mg, 0.115 mmol) and beating at 100° C. for 13 h under nitrogen. This gave after workup and purification using flash column chromatography [silica gel (25 g), eluting with MeOH in DCM from 0-8%] ethyl 2-(4-amino-6-(pyridin-4-yl)-9H-pyrimido[4,5-b]indol-9-yl)acetate (226a) (34 mg, 17% yield) as a white solid; $^1$H NMR (300 MHz, DMSO-$d_6$) δ 8.81 (d, J=1.7 Hz, 1H), 8.68-8.60 (m, 2H), 8.32 (s, 1H), 7.96-7.88 (m, 3H), 7.75 (d, J=8.6 Hz, 1H), 7.54 (s, 2H), 5.29 (s, 2H), 4.15 (q, J=7.1 Hz, 2H), 1.21 (t, J=7.1 Hz, 3H); MS (ES+): 348.20 (M+1).

Step-2: Preparation of 2-(4-amino-6-(pyridin-4-yl)-9H-pyrimido[4,5-b]indol-9-yl)acetic acid (226b)

Compound 226b was prepared according to the procedure reported in step-4 of scheme-17, from ethyl 2-(4-amino-6-(pyridin-4-yl)-9H-pyrimido[4,5-b]indol-9-yl)acetate (226a)

(32 mg, 0.092 mmol) in THF (3 mL) and methanol (3 mL) using a solution of lithium hydroxide hydrate (23.67 mg, 0.553 mmol) in water (3 mL) and stirring at RT for 14 h. This gave after workup 2-(4-amino-6-(pyridin-4-yl)-9H-pyrimido[4,5-b]indol-9-yl)acetic acid (226b) which was used as such for the next step; MS (ES+): 320.10 (M+1).

Step-3: Preparation of (1R,3S,5R)-2-(2-(4-amino-6-(pyridin-4-yl)-9H-pyrimido[4,5-b]indol-9-yl)acetyl)-N-(6-bromopyridin-2-yl)-2-azabicyclo[3.1.0]hexane-3-carboxamide (226c)

Compound 226c was prepared according to the procedure reported in step-3 of scheme-1, from 2-(4-amino-6-(pyridin-4-yl)-9H-pyrimido[4,5-b]indol-9-yl)acetic acid (226b) (0.029 g, 0.092 mmol) in DMF (8 mL) using HCl salt of (1R,3S,5R)—N-(6-bromopyridin-2-yl)-2-azabicyclo[3.1.0]hexane-3-carboxamide (4a) (44 mg, 0.138 mmol), HATU (70 mg, 0.184 mmol), DIPEA (0.080 mL, 0.460 mmol) and stirring at RT for 19 h. This gave after workup and purification by flash column chromatography [silica gel (12 g), eluting with MeOH in DCM from 0-10%] followed by purification using reverse phase column chromatography [C18 column, eluting with ACN in water (containing 0.1% HCl) from 0-100%] (1R,3S,5R)-2-(2-(4-amino-6 (pyridin-4-yl)-9H-pyrimido[4,5-b]indol-9-yl)acetyl)-N-(6-bromopyridin-2-yl)-2-azabicyclo[3.1.0]hexane-3-carboxamide (226c) (29 mg, 51% yield) HCl salt as a white solid; $^1$H NMR (300 MHz, DMSO-$d_6$) δ 10.77 (s, 1H), 9.19 (d, J=1.8 Hz, 1H), 8.97 (d, J=6.5 Hz, 2H), 8.70-8.53 (m, 5H), 8.25 (dd, J=8.9, 1.7 Hz, 1H), 8.00 (d, J=8.2 Hz, 1H), 7.89 (d, J=8.8 Hz, 1H), 7.70 (t, J=8.0 Hz, 1H), 7.31 (d, J=7.7 Hz, 1H), 5.82 (d, J=17.4 Hz, 1H), 5.47 (d, J=17.3 Hz, 1H), 4.42 (dd, J=9.1, 5.5 Hz, 1H), 4.03-3.83 (m, 1H), 2.45-2.08 (m, 2H), 2.00-1.79 (m, 1H), 1.21-0.98 (m, 1H), 0.88-0.68 (m, 1H); MS (ES+): 583.10 & 585.10 (M+1), MS (ES−): 581.10 & 583.10 (M−1); Analysis calculated for $C_{28}H_{23}BrN_8O_2 \cdot 2.75HCl \cdot 3.0H_2O$: C, 45.58; H, 4.34; N, 15.19. Found: C, 45.81; H, 4.30; N, 15.10.

Scheme 227

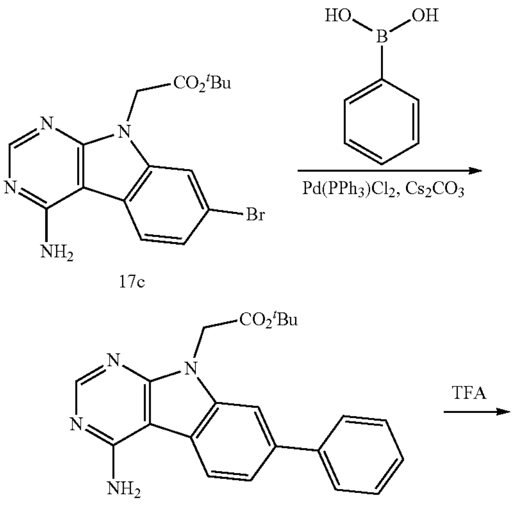

17c

227a

-continued

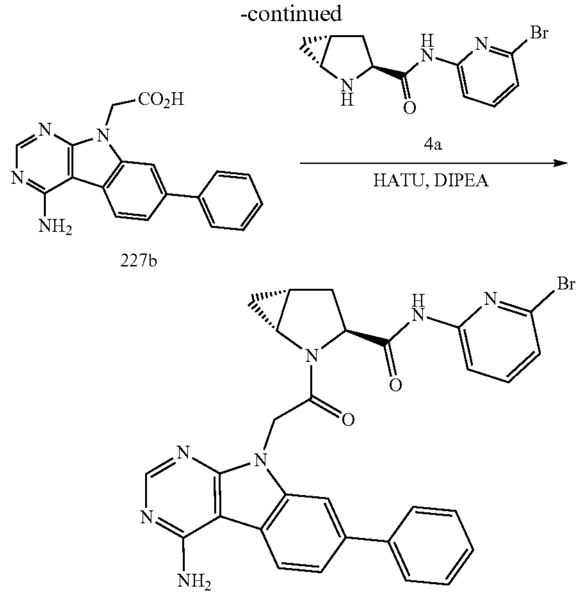

4a

227b

227c

Preparation of (1R,3S,5R)-2-(2-(4-amino-7-phenyl-9H-pyrimido[4,5-b]indol-9-yl)acetyl)-N-(6-bromopyridin-2-yl)-2-azabicyclo[3.1.0]hexane-3-carboxamide (227c)

Step-1: Preparation of tert-butyl 2-(4-amino-7-phenyl-9H-pyrimido[4,5-b]indol-9-yl)acetate (227a)

Compound 227a was prepared according to the procedure reported in step-1 of scheme-62, from tert-butyl 2-(4-amino-7-bromo-9H-pyrimido[4,5-b]indol-9-yl)acetate (17c) (400 mg, 1.06 mmol) in dioxane (10 mL) using phenyl boronic acid (194 mg, 1.591 mmol), a solution of 3.3 M aqueous $K_2CO_3$ (0.964 mL, 3.18 mmol), $Pd(PPh_3)_2Cl_2$ (74 mg, 0.106 mmol) and heating at 100° C. for 16 h under nitrogen. This gave after workup and purification using flash column chromatography [silica gel (12 g), eluting with MeOH in DCM from 0-4%] tert-butyl 2-(4-amino-7-phenyl-9H-pyrimido[4,5-b]indol-9-yl)acetate (227a) (242 mg, 61% yield) as a pale-brown solid: $^1$H NMR (300 MHz, DMSO-$d_6$) δ 8.42 (d, J=8.2 Hz, 1H), 8.30 (s, 1H), 7.92 (s, 1H), 7.82 (d, 2H), 7.60 (dd, J=8.1, 1.5 Hz, 1H), 7.51 (t, J=7.6 Hz, 2H), 7.43-7.37 (m, 1H), 7.35 (d, J=5.5 Hz, 2H), 5.22 (s, 2H), 1.41 (s, 9H); MS (ES+): 375 (M+1).

Step-2: Preparation of 2-(4-amino-7-phenyl-9H-pyrimido[4,5-b]indol-9-yl)acetic acid (227b)

Compound 227b was prepared according to the procedure reported in step-2 of scheme-1, from tert-butyl 2-(4-amino-7-phenyl-9H-pyrimido[4,5-b]indol-9-yl)acetate (227a) (242 mg, 0.646 mmol) in DCM (5 mL) using TFA (737 mg, 6.46 mmol) and stirring at RT for 16 h. This gave after work up TFA salt of 2-(4-amino-7-phenyl-9H-pyrimido[4,5-b]indol-9-yl)acetic acid (227b) (343 mg) which was used as such for the next step: $^1$H NMR (300 MHz, DMSO-$d_6$) δ 8.68-8.48 (m, 4H), 8.19 (s, 1H), 7.88 (d, J=1.5 Hz, 1H), 7.87 (s, 1H), 7.79 (dd, J=8.3, 1.5 Hz, 1H), 7.53 (dd, J=8.3, 6.9 Hz, 2H), 7.46-7.38 (m, 1H), 5.38 (s, 2H), $^{19}$F NMR (282 MHz, DMSO-$d_6$) δ−74.50; MS (ES+): 319 (M+1), (ES−): 317

(M−1): Analysis calculated for $C_{29}H_{24}BrN_7O_2 \cdot HCl \cdot 2.5H_2O$: C, 52.46; H, 4.55; Cl, 5.34; N, 14.77. Found: C, 52.45; H, 4.40. Cl, 5.47; N, 14.76.

Step-3: Preparation of (1R,3S,5R)-2-(2-(4-amino-7-phenyl-9H-pyrimido[4,5-b]indol-9-yl)acetyl)-N-(6-bromopyridin-2-yl)-2-azabicyclo[3.1.0]hexane-3-carboxamide (227c)

Compound 227c was prepared according to the procedure reported in step-3 of scheme-1, from TFA salt of 2-(4-amino-7-phenyl-9H-pyrimido[4,5-b]indol-9-yl)acetic acid (227b) (75 mg, 0.173 mmol) in DMF (5 mL) using HCl salt of (1R,3S,5R)—N-(6-bromopyridin-2-yl)-2-azabicyclo[3.1.0]hexane-3-carboxamide (4a) (55.3 mg, 0.173 mmol), HATU (79 mg, 0.208 mmol), DIPEA (112 mg, 0.867 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2 (4-amino-7-phenyl-9H-pyrimido[4,5-b]indol-9-yl)acetyl)-N-(6-bromopyridin-2-yl)-2-azabicyclo[3.1.0]hexane-3-carboxamide (227c) (54 mg, 53% yield) HCl salt as a white solid; $^1$H NMR (300 MHz, DMSO-$d_6$) δ 10.77 (s, 1H, $D_2O$ exchangeable), 8.71 (s, 2H, $D_2O$ exchangeable), 8.64 (s, 1H), 8.60 (d, J=8.3 Hz, 1H), 8.07-7.95 (m, 2H), 7.84 (d, J=1.5 Hz, 1H), 7.81 (s, 1H), 7.75 (dd, J=8.2, 1.5 Hz, 1H), 7.66 (t, J=8.0 Hz, 1H), 7.52 (t, J=7.6 Hz, 2H), 7.46-7.39 (m, 1H), 7.30 (d, J=7.7 Hz, 1H), 5.85 (d, J=17.3 Hz, 1H), 5.52 (d, J=17.2 Hz, 1H), 4.43 (dd, J=9.1, 5.5 Hz, 1H), 3.99-3.90 (m, 1H), 2.40-2.29 (m, 1H), 2.29-2.10 (m, 1H), 1.99-1.81 (m, 1H), 1.16-0.98 (m, 1H), 0.83-0.62 (m, 1H); MS (ES+): 582/584 (M+1), (ES−): 580/582 (M−1).

Preparation of (1R,3S,5R)-2-(2-(4-amino-7-phenyl-9H-pyrimido[4,5-b]indol-9-yl)acetyl)-N-(6-bromopyridin-2-yl)-5-methyl-2-azabicyclo[3.1.0]hexane-3-carboxamide (228a)

Compound 228a was prepared according to the procedure reported in step-3 of scheme-1, from TFA salt of 2-(4-amino-7-phenyl-9H-pyrimido[4,5-b]indol-9-yl)acetic acid (227b) (75 mg, 0.173 mmol) in DMF (5 mL) using HCl salt of (1R,3S,5R)—N-(6-bromopyridin-2-yl)-5-methyl-2-azabicyclo[3.1.0]hexane-3-carboxamide (8a) (57.7 mg, 0.173 mmol), HATU (79 mg, 0.208 mmol), DIPEA (112 mg, 0.867 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-7-phenyl-9H-pyrimido[4,5-b]indol-9-yl)acetyl)-N-(6-bromopyridin-2-yl)-5-methyl-2-azabicyclo[3.1.0]hexane-3-carboxamide (228a) (68 mg, 66% yield) HCl salt as a white solid; 1H NMR (300 MHz, DMSO-$d_6$) δ 10.77 (s, 1H, $D_2O$ exchangeable), 8.75 (s, 2H, $D_2O$ exchangeable), 8.64 (s, 1H), 8.60 (d, J=8.3 Hz, 1H), 7.99 (d, J=8.1 Hz, 2H), 7.84 (s, 1H), 7.82-7.72 (m, 2H), 7.67 (t, J=8.0 Hz, 1H), 7.53 (t, J=7.5 Hz, 2H), 7.43 (t, J=7.3 Hz, 1H), 7.30 (d, J=7.7 Hz, 1H), 5.81 (d, J=17.3 Hz, 1H), 5.47 (d, J=17.3 Hz, 1H), 4.39 (dd, J=9.1, 6.0 Hz, 1H), 3.74-368 (m, 1H), 2.49-2.42 (m, 1H), 1.99 (dd, J=13.2, 5.8 Hz, 1H), 1.32 (s, 3H), 1.03 (t, J=5.5 Hz, 1H), 0.96-0.82 (m, 1H); MS (ES+): 596/598 (M+1); (ES−): 594/596 (M−1); Analysis calculated for $C_{30}H_{26}BrN_7O_2 \cdot 1.15HCl \cdot 1.75H_2O$: C, 53.78; H, 4.61; Cl, 6.09; N, 14.64. Found: C, 53.70; H, 4.48; Cl, 6.02; N, 14.64.

Scheme 228

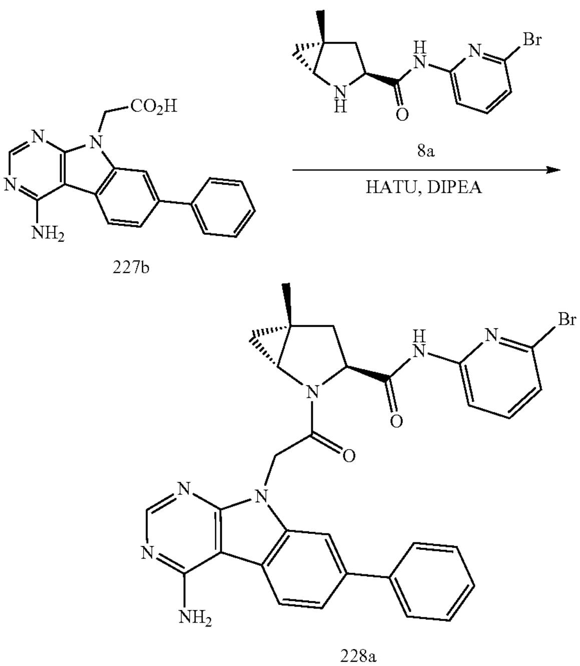

8a

227b

228a

Scheme 229

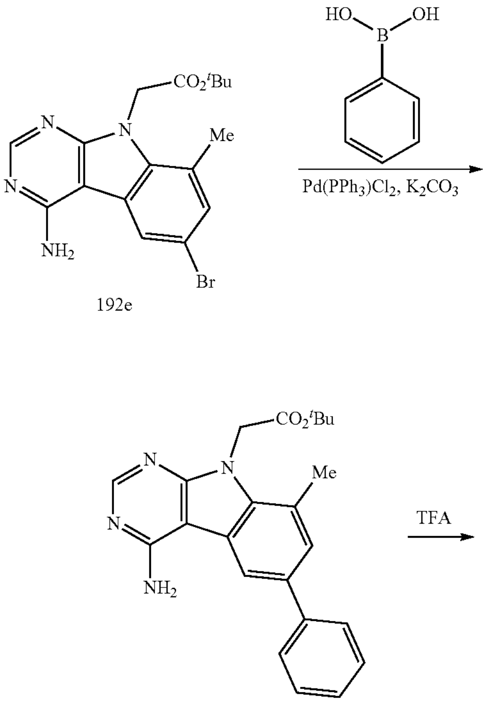

192e

229a

-continued

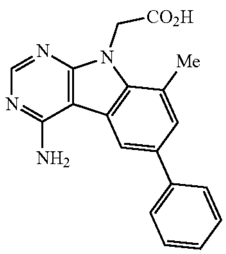

229b

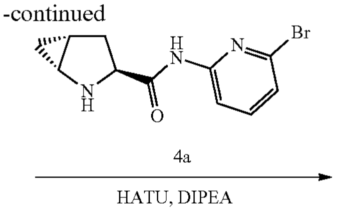

4a

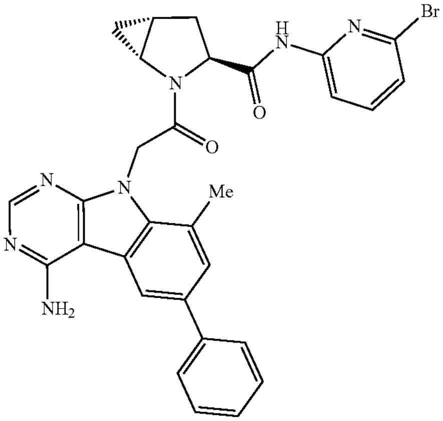

229c

Preparation of (1R,3S,5R)-2-(2-(4-amino-8-methyl-6-phenyl-9H-pyrimido[4,5-b]indol-9-yl)acetyl)-N-(6-bromopyridin-2-yl)-2-azabicyclo[3.1.0]hexane-3-carboxamide (229c)

Step-1: Preparation of tert-butyl 2-(4-amino-8-methyl-6-phenyl-9H-pyrimido[4,5-b]indol-9-yl)acetate (229a)

Compound 229a was prepared according to the procedure reported in step-1 of scheme-62, from tert-butyl 2-(4-amino-6-bromo-8-methyl-9H-pyrimido[4,5-b]indol-9-yl)acetate (192e) (300 mg, 0.767 mmol) in dioxane (4 mL) using phenyl boronic acid (140 mg, 1.150 mmol), a solution of 3.3 M aqueous $K_2CO_3$ (0.697 mL, 2.30 mmol), $Pd(PPh_3)_2Cl_2$ (53.8 mg, 0.077 mmol) and heating at 100° C. for 16 h under nitrogen. This gave after workup and purification using flash column chromatography [silica gel (24 g), eluting with MeOH in DCM from 0-3%] tert-butyl 2-(4-amino-8-methyl-6-phenyl-9H-pyrimido[4,5-b]indol-9-yl)acetate (229a) (200 mg, 67% yield) as a yellow solid; $^1H$ NMR (300 MHz, DMSO-$d_6$) δ 8.52-8.43 (m, 1H), 8.31 (s, 1H), 7.91-7.82 (m, 2H), 7.47 (dd, J=15.8, 8.1 Hz, 5H), 7.34 (t, J=7.3 Hz, 1H), 5.36 (s, 2H), 2.70 (s, 3H), 1.45 (s, 9H); MS (ES+): 389 (M+1), (ES−): 387 (M−1).

Step-2: Preparation of 2-(4-amino-8-methyl-6-phenyl-9H-pyrimido[4,5-b]indol-9-yl)acetic acid (229b)

Compound 229b was prepared according to the procedure reported in step-2 of scheme-1, from tert-butyl 2-(4-amino-8-methyl-6-phenyl-9H-pyrimido[4,5-b]indol-9-yl)acetate (229a) (198 mg, 0.510 mmol) in DCM (5 mL) using TFA (581 mg, 5.10 mmol) and stirring at RT for 16 h. This gave after work up TFA salt of 2-(4-amino-8-methyl-6-phenyl-9H-pyrimido[4,5-b]indol-9-yl)acetic acid (229b) (282 mg) which was used as such for the next step; $^1H$ NMR (300 MHz, DMSO-$d_6$) δ 8.59 (s, 1H), 8.54 (s, 1H), 8.35 (s, 2H), 7.86 (d, 2H), 7.63 (s, 1H), 7.51 (t, J=8.4, 6.9 Hz, 2H), 7.38 (t, J=7.2 Hz, 1H), 5.46 (s, 2H), 2.76 (s, 3H); $^{19}F$ NMR (282 MHz, DMSO) δ−74.28; MS (ES+): 333 (M+1); (ES−): 331 (M−1).

Step-3: Preparation of (1R,3S,5R)-2-(2-(4-amino-8-methyl-6-phenyl-9H-pyrimido[4,5-b]indol-9-yl)acetyl)-N-(6-bromopyridin-2-yl)-2-azabicyclo[3.1.0]hexane-3-carboxamide (229c)

Compound 229c was prepared according to the procedure reported in step-3 of scheme-1, from TFA salt of 2-(4-amino-8-methyl-6-phenyl-9H-pyrimido[4,5-b]indol-9-yl)acetic acid (229b) (75 mg, 0.168 mmol) in DMF (5 mL) using HCl salt of (1R,3S,5R)—N-(6-bromopyridin-2-yl)-2-azabicyclo[3.1.0]hexane-3-carboxamide (4a) (53.5 mg, 0.168 mmol), HATU (77 mg, 0.202 mmol), DIPEA (109 mg, 0.84 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-8-methyl-6-phenyl-9H-pyrimido[4,5-b]indol-9-yl)acetyl)-N-(6-bromopyridin-2-yl)-2-azabicyclo[3.1.0]hexane-3-carboxamide (229c) (82 mg, 82% yield) HCl salt as a white solid; 1H NMR (300 MHz, DMSO-$d_6$) δ 10.84 (s, 1H, $D_2O$ exchangeable), 8.83 (s, 2H, $D_2O$ exchangeable), 8.65 (s, 1H), 8.61 (s, 1H), 8.01 (d, J=8.2 Hz, 1H), 7.85 (d, J=7.6 Hz, 2H), 7.71 (t. J=8.0 Hz, 1H), 7.65 (s, 11H), 7.51 (t, J=7.6 Hz, 2H), 7.38 (t, J=7.4 Hz, 1H), 7.31 (d, J=7.7 Hz, 1H), 5.95 (d, J=17.9 Hz, 1H), 5.67 (d, J=17.9 Hz, 1H), 4.44 (dd, J=9.0, 5.7 Hz, 1H), 3.99-3.88 (m, 1H), 2.78 (s, 3H), 2.45-2.30 (m, 1H), 2.30-2.14 (m, 1H), 2.02-1.87 (m, 1H), 1.20-0.99 (m, 1H), 0.80-0.63 (m, 1H); MS (ES+): 596/598 (M+1); (ES−): 594/596 (M−1); Analysis calculated for $C_{30}H_{26}BrN_7O_2 \cdot HCl \cdot 2.25H_2O$: C, 53.50; H, 4.71; Cl, 5.26; N, 14.56. Found: C, 53.29; H, 4.53;

Scheme 230

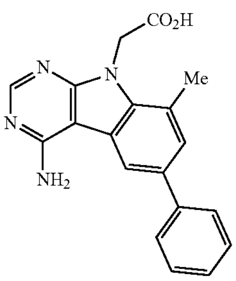

229b

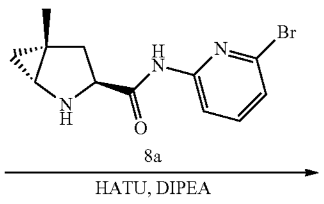

8a

-continued

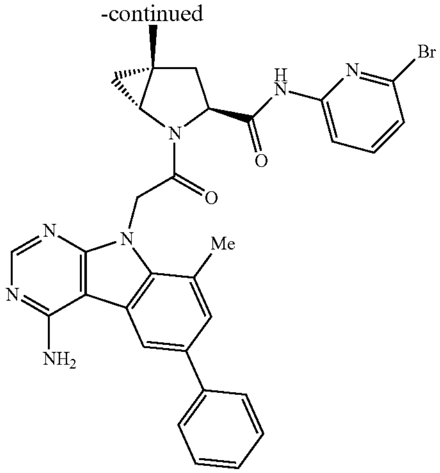

230a

Preparation of (1R,3S,5R)-2-(2-(4-amino-8-methyl-6-phenyl-9H-pyrimido[4,5-b]indol-9-yl)acetyl)-N-(6-bromopyridin-2-yl)-5-methyl-2-azabicyclo[3.1.0]hexane-3-carboxamide (230a)

Compound 230a was prepared according to the procedure reported in step-3 of scheme-1, from TFA salt of 2-(4-amino-8-methyl-6-phenyl-9H-pyrimido[4,5-b]indol-9-yl)acetic acid (229b) (75 mg, 0.168 mmol) in DMF (5 mL) using HCl salt of (1R,3S,5R)—N-(6-bromopyridin-2-yl)-5-methyl-2-azabicyclo[3.1.0]hexane-3-carboxamide (8a) (55.9 mg, 0.168 mmol), HATU (77 mg, 0.202 mmol), DIPEA (109 mg, 0.840 mmol) and stirring at RT for 16 h. This gave after workup and purification using flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-8-methyl-6-phenyl-9H-pyrimido[4,5-b]indol-9-yl)acetyl)-N-(6-bromopyridin-2-yl)-5-methyl-2-azabicyclo[3.1.0]hexane-3-carboxamide (230a) (68 mg, 66% yield) HCl salt as a white solid; $^1H$ NMR (300 MHz, DMSO-$d_6$) δ 10.84 (s, 1H, $D_2O$ exchangeable), 8.79 (s, 2H, $D_2O$ exchangeable), 8.64 (s, 1H), 8.61 (s, 1H), 8.02 (d, J=8.2 Hz, 1H), 7.85 (d, 2H), 7.71 (t, J=8.0 Hz, 1H), 7.64 (s, 1H), 7.50 (t, J=8.3, 6.9 Hz, 2H), 7.42-7.34 (m, 1H), 7.32 (d, J=7.7 Hz, 1H), 5.90 (d, J=18.0 Hz, 1H), 5.62 (d, J=17.9 Hz, 1H), 4.40 (dd, J=9.0, 6.1 Hz, 1H), 3.71 (dd, J=5.5, 2.3 Hz, 1H), 2.76 (s, 3H), 2.53-2.43 (m, 1H), 1.99 (dd, J=13.3, 6.1 Hz, 1H), 1.32 (s, 3H), 1.03 (t, J=5.5 Hz, 1H), 0.86 (dd, J=5.4, 2.4 Hz, 1H); MS (ES+): 610/612 (M+1), (ES−): 608/610 (M−1): Analysis calculated for $C_{31}H_{28}BrN_7O_2 \cdot 1.1HCl \cdot 2.25H_2O$: C, 53.87; H, 4.90; Cl, 5.64; N, 14.19. Found: C, 53.71; H, 4.64; Cl, 5.59; N, 14.27.

Scheme 231

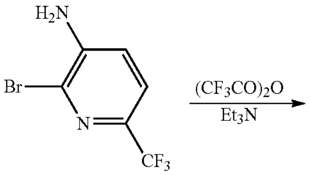

231a

-continued

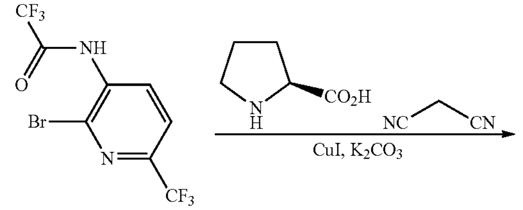

231b

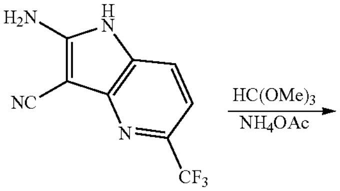

231c

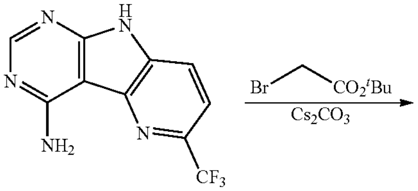

231d

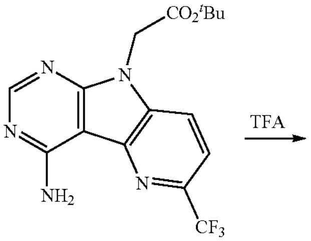

231e

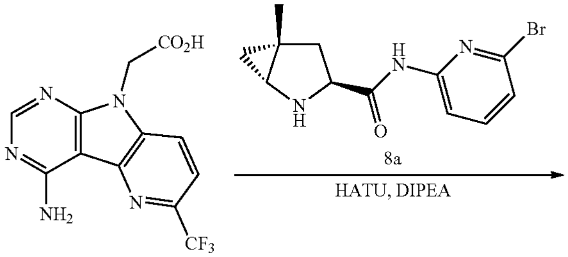

231f

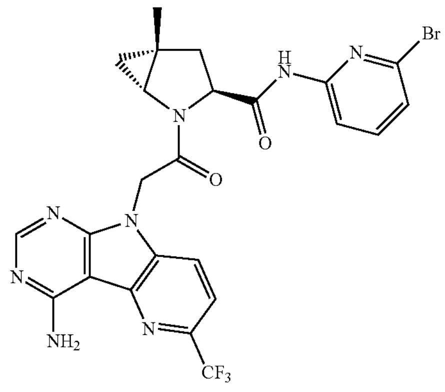

231g

Preparation of (1R,3S,5R)-2-(2-(4-amino-6-(trifluoromethyl)-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (231 g)

Step-1: Preparation of N-(2-bromo-6-(trifluoromethyl)pyridin-3-yl)-2,2,2-trifluoroacetamide (231b)

Compound 231b was prepared according to the procedure reported in step-1 of scheme-46, from 2-bromo-6-(trifluoromethyl)pyridin-3-amine (231a) (5 g, 20.75 mmol: CAS #117519-16-1) in DCM (30 mL) using triethylamine (3.57 g, 35.3 mmol), trifluoroacetic acid anhydride (6.54 g, 31.1 mmol) and stirring at RT for 1 h. This gave after workup N-(2-bromo-6-(trifluoromethyl)pyridin-3-yl)-2,2,2-trifluoroacetamide (231b) as a plum solid (6.94 g, 99% yield) and was used as such for next step: $^1H$ NMR (300 MHz, DMSO-$d_6$) δ 1.81 (s, 1H), 8.28 (d, J=8.1 Hz, 1H), 8.13 (d, J=8.1 Hz, 1H); $^{19}F$ NMR (282 MHz, DMSO-$d_6$) δ−66.38, −74.12.

Step-2: Preparation of 2-amino-5-(trifluoromethyl)-1H-pyrrolo[3,2-b]pyridine-3-carbonitrile (231c)

Compound 231c was prepared according to the procedure reported in step-1 of scheme-11, from N-(2-bromo-6-(trifluoromethyl)pyridin-3-yl)-2,2,2-trifluoroacetamide (231b) (6.94 g, 20.59 mmol) in DMSO (30 mL) using malononitrile (1.632 g, 24.71 mmol), L-proline (0.474 g, 4.12 mmol), CuI (0.392 g, 2.059 mmol), a solution of $K_2CO_3$ (5.69 g, 41.2 mmol) in water (30 mL) and heating at 60° C. for 16 h under an argon atmosphere. This gave after workup and purification [$SiO_2$ gel (40 g), eluting with EtOAc in hexane from 0-100%] 2-amino-5-(trifluoromethyl)-1H-pyrrolo[3,2-b]pyridine-3-carbonitrile (231c) (3.47 g, 75% yield) as a deep pink solid; $^1H$ NMR (300 MHz, DMSO-$d_6$) δ 11.27 (s, 1H), 7.60 (s, 2H), 7.53 (d, J=8.1 Hz, 1H), 7.34 (d, J=8.1 Hz, 1H); $^{19}F$ NMR (282 MHz, DMSO-$d_6$) δ−64.41; MS (ES+): 227 (M+1), (ES−): 225 (M−1).

Step-3: Preparation of 6-(trifluoromethyl)-9H-pyrido[2',3':4,5]pyrrolo[2,3-d]pyrimidin-4-amine (231d)

Compound 231d was prepared according to the procedure reported in step-2 of scheme-29, from 2-amino-5-(trifluoromethyl)-1H-pyrrolo[3,2-b]pyridine-3-carbonitrile (231c) (3.47 g, 15.34 mmol) in ethanol (10 mL) using $NH_4OAc$ (3.55 g, 46.0 mmol), $HC(OMe)_3$ (8.14 g, 77 mmol) and heating at 90° C. for 16 h. This gave after work up 6-(trifluoromethyl)-9H-pyrido[2',3':4,5]pyrrolo[2,3-d]pyrimidin-4-amine (231d) (1.90 g, 49% yield) as a pale-gray solid; $^1H$ NMR (300 MHz, DMSO-$d_6$) δ 12.49 (s, 1H), 8.43 (s, 1H), 8.03 (d, J=8.4 Hz, 1H), 7.84 (d, J=8.4 Hz, 1H). $^{19}F$ NMR (282 MHz, DMSO-$d_6$) δ−64.04; MS (ES+): 254 (M+1); (ES−): 252 (M−1).

Step-4: Preparation of tert-butyl 2-(4-amino-6-(trifluoromethyl)-9H-pyrido[2',3':4,5]pyrrolo[2,3-d]pyrimidin-9-yl)acetate (231e)

Compound 231e was prepared according to the procedure reported in step-1 of scheme-1, from 6-(trifluoromethyl)-9H-pyrido[2',3':4,5]pyrrolo[2,3-d]pyrimidin-4-amine (231d) (1.90 g, 7.50 mmol) in DMF (15 mL) using tert-butyl 2-bromoacetate (1.610 g, 8.25 mmol), $Cs_2CO_3$ (4.89 g, 15.01 mmol) and stirring at RT for 16 h. This gave after work up tert-butyl 2-(4-amino-6-(trifluoromethyl)-9H-pyrido[2',3':4,5] pyrrolo[2,3-d]pyrimidin-9-yl)acetate (231e) (1.74 g, 63% yield) as a pale gray solid: $^1H$ NMR (300 MHz, DMSO-$d_6$) δ 8.48 (s, 1H), 8.30 (d, J=8.5 Hz, 1H), 8.19 (s, 1H), 7.94 (d, J=8.6 Hz, 1H), 6.64 (s, 1H), 5.25 (s, 2H), 1.40 (s, 9H). $^{19}F$ NMR (282 MHz, DMSO-$d_6$) δ−64.07; MS (ES+): 368 (M+1), (ES−): 366 (M−1).

Step-5: Preparation of 2-(4-amino-6-(trifluoromethyl)-9H-pyrido[2',3':4,5]pyrrolo[2,3-d]pyrimidin-9-yl)acetic acid (231f)

Compound 231f was prepared according to the procedure reported in step-2 of scheme-1, from tert-butyl 2-(4-amino-6-(trifluoromethyl)-9H-pyrido[2',3':4,5]pyrrolo[2,3-d]pyrimidin-9-yl)acetate (231e) (1.00 g, 2.72 mmol) using TFA (3.10 g, 27.2 mmol) in DCM (5 mL) and stirring at RT for 16 h. This gave after work up TFA salt of 2-(4-amino-6-(trifluoromethyl)-9H-pyrido[2',3':4,5]pyrrolo[2,3-d]pyrimidin-9-yl)acetic acid (231f) (1.47 g) as a beige solid; $^1H$ NMR (300 MHz, DMSO-$d_6$) δ 8.55 (s, 1H), 8.39 (d, J=8.6 Hz, 1H), 7.98 (d, J=8.5 Hz, 1H), 5.30 (s, 2H); $^{19}F$ NMR (282 MHz, DMSO-$d_6$) δ−64.10, −74.90; MS (ES+): 312 (M+1).

Step-6: Preparation of (1R,3S,5R)-2-(2-(4-amino-6-(trifluoromethyl)-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (231 g)

Compound 231g was prepared according to the procedure reported in step-3 of scheme-1, from TFA salt of 2-(4-amino-6-(trifluoromethyl)-9H-pyrido[2',3':4,5]pyrrolo[2,3-d]pyrimidin-9-yl)acetic acid (231f) (75 mg, 0.176 mmol) in DMF (5 mL) using HCl salt of (1R,3S,5R)—N-(6-bromopyridin-2-yl)-5-methyl-2-azabicyclo[3.1.0]hexane-3-carboxamide (8a) (58.7 mg, 0.176 mmol), HATU (80 mg, 0.212 mmol), DIPEA (114 mg, 0.882 mmol) and stirring at RT for 16 h. This gave after workup and purification using flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-(trifluoromethyl)-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (231 g) (73 mg, 70% yield) HCl salt as a white solid; $^1H$ NMR (300 MHz, DMSO-$d_6$) δ 10.77 (s, 1H, $D_2O$ exchangeable), 8.74 (bs, 1H, $D_2O$ exchangeable), 8.65 (s, 1H), 8.33 (d, J=8.6 Hz, 1H), 8.01 (d, J=8.5 Hz, 2H), 7.70 (t, J=8.0 Hz, 1H), 7.47 (bs, 1H, $D_2O$ exchangeable), 7.32 (d, J=7.7 Hz, 1H), 5.79 (d, J=17.4 Hz, 1H), 5.43 (d, J=17.3 Hz, 1H), 4.38 (dd, J=9.1, 5.9 Hz, 1H), 3.62-3.52 (m, 1H), 2.49-2.42 (m, 1H), 1.99 (dd, J=13.2, 5.8 Hz, 1H), 1.31 (s, 3H), 1.02 (t, J=5.5 Hz, 1H), 0.96-0.88 (m, 1H). $^{19}F$ NMR (282 MHz, DMSO-$d_6$) δ−64.14; MS (ES+): 589/591 (M+1); (ES−): 587/589 (M−1); Analysis calculated for $C_{24}H_{20}BrF_3N_8O_2 \cdot 0.9HCl \cdot 1.75H_2O$: C, 44.10; H, 3.76; Cl, 4.88; N, 17.14. Found: C, 44.01; H, 3.64; Cl, 4.96; N, 17.07.

Scheme 232

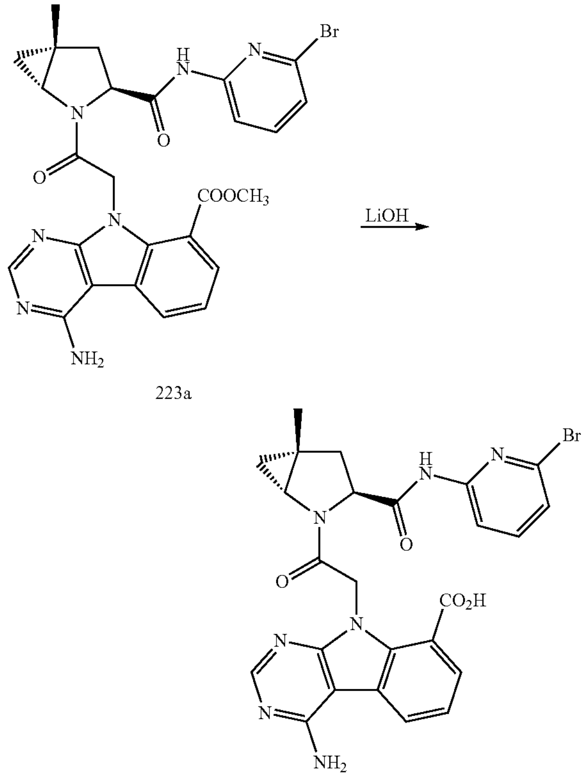

223a

232a

Scheme 233

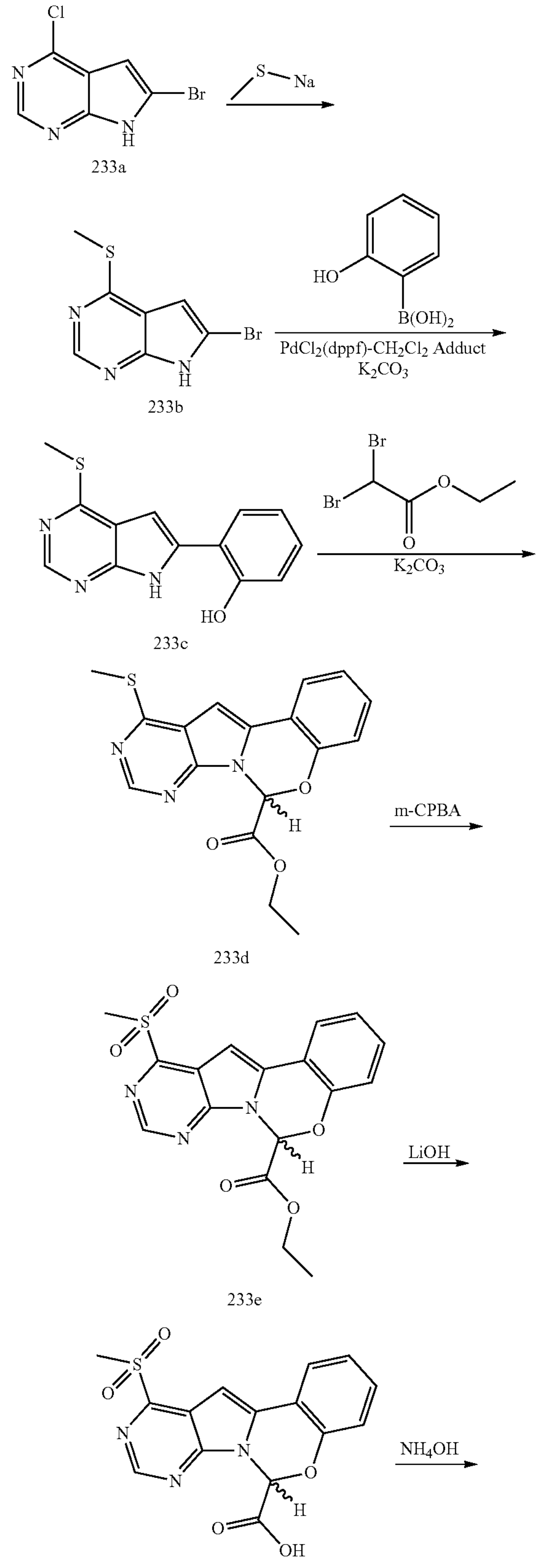

233a

233b

233c

233d

233e

233f

Preparation of 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-8-carboxylic acid (232a)

Compound 232a was prepared according to the procedure reported in step-4 of scheme-17, from methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-8-carboxylate (223a) (140 mg, 0.242 mmol) in THF (2 mL) and water (4 mL) using 1N aqueous lithium hydroxide hydrate (0.242 mL, 0.242 mmol) and stirring at RT for 16 h. This gave after workup and purification using reverse phase column chromatography [C18 column, eluting with ACN in water (containing 0.1% HCl) from 0-70%] 4-amino-9-(2-((1R,3S,5R)-3-((6-bromopyridin-2-yl)carbamoyl)-5-methyl-2-azabicyclo[3.1.0]hexan-2-yl)-2-oxoethyl)-9H-pyrimido[4,5-b]indole-8-carboxylic acid (232a) (17 mg, 12% yield) HCl salt as a white solid: $^1H$ NMR (300 MHz, DMSO-$d_6$) δ 10.71 (s, 1H), 8.69 (d, J=7.9 Hz, 1H), 8.62 (s, 1H), 8.54 (d, J=12.5 Hz, 3H), 7.98 (d, J=8.2 Hz, 1H), 7.89 (d, J=7.6 Hz, 1H), 7.67 (t, J=8.1 Hz, 1H), 7.46 (t, J=7.8 Hz, 1H), 7.29 (d, J=7.7 Hz, 1H), 5.98 (d, J=17.4 Hz, 1H), 5.68 (d, J=17.3 Hz, 1H), 4.31 (dd, J=9.0, 5.9 Hz, 1H), 3.54 (m, 1H), 2.49-2.32 (m, 1H), 1.95 (dd, J=13.2, 5.9 Hz, 1H), 1.29 (s, 3H), 1.08-0.91 (m, 2H); MS (ES+): 565.10; (ES−): 563.10 (M−1).

-continued

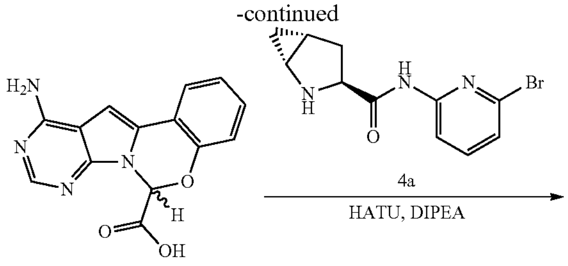

233g

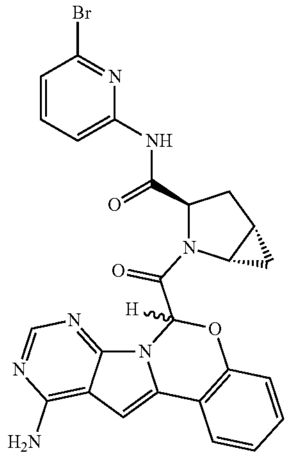

233h

Preparation of (1S,3R,5S)-2-(11-amino-6H-benzo[e] pyrimido[5',4':4,5]pyrrolo[1,2-c][,3]oxazine-6-carbonyl)-N-(6-bromopyridin-2-yl)-2-azabicyclo[3.1.0] hexane-3-carboxamide (233h)

Step-1: Preparation of 6-bromo-4-(methylthio)-7H-pyrrolo[2,3-d]pyrimidine (233b)

To a solution of 6-bromo-4-chloro-7H-pyrrolo[2,3-d]pyrimidine (233a) (1.02 g, 4.39 mmol; CAS #784150-41-0) in DMSO (10 mL) at 50° C. was added sodium methanethiolate (1.230 g, 17.55 mmol; CAS #5188-07-8) in three portions over a 3 h interval and heated at 50° C. overnight. The reaction mixture was poured into water (80 mL) and the solution was allowed to stand for 5 h. The solid obtained was collected by filtration washed with water, dried in vacuo to afford 6-bromo-4-(methylthio)-7H-pyrrolo[2,3-d]pyrimidine (233b) (1.01 g, 4.14 mmol, 94% yield) as a white solid; $^1$H NMR (300 MHz, DMSO-$d_6$) δ 12.99 (s, 1H), 8.58 (s, 1H), 6.66 (s, 1H), 2.64 (s, 3H); MS (ES+): 243.95/245.9 (M+1).

Step-2: Preparation of 2-(4-(methylthio)-7H-pyrrolo [2,3-d]pyrimidin-6-yl)phenol (233c)

Compound 233c was prepared according to the procedure reported in step-1 of scheme-62, from 6-bromo-4-(methylthio)-7H-pyrrolo[2,3-d]pyrimidine (233b) (922 mg, 3.78 mmol) in 1,4-dioxane (12 mL) using (2-hydroxyphenyl) boronic acid (625 mg, 4.53 mmol), a solution of $K_2CO_3$ (1566 mg, 11.33 mmol) in water (1.5 mL) and $PdCl_2$(dppf)-$CH_2Cl_2$ adduct (308 mg, 0.378 mmol) and heating at 80° C. for 6 h under nitrogen. This gave after workup and purification using flash column chromatography [silica gel (40 g), eluting with EtOAc/MeOH (9:1) in hexanes from 0-100%] 2-(4-(methylthio)-7H-pyrrolo[2,3-d]pyrimidin-6-yl)phenol (233c) (655 mg, 67% yield) as a yellow solid; $^1$H NMR (300 MHz, DMSO-$d_6$) δ 12.22 (s, 1H), 10.34 (s, 1H), 8.59 (s, 1H), 7.83 (dd, J=7.9, 1.6 Hz, 1H), 7.28-7.14 (m, 1H), 7.02 (dd, J=8.6, 1.3 Hz, 2H), 6.92 (t, J=7.4 Hz, 1H), 2.67 (s, 3H); MS (ES+): 258.0 (M+1).

Step-3: Preparation of ethyl 11-(methylthio)-6H-benzo[e]pyrimido[5',4':4,5]pyrrolo[1,2-c][1,3] oxazine-6-carboxylate (233d)

A mixture of 2-(4-(methylthio)-7H-pyrrolo[2,3-d]pyrimidin-6-yl)phenol (233c) (470 mg, 1.827 mmol), ethyl 2,2-dibromoacetate (1347 mg, 5.48 mmol) and potassium carbonate (757 mg, 5.48 mmol) in DMF (10 mL) was heated to 100° C., and stirred at 100° C. for 100 min. The reaction mixture was cooled to room temperature, diluted with EtOAc (200 mL), washed with water (100 mL), brine (100 mL), dried and concentrated in vacuo. The residue obtained was purified using flash column chromatography [silica gel (12 g), eluting with EtOAc/MeOH (9:1) in hexanes from 0-50%] to provide ethyl 11-(methylthio)-6H-benzo[e]pyrimido[5',4':4,5]pyrrolo[1,2-c][1,3]oxazine-6-carboxylate (233d) (298 mg, 48% yield) as a white yellow solid; $^1$H NMR (300 MHz, DMSO-$d_6$) δ 8.68 (s, 1H), 8.01 (dd, J=7.9, 1.6 Hz, 1H), 7.41 (td, J=7.7, 1.6 Hz, 1H), 7.29 (s, 1H), 7.26-7.17 (m, 3H), 4.12-3.98 (m, 2H), 2.71 (s, 31H), 1.01 (t, J=7.1 Hz, 3H).

Step-4: Preparation of ethyl 11-(methylsulfonyl)-6H-benzo[e]pyrimido[5',4':4,5]pyrrolo[1,2-c][1,3] oxazine-6-carboxylate (233e)

To a solution of ethyl 11-(methylthio)-6H-benzo[e]pyrimido[5',4':4,5]pyrrolo[1,2-c][1,3]oxazine-6-carboxylate (233d) (180 mg, 0.527 mmol) in DCM (35 mL) was added m-CPBA (354 mg) at 0°, warmed to RT and stirred overnight. An additional amount of m-CPBA (98 mg) was added, the mixture was stirred at RT for 2 h. The reaction mixture was diluted with DCM (25 mL), washed with Sat. $NaHCO_3$ (40 mL), dried, filtered and concentrated in vacuo to afford ethyl 11-(methylsulfonyl)-6H-benzo[e]pyrimido[5',4':4.5] pyrrolo[1,2-c][1,3]oxazine-6-carboxylate (233e) (197 mg, 100% yield) as a yellow solid which was used for the next step; MS (ES+): 374.10 (M+1);

Step-5: Preparation of 11-(methylsulfonyl)-6H-benzo[e]pyrimido[5',4':4,5]pyrrolo[1,2-c][1,3] oxazine-6-carboxylic acid (233f)

Compound 233f was prepared according to the procedure reported in step-4 of scheme-17, from ethyl 11-(methylsulfonyl)-6H-benzo[e]pyrimido[5',4':4,5]pyrrolo[1,2-c][1,3]oxazine-6-carboxylate (233e) (197 mg, 0.528 mmol) in MeOH (1.5 mL), THF (1.5 mL), acetonitrile (3 mL) using a solution of lithium hydroxide hydrate and stirring at RT. The reaction mixture was concentrated in vacuo and was used for the next step without further purification; MS (ES+): 346.0 (M+1);

Step-6: Preparation of 11-amino-6H-benzo[e]pyrimido[5',4':4,5]pyrrolo[1,2-c][1.3]oxazine-6-carboxylic acid (233 g)

To a solution of 11-(methylsulfonyl)-6H-benzo[e]pyrimido[5',4':4,5]pyrrolo[1,2-c][1,3]oxazine-6-carboxylic acid (233f) (182 mg) in 1,4-Dioxane (4 mL) was added ammonium hydroxide (3 mL, 23.11 mmol) and stirred at RT overnight. An additional amount of $NH_4OH$ (1 mL) was added and the reaction mixture was heated to 50° C. for 5 h. The reaction mixture was concentrated in vacuum and residue obtained was purified by reverse phase column chromatography [C18 (50 g), eluting with ACN in water (without HCl) from 0-100%] to provide 11-amino-6H-benzo[e]pyrimido[5',4':4,5]pyrrolo[1,2-c][1,3]oxazine-6-carboxylic acid (233 g) (90 mg, 61% yield) as a white solid; MS (ES+): 283.0 (M+1).

Step-7: Preparation of (1S,3R,5S)-2-(l-amino-6H-benzo[e]pyrimido[5',4':4,5]pyrrolo[1,2-c][1,3]oxazine-6-carbonyl)-N-(6-bromopyridin-2-yl)-2-azabicyclo[3.1.0]hexane-3-carboxamide (233h)

Compound 233h was prepared according to the procedure reported in step-3 of scheme-1, from 11-amino-6H-benzo[e]pyrimido[5',4':4,5]pyrrolo[1,2-c][1,3]oxazine-6-carboxylic acid (233 g) (40 mg, 0.142 mmol) in DMF (3 mL) using HCl salt of (1R,3S,5R)—N-(6-bromopyridin-2-yl)-2-azabicyclo[3.1.0]hexane-3-carboxamide (4a) (51 mg, 0.160 mmol), HATU (81 mg, 0.213 mmol), DIPEA (0.123 mL, 0.709 mmol) and stirring at RT for 14 h. This gave after workup and purification using reverse phase column chromatography [C18 column (50 g), eluting with ACN in water (containing 0.1% HCl) from 0-100%](1S,3R,5S)-2-(11-amino-6H-benzo[e]pyrimido[5',4':4,5]pyrrolo[1,2-c][,3]oxazine-6-carbonyl)-N-(6-bromopyridin-2-yl)-2-azabicyclo[3.1.0]hexane-3-carboxamide (233h) (48 mg, 62.0% yield) HCl salt as a white solid; $^1$H NMR (300 MHz, DMSO-$d_6$) δ 10.71 (d, J=2.2 Hz, 1H), 8.11-8.06 (m, 1H), 7.98-7.85 (m, 1H), 7.69-7.51 (m, 2H), 7.34-7.24 (m, 2H), 7.24-7.09 (m, 4H), 7.00-6.92 (m, 1H), 4.48-4.26 (m, 1H), 4.24-3.99 (m, 1H), 2.34-2.03 (m, 2H), 2.03-1.83 (m, 1H), 1.47-1.12 (m, 1H), 0.78-0.43 (m, 1H); $^1$H NMR (300 MHz, DMSO-$d_6$/$D_2O$) δ 8.13-8.01 (m, 1H), 7.98-7.84 (m, 1H), 7.70-7.46 (m, 2H), 7.38-7.23 (m, 2H), 7.23-7.09 (m, 2H), 7.02-6.93 (m, 1H), 4.33 (dd, J=28.1, 7.0 Hz, 1H), 4.11 (dt, J=30.4, 7.2 Hz, 1H), 2.33-2.02 (m, 2H), 1.99-1.83 (m, 1H), 1.47-1.12 (m, 1H), 0.78-0.43 (m, 1H). MS (ES+): 546.1, 548.1 (M+1); (ES−): 544.1, 546.1 (M−1): Analysis calculated for: $C_{25}H_{20}BrN_7O_3 \cdot 0.15HCl \cdot 0.5H_2O$: C, 53.54; H, 3.80; N, 17.48; Cl, 0.95. Found: C, 53.39; H, 3.70; N, 17.41; Cl, 0.95.

Scheme 234

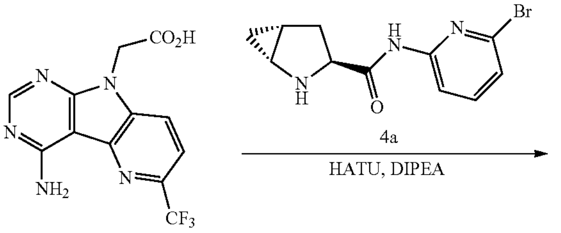

4a

231f

-continued

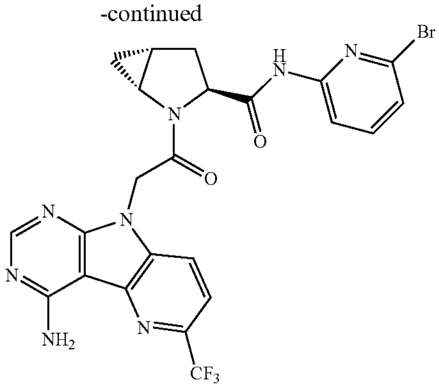

234a

Preparation of (1R,3S,5R)-2-(2-(4-amino-6-(trifluoromethyl)-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (234a)

Compound 234a was prepared according to the procedure reported in step-3 of scheme-1, from TFA salt of 2-(4-amino-6-(trifluoromethyl)-9H-pyrido[2',3':4,5]pyrrolo[2,3-d]pyrimidin-9-yl)acetic acid (231f) (75 mg, 0.176 mmol) in DMF (5 mL) using HCl salt of (1R,3S,5R)—N-(6-bromopyridin-2-yl)-2-azabicyclo[3.1.0]hexane-3-carboxamide (4a) (56.2 mg, 0.176 mmol), HATU (80 mg, 0.212 mmol), DIPEA (114 mg, 0.882 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-(trifluoromethyl)-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (234a) (67 mg, 66% yield) HCl salt as a white solid; 1H NMR (300 MHz, DMSO-$d_6$) δ 10.77 (s, 1H, $D_2O$ exchangeable), 8.82 (bs, 1H, $D_2O$ exchangeable), 8.67 (s, 1H), 8.34 (d, J=8.6 Hz, 1H), 8.06-7.97 (m, 2H), 7.70 (t, J=8.0 Hz, 1H), 7.45 (bs, 1H, $D_2O$ exchangeable), 7.32 (d, J=7.7 Hz, 11H), 5.84 (d, J=17.4 Hz, 1H), 5.49 (d, J=17.3 Hz, 1H), 4.43 (dd, J=9.1, 5.5 Hz, 1H), 3.90 (ddd, J=7.5, 5.4, 2.3 Hz, 1H), 2.40-2.27 (m, 1H), 2.27-2.16 (m, 1H), 1.99-1.86 (m, 1H), 1.20-1.00 (m, 1H), 0.88-0.68 (m, 1H); $^{19}$F NMR (282 MHz, DMSO-$d_6$) δ-64.12; MS (ES+): 575/577 (M+1), (ES−): 573/575 (M−1); Analysis calculated for $C_{23}H_{18}BrF_3N_8O_2 \cdot 1.15HCl \cdot 1.75H_2O$: C, 42.58; H, 3.52; Cl, 6.28; N, 17.27. Found: C, 42.53; H, 3.36; Cl, 6.33; N, 17.08.

Scheme 235

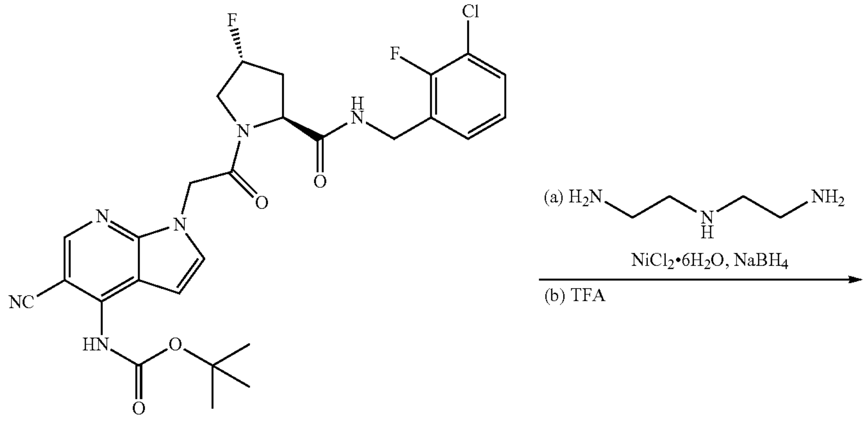

144e

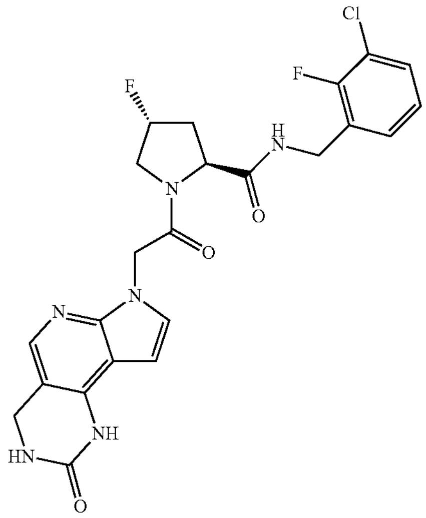

235a

Preparation of (2S,4R)—N-(3-chloro-2-fluorobenzyl)-4-fluoro-1-(2-(2-oxo-3,4-dihydro-1H-pyrrolo[3',2':5,6]pyrido[4,3-d]pyrimidin-7 (2H)-yl)acetyl)pyrrolidine-2-carboxamide (235a)

To a suspension of tert-butyl (1-(2-((2S,4R)-2-((3-chloro-2-fluorobenzyl)carbamoyl)-4-fluoropyrrolidin-1-yl)-2-oxoethyl)-5-cyano-1H-pyrrolo[2,3-b]pyridin-4-yl)carbamate (144e) (300 mg, 0.524 mmol) in methanol cooled with ice/water was added nickel(II) chloride hexahydrate (31.1 mg, 0.131 mmol), sodium borohydride (119 mg, 3.14 mmol) in several portions over a period of 10 min and stirred at RT for 1 h. The reaction mixture was treated with N1-(2-aminoethyl)ethane-1,2-diamine (0.113 mL, 1.047 mmol) stirred at RT for 0.5 h and concentrated to dryness. The residue was treated with ethyl acetate (120 mL) and washed with water (60 mL). The aqueous phase was extracted again with ethyl acetate (60 mL). The combined extracts were washed with brine (75 mL), dried, filtered and concentrated in vacuum. The crude product was purified by flash column chromatography [silica gel, eluting with dichloromethane/methanol (1:0 to 19:1)]. The product obtained was dissolved in DCM (10 mL) added TFA (0.077 mL, 1.040 mmol) and at RT for 22 h. The reaction mixture was concentrated to dryness and purified by reverse phase column chromatography using [C18 column (26 g), eluting with ACN in water (containing 0.1% HCl) from 0-100%] to give (2S,4R)—N-(3-chloro-2-fluorobenzyl)-4-fluoro-1-(2-(2-oxo-3,4-dihydro-1H-pyrrolo[3',2':5,6]pyrido[4,3-d]pyrimidin-7 (2H)-yl)acetyl)pyrrolidine-2-carboxamide (235a) (58 mg, 22% yield for two steps) HCl salt as a white solid; $^1H$ NMR (300 MHz, DMSO-$d_6$) (a mixture of two rotamers) δ 10.54 (s, 1H, $D_2O$ exchangeable), 9.01 & 8.66 (2t, J=6.0 Hz, 1H, $D_2O$ exchangeable), 7.97 (s, 1H), 7.50-7.29 (m, 3H, 1H $D_2O$ exchangeable), 7.16-7.03 (m, 1H), 6.95 (d, J=3.5 Hz, 1H), 6.84 (t, J=7.9 Hz, 11H), 5.56-5.07 (m, 3H), 4.84-3.71 (m, 7H), 2.59-2.23 (m, 1H), 2.23-1.81 (m, 1H); $^{19}F$ NMR (282 MHz, DMSO-$d_6$) (a mixture of two rotamers) δ−121.34 & −121.74 (1F), −175.94 & −176.13 (1F); MS (ES+): 503.10 & 505.10 (M+1); Analysis calculated for $C_{23}H_{21}ClF_2N_6O_3 \cdot 1.0\ HCl \cdot 2.25H_2O$: C, 47.64; H, 4.61; N, 14.49; Cl, 12.23. Found: C, 47.97; H, 4.46; N, 14.55; Cl, 11.93.

Scheme 236

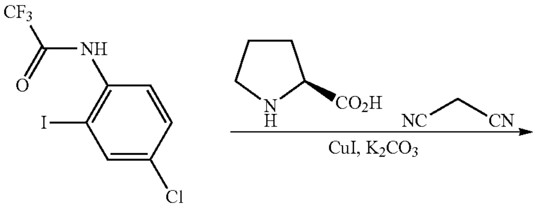

236a

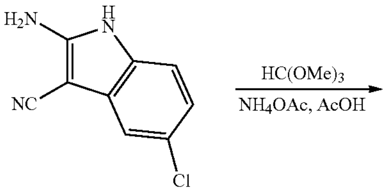

236b

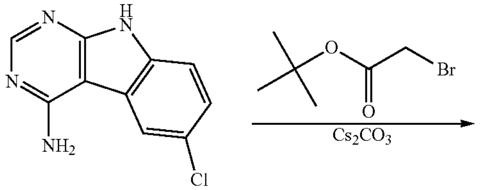

0.5AcOH
236c

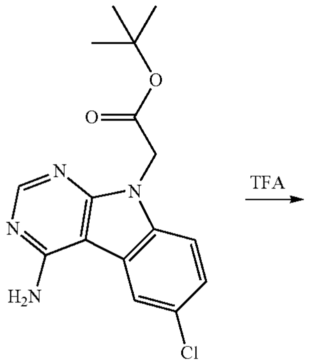

236d

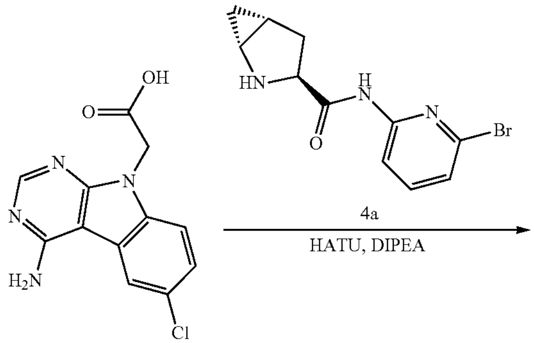

236e

-continued

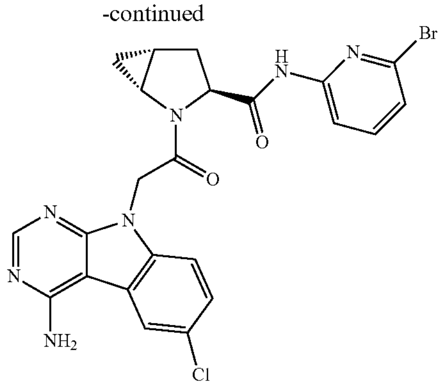

236f

Preparation of (1R,3S,5R)-2-(2-(4-amino-6-chloro-9H-pyrimido[4,5-b]indol-9-yl)acetyl)-N-(6-bromopyridin-2-yl)-2-azabicyclo[3.1.0]hexane-3-carboxamide (2360

Step-1: Preparation of 2-amino-5-chloro-1H-indole-3-carbonitrile (236b)

Compound 236b was prepared according to the procedure reported in step-1 of scheme-11, from N-(4-chloro-2-iodophenyl)-2,2,2-trifluoroacetamide (236a) (6.2 g, 17.74 mmol; CAS #784183-51-3) in DMSO (20 mL) using malononitrile (1.406 g, 21.29 mmol). L-proline (0.409 g, 3.55 mmol), CuI (0.338 g, 1.774 mmol), $K_2CO_3$ (4.90 g, 35.5 mmol) and heating at 60° C. for 16 h under an argon atmosphere. This gave after workup and purification using flash column chromatography [$SiO_2$ gel (40 g), eluting with EtOAc in hexane from 0-50%] 2-amino-5-chloro-1H-indole-3-carbonitrile (236b) (2.02 g, 59% yield) as a yellow solid; $^1H$ NMR (300 MHz, DMSO-$d_6$) δ 10.86 (s, 1H), 7.11 (d, J=8.3 Hz, 1H), 7.08 (d, J=2.1 Hz, 1H), 6.97 (s, 2H), 6.90 (dd, J=8.3, 2.1 Hz, 1H); MS (ES+): 192.0 (M+1); (ES−): 190.0 (M−1).

Step-2: Preparation of 6-chloro-9H-pyrimido[4,5-b]indol-4-amine (236c)

Compound 236c was prepared according to the procedure reported in step-1 of scheme-6, from 2-amino-5-chloro-1H-indole-3-carbonitrile (236b) (2.0 g, 10.44 mmol) using trimethyl orthoformate (22.84 mL, 209 mmol), AcOH (2.98 mL, 52.2 mmol) and $NH_4OAc$ (4.02 g, 52.2 mmol). This gave after workup 6-chloro-9H-pyrimido[4,5-b]indol-4-amine (236c) (2.3 g, 89% yield) as a pale-yellow solid; $^1H$ NMR (300 MHz, DMSO-$d_6$) δ 11.98 (s, 1H), 8.45 (d, J=2.0 Hz, 1H), 8.26 (s, 1H), 7.44 (d, J=8.6 Hz, 1H), 7.36 (dd, J=8.6, 2.0 Hz, 1H), 7.30 (s, 2H); MS (ES+): 219.00 (M+1).

Step-3: Preparation of tert-butyl 2-(4-amino-6-chloro-9H-pyrimido[4,5-b]indol-9-yl)acetate (236d)

Compound 236d was prepared according to the procedure reported in step-1 of scheme-1, from 6-chloro-9H-pyrimido[4,5-b]indol-4-amine (236c) (2.25 g, 9.05 mmol) in DMF (60 mL) using tert-butyl 2-bromoacetate (1.471 mL, 9.95 mmol), $Cs_2CO_3$ (6.49 g, 19.91 mmol) and stirring at RT for 2 h. This gave after workup and purification using reverse phase column chromatography [C18 column (150 g), eluting with ACN in water (containing 0.1% HCl) from 0-100%] tert-butyl 2-(4-amino-6-chloro-9H-pyrimido[4,5-b]indol-9- yl)acetate (236d) (1.216 g, 40% yield) as a pale yellow solid: $^1$H NMR (300 MHz, DMSO-$d_6$) δ 8.60 (d. J=2.0 Hz, 1H), 8.44 (s, 1H), 7.70 (d, J=8.7 Hz, 1H), 7.51 (dd, J=8.8, 2.0 Hz, 1H), 5.20 (s, 2H), 1.41 (s, 9H); MS (ES+): 333.10 (M+1).

Step-4: Preparation of 2-(4-amino-6-chloro-9H-pyrimido[4,5-b]indol-9-yl)acetic acid (236e)

Compound 236e was prepared according to the procedure reported in step-2 of scheme-1, from tert-butyl 2-(4-amino-6-chloro-9H-pyrimido[4,5-b]indol-9-yl)acetate (236d) (1 g, 3.00 mmol) using 20% TFA in DCM (17.25 mL, 45.1 mmol) and stirring at RT for 16 h. This gave after workup 2-(4-amino-6-chloro-9H-pyrimido[4,5-b]indol-9-yl)acetic acid (236e) (1.17 g, 100% yield) TFA salt as a pale-yellow solid; $^1$H NMR (300 MHz, DMSO-$d_6$) δ 8.66 (d, J=2.0 Hz, 1H), 8.54 (s, 1H), 8.35 (s, 2H), 7.81 (d, J=8.8 Hz, 1H), 7.56 (dd, J=8.8, 2.0 Hz, 1H), 5.25 (s, 2H); MS (ES+): 277.00 (M+1).

Step-5: Preparation of (1R,3S,5R)-2-(2-(4-amino-6-chloro-9H-pyrimido[4,5-b]indol-9-yl)acetyl)-N-(6-bromopyridin-2-yl)-2-azabicyclo[3.1.0]hexane-3-carboxamide (236f)

Compound 236f was prepared according to the procedure reported in step-3 of scheme-1, from TFA salt of 2-(4-amino-6-chloro-9H-pyrimido[4,5-b]indol-9-yl)acetic acid (236e) (60 mg, 0.154 mmol) in DMF (1.5 mL) using HCl salt of (1R,3S,5R)—N-(6-bromopyridin-2-yl)-2-azabicyclo[3.1.0]hexane-3-carboxamide (4a) (48.9 mg, 0.154 mmol), HATU (88 mg, 0.230 mmol), DIPEA (0.134 mL, 0.768 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-chloro-9H-pyrimido[4,5-b]indol-9-yl)acetyl)-N-(6-bromopyridin-2-yl)-2-azabicyclo[3.1.0]hexane-3-carboxamide (236f) (71 mg, 85% yield) HCl salt as a white solid; 1H NMR (300 MHz, DMSO-$d_6$) δ 10.77 (s, 1H, $D_2O$ exchangeable), 8.68 (d, J=2.0 Hz, 1H), 8.60 (s, 1H), 8.56 (s, 2H, $D_2O$ exchangeable), 8.01 (d, J=8.2 Hz, 1H), 7.77-7.67 (m, 2H), 7.58 (dd, J=8.8, 2.0 Hz, 1H), 7.33 (d, J=7.7 Hz, 1H), 5.77 (d, J=17.4 Hz, 1H), 5.42 (d, J=17.3 Hz, 1H), 4.41 (dd, J=9.0, 5.5 Hz, 1H), 3.90 (td, J=6.2, 5.3, 2.3 Hz, 1H), 2.38-2.12 (m, 2H), 1.97-1.85 (m, 1H), 1.07 (dt, J=9.2, 5.4 Hz, 1H), 0.78 (td, J=5.2, 2.4 Hz, 1H). MS (ES+): 540.1 (M+1): (ES−): 538.0 (M−1); Analysis calculated for $C_{23}H_{19}BrClN_7O_2$ 1.75$H_2O$, 0.9HCl: C, 45.65; H, 3.90; Cl, 11.13; N, 16.20. Found: C, 45.60; H, 3.80; Cl, 11.17; N, 15.84.

Scheme 237

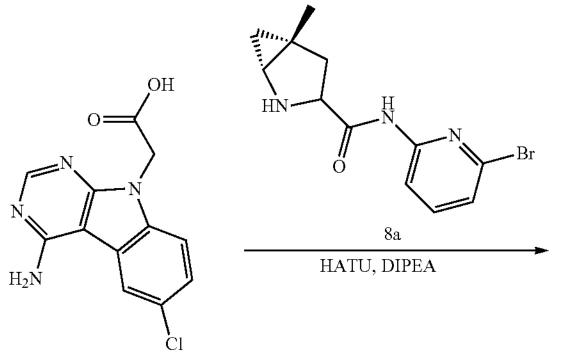

236e

-continued

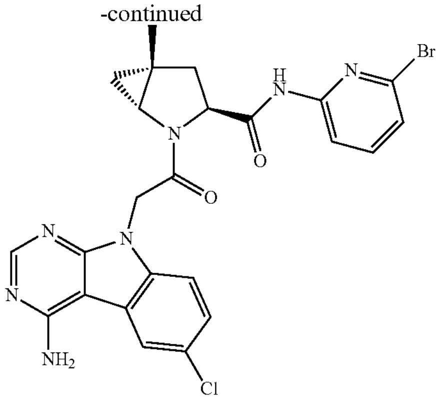

237a

Preparation of (1R,3S,5R)-2-(2-(4-amino-6-chloro-9H-pyrimido[4,5-b]indol-9-yl)acetyl)-N-(6-bromopyridin-2-yl)-5-methyl-2-azabicyclo[3.1.0]hexane-3-carboxamide (237a)

Compound 237a was prepared according to the procedure reported in step-3 of scheme-1, from TFA salt of 2-(4-amino-6-chloro-9H-pyrimido[4,5-b]indol-9-yl)acetic acid (236e) (60 mg, 0.154 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (51.1 mg, 0.154 mmol), HATU (88 mg, 0.230 mmol), DIPEA (0.134 mL, 0.768 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-chloro-9H-pyrimido[4,5-b]indol-9-yl)acetyl)-N-(6-bromopyridin-2-yl)-5-methyl-2-azabicyclo[3.1.0]hexane-3-carboxamide (237a) (59 mg, 69% yield) HCl salt as a white solid; $^1$H NMR (300 MHz, DMSO-$d_6$) δ 10.77 (s, 1H, $D_2O$ exchangeable), 8.68 (d, J=2.0 Hz, 1H), 8.67-8.54 (m, 3H, 2H $D_2O$ exchangeable), 8.01 (d, J=8.2 Hz, 1H), 7.78-7.66 (m, 2H), 7.58 (dd, J=8.7, 1.9 Hz, 1H), 7.33 (d, J=7.7 Hz, 1H), 5.73 (d, J=17.4 Hz, 1H), 5.37 (d, J=17.3 Hz, 1H), 4.37 (dd, J=9.1, 5.9 Hz, 1H), 3.68 (dd, J=5.5, 2.4 Hz, 1H), 2.57-2.52 (m, 1H), 1.98 (dd, J=13.3, 5.9 Hz, 1H), 1.31 (s, 3H), 1.01 (t, J=5.4 Hz, 1H), 0.93 (dd, J=5.5, 2.4 Hz, 1H). MS (ES+): 554.1 (M+1); (ES−): 552.1 (M−1); Analysis calculated for $C_{24}H_{21}BrClN_7O_2$ 2$H_2O$·HCl: C, 45.95; H, 4.18; Cl, 11.30; N, 15.63. Found: C, 46.26; H, 4.12. Cl, 10.92; N, 15.48.

Scheme 238

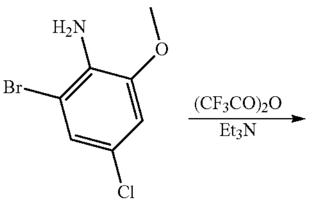

238a

-continued

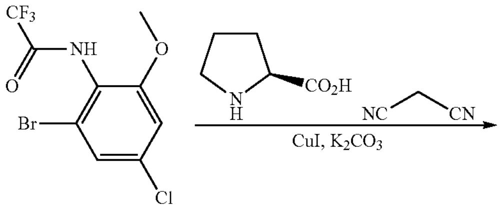

238b

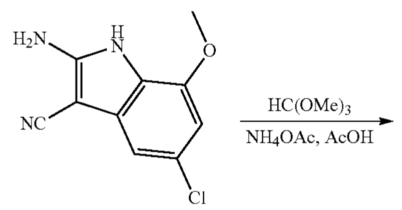

238c

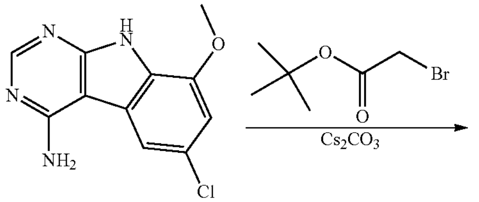

238d

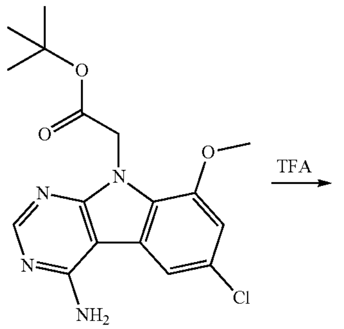

238e

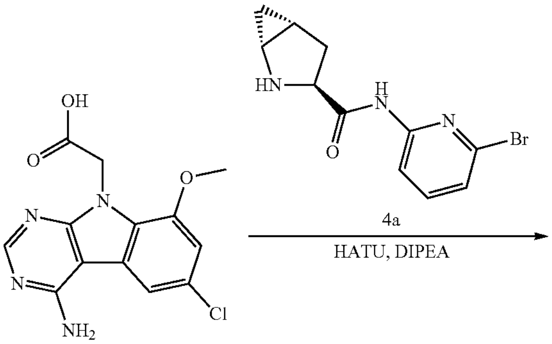

238f

-continued

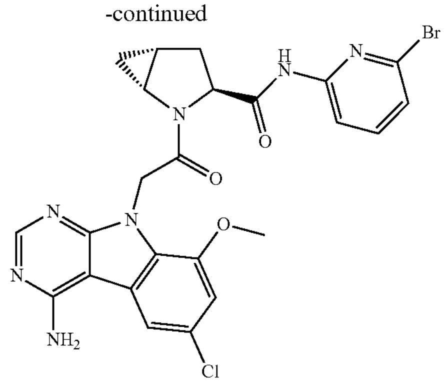

238g

Preparation of (1R,3S,5R)-2-(2-(4-amino-6-chloro-8-methoxy-9H-pyrimido[4,5-b]indol-9-yl)acetyl)-N-(6-bromopyridin-2-yl)-2-azabicyclo[3.1.0]hexane-3-carboxamide (238 g)

Step-1: Preparation of N-(2-bromo-4-chloro-6-methoxyphenyl)-2,2,2-trifluoroacetamide (238b)

Compound 238b was prepared according to the procedure reported in step-1 of scheme-46, from 2-bromo-4-chloro-6-methoxyaniline (238a) (5 g, 21.14 mmol: CAS #1261895-84-4) in DCM (75 mL) using triethylamine (5.01 mL, 35.9 mmol), trifluoroacetic acid anhydride (4.41 mL, 31.7 mmol) and stirring at RT for 16 h. This gave after workup N-(2-bromo-4-chloro-6-methoxyphenyl)-2,2,2-trifluoroacetamide (238b) (6.93 g, 99% yield) as a dark solid and was used as such for next step; $^1$H NMR (300 MHz, DMSO-$d_6$) δ 11.10 (s, 1H), 7.48 (d. J=2.1 Hz, 1H), 7.32 (d, J=2.2 Hz, 1H), 3.85 (s, 3H); MS (ES+): 331.90 (M+1).

Step-2: Preparation of 2-amino-5-chloro-7-methoxy-1H-indole-3-carbonitrile (238c)

Compound 238c was prepared according to the procedure reported in step-1 of scheme-11, from N-(2-bromo-4-chloro-6-methoxyphenyl)-2,2,2-trifluoroacetamide (238b) (6.9 g, 20.75 mmol) in DMSO (20 mL) using malononitrile (1.568 mL, 24.90 mmol), L-proline (0.478 g, 4.15 mmol), CuI (0.395 g, 2.075 mmol), a solution of $K_2CO_3$ (5.74 g, 41.5 mmol) in water (20 mL) and heating at 60° C. for 16 h under an argon atmosphere. This gave after workup and purification using flash column chromatography [$SiO_2$ gel (40 g), eluting with EtOAc in hexane from 0-50%] 2-amino-5-chloro-7-methoxy-1H-indole-3-carbonitrile (238c) (1.85 g, 40% yield) as a pale-yellow solid; $^1$H NMR (300 MHz, DMSO-$d_6$) δ 11.04 (s, 1H), 6.76 (d, J=1.7 Hz, 1H), 6.64 (d, J=1.8 Hz, 1H), 6.55 (s, 2H), 3.88 (s, 3H); MS (ES+): 222.00 (M+1).

Step-3: Preparation of 6-chloro-8-methoxy-9H-pyrimido[4,5-b]indol-4-amine (238d)

Compound 238d was prepared according to the procedure reported in step-1 of scheme-6, from 2-amino-5-chloro-7-methoxy-1H-indole-3-carbonitrile (238c) (1.8 g, 8.12 mmol) using trimethyl orthoformate (17.77 mL, 162 mmol), AcOH (2.322 mL, 40.6 mmol), $NH_4OAc$ (3.13 g, 40.6 mmol) and heating at 100° C. for 1 h. This gave after workup 6-chloro-8-methoxy-9H-pyrimido[4,5-b]indol-4-amine (238d) (2.33 g, 93% yield) ACOH salt as a pale-yellow solid; MS (ES+): 249.1 (M+1).

Step-4: Preparation of tert-butyl 2-(4-amino-6-chloro-8-methoxy-9H-pyrimido[4,5-b]indol-9-yl) acetate (238e)

Compound 238e was prepared according to the procedure reported in step-1 of scheme-1, from AcOH salt of 6-chloro-8-methoxy-9H-pyrimido[4,5-b]indol-4-amine (238d) (1 g, 3.24 mmol) in DMF (25 mL) using tert-butyl 2-bromoacetate (0.503 mL, 3.40 mmol), $Cs_2CO_3$ (2.64 g, 8.10 mmol) and stirring at RT for 15 h. This gave after workup and purification using reverse phase column chromatography [C18 column (50 g), eluting with ACN in water (containing 0.1% HCl) from 0-100%] tert-butyl 2-(4-amino-6-chloro-8-methoxy-9H-pyrimido[4,5-b]indol-9-yl)acetate (238e) (1.175 g, 9% yield) as a pale-yellow solid; $^1$H NMR (300 MHz, DMSO-$d_6$) δ 8.48 (s, 1H), 8.23 (d, J=1.7 Hz, 1H), 8.17 (s, 2H), 7.17 (d, J=1.7 Hz, 1H), 5.23 (s, 2H), 3.94 (s, 3H), 1.42 (s, 9H); MS (ES+): 363.10 (M+1).

Step-5: Preparation of 2-(4-amino-6-chloro-8-methoxy-9H-pyrimido[4,5-b]indol-9-yl)acetic acid (238f)

Compound 238f was prepared according to the procedure reported in step-2 of scheme-1, from tert-butyl 2-(4-amino-6-chloro-8-methoxy-9H-pyrimido[4,5-b]indol-9-yl)acetate (238e) (100 mg, 0.276 mmol) using 20% TFA in DCM (1582 μL, 4.13 mmol) and stirring at RT for 16 h. This gave after workup 2-(4-amino-6-chloro-8-methoxy-9H-pyrimido [4,5-b]indol-9-yl)acetic acid (238f) (115 mg, 99% yield) TFA salt as a pale-yellow solid: $^1$H NMR (300 MHz, DMSO-$d_6$) δ 8.48 (s, 1H), 8.23 (d, J=1.7 Hz, 1H), 8.15 (s, 2H), 7.18 (d, J=1.7 Hz, 1H), 5.28 (s, 2H), 3.94 (s, 3H); MS (ES+): 307.00 (M+1).

Step-6: Preparation of (1R,3S,5R)-2-(2-(4-amino-6-chloro-8-methoxy-9H-pyrimido[4,5-b]indol-9-yl) acetyl)-N-(6-bromopyridin-2-yl)-2-azabicyclo[3.1.0] hexane-3-carboxamide (238 g)

Compound 238g was prepared according to the procedure reported in step-3 of scheme-1, from TFA salt of 2-(4-amino-6-chloro-8-methoxy-9H-pyrimido[4,5-b]indol-9-yl)acetic acid (238f) (55 mg, 0.131 mmol) in DMF (1.5 mL) using HCl salt of (1R,3S,5R)—N-(6-bromopyridin-2-yl)-2-azabicyclo[3.1.0]hexane-3-carboxamide (4a) (41.6 mg, 0.131 mmol), HATU (74.6 mg, 0.196 mmol), DIPEA (0.114 mL, 0.654 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-chloro-8-methoxy-9H-pyrimido[4,5-b]indol-9-yl)acetyl)-N-(6-bromopyridin-2-yl)-2-azabicyclo [3.1.0]hexane-3-carboxamide (238 g) (52 mg, 70% yield) HCl salt as a white solid; $^1$H NMR (300 MHz, DMSO-$d_6$) δ 10.74 (s, 1H, $D_2O$ exchangeable), 8.67-8.46 (m, 3H, 2H $D_2O$ exchangeable), 8.26 (d, J=1.7 Hz, 1H), 8.02 (d, J=8.2 Hz, 1H), 7.71 (t, J=8.0 Hz, 1H), 7.32 (d, J=7.7 Hz, 1H), 7.19 (d, J=1.7 Hz, 1H), 5.78 (d, J=17.0 Hz, 1H), 5.54 (d, J=17.0 Hz, 11H), 4.42 (dd, J=9.0, 5.6 Hz, 1H), 3.95 (s, 3H), 3.89-3.75 (m, 1H), 2.41-2.15 (m, 2H), 2.00-1.86 (m, 1H), 1.11 (dt, J=9.3, 5.4 Hz, 1H), 0.74-0.56 (m, 1H). MS (ES+):

570.1 (M+1); (ES−): 568.1 (M−1); Analysis calculated for $C_{24}H_2BrClN_7O_3$ 2HCl·0.9HCl. C, 45.06; H, 4.08; Cl, 10.53; N, 15.33. Found: C, 45.34; H, 3.93; Cl, 10.64; N, 15.21.

Scheme 239

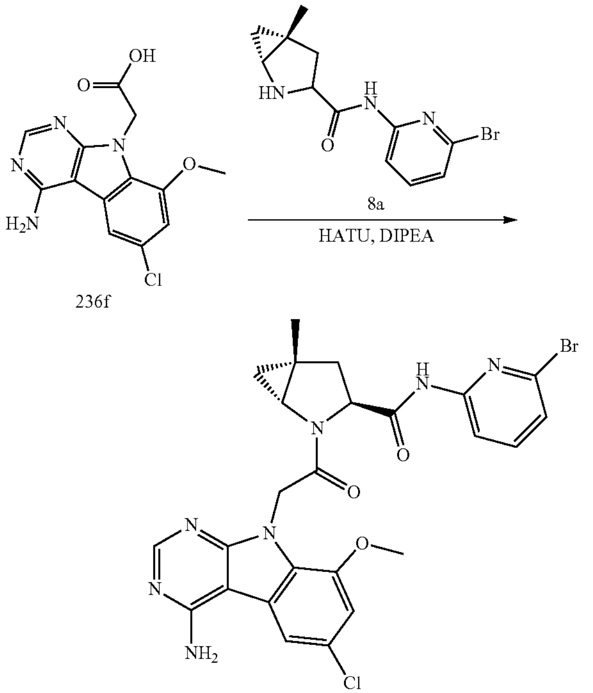

236f

239a

Preparation of (1R,3S,5R)-2-(2-(4-amino-6-chloro-8-methoxy-9H-pyrimido[4,5-b]indol-9-yl)acetyl)-N-(6-bromopyridin-2-yl)-5-methyl-2-azabicyclo[3.1.0] hexane-3-carboxamide (239a)

Compound 239a was prepared according to the procedure reported in step-3 of scheme-1, from TFA salt of 2-(4-amino-6-chloro-8-methoxy-9H-pyrimido[4,5-b]indol-9-yl)acetic acid (238f) (55 mg, 0.131 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (43.5 mg, 0.131 mmol), HATU (74.6 mg, 0.196 mmol), DIPEA (0.114 mL, 0.654 mmol) and stirring at RT for 16 h. This gave after workup and purification using flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-chloro-8-methoxy-9H-pyrimido[4,5-b]indol-9-yl)acetyl)-N-(6-bromopyridin-2-yl)-5-methyl-2-azabicyclo[3.1.0]hexane-3-carboxamide (239a) (40 mg, 52% yield) HCl salt as a white solid; $^1$H NMR (300 MHz, DMSO-$d_6$) δ 10.74 (s, 1H, $D_2O$ exchangeable), 8.59-8.46 (m, 3H, 2H $D_2O$ exchangeable), 8.25 (d, J=1.7 Hz, 1H), 8.02 (d, J=8.2 Hz, 1H), 7.71 (t, J=8.0 Hz, 1H), 7.32 (d, J=7.7 Hz, 1H), 7.18 (d, J=1.7 Hz, 1H), 5.78-5.66 (m, 1H), 5.49 (d, J=17.0 Hz, 1H), 4.38 (dd, J=9.0, 6.0 Hz, 1H), 3.94 (s, 3H), 3.63-3.61 (m, 1H), 2.47-2.39 (m, 1H), 1.99 (dd, J=13.3, 5.9 Hz, 1H), 1.31 (s, 3H), 1.05 (t, J=5.4 Hz, 1H), 0.82 (dd, J=5.3, 2.4 Hz, 1H). MS (ES+): 584.1 (M+1): (ES−): 582.0 (M−1);

Analysis calculated for $C_{25}H_{23}BrClN_7O_3$ $1.75H_2O{\cdot}HCl$: C, 45.99; H, 4.25; Cl, 10.86; N, 15.02. Found: C, 46.07; H, 4.22; Cl, 10.49; N, 14.90.

Scheme 240

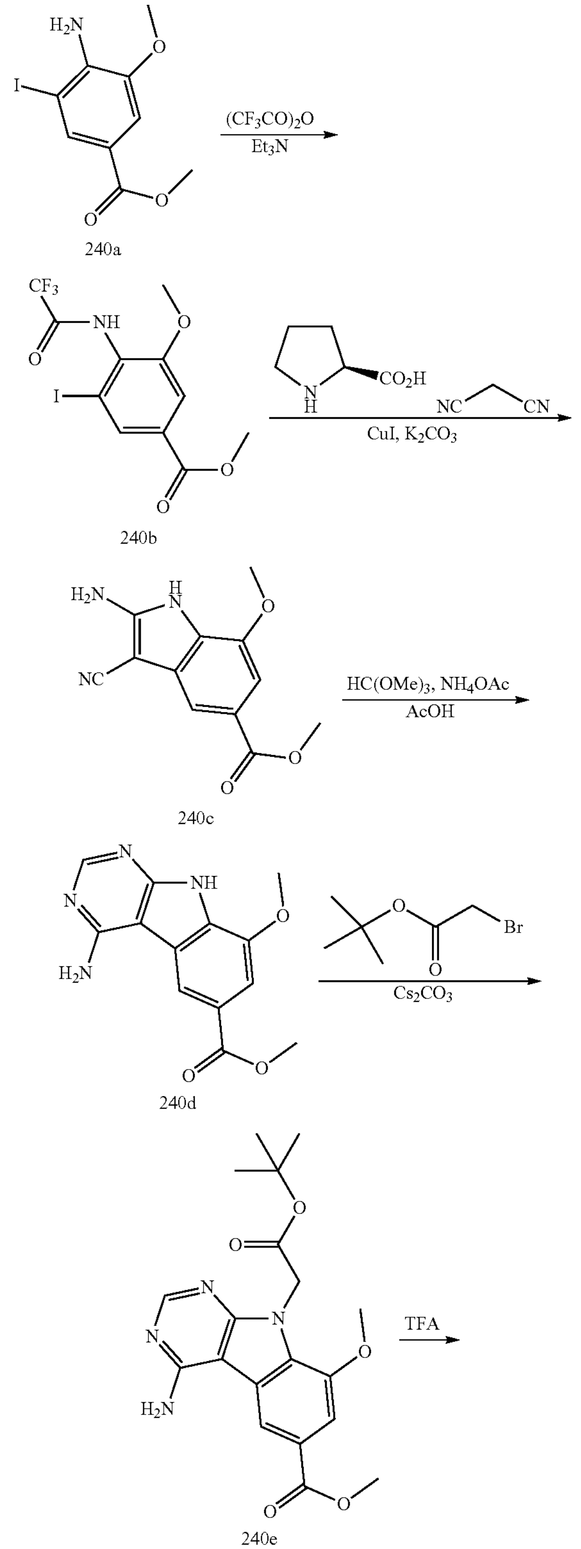

240a, 240b, 240c, 240d, 240e

-continued

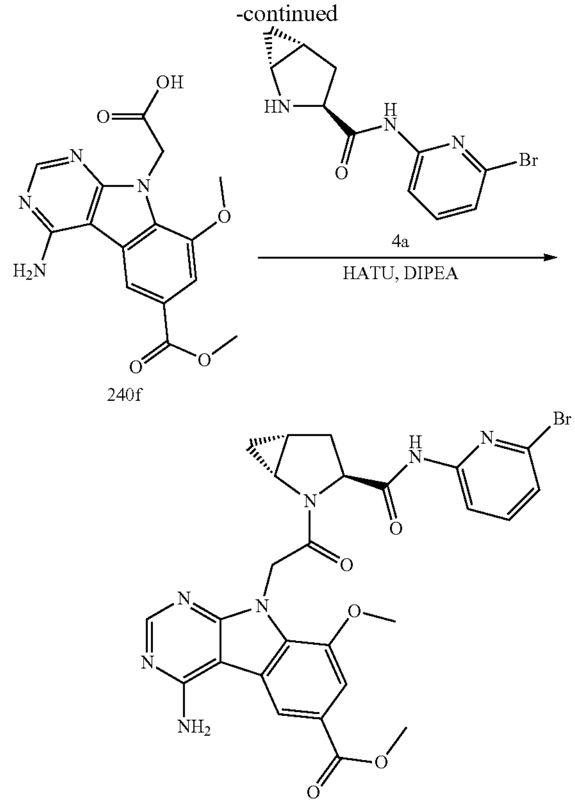

240f, 240g

Preparation of methyl 4-amino-9-(2-((1R,3S,5R)-3-((6-bromopyridin-2-yl)carbamoyl)-2-azabicyclo[3.1.0]hexan-2-yl)-2-oxoethyl)-8-methoxy-9H-pyrimido[4,5-b]indole-6-carboxylate (240 g)

Step-1: Preparation of methyl 3-iodo-5-methoxy-4-(2,2,2-trifluoroacetamido)benzoate (240b)

Compound 240b was prepared according to the procedure reported in step-1 of scheme-46, methyl 4-amino-3-iodo-5-methoxybenzoate (240a) (5 g, 16.28 mmol; CAS #180624-10-6) in DCM (60 mL) using triethylamine (3.86 mL, 27.7 mmol), trifluoroacetic acid anhydride (3.39 mL, 24.42 mmol) and stirring at RT for 16 h. This gave after workup and purification using flash column chromatography [$SiO_2$ gel (40 g), eluting with EtOAc in hexane from 0-50%] methyl 3-iodo-5-methoxy-4-(2,2,2-trifluoroacetamido)benzoate (240b) (5.51 g, 84% yield) as a yellow solid; $^1H$ NMR (300 MHz, DMSO-$d_6$) δ 11.25 (s, 1H), 8.02 (d, J=1.7 Hz, 1H), 7.61 (d, J=1.7 Hz, 1H), 3.89 (s, 3H), 3.87 (s, 3H).

Step-2: Preparation of methyl 2-amino-3-cyano-7-methoxy-1H-indole-5-carboxylate (240c)

Compound 240c was prepared according to the procedure reported in step-1 of scheme-11, from methyl 3-iodo-5-methoxy-4-(2,2,2-trifluoroacetamido)benzoate (240b) (5.5 g, 13.64 mmol) in DMSO (20 mL) using malononitrile (1.031 mL, 16.37 mmol), L-proline (0.314 g, 2.73 mmol), CuI (0.260 g, 1.364 mmol), a solution of $K_2CO_3$ (3.77 g, 27.3 mmol) in water (20 mL) and heating at 60° C. for 16 h under an argon atmosphere. This gave after workup and purification using flash column chromatography [$SiO_2$ gel (40 g), EtOAc in hexane from 0-50%] methyl 2-amino-3-cyano-7-methoxy-1H-indole-5-carboxylate (240c) (1.83 g, 55% yield) as a yellow solid; $^1$H NMR (300 MHz, DMSO-$d_6$) δ 11.30 (s, 1H), 7.46 (d, J=1.3 Hz, 1H), 7.16 (d, J=1.3 Hz, 1H), 6.66 (s, 2H), 3.93 (s, 3H), 3.84 (s, 3H); MS (ES+): 246.0 (M+1): (ES−): 244.1 (M−1).

Step-3: Preparation of methyl 4-amino-8-methoxy-9H-pyrimido[4,5-b]indole-6-carboxylate (240d)

Compound 240d was prepared according to the procedure reported in step-1 of scheme-6, from methyl 2-amino-3-cyano-7-methoxy-1H-indole-5-carboxylate (240c) (1.8 g, 7.34 mmol) using trimethyl orthoformate (16.06 mL, 147 mmol), AcOH (2.099 mL, 36.7 mmol), $NH_4OAc$ (2.83 g, 36.7 mmol) and stirring at 100° C. for 16 h. This gave after workup methyl 4-amino-8-methoxy-9H-pyrimido[4,5-b]indole-6-carboxylate (240d) (1.82 g, 87% yield) AcOH salt as a pale-yellow solid; $^1$H NMR (300 MHz, DMSO-$d_6$) δ 12.36 (s, 1H), 8.62 (d, J=1.2 Hz, 1H), 8.28 (s, 1H), 7.51 (d, J=1.3 Hz, 1H), 7.34 (s, 2H), 4.01 (s, 3H), 3.90 (s, 3H); MS (ES+): 273.10 (M+1).

Step-4: Preparation of methyl 4-amino-9-(2-(tert-butoxy)-2-oxoethyl)-8-methoxy-9H-pyrimido[4,5-b]indole-6-carboxylate (240e)

Compound 240e was prepared according to the procedure reported in step-1 of scheme-1, from AcOH salt of methyl 4-amino-8-methoxy-9H-pyrimido[4,5-b]indole-6-carboxylate (240d) (1 g, 3.67 mmol) in DMF (30 mL) using tert-butyl 2-bromoacetate (0.651 mL, 4.41 mmol), $Cs_2CO_3$ (2.99 g, 9.18 mmol) and stirring at RT for 30 min. This gave after workup methyl 4-amino-9-(2-(tert-butoxy)-2-oxoethyl)-8-methoxy-9H-pyrimido[4,5-b]indole-6-carboxylate (240e) (1.085 g, 76% yield) as a pale-yellow solid: 1H NMR (300 MHz, DMSO-$d_6$) δ 8.65 (d, J=1.3 Hz, 1H), 8.33 (s, 1H), 7.52 (t, J=2.0 Hz, 3H), 5.23 (s, 2H), 3.95 (s, 3H), 3.91 (s, 3H), 1.42 (s, 9H); MS (ES+): 387.20 (M+1).

Step-5: Preparation of 2-(4-amino-8-methoxy-6-(methoxycarbonyl)-9H-pyrimido[4,5-b]indol-9-yl) acetic acid (240f)

Compound 240f was prepared according to the procedure reported in step-2 of scheme-1, from methyl 4-amino-9-(2-(tert-butoxy)-2-oxoethyl)-8-methoxy-9H-pyrimido[4,5-b]indole-6-carboxylate (240e) (700 mg, 1.812 mmol) using 20% TFA in DCM (10.40 mL, 27.2 mmol) and stirring at RT for 16 h. This gave after workup 2-(4-amino-8-methoxy-6-(methoxycarbonyl)-9H-pyrimido[4,5-b]indol-9-yl)acetic acid (240f) (0.8 g, 99% yield) TFA salt as a pale-yellow solid; $^1$H NMR (300 MHz, DMSO-$d_6$) δ 8.76 (d, J=1.3 Hz, 1H), 8.53 (s, 1H), 8.37 (s, 2H), 7.60 (d, J=1.2 Hz, 1H), 5.35 (s, 2H), 3.98 (s, 3H), 3.93 (s, 3H); MS (ES+): 331.10 (M+1).

Step-6: Preparation of methyl 4-amino-9-(2-((1R, 3S,5R)-3-((6-bromopyridin-2-yl)carbamoyl)-2-azabicyclo[3.1.0]hexan-2-yl)-2-oxoethyl)-8-methoxy-9H-pyrimido[4,5-b]indole-6-carboxylate (240 g)

Compound 240g was prepared according to the procedure reported in step-3 of scheme-1, from TFA salt of 2-(4-amino-8-methoxy-6-(methoxycarbonyl)-9H-pyrimido[4,5-b]indol-9-yl)acetic acid (240f) (75 mg, 0.169 mmol) in DMF (1.5 mL) using HCl salt of (1R,3S,5R)—N-(6-bromopyridin-2-yl)-2-azabicyclo[3.1.0]hexane-3-carboxamide (4a) (53.8 mg, 0.169 mmol), HATU (96 mg, 0.253 mmol), DIPEA (0.147 mL, 0.844 mmol) and stirring at RT for 16 h. This gave after workup and purification by flash column chromatography [silica gel (12 g), DMA-80 in DCM from 0-100%] followed by purification using reverse phase column chromatography [C18 column (50 g), eluting with ACN in water (containing 0.1% HCl) from 0-100%] methyl 4-amino-9-(2-((1R,3S,5R)-3-((6-bromopyridin-2-yl)carbamoyl)-2-azabicyclo[3.1.0]hexan-2-yl)-2-oxoethyl)-8-methoxy-9H-pyrimido[4,5-b]indole-6-carboxylate (240 g) (70 mg, 70% yield) HCl salt as a white solid; 1H NMR (300 MHz, DMSO-$d_6$) δ 10.73 (s, 1H, $D_2O$ exchangeable), 8.75 (d, J=1.2 Hz, 1H), 8.57 (s, 1H), 8.60-8.37 (m, 2H, $D_2O$ exchangeable), 8.02 (d, J=8.2 Hz, 1H), 7.71 (t, J=8.0 Hz, 1H), 7.59 (d, J=1.2 Hz, 1H), 7.32 (d, J=7.7 Hz, 1H), 5.82 (d, J=17.0 Hz, 1H), 5.59 (d, J=17.0 Hz, 1H), 4.43 (dd, J=8.9, 5.6 Hz, 1H), 3.99 (s, 3H), 3.92 (s, 3H), 3.89-3.82 (m, 1H), 2.39-2.15 (m, 2H), 2.01-1.85 (m, 1H), 1.18-1.03 (m, 1H), 0.73-0.61 (m, 1H). MS (ES+): 594.1 (M+1); (ES−): 592.1 (M−1); Analysis calculated for $C_{26}H_{24}BrN_7O_2H_2O$, 0.9HCl: C, 47.08; H, 4.39; Cl, 4.81; N, 14.78. Found: C, 47.15; H, 4.28; Cl, 4.90; N, 14.68.

Scheme 241

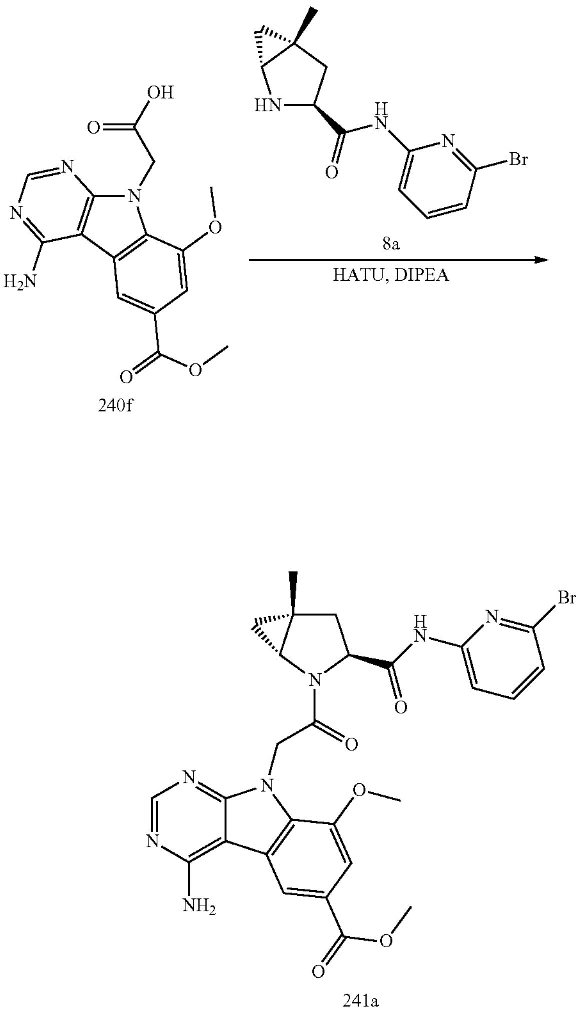

8a

240f

241a

Preparation of methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-8-methoxy-9H-pyrimido[4,5-b]indole-6-carboxylate (241a)

Compound 241a was prepared according to the procedure reported in step-3 of scheme-1, from TFA salt of 2-(4-amino-8-methoxy-6-(methoxycarbonyl)-9H-pyrimido[4,5-b]indol-9-yl)acetic acid (240f) (75 mg, 0.169 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (56.1 mg, 0.169 mmol), HATU (96 mg, 0.253 mmol), DIPEA (0.147 mL, 0.844 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] methyl 4-amino-9-(2-((1R,3S,5R)-3-((6-bromopyridin-2-yl)carbamoyl)-5-methyl-2-azabicyclo[3.1.0]hexan-2-yl)-2-oxoethyl)-8-methoxy-9H-pyrimido[4,5-b]indole-6-carboxylate (241a) (69 mg, 67% yield) HCl salt as a white solid; $^1$H NMR (300 MHz, DMSO-$d_6$) δ 10.73 (s, 1H, $D_2O$ exchangeable), 8.75 (d, J=1.3 Hz, 1H), 8.58 (s, 1H), 8.54 (s, 2H, $D_2O$ exchangeable), 8.02 (d, J=8.2 Hz, 11H), 7.70 (t, J=8.0 Hz, 1H), 7.58 (d, J=1.3 Hz, 1H), 7.31 (d, J=7.7 Hz, 1H), 5.77 (d, J=17.0 Hz, 1H), 5.54 (d, J=16.9 Hz, 1H), 4.39 (dd, J=8.9, 5.9 Hz, 1H), 3.98 (s, 3H), 3.92 (s, 3H), 3.63 (dd, J=5.5, 2.3 Hz, 1H), 2.49-2.40 (m, 1H), 2.00 (dd, J=13.2, 5.9 Hz, 1H), 1.32 (s, 3H), 1.12-0.99 (m, 1H), 0.85-0.77 (m, 1H); MS (ES+): 608.1 (M+1); (ES−): 606.1 (M−1); Analysis calculated for $C_{27}H_{26}BrN_7O_5$ 1.5$H_2O$, 0.9HCl: C, 48.53; H, 4.51; Cl, 4.77; N, 14.67. Found: C, 48.51; H, 4.47; Cl, 4.66; N, 14.59.

Scheme 242

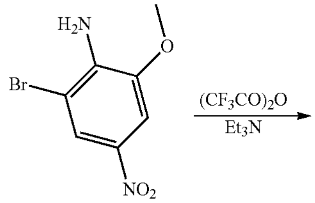

242a

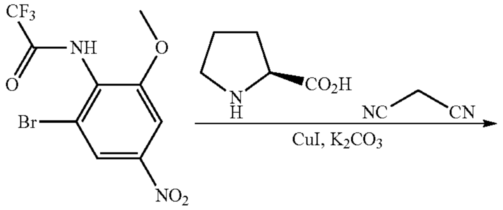

242b

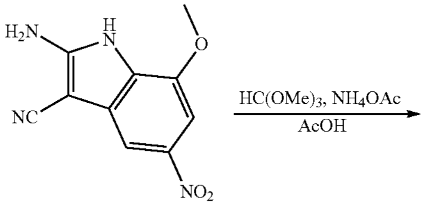

242c

-continued

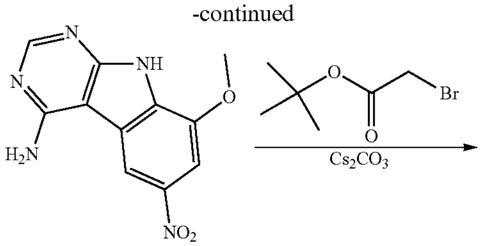

242d

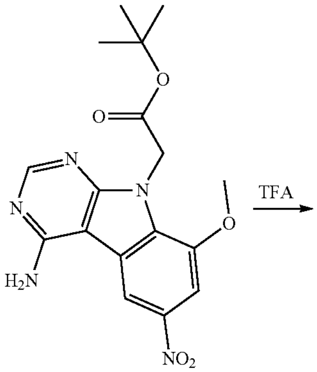

242e

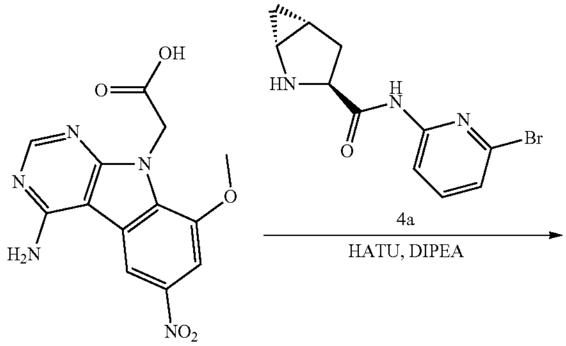

242f

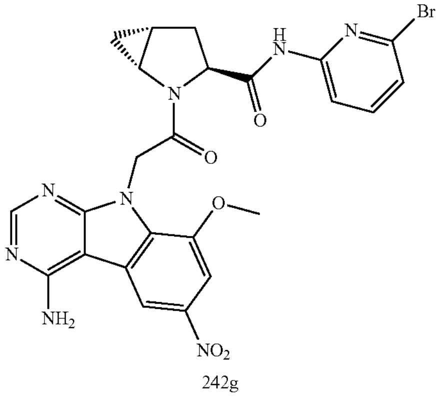 [SMILES: COc1cc([N+](=O)[O-])cc2c3c(N)ncnc3n(CC(=O)N3[C@@H]4C[C@@H]4C[C@H]3C(=O)Nc3cccc(Br)n3)c12]

242g

Preparation of (1R,3S,5R)-2-(2-(4-amino-8-methoxy-6-nitro-9H-pyrimido[4,5-b]indol-9-yl)acetyl)-N-(6-bromopyridin-2-yl)-2-azabicyclo[3.1.0]hexane-3-carboxamide (242 g)

Step-1: Preparation of N-(2-bromo-6-methoxy-4-nitrophenyl)-2,2,2-trifluoroacetamide (242b)

Compound 242b was prepared according to the procedure reported in step-1 of scheme-46, from 2-bromo-6-methoxy- 4-nitroaniline (242a) (5 g, 20.24 mmol; CAS #16618-66-9) in DCM (75 mL) using triethylamine (4.80 mL, 34.4 mmol), trifluoroacetic acid anhydride (4.22 mL, 30.40 mmol) and stirring at RT for 16 h. This gave after workup and purification using flash column chromatography [$SiO_2$ gel (40 g), eluting with EtOAc in hexane from 0-50%] N-(2-bromo-6-methoxy-4-nitrophenyl)-2,2,2-trifluoroacetamide (242b) (6.7 g, 96% yield) as a yellow solid, MS (ES+): 342.90 (M+1).

Step-2: Preparation of 2-amino-7-methoxy-5-nitro-1H-indole-3-carbonitrile (242c)

Compound 242c was prepared according to the procedure reported in step-1 of scheme-11, from N-(2-bromo-6-methoxy-4-nitrophenyl)-2,2,2-trifluoroacetamide (242b) (6.7 g, 19.53 mmol) in DMSO (20 mL) using malononitrile (1.476 mL, 23.44 mmol), L-proline (0.450 g, 3.91 mmol), CuI (0.372 g, 1.953 mmol), $K_2CO_3$ (5.40 g, 39.1 mmol) and heating at 60° C. for 16 h under an argon atmosphere. This gave after workup and purification using flash column chromatography [$SiO_2$ gel (40 g), eluting with EtOAc in hexane from 0-50%] 2-amino-7-methoxy-5-nitro-1H-indole-3-carbonitrile (242c) (290 mg, 6% yield) as a yellow solid; $^1$H NMR (300 MHz, DMSO-$d_6$) δ 11.71 (s, 1H), 7.69 (d, J=2.0 Hz, 1H), 7.47 (d, J=2.0 Hz, 1H), 6.91 (s, 2H), 3.99 (s, 3H).

Step-3: Preparation of 8-methoxy-6-nitro-9H-pyrimido[4,5-b]indol-4-amine (242d)

Compound 242d was prepared according to the procedure reported in step-1 of scheme-6, from 2-amino-7-methoxy-5-nitro-1H-indole-3-carbonitrile (242c) (0.28 g, 1.206 mmol) using trimethyl orthoformate (2.64 mL, 24.12 mmol), AcOH (0.345 mL, 6.03 mmol), $NH_4OAc$ (0.465 g, 6.03 mmol) and heating at 100° C. for 16 h. This gave after workup 8-methoxy-6-nitro-9H-pyrimido[4,5-b]indol-4-amine (242d) (245 mg, 78% yield) as a pale-yellow solid; $^1$H NMR (300 MHz, DMSO-$d_6$) δ 12.73 (s, 1H), 9.05 (d, J=1.9 Hz, 1H), 8.32 (s, 1H), 7.81 (d, J=1.9 Hz, 1H), 7.57 (s, 2H), 4.08 (s, 3H); MS (ES+): 260.00 (M+1).

Step-4: Preparation of tert-butyl 2-(4-amino-8-methoxy-6-nitro-9H-pyrimido[4,5-b]indol-9-yl)acetate (242e)

Compound 242e was prepared according to the procedure reported in step-1 of scheme-1, from 8-methoxy-6-nitro-9H-pyrimido[4,5-b]indol-4-amine (242d) (0.24 g, 0.926 mmol) in DMF (7 mL) using tert-butyl 2-bromoacetate (0.164 mL, 1.111 mmol), $Cs_2CO_3$ (0.754 g, 2.315 mmol) and stirring at RT for 30 min. This gave after workup tert-butyl 2-(4-amino-8-methoxy-6-nitro-9H-pyrimido[4,5-b]indol-9-yl) acetate (242e) (155 mg, 45% yield) as a pale-yellow solid; $^1$H NMR (300 MHz, DMSO-$d_6$) δ 9.08 (d, J=1.9 Hz, 1H), 8.38 (s, 1H), 7.83 (d, J=1.9 Hz, 1H), 7.75 (s, 2H), 5.26 (s, 2H), 4.03 (s, 3H), 1.42 (s, 9H); MS (ES+): 374.17 (M+1).

Step-5: Preparation of 2-(4-amino-8-methoxy-6-nitro-9H-pyrimido[4,5-b]indol-9-yl)acetic acid (242f)

Compound 242f was prepared according to the procedure reported in step-2 of scheme-1, from tert-butyl 2-(4-amino-8-methoxy-6-nitro-9H-pyrimido[4,5-b]indol-9-yl)acetate (242e) (150 mg, 0.402 mmol) using 20% TFA in DCM (2.306 μL, 6.03 mmol) and stirring at RT for 16 h. This gave after workup 2-(4-amino-8-methoxy-6-nitro-9H-pyrimido[4,5-b]indol-9-yl)acetic acid (242f) (170 mg, 98% yield) TFA salt as a pale-yellow solid; $^1$H NMR (300 MHz, DMSO-$d_6$) δ 9.15 (d, J=1.9 Hz, 1H), 8.53 (s, 1H), 8.38 (s, 2H), 7.88 (d, J=1.9 Hz, 1H), 5.35 (s, 2H), 4.04 (s, 3H); MS (ES+): 318.10 (M+1).

Step-6: Preparation of (1R,3S,5R)-2-(2-(4-amino-8-methoxy-6-nitro-9H-pyrimido[4,5-b]indol-9-yl) acetyl)-N-(6-bromopyridin-2-yl)-2-azabicyclo[3.1.0] hexane-3-carboxamide (242 g)

Compound 242g was prepared according to the procedure reported in step-3 of scheme-1, from TFA salt of 2-(4-amino-8-methoxy-6-nitro-9H-pyrimido[4,5-b]indol-9-yl)acetic acid (242) (60 mg, 0.139 mmol) in DMF (1.5 mL) using HCl salt of (1R,3S,5R)—N-(6-bromopyridin-2-yl)-2-azabicyclo [3.1.0]hexane-3-carboxamide (4a) (44.3 mg, 0.139 mmol), HATU (79 mg, 0.209 mmol). DIPEA (0.121 mL, 0.696 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-8-methoxy-6-nitro-9H-pyrimido[4,5-b]indol-9-yl) acetyl)-N-(6-bromopyridin-2-yl)-2-azabicyclo[3.1.0] hexane-3-carboxamide (242 g) (31 mg, 38% yield) HCl salt as a white solid $^1$H NMR (300 MHz, DMSO-$d_6$) δ 10.73 (s, 1H, $D_2O$ exchangeable), 9.15 (d, J=1.9 Hz, 1H), 8.66 (s, 2H, $D_2O$ exchangeable), 8.61 (s, 1H), 8.01 (d, J=8.2 Hz, 1H), 7.86 (d, J=1.9 Hz, 1H), 7.71 (t, J=8.0 Hz, 1H), 7.31 (d, J=7.7 Hz, 1H), 5.82 (d, J=17.1 Hz, 1H), 5.57 (d, J=17.0 Hz, 1H), 4.43 (dd, J=8.9, 5.6 Hz, 1H), 4.04 (s, 3H), 3.86 (td, J=6.2, 5.6, 2.2 Hz, 1H), 2.43-2.13 (m, 2H), 2.01-1.83 (m, 1H), 1.19-1.05 (m, 1H), 0.74-0.60 (m, 1H); MS (ES+): 581.1 (M+1); (ES−): 579.1 (M−1); Analysis calculated for $C_{24}H_{23}BrN_8O_5 \cdot 1.75H_2O \cdot 0.8HCl$: C, 44.89, H, 3.97; Cl, 4.42; N, 17.45. Found: C, 44.96; H, 3.81; Cl, 4.49; N, 17.30.

Scheme 243

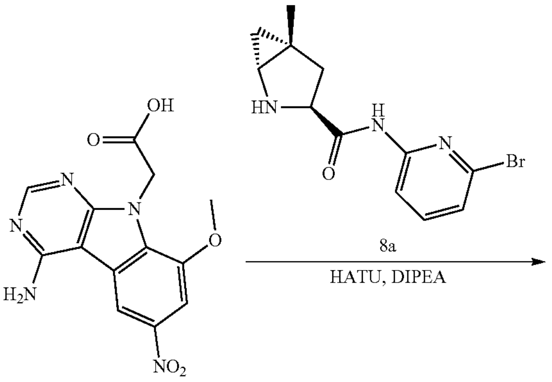

242f

-continued

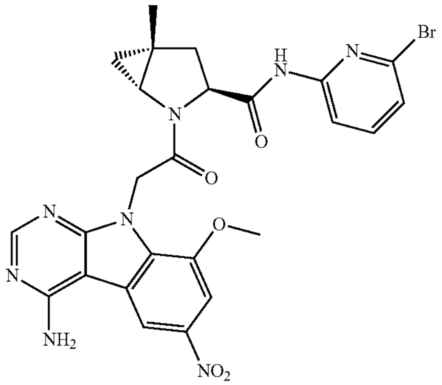

243a

Preparation of (1R,3S,5R)-2-(2-(4-amino-8-methoxy-6-nitro-9H-pyrimido[4,5-b]indol-9-yl)acetyl)-N-(6-bromopyridin-2-yl)-5-methyl-2-azabicyclo[3.1.0]hexane-3-carboxamide (243a)

Compound 243a was prepared according to the procedure reported in step-3 of scheme-1, from TFA salt of 2-(4-amino-8-methoxy-6-nitro-9H-pyrimido[4,5-b]indol-9-yl)acetic acid (242f) (60 mg, 0.139 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (46.3 mg, 0.139 mmol), HATU (79 mg, 0.209 mmol), DIPEA (0.121 mL, 0.696 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-8-methoxy-6-nitro-9H-pyrimido[4,5-b]indol-9-yl)acetyl)-N-(6-bromopyridin-2-yl)-5-methyl-2-azabicyclo[3.1.0]hexane-3-carboxamide (243a) (49 mg, 59% yield) HCl salt as a pale-yellow solid; $^1$H NMR (300 MHz, DMSO-$d_6$) δ 10.74 (s, 1H, $D_2O$ exchangeable), 9.15 (d, J=1.9 Hz, 1H), 8.79-8.42 (m, 3H, 2H $D_2O$ exchangeable), 8.02 (d, J=8.1 Hz, 1H), 7.85 (d, J=1.9 Hz, 1H), 7.70 (t, J=8.0 Hz, 1H), 7.31 (d, J=7.7 Hz, 1H), 5.77 (d, J=17.0 Hz, 1H), 5.52 (d, J=17.0 Hz, 1H), 4.39 (dd, J=9.0, 5.9 Hz, 1H), 4.03 (s, 3H), 3.63 (dd, J=5.6, 2.3 Hz, 1H), 2.48-2.41 (m, 1H), 2.00 (dd, J=13.3, 5.9 Hz, 1H), 1.32 (s, 3H), 1.11-1.00 (m, 1H), 0.90-0.77 (m, 1H). MS (ES+): 595.1 (M+1); (ES−): 593.1 (M−1); Analysis calculated for $C_{25}H_{23}BrN_8O_5$ $1.75H_2O \cdot 0.8HCl$: C, 45.77; H, 4.19; Cl, 4.32; N, 17.08. Found: C, 45.83; H, 3.98; Cl, 4.65. N, 17.07.

Scheme 244

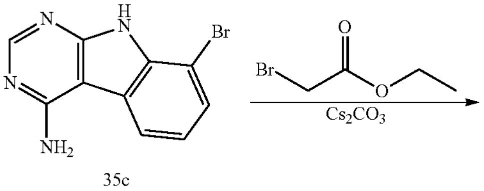

35c

-continued

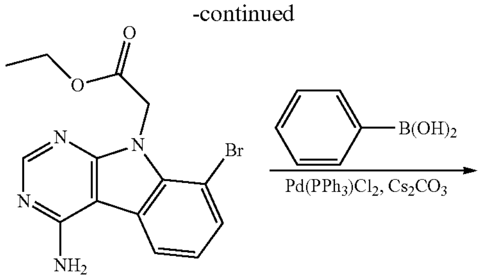

244a

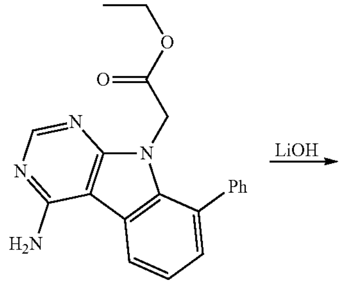

244b

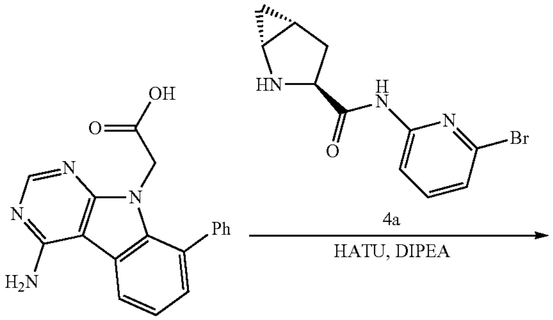

244c

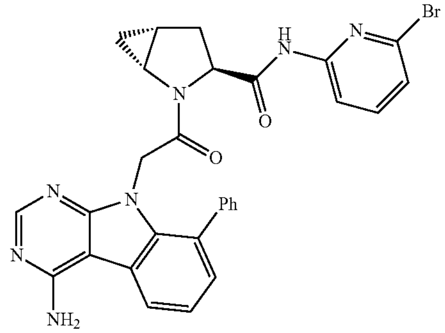

244d

Preparation of (1R,3S,5R)-2-(2-(4-amino-8-phenyl-9H-pyrimido[4,5-b]indol-9-yl)acetyl)-N-(6-bromopyridin-2-yl)-2-azabicyclo[3.1.0]hexane-3-carboxamide (244d)

Step-1: Preparation of ethyl 2-(4-amino-8-bromo-9H-pyrimido[4,5-b]indol-9-yl)acetate (244a)

Compound 244a was prepared according to the procedure reported in step-1 of scheme-1, from 8-bromo-9H-pyrimido[4,5-b]indol-4-amine (35c) (2 g, 7.60 mmol) in DMF (50 mL) using ethyl 2-bromoacetate (1.012 mL, 9.12 mmol), $Cs_2CO_3$ (3.72 g, 11.40 mmol) and stirring at RT for 1.5 h. This gave after workup and purification ethyl 2-(4-amino- 8-bromo-9H-pyrimido[4,5-b]indol-9-yl)acetate (244a) (1.35 g, 51% yield) as a pale-yellow solid; $^1$H NMR (300 MHz, DMSO-$d_6$) δ 8.40 (dd, J=7.8, 1.0 Hz, 1H), 8.34 (s, 1H), 7.60 (dd, J=7.9, 1.0 Hz, 1H), 7.54-7.43 (m, 2H), 7.22 (t, J=7.8 Hz, 1H), 5.55 (s, 2H), 4.18 (q, J=7.1 Hz, 2H), 1.22 (t, J=7.1 Hz, 3H); MS (ES+): 349.10 (M+1).

Step-2: Preparation of ethyl 2-(4-amino-8-phenyl-9H-pyrimido[4,5-b]indol-9-yl)acetate (244b)

Compound 244b was prepared according to the procedure reported in step-1 of scheme-62, from ethyl 2-(4-amino-8-bromo-9H-pyrimido[4,5-b]indol-9-yl)acetate (244a) (500 mg, 1.432 mmol) in dioxane (36 mL) using phenylboronic acid (0.262 g, 2.148 mmol), a solution of cesium carbonate (0.700 g, 2.148 mmol) in water (4.5 mL), $Pd(PPh_3)_2Cl_2$ (0.201 g, 0.286 mmol) and heating at 100° C. for 16 h under nitrogen. This gave after workup and purification using flash column chromatography [silica gel (40 g), eluting with MeOH/EtOAc (1:9) in hexane from 0-75%] ethyl 2-(4-amino-8-phenyl-9H-pyrimido[4,5-b]indol-9-yl)acetate (244b) (495 mg, 100% yield) as an off-white solid; $^1$H NMR (300 MHz, DMSO-$d_6$) δ 8.41 (dd, J=7.8, 1.2 Hz, 1H), 8.29 (s, 1H), 7.48 (dd, J=4.9, 1.8 Hz, 3H), 7.40 (s, 2H), 7.37-7.30 (m, 3H), 7.17 (dd, J=7.4, 1.1 Hz, 1H), 4.65 (s, 2H), 3.89 (q, J=7.1 Hz, 2H), 1.05 (t, J=7.1 Hz, 3H); MS (ES+): 347.20 (M+1).

Step-3: Preparation of 2-(4-amino-8-phenyl-9H-pyrimido[4,5-b]indol-9-yl)acetic acid (244c)

Compound 244c was prepared according to the procedure reported in step-4 of scheme-17, from ethyl 2-(4-amino-8-phenyl-9H-pyrimido[4,5-b]indol-9-yl)acetate (244b) (300 mg, 0.866 mmol) in THF (4.5 mL) and methanol (4.5 mL) using a solution of 1N lithium hydroxide hydrate (4.33 mL, 4.33 mmol) and stirring at RT for 19 h. This gave after work up 2-(4-amino-8-phenyl-9H-pyrimido[4,5-b]indol-9-yl)acetic acid (244c) (210 mg, 76% yield) which was used as such for the next step: $^1$H NMR (300 MHz, DMSO-$d_6$) δ 12.67 (s, 1H), 8.40 (dd, J=7.8, 1.2 Hz, 1H), 8.29 (s, 1H), 7.71-7.52 (m, 1H), 7.48 (dd, J=5.0, 2.0 Hz, 3H), 7.43-7.24 (m, 4H), 7.17 (dd, J=7.4, 1.1 Hz, 1H), 4.53 (s, 2H); MS (ES+): 319.10 (M+1).

Step-4: Preparation of (1R,3S,5R)-2-(2-(4-amino-8-phenyl-9H-pyrimido[4,5-b]indol-9-yl)acetyl)-N-(6-bromopyridin-2-yl)-2-azabicyclo[3.1.0]hexane-3-carboxamide (244d)

Compound 244d was prepared according to the procedure reported in step-3 of scheme-1, from 2-(4-amino-8-phenyl-9H-pyrimido[4,5-b]indol-9-yl)acetic acid (244c) (0.060 g, 0.188 mmol) in DMF (1.5 mL) using HCl salt of (1R,3S,5R)—N-(6-bromopyridin-2-yl)-2-azabicyclo[3.1.0]hexane-3-carboxamide (4a) (60.1 mg, 0.188 mmol), HATU (108 mg, 0.283 mmol), DIPEA (0.164 mL, 0.942 mmol) and stirring at RT for 16 h. his gave after workup and purification by flash column chromatography [silica gel (12 g), DMA80 in DCM from 0-100%] followed by purification using reverse phase column chromatography [C18 column (50 g), eluting with ACN in water (containing 0.1% HCl) from 0-100%] (1R,3S,5R)-2-(2-(4-amino-8-phenyl-9H-pyrimido[4,5-b]indol-9-yl)acetyl)-N-(6-bromopyridin-2-yl)-2-azabicyclo[3.1.0]hexane-3-carboxamide (244d) (69 mg, 63% yield) as a white solid; $^1$H NMR (300 MHz, DMSO-$d_6$) δ 10.70 (s, 1H, $D_2O$ exchangeable), 8.72-8.59 (m, 3H, 2H $D_2O$ exchangeable), 8.55 (dd, J=7.9, 1.2 Hz, 1H), 8.00 (d, J=8.2 Hz, 1H), 7.70 (t, J=8.0 Hz, 1H), 7.60-7.37 (m, 5H), 7.37-7.19 (m, 3H), 5.28 (d, J=17.6 Hz, 1H), 4.71 (d, J=17.6 Hz, 1H), 4.22 (t, J=7.3 Hz, 1H), 3.18-3.07 (m, 1H), 2.13 (dd, J=8.5, 3.4 Hz, 2H), 1.81-1.63 (m, 1H), 0.68-0.58 (m, 1H), 0.04-0.08 (m, 1H). MS (ES+): 582.1 (M+1); (ES−): 580.1 (M−1); Analysis calculated for $C_{29}H_{24}BrN_7O_2$ $1.75H_2O \cdot 0.9HCl$: C, 53.85; H, 4.43; Cl, 4.93; N, 15.16. Found: C, 54.03; H, 4.32; Cl, 5.11; N, 15.11.

Scheme 245

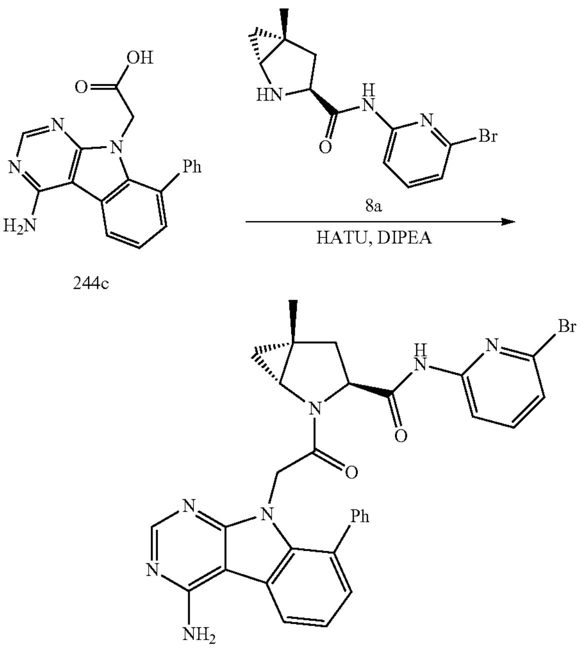

244c

245a

Preparation of (1R,3S,5R)-2-(2-(4-amino-8-phenyl-9H-pyrimido[4,5-b]indol-9-yl)acetyl)-N-(6-bromopyridin-2-yl)-5-methyl-2-azabicyclo[3.1.0]hexane-3-carboxamide (245a)

Compound 245a was prepared according to the procedure reported in step-3 of scheme-1, from 2-(4-amino-8-phenyl-9H-pyrimido[4,5-b]indol-9-yl)acetic acid (244c) (60 mg, 0.188 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (62.7 mg, 0.188 mmol), HATU (108 mg, 0.283 mmol), DIPEA (0.164 mL, 0.942 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-8-phenyl-9H-pyrimido[4,5-b]indol-9-yl)acetyl)-N-(6-bromopyridin-2-yl)-5-methyl-2-azabicyclo[3.1.0]hexane-3-carboxamide (245a) (71 mg, 63% yield) HCl salt as a white solid; 1H NMR (300 MHz, DMSO-$d_6$) δ 10.69 (s, 1H, $D_2O$ exchangeable), 8.63-8.41 (m, 4H, 2H $D_2O$ exchangeable), 8.00 (d, J=8.2 Hz, 1H), 7.68 (t, J=7.9 Hz, 1H), 7.62-7.36 (m, 5H), 7.36-7.06 (m, 3H), 5.21 (d, J=17.9 Hz, 1H), 4.65 (d, J=17.5 Hz, 1H), 4.17 (dd, J=8.8, 6.2 Hz, 1H), 2.95-2.81 (m, 1H), 2.35-2.17 (m, 1H), 1.88 (dd, J=13.0, 6.2 Hz, 1H), 1.18 (s, 3H), 0.64-0.51 (m, 1H), 0.28-0.12 (m, 1H). MS (ES+): 596.1 (M+1); (ES−): 594.1 (M−1); Analysis calculated for $C_3OH_{26}BrN_7O_2$ $1.75H_2O{\cdot}HCl$: C, 54.23; H, 4.63; Cl, 5.34; N, 14.76. Found: C, 54.38; H, 4.44; Cl, 5.04; N, 14.68.

Scheme 246

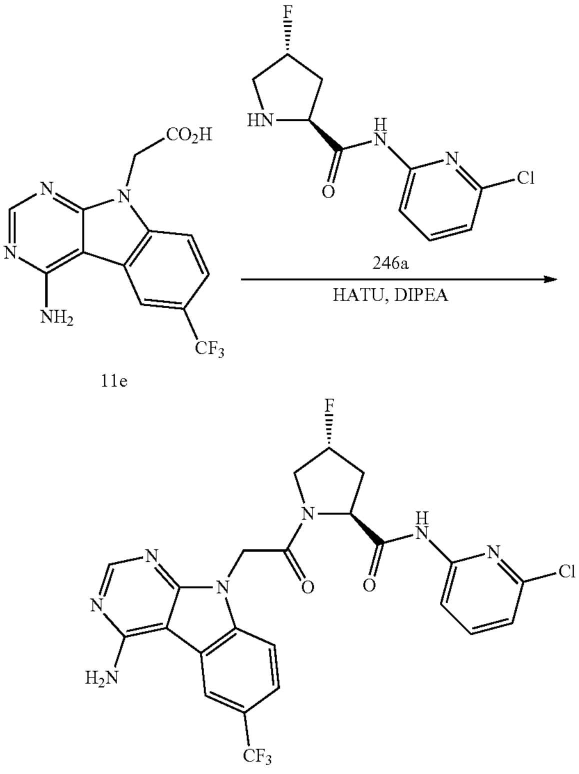

11e, 246a, 246b

Preparation of (2S,4R)-1-(2-(4-amino-6-(trifluoromethyl)-9H-pyrimido[4,5-b]indol-9-yl)acetyl)-N-(6-chloropyridin-2-yl)-4-fluoropyrrolidine-2-carboxamide (246b)

Compound 246b was prepared according to the procedure reported in step-3 of scheme-1, from HCl salt of 2-(4-amino-6-(trifluoromethyl)-9H-pyrimido[4,5-b]indol-9-yl)acetic acid (11e) (50 mg, 0.144 mmol), in DMF (1 mL) using TFA salt of (2S,4R)—N-(6-chloropyridin-2-yl)-4-fluoropyrrolidine-2-carboxamide (246a) (51.6 mg, 0.144 mmol; prepared according to the procedure reported by Wiles, Jason A. et al. PCT Int. Appl. (2017), WO 2017035351 A1 20170302). HATU (82 mg, 0.216 mmol). DIPEA (0.126 mL, 0.721 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (2S,4R)-1-(2-(4-amino-6-(trifluoromethyl)-9H-pyrimido[4,5-b]indol-9-yl)acetyl)-N-(6-chloropyridin-2-yl)-4-fluoropyrrolidine-2-carboxamide (246b) (51 mg, 66% yield) HCl salt as a white solid; $^1$H NMR (300 MHz, DMSO-$d_6$) (a mixture of two rotamers) δ 11.37 and 10.97 (2s, 1H, $D_2O$ exchangeable), 9.01 (s, 1H), 8.86 (s, 2H, $D_2O$ exchangeable), 8.67 and 8.64 (2s, 1H), 8.22-7.71 (m, 4H), 7.30 and 7.19 (2d, J=7.7 Hz, 1H), 5.76-5.01 (m, 3H), 4.62 (dd, J=9.6, 7.4 Hz, 1H), 4.33 (dd, J=22.2, 12.5 Hz, 1H), 4.09 (ddd, J=38.3, 12.5, 3.2 Hz, 1H), 2.65-2.54 (m, 1H), 2.31-2.02 (m, 1H). $^{19}$F NMR (282 MHz, DMSO-$d_6$) δ−58.61, −175.54. MS (ES+): 536.2 (M+1); (ES−): 534.1 (M−1); Analysis calculated for $C_{23}H_{18}ClF_4N_7O_2$ $2H_2O{\cdot}0.95HCl$: C, 45.54; H, 3.81; Cl, 11.40; N, 16.16. Found: C, 45.53; H, 3.72; Cl, 11.16; N, 15.83.

Scheme 247

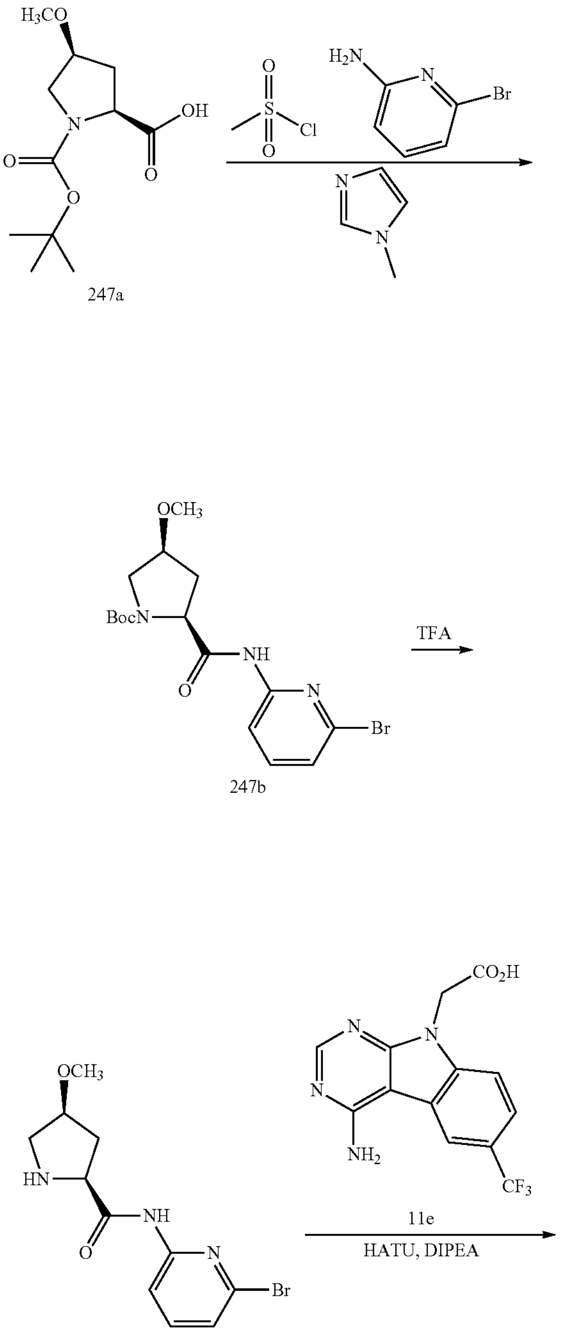

247a, 247b, 247c, 11e

-continued

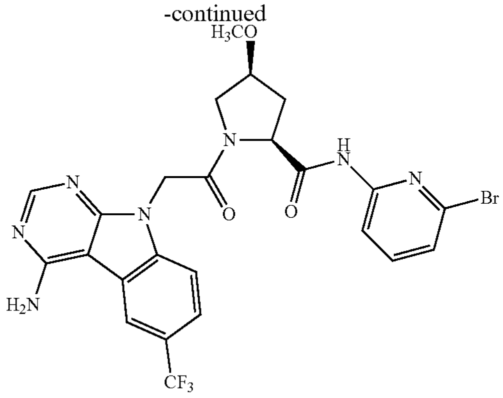

247d

Preparation of (2S,4S)-1-(2-(4-amino-6-(trifluoromethyl)-9H-pyrimido[4,5-b]indol-9-yl)acetyl)-N-(6-bromopyridin-2-yl)-4-methoxypyrrolidine-2-carboxamide (247d)

Step-1: Preparation of (2S,4S)-tert-butyl 2-((6-bromopyridin-2-yl)carbamoyl)-4-methoxypyrrolidine-1-carboxylate (247b)

Compound 247b was prepared according to the procedure reported in step-1 of scheme-53, from (2S,4S)-1-(tert-butoxycarbonyl)-4-methoxypyrrolidine-2-carboxylic acid (247a) (0.5 g, 2.039 mmol; CAS #83623-93-2) in DCM (15 mL) using 1-methyl-1H-imidazole (0.406 mL, 5.10 mmol), methanesulfonyl chloride (0.189 mL, 2.446 mmol), 6-bromopyridin-2-amine (0.353 g, 2.039 mmol) and stirring at RT for 18 h. This gave after workup (2S,4S)-tert-butyl 2-((6-bromopyridin-2-yl)carbamoyl)-4-methoxypyrrolidine-1-carboxylate (247b) (681 mg, 83% yield); $^{1}$H NMR (300 MHz, DMSO-$d_6$) δ 10.68 (d, J=27.7 Hz, 1H), 8.09 (q, J=11.2, 10.0 Hz, 1H), 7.75 (q, J=7.8 Hz, 1H), 7.35 (d, J=7.7 Hz, 1H), 4.34 (q, J=8.5, 7.9 Hz, 1H), 3.96 (t, J=5.7 Hz, 1H), 3.70-3.59 (m, 1H), 3.30-3.15 (m, 4H), 2.43 (d, J=17.1 Hz, 11H), 1.96-1.75 (m, 1H), 1.33 (d, J=42.4 Hz, 9H).

Step-2: Preparation of (2S,4S)—N-(6-bromopyridin-2-yl)-4-methoxypyrrolidine-2-carboxamide (247c)

Compound 247c was prepared according to the procedure reported in step-2 of scheme-1, from (2S,4S)-tert-butyl 2-((6-bromopyridin-2-yl)carbamoyl)-4-methoxypyrrolidine-1-carboxylate (247b) (670 mg, 1.674 mmol) in DCM (9 mL) using TFA (0.903 mL, 11.72 mmol) and stirring overnight at RT. This gave after workup TFA salt of (2S,4S)—N-(6-bromopyridin-2-yl)-4-methoxypyrrolidine-2-carboxamide (247c) (0.96 g, 98% yield) as a pale-yellow oil; 1H NMR (300 MHz, DMSO-$d_6$) δ 11.42 (s, 1H), 9.65 (s, 1H), 8.83 (s, 1H), 8.04 (d, J=8.3 Hz, 1H), 7.82 (t, J=8.0 Hz, 1H), 7.45 (dd, J=7.6, 3.1 Hz, 1H), 4.47 (s, 1H), 4.08 (d, J=5.2 Hz, 1H), 3.50-3.31 (m, 2H), 3.18 (s, 3H), 2.63-2.54 (m, 1H), 2.20 (dd, J=13.5, 4.7 Hz, 1H); MS (ES+): 300.00 (M+1).

Step-3: Preparation of (2S,4S)-1-(2-(4-amino-6-(trifluoromethyl)-9H-pyrimido[4,5-b]indol-9-yl)acetyl)-N-(6-bromopyridin-2-yl)-4-methoxypyrrolidine-2-carboxamide (247d)

Compound 247d was prepared according to the procedure reported in step-3 of scheme-1, from TFA salt of (2S,4S)—N-(6-bromopyridin-2-yl)-4-methoxypyrrolidine-2-carboxamide (247c) (84 mg, 0.144 mmol) in DMF (I mL) using HCl salt of 2-(4-amino-6-(trifluoromethyl)-9H-pyrimido[4,5-b]indol-9-yl)acetic acid (11e) (50 mg, 0.144 mmol), HATU (82 mg, 0.216 mmol), DIPEA (0.151 mL, 0.865 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (2S,4S)-1-(2-(4-amino-6-(trifluoromethyl)-9H-pyrimido[4,5-b]indol-9-yl)acetyl)-N-(6-bromopyridin-2-yl)-4-methoxypyrrolidine-2-carboxamide (247d) (55 mg, 64% yield) HCl salt as a white solid; $^{1}$H NMR (300 MHz, DMSO-$d_6$) (a mixture of two rotamers) δ 11.07 and 10.55 (2s, 1H, $D_2O$ exchangeable), 8.98 (s, 1H), 8.74-8.47 (m, 3H, 2H $D_2O$ exchangeable), 8.18-7.91 (m, 2H), 7.91-7.76 (m, 1H), 7.70 (t, J=8.0 Hz, 1H), 7.40 and 7.33 (2d, J=7.7 Hz, 1H), 5.61-5.40 (m, 2H), 4.51 (dd, J=9.1, 5.1 Hz, 1H), 4.21-4.08 (m, 2H), 3.85 (q, J=6.4 Hz, 1H), 3.30 and 3.15 (2s, 3H), 2.55-2.45 (m, 1H), 2.12-1.96 (m, 1H). $^{19}$F NMR (282 MHz, DMSO-$d_6$) δ−58.53. MS (ES+): 592.1 (M+1), 614.1 (M+Na); (ES−): 590.1 (M−1); Analysis calculated for $C_{24}H_{21}BrF_3N_7O_3 \cdot 1.5H_2O \cdot 1.15HCl$: C, 43.59; H, 3.83; Cl, 6.17; N, 14.83. Found: C, 43.64; H, 3.61; Cl, 6.14; N, 14.50.

Scheme 248

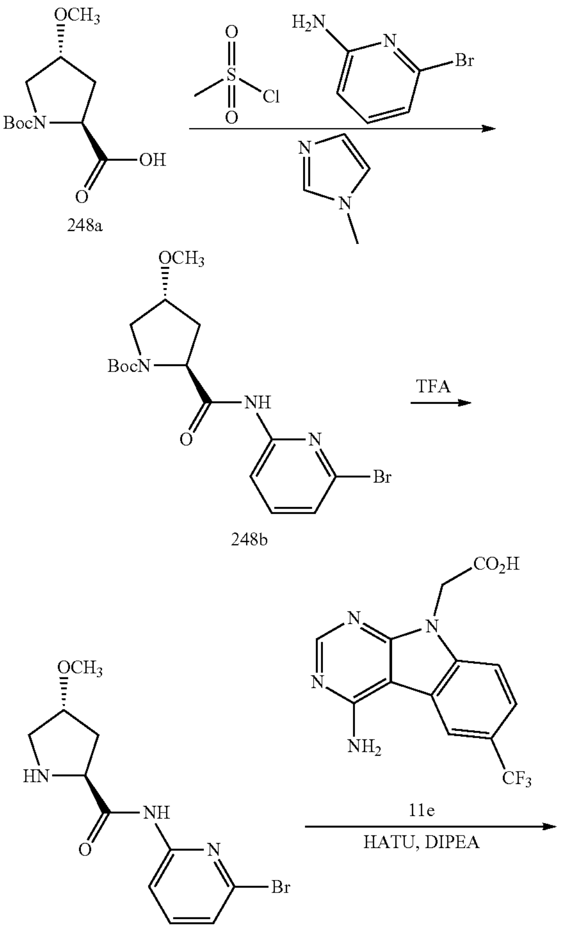

248a

248b

248c

-continued

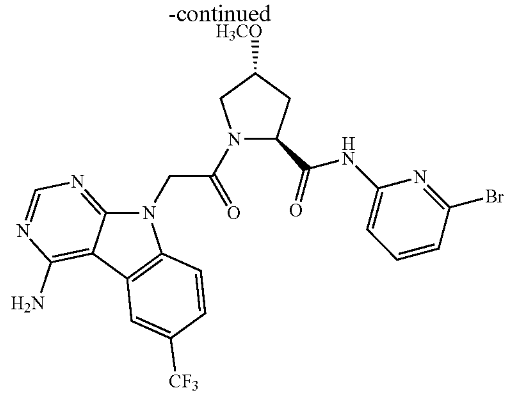

248d

Preparation of (2S,4R)-1-(2-(4-amino-6-(trifluoromethyl)-9H-pyrimido[4,5-b]indol-9-yl)acetyl)-N-(6-bromopyridin-2-yl)-4-methoxypyrrolidine-2-carboxamide (248d)

Step-1: Preparation of (2S,4R)-tert-butyl 2-((6-bromopyridin-2-yl)carbamoyl)-4-methoxypyrrolidine-1-carboxylate (248b)

Compound 248b was prepared according to the procedure reported in step-1 of scheme-53, from (2S,4R)-1-(tert-butoxycarbonyl)-4-methoxypyrrolidine-2-carboxylic acid (248a) (0.5 g, 2.039 mmol; CAS #83624-01-05) in DCM (15 mL) using 1-methyl-1H-imidazole (0.406 mL, 5.10 mmol), methanesulfonyl chloride (0.189 mL, 2.446 mmol), 6-bromopyridin-2-amine (0.353 g, 2.039 mmol) and stirring at RT for 18 h. This gave after workup (2S,4R)-tert-butyl 2-((6-bromopyridin-2-yl)carbamoyl)-4-methoxypyrrolidine-1-carboxylate (248b) (730 mg, 89% yield): $^1$H NMR (300 MHz, DMSO-$d_6$) δ 10.97 (d, J=18.3 Hz, 1H), 8.10 (dd, J=14.4, 8.1 Hz, 1H), 7.76 (q, J=8.2 Hz, 1H), 7.36 (d, J=7.7 Hz, 1H), 4.39 (q, J=8.2 Hz, 1H), 3.96 (d, J=5.1 Hz, 1H), 3.45 (q, J=3.5 Hz, 2H), 3.23 (s, 3H), 2.39-2.23 (m, 1H), 1.93 (ddd, J=13.4, 8.6, 4.9 Hz, 1H), 1.32 (d, J=42.4 Hz, 9H); MS (ES+): 400.10 (M+1).

Step-2: Preparation of (2S,4R)—N-(6-bromopyridin-2-yl)-4-methoxypyrrolidine-2-carboxamide (248c)

Compound 248c was prepared according to the procedure reported in step-2 of scheme-1, from (2S,4R)-tert-butyl 2-((6-bromopyridin-2-yl)carbamoyl)-4-methoxypyrrolidine-1-carboxylate (248b) (720 mg, 1.799 mmol) in DCM (10 mL) using TFA (0.970 mL, 12.59 mmol) and stirring overnight at RT. This gave after workup TFA salt of (2S,4R)—N-(6-bromopyridin-2-yl)-4-methoxypyrrolidine-2-carboxamide (248c) (1.05 g, 100% yield) as a pale-yellow oil; $^1$H NMR (300 MHz, DMSO-$d_6$) δ 11.44 (s, 1H), 9.70 (s, 1H), 8.90 (s, 1H), 8.06 (d, J=8.1 Hz, 1H), 7.82 (t, J=7.9 Hz, 1H), 7.44 (dd, J=7.8, 0.7 Hz, 1H), 4.50-4.38 (m, 1H), 4.18-4.10 (m, 1H), 3.42-3.32 (m, 2H), 3.27 (s, 3H), 2.65 (dd, J=13.7, 7.1 Hz, 1H), 2.07-1.93 (m, 1H); MS (ES+): 300.0 (M+1).

Step-3: Preparation of (2S,4R)-1-(2-(4-amino-6-(trifluoromethyl)-9H-pyrimido[4,5-b]indol-9-yl)acetyl)-N-(6-bromopyridin-2-yl)-4-methoxypyrrolidine-2-carboxamide (248d)

Compound 248d was prepared according to the procedure reported in step-3 of scheme-1, from TFA salt of (2S,4R)—N-(6-bromopyridin-2-yl)-4-methoxypyrrolidine-2-carboxamide (248c) (84 mg, 0.144 mmol) in DMF (1 mL) using HCl salt of 2-(4-amino-6-(trifluoromethyl)-9H-pyrimido[4,5-b]indol-9-yl)acetic acid (11e) (50 mg, 0.144 mmol), HATU (82 mg, 0.216 mmol), DIPEA (0.151 mL, 0.865 mmol) and stirring at RT for 16 h. This gave after workup and purification by flash column chromatography [silica gel (24 g), eluting with DMA-80 in DCM from 0-100%] (2S,4R)-1-(2-(4-amino-6-(trifluoromethyl)-9H-pyrimido[4,5-b]indol-9-yl)acetyl)-N-(6-bromopyridin-2-yl)-4-methoxypyrrolidine-2-carboxamide (248d) (57 mg, 67% yield) HCl salt as a white solid; $^1$H NMR (300 MHz, DMSO-$d_6$) (a mixture of two rotamers) δ 11.34 and 10.91 (2s, 1H, $D_2O$ exchangeable), 9.00 (s, 1H), 8.77 (s, 2H, $D_2O$ exchangeable), 8.65 and 8.61 (2s, 1H), 8.20 and 7.99 (2d, J=8.2 Hz, 1H), 7.94-7.79 (m, 2H), 7.69 (t, J=8.0 Hz, 1H), 7.42 and 7.30 (2d, 1H), 5.61 (d, J=17.3 Hz, 1H), 5.45 (d, J=17.3 Hz, 1H), 4.52 (t. J=8.0 Hz, 1H), 4.27-4.13 (m, 1H), 4.07-3.94 (m, 2H), 3.36 and 3.26 (2s, 3H), 2.40-2.29 (m, 1H), 2.11-1.94 (m, 1H). $^{19}$F NMR (282 MHz, DMSO-$d_6$) δ−58.57. MS (ES+): 592.1 (M+1), (ES−): 590.0 (M−1); Analysis calculated for $C_4H_{21}BrF_3N_7O_3$ $1.75H_2O{\cdot}1.1HCl$: C, 43.41; H, 3.89; Cl, 5.87; N, 14.77. Found: C, 43.38; H, 3.60; Cl, 5.84; N, 14.60.

Scheme 249

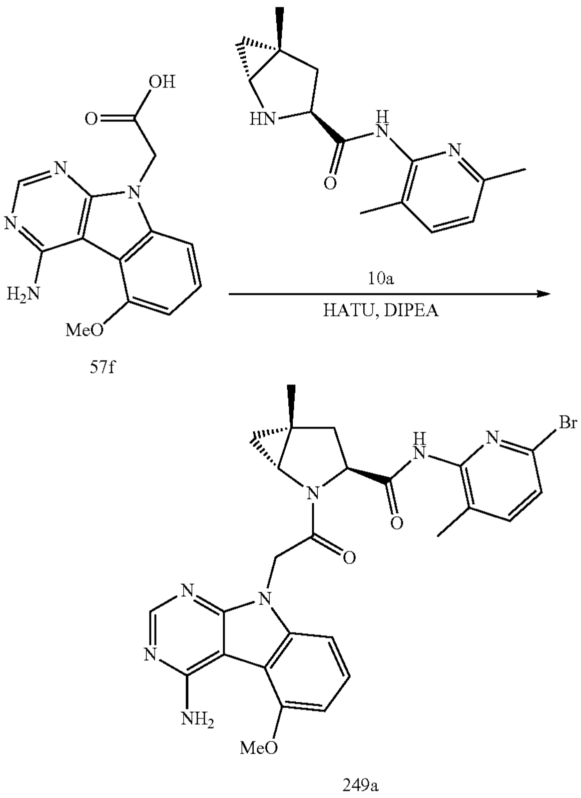

57f

249a

Preparation of (1R,3S,5R)-2-(2-(4-amino-5-methoxy-9H-pyrimido[4,5-b]indol-9-yl)acetyl)-N-(6-bromo-3-methylpyridin-2-yl)-5-methyl-2-azabicyclo[3.1.0]hexane-3-carboxamide (249a)

Compound 249a was prepared according to the procedure reported in step-3 of scheme-1, from TFA salt of 2-(4-amino-5-methoxy-9H-pyrimido[4,5-b]indol-9-yl)acetic acid (57f)

(60 mg, 0.155 mmol) in DMF (1.5 mL) using HCl salt of (1R,3S,5R)—N-(6-bromo-3-methylpyridin-2-yl)-5-methyl-2-azabicyclo[3.1.0]hexane-3-carboxamide (10a) (53.8 mg, 0.155 mmol). HATU (89 mg, 0.233 mmol), DIPEA (0.135 mL, 0.777 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-5-methoxy-9H-pyrimido[4,5-b]indol-9-yl)acetyl)-N-(6-bromo-3-methylpyridin-2-yl)-5-methyl-2-azabicyclo[3.1.0]hexane-3-carboxamide (249a) (52 mg, 59% yield) HCl salt as a white solid; $^1H$ NMR (300 MHz, DMSO-$d_6$) δ 10.31 (s, 1H, $D_2O$ exchangeable), 8.57 (s, 11H), 8.56-8.48 (m, 2H, $D_2O$ exchangeable), 8.41 (d, J=8.7 Hz, 1H), 7.62 (d, J=8.0 Hz, 1H), 7.45 (d, J=7.9 Hz, 1H), 7.26 (d, J=2.3 Hz, 1H), 7.04 (dd, J=8.7, 2.3 Hz, 1H), 5.63 (d, J=17.3 Hz, 11H), 5.42 (d, J=17.3 Hz, 11H), 4.36 (dd, J=9.3, 5.4 Hz, 11H), 3.78 (s, 3H), 3.69 (dd, J=5.6, 2.4 Hz, 1H), 2.63-2.53 (m, 1H), 2.09-2.00 (m, 1H), 1.99 (s, 3H), 1.35 (s, 3H), 1.09-1.01 (m, 1H), 1.01-0.90 (m, 1H). MS (ES+): 564.1 (M+1); (ES−): 562.1 (M−1); Analysis calculated for $C_{26}H_{26}BrN_7O_3$ $1.5H_2O{\cdot}HCl$: C, 49.73; H, 4.82; Cl, 5.65; N, 15.61. Found: C, 49.92; H, 4.81; Cl, 5.80; N, 15.54.

Scheme 250

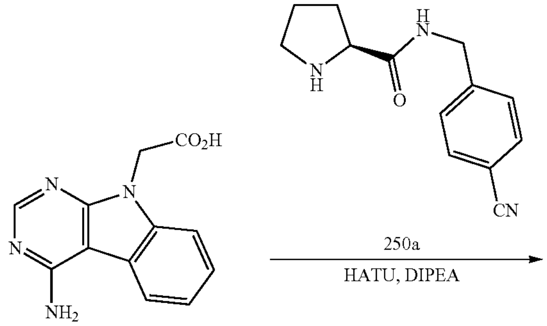

1c

-continued

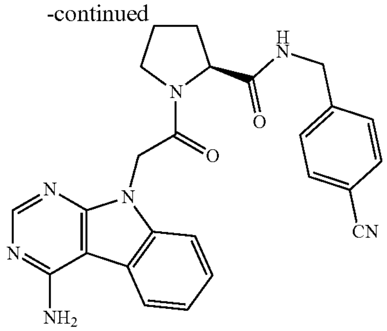

250b

Preparation of (S)-1-(2-(4-amino-9H-pyrimido[4,5-b]indol-9-yl)acetyl)-N-(4-cyanobenzyl)pyrrolidine-2-carboxamide (250b)

Compound 250b was prepared according to the procedure reported in step-3 of scheme-1, from TFA salt of 2-(4-amino-9H-pyrimido[4,5-b]indol-9-yl)acetic acid (1c) (75 mg, 0.211 mmol) in DMF (5 mL) using HCl salt of (S)—N-(4-cyanobenzyl)pyrrolidine-2-carboxamide (250a) (55.9 mg, 0.211 mmol; CAS #182291-72-1), HATU (89 mg, 0.233 mmol), DIPEA (136 mg, 1.053 mmol) and stirring at RT for 16 h. This gave after workup and purification by flash column chromatography [silica gel (12 g), eluting with MeOH in DCM from 0-6%] followed by purification using reverse phase column chromatography [C18 column (100 g), eluting with ACN in water (containing 0.1% HCl) from 0-100%] (S)-1-(2-(4-amino-9H-pyrimido[4,5-b]indol-9-yl)acetyl)-N-(4-cyanobenzyl)pyrrolidine-2-carboxamide (250b) (55 mg, 58% yield) HCl salt as a white solid; $^1H$ NMR (300 MHz, DMSO-$d_6$) δ 8.70-8.40 (m, 5H, 3H $D_2O$ exchangeable), 7.68 (td, J=5.2, 4.5, 2.4 Hz, 1H), 7.56-7.44 (m, 2H), 7.39 (qd, J=7.6, 3.9 Hz, 2H), 7.27 (d, J=8.1 Hz, 2H), 5.37 (s, 2H), 4.46-4.13 (m, 3H), 3.94-3.78 (m, 1H), 3.78-3.67 (m, 1H), 2.23-1.64 (m, 4H); MS (ES+): 454 (M+1); (ES−): 452 (M−1); IR 2233 (cm-1) Analysis calculated for $C_{25}H_{23}N_7O_2{\cdot}1.05HCl{\cdot}3.5H_2O$: C, 54.12; H, 5.64; Cl, 6.71; N, 17.67. Found: C, 54.43; H, 5.27; Cl, 6.90; N, 17.37.

Scheme 251

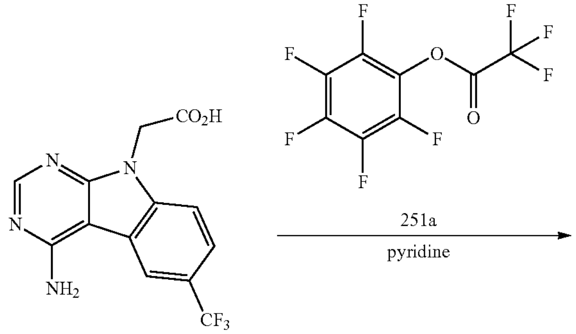

11e

-continued

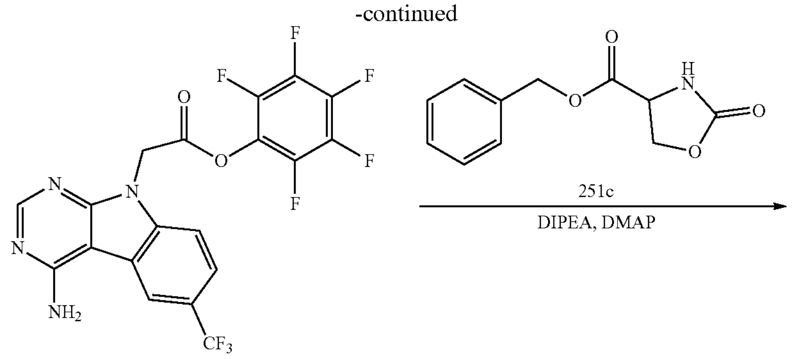

251b

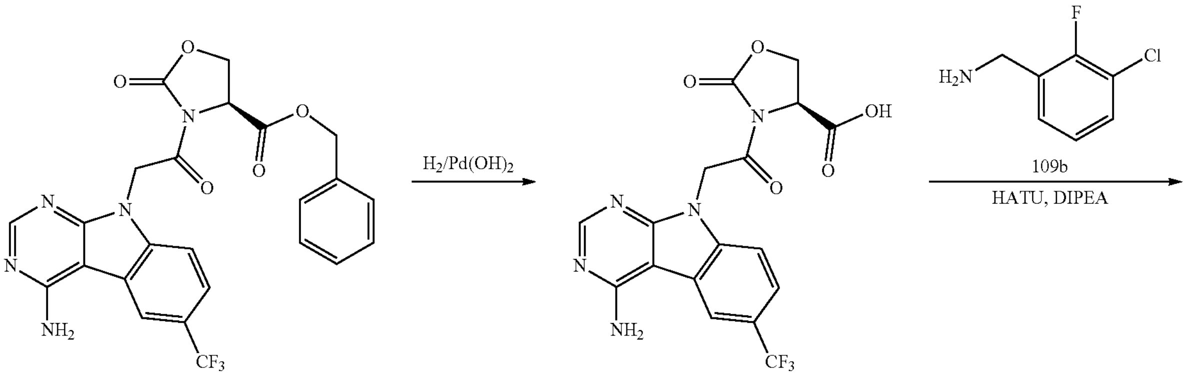

251d 251e

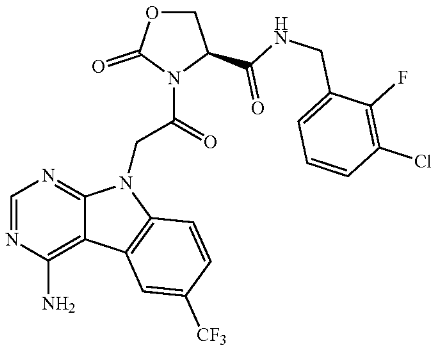

251f

Preparation of (S)-3-(2-(4-amino-6-(trifluoromethyl)-9H-pyrimido[4,5-b]indol-9-yl)acetyl)-N-(3-chloro-2-fluorobenzyl)-2-oxooxazolidine-4-carboxamide (2510)

Step-1: Preparation of perfluorophenyl 2-(4-amino-6-(trifluoromethyl)-9H-pyrimido[4,5-b]indol-9-yl) acetate (251b)

To a stirred solution of TFA salt of 2-(4-amino-6-(trifluoromethyl)-9H-pyrimido[4,5-b]indol-9-yl)acetic acid (11e) (500 mg, 1.179 mmol) in DMF (2 mL) was added pyridine (0.200 mL, 2.475 mmol) followed by pentafluorophenyl trifluoroacetate (251a) (0.253 mL, 1.473 mmol; CAS #14533-84-7) and stirred for 45 min at RT. The reaction mixture was diluted with ethyl acetate (50 mL), washed with 0.1N aqueous HCl (2×30 mL), 5% aqueous $NaHCO_3$ (1×30 mL), dried, filtered and concentrated in vacuo to afford perfluorophenyl 2-(4-amino-6-(trifluoromethyl)-9H-pyrimido[4,5-b]indol-9-yl)acetate (251b) (475 mg, 85% yield) as a white solid and was used as such for the next step; MS (ES+): 477.10 (M+1).

Step-2: Preparation of (S)-benzyl 3-(2-(4-amino-6-(trifluoromethyl)-9H-pyrimido[4,5-b]indol-9-yl) acetyl)-2-oxooxazolidine-4-carboxylate (251d)

To a stirred solution of (S)-benzyl 2-oxooxazolidine-4-carboxylate (251c) (218 mg, 0.987 mmol; CAS #203736-214) in dry DMF (1 mL) was added DIPEA (0.345 mL, 1.974 mmol), DMAP (12.06 mg, 0.099 mmol), followed by perfluorophenyl 2-(4-amino-6-(trifluoromethyl)-9H-pyrimido[4,5-b]indol-9-yl)acetate (251b) (470 mg, 0.987 mmol) and stirred for at RT 2 h. The reaction mixture was diluted with ethyl acetate (50 mL), washed with 0.1N aqueous HCl (2×30 mL), 5% aqueous $NaHCO_3$ (1×30 mL), dried, filtered and concentrated in vacuo. The residue obtained was purified using flash column chromatography [silica gel (24 g), eluting with DMA-80 in DCM from 0 to 50%] to give (S)-benzyl 3-(2-(4-amino-6-(trifluoromethyl)-9H-pyrimido[4,5-b]indol-9-yl)acetyl)-2-oxooxazolidine-4-carboxylate (251d) (140 mg, 28% yield) as a white solid: 1H NMR (300 MHz, DMSO-$d_6$) δ 8.84 (s, 1H), 8.34 (s, 1H), 7.69 (d, J=1.1 Hz, 2H), 7.63 (s, 2H), 7.32 (s, 5H), 5.92 (d, J=18.6 Hz, 1H), 5.74 (d, J=18.6 Hz, 1H), 5.17 (s, 2H), 5.06 (dd, J=9.4, 3.7 Hz, 1H), 4.78 (t, J=9.3 Hz, 1H), 4.64 (dd, J=9.2, 3.7 Hz, 1H); MS (ES+): 514.10 (M+1).

Step-3: Preparation of (S)-3-(2-(4-amino-6-(trifluoromethyl)-9H-pyrimido[4,5-b]indol-9-yl)acetyl)-2-oxooxazolidine-4-carboxylic acid (251e)

Compound 251e was prepared according to the procedure reported in step-2 of scheme-45, from (S)-benzyl 3-(2-(4-amino-6-(trifluoromethyl)-9H-pyrimido[4,5-b]indol-9-yl)acetyl)-2-oxooxazolidine-4-carboxylate (251d) (135 mg, 0.263 mmol) in MeOH (30 mL) using palladium hydroxide on carbon (36.9 mg, 0.053 mmol) in a hydrogen atmosphere (balloon) for 2 h at RT. The reaction mixture was filtered and filtrate was concentrated in vacuum to give (S)-3-(2-(4-amino-6-(trifluoromethyl)-9H-pyrimido[4,5-b]indol-9-yl)acetyl)-2-oxooxazolidine-4-carboxylic acid (251e) (0.070 g, 63% yield) as an off-white solid; $^1$H NMR (300 MHz, DMSO-$d_6$) δ 8.84 (s, 1H), 8.35 (s, 1H), 7.71 (d, J=1.1 Hz, 2H), 7.62 (s, 2H), 5.89 (d, J=18.6 Hz, 1H), 5.74 (d, J=18.7 Hz, 1H), 4.90-4.80 (m, 1H), 4.75 (t, J=9.1 Hz, 1H), 4.56 (dd, J=8.9, 3.3 Hz, 1H); MS (ES+): 424.10 (M+1).

Step-4: Preparation of (S)-3-(2-(4-amino-6-(trifluoromethyl)-9H-pyrimido[4,5-b]indol-9-yl)acetyl)-N-(3-chloro-2-fluorobenzyl)-2-oxooxazolidine-4-carboxamide (251f)

Compound 251f was prepared according to the procedure reported in step-3 of scheme-1, from (S)-3-(2-(4-amino-6-(trifluoromethyl)-9H-pyrimido[4,5-b]indol-9-yl)acetyl)-2-oxooxazolidine-4-carboxylic acid (251e) (30 mg, 0.071 mmol) in DMF (1 mL) using (3-chloro-2-fluorophenyl)methanamine (109b) (8.91 μL, 0.071 mmol; CAS #182291-72-1), HATU (40.4 mg, 0.106 mmol), DIPEA (0.037 mL, 0.213 mmol) and stirring at RT for 16 h. This gave after workup and purification by flash column chromatography [silica gel (12 g), eluting with DMA-80 in DCM from 0-100%] followed by purification using reverse phase column chromatography [C18 column (30 g), eluting with ACN in water (containing 0.1% HCl) from 0-100%] (S)-3-(2-(4-amino-6-(trifluoromethyl)-9H-pyrimido[4,5-b]indol-9-yl)acetyl)-N-(3-chloro-2-fluorobenzyl)-2-oxooxazolidine-4-carboxamide (251f) (12 mg, 30% yield) HCl salt as a white solid; $^1$H NMR (300 MHz, DMSO-$d_6$) δ 8.99-8.92 (m, 2H), 8.55 (s, 1H), 8.42 (s, 2H, $D_2O$ exchangeable), 7.81 (q, J=8.7 Hz, 2H), 7.48-7.36 (m, 1H), 7.21-7.11 (m, 1H), 7.00 (t, J=7.9 Hz, 1H), 6.01-5.73 (m, 2H), 4.86 (dd, J=9.3, 3.6 Hz, 1H), 4.73 (t, J=9.1 Hz, 1H), 4.37 (dt, J=15.1, 4.3 Hz, 3H). $^{19}$F NMR (282 MHz, DMSO) δ-58.50, −121.33. MS (ES+): 565.1 (M+1): (ES−): 563.0 (M−1).

Scheme 252

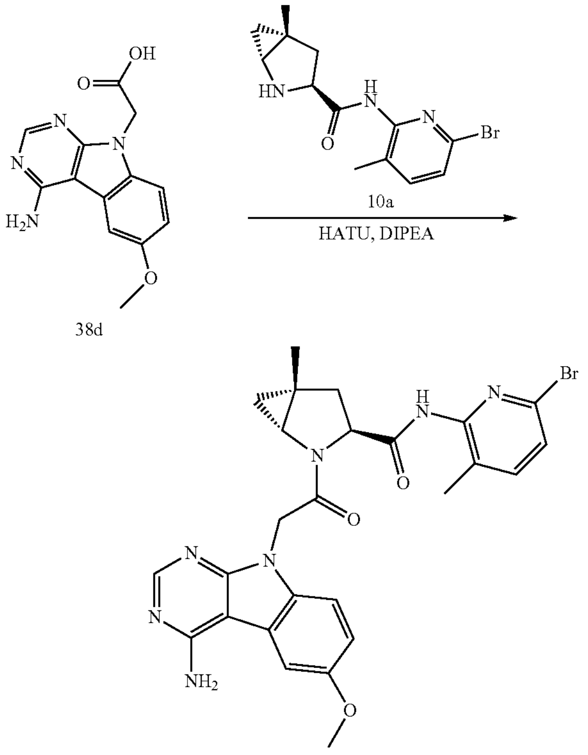

38d

10a

252a

Preparation of (1R,3S,5R)-2-(2-(4-amino-6-methoxy-9H-pyrimido[4,5-b]indol-9-yl)acetyl)-N-(6-bromo-3-methylpyridin-2-yl)-5-methyl-2-azabicyclo[3.1.0]hexane-3-carboxamide (252a)

Compound 252a was prepared according to the procedure reported in step-3 of scheme-1, from TFA salt of 2-(4-amino-6-methoxy-9H-pyrimido[4,5-b]indol-9-yl)acetic acid (38d) (60 mg, 0.155 mmol) in DMF (1.5 mL) using HCl salt of (1R,3S,5R)—N-(6-bromo-3-methylpyridin-2-yl)-5-methyl-2-azabicyclo[3.1.0]hexane-3-carboxamide (10a) (53.8 mg, 0.155 mmol), HATU (89 mg, 0.233 mmol), DIPEA (0.135 mL, 0.777 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-methoxy-9H-pyrimido[4,5-b]indol-9-yl)acetyl)-N-(6-bromo-3-methylpyridin-2-yl)-5-methyl-2-azabicyclo[3.1.0]hexane-3-carboxamide (252a) (50 mg, 57% yield) HCl salt as a white solid; $^1$H NMR (300 MHz, DMSO-$d_6$) δ 10.29 (s, 1H, $D_2O$ exchangeable), 8.63-8.45 (m, 3H, 2H $D_2O$ exchangeable), 8.06 (d, J=2.4 Hz, 1H), 7.62 (d, J=8.0 Hz, 1H), 7.57 (d, J=9.0 Hz, 1H), 7.45 (d, J=7.9 Hz, 1H), 7.15 (dd, J=8.9, 2.4 Hz, 1H), 5.64 (d, J=17.3 Hz, 1H), 5.37 (d, J=17.3 Hz, 1H), 4.36 (dd, J=9.2, 5.2 Hz, 1H), 3.89 (s, 3H), 3.65 (dd, J=5.4, 2.4 Hz, 1H), 2.60-2.54 (m, 1H), 2.09-2.03 (m, 1H), 2.01 (s, 3H), 1.33 (s, 3H), 1.08-1.00 (m, 1H), 1.00-0.93 (m, 1H). MS (ES+): 564.1 (M+1); (ES−): 562.1 (M−1); Analysis calculated for $C_{26}H_{26}BrN_7O_3$ 1.75$H_2O$·HCl: C, 49.38; H, 4.86; Cl, 5.61; N, 15.50. Found: C, 49.41; H, 4.63; Cl, 5.39; N, 15.43.

Scheme 253

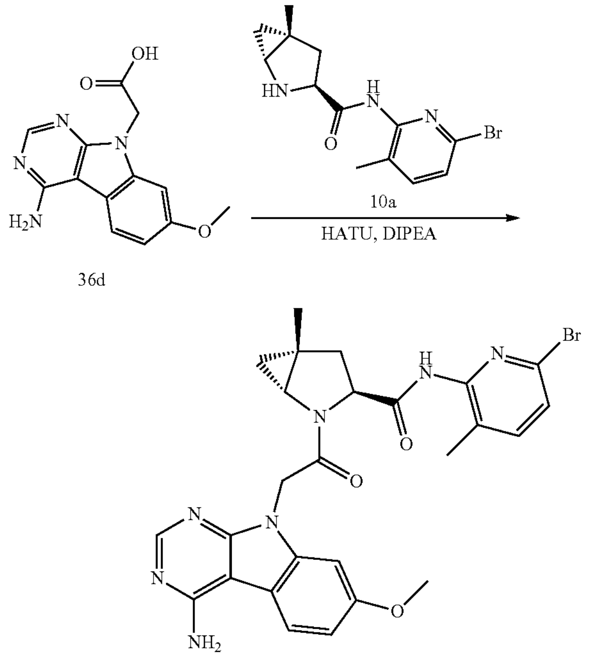

36d

253a

Scheme 254

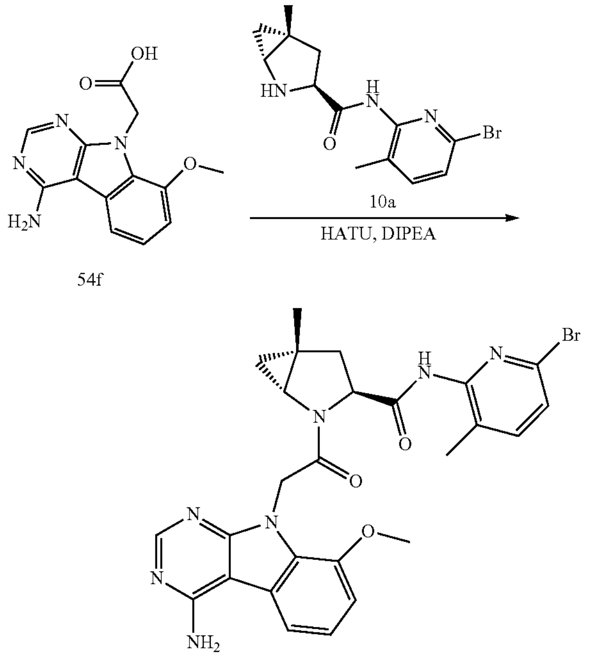

54f

254a

Preparation of (1R,3S,5R)-2-(2-(4-amino-7-methoxy-9H-pyrimido[4,5-b]indol-9-yl)acetyl)-N-(6-bromo-3-methylpyridin-2-yl)-5-methyl-2-azabicyclo[3.1.0]hexane-3-carboxamide (253a)

Compound 253a was prepared according to the procedure reported in step-3 of scheme-1, from TFA salt of 2-(4-amino-7-methoxy-9H-pyrimido[4,5-b]indol-9-yl)acetic acid (36d) (60 mg, 0.155 mmol) in DMF (1.5 mL) using HCl salt of (1R,3S,5R)—N-(6-bromo-3-methylpyridin-2-yl)-5-methyl-2-azabicyclo[3.1.0]hexane-3-carboxamide (10a) (53.8 mg, 0.155 mmol), HATU (89 mg, 0.233 mmol), DIPEA (0.135 mL, 0.777 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-7-methoxy-9H-pyrimido[4,5-b]indol-9-yl)acetyl)-N-(6-bromo-3-methylpyridin-2-yl)-5-methyl-2-azabicyclo[3.1.0]hexane-3-carboxamide (253a) (46 mg, 53% yield) HCl salt as a white solid; $^1H$ NMR (300 MHz, DMSO-$d_6$) δ 10.31 (s, 1H, $D_2O$ exchangeable), 8.67-8.46 (m, 3H, 2H $D_2O$ exchangeable), 8.42 (d, J=8.7 Hz, 1H), 7.62 (d, J=8.0 Hz, 1H), 7.45 (d, J=7.9 Hz, 1H), 7.26 (d, J=2.3 Hz, 1H), 7.05 (dd, J=8.7, 2.2 Hz, 1H), 5.63 (d, J=17.3 Hz, 1H), 5.42 (d, J=17.2 Hz, 1H), 4.36 (dd, J=9.3, 5.4 Hz, 1H), 3.78 (s, 3H), 3.69 (dd, J=5.6, 2.4 Hz, 1H), 2.61-2.53 (m, 1H), 2.04 (dd, J=13.5, 5.7 Hz, 1H), 1.99 (s, 3H), 1.35 (s, 3H), 1.12-0.98 (m, 1H), 0.98-0.90 (m, 1H). MS (ES+): 564.2 (M+1); (ES−): 562.2 (M−1); Analysis calculated for $C_{26}H_{26}BrN_7O_3$ $1.5H_2O·HCl$: C, 49.73; H, 4.82; Cl, 5.65; N, 15.61. Found: C, 49.88; H, 4.80; Cl, 5.77; N, 15.66.

Preparation of (1R,3S,5R)-2-(2-(4-amino-8-methoxy-9H-pyrimido[4,5-b]indol-9-yl)acetyl)-N-(6-bromo-3-methylpyridin-2-yl)-5-methyl-2-azabicyclo[3.1.0]hexane-3-carboxamide (254a)

Compound 254a was prepared according to the procedure reported in step-3 of scheme-1, from TFA salt of 2-(4-amino-8-methoxy-9H-pyrimido[4,5-b]indol-9-yl)acetic acid (54f) (60 mg, 0.155 mmol) in DMF (1.5 mL) using HCl salt of (1R,3S,5R)—N-(6-bromo-3-methylpyridin-2-yl)-5-methyl-2-azabicyclo[3.1.0]hexane-3-carboxamide (10a) (53.8 mg, 0.155 mmol), HATU (89 mg, 0.233 mmol), DIPEA (0.135 mL, 0.777 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-8-methoxy-9H-pyrimido[4,5-b]indol-9-yl)acetyl)-N-(6-bromo-3-methylpyridin-2-yl)-5-methyl-2-azabicyclo[3.1.0]hexane-3-carboxamide (254a) (55 mg, 63% yield) HCl salt as a white solid: $^1H$ NMR (300 MHz, DMSO-$d_6$) δ 10.28 (s, 1H, $D_2O$ exchangeable), 8.69-8.54 (m, 3H, 2H $D_2O$ exchangeable), 8.10 (d, J=7.9 Hz, 1H), 7.61 (d, J=8.0 Hz, 1H), 7.43 (d, J=7.9 Hz, 1H), 7.36 (t, J=8.0 Hz, 1H), 7.14 (d, J=8.1 Hz, 1H), 5.77 (d, J=17.0 Hz, 1H), 5.56 (d, J=16.9 Hz, 1H), 4.37 (dd, J=9.1, 5.3 Hz, 1H), 3.90 (s, 3H), 3.60 (dd, J=5.6, 2.4 Hz, 1H), 2.60-2.55 (m, 1H), 2.10-2.03 (m, 1H), 2.01 (s, 3H), 1.34 (s, 3H), 1.14-1.04 (m, 1H), 0.92-0.78 (m, 1H). MS (ES+): 564.1 (M+1); (ES−): 562.1 (M−1); Analysis calculated for $C_{26}H_{26}BrN_7O_3$ $1.5H_2O·HCl$: C, 49.73; H, 4.82; Cl, 5.65; N, 15.61. Found: C, 49.71; H, 4.81; Cl, 5.55; N, 15.62.

Scheme 255

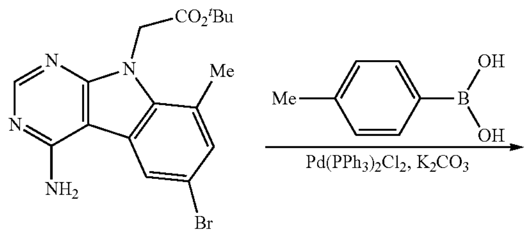

192e

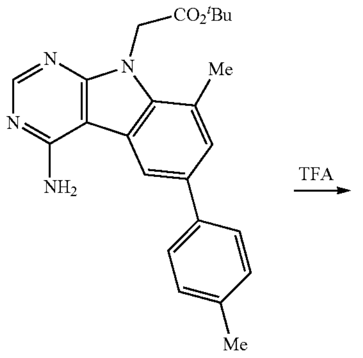

255a

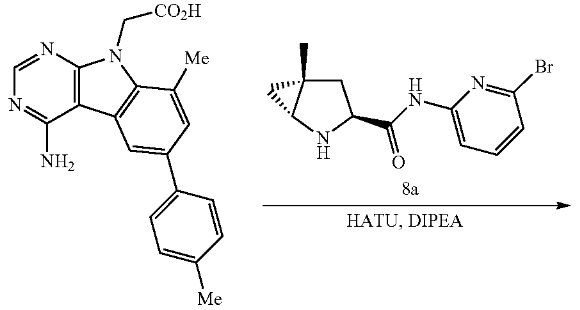

255b

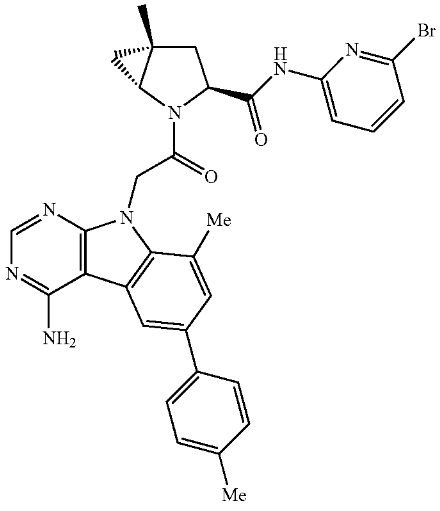

255c

Preparation of (1R,3S,5R)-2-(2-(4-amino-8-methyl-6-(p-tolyl)-9H-pyrimido[4,5-b]indol-9-yl)acetyl)-N-(6-bromopyridin-2-yl)-5-methyl-2-azabicyclo[3.1.0]hexane-3-carboxamide (255c)

Step-1: Preparation of tert-butyl 2-(4-amino-8-methyl-6-(p-tolyl)-9H-pyrimido[4,5-b]indol-9-yl)acetate (255a)

Compound 255a was prepared according to the procedure reported in step-1 of scheme-59, from tert-butyl 2-(4-amino-6-bromo-8-methyl-9H-pyrimido[4,5-b]indol-9-yl)acetate (192e) (300 mg, 0.767 mmol) in dioxane (4 mL) using p-tolylboronic acid (156 mg, 1.150 mmol), bis(triphenylphosphine)palladium(II) chloride (53.8 mg, 0.077 mmol) a solution of 3.3 M potassium carbonate (0.697 mL, 2.300 mmol) and stirring at 100° C. for 16 h. This gave after workup and purification by flash column chromatography [silica gel (12 g), eluting with MeOH in DCM from 0-3%] tert-butyl 2-(4-amino-8-methyl-6-(p-tolyl)-9H-pyrimido[4,5-b]indol-9-yl)acetate (255a) (190 mg, 62% yield) as a white solid; 1H NMR (300 MHz, DMSO-$d_6$) δ 8.44 (d, J=1.7 Hz, 1H), 8.30 (s, 1H), 7.78 (s, 1H), 7.76 (s, 11H), 7.48 (d, J=1.7 Hz, 1H), 7.42 (s, 2H), 7.30 (s, 1H), 7.27 (s, 1H), 5.35 (s, 2H), 2.69 (s, 3H), 2.36 (s, 314), 1.44 (s, 9H); MS (ES+): 403 (M+1), (ES−): 401 (M−1).

Step-2: Preparation of 2-(4-amino-8-methyl-6-(p-tolyl)-9H-pyrimido[4,5-b]indol-9-yl)acetic acid (255b)

Compound 255b was prepared according to the procedure reported in step-2 of scheme-1, from tert-butyl 2-(4-amino-8-methyl-6-(p-tolyl)-9H-pyrimido[4,5-b]indol-9-yl)acetate (255a) (190 mg, 0.472 mmol) in DCM (5 mL) using TFA (538 mg, 4.72 mmol) and stirring at RT for 16 h. This gave after work up TFA salt of 2-(4-amino-8-methyl-6-(p-tolyl)-9H-pyrimido[4,5-b]indol-9-yl)acetic acid (255b) (250 mg): $^1$H NMR (300 MHz, DMSO-$d_6$) δ 8.77-8.51 (m, 4H), 7.77 (d, 2H), 7.64 (s, 1H), 7.32 (d, J=8.0 Hz, 214), 5.47 (s, 2H), 2.75 (s, 3H), 2.38 (s, 3H); $^{19}$F NMR (282 MHz, DMSO) δ−74.46; MS (ES+): 347 (M+1), (ES−): 345 (M−1).

Step-3: Preparation of (1R,3S,5R)-2-(2-(4-amino-8-methyl-6-(p-tolyl)-9H-pyrimido[4,5-b]indol-9-yl)acetyl)-N-(6-bromopyridin-2-yl)-5-methyl-2-azabicyclo[3.1.0]hexane-3-carboxamide (255c)

Compound 255c was prepared according to the procedure reported in step-3 of scheme-1, from TFA salt of 2-(4-amino-8-methyl-6-(p-tolyl)-9H-pyrimido[4,5-b]indol-9-yl)acetic acid (255b) (75 mg, 0.163 mmol) in DMF (5 mL) using HCl salt of (1R,3S,5R)—N-(6-bromopyridin-2-yl)-5-methyl-2-azabicyclo[3.1.0]hexane-3-carboxamide (8a) (54.2 mg, 0.163 mmol), HATU (74.3 mg, 0.195 mmol) DIPEA (105 mg, 0.814 mmol) and stirring at RT for 16 h. This gave after workup and purification by flash column chromatography [silica gel (12 g), MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-8-methyl-6-(p-tolyl)-9H-pyrimido[4,5-b]indol-9-yl)acetyl)-N-(6-bromopyridin-2-yl)-5-methyl-2-azabicyclo[3.1.0]hexane-3-carboxamide (255c) (65 mg, 64% yield) HCl salt as a white solid; $^1$H NMR (300 MHz, DMSO-$d_6$) δ 10.84 (s, 1H, $D_2O$ exchangeable), 8.72 (bs, 2H, $D_2O$ exchangeable), 8.62 (s, 1H), 8.57 (s, 1H), 8.02 (d, J=8.2 Hz, 1H), 7.81-7.65

(m, 3H), 7.61 (s, 1H), 7.38-7.21 (m, 3H), 5.87 (d, J=17.9 Hz, 1H), 5.61 (d, J=17.9 Hz, 1H), 4.40 (dd, J=9.0, 6.2 Hz, 1H), 3.74-3.67 (m, 11H), 2.74 (s, 3H), 2.49-2.43 (m, 1H), 2.37 (s, 3H), 1.99 (dd, J=13.3, 6.1 Hz, 1H), 1.31 (s, 3H), 1.03 (t, J=5.5 Hz, 1H), 0.85 (dd, J=5.6, 2.4 Hz, 1H); MS (ES+) 624/626 (M+1), (ES−) 622/624 (M−1); Analysis calculated for $C_{32}H_{30}BrN_7O_2 \cdot 1.1HCl \cdot 2.25H_2O$: C, 54.50. H, 5.09; Cl, 5.53; N, 13.90. Found: C, 54.21; H, 5.00; Cl, 5.39; N, 13.87.

Scheme 256

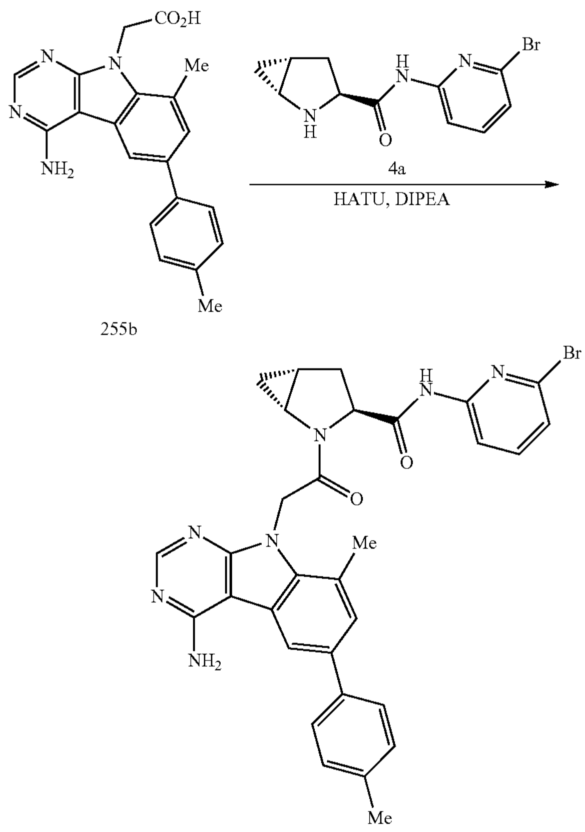

256a

Preparation of (1R,3S,5R)-2-(2-(4-amino-8-methyl-6-(p-tolyl)-9H-pyrimido[4,5-b]indol-9-yl)acetyl)-N-(6-bromopyridin-2-yl)-2-azabicyclo[3.1.0]hexane-3-carboxamide (256a)

Compound 256a was prepared according to the procedure reported in step-3 of scheme-1, from TFA salt of 2-(4-amino-8-methyl-6-(p-tolyl)-9H-pyrimido[4,5-b]indol-9-yl)acetic acid (255b) (75 mg, 0.163 mmol) in DMF (5 mL) using HCl salt of (1R,3S,5R)—N-(6-bromopyridin-2-yl)-2-azabicyclo[3.1.0]hexane-3-carboxamide (4a) (51.9 mg, 0.163 mmol), HATU (74.3 mg, 0.195 mmol), DIPEA (105 mg, 0.814 mmol) and stirring at RT for 16 h. This gave after workup and purification by flash column chromatography [silica gel (12 g), MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-8-methyl-6-(p-tolyl)-9H-pyrimido[4,5-b]indol-9-yl)acetyl)-N-(6-bromopyridin-2-yl)-2-azabicyclo[3.1.0]hexane-3-carboxamide (256a) (70 mg, 70% yield) HCl salt as a white solid; $^1H$ NMR (300 MHz, DMSO-$d_6$) δ 10.83 (s, 1H, $D_2O$ exchangeable), 8.80 (s, 2H, $D_2O$ exchangeable), 8.63 (s, 1H), 8.57 (s, 1H), 8.01 (d, J=8.1 Hz, 1H), 7.81-7.66 (m, 3H), 7.61 (s, 1H), 7.37-7.21 (m, 3H), 5.93 (d, J=18.0 Hz, 1H), 5.64 (d, J=17.9 Hz, 1H), 4.43 (dd, J=9.1, 5.7 Hz, 1H), 3.98-3.87 (m, 1H), 2.75 (s, 3H), 2.42-2.29 (m, 4H), 2.29-2.12 (m, 1H), 2.00-1.81 (m, 1H), 1.17-0.99 (m, 1H), 0.79-0.60 (m, 1H); MS (ES+): 610/612 (M+1), (ES−): 608/610 (M−1); Analysis calculated for $C_{31}H_{28}BrN_7O_2 \cdot 1.15\,HCl \cdot 1.75H_2O$: C, 54.44; H, 4.81; Cl, 5.96; N, 14.34. Found: C, 54.27; H, 4.91; Cl, 5.93; N, 14.46.

Scheme 257

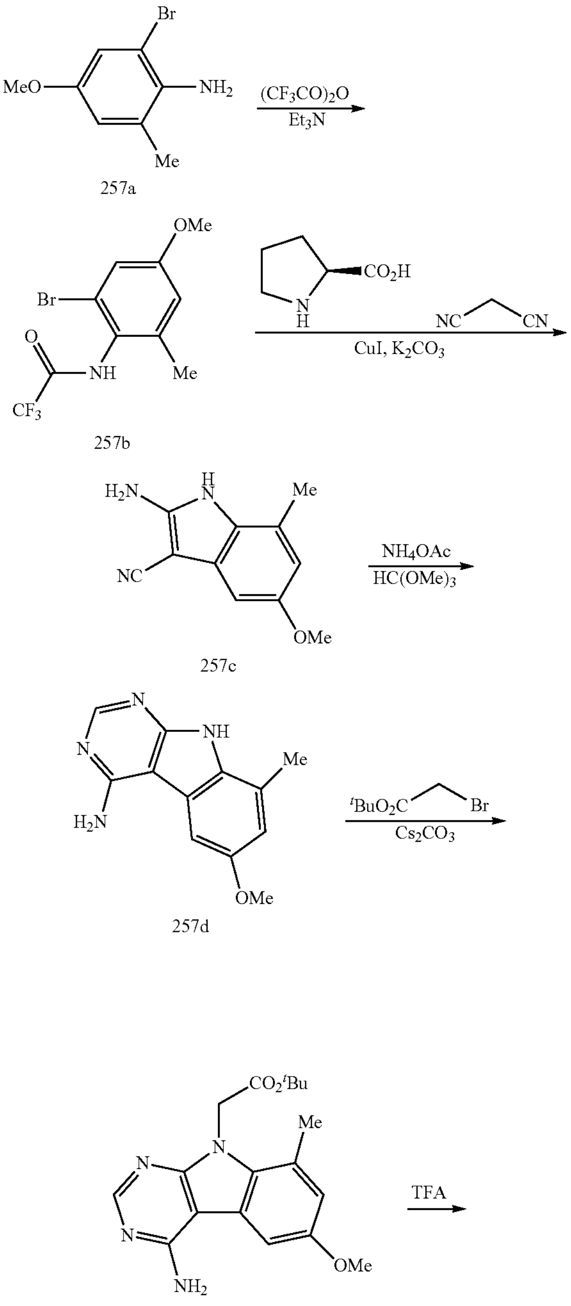

257e

-continued

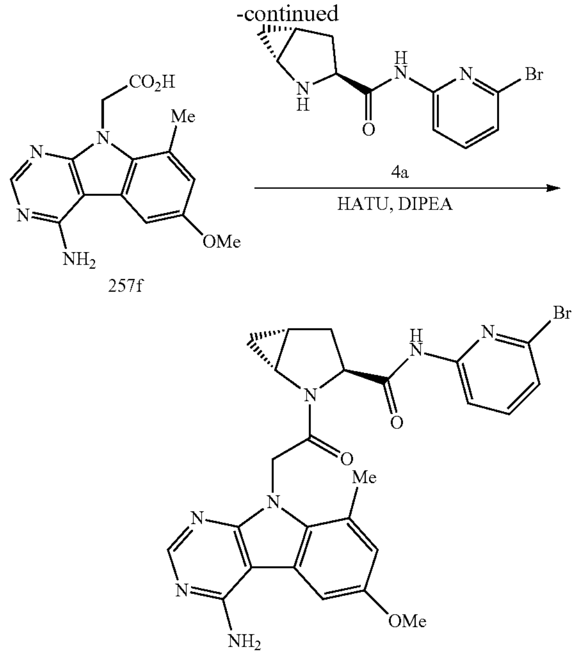

257f

257g

Preparation of (1R,3S,5R)-2-(2-(4-amino-6-methoxy-8-methyl-9H-pyrimido[4,5-b]indol-9-yl)acetyl)-N-(6-bromopyridin-2-yl)-2-azabicyclo[3.1.0]hexane-3-carboxamide (257 g)

Step-1: Preparation of N-(2-bromo-4-methoxy-6-methylphenyl)-2,2,2-trifluoroacetamide (257b)

Compound 257b was prepared according to the procedure reported in step-1 of scheme-46, from 2-bromo-4-methoxy-6-methylaniline (257a) (5.00 g, 23.14 mmol; CAS #1100394-71-5) in DCM (25 mL) using triethylamine (3.98 g, 39.3 mmol), a solution of trifluoroacetic acid anhydride (7.29 g, 34.7 mmol) in DCM (5 mL) and stirring at RT for 1 h. This gave after workup N-(2-bromo-4-methoxy-6-methylphenyl)-2,2,2-trifluoroacetamide (257b) (7.05 g, 98% yield) as a plum solid; $^1$H NMR (300 MHz, DMSO-$d_6$) δ 1.02 (s, 1H), 7.17 (d, J=2.8 Hz, 1H), 6.96 (d, 1H), 3.79 (s, 3H), 2.17 (s, 3H). $^{19}$F NMR (282 MHz, DMSO-$d_6$) δ−74.07; MS (ES−): 310/312 (M−1).

Step-2: Preparation of 2-amino-5-methoxy-7-methyl-1H-indole-3-carbonitrile (257c)

Compound 257c was prepared according to the procedure reported in step-1 of scheme-11, from N-(2-bromo-4-methoxy-6-methylphenyl)-2,2,2-trifluoroacetamide (257b) (7.05 g, 22.59 mmol) in DMSO (20 mL) using malononitrile (1.791 g, 27.1 mmol), L-proline (0.520 g, 4.52 mmol), CuI (0.430 g, 2.259 mmol), a solution of $K_2CO_3$ (6.24 g, 45.2 mmol) in water (20 mL) and heating at 60° C. for 16 h under an argon atmosphere. This gave after workup and purification [$SiO_2$ gel (40 g), MeOH in DCM from 0-6%] 2-amino-5-methoxy-7-methyl-1H-indole-3-carbonitrile (257c) (2.72 g, 60% yield) as a pale-brown solid; $^1$H NMR (300 MHz, DMSO-$d_6$) δ 10.57 (s, 1H), 6.51 (d, J=2.4 Hz, 1H), 6.43 (s, 2H), 6.35 (dd, J=2.4, 0.9 Hz, 1H), 3.71 (s, 3H), 2.29 (s, 3H); MS (ES+): 202 (M+1), (ES−): 200 (M−1).

Step-3: Preparation of 6-methoxy-8-methyl-9H-pyrimido[4,5-b]indol-4-amine (257d)

Compound 257d was prepared according to the procedure reported in step-2 of scheme-29, from 2-amino-5-methoxy-7-methyl-1H-indole-3-carbonitrile (257c) (2.72 g, 13.52 mmol) using $NH_4OAc$ (3.13 g, 40.6 mmol), HC(OMe); (7.17 g, 67.6 mmol) and heating at 90° C. for 16 h. This gave after work up 6-methoxy-8-methyl-9H-pyrimido[4,5-b]indol-4-amine (257d) (2.97 g, 96% yield) as a pale-yellow solid; 1H NMR (300 MHz, DMSO-$d_6$) δ 11.64 (s, 1H), 8.21 (s, 1H), 7.67 (d, J=2.4 Hz, 1H), 7.13 (s, 2H), 6.79 (d, J=2.3 Hz, 1H), 3.83 (s, 3H), 2.48 (s, 3H); MS (ES+): 229 (M+1), (ES−): 227 (M−1).

Step-4: Preparation of tert-butyl 2-(4-amino-6-methoxy-8-methyl-9H-pyrimido[4,5-b]indol-9-yl)acetate (257e)

Compound 257e was prepared according to the procedure reported in step-1 of scheme-1, from 6-methoxy-8-methyl-9H-pyrimido[4,5-b]indol-4-amine (257d) (2.00 g, 8.76 mmol) in DMF (15 mL) using tert-butyl 2-bromoacetate (1.880 g, 9.64 mmol). $Cs_2CO_3$ (5.71 g, 17.52 mmol) and stirring at RT for 16 h. This gave after work up and purification using flash column chromatography [$SiO_2$ gel (40 g), methanol in DCM from 0-4%] tert-butyl 2-(4-amino-6-methoxy-8-methyl-9H-pyrimido[4,5-b]indol-9-yl)acetate (257e) (1.37 g, 46% yield) as a tan solid; $^1$H NMR (300 MHz, DMSO-$d_6$) δ 8.25 (s, 1H), 7.71 (d, J=2.5 Hz, 1H), 7.30 (s, 2H), 6.79 (d, J=2.4 Hz, 1H), 5.28 (s, 2H), 3.85 (s, 3H), 2.58 (s, 3H), 1.42 (s, 9H).

Step-5: Preparation of 2-(4-amino-6-methoxy-8-methyl-9H-pyrimido[4,5-b]indol-9-yl)acetic acid (257f)

Compound 257f was prepared according to the procedure reported in step-2 of scheme-1, from tert-butyl 2-(4-amino-6-methoxy-8-methyl-9H-pyrimido[4,5-b]indol-9-yl)acetate (257e) (1.00 g, 2.92 mmol) in DCM (10 mL) using TFA (3.33 g, 29.2 mmol) and stirring at RT for 16 h. This gave after work up TFA salt of 2-(4-amino-6-methoxy-8-methyl-9H-pyrimido[4,5-b]indol-9-yl)acetic acid (257f) (1.51 g); $^1$H NMR (300 MHz, DMSO-$d_6$) δ 8.82 (s, 2H), 8.61 (s, 1H), 7.87 (d, J=2.4 Hz, 1H), 6.97 (d, J=2.4 Hz, 1H), 5.42 (s, 2H), 3.87 (s, 3H), 2.65 (s, 3H); $^{19}$F NMR (282 MHz, DMSO-$d_6$) δ−74.55; MS (ES+): 287 (M+1), (ES−): 285 (M−1).

Step-6: Preparation of (1R,3S,5R)-2-(2-(4-amino-6-methoxy-8-methyl-9H-pyrimido[4,5-b]indol-9-yl)acetyl)-N-(6-bromopyridin-2-yl)-2-azabicyclo[3.1.0]hexane-3-carboxamide (257 g)

Compound 257g was prepared according to the procedure reported in step-3 of scheme-1, from TFA salt of 2-(4-amino-6-methoxy-8-methyl-9H-pyrimido[4,5-b]indol-9-yl)acetic acid (257f) (125 mg, 0.312 mmol) in DMF (5 mL) using HCl salt of (1R,3S,5R)—N-(6-bromopyridin-2-yl)-2-azabicyclo[3.1.0]hexane-3-carboxamide (4a) (99 mg, 0.312 mmol), HATU (142 mg, 0.375 mmol), DIPEA (202 mg, 1.561 mmol) and stirring at RT for 16 h. This gave after workup and purification by flash column chromatography [silica gel (12 g), MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-methoxy-8- methyl-9H-pyrimido[4,5-b]indol-9-yl)acetyl)-N-(6-bromopyridin-2-yl)-2-azabicyclo[3.1.0]hexane-3-carboxamide (257 g) (116 mg, 68% yield) HCl salt as a white solid; 1H NMR (300 MHz, DMSO-$d_6$) δ 10.82 (s, 1H, $D_2O$ exchangeable), 8.69 (bs, 2H, $D_2O$ exchangeable), 8.58 (s, 1H), 8.00 (d, J=8.2 Hz, 1H), 7.85 (d, J=2.4 Hz, 1H), 7.71 (t, J=8.0 Hz, 1H), 7.31 (d, J=7.7 Hz, 1H), 6.94 (d, J=2.4 Hz, 1H), 5.88 (d, J=17.9 Hz, 1H), 5.60 (d, J=17.9 Hz, 1H), 4.42 (dd, J=9.1, 5.7 Hz, 1H), 3.96-3.87 (m, 1H), 3.85 (s, 3H), 2.66 (s, 3H), 2.42-2.28 (m, 1H), 2.25-2.12 (m, 1H), 2.00-1.83 (m, 1H), 1.13-0.99 (m, 1H), 0.71-0.62 (m, 1H); MS (ES+): 550/552 (M+1), (ES−): 548/550 (M−1); Analysis calculated for $C_{25}H_{24}BrN_7O_3 \cdot HCl \cdot 2.5H_2O$: C, 47.52; H, 4.79; Cl, 5.61; N, 15.52. Found: C, 47.55; H, 4.64; Cl, 5.61; N, 15.28.

Scheme 258

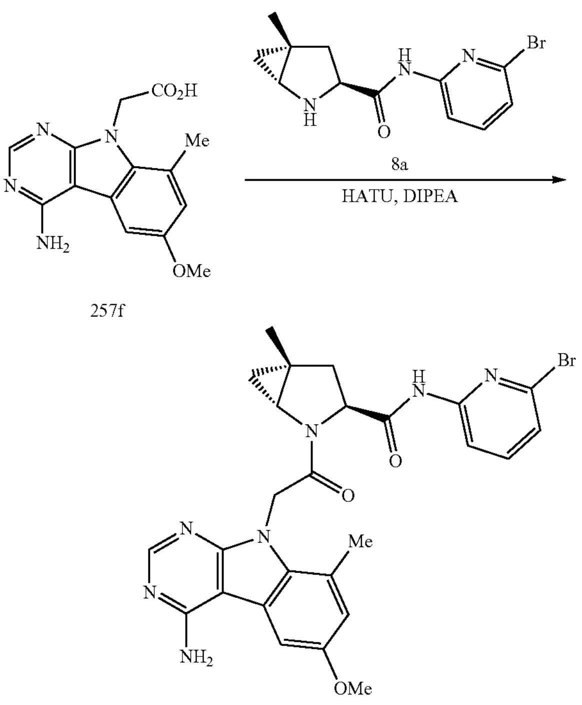

257f

258a

Preparation of (1R,3S,5R)-2-(2-(4-amino-6-methoxy-8-methyl-9H-pyrimido[4,5-b]indol-9-yl)acetyl)-N-(6-bromopyridin-2-yl)-5-methyl-2-azabicyclo[3.1.0]hexane-3-carboxamide (258a)

Compound 258a was prepared according to the procedure reported in step-3 of scheme-1, from TFA salt of 2-(4-amino-6-methoxy-8-methyl-9H-pyrimido[4,5-b]indol-9-yl)acetic acid (257f) (125 mg, 0.312 mmol) in DMF (5 mL) using HCl salt of (1R,3S,5R)—N-(6-bromopyridin-2-yl)-5-methyl-2-azabicyclo[3.1.0]hexane-3-carboxamide (8a) (104 mg, 0.312 mmol), HATU (142 mg, 0.375 mmol), DIPEA (202 mg, 1.561 mmol) and stirring at RT for 16 h. This gave after workup and purification by flash column chromatography [silica gel (12 g), MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-methoxy-8-methyl-9H-pyrimido[4,5-b]indol-9-yl)acetyl)-N-(6-bromopyridin-2-yl)-5-methyl-2-azabicyclo[3.1.0]hexane-3-carboxamide (258a) (131 mg, 74% yield) HCl salt as a white solid; $^1$H NMR (300 MHz, DMSO-$d_6$) δ 10.83 (s, 1H, $D_2O$ exchangeable), 8.67 (bs, 2H, $D_2O$ exchangeable), 8.58 (s, 1H), 8.02 (d, J=8.1 Hz, 1H), 7.85 (d, J=2.4 Hz, 1H), 7.71 (t, J=8.0 Hz, 1H), 7.32 (d, J=7.7 Hz, 1H), 6.94 (d, J=2.3 Hz, 1H), 5.84 (d, J=18.0 Hz, 1H), 5.57 (d, J=17.9 Hz, 1H), 4.38 (dd, J=9.0, 6.2 Hz, 1H), 3.86 (s, 3H), 3.72-3.66 (m, 1H), 2.65 (s, 3H), 2.49-2.39 (m, 1H), 1.98 (m, 1H), 1.31 (s, 3H), 1.01 (m, 1H), 0.83 (m, 1H); MS (ES+): 564/566 (M+1), (ES−): 562/564 (M−1); Analysis calculated for $C_{26}H_{26}BrN_7O_3 \cdot 1.2HCl \cdot 2.5H_2O$: C, 47.81; H, 4.97; Cl, 6.51; N, 15.01. Found: C, 47.85; H, 4.89; Cl, 6.51; N, 14.94.

Scheme 259

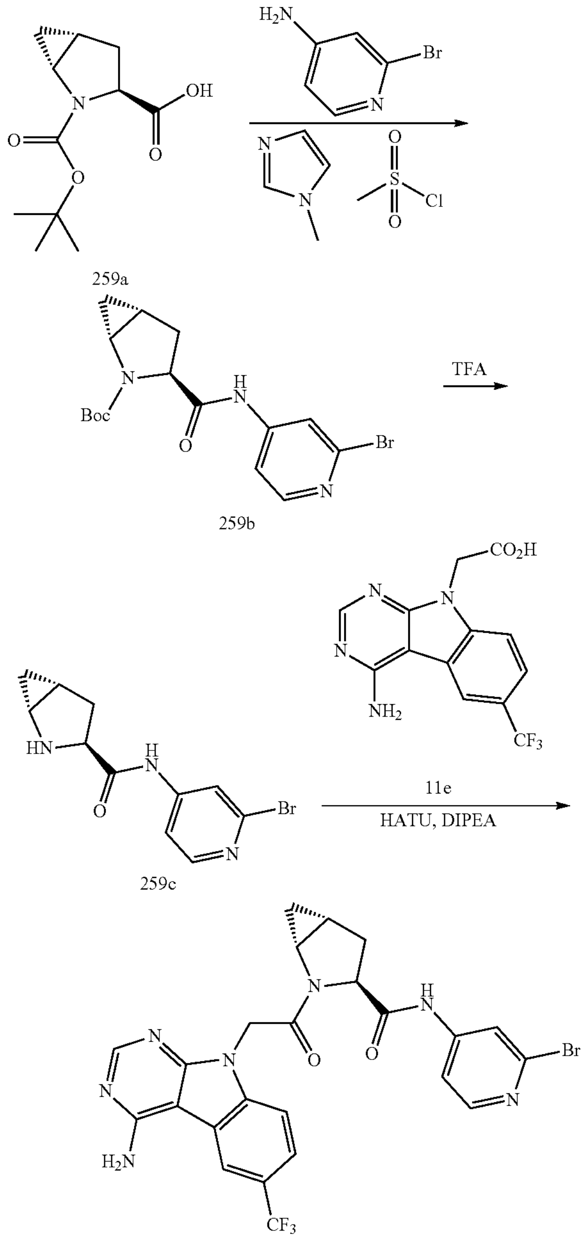

259a

259b

259c

259d

Preparation of (1R,3S,5R)-2-(2-(4-amino-6-(trifluoromethyl)-9H-pyrimido[4,5-b]indol-9-yl)acetyl)-N-(2-bromopyridin-4-yl)-2-azabicyclo[3.1.0]hexane-3-carboxamide (259d)

Step-1: Preparation of (1R,3S,5R)-tert-butyl 3-((2-bromopyridin-4-yl)carbamoyl)-2-azabicyclo[3.1.0]hexane-2-carboxylate (259b)

Compound 259b was prepared according to the procedure reported in step-1 of scheme-53, from (1R,3S,5R)-2-(tert-butoxycarbonyl)-2-azabicyclo[3.1.0]hexane-3-carboxylic acid (259a) (0.5 g, 2.200 mmol; CAS #197142-34-0) in DCM (15 mL) using 1-methyl-1H-imidazole (0.438 mL, 5.50 mmol), methanesulfonyl chloride (0.204 mL, 2.64 mmol), 2-bromopyridin-4-amine (0.381 g, 2.200 mmol; CAS #7598-35-8) and stirring at RT for 18 h. This gave after workup and purification by flash column chromatography [silica gel (24 g), EtOAc in hexane from 0-50%] (1R,3S,5R)-tert-butyl 3-((2-bromopyridin-4-yl)carbamoyl)-2-azabicyclo[3.1.0]hexane-2-carboxylate (259b) (0.798 g, 95% yield) as a colorless gum; MS (ES+): 382.1 (M+1).

Step-2: Preparation of (1R,3S,5R)—N-(2-bromopyridin-4-yl)-2-azabicyclo[3.1.0]hexane-3-carboxamide (259c)

Compound 259c was prepared according to the procedure reported in step-2 of scheme-1, from (1R,3S,5R)-tert-butyl 3-((2-bromopyridin-4-yl)carbamoyl)-2-azabicyclo[3.1.0]hexane-2-carboxylate (259b) (0.78 g, 2.041 mmol) in DCM (11 mL) using TFA (1.100 mL, 14.28 mmol) and stirring overnight at RT. This gave after work up and purification using reverse phase column chromatography [C18 column (50 g), eluting with ACN in water (containing 0.1% HCl) from 0-100%] HCl salt of (1R,3S,5R)—N-(2-bromopyridin-4-yl)-2-azabicyclo[3.1.0]hexane-3-carboxamide (259c) (450 mg, 69% yield); $^1$H NMR (300 MHz, DMSO-$d_6$) δ 11.53 (s, 1H), 10.11 (s, 1H), 9.28 (s, 1H), 8.32 (d, J=5.5 Hz, 1H), 7.92 (d, J=1.8 Hz, 1H), 7.60 (dd, J=5.6, 1.9 Hz, 1H), 4.24 (t, J=9.4 Hz, 1H), 3.45-3.29 (m, 1H), 2.65 (dd, J=12.8, 7.7 Hz, 1H), 2.11 (td, J=12.0, 4.8 Hz, 1H), 1.84 (dq, J=9.9, 5.1 Hz, 1H), 0.91-0.79 (m, 2H); MS (ES+): 282.0 (M+1).

Step-3: Preparation of (1R,3S,5R)-2-(2-(4-amino-6-(trifluoromethyl)-9H-pyrimido[4,5-b]indol-9-yl)acetyl)-N-(2-bromopyridin-4-yl)-2-azabicyclo[3.1.0]hexane-3-carboxamide (259d)

Compound 259d was prepared according to the procedure reported in step-3 of scheme-1, from HCl salt of (1R,3S,5R)—N-(2-bromopyridin-4-yl)-2-azabicyclo[3.1.0]hexane-3-carboxamide (259c) (55.1 mg, 0.173 mmol) in DMF (1.5 mL) using HCl salt of 2-(4-amino-6-(trifluoromethyl)-9H-pyrimido[4,5-b]indol-9-yl)acetic acid (11e) (60 mg, 0.173 mmol), HATU (99 mg, 0.260 mmol), DIPEA (0.151 mL, 0.865 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-(trifluoromethyl)-9H-pyrimido[4,5-b]indol-9-yl)acetyl)-N-(2-bromopyridin-4-yl)-2-azabicyclo[3.1.0]hexane-3-carboxamide (259d) (54 mg, 54% yield) HCl salt as a white solid; $^1$H NMR (300 MHz, DMSO-$d_6$) δ 10.59 (s, 1H, $D_2O$ exchangeable), 8.99 (s, 1H), 8.79-8.53 (m, 3H, 2H $D_2O$ exchangeable), 8.20 (d, J=5.6 Hz, 1H), 7.96-7.80 (m, 3H), 7.47 (dd, J=5.6, 1.9 Hz, 1H), 5.84 (d, J=17.4 Hz, 1H), 5.50 (d, J=17.3 Hz, 1H), 4.28 (dd, J=9.0, 6.0 Hz, 1H), 4.02-3.89 (m, 1H), 2.38 (dd, J=13.4, 9.2 Hz, 1H), 2.29-2.15 (m, 1H), 2.00-1.86 (m, 1H), 1.16-1.00 (m, 1H), 0.92-0.64 (m, 1H). $^{19}$F NMR (282 MHz, DMSO-$d_6$) δ−58.55. MS (ES+): 574.1/576.1 (M+1); (ES−): 572.1/574.1 (M−1): Analysis calculated for $C_{24}H_{19}BrF_3N_7O_2$ $2.5H_2O{\cdot}1.25HCl$: C, 43.35; H, 3.83; Cl, 6.66; N, 14.74. Found: C, 43.46; H, 3.57; Cl, 6.83. N, 14.67.

Scheme 260

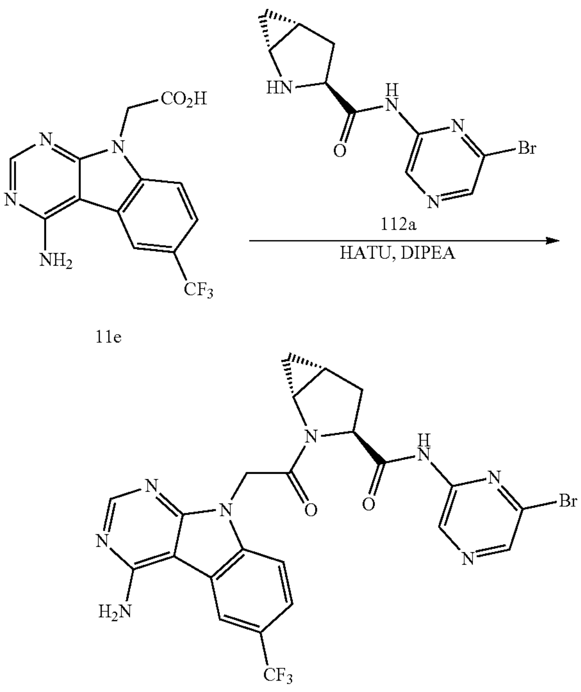

11e

112a

260a

Preparation of (1R,3S,5R)-2-(2-(4-amino-6-(trifluoromethyl)-9H-pyrimido[4,5-b]indol-9-yl)acetyl)-N-(6-bromopyrazin-2-yl)-2-azabicyclo[3.1.0]hexane-3-carboxamide (260a)

Compound 260a was prepared according to the procedure reported in step-3 of scheme-1, from HCl salt of 2-(4-amino-6-(trifluoromethyl)-9H-pyrimido[4,5-b]indol-9-yl)acetic acid (11e) (60 mg, 0.173 mmol) in DMF (1.5 mL) using HCl salt of (1R,3S,5R)—N-(6-bromopyrazin-2-yl)-2-azabicyclo[3.1.0]hexane-3-carboxamide (112a) (55.3 mg, 0.173 mmol), HATU (99 mg, 0.260 mmol), DIPEA (0.151 mL, 0.865 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%](1R,3S,5R)-2-(2-(4-amino-6-(trifluoromethyl)-9H-pyrimido[4,5-b]indol-9-yl)acetyl)-N-(6-bromopyrazin-2-yl)-2-azabicyclo[3.1.0]hexane-3-carboxamide (260a) (37 mg, 37% yield) HCl salt as a white solid: 1H NMR (300 MHz, DMSO-$d_6$) δ 11.14 (s, 1H, $D_2O$ exchangeable), 9.24 (s, 1H), 8.98 (s, 1H), 8.68-8.56 (m, 3H, 2H $D_2O$ exchangeable), 8.54 (s, 1H), 7.94-7.82 (m, 2H), 5.83 (d, J=17.4 Hz, 1H), 5.48 (d, J=17.3 Hz, 1H), 4.44 (dd, J=9.0, 5.6 Hz, 1H), 3.93 (td, J=6.5, 5.7, 2.3 Hz, 1H), 2.42-2.20 (m, 2H), 2.00-1.86 (m, 1H), 1.12-1.01 (m, 1H), 0.90-0.74 (m, 1H). $^{19}F$ NMR (282 MHz, DMSO) δ−58.53. MS (ES+): 575.1/577.1 (M+1); (ES−): 573.1/575.1 (M−1); Analysis calculated for $C_{23}H_{18}BrF_3N_8O_2$ $2.5H_2O \cdot 1.15HCl$: C, 41.71; H, 3.68; Cl, 6.16; N, 16.92. Found: C, 41.73; H, 3.45; Cl, 5.90; N, 16.76.

Scheme 261

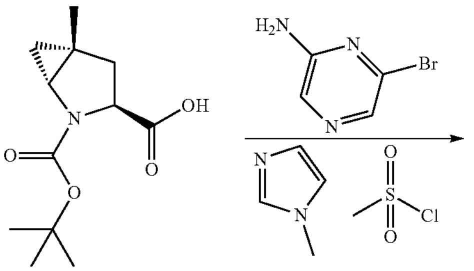

261a

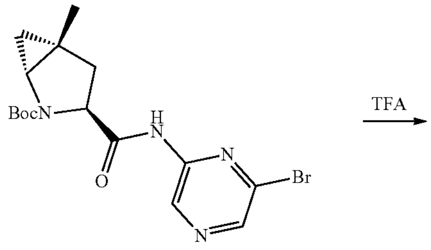

261b

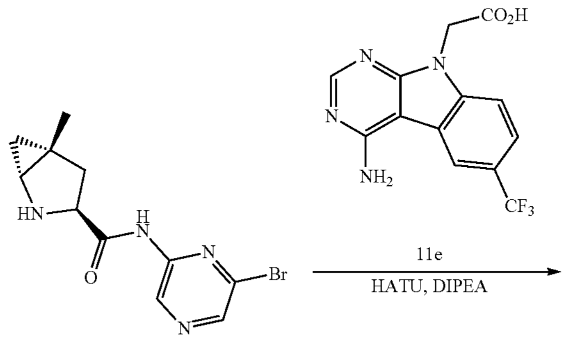

261c

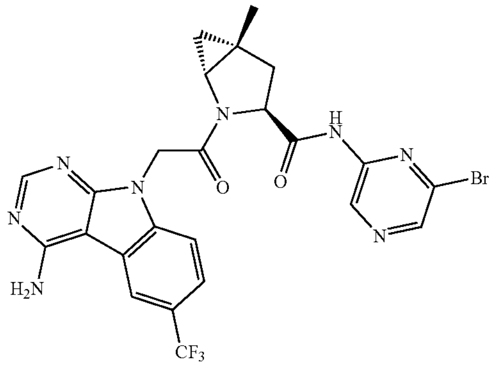

261d

Preparation of (1R,3S,5R)-2-(2-(4-amino-6-(trifluoromethyl)-9H-pyrimido[4,5-b]indol-9-yl)acetyl)-N-(6-bromopyrazin-2-yl)-5-methyl-2-azabicyclo[3.1.0]hexane-3-carboxamide (261d)

Step-1: Preparation of (1R,3S,5R)-tert-butyl 3-((6-bromopyrazin-2-yl)carbamoyl)-5-methyl-2-azabicyclo[3.1.0]hexane-2-carboxylate (261b)

Compound 261b was prepared according to the procedure reported in step-1 of scheme-53, from (1R,3S,5R)-2-(tert-butoxycarbonyl)-5-methyl-2-azabicyclo[3.1.0]hexane-3-carboxylic acid (261a) (0.53 g, 2.197 mmol; CAS #1306734-44-0) in DCM (15 mL) using 1-methyl-1H-imidazole (0.438 mL, 5.49 mmol), methanesulfonyl chloride (0.204 mL, 2.64 mmol) and 6-bromopyrazin-2-amine (0.382 g, 2.197 mmol; CAS #54237-53-5) and stirring at RT for 18 h. This gave after workup and purification using flash column chromatography [silica gel (24 g), eluting with EtOAc in hexane from 0-50%] (1R,3S,5R)-tert-butyl 3-((6-bromopyrazin-2-yl)carbamoyl)-5-methyl-2-azabicyclo[3.1.0]hexane-2-carboxylate (261b) (0.418 g, 48% yield) as a colorless gum; MS (ES+): 397.1/399.1 (M+1).

Step-2: Preparation of (1R,3S,5R)—N-(6-bromopyrazin-2-yl)-5-methyl-2-azabicyclo[3.1.0]hexane-3-carboxamide (261c)

Compound 261c was prepared according to the procedure reported in step-2 of scheme-1, from (1R,3S,5R)-tert-butyl 3-((6-bromopyrazin-2-yl)carbamoyl)-5-methyl-2-azabicyclo[3.1.0]hexane-2-carboxylate (261b) (0.41 g, 1.032 mmol) in DCM (6 mL) using TFA (0.557 mL, 7.22 mmol) and stirring overnight at RT. This gave after work up and purification using reverse phase column chromatography [C18 column (50 g), eluting with ACN in water (containing 0.1% HCl) from 0-100%] HCl salt of (1R,3S,5R)—N-(6-bromopyrazin-2-yl)-5-methyl-2-azabicyclo[3.1.0]hexane-3-carboxamide (261c) (232 mg, 67% yield); $^1H$ NMR (300 MHz, DMSO-$d_6$) δ 11.70 (s, 1H), 9.67 (s, 2H), 9.27 (s, 1H), 8.67 (s, 1H), 4.23 (dd, J=11.0, 7.7 Hz, 1H), 3.10 (dd, J=6.9, 2.4 Hz, 1H), 2.65 (dd, J=12.7, 7.7 Hz, 1H), 2.00 (t, J=11.8 Hz, 1H), 1.25 (s, 3H), 1.02 (dd, J=7.2, 2.4 Hz, 1H), 0.78 (t, J=7.0 Hz, 1H); MS (ES+): 297.0 (M+1).

Step-3: Preparation of (1R,3S,5R)-2-(2-(4-amino-6-(trifluoromethyl)-9H-pyrimido[4,5-b]indol-9-yl)acetyl)-N-(6-bromopyrazin-2-yl)-5-methyl-2-azabicyclo[3.1.0]hexane-3-carboxamide (261d)

Compound 261d was prepared according to the procedure reported in step-3 of scheme-1, from HCl salt of (1R,3S,5R)—N-(6-bromopyrazin-2-yl)-5-methyl-2-azabicyclo[3.1.0]hexane-3-carboxamide (261c) (58 mg, 0.173 mmol) in DMF (1.5 mL) using HCl salt of 2-(4-amino-6-(trifluoromethyl)-9H-pyrimido[4,5-b]indol-9-yl)acetic acid (11e) (60 mg, 0.173 mmol), HATU (99 mg, 0.260 mmol), DIPEA (0.151 mL, 0.865 mmol) and stirring at RT for 16 h. This gave after workup and purification by flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-(trifluoromethyl)-9H-pyrimido[4,5-b]indol-9-yl)acetyl)-N-(6-bromopyrazin-2-yl)-5-methyl-2-azabicyclo[3.1.0]hexane-3-carboxamide (261d) (62 mg, 61% yield) HCl salt as a white solid; 1H NMR (300 MHz, DMSO-$d_6$) δ 11.14 (s, 1H, $D_2O$ exchangeable), 9.25 (s, 1H), 8.95 (s, 1H), 8.56 (s, 1H), 8.54 (s, 1H), 8.40 (s, 2H, $D_2O$ exchangeable), 7.88-7.80 (m, 2H), 5.76 (d, J=17.4 Hz, 1H), 5.42 (d, J=17.3 Hz, 1H), 4.39 (dd, J=9.1, 6.0 Hz, 1H), 3.71 (dd, J=5.5, 2.5 Hz, 1H), 2.48-2.42 (m, 1H), 2.03 (dd. J=13.3, 6.0 Hz, 1H), 1.32 (s, 3H), 1.05-0.91 (m, 2H). $^{19}F$ NMR (282 MHz, DMSO-$d_6$) δ-58.48; MS (ES+): 589.1/591.1 (M+1); (ES−): 587.1/589.1 (M−1); Analysis calculated for $C_{24}H_{20}BrF_3N_8O_2$ 1.75$H_2O$·1.1HCl: C, 43.61; H, 3.75; Cl, 5.90; N, 16.95. Found: C, 43.54; H, 3.74; Cl, 5.59; N, 16.70.

Scheme 262

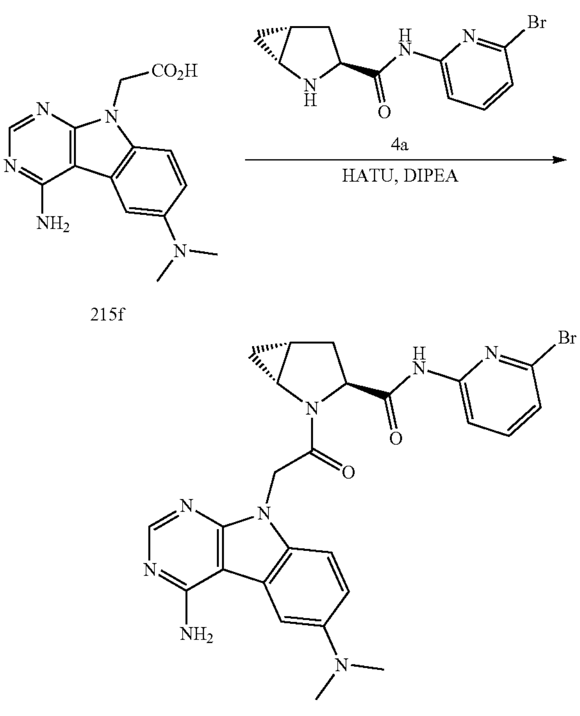

215f

4a

262a

Preparation of (1R,3S,5R)-2-(2-(4-amino-6-(dimethylamino)-9H-pyrimido[4,5-b]indol-9-yl)acetyl)-N-(6-bromopyridin-2-yl)-2-azabicyclo[3.1.0]hexane-3-carboxamide (262a)

Compound 262a was prepared according to the procedure reported in step-3 of scheme-1, from TFA salt of 2-(4-amino-6-(dimethylamino)-9H-pyrimido[4,5-b]indol-9-yl)acetic acid (215f) (75 mg, 0.188 mmol) in DMF (5 mL) using HCl salt of (1R,3S,5R)—N-(6-bromopyridin-2-yl)-2-azabicyclo[3.1.0]hexane-3-carboxamide (4a) (59.8 mg, 0.188 mmol), HATU (86 mg, 0.225 mmol), DIPEA (121 mg, 0.939 mmol) and stirring at RT for 16 h. This gave after workup and purification by flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-(dimethylamino)-9H-pyrimido[4,5-b]indol-9-yl)acetyl)-N-(6-bromopyridin-2-yl)-2-azabicyclo[3.1.0]hexane-3-carboxamide (262a) (13 mg, 13% yield) as a pale-yellow solid; $^1H$ NMR (300 MHz, DMSO-$d_6$) δ 10.77 (s, 1H, $D_2O$ exchangeable), 9.08-8.52 (m, 4H, 2H $D_2O$ exchangeable), 8.01 (d, J=8.2 Hz, 1H), 7.88-7.55 (m, 3H), 7.32 (d, J=7.7 Hz, 1H), 5.77 (d, J=17.4 Hz, 1H), 5.42 (d, J=17.2 Hz, 1H), 4.41 (dd, J=9.1, 5.6 Hz, 1H), 3.91 (td, J=6.4, 5.6, 2.4 Hz, 1H), 3.18 (s, 6H), 2.41-2.28 (m, 1H), 2.27-2.14 (m, 1H), 1.99-1.84 (m, 1H), 1.13-1.02 (m, 1H), 0.84-0.73 (m, 1H); MS (ES+): 549/551 (M+1); (ES−): 547/549 (M−1).

Scheme 263

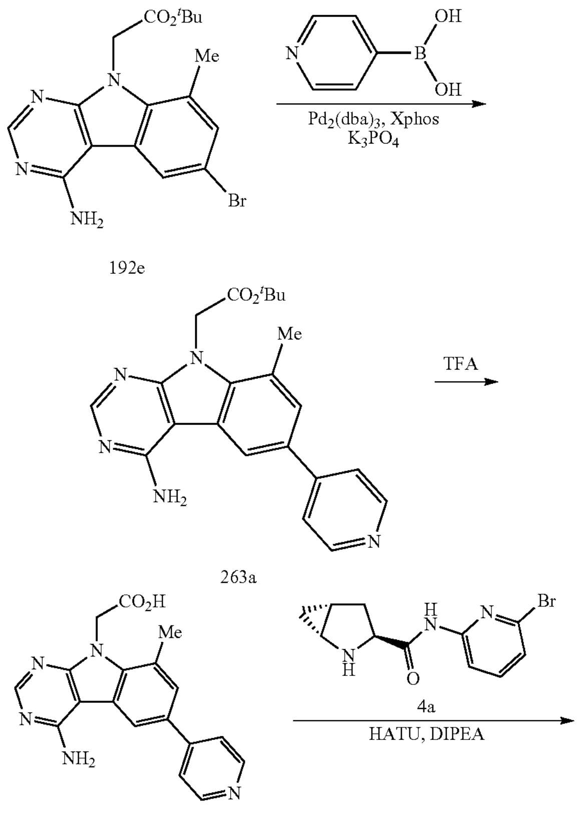

192e

263a

263b

4a

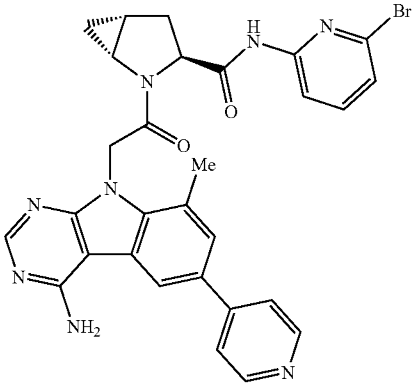

263c

Preparation of (1R,3S,5R)-2-(2-(4-amino-8-methyl-6-(pyridin-4-yl)-9H-pyrimido[4,5-b]indol-9-yl)acetyl)-N-(6-bromopyridin-2-yl)-2-azabicyclo[3.1.0]hexane-3-carboxamide (263c)

Step-1: Preparation of tert-butyl 2-(4-amino-8-methyl-6-(pyridin-4-yl)-9H-pyrimido[4,5-b]indol-9-yl)acetate (263a)

To a suspension of tert-butyl 2-(4-amino-6-bromo-8-methyl-9H-pyrimido[4,5-b]indol-9-yl)acetate (192e) (300 mg, 0.767 mmol), pyridin-4-ylboronic acid (141 mg, 1.150 mmol), $Pd_2(dba)_3$ (70.2 mg, 0.077 mmol), XPhos (73.1 mg, 0.153 mmol), and 1.27 M aqueous $K_3PO_4$ (1.207 mL, 1.533 mmol) in n-BuOH (4 mL) in a scintillation vial. The vial was flushed with nitrogen and then heated at 100° C. under nitrogen for 16 h. The resulting cooled deep red mixture was concentrated to dry ness and the residue was suspended in $H_2O$ (30 mL) and EtOAc (30 mL), stirred for 30 min, and then filtered. The filtered cake was washed with $H_2O$ (20 mL) and EtOAc (20 mL) to provide 263a as a pale-yellow solid. The filtrate separated from aqueous layer and the aqueous layer was extracted with EtOAc (25 mL). The combined organic extract was washed with $H_2O$ (25 mL), brine (25 mL), dried, filtered and concentrated, and residue obtained was purified by flash column chromatography (Silica gel, 12 g, 0-7% MeOH in DCM) to provide additional 263a as a white solid. Total yield: tert-butyl 2-(4-amino-8-methyl-6-(pyridin-4-yl)-9H-pyrimido[4,5-b]indol-9-yl)acetate (263a) (250 mg, 84% yield). $^1H$ NMR (300 MHz, DMSO-$d_6$) δ 8.76-8.55 (m, 3H), 8.33 (s, 1H), 8.01-7.88 (m, 2H), 7.69 (s, 1H), 7.52 (s, 2H), 5.38 (s, 2H), 2.72 (s, 3H), 1.44 (s, 9H). LC-MS: t=1.73 min MS (ES+) 390 (M+1), (ES−) 388 (M−1).

Step-2: Preparation of 2-(4-amino-8-methyl-6-(pyridin-4-yl)-9H-pyrimido[4,5-b]indol-9-yl)acetic acid (263b)

Compound 263b was prepared according to the procedure reported in step-2 of scheme-1, from tert-butyl 2-(4-amino-8-methyl-6-(pyridin-4-yl)-9H-pyrimido[4,5-b]indol-9-yl)acetate (263a) (250 mg, 0.642 mmol) in DCM (5 mL) using TFA (732 mg, 6.42 mmol) and stirring at RT for 16 h. This gave after work up TFA salt of 2-(4-amino-8-methyl-6-(pyridin-4-yl)-9H-pyrimido[4,5-b]indol-9-yl)acetic acid (263b) (394 mg); $^1H$ NMR (300 MHz, DMSO-$d_6$) δ 8.94 (d, J=6.1 Hz, 2H), 8.89 (s, 1H), 8.60-8.44 (m, 3H), 8.19 (s, 2H), 7.99 (s, 1H), 5.46 (s, 2H), 2.79 (s, 3H). $^{19}F$ NMR (282 MHz, DMSO-$d_6$) δ−74.43:

Step-3: Preparation of (1R,3S,5R)-2-(2-(4-amino-8-methyl-6-(pyridin-4-yl)-9H-pyrimido[4,5-b]indol-9-yl)acetyl)-N-(6-bromopyridin-2-yl)-2-azabicyclo[3.1.0]hexane-3-carboxamide (263c)

Compound 263c was prepared according to the procedure reported in step-3 of scheme-1, from TFA salt of 2-(4-amino-8-methyl-6-(pyridin-4-yl)-9H-pyrimido[4,5-b]indol-9-yl)acetic acid (263b) (56 mg, 0.125 mmol) in DMF (5 mL) using HCl salt of (1R,3S,5R)—N-(6-bromopyridin-2-yl)-2-azabicyclo[3.1.0]hexane-3-carboxamide (4a) (39.9 mg, 0.125 mmol), HATU (57.1 mg, 0.150 mmol), DIPEA (81 mg, 0.626 mmol) and stirring at RT for 16 h. This gave after workup and purification by flash column chromatography [silica gel (12 g), eluting with MeOH in DCM from 0-8%] followed by purification using reverse phase column chromatography [C18 column (100 g), eluting with ACN in water (containing 0.1% HCl) from 0-100%] (1R,3S,5R)-2-(2-(4-amino-8-methyl-6-(pyridin-4-yl)-9H-pyrimido[4,5-b]indol-9-yl)acetyl)-N-(6-bromopyridin-2-yl)-2-azabicyclo[3.1.0]hexane-3-carboxamide (263c) (32 mg, 43% yield) HCl salt as a pale-yellow solid; $^1H$ NMR (300 MHz, DMSO-$d_6$) δ 10.84 (s, 1H, $D_2O$ exchangeable), 9.02 (s, 1H), 8.96 (d, J=6.5 Hz, 2H), 8.83 (s, 2H, $D_2O$ exchangeable), 8.68-8.57 (m, 3H), 8.09-7.92 (m, 2H), 7.70 (t, J=8.0 Hz, 1H), 7.30 (d, J=7.7 Hz, 1H), 5.97 (d, J=18.0 Hz, 1H), 5.67 (d, J=17.9 Hz, 1H), 4.43 (dd, J=9.0, 5.7 Hz, 1H), 3.99-3.90 (m, 1H), 2.81 (s, 3H), 2.42-2.29 (m, 1H), 2.28-2.14 (m, 1H), 2.02-1.85 (m, 1H), 1.17-1.03 (m, 1H), 0.79-0.59 (m, 1H); MS (ES+): 597/599 (M+1), (ES−): 595/597 (M−1): Analysis calculated for $C_{29}H_{25}BrN_8O_2 \cdot 1.9HCl \cdot 4.25H_2O$: C, 46.86; H, 4.80; Cl, 9.06; N, 15.08. Found: C, 46.75; H, 4.43; Cl, 9.04; N, 14.85.

Scheme 264

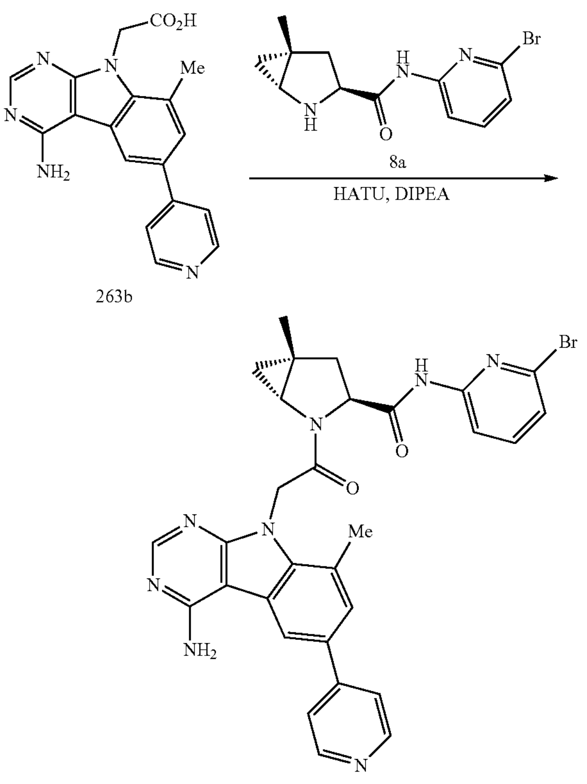

263b

8a

264a

Preparation of (1R,3S,5R)-2-(2-(4-amino-8-methyl-6-(pyridin-4-yl)-9H-pyrimido[4,5-b]indol-9-yl)acetyl)-N-(6-bromopyridin-2-yl)-5-methyl-2-azabicyclo[3.1.0]hexane-3-carboxamide (264a)

Compound 264a was prepared according to the procedure reported in step-3 of scheme-1, from TFA salt of 2-(4-amino-8-methyl-6-(pyridin-4-yl)-9H-pyrimido[4,5-b]indol-9-yl)acetic acid (263b) (75 mg, 0.168 mmol) in DMF (5 mL) using HCl salt of (1R,3S,5R)—N-(6-bromopyridin-2-yl)-5-methyl-2-azabicyclo[3.1.0]hexane-3-carboxamide (8a) (55.8 mg, 0.168 mmol), HATU (76 mg, 0.201 mmol), DIPEA (108 mg, 0.838 mmol) and stirring at RT for 16 h. This gave after workup and purification using flash column chromatography [silica gel (12 g), eluting with MeOH in DCM from 0-8%] followed by purification using reverse phase column chromatography [C18 column (100 g), eluting with ACN in water (containing 0.1% HCl) from 0-100%] (1R,3S,5R)-2-(2-(4-amino-8-methyl-6-(pyridin-4-yl)-9H-pyrimido[4,5-b]indol-9-yl)acetyl)-N-(6-bromopyridin-2-yl)-5-methyl-2-azabicyclo[3.1.0]hexane-3-carboxamide (264a) (69 mg, 67% yield) HCl salt as a pale-yellow solid; 1H NMR (300 MHz, DMSO-$d_6$) δ 10.85 (s, 1H, $D_2O$ exchangeable), 9.11 (bs, 2H, $D_2O$ exchangeable), 9.01 (s, 1H), 8.94 (d, J=6.3 Hz, 2H), 8.73-8.55 (m, 3H), 8.01 (d, J=8.2 Hz, 1H), 7.96 (s, 1H), 7.70 (t, J=8.0 Hz, 1H), 7.30 (d, J=7.7 Hz, 1H), 5.93 (d, J=18.0 Hz, 1H), 5.59 (d, J=17.9 Hz, 1H), 4.40 (dd, J=9.0, 6.2 Hz, 1H), 3.75 (m, 1H), 2.78 (s, 3H), 2.50-2.44 (m, 1H), 1.99 (m, 1H), 1.33 (s, 3H), 1.15-0.96 (m, 1H), 0.86 (m, 1H); MS (ES+): 611/613 (M+1), (ES−): 609/611 (M−1).

Scheme 265

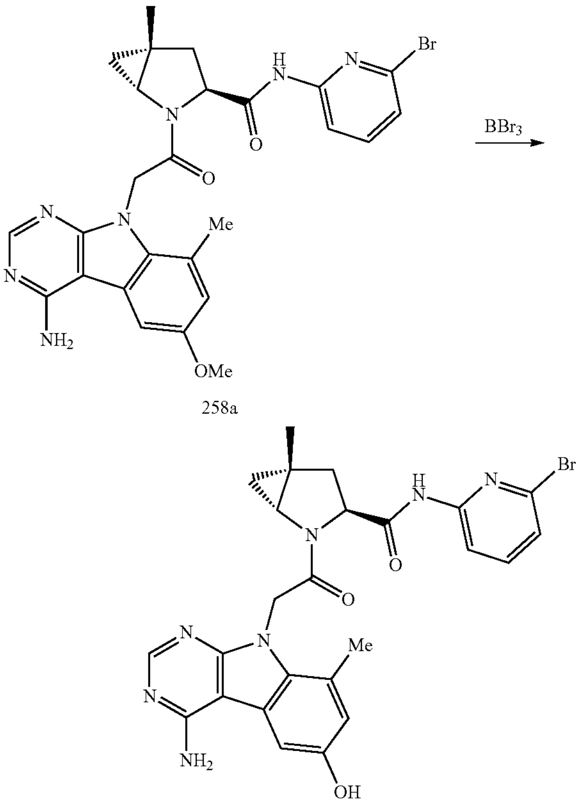

258a

265a

Preparation of (1R,3S,5R)-2-(2-(4-amino-6-hydroxy-8-methyl-9H-pyrimido[4,5-b]indol-9-yl)acetyl)-N-(6-bromopyridin-2-yl)-5-methyl-2-azabicyclo[3.1.0]hexane-3-carboxamide (265a)

Compound 265a was prepared according to the procedure reported in scheme-164, from (1R,3S,5R)-2-(2-(4-amino-6-methoxy-8-methyl-9H-pyrimido[4,5-b]indol-9-yl)acetyl)-N-(6-bromopyridin-2-yl)-5-methyl-2-azabicyclo[3.1.0]hexane-3-carboxamide (258a) (78 mg, 0.138 mmol) in DCM (5 mL) using a solution of 1.0 M $BBr_3$ in DCM (0.691 mL, 0.691 mmol) and stirring at RT for 16 h. This gave after work up and purification using reverse phase column chromatography [C18 column (100 g), eluting with ACN in water (containing 0.1% HCl) from 0-100%] (1R,3S,5R)-2-(2-(4-amino-6-hydroxy-8-methyl-9H-pyrimido[4,5-b]indol-9-yl)acetyl)-N-(6-bromopyridin-2-yl)-5-methyl-2-azabicyclo[3.1.0]hexane-3-carboxamide (265a) (30 mg, 36% yield) HCl salt as a white solid; $^1H$ NMR (300 MHz, DMSO-$d_6$) (a mixture of two rotamers) δ 10.89 and 10.82 (2s, 1H, $D_2O$ exchangeable), 9.39 (s, 1H, $D_2O$ exchangeable), 8.77-8.41 (m, 3H, 2H $D_2O$ exchangeable), 8.01 and 7.94 (2d, J=8.2 Hz, 1H), 7.77-7.62 (m, 2H), 7.35-7.27 (m, 1H), 6.82 (s, 1H), 5.80 (d, J=17.9 Hz, 1H), 5.53 (d, J=17.8 Hz, 1H), 4.38 (dd, J=9.1, 6.2 Hz, 1H), 3.72-3.63 (m, 1H), 2.65 and 2.60 (2s, 3H), 2.48-2.40 (m, 1H), 1.97 (m, 1H), 1.30 (s, 3H), 1.00 (m, 1H), 0.91-0.76 (m, 1H); MS (ES+): 550/552 (M+1), (ES−): 548/550 (M−1); Analysis calculated for $C_{25}H_{24}BrN_7O_3 \cdot 1.15HCl \cdot 2H_2O$: C, 47.79; H, 4.68; Cl, 6.49; N, 15.60. Found: C, 47.69; H, 4.42; Cl, 6.41; N, 15.42.

Scheme 266

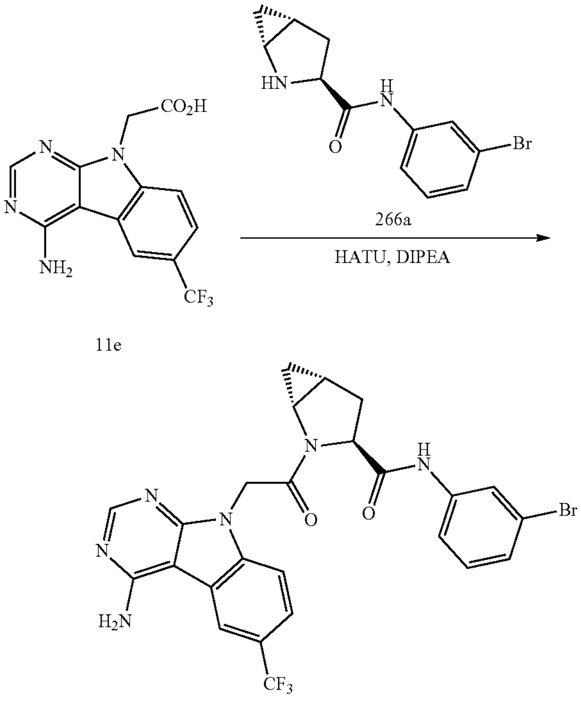

11e

266a

266b

Preparation of (1R,3S,5R)-2-(2-(4-amino-6-(trifluoromethyl)-9H-pyrimido[4,5-b]indol-9-yl)acetyl)-N-(3-bromophenyl)-2-azabicyclo[3.1.0]hexane-3-carboxamide (266b)

Compound 266b was prepared according to the procedure reported in step-3 of scheme-1, from HCl salt of 2-(4-amino-6-(trifluoromethyl)-9H-pyrimido[4,5-b]indol-9-yl)acetic acid (11e) (60 mg, 0.173 mmol) in DMF (1.5 mL) using HCl salt of (1R,3S,5R)—N-(3-bromophenyl)-2-azabicyclo[3.1.0]hexane-3-carboxamide (266a) [(55.0 mg, 0.173 mmol); prepared according to the procedure reported by Lorthiois, E. et al. in J. Med. Chem. (2017), 60(13), 5717-5735.], HATU (99 mg, 0.260 mmol), DIPEA (0.151 mL, 0.865 mmol) and stirring at RT for 16 h. This gave after workup and purification using flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-(trifluoromethyl)-9H-pyrimido[4,5-b]indol-9-yl)acetyl)-N-(3-bromophenyl)-2-azabicyclo[3.1.0]hexane-3-carboxamide (266b) (73 mg, 74% yield) as a white solid; $^1$H NMR (300 MHz, DMSO-$d_6$) δ 10.09 (s, 1H, $D_2O$ exchangeable), 8.99 (s, 1H), 8.65-8.45 (m, 3H, 2H $D_2O$ exchangeable), 7.97-7.81 (m, 3H), 7.45 (dt, J=6.9, 2.3 Hz, 1H), 7.28-7.18 (m, 2H), 5.82 (d, J=17.4 Hz, 1H), 5.50 (d, J=17.3 Hz, 1H), 4.27 (dd, J=9.0, 5.8 Hz, 1H), 3.99-3.87 (m, 1H), 2.42-2.28 (m, 1H), 2.28-2.17 (m, 1H), 1.99-1.86 (m, 1H), 1.14-1.02 (m, 1H), 0.83-0.74 (m, 1H); $^{19}$F NMR (282 MHz, DMSO-$d_6$) δ−58.53; MS (ES+): 573.1/575.1 (M+1); (ES−): 571.1/573.1 (M−1); Analysis calculated for $C_{25}H_{20}BrF_3N_6O_2 \cdot 1.25H_2O \cdot HCl$: C, 47.48; H, 3.75; Cl, 5.61; N, 13.29. Found: C, 47.47; H, 3.43; Cl, 5.35; N, 13.23.

Scheme 267

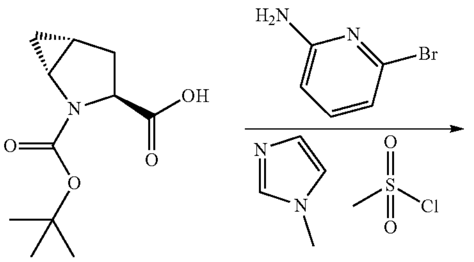

259a

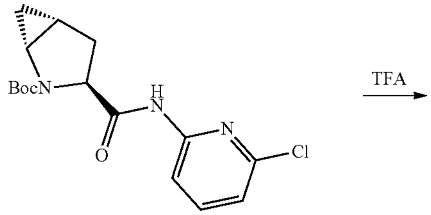

267a

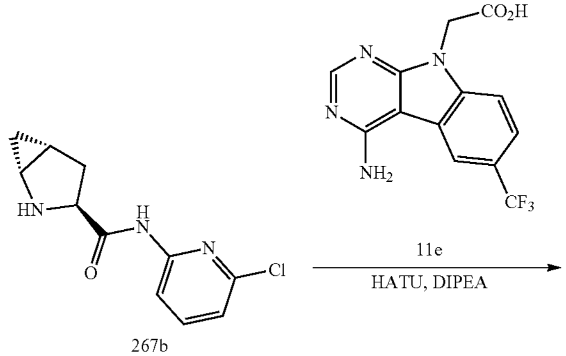

267b

-continued

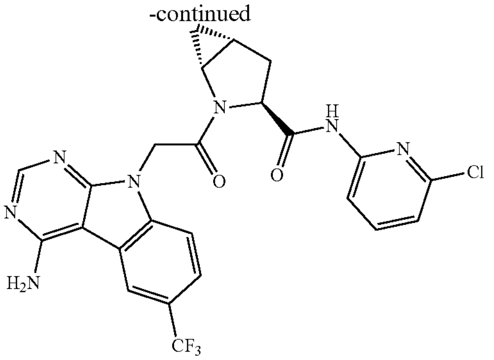

267c

Preparation of (1R,3S,5R)-2-(2-(4-amino-6-(trifluoromethyl)-9H-pyrimido[4,5-b]indol-9-yl)acetyl)-N-(6-chloropyridin-2-yl)-2-azabicyclo[3.1.0]hexane-3-carboxamide (267c)

Step-1: Preparation of (1R,3S,5R)-tert-butyl 3-((6-chloropyridin-2-yl)carbamoyl)-2-azabicyclo[3.1.0]hexane-2-carboxylate (267a)

Compound 267a was prepared according to the procedure reported in step-1 of scheme-53, from (1R,3S,5R)-2-tert-butoxycarbonyl)-2-azabicyclo[3.1.0]hexane-3-carboxylic acid (259a) (0.5 g, 2.200 mmol) in DCM (15 mL) using 1-methyl-1H-imidazole (0.438 mL, 5.50 mmol), methanesulfonyl chloride (0.204 mL, 2.64 mmol), 6-chloropyridin-2-amine (0.283 g, 2.200 mmol; CAS #45644-21-1) and stirring at RT for 18 h. This gave after workup and purification using flash column chromatography [silica gel (24 g), eluting with EtOAc in hexane from 0-50%] (1R,3S,5R)-tert-butyl 3-((6-chloropyridin-2-yl)carbamoyl)-2-azabicyclo[3.1.0]hexane-2-carboxylate (267a) (0.580 g, 78% yield) as a white solid; $^1$H NMR (300 MHz, DMSO-$d_6$) δ 10.80 (s, 1H), 8.11-8.01 (m, 1H), 7.86 (t, J=8.0 Hz, 1H), 7.22 (d, J=7.7 Hz, 1H), 4.20-4.00 (m, 1H), 3.44-3.37 (m, 1H), 2.30 (dd, J=13.2, 8.8 Hz, 1H), 2.21-2.01 (m, 1H), 1.59 (s, 1H), 1.45-1.08 (m, 9H), 0.80-0.65 (m, 1H), 0.48-0.27 (m, 1H); MS (ES+): 338.1 (M+1).

Step-2: Preparation of (1R,3S,5R)—N-(6-chloropyridin-2-yl)-2-azabicyclo[3.1.0]hexane-3-carboxamide (267b)

Compound 267b was prepared according to the procedure reported in step-2 of scheme-1, from (1R,3S,5R)-tert-butyl 3-((6-chloropyridin-2-yl)carbamoyl)-2-azabicyclo[3.1.0]hexane-2-carboxylate (267a) (0.565 g, 1.673 mmol) in DCM (9 mL) using TFA (0.902 mL, 11.71 mmol) and stirring overnight at RT. This gave after work up and purification using reverse phase column chromatography [C18 column (50 g), eluting with ACN in water (containing 0.1% HCl) from 0-100%] HCl salt of (1R,3S,5R)—N-(6-chloropyridin-2-yl)-2-azabicyclo[3.1.0]hexane-3-carboxamide (267b) (413 mg, 90% yield); 1H NMR (300 MHz, DMSO-$d_6$) δ 11.35 (s, 1H), 10.01 (s, 1H), 9.23 (s, 1H), 8.06-7.88 (m, 2H), 7.33 (dd, J=7.6, 0.9 Hz, 1H), 4.21-4.08 (m, 1H), 3.39-3.27 (m, 1H), 2.62 (dd, J=12.8, 7.7 Hz, 1H), 2.15-2.02 (m, 1H), 1.89-1.76 (m, 1H), 0.90-0.76 (m, 2H); MS (ES+): 238.1 (M+1).

Step-3: Preparation of (1R,3S,5R)-2-(2-(4-amino-6-(trifluoromethyl)-9H-pyrimido[4,5-b]indol-9-yl)acetyl)-N-(6-chloropyridin-2-yl)-2-azabicyclo[3.1.0]hexane-3-carboxamide (267c)

Compound 267c was prepared according to the procedure reported in step-3 of scheme-1, from HCl salt of (1R,3S,5R)—N-(6-chloropyridin-2-yl)-2-azabicyclo[3.1.0]hexane-3-carboxamide (267b) (47.4 mg, 0.173 mmol) in DMF (1.5 mL) using HCl salt of 2-(4-amino-6-(trifluoromethyl)-9H-pyrimido[4,5-b]indol-9-yl)acetic acid (11e) (60 mg, 0.173 mmol), HATU (99 mg, 0.260 mmol), DIPEA (0.151 mL, 0.865 mmol) and stirring at RT for 16 h. This gave after workup and purification using flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-(trifluoromethyl)-9H-pyrimido[4,5-b]indol-9-yl)acetyl)-N-(6-chloropyridin-2-yl)-2-azabicyclo[3.1.0]hexane-3-carboxamide (267c) (67 mg, 73% yield) as a white solid; $^1$H NMR (300 MHz, DMSO-$d_6$) δ 10.75 (s, 1H, $D_2O$ exchangeable), 8.98 (s, 1H), 8.61 (s, 1H), 8.58 (s, 2H, $D_2O$ exchangeable), 7.98 (d, J=8.2 Hz, 1H), 7.89-7.76 (m, 3H), 7.19 (d, J=7.7 Hz, 1H), 5.82 (d, J=17.4 Hz, 1H), 5.47 (d, J=17.3 Hz, 1H), 4.42 (dd, J=9.1, 5.5 Hz, 1H), 3.92 (td, J=6.2, 5.4, 2.3 Hz, 1H), 2.40-2.15 (m, 2H), 2.00-1.83 (m, 1H), 1.15-0.98 (m, 1H), 0.86-0.74 (m, 1H); $^{19}$F NMR (282 MHz, DMSO-$d_6$) δ-58.53. MS (ES+): 530.2 (M+1); (ES−): 528.1 (M−1): Analysis calculated for $C_{24}H_{21}ClF_3N_7O_2 \cdot 2H_2O \cdot 0.85HCl$: C, 48.29; H, 4.03; Cl, 10.99; N, 16.43. Found: C, 48.33; H, 3.79; Cl, 10.82; N, 16.28

Scheme 268

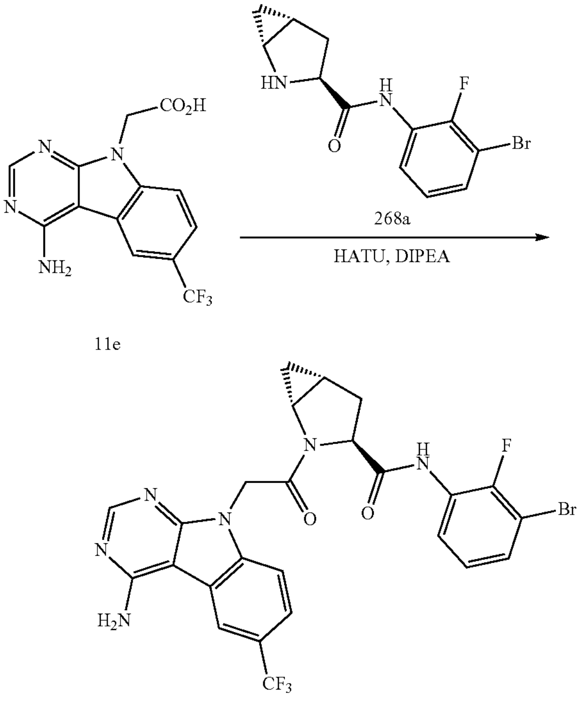

268a

11e

268b

Preparation of (1R,3S,5R)-2-(2-(4-amino-6-(trifluoromethyl)-9H-pyrimido[4,5-b]indol-9-yl)acetyl)-N-(3-bromo-2-fluorophenyl)-2-azabicyclo[3.1.0]hexane-3-carboxamide (268b)

Compound 268b was prepared according to the procedure reported in step-3 of scheme-1, from HCl salt of 2-(4-amino-6-(trifluoromethyl)-9H-pyrimido[4,5-b]indol-9-yl)acetic acid (11e) (60 mg, 0.173 mmol) in DMF (1.5 mL) using HCl salt of (1R,3S,5R)—N-(3-bromo-2-fluorophenyl)-2-azabicyclo[3.1.0]hexane-3-carboxamide (268a) (58.1 mg, 0.173 mmol); prepared according to the procedure reported by Lorthiois, E. et al. J. Med. Chem. (2017), 60(13), 5717-5735.1, HATU (99 mg, 0.260 mmol) and DIPEA (0.151 mL, 0.865 mmol) and stirring at RT for 16 h. This gave after workup and purification using flash column chromatography [silica gel (24 g), eluting with DMA80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-(trifluoromethyl)-9H-pyrimido[4,5-b]indol-9-yl)acetyl)-N-(3-bromo-2-fluorophenyl)-2-azabicyclo[3.1.0]hexane-3-carboxamide (268b) (98 mg, 96% yield) as a white solid; $^1$H NMR (300 MHz, DMSO-$d_6$) δ 9.85 (s, 1H, $D_2O$ exchangeable), 8.96 (s, 1H), 8.55 (s, 1H), 8.36 (s, 2H, $D_2O$ exchangeable), 7.90-7.78 (m, 2H), 7.78-7.67 (m, 1H), 7.49-7.38 (m, 1H), 7.11 (td, J=8.1, 1.4 Hz, 1H), 5.77 (d, J=17.5 Hz, 1H), 5.49 (d, J=17.3 Hz, 1H), 4.46 (dd, J=8.8, 5.5 Hz, 1H), 3.94-3.84 (m, 1H), 2.38-2.22 (m, 2H), 2.00-1.84 (m, 1H), 1.10 (m, 1H), 0.86-0.71 (m, 1H); $^{19}$F NMR (282 MHz, DMSO-$d_6$) δ-58.45, −117.67; MS (ES+): 591.1/593.1 (M+1); (ES−): 589.1/591.1 (M−1); Analysis calculated for $C_{25}H_{19}BrF_4N_6O_2 \cdot 1.5H_2O \cdot 0.95HCl$: C, 45.98; H, 3.54; Cl, 5.16; N, 12.87. Found: C, 45.92; H, 3.41; Cl, 4.94; N, 12.73.

Scheme 269

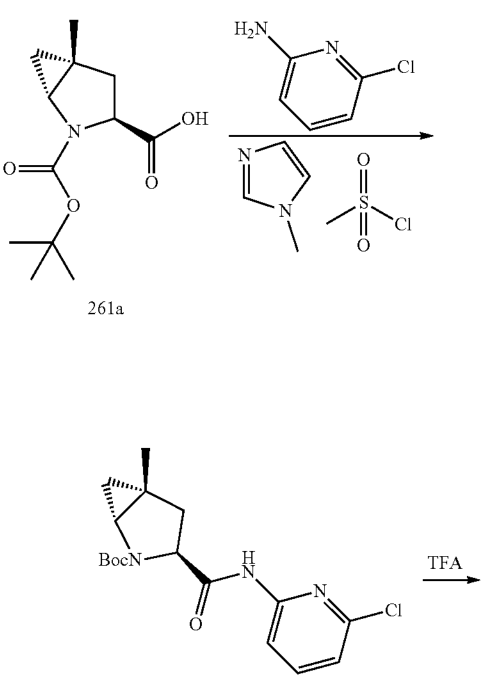

261a

269a

-continued

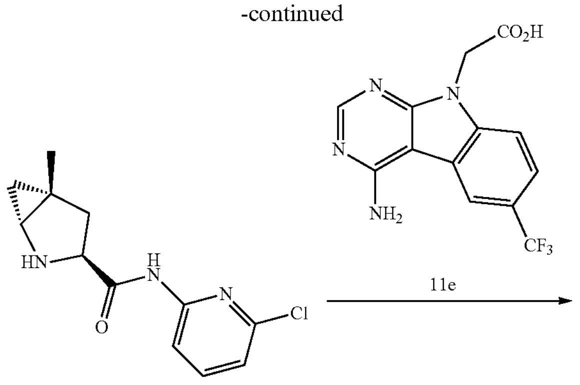

269b

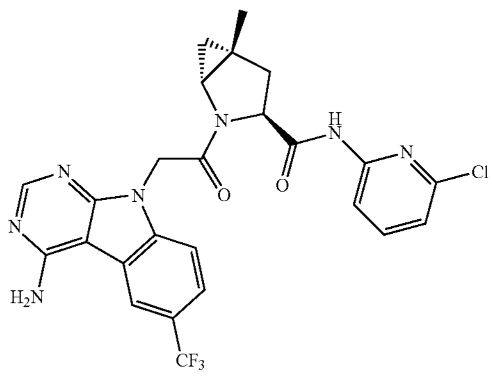

269c

Preparation of (1R,3S,5R)-2-(2-(4-amino-6-(trifluoromethyl)-9H-pyrimido[4,5-b]indol-9-yl)acetyl)-N-(6-chloropyridin-2-yl)-5-methyl-2-azabicyclo[3.1.0]hexane-3-carboxamide (269c)

Step-1: Preparation of (1R,3S,5R)-tert-butyl 3-((6-chloropyridin-2-yl)carbamoyl)-5-methyl-2-azabicyclo[3.1.0]hexane-2-carboxylate (269a)

Compound 269a was prepared according to the procedure reported in step-1 of scheme-53, from (1R,3S,5R)-2-(tert-butoxycarbonyl)-5-methyl-2-azabicyclo[3.1.0]hexane-3-carboxylic acid (261a) (0.531 g, 2.200 mmol) in DCM (15 mL) using 1-methyl-1H-imidazole (0.438 mL, 5.50 mmol), methanesulfonyl chloride (0.204 mL, 2.64 mmol), 6-chloropyridin-2-amine (0.283 g, 2.200 mmol; CAS #45644-21-1) and stirring at RT for 18 h. This gave after workup and purification using flash column chromatography [silica gel (24 g), eluting with EtOAc in hexane from 0-50%] (1R,3S,5R)-tert-butyl 3-((6-chloropyridin-2-yl)carbamoyl)-5-methyl-2-azabicyclo[3.1.0]hexane-2-carboxylate (269a) (0.667 g, 86% yield) as a white solid; $^1$H NMR (300 MHz, DMSO-$d_6$) δ 10.80 (s, 1H), 8.16-7.96 (m, 1H), 7.86 (t, J=7.9 Hz, 1H), 7.22 (d, J=7.7 Hz, 1H), 4.19-4.01 (m, 1H), 3.23-3.06 (m, 1H), 2.39 (dd, J=12.8, 8.7 Hz, 1H), 1.95-1.81 (m, 1H), 1.51-1.08 (m, 12H), 0.71-0.62 (m, 1H), 0.62-0.52 (m, 1H); MS (ES+): 352.1 (M+1).

Step-2: Preparation of (1R,3S,5R)—N-(6-chloropyridin-2-yl)-5-methyl-2-azabicyclo[3.1.0]hexane-3-carboxamide (269b)

Compound 269b was prepared according to the procedure reported in step-2 of scheme-1, from (1R,3S,5R)-tert-butyl 3-((6-chloropyridin-2-yl)carbamoyl)-5-methyl-2-azabicyclo[3.1.0]hexane-2-carboxylate (269a) (0.652 g, 1.853 mmol) in DCM (10 mL) using TFA (0.999 mL, 12.97 mmol) and stirring overnight at RT. This gave after work up and purification using reverse phase column chromatography [C18 column (50 g), eluting with ACN in water (containing 0.1% HCl) from 0-100%] HCl salt of (1R,3S,5R)—N-(6-chloropyridin-2-yl)-5-methyl-2-azabicyclo[3.1.0]hexane-3-carboxamide (269b) (532 mg, 100% yield): $^1$H NMR (300 MHz, DMSO-$d_6$) δ 11.34 (s, 1H), 9.85 (s, 1H), 9.24 (s, 1H), 8.08-7.85 (m, 2H), 7.40-7.21 (m, 1H), 4.27-4.08 (m, 1H), 3.09 (dd, J=7.0, 2.4 Hz, 1H), 2.65 (dd, J=12.6, 7.6 Hz, 1H), 1.97 (t, J=11.9 Hz, 1H), 1.25 (s, 3H), 1.05-0.94 (m, 1H), 0.82-0.72 (m, 1H); MS (ES+): 252.1 (M+1).

Step-3: Preparation of (1R,3S,5R)-2-(2-(4-amino-6-(trifluoromethyl)-9H-pyrimido[4,5-b]indol-9-yl)acetyl)-N-(6-chloropyridin-2-yl)-5-methyl-2-azabicyclo[3.1.0]hexane-3-carboxamide (269c)

Compound 269c was prepared according to the procedure reported in step-3 of scheme-1, from HCl salt of (1R,3S,5R)—N-(6-chloropyridin-2-yl)-5-methyl-2-azabicyclo[3.1.0]hexane-3-carboxamide (269b) (60 mg, 0.173 mmol) in DMF (1.5 mL) using HCl salt of 2-(4-amino-6-(trifluoromethyl)-9H-pyrimido[4,5-b]indol-9-yl)acetic acid (11e) [(58.1 mg, 0.173 mmol), HATU (99 mg, 0.260 mmol), DIPEA (0.151 mL, 0.865 mmol) and stirring at RT for 16 h. This gave after workup and purification using flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-(trifluoromethyl)-9H-pyrimido[4,5-b]indol-9-yl)acetyl)-N-(6-chloropyridin-2-yl)-5-methyl-2-azabicyclo[3.1.0]hexane-3-carboxamide (269c) (53 mg, 56% yield) HCl salt as a white solid; $^1$H NMR (300 MHz, DMSO-$d_6$) δ 10.75 (s, 1H, $D_2O$ exchangeable), 8.98 (s, 1H), 8.70-8.47 (m, 3H, 2H $D_2O$ exchangeable), 7.99 (d, J=8.2 Hz, 1H), 7.90-7.75 (m, 3H), 7.19 (d, J=7.7 Hz, 1H), 5.78 (d, J=17.4 Hz, 1H), 5.43 (d, J=17.3 Hz, 1H), 4.37 (dd, J=9.1, 6.0 Hz, 1H), 3.70 (m, 1H), 2.49-2.42 (m, 1H), 1.99 (m, 1H), 1.32 (s, 3H), 1.07-0.98 (m, 1H), 0.98-0.90 (m, 1H). MS (ES+): 544.2 (M+1); (ES−): 542.1 (M−1); Analysis calculated for $C_{25}H_{21}ClF_3N_7O_2 \cdot 2H_2O \cdot 0.75HCl$: C, 49.44; H, 4.27; Cl, 10.22; N, 16.14. Found: C, 49.65; H, 4.00; Cl, 9.94; N, 16.05.

Scheme 270

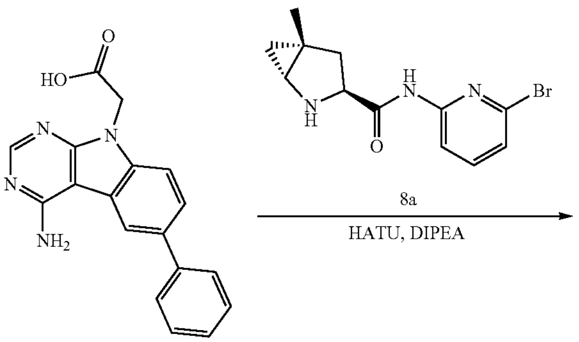

62b

-continued

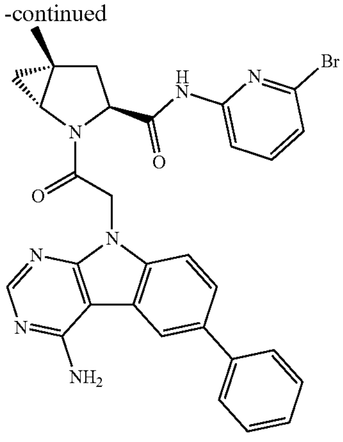

270a

Preparation of (1R,3S,5R)-2-(2-(4-amino-6-phenyl-9H-pyrimido[4,5-b]indol-9-yl)acetyl)-N-(6-bromopyridin-2-yl)-5-methyl-2-azabicyclo[3.1.0]hexane-3-carboxamide (270a)

Compound 270a was prepared according to the procedure reported in step-3 of scheme-1, from 2-(4-amino-6-phenyl-9H-pyrimido[4,5-b]indol-9-yl)acetic acid (62b) (90 mg, 0.283 mmol) in DMF (10 mL) using HCl salt of (1R,3S,5R)—N-(6-bromopyridin-2-yl)-5-methyl-2-azabicyclo[3.1.0]hexane-3-carboxamide (8a) (113 mg, 0.339 mmol), HATU (161 mg, 0.424 mmol), DIPEA (0.197 mL, 1.131 mmol) and stirring at RT for 16 h. This gave after workup and purification using flash column chromatography [silica gel (12 g), eluting with MeOH in DCM from 0-5%] followed by purification using reverse phase C18 column chromatography with water (containing 0.1% HCl)/acetonitrile (1:0 to 0:1) (1R,3S,5R)-2-(2-(4-amino-6-phenyl-9H-pyrimido[4,5-b]indol-9-yl)acetyl)-N-(6-bromopyridin-2-yl)-5-methyl-2-azabicyclo[3.1.0]hexane-3-carboxamide (270a) (58 mg, 34% yield) HCl salt as a white solid; $^1$H NMR (300 MHz, DMSO-$d_6$) δ 10.78 (s, 1H), 8.80 (d, J=1.6 Hz, 1H), 8.76 (s, 2H), 8.63 (s, 1H), 8.01 (d, J=8.2 Hz, 1H), 7.92-7.75 (m, 4H), 7.69 (t, J=8.0 Hz, 1H), 7.56-7.47 (m, 2H), 7.43-7.35 (m, 1H), 7.31 (d, J=7.7 Hz, 1H), 5.76 (d, J=17.3 Hz, 1H), 5.40 (d, J=17.3 Hz, 1H), 4.38 (dd, J=9.1, 6.0 Hz, 1H), 3.71 (dd, J=5.5, 2.4 Hz, 1H), 2.58-2.41 (m, 1H), 1.99 (dd, J=13.2, 5.9 Hz, 1H), 1.31 (s, 3H), 1.06-0.98 (m, 1H), 0.94 (m, 1H); MS (ES+): 596.15 & 598.15 (M+1), MS (ES−): 594.10 & 596.10 (M−1); Analysis calculated for $C_{30}H_{26}BrN_7O_2\cdot1.1HCl\cdot2H_2O$: C, 53.57; H, 4.66; N, 14.58; Cl, 5.80. Found: C, 53.76; H, 4.48; N, 14.50; Cl, 5.76

Scheme 271

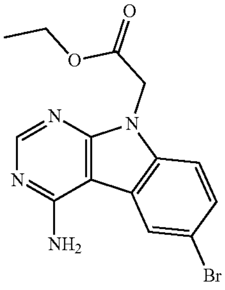

48a

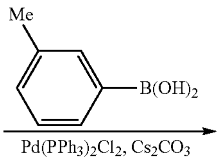

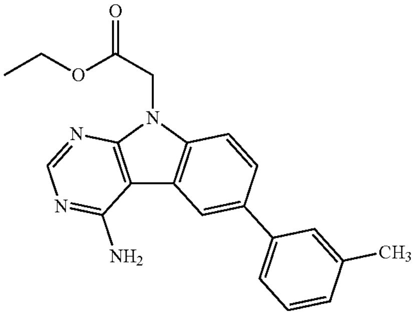

271a

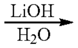

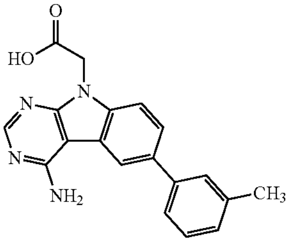

271b

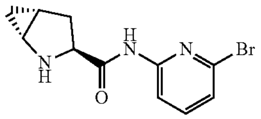

4a

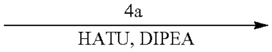

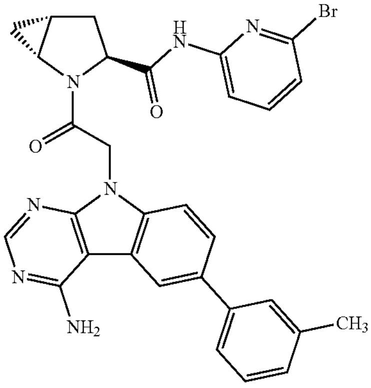

271c

Preparation of (1R,3S,5R)-2-(2-(4-amino-6-(m-tolyl)-9H-pyrimido[4,5-b]indol-9-yl)acetyl)-N-(6-bromopyridin-2-yl)-2-azabicyclo[3.1.0]hexane-3-carboxamide (271c)

Step-1: Preparation of ethyl 2-(4-amino-6-(m-tolyl)-9H-pyrimido[4,5-b]indol-9-yl)acetate (271a)

Compound 271a was prepared according to the procedure reported in step-1 of scheme-62, from ethyl 2-(4-amino-6- bromo-9H-pyrimido[4,5-b]indol-9-yl)acetate (48a) (200 mg, 0.573 mmol) in dioxane (18 mL) using m-tolylboronic acid (117 mg, 0.859 mmol), a solution of cesium carbonate (280 mg, 0.859 mmol) in water (2.2 mL), $Pd(PPh_3)_2Cl_2$ (80 mg, 0.115 mmol) and heating at 100° C. for 19 h under nitrogen. This gave after workup a mixture of ethyl 2-(4-amino-6-(m-tolyl)-9H-pyrimido[4,5-b]indol-9-yl)acetate (271a) and 2-(4-amino-6-m-tolyl-9H-pyrimido[4,5-b]indol-9-yl)acetic acid (271b) which was used as such for the next step; MS (ES+): 361.10 & 333.15 (M+1).

Step-2: Preparation of 2-(4-amino-6-(m-tolyl)-9H-pyrimido[4,5-b]indol-9-yl)acetic acid (271b)

Compound 271b was prepared according to the procedure reported in step-4 of scheme-17, from a mixture containing ethyl 2-(4-amino-6-(m-tolyl)-9H-pyrimido[4,5-b]indol-9-yl)acetate (271a) and 2-(4-amino-6-(m-tolyl)-9H-pyrimido [4,5-b]indol-9-yl)acetic acid (271b) (207 mg, 0.573 mmol) in THF (5 mL) and methanol (5 mL) using a solution of lithium hydroxide hydrate (147 mg, 3.44 mmol) in water (5 mL) and stirring at RT for 21 h. The residue obtained after work up was used as such for the next step; MS (ES+): 333.10 (M+1).

Step-3: Preparation of (1R,3S,5R)-2-(2-(4-amino-6-(m-tolyl)-9H-pyrimido[4,5-b]indol-9-yl)acetyl)-N-(6-bromopyridin-2-yl)-2-azabicyclo[3.1.0]hexane-3-carboxamide (271c)

Compound 271c was prepared according to the procedure reported in step-3 of scheme-1, from 2-(4-amino-6-(m-tolyl)-9H-pyrimido[4,5-b]indol-9-yl)acetic acid (271b) (0.090 mg, 0.271 mmol) in DMF (10 mL) using HCl salt of (1R,3S,5R)—N-(6-bromopyridin-2-yl)-2-azabicyclo[3.1.0] hexane-3-carboxamide (4a) (0.104 g, 0.325 mmol), HATU (0.154 g, 0.406 mmol), DIPEA (140 mg, 1.083 mmol) and stirring at RT for 19 h. This gave after workup and purification using flash column chromatography [silica gel (12 g), eluting with MeOH in DCM from 0-5%] followed by purification using reverse phase column chromatography [C18 column, eluting with ACN in water (containing 0.1% HCl) from 0-100%] (1R,3S,5R)-2-(2-(4-amino-6-(m-tolyl)-9H-pyrimido[4,5-b]indol-9-yl)acetyl)-N-(6-bromopyridin-2-yl)-2-azabicyclo[3.1.0]hexane-3-carboxamide (271c) (58 mg, 36% yield) HCl salt as a white solid; $^1H$ NMR (300 MHz, DMSO-$d_6$) δ 10.78 (s, 1H), 8.84-8.70 (m, 3H), 8.64 (s, 1H), 8.01 (d, J=8.2 Hz, 1H), 7.87 (dd, J=8.7, 1.6 Hz, 1H), 7.81-7.59 (m, 4H), 7.39 (t, J=7.6 Hz, 1H), 7.32 (d, J=7.7 Hz, 1H), 7.20 (d, J=7.5 Hz, 1H), 5.80 (d, J=17.4 Hz, 1H), 5.45 (d, J=17.3 Hz, 1H), 4.42 (dd, J=9.0, 5.6 Hz, 1H), 3.98-3.89 (m, 1H), 2.42 (s, 3H), 2.41-2.14 (m, 2H), 2.02-1.82 (m, 1H), 1.16-0.99 (m, 1H), 0.86-0.72 (m, 1H); MS (ES+): 596.20 & 598.10 (M+1), (ES−): 594.10 & 596.20 (M−1); Analysis calculated for $C_{30}H_{26}BrN_7O_2 \cdot HCl \cdot 2.25H_2O$: C, 53.50; H, 4.71; N, 14.56; Cl, 5.26. Found: C, 53.79; H, 4.62; N, 14.71; Cl, 5.19.

Scheme 272

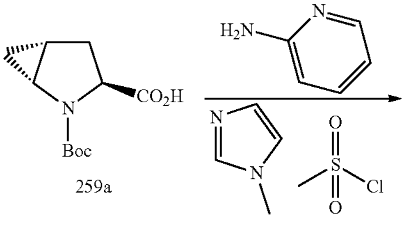

259a

-continued

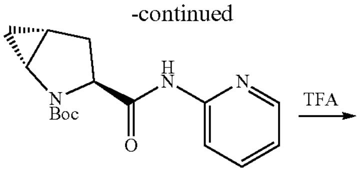

272a

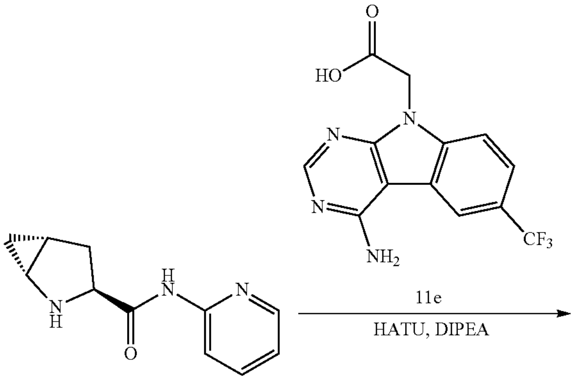

272b

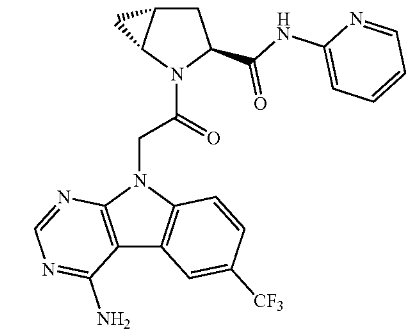

272c

Preparation of (1R,3S,5R)-2-(2-(4-amino-6-(trifluoromethyl)-9H-pyrimido[4,5-b]indol-9-yl)acetyl)-N-(pyridin-2-yl)-2-azabicyclo[3.1.0]hexane-3-carboxamide (272c)

Step-1: Preparation of (1R,3S,5R)-tert-butyl 3-(pyridin-2-ylcarbamoyl)-2-azabicyclo[3.1.0] hexane-2-carboxylate (272a)

Compound 272a was prepared according to the procedure reported in step-1 of scheme-53, from (1R,3S,5R)-2-(tert-butoxycarbonyl)-2-azabicyclo[3.1.0]hexane-3-carboxylic acid (259a) (2.415 g, 10.63 mmol) in DCM (10 mL) using 1-methyl-1H-imidazole (2.181 g, 26.6 mmol), methanesulfonyl chloride (1.461 g, 12.75 mmol) in DCM (2 mL), pyridin-2-amine (1.00 g, 10.63 mmol; CAS #504-29-0) and stirring at RT for 16 h. This gave after workup and purification by flash column chromatography [silica gel (80 g), eluting with EtOAc in hexane from 0-30%] (1R,3S,5R)-tert-butyl 3-(pyridin-2-ylcarbamoyl)-2-azabicyclo[3.1.0] hexane-2-carboxylate (272a) (2.54 g, 79% yield) as a sticky white solid; $^1H$ NMR (300 MHz, DMSO-$d_6$) δ 10.39 (s, 1H), 8.35-8.22 (m, 1H), 8.08 (d, J=8.4 Hz, 1H), 7.87-7.73 (m, 1H), 7.16-7.03 (m, 1H), 4.24-4.07 (m, 1H), 3.52-3.35 (m, 1H), 2.29 (dd, J=13.2, 8.8 Hz, 1H), 2.18-2.04 (m, 1H), 1.64-1.51 (m, 1H), 1.32 (2bs, 9H), 0.82-0.70 (m, 1H), 0.43-0.36 (m, 1H); MS (ES+): 304.20 (M+1).

Step-2: Preparation of (1R,3S,5R)—N-(pyridin-2-yl)-2-azabicyclo[3.1.0]hexane-3-carboxamide (272b)

Compound 272b was prepared according to the procedure reported in step-2 of scheme-1, from (1R,3S,5R)-tert-butyl 3-(pyridin-2-ylcarbamoyl)-2-azabicyclo[3.1.0]hexane-2-carboxylate (272a) (2.5 g, 8.24 mmol) in DCM (30 mL) using TFA (3.15 mL, 41.2 mmol) and stirring for 16 h at RT. This gave after work up TFA salt of (1R,3S,5R)—N-(pyridin-2-yl)-2-azabicyclo[3.1.0]hexane-3-carboxamide (272b) (6.0 g); MS (ES+): 204.10 (M+1).

Step-3: Preparation of (1R,3S,5R)-2-(2-(4-amino-6-(trifluoromethyl)-9H-pyrimido[4,5-b]indol-9-yl)acetyl)-N-(pyridin-2-yl)-2-azabicyclo[3.1.0]hexane-3-carboxamide (272c)

Compound 272c was prepared according to the procedure reported in step-3 of scheme-1, from TFA salt of (1R,3S,5R)—N-(pyridin-2-yl)-2-azabicyclo[3.1.0]hexane-3-carboxamide (272b) (0.127 mg, 0.4 mmol) in DMF (10 mL) using HCl salt of 2-(4-amino-6-(trifluoromethyl)-9H-pyrimido[4,5-b]indol-9-yl)acetic acid (11e) (69.3 mg, 0.2 mmol), HATU (152 mg, 0.400 mmol), DIPEA (0.174 mL, 1.0 mmol) and stirring at RT for 19 h. This gave after workup and purification using flash column chromatography [silica gel (12 g), eluting with MeOH in DCM from 0-8%] followed by purification using reverse phase column chromatography [C18 column, eluting with ACN in water (containing 0.1% HCl) from 0-50%] (1R,3S,5R)-2-(2-(4-amino-6-(trifluoromethyl)-9H-pyrimido[4,5-b]indol-9-yl)acetyl)-N-(pyridin-2-yl)-2-azabicyclo[3.1.0]hexane-3-carboxamide (272c) (56 mg, 57% yield) HCl as a white solid; $^1$H NMR (300 MHz, DMSO-$d_6$) δ 10.46 (s, 1H), 8.99 (s, 1H), 8.68 (s, 2H), 8.64 (s, 1H), 8.28 (d, J=4.9 Hz, 1H), 7.99 (d, J=8.4 Hz, 1H), 7.93-7.83 (m, 2H), 7.77 (t, J=8.3 Hz, 1H), 7.15-7.05 (m, 1H), 5.85 (d, J=17.4 Hz, 1H), 5.48 (d, J=17.2 Hz, 1H), 4.51-4.41 (m, 1H), 3.95-3.87 (m, 1H), 2.39-2.19 (m, 2H), 2.00-1.84 (m, 1H), 1.16-1.04 (m, 1H), 0.87-0.73 (m, 1H); MS (ES+): 496.15 (M+1); (ES−): 494.10 (M−1); Analysis calculated for $C_{24}H_{20}F_3N_7O_2 \cdot 1.8HCl \cdot 3H_2O$: C, 46.86; H, 4.56; Cl, 10.37; N, 15.94. Found: C, 46.80; H, 4.06; Cl, 10.11; N, 15.62.

Scheme 273

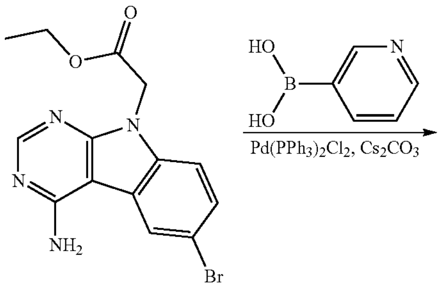

48a

-continued

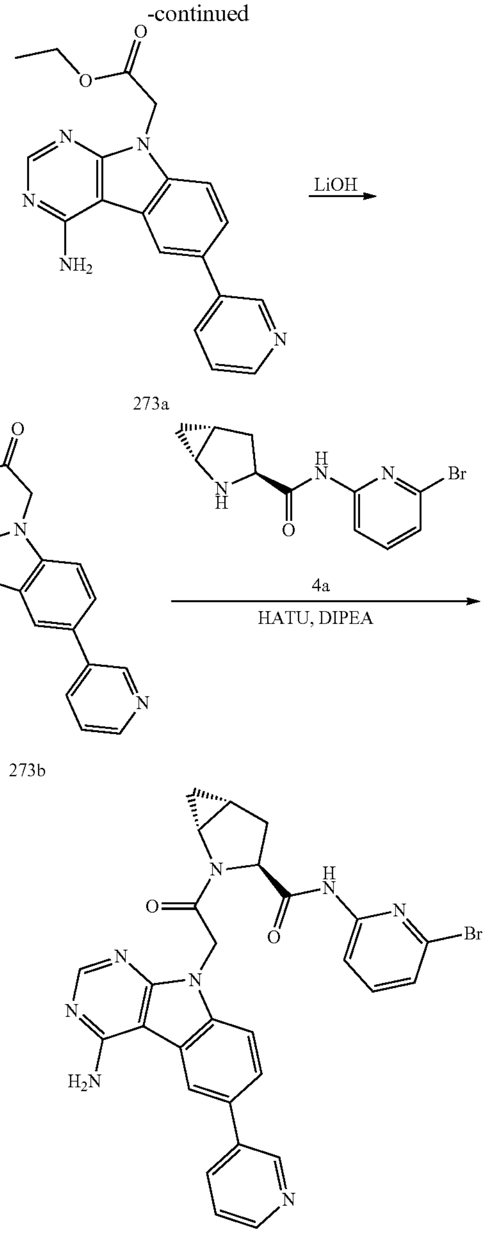

273c

Preparation of (1R,3S,5R)-2-(2-(4-amino-6-(pyridin-3-yl)-9H-pyrimido[4,5-b]indol-9-yl)acetyl)-N-(6-bromopyridin-2-yl)-2-azabicyclo[3.1.0]hexane-3-carboxamide (273c)

Step-1: Preparation of ethyl 2-(4-amino-6-(pyridin-3-yl)-9H-pyrimido[4,5-b]indol-9-yl)acetate (273a)

Compound 273a was prepared according to the procedure reported in step-1 of scheme-62, from ethyl 2-(4-amino-6-bromo-9H-pyrimido[4,5-b]indol-9-yl)acetate (48a) (200 mg, 0.573 mmol) in dioxane (18 mL) using pyridin-3-ylboronic acid (106 mg, 0.859 mmol: CAS #1692-25-7), bis(triphenylphosphine)palladium(II) chloride (80 mg, 0.115 mmol), a solution of cesium carbonate (280 mg, 0.859 mmol) in water (2.2 mL) and heating at 100° C. for 13 h.

This gave after workup a mixture of ethyl 2-(4-amino-6-(pyridin-3-yl)-9H-pyrimido[4,5-b]indol-9-yl)acetate (273a) MS (ES+): 348.15 (M+1) and 2-(4-amino-6-(pyridin-3-yl)-9H-pyrimido[4,5-b]indol-9-yl)acetic acid (273b) MS (ES+): 320.10 (M+1) which was used as such for the next step.

Step-2: Preparation of 2-(4-amino-6-(pyridin-3-yl)-9H-pyrimido[4,5-b]indol-9-yl)acetic acid (273b)

Compound 273b was prepared according to the procedure reported in step-4 of scheme-17, from the above mixture of ethyl 2-(4-amino-6-(pyridin-3-yl)-9H-pyrimido[4,5-b]indol-9-yl)acetate (273a) and 2-(4-amino-6-(pyridin-3-yl)-9H-pyrimido[4,5-b]indol-9-yl)acetic acid (273b) (0.573 mmol) in THF (5 mL) and methanol (5 mL) using a solution of lithium hydroxide hydrate (147 mg, 3.44 mmol) in water (5 mL) and stirring at RT for 18 h. This gave after work up 2-(4-amino-6-(pyridin-3-yl)-9H-pyrimido[4,5-b]indol-9-yl) acetic acid (273b) which was used as such for the next step; MS (ES+): 320.10 (M+1).

Step-3: Preparation of (1R,3S,5R)-2-(2-(4-amino-6-(pyridin-3-yl)-9H-pyrimido[4,5-b]indol-9-yl)acetyl)-N-(6-bromopyridin-2-yl)-2-azabicyclo[3.1.0]hexane-3-carboxamide (273c)

Compound 273c was prepared according to the procedure reported in step-3 of scheme-1, from 2-(4-amino-6-(pyridin-3-yl)-9H-pyrimido[4,5-b]indol-9-yl)acetic acid (273b) (65 mg, 0.204 mmol) in DMF (10 mL) using HCl salt of (1R,3S,5R)—N-(6-bromopyridin-2-yl)-2-azabicyclo[3.1.0] hexane-3-carboxamide (4a) (84 mg, 0.265 mmol), HATU (155 mg, 0.407 mmol), DIPEA (0.142 mL, 0.814 mmol) and stirring at RT for 21 h. This gave after workup and purification by flash column chromatography [silica gel (12 g), eluting with MeOH in DCM from 0-8%] followed by purification using reverse phase column chromatography [C18 column (50 g), eluting with ACN in water (containing 0.1% HCl) from 0-100%] (1R,3S,5R)-2-(2-(4-amino-6-(pyridin-3-yl)-9H-pyrimido[4,5-b]indol-9-yl)acetyl)-N-(6-bromopyridin-2-yl)-2-azabicyclo[3.1.0]hexane-3-carboxamide (273c) (48 mg, 40% yield) HCl salt as a white solid; $^1$H NMR (300 MHz, DMSO-$d_6$) δ 10.78 (s, 1H), 9.45 (d, J=2.2 Hz, 1H), 9.18 (d, J=1.7 Hz, 1H), 9.14 (bs, 3H), 9.03-8.96 (m, 1H), 8.86 (dd, J=5.5, 1.3 Hz, 1H), 8.71 (s, 1H), 8.16-8.06 (m, 2H), 8.00 (d, J=8.2 Hz, 1H), 7.91 (d, J=8.7 Hz, 1H), 7.70 (t, J=8.0 Hz, 1H), 7.31 (d, J=7.7 Hz, 1H), 5.85 (d, J=17.4 Hz, 1H), 5.48 (d, J=17.2 Hz, 1H), 4.43 (dd, J=9.0, 5.5 Hz, 1H), 4.01-3.87 (m, 1H), 2.43-2.14 (m, 2H), 2.01-1.83 (m, 1H), 1.18-1.01 (m, 1H), 0.90-0.71 (m, 1H); MS (ES+): 583.10 & 585.10 (M+1), MS (ES−): 581.10 & 583.10 (M−1): Analysis calculated for $C_{28}H_{23}BrN_8O_2 \cdot 2.25HCl \cdot 4.65H_2O$: C, 44.89; H, 4.65; N, 14.96; Cl, 10.65. Found: C, 45.29; H, 4.52; N, 14.35; Cl, 10.37.

Scheme 274

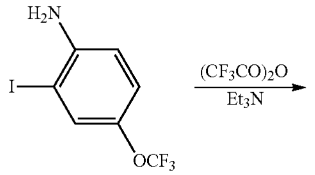

274a

-continued

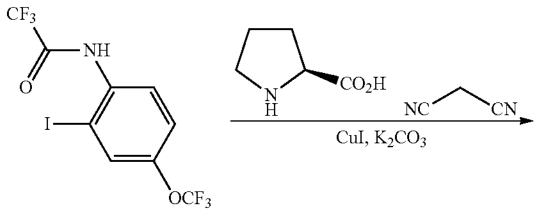

274b

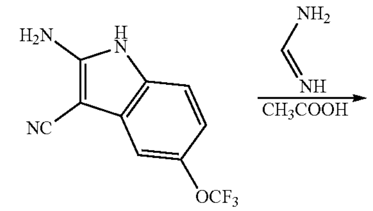

274c

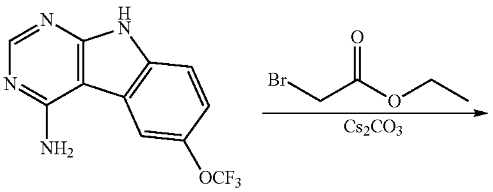

274d

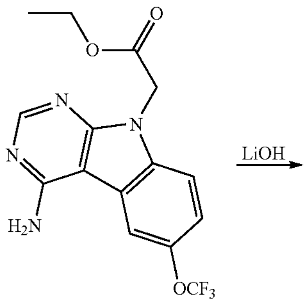

274e

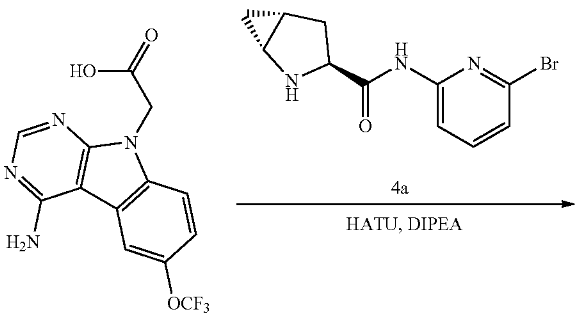

274f

-continued

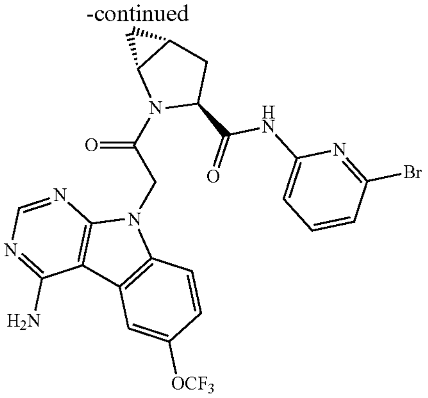

274g

Preparation of (1R,3S,5R)-2-(2-(4-amino-6-(trifluoromethoxy)-9H-pyrimido[4,5-b]indol-9-yl)acetyl)-N-(6-bromopyridin-2-yl)-2-azabicyclo[3.1.0]hexane-3-carboxamide (274 g)

Step-1: Preparation of 2,2,2-trifluoro-N-(2-iodo-4-(trifluoromethoxy)phenyl)acetamide (274b)

Compound 274b was prepared according to the procedure reported in step-1 of scheme-46, from 2-iodo-4-(trifluoromethoxy)aniline (274a) (10 g, 33.0 mmol; CAS #845866-79-7) in DCM (50 mL) using triethylamine (11.50 mL, 83 mmol), trifluoroacetic acid anhydride (6.88 mL, 49.5 mmol) and stirring at RT for 15 h. This gave after workup 2,2,2-trifluoro-N-(2-iodo-4-(trifluoromethoxy)phenyl)acetamide (274b) (15.94 g) which was used as such for next step; MS (ES−): 397.90 (M−1).

Step-2: Preparation of 2-amino-5-(trifluoromethoxy)-1H-indole-3-carbonitrile (274c)

Compound 274c was prepared according to the procedure reported in step-1 of scheme-11, from 2,2,2-trifluoro-N-(2-iodo-4-(trifluoromethoxy)phenyl)acetamide (274b) (13.17 g, 33 mmol) in DMSO (40 mL) using malononitrile (2.62 g, 39.6 mmol), L-proline (0.760 g, 6.60 mmol), CuI (0.628 g, 3.30 mmol), a solution of $K_2CO_3$ (9.12 g, 66.0 mmol) in water (40 mL) and heating at 60° C. for 19 h under an argon atmosphere. This gave after workup and purification using flash column chromatography [$SiO_2$ gel (120 g), eluting with EtOAc in hexane from 0-66%] 2-amino-5-(trifluoromethoxy)-1H-indole-3-carbonitrile (274c) (4.7 g, 59% yield) as a yellow solid; $^1$H NMR (300 MHz, DMSO-$d_6$) δ 10.93 (s, 1H), 7.17 (d, J=8.5 Hz, 1H), 7.03-6.98 (m, 3H), 6.88-6.82 (m, 1H); $^{19}$F NMR (282 MHz, DMSO-$d_6$) δ −56.92; MS (ES+): 242.00 (M+1); MS (ES−): 240.00 (M−1).

Step-3: Preparation of 6-(trifluoromethoxy)-9H-pyrimido[4,5-b]indol-4-amine (274d)

Compound 274d was prepared according to the procedure reported in step-2 of scheme-29, from 2-amino-5-(trifluoromethoxy)-1H-indole-3-carbonitrile (274c) (4.5 g, 18.66 mmol) in ethanol (85 mL) using formamidine acetate (15.70 g, 149 mmol) and refluxing for 19 h. This gave after work up 6-(trifluoromethoxy)-9H-pyrimido[4,5-b]indol-4-amine (274d) (2.873 g) as a gray solid which was used as such for the next step; $^1$H NMR (300 MHz, DMSO-$d_6$) δ 12.06 (s, 1H), 8.42 (d, J=2.3 Hz, 1H), 8.27 (s, 1H), 7.50 (d, J=8.7 Hz, 1H), 7.39-7.29 (m, 3H); $^{19}$F NMR (282 MHz, DMSO-$d_6$) δ−56.94; MS (ES+): 269.10 (M+1); MS (ES−): 267.00 (M−1).

Step-4: Preparation of ethyl 2-(4-amino-6-(trifluoromethoxy)-9H-pyrimido[4,5-b]indol-9-yl)acetate (274e)

Compound 274e was prepared according to the procedure reported in step-1 of scheme-1, from 6-(trifluoromethoxy)-9H-pyrimido[4,5-b]indol-4-amine (274d) (1.2 g, 4.47 mmol) in DMF (25 mL) using ethyl 2-bromoacetate (0.546 mL, 4.92 mmol), $Cs_2CO_3$ (3.64 g, 11.19 mmol) and stirring at RT for 20 h. This gave after work up ethyl 2-(4-amino-6-(trifluoromethoxy)-9H-pyrimido[4,5-b]indol-9-yl)acetate (274e) (495 mg, 31% yield) as an off-white solid; $^1$H NMR (300 MHz, DMSO-$d_6$) δ 8.48 (d, J=2.3 Hz, 1H), 8.32 (s, 1H), 7.72 (d, J=8.9 Hz, 1H), 7.51 (s, 2H), 7.44-7.37 (m, 1H), 5.27 (s, 2H), 4.14 (q, J=7.1 Hz, 2H), 1.20 (t, J=7.1 Hz, 3H); $^{19}$F NMR (282 MHz, DMSO-$d_6$) δ−56.97; MS (ES+): 355.10 (M+1).

Step-5: Preparation of 2-(4-amino-6-(trifluoromethoxy)-9H-pyrimido[4,5-b]indol-9-yl)acetic acid (274f)

Compound 274f was prepared according to the procedure reported in step-4 of scheme-17, from ethyl 2-(4-amino-6-(trifluoromethoxy)-9H-pyrimido[4,5-b]indol-9-yl)acetate (274e) (400 mg, 1.129 mmol) in THF (6 mL) and MeOH (6 mL) using a solution of lithium hydroxide hydrate (290 mg, 6.77 mmol) in water (6 mL) and stirring at RT for 17 h. This gave after work up 2-(4-amino-6-(trifluoromethoxy)-9H-pyrimido[4,5-b]indol-9-yl)acetic acid (274f) (356 mg, 97% yield): $^1$H NMR (300 MHz, DMSO-$d_6$) δ 13.09 (s, 1H), 8.49-8.46 (m, 1H), 8.32 (s, 1H), 7.71 (d, J=8.9 Hz, 1H), 7.49 (s, 2H), 7.43-7.37 (m, 1H), 5.17 (s, 2H); $^{19}$F NMR (282 MHz, DMSO-$d_6$) δ−56.96; MS (ES+): 327.10 (M+1); MS (ES−): 325.10 (M−1).

Step-6: Preparation of (1R,3S,5R)-2-(2-(4-amino-6-(trifluoromethoxy)-9H-pyrimido[4,5-b]indol-9-yl)acetyl)-N-(6-bromopyridin-2-yl)-2-azabicyclo[3.1.0]hexane-3-carboxamide (274 g)

Compound 274g was prepared according to the procedure reported in step-3 of scheme-1, from 2-(4-amino-6-(trifluoromethoxy)-9H-pyrimido[4,5-b]indol-9-yl)acetic acid (274f) (75 mg, 0.230 mmol) in DMF (10 mL) using HCl salt of (1R,3S,5R)—N-(6-bromopyridin-2-yl)-2-azabicyclo[3.1.0]hexane-3-carboxamide (4a) (88 mg, 0.276 mmol), HATU (175 mg, 0.460 mmol), DIPEA (0.160 mL, 0.92 mmol) and stirring at RT for 23 h. This gave after workup and purification by flash column chromatography [silica gel (25 g), eluting with MeOH in DCM from 0-5%] followed by purification using reverse phase column chromatography [C18 column (100 g), eluting with ACN in water (containing 0.1% HCl) from 0-100%] (1R,3S,5R)-2-(2-(4-amino-6-(trifluoromethoxy)-9H-pyrimido[4,5-b]indol-9-yl)acetyl)-N-(6-bromopyridin-2-yl)-2-azabicyclo[3.1.0]hexane-3-carboxamide (274 g) (87 mg, 64% yield) HCl salt as a white solid; $^1$H NMR (300 MHz, DMSO-$d_6$) δ 10.77 (s, 1H), 8.83 (s, 2H), 8.71-8.64 (m, 2H), 8.00 (d, J=8.2 Hz, 1H), 7.82 (d, J=9.0 Hz, 1H), 7.70 (t, J=8.0 Hz, 1H), 7.62-7.54 (m, 1H), 7.32 (d, J=7.7 Hz, 1H), 5.81 (d, J=17.4 Hz, 1H), 5.45 (d, J=17.3 Hz, 1H), 4.41 (dd, J=9.1, 5.5 Hz, 11H), 3.99-3.84 (m, 1H), 2.41-2.14 (m, 2H), 2.03-1.77 (m, 1H), 1.16-0.99 (m, 1H), 0.85-0.71 (m, 1H); $^{19}F$ NMR (282 MHz, DMSO-$d_6$) δ-57.02; MS (ES+): 590.10 & 592.10 (M+1); MS (ES−): 588.00 & 590.00 (M−1); Analysis calculated for $C_{24}H_{19}BrF_3N_7O_3 \cdot HCl \cdot H_2O$: C, 44.70; H, 3.44; N, 15.21; Cl, 5.50. Found: C, 44.48; H, 3.23; N, 15.18; Cl, 5.42.

Scheme 275

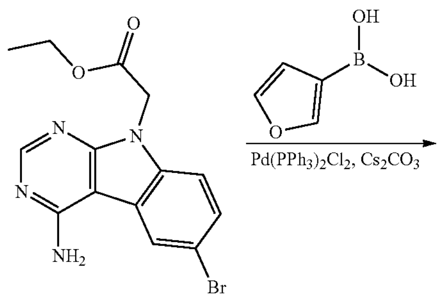

48a

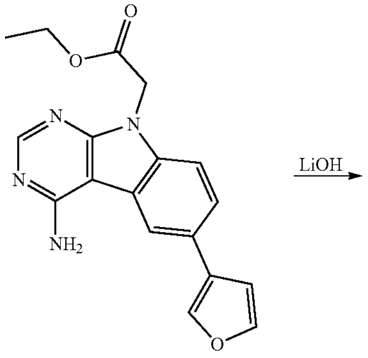

275a

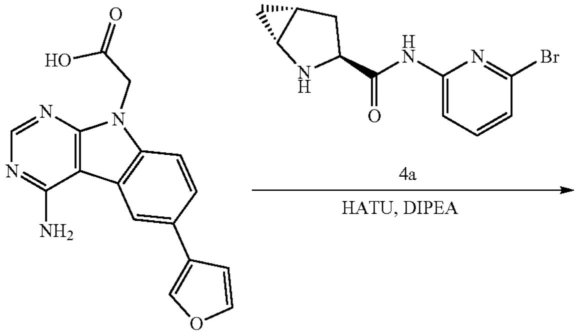

4a

275b

-continued

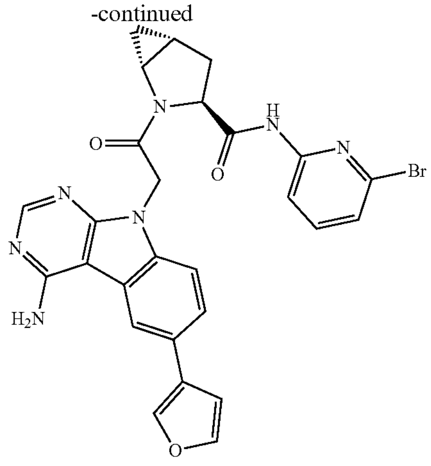

275c

Preparation of (1R,3S,5R)-2-(2-(4-amino-6-(furan-3-yl)-9H-pyrimido[4,5-b]indol-9-yl)acetyl)-N-(6-bromopyridin-2-yl)-2-azabicyclo[3.1.0]hexane-3-carboxamide (275c)

Step-1: Preparation of ethyl 2-(4-amino-6-(furan-3-yl)-9H-pyrimido[4,5-b]indol-9-yl)acetate (275a)

Compound 275a was prepared according to the procedure reported in step-1 of scheme-62, from ethyl 2-(4-amino-6-bromo-9H-pyrimido[4,5-b]indol-9-yl)acetate (48a) (200 mg, 0.573 mmol) in dioxane (18 mL) using furan-3-ylboronic acid (96 mg, 0.859 mmol), bis(triphenylphosphine) palladium(II) chloride (80 mg, 0.115 mmol) a solution of cesium carbonate (280 mg, 0.859 mmol) in water (2.2 mL) and heating at 100° C. for 19 h. This gave after workup a mixture of ethyl 2-(4-amino-6-(furan-3-yl)-9H-pyrimido[4,5-b]indol-9-yl)acetate (275a) and 2-(4-amino-6-(furan-3-yl)-9H-pyrimido[4,5-b]indol-9-yl)acetic acid (275b) which was used as such for the next step; MS (ES+): 337.10 (M+1) and MS (ES+): 309.10 (M+1).

Step-2: Preparation of 2-(4-amino-6-(furan-3-yl)-9H-pyrimido[4,5-b]indol-9-yl)acetic acid (275b)

Compound 275b was prepared according to the procedure reported in step-4 of scheme-17, from the above mixture of ethyl 2-(4-amino-6-(furan-3-yl)-9H-pyrimido[4,5-b]indol-9-yl)acetate (275a) and 2-(4-amino-6-(furan-3-yl)-9H-pyrimido[4,5-b]indol-9-yl)acetic acid (275b) (0.573 mmol) in THF (5 mL) and methanol (5 mL) using a solution of lithium hydroxide hydrate (147 mg, 3.44 mmol) in water (5 mL) and stirring at RT for 18 h. This gave after work up 2-(4-amino-6-(furan-3-yl)-9H-pyrimido[4,5-b]indol-9-yl)acetic acid (275b) (166 mg, 94% yield) which was used as such for the next step; MS (ES+): 309.10 (M+1).

Step-3: Preparation of (1R,3S,5R)-2-(2-(4-amino-6-(furan-3-yl)-9H-pyrimido[4,5-b]indol-9-yl)acetyl)-N-(6-bromopyridin-2-yl)-2-azabicyclo[3.1.0]hexane-3-carboxamide (275c)

Compound 275c was prepared according to the procedure reported in step-3 of scheme-1, from 2-(4-amino-6-(furan-3-yl)-9H-pyrimido[4,5-b]indol-9-yl)acetic acid (275b) (78 mg, 0.253 mmol) in DMF (10 mL) using HCl salt of (1R,3S,5R)—N-(6-bromopyridin-2-yl)-2-azabicyclo[3.1.0]hexane-3-carboxamide (4a) (97 mg, 0.304 mmol), HATU (192 mg, 0.506 mmol), DIPEA (0.176 mL, 1.012 mmol) and stirring at RT for 13 h. This gave after workup and purification using flash column chromatography [silica gel (12 g), eluting with MeOH in DCM from 0-5%] followed by purification using reverse phase column chromatography [C18 column (50 g), eluting with ACN in water (containing 0.1% HCl) from 0-100%] (1R,3S,5R)-2-(2-(4-amino-6-(furan-3-yl)-9H-pyrimido[4,5-b]indol-9-yl)acetyl)-N-(6-bromopyridin-2-yl)-2-azabicyclo[3.1.0]hexane-3-carboxamide (275c) (10 mg, 7% yield) HCl salt as a light yellow solid; $^1$H NMR (300 MHz, DMSO-$d_6$) δ 10.77 (s, 1H), 8.69 (s, 1H), 8.64-8.48 (m, 3H), 8.26 (s, 1H), 8.01 (d, J=8.1 Hz, 1H), 7.86-7.81 (m, 1H), 7.79 (t, J=1.7 Hz, 1H), 7.74-7.66 (m, 2H), 7.34-7.29 (m, 1H), 7.18-7.16 (m, 1H), 5.75 (d, J=17.3 Hz, 1H), 5.42 (d, J=17.3 Hz, 1H), 4.42 (dd, J=9.0, 5.6 Hz, 1H), 3.98-3.81 (m, 1H), 2.42-2.13 (m, 2H), 2.00-1.83 (m, 1H), 1.14-1.01 (m, 1H), 0.83-0.69 (m, 1H); MS (ES+): 572.10 & 574.10 (M+1); MS (ES−): 570.10 & 572.10 (M−1).

Scheme 276

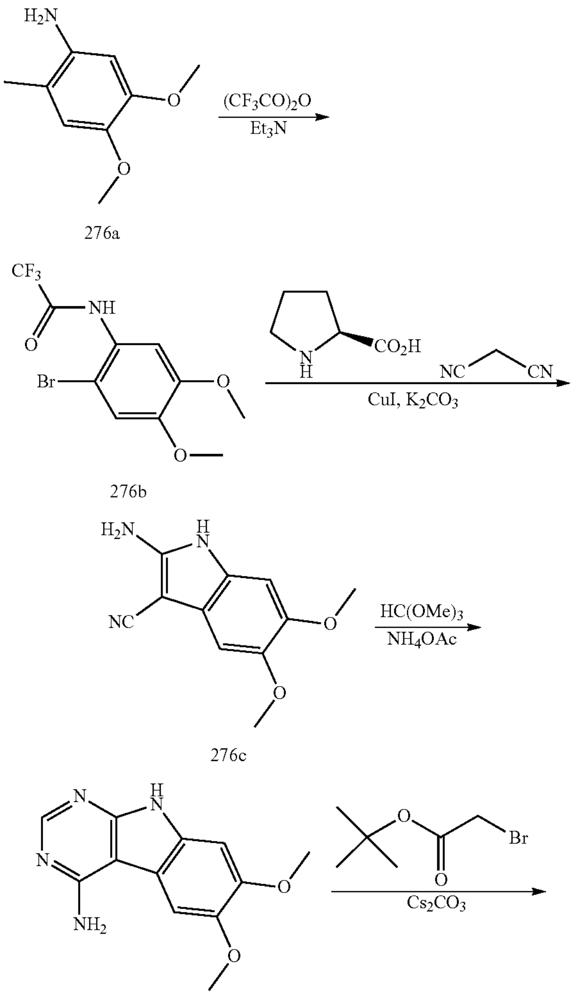

276a

276b

276c

276d

-continued

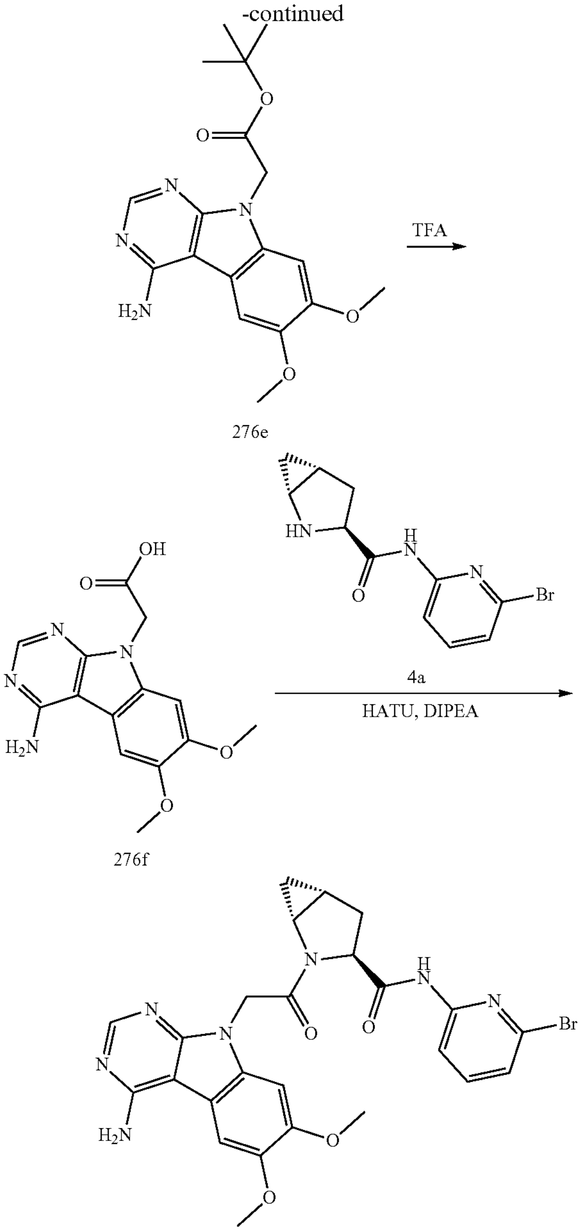

276e

276f

276g

Preparation of (1R,3S,5R)-2-(2-(4-amino-6,7-dimethoxy-9H-pyrimido[4,5-b]indol-9-yl)acetyl)-N-(6-bromopyridin-2-yl)-2-azabicyclo[3.1.0]hexane-3-carboxamide (276 g)

Step-1: Preparation of N-(2-bromo-4,5-dimethoxyphenyl)-2,2,2-trifluoroacetamide (276b)

Compound 276b was prepared according to the procedure reported in step-1 of scheme-46, from 2-bromo-4,5-dimethoxyaniline (276a) (5 g, 21.54 mmol; CAS #16791-41-6) in DCM (75 mL) using triethylamine (5.10 mL, 36.6 mmol), trifluoroacetic acid anhydride (4.49 mL, 32.3 mmol) and stirring at RT for 16 h. This gave after workup and purification by flash column chromatography [silica gel (40 g), eluting with EtOAc in hexane from 0-50%] N-(2-bromo-4, 5-dimethoxyphenyl)-2,2,2-trifluoroacetamide (276b) (1.49 g, 21% yield) as a pale-yellow solid which was used as such for next step: 1H NMR (300 MHz, DMSO-$d_6$) δ 11.13 (s, 1H), 7.26 (s, 1H), 7.05 (s, 1H), 3.81 (s, 3H), 3.76 (s, 3H); MS (ES+): 327.90 (M+1).

Step-2: Preparation of 2-amino-5,6-dimethoxy-1H-indole-3-carbonitrile (276c)

Compound 276c was prepared according to the procedure reported in step-1 of scheme-11, from N-(2-bromo-4,5-dimethoxyphenyl)-2,2,2-trifluoroacetamide (276b) (1.45 g, 4.42 mmol) in DMSO (5 mL) using malononitrile (0.334 mL, 5.30 mmol), L-proline (0.102 g, 0.884 mmol), CuI (84 mg, 0.442 mmol), a solution of $K_2CO_3$ (1.222 g, 8.84 mmol) in water (5 mL) and heating at 60° C. for 16 h under an argon atmosphere. This gave after workup and purification [sili-cagel (40 g), eluting with EtOAc in hexane from 0-50%] 2-amino-5,6-dimethoxy-1H-indole-3-carbonitrile (276c) (457 mg, 48% yield) as a yellow solid; $^1$H NMR (300 MHz, DMSO-$d_6$) δ 10.38 (s, 1H), 6.80 (s, 1H), 6.71 (s, 1H), 6.48 (s, 21H), 3.74 (s, 3H), 3.71 (s, 3H); MS (ES+): 218.10 (M+1).

Step-3: Preparation of 6,7-dimethoxy-9H-pyrimido[4,5-b]indol-4-amine (276d)

Compound 276d was prepared according to the procedure reported in step-2 of scheme-29, from 2-amino-5,6-dimethoxy-1H-indole-3-carbonitrile (276c) (0.45 g, 2.072 mmol) in ethanol (5 mL) using trimethyl orthoformate (2.266 mL, 20.72 mmol), $NH_4OAC$ (0.479 g, 6.21 mmol) and heating at 90° C. for 16 h. This gave after work up and purification using reverse phase column chromatography [C18 column (50 g), eluting with ACN in water (containing 0.1% HCl) from 0-100%] 6,7-dimethoxy-9H-pyrimido[4,5-b]indol-4-amine (276d) (282 mg, 49% yield) HCl salt as a pale-yellow solid; $^1$H NMR (300 MHz, DMSO-$d_6$) δ 12.87 (s, 1H), 8.70-8.55 (m, 2H), 8.49 (s, 1H), 8.03 (s, 1H), 7.11 (s, 1H), 3.89 (s, 3H), 3.88 (s, 3H); MS (ES+): 245.10 (M+1).

Step-4: Preparation of tert-butyl 2-(4-amino-6,7-dimethoxy-9H-pyrimido[4,5-b]indol-9-yl)acetate (276e)

Compound 276e was prepared according to the procedure reported in step-1 of scheme-1, from HCl salt of 6,7-dimethoxy-9H-pyrimido[4,5-b]indol-4-amine (276d) (275 mg, 0.980 mmol) in DMF (7 mL) using tert-butyl 2-bromoacetate (0.159 mL, 1.078 mmol), $Cs_2CO_3$ (702 mg, 2.155 mmol) and stirring at RT for 16 h. This gave after work up and purification using reverse phase column chromatography [C18 column (50 g), eluting with ACN in water (containing 0.1% HCl) from 0-100%] tert-butyl 2-(4-amino-6,7-dimethoxy-9H-pyrimido[4,5-b]indol-9-yl)acetate (276e) (283 mg, 81% yield) as a pale yellow solid; 1H NMR (300 MHz, DMSO-$d_6$) δ 8.63 (s, 2H), 8.54 (s, 1H), 8.06 (s, 1H), 7.47 (s, 1H), 5.28 (s, 2H), 3.90 (s, 3H), 3.88 (s, 3H), 1.42 (s, 9H); MS (ES+): 359.2 (M+1).

Step-5: Preparation of 2-(4-amino-6,7-dimethoxy-9H-pyrimido[4,5-b]indol-9-yl)acetic acid (276f)

Compound 276f was prepared according to the procedure reported in step-2 of scheme-1, from tert-butyl 2-(4-amino-6,7-dimethoxy-9H-pyrimido[4,5-b]indol-9-yl)acetate (276e) (270 mg, 0.753 mmol) using 20% TFA in DCM (4324 μL, 11.30 mmol) and stirring at RT for 16 h. This gave after work up TFA salt of 2-(4-amino-6,7-dimethoxy-9H-pyrimido[4,5-b]indol-9-yl)acetic acid (2760 (311 mg, 99% yield) as a pale-yellow solid; $^1$H NMR (300 MHz, DMSO-$d_6$) δ 8.50 (s, 1H), 8.47 (s, 2H), 8.03 (s, 1H), 7.51 (s, 1H), 5.27 (s, 2H), 3.89 (s, 3H), 3.89 (s, 3H); MS (ES+): 303.1 (M+1).

Step-6: Preparation of (1R,3S,5R)-2-(2-(4-amino-6,7-dimethoxy-9H-pyrimido[4,5-b]indol-9-yl)acetyl)-N-(6-bromopyridin-2-yl)-2-azabicyclo[3.1.0]hexane-3-carboxamide (276 g)

Compound 276g was prepared according to the procedure reported in step-3 of scheme-1, from TFA salt of 2-(4-amino-6,7-dimethoxy-9H-pyrimido[4,5-b]indol-9-yl)acetic acid (276f) (65.3 mg, 0.157 mmol) in DMF (1.5 mL) using HCl salt of (1R,3S,5R)—N-(6-bromopyridin-2-yl)-2-azabicyclo[3.1.0]hexane-3-carboxamide (4a) (50 mg, 0.157 mmol), HATU (90 mg, 0.235 mmol), DIPEA (0.137 mL, 0.785 mmol) and stirring at RT for 16 h. This gave after work up and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6,7-dimethoxy-9H-pyrimido[4,5-b]indol-9-yl)acetyl)-N-(6-bromopyridin-2-yl)-2-azabicyclo[3.1.0]hexane-3-carboxamide (276 g) (68 mg, 76% yield) HCl salt as a white solid; 1H NMR (300 MHz, DMSO-$d_6$) δ 10.73 (s, 1H, $D_2O$ exchangeable), 8.69 (s, 2H, $D_2O$ exchangeable), 8.55 (s, 1H), 8.06 (s, 1H), 8.01 (d, J=8.2 Hz, 1H), 7.72 (t, J=8.0 Hz, 1H), 7.36-7.29 (m, 2H), 5.72 (d, J=17.3 Hz, 1H), 5.46 (d, J=17.2 Hz, 1H), 4.42 (dd, J=9.1, 5.7 Hz, 1H), 3.93-3.89 (m, 7H), 2.35 (dd, J=13.4, 9.2 Hz, 1H), 2.29-2.14 (m, 1H), 1.98-1.85 (m, 1H), 1.08 (dt, J=8.3, 5.4 Hz, 1H), 0.75 (td, J=5.2, 2.4 Hz, 1H). MS (ES+): 566.1/568.1 (M+1); (ES−): 564.1/566.1 (M−1); Analysis calculated for $C_{25}H_{24}BrN_7O_4 \cdot 2.5H_2O \cdot 1.25HCl$: C, 45.70; H, 4.64; Cl, 6.75; N, 14.92. Found: C, 45.82; H, 4.63; Cl, 6.58; N, 14.82.

Scheme 277

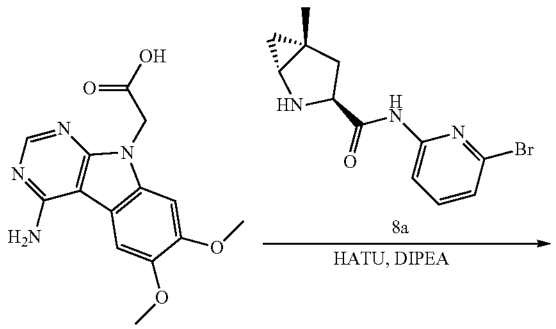

276f

-continued

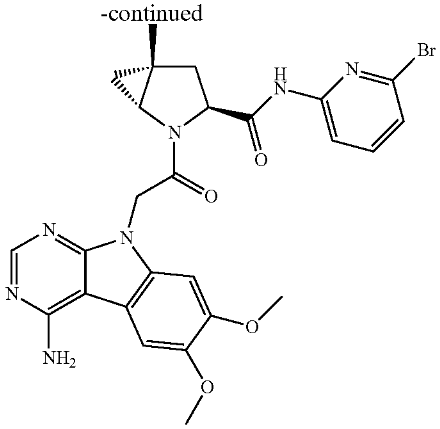

277a

Preparation of (1R,3S,5R)-2-(2-(4-amino-6,7-dimethoxy-9H-pyrimido[4,5-b]indol-9-yl)acetyl)-N-(6-bromopyridin-2-yl)-5-methyl-2-azabicyclo[3.1.0]hexane-3-carboxamide (277a)

Compound 277a was prepared according to the procedure reported in step-3 of scheme-1, from TFA salt of 2-(4-amino-6,7-dimethoxy-9H-pyrimido[4,5-b]indol-9-yl)acetic acid (276f) (65.1 mg, 0.156 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (52 mg, 0.156 mmol), HATU (89 mg, 0.234 mmol), DIPEA (0.136 mL, 0.782 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6,7-dimethoxy-9H-pyrimido[4,5-b]indol-9-yl)acetyl)-N-(6-bromopyridin-2-yl)-5-methyl-2-azabicyclo[3.1.0]hexane-3-carboxamide (277a) (51 mg, 56% yield) HCl salt as a white solid; 1H NMR (300 MHz, DMSO-$d_6$) δ 10.72 (s, 1H, $D_2O$ exchangeable), 8.70 (s, 2H, $D_2O$ exchangeable), 8.55 (s, 1H), 8.10-7.91 (m, 2H), 7.71 (t, J=8.0 Hz, 1H), 7.38-7.29 (m, 2H), 5.68 (d, J=17.3 Hz, 1H), 5.40 (d, J=17.2 Hz, 1H), 4.37 (dd, J=9.1, 6.1 Hz, 1H), 3.89 (s, 6H), 3.69 (dd, J=5.6, 2.4 Hz, 1H), 2.59-2.54 (m, 1H), 2.00 (dd, J=13.3, 6.0 Hz, 1H), 1.32 (s, 3H), 1.08-0.96 (m, 1H), 0.96-0.82 (m, 1H). MS (ES+): 580.1/582.1 (M+1): (ES−): 578.1/580.1 (M−1): Analysis calculated for $C_{26}H_{26}BrN_7O_4$ $2.75H_2O{\cdot}HCl$: C, 46.86; H, 4.92; Cl, 5.32; N, 14.71. Found: C, 46.80; H, 4.88; Cl, 5.17: N, 14.55.

Scheme 278

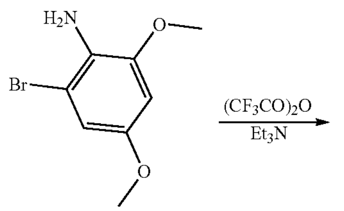

278a

-continued

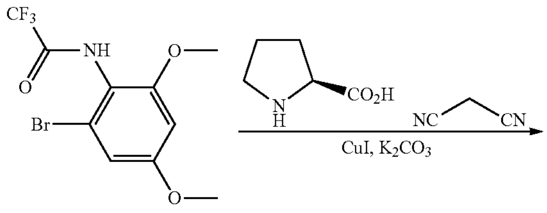

278b

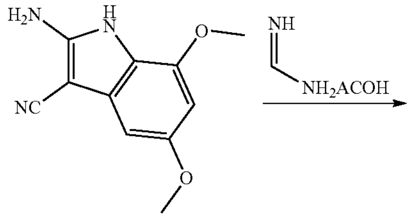

278c

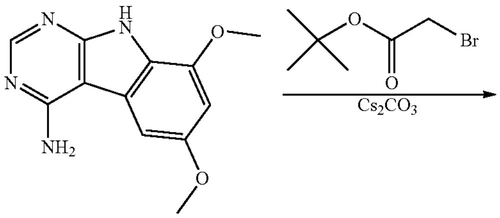

278d

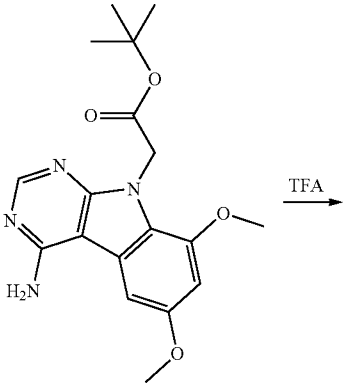

276e

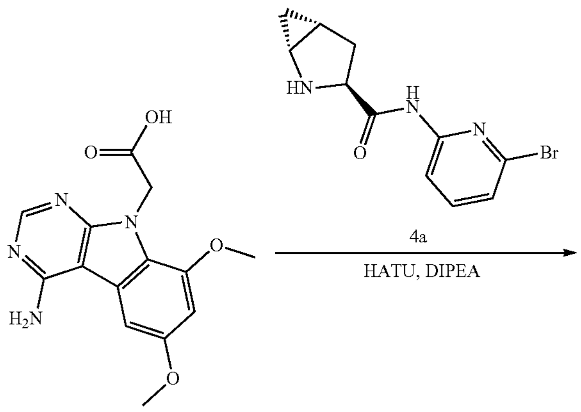

278f

-continued

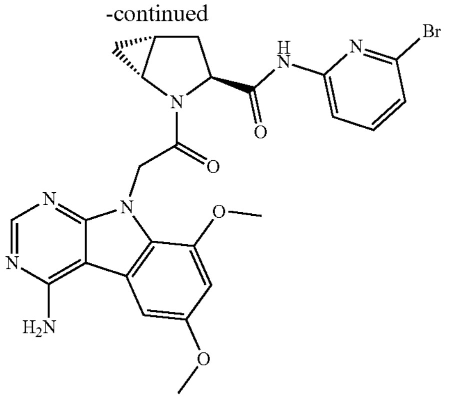

278g

Preparation of (1R,3S,5R)-2-(2-(4-amino-6,8-dimethoxy-9H-pyrimido[4,5-b]indol-9-yl)acetyl)-N-(6-bromopyridin-2-yl)-2-azabicyclo[3.1.0]hexane-3-carboxamide (278 g)

Step-1: Preparation of N-(2-bromo-4,6-dimethoxyphenyl)-2,2,2-trifluoroacetamide (278b)

Compound 278b was prepared according to the procedure reported in step-1 of scheme-46, from 2-bromo-4,6-dimethoxyaniline (278a) (1 g, 4.31 mmol: CAS #197803-53-5) in DCM (15 mL) using triethylamine (1.021 mL, 7.33 mmol), trifluoroacetic acid anhydride (0.898 mL, 6.46 mmol) and stirring at RT for 16 h. This gave after workup and purification by flash column chromatography [silicagel (24 g), eluting with EtOAc in hexane from 0-50%] N-(2-bromo-4,6-dimethoxyphenyl)-2,2,2-trifluoroacetamide (278b) (0.89 g, 63% yield) as a pale yellow solid; 1H NMR (300 MHz, DMSO-$d_6$) δ 10.81 (s, 1H), 6.89 (d, J=2.5 Hz, 1H), 6.72 (d, J=2.6 Hz, 1H), 3.82 (s, 3H), 3.79 (s, 3H); MS (ES+): 327.91 (M+1).

Step-2: Preparation of 2-amino-5,7-dimethoxy-1H-indole-3-carbonitrile (278c)

Compound 278c was prepared according to the procedure reported in step-1 of scheme-11, from N-(2-bromo-4,6-dimethoxyphenyl)-2,2,2-trifluoroacetamide (278b) (0.87 g, 2.65 mmol) in DMSO (3 mL) and using malononitrile (0.200 mL, 3.18 mmol), L-proline (0.061 g, 0.530 mmol), CuI (51 mg, 0.265 mmol), a solution of $K_2CO_3$ (0.733 g, 5.30 mmol) in water (3 mL) and heating at 60° C. for 16 h under an argon atmosphere. This gave after workup and purification [silica gel (40 g), eluting with EtOAc in hexane from 0-50%] 2-amino-5,7-dimethoxy-1H-indole-3-carbonitrile (278c) (279 mg, 48% yield) as a yellow solid: 1H NMR (300 MHz, DMSO-$d_6$) δ 10.63 (s, 1H), 6.31 (d, J=2.1 Hz, 1H), 6.29 (s, 2H), 6.21 (d, J=2.1 Hz, 1H), 3.83 (s, 3H), 3.73 (s, 3H); MS (ES+): 218.1 (M+1); (ES−): 216.0 (M−1).

Step-3: Preparation of 6,8-dimethoxy-9H-pyrimido[4,5-b]indol-4-amine (278d)

Compound 278d was prepared according to the procedure reported in step-2 of scheme-29, from 2-amino-5,7-dimethoxy-1H-indole-3-carbonitrile (278c) (0.270 g, 1.243 mmol) in ethanol (20 mL) using formamidine acetate (1046 mg, 9.94 mmol) and refluxing for 22 h. This gave after work up 6,8-dimethoxy-9H-pyrimido[4,5-b]indol-4-amine (278d) (206 mg, 68% yield) as a pale-yellow solid; $^1$H NMR (300 MHz, DMSO-$d_6$) δ 11.72 (s, 1H), 8.18 (s, 1H), 7.43 (d, J=2.0 Hz, 1H), 7.12 (s, 2H), 6.60 (d, J=2.0 Hz, 1H), 3.92 (s, 3H), 3.85 (s, 3H); MS (ES+): 245.1 (M+1).

Step-4: Preparation of tert-butyl 2-(4-amino-6,8-dimethoxy-9H-pyrimido[4,5-b]indol-9-yl)acetate (278e)

Compound 278e was prepared according to the procedure reported in step-1 of scheme-1, from 6,8-dimethoxy-9H-pyrimido[4,5-b]indol-4-amine (278d) (200 mg, 0.819 mmol) in DMF (6 mL) using tert-butyl 2-bromoacetate (0.133 mL, 0.901 mmol), $Cs_2CO_3$ (400 mg, 1.228 mmol) and stirring at RT for 16 h. This gave after work up and purification using reverse phase column chromatography [C18 column (50 g), eluting with ACN in water (containing 0.1% HCl) from 0-100%] tert-butyl 2-(4-amino-6,8-dimethoxy-9H-pyrimido[4,5-b]indol-9-yl)acetate (278e) (198 mg, 68% yield) as a pale yellow solid: $^1$H NMR (300 MHz, DMSO-$d_6$) δ 8.32 (s, 1H), 7.67 (s, 2H), 7.51 (d, J=2.0 Hz, 1H), 6.67 (d, J=2.0 Hz, 1H), 5.15 (s, 2H), 3.87 (s, 6H), 1.42 (s, 9H); MS (ES+): 359.1 (M+1).

Step-5: Preparation of 2-(4-amino-6,8-dimethoxy-9H-pyrimido[4,5-b]indol-9-yl)acetic acid (278f)

Compound 278f was prepared according to the procedure reported in step-2 of scheme-1, from tert-butyl 2-(4-amino-6,8-dimethoxy-9H-pyrimido[4,5-b]indol-9-yl)acetate (278e) (175 mg, 0.488 mmol) using 20% TFA in DCM (2803 μL, 7.32 mmol) and stirring at RT for 16 h. This gave after work up and purification TFA salt of 2-(4-amino-6,8-dimethoxy-9H-pyrimido[4,5-b]indol-9-yl)acetic acid (278f) (225 mg, 97% yield) as a pale-yellow solid; $^1$H NMR (300 MHz, DMSO-$d_6$) δ 8.51 (s, 1H), 8.44 (s, 2H), 7.59 (d, J=2.0 Hz, 1H), 6.76 (d, J=2.0 Hz, 1H), 5.27 (s, 2H), 3.90 (s, 3H), 3.89 (s, 3H); MS (ES+): 303.1 (M+1).

Step-6: Preparation of (1R,3S,5R)-2-(2-(4-amino-6,8-dimethoxy-9H-pyrimido[4,5-b]indol-9-yl)acetyl)-N-(6-bromopyridin-2-yl)-2-azabicyclo[3.1.0]hexane-3-carboxamide (278 g)

Compound 278g was prepared according to the procedure reported in step-3 of scheme-1, from TFA salt of 2-(4-amino-6,8-dimethoxy-9H-pyrimido[4,5-b]indol-9-yl)acetic acid (278f) (74.3 mg, 0.157 mmol) in DMF (1.5 mL) using HCl salt of (1R,3S,5R)—N-(6-bromopyridin-2-yl)-2-azabicyclo[3.1.0]hexane-3-carboxamide (4a) (50 mg, 0.157 mmol), HATU (90 mg, 0.235 mmol), DIPEA (0.137 mL, 0.785 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6,8-dimethoxy-9H-pyrimido[4,5-b]indol-9-yl)acetyl)-N-(6-bromopyridin-2-yl)-2-azabicyclo[3.1.0]hexane-3-carboxamide (278 g) (63 mg, 71% yield) HCl salt as a white solid; $^1$H NMR (300 MHz, DMSO-$d_6$) δ 10.74 (s, 1H, $D_2O$ exchangeable), 8.68 (s, 2H, $D_2O$ exchangeable), 8.57 (s, 1H), 8.02 (d, J=8.2 Hz, 1H), 7.71 (t, J=8.0 Hz, 1H), 7.61 (d, J=2.0 Hz, 1H), 7.32 (d, J=7.7 Hz, 1H), 6.75 (d, J=2.0 Hz, 1H), 5.75 (d, J 17.0 Hz, 1H), 5.53 (d, J=16.9 Hz, 1H), 4.43 (dd, J=8.9, 5.6 Hz, 1H), 3.91 (s, 3H), 3.88 (s, 3H), 3.86-3.78 (m, 1H), 2.39-2.14 (m, 2H), 2.00-1.85 (m, 1H), 1.15-1.05 (m, 1H), 0.71-0.60 (m, 1H). MS (ES+): 566.1/568.1 (M+1): (ES−): 564.1/566.1 (M−1); Analysis calculated for $C_{25}H_{24}BrN_7O_4{\cdot}1.5H_2O{\cdot}1.15HCl$: C, 47.26; H, 4.47; Cl, 6.42. N, 15.43. Found: C, 47.47; H, 4.81; Cl, 6.46; N, 15.10.

Scheme 279

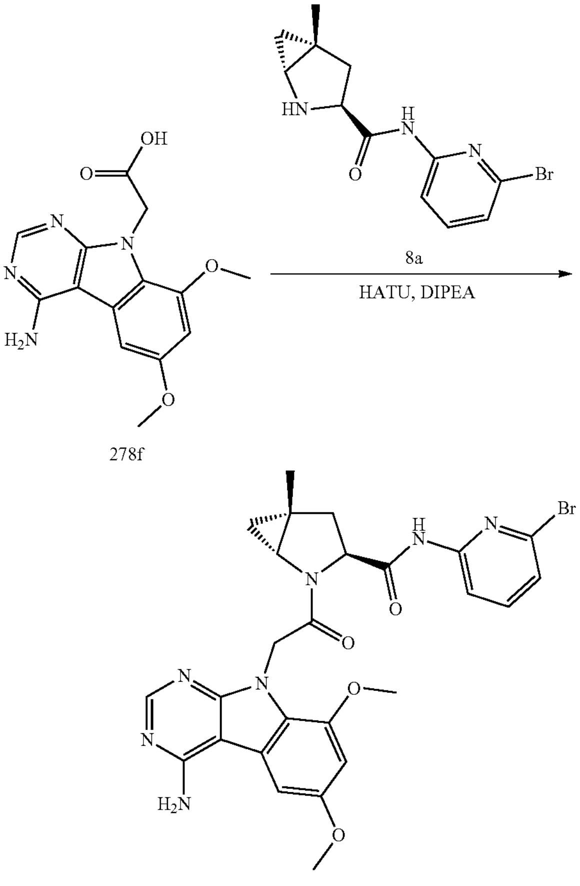

278f

279a

Step-6: Preparation of (1R,3S,5R)-2-(2-(4-amino-6,8-dimethoxy-9H-pyrimido[4,5-b]indol-9-yl)acetyl)-N-(6-bromopyridin-2-yl)-5-methyl-2-azabicyclo[3.1.0]hexane-3-carboxamide (279a)

Compound 279a was prepared according to the procedure reported in step-3 of scheme-1, from TFA salt of 2-(4-amino-6,8-dimethoxy-9H-pyrimido[4,5-b]indol-9-yl)acetic acid (278f) (74.3 mg, 0.157 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (52.2 mg, 0.157 mmol), HATU (90 mg, 0.236 mmol), DIPEA (0.137 mL, 0.785 mmol) and stirring at RT for 16 h. This gave after workup and purification by flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6,8-dimethoxy-9H-pyrimido[4,5-b]indol-9-yl)acetyl)-N-(6-bromopyridin-2-yl)-5-methyl-2-azabicyclo[3.1.0]hexane-3-carboxamide (279a) (53 mg, 58% yield) HCl salt as a white solid: $^1H$ NMR (300 MHz, DMSO-$d_6$) δ 10.74 (s, 1H, $D_2O$ exchangeable), 8.68 (s, 2H, $D_2O$ exchangeable), 8.56 (s, 1H), 8.02 (d, J=8.2 Hz, 1H), 7.71 (t, J=8.0 Hz, 1H), 7.60 (s, 1H), 7.32 (d, J=7.7 Hz, 1H), 6.75 (s, 1H), 5.70 (d, J=17.0 Hz, 1H), 5.48 (d, J=17.0 Hz, 1H), 4.38 (dd, J=8.9, 5.9 Hz, 1H), 3.90 (s, 3H), 3.88 (s, 3H), 3.63-3.58 (m, 1H), 2.48-2.36 (m, 1H), 1.99 (dd, J=13.4, 5.8 Hz, 1H), 1.31 (s, 3H), 1.08-1.01 (m, 1H), 0.88-0.78 (m, 1H). MS (ES+): 580.2/582.1 (M+1); (ES−): 578.1/580.1 (M−1); Analysis calculated for $C_{26}H_{26}BrN_7O_4{\cdot}2H_2O{\cdot}1.1HCl$: C, 47.56; H, 4.77; Cl, 5.94; N, 14.93. Found: C, 47.47; H, 4.81; Cl, 5.88; N, 14.86.

Scheme 280

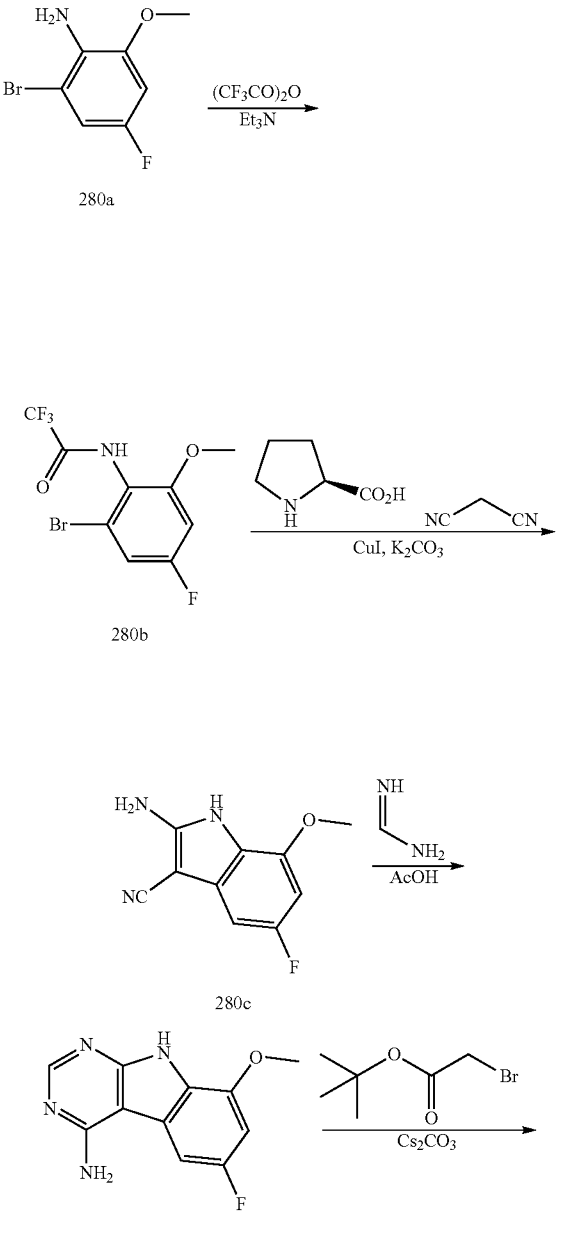

280a

280b

280c

280d

-continued

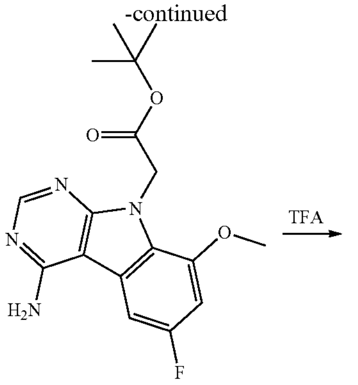

280e

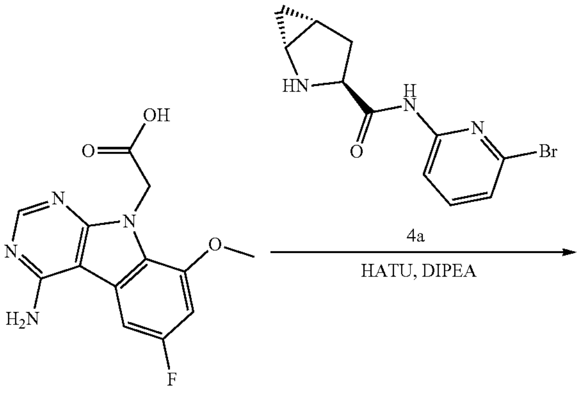

280f

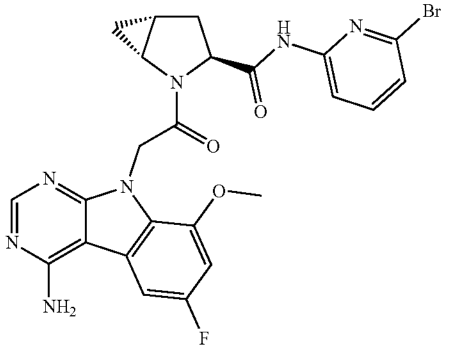

280g

Preparation of (1R,3S,5R)-2-(2-(4-amino-6-fluoro-8-methoxy-9H-pyrimido[4,5-b]indol-9-yl)acetyl)-N-(6-bromopyridin-2-yl)-2-azabicyclo[3.1.0]hexane-3-carboxamide (280 g)

Step-1: Preparation of N-(2-bromo-4-fluoro-6-methoxyphenyl)-2,2,2-trifluoroacetamide (280b)

Compound 280b was prepared according to the procedure reported in step-1 of scheme-46, from 2-bromo-4-fluoro-6-methoxyaniline (280a) (I g, 4.54 mmol; CAS #354574-32-6) in DCM (15 mL) using triethylamine (1.077 mL, 7.73 mmol), trifluoroacetic acid anhydride (0.948 mL, 6.82 mmol) and stirring at RT for 16 h. This gave after workup and purification using flash column chromatography [silica-gel (24 g), eluting with EtOAc in hexane from 0-50%] N-(2-bromo-4-fluoro-6-methoxyphenyl)-2,2,2-trifluoroacetamide (280b) (1.25 g, 87% yield) as a pale yellow solid; 1H NMR (300 MHz, DMSO-$d_6$) δ 11.01 (s, 1H), 7.30 (dd, J=8.2, 2.7 Hz, 1H), 7.18 (dd, J=10.8, 2.7 Hz, 1H), 3.83 (s, 3H); MS (ES+): 315.90 (M+1).

Step-2: Preparation of 2-amino-5-fluoro-7-methoxy-1H-indole-3-carbonitrile (280c)

Compound 280c was prepared according to the procedure reported in step-1 of scheme-11, from N-(2-bromo-4-fluoro-6-methoxyphenyl)-2,2,2-trifluoroacetamide (280b) (1.22 g, 3.86 mmol) in DMSO (5 mL) using malononitrile (0.292 mL, 4.63 mmol), L-proline (0.089 g, 0.772 mmol), CuI (74 mg, 0.386 mmol), a solution of $K_2CO_3$ (1.067 g, 7.72 mmol) in water (5 mL) and heating at 60° C. for 16 h under an argon atmosphere. This gave after workup and purification [sili-cagel (40 g), eluting with EtOAc in hexane from 0-50%] 2-amino-5-fluoro-7-methoxy-1H-indole-3-carbonitrile (280c) (538 mg, 68% yield) as a yellow solid; $^1$H NMR (300 MHz, DMSO-$d_6$) δ 10.90 (s, 1H), 6.60-6.40 (m, 4H), 3.87 (s, 3H); MS (ES+): 206.10 (M+1): (ES−): 204.10 (M−1).

Step-3: Preparation of 6-fluoro-8-methoxy-9H-pyrimido[4,5-b]indol-4-amine (280d)

Compound 280d was prepared according to the procedure reported in step-2 of scheme-29, from 2-amino-5-fluoro-7-methoxy-1H-indole-3-carbonitrile (280c) (0.520 g, 2.53 mmol) in ethanol (30 mL) using formamidine acetate (2132 mg, 20.27 mmol) and refluxing for 22 h. This gave after work up AcOH salt of 6-fluoro-8-methoxy-9H-pyrimido[4,5-b]indol-4-amine (280d) (665 mg, 90% yield) as a pale-yellow solid; $^1$H NMR (300 MHz, DMSO-$d_6$) δ 10.00 (s, 1H), 8.22 (s, 1H), 7.81 (dd, J=9.7, 2.2 Hz, 1H), 7.18 (s, 2H), 6.92 (dd, J=11.5, 2.2 Hz, 1H), 3.96 (s, 3H); MS (ES+): 233.1 (M+1).

Step-4: Preparation of tert-butyl 2-(4-amino-6-fluoro-8-methoxy-9H-pyrimido[4,5-b]indol-9-yl) acetate (280e)

Compound 280e was prepared according to the procedure reported in step-1 of scheme-1, from AcOH salt of 6-fluoro-8-methoxy-9H-pyrimido[4,5-b]indol-4-amine (280d) (650 mg, 1.576 mmol) in DMF (15 mL) using tert-butyl 2-bromoacetate (0.256 mL, 0.1.734 mmol), $Cs_2CO_3$ (1284 mg, 3.94 mmol) and stirring at RT for 16 h. This gave after work up and purification using reverse phase column chromatography [C18 column (50 g), eluting with ACN in water (containing 0.1% HCl) from 0-100%] tert-butyl 2-(4-amino-6-fluoro-8-methoxy-9H-pyrimido[4,5-b]indol-9-yl)acetate (280e) (546 mg, 25% yield) as a pale yellow solid; $^1$H NMR (300 MHz, DMSO-$d_6$) δ 8.54 (s, 1H), 8.43 (s, 2H), 8.02 (dd, J=9.4, 2.2 Hz, 1H), 7.11 (dd, J=11.4, 2.2 Hz, 1H), 5.25 (s, 2H), 3.94 (s, 3H), 1.43 (s, 9H); MS (ES+): 347.1 (M+1).

Step-5: Preparation of 2-(4-amino-6-fluoro-8-methoxy-9H-pyrimido[4,5-b]indol-9-yl)acetic acid (280f)

Compound 280f was prepared according to the procedure reported in step-2 of scheme-1, from tert-butyl 2-(4-amino-6-fluoro-8-methoxy-9H-pyrimido[4,5-b]indol-9-yl)acetate (280e) (125 mg, 0.361 mmol) using 20% TFA in DCM (2071 μL, 5.41 mmol) and stirring at RT for 16 h. This gave after work up TFA salt of 2-(4-amino-6-fluoro-8-methoxy-9H-pyrimido[4,5-b]indol-9-yl)acetic acid (280) (171 mg, 97% yield) as a pale-yellow solid; $^1$H NMR (300 MHz, DMSO-$d_6$) δ 8.55 (s, 1H), 8.46 (s, 2H), 8.02 (dd, J=9.4, 2.2 Hz, 1H), 7.13 (dd, J=11.5, 2.2 Hz, 1H), 5.30 (s, 2H), 3.94 (s, 3H); MS (ES+): 291.10 (M+1).

Step-6: Preparation of (1R,3S,5R)-2-(2-(4-amino-6-fluoro-8-methoxy-9H-pyrimido[4,5-b]indol-9-yl) acetyl)-N-(6-bromopyridin-2-yl)-2-azabicyclo[3.1.0] hexane-3-carboxamide (280 g)

Compound 280g was prepared according to the procedure reported in step-3 of scheme-1, from TFA salt of 2-(4-amino-6-fluoro-8-methoxy-9H-pyrimido[4,5-b]indol-9-yl)acetic acid (280f) (77 mg, 0.157 mmol) in DMF (7 mL) using HCl salt of (1R,3S,5R)—N-(6-bromopyridin-2-yl)-2-azabicyclo [3.1.0]hexane-3-carboxamide (4a) (50 mg, 0.157 mmol), HATU (90 mg, 0.235 mmol), DIPEA (0.137 mL, 0.785 mmol) and stirring at RT for 16 h. This gave after workup and purification using flash column chromatography [silica gel (12 g), DMA80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-fluoro-8-methoxy-9H-pyrimido[4,5-b]indol-9-yl)acetyl)-N-(6-bromopyridin-2-yl)-2-azabicyclo[3.1.0]hexane-3-carboxamide (280 g) (58 mg, 67% yield) HCl salt as a white solid; $^1$H NMR (300 MHz, DMSO-$d_6$) δ 10.75 (s, 1H, $D_2O$ exchangeable), 8.71 (s, 2H, $D_2O$ exchangeable), 8.62 (s, 1H), 8.08-7.91 (m, 2H), 7.71 (t, J=8.0 Hz, 1H), 7.32 (d, J=7.7 Hz, 1H), 7.11 (dd, J=11.5, 2.2 Hz, 1H), 5.78 (d, J=17.1 Hz, 1H), 5.54 (d, J=16.9 Hz, 1H), 4.43 (dd, J=8.9, 5.6 Hz, 1H), 3.95 (s, 3H), 3.84 (ddd, J=7.6, 5.3, 2.3 Hz, 1H), 2.41-2.14 (m, 2H), 2.00-1.86 (m, 1H), 1.11 (dt, J=9.8, 5.4 Hz, 1H), 0.66 (td, J=5.1, 2.4 Hz, 1H), $^{19}$F NMR (282 MHz, DMSO) δ−117.06. MS (ES+): 554.1/556.1 (M+1); (ES−): 552.1/554.1 (M−1); Analysis calculated for $C_{24}H_{21}BrFN_7O_3$ 1.75$H_2O$. HCl: C, 46.32; H, 4.13; Cl, 5.70; N, 15.75. Found: C, 46.24; H, 3.99; Cl, 5.70; N, 15.66.

Scheme 281

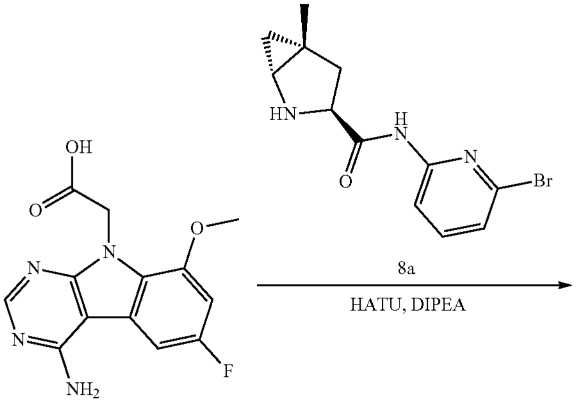

280f

-continued

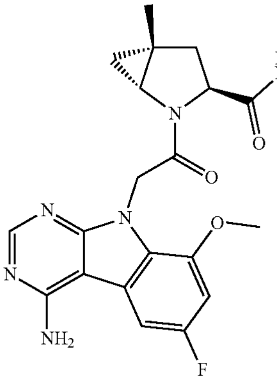

281a

Preparation of (1R,3S,5R)-2-(2-(4-amino-6-fluoro-8-methoxy-9H-pyrimido[4,5-b]indol-9-yl)acetyl)-N-(6-bromopyridin-2-yl)-5-methyl-2-azabicyclo[3.1.0] hexane-3-carboxamide (281a)

Compound 281a was prepared according to the procedure reported in step-3 of scheme-1, from TFA salt of 2-(4-amino-6-fluoro-8-methoxy-9H-pyrimido[4,5-b]indol-9-yl)acetic acid (280f) (77 mg, 0.157 mmol) in DMF (1.5 mL) using HCl salt of (1R,3S,5R)—N-(6-bromopyridin-2-yl)-5-methyl-2-azabicyclo[3.1.0]hexane-3-carboxamide (8a) (52.2 mg, 0.157 mmol), HATU (90 mg, 0.236 mmol), DIPEA (0.137 mL, 0.785 mmol) and stirring at RT for 16 h. This gave after workup and purification using flash column chromatography [silica gel (12 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-6-fluoro-8-methoxy-9H-pyrimido[4,5-b]indol-9-yl)acetyl)-N-(6-bromopyridin-2-yl)-5-methyl-2-azabicyclo[3.1.0]hexane-3-carboxamide (281a) (65 mg, 73% yield) HCl salt as a white solid; $^1$H NMR (300 MHz, DMSO-$d_6$) δ 10.74 (s, 1H, $D_2O$ exchangeable), 8.65-8.48 (m, 3H, 2H $D_2O$ exchangeable), 8.06-7.95 (m, 2H), 7.71 (t, J=8.0 Hz, 1H), 7.32 (d, J=7.7 Hz, 1H), 7.10 (dd, J=11.5, 2.2 Hz, 1H), 5.73 (d, J=17.0 Hz, 1H), 5.50 (d, J=16.9 Hz, 1H), 4.38 (dd, J=9.0, 5.9 Hz, 1H), 3.94 (s, 3H), 3.62 (dd, J=5.5, 2.3 Hz, 1H), 2.49-2.41 (m, 1H), 2.00 (dd, J=13.2, 5.9 Hz, 1H), 1.31 (s, 3H), 1.08-1.00 (m, 1H), 0.89-0.77 (m, 1H). $^{19}$F NMR (282 MHz, DMSO-$d_6$) δ−117.27. MS (ES+): 568.1/570.1 (M+1): (ES−): 566.1/568.1 (M−1); Analysis calculated for $C_{25}H_{23}BrFN_7O_3 \cdot 1.75H_2O \cdot HCl$: C, 47.18; H, 4.36; Cl, 5.57; N, 15.41. Found: C, 47.11; H, 4.33; Cl, 5.23; N, 15.33

Scheme 282

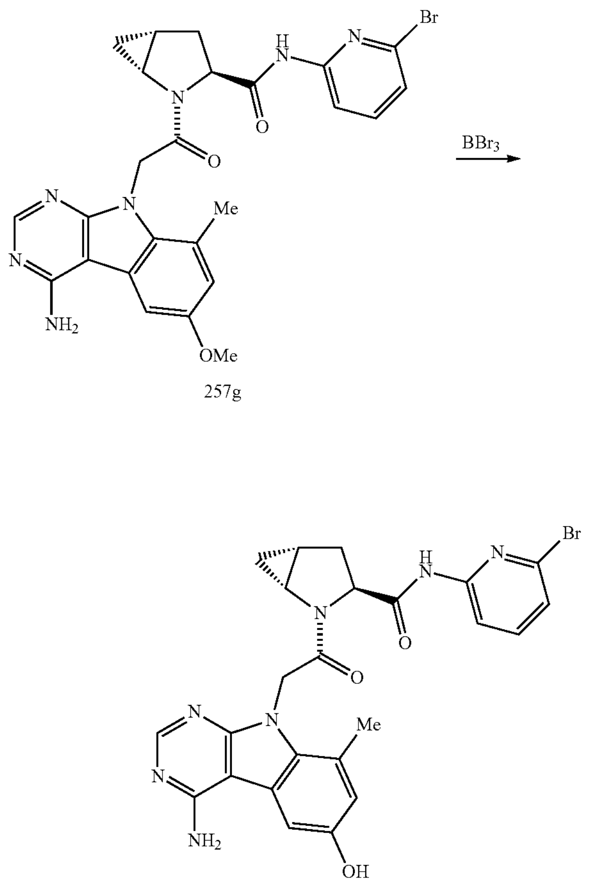

257g

282a

Preparation of (1R,3S,5R)-2-(2-(4-amino-6-hydroxy-8-methyl-9H-pyrimido[4,5-b]indol-9-yl)acetyl)-N-(6-bromopyridin-2-yl)-2-azabicyclo[3.1.0]hexane-3-carboxamide (282a)

Compound 282a was prepared according to the procedure reported in scheme-164, from (1R,3S,5R)-2-(2-(4-amino-6-methoxy-8-methyl-9H-pyrimido[4,5-b]indol-9-yl)acetyl)-N-(6-bromopyridin-2-yl)-2-azabicyclo[3.1.0]hexane-3-carboxamide (257 g) (64 mg, 0.116 mmol) in DCM (5 mL) using a solution of 1.0 M $BBr_3$ in DCM (0.581 mL, 0.581 mmol) and stirring at RT for 16 h. This gave after work up and purification using reverse phase column chromatography [C18 column (100 g), eluting with ACN in water (containing 0.1% HCl) from 0-100%] (1R,3S,5R)-2-(2-(4-amino-6-hydroxy-8-methyl-9H-pyrimido[4,5-b]indol-9-yl)acetyl)-N-(6-bromopyridin-2-yl)-2-azabicyclo[3.1.0]hexane-3-carboxamide (282a) (29 mg, 47% yield) HCl salt as a white solid; $^1H$ NMR (300 MHz, DMSO-$d_6$) (a mixture of two rotamers) δ 10.89 and 10.82 (2s, 1H, $D_2O$ exchangeable), 9.39 (s, 1H, $D_2O$ exchangeable), 8.55 (s, 1H), 8.47 (s, 2H, $D_2O$ exchangeable), 8.00 and 7.95 (2d, J=8.1 Hz, 1H), 7.71 (t, J=7.9 Hz, 1H), 7.65 (d, J=2.1 Hz, 1H), 7.36-7.26 (m, 1H), 6.81 (s, 1H), 5.84 (d, J=17.9 Hz, 1H), 5.57 (d, J=17.9 Hz, 1H), 4.41 (dd, J=9.0, 5.7 Hz, 1H), 3.95-3.82 (m, 1H), 2.65 and 2.61 (2s, 3H), 2.40-2.27 (m, 1H), 2.26-2.11 (m, 1H), 1.98-1.85 (m, 1H), 1.14-0.99 (m, 1H), 0.73-0.55 (m, 1H); MS (ES+): 536/538 (M+1); (ES−): 534/536 (M−1).

Scheme 283

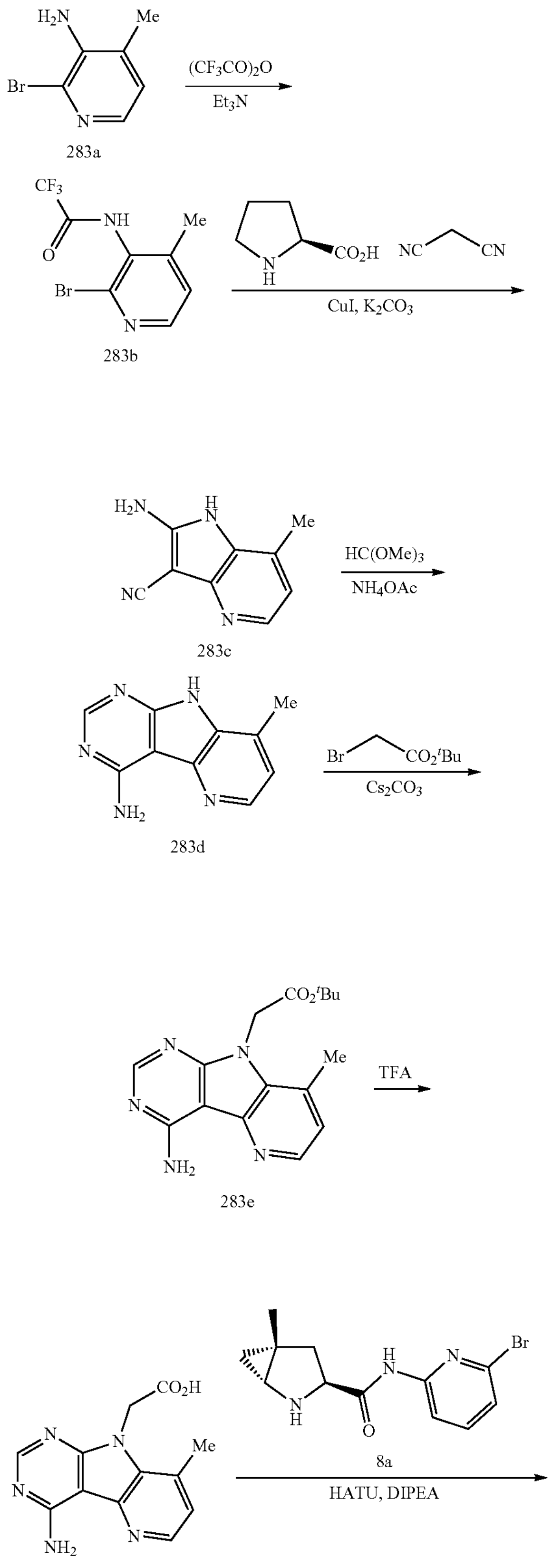

283a

283b

283c

283d

283e

8a

283f

-continued

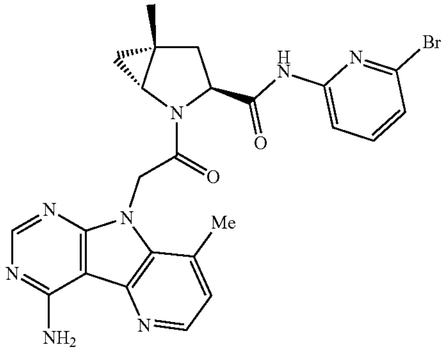

283g

Preparation of (1R,3S,5R)-2-(2-(4-amino-8-methyl-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (283 g)

Step-1: Preparation of N-(2-bromo-4-methylpyridin-3-yl)-2,2,2-trifluoroacetamide (283b)

Compound 283b was prepared according to the procedure reported in step-1 of scheme-46, from 2-bromo-4-methylpyridin-3-amine (283a) (5 g, 26.7 mmol: CAS #126325-50-6) in DCM (30 mL) using triethylamine (4.60 g, 45.4 mmol), trifluoroacetic acid anhydride (8.42 g, 40.1 mmol) and stirring at RT for 1 h. This gave after workup N-(2-bromo-4-methylpyridin-3-yl)-2,2,2-trifluoroacetamide (283b) (6.85 g, 91% yield) as a plum solid; $^1$H NMR (300 MHz, DMSO-$d_6$) δ 11.51 (s, 1H), 8.30 (d, J=4.9 Hz, 1H), 7.48 (d, J=4.9 Hz, 1H), 2.25 (s, 3H). $^{19}$F NMR (282 MHz, DMSO-$d_6$) δ −74.21; MS (ES+): 283/285, (ES−): 281/283 (M−1).

Step-2: Preparation of 2-amino-7-methyl-1H-pyrrolo[3,2-b]pyridine-3-carbonitrile (283c)

Compound 283c was prepared according to the procedure reported in step-1 of scheme-11, from N-(2-bromo-4-methylpyridin-3-yl)-2,2,2-trifluoroacetamide (283b) (6.85 g, 24.20 mmol) in DMSO (30 mL) and using malononitrile (1.919 g, 29.0 mmol), L-proline (0.557 g, 4.84 mmol), CuI (0.461 g, 2.420 mmol), a solution of $K_2CO_3$ (6.69 g, 48.4 mmol) in water (30 mL) and heating at 60° C. for 16 h under an argon atmosphere. This gave after workup and purification using flash column chromatography [silicagel (40 g), eluting with MeOH in DCM from 0-6%] 2-amino-7-methyl-1H-pyrrolo[3,2-b]pyridine-3-carbonitrile (283c) (0.39 g, 9% yield) as a yellow solid: 1H NMR (300 MHz, DMSO-$d_6$) δ 11.66 (s, 1H), 7.98 (d, J=5.6 Hz, 1H), 7.48 (s, 2H), 6.93 (d, J=5.6 Hz, 1H), 2.43 (s, 3H); MS (ES+): 173 (M+1), (ES−): 171 (M−1).

Step-3: Preparation of 8-methyl-9H-pyrido[2',3':4,5]pyrrolo[2,3-d]pyrimidin-4-amine (283d)

Compound 283d was prepared according to the procedure reported in step-2 of scheme-29, from 2-amino-7-methyl-1H-pyrrolo[3,2-b]pyridine-3-carbonitrile (283c) (0.39 g, 2.265 mmol) in ethanol (5 mL) using $NH_4OAc$ (0.524 g, 6.79 mmol), $HC(OMe)_3$ (2.404 g, 22.65 mmol) and heating at 90° C. for 16 h. This gave after work up 8-methyl-9H-pyrido[2',3':4,5]pyrrolo[2,3-d]pyrimidin-4-amine (283d) (196 mg, 43% yield) as a brown solid; $^1$H NMR (300 MHz, DMSO-$d_6$) δ 12.11 (s, 1H), 8.47-8.22 (m, 2H), 8.01 (s, 1H), 7.19 (d, J=4.9 Hz, 1H), 6.65 (s, 1H), 2.56 (s, 3H); MS (ES+): 200 (M+1), (ES−): 198 (M−1).

Step-4: Preparation of tert-butyl 2-(4-amino-8-methyl-9H-pyrido[2',3':4,5]pyrrolo[2,3-d]pyrimidin-9-yl)acetate (283e)

Compound 283e was prepared according to the procedure reported in step-1 of scheme-1, from 8-methyl-9H-pyrido[2',3':4,5]pyrrolo[2,3-d]pyrimidin-4-amine (283d) (190 mg, 0.954 mmol) in DMF (15 mL) using tert-butyl 2-bromoacetate (205 mg, 1.049 mmol), $Cs_2CO_3$ (622 mg, 1.908 mmol) and stirring at RT for 16 h. This gave after work up tert-butyl 2-(4-amino-8-methyl-9H-pyrido[2',3':4,5]pyrrolo[2,3-d]pyrimidin-9-yl)acetate (283e) (236 mg, 79% yield) as a white solid; $^1$H NMR (300 MHz, DMSO-$d_6$) δ 8.50-8.31 (m, 2H), 7.90 (s, 1H), 7.20 (d, J=5.0 Hz, 1H), 6.78 (s, 1H), 5.33 (s, 2H), 2.64 (s, 3H), 1.43 (s, 9H); MS (ES+): 314 (M+1), (ES−): 312 (M−1).

Step-5: Preparation of 2-(4-amino-8-methyl-9H-pyrido[2',3':4,5]pyrrolo[2,3-d]pyrimidin-9-yl)acetic acid (283f)

Compound 283f was prepared according to the procedure reported in step-2 of scheme-1, from tert-butyl 2-(4-amino-8-methyl-9H-pyrido[2',3':4,5]pyrrolo[2,3-d]pyrimidin-9-yl)acetate (283e) (236 mg, 0.753 mmol) in DCM (5 mL) using TFA (859 mg, 7.53 mmol) and stirring at RT for 16 h. This gave after work up TFA salt of 2-(4-amino-8-methyl-9H-pyrido[2',3':4,5]pyrrolo[2,3-d]pyrimidin-9-yl)acetic acid (283f) (356 mg) as a white solid; $^1$H NMR (300 MHz, DMSO-$d_6$) δ 8.75 (s, 1H), 8.58 (s, 1H), 8.53 (d, J=5.0 Hz, 1H), 7.93 (s, 1H), 7.37 (d, J=5.0 Hz, 1H), 5.43 (s, 2H), 2.72 (s, 3H); MS (ES+): 258 (M+1), (ES−): 256 (M−1).

Step-6: Preparation of (1R,3S,5R)-2-(2-(4-amino-8-methyl-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (283 g)

Compound 283g was prepared according to the procedure reported in step-3 of scheme-1, from TFA salt of 2-(4-amino-8-methyl-9H-pyrido[2',3':4,5]pyrrolo[2,3-d]pyrimidin-9-yl)acetic acid (283f) (75 mg, 0.202 mmol) in DMF (5 mL) using HCl salt of (1R,3S,5R)—N-(6-bromopyridin-2-yl)-5-methyl-2-azabicyclo[3.1.0]hexane-3-carboxamide (8a) (67.2 mg, 0.202 mmol), HATU (92 mg, 0.242 mmol), DIPEA (131 mg, 1.010 mmol) and stirring at RT for 16 h. This gave after workup and purification using flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (1R,3S,5R)-2-(2-(4-amino-8-methyl-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (283 g) (71 mg, 66% yield) HCl salt as a white solid: $^1$H NMR (300 MHz, DMSO-$d_6$) δ 10.84 (s, 1H, $D_2O$ exchangeable), 8.79 (s, 1H, $D_2O$ exchangeable), 8.61 (s, 1H), 8.53 (d, J=5.1 Hz, 1H), 8.34 (s, 2H, $D_2O$ exchangeable), 8.01 (d, J=8.2 Hz, 1H), 7.72 (t, J=8.0 Hz, 1H), 7.42 (d, J=5.3 Hz, 1H), 7.32 (d, J=7.7 Hz, 1H), 5.88 (d, J=18.0 Hz, 1H), 5.62 (d, J=17.9 Hz, 1H), 4.39 (dd, J=9.1, 6.1 Hz, 1H), 3.77-3.68

(m, 1H), 2.75 (s, 3H), 2.49-2.40 (m, 1H), 1.98 (dd, J=13.3, 6.0 Hz, 1H), 1.31 (s, 3H), 1.03 (t, J=5.5 Hz, 1H), 0.87 (dd, J=5.5, 2.3 Hz, 1H); MS (ES+): 535/537 (M+1); (ES−): 533/535 (M−1): Analysis calculated for $C_{24}H_{23}BrN_8O_2 \cdot 1.45HCl \cdot 2.25H_2O$: C, 45.84; H, 4.64; Cl, 8.18; N, 17.82. Found: C, 45.82; H, 4.56; Cl, 8.20; N, 17.70.

Scheme 284

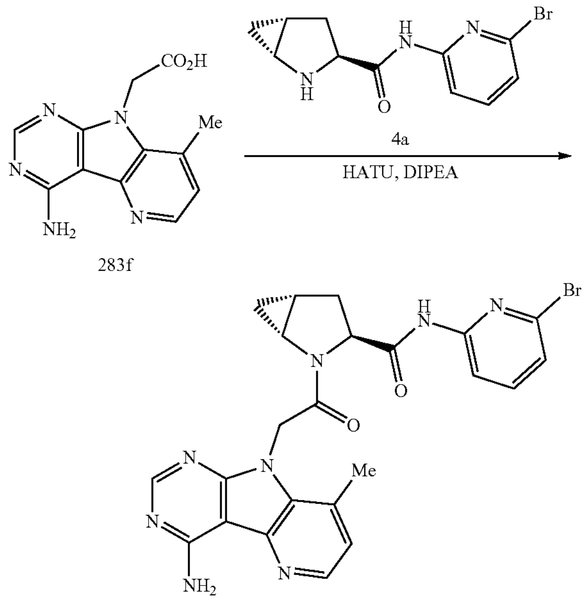

283f

4a

284a

Preparation of (1R,3S,5R)-2-(2-(4-amino-8-methyl-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (284a)

Compound 284a was prepared according to the procedure reported in step-3 of scheme-1, from TFA salt of 2-(4-amino-8-methyl-9H-pyrido[2',3':4,5]pyrrolo[2,3-d]pyrimidin-9-yl) acetic acid (283f) (75 mg, 0.202 mmol) in DMF (5 mL) using HCl salt of (1R,3S,5R)—N-(6-bromopyridin-2-yl)-2-azabicyclo[3.1.0]hexane-3-carboxamide (4a) (64.4 mg, 0.202 mmol), HATU (92 mg, 0.242 mmol) DIPEA (131 mg, 1.010 mmol) and stirring at RT for 16 h. This gave after workup and purification using flash column chromatography [silica gel (12 g), eluting with MeOH in DCM from 0-3%] followed by purification using reverse phase column chromatography [C18 column (100 g), eluting with ACN in water (containing 0.1% HCl) from 0-100%](1R,3S,5R)-2-(2-(4-amino-8-methyl-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (284a) (86 mg, 82% yield) HCl salt as a white solid: $^1H$ NMR (300 MHz, DMSO-$d_6$) δ 10.84 (s, 1H, $D_2O$ exchangeable), 8.91 (bs, 1H, $D_2O$ exchangeable), 8.65 (s, 1H), 8.60 (bs, 1H, $D_2O$ exchangeable), 8.55 (d, J=5.1 Hz, 1H), 8.00 (d, J=8.2 Hz, 1H), 7.71 (t, J=7.9 Hz, 1H), 7.46 (d, J=5.2 Hz, 1H), 7.32 (d, J=7.7 Hz, 1H), 5.95 (d, J=18.0 Hz, 1H), 5.68 (d, J=17.9 Hz, 1H), 4.47-4.39 (m, 1H), 3.97-3.90 (m, 1H), 2.78 (s, 3H), 2.43-2.29 (m, 1H), 2.29-2.15 (m, 1H), 2.02-1.81 (m, 1H), 1.19-1.01 (m, 1H), 0.79-0.66 (m, 1H); MS (ES+): 521/523 (M+1); (ES−): 519/521 (M−1).

Scheme 285

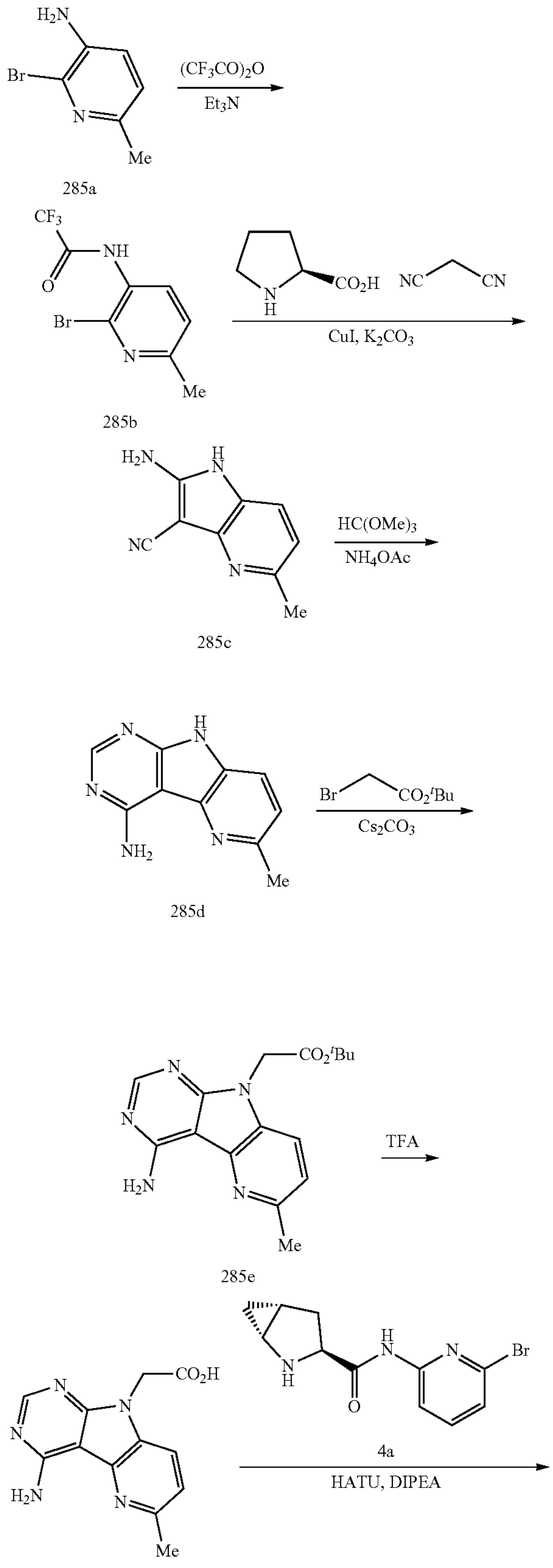

285a

285b

285c

285d

285e

285f

4a

-continued

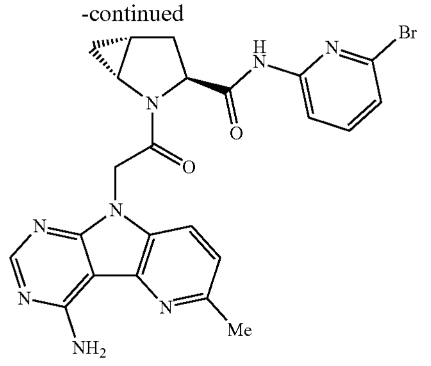

285g

Preparation of (1R,3S,5R)-2-(2-(4-amino-6-methyl-9H-pyrido[2',3':4,5]pyrrolo[2,3-d]pyrimidin-9-yl) acetyl)-N-(6-bromopyridin-2-yl)-2-azabicyclo[3.1.0] hexane-3-carboxamide (285 g)

Step-1: Preparation of N-(2-bromo-6-methylpyridin-3-yl)-2,2,2-trifluoroacetamide (285b)

Compound 285b was prepared according to the procedure reported in step-1 of scheme-46, from 2-bromo-6-methylpyridin-3-amine (285a) (5 g, 26.7 mmol: CAS #126325-53-9) in DCM (30 mL) using triethylamine (4.60 g, 45.4 mmol), trifluoroacetic acid anhydride (8.42 g, 40.1 mmol) and stirring at RT for 1 h. This gave after workup N-(2-bromo-6-methylpyridin-3-yl)-2,2,2-trifluoroacetamide (285b) (7.33 g, 97% yield) as a pale-yellow solid which was used as such for the next step: $^1$H NMR (300 MHz, DMSO-$d_6$) δ 11.42 (s, 1H), 7.81 (d, J=7.9 Hz, 1H), 7.41 (d, J=7.9 Hz, 1H), 2.50 (s, 3H). $^{19}$F NMR (282 MHz, DMSO-$d_6$) δ-74.21; MS (ES+): 283/285. (ES−): 281/283 (M−1).

Step-2: Preparation of 2-amino-5-methyl-1H-pyrrolo[3,2-b]pyridine-3-carbonitrile (285c)

Compound 285c was prepared according to the procedure reported in step-1 of scheme-11, from N-(2-bromo-6-methylpyridin-3-yl)-2,2,2-trifluoroacetamide (285b) (7.33 g, 25.90 mmol) in DMSO (30 mL) using malononitrile (2.053 g, 31.1 mmol), L-proline (0.596 g, 5.18 mmol), CuI (0.493 g, 2.59 mmol), a solution of $K_2CO_3$ (7.16 g, 51.8 mmol) in water (30 mL) and heating at 60° C. for 16 h under an argon atmosphere. This gave after workup 2-amino-5-methyl-1H-pyrrolo[3,2-b]pyridine-3-carbonitrile (285c) (2.27 g, 51% yield) as a pale-pink solid; $^1$H NMR (300 MHz, DMSO-$d_6$) δ 10.71 (s, 1H), 7.25 (d, J=7.9 Hz, 1H), 7.05 (s, 2H), 6.72 (d, J=7.9 Hz, 1H), 2.41 (s, 3H); MS (ES+): 173 (M+1), (ES−): 171 (M−1).

Step-3: Preparation of 6-methyl-9H-pyrido[2',3':4,5] pyrrolo[2,3-d]pyrimidin-4-amine (285d)

Compound 285d was prepared according to the procedure reported in step-2 of scheme-29, from 2-amino-5-methyl-1H-pyrrolo[3,2-b]pyridine-3-carbonitrile (285c) (1.79 g, 10.40 mmol) in ethanol (10 mL) using $NH_4OAc$ (2.404 g, 31.2 mmol), $HC(OMe)_3$ (11.03 g, 104 mmol) and heating at 90° C. for 16 h. This gave after work up 6-methyl-9H-pyrido [2',3':4.5]pyrrolo[2,3-d]pyrimidin-4-amine (285d) (1.04 g, 50% yield) as a beige solid; $^1$H NMR (300 MHz, DMSO-$d_6$) δ 11.88 (s, 1H), 8.32 (s, 1H), 7.73 (d, J=8.2 Hz, 2H), 7.23 (d, J=8.3 Hz, 1H), 6.53 (s, 1H), 2.63 (s, 3H); MS (ES+): 200 (M+1), (ES−): 198 (M−1).

Step-4: Preparation of tert-butyl 2-(4-amino-6-methyl-9H-pyrido[2',3':4,5]pyrrolo[2,3-d]pyrimidin-9-yl)acetate (285e)

Compound 285e was prepared according to the procedure reported in step-1 of scheme-1, from 6-methyl-9H-pyrido [2',3':4,5]pyrrolo[2,3-d]pyrimidin-4-amine (285d) (1.02 g, 0.5.12 mmol) in DMF (15 mL) using tert-butyl 2-bromoacetate (1.099 g, 5.63 mmol), $Cs_2CO_3$ (3.34 g, 10.24 mmol) and stirring at RT for 16 h. This gave after work up tert-butyl 2-(4-amino-6-methyl-9H-pyrido[2',3':4,5]pyrrolo[2,3-d]pyrimidin-9-yl)acetate (285e) (1.24 g, 77% yield) as a beige solid; 1H NMR (300 MHz, DMSO-$d_6$) δ 8.36 (s, 1H), 7.92 (d, J=8.4 Hz, 1H), 7.92 (s, 1H), 7.29 (d, J=8.3 Hz, 1H), 6.58 (s, 1H), 5.13 (s, 2H), 2.65 (s, 3H), 1.39 (s, 9H); MS (ES+): 314 (M+1).

Step-5: Preparation of 2-(4-amino-6-methyl-9H-pyrido[2',3':4,5]pyrrolo[2,3-d]pyrimidin-9-yl)acetic acid (285f)

Compound 285f was prepared according to the procedure reported in step-2 of scheme-1, from tert-butyl 2-(4-amino-6-methyl-9H-pyrido[2',3':4,5]pyrrolo[2,3-d]pyrimidin-9-yl) acetate (285e) (1.23 g, 3.93 mmol) using TFA (4.48 g, 39.3 mmol) in DCM (5 mL) and stirring at RT for 16 h. This gave after work up TFA salt of 2-(4-amino-6-methyl-9H-pyrido [2',3':4.5]pyrrolo[2,3-d]pyrimidin-9-yl)acetic acid (285f) (2.28 g) as a white solid; $^1$H NMR (300 MHz, DMSO-$d_6$) δ 8.87 (bs, 1H), 8.59 (s, 1H), 8.27 (d, J=8.6 Hz, 1H), 7.90 (bs, 1H), 7.51 (d, J=8.5 Hz, 1H), 5.28 (s, 2H), 2.73 (s, 3H). $^{19}$F NMR (282 MHz, DMSO-$d_6$) δ-74.81; MS (ES+): 258 (M+1); (ES−): 256 (M−1).

Step-6: Preparation of (1R,3S,5R)-2-(2-(4-amino-6-methyl-9H-pyrido[2',3':4.5]pyrrolo[2,3-d]pyrimidin-9-yl)acetyl)-N-(6-bromopyridin-2-yl)-2-azabicyclo [3.1.0]hexane-3-carboxamide (285 g)

Compound 285g was prepared according to the procedure reported in step-3 of scheme-1, from TFA salt of 2-(4-amino-6-methyl-9H-pyrido[2',3':4,5]pyrrolo[2,3-d]pyrimidin-9-yl) acetic acid (2850) (75 mg, 0.202 mmol) in DMF (5 mL) using HCl salt of (1R,3S,5R)—N-(6-bromopyridin-2-yl)-2-azabicyclo[3.1.0]hexane-3-carboxamide (4a) (64.4 mg, 0.202 mmol), HATU (92 mg, 0.242 mmol), DIPEA (131 mg, 1.010 mmol) and stirring at RT for 16 h. This gave after workup and purification using flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-methyl-9H-pyrido[2',3':4,5]pyrrolo[2,3-d] pyrimidin-9-yl)acetyl)-N-(6-bromopyridin-2-yl)-2-azabicyclo[3.1.0]hexane-3-carboxamide (285 g) (69 mg, 66% yield) HCl salt as a white solid; $^1$H NMR (300 MHz, DMSO-$d_6$) δ 10.76 (s, 1H, $D_2O$ exchangeable), 8.86 (bs, 2H, $D_2O$ exchangeable), 8.61 (s, 1H), 8.33 (d, J=7.7 Hz, 1H), 8.00 (d, J=8.1 Hz, 1H), 7.70 (t, J=8.0 Hz, 1H), 7.62 (d, J=8.5 Hz, 1H), 7.32 (d, J=7.7 Hz, 1H), 5.81 (d, J=17.3 Hz, 1H), 5.45 (d, J=17.3 Hz, 1H), 4.45-4.36 (m, 1H), 3.90-3.83 (m, 1H), 2.81 (s, 3H), 2.39-2.26 (m, 1H), 2.26-2.11 (m, 1H), 1.98-

1.84 (m, 1H), 1.13-1.01 (m, 11H), 0.85-0.72 (m, 1H); MS (ES+): 521/523 (M+1); (ES−): 519/521 (M−1).

Scheme 286

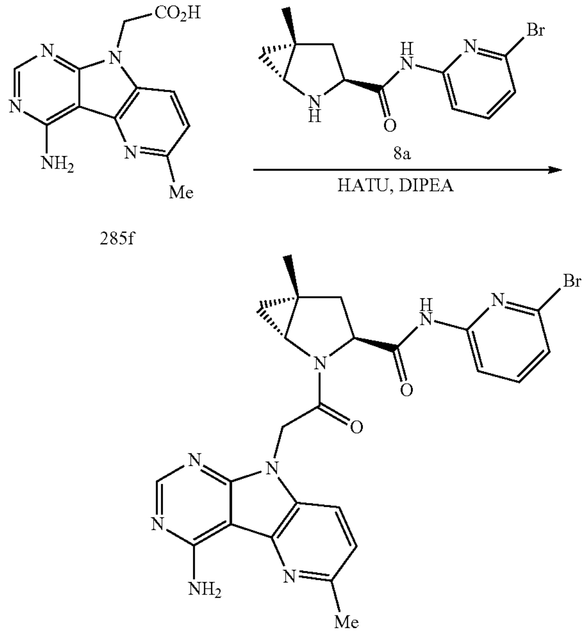

285f

286a

Preparation of (1R,3S,5R)-2-(2-(4-amino-6-methyl-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (286a)

Compound 286a was prepared according to the procedure reported in step-3 of scheme-1, from TFA salt of 2-(4-amino-6-methyl-9H-pyrido[2',3':4,5]pyrrolo[2,3-d]pyrimidin-9-yl) acetic acid (285f) (75 mg, 0.202 mmol) in DMF (5 mL) using HCl salt of (1R,3S,5R)—N-(6-bromopyridin-2-yl)-5-methyl-2-azabicyclo[3.1.0]hexane-3-carboxamide (8a) (67.2 mg, 0.202 mmol), HATU (92 mg, 0.242 mmol), DIPEA (131 mg, 1.010 mmol) and stirring at RT for 16 h. This gave after workup and purification using flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-methyl-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (286a) (65 mg, 60% yield) HCl salt as a white solid; $^1$H NMR (300 MHz, DMSO-$d_6$) δ 10.77 (s, 1H, $D_2O$ exchangeable), 8.88 (bs, 2H, $D_2O$ exchangeable), 8.61 (s, 1H), 8.33 (d, J=8.9, 2.6 Hz, 1H), 8.00 (d, J=8.1 Hz, 1H), 7.70 (t, J=8.0 Hz, 1H), 7.62 (d, J=8.6 Hz, 1H), 7.32 (d, J=7.7 Hz, 1H), 5.77 (d, J=17.3 Hz, 1H), 5.41 (d, J=17.3 Hz, 1H), 4.43-4.30 (m, 1H), 3.67-3.64 (m, 1H), 2.81 (s, 3H), 2.49-2.42 (m, 1H), 1.98 (dd, J=13.3, 5.8 Hz, 1H), 1.30 (s, 3H), 1.06-0.98 (m, 1H), 0.98-0.89 (m, 1H); MS (ES+): 535/537 (M+1), (ES−): 533/535 (M−1); Analysis calculated for $C_{24}H_{23}BrN_8O_2 \cdot 1.95HCl \cdot 4.25H_2O$: C, 42.20; H, 4.94; Cl, 10.12; N, 16.40. Found: C, 42.44; H, 4.61; Cl, 9.93; N, 16.00.

Scheme 287

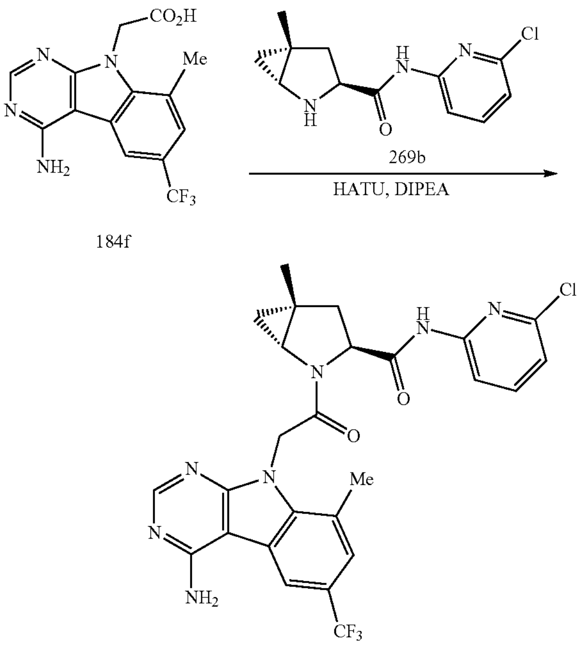

184f

287a

Preparation of (1R,3S,5R)-2-(2-(4-amino-8-methyl-6-(trifluoromethyl)-9H-pyrimido[4,5-b]indol-9-yl)acetyl)-N-(6-chloropyridin-2-yl)-5-methyl-2-azabicyclo[3.1.0]hexane-3-carboxamide (287a)

Compound 287a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (100 mg, 0.228 mmol) in DMF (5 mL) using HCl salt of (1R,3S,5R)—N-(6-chloropyridin-2-yl)-5-methyl-2-azabicyclo[3.1.0]hexane-3-carboxamide (269b) (65.8 mg, 0.228 mmol), HATU (130 mg, 0.342 mmol), DIPEA (147 mg, 1.141 mmol) and stirring at RT for 16 h. This gave after workup and purification using flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (1R,3S,5R)-2-(2-(4-amino-8-methyl-6-(trifluoromethyl)-9H-pyrimido[4,5-b]indol-9-yl)acetyl)-N-(6-chloropyridin-2-yl)-5-methyl-2-azabicyclo[3.1.0]hexane-3-carboxamide (287a) (58 mg, 46% yield) HCl salt as a white solid; $^1$H NMR (300 MHz, DMSO-$d_6$) δ 10.81 (s, 1H, $D_2O$ exchangeable), 8.79 (s, 1H), 8.64 (s, 1H), 8.64 (bs, 2H, $D_2O$ exchangeable), 7.98 (d, J=8.2 Hz, 1H), 7.81 (t, J=8.0 Hz, 1H), 7.60 (s, 11H), 7.18 (d, J=7.7 Hz, 1H), 5.92 (d, J=18.0 Hz, 1H), 5.65 (d, J=17.9 Hz, 1H), 4.38 (dd, J=9.1, 6.1 Hz, 1H), 3.74-3.69 (m, 1H), 2.76 (s, 3H), 2.49-2.36 (m, 1H), 1.98 (dd, J=13.3, 6.1 Hz, 1H), 1.31 (s, 3H), 1.03 (t, J=5.5 Hz, 1H), 0.89-0.82 (m, 1H); $^{19}$F NMR (282 MHz, DMSO-$d_6$) δ−58.77; MS (ES+): 558/560 (M+1); (ES−): 556/558 (M−1); Analysis calculated for $C_{26}H_{23}ClF_3N_7O_2 \cdot 0.75HCl \cdot 2.25H_2O$: C, 49.90; H, 4.55; Cl, 9.91; N, 15.67. Found: C, 50.06; H, 4.28; Cl, 9.86; N, 15.34.

Scheme 288

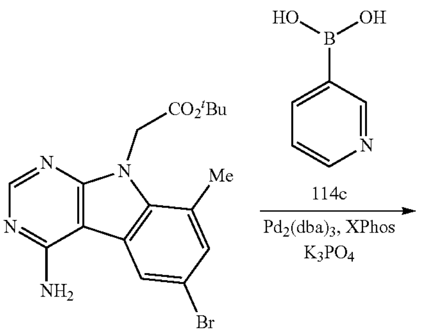

192e

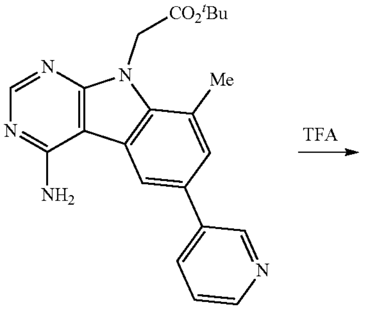

288a

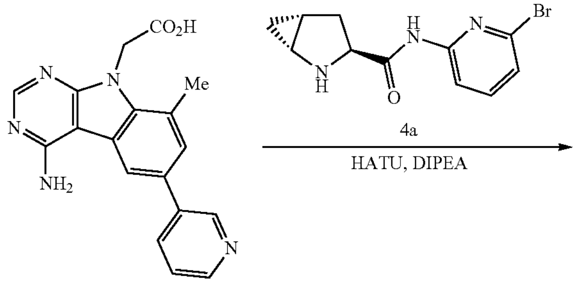

288b

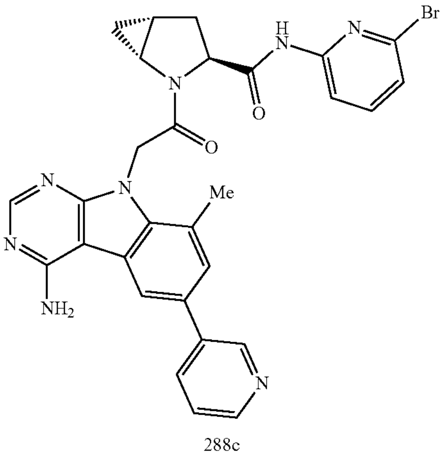

288c

Preparation of (1R,3S,5R)-2-(2-(4-amino-8-methyl-6-(pyridin-3-yl)-9H-pyrimido[4,5-b]indol-9-yl)acetyl)-N-(6-bromopyridin-2-yl)-2-azabicyclo[3.1.0]hexane-3-carboxamide (288c)

Step-1: Preparation of tert-butyl 2-(4-amino-8-methyl-6-(pyridin-3-yl)-9H-pyrimido[4,5-b]indol-9-yl)acetate (288a)

Compound 288a was prepared according to the procedure reported in step-1 of scheme-263, from tert-butyl 2-(4-amino-6-bromo-8-methyl-9H-pyrimido[4,5-b]indol-9-yl) acetate (192e) (300 mg, 0.767 mmol) in n-BuOH (4 mL) using pyridin-3-ylboronic acid (114c) (141 mg, 1.150 mmol), a solution of 1.27 M aqueous $K_3PO_4$ (1.207 mL, 1.533 mmol), $Pd_2$(dba); (70.2 mg, 0.077 mmol), XPhos (73.1 mg, 0.153 mmol) and heating at 100° C. for 16 h under nitrogen. This gave after workup and purification using flash column chromatography [silica gel (12 g), eluting with MeOH in DCM from 0-7%] tert-butyl 2-(4-amino-8-methyl-6-(pyridin-3-yl)-9H-pyrimido[4,5-b]indol-9-yl)acetate (288a) (260 mg, 87% yield) as a white solid; $^1$H NMR (300 MHz, DMSO-$d_6$) δ 9.11 (d, J=2.4 Hz, 1H), 8.66-8.49 (m, 2H), 8.32 (s, 1H), 8.25 (dt, J=8.1, 2.0 Hz, 1H), 7.58 (s, 1H), 7.56-7.35 (m, 3H), 5.37 (s, 2H), 2.71 (s, 3H), 1.44 (s, 9H); MS (ES+): 390 (M+1); (ES−): 388 (M−1).

Step-2: Preparation of 2-(4-amino-8-methyl-6-(pyridin-3-yl)-9H-pyrimido[4,5-b]indol-9-yl)acetic acid (288b)

Compound 288b was prepared according to the procedure reported in step-2 of scheme-1, from tert-butyl 2-(4-amino-8-methyl-6-(pyridin-3-yl)-9H-pyrimido[4,5-b]indol-9-yl) acetate (288a) (260 mg, 0.668 mmol) in DCM (5 mL) using TFA (761 mg, 6.68 mmol) and stirring at RT for 16 h. This gave after work up TFA salt of 2-(4-amino-8-methyl-6-(pyridin-3-yl)-9H-pyrimido[4,5-b]indol-9-yl)acetic acid (288b) (436 mg) and used as such for the next step: $^1$H NMR (300 MHz, DMSO-$d_6$) δ 9.26 (d, J=2.2 Hz, 1H), 8.87-8.71 (m, 2H), 8.68 (dd, J=8.1, 2.2 Hz, 1H), 8.64-8.42 (m, 3H), 7.88 (dd, J=8.2, 5.2 Hz, 1H), 7.81 (s, 1H), 5.48 (s, 2H), 2.78 (s, 3H); $^{19}$F NMR (282 MHz, DMSO-$d_6$) δ −74.60; MS (ES+): 334 (M+1); (ES−): 332 (M−1).

Step-3: Preparation of (1R,3S,5R)-2-(2-(4-amino-8-methyl-6-(pyridin-3-yl)-9H-pyrimido[4,5-b]indol-9-yl)acetyl)-N-(6-bromopyridin-2-yl)-2-azabicyclo[3.1.0]hexane-3-carboxamide (288c)

Compound 288c was prepared according to the procedure reported in step-3 of scheme-1, from TFA salt of 2-(4-amino-8-methyl-6-(pyridin-3-yl)-9H-pyrimido[4,5-b]indol-9-yl) acetic acid (288b) (75 mg, 0.168 mmol) in DMF (5 mL) using HCl salt of (1R,3S,5R)—N-(6-bromopyridin-2-yl)-2-azabicyclo[3.1.0]hexane-3-carboxamide (4a) (53.4 mg, 0.168 mmol). HATU (76 mg, 0.201 mmol), DIPEA (108 mg, 0.838 mmol) and stirring at RT for 16 h. This gave after workup and purification using flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-8-methyl-6-(pyridin-3-yl)-9H-pyrimido[4,5-b]indol-9-yl)acetyl)-N-(6-bromopyridin-2-yl)-2-azabicyclo[3.1.0]hexane-3-carboxamide (288c) (50 mg, 50% yield) HCl salt as a white solid; $^1$H NMR (300 MHz, DMSO-$d_6$)

δ 10.84 (s, 1H, $D_2O$ exchangeable), 9.45 (d, J=2.2 Hz, 1H), 9.12 (bs, 211 $D_2O$ exchangeable), 8.98 (dd, J=8.4, 1.7 Hz, 1H), 8.94 (d, J=1.7 Hz, 1H), 8.83 (d, 1H), 8.67 (s, 1H), 8.05 (dd, J=8.3, 5.5 Hz, 1H), 8.00 (d, J=8.2 Hz, 1H), 7.86 (s, 1H), 7.70 (t, J=8.0 Hz, 1H), 7.31 (d, J=7.7 Hz, 1H), 5.99 (d, J=18.0 Hz, 1H), 5.67 (d, J=17.9 Hz, 1H), 4.43 (dd, J=9.1, 5.8 Hz, 1H), 4.01-3.94 (m, 1H), 2.80 (s, 3H), 2.37 (dd, J=13.5, 9.1 Hz, 1H), 2.29-2.08 (m, 1H), 2.01-1.87 (m, 1H), 1.16-1.05 (m, 1H), 0.78-0.59 (m, 1H); MS (ES+): 597/599 (M+1): (ES−): 595/597 (M−1); Analysis calculated for $C_{29}H_{25}BrN_8O_2 \cdot 2.15HCl \cdot 4.25H_2O$: C, 46.29; H, 4.78; Cl, 10.13; N, 14.89. Found: C, 46.42; H, 4.44; Cl, 10.13; N, 14.82.

Scheme 289

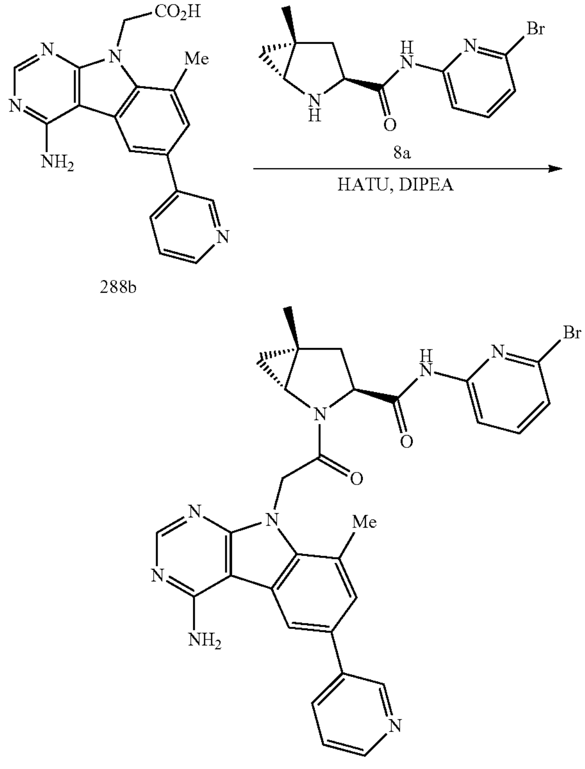

288b

8a

289a

Preparation of (1R,3S,5R)-2-(2-(4-amino-8-methyl-6-(pyridin-3-yl)-9H-pyrimido[4,5-b]indol-9-yl) acetyl)-N-(6-bromopyridin-2-yl)-5-methyl-2-azabicyclo[3.1.0]hexane-3-carboxamide (289a)

Compound 289a was prepared according to the procedure reported in step-3 of scheme-1, from TFA salt of 2-(4-amino-8-methyl-6-(pyridin-3-yl)-9H-pyrimido[4,5-b]indol-9-yl) acetic acid (288b) (75 mg, 0.168 mmol) in DMF (5 mL) using HCl salt of (1R,3S,5R)—N-(6-bromopyridin-2-yl)-5-methyl-2-azabicyclo[3.1.0]hexane-3-carboxamide (8a) (55.8 mg, 0.168 mmol), HATU (76 mg, 0.201 mmol), DIPEA (108 mg, 0.838 mmol) and stirring at RT for 16 h. This gave after workup and purification using flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (1R,3S,5R)-2-(2-(4-amino-8-methyl-6-(pyridin-3-yl)-9H-pyrimido[4,5-b]indol-9-yl)acetyl)-N-(6-bromopyridin-2-yl)-5-methyl-2-azabicyclo[3.1.0]hexane-3-carboxamide (289a) (36 mg, 35% yield) HCl salt as a white solid; $^1H$ NMR (300 MHz, DMSO-$d_6$) δ 10.84 (s, 1H, $D_2O$ exchangeable), 9.40 (s, 1H), 9.14-8.84 (m, 4H, in which 2H were $D_2O$ exchangeable), 8.84-8.78 (m, 1H), 8.66 (s, 1H), 8.10-7.95 (m, 2H), 7.85 (s, 1H), 7.71 (t, J=8.0 Hz, 1H), 7.31 (d, J=7.7 Hz, 1H), 5.93 (d, J=18.0 Hz, 1H), 5.64 (d, J=17.9 Hz, 1H), 4.39 (dd, J=9.0, 6.2 Hz, 1H), 3.73 (dd, J=5.4, 2.4 Hz, 1H), 2.78 (s, 3H), 2.49-2.44 (m, 1H), 1.99 (dd, J=13.4, 6.1 Hz, 1H), 1.32 (s, 3H), 1.04 (t, J=5.4 Hz, 1H), 0.92-0.82 (m, 1H); MS (ES+): 611/613 (M+1), (ES−): 609/611 (M−1).

Scheme 290

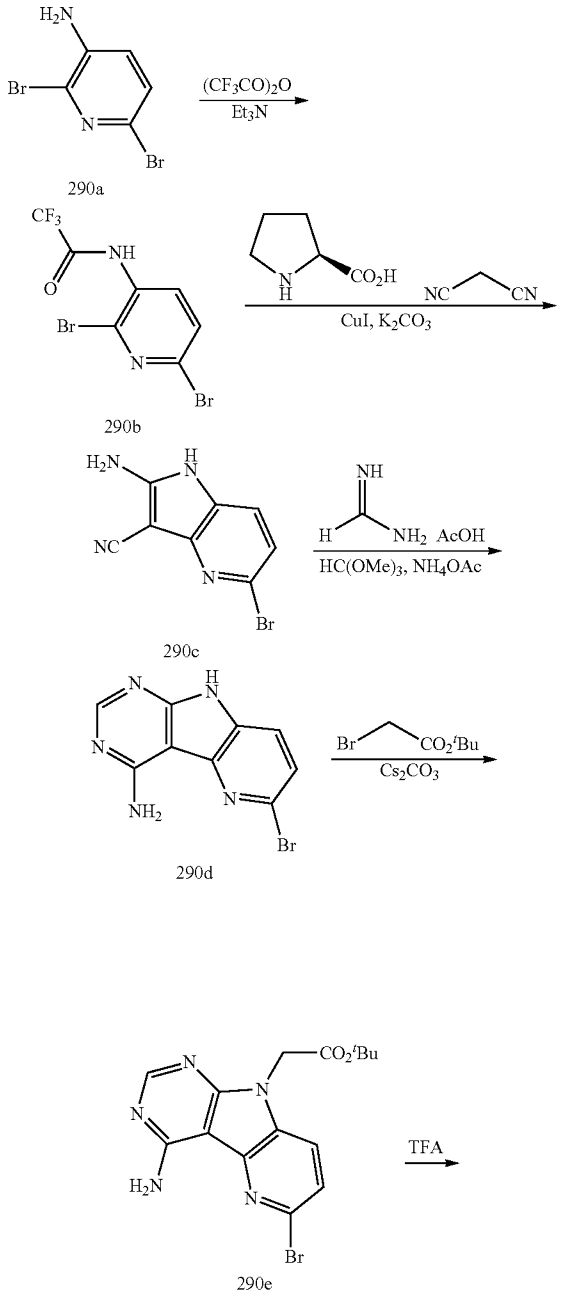

290a

290b

290c

290d

290e

-continued

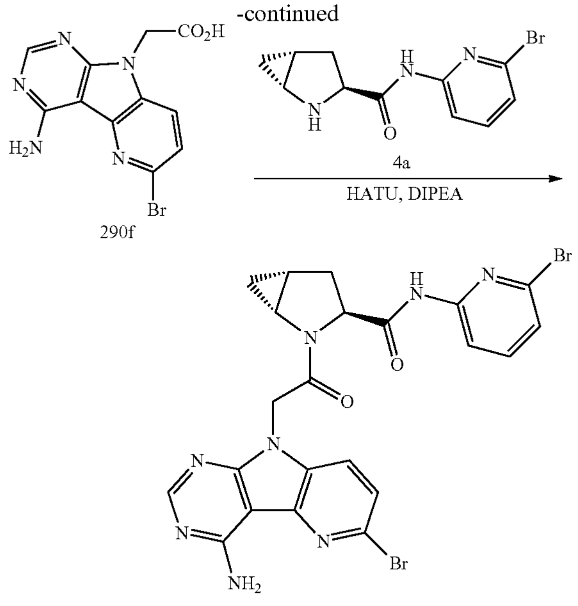

290f

4a

290g

Preparation of (1R,3S,5R)-2-(2-(4-amino-6-bromo-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (290 g)

Step-1: Preparation of N-(2,6-dibromopyridine-3-yl)-2,2,2-trifluoroacetamide (290b)

Compound 290b was prepared according to the procedure reported in step-1 of scheme-46, from 2,6-dibromopyridine-3-amine (290a) (10 g, 39.7 mmol; CAS #39856-57-0) in DCM (30 mL) using triethylamine (6.83 g, 67.5 mmol), trifluoroacetic acid anhydride (12.51 g, 59.5 mmol) and stirring at RT for 1 h. This gave after workup N-(2,6-dibromopyridine-3-yl)-2,2,2-trifluoroacetamide (290b) (13.78 g, 100% yield) as a pale-yellow solid and was used as such for next step; $^1$H NMR (300 MHz, DMSO-$d_6$) δ 11.68 (s, 1H), 8.61 (d, J=2.4 Hz, 1H), 8.35 (d, J=2.3 Hz, 1H); $^{19}$F NMR (282 MHz, DMSO-do) 6-74.16; MS (ES−): 345/347 (M−1).

Step-2: Preparation of 2-amino-5-bromo-1H-pyrrolo[3,2-b]pyridine-3-carbonitrile (290c)

Compound 290c was prepared according to the procedure reported in step-1 of scheme-11, from N-(2,6-dibromopyridine-3-yl)-2,2,2-trifluoroacetamide (290b) (13.78 g, 39.6 mmol) in DMSO (30 mL) using malononitrile (3.14 g, 47.5 mmol), L-proline (0.912 g, 7.92 mmol), CuI (0.754 g, 3.96 mmol), a solution of $K_2CO_3$ (10.95 g, 79 mmol) in water (30 mL) and heating at 60° C. for 16 h under an argon atmosphere. This gave after workup and 2-amino-5-bromo-1H-pyrrolo[3,2-b]pyridine-3-carbonitrile (290c) (7.03 g, 75% yield) as a beige solid; $^1$H NMR (300 MHz, DMSO-$d_6$) δ 10.95 (s, 1H), 8.36-7.90 (m, 1H), 7.55 (d, J=1.9 Hz, 1H), 7.39 (s, 2H); MS (ES+): 237/239 (M+1); (ES−): 235/237 (M−1).

Step-3: Preparation of 6-bromo-9H-pyrido[2',3':4,5]pyrrolo[2,3-d]pyrimidin-4-amine (290d)

Compound 290d was prepared according to the procedure reported in step-2 of scheme-29, from 2-amino-5-bromo-1H-pyrrolo[3,2-b]pyridine-3-carbonitrile (290c) (7.02 g, 29.6 mmol) in ethanol (20 mL) using $NH_4OAc$ (11.41 g, 148 mmol), formamidine acetate (9.25 g, 89 mmol), $HC(OMe)_3$ (31.4 g, 296 mmol) and heating at 90° C. for 16 h. This gave after work up 6-bromo-9H-pyrido[2',3':4,5]pyrrolo[2,3-d]pyrimidin-4-amine (290d) (7.68 g, 98% yield) as a beige solid; $^1$H NMR (300 MHz, DMSO-$d_6$) δ 12.20 (s, 1H), 8.56 (d, J=2.0 Hz, 1H), 8.37 (s, 1H), 8.03 (d, J=2.0 Hz, 1H), 7.87 (s, 1H), 6.75 (s, 1H); MS (ES+): 264/266 (M+1), (ES−): 262/264 (M−1).

Step-4: Preparation of tert-butyl 2-(4-amino-6-bromo-9H-pyrido[2',3':4,5]pyrrolo[2,3-d]pyrimidin-9-yl)acetate (290e)

Compound 290e was prepared according to the procedure reported in step-1 of scheme-1, from 6-bromo-9H-pyrido[2',3':4,5]pyrrolo[2,3-d]pyrimidin-4-amine (290d) (3.00 g, 11.36 mmol) in DMF (15 mL) using tert-butyl 2-bromoacetate (2.437 g, 12.50 mmol), $Cs_2CO_3$ (7.40 g, 22.72 mmol) and stirring at RT for 16 h. This gave after work up tert-butyl 2-(4-amino-6-bromo-9H-pyrido[2',3':4,5]pyrrolo[2,3-d]pyrimidin-9-yl)acetate (290e) (3.20 g, 75% yield) as a beige solid; $^1$H NMR (300 MHz, DMSO-$d_6$) δ 8.61 (d, J=1.9 Hz, 1H), 8.47 (d, J=1.9 Hz, 1H), 8.40 (s, 1H), 7.97 (bs, 1H), 6.86 (bs, 1H), 5.16 (s, 2H), 1.41 (s, 9H); MS (ES+): 378/380 (M+1).

Step-5: Preparation of 2-(4-amino-6-bromo-9H-pyrido[2',3':4,5]pyrrolo[2,3-d]pyrimidin-9-yl)acetic acid (290f)

Compound 290f was prepared according to the procedure reported in step-2 of scheme-1, from tert-butyl 2-(4-amino-6-bromo-9H-pyrido[2',3':4,5]pyrrolo[2,3-d]pyrimidin-9-yl)acetate (290e) (300 mg, 0.793 mmol) using TFA (904 mg, 7.93 mmol) in DCM (5 mL) and stirring at RT for 16 h. This gave after work up TFA salt of 2-(4-amino-6-bromo-9H-pyrido[2',3':4,5]pyrrolo[2,3-d]pyrimidin-9-yl)acetic acid (2901) (346 mg) as a beige solid: $^1$H NMR (300 MHz, DMSO-$d_6$) δ 8.66 (d, J=1.9 Hz, 1H), 8.58 (d, J=1.9 Hz, 1H), 8.56-8.29 (m, 2H), 7.27 (s, 1H), 5.22 (s, 2H); $^{19}$F NMR (282 MHz, DMSO-$d_6$) δ−74.62; MS (ES+): 322/324 (M+1); (ES−): 320/322 (M−1).

Step-6: Preparation of (1R,3S,5R)-2-(2-(4-amino-6-bromo-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (290 g)

Compound 290g was prepared according to the procedure reported in step-3 of scheme-1, from 2-(4-amino-6-bromo-9H-pyrido[2',3':4,5]pyrrolo[2,3-d]pyrimidin-9-yl)acetic acid (2900 (75 mg, 0.172 mmol) in DMF (5 mL) using HCl salt of (1R,3S,5R)—N-(6-bromopyridin-2-yl)-2-azabicyclo[3.1.0]hexane-3-carboxamide (4a) (54.8 mg, 0.172 mmol), HATU (78 mg, 0.206 mmol), DIPEA (111 mg, 0.860 mmol) and stirring at RT for 16 h. This gave after workup and purification using flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-6-bromo-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (290 g) (73 mg, 72% yield) HCl salt as a white solid: $^1$H NMR (300 MHz, DMSO-$d_6$) δ 10.80 (s, 1H, $D_2O$ exchangeable), 9.07 (bs, 2H, $D_2O$ exchangeable), 8.78-8.70 (m, 2H), 8.61 (d, J=2.0 Hz, 1H), 8.02 (d, J=8.1 Hz, 1H), 7.71 (t, J=7.9 Hz, 1H), 7.32 (d, J=7.7 Hz, 1H), 5.83 (d, J=17.4 Hz, 1H), 5.43 (d, J=17.3 Hz, 1H), 4.47-4.41 (m, 1H), 3.93-3.84 (m, 1H), 2.40-2.28 (m, 1H), 2.28-2.16 (m, 1H), 1.99-1.84 (m, 1H), 1.14-0.96 (m, 1H), 0.96-0.74 (m, 1H); MS (ES+): 585/587 (M+1), (ES−): 583/585 (M−1); Analysis calculated for $C_{22}H_{18}Br_2N_8O_2 \cdot 1.1HCl \cdot 2H_2O$: C, 39.89; H, 3.52; Cl, 5.89; N, 16.92. Found: C, 39.97; H, 3.29; Cl, 5.89; N, 16.88.

Scheme 291

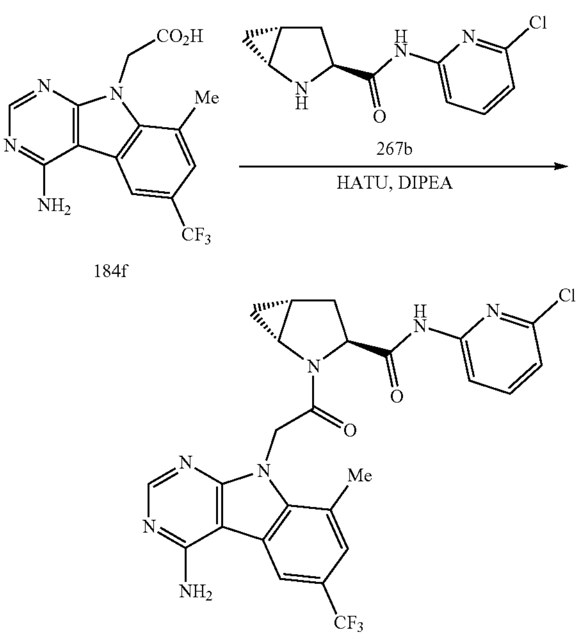

184f

267b

291a

Preparation of (1R,3S,5R)-2-(2-(4-amino-8-methyl-6-(trifluoromethyl)-9H-pyrimido[4,5-b]indol-9-yl)acetyl)-N-(6-chloropyridin-2-yl)-2-azabicyclo[3.1.0]hexane-3-carboxamide (291a)

Compound 291a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (100 mg, 0.228 mmol) in DMF (5 mL) using HCl salt of (1R,3S,5R)—N-(6-chloropyridin-2-yl)-2-azabicyclo[3.1.0]hexane-3-carboxamide (267b) (62.6 mg, 0.228 mmol), HATU (130 mg, 0.342 mmol), DIPEA (147 mg, 1.141 mmol) and stirring at RT for 16 h. This gave after workup and purification using flash column chromatography [silica gel (12 g), eluting with MeOH in DCM from 0-2%] followed by purification using reverse phase column chromatography [C18 column (100 g), eluting with ACN in water (containing 0.1% HCl) from 0-100%] (1R,3S,5R)-2-(2-(4-amino-8-methyl-6-(trifluoromethyl)-9H-pyrimido[4,5-b]indol-9-yl)acetyl)-N-(6-chloropyridin-2-yl)-2-azabicyclo[3.1.0]hexane-3-carboxamide (291a) (30 mg, 24% yield) HCl salt as a white solid: $^1H$ NMR (300 MHz, DMSO-$d_6$) δ 10.82 (s, 1H, $D_2O$ exchangeable), 8.81 (s, 1H), 8.78 (bs, 2H, $D_2O$ exchangeable), 8.66 (s, 1H), 7.98 (d, J=8.2 Hz, 1H), 7.82 (t, J=8.0 Hz, 1H), 7.62 (s, 1H), 7.19 (d, J=7.7 Hz, 1H), 5.98 (d, J=18.0 Hz, 1H), 5.70 (d, J=18.0 Hz, 1H), 4.43 (dd, J=9.1, 5.7 Hz, 1H), 3.98-3.93 (m, 1H), 2.79 (s, 3H), 2.42-2.30 (m, 1H), 2.30-2.10 (m, 1H), 2.01-1.84 (m, 1H), 1.20-1.02 (m, 1H), 0.78-0.58 (m, 1H); $^{19}F$ NMR (282 MHz, DMSO-$d_6$) δ−58.79. MS (ES+): 544/546 (M+1); (ES−): 542/544 (M−1); Analysis calculated for $C_{25}H_{21}ClF_3N_7O_2 \cdot HCl \cdot 3H_2O$: C, 47.33; H, 4.45; N, 15.45. Found: C, 47.40; H, 4.05; N, 15.36.

Scheme 292

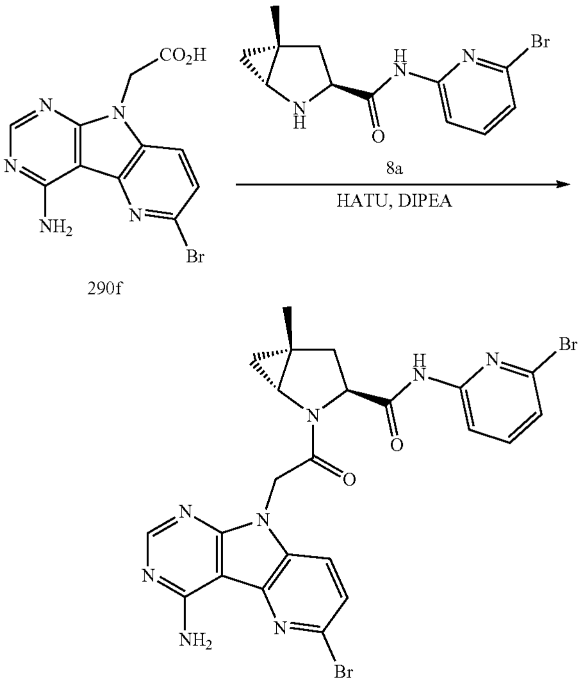

8a

290f

292a

Preparation of (1R,3S,5R)-2-(2-(4-amino-6-bromo-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (292a)

Compound 292a was prepared according to the procedure reported in step-3 of scheme-1, from TFA salt of 2-(4-amino-6-bromo-9H-pyrido[2',3':4,5]pyrrolo[2,3-d]pyrimidin-9-yl)acetic acid (290) (75 mg, 0.172 mmol) in DMF (5 mL) using HCl salt of (1R,3S,5R)—N-(6-bromopyridin-2-yl)-5-methyl-2-azabicyclo[3.1.0]hexane-3-carboxamide (8a) (57.2 mg, 0.172 mmol). HATU (78 mg, 0.206 mmol), DIPEA (111 mg, 0.860 mmol) and stirring at RT for 16 h. This gave after workup and purification using flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (1R,3S,5R)-2-(2-(4-amino-6-bromo-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (292a) (89 mg, 86% yield) HCl salt as a white solid; $^1H$ NMR (300 MHz, DMSO-$d_6$) δ 10.72 (s, 1H, $D_2O$ exchangeable), 8.70 (bs, 1H, $D_2O$ exchangeable), 8.63 (d, J=1.9 Hz, 1H), 8.56 (s, 1H), 8.46 (d, J=2.0 Hz, 1H), 8.14 (bs, 1H, $D_2O$ exchangeable), 7.95 (d, J=8.2 Hz, 1H), 7.63 (t, J=7.9 Hz, 1H), 7.25 (d, J=7.7 Hz, 1H), 5.67 (d, J=17.4 Hz, 1H), 5.29

(d, J=17.3 Hz, 1H), 4.32 (dd, J=9.1, 5.8 Hz, 1H), 3.58-3.55 (m, 1H), 2.42-2.32 (m, 1H), 1.91 (dd, J=13.3, 5.8 Hz, 1H), 1.24 (s, 3H), 1.00-0.83 (m, 2H); MS (ES+): 599/601 (M+1), (ES−): 597/599 (M−1); Analysis calculated for $C_{23}H_{20}Br_2N_8O_2 \cdot HCl \cdot 2H_2O$: C, 41.06; H, 3.75; Cl, 5.27; N, 16.66. Found: C, 41.06; H, 3.51; Cl, 5.21; N, 16.52.

Scheme 293

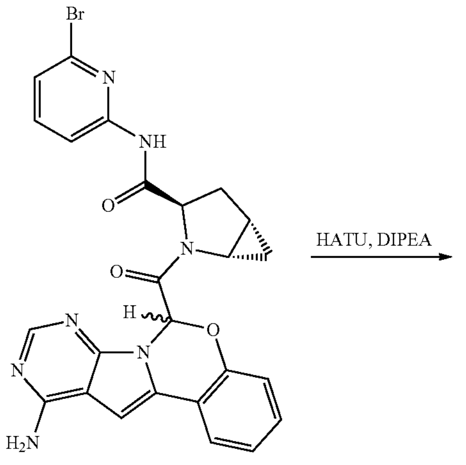

233h

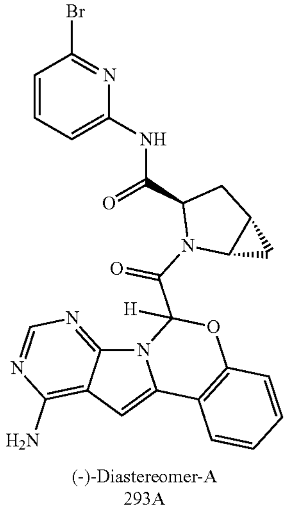

+

(-)-Diastereomer-A
293A

-continued

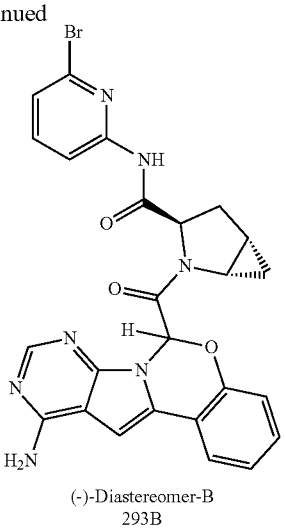

(-)-Diastereomer-B
293B

Preparation of (1S,3R,5S)-2-(11-amino-6H-benzo[e]pyrimido[5',4':4,5]pyrrolo[1,2-c][1,3]oxazine-6-carbonyl)-N-(6-bromopyridin-2-yl)-2-azabicyclo[3.1.0]hexane-3-carboxamide (293A; (−)-diastereoisomer-A), (1S,3R,5S)-2-(11-amino-6H-benzo[e]pyrimido[5',4':4.5]pyrrolo[1,2-c][1,3]oxazine-6-carbonyl)-N-(6-bromopyridin-2-yl)-2-azabicyclo[3.1.0]hexane-3-carboxamide (293B; (−)-diastereoisomer-B)

Compound (233h) was prepared according to procedure reported in scheme 233 from 11-amino-6H-benzo[e]pyrimido[5',4':4,5]pyrrolo[1,2-c][1,3]oxazine-6-carboxylic acid (233 g) (171 mg, 0.606 mmol) and (1R,3S,5R)—N-(6-bromopyridin-2-yl)-2-azabicyclo[3.1.0]hexane-3-carboxamide, HCl (4a) (212 mg, 0.666 mmol) in DMF (5 mL) using HATU (346 mg, 0.909 mmol), DIPEA (0.528 mL, 3.03 mmol) and stirring at RT for 48 h. This gave after workup and purification by flash column chromatography [silica (12 g), eluting with ethyl acetate/MeOH 9:1 in hexanes from 0-100%] to afford Compound (233h) as a mixture of diastereomers. The mixture was repurified by chromatography [silica (12 g), eluting with ethyl acetate/MeOH 9:1 in DCM from 0-100%] to afford pure individual diastereoisomer 293A and 293B. The following was the order and data for the compound that was eluted 1. (1S,3R,5S)-2-(11-amino-6H-benzo[e]pyrimido[5',4':4,5]pyrrolo[1,2-c][1,3]oxazine-6-carbonyl)-N-(6-bromopyridin-2-yl)-2-azabicyclo[3.1.0]hexane-3-carboxamide (293A; (−)-diastereoisomer-A) as a free base; $^1H$ NMR (300 MHz, MeOD-$d_4$) δ 8.11 (s, 1H), 7.95 (d, J=8.4 Hz, 1H), 7.68 (d, J=7.9 Hz, 1H), 7.52 (t, J=8.2 Hz, 1H), 7.37 (s, 1H), 7.27 (t, J=7.9 Hz, 1H), 7.21-7.03 (m, 3H), 6.92 (s, 1H), 4.33-4.11 (m, 2H), 2.47-2.19 (m, 2H), 2.05-1.99 (m, 1H), 1.27-1.23 (m, 1H), 0.79-0.59 (m, 1H); MS (ES+): 546.10, 548.10 (M+1): (ES−): 543.00, 544.00 (M−1); Optical rotation $[\alpha]_D$=−11.43 (c=0.14. MeOH); Compound (293A; (−)-diastereoisomer-A) was further purified by reverse-phase column chromatography [EZ-PREP. C-18 column, 50 g, eluting with 0.1% aqueous HCl in water and acetonitrile from 0-100%] to afford (1S,3R,5S)-2-(11-amino-6H-benzo[e]pyrimido[5',4':4,5]pyrrolo[1,2-c][1,3]oxazine-6-carbonyl)-N-(6-bromopyridin-2-yl)-2-azabicyclo[3.1.0]hexane-3-carboxamide (293A; (−)-diastereoisomer-A)

(42 mg, 13% yield) HCl salt as a white solid; $^1$H NMR (300 MHz, DMSO-$d_6$) δ 10.76 (s, 1H), 9.58 (s, 1H, $D_2O$ exchangeable), 8.76 (s, 1H, $D_2O$ exchangeable), 8.45 (s, 1H), 7.93 (d, J=8.2 Hz, 1H), 7.82-7.56 (m, 3H), 7.39 (d, J=6.8 Hz, 2H), 7.33-7.04 (m, 3H), 4.46-4.26 (m, 1H), 4.26-4.06 (m, 1H), 2.34-2.18 (m, 1H), 2.18-2.01 (m, 1H), 2.01-1.81 (m, 1H), 1.36-1.08 (m, 1H), 0.63-0.32 (m, 1H): $^1$H NMR (300 MHz, DMSO-$d_6$/$D_2O$) δ 10.71 (d, J=4.3 Hz, 1H), 8.41 (d, J=3.9 Hz, 1H), 7.91 (d, J=8.3 Hz, 1H), 7.74 (q. J=6.1, 4.5 Hz, 2H), 7.65 (t, J=7.9 Hz, 1H), 7.48-7.31 (m, 2H), 7.31-7.07 (m, 3H), 4.41-4.22 (m, 1H), 4.22-4.05 (m, 1H), 2.35-2.17 (m, 1H), 2.17-2.00 (m, 1H), 2.00-1.82 (m, 1H), 1.21 (q, J=6.3 Hz, 1H), 0.62-0.39 (m, 1H); MS (ES+): 546.1, 548.1 (M+1); (ES−): 544.1, 546.1 (M−1); LCMS, Rt=1.96 min, (wavelength=254 nM), 98.06%; Optical rotation $[\alpha]_D$=+5.88 (c=0.17. MeOH);

2. (1S,3R,5S)-2-(11-amino-6H-benzo[e]pyrimido[5',4':4,5]pyrrolo[1,2-c][1,3]oxazine-6-carbonyl)-N-(6-bromopyridin-2-yl)-2-azabicyclo[3.1.0]hexane-3-carboxamide (293B; (−)-diastereoisomer-B); $^1$H NMR (300 MHz, MeOD-$d_4$) δ 8.08 (s, 1H), 7.86 (d, J=8.3 Hz, 1H), 7.67 (d, J=7.6 Hz, 1H), 7.51 (t, J=8.0 Hz, 1H), 7.25-7.14 (m, 4H), 7.12-7.04 (m, 1H), 6.94 (s, 1H), 4.53-4.38 (m, 1H), 4.23-4.13 (m, 1H), 2.43-2.25 (m, 2H), 2.03-1.97 (m, 1H), 1.30-1.22 (m, 1H), 1.02-0.91 (m, 1H); MS (ES+): 546.10, 548.10 (M+1); Optical rotation $[\alpha]_D$=−223.88 (c=0.135, MeOH), Compound (293B; (−)-diastereoisomer-B) was further purified by reverse-phase column chromatography [EZ-PREP, C-18 column, 50 g, eluting with 0.1% aqueous HCl in water and acetonitrile from 0-100%] to afford (1S,3R,5S)-2-(11-amino-6H-benzo[e]pyrimido[5',4':4,5]pyrrolo[0,2-c][1,3]oxazine-6-carbonyl)-N-(6-bromopyridin-2-yl)-2-azabicyclo[3.1.0]hexane-3-carboxamide (293B; (−)-diastereoisomer-B) to afford (64 mg, 19% yield) HCl salt as a white solid; $^1$H NMR (300 MHz, DMSO-$d_6$) δ 10.79 (s, 1H), 9.60 (s, 1H, $D_2O$ exchangeable), 8.84 (s, 1H, $D_2O$ exchangeable), 8.49 (s, 1H), 7.92 (d, J=8.1 Hz, 1H), 7.84-7.62 (m, 2H), 7.57-7.38 (m, 3H), 7.38-7.16 (m, 3H), 5.21-4.35 (m, 1H), 4.35-4.10 (m, 1H), 2.44-2.14 (m, 2H), 2.02 (p, J=6.8 Hz, 1H), 1.34-1.05 (m, 1H), 0.90-0.67 (m, 1H); $^1$H NMR (300 MHz, DMSO-$d_6$/$D_2O$) δ 11.66-10.37 (m, 1H), 8.58-8.15 (m, 1H), 8.03-7.74 (m, 2H), 7.69 (t, J=7.9 Hz, 1H), 7.56-7.14 (m, 6H), 5.14-4.34 (m, 1H), 4.15 (d, J=6.5 Hz, 1H), 2.44-2.28 (m, 1H), 2.28-2.13 (m, 1H), 2.13-1.88 (m, 1H), 1.37-1.08 (m, 1H), 0.93-0.65 (m, 1H); MS (ES+): 546.1, 548.1 (M+1); (ES−): 544.1, 546.1 (M−1); LCMS, Rt=1.98 min, (wavelength=254 nM), 98.60%; Optical rotation $[\alpha]_D$=−256.15 (c=0.26, MeOH);

Scheme 294

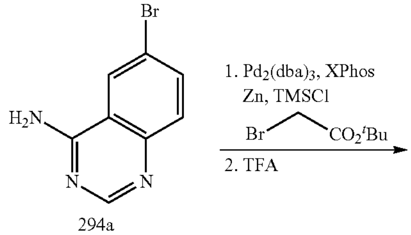

294a

-continued

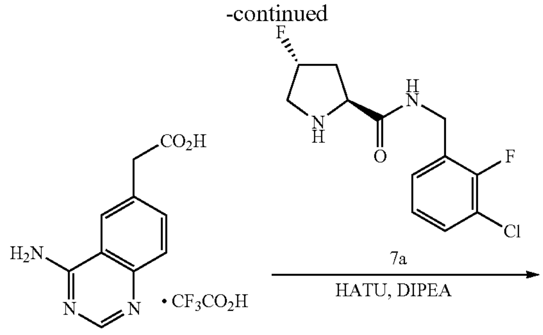

294b

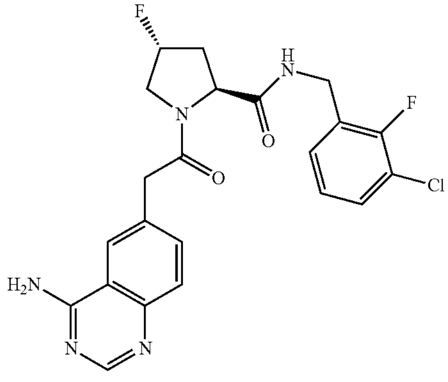

294c

Preparation of (2S,4R)-1-(2-(4-aminoquinazolin-6-yl)acetyl)-N-(3-chloro-2-fluorobenzyl)-4-fluoropyrrolidine-2-carboxamide (294c)

Step-1: Preparation of 2-(4-aminoquinazolin-6-yl)acetic acid (294b)

Compound 294b was prepared according to the procedure reported in step-1 of scheme-2, from 6-bromoquinazolin-4-amine (294a) (1.00 g, 4.46 mmol; CAS #21419-48-7) using zinc (1.752 g, 26.8 mmol), TMSCl (0.170 mL, 1.339 mmol) in THF (5 mL) and $Pd_2(dba)_3$ (0.204 g, 0.223 mmol) and XPhos (0.213 g, 0.446 mmol) in THF (10 mL) and heating at 60° C. under argon for 16 h. The cooled reaction mixture was diluted with $H_2O$ (30 mL) and EtOAc (30 mL), followed by addition of solid $NH_4Cl$ (2 g). After 15-min stirring at rt, TFA (10 mL) was added and stirring continued for 30 min. The mixture was then filtered. The filtered cake was washed thoroughly with $H_2O$ and EtOAc and filtrate was concentrated in vacuum to provide the product TFA salt of 2-(4-aminoquinazolin-6-yl)acetic acid (294b) (475 mg, 33.5% yield) as a brown solid. $^1$H NMR (300 MHz, DMSO-$d_6$) δ 9.70 (s, 2H), 8.75 (s, 1H), 8.24 (d, J=1.7 Hz, 11H), 7.90 (dd, J=8.5, 1.7 Hz, 1H), 7.69 (d, J=8.6 Hz, 1H), 3.72 (s, 2H). $^{19}$F NMR (282 MHz, DMSO-$d_6$) δ−74.74; MS (ES+): 204 (M+1): (ES−): 202 (M−1).

Step-2: Preparation of (2S,4R)-1-(2-(4-aminoquinazolin-6-yl)acetyl)-N-(3-chloro-2-fluorobenzyl)-4-fluoropyrrolidine-2-carboxamide (294c)

Compound 294c was prepared according to the procedure reported in step-3 of scheme-1, from TFA salt of 2-(4-aminoquinazolin-6-yl)acetic acid (294b) (163 mg, 0.515 mmol) in DMF (5 mL) using (2S,4R)—N-(3-chloro-2- fluorobenzyl)-4-fluoropyrrolidine-2-carboxamide (7a) (200 mg, 0.515 mmol), HATU (235 mg, 0.617 mmol), DIPEA (0.449 mL, 2.57 mmol) and stirring at RT for 16 h. This gave after workup and purification by flash column chromatography ($SiO_2$, 12 g, eluting with 0-5% MeOH in DCM) followed by reverse phase column chromatography [C-18 column, 100 g, eluting with 0.1% aqueous HCl in $H_2O$ and MeCN from 0-100%] (2S,4R)-1-(2-(4-aminoquinazolin-6-yl)acetyl)-N-(3-chloro-2-fluorobenzyl)-4-fluoropyrrolidine-2-carboxamide (294c) (21 mg, 9% yield) HCl salt as a white solid: $^1H$ NMR (300 MHz, DMSO-$d_6$) (mixture of two rotamers) δ 9.70 (bs, 2H, $D_2O$ exchangeable), 8.82 (s, 1H), 9.18 and 8.74 (2t, J=5.9 Hz, 1H), 8.36 and 8.30 (2s, 1H), 8.02-7.84 (m, 1H), 7.84-7.72 (m, 1H), 7.53-7.39 (m, 1H), 7.40-7.25 (m, 1H), 7.23-7.04 (m, 1H), 5.60-5.21 (m, 1H), 4.51-3.72 (m, 6H), 3.60-3.46 (m, 1H), 2.76-2.40 (m, 1H), 2.23-1.86 (m, 1H); $^{19}F$ NMR (282 MHz, DMSO-$d_6$) δ-121.25, -121.65, -176.17, -176.38; MS (ES+) 460/462 (M+1).

Scheme 295

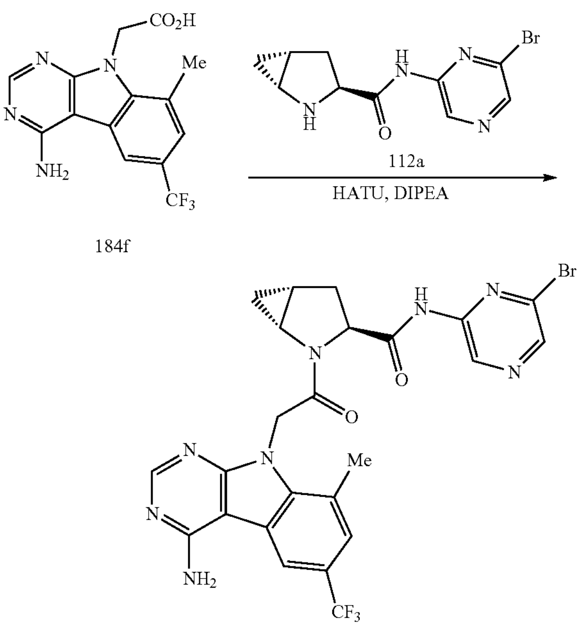

184f

295a

Preparation of (1R,3S,5R)-2-(2-(4-amino-8-methyl-6-(trifluoromethyl)-9H-pyrimido[4,5-b]indol-9-yl)acetyl)-N-(6-bromopyrazin-2-yl)-2-azabicyclo[3.1.0]hexane-3-carboxamide (295a)

Compound 295a was prepared according to the procedure reported in step-3 of scheme-1, from TFA salt of 2-(4-amino-8-methyl-6-(trifluoromethyl)-9H-pyrimido[4,5-b]indol-9-yl)acetic acid (1841) (75 mg, 0.171 mmol) in DMF (5 mL) using HCl salt of (1R,3S,5R)—N-(6-bromopyrazin-2-yl)-2-azabicyclo[3.1.0]hexane-3-carboxamide (112a) (54.7 mg, 0.171 mmol), HATU (98 mg, 0.257 mmol), DIPEA (111 mg, 0.856 mmol) and stirring at RT for 16 h. This gave after workup and purification using flash column chromatography [silica gel (12 g), eluting with MeOH in DCM from 0-3%] followed by purification using reverse phase column chromatography [C18 column (100 g), eluting with ACN in water (containing 0.1% HCl) from 0-100%] (1R,3S,5R)-2-(2-(4-amino-8-methyl-6-(trifluoromethyl)-9H-pyrimido[4,5-b]indol-9-yl)acetyl)-N-(6-bromopyrazin-2-yl)-2-azabicyclo[3.1.0]hexane-3-carboxamide (295a) (66 mg, 65% yield) HCl salt as a white solid: $^1H$ NMR (300 MHz, DMSO-$d_6$) δ 11.22 (s, 1H, $D_2O$ exchangeable), 9.23 (s, 1H), 8.92 (bs, 2H, $D_2O$ exchangeable), 8.82 (s, 1H), 8.70 (s, 1H), 8.53 (s, 1H), 7.64 (s, 1H), 6.00 (d, J=18.0 Hz, 1H), 5.71 (d, J=17.9 Hz, 1H), 4.47 (dd, J=9.0, 5.7 Hz, 1H), 4.00-3.92 (m, 1H), 2.79 (s, 3H), 2.44-2.31 (m, 1H), 2.31-2.17 (m, 1H), 2.02-1.88 (m, 1H), 1.19-1.02 (m, 1H), 0.80-0.64 (m, 1H); F NMR (282 MHz, DMSO-$d_6$) δ-58.83; MS (ES+): 589/591 (M+1), (ES-): 587/589 (M-1).

Scheme 296

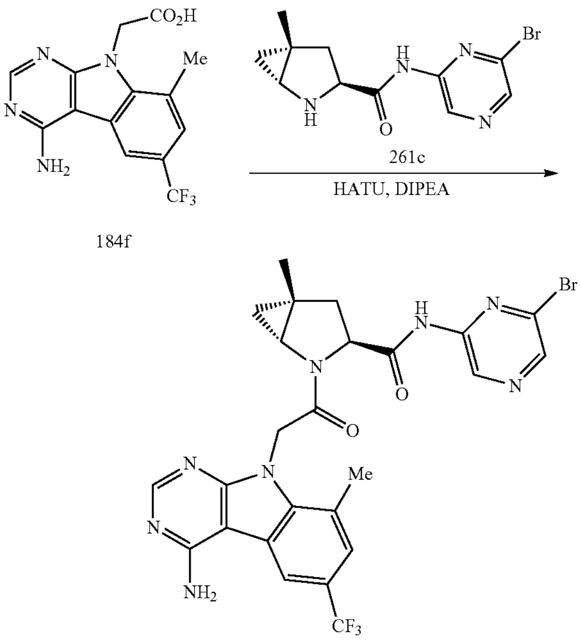

184f

296a

Preparation of (1R,3S,5R)-2-(2-(4-amino-8-methyl-6-(trifluoromethyl)-9H-pyrimido[4,5-b]indol-9-yl)acetyl)-N-(6-bromopyrazin-2-yl)-5-methyl-2-azabicyclo[3.1.0]hexane-3-carboxamide (296a)

Compound 296a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (75 mg, 0.171 mmol) in DMF (5 mL) using HCl salt of (1R,3S,5R)—N-(6-bromopyrazin-2-yl)-5-methyl-2-azabicyclo[3.1.0]hexane-3-carboxamide (261c) (57.1 mg, 0.171 mmol), HATU (98 mg, 0.257 mmol), DIPEA (111 mg, 0.856 mmol) and stirring at RT for 16 h. This gave after workup and purification using flash column chromatography [silica gel (12 g), eluting with MeOH in DCM from 0-2%] followed by purification using reverse phase column chromatography [C18 column (100 g), eluting with ACN in water (containing 0.1% HCl) from 0-100%] (1R,3S,5R)-2-(2-(4-amino-8-methyl-6-(trifluoromethyl)-9H-pyrimido[4,5-b]indol-9-yl)acetyl)-N-(6-bromopyrazin-2-yl)-5-methyl-2-azabicyclo[3.1.0]hexane-3-carboxamide (296a) (63 mg, 61% yield) HCl salt as a white solid: $^1H$ NMR (300 MHz, DMSO-$d_6$) δ 11.21 (s, 1H, $D_2O$ exchangeable), 9.24 (s, 1H), 8.91 (bs, 2H, $D_2O$ exchangeable), 8.85 (s, 1H), 8.69 (s, 1H), 8.53 (s, 1H), 7.62 (s, 1H), 5.94 (d, J=18.0 Hz, 1H), 5.66 (d, J=18.0 Hz, 1H), 4.42 (dd, J=9.1, 6.1 Hz, 1H), 3.76-3.71 (m, 1H), 2.76 (s, 3H), 2.57-2.51 (m, 1H), 2.10-1.94 (m, 1H), 1.31 (s, 3H), 1.08-0.98 (m, 1H), 0.94-0.82 (m, 1H); $^{19}F$ NMR (282 MHz, DMSO-$d_6$) δ-58.84; MS (ES+): 603/605 (M+1), (ES-): 601/603 (M-1).

Scheme 297

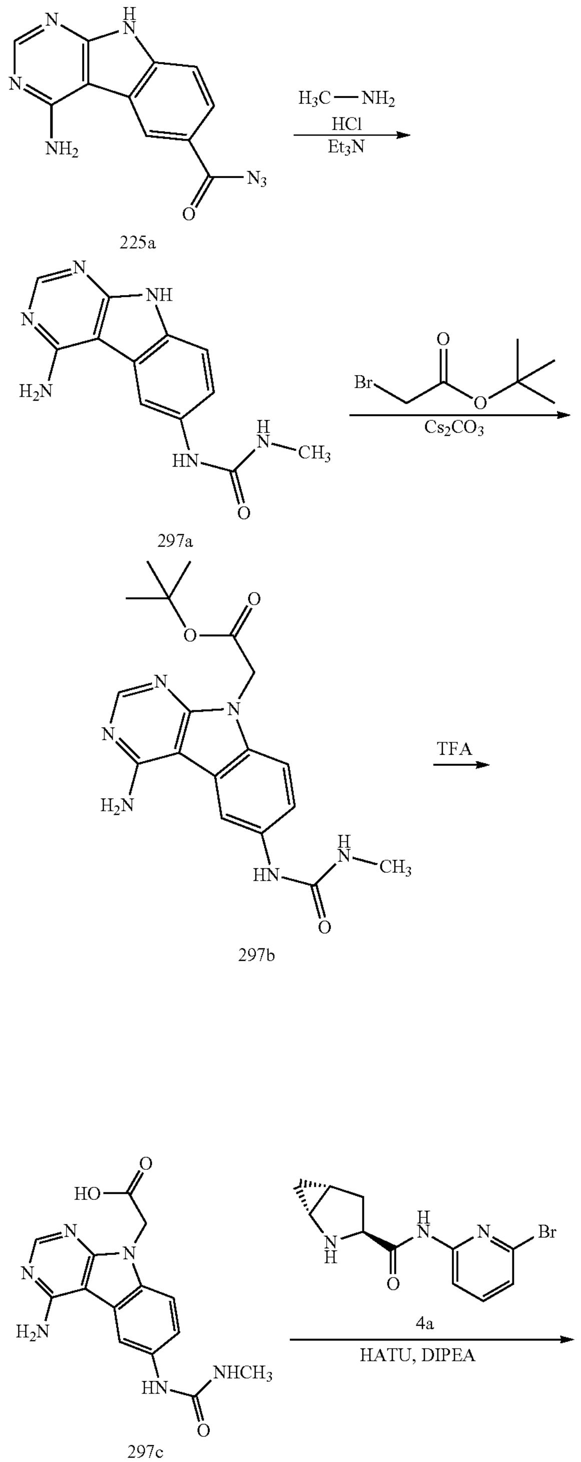

225a, 297a, 297b, 297c, 4a

-continued

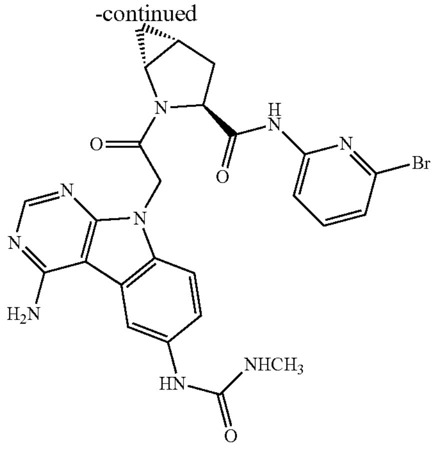

297d

Preparation of (1R,3S,5R)-2-(2-(4-amino-6-(3-methylureido)-9H-pyrimido[4,5-b]indol-9-yl)acetyl)-N-(6-bromopyridin-2-yl)-2-azabicyclo[3.1.0]hexane-3-carboxamide (297d)

Step-1: Preparation of 1-(4-amino-9H-pyrimido[4,5-b]indol-6-yl)-3-methylurea (297a)

A suspension of 4-amino-9H-pyrimido[4,5-b]indole-6-carbonyl azide (225a) (111 mg, 0.438 mmol) in toluene (4 mL) was added methanamine hydrochloride (177 mg, 2.63 mmol), triethylamine (0.916 mL, 6.57 mmol) and heated at 115° C. for 2 h in a microwave. The reaction mixture was cooled to RT, triturated with dichloromethane/methanol (9:1) (30 mL), filtered, washed with dichloromethane/methanol (9:1). The filtrate was concentrated and purified by flash column chromatography [silica gel (40 g), eluting with dichloromethane/methanol (1:0 to 9:1)] to afford 1-(4-amino-9H-pyrimido[4,5-b]indol-6-yl)-3-methylurea (297a) (44 mg, 39% yield) as a light brown gum; MS (ES+): 257.10 (M+Na).

Step-2: Preparation of tert-butyl 2-(4-amino-6-(3-methylureido)-9H-pyrimido[4,5-b]indol-9-yl)acetate (297b)

Compound 297b was prepared according to the procedure reported in step-1 of scheme-1, from 1-(4-amino-9H-pyrimido[4,5-b]indol-6-yl)-3-methylurea (297a) (42 mg, 0.164 mmol) in DMF (10 mL) using tert-butyl 2-bromoacetate (0.027 mL, 0.180 mmol) and $Cs_2CO_3$ (133 mg, 0.410 mmol) and stirring at RT for 17 h. This gave after work up tert-butyl 2-(4-amino-6-(3-methylureido)-9H-pyrimido[4,5-b]indol-9-yl)acetate (297b) (32 mg) and was used as such for the next step; MS (ES+): 371.20 (M+1).

Step-3: Preparation of 2-(4-amino-6-(3-methylureido)-9H-pyrimido[4,5-b]indol-9-yl)acetic acid (297c)

Compound 297c was prepared according to the procedure reported in step-2 of scheme-1, from tert-butyl 2-(4-amino-6-(3-methylureido)-9H-pyrimido[4,5-b]indol-9-yl)acetate (297b) (30 mg, 0.081 mmol) in DCM (10 mL) using TFA and stirring at RT. This gave after work which was used as such for the next step; MS (ES+): 315.10 (M+1).

Step-4: Preparation of (1R,3S,5R)-2-(2-(4-amino-6-(3-methylureido)-9H-pyrimido[4,5-b]indol-9-yl)acetyl)-N-(6-bromopyridin-2-yl)-2-azabicyclo[3.1.0]hexane-3-carboxamide (297d)

Compound 297d was prepared according to the procedure reported in step-3 of scheme-1, from TFA salt of 2-(4-amino-6-(3-methylureido)-9H-pyrimido[4,5-b]indol-9-yl)acetic acid (297c) (25.5 mg, 0.081 mmol) in DMF (10 mL) using HCl salt of (1R,3S,5R)—N-(6-bromopyridin-2-yl)-2-azabicyclo[3.1.0]hexane-3-carboxamide (4a) (51.6 mg, 0.162 mmol), HATU (61.6 mg, 0.0.162 mmol), DIPEA (0.071 mL, 0.405 mmol) and stirring at RT for 21 h. This gave after workup and purification using flash column chromatography [silica gel (12 g), eluting with MeOH in DCM from 0-10%] followed by treating with acetonitrile (2 mL) and 0.1% aq. HCl (10 mL) to afford (1R,3S,5R)-2-(2-(4-amino-6-(3-methylureido)-9H-pyrimido[4,5-b]indol-9-yl)acetyl)-N-(6-bromopyridin-2-yl)-2-azabicyclo[3.1.0]hexane-3-carboxamide (297d) (4 mg, 9% yield) HCl salt as a light brown solid; $^1$H NMR (300 MHz, DMSO-$d_6$) δ 10.76 (s, 1H), 8.55 (s, 1H), 8.42 (s, 1H), 8.27 (s, 1H), 8.01 (d, J=8.1 Hz, 1H), 7.70 (t, J=7.9 Hz, 1H), 7.55 (s, 2H), 7.32 (d, J=7.7 Hz, 1H), 6.19 (s, 1H), 5.71 (d, J=17.5 Hz, 1H), 5.37 (d, J=17.3 Hz, 1H), 4.51-4.33 (m, 1H), 3.98-3.85 (m, 1H), 2.70-2.63 (m, 3H), 2.40-2.14 (m, 2H), 1.97-1.83 (m, 1H), 1.14-0.98 (m, 1H), 0.81-0.71 (m, 1H); MS (ES+): 578.20 (M+1); (ES−): 576.10 (M−1).

Scheme 298

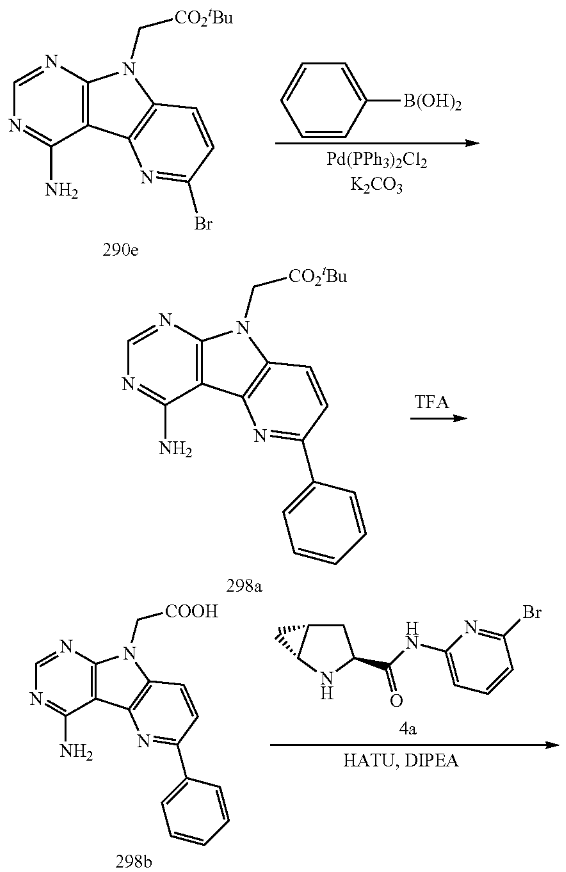

290e

298a

4a

298b

-continued

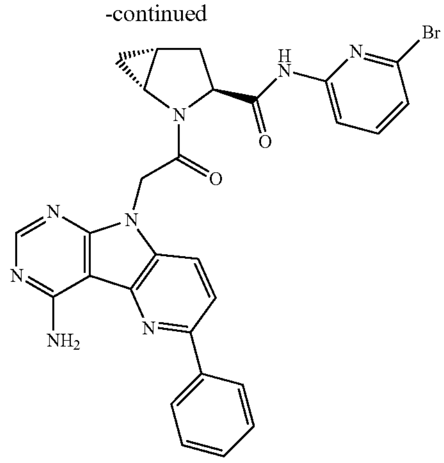

298c

Preparation of (1R,3S,5R)-2-(2-(4-amino-6-phenyl-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (298c)

Step-1: Preparation of tert-butyl 2-(4-amino-6-phenyl-9H-pyrido[2',3':4,5]pyrrolo[2,3-d]pyrimidin-9-yl)acetate (298a)

Compound 298a was prepared according to the procedure reported in step-1 of scheme-59, from tert-butyl 2-(4-amino-6-bromo-9H-pyrido[2',3':4,5]pyrrolo[2,3-d]pyrimidin-9-yl)acetate (290e) (300 mg, 0.793 mmol) in dioxane (4 mL) using phenyl boronic acid (145 mg, 1.190 mmol), bis(triphenylphosphine)palladium(II) chloride (55.7 mg, 0.079 mmol) a solution of 3.3 M potassium carbonate (0.721 mL, 2.380 mmol) and heating at 100° C. for 16 h. This gave after workup and purification using flash column chromatography [silica gel (24 g), eluting with MeOH in DCM from 0-3%] tert-butyl 2-(4-amino-6-phenyl-9H-pyrido[2',3':4,5]pyrrolo[2,3-d]pyrimidin-9-yl)acetate (298a) (281 mg, 94% yield) as a yellow solid; $^1$H NMR (300 MHz, DMSO-$d_6$) δ 8.85 (d, J=1.8 Hz, 1H), 8.42 (d, J=1.9 Hz, 1H), 8.39 (s, 1H), 8.15-7.66 (m, 3H), 7.61-7.50 (m, 2H), 7.49-7.40 (m, 1H), 6.85 (bs, 1H), 5.24 (s, 2H), 1.41 (s, 9H); MS (ES+): 376 (M+1).

Step-2: Preparation of 2-(4-amino-6-phenyl-9H-pyrido[2',3':4,5]pyrrolo[2,3-d]pyrimidin-9-yl)acetic acid (298b)

Compound 298b was prepared according to the procedure reported in step-2 of scheme-1, from tert-butyl 2-(4-amino-6-phenyl-9H-pyrido[2',3':4,5]pyrrolo[2,3-d]pyrimidin-9-yl)acetate (298a) (280 mg, 0.746 mmol) in DCM (5 mL) using TFA (850 mg, 7.46 mmol) and stirring at RT for 16 h. This gave after work up 2-(4-amino-6-phenyl-9H-pyrido[2',3':4,5]pyrrolo[2,3-d]pyrimidin-9-yl)acetic acid (298b) (386 mg) TFA salt as a pale-yellow solid; $^1$H NMR (300 MHz, DMSO-$d_6$) δ 8.98 (d, J=1.8 Hz, 1H), 8.80 (bs, 1H), 8.65 (d, J=1.9 Hz, 1H), 8.60 (s, 1H), 8.10 (bs, 1H), 7.92-7.86 (m, 2H), 7.65-7.52 (m, 2H), 7.53-7.42 (m, 1H), 5.36 (s, 2H); $^{19}$F NMR (282 MHz, DMSO) δ-74.76; MS (ES+): 320 (M+1); (ES−): 318 (M−1).

Step-3: Preparation of (1R,3S,5R)-2-(2-(4-amino-6-phenyl-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (298c)

Compound 298c was prepared according to the procedure reported in step-3 of scheme-1, from TFA salt of 2-(4-amino-6-phenyl-9H-pyrido[2',3':4,5]pyrrolo[2,3-d]pyrimidin-9-yl) acetic acid (298b) (75 mg, 0.173 mmol) in DMF (5 mL) using HCl salt of (1R,3S,5R)—N-(6-bromopyridin-2-yl)-2-azabicyclo[3.1.0]hexane-3-carboxamide (4a) (55.1 mg, 0.173 mmol), HATU (79 mg, 0.208 mmol), DIPEA (112 mg, 0.865 mmol) and stirring at RT for 16 h. This gave after workup and purification using flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (1R,3S,5R)-2-(2-(4-amino-6-phenyl-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (298c) (72 mg, 71% yield) HCl salt as a white solid; $^1$H NMR (300 MHz, DMSO-$d_6$) δ 10.79 (s, 1H, $D_2O$ exchangeable), 9.15-8.85 (bs, 1H, $D_2O$ exchangeable), 8.98 (d, J=1.8 Hz, 1H), 8.85-8.56 (bs, 1H, $D_2O$ exchangeable), 8.70 (s, 1H), 8.53 (d, J=1.9 Hz, 11H), 7.98 (d, J=8.2 Hz, 1H), 7.90-7.83 (m, 2H), 7.67 (t, J=8.0 Hz, 1H), 7.63-7.55 (m, 2H), 7.54-7.45 (m, 1H), 7.31 (d, J=7.7 Hz, 1H), 5.89 (d, J=17.3 Hz, 1H), 5.54 (d, J=17.3 Hz, 1H), 4.45 (dd, J=9.1, 5.5 Hz, 1H), 3.98-3.87 (m, 1H), 2.42-2.28 (m, 1H), 2.28-2.12 (m, 1H), 2.00-1.86 (m, 1H), 1.19-0.99 (m, 1H), 0.87-0.72 (m, 1H); MS (ES+): 583/585 (M+1), (ES−): 581/583 (M−1).

Preparation of (1R,3S,5R)-2-(2-(4-amino-6-phenyl-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (299a)

Compound 299a was prepared according to the procedure reported in step-3 of scheme-1, from TFA salt of 2-(4-amino-6-phenyl-9H-pyrido[2',3':4,5]pyrrolo[2,3-d]pyrimidin-9-yl) acetic acid (298b)(75 mg, 0.173 mmol) in DMF (5 mL) using HCl salt of (1R,3S,5R)—N-(6-bromopyridin-2-yl)-5-methyl-2-azabicyclo[3.1.0]hexane-3-carboxamide (8a)(57.6 mg, 0.173 mmol), HATU (79 mg, 0.208 mmol) DIPEA (112 mg, 0.865 mmol) and stirring at RT for 16 h. This gave after workup and purification using flash column chromatography [silica gel (12 g), eluting with MeOH in DCM from 0-5%] followed by purification using reverse phase column chromatography [C18 column (100 g), eluting with ACN in water (containing 0.1% HCl) from 0-100%] (1R,3S,5R)-2-(2-(4-amino-6-phenyl-9H-pyrido[2',3':4.5]pyrrolo[2,3-d]pyrimidin-9-yl)acetyl)-N-(6-bromopyridin-2-yl)-5-methyl-2-azabicyclo[3.1.0]hexane-3-carboxamide (299a) (67 mg, 65% yield) HCl salt as a white solid, $^1$H NMR (300 MHz, DMSO-$d_6$) δ 10.79 (s, 1H, $D_2O$ exchangeable), 9.19-8.84 (bs, 1H, $D_2O$ exchangeable), 8.98 (d, J=1.8 Hz, 1H), 8.84-8.58 (bs, 1H, $D_2O$ exchangeable), 8.70 (s, 1H), 8.53 (d, J=1.9 Hz, 1H), 7.99 (d, J=8.2 Hz, 1H), 7.90-7.81 (m, 2H), 7.67 (t, J=8.0 Hz, 1H), 7.63-7.54 (m, 2H), 7.54-7.46 (m, 1H), 7.30 (d, J=7.7 Hz, 1H), 5.85 (d, J=17.3 Hz, 1H), 5.48 (d, J=17.3 Hz, 1H), 4.40 (dd, J=9.1, 5.9 Hz, 1H), 3.76-3.61 (m, 1H), 2.48-2.38 (m, 1H), 1.99 (dd, J=13.3, 5.8 Hz, 1H), 1.32 (s, 3H), 1.08-1.00 (m, 1H), 1.00-0.88 (m, 1H); MS (ES+): 597/599 (M+1); (ES−): 595/597 (M−1).

Scheme 299

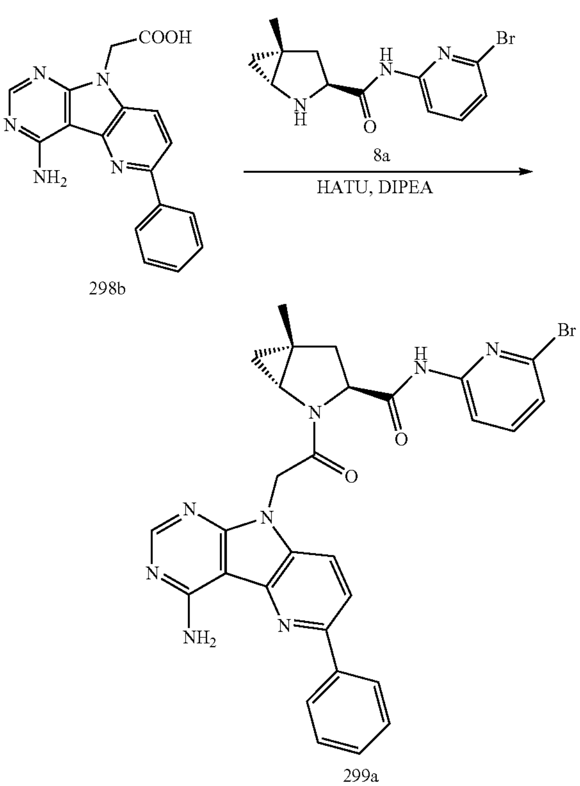

298b

299a

Scheme 300

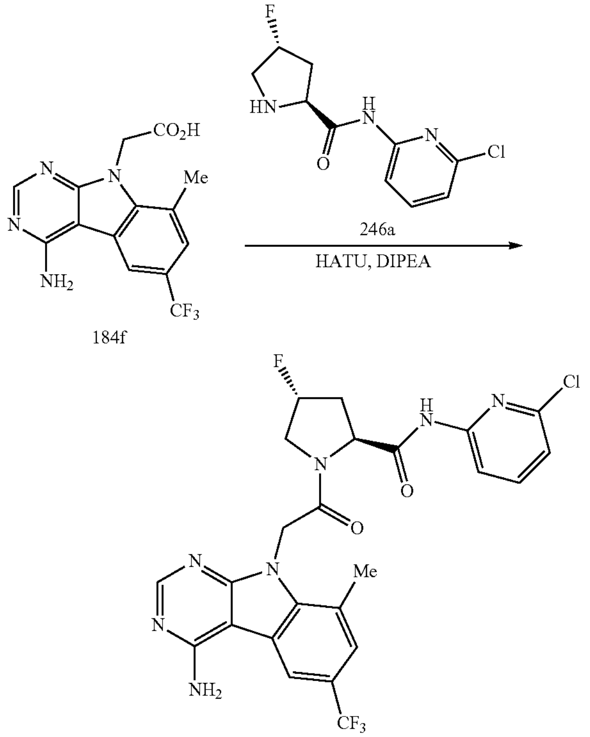

184f

300a

Preparation of (2S,4R)-1-(2-(4-amino-8-methyl-6-(trifluoromethyl)-9H-pyrimido[4,5-b]indol-9-yl)acetyl)-N-(6-chloropyridin-2-yl)-4-fluoropyrrolidine-2-carboxamide (300a)

Compound 300a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (61.3 mg, 0.140 mmol) in DMF (1.5 mL) using TFA salt of (2S,4R)—N-(6-chloropyridin-2-yl)-4-fluoropyrrolidine-2-carboxamide (246a) (50 mg, 0.140 mmol), HATU (80 mg, 0.210 mmol), DIPEA (0.122 mL, 0.699 mmol) and stirring at RT for 16 h. This gave after workup and purification using flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (2S,4R)-1-(2-(4-amino-8-methyl-6-(trifluoromethyl)-9H-pyrimido[4,5-b]indol-9-yl)acetyl)-N-(6-chloropyridin-2-yl)-4-fluoropyrrolidine-2-carboxamide (300a) (48 mg, 62% yield) HCl salt as a white solid: 1H NMR (300 MHz, DMSO-$d_6$) (a mixture of two rotamers) δ 11.37 and 11.03 (2s, 1H), 8.78 (s, 1H), 8.59 (s, 1H), 8.57-8.46 (m, 2H), 8.15 and 7.97 (2d, J=8.2 Hz, 1H), 7.82 (t, J=8.0 Hz, 1H), 7.59 (s, 1H), 7.31 and 7.19 (2d, J=7.7 Hz, 1H), 5.89-5.42 (m, 3H), 4.68 (t, J=8.5 Hz, 1H), 4.32 (dd, J=21.3, 12.6 Hz, 1H), 4.10-3.84 (m, 1H), 2.76 and 2.66 (2s, 3H), 2.61-2.53 (m, 1H), 2.28-2.02 (m, 1H); $^{19}$F NMR (282 MHz, DMSO-$d_6$) δ−58.73, −176.50; MS (ES+): 550.1 (M+1); (ES−): 548.1 (M−1).

Scheme 301

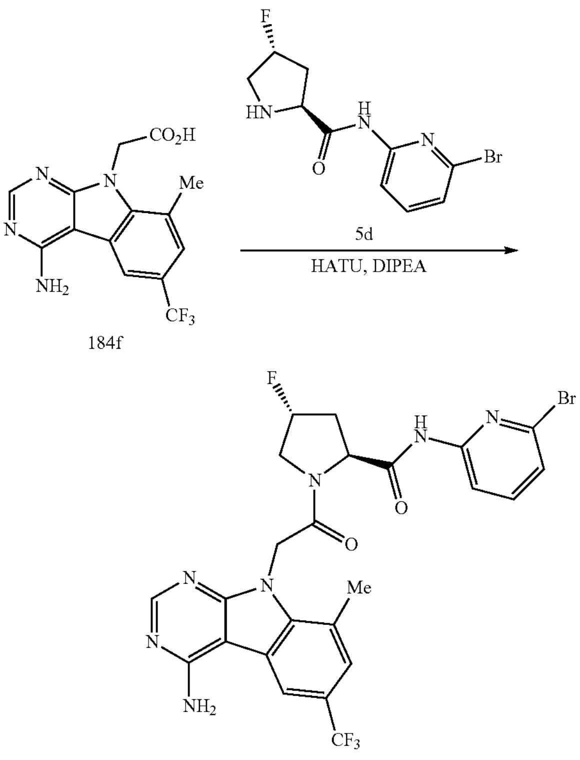

184f

5d

301a

Preparation of (2S,4R)-1-(2-(4-amino-8-methyl-6-(trifluoromethyl)-9H-pyrimido[4,5-b]indol-9-yl)acetyl)-N-(6-bromopyridin-2-yl)-4-fluoropyrrolidine-2-carboxamide (301a)

Compound 301a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (54.5 mg, 0.124 mmol) in DMF (1.5 mL) using TFA salt of (2S,4R)—N-(6-bromopyridin-2-yl)-4-fluoropyrrolidine-2-carboxamide (5d) (50 mg, 0.124 mmol), HATU (70.9 mg, 0.187 mmol), DIPEA (0.108 mL, 0.622 mmol) and stirring at RT for 16 h. This gave after workup and purification using flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (2S,4R)-1-(2-(4-amino-8-methyl-6-(trifluoromethyl)-9H-pyrimido[4,5-b]indol-9-yl)acetyl)-N-(6-bromopyridin-2-yl)-4-fluoropyrrolidine-2-carboxamide (301a) (53 mg, 72% yield) HCl salt as a white solid; $^1$H NMR (300 MHz, DMSO-$d_6$) (a mixture of two rotamers) δ 11.38 and 11.04 (2s, 1H, $D_2O$ exchangeable), 8.76 (s, 1H), 8.57 (s, 1H), 8.45 (s, 2H, $D_2O$ exchangeable), 8.18 and 7.99 (2d, J=8.2 Hz, 1H), 7.84 and 7.71 (2t, J=8.0 Hz, 1H), 7.58 (s, 1H), 7.44 and 7.32 (2d, J=7.7 Hz, 1H), 5.86-5.43 (m, 3H), 4.68 (t, J=8.5 Hz, 1H), 4.31 (dd, J=21.4, 12.6 Hz, 1H), 3.98 (dd, J=38.1, 12.5 Hz, 1H), 2.75 and 2.65 (2s, 3H), 2.61-2.54 (m, 1H), 2.30-2.02 (m, 1H); $^{19}$F NMR (282 MHz, DMSO-$d_6$) δ−58.70, −176.49; MS (ES+): 594.1/596.1 (M+1); (ES−): 592.1/594.1 (M−1).

Scheme 302

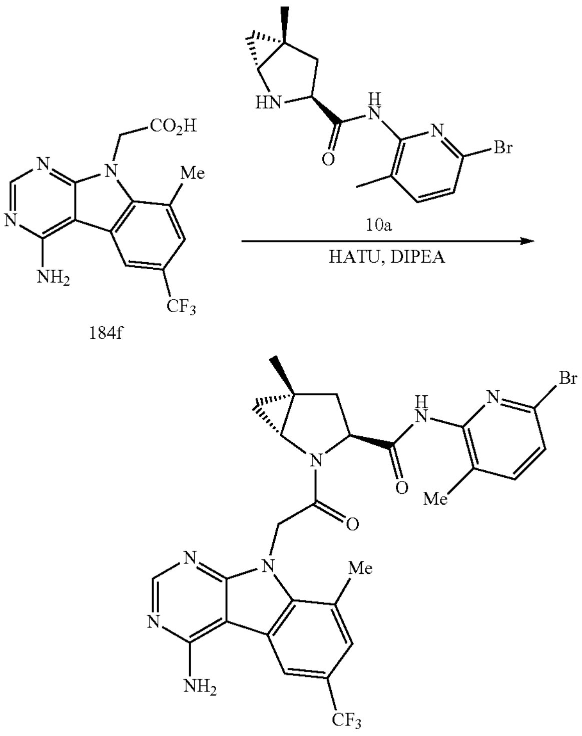

184f

10a

302a

Preparation of (1R,3S,5R)-2-(2-(4-amino-8-methyl-6-(trifluoromethyl)-9H-pyrimido[4,5-b]indol-9-yl)acetyl)-N-(6-bromo-3-methylpyridin-2-yl)-5-methyl-2-azabicyclo[3.1.0]hexane-3-carboxamide (302a)

Compound 302a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (63.2 mg, 0.144 mmol) in DMF (1.5 mL) using HCl salt of (1R,3S,5R)—N-(6-bromo-3-methylpyridin-2-yl)-5-methyl-2-azabicyclo[3.1.0]hexane-3-carboxamide (10a) (50 mg, 0.144 mmol), HATU (82 mg, 0.216 mmol), DIPEA (0.126 mL, 0.721 mmol) and stirring at RT for 16 h. This gave after workup and purification using flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-8-methyl-6-(trifluoromethyl)-9H-pyrimido[4,5-b]indol-9-yl)acetyl)-N-(6-bromo-3-methylpyridin-2-yl)-5-methyl-2-azabicyclo[3.1.0]hexane-3-carboxamide (302a) (64 mg, 72% yield) HCl salt as a white solid; $^1H$ NMR (300 MHz, DMSO-$d_6$) δ 10.33 (s, 1H, $D_2O$ exchangeable), 8.73 (s, 1H), 8.49 (s, 1H), 8.13 (s, 2H, $D_2O$ exchangeable), 7.61 (d, J=8.0 Hz, 1H), 7.53 (s, 1H), 7.43 (d, J=7.9 Hz, 1H), 5.86 (d, J=18.0 Hz, 1H), 5.65 (d, J=17.9 Hz, 1H), 4.37 (dd, J=9.1, 5.6 Hz, 1H), 3.70-3.65 (m, 1H), 2.73 (s, 3H), 2.60-2.57 (m, 1H), 2.08-2.02 (m, 1H), 2.01 (s, 3H), 1.33 (s, 3H), 1.07-1.00 (m, 1H), 0.94-0.85 (m, 1H); $^{19}F$ NMR (282 MHz, DMSO-$d_6$) δ-58.58; MS (ES+): 616.2/618.1 (M+1); (ES−): 614.1/616.1 (M−1).

Scheme 303

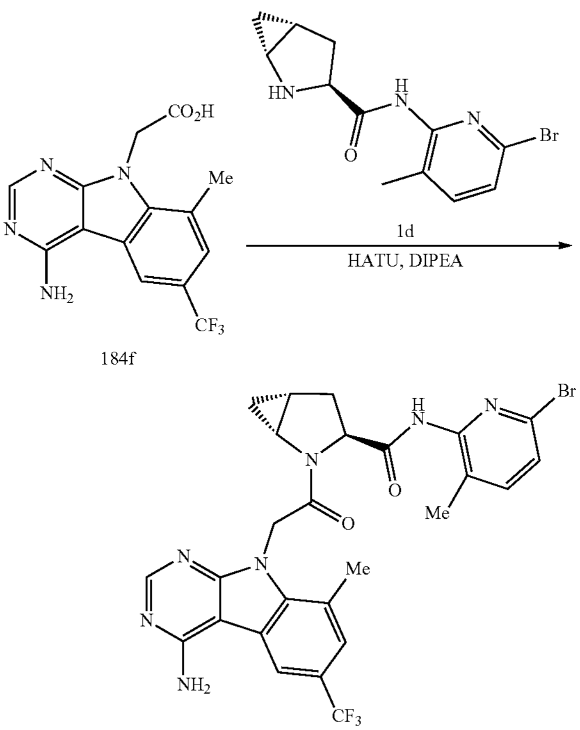

184f

303a

Preparation of (1R,3S,5R)-2-(2-(4-amino-8-methyl-6-(trifluoromethyl)-9H-pyrimido[4,5-b]indol-9-yl)acetyl)-N-(6-bromo-3-methylpyridin-2-yl)-2-azabicyclo[3.1.0]hexane-3-carboxamide (303a)

Compound 303a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (65.9 mg, 0.150 mmol) in DMF (1.5 mL) using HCl salt of (1R,3S,5R)—N-(6-bromo-3-methylpyridin-2-yl)-2-azabicyclo[3.1.0]hexane-3-carboxamide (1d) (50 mg, 0.150 mmol). HATU (86 mg, 0.225 mmol), DIPEA (0.131 mL, 0.752 mmol) and stirring at RT for 16 h. This gave after workup and purification using flash column chromatography [silica gel (24 g), eluting with DMA-80 in DCM from 0-100%] followed by purification using reverse phase column chromatography [C18 column (50 g), eluting with ACN in water (containing 0.1% HCl) from 0-100%] (1R,3S,5R)-2-(2-(4-amino-8-methyl-6-(trifluoromethyl)-9H-pyrimido[4,5-b]indol-9-yl)acetyl)-N-(6-bromo-3-methylpyridin-2-yl)-2-azabicyclo[3.1.0]hexane-3-carboxamide (303a) (45 mg, 50% yield) HCl salt as a white solid; $^1H$ NMR (300 MHz, DMSO-$d_6$) δ 10.32 (s, 1H, $D_2O$ exchangeable), 8.78 (s, 1H), 8.63-8.41 (m, 3H, 2H $D_2O$ exchangeable), 7.63-7.50 (m, 2H), 7.42 (d, J=7.9 Hz, 1H), 5.93 (d, J=18.3 Hz, 1H), 5.70 (d, J=17.9 Hz, 1H), 4.38 (dd, J=9.2, 5.5 Hz, 1H), 3.93-3.84 (m, 1H), 2.74 (s, 3H), 2.47-2.34 (m, 1H), 2.30-2.16 (m, 1H), 1.99 (s, 3H), 1.98-1.88 (m, 1H), 1.16-0.99 (m, 1H), 0.82-0.64 (m, 1H); $^{19}F$ NMR (282 MHz, DMSO-$d_6$) δ −58.69; MS (ES+): 602.1/604.1 (M+1): (ES−): 600.1/602.1 (M−1).

Scheme 304

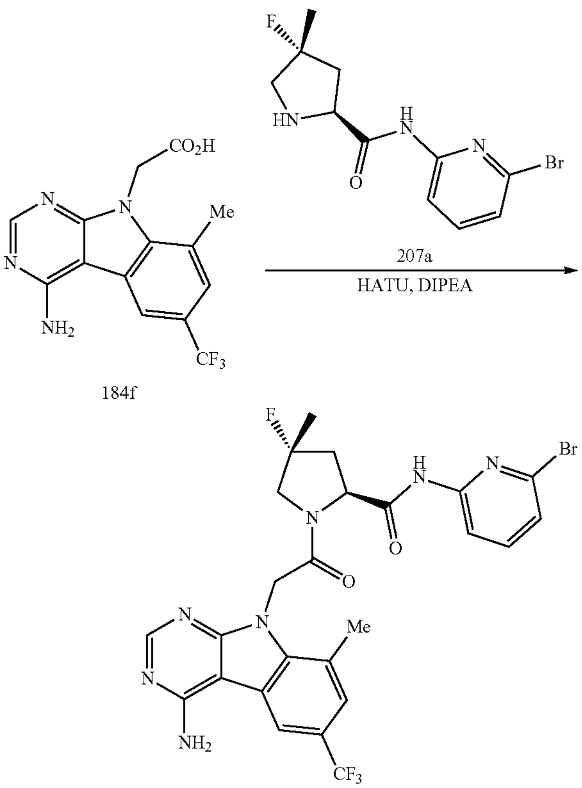

184f

304a

Preparation of (2S,4R)-1-(2-(4-amino-8-methyl-6-(trifluoromethyl)-9H-pyrimido[4,5-b]indol-9-yl)acetyl)-N-(6-bromopyridin-2-yl)-4-fluoro-4-methylpyrrolidine-2-carboxamide (304a)

Compound 304a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (60 mg, 0.137 mmol) in DMF (1.5 mL) using TFA salt of (2S,4R)—N-(6-bromopyridin-2-yl)-4-fluoro-4-methylpyrrolidine-2-carboxamide (207a) (57.0 mg, 0.137 mmol), HATU (78 mg, 0.205 mmol), DIPEA (0.119 mL, 0.684 mmol) and stirring at RT for 16 h. This gave after workup and purification as described in scheme-303, (2S,4R)-1-(2-(4-amino-8-methyl-6-(trifluoromethyl)-9H-pyrimido[4,5-b]indol-9-yl)acetyl)-N-(6-bromopyridin-2-yl)-4-fluoro-4-methylpyrrolidine-2-carboxamide (304a) (41 mg, 49% yield) HCl salt as a white solid; $^1$H NMR (300 MHz, DMSO-$d_6$) (a mixture of two rotamers) δ 11.36 and 11.02 (2s, 1H, $D_2O$ exchangeable), 8.76 (s, 1H), 8.56 (s, 1H), 8.42 (s, 2H, $D_2O$ exchangeable), 8.18 and 7.99 (2d, J=8.2 Hz, 1H), 7.84 and 7.71 (2t, J=8.0 Hz, 1H), 7.58 (s, 1H), 7.43 and 7.32 (2d, J=7.7 Hz, 1H), 5.76 (d, J=18.0 Hz, 1H), 5.54 (d, J=17.9 Hz, 1H), 4.68 (t, J=8.7 Hz, 1H), 4.41-4.20 (m, 1H), 3.96-3.81 (m, 1H), 2.75 (s, 3H), 2.62-2.56 (m, 1H), 2.23-1.95 (m, 1H), 1.62 (d, J=21.1 Hz, 3H); $^{19}$F NMR (282 MHz, DMSO) δ−58.70, −139.66; MS (ES+): 608.1/610.1 (M+1); (ES−): 606.1/608.1 (M−1): Analysis calculated for $C_{21}H_{22}BrF_4N_7O_2$ $2H_2O{\cdot}HCl$: C, 44.10; H, 4.00; Cl, 5.21; N, 14.40. Found: C, 43.75; H, 3.89; Cl, 5.56; N, 14.11.

Preparation of (2S,4R)-1-(2-(4-amino-8-methyl-6-(trifluoromethyl)-9H-pyrimido[4,5-b]indol-9-yl)acetyl)-N-(6-bromopyrazin-2-yl)-4-fluoro-4-methylpyrrolidine-2-carboxamide (305a)

Compound 305a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (60 mg, 0.137 mmol) in DMF (1.5 mL) using HCl salt of (2S,4R)—N-(6-bromopyrazin-2-yl)-4-fluoro-4-methylpyrrolidine-2-carboxamide (213c) (46.5 mg, 0.137 mmol), HATU (78 mg, 0.205 mmol), DIPEA (0.119 mL, 0.684 mmol) and stirring at RT for 16 h. This gave after workup and purification as described in scheme-303, (2S,4R)-1-(2-(4-amino-8-methyl-6-(trifluoromethyl)-9H-pyrimido[4,5-b]indol-9-yl)acetyl)-N-(6-bromopyrazin-2-yl)-4-fluoro-4-methylpyrrolidine-2-carboxamide (305a) (64 mg, 77% yield) HCl salt as a white solid: $^1$H NMR (300 MHz, DMSO-$d_6$) (a mixture of two rotamers) δ 11.68 and 11.38 (2s, 1H, $D_2O$ exchangeable), 9.40 and 9.22 (2s, 1H), 8.78 (s, 1H), 8.70-8.57 (m, 3H, 2H $D_2O$ exchangeable), 8.54 (s, 1H), 7.60 (d, J=1.7 Hz, 1H), 5.79 (d, J=18.0 Hz, 1H), 5.57 (d, J=18.0 Hz, 1H), 4.71 (dd, J=9.8, 7.5 Hz, 1H), 4.30 (dd, J=18.1, 12.1 Hz, 1H), 3.91 (dd, J=35.3, 12.1 Hz, 1H), 2.75 (s, 3H), 2.65-2.55 (m, 1H), 2.25-1.99 (m, 1H), 1.63 (d, J=21.0 Hz, 3H); $^{19}$F NMR (282 MHz, DMSO) δ−58.76, −139.68; MS (ES+): 609.1/611.1 (M+1); (ES−): 607.1/609.1 (M−1); Analysis calculated for $C_{24}H_{21}BrF_4N_8O_2$ $2H_2O{\cdot}HCl$: C, 42.27; H, 3.84; Cl, 5.20; N, 16.43. Found: C, 42.34; H, 3.78; Cl, 4.91; N, 16.16.

Scheme 305

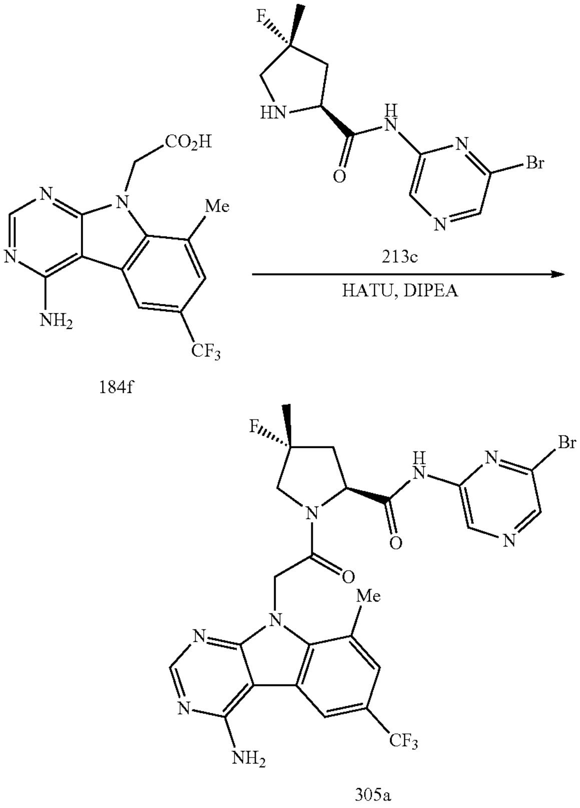

Scheme 306

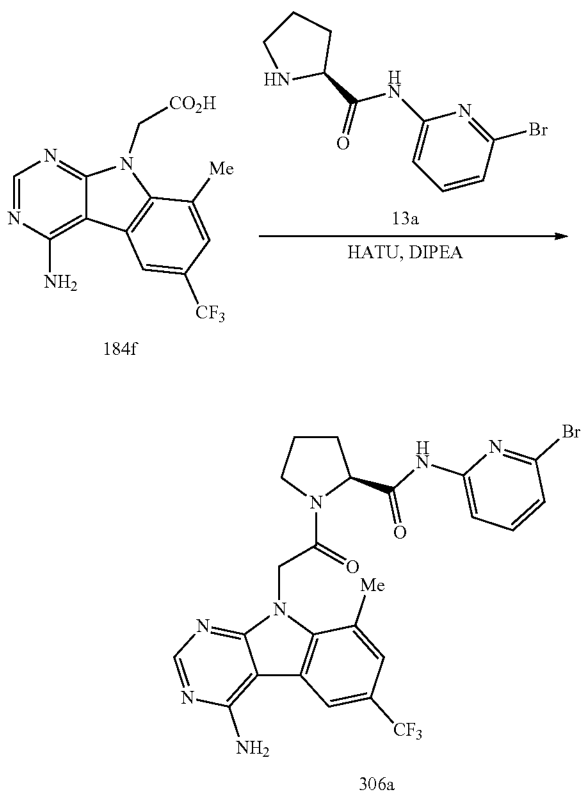

Preparation of (S)-1-(2-(4-amino-8-methyl-6-(trifluoromethyl)-9H-pyrimido[4,5-b]indol-9-yl)acetyl)-N-(6-bromopyridin-2-yl)pyrrolidine-2-carboxamide (306a)

Compound 306a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (60 mg, 0.137 mmol) in DMF (1.5 mL) using TFA salt of (S)—N-(6-bromopyridin-2-yl)pyrrolidine-2-carboxamide (13a) (52.6 mg, 0.137 mmol), HATU (78 mg, 0.205 mmol), DIPEA (0.119 mL, 0.684 mmol) and stirring at RT for 16 h. This gave after workup and purification as described in scheme-303, (S)-1-(2-(4-amino-8-methyl-6-(trifluoromethyl)-9H-pyrimido[4,5-b]indol-9-yl)acetyl)-N-(6-bromopyridin-2-yl)pyrrolidine-2-carboxamide (306a) (76 mg, 96% yield) HCl salt as a white solid; $^1H$ NMR (300 MHz, DMSO-$d_6$) (a mixture of two rotamers) δ 11.28 and 10.94 (2s, 1H, $D_2O$ exchangeable), 8.78 (s, 1H), 8.71-8.43 (m, 3H, 2H $D_2O$ exchangeable), 8.15 and 8.00 (2d, J=8.1 Hz, 1H), 7.82 and 7.71 (2t, J=8.0 Hz, 1H), 7.60 (d, J=1.7 Hz, 1H), 7.41 and 7.31 (2d, J=7.7 Hz, 1H), 5.66 (s, 2H), 4.56 (dd, J=8.4, 4.5 Hz, 1H), 3.84 (t, J=6.6 Hz, 2H), 2.77 (s, 3H), 2.33-2.16 (m, 1H), 2.13-2.00 (m, 2H), 2.00-1.85 (m, 1H); $^{19}F$ NMR (282 MHz, DMSO) δ−58.74: MS (ES+): 576.1/578.1 (M+1); (ES−): 574.1/576.0 (M−1); Analysis calculated for $C_{24}H_{21}BrF_3N_7O_2$ 1.5$H_2O$. HCl: C, 45.05; H, 3.94; Cl, 5.54; N, 15.32. Found: C, 45.19; H, 3.98; Cl, 5.28; N, 15.22.

Scheme 307

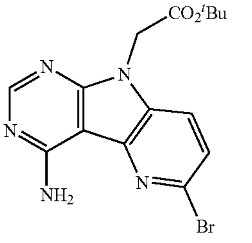

290e

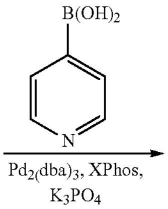

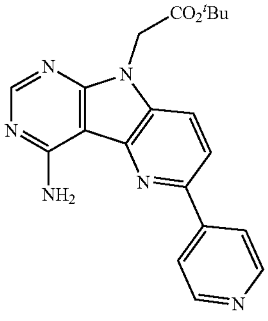

307a

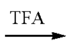

-continued

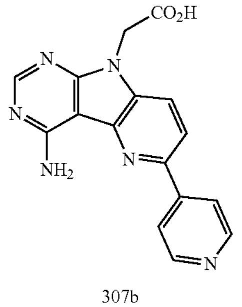

307b

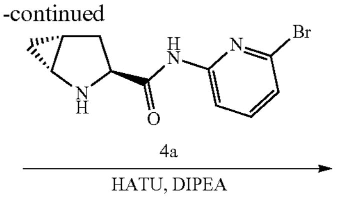

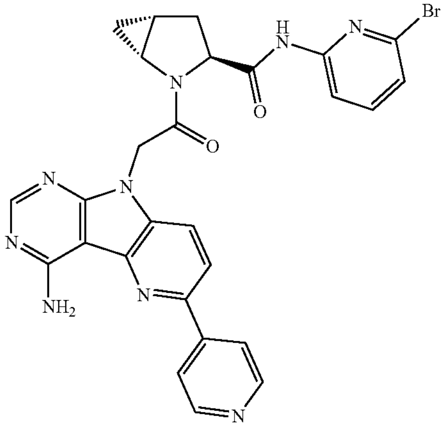

307c

Preparation of (1R,3S,5R)-2-(2-(4-amino-6-(pyridin-4-yl)-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (307c)

Step-1: Preparation of tert-butyl 2-(4-amino-6-(pyridin-4-yl)-9H-pyrido[2',3':4,5]pyrrolo[2,3-d]pyrimidin-9-yl)acetate (307a)

Compound 307a was prepared according to the procedure reported in step-1 of scheme-263, from tert-butyl 2-(4-amino-6-bromo-9H-pyrido[2',3':4,5]pyrrolo[2,3-d]pyrimidin-9-yl)acetate (290e) (300 mg, 0.793 mmol) in n-BuOH (4 mL) using pyridin-4-ylboronic acid (146 mg, 1.190 mmol), $Pd_2(dba)_3$ (72.6 mg, 0.079 mmol), XPhos (76 mg, 0.159 mmol), a solution of 1.27 M potassium phosphate (1.249 mL, 1.586 mmol) and heating at 100° C. for 16 h. This gave after workup and purification by flash column chromatography [silica gel (12 g), eluting with MeOH in DCM from 0-7%] tert-butyl 2-(4-amino-6-(pyridin-4-yl)-9H-pyrido[2',3':4,5]pyrrolo[2,3-d]pyrimidin-9-yl)acetate (307a) (275 mg, 92% yield) as a gray solid; $^1H$ NMR (300 MHz, DMSO-$d_6$) δ 8.99 (d, J=1.8 Hz, 1H), 8.73 (d, 2H), 8.61 (d, J=1.9 Hz, 1H), 8.41 (s, 1H), 8.01 (s, 1H), 7.91 (d, 2H), 6.89 (bs, 1H), 5.25 (s, 2H), 1.41 (s, 9H); MS (ES+): 377 (M+1).

Step-2: Preparation of 2-(4-amino-6-(pyridin-4-yl)-9H-pyrido[2',3':4,5]pyrrolo[2,3-d]pyrimidin-9-yl)acetic acid (307b)

Compound 307b was prepared according to the procedure reported in step-2 of scheme-1, from tert-butyl 2-(4-amino-6-(pyridin-4-yl)-9H-pyrido[2',3':4,5]pyrrolo[2,3-d]pyrimidin-9-yl)acetate (307a) (272 mg, 0.723 mmol) in DCM (5 mL) using TFA (824 mg, 7.23 mmol) and stirring at RT for 16 h. This gave after work up 2-(4-amino-6-(pyridin-4-yl)-9H-pyrido[2',3':4,5]pyrrolo[2,3-d]pyrimidin-9-yl)acetic acid (307b) (358 mg) TFA salt as a beige solid; $^1$H NMR (300 MHz, DMSO-$d_6$) δ 9.28 (d, J=1.9 Hz, 1H), 9.13-9.03 (m, 3H), 8.97 (bs, 1H), 8.68 (s, 1H), 8.60 (d, 2H), 8.30 (bs, 1H), 5.39 (s, 2H); MS (ES+) 321 (M+1); (ES−): 319.10 (M−1).

Step-3: Preparation of (1R,3S,5R)-2-(2-(4-amino-6-(pyridin-4-yl)-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (307c)

Compound 307c was prepared according to the procedure reported in step-3 of scheme-1, from TFA salt of 2-(4-amino-6-(pyridin-4-yl)-9H-pyrido[2',3':4,5]pyrrolo[2,3-d]pyrimidin-9-yl)acetic acid (307b) (75 mg, 0.173 mmol) in DMF (5 mL) using HCl salt of (1R,3S,5R)—N-(6-bromopyridin-2-yl)-2-azabicyclo[3.1.0]hexane-3-carboxamide (4a) (55.0 mg, 0.173 mmol), HATU (79 mg, 0.207 mmol), DIPEA (112 mg, 0.863 mmol) and stirring at RT for 16 h. This gave after workup and purification as described in scheme-299, (1R,3S,5R)-2-(2-(4-amino-6-(pyridin-4-yl)-9H-pyrido[2',3':4.5]pyrrolo[2,3-d]pyrimidin-9-yl)acetyl)-N-(6-bromopyridin-2-yl)-2-azabicyclo[3.1.0]hexane-3-carboxamide (307c) (52 mg, 52% yield) HCl salt as a white solid: 1H NMR (300 MHz, DMSO-$d_6$) δ 10.78 (s, 1H, $D_2O$ exchangeable), 9.20 (d, J=1.9 Hz, 1H), 9.02 (d, J=5.9 Hz, 2H), 8.86-8.68 (bs, 1H, $D_2O$ exchangeable), 8.77 (s, 1H), 8.63 (s, 1H), 8.46 (d, J=6.0 Hz, 2H), 8.13-7.78 (bs, 1H, $D_2O$ exchangeable), 7.97 (d, J=8.2 Hz, 1H), 7.68 (t, J=8.0 Hz, 1H), 7.30 (d, J=7.7 Hz, 1H), 5.85 (d, J=17.2 Hz, 1H), 5.53 (d, J=17.2 Hz, 1H), 4.49-4.41 (m, 1H), 3.95-3.87 (m, 11H), 2.39-2.29 (m, 1H), 2.29-2.17 (m, 1H), 2.01-1.81 (m, 1H), 1.20-1.04 (m, 1H), 0.90-0.74 (m, 1H); MS (ES+): 584/586 (M+1); (ES−): 582/584 (M−1); Analysis calculated for $C_{27}H_{22}BrN_9O_2$·2.2HCl·4.5$H_2O$: C, 43.49; H, 4.49; Cl, 10.46; N, 16.90. Found: C, 43.57; H, 4.29; Cl, 10.41; N, 16.69.

Scheme 308

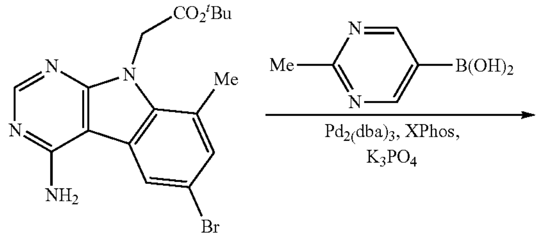

192e

-continued

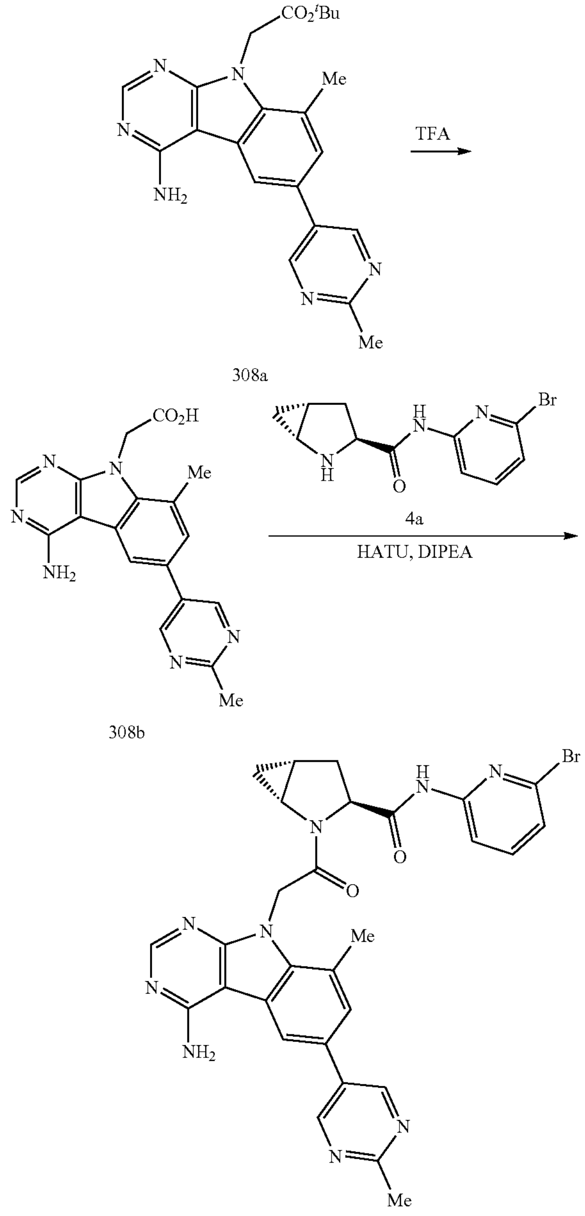

308a

308b

308c

Preparation of (1R,3S,5R)-2-(2-(4-amino-8-methyl-6-(2-methylpyrimidin-5-yl)-9H-pyrimido[4,5-b]indol-9-yl)acetyl)-N-(6-bromopyridin-2-yl)-2-azabicyclo[3.1.0]hexane-3-carboxamide (308c)

Step-1: Preparation of tert-butyl 2-(4-amino-8-methyl-6-(2-methylpyrimidin-5-yl)-9H-pyrimido[4,5-b]indol-9-yl)acetate (308a)

Compound 308a was prepared according to the procedure reported in step-1 of scheme-263, from tert-butyl 2-(4-amino-6-bromo-8-methyl-9H-pyrimido[4,5-b]indol-9-yl) acetate (192e) (500 mg, 1.278 mmol) in n-BuOH (20 mL) using (2-methylpyrimidin-5-yl)boronic acid (264 mg, 1.917 mmol), $Pd_2(dba)_3$ (117 mg, 0.128 mmol), XPhos (122 mg, 0.256 mmol), a solution of 1.27 M potassium phosphate (2.012 mL, 2.56 mmol) and heating at 100° C. for 16 h. This gave after workup and purification by flash column chromatography [silica gel (12 g), eluting with MeOH in DCM from 0-7%] tert-butyl 2-(4-amino-8-methyl-6-(2-methylpyrimidin-5-yl)-9H-pyrimido[4,5-b]indol-9-yl)acetate (308a) (475 mg, 92% yield) as a white solid; $^1$H NMR (300 MHz, DMSO-$d_6$) δ 9.21 (s, 2H), 8.59 (d, J=1.8 Hz, 1H), 8.33 (s, 1H), 7.64 (s, 1H), 7.49 (s, 2H), 5.37 (s, 2H), 2.71 (s, 3H), 2.68 (s, 3H), 1.44 (s, 9H); MS (ES+): 405 (M+1); (ES−): 403 (M−1).

Step-2: Preparation of 2-(4-amino-8-methyl-6-(2-methylpyrimidin-5-yl)-9H-pyrimido[4,5-b]indol-9-yl)acetic acid (308b)

Compound 308b was prepared according to the procedure reported in step-2 of scheme-1, from tert-butyl 2-(4-amino-8-methyl-6-(2-methylpyrimidin-5-yl)-9H-pyrimido[4,5-b]indol-9-yl)acetate (308a) (475 mg, 1.174 mmol) in DCM (20 mL) using TFA (1339 mg, 11.74 mmol) and stirring at RT for 16 h. This gave after work up TFA salt 2-(4-amino-8-methyl-6-(2-methylpyrimidin-5-yl)-9H-pyrimido[4,5-b]indol-9-yl) acetic acid (308b) (715 mg) as a pale yellow solid; $^1$H NMR (300 MHz, DMSO-$d_6$) δ 9.21 (s, 2H), 8.82 (bs, 2H), 8.73 (d, J=1.8 Hz, 1H), 8.65 (s, 1H), 7.80 (s, 1H), 5.48 (s, 2H), 2.77 (s, 3H), 2.70 (s, 3H); $^{19}$F NMR (282 MHz, DMSO-$d_6$) δ−74.78; MS (ES+): 349 (M+1); (ES−): 347 (M−1).

Step-3: Preparation of (1R,3S,5R)-2-(2-(4-amino-8-methyl-6-(2-methylpyrimidin-5-yl)-9H-pyrimido[4,5-b]indol-9-yl)acetyl)-N-(6-bromopyridin-2-yl)-2-azabicyclo[3.1.0]hexane-3-carboxamide (308c)

Compound 308c was prepared according to the procedure reported in step-3 of scheme-1, from TFA salt of 2-(4-amino-8-methyl-6-(2-methylpyrimidin-5-yl)-9H-pyrimido[4,5-b]indol-9-yl)acetic acid (308b) (75 mg, 0.162 mmol) in DMF (5 mL) using HCl salt of (1R,3S,5R)—N-(6-bromopyridin-2-yl)-2-azabicyclo[3.1.0]hexane-3-carboxamide (4a) (51.7 mg, 0.162 mmol), HATU (74.0 mg, 0.195 mmol), DIPEA (105 mg, 0.81 mmol) and stirring at RT for 16 h. This gave after workup and purification as described in scheme-299, (1R,3S,5R)-2-(2-(4-amino-8-methyl-6-(2-methylpyrimidin-5-yl)-9H-pyrimido[4,5-b]indol-9-yl)acetyl)-N-(6-bromopyridin-2-yl)-2-azabicyclo[3.1.0]hexane-3-carboxamide (308c) (70 mg, 71% yield) HCl salt as a white solid; $^1$H NMR (300 MHz, DMSO-$d_6$) δ 10.84 (s, 1H, $D_2O$ exchangeable), 9.23 (s, 2H), 9.06 (bs, 2H, $D_2O$ exchangeable), 8.77 (d, J=1.7 Hz, 1H), 8.69 (s, 1H), 8.00 (d, J=8.2 Hz, 1H), 7.79 (s, 1H), 7.70 (t, J=8.0 Hz, 1H), 7.31 (d, J=7.7 Hz, 1H), 5.97 (d, J=18.0 Hz, 1H), 5.67 (d, J=17.9 Hz, 1H), 4.43 (dd, J=9.1, 5.7 Hz, 1H), 3.98-3.91 (m, 1H), 2.78 (s, 3H), 2.69 (s, 3H), 2.42-2.29 (m, 1H), 2.29-2.10 (m, 1H), 2.02-1.87 (m, 1H), 1.17-1.02 (m, 1H), 0.79-0.62 (m, 1H); MS (ES+): 612/614 (M+1): (ES−): 610/612 (M−1); Analysis calculated for $C_{29}H_{26}BrN_9O_2 \cdot 1.5HCl \cdot 4H_2O$: C, 47.12; H, 4.84; Cl, 7.19; N, 17.05. Found: C, 47.26; H, 4.67; Cl, 7.17; N, 17.07.

Scheme 309

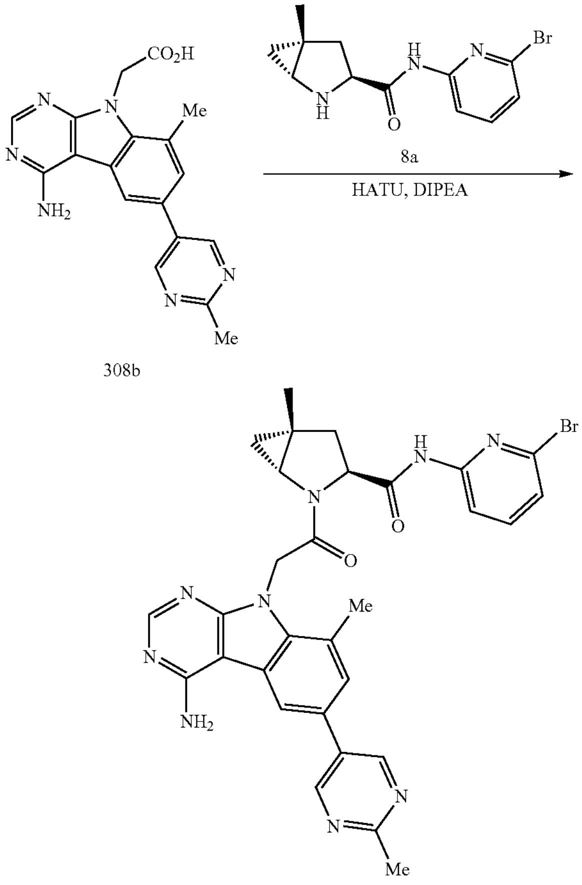

308b

8a

309a

Preparation of (1R,3S,5R)-2-(2-(4-amino-8-methyl-6-(2-methylpyrimidin-5-yl)-9H-pyrimido[4,5-b]indol-9-yl)acetyl)-N-(6-bromopyridin-2-yl)-5-methyl-2-azabicyclo[3.1.0]hexane-3-carboxamide (309a)

Compound 309a was prepared according to the procedure reported in step-3 of scheme-1, from TFA salt of 2-(4-amino-8-methyl-6-(2-methylpyrimidin-5-yl)-9H-pyrimido[4,5-b]indol-9-yl)acetic acid (308b) (75 mg, 0.162 mmol) in DMF (5 mL) using HCl salt of (1R,3S,5R)—N-(6-bromopyridin-2-yl)-5-methyl-2-azabicyclo[3.1.0]hexane-3-carboxamide (8a) (54 mg, 0.162 mmol), HATU (74.0 mg, 0.195 mmol), DIPEA (105 mg, 0.811 mmol) and stirring at RT for 16 h. This gave after workup and purification as described in scheme-299, (1R,3S,5R)-2-(2-(4-amino-8-methyl-6-(2-methylpyrimidin-5-yl)-9H-pyrimido[4,5-b]indol-9-yl) acetyl)-N-(6-bromopyridin-2-yl)-5-methyl-2-azabicyclo [3.1.0]hexane-3-carboxamide (309a) (64 mg, 63% yield) HCl salt as a white solid: $^1$H NMR (30) MHz, DMSO-$d_6$) δ 10.84 (s, 1H, $D_2O$ exchangeable), 9.23 (s, 1H), 9.21 (s, 1H), 9.01 (bs, 1H, $D_2O$ exchangeable), 8.89 (bs, 1H, $D_2O$ exchangeable), 8.76 (s, 1H), 8.71-8.64 (m, 1H), 8.02 (d, J=8.2 Hz, 1H), 7.79 (s, 1H), 7.71 (t, J=8.0 Hz, 1H), 7.32 (d, J=7.7 Hz, 1H), 5.92 (d, J=18.0 Hz, 1H), 5.63 (d, J=17.8 Hz, 1H), 4.39 (dd, J=9.0, 6.2 Hz, 1H), 3.75-3.70 (m, 1H), 2.77 (s, 3H), 2.69 (s, 3H), 2.49-2.44 (m, 1H), 1.99 (dd, J=13.3, 6.1 Hz, 1H), 1.32 (s, 3H), 1.11-0.99 (m, 1H), 0.92-0.81 (m, 1H); MS (ES+) 626/628 (M+1); (ES−) 624/626 (M−1); Analysis calculated for $C_{30}H_{28}BrN_9O_2 \cdot 1.6HCl \cdot 4H_2O$: C, 47.60; H, 5.01; Cl, 7.49; N, 16.65. Found: C, 47.59; H, 4.89; Cl, 7.36:

Scheme 310

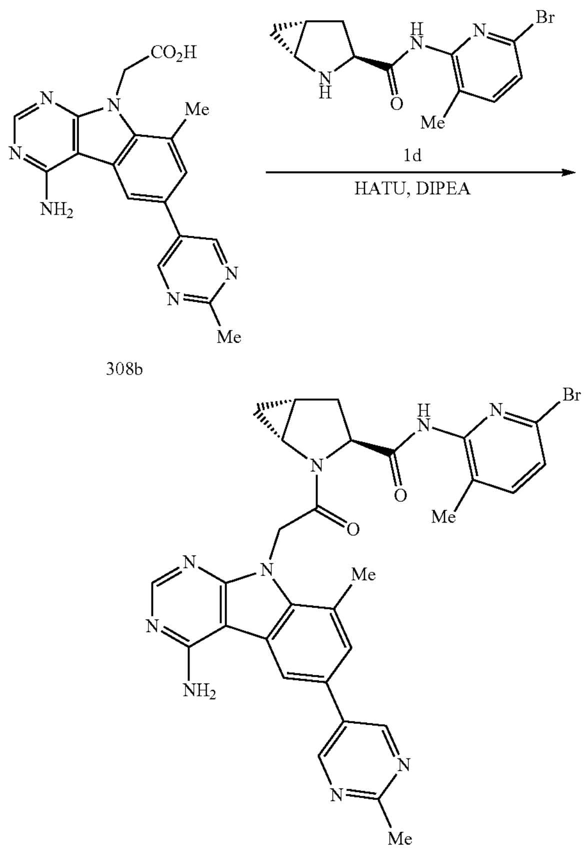

308b

310a

Preparation of (1R,3S,5R)-2-(2-(4-amino-8-methyl-6-(2-methylpyrimidin-5-yl)-9H-pyrimido[4,5-b]indol-9-yl)acetyl)-N-(6-bromo-3-methylpyridin-2-yl)-2-azabicyclo[3.1.0]hexane-3-carboxamide (310a)

Compound 310a was prepared according to the procedure reported in step-3 of scheme-1, from TFA salt of 2-(4-amino-8-methyl-6-(2-methylpyrimidin-5-yl)-9H-pyrimido[4,5-b]indol-9-yl)acetic acid (308b) (75 mg, 0.162 mmol) in DMF (5 mL) using HCl salt of (1R,3S,5R)—N-(6-bromo-3-methylpyridin-2-yl)-2-azabicyclo[3.1.0]hexane-3-carboxamide (1d) (54 mg, 0.162 mmol), HATU (74 mg, 0.195 mmol), DIPEA (105 mg, 0.811 mmol) and stirring at RT for 16 h. This gave after workup and purification as described in scheme-299, (1R,3S,5R)-2-(2-(4-amino-8-methyl-6-(2-methylpyrimidin-5-yl)-9H-pyrimido[4,5-b]indol-9-yl)acetyl)-N-(6-bromo-3-methylpyridin-2-yl)-2-azabicyclo[3.1.0]hexane-3-carboxamide (310a) (41 mg, 40% yield) HCl salt as a white solid: $^1$H NMR (300 MHz, DMSO-$d_6$) δ 10.35 (s, 1H, $D_2O$ exchangeable), 9.26 (s, 2H), 9.11 (bs, 2H, $D_2O$ exchangeable), 8.80 (s, 1H), 8.70 (s, 1H), 7.79 (s, 1H), 7.60 (d, J=8.0 Hz, 1H), 7.42 (d, J=7.9 Hz, 1H), 5.96 (d, J=18.0 Hz, 11H), 5.68 (d, J=17.8 Hz, 11H), 4.41 (dd, J=9.2, 5.6 Hz, 1H), 3.95-3.93 (m, 1H), 2.76 (s, 3H), 2.71 (s, 3H), 2.48-2.36 (m, 1H), 2.32-2.19 (m, 1H), 2.00 (s, 3H), 1.98-1.91 (m, 1H), 1.19-0.98 (m, 1H), 0.89-0.65 (m, 1H); MS (ES+) 626/628 (M+1); (ES−) 624/626 (M−1); Analysis calculated for $C_{30}H_{28}BrN_9O_2 \cdot 1.5HCl \cdot 5.25H_2O$: C, 46.45; H, 5.20; N, 16.25. Found: C, 46.48; H, 4.98; N, 16.02.

Scheme 311

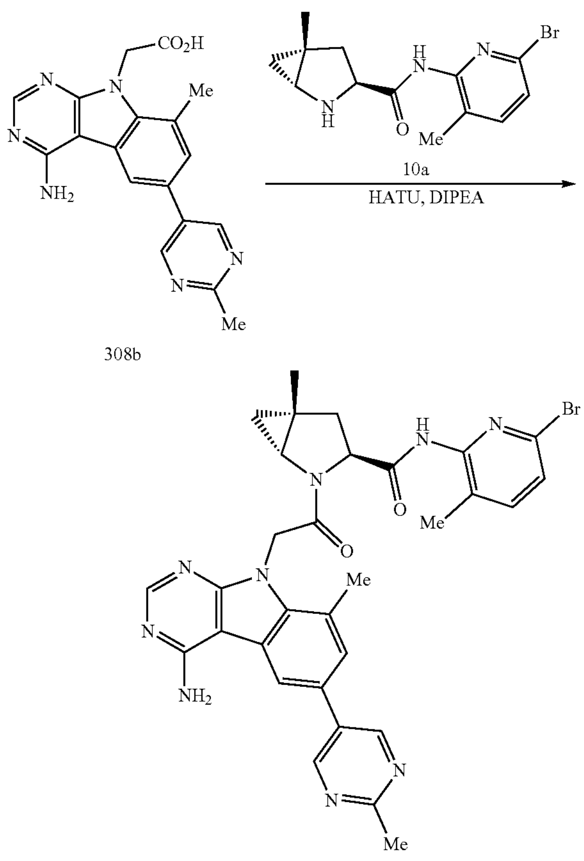

308b

311a

Preparation of (1R,3S,5R)-2-(2-(4-amino-8-methyl-6-(2-methylpyrimidin-5-yl)-9H-pyrimido[4,5-b]indol-9-yl)acetyl)-N-(6-bromo-3-methylpyridin-2-yl)-5-methyl-2-azabicyclo[3.1.0]hexane-3-carboxamide (311a)

Compound 311a was prepared according to the procedure reported in step-3 of scheme-1, from TFA salt of 2-(4-amino-8-methyl-6-(2-methylpyrimidin-5-yl)-9H-pyrimido[4,5-b]indol-9-yl)acetic acid (308b) (75 mg, 0.162 mmol) in DMF (5 mL) using HCl salt of (1R,3S,5R)—N-(6-bromo-3-methylpyridin-2-yl)-5-methyl-2-azabicyclo[3.1.0]hexane-3-carboxamide (10a) (56.2 mg, 0.162 mmol), HATU (74.0 mg, 0.195 mmol). DIPEA (105 mg, 0.811 mmol) and stirring at RT for 16 h. This gave after workup and purification as described in scheme-299, (1R,3S,5R)-2-(2-(4-amino-8-methyl-6-(2-methylpyrimidin-5-yl)-9H-pyrimido[4,5-b]indol-9-yl)acetyl)-N-(6-bromo-3-methylpyridin-2-yl)-5-methyl-2-azabicyclo[3.1.0]hexane-3-carboxamide (311a) (61 mg, 59% yield) HCl salt as a white solid; $^1$H NMR (300 MHz, DMSO-$d_6$) δ 10.37 (s, 1H, $D_2O$ exchangeable), 9.24 (s, 2H), 9.04 (bs, 2H, $D_2O$ exchangeable), 8.78 (d, J=1.7 Hz, 1H), 8.68 (s, 1H), 7.78 (s, 1H), 7.61 (d, J=8.0 Hz, 1H), 7.42

(d, J=7.9 Hz, 1H), 5.90 (d, J=18.0 Hz, 1H), 5.63 (d, J=17.9 Hz, 1H), 4.39 (dd, J=9.1, 5.7 Hz, 1H), 3.71-3.68 (m, 1H), 2.74 (s, 3H), 2.70 (s, 3H), 2.63-2.53 (m, 1H), 2.13-2.04 (m, 1H), 2.02 (s, 3H), 1.34 (s, 3H), 1.10-0.97 (m, 1H), 0.98-0.85 (m, 1H): MS (ES+): 640/642 (M+1), (ES−): 638/640 (M−1); Analysis calculated for $C_{31}H_{30}BrN_9O_2 \cdot 1.5HCl \cdot 3.5H_2O$: C, 49.10; H, 5.12; Cl, 7.01; N, 16.62. Found: C, 48.93; H, 4.95; Cl, 7.05; N, 16.39.

Scheme 312

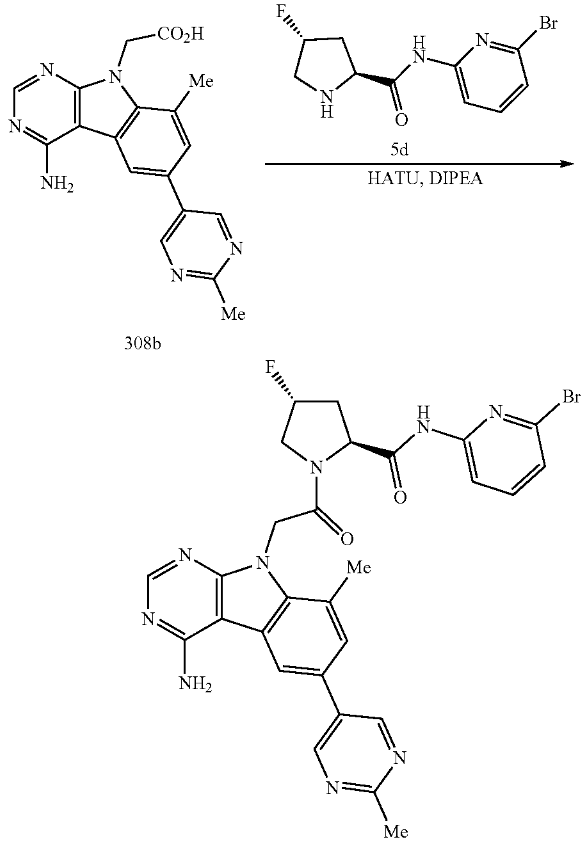

308b

312a

Preparation of (2S,4R)-1-(2-(4-amino-8-methyl-6-(2-methylpyrimidin-5-yl)-9H-pyrimido[4,5-b]indol-9-yl)acetyl)-N-(6-bromopyridin-2-yl)-4-fluoropyrrolidine-2-carboxamide (312a)

Compound 312a was prepared according to the procedure reported in step-3 of scheme-1, from TFA salt of 2-(4-amino-8-methyl-6-(2-methylpyrimidin-5-yl)-9H-pyrimido[4,5-b]indol-9-yl)acetic acid (308b) (75 mg, 0.162 mmol) in DMF (5 mL) using HCl salt of (2S,4R)—N-(6-bromopyridin-2-yl)-4-fluoropyrrolidine-2-carboxamide (5d) (52.6 mg, 0.162 mmol), HATU (74.0 mg, 0.195 mmol), DIPEA (105 mg, 0.811 mmol) and stirring at RT for 16 h. This gave after workup and purification as described in scheme-299, (2S,4R)-1-(2-(4-amino-8-methyl-6-(2-methylpyrimidin-5-yl)-9H-pyrimido[4,5-b]indol-9-yl)acetyl)-N-(6-bromopyridin-2-yl)-4-fluoropyrrolidine-2-carboxamide (312a) (26 mg, 26% yield) HCl salt as a white solid; 1H NMR (300 MHz, DMSO-$d_6$) δ (a mixture of two rotamers) 11.39 and 11.05 (2s, 1H, $D_2O$ exchangeable), 9.23 and 9.21 (2s, 2H), 8.94 (s, 2H, $D_2O$ exchangeable), 8.76 (d, J=1.7 Hz, 1H), 8.67 and 8.65 (2s, 1H), 8.18 and 7.99 (2d, J=8.2 Hz, 1H), 7.82 and 7.70 (2t, J=8.0 Hz, 1H), 7.79 (s, 1H), 7.44 and 7.31 (d, J=7.7 Hz, 1H), 5.91-5.09 (m, 3H), 4.69 (t, J=8.5 Hz, 1H), 4.42-4.22 (m, 1H), 4.10-3.93 (m, 1H), 2.77 (s, 3H), 2.69 (s, 3H), 2.32-2.16 (m, 1H), 2.16-2.01 (m, 1H); $^{19}F$ NMR (282 MHz, DMSO-$d_6$) δ−176.18; MS (ES+): 618/620 (M+1); (ES−): 616/618 (M−1).

Scheme 313

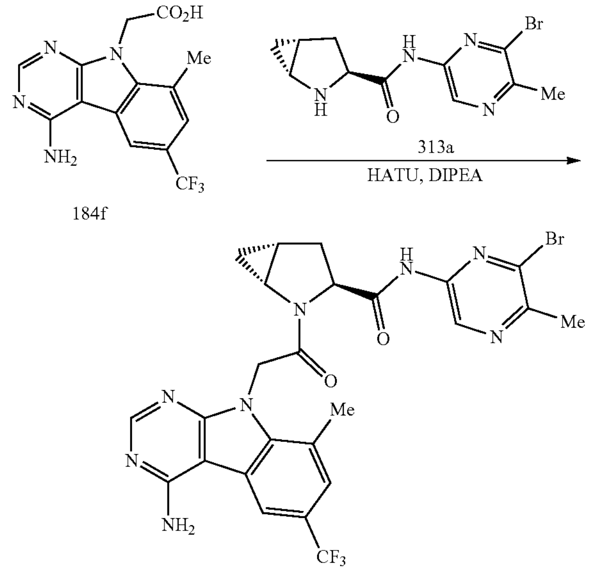

184f

313b

Preparation of (1R,3S,5R)-2-(2-(4-amino-8-methyl-6-(trifluoromethyl)-9H-pyrimido[4,5-b]indol-9-yl)acetyl)-N-(6-bromo-5-methylpyrazin-2-yl)-2-azabicyclo[3.1.0]hexane-3-carboxamide (313b)

Compound 313b was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (75 mg, 0.171 mmol) in DMF (5 mL) using HCl salt of (1R,3S,5R)—N-(6-bromo-5-methylpyrazin-2-yl)-2-azabicyclo[3.1.0]hexane-3-carboxamide (313a) (57.1 mg, 0.171 mmol; CAS #2086190-99-8), HATU (98 mg, 0.257 mmol), DIPEA (111 mg, 0.856 mmol) and stirring at RT for 16 h. This gave after workup and purification as described in scheme-299, (1R,3S,5R)-2-(2-(4-amino-8-methyl-6-(trifluoromethyl)-9H-pyrimido[4,5-b]indol-9-yl)acetyl)-N-(6-bromo-5-methylpyrazin-2-yl)-2-azabicyclo[3.1.0]hexane-3-carboxamide (313b) (52 mg, 50% yield) HCl salt as a white solid; 1H NMR (300 MHz, DMSO-$d_6$) δ 11.08 (s, 1H, $D_2O$ exchangeable), 9.10 (s, 1H), 8.80 (s, 1H), 8.71 (bs, 2H, $D_2O$ exchangeable), 8.65 (s, 1H), 7.61 (s, 1H), 5.98 (d, J=18.1 Hz, 1H), 5.70 (d, J=17.9 Hz, 1H), 4.44 (dd, J=9.1, 5.6 Hz, 1H), 3.98-3.90 (m, 1H), 2.77 (s, 3H), 2.52 (s, 3H), 2.43-2.29 (m, 1H), 2.29-2.14 (m, 1H), 2.01-1.87 (m, 1H), 1.17-0.99 (m, 1H), 0.82-0.62 (m, 1H); $^{19}F$ NMR (282 MHz, DMSO-$d_6$) δ −58.78; MS (ES+): 603/605 (M+1), (ES−): 601/603 (M−1); Analysis calculated for $C_{25}H_{22}BrF_3N_8O_2 \cdot 1.4HCl \cdot 1.5H_2O$: C, 44.06; H, 3.90; N, 16.44. Found: C, 44.02; H, 3.55; N, 16.44.

Scheme 314

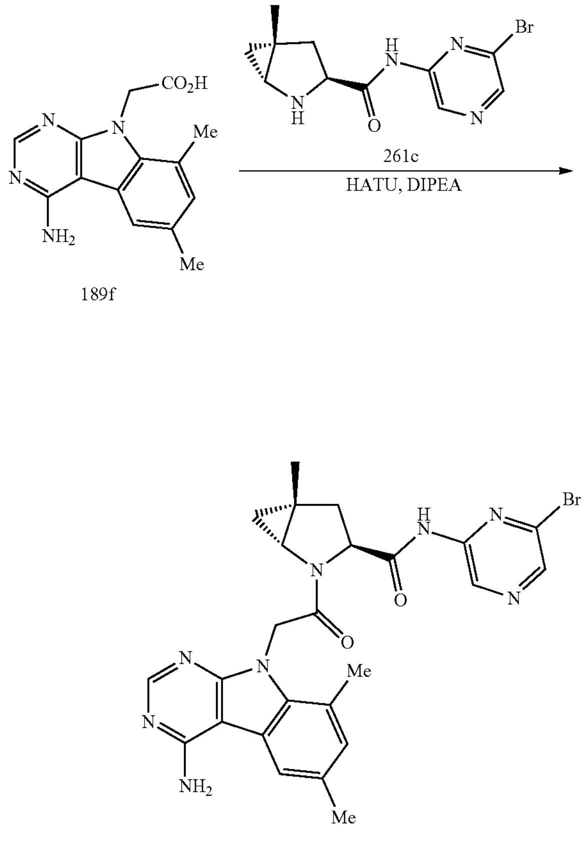

189f 261c 314a

Scheme 315

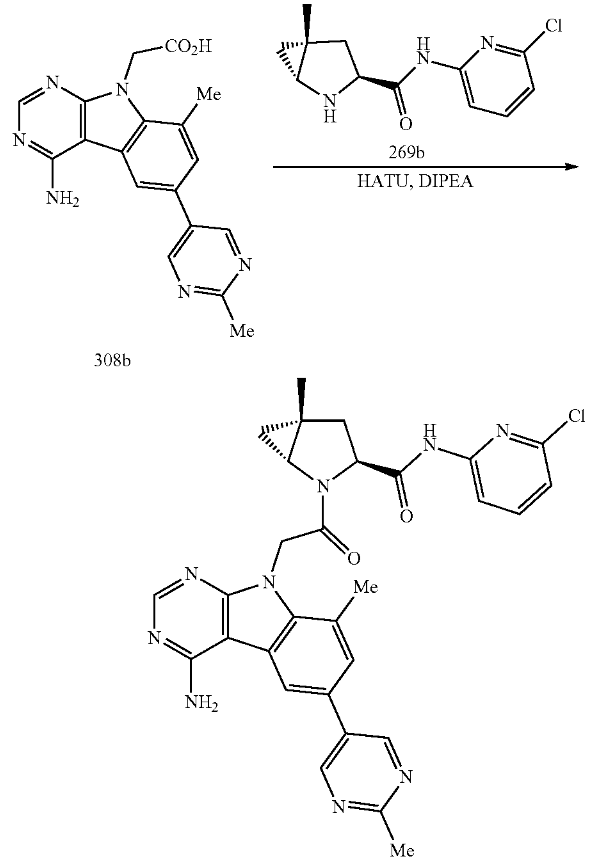

308b 269b 315a

Preparation of (1R,3S,5R)-2-(2-(4-amino-6,8-dimethyl-9H-pyrimido[4,5-b]indol-9-yl)acetyl)-N-(6-bromopyrazin-2-yl)-5-methyl-2-azabicyclo[3.1.0]hexane-3-carboxamide (314a)

Compound 314a was prepared according to the procedure reported in step-3 of scheme-1, from TFA salt of 2-(4-amino-6,8-dimethyl-9H-pyrimido[4,5-b]indol-9-yl)acetic acid (189f) (75 mg, 0.195 mmol) in DMF (5 mL) using HCl salt of (1R,3S,5R)—N-(6-bromopyrazin-2-yl)-5-methyl-2-azabicyclo[3.1.0]hexane-3-carboxamide (261c) (65.1 mg, 0.195 mmol), HATU (111 mg, 0.293 mmol), DIPEA (126 mg, 0.976 mmol) and stirring at RT for 16 h. This gave after workup and purification as described in scheme-299, (1R,3S,5R)-2-(2-(4-amino-6,8-dimethyl-9H-pyrimido[4,5-b]indol-9-yl)acetyl)-N-(6-bromopyrazin-2-yl)-5-methyl-2-azabicyclo[3.1.0]hexane-3-carboxamide (314a) (66 mg, 62% yield) HCl salt as a white solid: $^1$H NMR (300 MHz, DMSO-$d_6$) δ 11.20 (s, 1H, $D_2O$ exchangeable), 9.24 (s, 1H), 8.64 (bs, 2H, $D_2O$ exchangeable), 8.61 (s, 1H), 8.54 (s, 1H), 8.17 (s, 1H), 7.12 (s, 1H), 5.86 (d, J=18.0 Hz, 1H), 5.58 (d, J=17.9 Hz, 1H), 4.41 (dd, J=9.1, 6.1 Hz, 1H), 3.74-3.69 (m, 1H), 2.65 (s, 3H), 2.50-2.45 (m, 1H), 2.43 (s, 3H), 2.12-1.98 (m, 1H), 1.31 (s, 3H), 1.09-0.95 (m, 1H), 0.92-0.81 (m, 1H); MS (ES+): 549/551 (M+1): (ES−): 547/549 (M−1); Analysis calculated for $C_{25}H_{25}BrN_8O_2 \cdot 1.1HCl, 2H_2O$: C, 48.00; H, 4.85; Cl, 6.23; N, 17.91. Found: C, 47.84; H, 4.67; Cl, 6.10; N, 17.90.

Preparation of (1R,3S,5R)-2-(2-(4-amino-8-methyl-6-(2-methylpyrimidin-5-yl)-9H-pyrimido[4,5-b]indol-9-yl)acetyl)-N-(6-chloropyridin-2-yl)-5-methyl-2-azabicyclo[3.1.0]hexane-3-carboxamide (315a)

Compound 315a was prepared according to the procedure reported in step-3 of scheme-1, from TFA salt of 2-(4-amino-8-methyl-6-(2-methylpyrimidin-5-yl)-9H-pyrimido[4,5-b]indol-9-yl)acetic acid (308b) (75 mg, 0.162 mmol) in DMF (5 mL) using HCl salt of (1R,3S,5R)—N-(6-chloropyridin-2-yl)-5-methyl-2-azabicyclo[3.1.0]hexane-3-carboxamide (269b) (46.7 mg, 0.162 mmol), HATU (74.0 mg, 0.195 mmol), DIPEA (105 mg, 0.811 mmol) and stirring at RT for 16 h. This gave after workup and purification as described in scheme-299, (1R,3S,5R)-2-(2-(4-amino-8-methyl-6-(2-methylpyrimidin-5-yl)-9H-pyrimido[4,5-b]indol-9-yl)acetyl)-N-(6-chloropyridin-2-yl)-5-methyl-2-azabicyclo[3.1.0]hexane-3-carboxamide (315a) (47 mg, 50% yield) HCl salt as a white solid: $^1$H NMR (300 MHz, DMSO-$d_6$) δ 10.83 (s, 1H, $D_2O$ exchangeable), 9.24 (s, 2H), 9.06 (bs, 2H, $D_2O$ exchangeable), 8.77 (d, J=1.7 Hz, 1H), 8.69 (s, 1H), 7.99 (d, J=8.2 Hz, 1H), 7.87-7.74 (m, 2H), 7.18 (d, J=7.7 Hz, 1H), 5.92 (d, J=18.0 Hz, 1H), 5.62 (d, J=17.9 Hz, 1H), 4.40 (dd, J=9.0, 6.2 Hz, 1H), 3.76-3.70 (m, 1H), 2.76 (s, 3H), 2.70 (s, 3H), 2.49-2.43 (m, 1H), 1.99 (dd, J=13.3, 6.1 Hz, 1H), 1.32 (s, 3H), 1.08-0.95 (m, 1H), 0.94-0.76 (m, 1H); MS (ES+): 582/584 (M+1); (ES−): 580/582 (M−1);

Analysis calculated for $C_{30}H_{28}ClN_9O_2 \cdot 1.3HCl \cdot 3H_2O$: C, 52.72; H, 5.21; Cl, 11.93; N, 18.44. Found: C, 52.74; H, 5.19; Cl, 11.84; N, 18.36.

Scheme 316

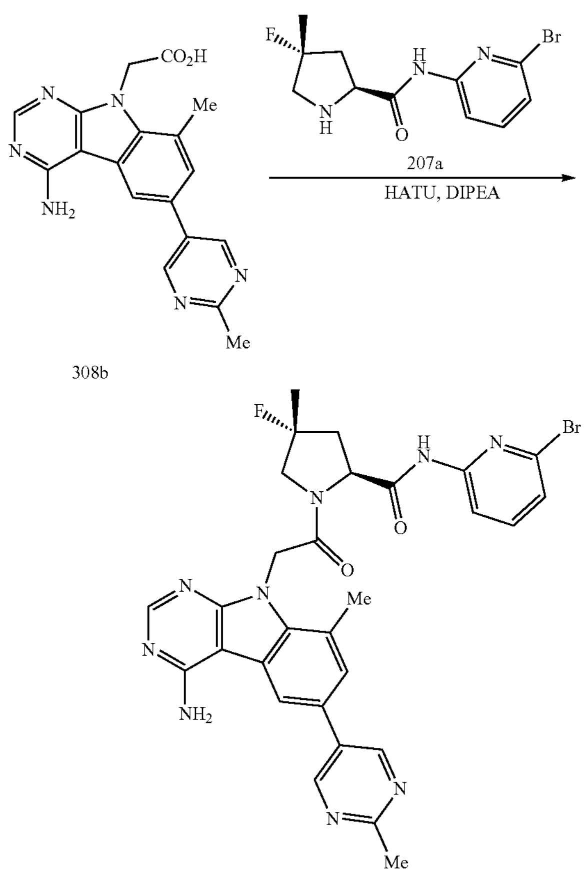

308b 207a 316a

Preparation of (2S,4R)-1-(2-(4-amino-8-methyl-6-(2-methylpyrimidin-5-yl)-9H-pyrimido[4,5-b]indol-9-yl)acetyl)-N-(6-bromopyridin-2-yl)-4-fluoro-4-methylpyrrolidine-2-carboxamide (316a)

Compound 316a was prepared according to the procedure reported in step-3 of scheme-1, from TFA salt of 2-(4-amino-8-methyl-6-(2-methylpyrimidin-5-yl)-9H-pyrimido[4,5-b]indol-9-yl)acetic acid (308b) (75 mg, 0.162 mmol) in DMF (5 mL) using TFA salt of (2S,4R)—N-(6-bromopyridin-2-yl)-4-fluoro-4-methylpyrrolidine-2-carboxamide (207a) (67.5 mg, 0.162 mmol), HATU (74.0 mg, 0.195 mmol), DIPEA (105 mg, 0.811 mmol) and stirring at RT for 16 h. This gave after workup and purification as described in scheme-299, (2S,4R)-1-(2-(4-amino-8-methyl-6-(2-methylpyrimidin-5-yl)-9H-pyrimido[4,5-b]indol-9-yl)acetyl)-N-(6-bromopyridin-2-yl)-4-fluoro-4-methylpyrrolidine-2-carboxamide (316a) (60 mg, 59% yield) HCl salt as a white solid; $^1H$ NMR (300 MHz, DMSO-$d_6$) δ (a mixture of two rotamers) 11.37 and 11.03 (2s, 1H, $D_2O$ exchangeable), 9.22 (s, 2H), 8.93 (bs, 2H, $D_2O$ exchangeable), 8.77 (s, 1H), 8.67 and 8.65 (2s, 1H), 8.19 and 7.99 (2d, J=8.2 Hz, 1H), 7.79 (d, J=1.6 Hz, 1H), 7.85 and 7.70 (2t, J=8.0 Hz, 1H), 7.44 and 7.32 (2d, J=7.7 Hz, 1H), 5.77 (d, J=18.0 Hz, 1H), 5.56 (d, J=17.9 Hz, 1H), 4.70 (dd, J=9.7, 7.5 Hz, 1H), 4.29 (dd, J=18.2, 12.3 Hz, 1H), 3.99-3.81 (m, 1H), 2.77 (s, 3H), 2.69 (s, 3H), 2.63-2.55 (m, 1H), 2.24-1.96 (m, 1H), 1.63 (d, J=21.1 Hz, 3H); $^{19}F$ NMR (282 MHz, DMSO-$d_6$) δ−139.89; MS (ES+): 632/634 (M+1); (ES−): 630/632 (M−1); Analysis calculated for $C_{29}H_{27}BrFN_9O_2 \cdot 1.55HCl \cdot 2.5H_2O$: C, 47.45; H, 4.61; Cl, 7.49; N, 17.17. Found: C, 47.48; H, 4.71; Cl, 7.45; N, 17.11.

Scheme 317

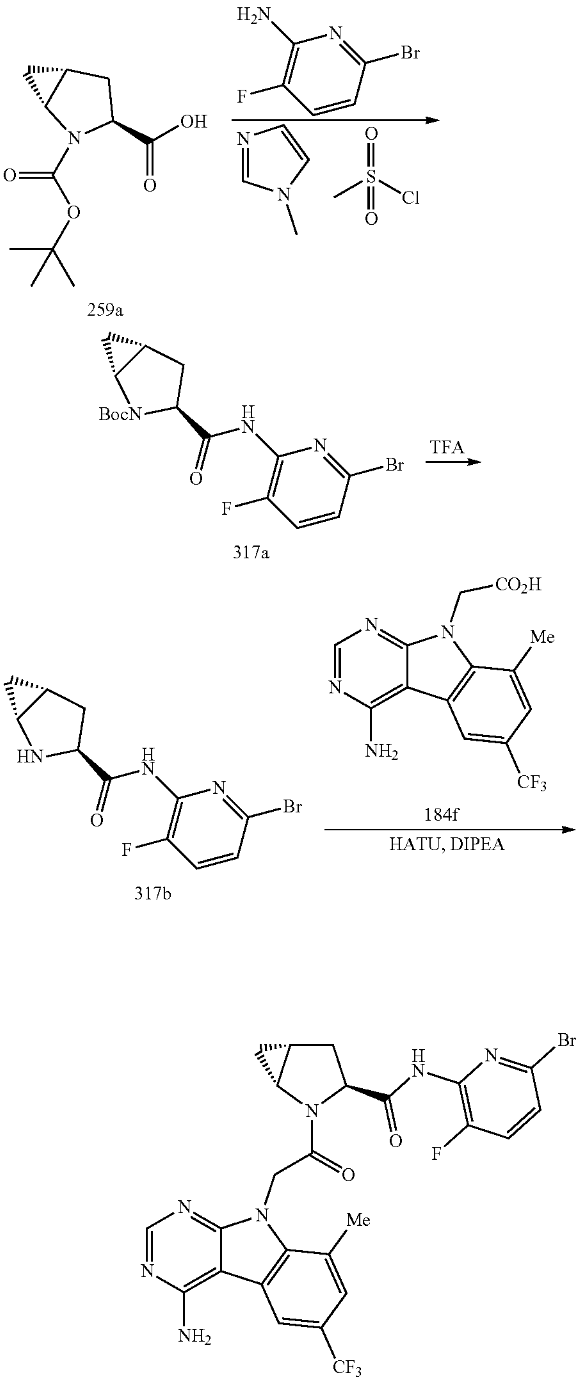

259a 317a 317b 184f 317c

Preparation of (1R,3S,5R)-2-(2-(4-amino-8-methyl-6-(trifluoromethyl)-9H-pyrimido[4,5-b]indol-9-yl) acetyl)-N-(6-bromo-3-fluoropyridin-2-yl)-2-azabicyclo[3.1.0]hexane-3-carboxamide (317c)

Step-1: Preparation of (1R,3S,5R)-tert-butyl 3-((6-bromo-3-fluoropyridin-2-yl)carbamoyl)-2-azabicyclo[3.1.0]hexane-2-carboxylate (317a)

Compound 317a was prepared according to the procedure reported in step-1 of scheme-53, from (1R,3S,5R)-2-(tert-butoxycarbonyl)-2-azabicyclo[3.1.0]hexane-3-carboxylic acid (259a) (0.5 g, 2.2 mmol) and 6-bromo-3-fluoropyridin-2-amine (0.42 g, 2.2 mmol: CAS #1379457-78-9) to afford after purification using flash column chromatography [silica gel (24 g), EtOAc in hexane from 0-50%] (1R,3S,5R)-tert-butyl 3-((6-bromo-3-fluoropyridin-2-yl)carbamoyl)-2-azabicyclo[3.1.0]hexane-2-carboxylate (317a) (180 mg, 20% yield) as a white solid; MS (ES+): 400.1/402.1 (M+1).

Step-2: Preparation of (1R,3S,5R)—N-(6-bromo-3-fluoropyridin-2-yl)-2-azabicyclo[3.1.0]hexane-3-carboxamide (317b)

Compound 317b was prepared according to the procedure reported in step-2 of scheme-1, from (1R,3S,5R)-tert-butyl 3-((6-bromo-3-fluoropyridin-2-yl)carbamoyl)-2-azabicyclo [3.1.0]hexane-2-carboxylate (317a) (0.18 g, 0.450 mmol) in DCM (2.5 mL) using TFA (0.243 mL, 3.15 mmol). This gave after work up TFA salt of (1R,3S,5R)—N-(6-bromo-3-fluoropyridin-2-yl)-2-azabicyclo[3.1.0]hexane-3-carboxamide (317b) (180 mg, 97% yield): $^1$H NMR (300 MHz, DMSO-$d_6$) δ 10.95 (d, J=13.0 Hz, 1H), 8.50 (dd, J=4.5, 2.5 Hz, 1H), 8.32 (d, J=5.7 Hz, 1H), 4.30-4.18 (m, 1H), 3.41-3.31 (m, 1H), 2.66-2.57 (m, 1H), 2.34-2.09 (m, 1H), 1.92-1.70 (m, 1H), 0.92-0.73 (m, 2H); $^{19}$F NMR (282 MHz, DMSO-$d_6$) δ −73.77, −142.14; MS (ES+): 300.0/302.0 (M+1).

Step-3: Preparation of (1R,3S,5R)-2-(2-(4-amino-8-methyl-6-(trifluoromethyl)-9H-pyrimido[4,5-b]indol-9-yl)acetyl)-N-(6-bromo-3-fluoropyridin-2-yl)-2-azabicyclo[3.1.0]hexane-3-carboxamide (317c)

Compound 317c was prepared according to the procedure reported in step-3 of scheme-1, from TFA salt of (1R,3S,5R)—N-(6-bromo-3-fluoropyridin-2-yl)-2-azabicyclo [3.1.0]hexane-3-carboxamide (317b) (56.7 mg, 0.137 mmol) in DMF (1.5 mL) using TFA salt of 2-(4-amino-8-methyl-6 trifluoromethyl)-9H-pyrimido[4,5-b]indol-9-yl) acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (1R,3S,5R)-2-(2-(4-amino-8-methyl-6-(trifluoromethyl)-9H-pyrimido[4,5-b]indol-9-yl) acetyl)-N-(6-bromo-3-fluoropyridin-2-yl)-2-azabicyclo [3.1.0]hexane-3-carboxamide (317c) (47 mg, 57% yield) HCl salt as a white solid; $^1$H NMR (300 MHz, DMSO-$d_6$) δ 10.49 (s, 1H, $D_2O$ exchangeable), 8.78 (s, 1H), 8.59 (s, 1H), 8.50 (s, 2H, $D_2O$ exchangeable), 8.37 (d, J=2.5 Hz, 1H), 8.34 (d, J=5.7 Hz, 1H), 7.61 (s, 1H), 5.97 (d, J=18.0 Hz, 1H), 5.70 (d, J=18.0 Hz, 1H), 4.59 (dd, J=8.9, 5.8 Hz, 1H), 4.01-3.89 (m, 1H), 2.78 (s, 3H), 2.42-2.20 (m, 2H), 2.02-1.86 (m, 1H), 1.15-1.05 (m, 1H), 0.77-0.68 (m, 1H); $^{19}$F NMR (282 MHz, DMSO-$d_6$) δ−58.71, −142.98; MS (ES+): 606.1/608.1 (M+1); (ES−): 604.1/606.1 (M−1); Analysis calculated for $C_{21}H_{20}BrF_4N_7O_2$ $2H_2O{\cdot}HCl$: C, 44.23; H, 3.71; Cl, 5.22; N, 14.44. Found: C, 44.06; H, 3.73; Cl, 4.96; N, 14.31.

Scheme 318

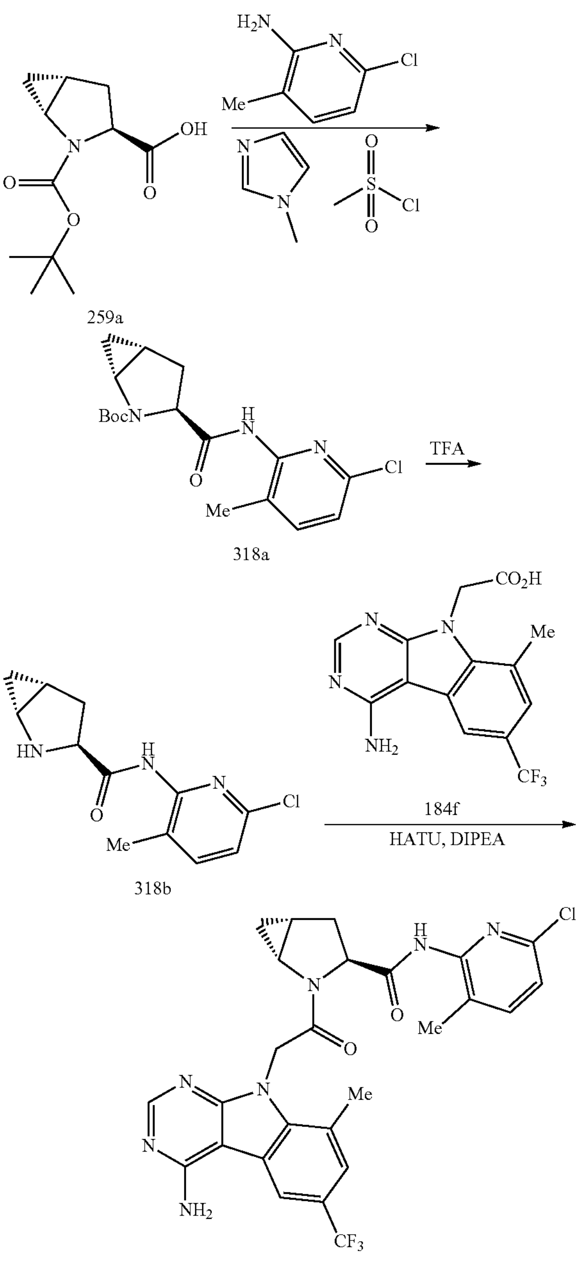

259a

318a

318b

318c

Preparation of (1R,3S,5R)-2-(2-(4-amino-8-methyl-6-(trifluoromethyl)-9H-pyrimido[4,5-b]indol-9-yl) acetyl)-N-(6-chloro-3-methylpyridin-2-yl)-2-azabicyclo[3.1.0]hexane-3-carboxamide (318c)

Step-1: Preparation of (1R,3S,5R)-tert-butyl 3-((6-chloro-3-methylpyridin-2-yl)carbamoyl)-2-azabicyclo[3.1.0]hexane-2-carboxylate (318a)

Compound 318a was prepared according to the procedure reported in step-1 of scheme-53, from (1R,3S,5R)-2-(tert-butoxycarbonyl)-2-azabicyclo[3.1.0]hexane-3-carboxylic acid (259a) (0.5 g, 2.2 mmol) in DCM (15 mL) and 6-chloro-3-methylpyridin-2-amine (0.314 g, 2.200 mmol; CAS #442128-86-1) to afford after purification as described in step-1 of scheme-317 (1R,3S,5R)-tert-butyl 3-((6-chloro-3-methylpyridin-2-yl)carbamoyl)-2-azabicyclo[3.1.0] hexane-2-carboxylate (318a) (0.46 g, 59% yield) as a white solid; MS (ES+): 352.1 (M+1).

Step-2: Preparation of (1R,3S,5R)—N-(6-chloro-3-methylpyridin-2-yl)-2-azabicyclo[3.1.0]hexane-3-carboxamide (318b)

Compound 318b was prepared according to the procedure reported in step-2 of scheme-1, from (1R,3S,5R)-tert-butyl 3-((6-chloro-3-methylpyridin-2-yl)carbamoyl)-2-azabicyclo [3.1.0]hexane-2-carboxylate (318a) (0.45 g, 1.279 mmol) in DCM (7 mL) using TFA (0.690 mL, 8.95 mmol). This gave after work up TFA salt of (1R,3S,5R)—N-(6-chloro-3-methylpyridin-2-yl)-2-azabicyclo[3.1.0]hexane-3-carboxamide (318b) (0.47 g); $^1$H NMR (300 MHz, DMSO-$d_6$) δ 10.79 (s, 1H), 9.86 (s, 1H), 9.23 (s, 1H), 7.83 (d, J=8.0 Hz, 1H), 7.42 (d, J=8.0 Hz, 1H), 4.34-4.15 (m, 1H), 3.37-3.26 (m, 1H), 2.68-2.58 (m, 1H), 2.15 (s, 3H), 2.15-2.05 (m, 1H), 1.95-1.75 (m, 1H), 0.97-0.78 (m, 2H); MS (ES+): 252.0 (M+1).

Step-3: Preparation of (1R,3S,5R)-2-(2-(4-amino-8-methyl-6-(trifluoromethyl)-9H-pyrimido[4,5-b]indol-9-yl)acetyl)-N-(6-chloro-3-methylpyridin-2-yl)-2-azabicyclo[3.1.0]hexane-3-carboxamide (318c)

Compound 318c was prepared according to the procedure reported in step-3 of scheme-1, from TFA salt of (1R,3S,5R)—N-(6-chloro-3-methylpyridin-2-yl)-2-azabicyclo [3.1.0]hexane-3-carboxamide (318b) (50.1 mg, 0.137 mmol) in DMF (1.5 mL) using TFA salt of 2-(4-amino-8-methyl-6-(trifluoromethyl)-9H-pyrimido[4,5-b]indol-9-yl) acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (1R,3S,5R)-2-(2-(4-amino-8-methyl-6-(trifluoromethyl)-9H-pyrimido[4,5-b]indol-9-yl) acetyl)-N-(6-chloro-3-methylpyridin-2-yl)-2-azabicyclo [3.1.0]hexane-3-carboxamide (318c) (19 mg, 25% yield) HCl salt as a white solid; 1H NMR (300 MHz, DMSO-$d_6$) δ10.30 (s, 1H, $D_2O$ exchangeable), 8.82 (s, 1H), 8.73 (s, 2H, $D_2O$ exchangeable), 8.65 (d, J=1.7 Hz, 1H), 7.71 (d, J=8.0 Hz, 1H), 7.61 (d, J=1.7 Hz, 1H), 7.30 (d, J=7.9 Hz, 1H), 5.96 (d, J=18.0 Hz, 1H), 5.72 (d, J=17.9 Hz, 1H), 4.40 (dd, J=9.2, 5.5 Hz, 1H), 3.99-3.88 (m, 1H), 2.76 (s, 3H), 2.42 (dd, J=13.4, 9.3 Hz, 1H), 2.33-2.19 (m, 1H), 2.02 (s, 3H), 2.01-1.90 (m, 1H), 1.17-1.03 (m, 1H), 0.82-0.66 (m, 1H); $^{19}$F NMR (282 MHz, DMSO) δ-58.69; MS (ES+): 558.2 (M+1); (ES−): 556.1 (M−1).

Scheme 319

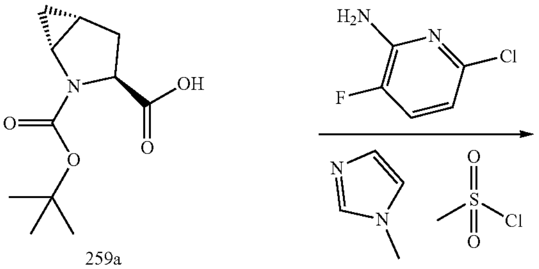

259a

-continued

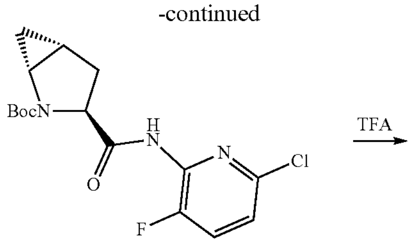

319a

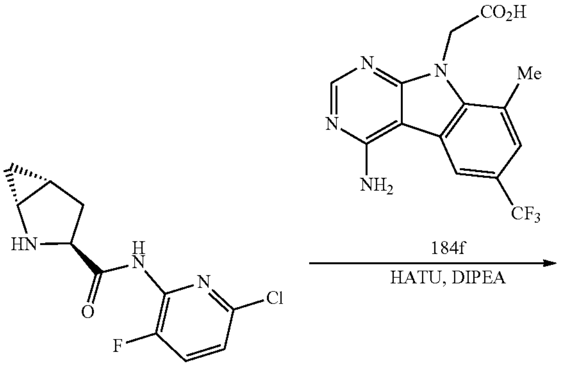

319b

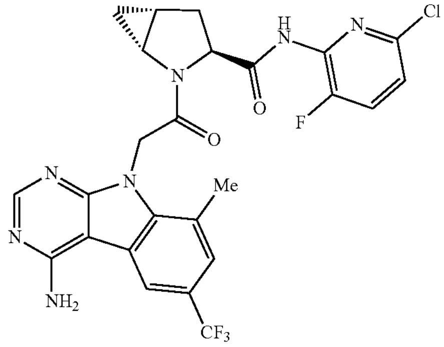

319c

Preparation of (1R,3S,5R)-2-(2-(4-amino-8-methyl-6-(trifluoromethyl)-9H-pyrimido[4,5-b]indol-9-yl) acetyl)-N-(6-chloro-3-fluoropyridin-2-yl)-2-azabicyclo[3.1.0]hexane-3-carboxamide (319c)

Step-1: Preparation of (1R,3S,5R)-tert-butyl 3-((6-chloro-3-fluoropyridin-2-yl)carbamoyl)-2-azabicyclo [3.1.0]hexane-2-carboxylate (319a)

Compound 319a was prepared according to the procedure reported in step-1 of scheme-53, from (1R,3S,5R)-2-tert-butoxycarbonyl)-2-azabicyclo[3.1.0]hexane-3-carboxylic acid (259a) (0.25 g, 1.1 mmol) and 6-chloro-3-fluoropyridin-2-amine (0.161 g, 1.1 mmol; CAS #1260672-14-7) to afford after purification as described in step-1 of scheme-317 (1R,3S,5R)-tert-butyl 3-((6-chloro-3-fluoropyridin-2-yl)carbamoyl)-2-azabicyclo[3.1.0]hexane-2-carboxylate (319a) (0.187 g, 48% yield) as a white solid; MS (ES+): 356.1 (M+1); 378.1 (M+Na).

Step-2: Preparation of (1R,3S,5R)—N-(6-chloro-3-fluoropyridin-2-yl)-2-azabicyclo[3.1.0]hexane-3-carboxamide (319b)

Compound 319b was prepared according to the procedure reported in step-2 of scheme-1, from (1R,3S,5R)-tert-butyl 3-((6-chloro-3-fluoropyridin-2-yl)carbamoyl)-2-azabicyclo [3.1.0]hexane-2-carboxylate (319a) (0.18 g, 0.506 mmol) in DCM (2.7 mL) using TFA (0.273 mL, 3.54 mmol). This gave after work up and purification using reverse phase column chromatography [C18 column (50 g), eluting with ACN in water (containing 0.1% HCl) from 0-100%] TFA/HCl salt of (1R,3S,5R)—N-(6-chloro-3-fluoropyridin-2-yl)-2-azabicyclo[3.1.0]hexane-3-carboxamide (319b) (0.19 g); $^{1}$H NMR (300 MHz, DMSO-$d_6$) δ 11.11 (s, 1H), 9.82 (s, 1H), 9.29 (s, 1H), 7.99 (t, J=8.9 Hz, 1H), 7.56 (dd, J=8.6, 3.0 Hz, 1H), 4.30-4.23 (m, 1H), 3.38-3.28 (m, 1H), 2.70-2.56 (m, 1H), 2.15-2.02 (m, 1H), 1.94-1.71 (m, 1H), 1.04-0.70 (m, 2H); MS (ES+): 256.1 (M+1).

Step-3: Preparation of (1R,3S,5R)-2-(2-(4-amino-8-methyl-6-(trifluoromethyl)-9H-pyrimido[4,5-b]indol-9-yl)acetyl)-N-(6-chloro-3-fluoropyridin-2-yl)-2-azabicyclo[3.1.0]hexane-3-carboxamide (319c)

Compound 319c was prepared according to the procedure reported in step-3 of scheme-1, from TFA salt of (1R,3S,5R)—N-(6-chloro-3-fluoropyridin-2-yl)-2-azabicyclo [3.1.0]hexane-3-carboxamide (319b) (50.6 mg, 0.137 mmol) in DMF (1.5 mL) using TFA salt of 2-(4-amino-8-methyl-6-(trifluoromethyl)-9H-pyrimido[4,5-b]indol-9-yl) acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (1R,3S,5R)-2-(2-(4-amino-8-methyl-6-(trifluoromethyl)-9H-pyrimido[4,5-b]indol-9-yl) acetyl)-N-(6-chloro-3-fluoropyridin-2-yl)-2-azabicyclo [3.1.0]hexane-3-carboxamide (319c) (27 mg, 35.1% yield) HCl salt as a white solid; $^{1}$H NMR (300 MHz, DMSO-$d_6$) δ 10.56 (s, 1H, $D_2O$ exchangeable), 8.81 (s, 1H), 8.68 (s, 2H, $D_2O$ exchangeable), 8.64 (s, 1H), 7.86 (t, J=8.9 Hz, 1H), 7.60 (s, 1H), 7.43 (dd, J=8.5, 2.9 Hz, 1H), 5.96 (d, J=18.0 Hz, 1H), 5.70 (d, J=17.9 Hz, 1H), 4.44 (dd, J=9.3, 5.3 Hz, 1H), 3.95-3.90 (m, 1H), 2.76 (s, 3H), 2.42 (dd, J=13.5, 9.4 Hz, 1H), 2.30-2.16 (m, 1H), 2.03-1.90 (m, 1H), 1.19-1.04 (m, 1H), 0.77-0.69 (m, 1H); $^{19}$F NMR (282 MHz, DMSO) δ−58.75, −125.59; MS (ES+): 562.2 (M+1): (ES−): 560.1 (M−1).

Scheme 320

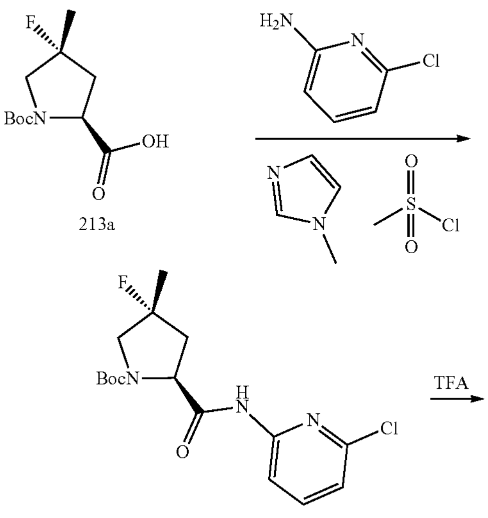

213a

320a

-continued

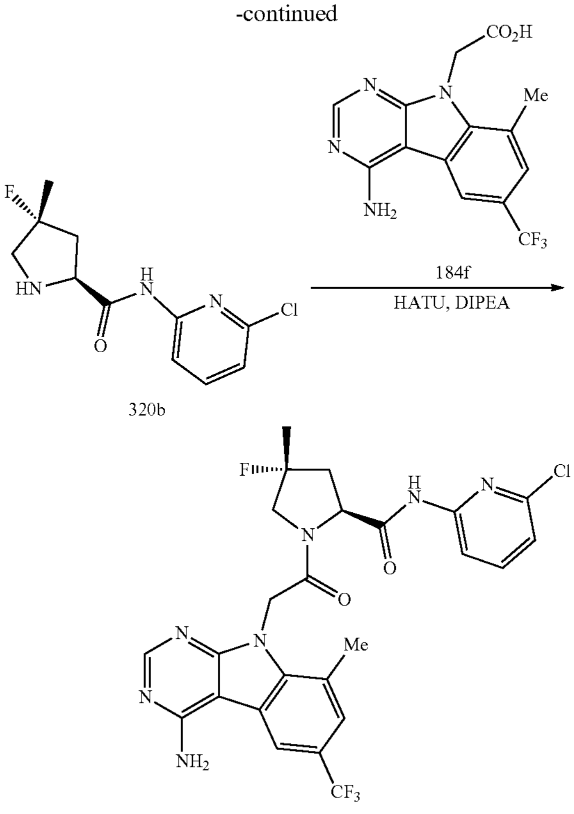

320b

320c

Preparation of (2S,4R)-1-(2-(4-amino-8-methyl-6-(trifluoromethyl)-9H-pyrimido[4,5-b]indol-9-yl) acetyl)-N-(6-chloropyridin-2-yl)-4-fluoro-4-methylpyrrolidine-2-carboxamide (320c)

Step-1: Preparation of (2S,4R)-tert-butyl 2-((6-chloropyridin-2-yl)carbamoyl)-4-fluoro-4-methylpyrrolidine-1-carboxylate (320a)

Compound 320a was prepared according to the procedure reported in step-1 of scheme-53, from (2S,4R)-1-(tert-butoxycarbonyl)-4-fluoro-4-methylpyrrolidine-2-carboxylic acid (213a) (0.35 g, 1.415 mmol) and 6-chloropyridin-2-amine (0.182 g, 1.415 mmol; CAS #45644-21-1) to afford after purification as described in step-1 of scheme-317. (2S,4R)-tert-butyl 2-((6-chloropyridin-2-yl)carbamoyl)-4-fluoro-4-methylpyrrolidine-1-carboxylate (320a) (0.362 g, 72% yield) as a white solid; MS (ES+): 358.2 (M+1); 380.1 (M+Na).

Step-2: Preparation of (2S,4R)—N-(6-chloropyridin-2-yl)-4-fluoro-4-methylpyrrolidine-2-carboxamide (320b)

Compound 320b was prepared according to the procedure reported in step-2 of scheme-1, from (2S,4R)-tert-butyl 2-((6-chloropyridin-2-yl)carbamoyl)-4-fluoro-4-methylpyrrolidine-1-carboxylate (320a) (0.36 g, 1.006 mmol) in DCM (5.5 mL) using TFA (0.543 mL, 7.04 mmol) to afford after work up TFA salt of (2S,4R)—N-(6-chloropyridin-2-yl)-4-fluoro-4-methylpyrrolidine-2-carboxamide (320b) (0.375 g): $^{1}$H NMR (300 MHz, DMSO-$d_6$) δ 11.45 (s, 1H), 9.99 (s, 1H), 9.12 (s, 1H), 8.05 (d, J=8.2 Hz, 1H), 7.95 (t, J=7.9 Hz, 1H), 7.33 (d, J=7.7 Hz, 1H), 4.76-4.51 (m, 1H), 3.68-3.29 (m, 2H), 2.88-2.67 (m, 1H), 2.35-2.11 (m, 11H), 1.55 (dd, J=21.3, 5.8 Hz, 3H); MS (ES+): 258.1 (M+1).

Step-3: Preparation of (2S,4R)-1-(2-(4-amino-8-methyl-6-(trifluoromethyl)-9H-pyrimido[4,5-b]indol-9-yl)acetyl)-N-(6-chloropyridin-2-yl)-4-fluoro-4-methylpyrrolidine-2-carboxamide (320c)

Compound 320c was prepared according to the procedure reported in step-3 of scheme-1, from TFA salt of (2S,4R)—N-(6-chloropyridin-2-yl)-4-fluoro-4-methylpyrrolidine-2-carboxamide (320b) (50.9 mg, 0.137 mmol) in DMF (1.5 mL) using TFA salt of 2-(4-amino-8-methyl-6-(trifluoromethyl)-9H-pyrimido[4,5-b]indol-9-yl)acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (2S,4R)-1-(2-(4-amino-8-methyl-6-(trifluoromethyl)-9H-pyrimido[4,5-b]indol-9-yl)acetyl)-N-(6-chloropyridin-2-yl)-4-fluoro-4-methylpyrrolidine-2-carboxamide (320c) (46 mg, 60% yield) HCl salt as a white solid: $^1$H NMR (300 MHz, DMSO-$d_6$) (a mixture of two rotamers) δ 11.34 and 11.00 (2s, 1H, $D_2O$ exchangeable), 8.76 (s, 1H), 8.57 (s, 1H), 8.45 (s, 2H, $D_2O$ exchangeable), 8.16 and 7.97 (2d, J=8.2 Hz, 1H), 7.82 (t, J=8.0 Hz, 1H), 7.58 (s, 114), 7.30 and 7.19 (2d, J=7.7 Hz, 114), 5.76 (d, J=18.0 Hz, 1H), 5.54 (d, J=17.9 Hz, 1H), 4.68 (t, J=8.6 Hz, 1H), 4.28 (dd, J=18.0, 12.0 Hz, 1H), 3.88 (dd, J=35.2, 12.0 Hz, 1H), 2.75 (s, 3H), 2.62-2.54 (m, 1H), 2.23-1.94 (m, 1H), 1.63 (d, J=21.1 Hz, 31H); $^{19}$F NMR (282 MHz, DMSO-$d_6$) δ−58.71, −139.94; MS (ES+): 564.2 (M+1); (ES−): 562.1 (M−1): Analysis calculated for $C_{25}H_{22}ClF_4N_7O_2$ $2H_2O$, 0.9HCl: C, 47.45; H, 4.28; Cl, 10.65; N, 15.49. Found: C, 47.18; H, 3.93; Cl, 10.40; N, 15.20.

Scheme 321

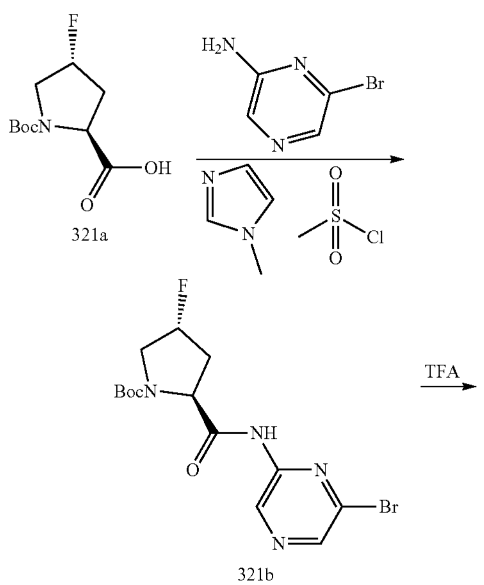

321a

321b

-continued

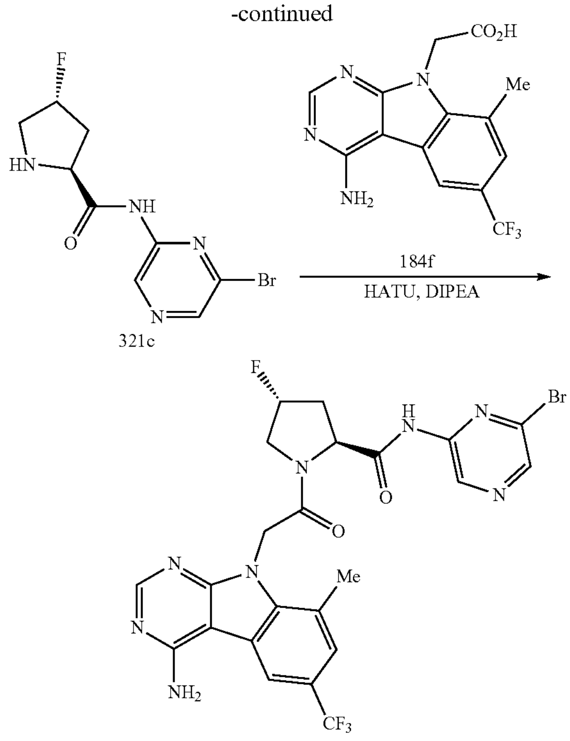

321c

321d

Preparation of (2S,4R)-1-(2-(4-amino-8-methyl-6-(trifluoromethyl)-9H-pyrimido[4,5-b]indol-9-yl)acetyl)-N-(6-bromopyrazin-2-yl)-4-fluoropyrrolidine-2-carboxamide (321d)

Step-1: Preparation of (2S,4R)-tert-butyl 2-((6-bromopyrazin-2-yl)carbamoyl)-4-fluoropyrrolidine-1-carboxylate (321b)

Compound 321b was prepared according to the procedure reported in step-1 of scheme-53, from (2S,4R)-1-(tert-butoxycarbonyl)-4-fluoropyrrolidine-2-carboxylic acid (321a) (0.5 g, 2.144 mmol; CAS #203866-14-2) and 6-bromopyrazin-2-amine (0.373 g, 2.144 mmol; CAS #54237-53-5) to afford after purification as described in step-1 of scheme-317, (2S,4R)-tert-butyl 2-((6-bromopyrazin-2-yl)carbamoyl)-4-fluoropyrrolidine-1-carboxylate (321b) (0.452 g, 54% yield) as a white solid; MS (ES+): 389.1/391.1 (M+1).

Step-2: Preparation of (2S,4R)—N-(6-bromopyrazin-2-yl)-4-fluoropyrrolidine-2-carboxamide (321c)

Compound 321c was prepared according to the procedure reported in step-2 of scheme-1, from (2S,4R)-tert-butyl 2-((6-bromopyrazin-2-yl)carbamoyl)-4-fluoropyrrolidine-1-carboxylate (321b) (0.45 g, 1.156 mmol) in DCM (6 mL) using TFA (0.624 mL, 8.09 mmol) to afford after work up TFA salt of (2S,4R)—N-(6-bromopyrazin-2-yl)-4-fluoropyrrolidine-2-carboxamide (321c) (0.569 g); $^1$H NMR (300 MHz, DMSO-$d_6$) δ 11.80 (s, 1H), 9.30 (s, 1H), 8.67 (s, 1H), 5.65-5.37 (m, 1H), 4.66 (dd, J=10.8, 7.4 Hz, 1H), 3.71-3.47 (m, 2H), 2.88-2.66 (m, 1H), 2.44-2.18 (m, 1H); MS (ES+): 289.0/290.9 (M+1).

Step-3: Preparation of (2S,4R)-1-(2-(4-amino-8-methyl-6-(trifluoromethyl)-9H-pyrimido[4,5-b]indol-9-yl)acetyl)-N-(6-bromopyrazin-2-yl)-4-fluoropyrrolidine-2-carboxamide (321d)

Compound 321d was prepared according to the procedure reported in step-3 of scheme-1, from TFA salt of (2S,4R)—N-(6-bromopyrazin-2-yl)-4-fluoropyrrolidine-2-carboxamide (321c) (70.8 mg, 0.137 mmol) in DMF (1.5 mL) using TFA salt of 2-(4-amino-8-methyl-6-(trifluoromethyl)-9H-pyrimido[4,5-b]indol-9-yl)acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (2S,4R)-1-(2-(4-amino-8-methyl-6-(trifluoromethyl)-9H-pyrimido[4,5-b]indol-9-yl)acetyl)-N-(6-bromopyrazin-2-yl)-4-fluoropyrrolidine-2-carboxamide (321d) (45 mg, 55% yield) HCl salt as a white solid; $^1H$ NMR (300 MHz, DMSO-$d_6$) (a mixture of two rotamers) δ 11.69 and 11.39 (2s, 1H, $D_2O$ exchangeable), 9.40 and 9.22 (2s, 1H), 8.77 (s, 1H), 8.65 and 8.58 (2s, 1H), 8.54 (s, 1H), 8.48 (s, 2H, $D_2O$ exchangeable), 7.59 (s, 1H), 6.00-5.45 (m, 3H), 4.70 (t, J=8.5 Hz, 1H), 4.33 (dd, J=21.4, 12.6 Hz, 1H), 4.15-3.88 (m, 1H), 2.75 (s, 3H), 2.67-2.57 (m, 1H), 2.38-2.07 (m, 1H); $^{19}F$ NMR (282 MHz, DMSO-$d_6$) δ−58.72, −176.42; MS (ES+): 595.1/597.1 (M+1): (ES−): 593.1/595.1 (M−1); Analysis calculated for $C_{23}H_{19}BrF_4N_8O_2$ $1.75H_2O{\cdot}HCl$: C, 41.65; H, 3.57; Cl, 5.34; N, 16.89. Found: C, 41.92; H, 3.47; Cl, 5.35; N, 16.51.

Scheme 322

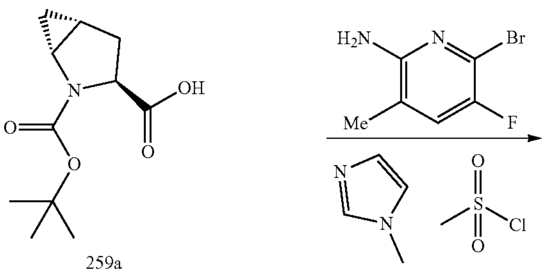

259a

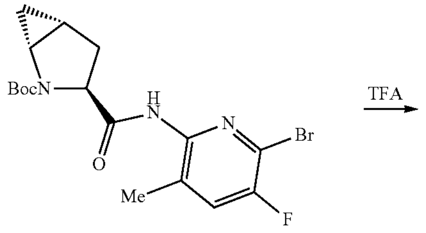

322a

-continued

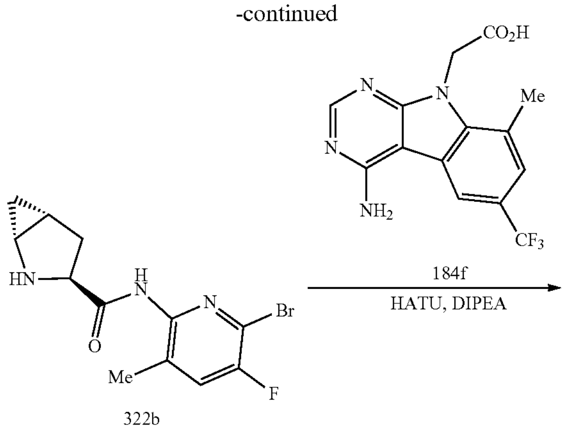

322b

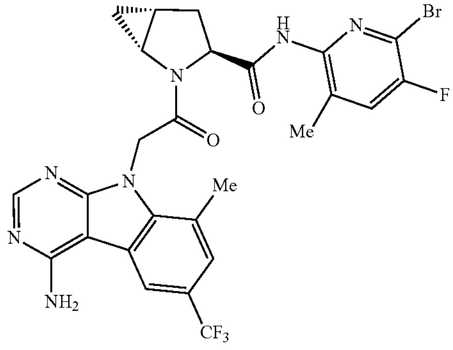

322c

Preparation of (1R,3S,5R)-2-(2-(4-amino-8-methyl-6-(trifluoromethyl)-9H-pyrimido[4,5-b]indol-9-yl)acetyl)-N-(6-bromo-5-fluoro-3-methylpyridin-2-yl)-2-azabicyclo[3.1.0]hexane-3-carboxamide (322c)

Step-1: Preparation of (1R,3S,5R)-tert-butyl 3-((6-bromo-5-fluoro-3-methylpyridin-2-yl)carbamoyl)-2-azabicyclo[3.1.0]hexane-2-carboxylate (322a)

Compound 322a was prepared according to the procedure reported in step-1 of scheme-53, from (1R,3S,5R)-2-(tert-butoxycarbonyl)-2-azabicyclo[3.1.0]hexane-3-carboxylic acid (259a) (0.322 g, 1.415 mmol) in DCM (12 mL) and 6-bromo-5-fluoro-3-methylpyridin-2-amine (0.290 g, 1.415 mmol; CAS #2086189-45-7) to afford after purification as described in step-1 of scheme-317, (1R,3S,5R)-tert-butyl 3-((6-bromo-5-fluoro-3-methylpyridin-2-yl)carbamoyl)-2-azabicyclo[3.1.0]hexane-2-carboxylate (322a) (0.463 g, 79% yield) as a white solid; MS (ES+): 414.1/416.1 (M+1).

Step-2: Preparation of (1R,3S,5R)—N-(6-bromo-5-fluoro-3-methylpyridin-2-yl)-2-azabicyclo[3.1.0]hexane-3-carboxamide (322b)

Compound 322b was prepared according to the procedure reported in step-2 of scheme-1, from (1R,3S,5R)-tert-butyl 3-((6-bromo-5-fluoro-3-methylpyridin-2-yl)carbamoyl)-2-azabicyclo[3.1.0]hexane-2-carboxylate (322a) (0.46 g, 1.110 mmol) in DCM (6 mL) using TFA (0.599 mL, 7.77 mmol) to afford after purification as described in step-2 of scheme-319 TFA salt of (1R,3S,5R)—N-(6-bromo-5-fluoro-3-methylpyridin-2-yl)-2-azabicyclo[3.1.0]hexane-3-carboxamide (322b) (0.54 g, 100% yield); $^1H$ NMR (300 MHz, DMSO-$d_6$) δ 10.81 (s, 1H), 9.88 (s, 1H), 9.21 (s, 1H), 7.93

(d, J=8.4 Hz, 1H), 4.48-3.96 (m, 1H), 3.46-3.19 (m, 1H), 2.67-2.54 (m, 1H), 2.23-2.05 (m, 4H), 1.91-1.80 (m, 1H), 1.02-0.87 (m, 1H), 0.88-0.74 (m, 1H); $^{19}F$ NMR (282 MHz, DMSO-$d_6$) δ-74.31, −117.92; MS (ES+): 314.0/316.0 (M+1).

Step-3: Preparation of (1R,3S,5R)-2-(2-(4-amino-8-methyl-6-(trifluoromethyl)-9H-pyrimido[4,5-b]indol-9-yl)acetyl)-N-(6-bromo-5-fluoro-3-methylpyridin-2-yl)-2-azabicyclo[3.1.0]hexane-3-carboxamide (322c)

Compound 322c was prepared according to the procedure reported in step-3 of scheme-1, from TFA salt of (1R,3S,5R)—N-(6-bromo-5-fluoro-3-methylpyridin-2-yl)-2-azabicyclo[3.1.0]hexane-3-carboxamide (322b) (66.4 mg, 0.137 mmol) in DMF (1.5 mL) using TFA salt of 2-(4-amino-8-methyl-6-(trifluoromethyl)-9H-pyrimido[4,5-b]indol-9-yl) acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (1R,3S,5R)-2-(2-(4-amino-8-methyl-6-(trifluoromethyl)-9H-pyrimido[4,5-b]indol-9-yl) acetyl)-N-(6-bromo-5-fluoro-3-methylpyridin-2-yl)-2-azabicyclo[3.1.0]hexane-3-carboxamide (322c) (45 mg, 55% yield) HCl salt as a white solid; $^1H$ NMR (300 MHz, DMSO-$d_6$) δ 10.34 (s, 1H, $D_2O$ exchangeable), 8.80 (s, 1H), 8.60 (s, 1H), 8.56 (s, 2H, $D_2O$ exchangeable), 7.82 (d, J=8.4 Hz, 1H), 7.59 (s, 1H), 5.94 (d, J=18.0 Hz, 1H), 5.71 (d, J=17.9 Hz, 1H), 4.37 (dd, J=9.2, 5.5 Hz, 1H), 3.97-3.86 (m, 1H), 2.75 (s, 3H), 2.42 (dd, J=13.4, 9.4 Hz, 1H), 2.33-2.17 (m, 1H), 2.02 (s, 3H), 2.00-1.88 (m, 1H), 1.21-1.05 (m, 1H), 0.79-0.68 (m, 1H); $^{19}F$ NMR (282 MHz, DMSO) δ-58.70, −119.16. MS (ES+): 620.1/622.1 (M+1); (ES−): 618.0/620.0 (M−1); Analysis calculated for $C_{26}H_{22}BrF_4N_7O_2 \cdot H_2O \cdot HCl$: C, 46.27; H, 3.73; Cl, 5.25; N, 14.53. Found: C, 46.1; H, 4.02; Cl, 5.16; N, 14.25.

Scheme 323

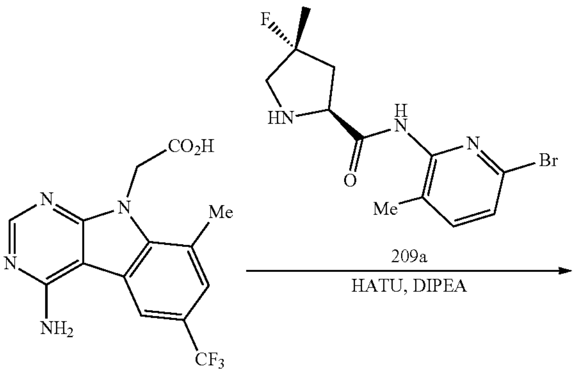

184f

-continued

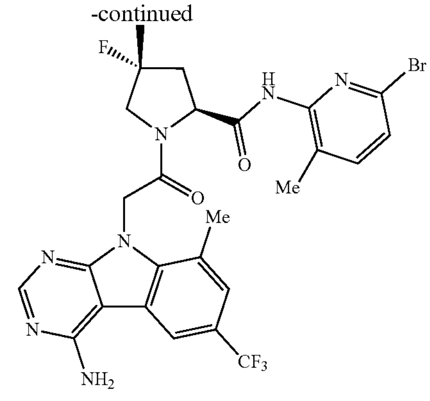

323a

Preparation of (2S,4R)-1-(2-(4-amino-8-methyl-6-(trifluoromethyl)-9H-pyrimido[4,5-b]indol-9-yl)acetyl)-N-(6-bromo-3-methylpyridin-2-yl)-4-fluoro-4-methylpyrrolidine-2-carboxamide (323a)

Compound 323a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (60 mg, 0.137 mmol) in DMF (1.5 mL) using HCl salt of (2S,4R)—N-(6-bromo-3-methylpyridin-2-yl)-4-fluoro-4-methylpyrrolidine-2-carboxamide (209a) (48.3 mg, 0.137 mmol), HATU (78 mg, 0.205 mmol), DIPEA (0.119 mL, 0.684 mmol) and stirring at RT for 16 h. This gave after workup and purification as described in scheme-303, (2S,4R)-1-(2-(4-amino-8-methyl-6-(trifluoromethyl)-9H-pyrimido[4,5-b]indol-9-yl)acetyl)-N-(6-bromo-3-methylpyridin-2-yl)-4-fluoro-4-methylpyrrolidine-2-carboxamide (323a) (45 mg, 53% yield) HCl salt as a white solid; $^1H$ NMR (300 MHz, DMSO-$d_6$) (a mixture of two rotamers) δ 10.83 and 10.50 (2s, 1H, $D_2O$ exchangeable), 8.72 (s, 1H), 8.48 and 8.46 (2s, 1H), 8.14 (s, 2H, $D_2O$ exchangeable), 7.73 and, 7.59 (2d, J=8.0 Hz, 1H), 7.55 and 7.51 (2s, 1H), 7.41 (d, J=7.9 Hz, 1H), 5.74 (d, J=18.0 Hz, 1H), 5.49 (d, J=17.9 Hz, 1H), 4.62 (dd, J=9.8, 7.5 Hz, 1H), 4.27 (dd, J=18.1, 12.0 Hz, 1H), 3.89 (dd, J=35.2, 12.0 Hz, 1H), 2.71 (s, 3H), 2.61-2.54 (m, 1H), 2.21-2.00 (m, 1H), 1.95 (s, 3H), 1.65 (d, J=21.1 Hz, 3H); $^{19}F$ NMR (282 MHz, DMSO-$d_6$) δ-58.59, −139.97. MS (ES+): 622.1/624.1 (M+1); (ES−): 620.1/622.1 (M−1); Analysis calculated for $C_{26}H_{24}BrF_4N_7O_2 \cdot 1.75H_2O \cdot HCl$: C, 45.23; H, 4.16; Cl, 5.14; N, 14.20. Found: C, 45.34; H, 4.07; Cl, 4.99; N, 14.15

Scheme 324

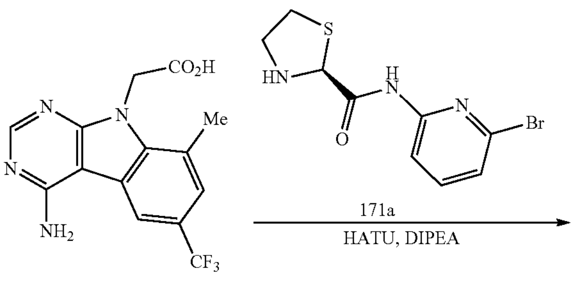

184f

-continued

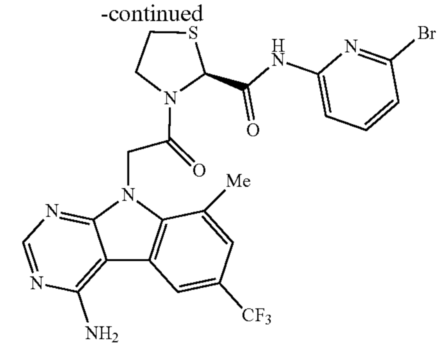

324a

Preparation of(S)-3-(2-(4-amino-8-methyl-6-(trifluoromethyl)-9H-pyrimido[4,5-b]indol-9-yl)acetyl)-N-(6-bromopyridin-2-yl)thiazolidine-2-carboxamide (324a)

Compound 324a was prepared according to the procedure reported in step-3 of scheme-1, from TFA salt of 2-(4-amino-8-methyl-6-(trifluoromethyl)-9H-pyrimido[4,5-b]indol-9-yl)acetic acid (184f) (60 mg, 0.137 mmol) in DMF (1.5 mL) using TFA salt of (S)—N-(6-bromopyridin-2-yl)thiazolidine-2-carboxamide (171a) (55.1 mg, 0.137 mmol), HATU (78 mg, 0.205 mmol), DIPEA (0.119 mL, 0.684 mmol) and stirring at RT for 16 h. This gave after workup and purification as described in scheme-303, (S)-3-(2-(4-amino-8-methyl-6-(trifluoromethyl)-9H-pyrimido[4,5-b]indol-9-yl)acetyl)-N-(6-bromopyridin-2-yl)thiazolidine-2-carboxamide (324a)(75 mg, 92% yield) HCl salt as a white solid; $^1$H NMR (300 MHz, DMSO-$d_6$) (a mixture of two rotamers) δ 11.30 and 11.08 (2s, 1H, $D_2O$ exchangeable), 8.78 (s, 1H), 8.59 (s, 1H), 8.51 (s, 2H, $D_2O$ exchangeable), 8.07 and 7.97 (2d, J=8.2 Hz, 1H), 7.82 and 7.74 (2t, J=8.0 Hz, 1H), 7.59 (s, 1H), 7.42 and 7.35 (2d, J=7.7 Hz, 1H), 5.86-5.54 (m, 3H), 4.42-4.28 (m, 1H), 4.18-4.05 (m, 1H), 3.44-3.31 (m, 2H), 2.75 (s, 3H); $^{19}$F NMR (282 MHz, DMSO-$d_6$) δ−58.74; MS (ES+): 594.1/596.1 (M+1); (ES−): 592.0/594.0 (M−1); Analysis calculated for $C_{23}H_{19}BrF_3N_7O_2S.1.25H_2O{\cdot}1.15HCl$: C, 41.93; H, 3.47; Cl, 6.19; N, 14.88. Found: C, 41.81. H, 3.38; Cl, 5.92; N, 14.71.

Scheme 325

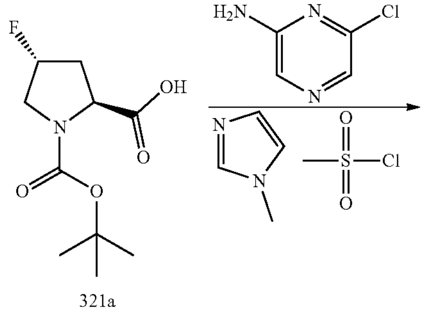

321a

-continued

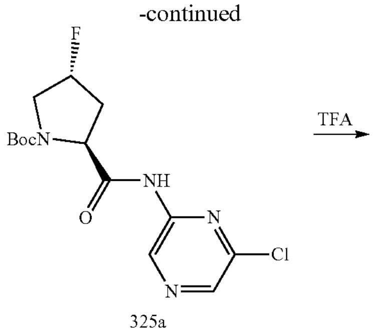

325a

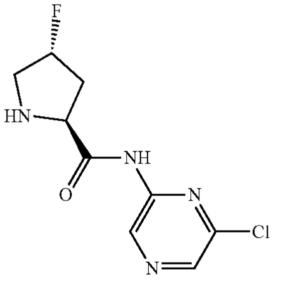

325b

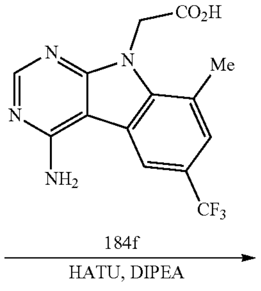

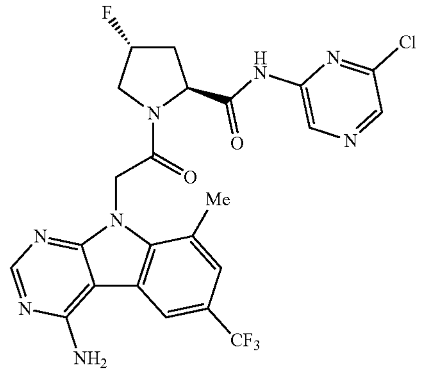

325c

Preparation of (2S,4R)-1-(2-(4-amino-8-methyl-6-(trifluoromethyl)-9H-pyrimido[4,5-b]indol-9-yl)acetyl)-N-(6-chloropyrazin-2-yl)-4-fluoropyrrolidine-2-carboxamide (325c)

Step-1: Preparation of (2S,4R)-tert-butyl 2-((6-chloropyrazin-2-yl)carbamoyl)-4-fluoropyrrolidine-1-carboxylate (325a)

Compound 325a was prepared according to the procedure reported in step-1 of scheme-53, from (2S,4R)-1-(tert-butoxycarbonyl)-4-fluoropyrrolidine-2-carboxylic acid (321a) (0.466 g, 2 mmol) in DCM (15 mL) and 6-chloropyrazin-2-amine (0.259 g, 2.00 mmol; CAS #33332-28-4) to afford after purification as described in step-1 of scheme-317, (2S,4R)-tert-butyl 2-((6-chloropyrazin-2-yl)carbamoyl)-4-fluoropyrrolidine-1-carboxylate (325a) (0.36 g, 52% yield) as a clear gel; MS (ES+): 345.1 (M+1).

Step-2: Preparation of (2S,4R)—N-(6-chloropyrazin-2-yl)-4-fluoropyrrolidine-2-carboxamide (325b)

Compound 325b was prepared according to the procedure reported in step-2 of scheme-1, from (2S,4R)-tert-butyl 2-((6-chloropyrazin-2-yl)carbamoyl)-4-fluoropyrrolidine-1-carboxylate (325a) (0.35 g, 1.015 mmol) in DCM (5.5 mL) using TFA (0.547 mL, 7.11 mmol) to afford after purification as described in step-2 of scheme-319, HCl salt of (2S,4R)—N-(6-chloropyrazin-2-yl)-4-fluoropyrrolidine-2-carboxamide (325b) (0.220 g, 77% yield); $^1$H NMR (300 MHz, DMSO-$d_6$) δ 11.77 (s, 1H), 9.29 (s, 1H), 8.62 (s, 1H), 5.51 (d, J=52.4 Hz, 1H), 4.64 (dd, J=10.9, 7.3 Hz, 1H), 3.67-3.61 (m, 1H), 3.59-3.47 (m, 1H), 2.93-2.67 (m, 1H), 2.45-2.17 (m, 1H); $^{19}$F NMR (282 MHz, DMSO-$d_6$) δ−175.30; MS (ES+): 245.0 (M+1).

Step-3: Preparation of (2S,4R)-1-(2-(4-amino-8-methyl-6-(trifluoromethyl)-9H-pyrimido[4,5-b]indol-9-yl)acetyl)-N-(6-chloropyrazin-2-yl)-4-fluoropyrrolidine-2-carboxamide (325c)

Compound 325c was prepared according to the procedure reported in step-3 of scheme-1, from HCl salt of (2S,4R)—N-(6-chloropyrazin-2-yl)-4-fluoropyrrolidine-2-carboxamide (325b) (38.5 mg, 0.137 mmol) in DMF (1.5 mL) using TFA salt of 2-(4-amino-8-methyl-6-(trifluoromethyl)-9H-pyrimido[4,5-b]indol-9-yl)acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (2S,4R)-1-(2-(4-amino-8-methyl-6-(trifluoromethyl)-9H-pyrimido[4,5-b]indol-9-yl)acetyl)-N-(6-chloropyrazin-2-yl)-4-fluoropyrrolidine-2-carboxamide (325c) (69 mg, 91% yield) HCl salt as a white solid: $^1$H NMR (300 MHz, DMSO-$d_6$) (a mixture of two rotamers) δ 11.68 and 11.37 (2s, 1H, $D_2O$ exchangeable), 9.38 and 9.21 (2s, 1H), 8.78 (s, 1H), 8.67-8.50 (m, 3H, 2H $D_2O$ exchangeable), 8.48 (s, 1H), 7.60 (s, 1H), 5.93-5.46 (m, 3H), 4.70 (t, J=8.5 Hz, 1H), 4.34 (dd, J=21.4, 12.6 Hz, 11H), 4.01 (dd, J=38.1, 12.5 Hz, 1H), 2.75 (s, 3H), 2.64-2.55 (m, 1H), 2.35-2.06 (m, 1H); $^{19}$F NMR (282 MHz, DMSO-$d_6$) δ−58.74, −176.51. MS (ES+): 551.2 (M+1); (ES−): 549.1 (M−1); Analysis calculated for $C_{23}H_{19}ClF_4N_8O_2$ 1.75$H_2O$, 0.85HCl: C, 45.03; H, 3.84; Cl, 10.69; N, 18.27. Found: C, 45.06; H, 3.84; Cl, 10.59: N, 18.07.

Scheme 326

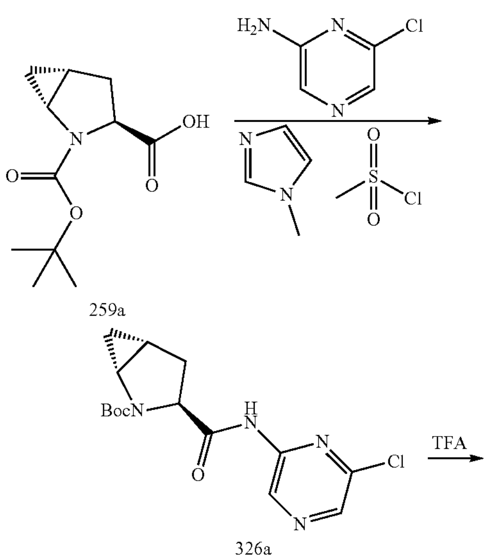

259a

326a

-continued

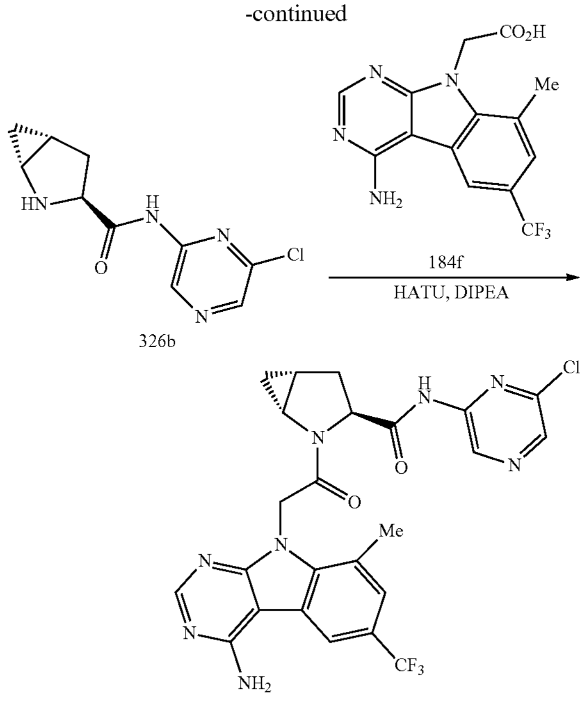

326b

326c

Preparation of (1R,3S,5R)-2-(2-(4-amino-8-methyl-6-(trifluoromethyl)-9H-pyrimido[4,5-b]indol-9-yl)acetyl)-N-(6-chloropyrazin-2-yl)-2-azabicyclo[3.1.0]hexane-3-carboxamide (326c)

Step-1: Preparation of (1R,3S,5R)-tert-butyl 3-((6-chloropyrazin-2-yl)carbamoyl)-2-azabicyclo[3.1.0]hexane-2-carboxylate (326a)

Compound 326a was prepared according to the procedure reported in step-1 of scheme-53, from (1R,3S,5R)-2-(tert-butoxycarbonyl)-2-azabicyclo[3.1.0]hexane-3-carboxylic acid (259a) (0.455 g, 2 mmol) and 6-chloropyrazin-2-amine (0.259 g, 2 mmol; CAS #33332-28-4) to afford after purification as described in step-1 of scheme-317 (1R,3S,5R)-tert-butyl 3-((6-chloropyrazin-2-yl)carbamoyl)-2-azabicyclo[3.1.0]hexane-2-carboxylate (326a) (0.245 g, 36% yield) as a clear gel; MS (ES+): 339.1 (M+1).

Step-2: Preparation of (1R,3S,5R)—N-(6-chloropyrazin-2-yl)-2-azabicyclo[3.1.0]hexane-3-carboxamide (326b)

Compound 326b was prepared according to the procedure reported in step-2 of scheme-1, from (1R,3S,5R)-tert-butyl 3-((6-chloropyrazin-2-yl)carbamoyl)-2-azabicyclo[3.1.0]hexane-2-carboxylate (326a) (0.24 g, 0.708 mmol) in DCM (4 mL) using TFA (0.382 mL, 4.96 mmol) to afford after purification as described in step-2 of scheme-319, (1R,3S,5R)—N-(6-chloropyrazin-2-yl)-2-azabicyclo[3.1.0]hexane-3-carboxamide (326b) (0.14 g, 72% yield) HCl salt; $^1$H NMR (300 MHz, DMSO-$d_6$) δ 11.66 (s, 1H), 9.26 (s, 1H), 8.61 (s, 1H), 4.21 (dd, J=10.9, 7.8 Hz, 1H), 3.32-3.26 (m, 1H), 2.62 (dd, J=12.8, 7.8 Hz, 1H), 2.22-1.99 (m, 1H), 1.92-1.68 (m, 1H), 1.00-0.58 (m, 2H); MS (ES+): 239.0 (M+1).

Step-3: Preparation of (1R,3S,5R)-2-(2-(4-amino-8-methyl-6-(trifluoromethyl)-9H-pyrimido[4,5-b]indol-9-yl)acetyl)-N-(6-chloropyrazin-2-yl)-2-azabicyclo[3.1.0]hexane-3-carboxamide (326c)

Compound 326c was prepared according to the procedure reported in step-3 of scheme-1, from HCl salt of (1R,3S,5R)—N-(6-chloropyrazin-2-yl)-2-azabicyclo[3.1.0]hexane-3-carboxamide (326b) (37.7 mg, 0.137 mmol) in DMF (1.5 mL) using TFA salt of 2-(4-amino-8-methyl-6-(trifluoromethyl)-9H-pyrimido[4,5-b]indol-9-yl)acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (1R,3S,5R)-2-(2-(4-amino-8-methyl-6-(trifluoromethyl)-9H-pyrimido[4,5-b]indol-9-yl)acetyl)-N-(6-chloropyrazin-2-yl)-2-azabicyclo[3.1.0]hexane-3-carboxamide (326c) (67 mg, 90% yield) HCl salt as a white solid; $^1$H NMR (300 MHz, DMSO-$d_6$) δ 11.19 (s, 1H, $D_2O$ exchangeable), 9.23 (s, 1H), 8.79 (s, 1H), 8.63 (s, 3H, 2H $D_2O$ exchangeable), 8.48 (s, 1H), 7.62 (s, 1H), 5.99 (d, J=18.0 Hz, 1H), 5.71 (d, J=18.0 Hz, 1H), 4.46 (dd, J=9.1, 5.7 Hz, 1H), 4.03-3.80 (m, 11H), 2.78 (s, 3H), 2.38 (dd, J=13.5, 9.2 Hz, 1H), 2.32-2.18 (m, 1H), 2.02-1.87 (m, 1H), 1.21-1.01 (m, 1H), 0.78-0.67 (m, 1H); $^{19}$F NMR (282 MHz, DMSO-$d_6$) δ-58.76; MS (ES+): 545.2 (M+1); (ES−): 543.1 (M−1); Analysis calculated for $C_{24}H_{20}ClF_3N_8O_2 \cdot 2H_2O$, 0.75HCl: C, 47.39; H, 4.10; Cl, 10.20; N, 18.42. Found: C, 47.57; H, 3.92; Cl, 10.02; N, 18.31.

Scheme 327

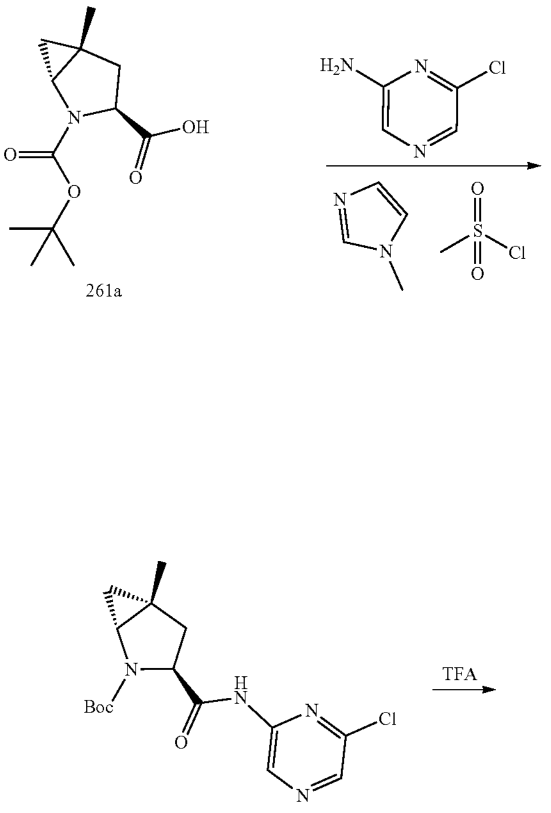

261a

327a

-continued

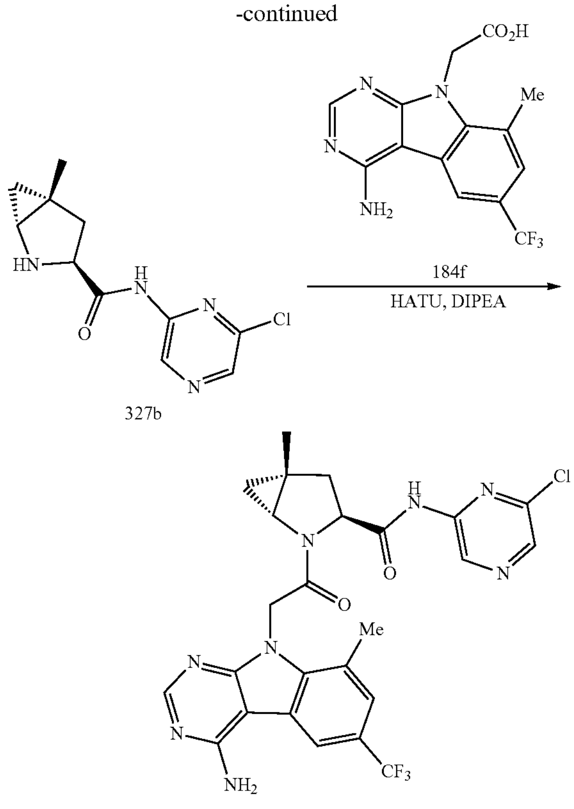

327b

327c

Preparation of (1R,3S,5R)-2-(2-(4-amino-8-methyl-6-(trifluoromethyl)-9H-pyrimido[4,5-b]indol-9-yl)acetyl)-N-(6-chloropyrazin-2-yl)-5-methyl-2-azabicyclo[3.1.0]hexane-3-carboxamide (327c)

Step-1: Preparation of (1R,3S,5R)-tert-butyl 3-((6-chloropyrazin-2-yl)carbamoyl)-5-methyl-2-azabicyclo[3.1.0]hexane-2-carboxylate (327a)

Compound 327a was prepared according to the procedure reported in step-1 of scheme-53, from (1R,3S,5R)-2-tert-butoxycarbonyl)-5-methyl-2-azabicyclo[3.1.0]hexane-3-carboxylic acid (261a) (0.483 g, 2 mmol) and 6-chloropyrazin-2-amine (0.259 g, 2 mmol) to afford after purification as described in step-1 of scheme-317, (1R,3S,5R)-tert-butyl 3-((6-chloropyrazin-2-yl)carbamoyl)-5-methyl-2-azabicyclo[3.1.0]hexane-2-carboxylate (327a) (0.091 g, 13% yield) as a clear gel; MS (ES+): 353.1 (M+1).

Step-2: Preparation of (1R,3S,5R)—N-(6-chloropyrazin-2-yl)-5-methyl-2-azabicyclo[3.1.0]hexane-3-carboxamide (327b)

Compound 327b was prepared according to the procedure reported in step-2 of scheme-1, from (1R,3S,5R)-tert-butyl 3-((6-chloropyrazin-2-yl)carbamoyl)-5-methyl-2-azabicyclo[3.1.0]hexane-2-carboxylate (327a)(0.085 g, 0.241 mmol) in DCM (1.5 mL) using TFA (0.130 mL, 1.686 mmol) to afford after purification as described in step-2 of scheme-319, (1R,3S,5R)—N-(6-chloropyrazin-2-yl)-5-methyl-2-azabicyclo[3.1.0]hexane-3-carboxamide (327b) (0.055 g, 79% yield) HCl salt; $^1$H NMR (300 MHz, DMSO-$d_6$) δ 11.68 (s, 1H), 9.26 (s, 1H), 8.61 (s, 1H), 4.24 (dd, J=11.1, 7.7 Hz, 1H), 3.10 (dd, J=6.9, 2.4 Hz, 1H), 2.74-2.60 (m, 1H), 2.00 (t, J=11.8 Hz, 1H), 1.26 (s, 3H), 1.03 (dd, J=7.2, 2.5 Hz, 1H), 0.79 (t, J=7.0 Hz, 1H); MS (ES+): 253.1 (M+1).

Step-3: Preparation of (1R,3S,5R)-2-(2-(4-amino-8-methyl-6-(trifluoromethyl)-9H-pyrimido[4,5-b]indol-9-yl)acetyl)-N-(6-chloropyrazin-2-yl)-5-methyl-2-azabicyclo[3.1.0]hexane-3-carboxamide (327c)

Compound 327c was prepared according to the procedure reported in step-3 of scheme-1, from HCl salt of (1R,3S,5R)—N-(6-chloropyrazin-2-yl)-5-methyl-2-azabicyclo[3.1.0]hexane-3-carboxamide (327b) (39.6 mg, 0.137 mmol) in DMF (1.5 mL) using TFA salt of 2-(4-amino-8-methyl-6-(trifluoromethyl)-9H-pyrimido[4,5-b]indol-9-yl) acetic acid (184f) (60 mg, 0.137 mmol). HATU (78 mg, 0.205 mmol), DIPEA (0.119 mL, 0.684 mmol) and stirring at RT for 16 h. This gave after workup and purification as described in scheme-303, (1R,3S,5R)-2-(2-(4-amino-8-methyl-6-(trifluoromethyl)-9H-pyrimido[4,5-b]indol-9-yl) acetyl)-N-(6-chloropyrazin-2-yl)-5-methyl-2-azabicyclo[3.1.0]hexane-3-carboxamide (327c) (64 mg, 84% yield) HCl salt as a white solid; 1H NMR (300 MHz, DMSO-$d_6$) δ 11.18 (s, 1H, $D_2O$ exchangeable), 9.23 (s, 1H), 8.78 (s, 1H), 8.60 (s, 1H), 8.53 (s, 2H, $D_2O$ exchangeable), 8.48 (s, 1H), 7.60 (s, 1H), 5.93 (d, J=18.0 Hz, 1H), 5.66 (d, J=17.9 Hz, 1H), 4.41 (dd, J=9.1, 6.1 Hz, 1H), 3.73 (dd, J=5.5, 2.3 Hz, 1H), 2.76 (s, 3H), 2.56-2.52 (m, 1H), 2.03 (dd, J=13.3, 6.0 Hz, 1H), 1.32 (s, 3H), 1.08-0.99 (m, 1H), 0.92-0.83 (m, 1H); $^{19}F$ NMR (282 MHz, DMSO-$d_6$) δ −58.73; MS (ES+): 559.1 (M+1); (ES−): 557.1 (M−1); Analysis calculated for $C_{25}H_{22}ClF_3N_8O_2$ 2.25$H_2O$, 0.75HCl: C, 47.90; H, 4.38; Cl, 9.90; N, 17.88. Found: C, 47.92; H, 4.18; Cl, 9.91; N, 17.77.

Scheme 328

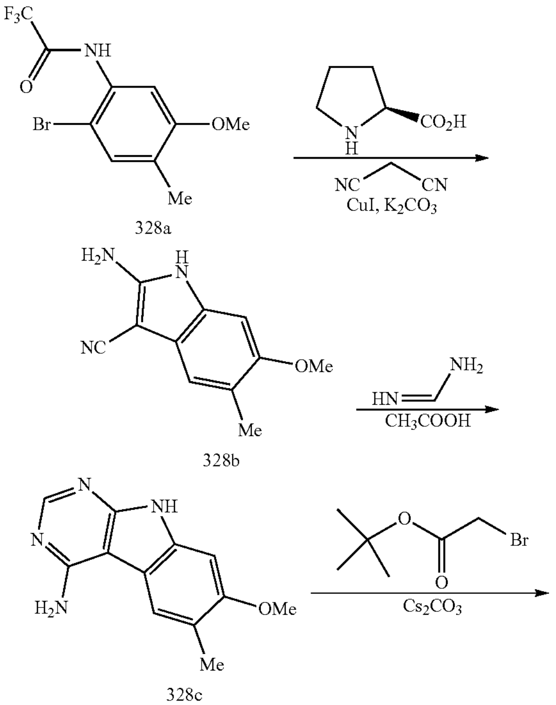

328a

328b

328c

-continued

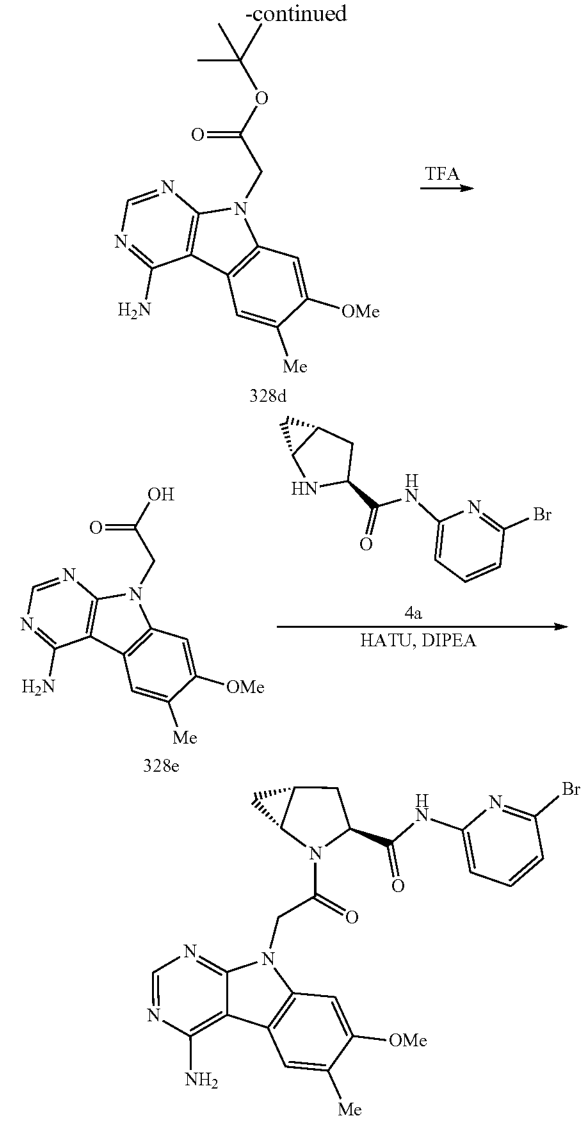

328d

328e

328f

Preparation of (1R,3S,5R)-2-(2-(4-amino-7-methoxy-6-methyl-9H-pyrimido[4,5-b]indol-9-yl) acetyl)-N-(6-bromopyridin-2-yl)-2-azabicyclo[3.1.0] hexane-3-carboxamide (328f)

Step-1: Preparation of 2-amino-6-methoxy-5-methyl-1H-indole-3-carbonitrile (328b)

Compound 328b was prepared according to the procedure reported in step-1 of scheme-11, from N-(2-bromo-5-methoxy-4-methylphenyl)-2,2,2-trifluoroacetamide (328a) (7.4 g, 23.71 mmol; CAS #1262881-27-5) in DMSO (30 mL) using malononitrile (1.792 mL, 28.5 mmol), L-proline (0.546 g, 4.74 mmol), CuI (452 mg, 2.371 mmol), a solution of $K_2CO_3$ (6.55 g, 47.4 mmol) in water (30 mL) and heating at 60° C. for 16 h under an argon atmosphere. This gave after workup and purification [$SiO_2$ gel (80 g), EtOAc/methanol (9:1) in hexane from 0-50%] 2-amino-6-methoxy-5-methyl-1H-indole-3-carbonitrile (328b) (1.95 g, 41% yield) as a grey solid; $^1H$ NMR (300 MHz, DMSO-$d_6$) δ 10.43 (s, 1H), 6.89 (s, 1H), 6.75 (s, 1H), 6.49 (s, 2H), 3.73 (s, 3H), 2.21-2.07 (m, 3H); MS (ES+): 202.1 (M+1); (ES−): 200.1 (M−1).

Step-2: Preparation of 7-methoxy-6-methyl-9H-pyrimido[4,5-b]indol-4-amine (328c)

Compound 328c was prepared according to the procedure reported in step-2 of scheme-29, from 2-amino-6-methoxy-5-methyl-1H-indole-3-carbonitrile (328b) (1.9 g, 9.44 mmol) in ethanol (60 mL) using formamidine acetate (7.94 g, 76 mmol) to afford after workup AcOH salt of 7-methoxy-6-methyl-9H-pyrimido[4,5-b]indol-4-amine (328c) (2.72 g, 81% yield) as a pale-yellow solid; 1H NMR (300 MHz, DMSO-$d_6$) δ 8.53 (s, 1H), 8.45 (s, 1H), 8.32 (s, 1H), 7.46 (s, 1H), 5.29 (s, 2H), 3.92 (s, 3H), 2.32 (s, 3H); MS (ES+): 229.1 (M+1).

Step-3: Preparation of tert-butyl 2-(4-amino-7-methoxy-6-methyl-9H-pyrimido[4,5-b]indol-9-yl) acetate (328d)

To a mixture of 7-methoxy-6-methyl-9H-pyrimido[4,5-b]indol-4-amine (328c) AcOH salt (2 g, 6.94 mmol) in DMF (50 mL) was added cesium carbonate (6.78 g, 20.81 mmol) at 0° C. under $N_2$ and stirred at the same temperature for 20 min. To this mixture was added tert-butyl 2-bromoacetate (1.128 mL, 7.63 mmol) and allowed to RT over a period of 16 h at RT. The reaction mixture was quenched by adding water. The solid separated was filtered and purified by reverse phase column chromatography [C18 column (50 g), eluting with ACN in water (containing 0.1% HCl) from 0-100%] to afford tert-butyl 2-(4-amino-7-methoxy-6-methyl-9H-pyrimido[4,5-b]indol-9-yl)acetate (328d) (0.2 g, 8% yield) as a pale yellow solid: $^1$H NMR (300 MHz, DMSO-$d_6$) δ 8.24 (s, 1H), 8.15 (s, 1H), 7.19 (s, 3H), 5.12 (s, 2H), 3.88 (s, 3H), 2.29 (s, 3H), 1.41 (s, 9H); MS (ES+): 343.2 (M+1).

Step-4: Preparation of 2-(4-amino-7-methoxy-6-methyl-9H-pyrimido[4,5-b]indol-9-yl)acetic acid (328e)

Compound 328e was prepared according to the procedure reported in step-2 of scheme-1, from tert-butyl 2-(4-amino-7-methoxy-6-methyl-9H-pyrimido[4,5-b]indol-9-yl)acetate (328d) (0.19 g, 0.555 mmol) using 20% TFA in DCM (3.18 mL, 8.32 mmol) to afford the TFA salt of 2-(4-amino-7-methoxy-6-methyl-9H-pyrimido[4,5-b]indol-9-yl)acetic acid (328e) (285 mg) as a pale-yellow solid; $^1$H NMR (300 MHz, DMSO-$d_6$) δ 8.53 (s, 1H), 8.45 (s, 1H), 8.32 (s, 1H), 7.46 (s, 1H), 5.29 (s, 2H), 3.92 (s, 3H), 2.32 (s, 3H); MS (ES+): 287.10 (M+1).

Step-5: Preparation of (1R,3S,5R)-2-(2-(4-amino-7-methoxy-6-methyl-9H-pyrimido[4,5-b]indol-9-yl) acetyl)-N-(6-bromopyridin-2-yl)-2-azabicyclo[3.1.0] hexane-3-carboxamide (328f)

Compound 328f was prepared according to the procedure reported in step-3 of scheme-1, from TFA salt of 2-(4-amino-7-methoxy-6-methyl-9H-pyrimido[4,5-b]indol-9-yl)acetic acid (328e) (81 mg, 0.157 mmol) in DMF (2 mL) using HCl salt of (1R,3S,5R)—N-(6-bromopyridin-2-yl)-2-azabicyclo [3.1.0]hexane-3-carboxamide (4a) (50 mg, 0.157 mmol), HATU (90 mg, 0.235 mmol), DIPEA (0.137 mL, 0.785 mmol) and stirring at RT for 16 h. This gave after workup and purification as described in scheme-303, (1R,3S,5R)-2-(2-(4-amino-7-methoxy-6-methyl-9H-pyrimido[4,5-b]indol-9-yl)acetyl)-N-(6-bromopyridin-2-yl)-2-azabicyclo [3.1.0]hexane-3-carboxamide (328f) (51 mg, 59% yield) HCl salt as a white solid; $^1$H NMR (300 MHz, DMSO-$d_6$) δ 10.73 (s, 1H, $D_2O$ exchangeable), 8.54 (s, 1H), 8.43 (s, 2H, $D_2O$ exchangeable), 8.31 (s, 1H), 8.01 (d, J=8.2 Hz, 1H), 7.72 (t, J=8.0 Hz, 1H), 7.33 (d, J=7.7 Hz, 1H), 7.25 (s, 1H), 5.71 (d, J=17.2 Hz, 1H), 5.46 (d, J=17.2 Hz, 1H), 4.41 (dd, J=9.1, 5.6 Hz, 1H), 4.00-3.86 (m, 4H), 2.46-2.12 (m, 5H), 2.00-1.88 (m, 1H), 1.12-1.01 (m, 1H), 0.79-0.65 (m, 1H). MS (ES+): 550.1/552.1 (M+1): (ES−): 548.1/550.1 (M−1); Analysis calculated for $C_{23}H_{24}BrN_7O_3$ $2H_2O{\cdot}HCl$: C, 48.20; H, 4.69; Cl, 5.69: N, 15.74. Found: C, 48.19; H, 4.35; Cl, 5.70; N, 15.69.

Scheme 329

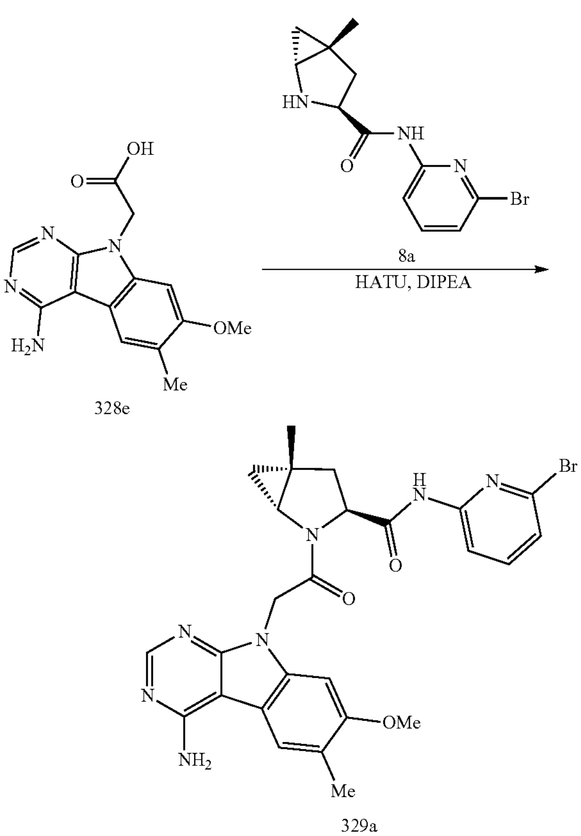

328e

329a

Preparation of (1R,3S,5R)-2-(2-(4-amino-7-methoxy-6-methyl-9H-pyrimido[4,5-b]indol-9-yl) acetyl)-N-(6-bromopyridin-2-yl)-5-methyl-2-azabicyclo[3.1.0]hexane-3-carboxamide (329a)

Compound 329a was prepared according to the procedure reported in step-3 of scheme-1, from TFA salt of 2-(4-amino-7-methoxy-6-methyl-9H-pyrimido[4,5-b]indol-9-yl)acetic acid (328e) (81 mg, 0.157 mmol) in DMF (2 mL) using HCl salt of (1R,3S,5R)—N-(6-bromopyridin-2-yl)-5-methyl-2-azabicyclo[3.1.0]hexane-3-carboxamide (8a) (52.2 mg, 0.157 mmol), HATU (90 mg, 0.236 mmol), DIPEA (0.137 mL, 0.785 mmol) and stirring at RT for 16 h. This gave after workup and purification as described in scheme-303, (1R, 3S,5R)-2-(2-(4-amino-7-methoxy-6-methyl-9H-pyrimido

[4,5-b]indol-9-yl)acetyl)-N-(6-bromopyridin-2-yl)-5-methyl-2-azabicyclo[3.1.0]hexane-3-carboxamide (329a) (56 mg, 63% yield) HCl salt as a white solid; $^1$H NMR (300 MHz, DMSO-$d_6$) δ 10.72 (s, 1H, $D_2O$ exchangeable), 8.53 (s, 1H), 8.40 (s, 2H, $D_2O$ exchangeable), 8.30 (s, 1H), 8.02 (d, J=8.2 Hz, 1H), 7.72 (t, J=8.0 Hz, 1H), 7.33 (d, J=7.7 Hz, 1H), 7.25 (s, 1H), 5.67 (d, J=17.3 Hz, 1H), 5.40 (d, J=17.2 Hz, 1H), 4.37 (dd, J=9.1, 6.1 Hz, 1H), 3.92 (s, 3H), 3.70 (dd, J=5.6, 2.3 Hz, 1H), 2.50-2.43 (m, 1H), 2.30 (s, 3H), 2.00 (dd, J=13.2, 6.0 Hz, 1H), 1.32 (s, 3H), 1.10-0.97 (m, 1H), 0.97-0.82 (m, 1H); MS (ES+): 564.1/566.1 (M+1); (ES−): 562.1/564.0 (M−1); Analysis calculated for $C_{26}H_{26}BrN_7O_3$ $1.75H_2O$, 1.15HCl: C, 48.95; H, 4.84; Cl, 6.39; N, 15.37. Found: C, 48.93; H, 4.87; Cl, 6.37; N, 15.47.

Scheme 330

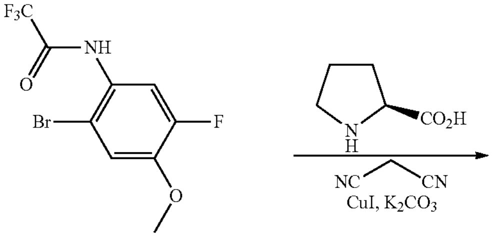

330a

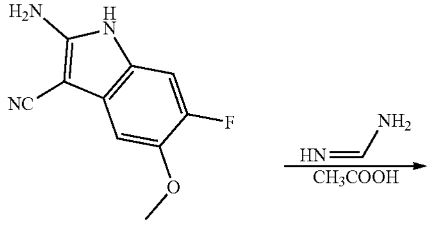

330b

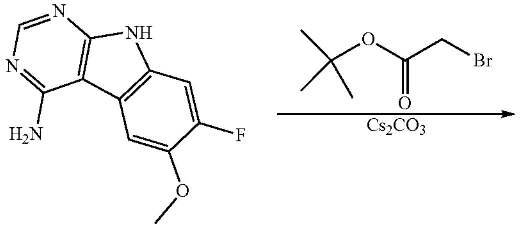

330c

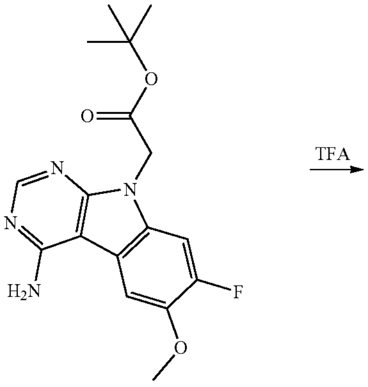

330d

-continued

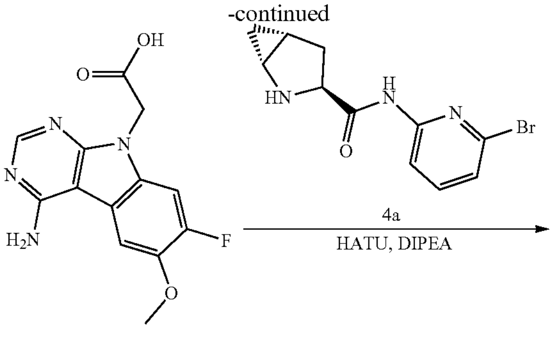

330e

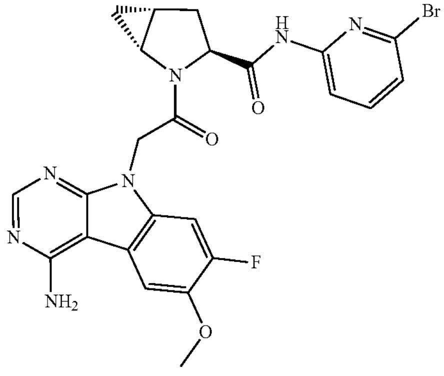

330f

Preparation of (1R,3S,5R)-2-(2-(4-amino-7-fluoro-6-methoxy-9H-pyrimido[4,5-b]indol-9-yl)acetyl)-N-(6-bromopyridin-2-yl)-2-azabicyclo[3.1.0]hexane-3-carboxamide (330f)

Step-1: Preparation of 2-amino-6-fluoro-5-methoxy-1H-indole-3-carbonitrile (330b)

Compound 330b was prepared according to the procedure reported in step-1 of scheme-11, from N-(2-bromo-5-fluoro-4-methoxyphenyl)-2,2,2-trifluoroacetamide (330a) (3.5 g, 11.07 mmol; CAS #1262881-29-7) in DMSO (15 mL) using malononitrile (0.837 mL, 13.29 mmol), L-proline (0.255 g, 2.215 mmol), CuI (211 mg, 1.107 mmol), a solution of $K_2CO_3$ (3.06 g, 22.15 mmol) in water (15 mL) to afford after workup and purification as described in step-1 of scheme-328, 2-amino-6-fluoro-5-methoxy-1H-indole-3-carbonitrile (330b)(0.95 g, 42% yield) as a yellow solid; MS (ES+): 206.1 (M+1); (ES−): 204.0 (M−1).

Step-2: Preparation of 7-fluoro-6-methoxy-9H-pyrimido[4,5-b]indol-4-amine (330c)

Compound 330c was prepared according to the procedure reported in step-2 of scheme-29, from 2-amino-6-fluoro-5-methoxy-1H-indole-3-carbonitrile (330b) (0.9 g, 4.39 mmol) in ethanol (30 mL) using formamidine acetate (3.69 g, 35.1 mmol) to afford after workup AcOH salt of 7-fluoro-6-methoxy-9H-pyrimido[4,5-b]indol-4-amine (330c) (0.98 g, 85% yield) as a pale-yellow solid; $^1$H NMR (300 MHz, DMSO-$d_6$) δ 11.74 (s, 1H), 8.20 (s, 1H), 8.04 (d, J=8.4 Hz, 1H), 7.35-7.16 (m, 3H), 3.93 (s, 3H); MS (ES+): 233.1 (M+1).

Step-3: Preparation of tert-butyl 2-(4-amino-7-fluoro-6-methoxy-9H-pyrimido[4,5-b]indol-9-yl) acetate (330d)

Compound 330d was prepared according to the procedure reported in step-1 of scheme-1/step-3 of scheme-328, from AcOH salt of 7-fluoro-6-methoxy-9H-pyrimido[4,5-b]indol-4-amine (330c) (950 mg, 3.62 mmol) in DMF (25 mL) using tert-butyl 2-bromoacetate (0.589 mL, 3.98 mmol) and $Cs_2CO_3$ (2.95 g, 9.06 mmol) to afford after workup and purification as described in step-3 of scheme-328, tert-butyl 2-(4-amino-7-fluoro-6-methoxy-9H-pyrimido[4,5-b]indol-9-yl)acetate (330d) (0.89 g, 71% yield) as a pale yellow solid; MS (ES+): 347.2 (M+1).

Step-4: Preparation of 2-(4-amino-7-fluoro-6-methoxy-9H-pyrimido[4,5-b]indol-9-yl)acetic acid (330e)

Compound 330e was prepared according to the procedure reported in step-2 of scheme-1, from tert-butyl 2-(4-amino-7-fluoro-6-methoxy-9H-pyrimido[4,5-b]indol-9-yl)acetate (330d) (0.87 g, 2.51 mmol) using 20% TFA in DCM (14.42 mL, 37.7 mmol) to afford after workup TFA salt of 2-(4-amino-7-fluoro-6-methoxy-9H-pyrimido[4,5-b]indol-9-yl) acetic acid (330e) (1.3 g) as a pale-yellow solid; $^1$H NMR (300 MHz, DMSO-$d_6$) δ 8.73 (s, 2H), 8.58 (s, 1H), 8.24 (d, J=8.2 Hz, 1H), 7.91 (d, J=11.7 Hz, 1H), 5.24 (s, 2H), 3.98 (s, 3H); MS (ES+): 291.1 (M+1).

Scheme 331

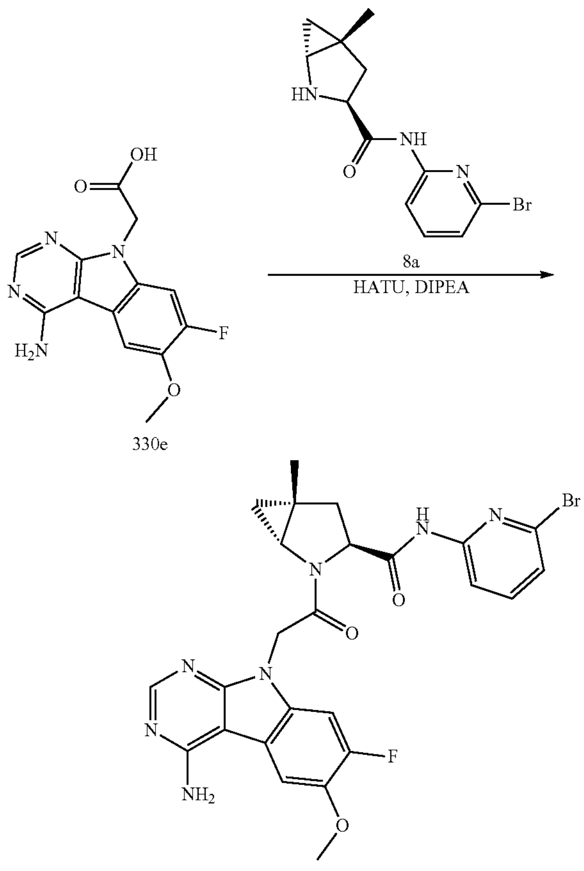

330e

331a

Step-5: Preparation of (1R,3S,5R)-2-(2-(4-amino-7-fluoro-6-methoxy-9H-pyrimido[4,5-b]indol-9-yl) acetyl)-N-(6-bromopyridin-2-yl)-2-azabicyclo[3.1.0] hexane-3-carboxamide (330f)

Compound 330f was prepared according to the procedure reported in step-3 of scheme-1, from TFA salt of 2-(4-amino-7-fluoro-6-methoxy-9H-pyrimido[4,5-b]indol-9-yl)acetic acid (330e) (81 mg, 0.157 mmol) in DMF (2 mL) using HCl salt of (1R,3S,5R)—N-(6-bromopyridin-2-yl)-2-azabicyclo [3.1.0]hexane-3-carboxamide (4a) (50 mg, 0.157 mmol), HATU (90 mg, 0.235 mmol), DIPEA (0.137 mL, 0.785 mmol) and stirring at RT for 16 h. This gave after workup and purification as described in scheme-303, (1R,3S,5R)-2-(2-(4-amino-7-fluoro-6-methoxy-9H-pyrimido[4,5-b]indol-9-yl)acetyl)-N-(6-bromopyridin-2-yl)-2-azabicyclo[3.1.0] hexane-3-carboxamide (330f) (56 mg, 64.4% yield) HCl salt as a white solid; $^1$H NMR (300 MHz, DMSO-$d_6$) δ 10.77 (s, 1H, $D_2O$ exchangeable), 8.54 (s, 3H, 2H $D_2O$ exchangeable), 8.24 (d, J=8.2 Hz, 1H), 8.01 (d, J=8.1 Hz, 1H), 7.77-7.63 (m, 2H), 7.32 (d, J=7.7 Hz, 1H), 5.71 (d, J=17.4 Hz, 1H), 5.36 (d, J=17.3 Hz, 1H), 4.42 (dd, J=9.0, 5.4 Hz, 1H), 3.97 (s, 3H), 3.93-3.81 (m, 1H), 2.39-2.27 (m, 1H), 2.27-2.14 (m, 1H), 2.00-1.82 (m, 1H), 1.19-0.96 (m, 1H), 0.84-0.75 (m, 1H). $^{19}$F NMR (282 MHz, DMSO-$d_6$) δ−133.52. MS (ES+): 554.1/556.1 (M+1): (ES−): 552.1/554.1 (M−1); Analysis calculated for $C_{24}H_{21}BrFN_7O_3$ $2H_2O$, 0.9HCl: C, 46.25; H, 4.19; Cl, 5.12; N, 15.73. Found: C, 46.18: H, 3.92; Cl, 5.08; N, 15.62.

Preparation of (1R,3S,5R)-2-(2-(4-amino-7-fluoro-6-methoxy-9H-pyrimido[4,5-b]indol-9-yl)acetyl)-N-(6-bromopyridin-2-yl)-5-methyl-2-azabicyclo[3.1.0] hexane-3-carboxamide (331a)

Compound 331a was prepared according to the procedure reported in step-3 of scheme-1, from TFA salt of 2-(4-amino-7-fluoro-6-methoxy-9H-pyrimido[4,5-b]indol-9-yl)acetic acid (330e) (78 mg, 0.150 mmol) in DMF (2 mL) using HCl salt of (1R,3S,5R)—N-(6-bromopyridin-2-yl)-5-methyl-2-azabicyclo[3.1.0]hexane-3-carboxamide (8a) (50 mg, 0.150 mmol), HATU (86 mg, 0.225 mmol), DIPEA (0.131 mL, 0.752 mmol) and stirring at RT for 16 h. This gave after workup and purification using as described in scheme-303, (1R,3S,5R)-2-(2-(4-amino-7-fluoro-6-methoxy-9H-pyrimido[4,5-b]indol-9-yl)acetyl)-N-(6-bromopyridin-2-yl)-5-methyl-2-azabicyclo[3.1.0]hexane-3-carboxamide (331a) (48 mg, 56% yield) HCl salt as a white solid; $^1$H NMR (300 MHz, DMSO-$d_6$) δ 10.77 (s, 1H, $D_2O$ exchangeable), 8.64-8.28 (m, 3H, 2H $D_2O$ exchangeable), 8.21 (d, J=8.2 Hz, 1H), 8.02 (d, J=8.1 Hz, 1H), 7.80-7.58 (m, 2H), 7.32 (d, J=7.7 Hz, 1H), 5.66 (d, J=17.4 Hz, 1H), 5.30 (d, J=17.3 Hz, 1H), 4.37 (dd, J=9.1, 5.9 Hz, 1H), 3.96 (s, 3H), 3.70-3.64 (m, 1H), 2.48-2.41 (m, 1H), 1.98 (dd, J=13.3, 5.8 Hz, 1H), 1.31 (s, 3H), 1.06-0.90 (m, 2H); $^{19}$F NMR (282 MHz, DMSO-$d_6$) δ−133.30. MS (ES+): 568.1/570.1 (M+1): (ES−): 566.1/568.1 (M−1); Analysis calculated for $C_{25}H_2BrFN_7O_3$ $2H_2O{\cdot}1.1HCl$: C, 46.59; H, 4.39; Cl, 6.05; N, 15.21. Found: C, 46.52; H, 4.33; Cl, 6.12; N, 15.15.

Scheme 332

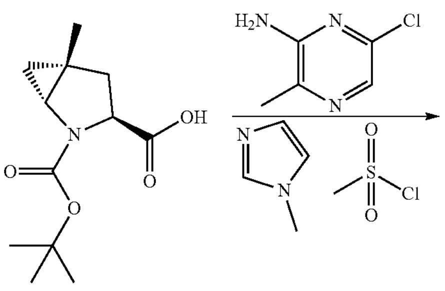

261a

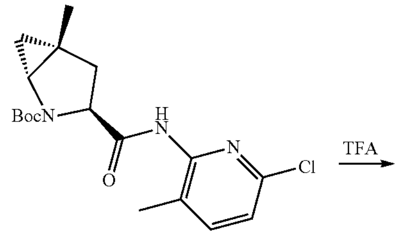

332a

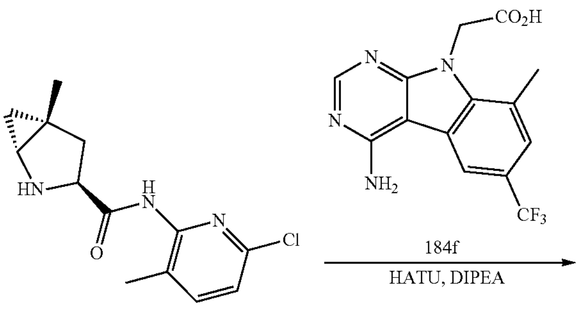

332b

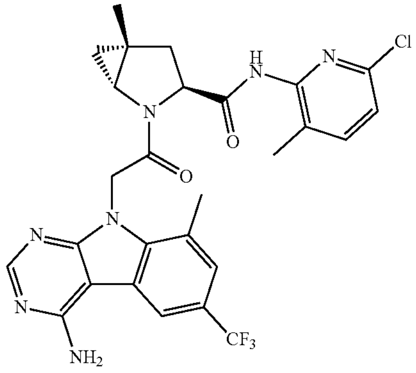

332c

Preparation of (1R,3S,5R)-2-(2-(4-amino-8-methyl-6-(trifluoromethyl)-9H-pyrimido[4,5-b]indol-9-yl)acetyl)-N-(6-chloro-3-methylpyridin-2-yl)-5-methyl-2-azabicyclo[3.1.0]hexane-3-carboxamide (332c)

Step-1: Preparation of (1R,3S,5R)-tert-butyl 3-((6-chloro-3-methylpyridin-2-yl)carbamoyl)-5-methyl-2-azabicyclo[3.1.0]hexane-2-carboxylate (332a)

Compound 332a was prepared according to the procedure reported in step-1 of scheme-53, from (1R,3S,5R)-2-(tert-butoxycarbonyl)-5-methyl-2-azabicyclo[3.1.0]hexane-3- carboxylic acid (261a) (0.35 g, 1.451 mmol) and 6-chloro-3-methylpyridin-2-amine (0.207 g, 1.451 mmol) to afford after purification as described in step-1 of scheme-317. (1R,3S,5R)-tert-butyl 3-((6-chloro-3-methylpyridin-2-yl)carbamoyl)-5-methyl-2-azabicyclo[3.1.0]hexane-2-carboxylate (332a) (0.196 g, 37% yield) as a white solid; MS (ES+): 366.2 (M+1).

Step-2: Preparation of (1R,3S,5R)—N-(6-chloro-3-methylpyridin-2-yl)-5-methyl-2-azabicyclo[3.1.0]hexane-3-carboxamide (332b)

Compound 332b was prepared according to the procedure reported in step-2 of scheme-1, from (1R,3S,5R)-tert-butyl 3-((6-chloro-3-methylpyridin-2-yl)carbamoyl)-5-methyl-2-azabicyclo[3.1.0]hexane-2-carboxylate (332a) (0.19 g, 0.519 mmol) in DCM (2.8 mL) using TFA (0.280 mL, 3.64 mmol) to afford after purification as described in step-2 of scheme-319, (1R,3S,5R)—N-(6-chloro-3-methylpyridin-2-yl)-5-methyl-2-azabicyclo[3.1.0]hexane-3-carboxamide (332b) (137 mg, 99% yield); $^1$H NMR (300 MHz, DMSO-$d_6$) δ 10.89 (s, 1H), 10.12 (s, 1H), 9.19 (d, J=10.0 Hz, 1H), 7.82 (d, J=8.0 Hz, 1H), 7.41 (d, J=8.0 Hz, 1H), 4.36-4.22 (m, 1H), 3.11-3.04 (m, 1H), 2.65 (dd, J=12.6, 7.6 Hz, 1H), 2.16 (s, 3H), 2.05-1.95 (m, 1H), 1.27 (s, 3H), 1.13-1.03 (m, 1H), 0.84-0.72 (m, 1H); MS (ES+): 266.1 (M+1).

Step-3: Preparation of (1R,3S,5R)-2-(2-(4-amino-8-methyl-6-(trifluoromethyl)-9H-pyrimido[4,5-b]indol-9-yl)acetyl)-N-(6-chloro-3-methylpyridin-2-yl)-5-methyl-2-azabicyclo[3.1.0]hexane-3-carboxamide (332c)

Compound 332c was prepared according to the procedure reported in step-3 of scheme-1, from HCl salt of (1R,3S,5R)—N-(6-chloro-3-methylpyridin-2-yl)-5-methyl-2-azabicyclo[3.1.0]hexane-3-carboxamide (332b) (41.4 mg, 0.137 mmol) in DMF (1.5 mL) using TFA salt of 2-(4-amino-8-methyl-6-(trifluoromethyl)-9H-pyrimido[4,5-b]indol-9-yl)acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (1R,3S,5R)-2-(2-(4-amino-8-methyl-6-(trifluoromethyl)-9H-pyrimido[4,5-b]indol-9-yl)acetyl)-N-(6-chloro-3-methylpyridin-2-yl)-5-methyl-2-azabicyclo[3.1.0]hexane-3-carboxamide (332c) (55 mg, 70% yield) HCl salt as a white solid; $^1$H NMR (300 MHz, DMSO-$d_6$) δ 10.31 (s, 1H, $D_2O$ exchangeable), 8.79 (s, 1H), 8.59 (s, 1H), 8.53 (s, 2H, $D_2O$ exchangeable), 7.72 (d, J=8.0 Hz, 1H), 7.58 (s, 1H), 7.31 (d, J=7.9 Hz, 1H), 5.90 (d, J=18.0 Hz, 1H), 5.66 (d, J=17.9 Hz, 1H), 4.38 (dd, J=9.1, 5.6 Hz, 1H), 3.69 (dd, J=5.6, 2.4 Hz, 1H), 2.74 (s, 3H), 2.62-2.56 (m, 1H), 2.10-1.94 (m, 4H), 1.33 (s, 3H), 1.12-0.98 (m, 1H), 0.96-0.78 (m, 1H). $^{19}$F NMR (282 MHz, DMSO-$d_6$) δ-58.70; MS (ES+): 572.2 (M+1); (ES−): 570.1 (M−1); Analysis calculated for $C_{27}H_{25}ClF_3N_7O_2$ $2.25H_2O \cdot 0.75HCl$: C, 50.68; H, 4.77; Cl, 9.70; N, 15.32. Found: C, 50.55; H, 4.68; Cl, 9.70; N, 15.18.

Scheme 333

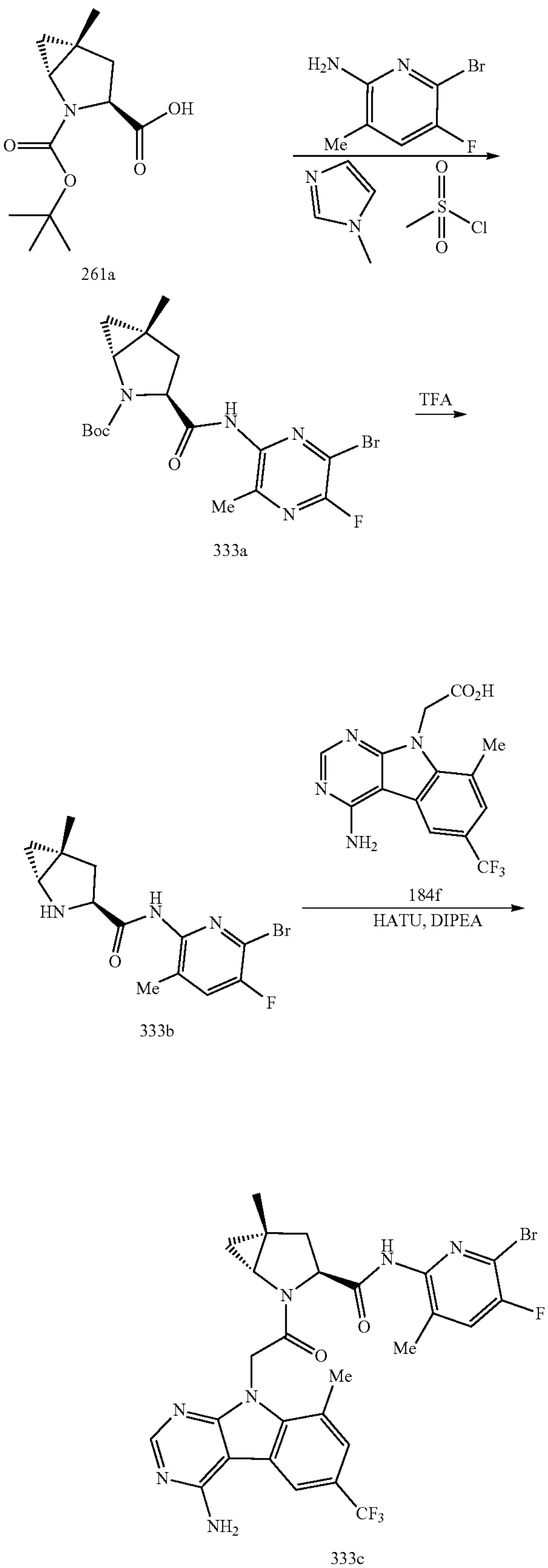

261a

333a

333b

333c

Preparation of (1R,3S,5R)-2-(2-(4-amino-8-methyl-6-(trifluoromethyl)-9H-pyrimido[4,5-b]indol-9-yl)acetyl)-N-(6-bromo-5-fluoro-3-methylpyridin-2-yl)-5-methyl-2-azabicyclo[3.1.0]hexane-3-carboxamide (333c)

Step-1: Preparation of (1R,3S,5R)-tert-butyl 3-((6-bromo-5-fluoro-3-methylpyridin-2-yl)carbamoyl)-5-methyl-2-azabicyclo[3.1.0]hexane-2-carboxylate (333a)

Compound 333a was prepared according to the procedure reported in step-1 of scheme-53, from (1R,3S,5R)-2-tert-butoxycarbonyl)-5-methyl-2-azabicyclo[3.1.0]hexane-3-carboxylic acid (261a) (0.35 g, 1.451 mmol) and 6-bromo-5-fluoro-3-methylpyridin-2-amine (0.297 g, 1.451 mmol) to afford after purification as described in step-1 of scheme-317, (1R,3S,5R)-tert-butyl 3-((6-bromo-5-fluoro-3-methylpyridin-2-yl)carbamoyl)-5-methyl-2-azabicyclo[3.1.0]hexane-2-carboxylate (333a) (0.560 g, 90% yield) as a white solid; MS (ES+): 428.1/430.1 (M+1).

Step-2: Preparation of (1R,3S,5R)—N-(6-bromo-5-fluoro-3-methylpyridin-2-yl)-5-methyl-2-azabicyclo[3.1.0]hexane-3-carboxamide (333b)

Compound 333b was prepared according to the procedure reported in step-2 of scheme-1, from (1R,3S,5R)-tert-butyl 3-((6-bromo-5-fluoro-3-methylpyridin-2-yl)carbamoyl)-5-methyl-2-azabicyclo[3.1.0]hexane-2-carboxylate (333a) (0.550 g, 1.284 mmol) in DCM (7 mL) using TFA (0.693 mL, 8.99 mmol) to afford after purification as described in step-2 of scheme-319, (1R,3S,5R)—N-(6-bromo-5-fluoro-3-methylpyridin-2-yl)-5-methyl-2-azabicyclo[3.1.0]hexane-3-carboxamide (333b) (408 mg, 97% yield); $^1$H NMR (300 MHz, DMSO-$d_6$) δ 10.92 (s, 1H), 10.08 (s, 1H), 9.27-9.11 (m, 1H), 7.93 (d, J=8.4 Hz, 1H), 4.38-4.21 (m, 1H), 3.07 (d, J=6.6 Hz, 1H), 2.65 (dd, J=12.6, 7.6 Hz, 1H), 2.17 (s, 3H), 1.99 (t, J=11.8 Hz, 1H), 1.27 (s, 3H), 1.15-1.01 (m, 1H), 0.81-0.71 (m, 1H); MS (ES+): 328.1/330.1 (M+1).

Step-3: Preparation of (1R,3S,5R)-2-(2-(4-amino-8-methyl-6-(trifluoromethyl)-9H-pyrimido[4,5-b]indol-9-yl)acetyl)-N-(6-bromo-5-fluoro-3-methylpyridin-2-yl)-5-methyl-2-azabicyclo[3.1.0]hexane-3-carboxamide (333c)

Compound 333c was prepared according to the procedure reported in step-3 of scheme-1, from HCl salt of (1R,3S,5R)—N-(6-bromo-5-fluoro-3-methylpyridin-2-yl)-5-methyl-2-azabicyclo[3.1.0]hexane-3-carboxamide (333b) (49.9 mg, 0.137 mmol) in DMF (1.5 mL) using TFA salt of 2-(4-amino-8-methyl-6-(trifluoromethyl)-9H-pyrimido[4,5-b]indol-9-yl)acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (1R,3S,5R)-2-(2-(4-amino-8-methyl-6-(trifluoromethyl)-9H-pyrimido[4,5-b]indol-9-yl)acetyl)-N-(6-bromo-5-fluoro-3-methylpyridin-2-yl)-5-methyl-2-azabicyclo[3.1.0]hexane-3-carboxamide (333c) (68 mg, 78% yield) HCl salt as a white solid; $^1$H NMR (300 MHz, DMSO-$d_6$) δ 10.36 (s, 1H, $D_2O$ exchangeable), 8.80 (s, 1H), 8.74-8.44 (m, 3H, 2H $D_2O$ exchangeable), 7.82 (d, J=8.5 Hz, 1H), 7.59 (s, 1H), 5.90 (d, J=18.0 Hz, 1H), 5.66 (d, J=17.9 Hz, 1H), 4.35 (dd, J=9.2, 5.7 Hz, 1H), 3.69 (dd, J=5.6, 2.4 Hz, 1H), 2.74 (s, 3H), 2.62-2.54 (m, 1H), 2.08-1.97 (m, 4H), 1.33 (s, 3H), 1.09-0.96 (m, 1H), 0.94-0.86 (m, 1H). $^{19}$F NMR (282 MHz, DMSO-$d_6$) δ−58.72, −119.20. MS (ES+): 634.1/636.1 (M+1); (ES−): 632.1/634.1 (M−1); Analysis calculated for $C_{27}H_{24}BrF_4N_7O_2H_2O{\cdot}HCl$: C, 47.07; H, 3.95; Cl, 5.15; N, 14.23. Found: C, 47.00; H, 3.75; Cl, 4.92; N, 14.06.

Scheme 334

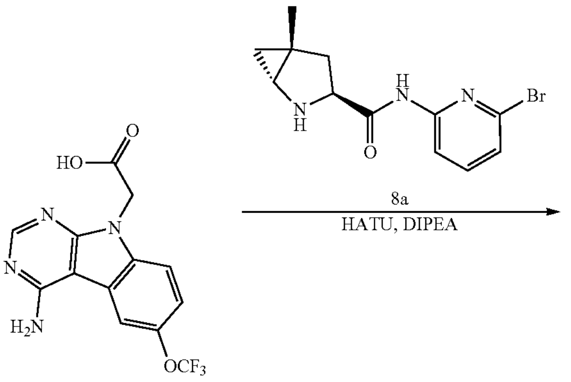

274f

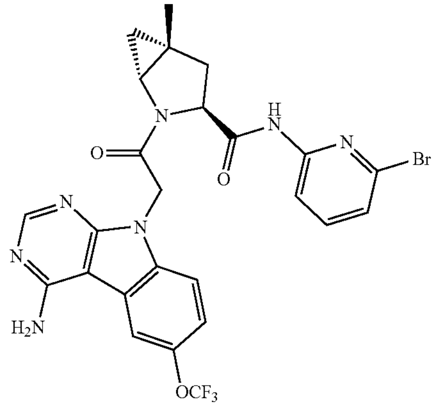

334a

Preparation of (1R,3S,5R)-2-(2-(4-amino-6-(trifluoromethoxy)-9H-pyrimido[4,5-b]indol-9-yl)acetyl)-N-(6-bromopyridin-2-yl)-5-methyl-2-azabicyclo[3.1.0]hexane-3-carboxamide (334a)

Compound 334a was prepared according to the procedure reported in step-3 of scheme-1, from 2-(4-amino-6-(trifluoromethoxy)-9H-pyrimido[4,5-b]indol-9-yl)acetic acid (274f) (75 mg, 0.23 mmol) in DMF (10 mL) using HCl salt of (1R,3S,5R)—N-(6-bromopyridin-2-yl)-5-methyl-2-azabicyclo[3.1.0]hexane-3-carboxamide (8a) (92 mg, 0.276 mmol), HATU (175 mg, 0.460 mmol), DIPEA (0.160 mL, 0.920 mmol) and stirring at RT for 20 h. This gave after workup and purification as described in scheme-299, (1R,3S,5R)-2-(2-(4-amino-6-(trifluoromethoxy)-9H-pyrimido[4,5-b]indol-9-yl)acetyl)-N-(6-bromopyridin-2-yl)-5-methyl-2-azabicyclo[3.1.0]hexane-3-carboxamide (334a) (109 mg, 78% yield) HCl salt as a white solid; $^1$H NMR (300 MHz, DMSO-$d_6$) δ 10.76 (s, 1H, $D_2O$ exchangeable), 8.64-8.59 (m, 1H), 8.56 (s, 1H), 8.44 (s, 2H, $D_2O$ exchangeable), 8.01 (d, J=8.2 Hz, 1H), 7.76 (d, J=9.0 Hz, 1H), 7.70 (t, J=8.0 Hz, 1H), 7.57-7.48 (m, 1H), 7.32 (d, J=7.7 Hz, 1H), 5.72 (d, J=17.4 Hz, 1H), 5.38 (d, J-=17.3 Hz, H), 4.36 (dd, =9.0, 6.0 Hz, 1H), 3.71-3.64 (m, 1H), 2.56-2.41 (m, 1H), 1.98 (dd, J=13.3, 5.9 Hz, 1H), 1.30 (s, 3H), 1.05-0.97 (m, 1H), 0.97-0.90 (m, 1H); $^{19}$F NMR (282 MHz, DMSO-$d_6$) δ−57.00; MS (ES+): 604.10 & 606.10 (M+1); MS (ES−): 602.00 & 604.00 (M−1); Analysis calculated for $C_{25}H_{21}BrF_3N_7O_3{\cdot}HCl{\cdot}1.25H_2O$: C, 45.26; H, 3.72; N, 14.78; Cl, 5.34. Found: C, 45.13; H, 3.83; N, 14.66; Cl, 5.08.

Scheme 335

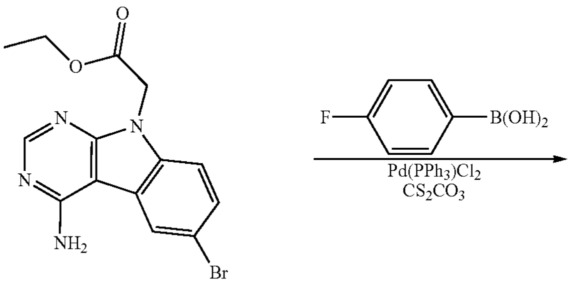

48a

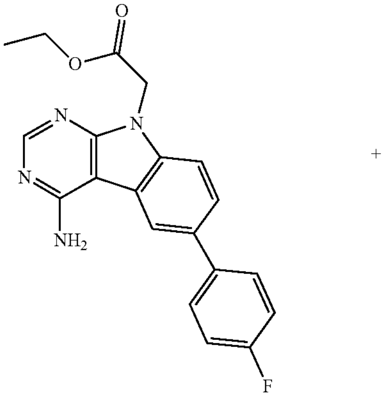

335a

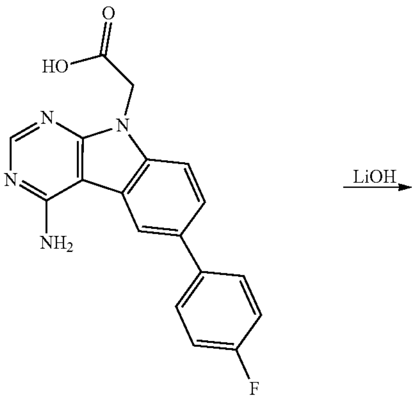

335b

-continued

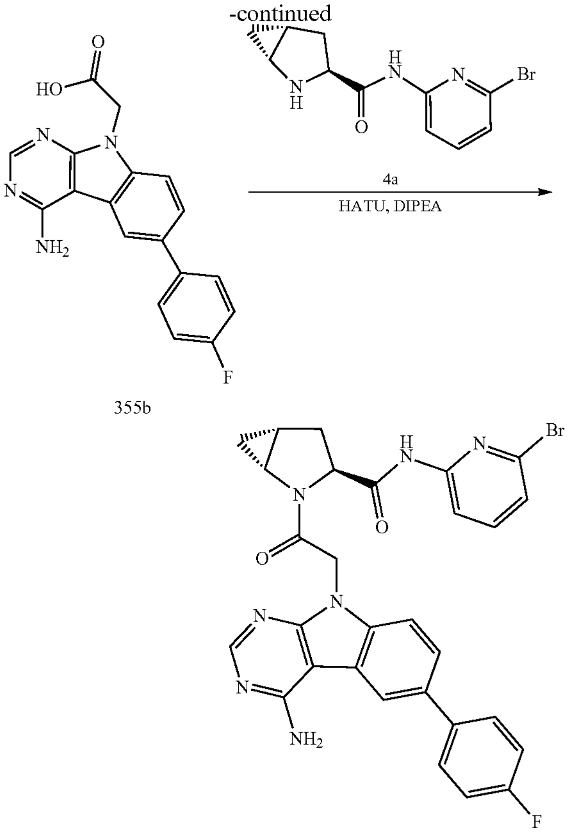

355b

355c

Preparation of (1R,3S,5R)-2-(2-(4-amino-6-(4-fluorophenyl)-9H-pyrimido[4,5-b]indol-9-yl)acetyl)-N-(6-bromopyridin-2-yl)-2-azabicyclo[3.1.0]hexane-3-carboxamide (335c)

Step-1: Preparation of ethyl 2-(4-amino-6-(4-fluorophenyl)-9H-pyrimido[4,5-b]indol-9-yl)acetate (335a)

Compound 335a was prepared and purified according to the procedure reported in step-1 of scheme-62, from ethyl 2-(4-amino-6-bromo-9H-pyrimido[4,5-b]indol-9-yl)acetate (48a) (200 mg, 0.573 mmol) in dioxane (18 mL) using (4-fluorophenyl)boronic acid (120 mg, 0.859 mmol), cesium carbonate (280 mg, 0.859 mmol) in water (2.2 mL), $Pd(PPh_3)_2Cl_2$, (80 mg, 0.115 mmol) and heating at 100° C. for 18 h to give a mixture of ethyl 2-(4-amino-6-(4-fluorophenyl)-9H-pyrimido[4,5-b]indol-9-yl)acetate (335a) and 2-(4-amino-6-(4-fluorophenyl)-9H-pyrimido[4,5-b]indol-9-yl)acetic acid (335b) which was used as such for the next step; MS (ES+): 337.10 & 365.10 (M+1).

Step-2: Preparation of 2-(4-amino-6-(4-fluorophenyl)-9H-pyrimido[4,5-b]indol-9-yl)acetic acid (335b)

Compound 335b was prepared according to the procedure reported in step-4 of scheme-17, from mixture of ethyl 2-(4-amino-6-(4-fluorophenyl)-9H-pyrimido[4,5-b]indol-9-yl)acetate (335a) and 2-(4-amino-6-(4-fluorophenyl)-9H-pyrimido[4,5-b]indol-9-yl)acetic acid (335b) obtained in step-1 of this scheme (0.573 mmol) in THF (5 mL) and methanol (5 mL) using a solution of lithium hydroxide hydrate (147 mg, 3.44 mmol) in water (5 mL) and stirring at RT for 12 h. The reaction mixture was concentrated to dryness diluted with water (12 mL), acidified with 4 N HCl to pH about 6 followed by filtration, washing with water, and drying under vacuum to afford a gray solid of 2-(4-amino-6-(4-fluorophenyl)-9H-pyrimido[4,5-b]indol-9-yl)acetic acid (335b) (120 mg) which was used as such for the next step: MS (ES+): 337.10 (M+1).

Step-3: Preparation of (1R,3S,5R)-2-(2-(4-amino-6-(4-fluorophenyl)-9H-pyrimido[4,5-b]indol-9-yl)acetyl)-N-(6-bromopyridin-2-yl)-2-azabicyclo[3.1.0]hexane-3-carboxamide (335c)

Compound 335c was prepared according to the procedure reported in step-3 of scheme-1, from 2-(4-amino-6-(4-fluorophenyl)-9H-pyrimido[4,5-b]indol-9-yl)acetic acid (335b) (60 mg, 0.178 mmol) in DMF (10 mL) using HCl salt of (1R,3S,5R)—N-(6-bromopyridin-2-yl)-2-azabicyclo[3.1.0]hexane-3-carboxamide (4a) (68.2 mg, 0.214 mmol), HATU (136 mg, 0.357 mmol), DIPEA (0.124 mL, 0.714 mmol) and stirring at RT for 20 h. This gave after workup and purification as described in scheme-299, (1R,3S,5R)-2-(2-(4-amino-6-(4-fluorophenyl)-9H-pyrimido[4,5-b]indol-9-yl)acetyl)-N-(6-bromopyridin-2-yl)-2-azabicyclo[3.1.0]hexane-3-carboxamide (335c) (52 mg, 49% yield) HCl salt as a white solid; $^1H$ NMR (300 MHz, DMSO-$d_6$) δ 10.77 (s, 1H, $D_2O$ exchangeable), 8.78 (d, 1H), 8.67 (s, 3H, $D_2O$ exchangeable), 8.62 (s, 1H), 8.01 (d, J=8.2 Hz, 1H), 7.92-7.83 (m, 3H), 7.77 (d, J=8.7 Hz, 1H), 7.70 (t, J=8.0 Hz, 1H), 7.40-7.28 (m, 3H), 5.79 (d, J=17.4 Hz, 1H), 5.45 (d, J=17.3 Hz, 1H), 4.42 (dd, J=9.0, 5.6 Hz, 1H), 4.05-3.81 (m, 1H), 2.44-2.14 (m, 2H), 2.02-1.84 (m, 1H), 1.17-1.01 (m, 1H), 0.85-0.69 (m, 1H); $^{19}F$ NMR (282 MHz, DMSO-$d_6$) δ-116.03; MS (ES+): 600.10 & 602.15 (M+1); MS (ES−): 598.10 & 600.05 (M−1); Analysis calculated for $C_{29}H_{23}BrFN_7O_2 \cdot 1.15HCl \cdot 1.75H_2O$: C, 51.69; H, 4.14; N, 14.55. Cl, 6.05. Found: C, 51.71; H, 4.14; N, 14.42; Cl, 5.91.

Scheme 336

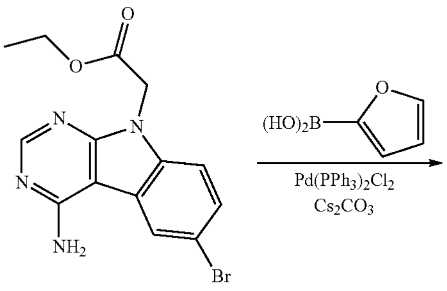

48a

-continued

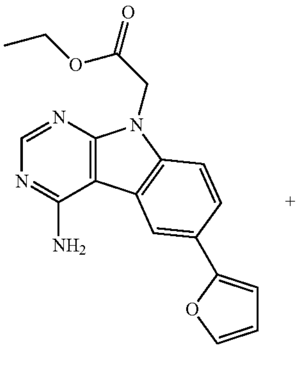

336a

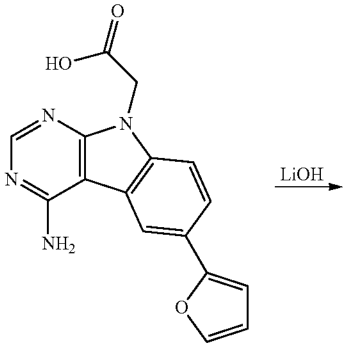

336b

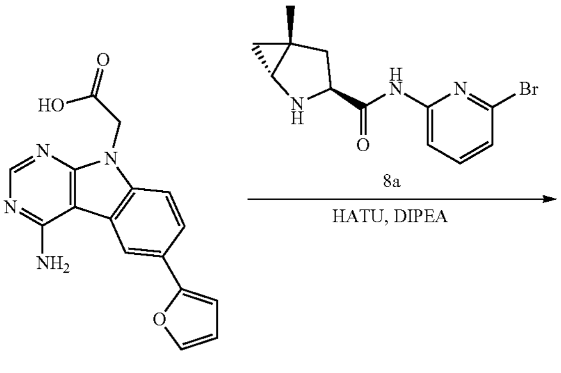

8a

336b

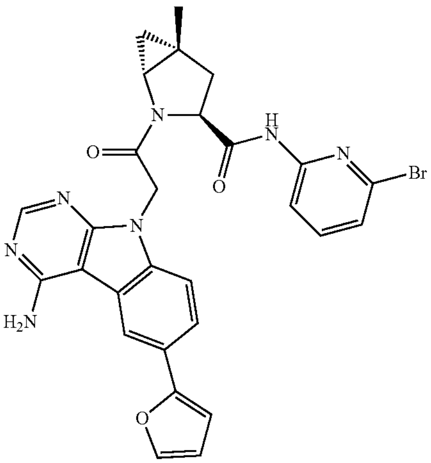

336c

Preparation of (1R,3S,5R)-2-(2-(4-amino-6-(furan-2-yl)-9H-pyrimido[4,5-b]indol-9-yl)acetyl)-N-(6-bromopyridin-2-yl)-5-methyl-2-azabicyclo[3.1.0]hexane-3-carboxamide (336c)

Step-1: Preparation of ethyl 2-(4-amino-6-(furan-2-yl)-9H-pyrimido[4,5-b]indol-9-yl)acetate (336a)

Compound 336a was prepared and purified according to the procedure reported in step-1 of scheme-62, from ethyl 2-(4-amino-6-bromo-9H-pyrimido[4,5-b]indol-9-yl)acetate (48a) (200 mg, 0.573 mmol) in dioxane (18 mL) using furan-2-ylboronic acid (96 mg, 0.859 mmol), cesium carbonate (280 mg, 0.859 mmol) in water (2.2 mL), $Pd(PPh_3)_2Cl_2$ (80 mg, 0.115 mmol) to give a mixture of ethyl 2-(4-amino-6-(furan-2-yl)-9H-pyrimido[4,5-b]indol-9-yl)acetate (336a) and 2-(4-amino-6-(furan-2-yl)-9H-pyrimido[4,5-b]indol-9-yl)acetic acid (336b) and this was used as such for the next step; MS (ES+): 309.10 & 337.20.

Step-2: Preparation of 2-(4-amino-6-(furan-2-yl)-9H-pyrimido[4,5-b]indol-9-yl)acetic acid (336b)

Compound 336b was prepared according to the procedure reported in step-4 of scheme-17, from a mixture of ethyl 2-(4-amino-6-(furan-2-yl)-9H-pyrimido[4,5-b]indol-9-yl) acetate (336a) and 2-(4-amino-6-(furan-2-yl)-9H-pyrimido [4,5-b]indol-9-yl)acetic acid (336b) from step-1 above (0.573 mmol) in THF (5 mL) and methanol (5 mL) using a solution of lithium hydroxide hydrate (147 mg, 3.44 mmol) in water (5 mL) and stirring at RT for 23 h. This gave after workup a dark brown solid (190 mg) which was used as such for the next step: MS (ES+): 309.10 (M+1)

Step-3: Preparation of (1R,3S,5R)-2-(2-(4-amino-6-(furan-2-yl)-9H-pyrimido[4,5-b]indol-9-yl)acetyl)-N-(6-bromopyridin-2-yl)-5-methyl-2-azabicyclo[3.1.0]hexane-3-carboxamide (336c)

Compound 336c was prepared according to the procedure reported in step-3 of scheme-1, from 2-(4-amino-6-(furan-2-yl)-9H-pyrimido[4,5-b]indol-9-yl)acetic acid (336b) (90 mg, 0.292 mmol) in DMF (10 mL) using HCl salt of (1R,3S,5R)—N-(6-bromopyridin-2-yl)-5-methyl-2-azabicyclo[3.1.0]hexane-3-carboxamide (8a) (97 mg, 0.292 mmol), HATU (222 mg, 0.584 mmol), DIPEA (0.203 mL, 1.168 mmol) and stirring at RT for 20 h. This gave after workup and purification as described in scheme-299, (1R,3S,5R)-2-(2-(4-amino-6-(furan-2-yl)-9H-pyrimido[4,5-b]indol-9-yl)acetyl)-N-(6-bromopyridin-2-yl)-5-methyl-2-azabicyclo[3.1.0]hexane-3-carboxamide (336c) (29 mg, 17% yield for three steps) HCl salt as a light brown solid. $^1H$ NMR (300 MHz, DMSO-$d_6$) δ 10.77 (s, 1H, $D_2O$ exchangeable), 8.83 (d, J=1.6 Hz, 1H), 8.67 (s, 2H, $D_2O$ exchangeable), 8.60 (s, 1H), 8.01 (d, J=8.2 Hz, 1H), 7.90 (dd, J=8.6, 1.5 Hz, 1H), 7.80-7.78 (m, 1H), 7.73 (d, J=8.5 Hz, 1H), 7.68 (d, J=8.0 Hz, 1H), 7.31 (d, J=7.7 Hz, 1H), 7.04 (d, J=3.4 Hz, 1H), 6.65 (dd, J=3.4, 1.8 Hz, 1H), 5.72 (d, J=17.3 Hz, 1H), 5.37 (d, J=17.3 Hz, 1H), 4.37 (dd, J=9.2, 5.8 Hz, 1H), 3.69 (dd, J=5.6, 2.3 Hz, 1H), 2.60-2.38 (m, 1H), 1.98 (dd, J=13.4, 5.9 Hz, 1H), 1.31 (s, 3H), 1.06-0.97 (m, 1H), 0.97-0.87 (m, 1H); MS (ES+): 586.10 & 588.20 (M+1); MS (ES−): 584.10 & 586.05 (M−1): Analysis calculated for $C_{28}H_{24}BrN_7O_3 \cdot 1.0HCl \cdot 2.25H_2O$: C, 50.69; H, 4.48; N, 14.78; Cl, 5.34. Found: C, 50.60; H, 4.34; N, 14.64; Cl, 5.09.

Scheme 337

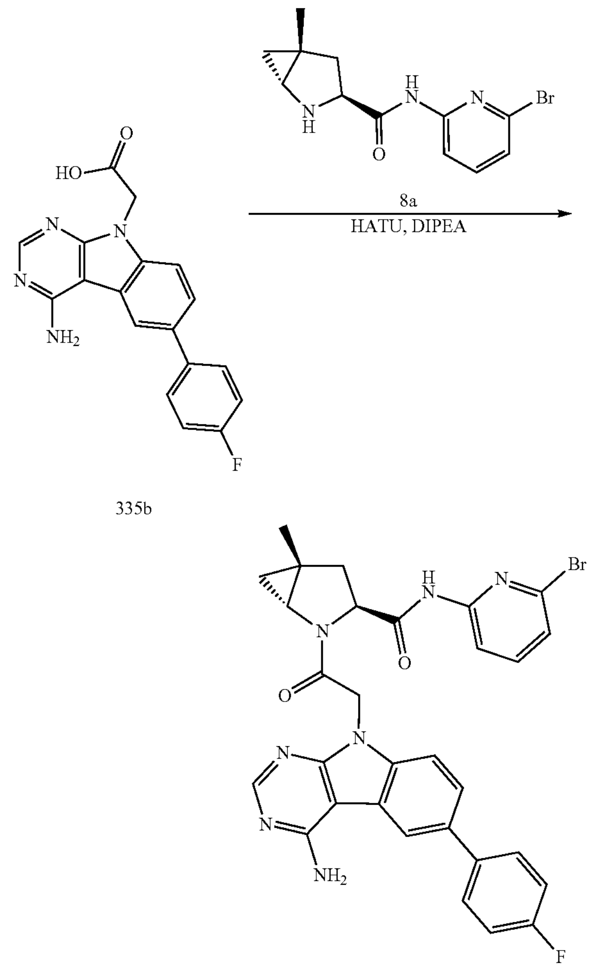

335b

337a

Preparation of (1R,3S,5R)-2-(2-(4-amino-6-(4-fluorophenyl)-9H-pyrimido[4,5-b]indol-9-yl)acetyl)-N-(6-bromopyridin-2-yl)-5-methyl-2-azabicyclo[3.1.0]hexane-3-carboxamide (337a)

Compound 337a was prepared according to the procedure reported in step-3 of scheme-1, from 2-(4-amino-6-(4-fluorophenyl)-9H-pyrimido[4,5-b]indol-9-yl)acetic acid (335b) (60 mg, 0.178 mmol) in DMF (10 mL) using HCl salt of (1R,3S,5R)—N-(6-bromopyridin-2-yl)-5-methyl-2-azabicyclo[3.1.0]hexane-3-carboxamide (8a) (71.2 mg, 0.214 mmol), HATU (136 mg, 0.357 mmol), DIPEA (0.124 mL, 0.714 mmol) and stirring at RT for 20 h. This gave after workup and purification as described in scheme-299, (1R,3S,5R)-2-(2-(4-amino-6-(4-fluorophenyl)-9H-pyrimido[4,5-b]indol-9-yl)acetyl)-N-(6-bromopyridin-2-yl)-5-methyl-2-azabicyclo[3.1.0]hexane-3-carboxamide (337a) (48 mg, 44% yield) HCl salt as a white solid; $^1$H NMR (300 MHz, DMSO-$d_6$) δ 10.78 (s, 1H, $D_2O$ exchangeable), 8.77 (d, J=1.7 Hz, 1H), 8.66 (s, 3H, $D_2O$ exchangeable), 8.61 (s, 1H), 8.01 (d, J=8.2 Hz, 1H), 7.92-7.82 (m, 3H), 7.76 (d, J=8.7 Hz, 1H), 7.69 (t, J=7.9 Hz, 1H), 7.39-7.29 (m, 3H), 5.75 (d, J=17.3 Hz, 1H), 5.40 (d, J=17.3 Hz, 1H), 4.37 (dd, J=9.1, 6.0 Hz, 1H), 3.71 (dd, J=5.6, 2.4 Hz, 1H), 2.63-2.37 (m, 1H), 1.99 (dd, J=13.1, 5.9 Hz, 1H), 1.31 (s, 3H), 1.07-0.98 (m, 1H), 0.98-0.89 (m, 1H); $^{19}$F NMR (282 MHz, DMSO-$d_6$) δ−116.03; MS (ES+): 614.10 & 616.15 (M+1); MS (ES−): 612.10 & 614.10 (M−1); Analysis calculated for $C_{30}H_{25}BrFN_7O_2 \cdot 1.1HCl \cdot 1.6H_2O$: C, 52.72; H, 4.32; N, 14.35; Cl, 5.71. Found: C, 52.79; H, 4.25; N, 14.28; Cl, 5.52.

Scheme 338

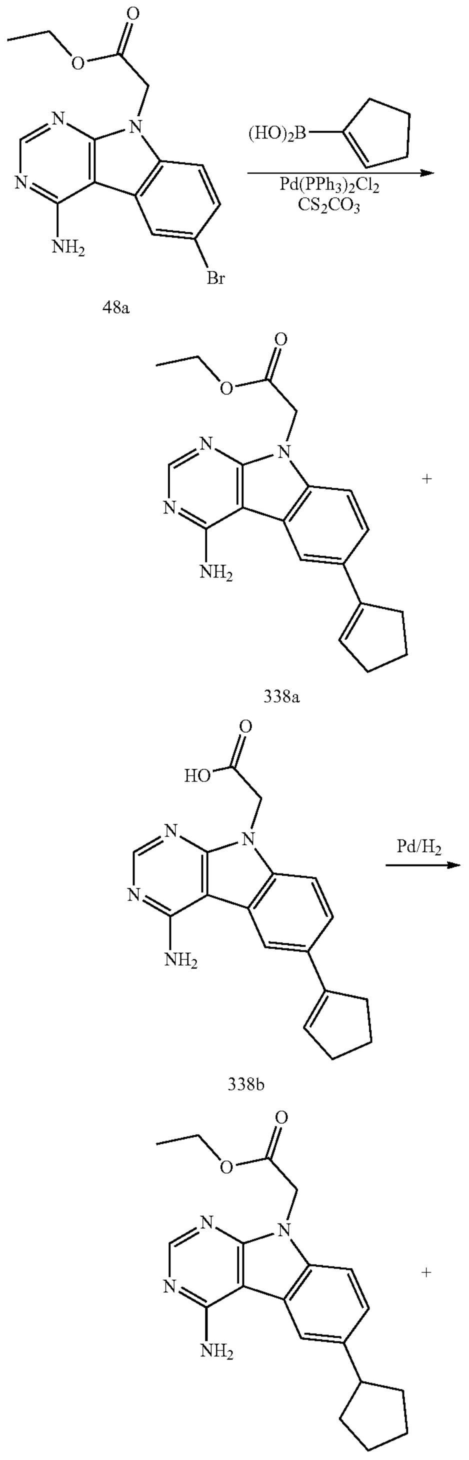

48a

338a

338b

338c

-continued

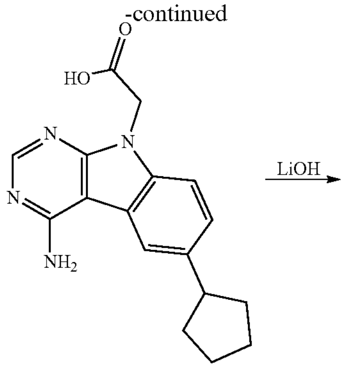

338d

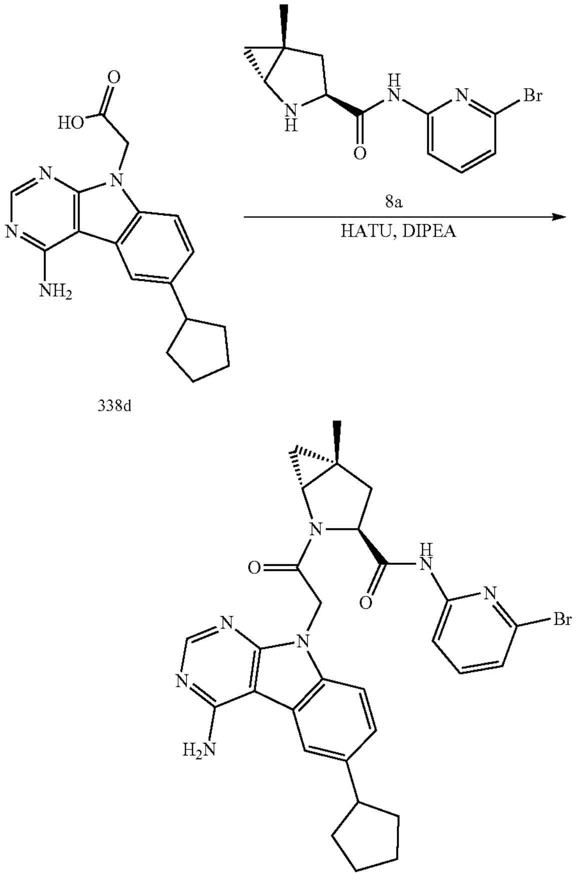

338d

8a

338e

Preparation of (1R,3S,5R)-2-(2-(4-amino-6-cyclopentyl-9H-pyrimido[4,5-b]indol-9-yl)acetyl)-N-(6-bromopyridin-2-yl)-5-methyl-2-azabicyclo[3.1.0]hexane-3-carboxamide (338e)

Step-1: Preparation of ethyl 2-(4-amino-6-(cyclopent-1-en-1-yl)-9H-pyrimido[4,5-b]indol-9-yl)acetate (338a) and 2-(4-amino-6-(cyclopent-1-en-1-yl)-9H-pyrimido[4,5-b]indol-9-yl)acetic acid (338b)

Compound 338a was prepared and purified according to the procedure reported in step-1 of scheme-62, from ethyl 2-(4-amino-6-bromo-9H-pyrimido[4,5-b]indol-9-yl)acetate (48a) (200 mg, 0.573 mmol) in dioxane (18 mL) using cyclopent-1-en-1-ylboronic acid (96 mg, 0.859 mmol), cesium carbonate (280 mg, 0.859 mmol) in water (2.2 mL), $Pd(PPh_3)_2Cl_2$ (80 mg, 0.115 mmol) to give a mixture of ethyl 2-(4-amino-6-(cyclopent-1-en-1-yl)-9H-pyrimido[4,5-b]indol-9-yl)acetate (338a) and 2-(4-amino-6-(cyclopent-1-en-1-yl)-9H-pyrimido[4,5-b]indol-9-yl)acetic acid (338b) which was used as such for the next step; MS (ES+): 309.10 & 337.20 (M+1).

Step-2: ethyl 2-(4-amino-6-cyclopentyl-9H-pyrimido[4,5-b]indol-9-yl)acetate (338c) and 2-(4-amino-6-cyclopentyl-9H-pyrimido[4,5-b]indol-9-yl) acetic acid (338d)

To a solution of mixture of ethyl 2-(4-amino-6-(cyclopent-1-en-1-yl)-9H-pyrimido[4,5-b]indol-9-yl)acetate (338a) and 2-(4-amino-6-(cyclopent-1-en-1-yl)-9H-pyrimido[4,5-b]indol-9-yl)acetic acid (338b) from step-1 above (0.097 g, 0.287 mmol) in ethyl acetate (5 mL), ethanol (5 mL) and MeOH (5 mL) was treated with palladium (0.046 g, 0.043 mmol) and hydrogenated for 29 h. Reaction mixture was filtered, washed with ethyl acetate/methanol (9:1), and concentrated to obtained residue containing mixture of Ethyl 2-(4-amino-6-cyclopentyl-9H-pyrimido[4,5-b]indol-9-yl) acetate (338c) and 2-(4-amino-6-cyclopentyl-9H-pyrimido [4,5-b]indol-9-yl)acetic acid (338d) (206 mg) which was used as such for next step; MS (ES+): 311.10 & 339.20 (M+1).

Step-3: Preparation of 2-(4-amino-6-cyclopentyl-9H-pyrimido[4,5-b]indol-9-yl)acetic acid (338d)

Compound 338d was prepared according to the procedure reported in step-4 of scheme-17, from mixture of Ethyl 2-(4-amino-6-cyclopentyl-9H-pyrimido[4,5-b]indol-9-yl) acetate (338c) and 2-(4-amino-6-cyclopentyl-9H-pyrimido [4,5-b]indol-9-yl)acetic acid (338d) (97 mg, 0.287 mmol) in THF (3 mL) and methanol (3 mL) using a solution of lithium hydroxide hydrate (73.7 mg, 1.722 mmol) in water (3 mL) and stirring at RT for 32 h. This gave after workup 2-(4-amino-6-cyclopentyl-9H-pyrimido[4,5-b]indol-9-yl)acetic acid (338d) as a gray solid (56 mg) which was used as such for the next step; MS (ES+): 311.20 (M+1).

Step-4: Preparation of (1R,3S,5R)-2-(2-(4-amino-6-cyclopentyl-9H-pyrimido[4,5-b]indol-9-yl)acetyl)-N-(6-bromopyridin-2-yl)-5-methyl-2-azabicyclo [3.1.0]hexane-3-carboxamide (338e)

Compound 338e was prepared according to the procedure reported in step-3 of scheme-1, from 2-(4-amino-6-cyclopentyl-9H-pyrimido[4,5-b]indol-9-yl)acetic acid (338d) (52 mg, 0.168 mmol) in DMF (8 mL) using HCl salt of (1R, 3S,5R)—N-(6-bromopyridin-2-yl)-5-methyl-2-azabicyclo [3.1.0]hexane-3-carboxamide (8a) (66.9 mg, 0.201 mmol), HATU (127 mg, 0.335 mmol), DIPEA (0.117 mL, 0.670 mmol) and stirring at RT for 19 h. This gave after workup as described in scheme-299, (1R,3S,5R)-2-(2-(4-amino-6-cyclopentyl-9H-pyrimido[4,5-b]indol-9-yl)acetyl)-N-(6-bromopyridin-2-yl)-5-methyl-2-azabicyclo[3.1.0]hexane-3-carboxamide (338e) (22 mg, 22% yield) HCl salt as a light brown solid; $^1H$ NMR (300 MHz, DMSO-$d_6$) δ 10.76 (s, 1H, $D_2O$ exchangeable), 8.61 (s, 3H, $D_2O$ exchangeable), 8.59 (s, 1H), 8.37 (s, 1H), 8.01 (d, J=8.2 Hz, 1H), 7.70 (t, J=8.0 Hz, 1H), 7.59 (d, J=8.5 Hz, 1H), 7.48-7.43 (m, 1H), 7.32 (d, J=7.7 Hz, 1H), 5.69 (d, J=17.3 Hz, 1H), 5.35 (d, J=17.3 Hz, 1H), 4.35 (dd, J=9.0, 6.0 Hz, 1H), 3.69 (dd, J=5.6, 2.4 Hz, 1H), 3.20-3.03 (m, 1H), 2.59-2.38 (m, 1H), 2.19-1.55 (m, 9H), 1.30 (s, 3H), 1.05-0.97 (m, 1H), 0.95-0.88 (m, 1H); MS (ES+): 588.20 & 590.20 (M+1); MS (ES−): 586.10 & 588.10 (M−1).

Scheme 339

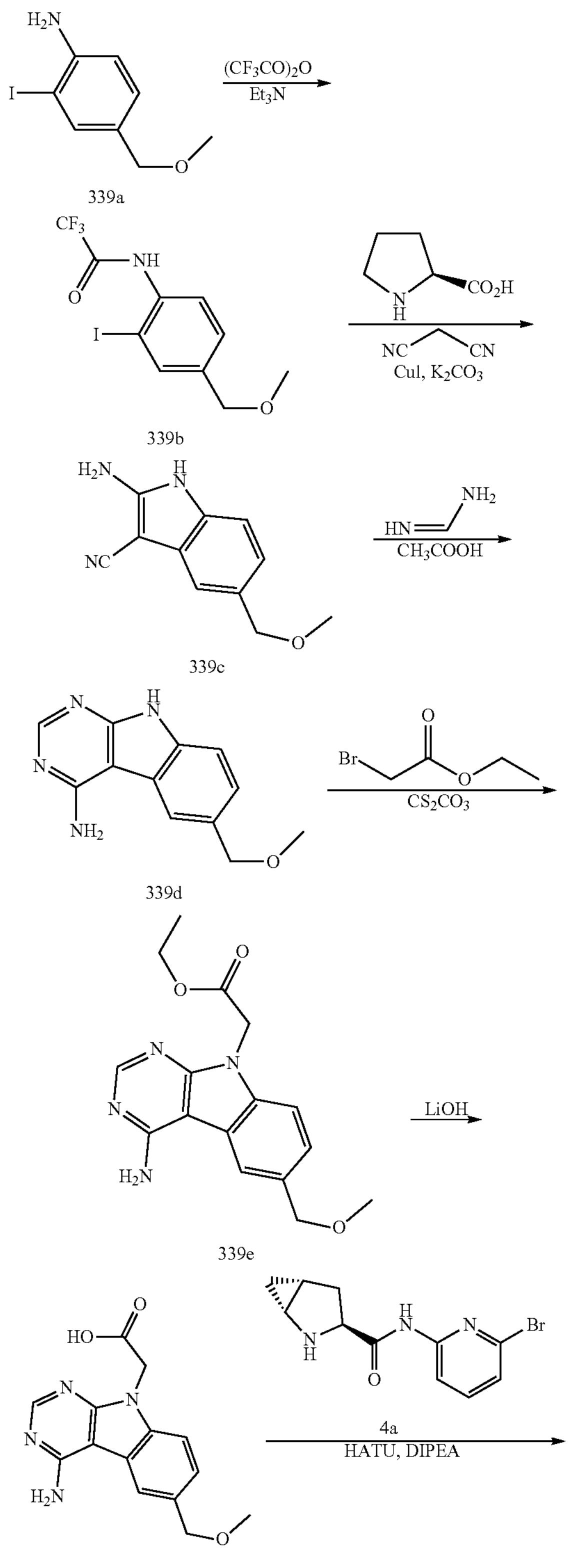

-continued

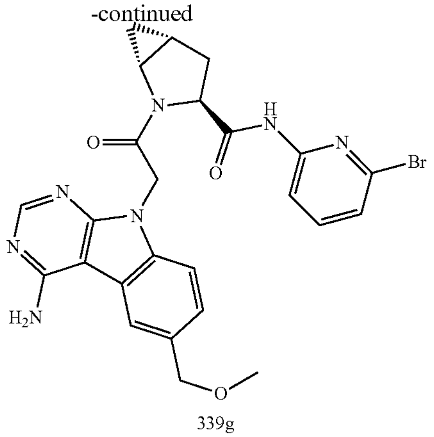

339g

Preparation of (1R,3S,5R)-2-(2-(4-amino-6-(methoxymethyl)-9H-pyrimido[4,5-b]indol-9-yl)acetyl)-N-(6-bromopyridin-2-yl)-2-azabicyclo[3.1.0]hexane-3-carboxamide (339 g)

Step-1: Preparation of 2,2,2-trifluoro-N-(2-iodo-4-(methoxymethyl)phenyl)acetamide (339b)

Compound 339b was prepared according to the procedure reported in step-1 of scheme-46, from 2-iodo-4-(methoxymethyl)aniline (339a)(6.538 g, 24.85 mmol; CAS #1697458-72-2) in DCM (40 mL) using triethylamine (8.66 mL, 62.1 mmol), trifluoroacetic acid anhydride (5.18 mL, 37.3 mmol) and stirring at RT for 20 h. This gave after workup 2,2,2-trifluoro-N-(2-iodo-4-(methoxymethyl)phenyl)acetamide (339b) (10.39 g) as a yellow solid and was used as such for next step; MS (ES−): 358.00 (M−1).

Step-2: Preparation of 2-amino-5-(methoxymethyl)-1H-indole-3-carbonitrile (339c)

Compound 339c was prepared according to the procedure reported in step-1 of scheme-11, from 2,2,2-trifluoro-N-(2-iodo-4-(methoxymethyl)phenyl)acetamide (339b) (8.92 g, 24.85 mmol) in DMSO (30 mL) using malononitrile (1.970 g, 29.8 mmol), L-proline (0.572 g, 4.97 mmol), CuI (0.473 g, 2.485 mmol), and $K_2CO_3$ (6.87 g, 49.7 mmol) in water (30 mL) to afford after workup and purification as described in step-1 of scheme-328, 2-amino-5-(methoxymethyl)-1H-indole-3-carbonitrile (339c) (2.68 g, 54% yield) as a yellow solid; $^1H$ NMR (300 MHz, DMSO-$d_6$) δ 10.69 (s, 1H), 7.11-7.04 (m, 2H), 6.88-6.82 (m, 1H), 6.75 (s, 2H), 4.38 (s, 2H), 3.24 (s, 3H); MS (ES+): 202.10 (M+1).

Step-3: Preparation of 6-(methoxymethyl)-9H-pyrimido[4,5-b]indol-4-amine (339d)

Compound 339d was prepared according to the procedure reported in step-2 of scheme-29, from 2-amino-5-(methoxymethyl)-1H-indole-3-carbonitrile (339c)(2.55 g, 12.67 mmol) in ethanol (60 mL) using formamidine acetate (10.66 g, 101 mmol) and refluxing for 19 h. This gave after workup 6-(methoxymethyl)-9H-pyrimido[4,5-b]indol-4-amine (339d) (910 mg) as a light brown solid which was used as such for the next step; $^1H$ NMR (300 MHz, DMSO-$d_6$) δ 11.81 (s, 1H), 8.27 (s, 1H), 8.23 (s, 1H), 7.40

(d, J=8.2 Hz, 1H), 7.32 (dd, J=8.2, 1.5 Hz, 1H), 7.14 (s, 2H), 4.51 (s, 2H), 3.29 (s, 3H); MS (ES+): 229.10 (M+1).

Step-4: Preparation of ethyl 2-(4-amino-6-(methoxymethyl)-9H-pyrimido[4,5-b]indol-9-yl) acetate (339e)

Compound 339e was prepared according to the procedure reported in step-1 of scheme-1, from 6-(methoxymethyl)-9H-pyrimido[4,5-b]indol-4-amine (339d) (850 mg, 3.72 mmol) in DMF (20 mL) using ethyl 2-bromoacetate (0.454 mL, 4.10 mmol), $Cs_2CO_3$ (3033 mg, 9.31 mmol) and stirring at RT for 26 h. This gave after workup ethyl 2-(4-amino-6-(methoxymethyl)-9H-pyrimido[4,5-b]indol-9-yl)acetate (339e) (780 mg) as a light-yellow solid; $^1$H NMR (300 MHz, DMSO-$d_6$) δ 8.35-8.32 (m, 1H), 8.28 (s, 1H), 7.56 (d, J=8.3 Hz, 1H), 7.38 (dd, J=8.4, 1.5 Hz, 1H), 7.30 (s, 2H), 5.23 (s, 2H), 4.53 (s, 2H), 4.14 (q, J=7.1 Hz, 2H), 3.30 (s, 3H), 1.20 (t. J=7.1 Hz, 3H); MS (ES+): 315.15 (M+1).

Step-5: Preparation of 2-(4-amino-6-(methoxymethyl)-9H-pyrimido[4,5-b]indol-9-yl)acetic acid (339f)

Compound 339f was prepared according to the procedure reported in step-4 of scheme-17, from ethyl 2-(4-amino-6-(methoxymethyl)-9H-pyrimido[4,5-b]indol-9-yl)acetate (339e) (600 mg, 1.909 mmol) in THF (8 mL) and methanol (8 mL) using a solution of lithium hydroxide hydrate (490 mg, 11.45 mmol) in water (8 mL) and stirring at RT for 19 h. This gave after workup 2-(4-amino-6-(methoxymethyl)-9H-pyrimido[4,5-b]indol-9-yl)acetic acid (339f) (1.205 g) as a white solid which was used as such for next step; MS (ES+): 287.10 (M+1).

Step-6: Preparation of (1R,3S,5R)-2-(2-(4-amino-6-(methoxymethyl)-9H-pyrimido[4,5-b]indol-9-yl) acetyl)-N-(6-bromopyridin-2-yl)-2-azabicyclo[3.1.0] hexane-3-carboxamide (339 g)

Compound 339g was prepared according to the procedure reported in step-3 of scheme-1, from 2-(4-amino-6-(methoxymethyl)-9H-pyrimido[4,5-b]indol-9-yl)acetic acid (339f) (0.23 mmol) in DMF (10 mL) using HCl salt of (1R,3S,5R)—N-(6-bromopyridin-2-yl)-2-azabicyclo[3.1.0] hexane-3-carboxamide (4a) (0.088 g, 0.276 mmol), HATU (0.175 g, 0.460 mmol), DIPEA (0.160 mL, 0.92 mmol) and stirring at RT overnight. This gave after workup and purification as described in scheme-299, (1R,3S,5R)-2-(2-(4-amino-6-(methoxymethyl)-9H-pyrimido[4,5-b]indol-9-yl) acetyl)-N-(6-bromopyridin-2-yl)-2-azabicyclo[3.1.0] hexane-3-carboxamide (339 g) (83 mg, 66% yield) HCl salt as a white solid; 1H NMR (300 MHz, DMSO-$d_6$) δ 10.76 (s, 1H, $D_2O$ exchangeable), 8.75 (s, 2H, $D_2O$ exchangeable), 8.64 (s, 1H), 8.52 (s, 1H), 8.00 (d, J=8.2 Hz, 1H), 7.80-7.63 (m, 2H), 7.54 (d, J=8.4 Hz, 1H), 7.31 (d, J=7.7 Hz, 1H), 5.77 (d, J=17.4 Hz, 1H), 5.42 (d, J=17.3 Hz, 1H), 4.56 (s, 2H), 4.47-4.35 (m, 1H), 3.98-3.83 (m, 1H), 3.32 (s, 3H), 2.40-2.10 (m, 2H), 1.99-1.82 (m, 1H), 1.19-0.96 (m, 1H), 0.89-0.65 (m, 1H); MS (ES+): 550.10 & 552.15 (M+1); MS (ES−): 548.10 & 550.10 (M−1); Analysis calculated for $C_{25}H_{24}BrN_7O_3·1.15HCl·1.0H_2O$: C, 49.20; H, 4.48; N, 16.06; Cl, 6.68. Found: C, 49.30; H, 4.44; N, 15.99; Cl, 6.56.

Scheme 340

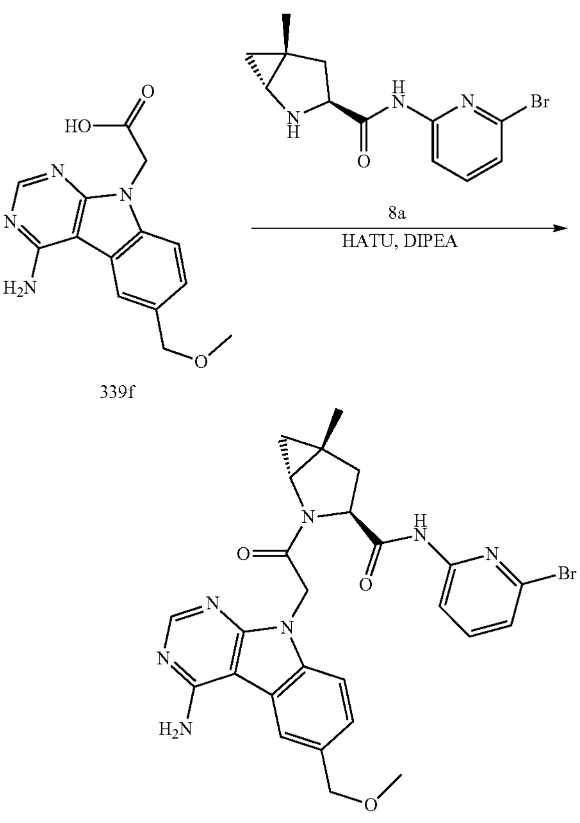

Preparation of (1R,3S,5R)-2-(2-(4-amino-6-(methoxymethyl)-9H-pyrimido[4,5-b]indol-9-yl) acetyl)-N-(6-bromopyridin-2-yl)-5-methyl-2-azabicyclo[3.1.0]hexane-3-carboxamide (340a)

Compound 340a was prepared according to the procedure reported in step-3 of scheme-1, from 2-(4-amino-6-(methoxymethyl)-9H-pyrimido[4,5-b]indol-9-yl)acetic acid (339f) (0.23 mmol) in DMF (10 mL) using HCl salt of (1R,3S,5R)—N-(6-bromopyridin-2-yl)-5-methyl-2-azabicyclo[3.1.0]hexane-3-carboxamide (8a) (92 mg, 0.276 mmol), HATU (175 mg, 0.460 mmol), DIPEA (0.160 mL, 0.920 mmol) and stirring at RT overnight. This gave after workup and purification as described in scheme-299, (1R,3S,5R)-2-(2-(4-amino-6-(methoxymethyl)-9H-pyrimido[4,5-b]indol-9-yl)acetyl)-N-(6-bromopyridin-2-yl)-5-methyl-2-azabicyclo[3.1.0]hexane-3-carboxamide (340a) (80 mg, 62% yield) HCl salt as a white solid: $^1$H NMR (300 MHz, DMSO-$d_6$) δ 10.77 (s, 1H, $D_2O$ exchangeable), 8.69 (s, 2H, $D_2O$ exchangeable), 8.62 (s, 1H), 8.50 (s, 1H), 8.00 (d, J=8.2 Hz, 1H), 7.75-7.64 (m, 2H), 7.53 (dd, J=8.5, 1.5 Hz, 1H), 7.31 (d, J=7.7 Hz, 1H), 5.72 (d, J=17.4 Hz, 1H), 5.37 (d, J=17.3 Hz, 1H), 4.56 (s, 2H), 4.37 (dd, J=9.1, 6.0 Hz, 1H), 3.69 (dd, J=5.5, 2.4 Hz, 1H), 3.31 (s, 3H), 2.55-2.41 (m, 1H), 1.98 (dd, J=13.2, 5.9 Hz, 1H), 1.30 (s, 3H), 1.01 (t, J=5.5 Hz, 1H), 0.93 (dd, J=5.4, 2.4 Hz, 1H); MS (ES+): 564.10 & 566.10 (M+1); MS (ES−): 562.10 & 564.10 (M−1): Analysis calculated for $C_{26}H_{26}BrN_7O_3·1.0HCl·1.5H_2O$: C, 49.73; H, 4.82: N, 15.61; Cl, 5.65. Found: C, 49.79; H, 4.86; N, 15.71; Cl, 5.38.

Scheme 341

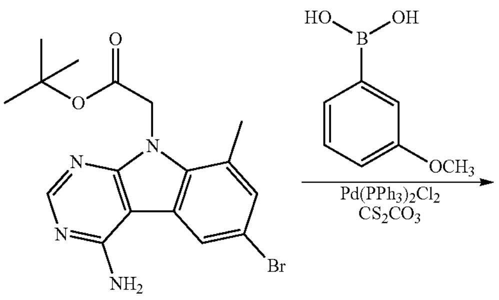

192e

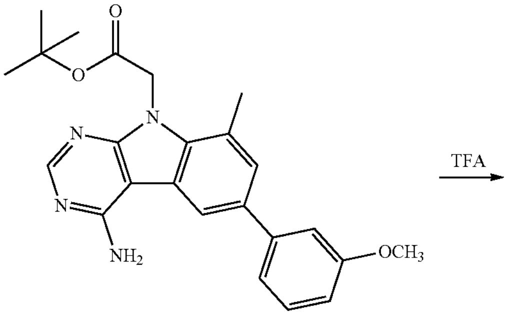

341a

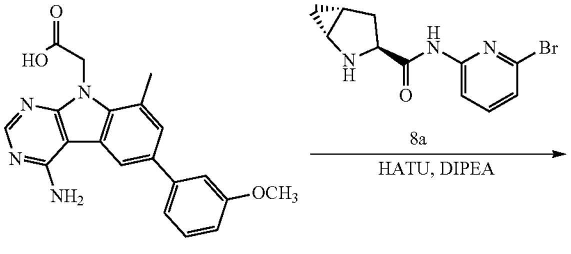

341b

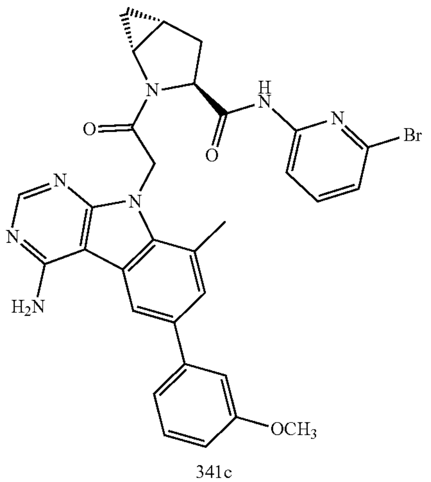

341c

Preparation of (1R,3S,5R)-2-(2-(4-amino-6-(3-methoxyphenyl)-8-methyl-9H-pyrimido[4,5-b]indol-9-yl)acetyl)-N-(6-bromopyridin-2-yl)-2-azabicyclo[3.1.0]hexane-3-carboxamide (341c)

Step-1: Preparation of tert-butyl 2-(4-amino-6-(3-methoxyphenyl)-8-methyl-9H-pyrimido[4,5-b]indol-9-yl)acetate (341a)

Compound 341a was prepared and purified according to the procedure reported in step-1 of scheme-62, from tert-butyl 2-(4-amino-6-bromo-8-methyl-9H-pyrimido[4,5-b]indol-9-yl)acetate (192e) (200 mg, 0.511 mmol) in dioxane (18 mL) using (3-methoxyphenyl)boronic acid (117 mg, 0.767 mmol), cesium carbonate (250 mg, 0.767 mmol) in water (2.2 mL), $Pd(PPh_3)_2Cl_2$ (71.8 mg, 0.102 mmol) to afford tert-butyl 2-(4-amino-6-(3-methoxyphenyl)-8-methyl-9H-pyrimido[4,5-b]indol-9-yl)acetate (341a) (110 mg, 51% yield) as a white solid; MS (ES+): 419.20 (M+1).

Step-2: Preparation of 2-(4-amino-6-(3-methoxyphenyl)-8-methyl-9H-pyrimido[4,5-b]indol-9-yl) acetic acid (341b)

Compound 341b was prepared according to the procedure reported in step-2 of scheme-1, from tert-butyl 2-(4-amino-6-(3-methoxyphenyl)-8-methyl-9H-pyrimido[4,5-b]indol-9-yl)acetate (341a) (105 mg, 0.251 mmol) in DCM (10 mL) using TFA (0.483 mL, 6.27 mmol) and stirring at RT for 27 h. This gave after workup 2-(4-amino-6-(3-methoxyphenyl)-8-methyl-9H-pyrimido[4,5-b]indol-9-yl)acetic acid (341b) and was used as such for the next step; MS (ES+): 363.10 (M+1).

Step-3: Preparation of (1R,3S,5R)-2-(2-(4-amino-6-(3-methoxyphenyl)-8-methyl-9H-pyrimido[4,5-b]indol-9-yl)acetyl)-N-(6-bromopyridin-2-yl)-2-azabicyclo[3.1.0]hexane-3-carboxamide (341c)

Compound 341c was prepared according to the procedure reported in step-3 of scheme-1, from 2-(4-amino-6-(3-methoxyphenyl)-8-methyl-9H-pyrimido[4,5-b]indol-9-yl) acetic acid (341b) (0.125 mmol) in DMF (8 mL) using HCl salt of (1R,3S,5R)—N-(6-bromopyridin-2-yl)-2-azabicyclo[3.1.0]hexane-3-carboxamide (4a) (0.048 g, 0.150 mmol), HATU (0.095 g, 0.250 mmol), DIPEA (0.109 mL, 0.625 mmol) and stirring at RT for 22 h. This gave after workup and purification as described in scheme-299, (1R,3S,5R)-2-(2-(4-amino-6-(3-methoxyphenyl)-8-methyl-9H-pyrimido[4,5-b]indol-9-yl)acetyl)-N-(6-bromopyridin-2-yl)-2-azabicyclo[3.1.0]hexane-3-carboxamide (341c) (26 mg, 33% yield) HCl salt as a white solid; $^1H$ NMR (300 MHz, DMSO-$d_6$) δ 10.83 (s, 1H, $D_2O$ exchangeable), 8.69 (s, 2H, $D_2O$ exchangeable), 8.62 (s, 1H), 8.59-8.56 (m, 1H), 8.01 (d, J=8.2 Hz, 1H), 7.71 (t, J=8.0 Hz, 1H), 7.64 (s, 1H), 7.45-7.35 (m, 3H), 7.31 (d, J=7.7 Hz, 1H), 7.01-6.90 (m, 1H), 5.94 (d, J=18.0 Hz, 1H), 5.66 (d, J=17.9 Hz, 1H), 4.43 (dd, J=9.0, 5.7 Hz, 1H), 3.98-3.89 (m, 1H), 3.85 (s, 3H), 2.77 (s, 3H), 2.45-2.29 (m, 1H), 2.28-2.14 (m, 1H), 2.01-1.86 (m, 1H), 1.15-1.03 (m, 1H), 0.78-0.56 (m, 1H); MS (ES+): 626.10 & 628.20 (M+1); MS (ES−): 624.10 & 626.10 (M−1); Analysis calculated for $C_{31}H_{28}BrN_7O_3 \cdot 1.0HCl \cdot 2.0H_2O$: C, 53.27; H, 4.76; N, 14.03. Found: C, 53.14; H, 4.60; N, 13.87.

Scheme 342

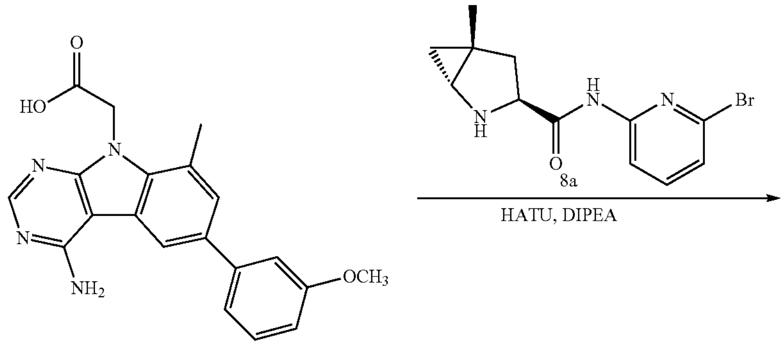

341b

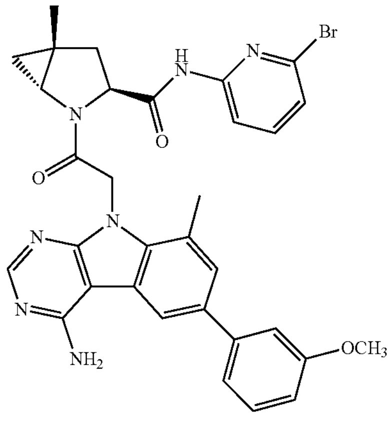

342a

Preparation of (1R,3S,5R)-2-(2-(4-amino-6-(3-methoxyphenyl)-8-methyl-9H-pyrimido[4,5-b]indol-9-yl)acetyl)-N-(6-bromopyridin-2-yl)-5-methyl-2-azabicyclo[3.1.0]hexane-3-carboxamide (342a)

Compound 342a was prepared according to the procedure reported in step-3 of scheme-1, from 2-(4-amino-6-(3-methoxyphenyl)-8-methyl-9H-pyrimido[4,5-b]indol-9-yl) acetic acid (341b) (0.125 mmol) in DMF (8 mL) using HCl salt of (1R,3S,5R)—N-(6-bromopyridin-2-yl)-5-methyl-2-azabicyclo[3.1.0]hexane-3-carboxamide (8a) (49.9 mg, 0.150 mmol), HATU (95 mg, 0.250 mmol), DIPEA (0.109 mL, 0.625 mmol) and stirring at RT for 22 h. This gave after workup and purification as described in scheme-299, (1R, 3S,5R)-2-(2-(4-amino-6-(3-methoxyphenyl)-8-methyl-9H-pyrimido[4,5-b]indol-9-yl)acetyl)-N-(6-bromopyridin-2-yl)-5-methyl-2-azabicyclo[3.1.0]hexane-3-carboxamide (342a) (27 mg, 34% yield) HCl salt as a white solid; 1H NMR (300 MHz, DMSO-$d_6$) δ 10.82 (s, 1H, $D_2O$ exchangeable), 8.57 (s, 1H), 8.56-8.48 (m, 4H, 3H $D_2O$ exchangeable), 8.01 (d, J=8.2 Hz, 1H), 7.70 (t. J=8.0 Hz, 1H), 7.61 (s, 1H), 7.43-7.35 (m, 3H), 7.31 (d, J=7.7 Hz, 1H), 7.01-6.89 (m, 1H), 5.88 (d, J=17.9 Hz, 1H), 5.61 (d, J=17.8 Hz, 1H), 4.39 (dd, J=8.9, 6.2 Hz, 1H), 3.85 (s, 3H), 3.74-3.68 (m, 1H), 2.74 (s, 3H), 2.58-2.42 (m, 1H), 1.98 (dd, J=13.2, 6.1 Hz, 1H), 1.31 (s, 3H), 1.02 (t, J=5.4 Hz, 1H), 0.87-0.82 (m, 1H); MS (ES+): 640.20 & 642.15 (M+1); MS (ES−): 638.10 & 640.10 (M−1); Analysis calculated for $C_{32}H_{30}BrN_7O_3 \cdot 1.0HCl \cdot 1.75H_2O$: C, 54.25; H, 4.91; N, 13.84. Found: C, 54.21; H, 4.81; N, 13.72.

Scheme 343

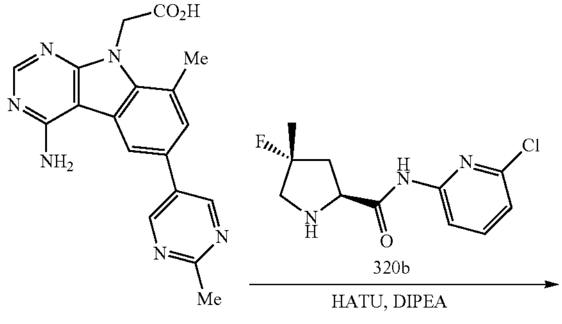

308b

-continued

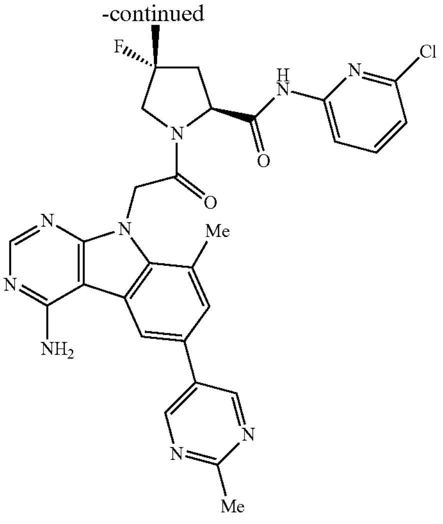

343a

Scheme 344

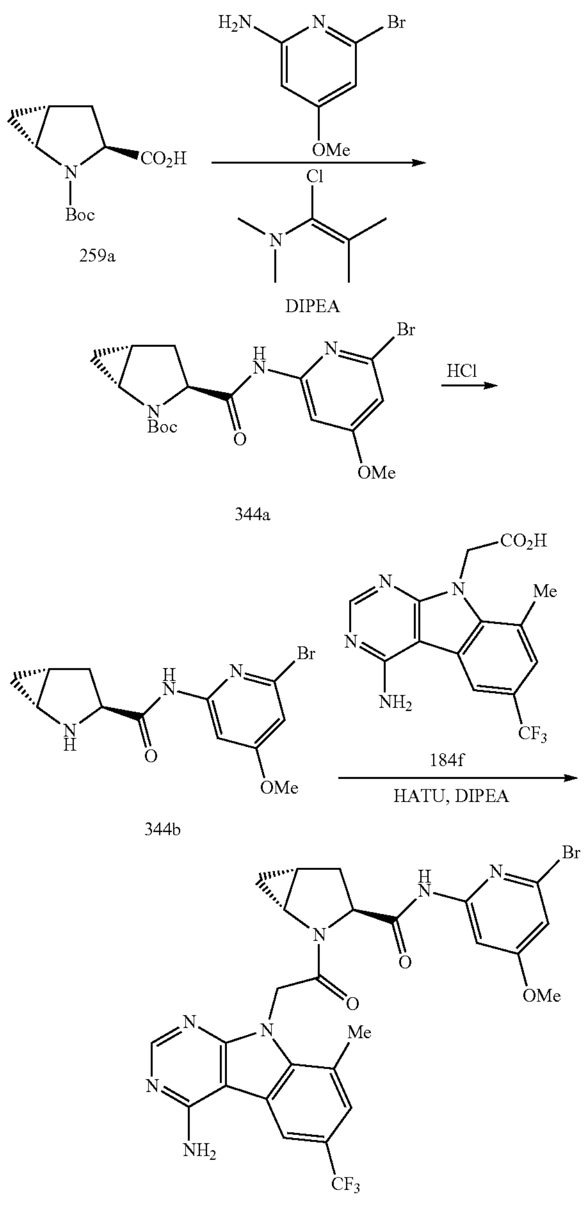

259a

344a

344b

344c

Preparation of (2S,4R)-1-(2-(4-amino-8-methyl-6-(2-methylpyrimidin-5-yl)-9H-pyrimido[4,5-b]indol-9-yl)acetyl)-N-(6-chloropyridin-2-yl)-4-fluoro-4-methylpyrrolidine-2-carboxamide (343a)

Compound 343a was prepared according to the procedure reported in step-3 of scheme-1, from TFA salt of 2-(4-amino-8-methyl-6-(2-methylpyrimidin-5-yl)-9H-pyrimido[4,5-b]indol-9-yl)acetic acid (308b) (75 mg, 0.162 mmol) in DMF (5 mL) using TFA salt of (2S,4R)—N-(6-chloropyridin-2-yl)-4-fluoro-4-methylpyrrolidine-2-carboxamide (320b) (60.3 mg, 0.162 mmol), HATU (74.0 mg, 0.195 mmol), DIPEA (105 mg, 0.811 mmol) and stirring at RT for 16 h. This gave after workup and purification as described in scheme-299, (2S,4R)-1-(2-(4-amino-8-methyl-6-(2-methylpyrimidin-5-yl)-9H-pyrimido[4,5-b]indol-9-yl)acetyl)-N-(6-chloropyridin-2-yl)-4-fluoro-4-methylpyrrolidine-2-carboxamide (343a) (43 mg, 45% yield) HCl salt as a white solid; $^{1}H$ NMR (300 MHz, DMSO-$d_6$) δ (a mixture of two rotamers) 11.37 and 11.01 (2s, 1H, $D_2O$ exchangeable), 9.24 and 9.23 (2s, 2H), 9.04 (bs, 2H, $D_2O$ exchangeable), 8.80 and 8.77 (2s, 1H), 8.68 (s, 1H), 7.97 (d, J=8.2 Hz, 1H), 7.87-7.75 (m, 2H), 7.18 (d, J=7.7 Hz, 1H), 5.77 (d, J=18.0 Hz, 1H), 5.56 (d, J=17.7 Hz, 11H), 4.70 (dd, J=9.7, 7.5 Hz, 1H), 4.37-4.22 (m, 1H), 3.98-3.93 (m, 1H), 2.77 (s, 3H), 2.70 (s, 3H), 2.65-2.56 (m, 1H), 2.22-1.97 (m, 1H), 1.64 (d, J=21.1 Hz, 3H); $^{19}F$ NMR (282 MHz, DMSO-$d_6$) δ−139.90; MS (ES+): 588/590 (M+1): (ES−): 586/588 (M−1); Analysis calculated for $C_{29}H_{22}ClFN_9O_2 \cdot 1.35HCl.3.25H_2O$: C, 50.06; H, 5.05; Cl, 11.97; N, 18.12. Found: C, 50.03; H, 4.93; Cl, 12.07; N, 17.91.

Preparation of (1R,3S,5R)-2-(2-(4-amino-8-methyl-6-(trifluoromethyl)-9H-pyrimido[4,5-b]indol-9-yl)acetyl)-N-(6-bromo-4-methoxypyridin-2-yl)-2-azabicyclo[3.1.0]hexane-3-carboxamide (344c)

Step-1: Preparation of (1R,3S,5R)-tert-butyl 3-((6-bromo-4-methoxypyridin-2-yl)carbamoyl)-2-azabicyclo[3.1.0]hexane-2-carboxylate (344a)

An aliquot of 1-chloro-N,N,2-trimethylprop-1-en-1-amine (0.090 mL, 0.677 mmol) was added drop wise to a solution of (1R,3S,5R)-2-(tert-butoxycarbonyl)-2-azabicyclo[3.1.0]hexane-3-carboxylic acid (259a) (140 mg, 0.616 mmol) in DCM (10 mL) at 0° C., and the mixture was stirred at 0° C. for 1 h, followed by addition of 6-bromo-4- methoxypyridin-2-amine (125 mg, 0.616 mmol), DIPEA (159 mg, 1.231 mmol) and stirring at RT for 16 h. The reaction mixture was diluted with DCM (15 mL), washed with $H_2O$ (20 mL×2), brine (20 mL) dried, filtered, concentrated and the residue obtained was purified using flash column chromatography [$SiO_2$ gel, eluting with EtOAc in hexane from 0-20%] to provide (1R,3S,5R)-tert-butyl 3-((6-bromo-4-methoxypyridin-2-yl)carbamoyl)-2-azabicyclo[3.1.0]hexane-2-carboxylate (344a) (155 mg, 61% yield) as a pale-yellow solid; $^1$H NMR (300 MHz, DMSO-$d_6$) δ 10.74 (s, 1H), 7.69 (s, 1H), 6.99 (d, J=2.0 Hz, 1H), 4.26-4.01 (m, 1H), 3.85 (s, 3H), 3.47-3.35 (m, 1H), 2.37-2.18 (m, 1H), 2.18-2.01 (m, 1H), 1.68-1.49 (m, 1H), 1.33 (d, J=46.4 Hz, 9H), 0.83-0.65 (m, 1H), 0.47-0.31 (m, 1H); MS (ES+): 412/414 (M+1); (ES−): 410/412 (M−1).

Step-2: Preparation of (1R,3S,5R)—N-(6-bromo-4-methoxypyridin-2-yl)-2-azabicyclo[3.1.0]hexane-3-carboxamide (344b)

A mixture of (1R,3S,5R)-tert-butyl 3-((6-bromo-4-methoxypyridin-2-yl)carbamoyl)-2-azabicyclo[3.1.0]hexane-2-carboxylate (344a) (155 mg, 0.376 mmol), 4 M HCl in dioxane (0.94 mL, 3.76 mmol) were suspended in DCM (5 mL), stirred at RT for 16 h and concentrated in vacuum to dryness. The residue was triturated with ether and the solid obtained was collected by filtration to provide the HCl salt of (1R,3S,5R)—N-(6-bromo-4-methoxypyridin-2-yl)-2-azabicyclo[3.1.0]hexane-3-carboxamide (344b) (130 mg, 99% yield) as a white solid; $^1$H NMR (300 MHz, DMSO-$d_6$) δ 11.32 (s, 1H), 10.51 (bs. J=6.9 Hz, 1H), 9.18 (bs, 1H), 7.60 (d, J=2.0 Hz, 1H), 7.09 (d, J=2.0 Hz, 1H), 4.29-4.04 (m, 1H), 3.87 (s, 3H), 3.39-3.25 (m, 1H), 2.69-2.54 (m, 1H), 2.16-1.96 (m, 1H), 1.90-1.73 (m, 1H), 0.95-0.65 (m, 2H); MS (ES+): 312/314 (M+1); (ES−): 310/312 (M−1).

Step-3: Preparation of (1R,3S,5R)-2-(2-(4-amino-8-methyl-6-(trifluoromethyl)-9H-pyrimido[4,5-b]indol-9-yl)acetyl)-N-(6-bromo-4-methoxypyridin-2-yl)-2-azabicyclo[3.1.0]hexane-3-carboxamide (344c)

Compound 344c was prepared according to the procedure reported in step-3 of scheme-1, from HCl salt of (1R,3S,5R)—N-(6-bromo-4-methoxypyridin-2-yl)-2-azabicyclo[3.1.0]hexane-3-carboxamide (344b) (59.7 mg, 0.171 mmol) in DMF (5 mL) using HCl salt of 2-(4-amino-8-methyl-6-(trifluoromethyl)-9H-pyrimido[4,5-b]indol-9-yl)acetic acid (184f) (75 mg, 0.171 mmol), HATU (98 mg, 0.257 mmol), DIPEA (111 mg, 0.856 mmol) and stirring at RT for 16 h. This gave after workup and purification as described in scheme-299, (1R,3S,5R)-2-(2-(4-amino-8-methyl-6-(trifluoromethyl)-9H-pyrimido[4,5-b]indol-9-yl)acetyl)-N-(6-bromo-4-methoxypyridin-2-yl)-2-azabicyclo[3.1.0]hexane-3-carboxamide (344c) (27 mg, 34% yield) HCl salt as a white solid; $^1$H NMR (300 MHz, DMSO-$d_6$) δ 10.77 (s, 1H, $D_2O$ exchangeable), 9.03 (bs, 2H, $D_2O$ exchangeable), 8.83 (s, 1H), 8.72 (s, 1H), 7.64 (d, J=1.7 Hz, 1H), 7.60 (d, J=2.0 Hz, 1H), 6.95 (d, J=2.0 Hz, 1H), 5.98 (d, J=18.1 Hz, 1H), 5.69 (d, J=18.0 Hz, 1H), 4.49-4.37 (m, 1H), 3.96-3.90 (m, 1H), 3.82 (s, 3H), 2.78 (s, 3H), 2.41-2.27 (m, 1H), 2.26-2.13 (m, 1H), 2.02-1.83 (m, 1H), 1.15-1.01 (m, 1H), 0.78-0.59 (m, 1H); F NMR (282 MHz, DMSO-$d_6$) δ−58.86; MS (ES+): 618/620 (M+1); (ES−): 616/618 (M−1); Analysis calculated for $C_{26}H_{23}BrF_3N_7O_3$·1.1HCl·1.75$H_2O$: C, 45.26; H, 4.03; Cl, 5.65; N, 14.21. Found: C, 45.34; H, 3.95; Cl, 5.74; N, 14.16.

Scheme 345

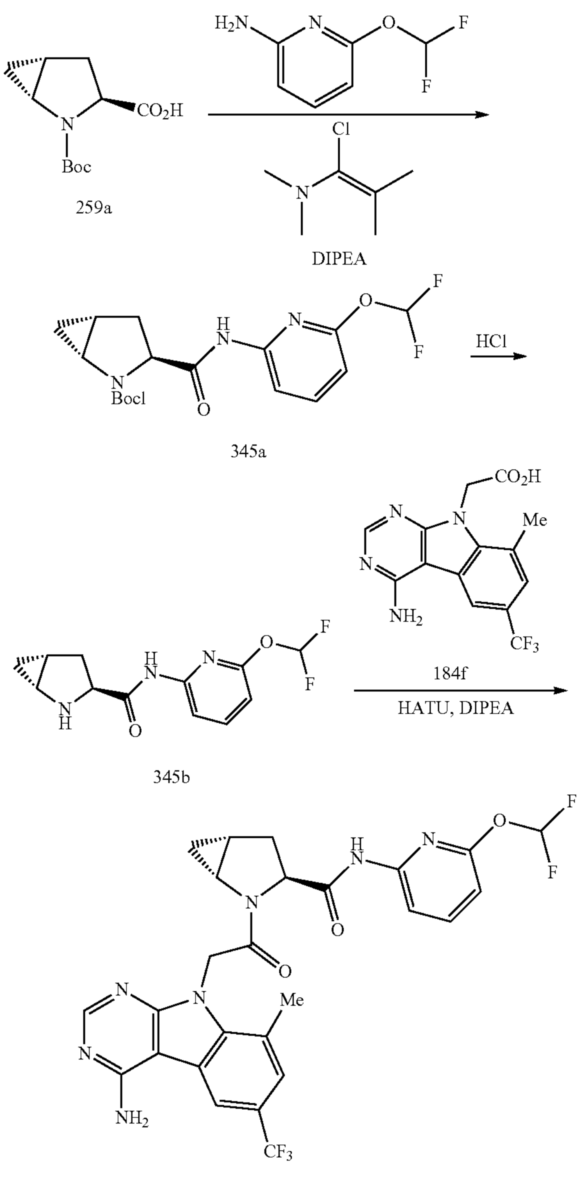

259a
345a
345b
345c

Preparation of (1R,3S,5R)-2-(2-(4-amino-8-methyl-6-(trifluoromethyl)-9H-pyrimido[4,5-b]indol-9-yl)acetyl)-N-(6-(difluoromethoxy)pyridin-2-yl)-2-azabicyclo[3.1.0]hexane-3-carboxamide (345c)

Step-1: Preparation of (1R,3S,5R)-tert-butyl 3-((6-(difluoromethoxy)pyridin-2-yl)carbamoyl)-2-azabicyclo[3.1.0]hexane-2-carboxylate (345a)

Compound 345a was prepared and purified according to the procedure reported in step-1 of scheme-344, from (1R,3S,5R)-2-(tert-butoxycarbonyl)-2-azabicyclo[3.1.0]hexane-3-carboxylic acid (259a) (177 mg, 0.781 mmol) in DCM (5 mL) using 1-chloro-N,N,2-trimethylprop-1-en-1-amine (0.114 mL, 0.859 mmol), 6-(difluoromethoxy)pyridin-2-amine (125 mg, 0.781 mmol) and DIPEA (202 mg, 1.561 mmol) to afford (1R,3S,5R)-tert-butyl 3-(6-(difluoromethoxy)pyridin-2-ylcarbamoyl)-2-azabicyclo[3.1.0] hexane-2-carboxylate (345a) (170 mg, 59% yield) as a pale-yellow solid; $^1$H NMR (300 MHz, DMSO-$d_6$) δ 10.44 (s, 1H), 8.04-7.85 (m, 2H), 7.57 (s, 1H), 6.88-6.64 (m, 1H), 4.34-4.05 (m, 1H), 3.35 (s, 1H), 2.38-2.21 (m, 1H), 2.21-2.02 (m, 1H), 1.71-1.53 (m, 1H), 1.32 (s, 9H), 0.84-0.64 (m, 1H), 0.50-0.33 (m, 1H); $^{19}$F NMR (282 MHz, DMSO-$d_6$) δ−86.36; MS (ES+): 370 (M+1); (ES−): 368 (M−1).

Step-2: Preparation of (1R,3S,5R)—N-(6-(difluoromethoxy)pyridin-2-yl)-2-azabicyclo[3.1.0]hexane-3-carboxamide (345b)

Compound 345b was prepared according to the procedure reported in step-2 of scheme-344, from (1R,3S,5R)-tert-butyl 3-((6-(difluoromethoxy)pyridin-2-yl)carbamoyl)-2-azabicyclo[3.1.0]hexane-2-carboxylate (345a) (165 mg, 0.447 mmol) in DCM (5 mL) using 4 M HCl in dioxane (1.117 mL, 4.47 mmol) and stirring at RT for 16 h. This gave after work up HCl salt of (1R,3S,5R)—N-(6-(difluoromethoxy)pyridin-2-yl)-2-azabicyclo[3.1.0]hexane-3-carboxamide (345b) (123 mg, 90% yield) as a white solid $^1$H NMR (300 MHz, DMSO-$d_6$) δ 11.08 (s, 1H), 7.98 (t, J=8.0 Hz, 1H), 7.86 (d, J=8.1 Hz, 1H), 7.58 (t, J=72.8 Hz, 1H), 6.88 (d, J=7.9 Hz, 1H), 4.34-4.08 (m, 1H), 3.33-3.18 (m, 1H), 2.66-2.54 (m, 1H), 2.19-1.98 (m, 1H), 1.91-1.62 (m, 1H), 0.91-0.76 (m, 2H); $^{19}$F NMR (282 MHz, DMSO-$d_6$) δ−86.32; MS (ES+): 270 (M+1); (ES−): 268 (M−1)

Step-3: Preparation of (1R,3S,5R)-2-(2-(4-amino-8-methyl-6-(trifluoromethyl)-9H-pyrimido[4,5-b]indol-9-yl)acetyl)-N-(6-(difluoromethoxy)pyridin-2-yl)-2-azabicyclo[3.1.0]hexane-3-carboxamide (345c)

Compound 345c was prepared according to the procedure reported in step-3 of scheme-1, from HCl salt of (1R,3S,5R)—N-(6-(difluoromethoxy)pyridin-2-yl)-2-azabicyclo [3.1.0]hexane-3-carboxamide (345b) (52.3 mg, 0.171 mmol) in DMF (5 mL) using TFA salt of 2-(4-amino-8-methyl-6-(trifluoromethyl)-9H-pyrimido[4,5-b]indol-9-yl) acetic acid (184f) (75 mg, 0.171 mmol), HATU (98 mg, 0.257 mmol), DIPEA (111 mg, 0.856 mmol) and stirring at RT for 16 h. This gave after workup and purification as described in scheme-299, (1R,3S,5R)-2-(2-(4-amino-8-methyl-6-(trifluoromethyl)-9H-pyrimido[4,5-b]indol-9-yl) acetyl)-N-(6-(difluoromethoxy)pyridin-2-yl)-2-azabicyclo [3.1.0]hexane-3-carboxamide (345c) (56 mg, 57% yield) HCl salt as a white solid; $^1$H NMR (300 MHz, DMSO-$d_6$) δ 10.54 (s, 1H, $D_2O$ exchangeable), 8.86 (bs, 2H, $D_2O$ exchangeable), 8.82 (s, 1H), 8.68 (s, 1H), 7.91-7.80 (m, 2H), 7.63 (d, J=1.7 Hz, 1H), 7.50 (t, J=73.0 Hz, 1H), 6.82-6.67 (m, 1H), 5.99 (d, J=18.0 Hz, 1H), 5.70 (d, J=18.0 Hz, 1H), 4.49 (dd, J=9.0, 5.7 Hz, 1H), 3.99-3.91 (m, 1H), 2.79 (s, 3H), 2.42-2.30 (m, 1H), 2.28-2.14 (m, 1H), 2.03-1.87 (m, 1H), 1.17-1.04 (m, 1H), 0.70 (m, J=5.2, 2.4 Hz, 1H), $^{19}$F NMR (282 MHz, DMSO-$d_6$) δ−58.82, −86.30, −86.40; MS (ES+): 576 (M+1); (ES−): 574 (M−1); Analysis calculated for $C_{26}H_{22}F_5N_7O_3 \cdot HCl \cdot 1.5H_2O$: C, 48.87; H, 4.10; Cl, 5.55; N, 15.34. Found: C, 48.78; H, 4.12; Cl, 5.53; N, 15.26.

Scheme 346

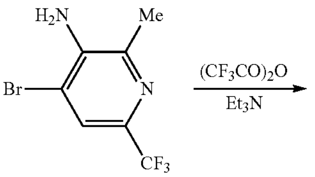

346a

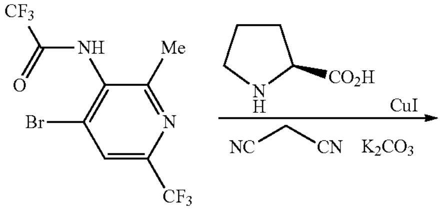

346b

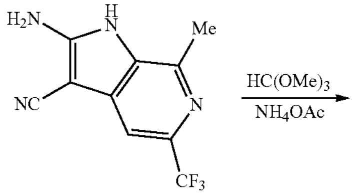

346c

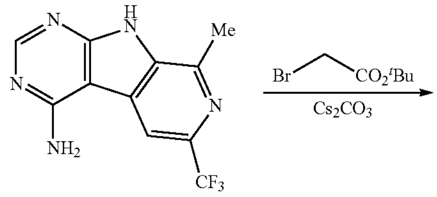

346d

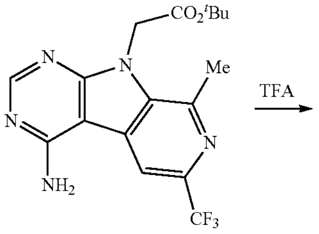

346e

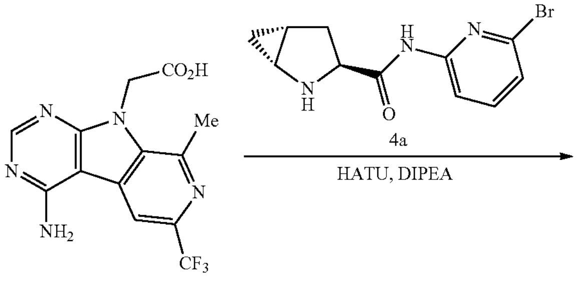

346f

-continued

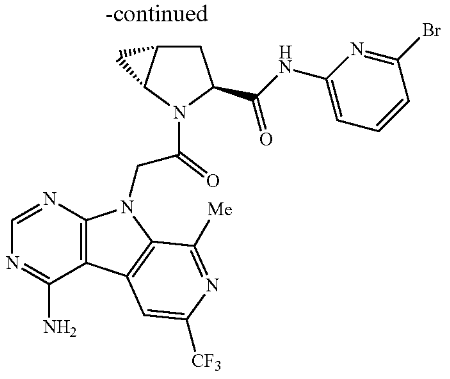

346g

Preparation of (1R,3S,5R)-2-(2-(4-amino-8-methyl-6-(trifluoromethyl)-9H-pyrido[4',3':4,5]pyrrolo[2,3-d]pyrimidin-9-yl)acetyl)-N-(6-bromopyridin-2-yl)-2-azabicyclo[3.1.0]hexane-3-carboxamide (346 g)

Step-1: Preparation of N-(4-bromo-2-methyl-6-(trifluoromethyl)pyridin-3-yl)-2,2,2-trifluoroacetamide (346b)

Compound 346b was prepared according to the procedure reported in step-1 of scheme-46, from 4-bromo-2-methyl-6-(trifluoromethyl)pyridin-3-amine (346a)(6.16 g, 24.15 mmol; CAS #1990462-02-6) in DCM (25 mL) using triethylamine (4.15 g, 41.1 mmol), trifluoroacetic acid anhydride (7.61 g, 36.2 mmol) to afford after workup N-(4-bromo-2-methyl-6-(trifluoromethyl)pyridin-3-yl)-2,2,2-trifluoroacetamide (346b) (8.08 g, 95% yield) as a pale-yellow solid and was used as such for next step; $^{1}H$ NMR (300 MHz, DMSO-$d_6$) δ 11.84 (s, 1H), 8.32 (s, 1H), 2.51 (s, 3H); $^{19}F$ NMR (282 MHz, DMSO-$d_6$) δ−66.43, −74.09; MS (ES+): 351/353 (M+1); (ES−): 349/351 (M−1).

Step-2: Preparation of 2-amino-7-methyl-5-(trifluoromethyl)-1H-pyrrolo[2,3-c]pyridine-3-carbonitrile (346c)

Compound 346c was prepared and purified according to the procedure reported in step-1 of scheme-11, from N-(4-bromo-2-methyl-6-(trifluoromethyl)pyridin-3-yl)-2,2,2-trifluoroacetamide (346b) (8.08 g, 23.02 mmol) in DMSO (30 mL) using malononitrile (1.825 g, 27.6 mmol), L-proline (0.530 g, 4.60 mmol). CuI (0.438 g, 2.302 mmol), a solution of $K_2CO_3$ (6.36 g, 46.0 mmol) in water (30 mL) to afford 2-amino-7-methyl-5-(trifluoromethyl)-1H-pyrrolo[2,3-c]pyridine-3-carbonitrile (346c) (3.76 g, 68% yield) as a yellow solid; $^{1}H$ NMR (300 MHz, DMSO-$d_6$) δ 11.68 (s, 1H), 7.40 (s, 1H), 7.27 (s, 2H), 2.57 (s, 3H); $^{19}F$ NMR (282 MHz, DMSO-$d_6$) δ−64.65; MS (ES+): 241 (M+1); (ES−): 239 (M−1).

Step-3: Preparation of 8-methyl-6-(trifluoromethyl)-9H-pyrido[4',3':4,5]pyrrolo[2,3-d]pyrimidin-4-amine (346d)

Compound 346d was prepared according to the procedure reported in step-2 of scheme-29, from 2-amino-7-methyl-5-(trifluoromethyl)-1H-pyrrolo[2,3-c]pyridine-3-carbonitrile (346c) (3.76 g, 15.65 mmol) in ethanol (10 mL) using trimethoxymethane (16.61 g, 157 mmol), $NH_4OAc$ (3.62 g, 47.0 mmol) and heating at 90° C. for 16 h. This gave after workup 8-methyl-6-(trifluoromethyl)-9H-pyrido[4',3':4,5]pyrrolo[2,3-d]pyrimidin-4-amine (346d) (3.53 g, 84% yield) as a pale-yellow solid; $^{1}H$ NMR (300 MHz, DMSO-$d_6$) δ 12.66 (s, 1H), 8.78 (s, 1H), 8.40 (s, 1H), 7.72 (bs, 2H), 2.79 (s, 3H); $^{19}F$ NMR (282 MHz, DMSO)-$d_6$ δ−63.78; MS (ES+): 268 (M+1); (ES−): 266 (M−1).

Step-4: Preparation of tert-butyl 2-(4-amino-8-methyl-6-(trifluoromethyl)-9H-pyrido[4',3':4,5]pyrrolo[2,3-d]pyrimidin-9-yl)acetate (346e)

Compound 346e was prepared according to the procedure reported in step-1 of scheme-1, from 8-methyl-6trifluoromethyl)-9H-pyrido[4',3':4,5]pyrrolo[2,3-d]pyrimidin-4-amine (346d) (3.53 g, 13.21 mmol) in DMF (20 mL) using tert-butyl 2-bromoacetate (3.09 g, 15.85 mmol), $Cs_2CO_3$ (8.61 g, 26.4 mmol) and stirring at RT for 16 h. This gave after workup tert-butyl 2-(4-amino-8-methyl-6-(trifluoromethyl)-9H-pyrido[4',3':4,5]pyrrolo[2,3-d]pyrimidin-9-yl)acetate (346e) (3.46 g, 69% yield) as a pale-yellow solid; $^{1}H$ NMR (300 MHz, DMSO-$d_6$) δ8.86 (s, 1H), 8.45 (s, 1H), 7.91 (bs, 2H), 5.44 (s, 2H), 2.88 (s, 3H), 1.44 (s, 9H); $^{19}F$ NMR (282 MHz, DMSO-$d_6$) δ−64.14; MS (ES+): 382 (M+1); (ES−): 380 (M−1).

Step-5: Preparation of 2-(4-amino-8-methyl-6-(trifluoromethyl)-9H-pyrido[4',3':4,5]pyrrolo[2,3-d]pyrimidin-9-yl)acetic acid (346f)

Compound 346f was prepared according to the procedure reported in step-2 of scheme-1, from tert-butyl 2-(4-amino-8-methyl-6-(trifluoromethyl)-9H-pyrido[4',3':4,5]pyrrolo[2,3-d]pyrimidin-9-yl)acetate (346e) (366 mg, 0.960 mmol) using TFA (1094 mg, 9.60 mmol) in DCM (5 mL) to afford after workup TFA salt of 2-(4-amino-8-methyl-6-(trifluoromethyl)-9H-pyrido[4',3':4,5]pyrrolo[2,3-d]pyrimidin-9-yl)acetic acid (346f) (0.280 g, 66% yield) as a pale-yellow solid; $^{1}H$ NMR (300 MHz, DMSO-$d_6$) δ 8.88 (s, 1H), 8.48 (s, 1H), 8.04 (bs, 2H), 5.47 (s, 2H), 2.91 (s, 3H); $^{19}F$ NMR (282 MHz, DMSO-$d_6$) δ−64.16, −74.52; MS (ES+): 326 (M+1), (ES−): 324 (M−1).

Step-6: Preparation of (1R,3S,5R)-2-(2-(4-amino-8-methyl-6-(trifluoromethyl)-9H-pyrido[4',3':4,5]pyrrolo[2,3-d]pyrimidin-9-yl)acetyl)-N-(6-bromopyridin-2-yl)-2-azabicyclo[3.1.0]hexane-3-carboxamide (346 g)

Compound 346g was prepared according to the procedure reported in step-3 of scheme-1, from TFA salt of 2-(4-amino-8-methyl-6-(trifluoromethyl)-9H-pyrido[4',3':4,5]pyrrolo[2,3-d]pyrimidin-9-yl)acetic acid (346f) (60 mg, 0.137 mmol) in DMF (5 mL) using HCl salt of (1R,3S,5R)—N-(6-bromopyridin-2-yl)-2-azabicyclo[3.1.0]hexane-3-carboxamide (4a) (43.5 mg, 0.137 mmol), HATU (62.3 mg, 0.164 mmol), DIPEA (88 mg, 0.683 mmol) and stirring at RT for 16 h. This gave after workup and purification as described in scheme-299, (1R,3S,5R)-2-(2-(4-amino-8-methyl-6-(trifluoromethyl)-9H-pyrido[4',3':4,5]pyrrolo[2,3-d]pyrimidin-9-yl)acetyl)-N-(6-bromopyridin-2-yl)-2-azabicyclo[3.1.0]hexane-3-carboxamide (346 g) (72 mg, 89% yield) HCl salt as a white solid; $^{1}H$ NMR (300 MHz, DMSO-$d_6$) δ 10.85 (s, 1H, $D_2O$ exchangeable), 8.99 (s, 1H), 8.95 (bs, 2H, $D_2O$ exchangeable), 8.71 (s, 1H), 8.01 (d, J=8.1 Hz, 1H), 7.71 (t, J=8.0 Hz, 1H), 7.31 (d, J=7.7 Hz, 1H), 6.03 (d, J=18.0 Hz, 1H), 5.73 (d, J=17.9 Hz, 1H), 4.46-4.40 (m, 1H), 4.00-3.92 (m, 1H), 2.43-2.30 (m, 1H), 2.28-2.12 (m, 1H), 2.04-1.82 (m, 1H), 1.10 (m, J=8.8, 5.4 Hz, 1H), 0.80-0.59 (m, 1H); $^{19}F$ NMR (282 MHz, DMSO-$d_6$) δ−64.39; MS (ES+): 589/591 (M+1); (ES−): 587/589 (M−1); Analysis calculated for $C_{24}H_{20}BrF_3NaO_2$·1.1HCl·$2H_2O$: C, 43.31; H, 3.80; Cl, 5.86; N, 16.84. Found: C, 43.24; H, 3.73; Cl, 5.97; N, 16.73.

2.50-2.41 (m, 1H), 1.99 (dd, J=13.3, 6.1 Hz, 1H), 1.32 (s, 3H), 1.07-0.98 (m, 1H), 0.96-0.82 (m, 1H); $^{19}F$ NMR (282 MHz, DMSO-$d_6$) δ−64.32; MS (ES+): 603/605 (M+1); (ES−): 601/603 (M−1); Analysis calculated for $C_{25}H_{22}BrF_3N_8O_2$·0.95HCl·$1.75H_2O$: C, 44.85; H, 3.98; Cl, 5.03; N, 16.74. Found: C, 44.76: H, 3.80; Cl, 5.06; N, 16.60.

Scheme 347

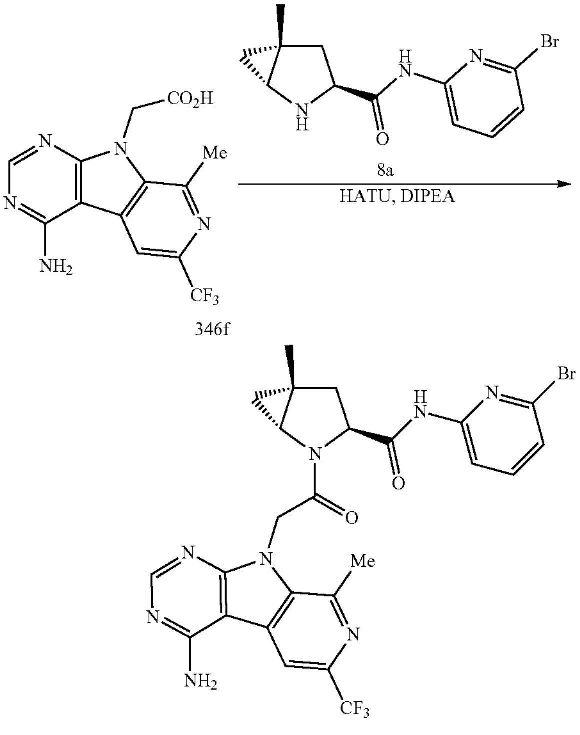

346f, 8a, 347a

Scheme 348

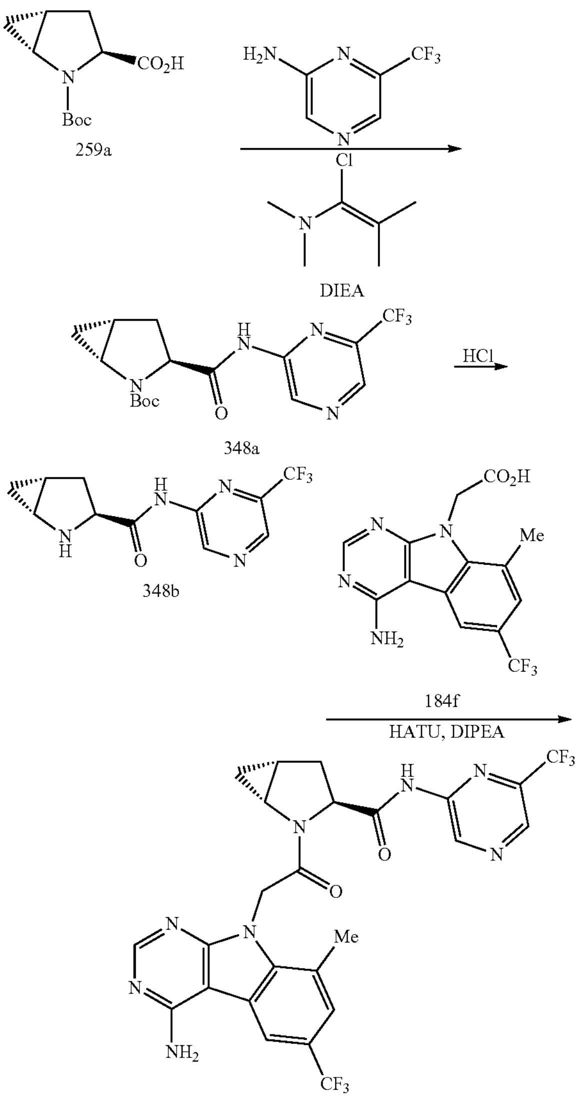

259a, 348a, 348b, 184f, 348c

Preparation of (1R,3S,5R)-2-(2-(4-amino-8-methyl-6-(trifluoromethyl)-9H-pyrido[4',3':4,5]pyrrolo[2,3-d]pyrimidin-9-yl)acetyl)-N-(6-bromopyridin-2-yl)-5-methyl-2-azabicyclo[3.1.0]hexane-3-carboxamide (347a)

Compound 347a was prepared according to the procedure reported in step-3 of scheme-1, from TFA salt of 2-(4-amino-8-methyl-6-(trifluoromethyl)-9H-pyrido[4',3':4,5]pyrrolo[2,3-d]pyrimidin-9-yl)acetic acid (346f) (60 mg, 0.137 mmol) in DMF (5 mL) using HCl salt of (1R,3S,5R)—N-(6-bromopyridin-2-yl)-5-methyl-2-azabicyclo[3.1.0]hexane-3-carboxamide (8a) (45.4 mg, 0.137 mmol), HATU (62.3 mg, 0.164 mmol), DIPEA (88 mg, 0.683 mmol) and stirring at RT for 16 h. This gave after workup and purification as described in scheme-299. (1R,3S,5R)-2-(2-(4-amino-8-methyl-6-(trifluoromethyl)-9H-pyrido[4',3':4,5]pyrrolo[2,3-d]pyrimidin-9-yl)acetyl)-N-(6-bromopyridin-2-yl)-5-methyl-2-azabicyclo[3.1.0]hexane-3-carboxamide (347a) (63 mg, 76% yield) HCl salt as a white solid; $^1H$ NMR (300 MHz, DMSO-$d_6$) δ 10.84 (s, 1H, $D_2O$ exchangeable), 8.95 (s, 1H), 8.66 (bs, 2H, $D_2O$ exchangeable), 8.63 (s, 1H), 8.02 (d, J=8.2 Hz, 1H), 7.71 (t, J=8.0 Hz, 1H), 7.32 (d, J=7.7 Hz, 1H), 5.95 (d, J=18.0 Hz, 1H), 5.68 (d, J=17.9 Hz, 1H), 4.39 (dd, J=9.1, 6.2 Hz, 1H), 3.77-3.73 (m, 1H), 2.93 (s, 3H), Preparation of (1R,3S,5R)-2-(2-(4-amino-8-methyl-6-(trifluoromethyl)-9H-pyrimido[4,5-b]indol-9-yl)acetyl)-N-(6-(trifluoromethyl)pyrazin-2-yl)-2-azabicyclo[3.1.0]hexane-3-carboxamide (348c)

Step-1: Preparation of (1R,3S,5R)-tert-butyl 3-((6-(trifluoromethyl)pyrazin-2-yl)carbamoyl)-2-azabicyclo[3.1.0]hexane-2-carboxylate (348a)

Compound 348a was prepared and purified according to the procedure reported in step-1 of scheme-344, from (1R,3S,5R)-2-(tert-butoxycarbonyl)-2-azabicyclo[3.1.0]hexane- 3-carboxylic acid (259a) (174 mg, 0.766 mmol) in DCM (10 mL) using 1-chloro-N,N,2-trimethylprop-1-en-1-amine (0.112 mL, 0.843 mmol), 6-(trifluoromethyl)pyrazin-2-amine (125 mg, 0.766 mmol). DIPEA (198 mg, 1.533 mmol) to afford (1R,3S,5R)-tert-butyl 3-((6-(trifluoromethyl) pyrazin-2-yl)carbamoyl)-2-azabicyclo[3.1.0]hexane-2-carboxylate (348a) (63 mg, 22% yield) as a pale-yellow solid; MS (ES+): 373 (M+1); (ES−): 371 (M−1).

Step-2: Preparation of (1R,3S,5R)—N-(6-(trifluoromethyl)pyrazin-2-yl)-2-azabicyclo[3.1.0]hexane-3-carboxamide (348b)

Compound 348b was prepared according to the procedure reported in step-2 of scheme-344, from (1R,3S,5R)-tert-butyl 3-((6-(trifluoromethyl)pyrazin-2-yl)carbamoyl)-2-azabicyclo[3.1.0]hexane-2-carboxylate (348a) (63 mg, 0.169 mmol) in DCM (5 mL) using 4 M HCl in dioxane (0.423 mL, 1.692 mmol) to afford HCl salt of (1R,3S,5R)—N-(6-(trifluoromethyl)pyrazin-2-yl)-2-azabicyclo[3.1.0] hexane-3-carboxamide (348b) (42 mg, 80% yield) as a white solid; $^1$H NMR (300 MHz, DMSO-$d_6$) δ 11.88 (s, 1H), 9.58 (s, 1H), 8.98 (s, 1H), 4.25 (dd, J=10.8, 7.8 Hz, 1H), 3.40-3.30 (m, 1H), 2.64 (dd, J=12.8, 7.8 Hz, 1H), 2.23-2.04 (m, 1H), 1.90-1.74 (m, 1H), 0.93-0.76 (m, 2H); $^{19}$F NMR (282 MHz, DMSO-$d_6$) δ−66.42; MS (ES+): 273 (M+1); (ES−): 271 (M−1).

Step-3: Preparation of (1R,3S,5R)-2-(2-(4-amino-8-methyl-6-(trifluoromethyl)-9H-pyrimido[4,5-b]indol-9-yl)acetyl)-N-(6-(trifluoromethyl)pyrazin-2-yl)-2-azabicyclo[3.1.0]hexane-3-carboxamide (348c)

Compound 348c was prepared according to the procedure reported in step-3 of scheme-1, from HCl salt of (1R,3S,5R)—N-(6-(trifluoromethyl)pyrazin-2-yl)-2-azabicyclo [3.1.0]hexane-3-carboxamide (348b) (42.3 mg, 0.137 mmol) in DMF (5 mL) using TFA salt of 2-(4-amino-8-methyl-6-(trifluoromethyl)-9H-pyrimido[4,5-b]indol-9-yl) acetic acid (184f) (60 mg, 0.137 mmol), HATU (78 mg, 0.205 mmol), DIPEA (88 mg, 0.684 mmol) and stirring at RT for 16 h. This gave after workup and purification as described in scheme-299, (1R,3S,5R)-2-(2-(4-amino-8-methyl-6-(trifluoromethyl)-9H-pyrimido[4,5-b]indol-9-yl) acetyl)-N-(6-(trifluoromethyl)pyrazin-2-yl)-2-azabicyclo [3.1.0]hexane-3-carboxamide (348c) (58 mg, 73% yield) HCl salt as a white solid; $^1$H NMR (300 MHz, DMSO-$d_6$) δ 11.38 (s, 1H, $D_2O$ exchangeable), 9.55 (s, 1H), 8.85 (s, 1H), 8.80 (s, 1H), 8.70 (bs, 2H, $D_2O$ exchangeable), 8.64 (s, 1H), 7.61 (d, J=1.7 Hz, 1H), 5.99 (d, J=18.0 Hz, 1H), 5.71 (d, J=17.9 Hz, 1H), 4.51 (dd, J=9.0, 5.8 Hz, 1H), 4.01-3.91 (m, 1H), 2.79 (s, 3H), 2.46-2.34 (m, 1H), 2.34-2.22 (m, 1H), 2.03-1.89 (m, 1H), 1.16-1.03 (m, 1H), 0.81-0.66 (m, 1H); $^{19}$F NMR (282 MHz, DMSO-$d_6$) δ−58.78, −66.52; MS (ES+): 579 (M+1), (ES−): 577 (M−1); Analysis calculated for $C_{25}H_{20}F_6N_8O_2 \cdot 1.1HCl \cdot H_2O$: C, 47.17; H, 3.66; Cl, 6.13. N, 17.60. Found: C, 47.00; H, 3.61; Cl, 6.09; N, 17.45.

Scheme 349

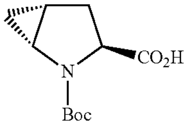

259a

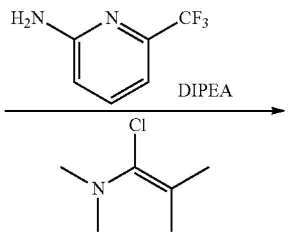

-continued

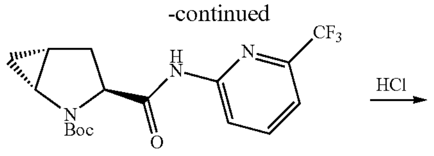

349a

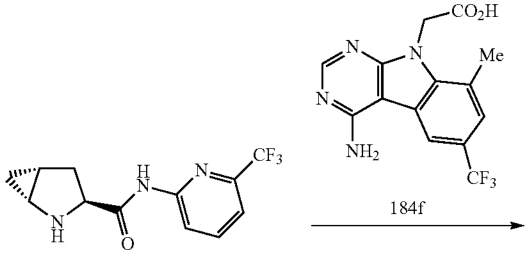

349b

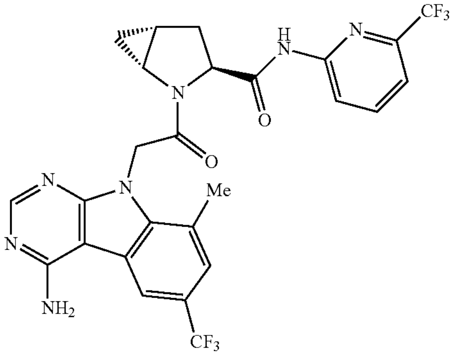

349c

Preparation of (1R,3S,5R)-2-(2-(4-amino-8-methyl-6-(trifluoromethyl)-9H-pyrimido[4,5-b]indol-9-yl) acetyl)-N-(6-(trifluoromethyl)pyridin-2-yl)-2-azabicyclo[3.1.0]hexane-3-carboxamide (349c)

Step-1: Preparation of (1R,3S,5R)-tert-butyl 3-((6-(trifluoromethyl)pyridin-2-yl)carbamoyl)-2-azabicyclo[3.1.0]hexane-2-carboxylate (349a)

Compound 349a was prepared according to the procedure reported in step-1 of scheme-345, from (1R,3S,5R)-2-(tert-butoxycarbonyl)-2-azabicyclo[3.1.0]hexane-3-carboxylic acid (259a) (350 mg, 1.542 mmol) in DCM (5 mL) using 1-chloro-N,N,2-trimethylprop-1-en-1-amine (0.224 mL, 1.696 mmol), 6-(trifluoromethyl)pyridin-2-amine (250 mg, 1.542 mmol), DIPEA (399 mg, 3.08 mmol) to afford after work up and purification using flash column chromatography [$SiO_2$ gel, eluting with EtOAc in hexane from 0-15%] followed by purification using reverse phase column chromatography [C18 column (100 g), eluting with ACN in water (containing 0.1% HCl) from 0-100%] (1R,3S,5R)-tert-butyl 3-((6-(trifluoromethyl)pyridin-2-yl)carbamoyl)-2-azabicyclo[3.1.0]hexane-2-carboxylate (349a) (280 mg, 49% yield) as a white solid: $^1$H NMR (300 MHz, DMSO-$d_6$) δ 10.92 (s, 1H), 8.38 (d, J=8.4 Hz, 1H), 8.09 (t, J=8.1 Hz, 1H), 7.61 (d, J=7.5 Hz, 1H), 4.36-4.03 (m, 1H), 3.53-3.37 (m, 1H), 2.39-2.23 (m, 1H), 2.23-2.02 (m, 1H), 1.74-1.52 (m, 1H), 1.37 (d, 9H), 0.89-0.65 (m, 1H), 0.53-0.31 (m, 1H); $^{19}$F NMR (282 MHz, DMSO-$d_6$) δ−66.61; MS (ES+): 394 (M+Na); (ES−): 370 (M−1).

Step-2: Preparation of (1R,3S,5R)—N-(6-(trifluoromethyl)pyridin-2-yl)-2-azabicyclo[3.1.0]hexane-3-carboxamide (349b)

Compound 349b was prepared according to the procedure reported in step-2 of scheme-344, from (1R,3S,5R)-tert-butyl 3-((6-(trifluoromethyl)pyridin-2-yl)carbamoyl)-2-azabicyclo[3.1.0]hexane-2-carboxylate (349a) (280 mg, 0.754 mmol) in DCM (5 mL) using 4 M HCl in dioxane (1.885 mL, 7.54 mmol) to afford HCl salt of (1R,3S,5R)—N-(6-(trifluoromethyl)pyridin-2-yl)-2-azabicyclo[3.1.0]hexane-3-carboxamide (349b) (230 mg, 99% yield) as a white solid; $^1$H NMR (300 MHz, DMSO-$d_6$) δ 11.48 (s, 1H), 8.32 (d, J=8.5 Hz, 1H), 8.17 (t, J=8.0 Hz, 1H), 7.71 (d, J=7.5 Hz, 1H), 4.38-4.07 (m, 1H), 3.41-3.29 (m, 1H), 2.62 (dd, J=12.8, 7.7 Hz, 1H), 2.27-2.05 (m, 1H), 1.98-1.72 (m, 1H), 0.98-0.58 (m, 2H); $^{19}$F NMR (282 MHz, DMSO-$d_6$) δ−66.61; MS (ES+): 272 (M+1).

Step-3: Preparation of (1R,3S,5R)-2-(2-(4-amino-8-methyl-6-(trifluoromethyl)-9H-pyrimido[4,5-b]indol-9-yl)acetyl)-N-(6-(trifluoromethyl)pyridin-2-yl)-2-azabicyclo[3.1.0]hexane-3-carboxamide (349c)

Compound 349c was prepared according to the procedure reported in step-3 of scheme-1, from HCl salt of (1R,3S,5R)—N-(6-(trifluoromethyl)pyridin-2-yl)-2-azabicyclo[3.1.0]hexane-3-carboxamide (349b) (42.1 mg, 0.137 mmol) in DMF (5 mL) using TFA salt of 2-(4-amino-8-methyl-6-(trifluoromethyl)-9H-pyrimido[4,5-b]indol-9-yl)acetic acid (184f) (60 mg, 0.137 mmol), HATU (78 mg, 0.205 mmol), DIPEA (88 mg, 0.684 mmol) and stirring at RT for 16 h. This gave after workup and purification as described in scheme-299, (1R,3S,5R)-2-(2-(4-amino-8-methyl-6-(trifluoromethyl)-9H-pyrimido[4,5-b]indol-9-yl)acetyl)-N-(6-(trifluoromethyl)pyridin-2-yl)-2-azabicyclo[3.1.0]hexane-3-carboxamide (349c) (54 mg, 68% yield) HCl salt as a white solid; $^1$H NMR (300 MHz, DMSO-$d_6$) δ 10.% (s, 1H, $D_2O$ exchangeable), 8.80 (s, 1H), 8.77 (bs, 2H, $D_2O$ exchangeable), 8.66 (s, 1H), 8.29 (d, J=8.5 Hz, 1H), 8.05 (t, J=8.0 Hz, 1H), 7.61 (s, 1H), 7.58 (d, J=7.6 Hz, 1H), 5.99 (d, J=18.0 Hz, 1H), 5.70 (d, J=18.0 Hz, 1H), 4.49 (dd, J=9.0, 5.7 Hz, 1H), 4.01-3.90 (m, 1H), 2.79 (s, 3H), 2.44-2.31 (m, 1H), 2.30-2.16 (m, 1H), 2.03-1.86 (m, 1H), 1.18-0.98 (m, 1H), 0.78-0.62 (m, 1H); $^{19}$F NMR (282 MHz, DMSO-$d_6$) δ−58.80, −66.65; MS (ES+): 578 (M+1), (ES−): 576 (M−1); Analysis calculated for $C_{26}H_{21}F_6N_7O_2 \cdot 1.1HCl \cdot 1.25H_2O$: C, 48.79; H, 3.87; Cl, 6.09; N, 15.32. Found: C, 48.59; H, 3.85; Cl, 5.97; N, 15.33.

-continued

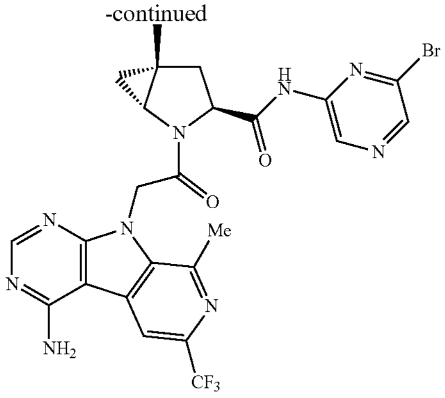

350a

Preparation of (1R,3S,5R)-2-(2-(4-amino-8-methyl-6-(trifluoromethyl)-9H-pyrido[4',3':4,5]pyrrolo[2,3-d]pyrimidin-9-yl)acetyl)-N-(6-bromopyrazin-2-yl)-5-methyl-2-azabicyclo[3.1.0]hexane-3-carboxamide (350a)

Compound 350a was prepared according to the procedure reported in step-3 of scheme-1, from TFA salt of 2-(4-amino-8-methyl-6-(trifluoromethyl)-9H-pyrido[4',3':4,5]pyrrolo[2,3-d]pyrimidin-9-yl)acetic acid (346f) (60 mg, 0.137 mmol) in DMF (5 mL) using HCl salt of (1R,3S,5R)—N-(6-bromopyrazin-2-yl)-5-methyl-2-azabicyclo[3.1.0]hexane-3-carboxamide (261c) (45.6 mg, 0.137 mmol), HATU (62.3 mg, 0.164 mmol), DIPEA (88 mg, 0.683 mmol) and stirring at RT for 16 h. This gave after workup and purification as described in scheme-299, (1R,3S,5R)-2-(2-(4-amino-8-methyl-6-(trifluoromethyl)-9H-pyrido[4',3':4,5]pyrrolo[2,3-d]pyrimidin-9-yl)acetyl)-N-(6-bromopyrazin-2-yl)-5-methyl-2-azabicyclo[3.1.0]hexane-3-carboxamide (350a) (57 mg, 69% yield) HCl salt as a white solid: $^1$H NMR (300 MHz, DMSO-$d_6$) δ 11.21 (s, 1H, $D_2O$ exchangeable), 9.24 (s, 1H), 8.95 (s, 1H), 8.68 (bs, 2H, $D_2O$ exchangeable), 8.64 (s, 1H), 8.53 (s, 1H), 5.96 (d, J=18.0 Hz, 1H), 5.68 (d, J=17.9 Hz, 1H), 4.41 (dd, J=9.1, 6.2 Hz, 1H), 3.80-3.70 (m, 1H), 2.92 (s, 3H), 2.60-2.52 (m, 1H), 2.03 (dd, J=13.2, 6.1 Hz, 1H), 1.32 (s, 3H), 1.09-0.99 (m, 1H), 0.96-0.86 (m, 1H). $^{19}$F NMR (282 MHz, DMSO-$d_6$) δ−64.34; MS (ES+): 604/606 (M+1); (ES−): 602/604 (M−1); Analysis calculated for $C_4H_{21}BrF_3N_9O_2 \cdot 1.45HCl \cdot 2H_2O$: C, 41.58; H, 3.85; Cl, 7.42; N, 18.18. Found: C, 41.70; H, 3.67; Cl, 7.44; N, 18.08.

Scheme 350

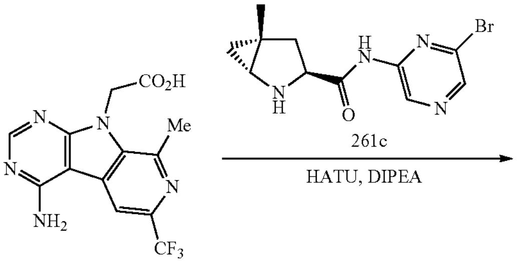

346f

Scheme 351

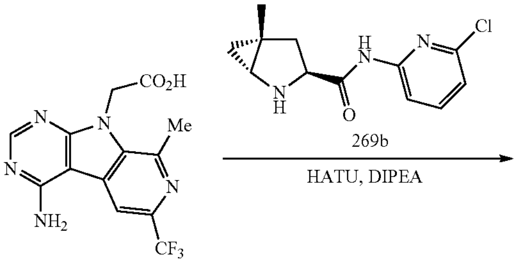

346f

-continued

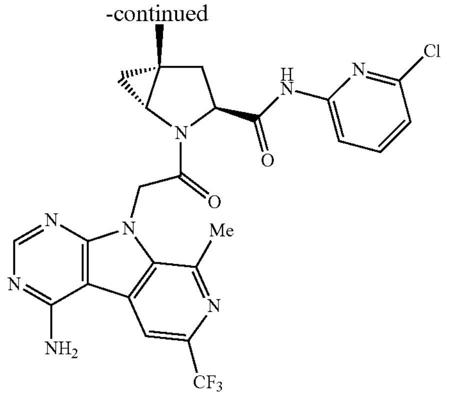

351a

Preparation of (1R,3S,5R)-2-(2-(4-amino-8-methyl-6-(trifluoromethyl)-9H-pyrido[4',3':4.5]pyrrolo[2,3-d]pyrimidin-9-yl)acetyl)-N-(6-chloropyridin-2-yl)-5-methyl-2-azabicyclo[3.1.0]hexane-3-carboxamide (351a)

Compound 351a was prepared according to the procedure reported in step-3 of scheme-1, from TFA salt of 2-(4-amino-8-methyl-6-(trifluoromethyl)-9H-pyrido[4',3':4,5]pyrrolo[2,3-d]pyrimidin-9-yl)acetic acid (346f) (55 mg, 0.125 mmol) in DMF (5 mL) using HCl salt of (1R,3S,5R)—N-(6-chloropyridin-2-yl)-5-methyl-2-azabicyclo[3.1.0]hexane-3-carboxamide (269b) (36.1 mg, 0.125 mmol), HATU (57.1 mg, 0.150 mmol), DIPEA (81 mg, 0.626 mmol) and stirring at RT for 16 h. This gave after workup and purification as described in scheme-299, (1R,3S,5R)-2-(2-(4-amino-8-methyl-6-(trifluoromethyl)-9H-pyrido[4',3':4,5]pyrrolo[2,3-d]pyrimidin-9-yl)acetyl)-N-(6-chloropyridin-2-yl)-5-methyl-2-azabicyclo[3.1.0]hexane-3-carboxamide (351a) (56 mg, 80% yield) HCl salt as a white solid; $^{1}H$ NMR (300 MHz, DMSO-$d_6$) δ 10.82 (s, 1H, $D_2O$ exchangeable), 8.97 (s, 1H), 8.81 (bs, 2H, $D_2O$ exchangeable), 8.67 (s, 1H), 7.99 (d, J=8.2 Hz, 1H), 7.81 (t, J=8.0 Hz, 1H), 7.18 (d, J=7.6 Hz, 1H), 5.96 (d, J=18.1 Hz, 1H), 5.68 (d, J=17.9 Hz, 1H), 4.39 (dd, J=9.1, 6.2 Hz, 1H), 3.78-3.69 (m, 1H), 2.93 (s, 3H), 2.49-2.43 (m, 1H), 1.99 (dd, J=13.3, 6.1 Hz, 1H), 1.31 (s, 3H), 1.08-0.98 (m, 1H), 0.92-0.81 (m, 1H); $^{19}F$ NMR (282 MHz, DMSO-$d_6$) δ-64.37; MS (ES+): 559/561 (M+1): (ES−): 557/559 (M−1); Analysis calculated for $C_{25}H_{22}ClF_3N_8O_2 \cdot 0.95HCl \cdot 2H_2O$: C, 47.69; H, 4.31; Cl, 10.98; N, 17.80. Found: C, 47.78; H, 4.27; Cl, 10.90; N, 17.77.

Scheme 352

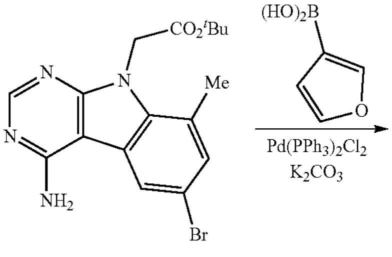

192e

-continued

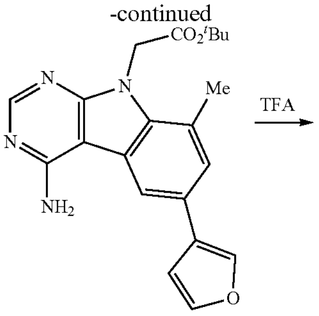

352a

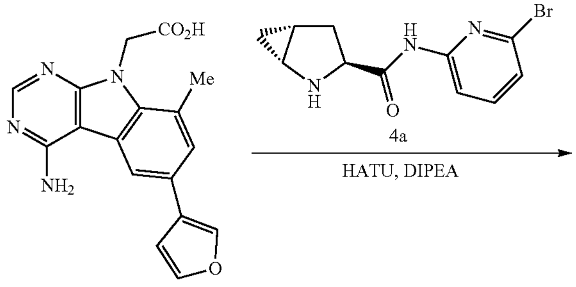

352b

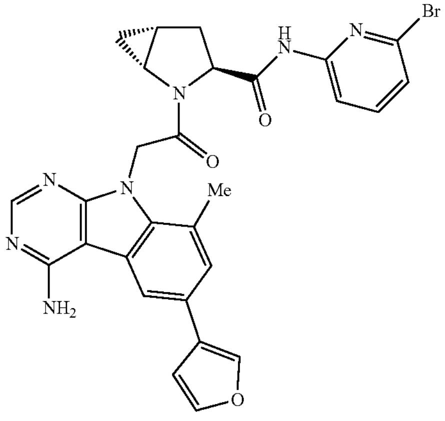

352c

Preparation of (1R,3S,5R)-2-(2-(4-amino-6-(furan-3-yl)-8-methyl-9H-pyrimido[4,5-b]indol-9-yl)acetyl)-N-(6-bromopyridin-2-yl)-2-azabicyclo[3.1.0]hexane-3-carboxamide (352c)

Step-1: Preparation of tert-butyl 2-(4-amino-6-(furan-3-yl)-8-methyl-9H-pyrimido[4,5-b]indol-9-yl)acetate (352a)

Compound 352a was prepared according to the procedure reported in step-1 of scheme-62, from tert-butyl 2-(4-amino-6-bromo-8-methyl-9H-pyrimido[4,5-b]indol-9-yl)acetate (192e) (200 mg, 0.511 mmol) in dioxane (4 mL) using furan-3-ylboronic acid (57.2 mg, 0.511 mmol), bis(triphenylphosphine)palladium(II) chloride (35.9 mg, 0.051 mmol), a solution of 3.3 M potassium carbonate (0.465 mL, 1.533 mmol) and heating at 100° C. for 16 h. This gave after workup and purification using flash column chromatography [silica gel (24 g), eluting with MeOH in DCM from 0-3%]

tert-butyl 2-(4-amino-6-(furan-3-yl)-8-methyl-9H-pyrimido[4,5-b]indol-9-yl)acetate (352a) (74 mg, 38% yield) as a yellow solid; $^1$H NMR (300 MHz, DMSO-$d_6$) δ 8.35 (s, 1H), 8.30 (s, 1H), 8.23 (s, 1H), 7.76 (t, J=1.7 Hz, 1H), 7.47 (s, 1H), 7.40 (bs, 2H), 7.19 (d, J=1.9 Hz, 1H), 5.33 (s, 2H), 2.64 (s, 3H), 1.43 (s, 9H); MS (ES+): 379 (M+1); (ES−): 377 (M−1).

Step-2: Preparation of 2-(4-amino-6-(furan-3-yl)-8-methyl-9H-pyrimido[4,5-b]indol-9-yl)acetic acid (352b)

Compound 352b was prepared according to the procedure reported in step-2 of scheme-1, from tert-butyl 2-(4-amino-6-(furan-3-yl)-8-methyl-9H-pyrimido[4,5-b]indol-9-yl)acetate (352a) (72 mg, 0.190 mmol) in DCM (5 mL) using TFA (217 mg, 1.903 mmol) to afford TFA salt of 2-(4-amino-6-(furan-3-yl)-8-methyl-9H-pyrimido[4,5-b]indol-9-yl)acetic acid (352b) (105 mg) as a brown solid; MS (ES+): 323 (M+1); (ES−): 321 (M−1).

Step-3: Preparation of (1R,3S,5R)-2-(2-(4-amino-6-(furan-3-yl)-8-methyl-9H-pyrimido[4,5-b]indol-9-yl)acetyl)-N-(6-bromopyridin-2-yl)-2-azabicyclo[3.1.0]hexane-3-carboxamide (352c)

Compound 352c was prepared according to the procedure reported in step-3 of scheme-1, from TFA salt of 2-(4-amino-6-(furan-3-yl)-8-methyl-9H-pyrimido[4,5-b]indol-9-yl)acetic acid (352b) (50 mg, 0.115 mmol) in DMF (5 mL) using HCl salt of (1R,3S,5R)—N-(6-bromopyridin-2-yl)-2-azabicyclo[3.1.0]hexane-3-carboxamide (4a) (36.5 mg, 0.115 mmol), HATU (52.3 mg, 0.138 mmol), DIPEA (74.0 mg, 0.573 mmol) and stirring at RT for 16 h. This gave after workup and purification as described in scheme-299, (1R,3S,5R)-2-(2-(4-amino-6-(furan-3-yl)-8-methyl-9H-pyrimido[4,5-b]indol-9-yl)acetyl)-N-(6-bromopyridin-2-yl)-2-azabicyclo[3.1.0]hexane-3-carboxamide (352c) (34 mg, 51% yield) HCl salt as a white solid: $^1$H NMR (300 MHz, DMSO-$d_6$) δ 10.84 (s, 1H, $D_2O$ exchangeable), 8.74 (bs, 2H, $D_2O$ exchangeable), 8.61 (s, 1H), 8.52 (s, 1H), 8.27 (s, 1H), 8.01 (d, J=8.2 Hz, 1H), 7.78 (t, J=1.7 Hz, 1H), 7.71 (t, J=8.0 Hz, 1H), 7.60 (s, 1H), 7.31 (d, J=7.7 Hz, 1H), 7.19 (d, J=1.9 Hz, 1H), 5.91 (d, J=17.9 Hz, 1H), 5.63 (d, J=17.9 Hz, 1H), 4.43 (dd, J=9.1, 5.7 Hz, 1H), 3.98-3.89 (m, 1H), 2.73 (s, 3H), 2.42-2.29 (m, 1H), 2.30-2.12 (m, 1H), 2.01-1.84 (m, 1H), 1.22-0.95 (m, 1H), 0.77-0.60 (m, 1H); MS (ES+): 586/588 (M+1), (ES−): 584/586 (M−1); Analysis calculated for $C_{28}H_{24}BrN_7O_3 \cdot HCl \cdot 2.75H_2O$: C, 50.01; H, 4.57; Cl, 5.27; N, 14.58. Found: C, 49.94; H, 4.36; Cl, 5.41; N, 14.67.

Scheme 353

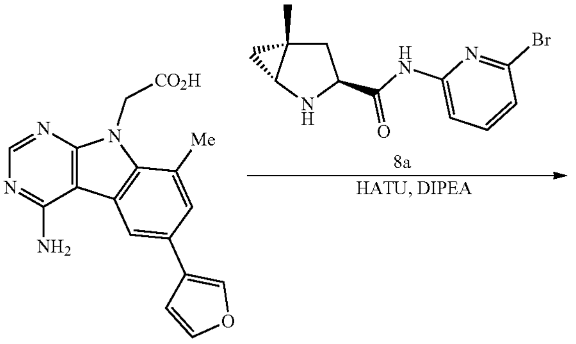

352b

-continued

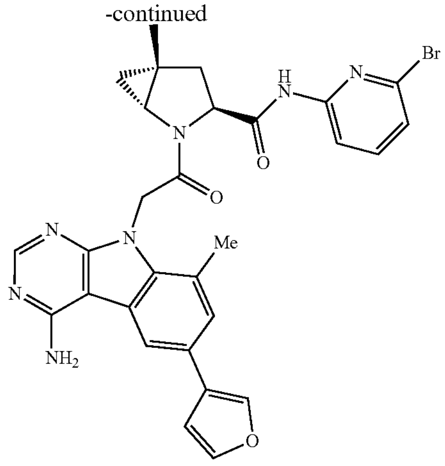

353a

Preparation of (1R,3S,5R)-2-(2-(4-amino-6-(furan-3-yl)-8-methyl-9H-pyrimido[4,5-b]indol-9-yl)acetyl)-N-(6-bromopyridin-2-yl)-5-methyl-2-azabicyclo[3.1.0]hexane-3-carboxamide (353a)

Compound 353a was prepared according to the procedure reported in step-3 of scheme-1, from TFA salt of 2-(4-amino-6-(furan-3-yl)-8-methyl-9H-pyrimido[4,5-b]indol-9-yl)acetic acid (352b) (50 mg, 0.115 mmol) in DMF (5 mL) using HCl salt of (1R,3S,5R)—N-(6-bromopyridin-2-yl)-5-methyl-2-azabicyclo[3.1.0]hexane-3-carboxamide (8a) (38.1 mg, 0.115 mmol), HATU (52.3 mg, 0.138 mmol), DIPEA (74.0 mg, 0.573 mmol) and stirring at RT for 16 h. This gave after workup and purification as described in scheme-299, (1R,3S,5R)-2-(2-(4-amino-6-(furan-3-yl)-8-methyl-9H-pyrimido[4,5-b]indol-9-yl)acetyl)-N-(6-bromopyridin-2-yl)-5-methyl-2-azabicyclo[3.1.0]hexane-3-carboxamide (353a) (37 mg, 54% yield) HCl salt as a white solid; 1H NMR (300 MHz, DMSO-$d_6$) δ 10.83 (s, 1H $D_2O$ exchangeable), 8.71 (bs, 2H, $D_2O$ exchangeable), 8.59 (s, 1H), 8.51 (s, 1H), 8.28 (s, 1H), 8.02 (d, J=8.2 Hz, 1H), 7.81-7.76 (m, 1H), 7.71 (t, J=8.0 Hz, 1H), 7.59 (s, 1H), 7.31 (d, J=7.7 Hz, 1H), 7.19 (d, J=1.9 Hz, 1H), 5.83 (d, J=18.0 Hz, 1H), 5.56 (d, J=17.9 Hz, 1H), 4.39 (dd, J=9.0.6.2 Hz, 1H), 3.70-3.64 (m, 1H), 2.69 (s, 3H), 2.49-2.43 (m, 1H), 1.98 (dd, J=13.3, 6.0 Hz, 1H), 1.31 (s, 3H), 1.08-0.94 (m, 1H), 0.92-0.79 (m, 1H); MS (ES+): 600/602 (M+1); (ES−): 598/600 (M−1): Analysis calculated for $C_{29}H_{26}BrN_7O_3 \cdot 1.05HCl \cdot 2.75H_2$, O: C, 50.61; H, 4.77; Cl, 5.41; N, 14.24. Found: C, 50.69; H, 4.66; Cl, 5.31; N, 14.36.

Scheme 354

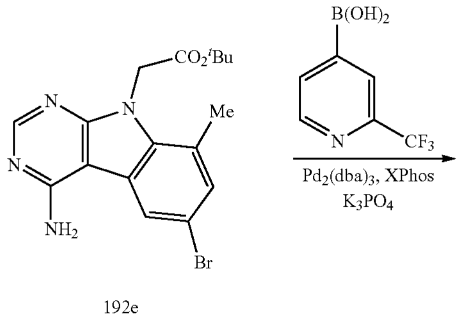

192e

-continued

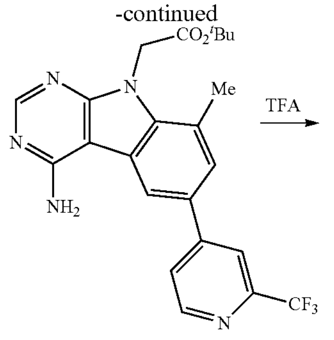

354a

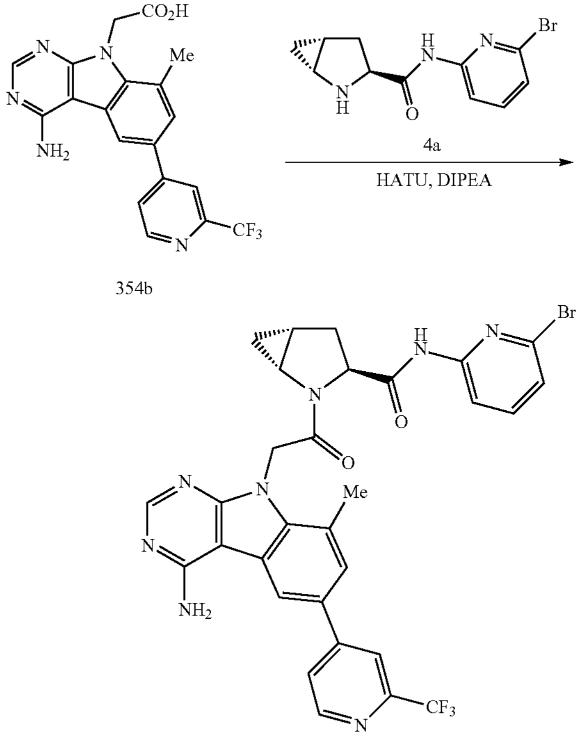

4a

354b

354c

Preparation of (1R,3S,5R)-2-(2-(4-amino-8-methyl-6-(2-(trifluoromethyl)pyridin-4-yl)-9H-pyrimido[4,5-b]indol-9-yl)acetyl)-N-(6-bromopyridin-2-yl)-2-azabicyclo[3.1.0]hexane-3-carboxamide (354c)

Step-1: Preparation of tert-butyl 2-(4-amino-8-methyl-6-(2-(trifluoromethyl)pyridin-4-yl)-9H-pyrimido[4,5-b]indol-9-yl)acetate (354a)

Compound 354a was prepared according to the procedure reported in scheme-263, from tert-butyl 2-(4-amino-6-bromo-8-methyl-9H-pyrimido[4,5-b]indol-9-yl)acetate (192e) (200 mg, 0.511 mmol) in n-BuOH (4 mL) using (2-(trifluoromethyl)pyridin-4-yl)boronic acid (146 mg, 0.767 mmol). $Pd_2(dba)_3$ (46.8 mg, 0.051 mmol), XPhos (48.7 mg, 0.102 mmol), a solution of 1.27 M potassium phosphate (0.805 mL, 1.022 mmol) and heating at 100° C. for 16 h. This gave after workup and purification using flash column chromatography [silica gel (12 g), eluting with MeOH in DCM from 0-7%] tert-butyl 2-(4-amino-8-methyl-6-(2-(trifluoromethyl)pyridin-4-yl)-9H-pyrimido[4,5-b]indol-9-yl)acetate (354a) (169 mg, 72% yield); $^1H$ NMR (300 MHz, DMSO-$d_6$) δ 8.82 (d, J=5.2 Hz, 1H), 8.76-8.66 (m, 1H), 8.42 (d, J=1.6 Hz, 1H), 8.35 (s, 1H), 8.26 (dt, J=5.6, 1.2 Hz, 1H), 7.82 (d, J=1.7 Hz, 1H), 7.58 (bs, 2H), 5.39 (s, 2H), 2.74 (s, 3H), 1.44 (s, 9H); $^{19}F$ NMR (282 MHz, DMSO-$d_6$) δ−66.17. MS (ES+): 458 (M+1); (ES−): 456 (M−1).

Step-2: Preparation of 2-(4-amino-8-methyl-6-(2-(trifluoromethyl)pyridin-4-yl)-9H-pyrimido[4,5-b]indol-9-yl)acetic acid (354b)

Compound 354b was prepared according to the procedure reported in step-2 of scheme-1, from tert-butyl 2-(4-amino-8-methyl-6-(2-(trifluoromethyl)pyridin-4-yl)-9H-pyrimido[4,5-b]indol-9-yl)acetate (354a) (167 mg, 0.365 mmol) in DCM (5 mL) using TFA (416 mg, 3.65 mmol) to afford after workup TFA salt of 2-(4-amino-8-methyl-6-(2-(trifluoromethyl)pyridin-4-yl)-9H-pyrimido[4,5-b]indol-9-yl)acetic acid (354b) (233 mg) as a pale-yellow solid; $^1H$ NMR (300 MHz, DMSO-$d_6$) δ 8.86 (d, J=5.2 Hz, 1H), 8.81 (d, J=1.8 Hz, 1H), 8.57 (s, 1H), 8.45 (s, 2H), 8.41 (d, J=1.7 Hz, 1H), 8.26 (dd, J=5.2, 1.7 Hz, 1H), 7.93 (d, J=1.6 Hz, 1H), 5.48 (s, 2H), 2.79 (s, 3H); $^{19}F$ NMR (282 MHz, DMSO-$d_6$) δ−66.19, −74.61; MS (ES+): 402 (M+1); (ES−): 400 (M−1).

Step-3: Preparation of (1R,3S,5R)-2-(2-(4-amino-8-methyl-6-(2-(trifluoromethyl)pyridin-4-yl)-9H-pyrimido[4,5-b]indol-9-yl)acetyl)-N-(6-bromopyridin-2-yl)-2-azabicyclo[3.1.0]hexane-3-carboxamide (354c)

Compound 354c was prepared according to the procedure reported in step-3 of scheme-1, from TFA salt of 2-(4-amino-8-methyl-6-(2-(trifluoromethyl)pyridin-4-yl)-9H-pyrimido[4,5-b]indol-9-yl)acetic acid (354b) (60 mg, 0.116 mmol) in DMF (5 mL) using HCl salt of (1R,3S,5R)—N-(6-bromopyridin-2-yl)-2-azabicyclo[3.1.0]hexane-3-carboxamide (4a) (37.1 mg, 0.116 mmol), HATU (53.1 mg, 0.140 mmol), DIPEA (75 mg, 0.582 mmol) and stirring at RT for 16 h. This gave after workup and purification as described in scheme-299, (1R,3S,5R)-2-(2-(4-amino-8-methyl-6-(2-(trifluoromethyl)pyridin-4-yl)-9H-pyrimido[4,5-b]indol-9-yl)acetyl)-N-(6-bromopyridin-2-yl)-2-azabicyclo[3.1.0]hexane-3-carboxamide (354c) (52 mg, 67% yield) HCl salt as a white solid; $^1H$ NMR (300 MHz, DMSO-$d_6$) δ 10.84 (s, 1H, $D_2O$ exchangeable), 8.85 (d, J=5.6 Hz, 1H), 8.84 (s, 1H), 8.79 (bs, 2H, $D_2O$ exchangeable), 8.65 (s, 1H), 8.40 (d, J=1.7 Hz, 1H), 8.26 (dd, J=5.3, 1.7 Hz, 1H), 8.01 (d, J=8.2 Hz, 1H), 7.93 (s, 1H), 7.71 (t, J=8.0 Hz, 1H), 7.31 (d, J=7.7 Hz, 1H), 5.97 (d, J=18.0 Hz, 1H), 5.68 (d, J=17.9 Hz, 1H), 4.44 (dd, J=9.0, 5.7 Hz, 1H), 4.00-3.92 (m, 1H), 2.81 (s, 3H), 2.43-2.30 (m, 1H), 2.30-2.11 (m, 1H), 2.05-1.85 (m, 1H), 1.18-1.00 (m, 1H), 0.81-0.60 (m, 1H); $^{19}F$ NMR (282 MHz, DMSO-$d_6$) δ−66.18; MS (ES+): 665/667 (M+1), (ES−): 663/665 (M−1); Analysis calculated for $C_{30}H_{24}BrF_3N_8O_2{\cdot}1.3HCl{\cdot}1.75H_2O$: C, 48.40; H, 3.90; Cl, 6.19; N, 15.05. Found: C, 48.48; H, 3.70; Cl, 6.30. N, 14.97.

Scheme 355

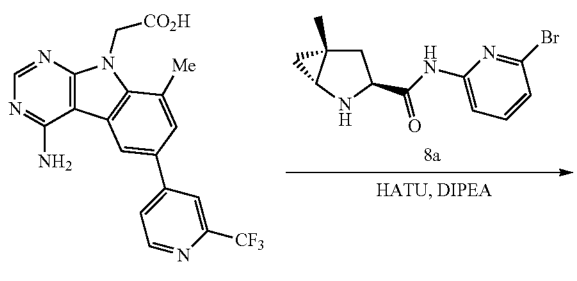

8a

354b

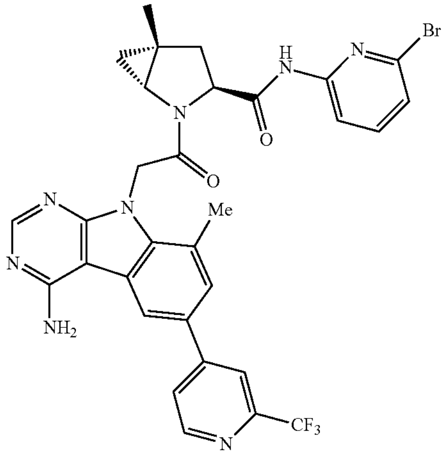

355a

Preparation of (1R,3S,5R)-2-(2-(4-amino-8-methyl-6-(2-(trifluoromethyl)pyridin-4-yl)-9H-pyrimido[4,5-b]indol-9-yl)acetyl)-N-(6-bromopyridin-2-yl)-5-methyl-2-azabicyclo[3.1.0]hexane-3-carboxamide (355a)

Compound 355a was prepared according to the procedure reported in step-3 of scheme-1, from TFA salt of 2-(4-amino-8-methyl-6-(2-(trifluoromethyl)pyridin-4-yl)-9H-pyrimido[4,5-b]indol-9-yl)acetic acid (354b) (60 mg, 0.116 mmol) in DMF (5 mL) using HCl salt of (1R,3S,5R)—N-(6-bromopyridin-2-yl)-5-methyl-2-azabicyclo[3.1.0]hexane-3-carboxamide (8a) (38.7 mg, 0.116 mmol), HATU (53.1 mg, 0.140 mmol), DIPEA (75 mg, 0.582 mmol) and stirring at RT for 16 h. This gave after workup and purification as described in scheme-299. (1R,3S,5R)-2-(2-(4-amino-8-methyl-6-(2-(trifluoromethyl)pyridin-4-yl)-9H-pyrimido[4,5-b]indol-9-yl)acetyl)-N-(6-bromopyridin-2-yl)-5-methyl-2-azabicyclo[3.1.0]hexane-3-carboxamide (355a) (55 mg, 70% yield) HCl salt as a white solid: $^1$H NMR (300 MHz, DMSO-$d_6$) δ 10.84 (s, 1H, $D_2O$ exchangeable), 8.99-8.69 (m, 4H, in which 2H were $D_2O$ exchangeable), 8.65 (s, 1H), 8.39 (d, J=1.7 Hz, 1H), 8.26 (dd, J=5.2, 1.7 Hz, 1H), 8.02 (d, J=8.2 Hz, 1H), 7.92 (d, J=1.7 Hz, 1H), 7.71 (t, J=8.0 Hz, 1H), 7.31 (d, J=7.7 Hz, 1H), 5.91 (d, J=18.0 Hz, 1H), 5.63 (d, J=17.9 Hz, 1H), 4.40 (dd, J=9.0, 6.1 Hz, 1H), 3.74-3.69 (m, 1H), 2.79 (s, 3H), 2.49-2.44 (m, 1H), 1.99 (dd, J=13.2, 6.0 Hz, 1H), 1.32 (s, 3H), 1.08-0.96 (m, 1H), 0.93-0.81 (m, 1H); $^{19}$F NMR (282 MHz, DMSO-$d_6$) δ−66.18; MS (ES+): 679/681 (M+1); (ES−): 677/679 (M−1); Analysis calculated for $C_3H_{26}BrF_3N_8O_2 \cdot 0.25HCl \cdot 4H_2O$: C, 48.95; H, 4.54; Cl, 1.17; N, 14.73. Found: C, 48.94; H, 3.99; Cl, 1.07; N, 14.73.

Scheme 356

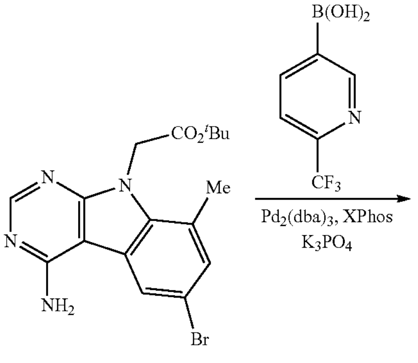

192e

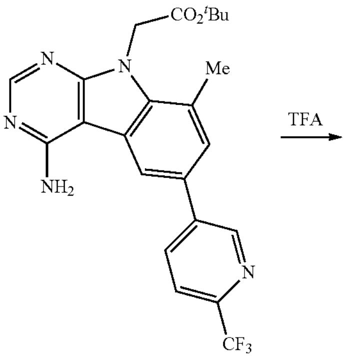

356a

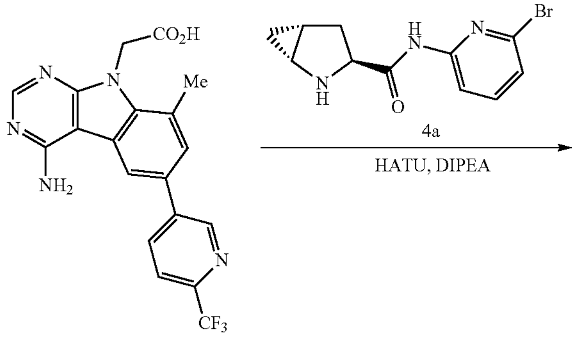

4a

356b

-continued

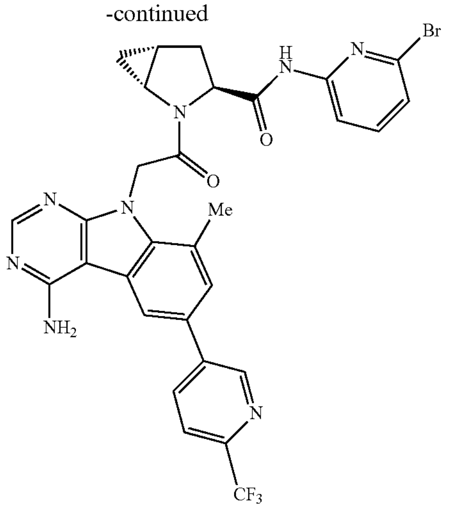

356c

Preparation of (1R,3S,5R)-2-(2-(4-amino-8-methyl-6-(6-(trifluoromethyl)pyridin-3-yl)-9H-pyrimido[4,5-b]indol-9-yl)acetyl)-N-(6-bromopyridin-2-yl)-2-azabicyclo[3.1.0]hexane-3-carboxamide (356c)

Step-1: Preparation of tert-butyl 2-(4-amino-8-methyl-6-(6-(trifluoromethyl)pyridin-3-yl)-9H-pyrimido[4,5-b]indol-9-yl)acetate (356a)

Compound 356a was prepared according to the procedure reported in scheme-263 and step-1 of scheme-354, from tert-butyl 2-(4-amino-6-bromo-8-methyl-9H-pyrimido[4,5-b]indol-9-yl)acetate (192e) (200 mg, 0.511 mmol) and (6-(trifluoromethyl)pyridin-3-yl)boronic acid (146 mg, 0.767 mmol) to afford tert-butyl 2-(4-amino-8-methyl-6-(6-(trifluoromethyl)pyridin-3-yl)-9H-pyrimido[4,5-b]indol-9-yl) acetate (356a) (214 mg, 92% yield) as a white solid; $^1$H NMR (300 MHz, DMSO-$d_6$) δ 9.30 (d, J=2.4 Hz, 1H), 8.66 (s, 11H), 8.54 (d, J=8.3 Hz, 1H), 8.34 (d, J=1.8 Hz, 11H), 8.01 (dd, J=8.3, 1.8 Hz, 1H), 7.70 (s, 1H), 7.52 (bs, 2H), 5.38 (s, 2H), 2.73 (s, 3H), 1.45 (s, 9H); $^{19}$F NMR (282 MHz, DMSO $d_6$) δ −66.02; MS (ES+): 458 (M+1); (ES−): 456 (M−1).

Step-2: Preparation of 2-(4-amino-8-methyl-6-(6-(trifluoromethyl)pyridin-3-yl)-9H-pyrimido[4,5-b]indol-9-yl)acetic acid (356b)

Compound 356b was prepared according to the procedure reported in step-2 of scheme-1, from tert-butyl 2-(4-amino-8-methyl-6-(6-(trifluoromethyl)pyridin-3-yl)-9H-pyrimido[4,5-b]indol-9-yl)acetate (356a) (210 mg, 0.459 mmol) in DCM (5 mL) using TFA (523 mg, 4.59 mmol) to afford TFA salt of 2-(4-amino-8-methyl-6-(6-(trifluoromethyl)pyridin-3-yl)-9H-pyrimido[4,5-b]indol-9-yl)acetic acid (356b) (298 mg) as a pale-yellow solid; $^1$H NMR (300 MHz, DMSO-$d_6$) δ 9.30 (d, J=2.2 Hz, 1H), 8.77 (d, J=1.8 Hz, 1H), 8.58 (s, 1H), 8.55 (dd, J=8.4, 2.2 Hz, 1H), 8.49 (s, 1H), 8.05 (d, J=8.3 Hz, 1H), 7.82 (d, J=1.7 Hz, 1H), 5.48 (s, 2H), 2.78 (s, 3H); $^{19}$F NMR (282 MHz, DMSO $d_6$) δ−66.07, −74.59; MS (ES+): 402 (M+1); (ES−): 400 (M−1).

Step-3: Preparation of (1R,3S,5R)-2-(2-(4-amino-8-methyl-6-(6-(trifluoromethyl)pyridin-3-yl)-9H-pyrimido[4,5-b]indol-9-yl)acetyl)-N-(6-bromopyridin-2-yl)-2-azabicyclo[3.1.0]hexane-3-carboxamide (356c)

Compound 356c was prepared according to the procedure reported in step-3 of scheme-1, from TFA salt of 2-(4-amino-8-methyl-6-(6-(trifluoromethyl)pyridin-3-yl)-9H-pyrimido[4,5-b]indol-9-yl)acetic acid (356b) (60 mg, 0.116 mmol) in DMF (5 mL) using HCl salt of (1R,3S,5R)—N-(6-bromopyridin-2-yl)-2-azabicyclo[3.1.0]hexane-3-carboxamide (4a) (37.1 mg, 0.116 mmol), HATU (53.1 mg, 0.140 mmol), DIPEA (75 mg, 0.582 mmol) and stirring at RT for 16 h. This gave after workup and purification as described in scheme-299, (1R,3S,5R)-2-(2-(4-amino-8-methyl-6-(6-(trifluoromethyl)pyridin-3-yl)-9H-pyrimido[4,5-b]indol-9-yl)acetyl)-N-(6-bromopyridin-2-yl)-2-azabicyclo[3.1.0]hexane-3-carboxamide (356c) (47 mg, 61% yield) HCl salt as a white solid; $^1$H NMR (300 MHz, DMSO-$d_6$) δ 10.84 (s, 1H, $D_2O$ exchangeable), 9.29 (d, J=2.2 Hz, 1H), 8.78 (d, J=1.8 Hz, 1H), 8.68 (bs, 2H, $D_2O$ exchangeable), 8.62 (s, 1H), 8.54 (dd, J=8.1, 2.2 Hz, 1H), 8.10-7.97 (m, 2H), 7.80 (s, 1H), 7.71 (t, J=8.0 Hz, 1H), 7.32 (d, J=7.7 Hz, 1H), 5.96 (d, J=18.0 Hz, 1H), 5.68 (d, J=17.9 Hz, 1H), 4.44 (dd, J=9.0, 5.7 Hz, 1H), 4.01-3.90 (m, 1H), 2.80 (s, 3H), 2.44-2.30 (m, 1H), 2.30-2.13 (m, 1H), 2.03-1.86 (m, 1H), 1.18-1.04 (m, 1H), 0.80-0.63 (m, 1H); $^{19}$F NMR (282 MHz, DMSO-$d_6$) δ−66.08; MS (ES+): 665/667 (M+1); (ES−): 663/665 (M−1); Analysis calculated for $C_{30}H_{24}BrF_3N_8O_2 \cdot 1.1HCl \cdot 2.5H_2O$: C, 48.00; H, 4.04; Cl, 5.20: N, 14.93. Found: C, 48.10; H, 3.54; Cl, 5.27; N, 14.93.

Scheme 357

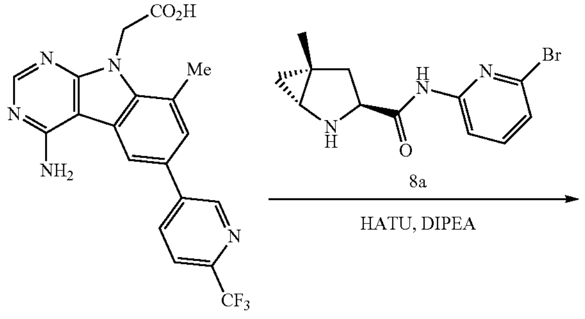

356b

-continued

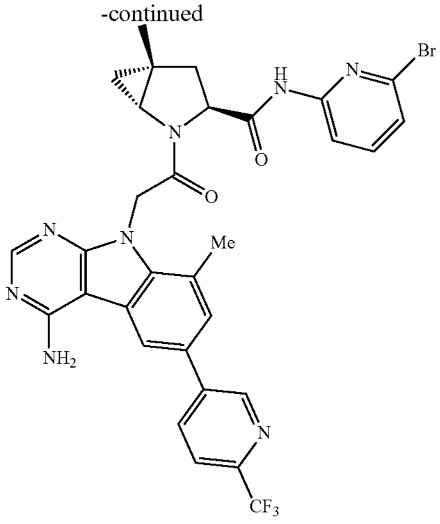

357a

Preparation of (1R,3S,5R)-2-(2-(4-amino-8-methyl-6-(6-(trifluoromethyl)pyridin-3-yl)-9H-pyrimido[4,5-b]indol-9-yl)acetyl)-N-(6-bromopyridin-2-yl)-5-methyl-2-azabicyclo[3.1.0]hexane-3-carboxamide (357a)

Compound 357a was prepared according to the procedure reported in step-3 of scheme-1, from TFA salt of 2-(4-amino-8-methyl-6-(6-(trifluoromethyl)pyridin-3-yl)-9H-pyrimido[4,5-b]indol-9-yl)acetic acid (356b) (60 mg, 0.116 mmol) in DMF (5 mL) using HCl salt of (1R,3S,5R)—N-(6-bromopyridin-2-yl)-5-methyl-2-azabicyclo[3.1.0]hexane-3-carboxamide (8a) (38.7 mg, 0.116 mmol), HATU (53.1 mg, 0.140 mmol), DIPEA (75 mg, 0.582 mmol) and stirring at RT for 16 h. This gave after workup and purification as described in scheme-299, (1R,3S,5R)-2-(2-(4-amino-8-methyl-6-(6-(trifluoromethyl)pyridin-3-yl)-9H-pyrimido[4,5-b]indol-9-yl)acetyl)-N-(6-bromopyridin-2-yl)-5-methyl-2-azabicyclo[3.1.0]hexane-3-carboxamide (357a) (50 mg, 63% yield) HCl salt as a white solid; $^1$H NMR (300 MHz, DMSO-$d_6$) δ 10.84 (s, 1H, $D_2O$ exchangeable), 9.29 (d, J=2.2 Hz, 1H), 8.99-8.69 (m, 3H, in which 2H were $D_2O$ exchangeable), 8.63 (s, 1H), 8.54 (dd, J=8.0, 2.3 Hz, 1H), 8.04 (d, J=3.0 Hz, 1H), 8.01 (d, J=3.0 Hz, 1H), 7.79 (s, 1H), 7.71 (t, J=8.0 Hz, 1H), 7.31 (d, J=7.7 Hz, 1H), 5.90 (d, J=18.0 Hz, 1H), 5.61 (d, J=17.8 Hz, 1H), 4.40 (dd, J=9.0, 6.2 Hz, 1H), 3.75-3.68 (m, 1H), 2.77 (s, 3H), 2.49-2.39 (m, 1H), 1.99 (dd, J=13.3, 6.0 Hz, 1H), 1.32 (s, 3H), 1.07-0.96 (m, 1H), 0.90-0.74 (m, 1H); $^{19}$F NMR (282 MHz, DMSO-$d_6$) δ−66.09; MS (ES+): 679/681 (M+1); (ES−): 677/679 (M−1); Analysis calculated for $C_{31}H_{26}BrF_3N_8O_2 \cdot 1.15HCl \cdot 2H_2O$: C, 49.16; H, 4.15; Cl, 5.38; N, 14.79. Found: C, 49.25; H, 3.91; Cl, 5.37; N, 14.83.

Scheme 358

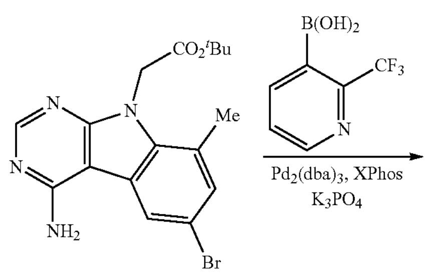

192e

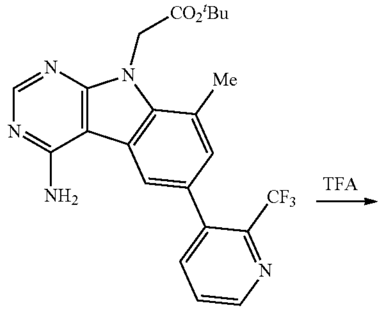

358a

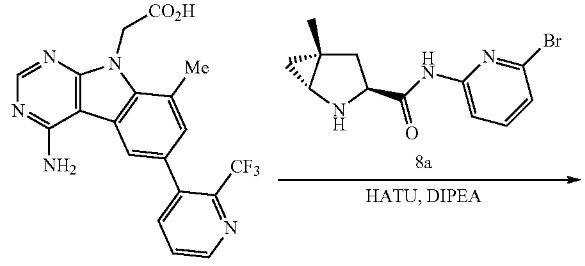

358b

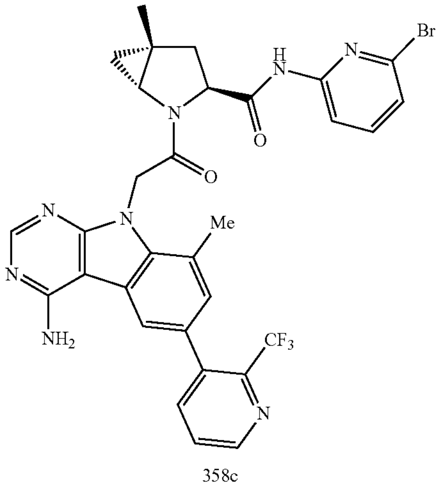

358c

Preparation of (1R,3S,5R)-2-(2-(4-amino-8-methyl-6-(2-(trifluoromethyl)pyridin-3-yl)-9H-pyrimido[4,5-b]indol-9-yl)acetyl)-N-(6-bromopyridin-2-yl)-5-methyl-2-azabicyclo[3.1.0]hexane-3-carboxamide (35c)

Step-1: Preparation of tert-butyl 2-(4-amino-8-methyl-6-(2-(trifluoromethyl)pyridin-3-yl)-9H-pyrimido[4,5-b]indol-9-yl)acetate (358a)

Compound 358a was prepared according to the procedure reported in scheme-263 and step-1 of scheme-354, from tert-butyl 2-(4-amino-6-bromo-8-methyl-9H-pyrimido[4,5-b]indol-9-yl)acetate (192e) (200 mg, 0.511 mmol) and (2-(trifluoromethyl)pyridin-3-yl)boronic acid (98 mg, 0.511 mmol) to afford tert-butyl 2-(4-amino-8-methyl-6-(2-(trifluoromethyl)pyridin-3-yl)-9H-pyrimido[4,5-b]indol-9-yl) acetate (358a) (21 mg, 9% yield); MS (ES+): 458 (M+1): (ES−): 456 (M−1).

Step-2: Preparation of 2-(4-amino-8-methyl-6-(2-(trifluoromethyl)pyridin-3-yl)-9H-pyrimido[4,5-b]indol-9-yl)acetic acid (358b)

Compound 358b was prepared according to the procedure reported in step-2 of scheme-1, from tert-butyl 2-(4-amino-8-methyl-6-(2-(trifluoromethyl)pyridin-3-yl)-9H-pyrimido[4,5-b]indol-9-yl)acetate (358a) (21 mg, 0.456 mmol) in DCM (5 mL) using TFA (52.3 mg, 0.459 mmol) to afford TFA salt of 2-(4-amino-8-methyl-6-(2-(trifluoromethyl)pyridin-3-yl)-9H-pyrimido[4,5-b]indol-9-yl)acetic acid (358b) (26 mg) as a pale-yellow solid; MS (ES+): 402 (M+1); (ES−): 400 (M−1).

Step-3: Preparation of (1R,3S,5R)-2-(2-(4-amino-8-methyl-6-(2-(trifluoromethyl)pyridin-3-yl)-9H-pyrimido[4,5-b]indol-9-yl)acetyl)-N-(6-bromopyridin-2-yl)-5-methyl-2-azabicyclo[3.1.0]hexane-3-carboxamide (358c)

Compound 358c was prepared according to the procedure reported in step-3 of scheme-1, from TFA salt of 2-(4-amino-8-methyl-6-(2-(trifluoromethyl)pyridin-3-yl)-9H-pyrimido[4,5-b]indol-9-yl)acetic acid (358b) (26 mg, 0.050 mmol) in DMF (5 mL) using HCl salt of (1R,3S,5R)—N-(6-bromopyridin-2-yl)-5-methyl-2-azabicyclo[3.1.0]hexane-3-carboxamide (8a) (16.78 mg, 0.050 mmol), HATU (23.02 mg, 0.061 mmol), DIPEA (32.6 mg, 0.252 mmol) and stirring at RT for 16 h. This gave after workup and purification as described in scheme-299, (1R,3S,5R)-2-(2-(4-amino-8-methyl-6-(2-(trifluoromethyl)pyridin-3-yl)-9H-pyrimido[4,5-b]indol-9-yl)acetyl)-N-(6-bromopyridin-2-yl)-5-methyl-2-azabicyclo[3.1.0]hexane-3-carboxamide (358c) (21 mg, 0.031 mmol, 61.3% yield) HCl salt as a pale-yellow solid; $^1$H NMR (300 MHz, DMSO-$d_6$) δ 10.85 (s, 1H $D_2O$ exchangeable), 8.81 (d, J=4.7 Hz, 1H), 8.61 (d, J=2.0 Hz, 1H), 8.42 (bs, 2H, $D_2O$ exchangeable), 8.38 (s, 1H), 8.12-7.95 (m, 2H), 7.83 (dd, J=7.8, 4.7 Hz, 1H), 7.71 (t, J=7.9 Hz, 1H), 7.32 (d, J=7.8 Hz, 1H), 7.26 (s, 1H), 5.92 (d, J=17.9 Hz, 1H), 5.65 (d, J=18.0 Hz, 1H), 4.49-4.33 (m, 1H), 3.74-3.69 (m, 1H), 2.73 (s, 3H), 2.49-2.45 (m, 1H), 1.99 (dd, J=13.2, 6.1 Hz, 1H), 1.32 (s, 3H), 1.10-0.97 (m, 1H), 0.93-0.80 (m, 1H); $^{19}$F NMR (282 MHz, DMSO-$d_6$) δ−59.64; MS (ES+): 679/681 (M+1); (ES−): 677/679 (M−1).

Scheme 359

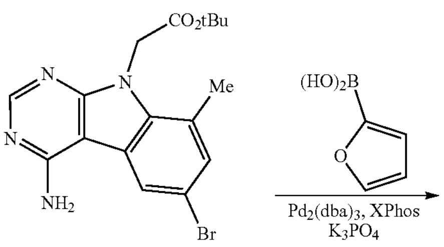

192e

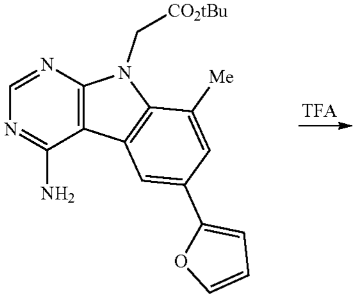

359a

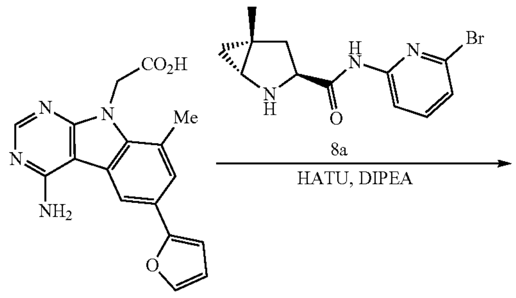

359b

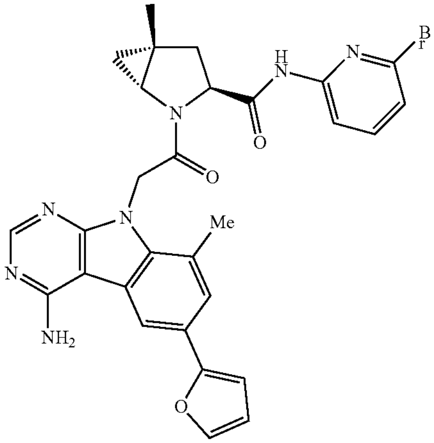

359c

Preparation of (1R,3S,5R)-2-(2-(4-amino-6-(furan-2-yl)-8-methyl-9H-pyrimido[4,5-b]indol-9-yl)acetyl)-N-(6-bromopyridin-2-yl)-5-methyl-2-azabicyclo[3.1.0]hexane-3-carboxamide (359c)

Step-1: Preparation of tert-butyl 2-(4-amino-6-(furan-2-yl)-8-methyl-9H-pyrimido[4,5-b]indol-9-yl)acetate (359a)

Compound 359a was prepared according to the procedure reported in scheme-263 and step-1 of scheme-354, from tert-butyl 2-(4-amino-6-bromo-8-methyl-9H-pyrimido[4,5-b]indol-9-yl)acetate (192e) (180 mg, 0.460 mmol) and furan-2-ylboronic acid (103 mg, 0.920 mmol), to afford tert-butyl 2-(4-amino-6-(furan-2-yl)-8-methyl-9H-pyrimido[4,5-b]indol-9-yl)acetate (359a) (158 mg, 91% yield) as a pale-yellow solid; $^1$H NMR (300 MHz, DMSO-$d_6$) δ 8.49 (d, J=1.7 Hz, 1H), 8.31 (s, 1H), 7.74 (d, J=1.8 Hz, 1H), 7.54 (s, 1H), 7.42 (bs, 2H), 7.03 (d, J=3.3 Hz, 1H), 6.62 (dd, J=3.4, 1.8 Hz, 1H), 5.34 (s, 2H), 2.67 (s, 3H), 1.43 (s, 9H); MS (ES+): 379 (M+1); (ES−): 377 (M−1).

Step-2: Preparation of 2-(4-amino-6-(furan-2-yl)-8-methyl-9H-pyrimido[4,5-b]indol-9-yl)acetic acid (359b)

Compound 359b was prepared according to the procedure reported in step-2 of scheme-1, from tert-butyl 2-(4-amino-6-(furan-2-yl)-8-methyl-9H-pyrimido[4,5-b]indol-9-yl)acetate (359a) (158 mg, 0.418 mmol) in DCM (5 mL) using TFA (476 mg, 4.18 mmol) to afford TFA salt of 2-(4-amino-6-(furan-2-yl)-8-methyl-9H-pyrimido[4,5-b]indol-9-yl)acetic acid (359b) (196 mg) as a green solid; $^1$H NMR (300 MHz, DMSO-$d_6$) δ 8.54 (d, J=1.6 Hz, 1H), 8.52-8.45 (m, 3H), 7.70 (d, J=1.8 Hz, 1H), 7.58 (s, 1H), 6.96 (d, J=3.3 Hz, 1H), 6.57 (dd. J=3.4, 1.8 Hz, 1H), 5.36 (s, 2H), 2.64 (s, 3H); MS (ES+): 323 (M+1), (ES−): 321 (M−1).

Step-3: Preparation of (1R,3S,5R)-2-(2-(4-amino-6-(furan-2-yl)-8-methyl-9H-pyrimido[4,5-b]indol-9-yl)acetyl)-N-(6-bromopyridin-2-yl)-5-methyl-2-azabicyclo[3.1.0]hexane-3-carboxamide (359c)

Compound 359c was prepared according to the procedure reported in step-3 of scheme-1, from TFA salt of 2-(4-amino-6-(furan-2-yl)-8-methyl-9H-pyrimido[4,5-b]indol-9-yl)acetic acid (359b) (60 mg, 0.138 mmol) in DMF (5 mL) using HCl salt of (1R,3S,5R)—N-(6-bromopyridin-2-yl)-5-methyl-2-azabicyclo[3.1.0]hexane-3-carboxamide (8a) (45.7 mg, 0.138 mmol), HATU (62.7 mg, 0.165 mmol), DIPEA (89 mg, 0.688 mmol) and stirring at RT for 16 h. This gave after workup and purification as described in scheme-299, (1R,3S,5R)-2-(2-(4-amino-6-(furan-2-yl)-8-methyl-9H-pyrimido[4,5-b]indol-9-yl)acetyl)-N-(6-bromopyridin-2-yl)-5-methyl-2-azabicyclo[3.1.0]hexane-3-carboxamide (359c) (27 mg, 33% yield) HCl salt as a white solid; 1H NMR (300 MHz, DMSO-$d_6$) δ 10.83 (s, 1H, $D_2O$ exchangeable), 8.60 (s, 1H), 8.55 (s, 1H), 8.46 (bs, 2H, $D_2O$ exchangeable), 8.02 (d, J=8.2 Hz, 1H), 7.77 (d, J=1.7 Hz, 1H), 7.71 (t, J=8.0 Hz, 1H), 7.63 (s, 1H), 7.31 (d, J=7.7 Hz, 1H), 7.03 (d, J=3.4 Hz, 1H), 6.69-6.59 (m, 1H), 5.86 (d, J=17.8 Hz, 1H), 5.59 (d, J=17.8 Hz, 1H), 4.39 (dd, J=9.1, 6.2 Hz, 1H), 3.73-3.67 (m, 1H), 2.72 (s, 3H), 2.49-2.42 (m, 1H), 1.99 (dd, J=13.3, 6.1 Hz, 1H), 1.31 (s, 3H), 1.09-0.96 (m, 1H), 0.91-0.73 (m, 1H); MS (ES+): 600/602 (M+1); (ES−): 598/600 (M−1).

Scheme 360

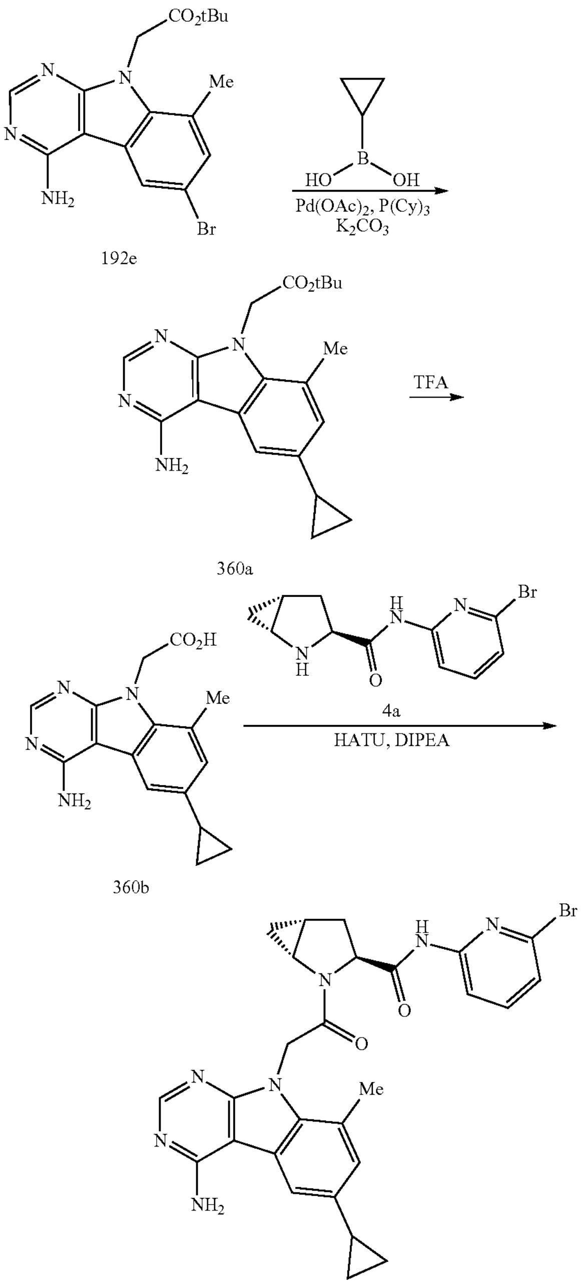

192e

360a

360b

360c

Preparation of (1R,3S,5R)-2-(2-(4-amino-6-cyclopropyl-8-methyl-9H-pyrimido[4,5-b]indol-9-yl)acetyl)-N-(6-bromopyridin-2-yl)-2-azabicyclo[3.1.0]hexane-3-carboxamide (360c)

Step-1: Preparation of tert-butyl 2-(4-amino-6-cyclopropyl-8-methyl-9H-pyrimido[4,5-b]indol-9-yl)acetate (360a)

Compound 360a was prepared according to the procedure reported in step-1 of scheme-59 and step-1 of scheme-354, from tert-butyl 2-(4-amino-6-bromo-8-methyl-9H-pyrimido

[4,5-b]indol-9-yl)acetate (192e) (180 mg, 0.460 mmol) and cyclopropyl boronic acid (79 mg, 0.920 mmol) to afford tert-butyl 2-(4-amino-6-cyclopropyl-8-methyl-9H-pyrimido [4,5-b]indol-9-yl)acetate (360a) (157 mg, 97% yield); $^1$H NMR (300 MHz, DMSO-$d_6$) δ 8.80 (bs, 2H), 8.63 (s, 1H), 8.00 (d, J=1.7 Hz, 1H), 7.11 (d, J=1.6 Hz, 1H), 5.41 (s, 2H), 2.63 (s, 3H), 2.13-1.91 (m, 1H), 1.44 (s, 9H), 1.07-0.95 (m, 2H), 0.89-0.73 (m, 2H); MS (ES+): 353 (M+1); (ES−): 351 (M−1).

Step-2: Preparation of 2-(4-amino-6-cyclopropyl-8-methyl-9H-pyrimido[4,5-b]indol-9-yl)acetic acid (360b)

Compound 360b was prepared according to the procedure reported in step-2 of scheme-1, from tert-butyl 2-(4-amino-6-cyclopropyl-8-methyl-9H-pyrimido[4,5-b]indol-9-yl)acetate (360a) (151 mg, 0.428 mmol) in DCM (5 mL) using TFA (489 mg, 4.28 mmol) to afford TFA salt of 2-(4-amino-6-cyclopropyl-8-methyl-9H-pyrimido[4,5-b]indol-9-yl)acetic acid (360b) (186 mg) as a white solid; $^1$H NMR (300 MHz, DMSO-$d_6$) δ 8.63 (bs, 2H), 8.59 (s, 1H), 7.96 (d, J=1.7 Hz, 1H), 7.10 (s, 1H), 5.41 (s, 2H), 2.65 (s, 3H), 2.13-1.94 (m, 1H), 1.09-0.93 (m, 2H), 0.88-0.72 (m, 2H); MS (ES+): 297 (M+1); (ES−): 295 (M−1).

Step-3: Preparation of (1R,3S,5R)-2-(2-(4-amino-6-cyclopropyl-8-methyl-9H-pyrimido[4,5-b]indol-9-yl)acetyl)-N-(6-bromopyridin-2-yl)-2-azabicyclo [3.1.0]hexane-3-carboxamide (360c)

Compound 360c was prepared according to the procedure reported in step-3 of scheme-1, from TFA salt of 2-(4-amino-6-cyclopropyl-8-methyl-9H-pyrimido[4,5-b]indol-9-yl)acetic acid (360b) (66 mg, 0.161 mmol) in DMF (5 mL) using HCl salt of (1R,3S,5R)—N-(6-bromopyridin-2-yl)-2-azabicyclo[3.1.0]hexane-3-carboxamide (4a) (51.2 mg, 0.161 mmol), HATU (73.4 mg, 0.193 mmol), DIPEA (104 mg, 0.804 mmol) and stirring at RT for 16 h. This gave after workup and purification as described in scheme-299, (1R, 3S,5R)-2-(2-(4-amino-6-cyclopropyl-8-methyl-9H-pyrimido[4,5-b]indol-9-yl)acetyl)-N-(6-bromopyridin-2-yl)-2-azabicyclo[3.1.0]hexane-3-carboxamide (360c) (39 mg, 43% yield) HCl salt as a white solid: $^1$H NMR (300 MHz, DMSO-$d_6$) δ 10.82 (s, 1H, $D_2O$ exchangeable), 8.89-8.33 (m, 3H, in which 2H were $D_2O$ exchangeable), 8.01 (d, J=8.2 Hz, 1H), 7.96 (d, J=1.7 Hz, 1H), 7.71 (t, J=8.0 Hz, 1H), 7.32 (d, J=7.7 Hz, 1H), 7.06 (s, 1H), 5.88 (d, J=17.9 Hz, 1H), 5.61 (d, J=17.9 Hz, 1H), 4.42 (dd, J=9.1, 5.7 Hz, 1H), 3.98-3.86 (m, 1H), 2.66 (s, 3H), 2.42-2.28 (m, 1H), 2.27-2.13 (m, 1H), 2.08-1.97 (m, 1H), 1.96-1.86 (m, 1H), 1.14-1.02 (m, 1H), 1.02-0.92 (m, 2H), 0.87-0.77 (m, 2H), 0.73-0.64 (m, 1H); MS (ES+): 560/562 (M+1): (ES−): 558/560 (M−1): Analysis calculated for $C_{27}H_{26}BrN_7O_2 \cdot 1.35HCl \cdot 2.75H_2O$: C, 49.19; H, 5.02; Cl, 7.26; N, 14.87. Found: C, 49.09; H, 4.77; Cl, 7.30; N, 14.93.

Scheme 361

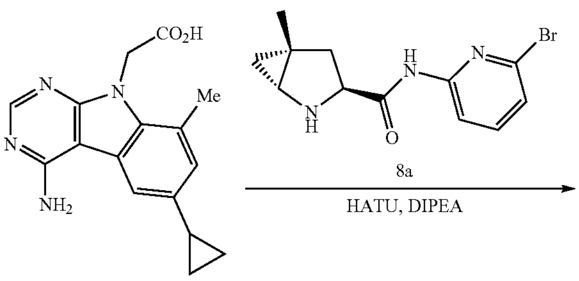

360b

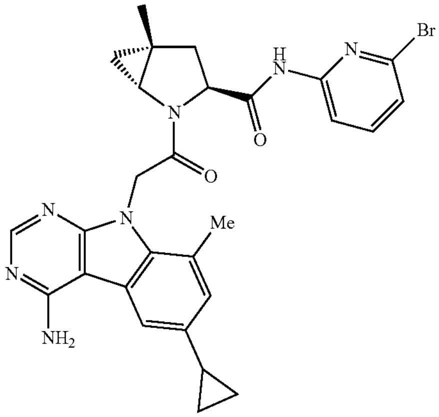

361a

Preparation of (1R,3S,5R)-2-(2-(4-amino-6-cyclopropyl-8-methyl-9H-pyrimido[4,5-b]indol-9-yl) acetyl)-N-(6-bromopyridin-2-yl)-5-methyl-2-azabicyclo[3.1.0]hexane-3-carboxamide (361a)

Compound 361a was prepared according to the procedure reported in step-3 of scheme-1, from TFA salt of 2-(4-amino-6-cyclopropyl-8-methyl-9H-pyrimido[4,5-b]indol-9-yl)acetic acid (360b) (60 mg, 0.146 mmol) in DMF (5 mL) using HCl salt of (1R,3S,5R)—N-(6-bromopyridin-2-yl)-5-methyl-2-azabicyclo[3.1.0]hexane-3-carboxamide (8a) (48.6 mg, 0.146 mmol), HATU (66.7 mg, 0.175 mmol), DIPEA (94 mg, 0.731 mmol) and stirring at RT for 16 h. This gave after workup and purification as described in scheme-299, (1R,3S,5R)-2-(2-(4-amino-6-cyclopropyl-8-methyl-9H-pyrimido[4,5-b]indol-9-yl)acetyl)-N-(6-bromopyridin-2-yl)-5-methyl-2-azabicyclo[3.1.0]hexane-3-carboxamide (361a) (49 mg, 58% yield) HCl salt as a white solid: $^1$H NMR (300 MHz, DMSO-$d_6$) δ 10.82 (s, 1H, $D_2O$ exchangeable), 8.73 (bs, 2H, $D_2O$ exchangeable), 8.61 (s, 1H), 8.01 (d, J=8.2 Hz, 1H), 7.96 (d, J=1.7 Hz, 1H), 7.71 (t, J=8.0 Hz, 1H), 7.32 (d, J=7.7 Hz, 1H), 7.06 (d, J=1.6 Hz, 1H), 5.83 (d, J=17.9 Hz, 1H), 5.56 (d, J=17.9 Hz, 1H), 4.38 (dd, J=9.0, 6.1 Hz, 1H), 3.72-3.66 (m, 1H), 2.64 (s, 3H), 2.49-2.36 (m, 1H), 2.07-1.89 (m, 2H), 1.31 (s, 3H), 1.06-0.91 (m, 3H), 0.89-0.76 (m, 3H); MS (ES+): 574/576 (M+1); (ES−): 572/574 (M−1); Analysis calculated for $C_{28}H_{28}BrN_7O_2 \cdot HCl \cdot 2H_2O$: C, 51.98; H, 5.14; Cl, 5.48; N, 15.15. Found: C, 51.82; H, 5.01; Cl, 5.44; N, 15.22.

Scheme 362

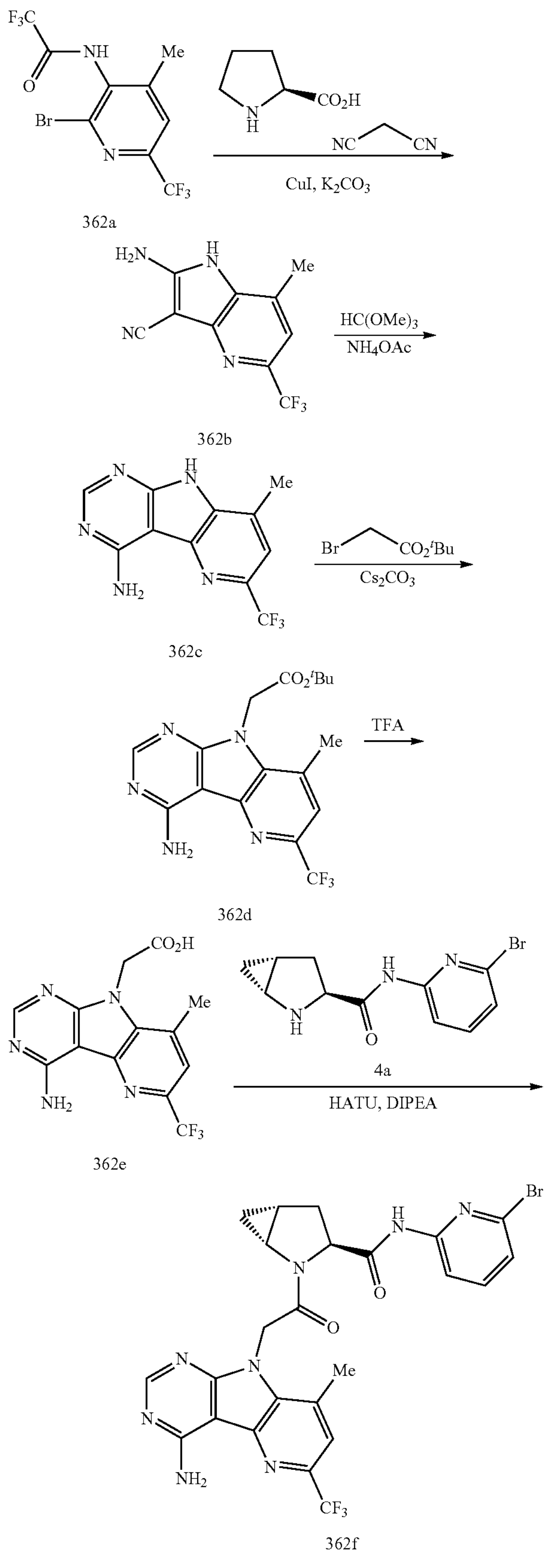

Preparation of (1R,3S,5R)-2-(2-(4-amino-8-methyl-6-(trifluoromethyl)-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (362f)

Step-1: Preparation of 2-amino-7-methyl-5-(trifluoromethyl)-1H-pyrrolo[3,2-b]pyridine-3-carbonitrile (362b)

Compound 362b was prepared according to the procedure reported in step-1 of scheme-11, from N-(2-bromo-4-methyl-6-(trifluoromethyl)pyridin-3-yl)-2,2,2-trifluoroacetamide (362a) (4.87 g, 13.87 mmol; CAS #2055497-18-0) in DMSO (30 mL) using malononitrile (1.100 g, 16.65 mmol), L-proline (0.319 g, 2.77 mmol), CuI (0.264 g, 1.387 mmol), a solution of $K_2CO_3$ (3.83 g, 27.7 mmol) in water (10 mL) to afford after purification [$SiO_2$ gel (80 g), MeOH in DCM from 0-10%] 2-amino-7-methyl-5-(trifluoromethyl)-1H-pyrrolo[3,2-b]pyridinic-3-carbonitrile (362b) (3.38 g) as a pale-yellow solid; $^1$H NMR (300 MHz, DMSO-$d_6$) δ 11.52 (s, 1H), 7.31 (s, 2H), 7.22 (s, 1H), 2.43 (s, 3H); $^{19}$F NMR (282 MHz, DMSO) δ−64.38; MS (ES+): 241 (M+1): (ES−): 239 (M−1).

Step-2: Preparation of 8-methyl-6-(trifluoromethyl)-9H-pyrido[2',3':4,5]pyrrolo[2,3-d]pyrimidin-4-amine (362c)

Compound 362c was prepared according to the procedure reported in step-2 of scheme-29, from 2-amino-7-methyl-5-(trifluoromethyl)-1H-pyrrolo[3,2-b]pyridine-3-carbonitrile (362b) (3.38 g, 14.07 mmol) using trimethoxymethane (7.47 g, 70.4 mmol) and $NH_4OAc$ (3.25 g, 42.2 mmol) to afford 8-methyl-6-(trifluoromethyl)-9H-pyrido[2',3':4,5]pyrrolo[2,3-d]pyrimidin-4-amine (362c) (3.28 g, 87% yield) as a green solid; $^1$H NMR (300 MHz, DMSO-$d_6$) δ 12.57 (s, 1H), 8.43 (s, 1H), 7.99 (s, 1H), 7.72 (s, 1H), 6.46 (s, 1H), 2.66 (s, 3H); $^{19}$F NMR (282 MHz, DMSO-$d_6$) δ−64.00. MS (ES+): 268 (M+1); (ES−): 266 (M−1).

Step-3: Preparation of tert-butyl 2-(4-amino-8-methyl-6-(trifluoromethyl)-9H-pyrido[2',3':4,5]pyrrolo[2,3-d]pyrimidin-9-yl)acetate (362d)

Compound 362d was prepared according to the procedure reported in step-1 of scheme-1, from 8-methyl-6-(trifluoromethyl)-9H-pyrido[2',3':4,5]pyrrolo[2,3-d]pyrimidin-4-amine (362c) (3.28 g, 12.27 mmol) in DMF (15 mL) using tert-butyl 2-bromoacetate (2.63 g, 13.50 mmol) and $Cs_2CO_3$ (8.0 g, 24.55 mmol) to afford tert-butyl 2-(4-amino-8-methyl-6-(trifluoromethyl)-9H-pyrido[2',3':4,5]pyrrolo[2,3-d]pyrimidin-9-yl)acetate (362d) (3.21 g, 69% yield) as a pale-yellow solid; $^1$H NMR (300 MHz, DMSO-$d_6$) δ 8.48 (s, 1H), 8.20 (s, 1H), 7.75 (s, 1H), 6.64 (s, 1H), 5.39 (s, 2H), 2.74 (s, 3H), 1.43 (s, 9H); $^{19}$F NMR (282 MHz, DMSO-$d_6$) δ−64.31; MS (ES+) 382 (M+1).

Step-4: Preparation of 2-(4-amino-8-methyl-6-(trifluoromethyl)-9H-pyrido[2',3':4,5]pyrrolo[2,3-d]pyrimidin-9-yl)acetic acid (362e)

Compound 362e was prepared according to the procedure reported in step-2 of scheme-1, from tert-butyl 2-(4-amino-8-methyl-6-(trifluoromethyl)-9H-pyrido[2',3':4,5]pyrrolo[2,3-d]pyrimidin-9-yl)acetate (362d) (3.21 g, 8.42 mmol) using TFA (9.6 g, 84 mmol) in DCM (10 mL) to afford TFA salt of 2-(4-amino-8-methyl-6-(trifluoromethyl)-9H-pyrido[2', 3':4,5]pyrrolo[2,3-d]pyrimidin-9-yl)acetic acid (362e) (3.16 g, 85% yield) as a pale-yellow solid $^1$H NMR (300 MHz, DMSO-$d_6$) δ 8.57 (s, 2H), 7.80 (s, 1H), 7.09 (bs, 1H), 5.43 (s, 2H), 2.78 (s, 3H); $^{19}$F NMR (282 MHz, DMSO) δ−64.34, −74.87; MS (ES+): 326 (M+1); (ES−): 324 (M−1).

Step-5: Preparation of (1R,3S,5R)-2-(2-(4-amino-8-methyl-6-(trifluoromethyl)-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (362f)

Compound 362f was prepared according to the procedure reported in step-3 of scheme-1, from TFA salt of 2-(4-amino-8-methyl-6-(trifluoromethyl)-9H-pyrido[2',3':4,5]pyrrolo[2,3-d]pyrimidin-9-yl)acetic acid (362e) (75 mg, 0.171 mmol) in DMF (5 mL) using HCl salt of (1R,3S,5R)—N-(6-bromopyridin-2-yl)-2-azabicyclo[3.1.0]hexane-3-carboxamide (4a) (54.4 mg, 0.171 mmol), HATU (78 mg, 0.205 mmol), DIPEA (110 mg, 0.854 mmol) and stirring at RT for 16 h. This gave after workup and purification as described in scheme-299, (1R,3S,5R)-2-(2-(4-amino-8-methyl-6-(trifluoromethyl)-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (362f) (76 mg, 76% yield) HCl salt as a white solid; $^1$H NMR (300 MHz, DMSO-$d_6$) δ 10.77 (s, 1H, $D_2O$ exchangeable), 8.52 (bs, 2H, in which 1H was $D_2O$ exchangeable), 7.93 (d, J=8.2 Hz, 1H), 7.71 (s, 1H), 7.64 (t, J=8.0 Hz, 1H), 7.25 (d, J=7.7 Hz, 1H), 7.13 (bs, 1H, $D_2O$ exchangeable), 5.84 (d, J=18.0 Hz, 1H), 5.59 (d, J=17.9 Hz, 1H), 4.36 (dd, J=9.1, 5.7 Hz, 1H), 3.91-3.83 (m, 1H), 2.72 (s, 3H), 2.36-2.22 (m, 1H), 2.19-2.08 (m, 1H), 1.93-1.77 (m, 1H), 1.09-0.94 (m, 1H), 0.71-0.58 (m, 1H); $^{19}$F NMR (282 MHz, DMSO-$d_6$) δ−64.32: MS (ES+): 589/591 (M+1); (ES−): 587/589 (M−1).

Scheme 363

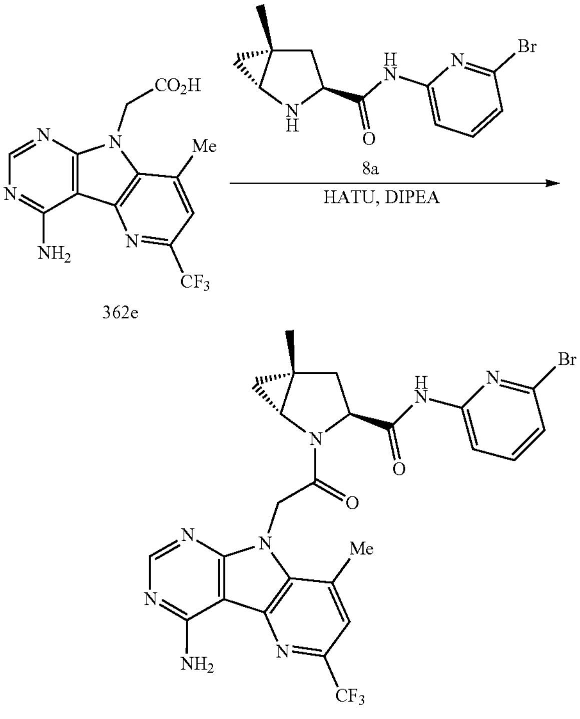

8a

362e

363a

Preparation of (1R,3S,5R)-2-(2-(4-amino-8-methyl-6-(trifluoromethyl)-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (363a)

Compound 363a was prepared according to the procedure reported in step-3 of scheme-1, from TFA salt of 2-(4-amino-8-methyl-6-(trifluoromethyl)-9H-pyrido[2',3':4,5]pyrrolo[2,3-d]pyrimidin-9-yl)acetic acid (362e) (75 mg, 0.171 mmol) in DMF (5 mL) using HCl salt of (1R,3S,5R)—N-(6-bromopyridin-2-yl)-5-methyl-2-azabicyclo[3.1.0]hexane-3-carboxamide (8a) (56.8 mg, 0.171 mmol). HATU (78 mg, 0.205 mmol), DIPEA (110 mg, 0.854 mmol) and stirring at RT for 16 h. This gave after workup and purification as described in scheme-299, (1R,3S,5R)-2-(2-(4-amino-8-methyl-6-(trifluoromethyl)-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (363a) (71 mg, 69% yield) HCl salt as a white solid: $^1$H NMR (300 MHz, DMSO-$d_6$) δ 10.84 (s, 1H, $D_2O$ exchangeable), 8.82 (bs, 1H, $D_2O$ exchangeable), 8.63 (s, 1H), 8.01 (d, J=8.1 Hz, 1H), 7.80 (s, 1H), 7.71 (t, J=7.9 Hz, 1H), 7.41 (bs, 1H, $D_2O$ exchangeable), 7.32 (d, J=7.7 Hz, 1H), 5.88 (d, J=18.0 Hz, 1H), 5.62 (d, J=17.9 Hz, 1H), 4.39 (dd, J=9.1, 6.1 Hz, 1H), 3.76-3.67 (m, 1H), 2.78 (s, 3H), 2.50-2.38 (m, 1H), 1.98 (dd, J=13.3, 6.0 Hz, 1H), 1.31 (s, 3H), 1.08-0.98 (m, 1H), 0.93-0.78 (m, 1H); $^{19}$F NMR (282 MHz, DMSO-$d_6$) δ−64.34; MS (ES+): 603/605 (M+1); (ES−): 601/603 (M−1).

Scheme 364

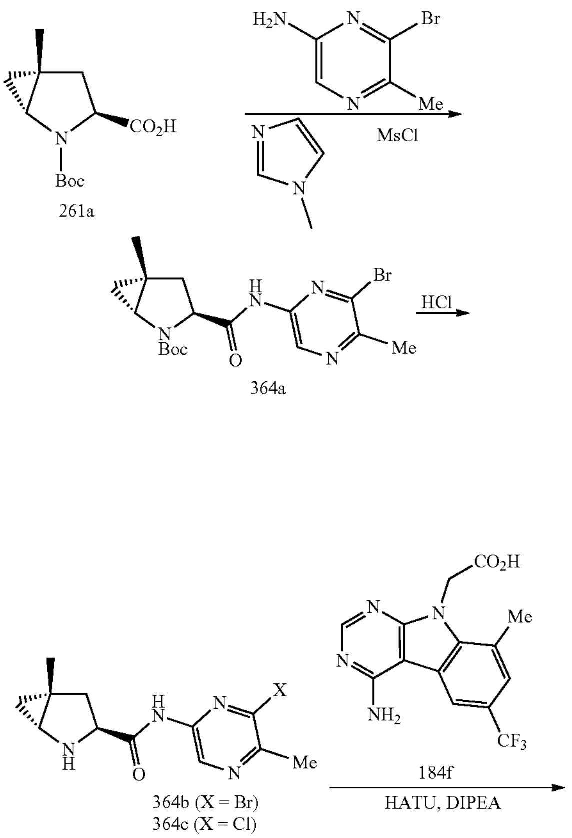

261a

364a 364b (X = Br)
364c (X = Cl)

184f

-continued

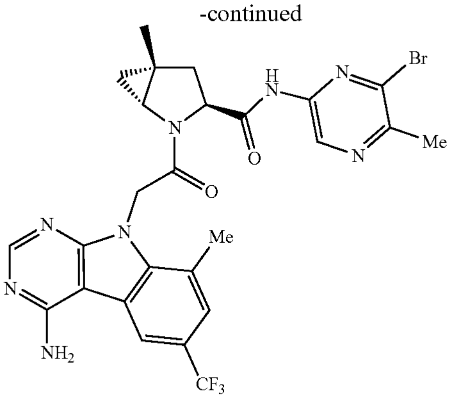

+

364d

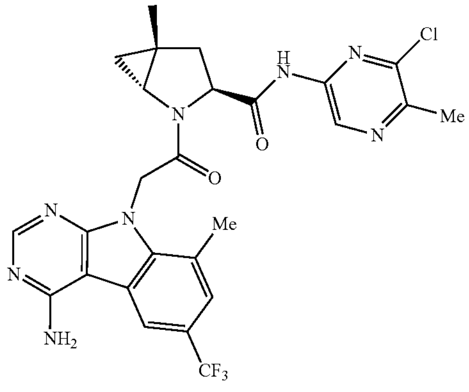

364e

Preparation of (1R,3S,5R)-2-(2-(4-amino-8-methyl-6-(trifluoromethyl)-9H-pyrimido[4,5-b]indol-9-yl)acetyl)-N-(6-chloro-5-methylpyrazin-2-yl)-5-methyl-2-azabicyclo[3.1.0]hexane-3-carboxamide (364e) and (1R,3S,5R)-2-(2-(4-amino-8-methyl-6-(trifluoromethyl)-9H-pyrimido[4,5-b]indol-9-yl)acetyl)-N-(6-bromo-5-methylpyrazin-2-yl)-5-methyl-2-azabicyclo[3.1.0]hexane-3-carboxamide (364d)

Step-1: Preparation of (1R,3S,5R)-tert-butyl 3-((6-bromo-5-methylpyrazin-2-yl)carbamoyl)-5-methyl-2-azabicyclo[3.1.0]hexane-2-carboxylate (364a)

Compound 364a was prepared according to the procedure reported in step-1 of scheme-53 and step-1 of scheme-317, from (1R,3S,5R)-2-(tert-butoxycarbonyl)-5-methyl-2-azabicyclo[3.1.0]hexane-3-carboxylic acid (261a) (0.321 g, 1.330 mmol) and 6-bromo-5-methylpyrazin-2-amine (0.25 g, 1.330 mmol) to afford (1R,3S,5R)-tert-butyl 3-((6-bromo-5-methylpyrazin-2-yl)carbamoyl)-5-methyl-2-azabicyclo[3.1.0]hexane-2-carboxylate (364a) (0.36 g, 66% yield) as a white crystalline solid; 1H NMR (300 MHz, DMSO-$d_6$) δ 11.13-10.84 (m, 1H), 9.33-9.08 (m, 1H), 4.23-4.03 (m, 1H), 3.24-3.09 (m, 1H), 2.56 (s, 3H), 2.40 (dd, J=12.9, 8.8 Hz, 1H), 1.98-1.77 (m, 1H), 1.32 (d, 9H), 1.19 (s, 3H), 0.75-0.55 (m, 2H); MS (ES+): 411/413 (M+1); (ES−): 409/411 (M−1).

Step-2: Preparation of (1R,3S,5R)—N-(6-bromo-5-methylpyrazin-2-yl)-5-methyl-2-azabicyclo[3.1.0]hexane-3-carboxamide (364b) and (1R,3S,5R)—N-(6-chloro-5-methylpyrazin-2-yl)-5-methyl-2-azabicyclo[3.1.0]hexane-3-carboxamide (364c)

Compounds 364b and 364c were prepared according to the procedure reported in step-2 of scheme-344, from (1R,3S,5R)-tert-butyl 3-((6-bromo-5-methylpyrazin-2-yl)carbamoyl)-5-methyl-2-azabicyclo[3.1.0]hexane-2-carboxylate (364a) (360 mg, 0.875 mmol) in DCM (5 mL) using 4 M HCl in dioxane (2.188 mL, 8.75 mmol) to afford 318 mg HCl salt of a mixture of two products (1R,3S,5R)—N-(6-bromo-5-methylpyrazin-2-yl)-5-methyl-2-azabicyclo[3.1.0]hexane-3-carboxamide (364b); MS (ES+): 311/313 (M+1); (ES−): 309/311 (M−1), and (1R,3S,5R)—N-(6-chloro-5-methylpyrazin-2-yl)-5-methyl-2-azabicyclo[3.1.0]hexane-3-carboxamide (364c); MS (ES+): 267/269 (M+1); (ES−): 265/267 (M−1) as white solids.

Step-3: Preparation of (1R,3S,5R)-2-(2-(4-amino-8-methyl-6-(trifluoromethyl)-9H-pyrimido[4,5-b]indol-9-yl)acetyl)-N-(6-chloro-5-methylpyrazin-2-yl)-5-methyl-2-azabicyclo[3.1.0]hexane-3-carboxamide (364e) and (1R,3S,5R)-2-(2-(4-amino-8-methyl-6-(trifluoromethyl)-9H-pyrimido[4,5-b]indol-9-yl)acetyl)-N-(6-bromo-5-methylpyrazin-2-yl)-5-methyl-2-azabicyclo[3.1.0]hexane-3-carboxamide (364d)

Compounds 364d and 364e were prepared according to the procedure reported in step-3 of scheme-1, from above mixture of (1R,3S,5R)—N-(6-bromo-5-methylpyrazin-2-yl)-5-methyl-2-azabicyclo[3.1.0]hexane-3-carboxamide (364b) and (1R,3S,5R)—N-(6-chloro-5-methylpyrazin-2-yl)-5-methyl-2-azabicyclo[3.1.0]hexane-3-carboxamide (364c) (99 mg, 0.285 mmol) in DMF (5 mL) using HCl salt of 2-(4-amino-8-methyl-6-(trifluoromethyl)-9H-pyrimido[4,5-b]indol-9-yl)acetic acid (184f) (125 mg, 0.285 mmol), HATU (163 mg, 0.428 mmol), DIPEA (184 mg, 1.426 mmol) and stirring at RT for 16 h. This gave after workup and purification as described in scheme-299, (1R,3S,5R)-2-(2-(4-amino-8-methyl-6-(trifluoromethyl)-9H-pyrimido[4,5-b]indol-9-yl)acetyl)-N-(6-chloro-5-methylpyrazin-2-yl)-5-methyl-2-azabicyclo[3.1.0]hexane-3-carboxamide (364e) (10 mg, 6% yield) HCl salt as a white solid; $^1$H NMR (300 MHz, DMSO-$d_6$) δ 11.05 (s, 1H, $D_2O$ exchangeable), 9.10 (s, 1H), 8.79 (s, 1H), 8.65 (bs, 2H, $D_2O$ exchangeable), 8.63 (s, 1H), 7.60 (d, J=1.7 Hz, 1H), 5.93 (d, J=18.0 Hz, 1H), 5.65 (d, J=18.0 Hz, 1H), 4.40 (dd, J=9.1, 6.1 Hz, 1H), 3.74-3.69 (m, 1H), 2.76 (s, 3H), 2.51 (s, 3H), 2.49-2.44 (m, 1H), 2.01 (dd, J=13.3, 6.0 Hz, 1H), 1.32 (s, 3H), 1.08-0.97 (m, 1H), 0.94-0.81 (m, 1H); $^{19}$F NMR (282 MHz, DMSO-$d_6$) δ−58.76; MS (ES+): 573/575 (M+1); (ES−): 571/573 (M−1); and (1R,3S,5R)-2-(2-(4-amino-8-methyl-6-(trifluoromethyl)-9H-pyrimido[4,5-b]indol-9-yl)acetyl)-N-(6-bromo-5-methylpyrazin-2-yl)-5-methyl-2-azabicyclo[3.1.0]hexane-3-carboxamide (364d) (77 mg, 44% yield) HCl salt as a white solid; $^1$H NMR (300 MHz, DMSO-$d_6$) δ 11.08 (s, 1H, $D_2O$ exchangeable), 9.11 (s, 1H), 8.80 (bs, 3H, in which 2H were $D_2O$ exchangeable), 8.66 (s, 1H), 7.62 (s, 1H), 5.94 (d, J=18.0 Hz, 1H), 5.66 (d, J=18.0 Hz, 1H), 4.40 (dd, J=9.1, 6.1 Hz, 1H), 3.75-3.69 (m, 1H), 2.76 (s, 3H), 2.52 (s, 3H), 2.50-2.45 (m, 1H), 2.01 (dd, J=13.2, 6.0 Hz, 1H), 1.32 (s, 3H), 1.11-0.98 (m, 1H), 0.98-0.78 (m, 1H); $^{19}$F NMR (282 MHz, DMSO-$d_6$) δ−58.80; MS (ES+): 617/619 (M+1): (ES−): 615/617 (M−1); Analysis calculated for $C_{26}H_{24}BrF_3N_8O_2 \cdot 1.25HCl \cdot 2.5H_2O$: C, 44.10; H, 4.31; Cl, 6.26; N, 15.83. Found: C, 43.91; H, 4.15; Cl, 6.31; N, 15.93

Scheme 365

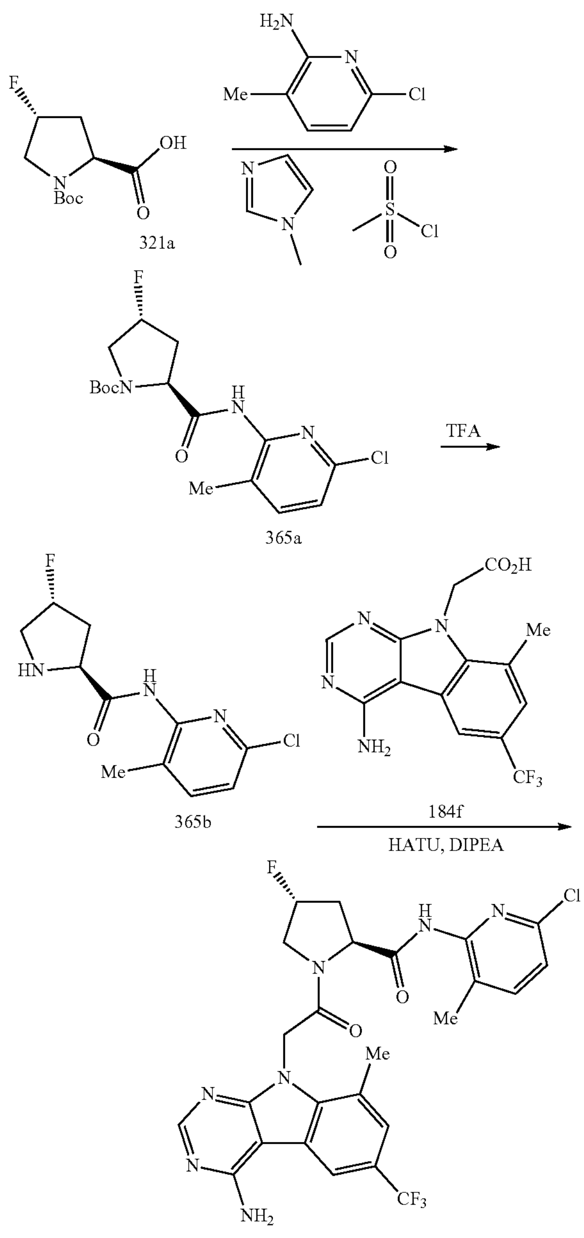

321a

365a

365b

184f

365c

Preparation of (2S,4R)-1-(2-(4-amino-8-methyl-6-(trifluoromethyl)-9H-pyrimido[4,5-b]indol-9-yl) acetyl)-N-(6-chloro-3-methylpyridin-2-yl)-4-fluoro-pyrrolidine-2-carboxamide (365c)

Step-1: Preparation of (2S,4R)-tert-butyl 2-((6-chloro-3-methylpyridin-2-yl)carbamoyl)-4-fluoropyrrolidine-1-carboxylate (365a)

Compound 365a was prepared according to the procedure reported in step-1 of scheme-53, from (2S,4R)-1-(tert-butoxycarbonyl)-4-fluoropyrrolidine-2-carboxylic acid (321a) (0.340 g, 1.458 mmol) and 6-chloro-3-methylpyridin-2-amine (0.208 g, 1.458 mmol) to afford after purification as reported in step-1 of scheme-317, (2S,4R)-tert-butyl 2-((6-chloro-3-methylpyridin-2-yl)carbamoyl)-4-fluoropyrrolidine-1-carboxylate (365a) (0.150 g, 29% yield) as a white solid; MS (ES+): 358.1 (M+1); 380.1 (M+Na); (ES−): 356.1 (M−1).

Step-2: Preparation of (2S,4R)—N-(6-chloro-3-methylpyridin-2-yl)-4-fluoropyrrolidine-2-carboxamide (365b)

Compound 365b was prepared according to the procedure reported in step-2 of scheme-1, from (2S,4R)-tert-butyl 2-((6-chloro-3-methylpyridin-2-yl)carbamoyl)-4-fluoropyrrolidine-1-carboxylate (365a) (0.145 g, 0.405 mmol) in DCM (2.2 mL) using TFA (0.219 mL, 2.84 mmol) to afford after purification as reported in step-2 of scheme-319, HCl salt of (2S,4R)—N-(6-chloro-3-methylpyridin-2-yl)-4-fluoropyrrolidine-2-carboxamide (365b) (0.086 mg, 82% yield); $^1$H NMR (300 MHz, DMSO-$d_6$) δ 10.96 (s, 1H), 10.22 (s, 1H), 9.05 (s, 1H), 7.83 (d, J=8.0 Hz, 1H), 7.42 (d, J=8.0 Hz, 1H), 5.69-5.34 (m, 1H), 4.66 (s, 1H), 3.59 (d, J=28.5 Hz, 2H), 2.87-2.72 (m, 1H), 2.40-2.22 (m, 1H), 2.18 (s, 3H); MS (ES+): 258.0 (M+1).

Step-3: Preparation of (2S,4R)-1-(2-(4-amino-8-methyl-6-(trifluoromethyl)-9H-pyrimido[4,5-b]indol-9-yl)acetyl)-N-(6-chloro-3-methylpyridin-2-yl)-4-fluoropyrrolidine-2-carboxamide (365c)

Compound 365c was prepared according to the procedure reported in step-3 of scheme-1, from HCl salt of (2S,4R)—N-(6-chloro-3-methylpyridin-2-yl)-4-fluoropyrrolidine-2-carboxamide (365b) (40.3 mg, 0.137 mmol) in DMF (1.5 mL) using TFA salt of 2-(4-amino-8-methyl-6-(trifluoromethyl)-9H-pyrimido[4,5-b]indol-9-yl)acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (2S,4R)-1-(2-(4-amino-8-methyl-6-(trifluoromethyl)-9H-pyrimido[4,5-b]indol-9-yl)acetyl)-N-(6-chloro-3-methylpyridin-2-yl)-4-fluoropyrrolidine-2-carboxamide (365c) (37 mg, 48% yield) HCl salt as a white solid: $^1$H NMR (300 MHz, DMSO-$d_6$) (a mixture of two rotamers) δ 10.99 and 10.52 (2s, 1H, $D_2O$ exchangeable), 8.92 (s, 2H, $D_2O$ exchangeable), 8.83 (s, 1H), 8.68 (s, 1H), 7.83 and 7.69 (2d, J=8.0 Hz, 1H), 7.64 and 7.61 (2s, 1H), 7.40 and 7.29 (2d, J=7.9 Hz, 1H), 5.83 (d, J=18.1 Hz, 1H), 5.69-5.41 (m, 2H), 4.63 (t, J=8.5 Hz, 1H), 4.37-4.26 (m, 1H), 4.08-3.92 (m, 1H), 2.74 (s, 3H), 2.66-2.55 (m, 1H), 2.32-2.08 (m, 1H), 1.97 (s, 3H); $^{19}$F NMR (282 MHz, DMSO-$d_6$) δ−58.82, −176.22; MS (ES+): 564.2 (M+1); 586.1 (M+Na); (ES−): 562.1 (M−1): Analysis calculated for $C_{25}H_{22}ClF_4N_7O_2$ $2H_2O \cdot 0.85HCl$: C, 47.59; H, 4.29; Cl, 10.40; N, 15.54. Found: C, 47.87; H, 4.01; Cl, 10.51; N, 15.43.

Scheme 366

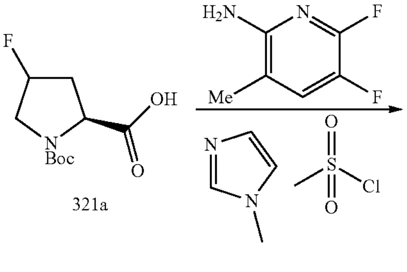

321a

-continued

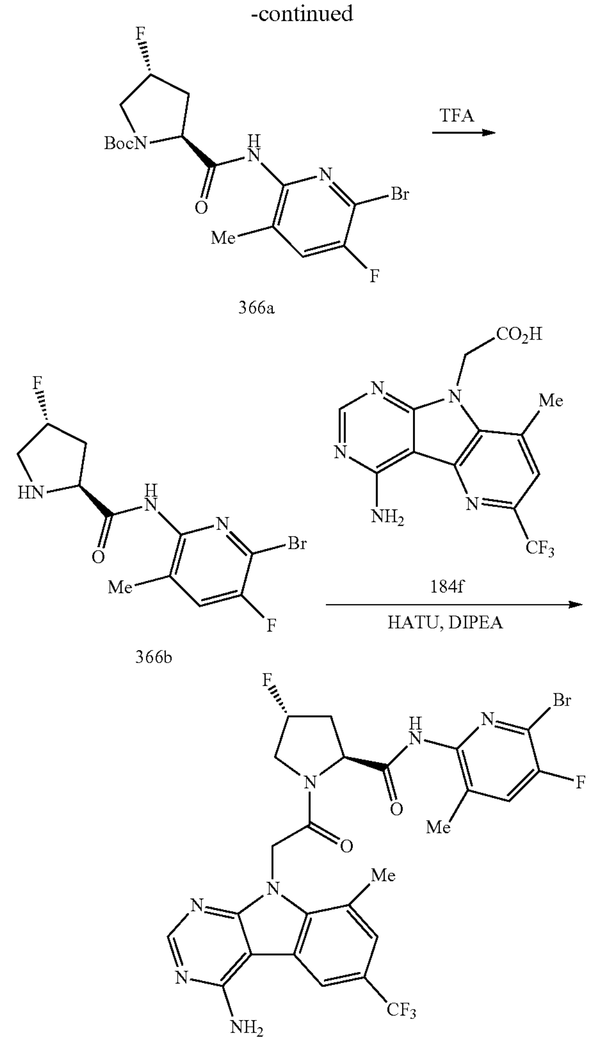

366a

366b

366c

Preparation of (2S,4R)-1-(2-(4-amino-8-methyl-6-(trifluoromethyl)-9H-pyrimido[4,5-b]indol-9-yl) acetyl)-N-(6-bromo-5-fluoro-3-methylpyridin-2-yl)-4-fluoropyrrolidine-2-carboxamide (366c)

Step-1: Preparation of (2S,4R)-tert-butyl 2-((6-bromo-5-fluoro-3-methylpyridin-2-yl)carbamoyl)-4-fluoropyrrolidine-1-carboxylate (366a)

Compound 366a was prepared according to the procedure reported in step-1 of scheme-53, from (2S,4R)-1-(tert-butoxycarbonyl)-4-fluoropyrrolidine-2-carboxylic acid (321a) (0.340 g, 1.458 mmol) and 6-bromo-5-fluoro-3-methylpyridin-2-amine (0.299 g, 1.458 mmol) to afford after purification as reported in step-1 of scheme-317, (2S,4R)-tert-butyl 2-((6-bromo-5-fluoro-3-methylpyridin-2-yl)carbamoyl)-4-fluoropyrrolidine-1-carboxylate (366a) (0.445 g, 73% yield) as a white solid; MS (ES+): 420.1/422.1 (M+1); 442.0/444.0 (M+Na).

Step-2: Preparation of (2S,4R)—N-(6-bromo-5-fluoro-3-methylpyridin-2-yl)-4-fluoropyrrolidine-2-carboxamide (366b)

Compound 366b was prepared according to the procedure reported in step-2 of scheme-1, from (2S,4R)-tert-butyl 2-((6-bromo-5-fluoro-3-methylpyridin-2-yl)carbamoyl)-4-fluoropyrrolidine-1-carboxylate (366a) (0.435 g, 1.035 mmol) in DCM (5.6 mL) using TFA (0.558 mL, 7.25 mmol) to afford after purification as reported in step-2 of scheme-319, HCl salt of (2S,4R)—N-(6-bromo-5-fluoro-3-methylpyridin-2-yl)-4-fluoropyrrolidine-2-carboxamide (366b) (0.324 mg, 98% yield); $^1$H NMR (300 MHz, DMSO-$d_6$) δ 10.98 (s, 1H), 10.18 (s, 1H), 9.06 (s, 1H), 7.94 (d, J=8.4 Hz, 11H), 5.53 (dd, J=53.5, 3.5 Hz, 1H), 4.64 (t, J=9.2 Hz, 1H), 3.68-3.60 (m, 1H), 3.57-3.51 (m, 1H), 2.88-2.69 (m, 1H), 2.42-2.23 (m, 1H), 2.19 (s, 3H); MS (ES+): 320.0/322.0 (M+1).

Step-3: Preparation of (2S,4R)-1-(2-(4-amino-8-methyl-6-(trifluoromethyl)-9H-pyrimido[4,5-b]indol-9-yl)acetyl)-N-(6-bromo-5-fluoro-3-methylpyridin-2-yl)-4-fluoropyrrolidine-2-carboxamide (366c)

Compound 366c was prepared according to the procedure reported in step-3 of scheme-1, from HCl salt of (2S,4R)—N-(6-bromo-5-fluoro-3-methylpyridin-2-yl)-4-fluoropyrrolidine-2-carboxamide (366b) (48.8 mg, 0.137 mmol) in DMF (1.5 mL) using TFA salt of 2-(4-amino-8-methyl-6-(trifluoromethyl)-9H-pyrimido[4,5-b]indol-9-yl)acetic acid (184f) (60 mg, 0.137 mmol), HATU (78 mg, 0.205 mmol), DIPEA (0.119 mL, 0.684 mmol) and stirring at RT for 16 h. This gave after workup and purification as described in scheme-303, (2S,4R)-1-(2-(4-amino-8-methyl-6-(trifluoromethyl)-9H-pyrimido[4,5-b]indol-9-yl)acetyl)-N-(6-bromo-5-fluoro-3-methylpyridin-2-yl)-4-fluoropyrrolidine-2-carboxamide (366c) (63 mg, 74% yield) HCl salt as a white solid: 1H NMR (300 MHz, DMSO-$d_6$) (a mixture of two rotamers) δ 10.88 and 10.54 (2s, 1H, $D_2O$ exchangeable), 8.78 (s, 1H), 8.57 (s, 1H), 8.48 (s, 2H, $D_2O$ exchangeable), 7.94 and 7.80 (2d, J=8.5 Hz, 1H), 7.59 and 7.56 (2s, 1H), 5.80 (d, J=18.0 Hz, 1H), 5.69-5.46 (m, 2H), 4.60 (t, J=8.5 Hz, 1H), 4.31 (dd, J=21.4, 12.7 Hz, 1H), 4.07-3.90 (m, 1H), 2.72 (s, 3H), 2.68-2.58 (m, 1H), 2.32-2.07 (m, 1H), 1.98 (s, 3H). $^{19}$F NMR (282 MHz, DMSO-$d_6$) δ−58.69, −119.17, −176.67. MS (ES+): 626.1/628.1 (M+1); (ES−): 624.0/626.0 (M−1): Analysis calculated for $C_{21}H_{21}BrF_5N_7O_2$ $1.5H_2O{\cdot}HCl$: C, 43.53; H, 3.65; Cl, 5.14; N, 14.21. Found: C, 43.65; H, 3.48; Cl, 5.01; N, 14.04.

Scheme 367

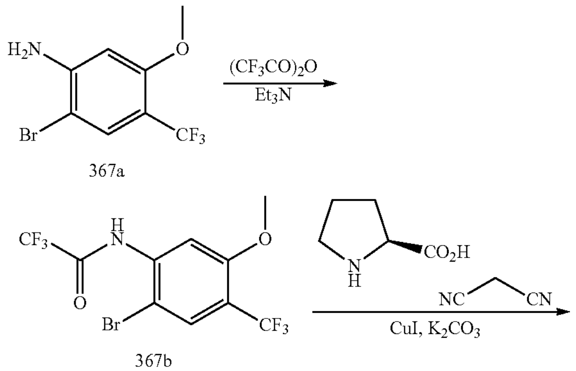

367a

367b

-continued

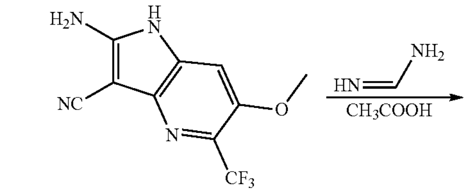

367c

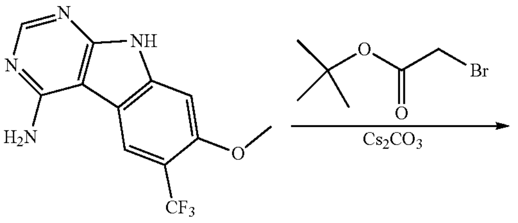

367d

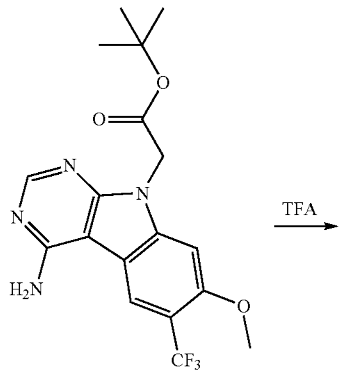

367e

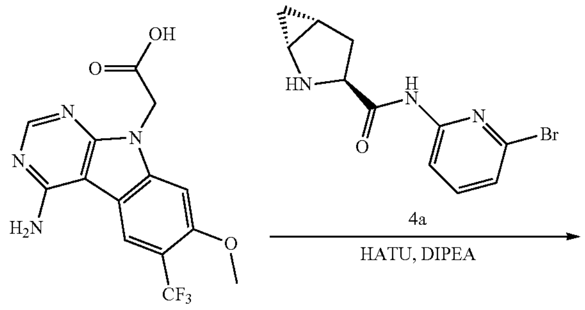

367f

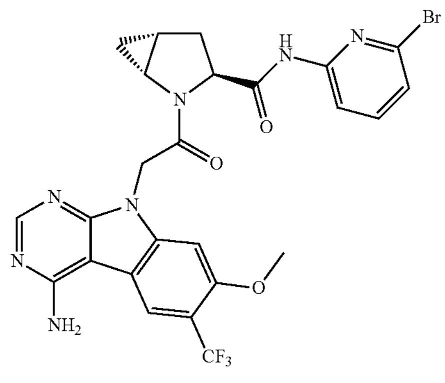

367g

Preparation of (1R,3S,5R)-2-(2-(4-amino-7-methoxy-6-(trifluoromethyl)-9H-pyrimido[4,5-b]indol-9-yl)acetyl)-N-(6-bromopyridin-2-yl)-2-azabicyclo[3.1.0]hexane-3-carboxamide (367 g)

Step-1: Preparation of N-(2-bromo-5-methoxy-4-(trifluoromethyl)phenyl)-2,2,2-trifluoroacetamide (367b)

Compound 367b was prepared according to the procedure reported in step-1 of scheme-46, from 2-bromo-5-methoxy-4-(trifluoromethyl)aniline (367a)(1 g, 3.70 mmol; CAS #694514-19-7) in DCM (15 mL) using triethylamine (0.877 mL, 6.30 mmol), trifluoroacetic acid anhydride (0.772 mL, 5.55 mmol) and stirring at RT for 16 h. This gave after workup and purification using flash column chromatography [silica gel (24 g), eluting with EtOAc in hexane from 0 to 50%] N-(2-bromo-5-methoxy-4-(trifluoromethyl)phenyl)-2,2,2-trifluoroacetamide (367b) (1.35 g, 100% yield) as a pale yellow solid; $^1$H NMR (300 MHz, DMSO-$d_6$) δ 11.57 (s, 1H), 7.96 (s, 1H), 7.47 (s, 1H), 3.91 (s, 3H); $^{19}$F NMR (282 MHz, DMSO-$d_6$) δ−61.15, −74.02; MS (ES−): 363.9 (M−1).

Step-2: Preparation of 2-amino-6-methoxy-5-(trifluoromethyl)-1H-indole-3-carbonitrile (367c)

Compound 367c was prepared according to the procedure reported in step-1 of scheme-11, from N-(2-bromo-5-methoxy-4-(trifluoromethyl)phenyl)-2,2,2-trifluoroacetamide (367b) (1.3 g, 3.55 mmol) in DMSO (5 mL) and using malononitrile (0.268 mL, 4.26 mmol), L-proline (0.082 g, 0.710 mmol), CuI (0.068 g, 0.355 mmol) and $K_2CO_3$ (0.982 g, 7.10 mmol) to afford after workup and purification as described in step-1 of scheme-328, 2-amino-6-methoxy-5-(trifluoromethyl)-1H-indole-3-carbonitrile (367c) (0.106 g, 12% yield) as a yellow solid; 1H NMR (300 MHz, DMSO-$d_6$) δ 10.98 (s, 1H), 7.31 (s, 1H), 7.07 (s, 1H), 6.99 (s, 2H), 3.89 (s, 3H); $^{19}$F NMR (282 MHz, DMSO) δ−59.05; MS (ES+): 256.1 (M+1); (ES−): 254.0 (M−1).

Step-3: Preparation of 7-methoxy-6-(trifluoromethyl)-9H-pyrimido[4,5-b]indol-4-amine (367d)

Compound 367d was prepared according to the procedure reported in step-2 of scheme-29, from 2-amino-6-methoxy-5-(trifluoromethyl)-1H-indole-3-carbonitrile (367c) (0.1 g, 0.392 mmol) in ethanol (10 mL) using formamidine acetate (0.33 g, 3.13 mmol) and refluxing for 22 h. The mixture was purified using reverse-phase column chromatography [C18 column (50 g), eluting with ACN in water (containing 0.1% HCl) from 0-100%]] to afford 7-methoxy-6-(trifluoromethyl)-9H-pyrimido[4,5-b]indol-4-amine (367d) (80 mg, 72% yield) HCl salt as a pale yellow solid; $^1$H NMR (300 MHz, DMSO-$d_6$) δ 13.07 (s, 1H), 8.81 (s, 1H), 8.59-8.42 (m, 3H), 7.27 (s, 1H), 3.99 (s, 3H); MS (ES+): 283.1 (M+1).

Step-4: Preparation of tert-butyl 2-(4-amino-7-methoxy-6-(trifluoromethyl)-9H-pyrimido[4,5-b]indol-9-yl)acetate (367e)

Compound 367e was prepared according to the procedure reported in step-2 of scheme-16, from HCl salt of 7-methoxy-6-(trifluoromethyl)-9H-pyrimido[4,5-b]indol-4-amine (367d) (75 mg, 0.235 mmol) in DMF (3 mL) using tert-butyl 2-bromoacetate (0.038 mL, 0.259 mmol), $Cs_2CO_3$ (192 mg, 0.588 mmol) and stirring at RT for 16 h. The solid separated was collected by filtration to give tert-butyl 2-(4- amino-7-methoxy-6-(trifluoromethyl)-9H-pyrimido[4,5-b]indol-9-yl)acetate (367e) (85 mg, 91% yield) as a pale yellow solid: MS (ES+): 397.1 (M+1).

Step-5: Preparation of 2-(4-amino-7-methoxy-6-(trifluoromethyl)-9H-pyrimido[4,5-b]indol-9-yl) acetic acid (367f)

Compound 367f was prepared according to the procedure reported in step-2 of scheme-1, from tert-butyl 2-(4-amino-7-methoxy-6-(trifluoromethyl)-9H-pyrimido[4,5-b]indol-9-yl)acetate (367e) (83 mg, 0.209 mmol) using 20% TFA in DCM (1202 μL, 3.14 mmol)) to afford TFA salt of 2-(4-amino-7-methoxy-6-(trifluoromethyl)-9H-pyrimido[4,5-b]indol-9-yl)acetic acid (367f) (70 mg, 98% yield) as a pale-yellow solid. $^{1}$H NMR (300 MHz, DMSO-$d_6$) δ 8.75 (s, 1H), 8.45 (s, 1H), 8.01 (d, J=31.6 Hz, 1H), 7.67 (s, 1H), 5.27 (s, 2H), 3.99 (s, 3H); MS (ES+): 341.1 (M+1).

Step-6: Preparation of (1R,3S,5R)-2-(2-(4-amino-7-methoxy-6-(trifluoromethyl)-9H-pyrimido[4,5-b]indol-9-yl)acetyl)-N-(6-bromopyridin-2-yl)-2-azabicyclo[3.1.0]hexane-3-carboxamide (367 g)

Compound 367g was prepared according to the procedure reported in step-3 of scheme-1, from TFA salt of 2-(4-amino-7-methoxy-6-(trifluoromethyl)-9H-pyrimido[4,5-b]indol-9-yl)acetic acid (367f) (45.4 mg, 0.1 mmol) in DMF (1 mL) using HCl salt of (1R,3S,5R)—N-(6-bromopyridin-2-yl)-2-azabicyclo[3.1.0]hexane-3-carboxamide (4a) (31.9 mg, 0.100 mmol), HATU (57.0 mg, 0.150 mmol), DIPEA (0.087 mL, 0.500 mmol) and stirring at RT for 1 h. This gave after workup and purification as described in scheme-303, (1R,3S,5R)-2-(2-(4-amino-7-methoxy-6-(trifluoromethyl)-9H-pyrimido[4,5-b]indol-9-yl)acetyl)-N-(6-bromopyridin-2-yl)-2-azabicyclo[3.1.0]hexane-3-carboxamide (367 g) (48 mg, 79% yield) HCl salt as a white solid; $^{1}$H NMR (300 MHz, DMSO-$d_6$) δ 10.73 (s, 1H, $D_2O$ exchangeable), 8.84 (s, 11H), 8.71-8.52 (m, 3H, 2H $D_2O$ exchangeable), 8.02 (d, J=8.1 Hz, 11H), 7.72 (t, J=8.0 Hz, 1H), 7.52 (s, 11H), 7.33 (d, J=7.7 Hz, 11H), 5.77 (d, J=17.3 Hz, 11H), 5.51 (d, J=17.2 Hz, 1H), 4.42 (dd, J=9.1, 5.7 Hz, 1H), 4.01 (s, 3H), 3.93 (td, J=6.2, 5.3, 2.3 Hz, 1H), 2.36 (dd, J=13.4, 9.2 Hz, 11H), 2.31-2.16 (m, 1H), 2.00-1.88 (m, 1H), 1.17-1.02 (m, 1H), 0.82-0.73 (m, 1H); $^{19}$F NMR (282 MHz, DMSO-$d_6$) δ–59.20; MS (ES+): 604.1/606.1 (M+1); (ES–): 602.0/604.1 (M–1); Analysis calculated for $C_{25}H_{21}BrF_3N_7O_3 \cdot 3.5H_2O \cdot 0.65HCl$: C, 43.45; H, 4.18; Cl, 3.33; N, 14.19. Found: C, 43.07; H, 3.76; Cl, 3.04; N, 13.78.

Scheme 368

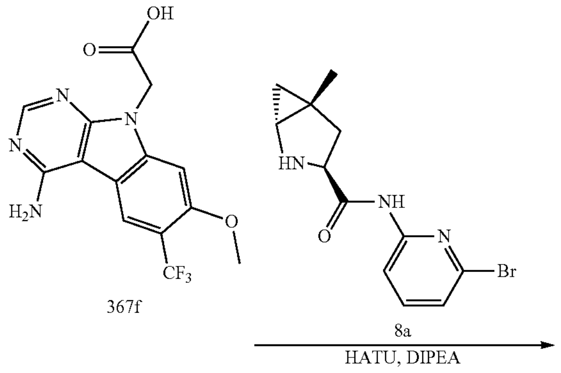

367f

8a

-continued

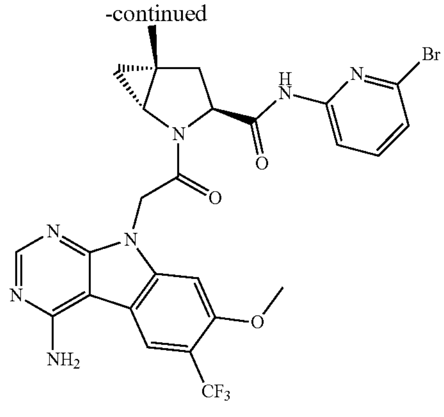

368a

Preparation of (1R,3S,5R)-2-(2-(4-amino-7-methoxy-6-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (368a)

Compound 368a was prepared according to the procedure reported in step-3 of scheme-1, from TFA salt of 2-(4-amino-7-methoxy-6-(trifluoromethyl)-9H-pyrimido[4,5-b]indol-9-yl)acetic acid (367f) (45.4 mg, 0.1 mmol) in DMF (1 mL) using HCl salt of (1R,3S,5R)—N-(6-bromopyridin-2-yl)-5-methyl-2-azabicyclo[3.1.0]hexane-3-carboxamide (8a) (33.3 mg, 0.100 mmol), HATU (57.0 mg, 0.150 mmol), DIPEA (0.087 mL, 0.500 mmol) and stirring at RT for 1 h. This gave after workup and purification as described in scheme-303, (1R,3S,5R)-2-(2-(4-amino-7-methoxy-6-(trifluoromethyl)-9H-pyrimido[4,5-b]indol-9-yl)acetyl)-N-(6-bromopyridin-2-yl)-5-methyl-2-azabicyclo[3.1.0]hexane-3-carboxamide (368a) (44 mg, 71% yield) HCl salt as a white solid; $^{1}$H NMR (300 MHz, DMSO-$d_6$) δ 10.72 (s, 1H, $D_2O$ exchangeable), 8.85 (s, 1H), 8.70 (s, 2H, $D_2O$ exchangeable), 8.61 (s, 1H), 8.02 (d, J=8.2 Hz, 1H), 7.72 (t, J=8.0 Hz, 1H), 7.53 (s, 1H), 7.33 (d, J=7.7 Hz, 1H), 5.74 (d, J=17.3 Hz, 1H), 5.46 (d, J=17.2 Hz, 1H), 4.38 (dd, J=9.1, 6.1 Hz, 1H), 4.00 (s, 31), 3.70 (dd, J=5.5, 2.4 Hz, 1H), 2.57-2.53 (m, 1H), 2.01 (dd, J=13.3, 6.0 Hz, 1H), 1.33 (s, 3H), 1.09-0.97 (m, 1H), 0.97-0.88 (m, 1H); $^{19}$F NMR (282 MHz, DMSO-$d_6$) δ–59.24; MS (ES+): 618.1/620.1 (M+1): (ES–): 616.1/618.0 (M–1); Analysis calculated for $C_{26}H_{23}BrF_3N_7O_3$ $2H_2O \cdot 1.2HCl$: C, 44.73; H, 4.07; Cl, 6.09; N, 14.04. Found: C, 44.79; H, 4.07; Cl, 5.87; N, 13.85.

Scheme 369

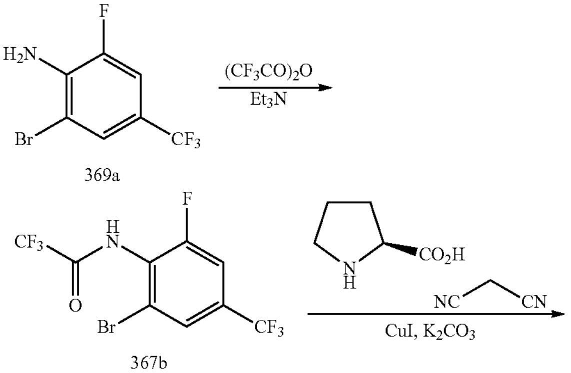

369a

367b

-continued

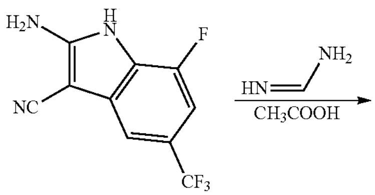

369c

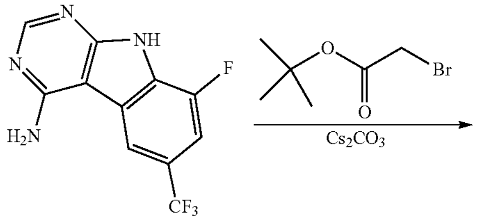

369d

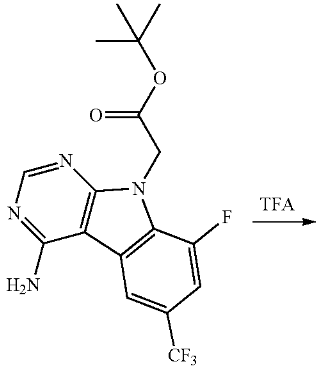

369e

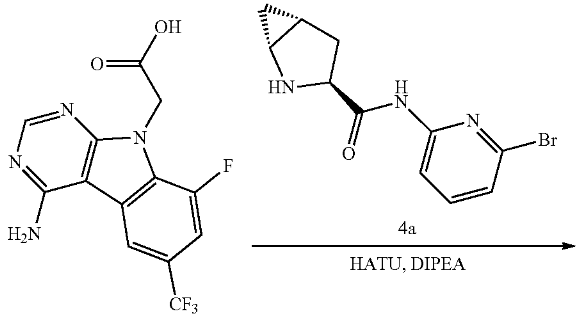

369f

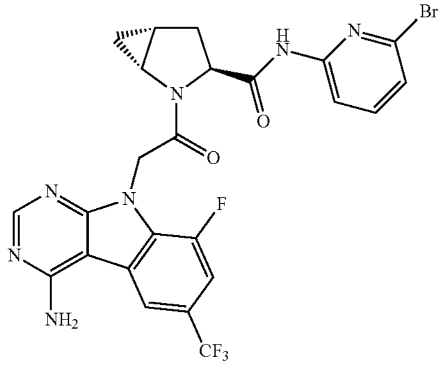

369g

Preparation of (1R,3S,5R)-2-(2-(4-amino-8-fluoro-6-(trifluoromethyl)-9H-pyrimido[4,5-b]indol-9-yl)acetyl)-N-(6-bromopyridin-2-yl)-2-azabicyclo[3.1.0]hexane-3-carboxamide (369 g)

Step-1: Preparation of N-(2-bromo-6-fluoro-4-(trifluoromethyl)phenyl)-2,2,2-trifluoroacetamide (369b)

Compound 369b was prepared according to the procedure reported in step-1 of scheme-46, from 2-bromo-6-fluoro-4-(trifluoromethyl)aniline (369a) (1 g, 3.88 mmol; CAS #1034325-63-7) in DCM (15 mL) using triethylamine (0.918 mL, 6.59 mmol), trifluoroacetic acid anhydride (0.808 mL, 5.81 mmol) to afford after purification as reported in step-1 of scheme-367 N-(2-bromo-6-fluoro-4-(trifluoromethyl)phenyl)-2,2,2-trifluoroacetamide (369b) (1.276 g, 93% yield) as a pale yellow solid; $^1H$ NMR (300 MHz, DMSO-$d_6$) δ 11.84 (s, 1H), 8.13 (s, 1H), 8.04 (dd, J=9.4, 1.9 Hz, 1H); MS (ES−): 351.9/353.9 (M−1).

Step-2: Preparation of 2-amino-7-fluoro-5-(trifluoromethyl)-1H-indole-3-carbonitrile (369c)

Compound 369c was prepared according to the procedure reported in step-1 of scheme-11, from N-(2-bromo-6-fluoro-4-(trifluoromethyl)phenyl)-2,2,2-trifluoroacetamide (369b) (1.25 g, 3.53 mmol) in DMSO (5 mL) using malononitrile (0.267 mL, 4.24 mmol), L-proline (0.081 g, 0.706 mmol), CuI (0.067 g, 0.353 mmol), a solution of $K_2CO_3$ (0.976 g, 7.06 mmol) in water (5 mL) to afford after purification as reported in step-2 of scheme-367, 2-amino-7-fluoro-5-(trifluoromethyl)-1H-indole-3-carbonitrile (369c)(0.125 g, 15% yield) as a yellow solid; $^1H$ NMR (300 MHz, DMSO-$d_6$) δ 11.89 (s, 1H), 7.26 (s, 1H), 7.17 (d, J=11.0 Hz, 1H), 7.11 (s, 2H); MS (ES+): 244.0 (M+1): (ES−): 242.0 (M−1).

Step-3: Preparation of 8-fluoro-6-(trifluoromethyl)-9H-pyrimido[4,5-b]indol-4-amine (369d)

Compound 369d was prepared according to the procedure reported in step-2 of scheme-29, from 2-amino-7-fluoro-5-(trifluoromethyl)-1H-indole-3-carbonitrile (369c) (0.120 g, 0.494 mmol) in ethanol (10 mL) using formamidine acetate (0.415 g, 3.95 mmol) to afford after purification as reported in step-3 of scheme-367, 8-fluoro-6-(trifluoromethyl)-9H-pyrimido[4,5-b]indol-4-amine (369d) (61 mg, 46% yield) HCl salt as a pale yellow solid; $^1H$ NMR (300 MHz, DMSO-$d_6$) δ 13.69 (s, 1H), 8.83 (s, 1H), 8.67 (s, 2H), 8.60 (s, 1H), 7.79 (dd, J=11.0, 1.4 Hz, 1H); MS (ES+): 271.1 (M+1).

Step-4: Preparation of tert-butyl 2-(4-amino-8-fluoro-6-(trifluoromethyl)-9H-pyrimido[4,5-b]indol-9-yl)acetate (369e)

Compound 369e was prepared according to the procedure reported in step-2 of scheme-16, from HCl salt of 8-fluoro-6-(trifluoromethyl)-9H-pyrimido[4,5-b]indol-4-amine (369d) (60 mg, 0.196 mmol) in DMF (3 mL) using tert-butyl 2-bromoacetate (0.032 mL, 0.215 mmol), $Cs_2CO_3$ (159 mg, 0.489 mmol) and stirring at RT for 16 h. The solid separated was collected by filtration to give tert-butyl 2-(4-amino-8-fluoro-6-(trifluoromethyl)-9H-pyrimido[4,5-b]indol-9-yl)acetate (369e) (30 mg, 40% yield) as a pale yellow solid; MS (ES+): 385.1 (M+1).

Step-5: Preparation of 2-(4-amino-8-fluoro-6-(trifluoromethyl)-9H-pyrimido[4,5-b]indol-9-yl)acetic acid (369f)

Compound 369f was prepared according to the procedure reported in step-2 of scheme-1, from tert-butyl 2-(4-amino-8-fluoro-6-(trifluoromethyl)-9H-pyrimido[4,5-b]indol-9-yl) acetate (369e) (28 mg, 0.073 mmol) using 20% TFA in DCM (418 μL, 1.093 mmol)) to afford 2-(4-amino-8-fluoro-6-(trifluoromethyl)-9H-pyrimido[4,5-b]indol-9-yl)acetic acid (369f) (23 mg, 96% yield) TFA salt as a pale-yellow solid; $^1$H NMR (300 MHz, DMSO-$d_6$) δ 8.73 (s, 1H), 8.41 (s, 1H), 7.80 (s, 2H), 7.70 (d, J=12.3 Hz, 1H), 5.25 (s, 2H); MS (ES+): 329.0 (M+1).

Step-6: Preparation of (1R,3S,5R)-2-(2-(4-amino-8-fluoro-6-(trifluoromethyl)-9H-pyrimido[4,5-b]indol-9-yl)acetyl)-N-(6-bromopyridin-2-yl)-2-azabicyclo[3.1.0]hexane-3-carboxamide (369 g)

Compound 369g was prepared according to the procedure reported in step-3 of scheme-1, from TFA salt of 2-(4-amino-8-fluoro-6-(trifluoromethyl)-9H-pyrimido[4,5-b]indol-9-yl) acetic acid (369f) (31.0 mg, 0.07 mmol) in DMF (1 mL) using HCl salt of (1R,3S,5R)—N-(6-bromopyridin-2-yl)-2-azabicyclo[3.1.0]hexane-3-carboxamide (4a) (22.30 mg, 0.070 mmol), HATU (39.9 mg, 0.105 mmol), DIPEA (0.061 mL, 0.350 mmol) and stirring at RT for 16 h. This gave after workup and purification as described in scheme-303, (1R,3S,5R)-2-(2-(4-amino-8-fluoro-6-(trifluoromethyl)-9H-pyrimido[4,5-b]indol-9-yl)acetyl)-N-(6-bromopyridin-2-yl)-2-azabicyclo[3.1.0]hexane-3-carboxamide (369 g) (35 mg, 84% yield) HCl salt as a white solid; $^1$H NMR (300 MHz, DMSO-$d_6$) δ 10.78 (s, 1H, $D_2O$ exchangeable), 8.81 (s, 1H), 8.60 (s, 1H), 8.48 (s, 2H, $D_2O$ exchangeable), 8.01 (d, J=8.2 Hz, 1H), 7.81-7.65 (m, 2H), 7.32 (d, J=7.7 Hz, 1H), 5.90-5.73 (m, 1H), 5.50 (dd, J=17.3, 2.0 Hz, 1H), 4.43 (dd, J=9.0, 5.6 Hz, 1H), 3.91-3.83 (m, 1H), 2.34 (dd, J=13.4, 9.1 Hz, 1H), 2.30-2.15 (m, 1H), 2.00-1.86 (m, 1H), 1.16-1.05 (m, 1H), 0.70-0.58 (m, 1H); $^{19}$F NMR (282 MHz, DMSO-$d_6$) δ−58.66, −132.55; MS (ES+): 592.1/594.1 (M+1); (ES−): 590.0/592.0 (M−1); Analysis calculated for $C_{24}H_{18}BrF_4N_7O_2$ $2H_2O{\cdot}HCl$: C, 43.36; H, 3.49; Cl, 5.33; N, 14.75. Found: C, 43.40; H, 3.46; Cl, 5.47; N, 14.64.

Scheme 370

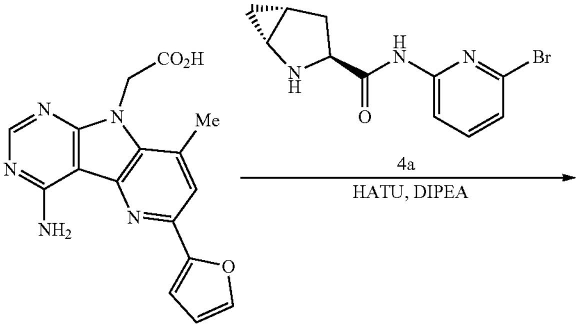

359b

-continued

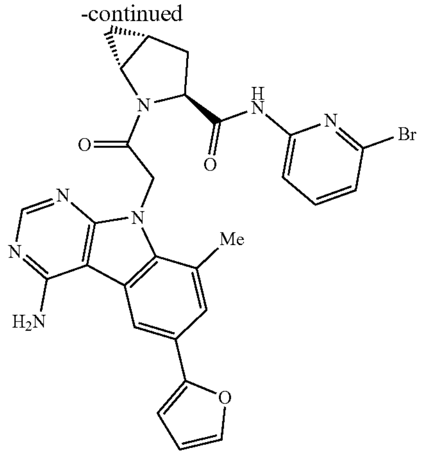

370a

Preparation of (1R,3S,5R)-2-(2-(4-amino-6-(furan-2-yl)-8-methyl-9H-pyrimido[4,5-b]indol-9-yl)acetyl)-N-(6-bromopyridin-2-yl)-2-azabicyclo[3.1.0]hexane-3-carboxamide (370a)

Compound 370a was prepared according to the procedure reported in step-3 of scheme-1, from TFA salt of 2-(4-amino-6-(furan-2-yl)-8-methyl-9H-pyrimido[4,5-b]indol-9-yl)acetic acid (359b) (100 mg, 0.182 mmol) in DMF (8 mL) using HCl salt of (1R,3S,5R)—N-(6-bromopyridin-2-yl)-2-azabicyclo[3.1.0]hexane-3-carboxamide (4a) (69.5 mg, 0.218 mmol), HATU (138 mg, 0.363 mmol), DIPEA (0.158 mL, 0.908 mmol) and stirring at RT for 18 h. This gave after workup and purification as described in scheme-299, (1R,3S,5R)-2-(2-(4-amino-6-(furan-2-yl)-8-methyl-9H-pyrimido[4,5-b]indol-9-yl)acetyl)-N-(6-bromopyridin-2-yl)-2-azabicyclo[3.1.0]hexane-3-carboxamide (370a) (9 mg, 8% yield) HCl salt as a white solid; $^1$H NMR (300 MHz, DMSO-$d_6$) δ 10.83 (s, 1H), 8.61 (s, 1H), 8.57 (s, 1H), 8.52 (s, 2H, $D_2O$ exchangeable), 8.01 (d, J=8.1 Hz, 1H), 7.77 (d, 11H), 7.70 (t, J=8.0 Hz, 1H), 7.64 (s, 1H), 7.31 (d, J=7.7 Hz, 1H), 7.03 (d, J=3.4 Hz, 1H), 6.65-6.62 (m, 1H), 5.91 (d, J=18.0 Hz, 1H), 5.64 (d, J=17.9 Hz, 1H), 4.43 (dd, J=9.1, 5.8 Hz, 1H), 3.99-3.84 (m, 1H), 2.74 (s, 3H), 2.43-2.12 (m, 2H), 2.01-1.81 (m, 1H), 1.18-0.98 (m, 1H), 0.75-0.63 (m, 1H): MS (ES+): 586.1 (M+1); (ES−): 584.0 (M−1).

Scheme 371

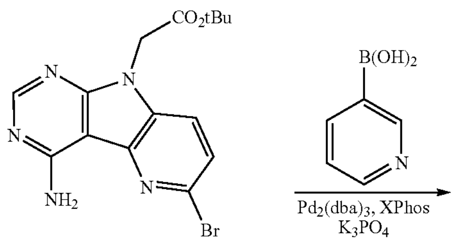

290e

-continued

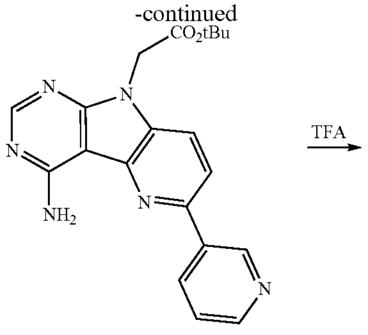

371a

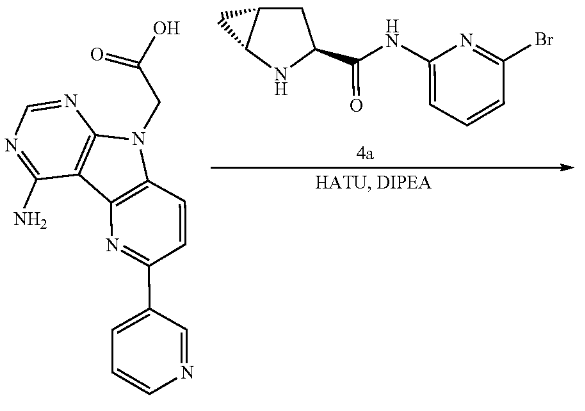

371b

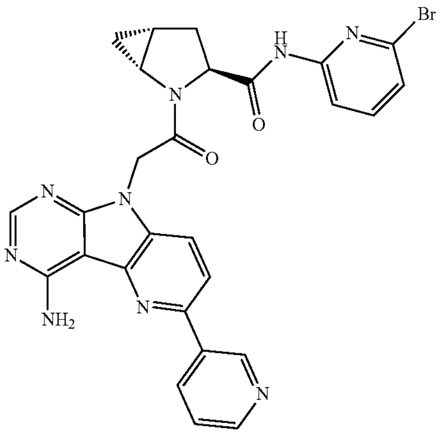

371c

Preparation of (1R,3S,5R)-2-(2-(4-amino-6-(pyridin-3-yl)-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (371c)

Step-1: Preparation of tert-butyl 2-(4-amino-6-(pyridin-3-yl)-9H-pyrido[2',3':4,5]pyrrolo[2,3-d]pyrimidin-9-yl)acetate (371a)

Compound 371a was prepared according to the procedure reported in in scheme-263 and step-1 of scheme-354, from tert-butyl 2-(4-amino-6-bromo-9H-pyrido[2',3':4,5]pyrrolo[2,3-d]pyrimidin-9-yl)acetate (290e) (300 mg, 0.793 mmol) and pyridin-3-ylboronic acid (146 mg, 1.190 mmol) to afford tert-butyl 2-(4-amino-6-(pyridin-3-yl)-9H-pyrido[2',3':4,5]pyrrolo[2,3-d]pyrimidin-9-yl)acetate (371a) (260 mg, 87% yield); $^{1}$H NMR (300 MHz, DMSO-$d_6$) δ 9.08 (d, J=1.9 Hz, 1H), 8.91 (d, J=1.9 Hz, 1H), 8.65 (dd, J=4.8, 1.6 Hz, 1H), 8.54 (d, J=1.9 Hz, 1H), 8.41 (s, 1H), 8.26 (dt, J=8.1, 1.9 Hz, 1H), 8.03 (bs, 1H), 7.70-7.46 (m, 1H), 6.86 (bs, 1H), 5.23 (s, 2H), 1.41 (s, 9H); MS (ES+): 377 (M+1).

Step-2: Preparation of 2-(4-amino-6-(pyridin-3-yl)-9H-pyrido[2',3':4,5]pyrrolo[2,3-d]pyrimidin-9-yl) acetic acid (371b)

Compound 371b was prepared according to the procedure reported in step-2 of scheme-1, from tert-butyl 2-(4-amino-6-(pyridin-3-yl)-9H-pyrido[2',3':4,5]pyrrolo[2,3-d]pyrimidin-9-yl)acetate (371a) (260 mg, 0.691 mmol) in DCM (5 mL) using TFA (788 mg, 6.91 mmol) to afford TFA salt of 2-(4-amino-6-(pyridin-3-yl)-9H-pyrido[2',3':4,5]pyrrolo[2,3-d]pyrimidin-9-yl)acetic acid (371b) (344 mg) as a pale-yellow solid; $^{1}$H NMR (300 MHz, DMSO-$d_6$) δ 9.18 (s, 1H), 9.01 (d, J=3.3 Hz, 1H), 8.71 (d, J=11.4 Hz, 2H), 8.58-8.26 (m, 3H), 7.74 (s, 1H), 7.52 (s, 1H), 5.29 (s, 2H); MS (ES+): 321 (M+1), (ES−): 319 (M−1).

Step-3: Preparation of (1R,3S,5R)-2-(2-(4-amino-6-(pyridin-3-yl)-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (371c)

Compound 371c was prepared according to the procedure reported in step-3 of scheme-1, from TFA salt of 2-(4-amino-6-(pyridin-3-yl)-9H-pyrido[2',3':4,5]pyrrolo[2,3-d]pyrimidin-9-yl)acetic acid (371b) (75 mg, 0.173 mmol) in DMF (8 mL) using HCl salt of (1R,3S,5R)—N-(6-bromopyridin-2-yl)-2-azabicyclo[3.1.0]hexane-3-carboxamide (4a) (66 mg, 0.207 mmol), HATU (131 mg, 0.345 mmol), DIPEA (0.150 mL, 0.863 mmol) and stirring at RT for 18 h. This gave after workup and purification as described in scheme-299, (1R,3S,5R)-2-(2-(4-amino-6-(pyridin-3-yl)-9H-pyrido[2',3':4,5]pyrrolo[2,3-d]pyrimidin-9-yl)acetyl)-N-(6-bromopyridin-2-yl)-2-azabicyclo[3.1.0]hexane-3-carboxamide (371c) (47 mg, 47% yield) HCl salt as a pale-yellow solid; $^{1}$H NMR (300 MHz, DMSO-$d_6$) δ 10.78 (s, 1H, $D_2O$ exchangeable), 9.45 (d, J=2.0 Hz, 1H), 9.22 (s, 2H, $D_2O$ exchangeable), 9.15 (d, J=1.9 Hz, 1H), 9.00-8.93 (m, 2H), 8.83 (d, J=1.9 Hz, 1H), 8.77 (s, 1H), 8.16 (dd, J=7.9, 5.8 Hz, 1H), 7.95 (d, J=8.2 Hz, 1H), 7.67 (t, J=8.0 Hz, 1H), 7.29 (d, J=7.7 Hz, 1H), 5.91 (d, J=17.3 Hz, 1H), 5.55 (d, J=17.2 Hz, 1H), 4.45 (dd, J=9.0, 5.5 Hz, 1H), 3.97-3.89 (m, 1H), 2.42-2.15 (m, 2H), 2.00-1.85 (m, 1H), 1.17-1.03 (m, 1H), 0.88-0.76 (m, 1H); MS (ES+): 584.10 (M+1); (ES−): 582.00 (M−1).

Scheme 372

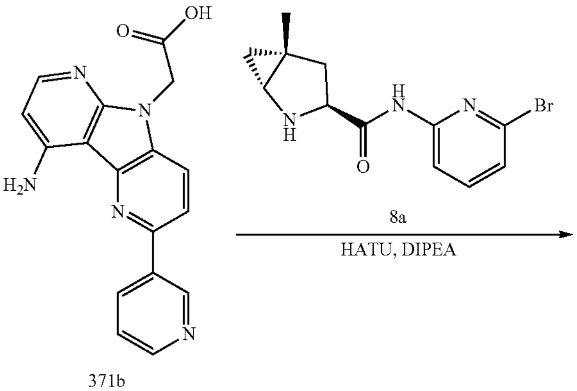

371b

-continued

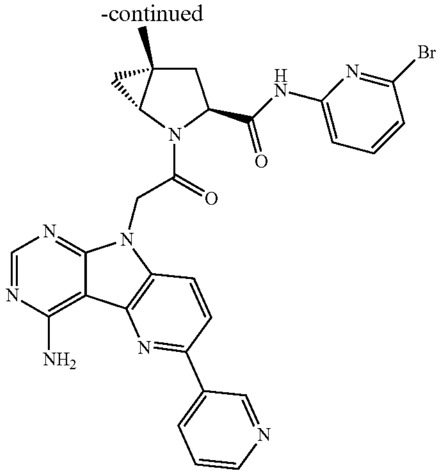

372a

Preparation of (1R,3S,5R)-2-(2-(4-amino-6-(pyridin-3-yl)-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (372a)

Compound 372a was prepared according to the procedure reported in step-3 of scheme-1, from TFA salt of 2-(4-amino-6-(pyridin-3-yl)-9H-pyrido[2',3':4,5]pyrrolo[2,3-d]pyrimidin-9-yl)acetic acid (371b) (75 mg, 0.234 mmol) in DMF (8 mL) using HCl salt of (1R,3S,5R)—N-(6-bromopyridin-2-yl)-5-methyl-2-azabicyclo[3.1.0]hexane-3-carboxamide (8a) (93 mg, 0.281 mmol), HATU (178 mg, 0.468 mmol), DIPEA (0.204 mL, 1.171 mmol) and stirring at RT for 18 h. This gave after workup and purification as described in scheme-299, (1R,3S,5R)-2-(2-(4-amino-6-(pyridin-3-yl)-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (372a) (48 mg, 34% yield) HCl salt as a pale-yellow solid; $^1$H NMR (300 MHz, DMSO-$d_6$) δ 10.78 (s, 1H, $D_2O$ exchangeable), 9.33 (s, 1H), 9.10 (d, J=2.8 Hz, 1H), 8.89 (s, 1H), 8.81-8.63 (m, 3H), 8.09-7.89 (m, 2H), 7.67 (t, J=8.0 Hz, 1H), 7.29 (d, J=7.7 Hz, 1H), 5.83 (d, J=17.4 Hz, 1H), 5.48 (d, J=17.3 Hz, 1H), 4.40 (dd, J=9.0, 5.9 Hz, 1H), 3.73-3.63 (m, 1H), 2.50-2.41 (m, 1H), 1.99 (dd, J=13.3, 5.8 Hz, 1H), 1.09-1.00 (m, 1H), 1.00-0.92 (m, 1H); MS (ES+): 598.1 (M+1): (ES−): 596.1 (M−1).

Scheme 373

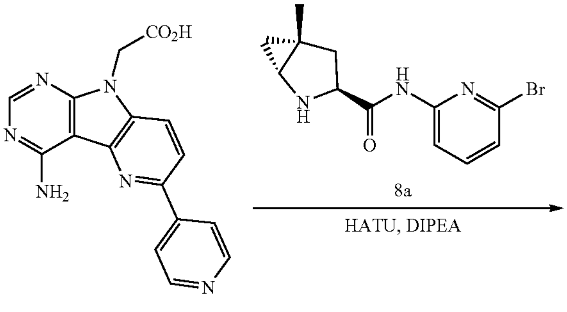

307b

8a

-continued

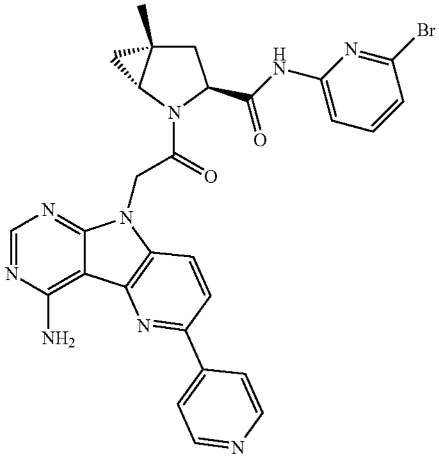

373a

Preparation of (1R,3S,5R)-2-(2-(4-amino-6-(pyridin-4-yl)-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (373a)

Compound 373a was prepared according to the procedure reported in step-3 of scheme-1, from TFA salt of 2-(4-amino-6-(pyridin-4-yl)-9H-pyrido[2',3':4,5]pyrrolo[2,3-d]pyrimidin-9-yl)acetic acid (307b) (80 mg, 0.250 mmol) in DMF (8 mL) using HCl salt of (1R,3S,5R)—N-(6-bromopyridin-2-yl)-5-methyl-2-azabicyclo[3.1.0]hexane-3-carboxamide (8a) (100 mg, 0.300 mmol), HATU (190 mg, 0.500 mmol), DIPEA (0.218 mL, 1.249 mmol) and stirring at RT for 18 h. This gave after workup and purification as described in scheme-299, (1R,3S,5R)-2-(2-(4-amino-6-(pyridin-4-yl)-9H-pyrido[2',3':4,5]pyrrolo[2,3-d]pyrimidin-9-yl)acetyl)-N-(6-bromopyridin-2-yl)-5-methyl-2-azabicyclo[3.1.0]hexane-3-carboxamide (373a) (72 mg, 48% yield) HCl salt as a pale-yellow solid; $^1$H NMR (300 MHz, DMSO-$d_6$) δ 10.77 (s, 1H, $D_2O$ exchangeable), 9.23 (d, J=1.9 Hz, 1H), 9.09-9.02 (m, 2H), 8.96 (s, 2H, $D_2O$ exchangeable), 8.84 (d, J=2.0 Hz, 1H), 8.68 (s, 1H), 8.56-8.48 (m, 2H), 8.26 (s, 1H, $D_2O$ exchangeable), 7.97 (d, J=8.1 Hz, 1H), 7.67 (t, J=8.0 Hz, 1H), 7.29 (d, J=7.7 Hz, 1H), 5.84 (d, J=17.3 Hz, 1H), 5.50 (d, J=17.2 Hz, 1H), 4.40 (dd, J=9.1, 5.9 Hz, 1H), 3.69 (dd, J=5.6, 2.4 Hz, 1H), 2.55-2.40 (m, 1H), 1.99 (dd, J=13.2, 5.8 Hz, 1H), 1.32 (s, 3H), 1.08-1.01 (m, 1H), 1.00-0.94 (m, 1H); MS (ES+): 598.10 (M+1); (ES−): 596.0 (M−1).

Scheme 374

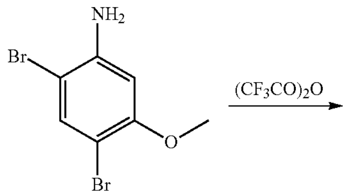

374a

-continued

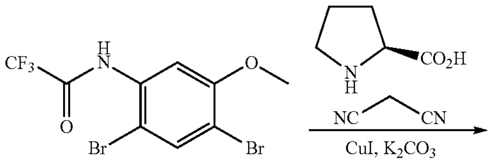

374b

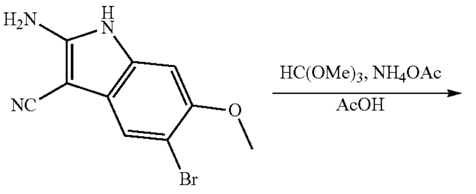

374c

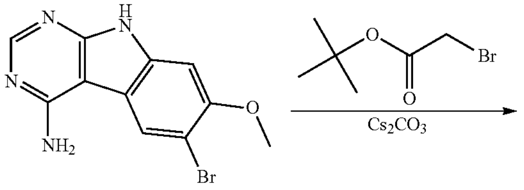

374d

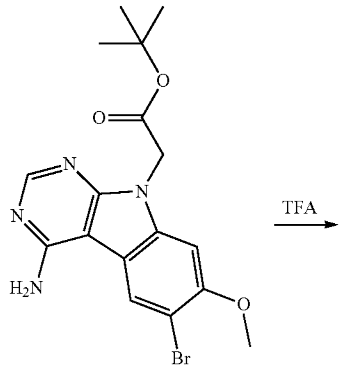

374e

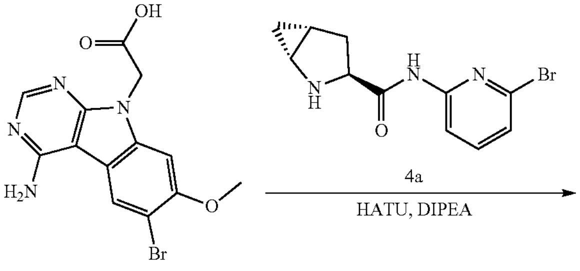

347f

-continued

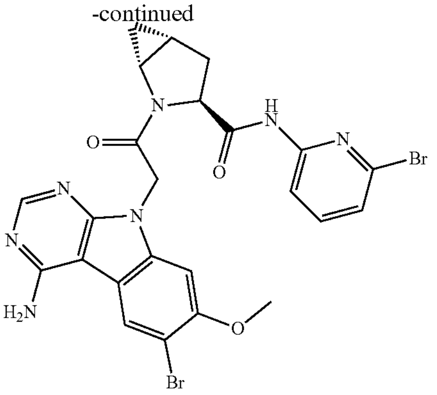

374g

Preparation of (1R,3S,5R)-2-(2-(4-amino-6-bromo-7-methoxy-9H-pyrimido[4,5-b]indol-9-yl)acetyl)-N-(6-bromopyridin-2-yl)-2-azabicyclo[3.1.0]hexane-3-carboxamide (374 g)

Step-1: Preparation of N-(2,4-dibromo-5-methoxyphenyl)-2,2,2-trifluoroacetamide (374b)

Compound 374b was prepared according to the procedure reported in step-1 of scheme-46, from 2,4-dibromo-5-methoxyaniline (374a) (5.0 g, 17.80 mmol; CAS #35736-52-8) in DCM (50 mL) using trifluoroacetic acid anhydride (3.78 mL, 26.68 mmol) and stirring at RT for 1 h. This gave after workup N-(2,4-dibromo-5-methoxyphenyl)-2,2,2-trifluoroacetamide (374b) (6.5 g, 97% yield) as a pale yellow solid; $^1H$ NMR (300 MHz, DMSO-$d_6$) δ 11.37 (s, 1H), 7.99 (s, 1H), 7.27 (s, 1H), 3.86 (s, 3H).

Step-2: Preparation of 2-amino-5-bromo-6-methoxy-1H-indole-3-carbonitrile (374c)

Compound 374c was prepared according to the procedure reported in step-1 of scheme-11, from N-(2,4-dibromo-5-methoxyphenyl)-2,2,2-trifluoroacetamide (374b) (6.1 g, 16.18 mmol) in DMSO (24.4 mL) using malononitrile (1.28 g, 19.41 mmol), L-proline (0.37 g, 3.23 mmol), CuI (0.31 g, 1.61 mmol), a solution of $K_2CO_3$ (2.80 g, 20.22 mmol) in water (3.05 mL) and heating at 65° C. for 16 h under an argon atmosphere. This gave after workup and purification by flash column chromatography [$SiO_2$ gel, eluting with EtOAc in n-heptane from 0-100%] 2-amino-5-bromo-6-methoxy-1H-indole-3-carbonitrile (374c) (1.48 g, 34% yield) as a reddish solid; $^1H$ NMR (300 MHz, DMSO-$d_6$) δ 10.69 (s, 1H), 7.24-7.19 (m, 1H), 6.95-6.89 (m, 1H), 6.79 (s, 2H), 3.79 (s, 3H).

Step-3: Preparation of 6-bromo-7-methoxy-9H-pyrimido[4,5-b]indol-4-amine (374d)

Compound 374d was prepared according to the procedure reported in step-1 of scheme-6, from 2-amino-5-bromo-6-methoxy-1H-indole-3-carbonitrile (374c) (1.6 g, 6.01 mmol) using trimethyl orthoformate (19.73 mL, 180.3 mmol), AcOH (1.72 mL, 30.05 mmol) and $NH_4OAc$ (2.32 g, 30.05) at RT. This gave after workup AcOH salt of 6-bromo-7-methoxy-9H-pyrimido[4,5-b]indol-4-amine (374d) (1.65 g, 78% yield) as a greenish solid; MS (ES−) 291.3 (M−1).

Step-4: Preparation of tert-butyl 2-(4-amino-6-bromo-7-methoxy-9H-pyrimido[4,5-b]indol-9-yl) acetate (374e)

Compound 374e was prepared according to the procedure reported in step-2 of scheme-16, from AcOH salt of 6-bromo-7-methoxy-9H-pyrimido[4,5-b]indol-4-amine (374d) (1.65 g, 4.67 mmol) in DMF (66 mL) using tert-butyl 2-bromoacetate (0.83 mL, 5.62 mmol) and $Cs_2CO_3$ (3.67 g, 11.24 mmol) and stirring at RT for 16 h. This gave after workup and purification by flash column chromatography [$SiO_2$ gel, eluting with MeOH in DCM from 0-10%] tert-butyl 2-(4-amino-6-bromo-7-methoxy-9H-pyrimido[4,5-b]indol-9-yl)acetate (374e) (0.97 g, 51% yield) as an off white solid; $^1H$ NMR (300 MHz, DMSO-$d_6$) δ 8.62 (s, 1H), 8.24 (s, 1H), 7.40 (s, 1H), 7.27 (s, 2H), 5.14 (s, 2H), 3.92 (s, 3H), 1.40 (s, 9H).

Step-5: Preparation of 2-(4-amino-6-bromo-7-methoxy-9H-pyrimido[4,5-b]indol-9-yl)acetic acid (374f)

Compound 374f was prepared according to the procedure reported in step-2 of scheme-1, from tert-butyl 2-(4-amino-6-bromo-7-methoxy-9H-pyrimido[4,5-b]indol-9-yl)acetate (374e) (0.97 g, 2.38 mmol) in DCM (4.0 mL) using TFA (4.0 mL, 52.36 mmol) in DCM (11.60 mL) to afford 2-(4-amino-6-bromo-7-methoxy-9H-pyrimido[4,5-b]indol-9-yl)acetic acid (374f) (1.1 g, 99% yield) TFA salt as an off white solid: 1H NMR (300 MHz, DMSO-$d_6$) δ 8.80 (s, 1H), 8.52 (s, 1H), 8.44 (s, 2H), 7.62 (s, 1H), 5.27 (s, 2H), 3.96 (s, 3H).

Step-6: Preparation of (1R,3S,5R)-2-(2-(4-amino-6-bromo-7-methoxy-9H-pyrimido[4,5-b]indol-9-yl) acetyl)-N-(6-bromopyridin-2-yl)-2-azabicyclo[3.1.0] hexane-3-carboxamide (374 g)

Compound 374g was prepared according to the procedure reported in step-3 of scheme-1, from TFA salt of 2-(4-amino-6-bromo-7-methoxy-9H-pyrimido[4,5-b]indol-9-yl)acetic acid (374f) (87 mg, 0.15 mmol) in DMF (8 mL) using HCl salt of (1R,3S,5R)—N-(6-bromopyridin-2-yl)-2-azabicyclo [3.1.0]hexane-3-carboxamide (4a) (57.3 mg, 0.180 mmol), HATU (114 mg, 0.300 mmol), DIPEA (0.131 mL, 0.750 mmol) and stirring at RT for 18 h. This gave after workup and purification as described in scheme-299, (1R,3S,5R)-2-(2-(4-amino-6-bromo-7-methoxy-9H-pyrimido[4,5-b]indol-9-yl)acetyl)-N-(6-bromopyridin-2-yl)-2-azabicyclo[3.1.0] hexane-3-carboxamide (374 g) (67 mg, 73% yield) HCl salt as a white solid; $^1H$ NMR (300 MHz, DMSO-$d_6$) δ 10.71 (s, 1H, $D_2O$ exchangeable), 8.82 (s, 1H), 8.56 (s, 1H), 8.53 (s, 3H, $D_2O$ exchangeable), 8.00 (d, J=8.2 Hz, 1H), 7.71 (t, J=8.0 Hz, 1H), 7.42 (s, 1H), 7.32 (d, J=7.7 Hz, 1H), 5.72 (d, J=17.3 Hz, 1H), 5.46 (d, J=17.2 Hz, 1H), 4.41 (dd, J=9.1, 5.7 Hz, 1H), 3.97 (s, 3H), 3.94-3.86 (m, 1H), 2.42-2.15 (m, 2H), 2.01-1.79 (m, 1H), 1.13-0.97 (m, 1H), 0.82-0.67 (m, 1H); MS (ES+): 614/616 (M+1).

Scheme 375

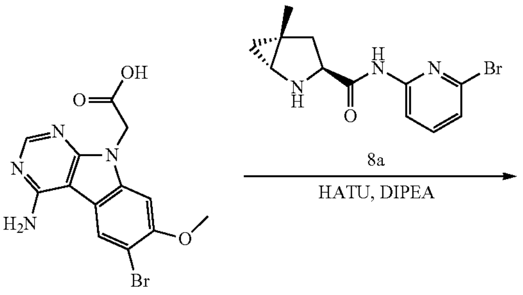

374f

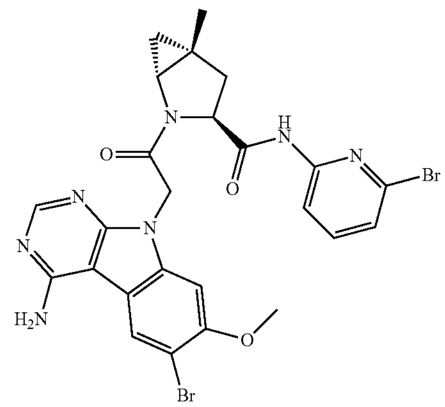

375a

Preparation of (1R,3S,5R)-2-(2-(4-amino-6-bromo-7-methoxy-9H-pyrimido[4,5-b]indol-9-yl)acetyl)-N-(6-bromopyridin-2-yl)-5-methyl-2-azabicyclo[3.1.0] hexane-3-carboxamide (375a)

Compound 375a was prepared according to the procedure reported in step-3 of scheme-1, from TFA salt of 2-(4-amino-6-bromo-7-methoxy-9H-pyrimido[4,5-b]indol-9-yl)acetic acid (374f) (87 mg, 0.15 mmol) in DMF (8 mL) using HCl salt of (1R,3S,5R)—N-(6-bromopyridin-2-yl)-5-methyl-2-azabicyclo[3.1.0]hexane-3-carboxamide (8a) (59.9 mg, 0.1800 mmol), HATU (114 mg, 0.300 mmol), DIPEA (0.131 mL, 0.750 mmol) and stirring at RT for 18 h. This gave after work up and purification as described in scheme-299, (1R,3S,5R)-2-(2-(4-amino-6-bromo-7-methoxy-9H-pyrimido[4,5-b]indol-9-yl)acetyl)-N-(6-bromopyridin-2-yl)-5-methyl-2-azabicyclo[3.1.0]hexane-3-carboxamide (375a) (47 mg, 50% yield) HCl salt as a white solid: $^1H$ NMR (300 MHz, DMSO-$d_6$) δ 10.70 (s, 1H, $D_2O$ exchangeable), 8.81 (s, 1H), 8.55 (s, 1H), 8.51 (s, 2H, $D_2O$ exchangeable), 8.01 (d, J=8.2 Hz, 1H), 7.71 (t, J=8.0 Hz, 1H), 7.42 (s, 1H), 7.32 (d, J=7.7 Hz, 1H), 5.68 (d, J=17.4 Hz, 1H), 5.41 (d, J=17.2 Hz, 1H), 4.36 (dd, J=9.1, 6.0 Hz, 1H), 3.96 (s, 3H), 3.73-3.63 (m, 1H), 2.56-2.40 (m, 1H), 1.99 (dd, J=13.1, 6.1 Hz, 1H), 1.32 (s, 3H), 1.07-0.96 (m, 1H), 0.94-0.87 (m, 1H): MS (ES+): 628/630 (M+1).

Scheme 376

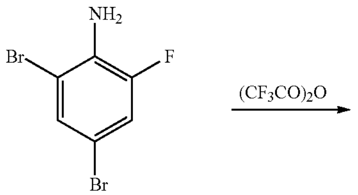

376a

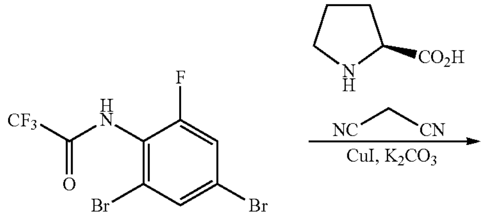

376b

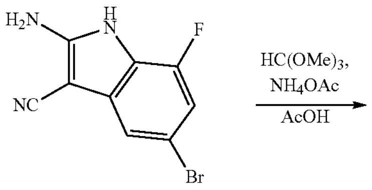

376c

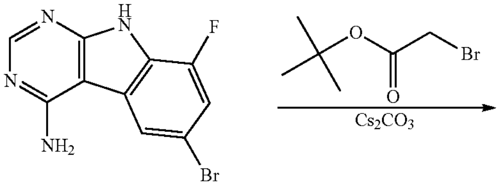

376d

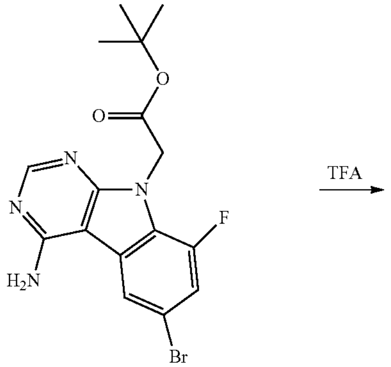

376e

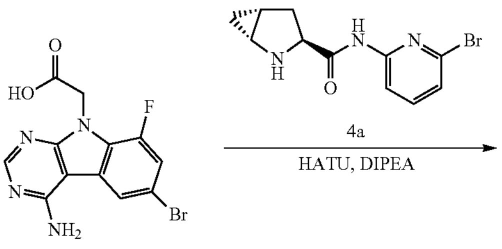

376f

-continued

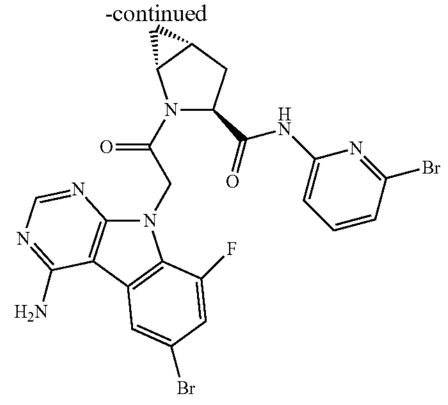

376g

Preparation of (1R,3S,5R)-2-(2-(4-amino-6-bromo-8-fluoro-9H-pyrimido[4,5-b]indol-9-yl)acetyl)-N-(6-bromopyridin-2-yl)-2-azabicyclo[3.1.0]hexane-3-carboxamide (376 g)

Step-1: Preparation of N-(2,4-dibromo-6-fluorophenyl)-2,2,2-trifluoroacetamide (376b)

Compound 376b was prepared according to the procedure reported in step-1 of scheme-46, from 2,4-dibromo-6-fluoroaniline (376a) (10.0 g, 37.19 mmol; CAS #141474-37-5) in DCM (100 mL) using trifluoroacetic acid anhydride (8.4 mL, 55.78 mmol) to afford N-(2,4-dibromo-6-fluorophenyl)-2,2,2-trifluoroacetamide (376b) (13.27 g, 98% yield) as an off white solid: $^1$H NMR (300 MHz, DMSO-$d_6$) δ 11.55 (s, 1H), 7.97 (t, J=1.9 Hz, 1H), 7.87 (dd, J=9.1, 2.1 Hz, 1H).

Step-2: Preparation of 2-amino-5-bromo-7-fluoro-1H-indole-3-carbonitrile (376c)

Compound 376c was prepared according to the procedure reported in step-1 of scheme-11 and step-2 of scheme-374, from N-(2,4-dibromo-6-fluorophenyl)-2,2,2-trifluoroacetamide (376b) (7.40 g, 20.28 mmol) in DMSO (20.0 mL) using malononitrile (1.35 mL, 24.32 mmol), L-proline (0.47 mg, 4.06 mmol), CuI (386 mg, 2.03 mmol), a solution of $K_2CO_3$ (3.50 g, 25.34 mmol) in water (1.4 mL) to afford 2-amino-5-bromo-7-fluoro-1H-indole-3-carbonitrile (376c) (1.84 g, 36% yield) as a brown solid; $^1$H NMR (300 MHz, DMSO-$d_6$) δ 11.57 (s, 1H), 7.14-7.07 (m, 1H), 7.06-7.00 (m, 1H), 6.97 (s, 2H).

Step-3: Preparation of 6-bromo-8-fluoro-9H-pyrimido[4,5-b]indol-4-amine (376d)

Compound 376d was prepared according to the procedure reported in step-1 of scheme-6 and step-3 of scheme-374, from 2-amino-5-bromo-7-fluoro-1H-indole-3-carbonitrile (376c) (3.40 g, 13.38 mmol) using trimethyl orthoformate (42.61 g, 401.47 mmol), AcOH (4.017 g, 66.9 mmol), $NH_4OAc$ (5.156 g, 66.9 mmol) to afford AcOH salt of 6-bromo-8-fluoro-9H-pyrimido[4,5-b]indol-4-amine (376d) (3.50 g, 93% yield) as an off white solid $^1$H NMR (300 MHz, DMSO-$d_6$) δ 12.54 (s, 1H), 8.46 (d, J=1.6 Hz, 1H), 8.30 (s, 1H), 7.50 (dd, J=10.4, 1.5 Hz, 1H), 7.42 (s, 2H).

Step-4: Preparation of tert-butyl 2-(4-amino-6-bromo-8-fluoro-9H-pyrimido[4,5-b]indol-9-yl)acetate (376e)

Compound 376e was prepared according to the procedure reported in step-2 of scheme-16 and step-4 of scheme-374, from AcOH salt of 6-bromo-8-fluoro-9H-pyrimido[4,5-b]indol-4-amine (376d) (3.50 g, 12.45 mmol) in DMF (140 mL) using tert-butyl 2-bromoacetate (2.43 g, 12.45 mmol), $Cs_2CO_3$ (8.11 g, 24.90 mmol) to afford tert-butyl 2-(4-amino-6-bromo-8-fluoro-9H-pyrimido[4,5-b]indol-9-yl)acetate (376e) (3.10 g, 63% yield) as an off white solid: $^1$H NMR (300 MHz, DMSO-$d_6$) δ 8.51 (d, J=1.6 Hz, 1H), 8.35 (s, 1H), 7.68-7.46 (m, 3H), 5.25-5.07 (m, 2H), 1.40 (s, 9H).

Step-5: Preparation of 2-(4-amino-6-bromo-8-fluoro-9H-pyrimido[4,5-b]indol-9-yl)acetic acid (376f)

Compound 376f was prepared according to the procedure reported in step-2 of scheme-1, from tert-butyl 2-(4-amino-6-bromo-8-fluoro-9H-pyrimido[4,5-b]indol-9-yl)acetate (376e) (3.0 g 7.59 mmol) in DCM (50 mL) using TFA (12.77 mL, 166.99 mmol) to afford 2-(4-amino-6-bromo-8-fluoro-9H-pyrimido[4,5-b]indol-9-yl)acetic acid (376f) (3.5 g) TFA salt as an off white solid; 1H NMR (300 MHz, DMSO-$d_6$) δ 8.60 (d, J=1.7 Hz, 1H), 8.49 (s, 1H), 8.16 (s, 2H), 7.64 (dd, J=11.7, 1.6 Hz, 1H), 5.22 (d, J=1.9 Hz, 2H).

Step-6: Preparation of (1R,3S,5R)-2-(2-(4-amino-6-bromo-8-fluoro-9H-pyrimido[4,5-b]indol-9-yl)acetyl)-N-(6-bromopyridin-2-yl)-2-azabicyclo[3.1.0]hexane-3-carboxamide (376 g)

Compound 376g was prepared according to the procedure reported in step-3 of scheme-1, from TFA salt of 2-(4-amino-6-bromo-8-fluoro-9H-pyrimido[4,5-b]indol-9-yl)acetic acid (376f) (85 mg, 0.15 mmol) in DMF (8 mL) using HCl salt of (1R,3S,5R)—N-(6-bromopyridin-2-yl)-2-azabicyclo[3.1.0]hexane-3-carboxamide (4a) (57.3 mg, 0.180 mmol), HATU (114 mg, 0.300 mmol), DIPEA (0.131 mL, 0.750 mmol) and stirring at RT for 18 h. This gave after workup and purification as described in scheme-299, (1R,3S,5R)-2-(2-(4-amino-6-bromo-8-fluoro-9H-pyrimido[4,5-b]indol-9-yl)acetyl)-N-(6-bromopyridin-2-yl)-2-azabicyclo[3.1.0]hexane-3-carboxamide (376 g) (52 mg, 58% yield) HCl salt as a white solid; $^1$H NMR (300 MHz, DMSO-$d_6$) δ 10.76 (s, 1H), 8.61 (s, 1H), 8.55 (s, 1H), 8.32 (s, 2H, $D_2O$ exchangeable), 8.08-7.92 (m, 1H), 7.79-7.56 (m, 2H), 7.39-7.22 (m, 1H), 5.76 (d, J=17.7 Hz, 1H), 5.42 (d, J=17.4 Hz, 1H), 4.53-4.26 (m, 1H), 3.95-3.77 (m, 1H), 2.43-2.13 (m, 2H), 2.02-1.81 (m, 1H), 1.14-1.01 (m, 1H), 0.72-0.50 (m, 1H); MS (ES+): 602.00 & 604.00 (M+1).

-continued

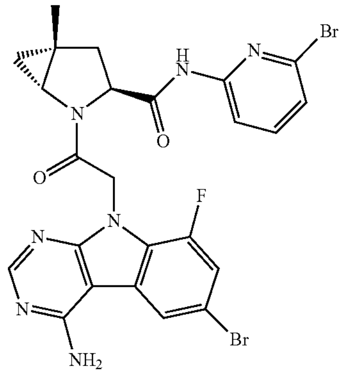

377a

Preparation of (1R,3S,5R)-2-(2-(4-amino-6-bromo-8-fluoro-9H-pyrimido[4,5-b]indol-9-yl)acetyl)-N-(6-bromopyridin-2-yl)-5-methyl-2-azabicyclo[3.1.0]hexane-3-carboxamide (377a)

Compound 377a was prepared according to the procedure reported in step-3 of scheme-1, from TFA salt of 2-(4-amino-6-bromo-8-fluoro-9H-pyrimido[4,5-b]indol-9-yl)acetic acid (3760 (85 mg, 0.15 mmol) in DMF (8 mL) using HCl salt of (1R,3S,5R)—N-(6-bromopyridin-2-yl)-5-methyl-2-azabicyclo[3.1.0]hexane-3-carboxamide (8a) (59.9 mg, 0.180 mmol), HATU (114 mg, 0.300 mmol), DIPEA (0.131 mL, 0.750 mmol) and stirring at RT for 18 h. This gave after workup and purification as described in scheme-299, (1R,3S,5R)-2-(2-(4-amino-6-bromo-8-fluoro-9H-pyrimido[4,5-b]indol-9-yl)acetyl)-N-(6-bromopyridin-2-yl)-5-methyl-2-azabicyclo[3.1.0]hexane-3-carboxamide (377a) (84 mg, 91% yield) HCl salt as a white solid: 1H NMR (300 MHz, DMSO-$d_6$) δ 10.77 (s, 1H), 8.70-8.49 (m, 4H, 2H $D_2O$ exchangeable), 8.05-7.96 (m, 1H), 7.78-7.55 (m, 2H), 7.37-7.23 (m, 1H), 5.72 (d, J=17.5 Hz, 1H), 5.38 (d, J=17.5 Hz, 1H), 4.43-4.32 (m, 1H), 3.13-2.98 (m, 1H), 2.61-2.32 (m, 1H), 2.17-1.76 (m, 1H), 1.29 (s, 3H), 1.08-0.95 (m, 1H), 0.83-0.70 (m, 1H); $^{19}$F NMR (282 MHz, DMSO-$d_6$) δ-131.77; MS (ES+): 616.00 & 618.00 (M+1).

Scheme 377

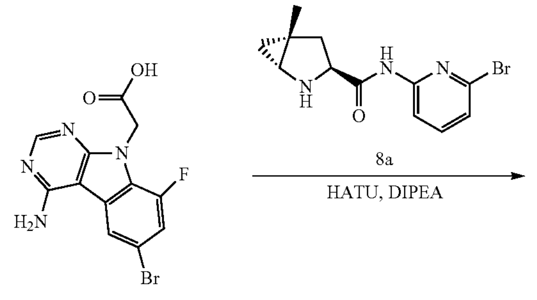

376f

Scheme 378

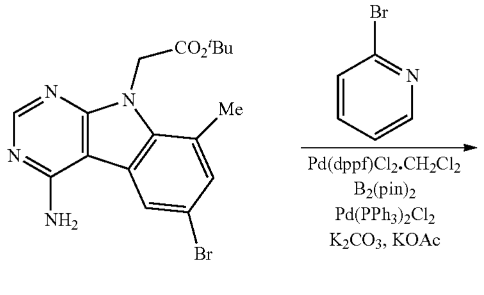

192e

-continued

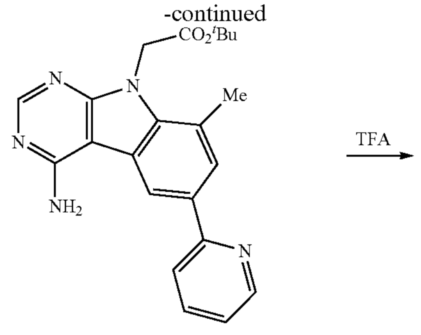

378a

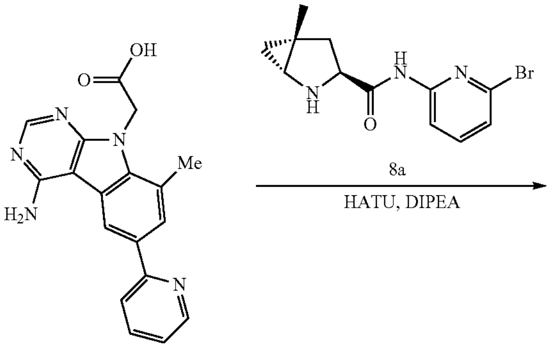

378b

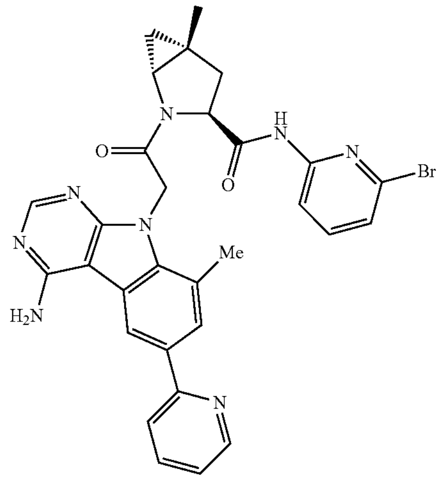

378c

Preparation of (1R,3S,5R)-2-(2-(4-amino-8-methyl-6-(pyridin-2-yl)-9H-pyrimido[4,5-b]indol-9-yl)acetyl)-N-(6-bromopyridin-2-yl)-5-methyl-2-azabicyclo[3.1.0]hexane-3-carboxamide (378c)

Step-1: Preparation of tert-butyl 2-(4-amino-8-methyl-6-(pyridin-2-yl)-9H-pyrimido[4,5-b]indol-9-yl)acetate (378a)

A mixture of tert-butyl 2-(4-amino-6-bromo-8-methyl-9H-pyrimido[4,5-b]indol-9-yl)acetate (192e) (300 mg, 0.767 mmol), $B_2(pin)_2$ (292 mg, 1.150 mmol), Pd(dppf) $Cl_2CH_2Cl_2$ (62.6 mg, 0.077 mmol), KOAc (226 mg, 2.300 mmol) in anhydrous dioxane (15 mL) was heated at 100° C. for 16 h under nitrogen. To this mixture 2-bromopyridine (182 mg, 1.150 mmol), $Pd(PPh_3)_2Cl_2$ (53.8 mg, 0.077 mmol) and 3.3 M aqueous $K_2CO_3$ (0.697 mL, 2.300 mmol) were added and the mixture was stirred at 100° C. for 16 h under nitrogen. The resulting mixture was diluted with EtOAc (50 mL) and filtered. The filtrate was washed with $H_2O$ (25 mL×3), brine (25 mL), dried, filtered and concentrated in vacuum. The residue obtained was purified using flash column chromatography [$SiO_2$ gel (12 g), eluting with DMA-80 in DCM from 0-20%] to provide tert-butyl 2-(4-amino-8-methyl-6-(pyridin-2-yl)-9H-pyrimido[4,5-b]indol-9-yl)acetate (378a) (60 mg, 20% yield) as a yellow semi-solid; $^1H$ NMR (300 MHz, DMSO-$d_6$) δ 8.75 (d, J=3.7 Hz, 1H), 8.66 (s, 1H), 8.43-8.21 (m, 2H), 8.08 (s, 1H), 7.92 (t, J=8.7 Hz, 1H), 7.48 (s, 2H), 7.32 (d, J=6.6 Hz, 1H), 5.37 (s, 2H), 2.71 (s, 3H), 1.44 (s, 9H); MS (ES+): 390 (M+1), (ES−): 388 (M−1).

Step-2: Preparation of 2-(4-amino-8-methyl-6-(pyridin-2-yl)-9H-pyrimido[4,5-b]indol-9-yl)acetic acid (378b)

Compound 378b was prepared according to the procedure reported in step-2 of scheme-1, from tert-butyl 2-(4-amino-8-methyl-6-(pyridin-2-yl)-9H-pyrimido[4,5-b]indol-9-yl) acetate (378a) (60 mg, 0.154 mmol) in DCM (5 mL) using TFA (176 mg, 1.541 mmol) to afford after purification as reported in step-2 of scheme-319, 2-(4-amino-8-methyl-6-(pyridin-2-yl)-9H-pyrimido[4,5-b]indol-9-yl)acetic acid (378b) (33 mg, 58% yield) HCl salt as a white solid; $^1H$ NMR (300 MHz, DMSO-$d_6$) δ 9.23 (s, 1H), 9.15 (bs, 2H), 8.81 (dd, J=5.5, 1.7 Hz, 1H), 8.71 (s, 1H), 8.57 (d, J=8.2 Hz, 1H), 8.38 (t, J=7.8 Hz, 1H), 8.21 (s, 1H), 7.84-7.66 (m, 1H), 5.52 (s, 2H), 2.79 (s, 3H); MS (ES+): 334 (M+1), (ES−): 332 (M−1).

Step-3: Preparation of (1R,3S,5R)-2-(2-(4-amino-8-methyl-6-(pyridin-2-yl)-9H-pyrimido[4,5-b]indol-9-yl)acetyl)-N-(6-bromopyridin-2-yl)-5-methyl-2-azabicyclo[3.1.0]hexane-3-carboxamide (378c)

Compound 378c was prepared according to the procedure reported in step-3 of scheme-1, from HCl salt of 2-(4-amino-8-methyl-6-(pyridin-2-yl)-9H-pyrimido[4,5-b]indol-9-yl) acetic acid (378b) (30 mg, 0.081 mmol) in DMF (5 mL) using HCl salt of (1R,3S,5R)—N-(6-bromopyridin-2-yl)-5-methyl-2-azabicyclo[3.1.0]hexane-3-carboxamide (8a) (32.4 mg, 0.097 mmol), HATU (61.7 mg, 0.162 mmol), DIPEA (0.071 mL, 0.406 mmol) and stirring at RT for 18 h. This gave after workup and purification as described in scheme-299, (1R,3S,5R)-2-(2-(4-amino-8-methyl-6-(pyridin-2-yl)-9H-pyrimido[4,5-b]indol-9-yl)acetyl)-N-(6-bromopyridin-2-yl)-5-methyl-2-azabicyclo[3.1.0]hexane-3-carboxamide (378c) (32 mg, 65% yield) HCl salt as a white solid; $^1H$ NMR (300 MHz, DMSO-$d_6$) δ 10.84 (s, 1H), 9.08 (s, 1H), 8.95 (s, 2H, $D_2O$ exchangeable), 8.80-8.74 (m, 1H), 8.68 (s, 1H), 8.43 (d, J=8.1 Hz, 1H), 8.24 (t, J=7.8 Hz, 1H), 8.14 (s, 1H), 8.01 (d, J=8.2 Hz, 1H), 7.70 (t, J=8.0 Hz, 1H), 7.66-7.58 (m, 1H), 7.31 (d, J=7.7 Hz, 1H), 5.94 (d, J=18.0 Hz, 1H), 5.65 (d, J=17.9 Hz, 1H), 4.40 (dd, J=9.0, 6.2 Hz, 1H), 3.72 (dd, J=5.5, 2.4 Hz, 1H), 2.79 (s, 3H), 2.56-2.42 (m, 1H), 1.99 (dd, J=13.2, 6.0 Hz, 1H), 1.31 (s, 3H), 1.08-0.99 (m, 1H), 0.89-0.83 (m, 1H); MS (ES+): 611.10 (M+1); (ES−): 609.10 (M−1).

Scheme 379

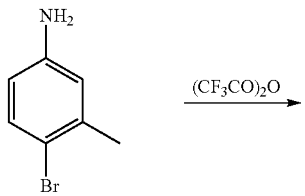

379a

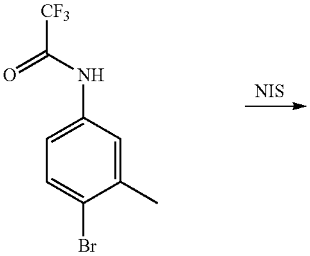

379b

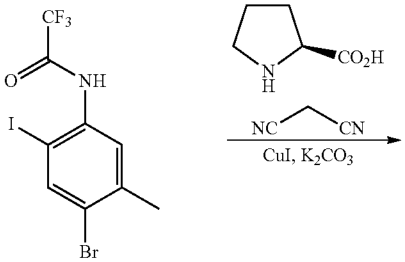

379c

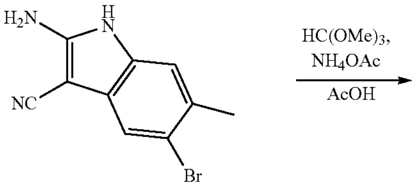

379d

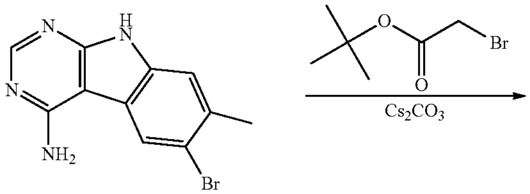

379e

-continued

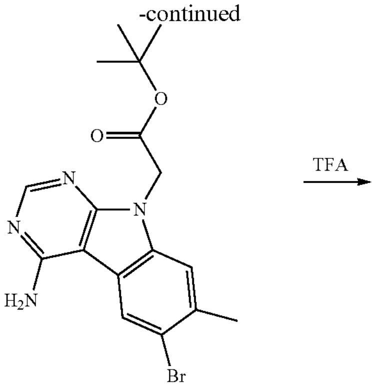

379f

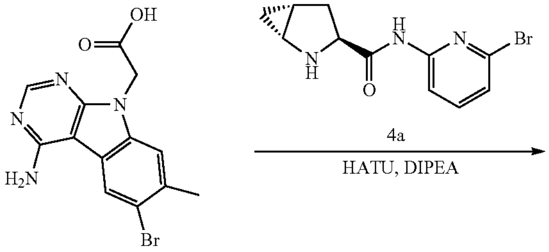

379g

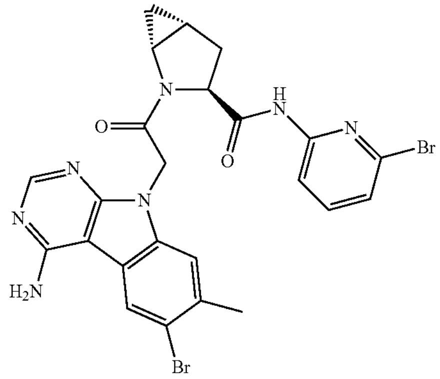

379h

Preparation of (1R,3S,5R)-2-(2-(4-amino-6-bromo-7-methyl-9H-pyrimido[4,5-b]indol-9-yl)acetyl)-N-(6-bromopyridin-2-yl)-2-azabicyclo[3.1.0]hexane-3-carboxamide (379h)

Step-1: Preparation of N-(4-bromo-3-methylphenyl)-2,2,2-trifluoroacetamide (379b)

Compound 379b was prepared according to the procedure reported in step-1 of scheme-46, from 4-bromo-3-methylaniline (379a) (15.0 g, 80.62 mmol; CAS #6933-10-4) in DCM (30 mL) using trifluoroacetic acid anhydride (25.40 g, 120.93 mmol) and stirring at RT for 30 min. This gave after workup N-(4-bromo-3-methylphenyl)-2,2,2-trifluoroacetamide (379b) (22.8 g) as a brown solid: $^1H$ NMR (300 MHz, DMSO-$d_6$) δ 11.31 (s, 1H), 7.88-7.54 (m, 2H), 7.45 (dd, J=8.6, 2.6 Hz, 1H), 2.35 (s, 3H).

Step-2: Preparation of N-(4-bromo-2-iodo-5-methylphenyl)-2,2,2-trifluoroacetamide (379c)

To a stirred solution of N-(4-bromo-3-methylphenyl)-2,2,2-trifluoroacetamide (379b) (22.8 g, 80.83 mmol) in acetonitrile (228 mL) was added at RT NIS (18.18 g, 80.83 mmol), triflic acid (0.6 g, 4.05 mmol) and stirred overnight at RT. Reaction quenched with water (250.0 mL), extracted with ethyl acetate (2×250 mL). The combined organic layers were washed with brine (150 mL), dried, filtered and concentrated to give N-(4-bromo-2-iodo-5-methylphenyl)-2,2,2-trifluoroacetamide (379c) (31.4 g, 95% yield) as a brown solid; $^1$H NMR (300 MHz, DMSO-$d_6$) δ 11.29 (s, 1H), 8.13 (s, 1H), 7.41 (s, 1H), 2.31 (s, 3H).

Step-3: Preparation of 2-amino-5-bromo-6-methyl-1H-indole-3-carbonitrile (379d)

Compound 379d was prepared according to the procedure reported in step-1 of scheme-11 and step-2 of scheme-374, from N-(4-bromo-2-iodo-5-methylphenyl)-2,2,2-trifluoroacetamide (379c) (10.0 g, 24.51 mmol) in DMSO (40.0 mL) using malononitrile (1.94 g, 29.41 mmol), L-proline (0.569 g, 4.92 mmol), CuI (0.47 g, 2.45 mmol), a solution of $K_2CO_3$ (4.064 g, 29.41 mmol) in water (0.5 mL) to afford 2-amino-5-bromo-6-methyl-1H-indole-3-carbonitrile (379d) (4.0 g, 65% yield) as a yellow solid: $^1$H NMR (300 MHz, DMSO-$d_6$) δ 10.77 (s, 1H), 7.25-7.23 (m, 1H), 7.09 (s, 1H), 6.88 (s, 2H), 2.35-2.31 (m, 3H).

Step-4: Preparation of 6-bromo-7-methyl-9H-pyrimido[4,5-b]indol-4-amine (379e)

Compound 379e was prepared according to the procedure reported in step-1 of scheme-6, from 2-amino-5-bromo-6-methyl-1H-indole-3-carbonitrile (379d)(4.0 g, 15.99 mmol) using trimethyl orthoformate (50.90 g, 479.7 mmol), AcOH (4.80 g) and $NH_4OAc$ (6.16 g, 79.96 mmol) at 100° C. for 16 h. This gave after workup AcOH salt of 6-bromo-7-methyl-9H-pyrimido[4,5-b]indol-4-amine (379e) (3.13 g, 58% yield) as a gray solid; MS (ES+): 277.1 (M+1).

Step-5: Preparation of tert-butyl 2-(4-amino-6-bromo-7-methyl-9H-pyrimido[4,5-b]indol-9-yl)acetate (379f)

Compound 379f was prepared according to the procedure reported in step-2 of scheme-16 and step-4 of scheme-374, from AcOH salt of 6-bromo-7-methyl-9H-pyrimido[4,5-b]indol-4-amine (379e) (3.13 g, 9.28 mmol) in DMF (125.2 mL) using tert-butyl 2-bromoacetate (20.2 g, 11.29 mmol), $Cs_2CO_3$ (7.35 g, 22.59 mmol) to afford tert-butyl 2-(4-amino-6-bromo-7-methyl-9H-pyrimido[4,5-b]indol-9-yl)acetate (379f) (1.32 g, 36% yield) as a yellow solid; $^1$H NMR (300 MHz, DMSO-$d_6$) δ 8.64 (s, 1H), 8.27 (d, J=0.8 Hz, 1H), 7.60 (s, 1H), 7.36 (s, 2H), 5.07 (s, 2H), 2.49 (s, 3H), 1.57-1.30 (m, 9H).

Step-6: Preparation of 2-(4-amino-6-bromo-7-methyl-9H-pyrimido[4,5-b]indol-9-yl)acetic acid (379 g)

Compound 379g was prepared according to the procedure reported in step-2 of scheme-1, from tert-butyl 2-(4-amino-6-bromo-7-methyl-9H-pyrimido[4,5-b]indol-9-yl)acetate (379f) (1.3 g, 3.32 mmol) in DCM (10 mL) using TFA (8.33 g, 73.10 mmol) in DCM (15 mL) to afford 2-(4-amino-6-bromo-7-methyl-9H-pyrimido[4,5-b]indol-9-yl)acetic acid (379 g) (1.35 g, 91% yield) TFA salt as an off white solid; $^1$H NMR (300 MHz, DMSO-$d_6$) δ 8.60 (s, 1H), 8.45 (s, 1H), 7.62 (s, 1H), 5.16 (s, 2H), 2.45 (s, 3H).

Step-7: Preparation of (1R,3S,5R)-2-(2-(4-amino-6-bromo-7-methyl-9H-pyrimido[4,5-b]indol-9-yl)acetyl)-N-(6-bromopyridin-2-yl)-2-azabicyclo[3.1.0]hexane-3-carboxamide (379h)

Compound 379h was prepared according to the procedure reported in step-3 of scheme-1, from TFA salt of 2-(4-amino-6-bromo-7-methyl-9H-pyrimido[4,5-b]indol-9-yl)acetic acid (379 g) (84 mg, 0.15 mmol) in DMF (8 mL) using HCl salt of (1R,3S,5R)—N-(6-bromopyridin-2-yl)-2-azabicyclo[3.1.0]hexane-3-carboxamide (4a) (57.3 mg, 0.180 mmol), HATU (114 mg, 0.300 mmol), DIPEA (0.131 mL, 0.750 mmol) and stirring at RT for 18 h. This gave after workup and purification as described in scheme-299, (1R,3S,5R)-2-(2-(4-amino-6-bromo-7-methyl-9H-pyrimido[4,5-b]indol-9-yl)acetyl)-N-(6-bromopyridin-2-yl)-2-azabicyclo[3.1.0]hexane-3-carboxamide (379h) (45 mg, 50% yield) HCl salt as a white solid; $^1$H NMR (300 MHz, DMSO-$d_6$) δ 10.76 (s, 1H), 8.80 (s, 1H), 8.56 (s, 1H), 8.48 (s, 3H, $D_2O$ exchangeable), 8.06-7.93 (m, 1H), 7.76-7.62 (m, 2H), 7.36-7.25 (m, 1H), 5.70 (d, J=17.6 Hz, 1H), 5.37 (d, J=17.9 Hz, 1H), 4.52-4.31 (m, 1H), 3.99-3.82 (m, 1H), 2.41-2.13 (m, 2H), 2.00-1.81 (m, 1H), 1.11-0.97 (m, 1H), 0.88-0.62 (m, 1H); MS (ES+): 598.00 (M+1); (ES−): 595.95 (M−1).

Scheme 380

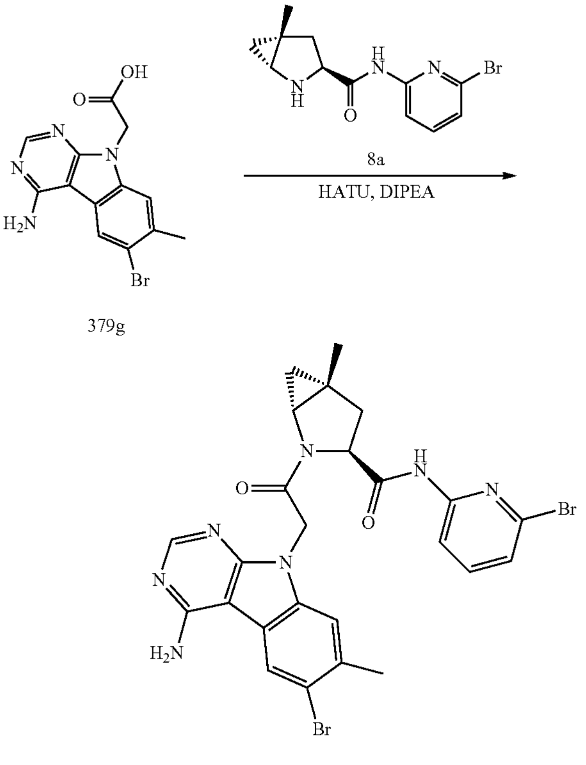

Preparation of (1R,3S,5R)-2-(2-(4-amino-6-bromo-7-methyl-9H-pyrimido[4,5-b]indol-9-yl)acetyl)-N-(6-bromopyridin-2-yl)-5-methyl-2-azabicyclo[3.1.0]hexane-3-carboxamide (380a)

Compound 380a was prepared according to the procedure reported in step-3 of scheme-1, from TFA salt of 2-(4-amino- 6-bromo-7-methyl-9H-pyrimido[4,5-b]indol-9-yl)acetic acid (379 g) (84 mg, 0.15 mmol) in DMF (8 mL) using HCl salt of (1R,3S,5R)—N-(6-bromopyridin-2-yl)-5-methyl-2-azabicyclo[3.1.0]hexane-3-carboxamide (8a) (59.9 mg, 0.180 mmol), HATU (114 mg, 0.300 mmol), DIPEA (0.131 mL, 0.750 mmol) and stirring at RT for 18 h. This gave after workup and purification as described in scheme-299, (1R, 3S,5R)-2-(2-(4-amino-6-bromo-7-methyl-9H-pyrimido[4,5-b]indol-9-yl)acetyl)-N-(6-bromopyridin-2-yl)-5-methyl-2-azabicyclo[3.1.0]hexane-3-carboxamide (380a) (73 mg, 79% yield) HCl salt as a white solid: $^{1}H$ NMR (300 MHz, DMSO-$d_6$) δ 10.76 (s, 1H, $D_2O$ exchangeable), 8.80 (s, 1H), 8.70-8.47 (m, 3H, 2H $D_2O$ exchangeable), 8.06-7.94 (m, 1H), 7.77-7.58 (m, 2H), 7.35-7.25 (m, 1H), 5.65 (d, J=17.2, 3.8 Hz, 1H), 5.31 (d, J=17.4 Hz, 1H), 4.42-4.30 (m, 1H), 3.70-3.61 (m, 1H), 2.65-2.33 (m, 4H), 2.09-1.89 (m, 1H), 1.30 (s, 3H), 1.07-0.87 (m, 2H); MS (ES+): 612.00 (M+1); (ES−): 609.90 (M−1).

Scheme 381

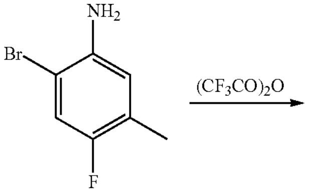

381a

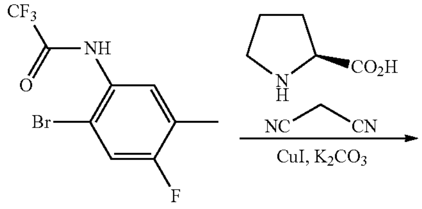

381b

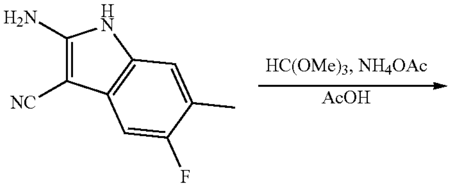

381c

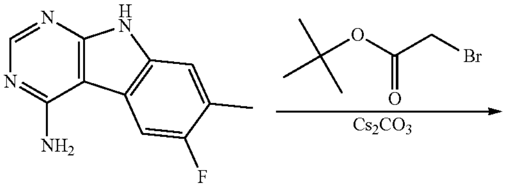

381d

-continued

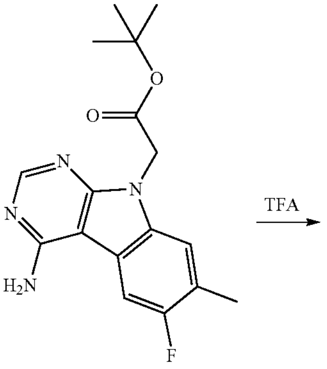

381e

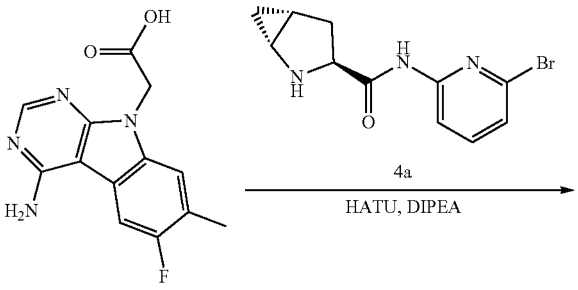

381f

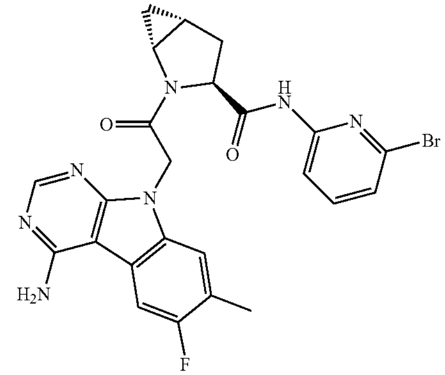

381g

Preparation of (1R,3S,5R)-2-(2-(4-amino-6-fluoro-7-methyl-9H-pyrimido[4,5-b]indol-9-yl)acetyl)-N-(6-bromopyridin-2-yl)-2-azabicyclo[3.1.0]hexane-3-carboxamide (381 g)

Step-1: Preparation of N (2-bromo-4-fluoro-5-methylphenyl)-2,2,2-trifluoroacetamide (381b)

Compound 381b was prepared according to the procedure reported in step-1 of scheme-46, from 2-bromo-4-fluoro-5-methylaniline (381a)(4.0 g, 19.60 mmol: CAS #1065076-39-2) in DCM (20 mL) using trifluoroacetic acid anhydride (6.17 g, 29.40 mmol) and stirring at RT for 1 h. This gave after workup N-(2-bromo-4-fluoro-5-methylphenyl)-2,2,2-trifluoroacetamide (381b) (6.25 g) as a light violet color solid; 1H NMR (300 MHz, DMSO-46) δ 11.26 (s, 1H), 7.66 (d, J=9.1 Hz, 1H), 7.43 (d, J=7.6 Hz, 1H), 2.22 (d, J=2.1 Hz, 3H).

Step-2: Preparation of 2-amino-5-fluoro-6-methyl-1H-indole-3-carbonitrile (381c)

Compound 381c was prepared according to the procedure reported in step-1 of scheme-11 and step-2 of scheme-374, from N-(2-bromo-4-fluoro-5-methylphenyl)-2,2,2-trifluoro-acetamide (381b) (6.25 g, 20.83 mmol) in DMSO (16 mL) using malononitrile (1.65 g, 24.99 mmol), L-proline (0.48 g, 4.16 mmol), CuI (0.40 g, 2.08 mmol), a solution of $K_2CO_3$ (5.75 g, 41.64 mmol) in water (16 mL) to afford 2-amino-5-fluoro-6-methyl-1H-indole-3-carbonitrile (381c) (1.4 g, 36% yield) as a gray solid: $^1$H NMR (300 MHz, DMSO-$d_6$) δ 10.64 (s, 1H), 6.97 (d, J=6.5 Hz, 1H), 6.82 (d, J=10.2 Hz, 1H), 6.77 (s, 2H), 2.21 (d, J=2.2 Hz, 3H).

Step-3: Preparation of 6-fluoro-7-methyl-9H-pyrimido[4,5-b]indol-4-amine (381d)

Compound 381d was prepared according to the procedure reported in step-1 of scheme-6 and step-3 of scheme-374, from 2-amino-5-fluoro-6-methyl-1H-indole-3-carbonitrile (381c) (1.35 g, 7.14 mmol) using trimethyl orthoformate (22.69 g, 213.9 mmol), AcOH (2.03 mL) $NH_4OAc$ (2.75 g, 35.67 mmol) to afford AcOH salt of 6-fluoro-7-methyl-9H-pyrimido[4,5-b]indol-4-amine (381d) (1.0 g, 65% yield) as a gray solid: $^1$H NMR (30) MHz, DMSO-$d_6$) δ 11.77 (s, 1H), 8.22 (s, 1H), 8.15 (d, J=10.9 Hz, 1H), 7.29 (d, J=6.6 Hz, 1H), 7.16 (s, 2H), 2.37 (d, J=2.2 Hz, 3H).

Step-4: Preparation of tert-butyl 2-(4-amino-6-fluoro-7-methyl-9H-pyrimido[4,5-b]indol-9-yl)acetate (381e)

Compound 381e was prepared according to the procedure reported in step-2 of scheme-16 and step-2 of scheme-374, from AcOH salt of 6-fluoro-7-methyl-9H-pyrimido[4,5-b]indol-4-amine (381d) (1.0 g, 3.82 mmol) in DMF (40 mL) using tert-butyl 2-bromoacetate (0.745 g, 3.82 mmol), $Cs_2CO_3$ (2.49 g, 7.65 mmol) to afford tert-butyl 2-(4-amino-6-fluoro-7-methyl-9H-pyrimido[4,5-b]indol-9-yl)acetate (381e) (1.21 g, 80% yield) as an off white solid; $^1$H NMR (300 MHz, DMSO-$d_6$) δ 8.26 (s, 1H), 8.21 (d, J=10.7 Hz, 1H), 7.47 (d, J=6.4 Hz, 1H), 7.29 (s, 2H), 5.07 (s, 2H), 2.39 (d, J=2.2 Hz, 3H), 1.40 (s, 9H).

Step-5: Preparation of 2-(4-amino-6-fluoro-7-methyl-9H-pyrimido[4,5-b]indol-9-yl)acetic acid (381f)

Compound 381f was prepared according to the procedure reported in step-2 of scheme-1, from tert-butyl 2-(4-amino-6-fluoro-7-methyl-9H-pyrimido[4,5-b]indol-9-yl)acetate (381e) (1.44 g, 4.36 mmol) in DCM (6 mL) using TFA (10.93 g, 95.90 mmol) in DCM (18 mL) to afford 2-(4-amino-6-fluoro-7-methyl-9H-pyrimido[4,5-b]indol-9-yl) acetic acid (381f) (1.62 g, 96% yield) TFA salt as an off white solid: $^1$H NMR (300 MHz, DMSO-$d_6$) δ 8.71 (s, 2H), 8.60 (s, 1H), 8.37 (d, J=10.5 Hz, 1H), 7.74 (d, J=6.3 Hz, 1H), 5.23 (s, 2H), 2.42 (d, J=2.2 Hz, 3H).

Step-6: Preparation of (1R,3S,5R)-2-(2-(4-amino-6-fluoro-7-methyl-9H-pyrimido[4,5-b]indol-9-yl) acetyl)-N-(6-bromopyridin-2-yl)-2-azabicyclo[3.1.0] hexane-3-carboxamide (381 g)

Compound 381g was prepared according to the procedure reported in step-3 of scheme-1, from TFA salt of 2-(4-amino-6-fluoro-7-methyl-9H-pyrimido[4,5-b]indol-9-yl)acetic acid (381f) (75 mg, 0.15 mmol) in DMF (8 mL) using HCl salt of (1R,3S,5R)—N-(6-bromopyridin-2-yl)-2-azabicyclo[3.1.0]hexane-3-carboxamide (4a) (57.3 mg, 0.180 mmol), HATU (114 mg, 0.300 mmol), DIPEA (0.131 mL, 0.750 mmol) and stirring at RT for 22 h. This gave after workup and purification as described in scheme-299, (1R,3S,5R)-2-(2-(4-amino-6-fluoro-7-methyl-9H-pyrimido[4,5-b]indol-9-yl)acetyl)-N-(6-bromopyridin-2-yl)-2-azabicyclo[3.1.0] hexane-3-carboxamide (381 g) (36 mg, 45% yield) HCl salt as a white solid: $^1$H NMR (300 MHz, DMSO-$d_6$) δ 10.77 (s, 1H), 8.66 (s, 2H), 8.61 (s, 1H), 8.41 (d, J=10.4 Hz, 1H), 8.01 (d, J=8.2 Hz, 1H), 7.71 (t, J=8.0 Hz, 1H), 7.64 (d, J=6.3 Hz, 1H), 7.32 (d, J=7.8 Hz, 1H), 5.73 (d, J=17.3 Hz, 1H), 5.39 (d, J=17.3 Hz, 1H), 4.42 (dd, J=9.1, 5.6 Hz, 1H), 3.97-3.83 (m, 1H), 2.42 (s, 3H), 2.39-2.16 (m, 2H), 1.99-1.85 (m, 1H), 1.13-1.00 (m, 1H), 0.84-0.75 (m, 1H); MS (ES+): 538.1 (M+1): (ES−): 536.0 (M−1).

Scheme 382

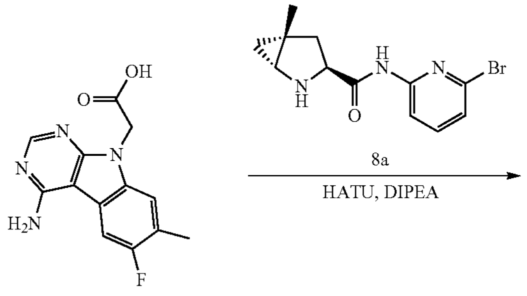

381f

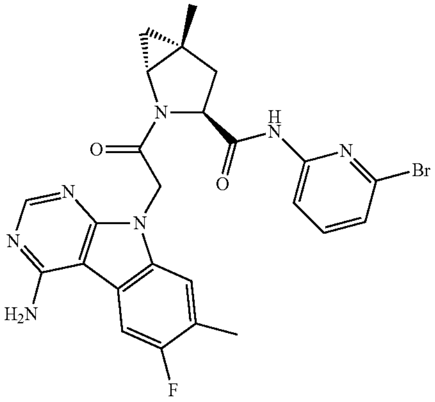

382a

Preparation of (1R,3S,5R)-2-(2-(4-amino-6-fluoro-7-methyl-9H-pyrimido[4,5-b]indol-9-yl)acetyl)-N-(6-bromopyridin-2-yl)-5-methyl-2-azabicyclo[3.1.0] hexane-3-carboxamide (382a)

Compound 382a was prepared according to the procedure reported in step-3 of scheme-1, from TFA salt of 2-(4-amino-6-fluoro-7-methyl-9H-pyrimido[4,5-b]indol-9-yl)acetic acid (381f) (75 mg, 0.15 mmol) in DMF (8 mL) using HCl salt of (1R,3S,5R)—N-(6-bromopyridin-2-yl)-5-methyl-2-azabicyclo[3.1.0]hexane-3-carboxamide (8a) (59.9 mg, 0.180 mmol), HATU (114 mg, 0.3 mmol), DIPEA (0.131 mL, 0.750 mmol) and stirring at RT for 18 h. This gave after workup and purification as described in scheme-299, (1R, 3S,5R)-2-(2-(4-amino-6-fluoro-7-methyl-9H-pyrimido[4,5-b]indol-9-yl)acetyl)-N-(6-bromopyridin-2-yl)-5-methyl-2-azabicyclo[3.1.0]hexane-3-carboxamide (382a) (77 mg, 93% yield) HCl salt as a white solid; $^1$H NMR (300 MHz, DMSO-$d_6$) δ 10.77 (s, 1H), 8.67 (s, 2H, $D_2O$ exchangeable), 8.60 (s, 1H), 8.41 (d, J=10.4 Hz, 1H), 8.01 (d, J=8.2 Hz, 1H), 7.70 (t, J=8.0 Hz, 1H), 7.64 (d, J=6.4 Hz, 1H), 7.32 (d, J=7.7 Hz, 1H), 5.69 (d, J=17.4 Hz, 1H), 5.34 (d, J=17.3 Hz, 1H), 4.42-4.31 (m, 1H), 3.67 (d, J=6.1 Hz, 1H), 2.47-2.43 (m, 1H), 2.42 (s, 3H), 2.04-1.91 (m, 1H), 1.31 (s, 3H), 1.06-0.87 (m, 2H); $^{19}$F NMR (282 MHz, DMSO-$d_6$) δ−123.40; MS (ES+): 552.10 (M+1); (ES−): 550.0 (M−1).

Scheme 383

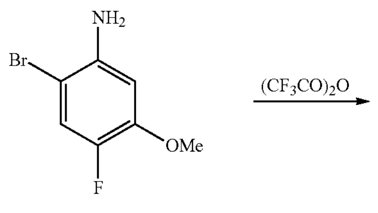

383a

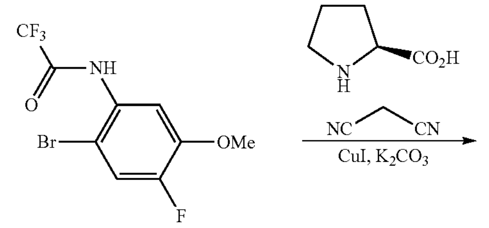

383b

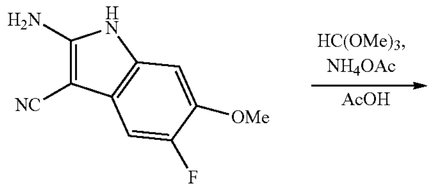

383c

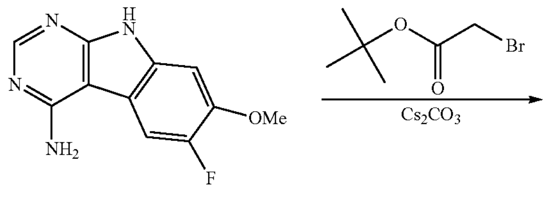

383d

-continued

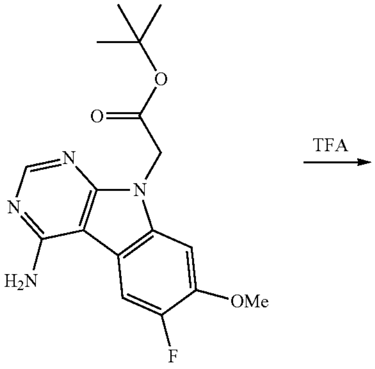

383e

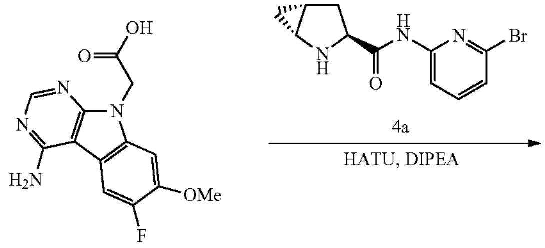

383f

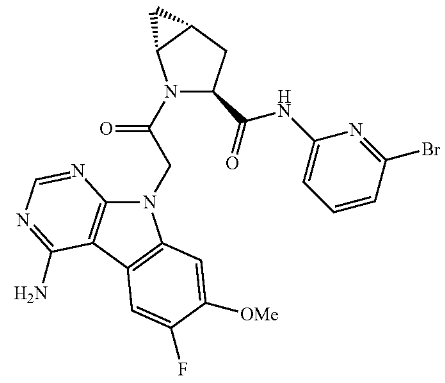

383g

Preparation of (1R,3S,5R)-2-(2-(4-amino-6-fluoro-7-methoxy-9H-pyrimido[4,5-b]indol-9-yl)acetyl)-N-(6-bromopyridin-2-yl)-2-azabicyclo[3.1.0]hexane-3-carboxamide (383 g)

Step-1: Preparation of N-(2-bromo-4-fluoro-5-methoxyphenyl)-2,2,2-trifluoroacetamide (383b)

Compound 383b was prepared according to the procedure reported in step-1 of scheme-46, from 2-bromo-4-fluoro-5-methoxyaniline (383a)(5.0 g, 22.72 mmol; CAS #420786-92-1) in DCM (50 mL) using trifluoroacetic acid anhydride (4.80 mL, 34.08 mmol) and stirring at RT for 1 h. This gave after workup N-(2-bromo-4-fluoro-5-methoxyphenyl)-2,2,2-trifluoroacetamide (383b) (7.0 g, 97% yield) as a light purple solid: $^1$H NMR (300 MHz, DMSO-$d_6$) δ 11.29 (s, 1H), 7.73 (dd, J=10.8, 1.2 Hz, 1H), 7.34 (dd, J=8.5, 1.2 Hz, 1H), 3.84 (d, J=1.3 Hz, 3H).

Step-2: Preparation of 2-amino-5-fluoro-6-methoxy-1H-indole-3-carbonitrile (383c)

Compound 383c was prepared according to the procedure reported in step-1 of scheme-11 and step-2 of scheme-374, from N-(2-bromo-4-fluoro-5-methoxyphenyl)-2,2,2-trifluoroacetamide (383b) (6.5 g, 20.57 mmol) in DMSO (26 mL) using malononitrile (1.63 g, 24.67 mmol), L-proline (0.47 g, 4.11 mmol), CuI (0.39 g, 2.05 mmol), a solution of $K_2CO_3$ (4.26 g, 30.84 mmol) in water (6.5 mL) to afford 2-amino-5-fluoro-6-methoxy-1H-indole-3-carbonitrile (383c) (1.42 g, 34% yield) as a black solid; $^1$H NMR (300 MHz, DMSO-$d_6$) δ 10.58 (s, 1H), 6.94 (s, 1H), 6.91 (d, J=4.3 Hz, 1H), 6.68 (s, 2H), 3.78 (s, 3H).

Step-3: Preparation of 6-fluoro-7-methoxy-9H-pyrimido[4,5-b]indol-4-amine (383d)

Compound 383d was prepared according to the procedure reported in step-1 of scheme-6 and step-3 of scheme-374, from 2-amino-5-fluoro-6-methoxy-1H-indole-3-carbonitrile (383c) (1.48 g, 7.21 mmol) using trimethyl orthoformate (23.67 mL, 216.3 mmol), AcOH (2.06 mL, 36.05 mmol), $NH_4OAc$ (2.78 g, 36.05 mmol) to afford 6-fluoro-7-methoxy-9H-pyrimido[4,5-b]indol-4-amine (383d) (1.20 g, 72% yield) as a light brown solid; 1H NMR (300 MHz, DMSO-$d_6$) δ 11.80 (s, 1H), 8.40-8.10 (m, 2H), 7.22-6.98 (m, 3H), 3.91 (s, 3H).

Step-4: Preparation of tert-butyl 2-(4-amino-6-fluoro-7-methoxy-9H-pyrimido[4,5-b]indol-9-yl) acetate (383e)

Compound 383e was prepared according to the procedure reported in step-2 of scheme-16 and step-4 of scheme-374, from 6-fluoro-7-methoxy-9H-pyrimido[4,5-b]indol-4-amine (383d) (1.20 g, 5.17 mmol) in DMF (48 mL) using tert-butyl 2-bromoacetate (0.95 mL, 6.19 mmol), $Cs_2CO_3$ (3.86 g, 11.35 mmol) to afford tert-butyl 2-(4-amino-6-fluoro-7-methoxy-9H-pyrimido[4,5-b]indol-9-yl)acetate (383e) (0.95 g, 53% yield) as an off white solid; 1H NMR (300 MHz, DMSO-$d_6$) δ 8.28 (d, J=12.1 Hz, 1H), 8.23 (s, 1H), 7.44 (d, J=7.4 Hz, 1H), 7.22 (s, 2H), 5.13 (s, 2H), 3.92 (s, 3H), 1.40 (s, 10H).

Step-5: Preparation of 2-(4-amino-6-fluoro-7-methoxy-9H-pyrimido[4,5-b]indol-9-yl)acetic acid (383f)

Compound 383f was prepared according to the procedure reported in step-2 of scheme-1, from tert-butyl 2-(4-amino-6-fluoro-7-methoxy-9H-pyrimido[4,5-b]indol-9-yl)acetate (383e) (0.95 g, 2.74 mmol) in DCM (4.75 mL) using TFA (4.62 mL, 60.28 mmol) in DCM (10.45 mL) to afford 2-(4-amino-6-fluoro-7-methoxy-9H-pyrimido[4,5-b]indol-9-yl)acetic acid (383f) (1.10 g, 99.2% yield) TFA salt as an off white solid; $^1$H NMR (300 MHz, DMSO-$d_6$) δ 8.62-8.51 (m, 3H), 8.47 (d, J=11.9 Hz, 1H), 7.71 (d, J=7.3 Hz, 1H), 5.29 (s, 2H), 3.96 (s, 3H).

Step-6: Preparation of (1R,3S,5R)-2-(2-(4-amino-6-fluoro-7-methoxy-9H-pyrimido[4,5-b]indol-9-yl) acetyl)-N-(6-bromopyridin-2-yl)-2-azabicyclo[3.1.0] hexane-3-carboxamide (383 g)

Compound 383g was prepared according to the procedure reported in step-3 of scheme-1, from TFA salt of 2-(4-amino-6-fluoro-7-methoxy-9H-pyrimido[4,5-b]indol-9-yl)acetic acid (383f) (78 mg, 0.15 mmol) in DMF (8 mL) using HCl salt of (1R,3S,5R)—N-(6-bromopyridin-2-yl)-2-azabicyclo [3.1.0]hexane-3-carboxamide (4a) (57.3 mg, 0.180 mmol), HATU (114 mg, 0.300 mmol), DIPEA (0.131 mL, 0.750 mmol) and stirring at RT for 18 h. This gave after workup and purification as described in scheme-299, (1R,3S,5R)-2-(2-(4-amino-6-fluoro-7-methoxy-9H-pyrimido[4,5-b]indol-9-yl)acetyl)-N-(6-bromopyridin-2-yl)-2-azabicyclo[3.1.0] hexane-3-carboxamide (383 g) (36 mg, 43% yield) HCl salt as a white solid; $^1$H NMR (300 MHz, DMSO-$d_6$) δ 10.72 (s, 1H), 8.55 (s, 1H), 8.52-8.43 (m, 3H, 2H $D_2O$ exchangeable), 8.00 (d, J=8.2 Hz, 1H), 7.71 (t, J=7.9 Hz, 1H), 7.49 (d, J=7.2 Hz, 1H), 7.33 (d, J=7.7 Hz, 1H), 5.72 (d, J=17.3 Hz, 1H), 5.46 (d, J=17.3 Hz, 1H), 4.48-4.37 (m, 1H), 3.97 (s, 3H), 3.93-3.82 (m, 1H), 2.40-2.13 (m, 2H), 2.00-1.83 (m, 1H), 1.15-0.96 (m, 1H), 0.85-0.66 (m, 1H); $^{19}$F NMR (282 MHz, DMSO-$d_6$) δ−140.13; MS (ES+): 554.10 (M+1); (ES−): 552.0 (M−1).

Scheme 384

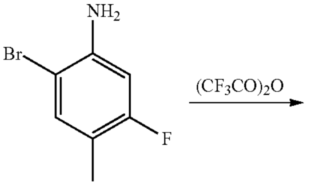

384a

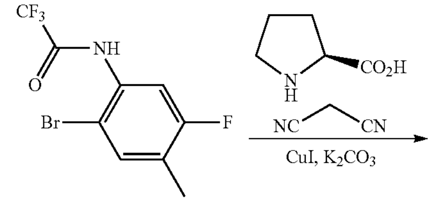

384b

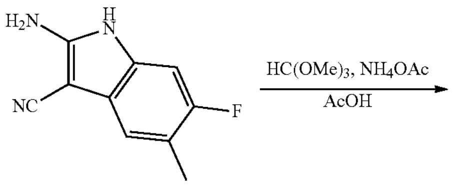

384c

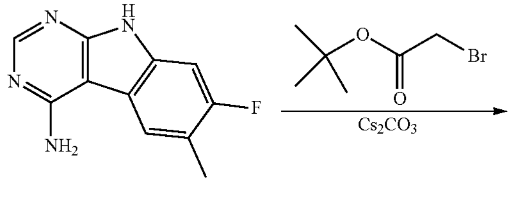

384d

-continued

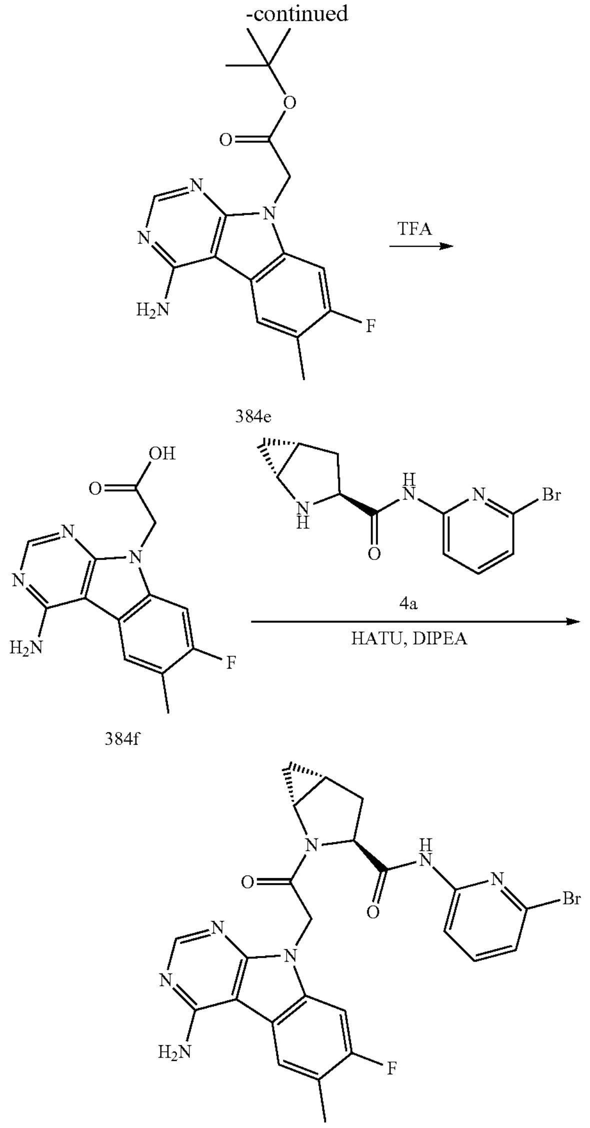

384e

384f

4a

384g

Preparation of (1R,3S,5R)-2-(2-(4-amino-7-fluoro-6-methyl-9H-pyrimido[4,5-b]indol-9-yl)acetyl)-N-(6-bromopyridin-2-yl)-2-azabicyclo[3.1.0]hexane-3-carboxamide (384 g)

Step-1: Preparation of N-(2-bromo-5-fluoro-4-methylphenyl)-2,2,2-trifluoroacetamide (384b)

Compound 384b was prepared according to the procedure reported in step-1 of scheme-46, from 2-bromo-5-fluoro-4-methylaniline (384a) (3.0 g, 14.70 mmol; CAS #202865-78-9) in DCM (30 mL) using trifluoroacetic acid anhydride (4.63 g, 22.05 mmol) and stirring at RT for 1 h. This gave after workup N-(2-bromo-5-fluoro-4-methylphenyl)-2,2,2-trifluoroacetamide (384b) (3.5 g, 79% yield) as a dark brown solid; $^1$H NMR (300 MHz, DMSO-$d_6$) δ 11.33 (s, 1H), 7.73 (d, J=7.7 Hz, 1H), 7.39 (d, J=10.0 Hz, 1H), 2.26 (d, J=2.0 Hz, 3H).

Step-2: Preparation of 2-amino-6-fluoro-5-methyl-1H-indole-3-carbonitrile (384c)

Compound 384c was prepared according to the procedure reported in step-1 of scheme-11 and step-2 of scheme-374, from N-(2-bromo-5-fluoro-4-methylphenyl)-2,2,2-trifluoroacetamide (384b) (5.0 g, 16.66 mmol) in DMSO (15 mL) using malononitrile (1.32 g, 19.98 mmol), L-proline (0.38 g, 3.32 mmol), CuI (0.31 g, 1.66 mmol), a solution of $K_2CO_3$ (4.60 g, 33.35 mmol) in water (15 mL) to afford 2-amino-6-fluoro-5-methyl-1H-indole-3-carbonitrile (384c) (1.5 g, 48% yield) as a white solid; $^1$H NMR (300 MHz, DMSO-$d_6$) δ10.62 (s, 1H), 6.96 (d, J=7.1 Hz, 1H), 6.91 (d, J=10.3 Hz, 1H), 6.73 (s, 2H), 2.22 (s, 3H).

Step-3: Preparation of 7-fluoro-6-methyl-9H-pyrimido[4,5-b]indol-4-amine (384d)

Compound 384d was prepared according to the procedure reported in step-1 of scheme-6 and step-3 of scheme-374, from 2-amino-6-fluoro-5-methyl-1H-indole-3-carbonitrile (384c) (1.5 g, 7.93 mmol) using trimethyl orthoformate (25.24 g, 237.85 mmol), AcOH (7.5 mL), $NH_4OAc$ (3.05 g, 39.65 mmol) to afford 7-fluoro-6-methyl-9H-pyrimido[4,5-b]indol-4-amine (384d) (1.2 g, 70% yield) as an off-white solid.

Step-4: Preparation of tert-butyl 2-(4-amino-7-fluoro-6-methyl-9H-pyrimido[4,5-b]indol-9-yl)acetate (384e)

Compound 384e was prepared according to the procedure reported in step-2 of scheme-16 and step-4 of scheme-374, from 7-fluoro-6-methyl-9H-pyrimido[4,5-b]indol-4-amine (384d) (1.2 g, 5.55 mmol) in DMF (36.0 mL) using tert-butyl 2-bromoacetate (1.07 g, 5.55 mmol), $Cs_2CO_3$ (3.60 g, 11.09 mmol) to afford tert-butyl 2-(4-amino-7-fluoro-6-methyl-9H-pyrimido[4,5-b]indol-9-yl)acetate (384e) (500.0 mg, 27% yield) as an off-white solid: $^1$H NMR (300 MHz, DMSO-$d_6$) δ 8.30-8.24 (m, 2H), 7.47 (d, J=10.7 Hz, 1H), 7.25 (s, 2H), 5.08 (s, 2H), 2.37 (d, J=2.2 Hz, 3H), 1.40 (s, 9H).

Step-5: Preparation of 2-(4-amino-7-fluoro-6-methyl-9H-pyrimido[4,5-b]indol-9-yl)acetic acid (384f)

Compound 384f was prepared according to the procedure reported in step-2 of scheme-1, from tert-butyl 2-(4-amino-7-fluoro-6-methyl-9H-pyrimido[4,5-b]indol-9-yl)acetate (384e) (700.0 mg, 2.12 mmol) in DCM (7.0 mL) using TFA (5.31 g, 46.6 mmol) in DCM (10 mL) to afford 2-(4-amino-7-fluoro-6-methyl-9H-pyrimido[4,5-b]indol-9-yl)acetic acid (384f) (590.0 mg, 72% yield) TFA salt as an off white solid: $^1$H NMR (300 MHz, DMSO-$d_6$) δ 8.52 (s, 1H), 8.47-8.29 (m, 3H), 7.70 (d, J=10.6 Hz, 1H), 5.21 (s, 2H), 2.40 (d, J=2.1 Hz, 3H).

Step-6: Preparation of (1R,3S,5R)-2-(2-(4-amino-7-fluoro-6-methyl-9H-pyrimido[4,5-b]indol-9-yl) acetyl)-N-(6-bromopyridin-2-yl)-2-azabicyclo[3.1.0] hexane-3-carboxamide (384 g)

Compound 384g was prepared according to the procedure reported in step-3 of scheme-1, from TFA salt of 2-(4-amino-7-fluoro-6-methyl-9H-pyrimido[4,5-b]indol-9-yl)acetic acid (384f) (75 mg, 0.15 mmol) in DMF (8 mL) using HCl salt of (1R,3S,5R)—N-(6-bromopyridin-2-yl)-2-azabicyclo[3.1.0]hexane-3-carboxamide (4a) (57.3 mg, 0.180 mmol), HATU (114 mg, 0.300 mmol), DIPEA (97 mg, 0.750 mmol) and stirring at RT for 18 h. This gave after workup and purification as described in scheme-299, (1R,3S,5R)-2-(2-(4-amino-7-fluoro-6-methyl-9H-pyrimido[4,5-b]indol-9-yl)acetyl)-N-(6-bromopyridin-2-yl)-2-azabicyclo[3.1.0]hexane-3-carboxamide (384 g) (50 mg, 62% yield) HCl salt as a white solid, $^1H$ NMR (300 MHz, DMSO-$d_6$) δ 10.76 (s, 1H), 8.58 (s, 1H), 8.55 (s, 2H, $D_2O$ exchangeable), 8.46 (d, J=7.3 Hz, 1H), 8.00 (d, J=8.2 Hz, 1H), 7.70 (t, J=8.0 Hz, 1H), 7.62 (d, J=10.5 Hz, 1H), 7.31 (d, J=7.7 Hz, 1H), 5.73 (d, J=17.4 Hz, 1H), 5.37 (d, J=17.3 Hz, 1H), 4.42 (dd, J=9.0, 5.6 Hz, 1H), 3.92-3.83 (m, 1H), 2.39 (s, 3H), 2.37-2.14 (m, 2H), 1.98-1.84 (m, 1H), 1.13-0.97 (m, 1H), 0.85-0.74 (m, 1H); $^{19}F$ NMR (282 MHz, DMSO-$d_6$) δ−117.36; MS (ES+): 538.10 (M+1); (ES−): 536.10 (M−1).

Scheme 385

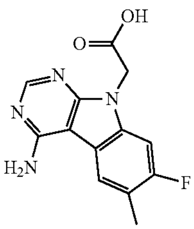

384f

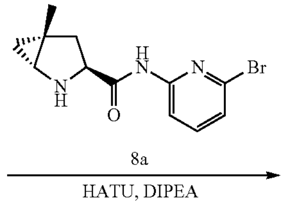

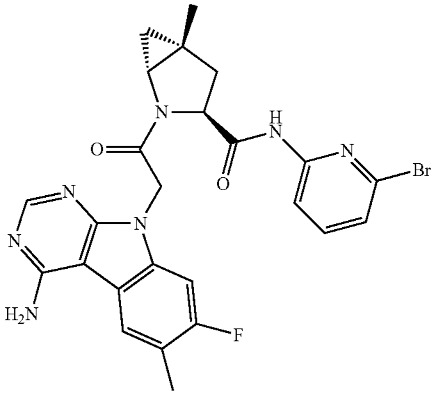

385a

Preparation of (1R,3S,5R)-2-(2-(4-amino-7-fluoro-6-methyl-9H-pyrimido[4,5-b]indol-9-yl)acetyl)-N-(6-bromopyridin-2-yl)-5-methyl-2-azabicyclo[3.1.0]hexane-3-carboxamide (385a)

Compound 385a was prepared according to the procedure reported in step-3 of scheme-1, from TFA salt of 2-(4-amino-7-fluoro-6-methyl-9H-pyrimido[4,5-b]indol-9-yl)acetic acid (384f) (75 mg, 0.15 mmol) in DMF (8 mL) using HCl salt of (1R,3S,5R)—N-(6-bromopyridin-2-yl)-5-methyl-2-azabicyclo[3.1.0]hexane-3-carboxamide (8a) (60 mg, 0.180 mmol), HATU (114 mg, 0.300 mmol), DIPEA (97 mg, 0.750 mmol) and stirring at RT for 18 h. This gave after workup and purification as described in scheme-299, (1R,3S,5R)-2-(2-(4-amino-7-fluoro-6-methyl-9H-pyrimido[4,5-b]indol-9-yl)acetyl)-N-(6-bromopyridin-2-yl)-5-methyl-2-azabicyclo[3.1.0]hexane-3-carboxamide (385a) (75 mg, 82% yield) HCl salt as a white solid; $^1H$ NMR (300 MHz, DMSO-$d_6$) δ 10.77 (s, 1H), 8.71 (s, 2H, $D_2O$ exchangeable), 8.61 (s, 1H), 8.48 (d, J=7.2 Hz, 1H), 8.01 (d, J=8.2 Hz, 1H), 7.69 (t, J=8.0 Hz, 1H), 7.62 (d, J=10.4 Hz, 1H), 7.31 (d, J=7.7 Hz, 1H), 5.69 (d, J=17.4 Hz, 1H), 5.32 (d, J=17.3 Hz, 1H), 4.37 (dd, J=9.0, 5.9 Hz, 1H), 3.71-3.63 (m, 1H), 2.47-2.41 (m, 1H), 2.39 (s, 3H), 1.97 (dd, J=13.3, 5.8 Hz, 1H), 1.30 (s, 3H), 1.06-0.89 (m, 2H); $^{19}F$ NMR (282 MHz, DMSO-$d_6$) δ−116.70; MS (ES+): 552.10 (M+1); (ES−): 550.0 (M−1).

Scheme 386

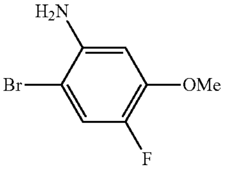

$(CF_3CO)_2O$

386a

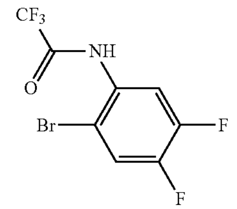

386b

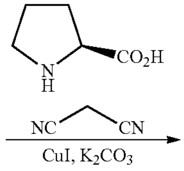

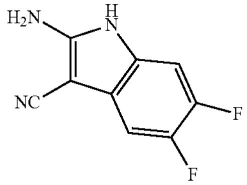

386c $HC(OMe)_3$,
$NH_4OAc$
AcOH

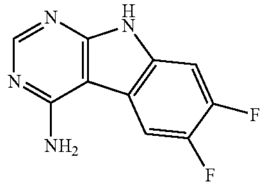

386d

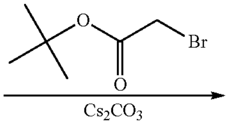

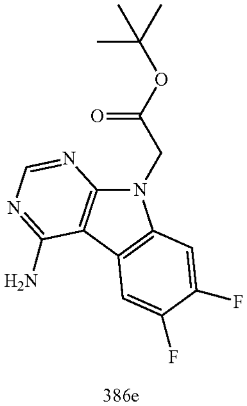

386e

TFA

-continued

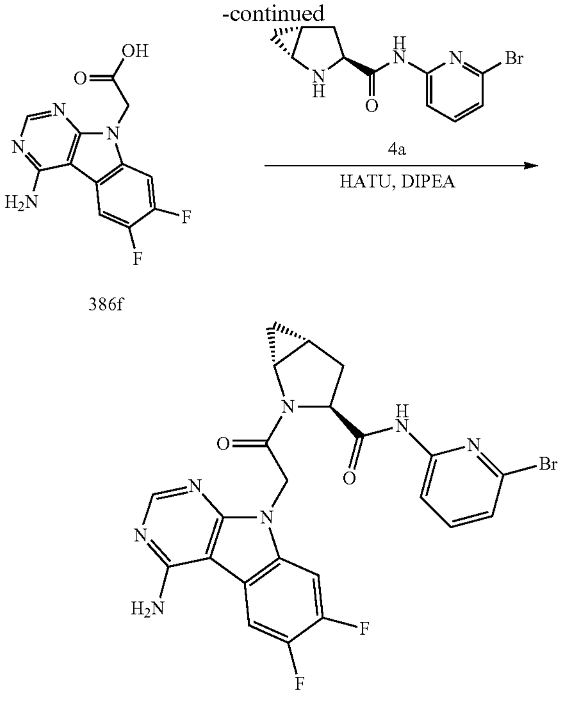

386f

386g

Preparation of (1R,3S,5R)-2-(2-(4-amino-6,7-difluoro-9H-pyrimido[4,5-b]indol-9-yl)acetyl)-N-(6-bromopyridin-2-yl)-2-azabicyclo[3.1.0]hexane-3-carboxamide (386 g)

Step-1: Preparation of N-(2-bromo-4,5-difluorophenyl)-2,2,2-trifluoroacetamide (386b)

Compound 386b was prepared according to the procedure reported in step-1 of scheme-46, from 2-bromo-4,5-difluoroaniline (386a)(3.0 g, 14.70 mmol; CAS #64695-79-0) in DCM (30 mL) using trifluoroacetic acid anhydride (4.54 g, 21.62 mmol) and stirring at RT for 1 h. This gave after workup N-(2-bromo-4,5-difluorophenyl)-2,2,2-trifluoroacetamide (386b) (3.5 g, 79% yield) as a dark brown solid; $^1$H NMR (300 MHz, DMSO-$d_6$) δ 11.43 (s, 1H), 8.11-7.98 (m, 1H), 7.78 (dd, J=11.2, 7.9 Hz H).

Step-2: Preparation of 2-amino-5,6-difluoro-1H-indole-3-carbonitrile (386c)

Compound 386c was prepared according to the procedure reported in step-1 of scheme-46 and step-2 of scheme-374, from N-(2-bromo-4,5-difluorophenyl)-2,2,2-trifluoroacetamide (386b) (4.5 g, 14.80 mmol) in DMSO (13.5 mL) using malononitrile (1.17 g, 17.71 mmol), L-proline (0.34 g, 2.95 mmol), CuI (0.28 g, 1.47 mmol), a solution of $K_2CO_3$ (4.09 g, 29.60 mmol) in water (13.5 mL) to afford 2-amino-5,6-difluoro-1H-indole-3-carbonitrile (386c) (1.4 g, 49% yield) as a white solid; $^1$H NMR (300 MHz, DMSO-$d_6$) δ 10.80 (s, 1H), 7.12 (ddd, J=20.0, 10.9, 7.3 Hz, 2H), 6.93 (s, 2H).

Step-3: Preparation of 6,7-difluoro-9H-pyrimido[4,5-b]indol-4-amine (386d)

Compound 386d was prepared according to the procedure reported in step-1 of scheme-6 and step-3 of scheme-374, from 2-amino-5,6-difluoro-1H-indole-3-carbonitrile (386c) (1.4 g, 7.25 mmol) using trimethyl orthoformate (23.07 g, 217.43 mmol), AcOH (7 mL), $NH_4OAc$ (2.79 g, 36.23 mmol) to afford 6,7-difluoro-9H-pyrimido[4,5-b]indol-4-amine (386d) (500 mg, 32% yield) as a brown solid.

Step-4: Preparation of tert-butyl 2-(4-amino-6,7-difluoro-9H-pyrimido[4,5-b]indol-9-yl)acetate (386e)

Compound 386e was prepared according to the procedure reported in step-2 of scheme-16 and step-4 of scheme-374, from 6,7-difluoro-9H-pyrimido[4,5-b]indol-4-amine (386d) (500 mg, 2.27 mmol) in DMF (6.5 mL) using tert-butyl 2-bromoacetate (443.0 mg, 2.27 mmol), $Cs_2CO_3$ (1.48 g, 4.54 mmol) to afford tert-butyl 2-(4-amino-6,7-difluoro-9H-pyrimido[4,5-b]indol-9-yl)acetate (386e) (220.0 mg, 29% yield) as an off-white solid.

Step-5: Preparation of 2-(4-amino-6,7-difluoro-9H-pyrimido[4,5-b]indol-9-yl)acetic acid (386f)

Compound 386f was prepared according to the procedure reported in step-2 of scheme-1, from tert-butyl 2-(4-amino-6,7-difluoro-9H-pyrimido[4,5-b]indol-9-yl)acetate (386e) (500.0 mg, 1.50 mmol) in DCM (5.0 mL) using TFA (3.75 g, 32.90 mmol) in DCM (10 mL) to afford 2-(4-amino-6,7-difluoro-9H-pyrimido[4,5-b]indol-9-yl)acetic acid (386f) (360.0 mg, 61% yield) TFA salt as a white solid: $^1$H NMR (300 MHz, DMSO-$d_6$) δ 8.60 (dd, J=11.5, 7.9 Hz, 1H), 8.46 (s, 1H), 8.09 (s, 2H), 7.99 (dd, J=11.3, 6.9 Hz, 1H), 5.20 (s, 2H).

Step-6: Preparation of (1R,3S,5R)-2-(2-(4-amino-6,7-difluoro-9H-pyrimido[4,5-b]indol-9-yl)acetyl)-N-(6-bromopyridin-2-yl)-2-azabicyclo[3.1.0]hexane-3-carboxamide (386 g)

Compound 386g was prepared according to the procedure reported in step-3 of scheme-1, from TFA salt of 2-(4-amino-6,7-difluoro-9H-pyrimido[4,5-b]indol-9-yl)acetic acid (386f) (76 mg, 0.15 mmol) in DMF (8 mL) using HCl salt of (1R,3S,5R)—N-(6-bromopyridin-2-yl)-2-azabicyclo[3.1.0]hexane-3-carboxamide (4a) (52 mg, 0.180 mmol), HATU (114 mg, 0.300 mmol), DIPEA (97 mg, 0.750 mmol) and stirring at RT for 18 h. This gave after workup and purification as described in scheme-299, (1R,3S,5R)-2-(2-(4-amino-6,7-difluoro-9H-pyrimido[4,5-b]indol-9-yl)acetyl)-N-(6-bromopyridin-2-yl)-2-azabicyclo[3.1.0]hexane-3-carboxamide (386 g) (57 mg, 64% yield) HCl salt as a white solid; $^1$H NMR (300 MHz, DMSO-$d_6$) δ 10.76 (s, 1H), 8.82-8.54 (m, 4H, 2H exchangeable), 8.06-7.87 (m, 2H), 7.70 (t, J=7.9 Hz, 1H), 7.32 (d, J=7.7 Hz, 11H), 5.76 (d, J=17.4 Hz, 1H), 5.39 (d, J=17.4 Hz, 1H), 4.42 (dd, J=9.0, 5.5 Hz, 1H), 3.94-3.83 (m, 1H), 2.41-2.11 (m, 2H), 2.00-1.82 (m, 1H), 1.14-0.99 (m, 1H), 0.90-0.74 (m, 1H); $^{19}$F NMR (282 MHz, DMSO-$d_6$) δ−138.00, −144.42; MS (ES+): 542.10 (M+1): (ES−): 540.0 (M−1).

Scheme 387

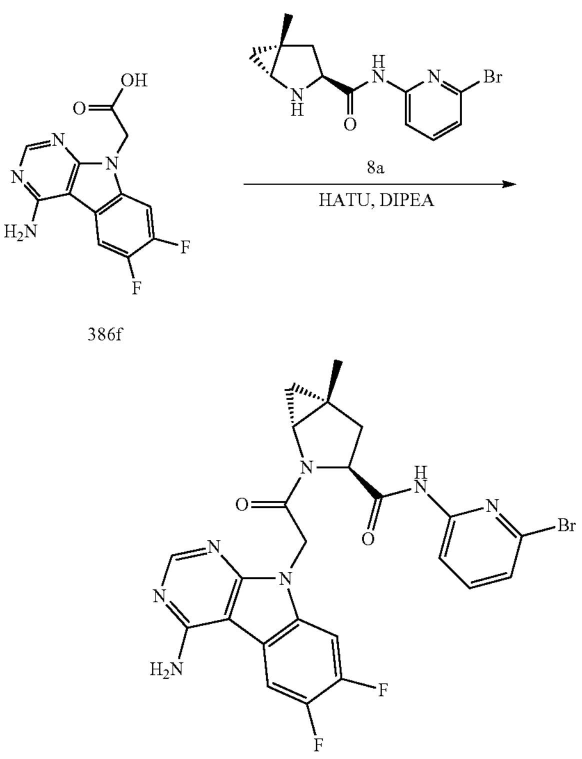

386f

387a

Scheme 388

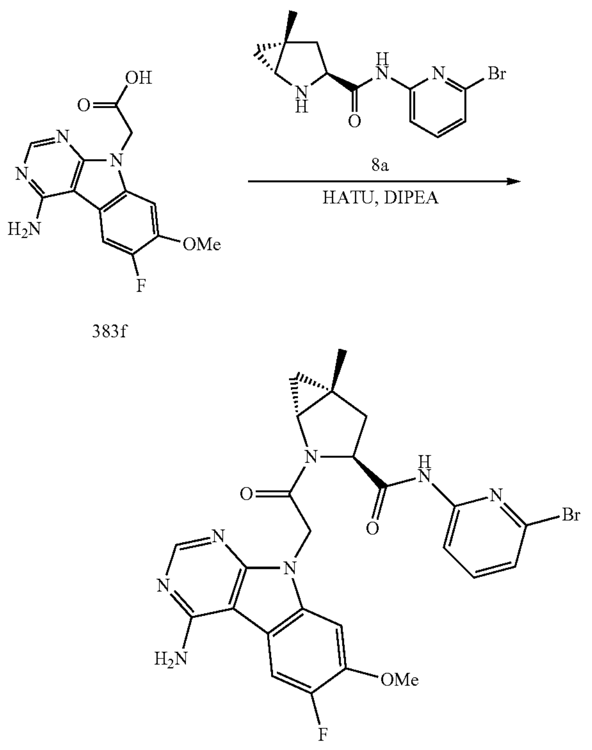

383f

388a

Preparation of (1R,3S,5R)-2-(2-(4-amino-6,7-difluoro-9H-pyrimido[4,5-b]indol-9-yl)acetyl)-N-(6-bromopyridin-2-yl)-5-methyl-2-azabicyclo[3.1.0]hexane-3-carboxamide (387a)

Compound 387a was prepared according to the procedure reported in step-3 of scheme-1, from TFA salt of 2-(4-amino-6,7-difluoro-9H-pyrimido[4,5-b]indol-9-yl)acetic acid (386) (76 mg, 0.15 mmol) in DMF (8 mL) using HCl salt of (1R,3S,5R)—N-(6-bromopyridin-2-yl)-5-methyl-2-azabicyclo[3.1.0]hexane-3-carboxamide (8a) (60 mg, 0.180 mmol), HATU (114 mg, 0.300 mmol), DIPEA (97 mg, 0.750 mmol) and stirring at RT for 18 h. This gave after workup and purification as described in scheme-299, (1R,3S,5R)-2-(2-(4-amino-6,7-difluoro-9H-pyrimido[4,5-b]indol-9-yl)acetyl)-N-(6-bromopyridin-2-yl)-5-methyl-2-azabicyclo[3.1.0]hexane-3-carboxamide (387a) (55 mg, 60% yield) HCl salt as a white solid: $^1H$ NMR (300 MHz, DMSO-$d_6$) δ 10.77 (s, 1H), 8.76-8.63 (m, 1H), 8.62-8.50 (m, 3H, 2H $D_2O$ exchangeable), 8.01 (d, J=8.2 Hz, 1H), 7.93 (dd, J=11.2, 6.9 Hz, 1H), 7.71 (t, J=8.0 Hz, 1H), 7.32 (d, J=7.7 Hz, 1H), 5.71 (d, J=17.4 Hz, 1H), 5.34 (d, J=17.3 Hz, 1H), 4.38 (t, J=7.5 Hz, 1H), 3.71-3.62 (m, 1H), 2.51-2.39 (m, 1H), 1.99 (dd, J=13.1, 5.8 Hz, 1H), 1.31 (s, 3H), 1.08-0.90 (m, 2H); $^{19}F$ NMR (282 MHz, DMSO-$d_6$) δ −138.26, −144.69; MS (ES+): 556.10 (M+1): (ES−): 554.0 (M−1).

Preparation of (1R,3S,5R)-2-(2-(4-amino-6-fluoro-7-methoxy-9H-pyrimido[4,5-b]indol-9-yl)acetyl)-N-(6-bromopyridin-2-yl)-5-methyl-2-azabicyclo[3.1.0]hexane-3-carboxamide (388a)

Compound 388a was prepared according to the procedure reported in step-3 of scheme-1, from TFA salt of 2-(4-amino-6-fluoro-7-methoxy-9H-pyrimido[4,5-b]indol-9-yl)acetic acid (383f) (78 mg, 0.15 mmol) in DMF (8 mL) using HCl salt of (1R,3S,5R)—N-(6-bromopyridin-2-yl)-5-methyl-2-azabicyclo[3.1.0]hexane-3-carboxamide (8a) (59.9 mg, 0.180 mmol), HATU (114 mg, 0.300 mmol), DIPEA (0.131 mL, 0.750 mmol) and stirring at RT for 18 h. This gave after workup and purification as described in scheme-299, (1R,3S,5R)-2-(2-(4-amino-6-fluoro-7-methoxy-9H-pyrimido[4,5-b]indol-9-yl)acetyl)-N-(6-bromopyridin-2-yl)-5-methyl-2-azabicyclo[3.1.0]hexane-3-carboxamide (388a) (40 mg, 47% yield) HCl salt as a white solid; $^1H$ NMR (300 MHz, DMSO-$d_6$) δ 10.71 (s, 1H), 8.65 (s, 2H, $D_2O$ exchangeable), 8.58 (s, 1H), 8.50 (d, J=11.9 Hz, 1H), 8.01 (d, J=8.2 Hz, 1H), 7.71 (t, J=8.0 Hz, 1H), 7.51 (d, J=7.4 Hz, 1H), 7.32 (d, J=7.7 Hz, 1H), 5.70 (d, J=17.3 Hz, 1H), 5.42 (d, J=17.3 Hz, 1H), 4.37 (t, J=7.5 Hz, 1H), 3.96 (s, 3H), 3.72-3.66 (m, 1H), 2.52-2.42 (m, 1H), 2.00 (dd, J=13.4, 5.9 Hz, 1H), 1.32 (s, 3H), 1.06-0.87 (m, 2H); $^{19}F$ NMR (282 MHz, DMSO-$d_6$) δ−139.92; MS (ES+): 568.10 (M+1): (ES−): 566.0 (M−1).

Scheme 389

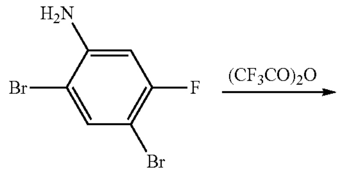

389a

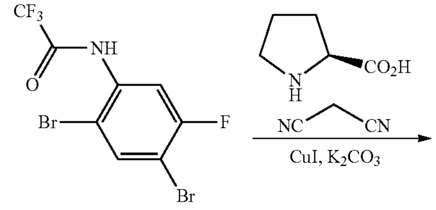

389b

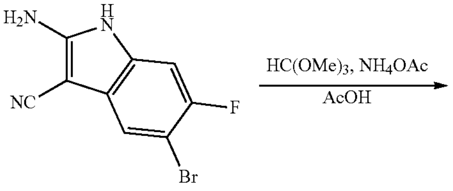

389c

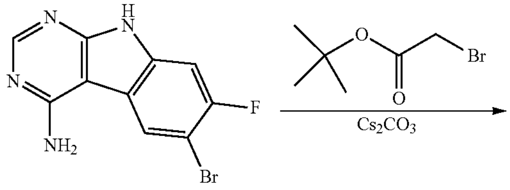

389d

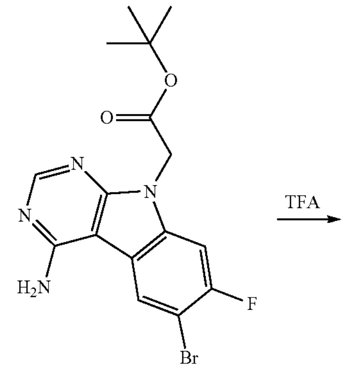

389e

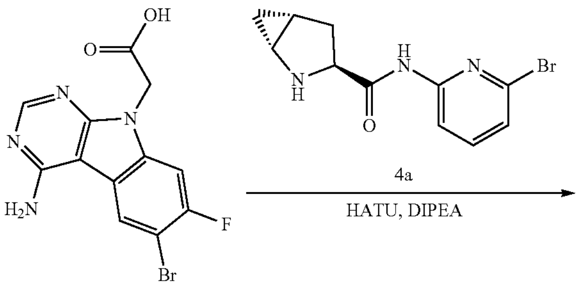

389f

-continued

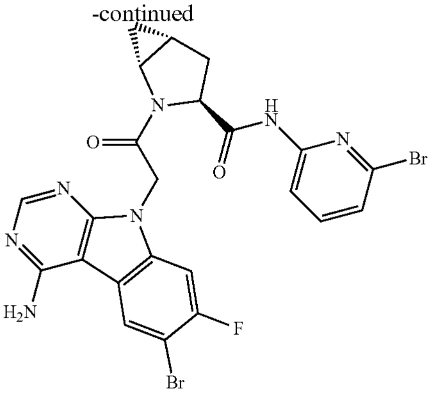

389g

Preparation of (1R,3S,5R)-2-(2-(4-amino-6-bromo-7-fluoro-9H-pyrimido[4,5-b]indol-9-yl)acetyl)-N-(6-bromopyridin-2-yl)-2-azabicyclo[3.1.0]hexane-3-carboxamide (389 g)

Step-1: Preparation of N-(2,4-dibromo-5-fluorophenyl)-2,2,2-trifluoroacetamide (389b)

Compound 389b was prepared according to the procedure reported in step-1 of scheme-46, from 2,4-dibromo-5-fluoroaniline (389a)(5 g, 18.59 mmol; CAS #1000578-04-0) in DCM (25 mL) using trifluoroacetic acid anhydride (5.86 g, 27.89 mmol) and stirring at RT for 1 h. This gave after workup N-(2,4-dibromo-5-fluorophenyl)-2,2,2-trifluoroacetamide (389b) (6.4 g, 94% yield) as an off-white solid; $^1$H NMR (300 MHz, DMSO-$d_6$) δ 11.47 (s, 1H), 8.22 (dd, J=7.1, 2.1 Hz, 1H), 7.69 (dd, J=9.2, 2.0 Hz, 1H).

Step-2: Preparation of 2-amino-5-bromo-6-fluoro-1H-indole-3-carbonitrile (389c)

Compound 389c was prepared according to the procedure reported in step-1 of scheme-11 and step-2 of scheme-374, from N-(2,4-dibromo-5-fluorophenyl)-2,2,2-trifluoroacetamide (389b) (6.4 g, 17.54 mmol) in DMSO (20 mL) using malononitrile (1.39 g, 21.046 mmol), L-proline (0.404 g, 3.51 mmol), CuI (0.334 g, 1.75 mmol), a solution of $K_2CO_3$ (3.647 g, 26.31 mmol) in DMW (6.4 mL) to afford 2-amino-5-bromo-6-fluoro-1H-indole-3-carbonitrile (389c) (1.7 g, 38% yield) as a yellow solid; 1H NMR (300 MHz, DMSO-$d_6$) δ 10.93 (s, 1H), 7.27 (d, J=6.4 Hz, 1H), 7.13 (d, J=9.2 Hz, 1H), 7.01 (s, 21).

Step-3: Preparation of 6-bromo-7-fluoro-9H-pyrimido[4,5-b]indol-4-amine (389d)

Compound 389d was prepared according to the procedure reported in step-1 of scheme-6 and step-3 of scheme-374, from 2-amino-5-bromo-6-fluoro-1H-indole-3-carbonitrile (389c) (1.8 g, 7.08 mmol) using trimethyl orthoformate (22.55 g, 212.55 mmol), AcOH (2.127 g, 35.425 mmol), $NH_4OAc$ (2.731 g, 35.425 mmol) to afford 6-bromo-7-fluoro-9H-pyrimido[4,5-b]indol-4-amine (389d)(1.52 g, 76% yield) as a brown solid; $^1$H NMR (300 MHz, DMSO-$d_6$) δ 12.12 (s, 1H), 8.70 (d, J=6.8 Hz, 1H), 8.26 (s, 1H), 7.39 (d, J=9.4 Hz, 1H), 7.34 (s, 2H).

Step-4: Preparation of tert-butyl 2-(4-amino-6-bromo-7-fluoro-9H-pyrimido[4,5-b]indol-9-yl)acetate (389e)

Compound 389e was prepared according to the procedure reported in step-2 of scheme-16 and step-4 of scheme-374, from 6-bromo-7-fluoro-9H-pyrimido[4,5-b]indol-4-amine (389d) (1.5 g, 5.34 mmol) in DMF (60 mL) using tert-butyl 2-bromoacetate (1.15 g, 5.87 mmol), $Cs_2CO_3$ (3.65 g, 11.21 mmol) to afford tert-butyl 2-(4-amino-6-bromo-7-fluoro-9H-pyrimido[4,5-b]indol-9-yl)acetate (389e) (1.5 g, 71% yield) as a brown solid; 1H NMR (300 MHz, DMSO-$d_6$) δ 8.78-8.72 (m, 1H), 8.30 (d, J=1.0 Hz, 1H), 7.82-7.76 (m, 1H), 7.46 (s, 2H), 5.12 (s, 2H), 1.42-1.37 (m, 9H).

Step-5: Preparation of 2-(4-amino-6-bromo-7-fluoro-9H-pyrimido[4,5-b]indol-9-yl)acetic acid (389f)

Compound 389f was prepared according to the procedure reported in step-2 of scheme-1, from tert-butyl 2-(4-amino-6-bromo-7-fluoro-9H-pyrimido[4,5-b]indol-9-yl)acetate (389e) (1.5 g, 3.80 mmol) in DCM (24 mL) using TFA (9.52 g, 83.50 mmol) to afford 2-(4-amino-6-bromo-7-fluoro-9H-pyrimido[4,5-b]indol-9-yl)acetic acid (389f) (1.8 g) TFA salt as an off-white solid: $^1$H NMR (300 MHz, DMSO-$d_6$) δ 8.86 (d, J=6.7 Hz, 1H), 8.48 (s, 1H), 8.18 (s, 2H), 7.95 (d, J=9.8 Hz, 1H), 5.20 (s, 2H).

Step-6: Preparation of (1R,3S,5R)-2-(2-(4-amino-6-bromo-7-fluoro-9H-pyrimido[4,5-b]indol-9-yl)acetyl)-N-(6-bromopyridin-2-yl)-2-azabicyclo[3.1.0]hexane-3-carboxamide (389 g)

Compound 389g was prepared according to the procedure reported in step-3 of scheme-1, from TFA salt of 2-(4-amino-6-bromo-7-fluoro-9H-pyrimido[4,5-b]indol-9-yl)acetic acid (389f) (85 mg, 0.15 mmol) in DMF (8 mL) using HCl salt of (1R,3S,5R)—N-(6-bromopyridin-2-yl)-2-azabicyclo[3.1.0]hexane-3-carboxamide (4a) (57.3 mg, 0.180 mmol), HATU (114 mg, 0.300 mmol), DIPEA (97 mg, 0.75 mmol) and stirring at RT for 18 h. This gave after workup and purification as described in scheme-299, (1R,3S,5R)-2-(2-(4-amino-6-bromo-7-fluoro-9H-pyrimido[4,5-b]indol-9-yl)acetyl)-N-(6-bromopyridin-2-yl)-2-azabicyclo[3.1.0]hexane-3-carboxamide (389 g) (62 mg, 69% yield) HCl salt as a white solid; $^1$H NMR (300 MHz, DMSO-$d_6$) δ 10.76 (s, 1H), 8.88 (d, J=6.7 Hz, 1H), 8.52 (s, 1H), 8.28 (s, 2H, $D_2O$ exchangeable), 8.00 (d, J=8.2 Hz, 1H), 7.83 (d, J=9.7 Hz, 1H), 7.70 (t, J=8.0 Hz, 1H), 7.32 (d, J=7.7 Hz, 1H), 5.71 (d, J=17.4 Hz, 1H), 5.35 (d, J=17.4 Hz, 1H), 4.41 (dd, J=9.3, 5.5 Hz, 1H), 3.90-3.80 (m, 1H), 2.39-2.12 (m, 2H), 1.98-1.84 (m, 1H), 1.11-0.98 (m, 1H), 0.87-0.75 (m, 1H); MS (ES+): 601.90 (M+1).

Scheme 390

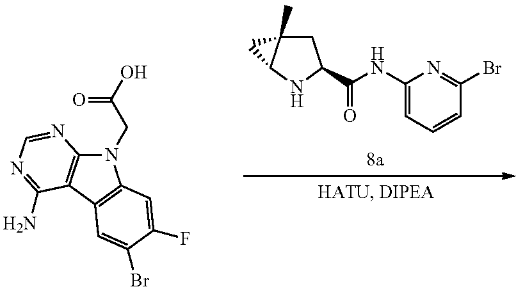

389f

8a

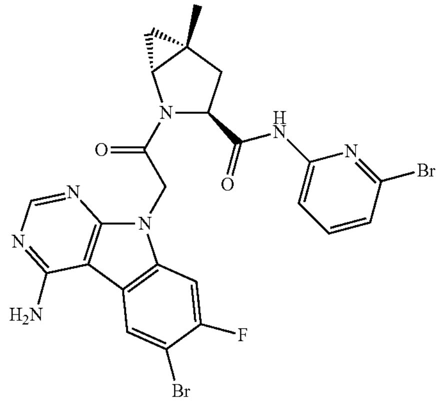

390a

Preparation of (1R,3S,5R)-2-(2-(4-amino-6-bromo-7-fluoro-9H-pyrimido[4,5-b]indol-9-yl)acetyl)-N-(6-bromopyridin-2-yl)-5-methyl-2-azabicyclo[3.1.0]hexane-3-carboxamide (390a)

Compound 390a was prepared according to the procedure reported in step-3 of scheme-1, from TFA salt of 2-(4-amino-6-bromo-7-fluoro-9H-pyrimido[4,5-b]indol-9-yl)acetic acid (3890 85 mg, 0.15 mmol) in DMF (8 mL) using HCl salt of (1R,3S,5R)—N-(6-bromopyridin-2-yl)-5-methyl-2-azabicyclo[3.1.0]hexane-3-carboxamide (8a) (60 mg, 0.180 mmol), HATU (114 mg, 0.300 mmol). DIPEA (97 mg, 0.750 mmol) and stirring at RT for 18 h. This gave after workup and purification as described in scheme-299, (1R,3S,5R)-2-(2-(4-amino-6-bromo-7-fluoro-9H-pyrimido[4,5-b]indol-9-yl)acetyl)-N-(6-bromopyridin-2-yl)-5-methyl-2-azabicyclo[3.1.0]hexane-3-carboxamide (390a) (85 mg, 84% yield) HCl salt as a white solid: $^1$H NMR (300 MHz, DMSO-$d_6$) δ 10.76 (s, 1H), 8.89 (d, J=6.6 Hz, 1H), 8.53 (s, 1H), 8.35 (s, 2H, $D_2O$ exchangeable), 8.01 (d, J=8.2 Hz, 1H), 7.83 (d, J=9.6 Hz, 1H), 7.70 (t, J=8.0 Hz, 1H), 7.31 (d, J=7.7 Hz, 1H), 5.68 (d, J=17.4 Hz, 1H), 5.31 (d, J=17.2 Hz, 1H), 4.42-4.27 (m, 1H), 3.68-3.61 (m, 1H), 2.49-2.40 (m, 1H), 1.99-1.89 (m, 1H), 1.30 (s, 3H), 1.04-0.90 (m, 2H); MS (ES+): 616.00 (M+1): (ES−): 613.85 (M−1).

Scheme 391

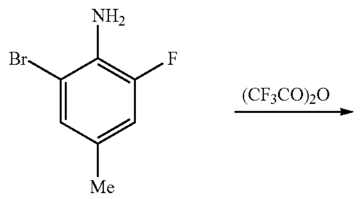

391a

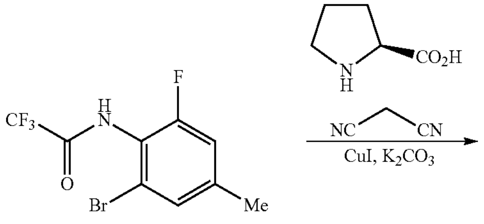

391b

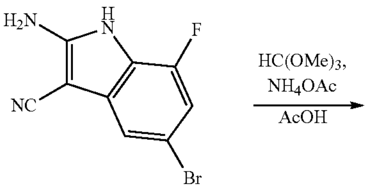

391c

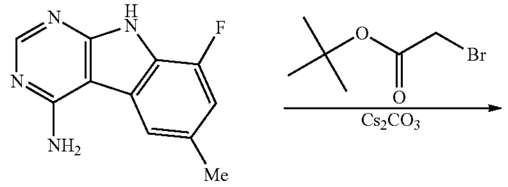

391d

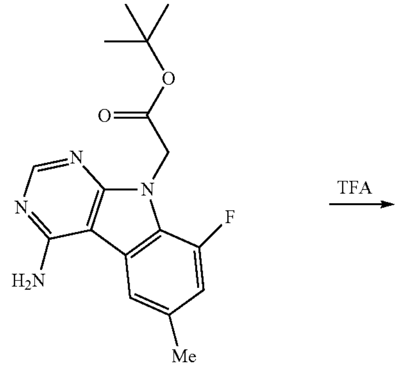

391e

-continued

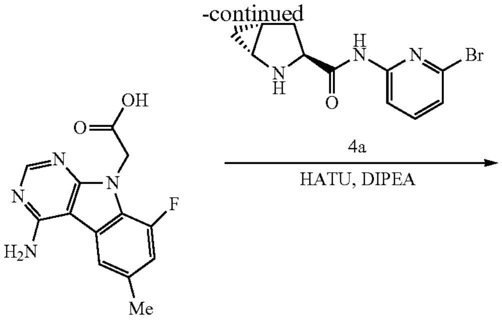

391f

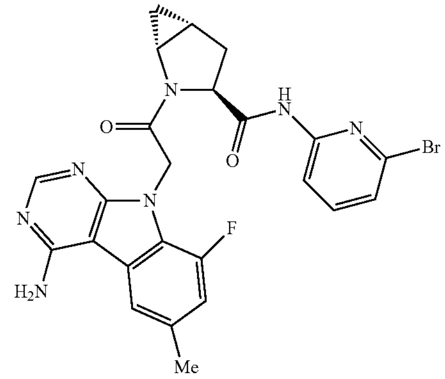

391g

Preparation of (1R,3S,5R)-2-(2-(4-amino-8-fluoro-6-methyl-9H-pyrimido[4,5-b]indol-9-yl)acetyl)-N-(6-bromopyridin-2-yl)-2-azabicyclo[3.1.0]hexane-3-carboxamide (391 g)

Step-1: Preparation of N-(2-bromo-6-fluoro-4-methylphenyl)-2,2,2-trifluoroacetamide (391b)

Compound 391b was prepared according to the procedure reported in step-1 of scheme-46, from 2-bromo-6-fluoro-4-methylaniline (391a) (5 g, 24.50 mmol; CAS #18349-09-2) in DCM (25 mL) using trifluoroacetic acid anhydride (7.72 g, 36.76 mmol) in DCM (25 mL) and stirring at RT for 1 h. This gave after workup N-(2-bromo-6-fluoro-4-methylphenyl)-2,2,2-trifluoroacetamide (391b) (6.8 g, 93% yield) as a black solid; $^1$H NMR (300 MHz, DMSO-$d_6$) δ 11.35 (s, 1H), 7.48 (s, 1H), 7.35-7.24 (m, 1H), 2.35 (s, 3H).

Step-2: Preparation of 2-amino-7-fluoro-5-methyl-1H-indole-3-carbonitrile (391c)

Compound 391c was prepared according to the procedure reported in step-1 of scheme-11 and step-2 of scheme-374, from N-(2-bromo-6-fluoro-4-methylphenyl)-2,2,2-trifluoroacetamide (391b) (6.2 g, 20.66 mmol) in DMSO (19.3 mL) using malononitrile (1.64 g, 24.80 mmol), L-proline (0.476 g, 4.13 mmol), CuI (0.393 g, 2.07 mmol), a solution of $K_2CO_3$ (4.28 g, 30.99 mmol) in DMW (6.2 mL) to afford 2-amino-7-fluoro-5-methyl-1H-indole-3-carbonitrile (391c) (1.55 g, 40% yield) as a brown solid; $^1$H NMR (300 MHz, DMSO-$d_6$) δ 11.16 (s, 1H), 6.77 (s, 1H), 6.68 (s, 2H), 6.63-6.53 (m, 1H), 2.31 (s, 3H).

Step-3: Preparation of 8-fluoro-6-methyl-9H-pyrimido[4,5-b]indol-4-amine (391d)

Compound 391d was prepared according to the procedure reported in step-1 of scheme-6 and step-3 of scheme-374, from 2-amino-7-fluoro-5-methyl-1H-indole-3-carbonitrile (391c) (1.6 g, 8.46 mmol) using trimethyl orthoformate (26.92 g, 253.71 mmol), AcOH (2.54 g, 42.29 mmol), $NH_4OAc$ (3.26 g, 42.29 mmol) to afford 8-fluoro-6-methyl-9H-pyrimido[4,5-b]indol-4-amine (391d) (1.45 g, 79% yield) as an off-white solid; $^1$H NMR (300 MHz, DMSO-$d_6$) δ 12.19 (s, 1H), 8.26 (d, J=1.0 Hz, 1H), 8.03-7.93 (m, 1H), 7.21 (s, 2H), 7.06 (d, J=12.0 Hz, 1H), 2.46 (s, 3H).

Step-4: Preparation of tert-butyl 2-(4-amino-8-fluoro-6-methyl-9H-pyrimido[4,5-b]indol-9-yl)acetate (391e)

Compound 391e was prepared according to the procedure reported in step-2 of scheme-16 and step-4 of scheme-374, from 8-fluoro-6-methyl-9H-pyrimido[4,5-b]indol-4-amine (391d) (1.45 g, 6.71 mmol) in DMF (58 mL) using tert-butyl 2-bromoacetate (1.44 g, 7.38 mmol), $Cs_2CO_3$ (4.588 g, 14.08 mmol) to afford tert-butyl 2-(4-amino-8-fluoro-6-methyl-9H-pyrimido[4,5-b]indol-9-yl)acetate (391e) (1.6 g, 72% yield) as an off-white solid: $^1$H NMR (300 MHz, DMSO-$d_4$) δ 8.30 (s, 1H), 8.08-8.01 (m, 1H), 7.37 (s, 2H), 7.09 (d, J=13.1 Hz, 1H), 5.12 (d, J=1.8 Hz, 2H), 2.46 (s, 3H), 1.40 (s, 9H).

Step-5: Preparation of 2-(4-amino-8-fluoro-6-methyl-9H-pyrimido[4,5-b]indol-9-yl)acetic acid (391f)

Compound 391f was prepared according to the procedure reported in step-2 of scheme-1, from tert-butyl 2-(4-amino-8-fluoro-6-methyl-9H-pyrimido[4,5-b]indol-9-yl)acetate (391e) (1.6 g, 4.84 mmol) in DCM (25.6 mL) using TFA (12.15 g, 106.55 mmol) to afford 2-(4-amino-8-fluoro-6-methyl-9H-pyrimido[4,5-b]indol-9-yl)acetic acid (391f) (1.85 g, 98% yield) TFA salt as a cream color solid; $^1$H NMR (300 MHz, DMSO-$d_6$) δ 8.56 (d, J=0.9 Hz, 1H), 8.46 (s, 2H), 8.15 (s, 1H), 7.23 (d, J=13.3 Hz, 1H), 5.25-5.21 (m, 2H), 2.49 (s, 3H).

Step-6: Preparation of (1R,3S,5R)-2-(2-(4-amino-8-fluoro-6-methyl-9H-pyrimido[4,5-b]indol-9-yl) acetyl)-N-(6-bromopyridin-2-yl)-2-azabicyclo[3.1.0] hexane-3-carboxamide (391 g)

Compound 391g was prepared according to the procedure reported in step-3 of scheme-1, from TFA salt of 2-(4-amino-8-fluoro-6-methyl-9H-pyrimido[4,5-b]indol-9-yl)acetic acid (391f) (75 mg, 0.15 mmol) in DMF (8 mL) using HCl salt of (1R,3S,5R)—N-(6-bromopyridin-2-yl)-2-azabicyclo [3.1.0]hexane-3-carboxamide (4a) (57.3 mg, 0.180 mmol), HATU (114 mg, 0.300 mmol), DIPEA (97 mg, 0.750 mmol) and stirring at RT for 18 h. This gave after workup and purification as described in scheme-299, (1R,3S,5R)-2-(2-(4-amino-8-fluoro-6-methyl-9H-pyrimido[4,5-b]indol-9-yl) acetyl)-N-(6-bromopyridin-2-yl)-2-azabicyclo[3.1.0] hexane-3-carboxamide (391 g) (56 mg, 69% yield) HCl salt as a white solid; $^1$H NMR (300 MHz, DMSO-$d_6$) δ 10.76 (s, 1H, $D_2O$ exchangeable), 8.61 (s, 1H), 8.58 (s, 2H, $D_2O$ exchangeable), 8.18 (s, 1H), 8.01 (d, J=8.2 Hz, 11H), 7.70 (t, J=8.0 Hz, 1H), 7.31 (d, J=7.7 Hz, 1H), 7.22 (d, J=13.2 Hz, 1H), 5.77 (d, J=17.4 Hz, 1H), 5.48-5.38 (m, 1H), 4.42 (dd, J=9.1, 5.6 Hz, 1H), 3.91-3.81 (m, 1H), 2.48 (s, 3H), 2.39-2.14 (m, 2H), 2.02-1.83 (m, 1H), 1.16-0.97 (m, 1H), 0.68-0.53 (m, 1H); $^{19}$F NMR (282 MHz, DMSO-$d_6$) δ−135.24; MS (ES+): 538.10 (M+1); (ES−): 536.10 (M−1).

Scheme 392

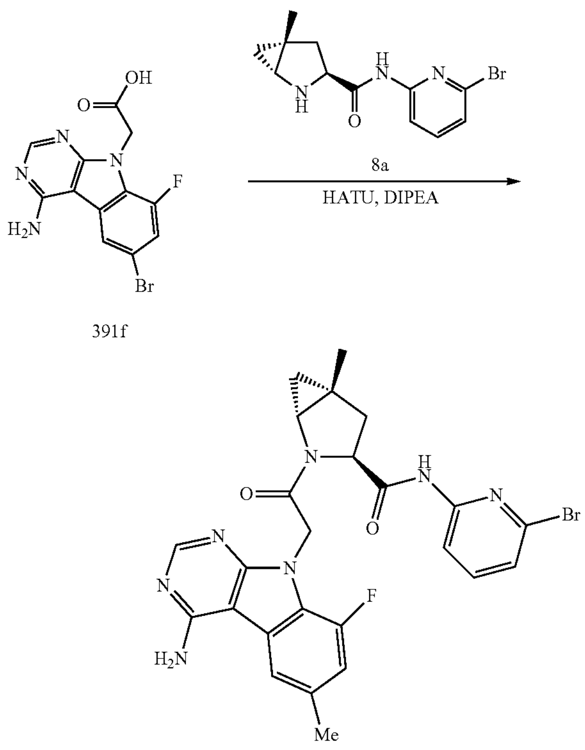

391f

392a

Preparation of (1R,3S,5R)-2-(2-(4-amino-8-fluoro-6-methyl-9H-pyrimido[4,5-b]indol-9-yl)acetyl)-N-(6-bromopyridin-2-yl)-5-methyl-2-azabicyclo[3.1.0] hexane-3-carboxamide (392a)

Compound 392a was prepared according to the procedure reported in step-3 of scheme-1, from TFA salt of 2-(4-amino-8-fluoro-6-methyl-9H-pyrimido[4,5-b]indol-9-yl)acetic acid (391) (75 mg, 0.15 mmol) in DMF (8 mL) using HCl salt of (1R,3S,5R)—N-(6-bromopyridin-2-yl)-5-methyl-2-azabicyclo[3.1.0]hexane-3-carboxamide (8a) (59.9 mg, 0.180 mmol), HATU (114 mg, 0.300 mmol), DIPEA (97 mg, 0.750 mmol) and stirring at RT for 18 h. This gave after workup and purification as described in scheme-299, (1R,3S,5R)-2-(2-(4-amino-8-fluoro-6-methyl-9H-pyrimido[4,5-b]indol-9-yl)acetyl)-N-(6-bromopyridin-2-yl)-5-methyl-2-azabicyclo [3.1.0]hexane-3-carboxamide (392a) (31 mg, 37% yield) HCl salt as a white solid: $^1$H NMR (300 MHz, DMSO-$d_6$) δ 10.76 (s, 1H, $D_2O$ exchangeable), 8.59 (s, 1H), 8.51 (s, 211 $D_2O$ exchangeable), 8.17 (s, 1H), 8.01 (d, J=8.2 Hz, 11H), 7.70 (t, J=8.0 Hz, 1H), 7.31 (d, J=7.7 Hz, 1H), 7.21 (d, J=13.1 Hz, 1H), 5.72 (d, J=17.5 Hz, 1H), 5.38 (d, J=17.5 Hz, 1H), 4.37 (dd, J=9.0, 5.9 Hz, 1H), 3.64 (dd, J=5.5, 2.3 Hz, 1H), 2.49-2.42 (m, 4H), 1.98 (dd, J=13.3, 5.9 Hz, 1H), 1.29 (s, 3H), 1.06-0.97 (m, 1H), 0.83-0.74 (m, 1H); $^{19}$F NMR (282 MHz, DMSO-$d_6$) δ−135.26; MS (ES+): 552.10 (M+1); (ES−): 549.95 (M−1).

Example 393

The $IC_{50}$ value of a compound (i.e., the concentration of the compound that inhibits 50% of the enzymatic activity)

was calculated according to the procedure reported in U.S. Pat. No. 6,653,340 B1, e.g., column 74 (incorporated by reference).

Specifically, the compounds were dissolved in a stock solution of DMSO at 10.0 or 100 mM. A portion of this stock solution was added to assay buffer in a final volume of 50 µL. Controls included buffer alone and enzyme solutions to which DMSO was added. Substrate was added to the reaction wells immediately or after incubation at room temperature. The reaction rates were measured spectrophotometrically by the generation of product at 405 nm for 600 sec. Background absorbance at 690 nm was measured and subtracted from the absorbance at 405 nm for each well.

The reaction rate for enzyme alone was compared to the rate of enzyme in the presence of inhibitor and the percent inhibition was calculated as shown below:

Percent Inhibition=[Rate without inhibitor−Rate with inhibitor)/(Rate without inhibitor)]−100

Factor D Esterolytic Assay:

An established esterolytic assay for the measurement of Factor D activity and inhibition of Factor D activity was used (Kam, C. M.; McRae, B. J.; Harper, J. W.; Niemann, M. A.; Volanakis, J. E.; Powers, J. C. Human complement proteins D. C2, and B Active site mapping with peptide thioester substrates. J Biol. Chem. 1987, 262, 3444-3451). For this assay Z-Lys-SBzl, 1.29 mM (Kim, S.; Narayana, S. V. L; Volanakis, J. E. Mutational analysis of the substrate binding site of human complement Factor D. Biochemistry, 1994, 33, 14393-14399) was used as the substrate for Factor D (104 mM). Hydrolysis of this compound by Factor D liberated a free sulfhydryl group which is then reacted with 5,5'-dithiobis(2-nitrobenzoic acid) producing an intense yellow color (Habeeb, A. F. S. A. Reaction of protein sulfhydryl groups with Ellman's Reagent. Methods in Enzymol. 1976, 25, 457-464). The assays were performed in 96 well microtiter plates and rates of hydrolysis were monitored at 405 nm on a Biotek Synergy H1 plate reader. Hydrolysis rates were reported as change in mOD/min. The assay was conducted in 100 mM HEPES, 500 mM NaCl, pH 7.5 containing 10% DMSO in a final volume of 50 µL per well.

An $IC_{50}$, a compound concentration which inhibits 50% of the enzymatic activity, was calculated. Compounds in the examples were tested a minimum of three times. In the table below, three plus symbols (+++) are used to indicate compounds with an $IC_{50}$ value of greater than 1 micromolar (>1000 nM) concentration; Two (++) indicate compounds with an $IC_{50}$ value between 1 and 0.1 micromolar (1000-100 nM) concentration; One (+) indicate compounds with an $IC_{50}$ value less than 0.1 micromolar (<100 nM) concentration.

TABLE 1

Measured Ki ($IC_{50}$) Value for Compounds.

| Compound | $IC_{50}$ |
|---|---|
| 75d | +++ |
| 76b | +++ |
| 77b | +++ |
| 78a | ++ |
| 79a | ++ |
| 80a | + |
| 81a | + |
| 82a | +++ |
| 83d | ++ |
| 84a | ++ |
| 85b | +++ |
| 86b | ++ |
| 87f | +++ |
| 88f | +++ |
| 89b | ++ |
| 90d | +++ |
| 91a | + |
| 92b | +++ |
| 93a | ++ |
| 94b | +++ |
| 95c | +++ |
| 96e | +++ |
| 97b | +++ |
| 98b | ++ |
| 99b | +++ |
| 100b | +++ |
| 101b | ++ |
| 102b | ++ |
| 103b | ++ |
| 104a | + |
| 105b | ++ |
| 111b | ++ |
| 107b | +++ |
| 108b | +++ |
| 109e | ++ |
| 110d | +++ |
| 106b | +++ |
| 112b | + |
| 119a | ++ |
| 120c | +++ |
| 121d | +++ |
| 122c | ++ |
| 123g | +++ |
| 118a | +++ |
| 117d | ++ |
| 116b | ++ |
| 115e | ++ |
| 114f | + |
| 113a | ++ |
| 66b | ++ |
| 124b | +++ |
| 68a | ++ |
| 67c | ++ |
| 65a | + |
| 64a | + |
| 130e | ++ |
| 131e | ++ |
| 132d | +++ |
| 133b | + |
| 20a | + |
| 134b | + |
| 135a | ++ |
| 136a | +++ |
| 137b | + |
| 140a | +++ |
| 141a | +++ |
| 138d | ++ |
| 139b | + |
| 125d | ++ |
| 126f | ++ |
| 142d | +++ |
| 143d | ++ |
| 144g | ++ |
| 145a | ++ |
| 146a | +++ |
| 235a | +++ |
| 147a | +++ |
| 148d | ++ |
| 19a | + |
| 3b | + |
| 149b | ++ |
| 4b | + |
| 5e | ++ |
| 150d | ++ |
| 69a | ++ |
| 70a | ++ |
| 2d | +++ |

TABLE 1-continued

| Measured Ki ($IC_{50}$) Value for Compounds. | |
|---|---|
| Compound | $IC_{50}$ |
| 71a | ++ |
| 72a | ++ |
| 9a | + |
| 151a | ++ |
| 152d | ++ |
| 1e | + |
| 6e | + |
| 7b | + |
| 21a | + |
| 73a | + |
| 74a | ++ |
| 153a | +++ |
| 27a | + |
| 25a | + |
| 26a | + |
| 8b | + |
| 28a | + |
| 10b | + |
| 11f | + |
| 12a | + |
| 127d | +++ |
| 128a | +++ |
| 154e | ++ |
| 34e | + |
| 13b | ++ |
| 14a | + |
| 15a | + |
| 155f | +++ |
| 156e | ++ |
| 45d | + |
| 41f | + |
| 37a | + |
| 42a | + |
| 16e | + |
| 36e | + |
| 39f | + |
| 23f | + |
| 40a | + |
| 24a | + |
| 50f | ++ |
| 157a | ++ |
| 158e | ++ |
| 32f | + |
| 43a | + |
| 35f | + |
| 30f | + |
| 47g | + |
| 48d | + |
| 38e | + |
| 51g | + |
| 52f | + |
| 54g | + |
| 44a | + |
| 29f | + |
| 22c | +++ |
| 22d | +++ |
| 33e | + |
| 49c | + |
| 58c | + |
| 59c | + |
| 17f | + |
| 18a | + |
| 31f | + |
| 60c | + |
| 61a | + |
| 129f | ++ |
| 46g | ++ |
| 62c | + |
| 63d | + |
| 53d | ++ |
| 55a | + |
| 56g | ++ |
| 57g | + |
| 159a | + |
| 160a | + |
| 171b | + |

TABLE 1-continued

| Measured Ki ($IC_{50}$) Value for Compounds. | |
|---|---|
| Compound | $IC_{50}$ |
| 172a | + |
| 173a | + |
| 161a | + |
| 174g | +++ |
| 175a | +++ |
| 176a | ++ |
| 169f | + |
| 177d | ++ |
| 178d | ++ |
| 162g | + |
| 163g | + |
| 164a | + |
| 165a | + |
| 170c | + |
| 179d | +++ |
| 180e | ++ |
| 166a | + |
| 167a | + |
| 168g | + |
| 187c | + |
| 188g | + |
| 195e | + |
| 198a | + |
| 199a | + |
| 200a | + |
| 194a | + |
| 201e | ++ |
| 211e | ++ |
| 212e | ++ |
| 181a | + |
| 182a | + |
| 183a | + |
| 207b | + |
| 208d | + |
| 203a | + |
| 204a | + |
| 184g | + |
| 185a | + |
| 186a | + |
| 206c | ++ |
| 209b | + |
| 210d | ++ |
| 189g | + |
| 193a | + |
| 190a | + |
| 191a | + |
| 192g | + |
| 196d | + |
| 197c | + |
| 214b | + |
| 213d | + |
| 215g | + |
| 216g | + |
| 217a | + |
| 220a | ++ |
| 202a | + |
| 205c | + |
| 221c | + |
| 236f | + |
| 237a | + |
| 238g | + |
| 239a | + |
| 222a | +++ |
| 240g | + |
| 241a | + |
| 242g | + |
| 243a | + |
| 244d | + |
| 245a | + |
| 218a | + |
| 223a | + |
| 224b | +++ |
| 225e | + |
| 226c | + |
| 219a | + |
| 227c | + |

TABLE 1-continued

Measured Ki ($IC_{50}$) Value for Compounds.

| Compound | $IC_{50}$ |
|---|---|
| 228a | + |
| 251f | ++ |
| 233h | + |
| 229c | + |
| 230a | + |
| 231g | + |
| 246b | + |
| 247d | ++ |
| 248d | +++ |
| 232a | + |
| 234a | + |
| 250b | +++ |
| 270a | + |
| 271c | + |
| 249a | + |
| 252a | + |
| 253a | + |
| 254a | + |
| 263c | + |
| 272c | ++ |
| 255c | + |
| 256a | + |
| 273c | + |
| 257g | + |
| 258a | + |
| 259d | ++ |
| 260a | + |
| 261d | + |
| 262a | + |
| 264a | + |
| 265a | + |
| 266b | + |
| 267c | + |
| 268b | + |
| 269c | + |
| 274g | + |
| 275c | + |
| 276g | + |
| 277a | + |
| 278g | + |
| 279a | + |
| 280g | + |
| 281a | + |
| 282a | + |
| 283g | + |
| 284a | + |
| 285g | + |
| 286a | + |
| 287a | + |
| 288c | + |
| 289a | + |
| 290g | + |
| 291a | + |
| 292a | + |
| 293a | ++ |
| 293b | + |
| 294c | +++ |
| 295a | + |
| 296a | + |
| 297d | + |
| 298c | + |
| 299a | + |
| 300a | + |
| 301a | + |
| 302a | + |
| 303a | + |
| 307c | + |
| 304a | + |
| 305a | + |
| 308c | + |
| 309a | + |
| 310a | + |
| 311a | + |
| 317c | ++ |
| 318c | + |
| 319c | + |

TABLE 1-continued

Measured Ki ($IC_{50}$) Value for Compounds.

| Compound | $IC_{50}$ |
|---|---|
| 320c | + |
| 321d | + |
| 322c | + |
| 334a | + |
| 335c | + |
| 313b | + |
| 314a | + |
| 312a | + |
| 323a | + |
| 324a | + |
| 306a | + |
| 325c | + |
| 326c | + |
| 327c | + |
| 328f | + |
| 329a | + |
| 330f | + |
| 331a | + |
| 336c | + |
| 337a | + |
| 315a | + |
| 316a | + |
| 343a | + |
| 344c | + |
| 345c | + |
| 346g | + |
| 347a | + |
| 338e | + |
| 339g | + |
| 348c | + |
| 349c | + |
| 350a | + |
| 351a | + |
| 332c | + |
| 333c | + |
| 365c | + |
| 366c | + |
| 352c | + |
| 353a | + |
| 354c | + |
| 355a | + |
| 340a | + |
| 341c | + |
| 342a | + |
| 356c | + |
| 357a | + |
| 358c | ++ |
| 359c | + |
| 360c | + |
| 361a | + |
| 367g | + |
| 368a | + |
| 369g | + |
| 362f | + |
| 363a | + |
| 364d | + |
| 364e | + |
| 381g | + |
| 382a | + |
| 385a | + |
| 384g | + |
| 386g | + |
| 387a | + |
| 383g | + |
| 388a | + |
| 389g | + |
| 390a | + |
| 376g | + |
| 377a | + |
| 379h | + |
| 380a | + |
| 374g | + |
| 375a | + |
| 391g | + |
| 392a | + |
| 370a | + |

TABLE 1-continued

Measured Ki ($IC_{50}$) Value for Compounds.

| Compound | $IC_{50}$ |
|---|---|
| 378c | + |
| 371c | ++ |
| 372a | ++ |
| 373a | ++ |

Three (+++) is used to denote compounds with an $IC_{50}$ value of greater than 1micromolar (>1000 nM) concentration; Two (++) indicate compounds with an $IC_{50}$ value between 1 and 0.1 micromolar (1000-100 nM) concentration: One (+) indicate compounds with an $IC_{50}$ value less than 0.1 micromolar (<100 nM) concentration.

INCORPORATION BY REFERENCE

All of the U.S. patents and U.S. and PCT published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound represented by Formula (I), or a pharmaceutically acceptable salt thereof:

(I-b)

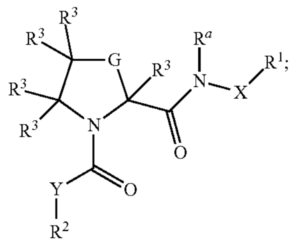

wherein, independently for each occurrence:

X is a bond or $C(R^X)_2$;

Y is a bond, $C(R^Y)_2$, or —$N(R^b)$—;

G is S or $C(R^3)_2$;

$R^a$ and $R^b$ are each independently H or $(C_1\text{-}C_6)$alkyl;

$R^1$ represents optionally substituted aryl or heteroaryl;

$R^2$ represents

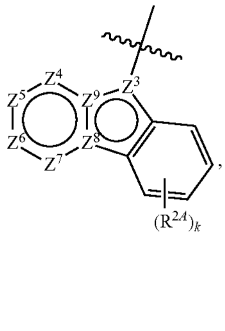

,

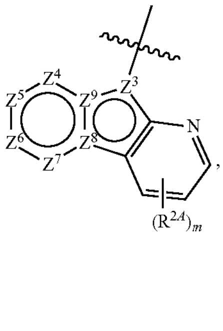

,

-continued

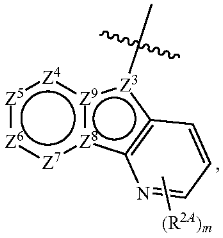

,

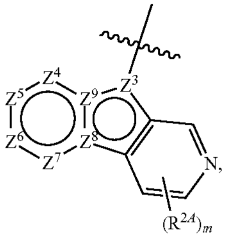

, or

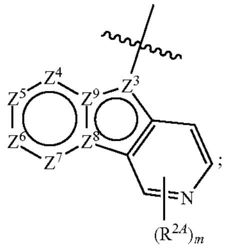

;

$R^3$ is independently for each occurrence H, halogen, —CN, —$NH_2$, —$CH_2NH_2$, $(C_1\text{-}C_6)$alkoxy or $(C_1\text{-}C_6)$alkyl; or two vicinal occurrences of $R^3$ taken together with the carbon atoms to which they are bonded form an optionally substituted fused $(C_3\text{-}C_7)$cycloalkyl or $(C_6)$aryl; or two geminal occurrences of $R^3$ taken together with the carbon atom to which they are bonded form an optionally substituted spiro $(C_3\text{-}C_7)$cycloalkyl; or two hominal occurrences of $R^3$ taken together with the carbon atoms to which they are bonded form an optionally substituted bridged $(C_3\text{-}C_7)$cycloalkyl;

$R^X$ is independently for each occurrence H, $(C_1\text{-}C_6)$alkyl, or $(C_3\text{-}C_7)$cycloalkyl;

$R^Y$ is independently for each occurrence H, $(C_1\text{-}C_6)$alkyl, or $(C_3\text{-}C_7)$cycloalkyl;

optional substituents on $R^1$ each independently represent halogen, —CN, —$NO_2$, —$OR^{13}$, —$NR^{13}R^{14}$, —$C(O)R^{13}$, —$C(O)OR^{13}$, —$C(O)NR^{13}R^{14}$, —$OC(O)R^{13}$, —$NR^{13}C(O)R^{14}$, —$OC(O)NR^{13}R^{14}$, —$OC(O)OR^{13}$, —$NR^{13}C(O)OR^{14}$, —$NR^{13}C(O)NR^{13}R^{14}$, —$OS(O)_p(R^{13})$, —$SR^{13}$, —$NR^{13}S(O)_p(R^{14})$, or optionally substituted alkyl, alkenyl, alkynyl, haloalkyl, hydroxyalkyl, alkoxyalkyl, cycloalkoxyalkyl, aryloxyalkyl, aralkyl, heteroaralkyl, heteroaryl, aryl, aryloxy, cycloalkyl, (cycloalkyl)alkyl, heterocycloalkyl, or (heterocycloalkyl)alkyl;

or wherein two substituents on $R^1$, taken together with the intervening atoms, form a ring;

$R^{13}$ and $R^{14}$, independently for each occurrence, represent H or optionally substituted alkyl, haloalkyl, alkenyl, alkynyl, aryl, or heteroaryl;

p is 0, 1, or 2;

$Z^3$ represents N;

$Z^4$ represents N or $CR^{4Z}$;

$Z^5$ represents N or $CR^{5Z}$;

$Z^6$ represents N or $CR^{6Z}$;

$Z^7$ represents N or $CR^{7Z}$;

$Z^8$ represents C;

$Z^9$ represents N or C;

k is an integer from 1-4;

m is an integer from 1-3; and each occurrence of $R^{4Z}$, $R^{5Z}$, $R^{6Z}$, $R^{7Z}$, $R^{2A}$ independently represents H, halogen, —CN, —$NO_2$, —$OR^{13}$, —$NR^{13}R^{14}$, —$C(O)R^{13}$, —$C(O)OR^{13}$, —$C(O)NR^{13}R^{14}$, —$OC(O)R^{13}$, —$NR^{13}C(O)R^{14}$, —$OC(O)NR^{13}R^{14}$, —$OC(O)OR^{13}$, —$NR^{13}C(O)OR^{14}$, $—NR^{13}C(O)NR^{13}R^{14}$, $—OS(O)_p(R^{13})$, $—SR^{13}$, $—NR^{13}S(O)_p(R^{14})$, or optionally substituted alkyl, alkenyl, alkynyl, haloalkyl, hydroxyalkyl, alkoxyalkyl, cycloalkoxyalkyl, aryloxyalkyl, aralkyl, heteroaralkyl, heteroaryl, aryl, aryloxy, cycloalkyl, (cycloalkyl)alkyl, heterocycloalkyl, or (heterocycloalkyl)alkyl; or wherein an occurrence of $R^{6Z}$ and an occurrence of $R^{7Z}$ taken together with the intervening atoms form a ring.

2. The compound of claim 1, wherein Y represents $C(R^Y)_2$.

3. The compound of claim 1, wherein Y represents $CH_2$.

4. The compound of claim 1, wherein X represents a bond.

5. The compound of claim 1, wherein X represents $CH_2$.

6. The compound of claim 1, wherein $R^1$ represents optionally substituted heteroaryl.

7. The compound of claim 1, wherein $R^1$ represents optionally substituted phenyl (e.g., 3-halophenyl, or 2,3-dihalophenyl), pyridinyl (e.g., 6-halopyridin-2-yl), or pyrazinyl (e.g., 6-halopyrazin-2-yl).

8. The compound of claim 1, wherein $R^1$ represents

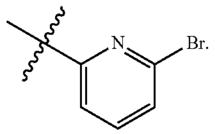 [SMILES: *c1cccc(Br)n1]

9. The compound of claim 1, wherein $R^1$ represents

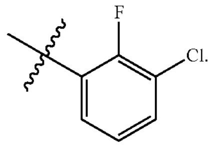 [SMILES: *c1cccc(Cl)c1F]

10. The compound of claim 1, wherein $R^2$ represents

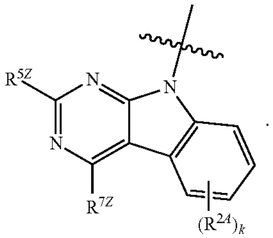

11. The compound of claim 10, wherein $R^2$ represents

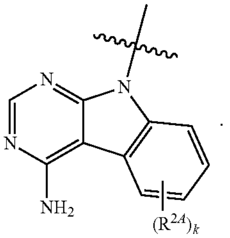

12. The compound of claim 10, wherein k represents 2.

13. The compound of claim 1, wherein $R^2$ represents

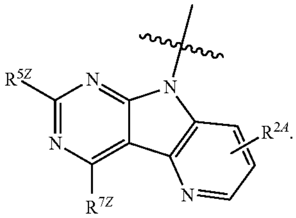

14. The compound of claim 1, wherein $R^{7Z}$ represents $—NR^{13}R^{14}$.

15. The compound of claim 1, wherein $R^{7Z}$ represents $—NH_2$.

16. The compound of claim 1, wherein $R^{6Z}$ represents $—C(O)R^{13}$, $—C(O)OR^{13}$, $—C(O)NR^{13}R^{14}$, or hydroxyalkyl.

17. The compound of claim 1, wherein $R^{5Z}$ represents alkyl, halo, or $—NR^{13}R^{14}$.

18. The compound of claim 1, wherein $R^{1Z}$ represents —CN, halo, haloalkyl, optionally substituted aryl, optionally substituted heteroaryl, optionally substituted alkyl, $—C(O)R^{13}$, $—SR^{13}$, $—NR^{13}R^{14}$, $—OR^{13}$, $—C(O)OR^{13}$, $—C(O)NR^{13}R^{14}$, or $—NR^{13}C(O)R^{14}$.

19. The compound of claim 1, wherein each occurrence of $R^{2A}$ independently represents —CN, $—NO_2$, halo, haloalkyl, optionally substituted aryl, optionally substituted heteroaryl, optionally substituted alkyl, optionally substituted alkenyl, optionally substituted hydroxyalkyl, $—C(O)R^{13}$, $—C(O)OR^{13}$, $—NR^{13}C(O)OR^{14}$, $—SR^{13}$, $—NR^{13}R^{14}$, $—OR^{13}$, $—C(O)NR^{13}R^{14}$, or $—NR^{13}C(O)R^{14}$.

20. The compound of claim 1, wherein G is $C(R^3)_2$.

21. The compound of claim 1, having the structure of formula (Ia):

(Ia)

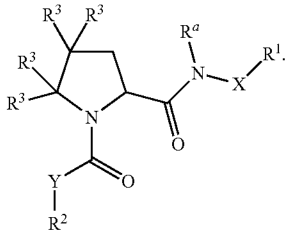

22. The compound of claim 1, wherein two vicinal occurrences of $R^3$ taken together with the carbon atoms to which they are bonded form an optionally substituted fused $C_3$-cycloalkyl.

23. The compound of claim 1, wherein at least one occurrence of $R^3$ is halo.

24. The compound of claim 1, wherein at least one occurrence of $R^3$ is methyl.

25. The compound of claim 1, or a pharmaceutically acceptable salt thereof, selected from the following table:
| # | Structure | # | Structure |
|---|---|---|---|
| 20a | 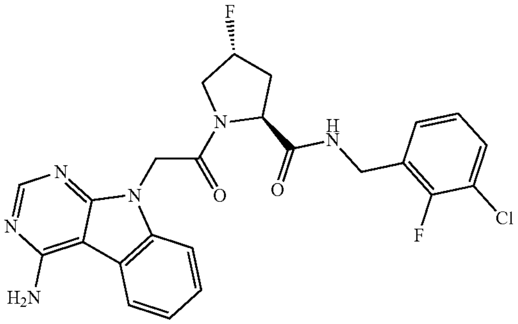 [SMILES: Nc1ncnc2c1c1ccccc1n2CC(=O)N1C[C@H](F)C[C@H]1C(=O)NCc1cccc(Cl)c1F] | 24a | 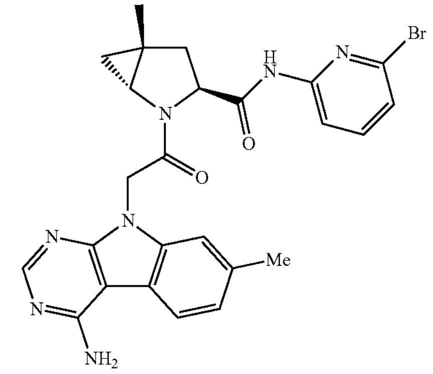 [SMILES: Cc1ccc2c3c(N)ncnc3n(CC(=O)N3[C@H](C(=O)Nc4cccc(Br)n4)C[C@@]4(C)C[C@@H]34)c2c1] |
| 19a | 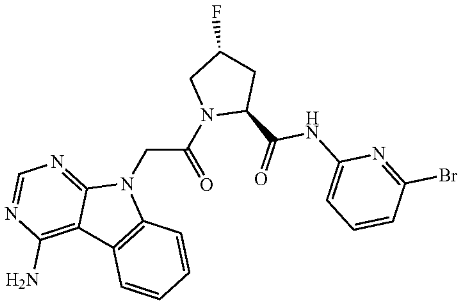 [SMILES: Nc1ncnc2c1c1ccccc1n2CC(=O)N1C[C@H](F)C[C@H]1C(=O)Nc1cccc(Br)n1] | 50f | 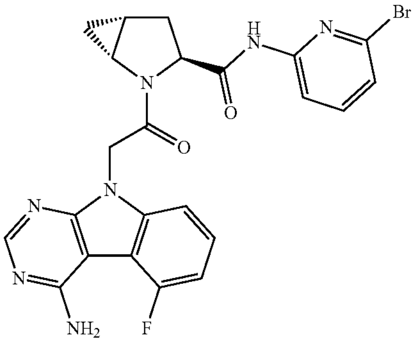 [SMILES: Nc1ncnc2c1c1c(F)cccc1n2CC(=O)N1[C@@H]2C[C@@H]2C[C@H]1C(=O)Nc1cccc(Br)n1] |
| 3b | 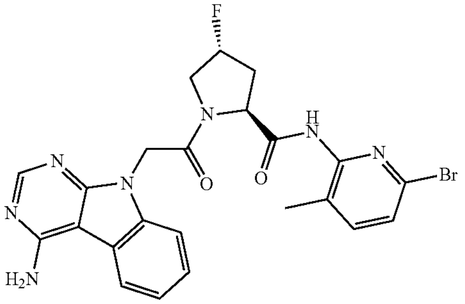 [SMILES: Cc1ccc(Br)nc1NC(=O)[C@@H]1C[C@@H](F)CN1C(=O)Cn1c2ccccc2c2c(N)ncnc21] | 32f | 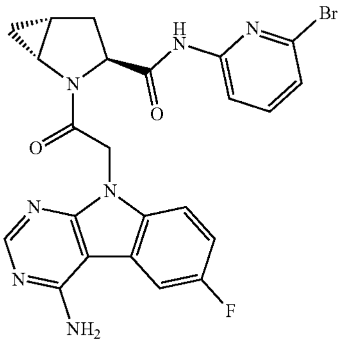 [SMILES: Nc1ncnc2c1c1cc(F)ccc1n2CC(=O)N1[C@@H]2C[C@@H]2C[C@H]1C(=O)Nc1cccc(Br)n1] |
| 4b | 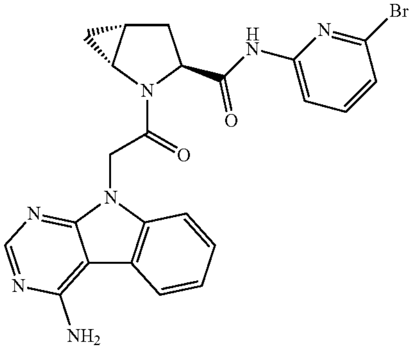 [SMILES: Nc1ncnc2c1c1ccccc1n2CC(=O)N1[C@@H]2C[C@@H]2C[C@H]1C(=O)Nc1cccc(Br)n1] | 43a | 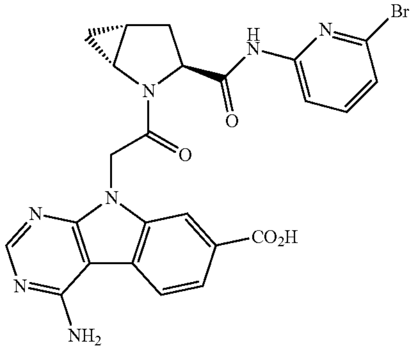 [SMILES: Nc1ncnc2c1c1ccc(C(=O)O)cc1n2CC(=O)N1[C@@H]2C[C@@H]2C[C@H]1C(=O)Nc1cccc(Br)n1] |

-continued
| # | Structure | # | Structure |
| --- | --- | --- | --- |
| 9a | 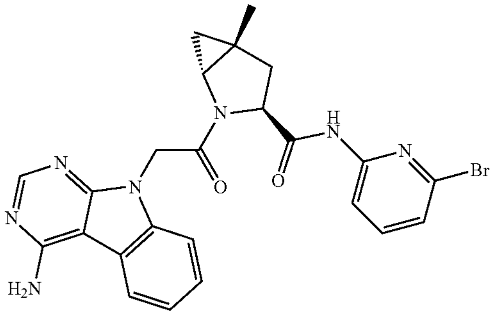 [SMILES: C[C@@]12C[C@@H](C(=O)Nc3cccc(Br)n3)N(C(=O)Cn3c4ccccc4c4c(N)ncnc43)[C@@H]1C2] | 35f | 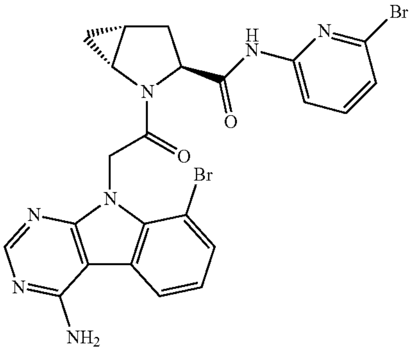 [SMILES: Nc1ncnc2c1c1cccc(Br)c1n2CC(=O)N1[C@@H]2C[C@@H]2C[C@H]1C(=O)Nc1cccc(Br)n1] |
| 1e | 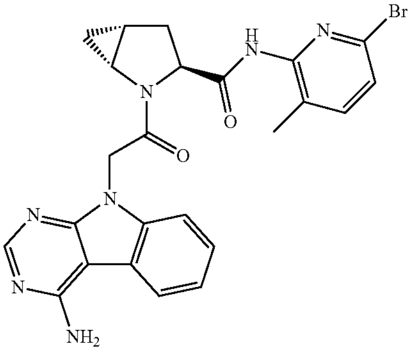 [SMILES: Cc1ccc(Br)nc1NC(=O)[C@@H]1C[C@H]2C[C@H]2N1C(=O)Cn1c2ccccc2c2c(N)ncnc21] | 30f | 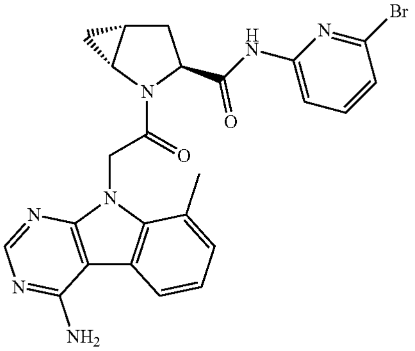 [SMILES: Cc1cccc2c3c(N)ncnc3n(CC(=O)N3[C@@H]4C[C@@H]4C[C@H]3C(=O)Nc3cccc(Br)n3)c12] |
| 6e | 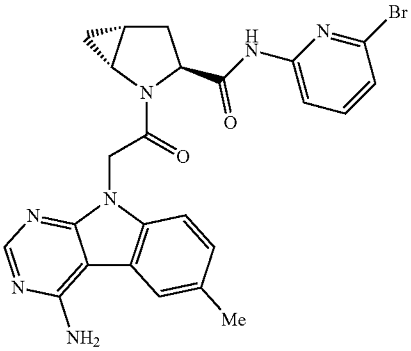 | 47g | 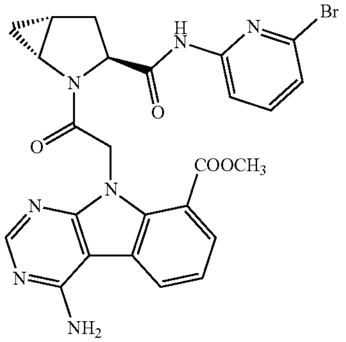 [SMILES: COC(=O)c1cccc2c3c(N)ncnc3n(CC(=O)N3[C@@H]4C[C@@H]4C[C@H]3C(=O)Nc3cccc(Br)n3)c12] |
| 7b | 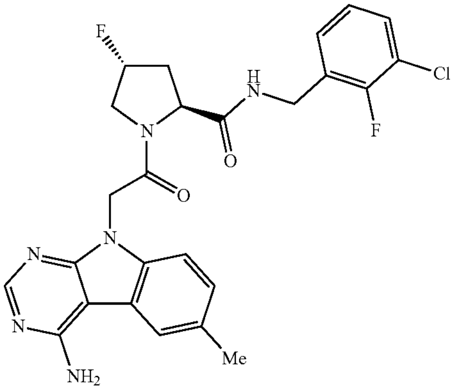 [SMILES: Cc1ccc2c(c1)c1c(N)ncnc1n2CC(=O)N1C[C@H](F)C[C@H]1C(=O)NCc1cccc(Cl)c1F] | 48d | 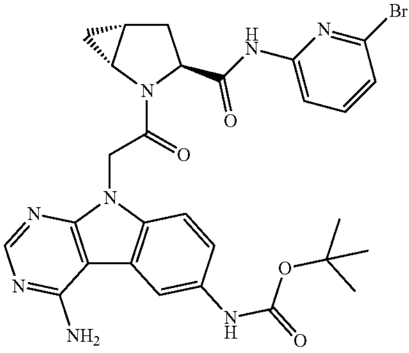 [SMILES: CC(C)(C)OC(=O)Nc1ccc2c(c1)c1c(N)ncnc1n2CC(=O)N1[C@@H]2C[C@@H]2C[C@H]1C(=O)Nc1cccc(Br)n1] |

-continued
| # | Structure | # | Structure |
|---|---|---|---|
| 21a | 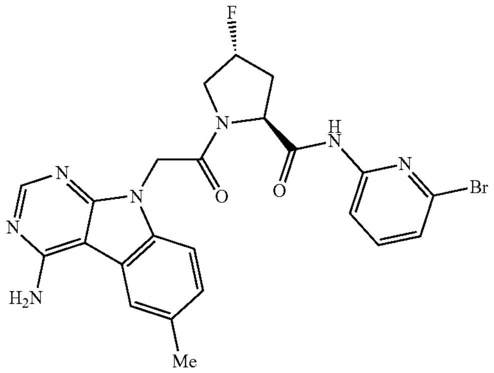 [SMILES: Cc1ccc2c(c1)c1c(N)ncnc1n2CC(=O)N1C[C@H](F)C[C@H]1C(=O)Nc1cccc(Br)n1] | 38e | 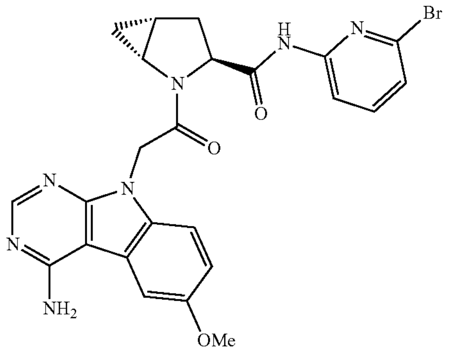 [SMILES: COc1ccc2c(c1)c1c(N)ncnc1n2CC(=O)N1[C@@H]2C[C@@H]2C[C@H]1C(=O)Nc1cccc(Br)n1] |
| 27a | 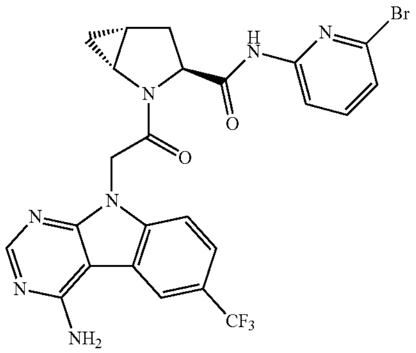 [SMILES: Nc1ncnc2c1c1cc(C(F)(F)F)ccc1n2CC(=O)N1[C@@H]2C[C@@H]2C[C@H]1C(=O)Nc1cccc(Br)n1] | 51g | 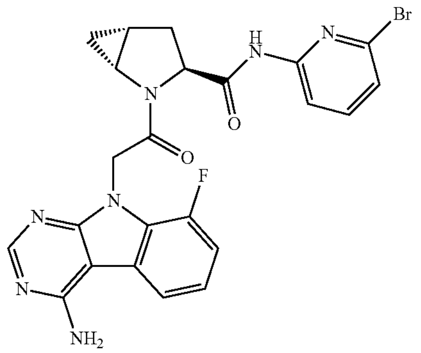 [SMILES: Nc1ncnc2c1c1cccc(F)c1n2CC(=O)N1[C@@H]2C[C@@H]2C[C@H]1C(=O)Nc1cccc(Br)n1] |
| 25a | 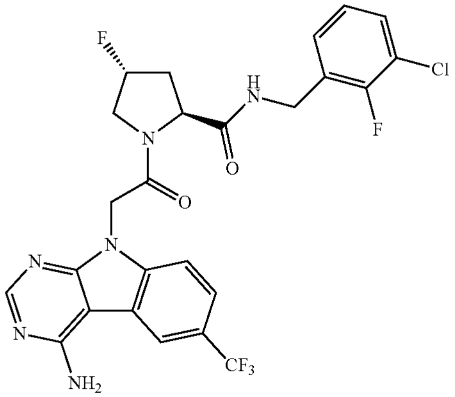 [SMILES: Nc1ncnc2c1c1cc(C(F)(F)F)ccc1n2CC(=O)N1C[C@H](F)C[C@H]1C(=O)NCc1cccc(Cl)c1F] | 52f | 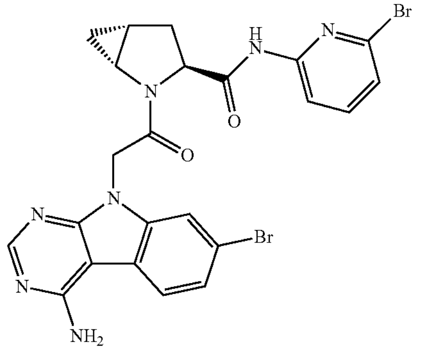 [SMILES: Nc1ncnc2c1c1ccc(Br)cc1n2CC(=O)N1[C@@H]2C[C@@H]2C[C@H]1C(=O)Nc1cccc(Br)n1] |
| 26a | 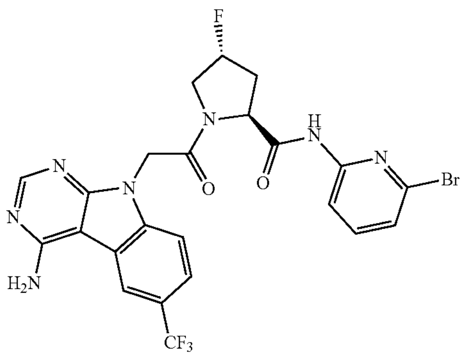 [SMILES: Nc1ncnc2c1c1cc(C(F)(F)F)ccc1n2CC(=O)N1C[C@H](F)C[C@H]1C(=O)Nc1cccc(Br)n1] | 54g | 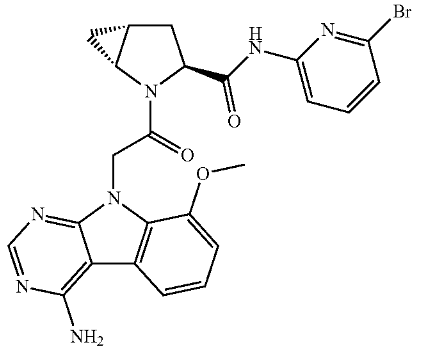 [SMILES: COc1cccc2c3c(N)ncnc3n(CC(=O)N3[C@@H]4C[C@@H]4C[C@H]3C(=O)Nc3cccc(Br)n3)c12] |

-continued
| # | Structure | # | Structure |
|---|---|---|---|
| 8b | 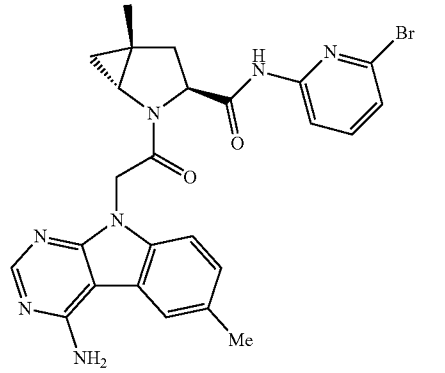 [SMILES: Cc1ccc2c(c1)c1c(N)ncnc1n2CC(=O)N1[C@H](C(=O)Nc2cccc(Br)n2)C[C@@]2(C)C[C@@H]12] | 44a | 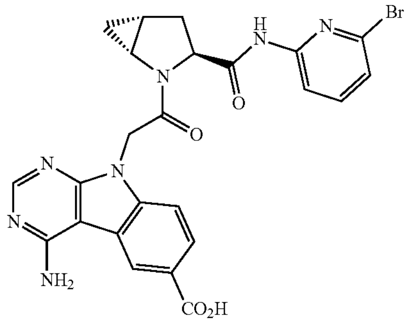 [SMILES: Nc1ncnc2c1c1cc(C(=O)O)ccc1n2CC(=O)N1[C@@H]2C[C@@H]2C[C@H]1C(=O)Nc1cccc(Br)n1] |
| 28a | 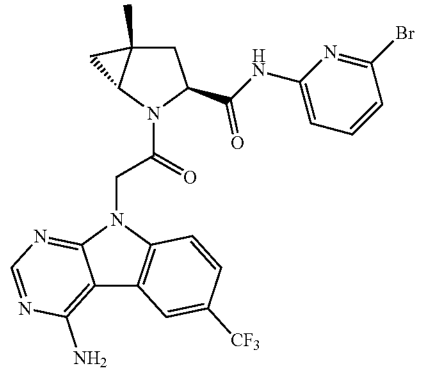 | 29f | 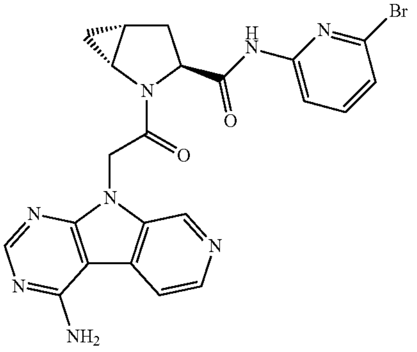 [SMILES: Nc1ncnc2c1c1ccncc1n2CC(=O)N1[C@@H]2C[C@@H]2C[C@H]1C(=O)Nc1cccc(Br)n1] |
| 10b | 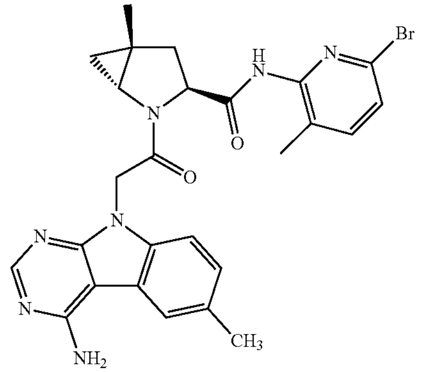 [SMILES: Cc1ccc2c(c1)c1c(N)ncnc1n2CC(=O)N1[C@H](C(=O)Nc2nc(Br)ccc2C)C[C@@]2(C)C[C@@H]12] | 22c and 22d | 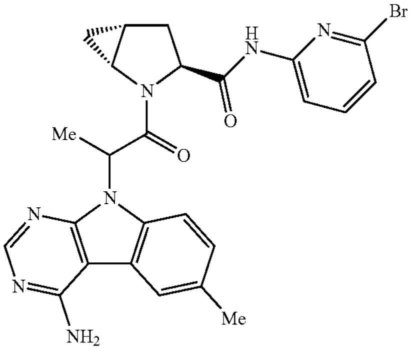 (+) and (-) isomer |
| 11f | 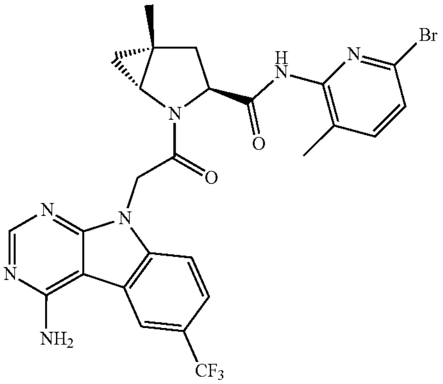 [SMILES: Cc1ccc(Br)nc1NC(=O)[C@@H]1C[C@@]2(C)C[C@H]2N1C(=O)Cn1c2ccc(C(F)(F)F)cc2c2c(N)ncnc21] | 33e | 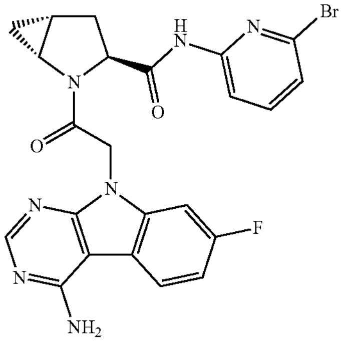 [SMILES: Nc1ncnc2c1c1ccc(F)cc1n2CC(=O)N1[C@@H]2C[C@@H]2C[C@H]1C(=O)Nc1cccc(Br)n1] |

-continued
| # | Structure | # | Structure |
|---|---|---|---|
| 12a | 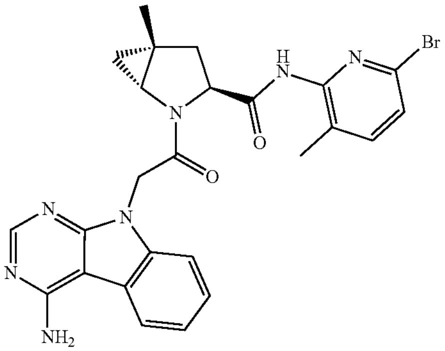 [SMILES: Cc1ccc(Br)nc1NC(=O)[C@@H]1C[C@@]2(C)C[C@H]2N1C(=O)Cn1c2ccccc2c2c(N)ncnc21] | 49c | 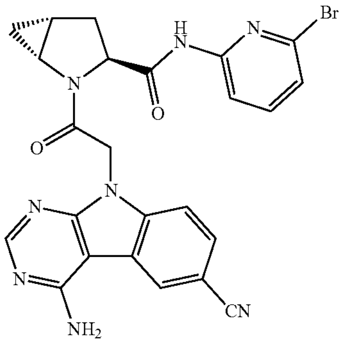 [SMILES: N#Cc1ccc2c(c1)c1c(N)ncnc1n2CC(=O)N1[C@@H]2C[C@@H]2C[C@H]1C(=O)Nc1cccc(Br)n1] |
| 34e | 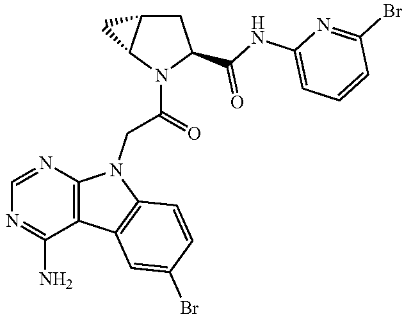 [SMILES: Nc1ncnc2c1c1cc(Br)ccc1n2CC(=O)N1[C@@H]2C[C@@H]2C[C@H]1C(=O)Nc1cccc(Br)n1] | 58c | 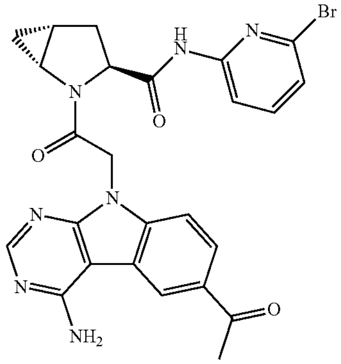 [SMILES: CC(=O)c1ccc2c(c1)c1c(N)ncnc1n2CC(=O)N1[C@@H]2C[C@@H]2C[C@H]1C(=O)Nc1cccc(Br)n1] |
| 13b | 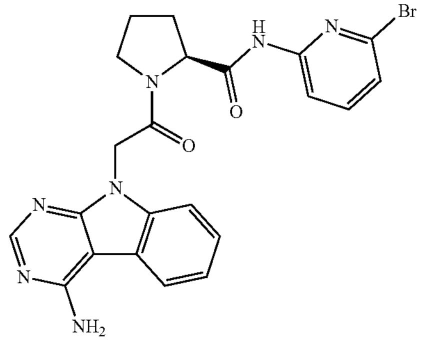 [SMILES: Nc1ncnc2c1c1ccccc1n2CC(=O)N1CCC[C@H]1C(=O)Nc1cccc(Br)n1] | 59c | 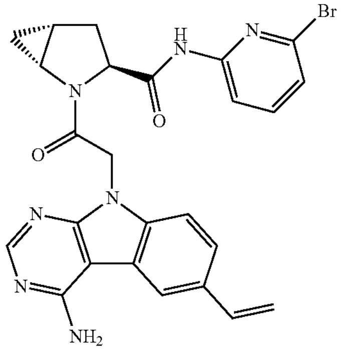 [SMILES: C=Cc1ccc2c(c1)c1c(N)ncnc1n2CC(=O)N1[C@@H]2C[C@@H]2C[C@H]1C(=O)Nc1cccc(Br)n1] |
| 14a | 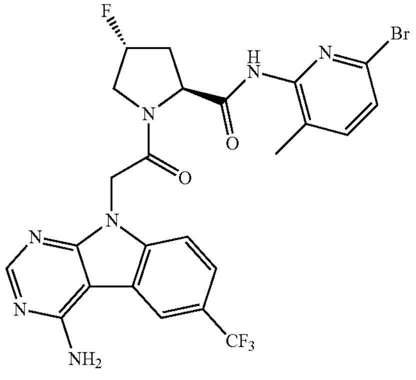 [SMILES: Cc1ccc(Br)nc1NC(=O)[C@@H]1C[C@@H](F)CN1C(=O)Cn1c2ccc(C(F)(F)F)cc2c2c(N)ncnc21] | 17f | 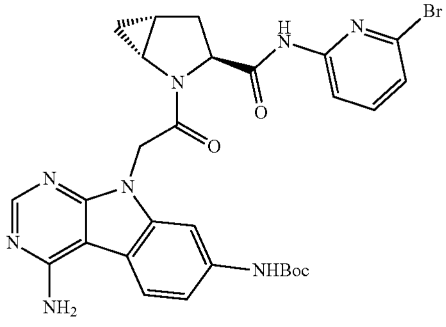 [SMILES: CC(C)(C)OC(=O)Nc1ccc2c3c(N)ncnc3n(CC(=O)N3[C@@H]4C[C@@H]4C[C@H]3C(=O)Nc3cccc(Br)n3)c2c1] |

-continued
| # | Structure | # | Structure |
|---|---|---|---|
| 15a | 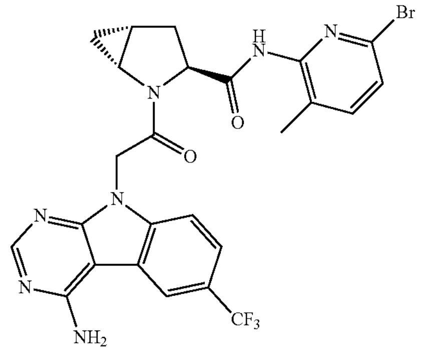 [SMILES: Cc1ccc(Br)nc1NC(=O)[C@@H]1C[C@H]2C[C@H]2N1C(=O)Cn1c2ccc(C(F)(F)F)cc2c2c(N)ncnc21] | 18a | 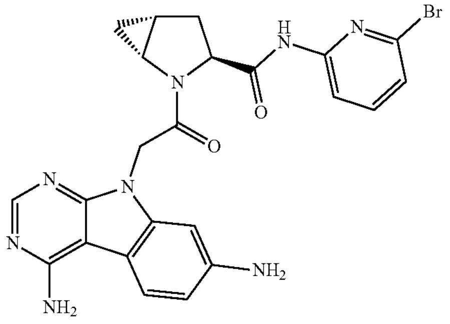 [SMILES: Nc1ccc2c3c(N)ncnc3n(CC(=O)N3[C@@H]4C[C@@H]4C[C@H]3C(=O)Nc3cccc(Br)n3)c2c1] |
| 37a | 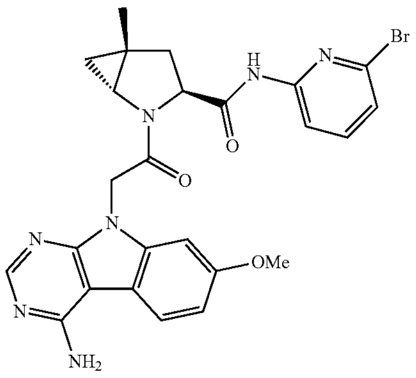 [SMILES: COc1ccc2c3c(N)ncnc3n(CC(=O)N3[C@H](C(=O)Nc4cccc(Br)n4)C[C@@]4(C)C[C@@H]34)c2c1] | 31f | 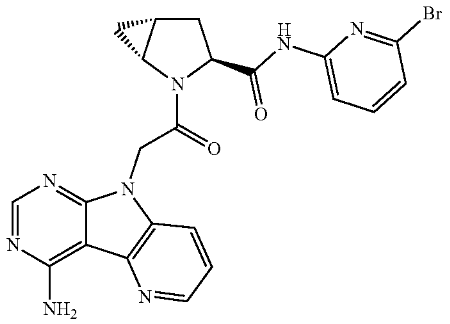 [SMILES: Nc1ncnc2c1c1ncccc1n2CC(=O)N1[C@@H]2C[C@@H]2C[C@H]1C(=O)Nc1cccc(Br)n1] |
| 218a | 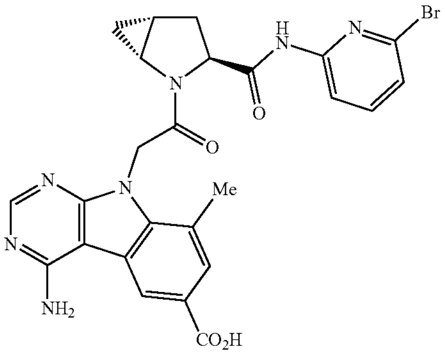 [SMILES: Cc1cc(C(=O)O)cc2c3c(N)ncnc3n(CC(=O)N3[C@@H]4C[C@@H]4C[C@H]3C(=O)Nc3cccc(Br)n3)c12] | 60c | 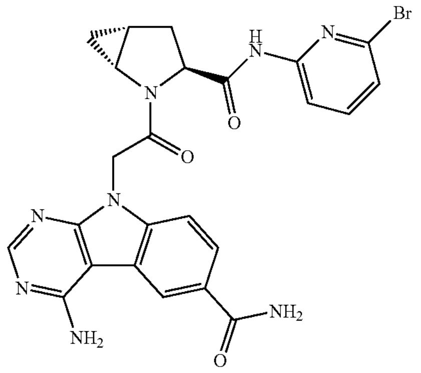 [SMILES: NC(=O)c1ccc2c(c1)c1c(N)ncnc1n2CC(=O)N1[C@@H]2C[C@@H]2C[C@H]1C(=O)Nc1cccc(Br)n1] |
| 223a | 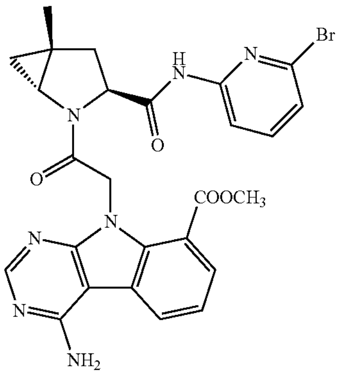 [SMILES: COC(=O)c1cccc2c3c(N)ncnc3n(CC(=O)N3[C@H](C(=O)Nc4cccc(Br)n4)C[C@@]4(C)C[C@@H]34)c12] | 61a | 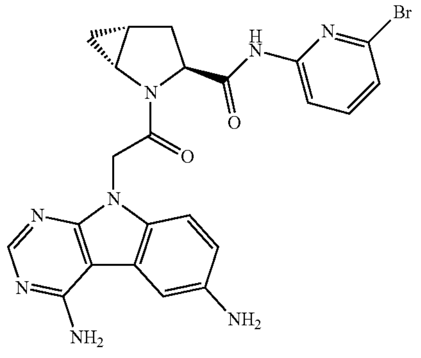 [SMILES: Nc1ccc2c(c1)c1c(N)ncnc1n2CC(=O)N1[C@@H]2C[C@@H]2C[C@H]1C(=O)Nc1cccc(Br)n1] |

-continued
| # | Structure | # | Structure |
|---|---|---|---|
| 224b | 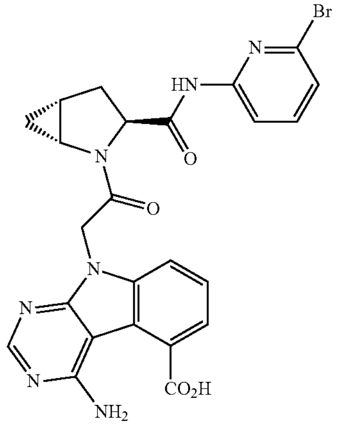 [SMILES: Nc1ncnc2c1c1c(C(=O)O)cccc1n2CC(=O)N1[C@@H]2C[C@@H]2C[C@H]1C(=O)Nc1cccc(Br)n1] | 46g | 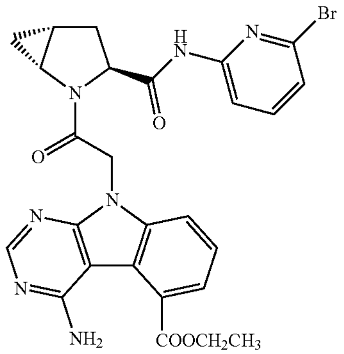 |
| 225e | 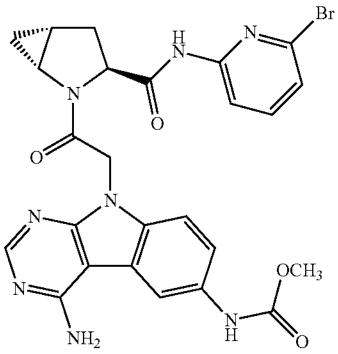 [SMILES: COC(=O)Nc1ccc2c(c1)c1c(N)ncnc1n2CC(=O)N1[C@@H]2C[C@@H]2C[C@H]1C(=O)Nc1cccc(Br)n1] | 62c | 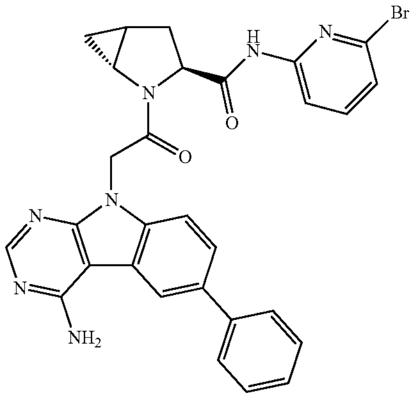 |
| 226c | 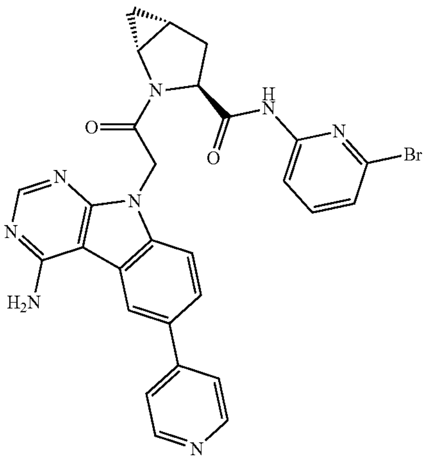 [SMILES: Nc1ncnc2c1c1cc(-c3ccncc3)ccc1n2CC(=O)N1[C@@H]2C[C@@H]2C[C@H]1C(=O)Nc1cccc(Br)n1] | 63d | 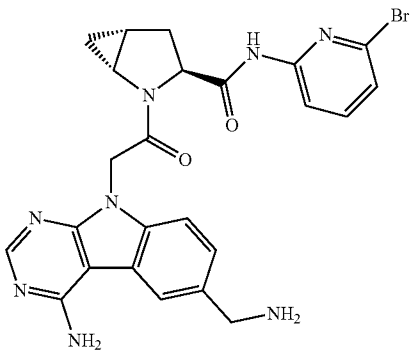 [SMILES: NCc1ccc2c(c1)c1c(N)ncnc1n2CC(=O)N1[C@@H]2C[C@@H]2C[C@H]1C(=O)Nc1cccc(Br)n1] |

-continued
| # | Structure | # | Structure |
|---|---|---|---|
| 219a | 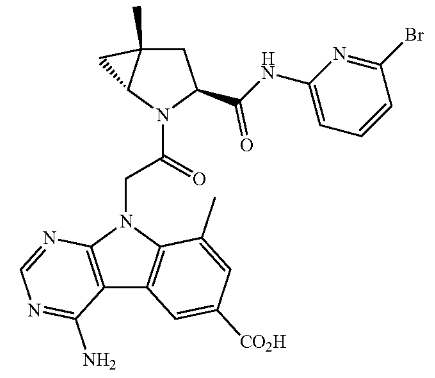 [SMILES: Cc1cc(C(=O)O)cc2c3c(N)ncnc3n(CC(=O)N3[C@H](C(=O)Nc4cccc(Br)n4)C[C@@]4(C)C[C@@H]34)c12] | 53d | 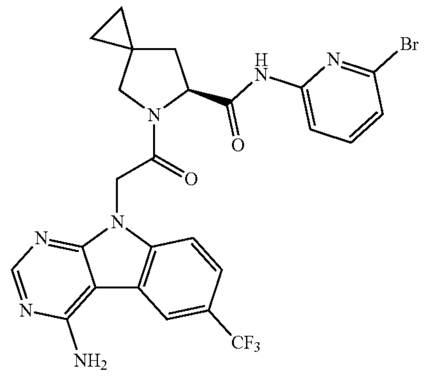 [SMILES: Nc1ncnc2c1c1cc(C(F)(F)F)ccc1n2CC(=O)N1CC2(CC2)C[C@H]1C(=O)Nc1cccc(Br)n1] |
| 227c | 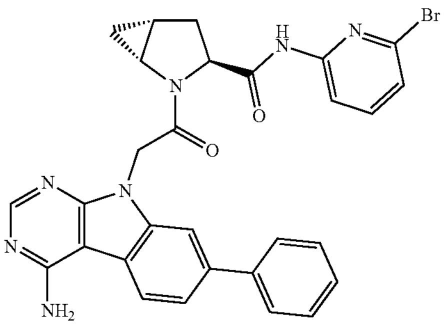 [SMILES: Nc1ncnc2c1c1ccc(-c3ccccc3)cc1n2CC(=O)N1[C@@H]2C[C@@H]2C[C@H]1C(=O)Nc1cccc(Br)n1] | 55a | 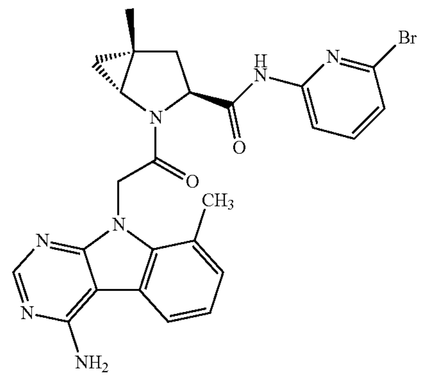 |
| 228a | 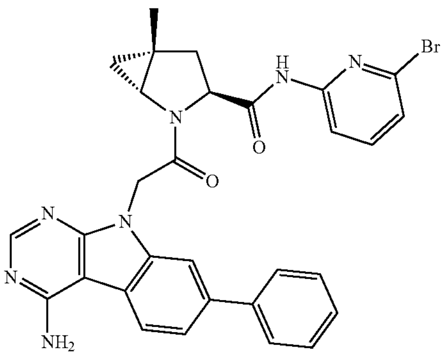 [SMILES: C[C@@]12C[C@@H](C(=O)Nc3cccc(Br)n3)N(C(=O)Cn3c4cc(-c5ccccc5)ccc4c4c(N)ncnc43)[C@@H]1C2] | 56g | 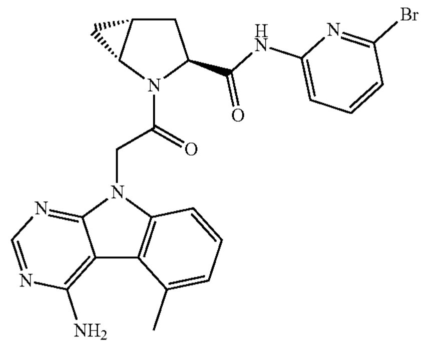 [SMILES: Cc1cccc2c1c1c(N)ncnc1n2CC(=O)N1[C@@H]2C[C@@H]2C[C@H]1C(=O)Nc1cccc(Br)n1] |
| | | 57g | 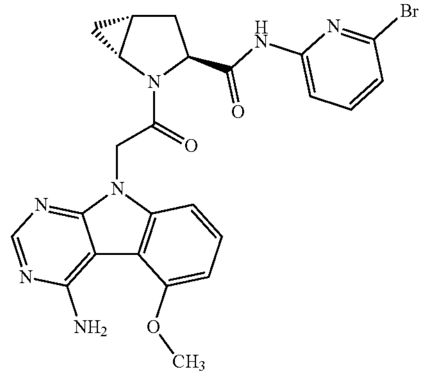 [SMILES: COc1cccc2c1c1c(N)ncnc1n2CC(=O)N1[C@@H]2C[C@@H]2C[C@H]1C(=O)Nc1cccc(Br)n1] |

-continued
| # | Structure | # | Structure |
|---|---|---|---|
| 229c | 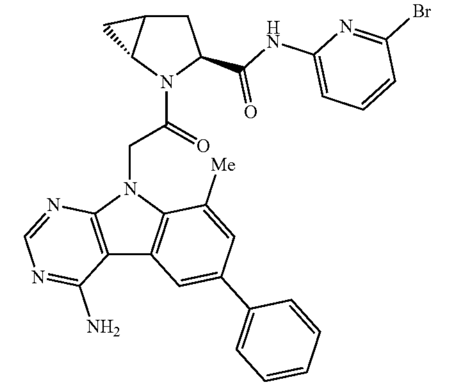 | 159a | 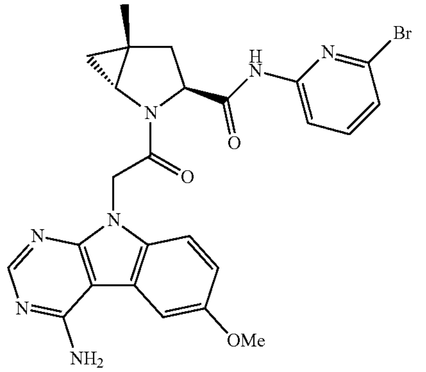 [SMILES: COc1ccc2c(c1)c1c(N)ncnc1n2CC(=O)N1[C@H](C(=O)Nc2cccc(Br)n2)C[C@@]2(C)C[C@@H]12] |
| 230a | 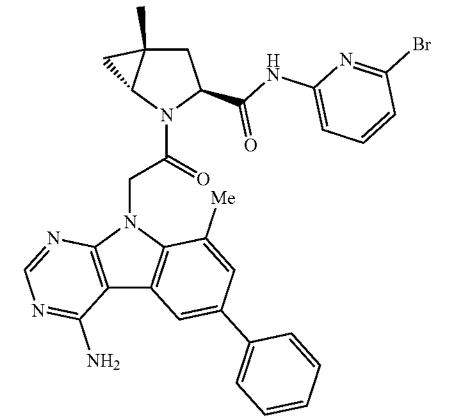 [SMILES: Cc1cc(-c2ccccc2)cc2c3c(N)ncnc3n(CC(=O)N3[C@H](C(=O)Nc4cccc(Br)n4)C[C@@]4(C)C[C@@H]34)c12] | 160a | 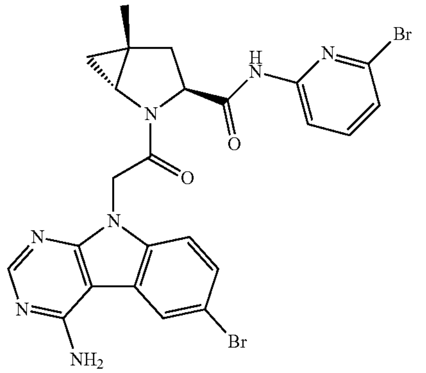 [SMILES: C[C@@]12C[C@@H](C(=O)Nc3cccc(Br)n3)N(C(=O)Cn3c4ccc(Br)cc4c4c(N)ncnc43)[C@@H]1C2] |
| 231g | 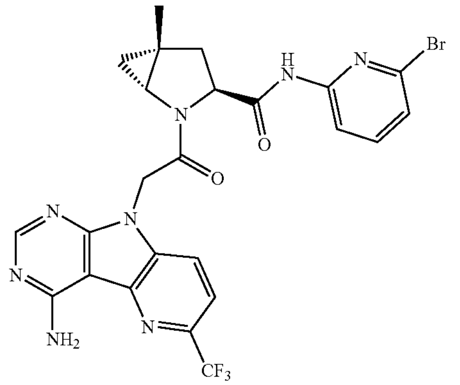 [SMILES: C[C@@]12C[C@@H](C(=O)Nc3cccc(Br)n3)N(C(=O)Cn3c4ccc(C(F)(F)F)nc4c4c(N)ncnc43)[C@@H]1C2] | 171b | 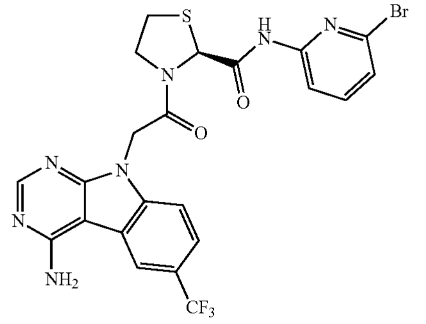 [SMILES: Nc1ncnc2c1c1cc(C(F)(F)F)ccc1n2CC(=O)N1CCS[C@H]1C(=O)Nc1cccc(Br)n1] |
| 246b | 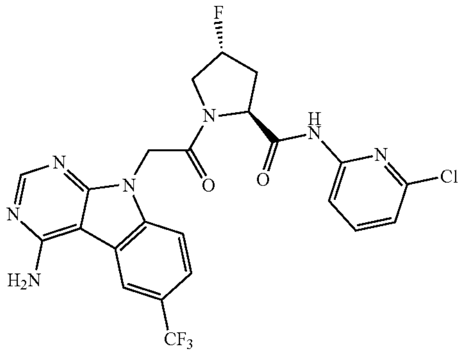 | 172a | 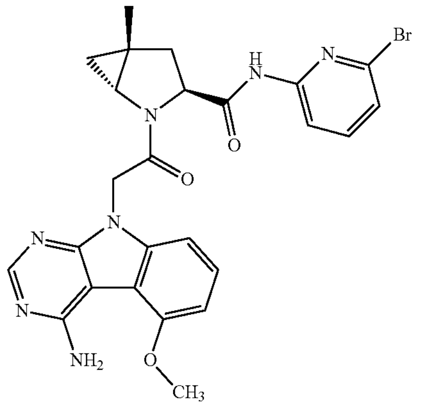 [SMILES: COc1cccc2c1c1c(N)ncnc1n2CC(=O)N1[C@H](C(=O)Nc2cccc(Br)n2)C[C@@]2(C)C[C@@H]12] |

-continued
| # | Structure | # | Structure |
|---|---|---|---|
| 247d | 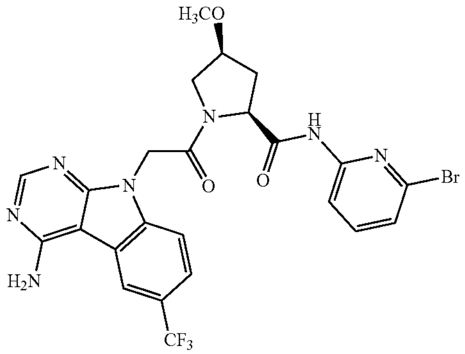 | 173a | 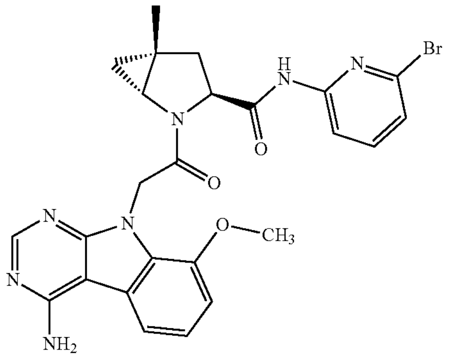 [SMILES: COc1cccc2c3c(N)ncnc3n(CC(=O)N3[C@H](C(=O)Nc4cccc(Br)n4)C[C@@]4(C)C[C@@H]34)c12] |
| 248d | 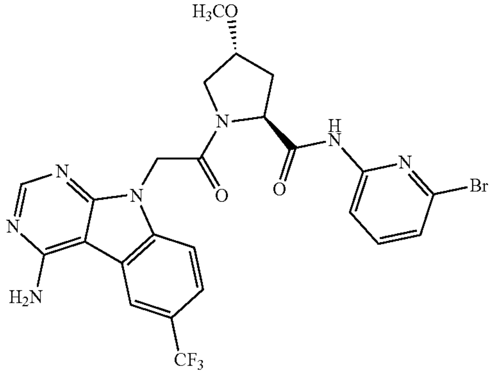 [SMILES: CO[C@@H]1C[C@@H](C(=O)Nc2cccc(Br)n2)N(C(=O)Cn2c3ccc(C(F)(F)F)cc3c3c(N)ncnc32)C1] | 161a | 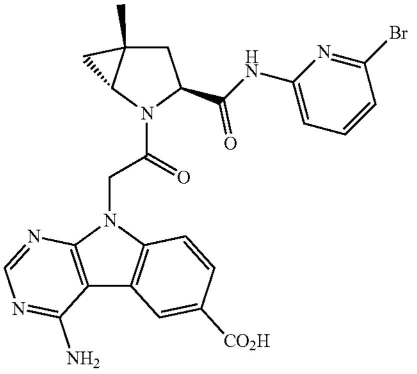 [SMILES: C[C@@]12C[C@@H](C(=O)Nc3cccc(Br)n3)N(C(=O)Cn3c4ccc(C(=O)O)cc4c4c(N)ncnc43)[C@@H]1C2] |
| 232a | 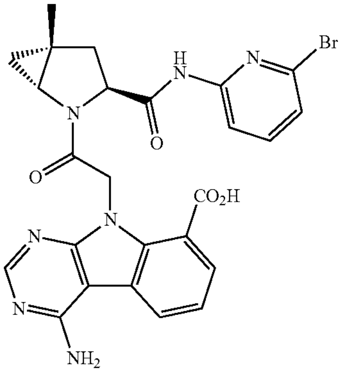 [SMILES: C[C@@]12C[C@@H](C(=O)Nc3cccc(Br)n3)N(C(=O)Cn3c4ncnc(N)c4c4cccc(C(=O)O)c43)[C@@H]1C2] | 174g | 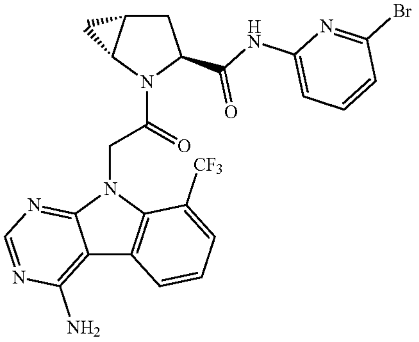 [SMILES: Nc1ncnc2c1c1cccc(C(F)(F)F)c1n2CC(=O)N1[C@@H]2C[C@@H]2C[C@H]1C(=O)Nc1cccc(Br)n1] |
| 234a | 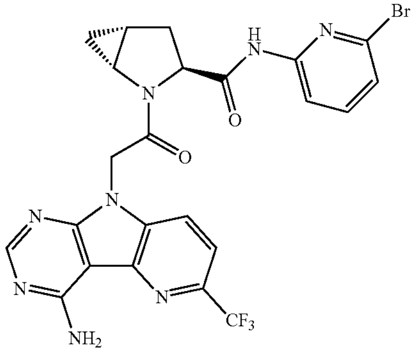 [SMILES: Nc1ncnc2c1c1nc(C(F)(F)F)ccc1n2CC(=O)N1[C@@H]2C[C@@H]2C[C@H]1C(=O)Nc1cccc(Br)n1] | 175a | 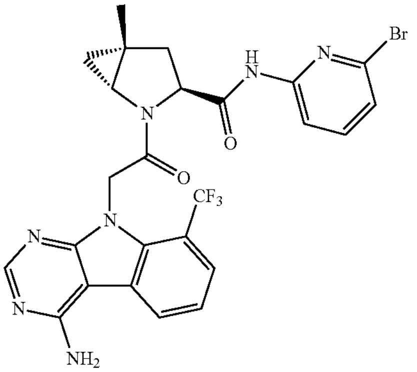 |

-continued
| # | Structure | # | Structure |
|---|---|---|---|
| 267c | 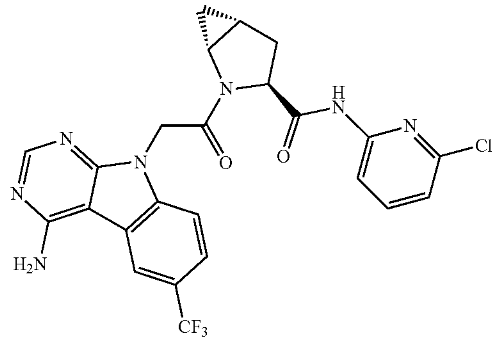 [SMILES: Nc1ncnc2c1c1cc(C(F)(F)F)ccc1n2CC(=O)N1[C@@H]2C[C@@H]2C[C@H]1C(=O)Nc1cccc(Cl)n1] | 176a | 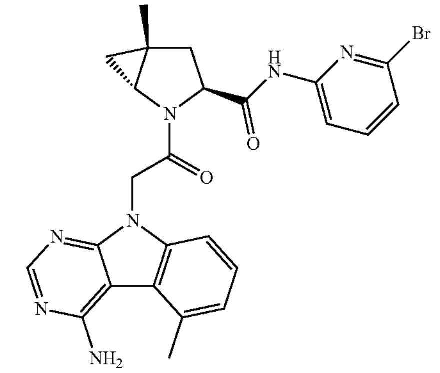 [SMILES: Cc1cccc2c1c1c(N)ncnc1n2CC(=O)N1[C@H](C(=O)Nc2cccc(Br)n2)C[C@@]2(C)C[C@@H]12] |
| 268b | 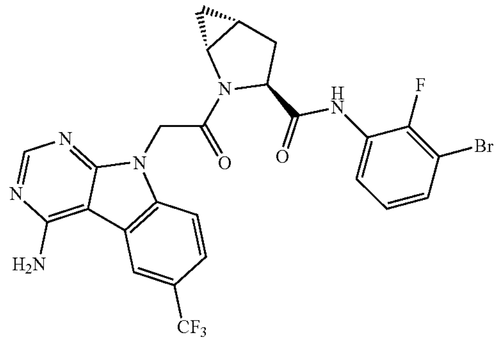 [SMILES: Nc1ncnc2c1c1cc(C(F)(F)F)ccc1n2CC(=O)N1[C@@H]2C[C@@H]2C[C@H]1C(=O)Nc1cccc(Br)c1F] | 169f | 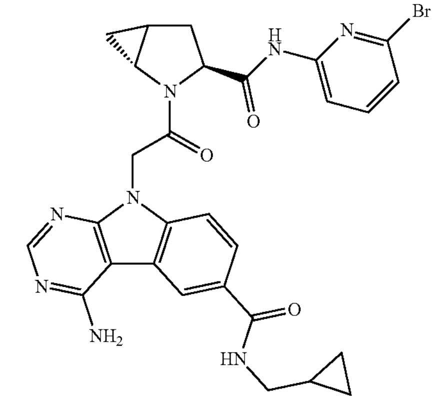 |
| 269c | 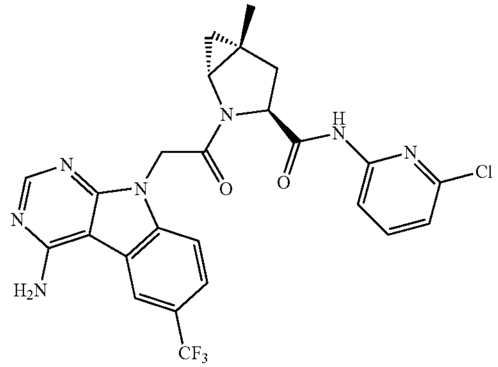 [SMILES: C[C@@]12C[C@@H](C(=O)Nc3cccc(Cl)n3)N(C(=O)Cn3c4ccc(C(F)(F)F)cc4c4c(N)ncnc43)[C@@H]1C2] | 177d | 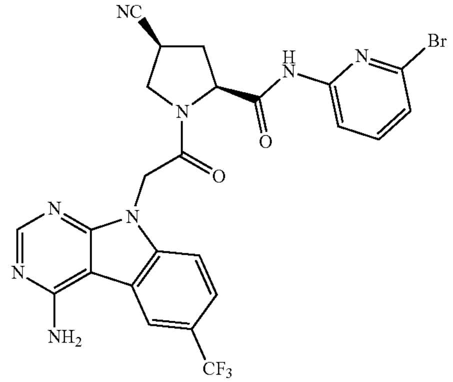 [SMILES: N#C[C@H]1C[C@@H](C(=O)Nc2cccc(Br)n2)N(C(=O)Cn2c3ccc(C(F)(F)F)cc3c3c(N)ncnc32)C1] |
| 274g | 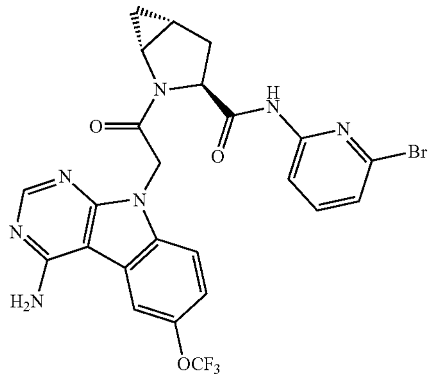 [SMILES: Nc1ncnc2c1c1cc(OC(F)(F)F)ccc1n2CC(=O)N1[C@@H]2C[C@@H]2C[C@H]1C(=O)Nc1cccc(Br)n1] | 178d | 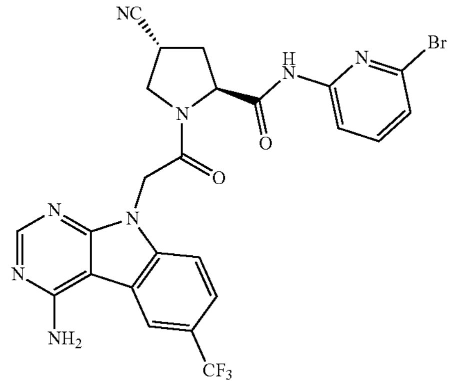 [SMILES: N#C[C@@H]1C[C@@H](C(=O)Nc2cccc(Br)n2)N(C(=O)Cn2c3ccc(C(F)(F)F)cc3c3c(N)ncnc32)C1] |

-continued
| # | Structure | # | Structure |
|---|---|---|---|
| 276g | 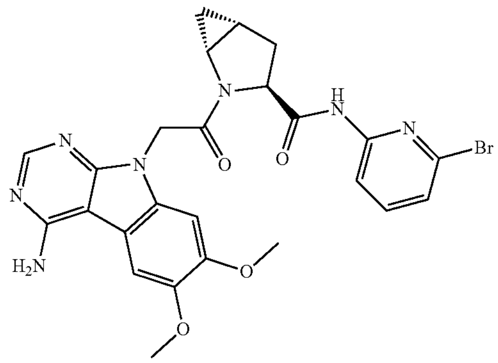 [SMILES: COc1cc2c3c(N)ncnc3n(CC(=O)N3[C@@H]4C[C@@H]4C[C@H]3C(=O)Nc3cccc(Br)n3)c2cc1OC] | 162g | 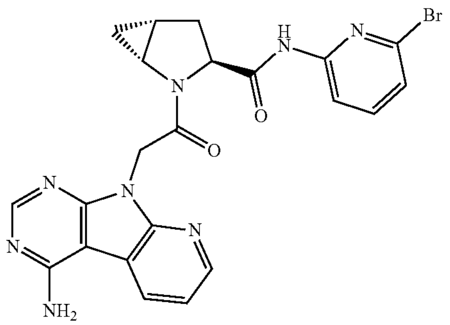 [SMILES: Nc1ncnc2c1c1cccnc1n2CC(=O)N1[C@@H]2C[C@@H]2C[C@H]1C(=O)Nc1cccc(Br)n1] |
| 277a | 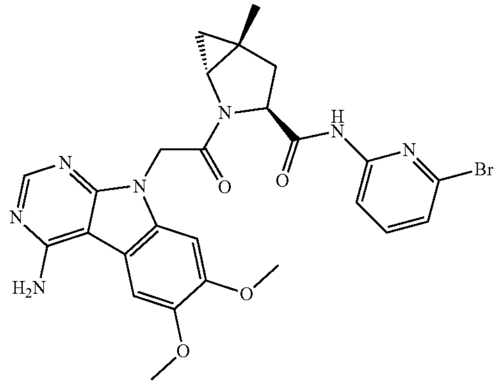 [SMILES: COc1cc2c3c(N)ncnc3n(CC(=O)N3[C@H](C(=O)Nc4cccc(Br)n4)C[C@@]4(C)C[C@@H]34)c2cc1OC] | 163g | 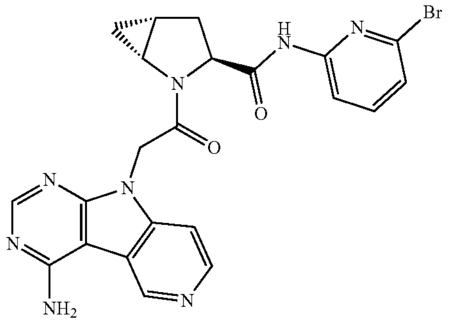 [SMILES: Nc1ncnc2c1c1cnccc1n2CC(=O)N1[C@@H]2C[C@@H]2C[C@H]1C(=O)Nc1cccc(Br)n1] |
| 278g | 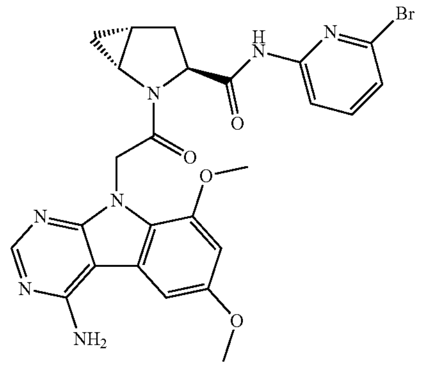 [SMILES: COc1cc(OC)c2c(c1)c1c(N)ncnc1n2CC(=O)N1[C@@H]2C[C@@H]2C[C@H]1C(=O)Nc1cccc(Br)n1] | 164a | 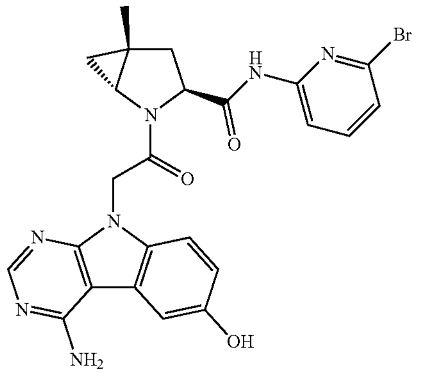 [SMILES: C[C@@]12C[C@@H](C(=O)Nc3cccc(Br)n3)N(C(=O)Cn3c4ccc(O)cc4c4c(N)ncnc43)[C@@H]1C2] |
| 279a | 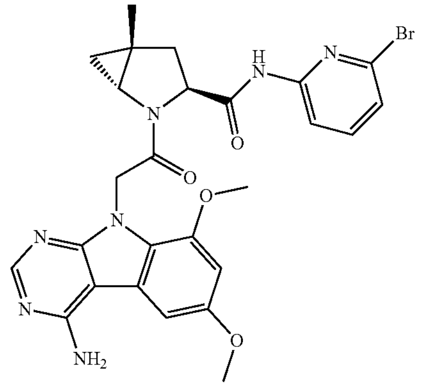 [SMILES: COc1cc(OC)c2c(c1)c1c(N)ncnc1n2CC(=O)N1[C@H](C(=O)Nc2cccc(Br)n2)C[C@@]2(C)C[C@@H]12] | 165a | 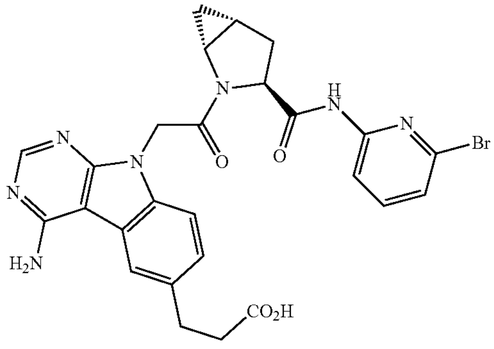 [SMILES: Nc1ncnc2c1c1cc(CCC(=O)O)ccc1n2CC(=O)N1[C@@H]2C[C@@H]2C[C@H]1C(=O)Nc1cccc(Br)n1] |

-continued
| # | Structure | # | Structure |
|---|---|---|---|
| 280g | 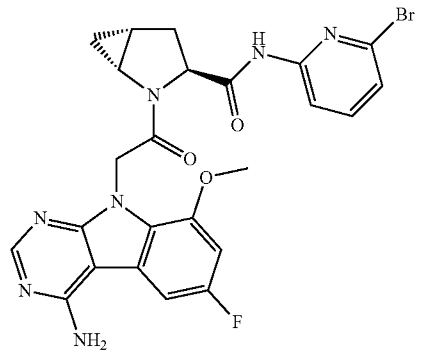 [SMILES: COc1cc(F)cc2c3c(N)ncnc3n(CC(=O)N3[C@@H]4C[C@@H]4C[C@H]3C(=O)Nc3cccc(Br)n3)c12] | 170c | 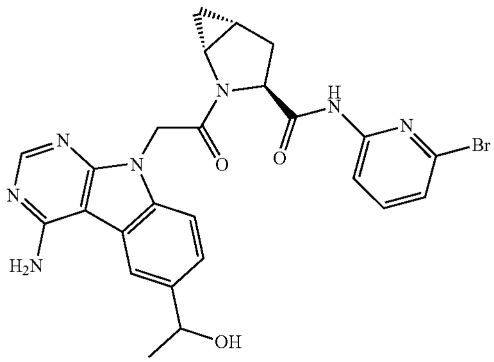 [SMILES: CC(O)c1ccc2c(c1)c1c(N)ncnc1n2CC(=O)N1[C@@H]2C[C@@H]2C[C@H]1C(=O)Nc1cccc(Br)n1] |
| 281a | 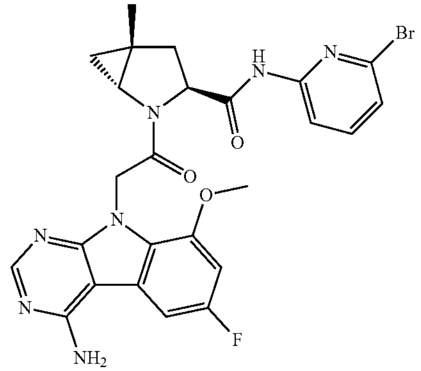 [SMILES: COc1cc(F)cc2c3c(N)ncnc3n(CC(=O)N3[C@H](C(=O)Nc4cccc(Br)n4)C[C@@]4(C)C[C@@H]34)c12] | 179d | 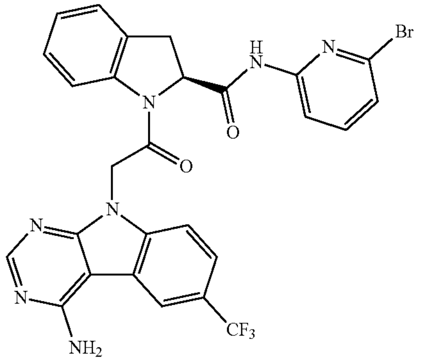 [SMILES: Nc1ncnc2c1c1cc(C(F)(F)F)ccc1n2CC(=O)N1c2ccccc2C[C@H]1C(=O)Nc1cccc(Br)n1] |
| 282a | 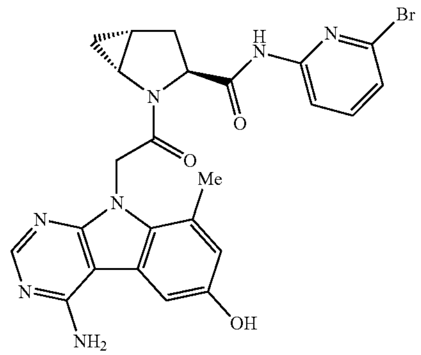 [SMILES: Cc1cc(O)cc2c3c(N)ncnc3n(CC(=O)N3[C@@H]4C[C@@H]4C[C@H]3C(=O)Nc3cccc(Br)n3)c12] | 180e | 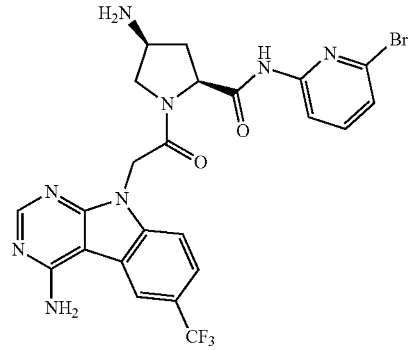 [SMILES: Nc1ncnc2c1c1cc(C(F)(F)F)ccc1n2CC(=O)N1C[C@@H](N)C[C@H]1C(=O)Nc1cccc(Br)n1] |
| 283g | 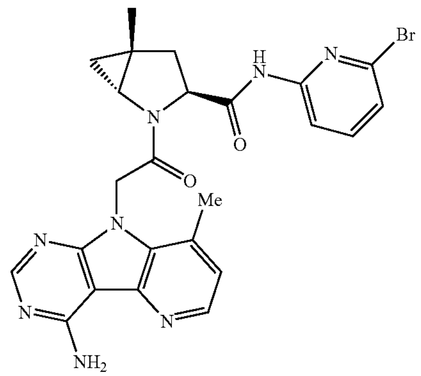 [SMILES: Cc1ccnc2c3c(N)ncnc3n(CC(=O)N3[C@H](C(=O)Nc4cccc(Br)n4)C[C@@]4(C)C[C@@H]34)c12] | 166a | 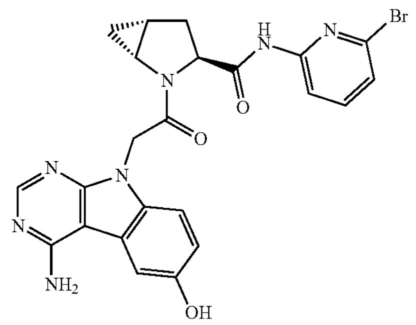 |

-continued
| # | Structure | # | Structure |
|---|---|---|---|
| 292a | 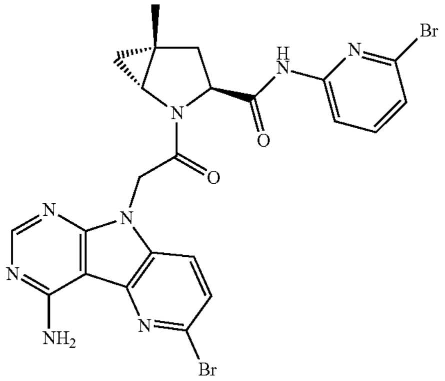 [SMILES: C[C@@]12C[C@@H](C(=O)Nc3cccc(Br)n3)N(C(=O)Cn3c4ccc(Br)nc4c4c(N)ncnc43)[C@@H]1C2] | 167a | 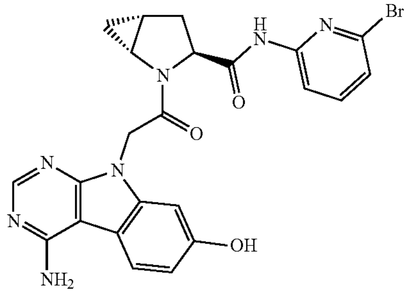 [SMILES: Nc1ncnc2c1c1ccc(O)cc1n2CC(=O)N1[C@@H]2C[C@@H]2C[C@H]1C(=O)Nc1cccc(Br)n1] |
| 297d | 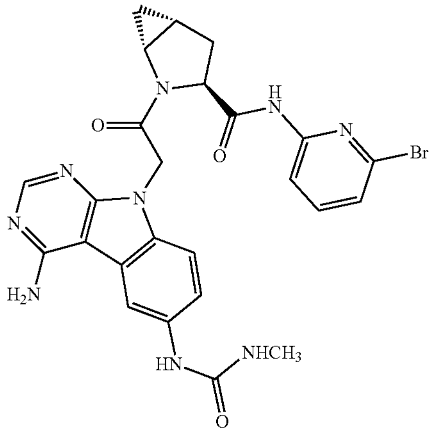 [SMILES: CNC(=O)Nc1ccc2c(c1)c1c(N)ncnc1n2CC(=O)N1[C@@H]2C[C@@H]2C[C@H]1C(=O)Nc1cccc(Br)n1] | 168g | 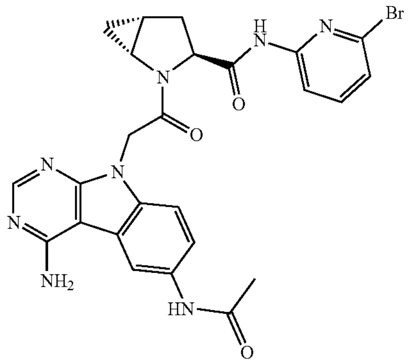 [SMILES: CC(=O)Nc1ccc2c(c1)c1c(N)ncnc1n2CC(=O)N1[C@@H]2C[C@@H]2C[C@H]1C(=O)Nc1cccc(Br)n1] |
| 299a | 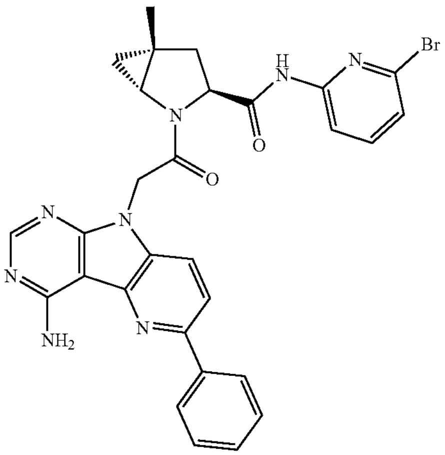 [SMILES: C[C@@]12C[C@@H](C(=O)Nc3cccc(Br)n3)N(C(=O)Cn3c4ccc(-c5ccccc5)nc4c4c(N)ncnc43)[C@@H]1C2] | 187c | 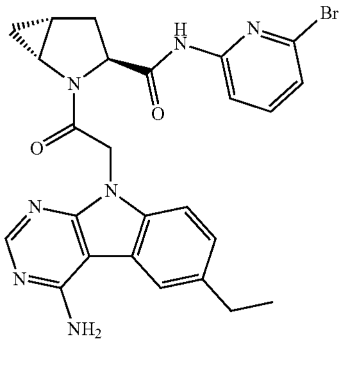 [SMILES: CCc1ccc2c(c1)c1c(N)ncnc1n2CC(=O)N1[C@@H]2C[C@@H]2C[C@H]1C(=O)Nc1cccc(Br)n1] |

-continued
| # | Structure | # | Structure |
| --- | --- | --- | --- |
| 301a | 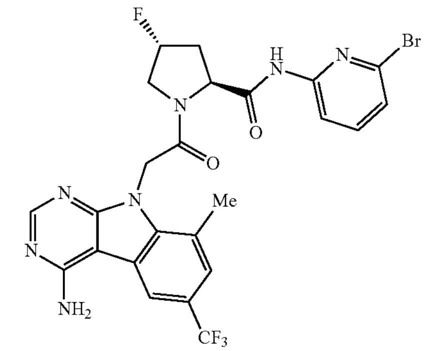 [SMILES: Cc1cc(C(F)(F)F)cc2c3c(N)ncnc3n(CC(=O)N3C[C@H](F)C[C@H]3C(=O)Nc3cccc(Br)n3)c12] | 188g | 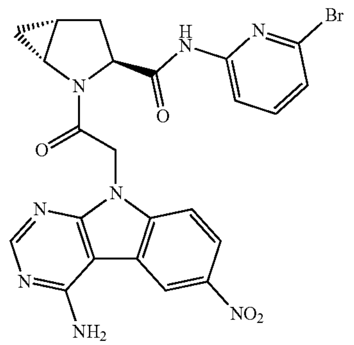 [SMILES: Nc1ncnc2c1c1cc([N+](=O)[O-])ccc1n2CC(=O)N1[C@@H]2C[C@@H]2C[C@H]1C(=O)Nc1cccc(Br)n1] |
| 303a | 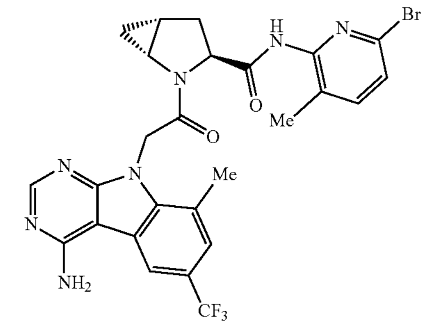 [SMILES: Cc1ccc(Br)nc1NC(=O)[C@@H]1C[C@H]2C[C@H]2N1C(=O)Cn1c2ncnc(N)c2c2cc(C(F)(F)F)cc(C)c21] | 195e | 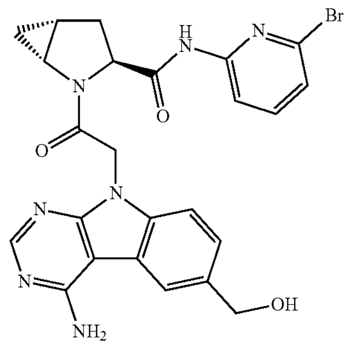 [SMILES: Nc1ncnc2c1c1cc(CO)ccc1n2CC(=O)N1[C@@H]2C[C@@H]2C[C@H]1C(=O)Nc1cccc(Br)n1] |
| 304a | 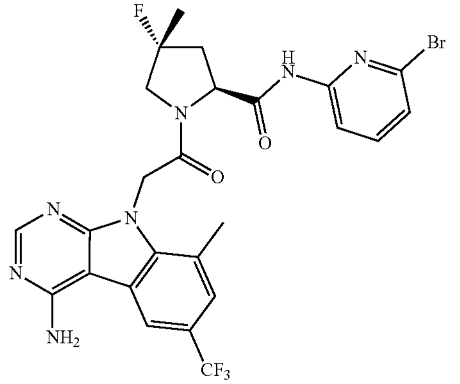 | 198a | 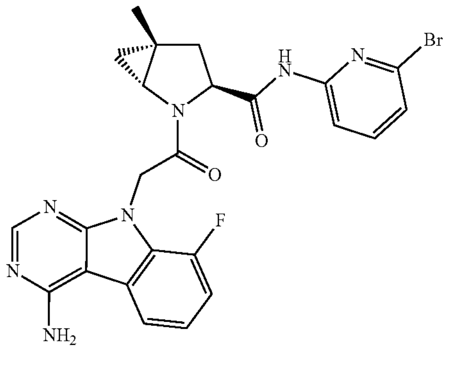 [SMILES: C[C@@]12C[C@@H](C(=O)Nc3cccc(Br)n3)N(C(=O)Cn3c4ncnc(N)c4c4cccc(F)c43)[C@@H]1C2] |
| 308c | 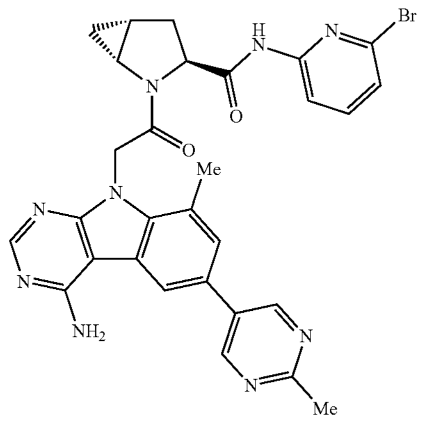 [SMILES: Cc1ncc(-c2cc(C)c3c(c2)c2c(N)ncnc2n3CC(=O)N2[C@@H]3C[C@@H]3C[C@H]2C(=O)Nc2cccc(Br)n2)cn1] | 199a | 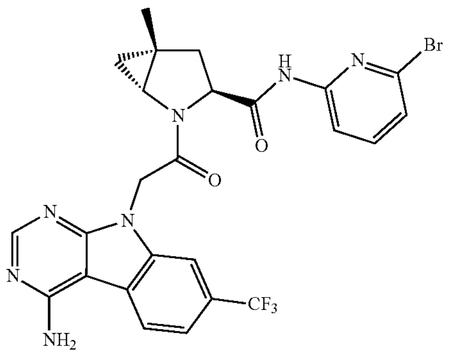 [SMILES: C[C@@]12C[C@@H](C(=O)Nc3cccc(Br)n3)N(C(=O)Cn3c4cc(C(F)(F)F)ccc4c4c(N)ncnc43)[C@@H]1C2] |

-continued
| # | Structure | # | Structure |
|---|---|---|---|
| 310a | 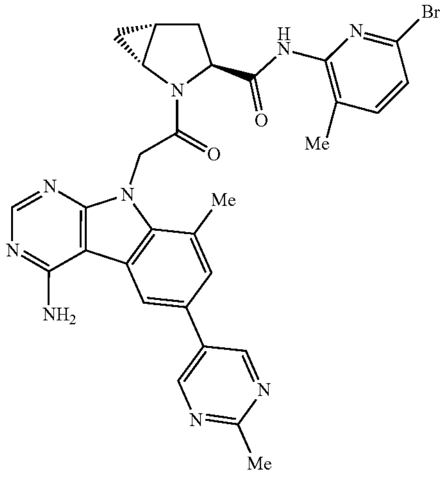 [SMILES: Cc1ncc(-c2cc(C)c3c(c2)c2c(N)ncnc2n3CC(=O)N2[C@@H]3C[C@@H]3C[C@H]2C(=O)Nc2nc(Br)ccc2C)cn1] | 200a | 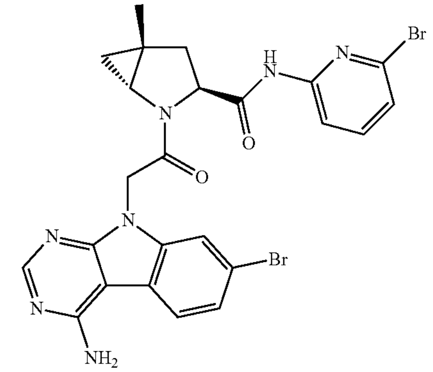 [SMILES: C[C@@]12C[C@@H](C(=O)Nc3cccc(Br)n3)N(C(=O)Cn3c4cc(Br)ccc4c4c(N)ncnc43)[C@@H]1C2] |
| 317c | 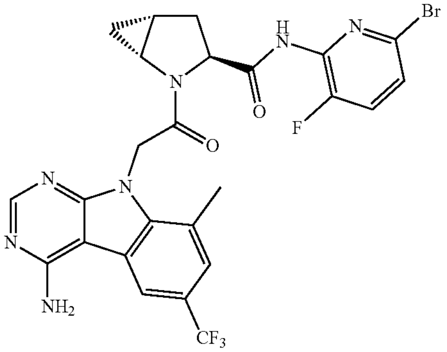 [SMILES: Cc1cc(C(F)(F)F)cc2c3c(N)ncnc3n(CC(=O)N3[C@@H]4C[C@@H]4C[C@H]3C(=O)Nc3nc(Br)ccc3F)c12] | 194a | 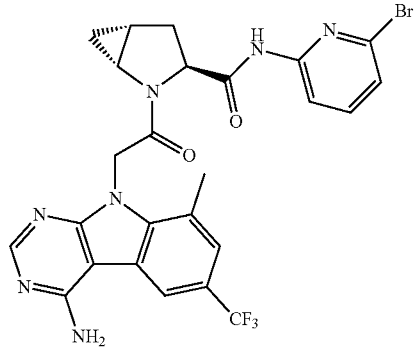 [SMILES: Cc1cc(C(F)(F)F)cc2c3c(N)ncnc3n(CC(=O)N3[C@@H]4C[C@@H]4C[C@H]3C(=O)Nc3cccc(Br)n3)c12] |
| 319c | 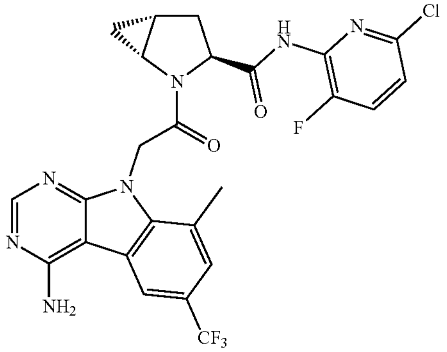 [SMILES: Cc1cc(C(F)(F)F)cc2c3c(N)ncnc3n(CC(=O)N3[C@@H]4C[C@@H]4C[C@H]3C(=O)Nc3nc(Cl)ccc3F)c12] | 201e | 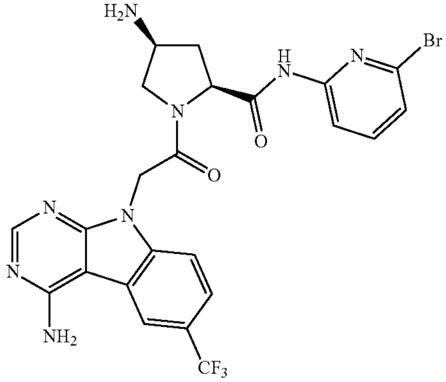 |
| 321d | 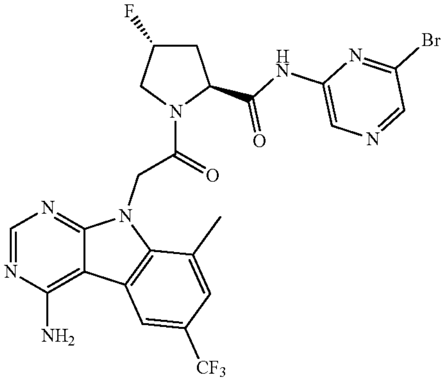 | 211e | 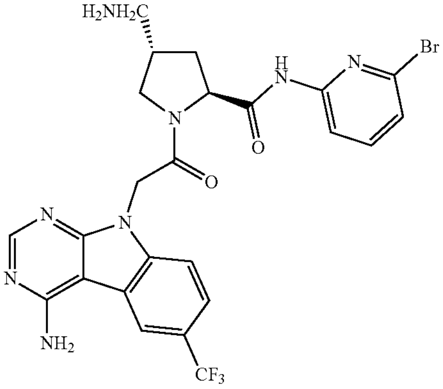 |

-continued
| # | Structure | # | Structure |
|---|---|---|---|
| 334a | 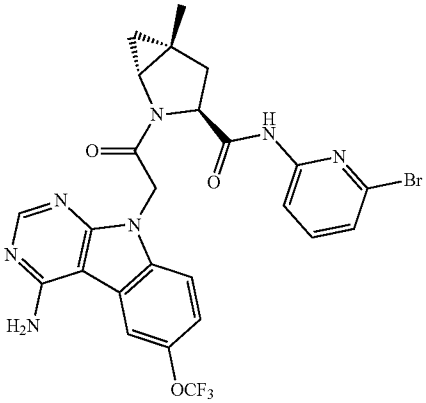 [SMILES: C[C@@]12C[C@@H](C(=O)Nc3cccc(Br)n3)N(C(=O)Cn3c4ccc(OC(F)(F)F)cc4c4c(N)ncnc43)[C@@H]1C2] | 212e | 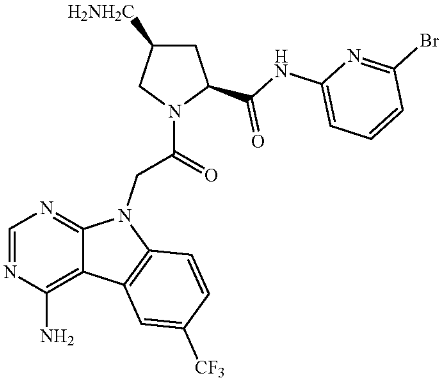 |
| 313b | 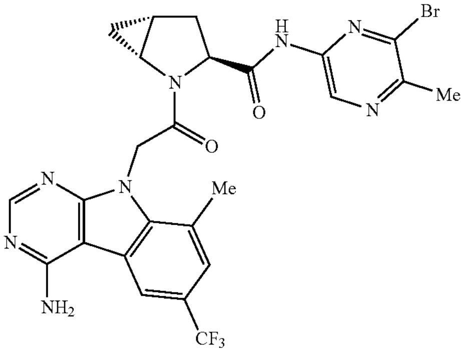 [SMILES: Cc1ncc(NC(=O)[C@@H]2C[C@H]3C[C@H]3N2C(=O)Cn2c3ncnc(N)c3c3cc(C(F)(F)F)cc(C)c32)nc1Br] | 181a | 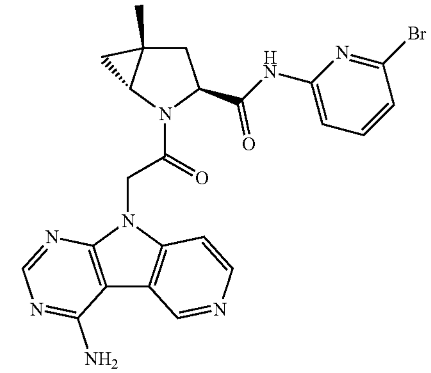 [SMILES: C[C@@]12C[C@@H](C(=O)Nc3cccc(Br)n3)N(C(=O)Cn3c4ccncc4c4c(N)ncnc43)[C@@H]1C2] |
| 312a | 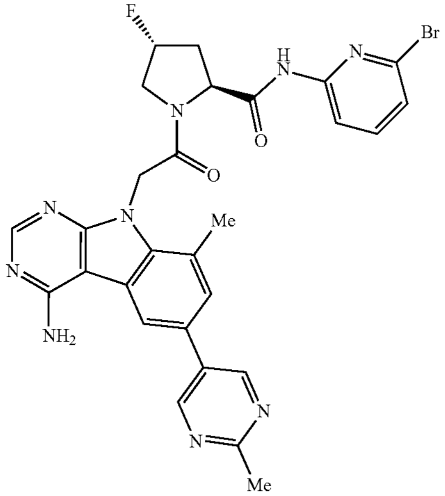 [SMILES: Cc1ncc(-c2cc(C)c3c(c2)c2c(N)ncnc2n3CC(=O)N2C[C@H](F)C[C@H]2C(=O)Nc2cccc(Br)n2)cn1] | 182a | 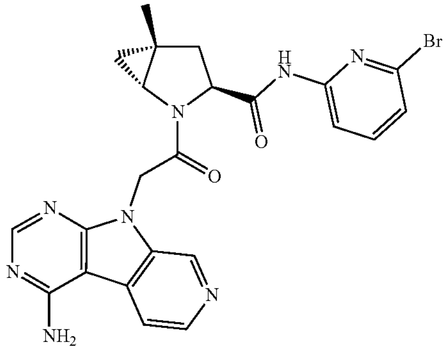 [SMILES: C[C@@]12C[C@@H](C(=O)Nc3cccc(Br)n3)N(C(=O)Cn3c4cnccc4c4c(N)ncnc43)[C@@H]1C2] |

-continued
| # | Structure | # | Structure |
|---|---|---|---|
| 324a | 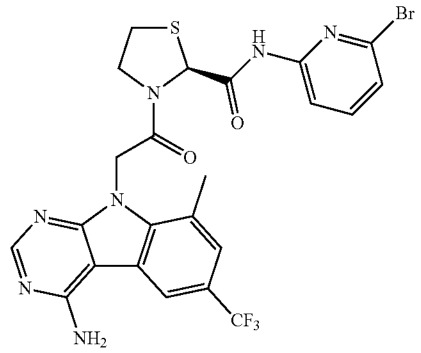 [SMILES: Cc1cc(C(F)(F)F)cc2c3c(N)ncnc3n(CC(=O)N3CCS[C@H]3C(=O)Nc3cccc(Br)n3)c12] | 183a | 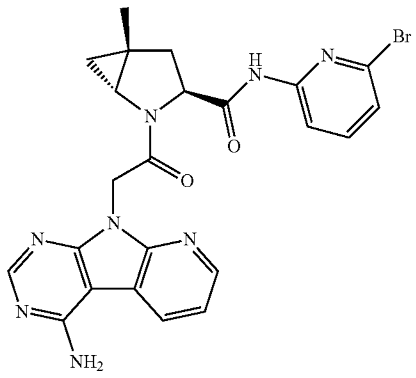 [SMILES: C[C@@]12C[C@@H](C(=O)Nc3cccc(Br)n3)N(C(=O)Cn3c4ncccc4c4c(N)ncnc43)[C@@H]1C2] |
| 325c | 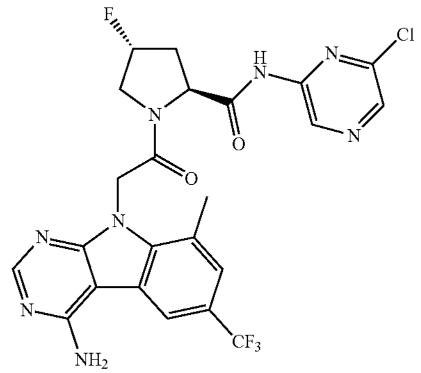 [SMILES: Cc1cc(C(F)(F)F)cc2c3c(N)ncnc3n(CC(=O)N3C[C@H](F)C[C@H]3C(=O)Nc3cncc(Cl)n3)c12] | 207b | 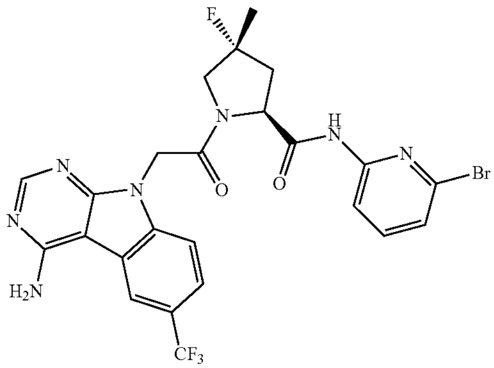 |
| 327c | 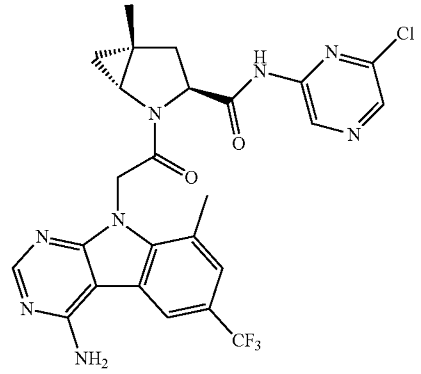 [SMILES: Cc1cc(C(F)(F)F)cc2c3c(N)ncnc3n(CC(=O)N3[C@H](C(=O)Nc4cncc(Cl)n4)C[C@@]4(C)C[C@@H]34)c12] | 208d | 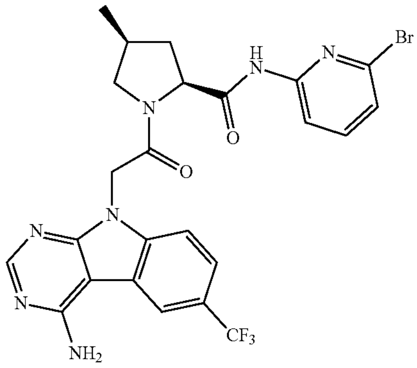 [SMILES: C[C@H]1C[C@@H](C(=O)Nc2cccc(Br)n2)N(C(=O)Cn2c3ccc(C(F)(F)F)cc3c3c(N)ncnc32)C1] |
| 329a | 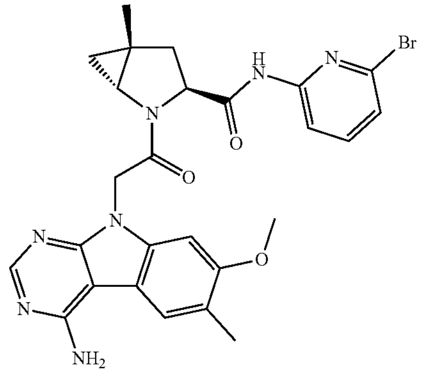 [SMILES: COc1cc2c(cc1C)c1c(N)ncnc1n2CC(=O)N1[C@H](C(=O)Nc2cccc(Br)n2)C[C@@]2(C)C[C@@H]12] | 203a | 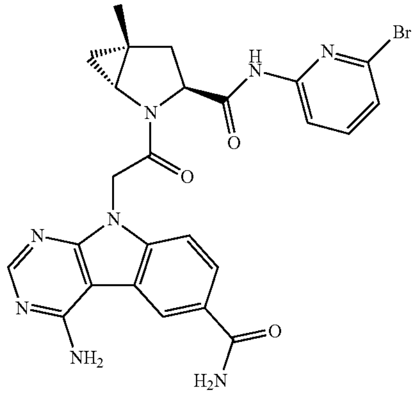 [SMILES: C[C@@]12C[C@@H](C(=O)Nc3cccc(Br)n3)N(C(=O)Cn3c4ccc(C(N)=O)cc4c4c(N)ncnc43)[C@@H]1C2] |

-continued
| # | Structure | # | Structure |
|---|---|---|---|
| 331a | 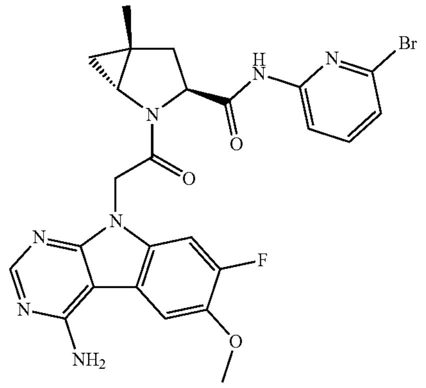 [SMILES: COc1cc2c3c(N)ncnc3n(CC(=O)N3[C@H](C(=O)Nc4cccc(Br)n4)C[C@@]4(C)C[C@@H]34)c2cc1F] | 204a | 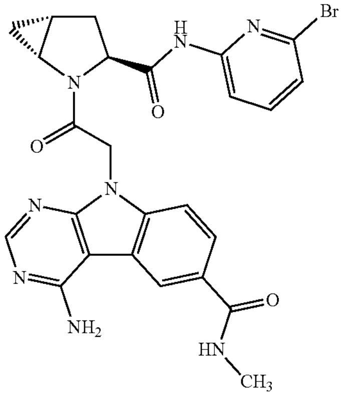 [SMILES: CNC(=O)c1ccc2c(c1)c1c(N)ncnc1n2CC(=O)N1[C@@H]2C[C@@H]2C[C@H]1C(=O)Nc1cccc(Br)n1] |
| 337a | 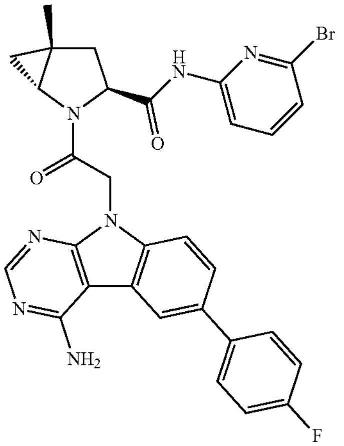 [SMILES: C[C@@]12C[C@@H](C(=O)Nc3cccc(Br)n3)N(C(=O)Cn3c4ccc(-c5ccc(F)cc5)cc4c4c(N)ncnc43)[C@@H]1C2] | 184g | 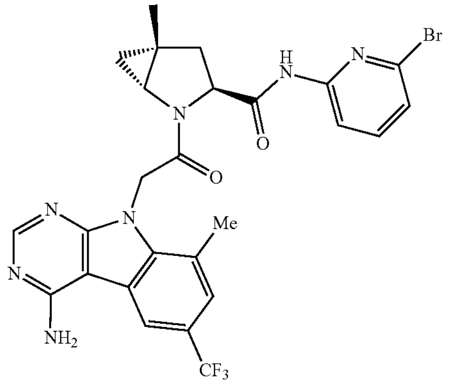 [SMILES: Cc1cc(C(F)(F)F)cc2c3c(N)ncnc3n(CC(=O)N3[C@H](C(=O)Nc4cccc(Br)n4)C[C@@]4(C)C[C@@H]34)c12] |
| 316a | 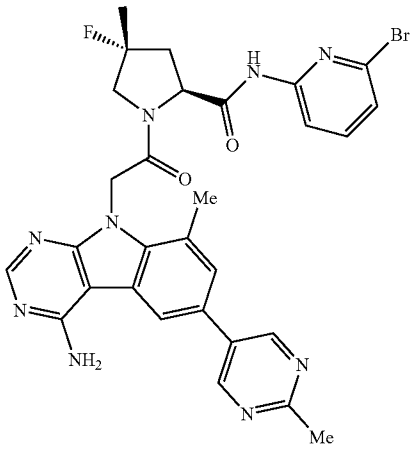 [SMILES: Cc1ncc(-c2cc(C)c3c(c2)c2c(N)ncnc2n3CC(=O)N2C[C@](C)(F)C[C@H]2C(=O)Nc2cccc(Br)n2)cn1] | 185a | 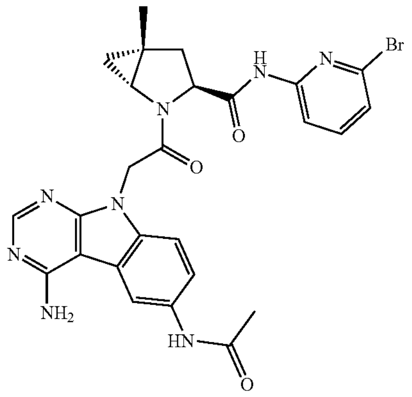 [SMILES: CC(=O)Nc1ccc2c(c1)c1c(N)ncnc1n2CC(=O)N1[C@H](C(=O)Nc2cccc(Br)n2)C[C@@]2(C)C[C@@H]12] |

-continued
| # | Structure | # | Structure |
|---|---|---|---|
| 344c | 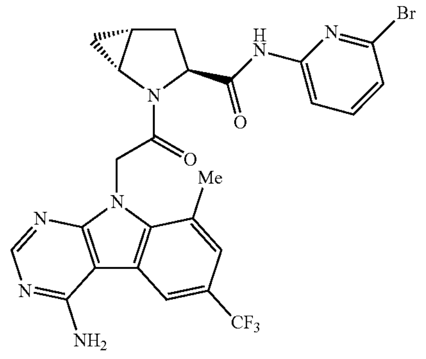 [SMILES: Cc1cc(C(F)(F)F)cc2c3c(N)ncnc3n(CC(=O)N3[C@@H]4C[C@@H]4C[C@H]3C(=O)Nc3cccc(Br)n3)c12] | 186a | 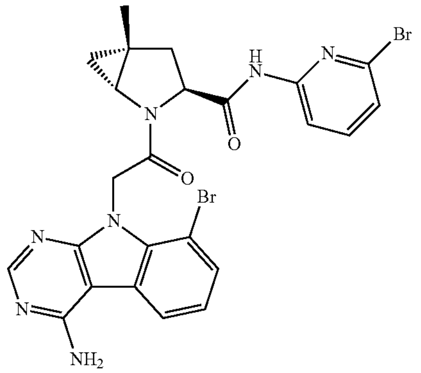 [SMILES: C[C@@]12C[C@@H](C(=O)Nc3cccc(Br)n3)N(C(=O)Cn3c4ncnc(N)c4c4cccc(Br)c43)[C@@H]1C2] |
| 346g | 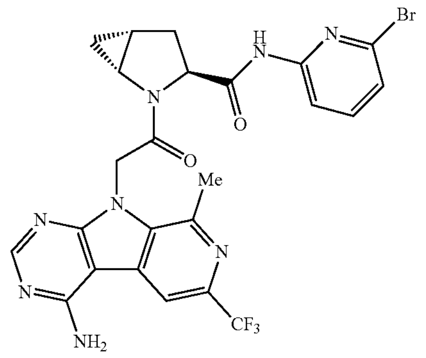 | 206c | 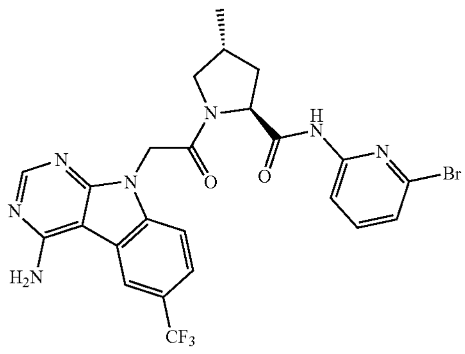 [SMILES: C[C@@H]1C[C@@H](C(=O)Nc2cccc(Br)n2)N(C(=O)Cn2c3ccc(C(F)(F)F)cc3c3c(N)ncnc32)C1] |
| 338e | 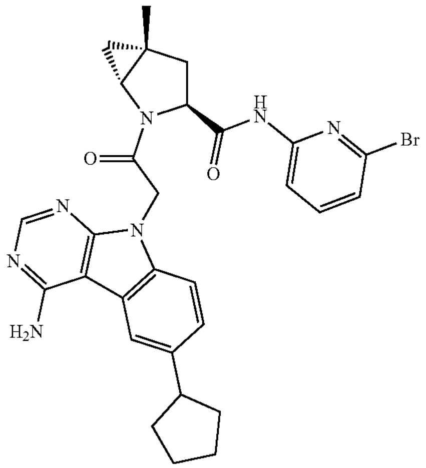 [SMILES: C[C@@]12C[C@@H](C(=O)Nc3cccc(Br)n3)N(C(=O)Cn3c4ccc(C5CCCC5)cc4c4c(N)ncnc43)[C@@H]1C2] | 209b | 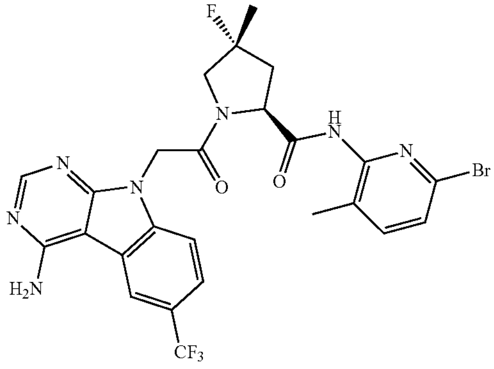 [SMILES: Cc1ccc(Br)nc1NC(=O)[C@@H]1C[C@@](C)(F)CN1C(=O)Cn1c2ccc(C(F)(F)F)cc2c2c(N)ncnc21] |
| 348c | 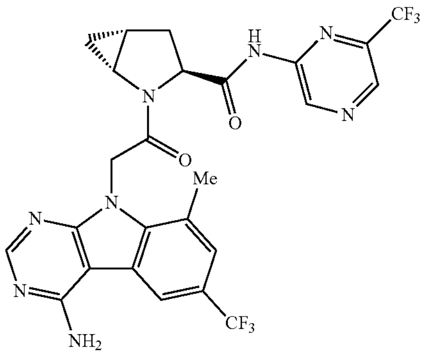 [SMILES: Cc1cc(C(F)(F)F)cc2c3c(N)ncnc3n(CC(=O)N3[C@@H]4C[C@@H]4C[C@H]3C(=O)Nc3cncc(C(F)(F)F)n3)c12] | 210d | 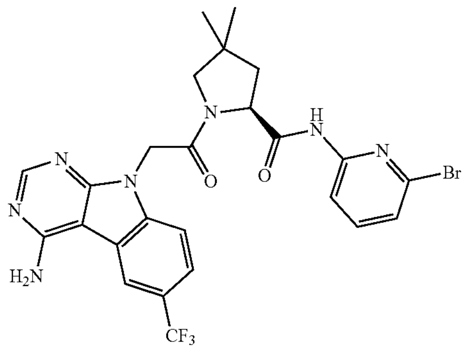 [SMILES: CC1(C)C[C@@H](C(=O)Nc2cccc(Br)n2)N(C(=O)Cn2c3ccc(C(F)(F)F)cc3c3c(N)ncnc32)C1] |

-continued
| # | Structure | # | Structure |
|---|---|---|---|
| 350a | 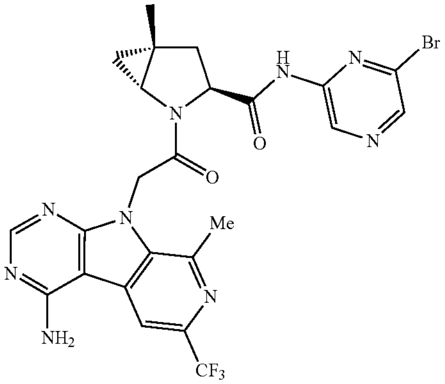 [SMILES: Cc1nc(C(F)(F)F)cc2c3c(N)ncnc3n(CC(=O)N3[C@H](C(=O)Nc4cncc(Br)n4)C[C@@]4(C)C[C@@H]34)c12] | 189g | 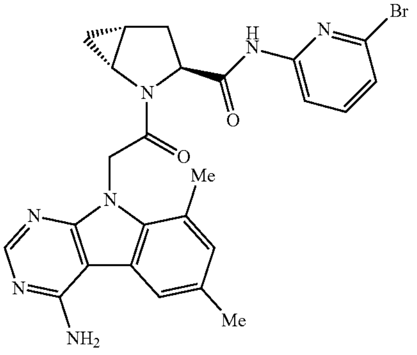 [SMILES: Cc1cc(C)c2c(c1)c1c(N)ncnc1n2CC(=O)N1[C@@H]2C[C@@H]2C[C@H]1C(=O)Nc1cccc(Br)n1] |
| 332c | 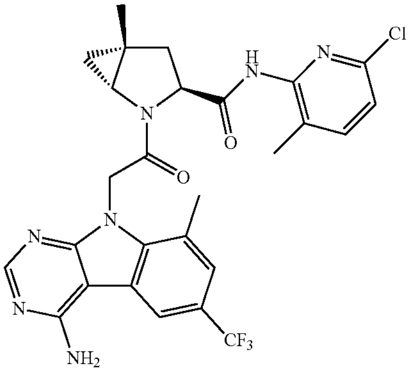 [SMILES: Cc1ccc(Cl)nc1NC(=O)[C@@H]1C[C@@]2(C)C[C@H]2N1C(=O)Cn1c2ncnc(N)c2c2cc(C(F)(F)F)cc(C)c21] | 193a | 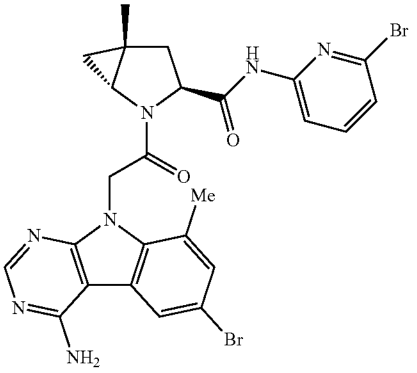 |
| 365c | 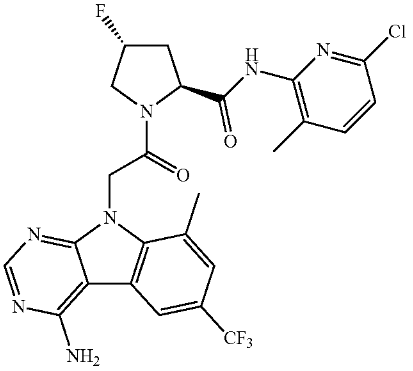 [SMILES: Cc1ccc(Cl)nc1NC(=O)[C@@H]1C[C@@H](F)CN1C(=O)Cn1c2ncnc(N)c2c2cc(C(F)(F)F)cc(C)c21] | 190a | 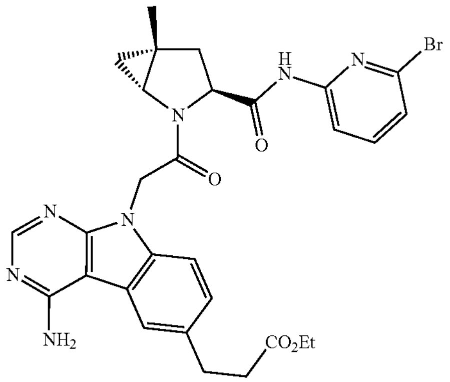 [SMILES: CCOC(=O)CCc1ccc2c(c1)c1c(N)ncnc1n2CC(=O)N1[C@H](C(=O)Nc2cccc(Br)n2)C[C@@]2(C)C[C@@H]12] |
| 352c | 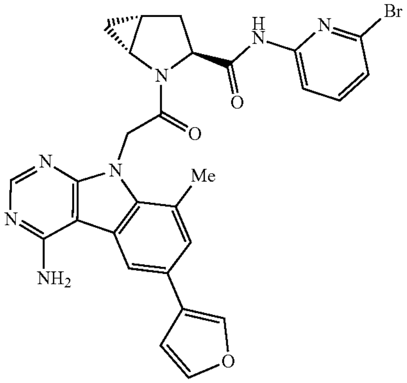 [SMILES: Cc1cc(-c2ccoc2)cc2c3c(N)ncnc3n(CC(=O)N3[C@@H]4C[C@@H]4C[C@H]3C(=O)Nc3cccc(Br)n3)c12] | 191a | 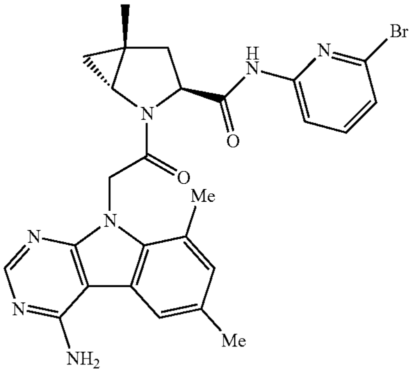 [SMILES: Cc1cc(C)c2c(c1)c1c(N)ncnc1n2CC(=O)N1[C@H](C(=O)Nc2cccc(Br)n2)C[C@@]2(C)C[C@@H]12] |

-continued
| # | Structure | # | Structure |
|---|---|---|---|
| 354c | 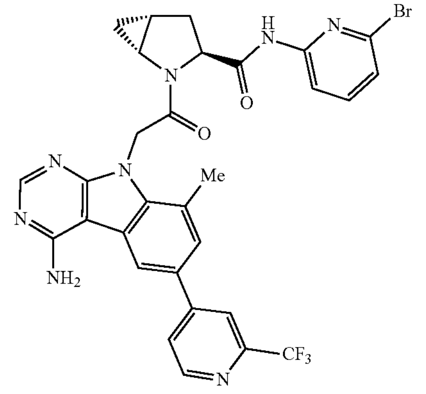 [SMILES: Cc1cc(-c2ccnc(C(F)(F)F)c2)cc2c3c(N)ncnc3n(CC(=O)N3[C@@H]4C[C@@H]4C[C@H]3C(=O)Nc3cccc(Br)n3)c12] | 192g | 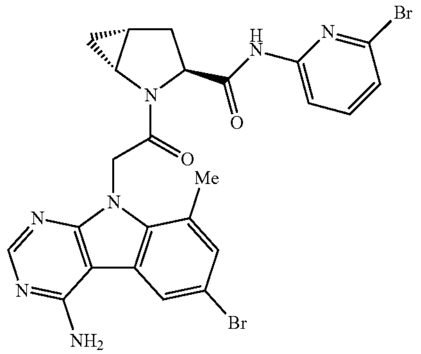 |
| 340a | 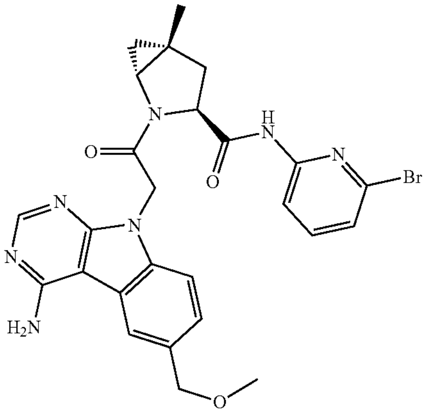 [SMILES: COCc1ccc2c(c1)c1c(N)ncnc1n2CC(=O)N1[C@H](C(=O)Nc2cccc(Br)n2)C[C@@]2(C)C[C@@H]12] | 196d | 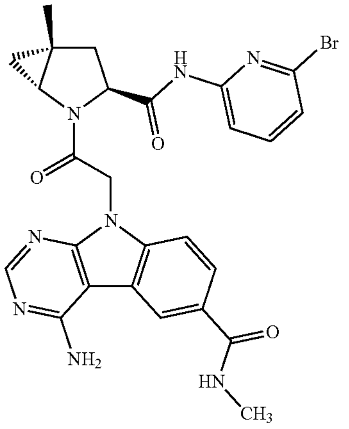 [SMILES: CNC(=O)c1ccc2c(c1)c1c(N)ncnc1n2CC(=O)N1[C@H](C(=O)Nc2cccc(Br)n2)C[C@@]2(C)C[C@@H]12] |
| 342a | 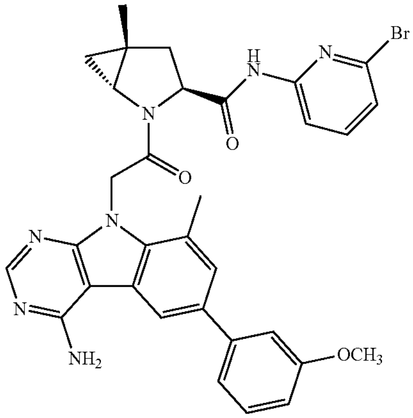 [SMILES: COc1cccc(-c2cc(C)c3c(c2)c2c(N)ncnc2n3CC(=O)N2[C@H](C(=O)Nc3cccc(Br)n3)C[C@@]3(C)C[C@@H]23)c1] | 197c | 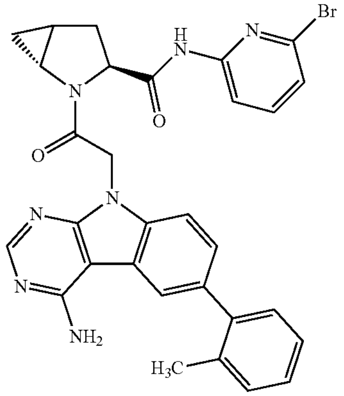 |

-continued
| # | Structure | # | Structure |
|---|---|---|---|
| 357a | 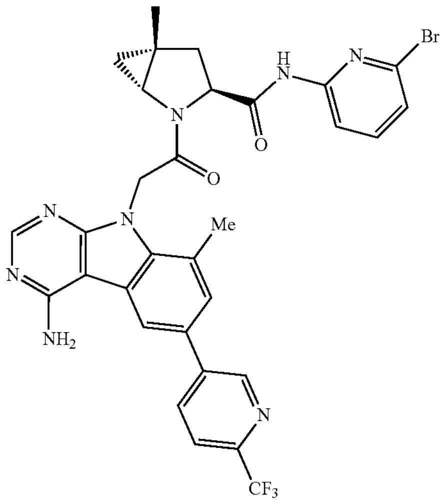 [SMILES: Cc1cc(-c2ccc(C(F)(F)F)nc2)cc2c3c(N)ncnc3n(CC(=O)N3[C@H](C(=O)Nc4cccc(Br)n4)C[C@@]4(C)C[C@@H]34)c12] | 214b | 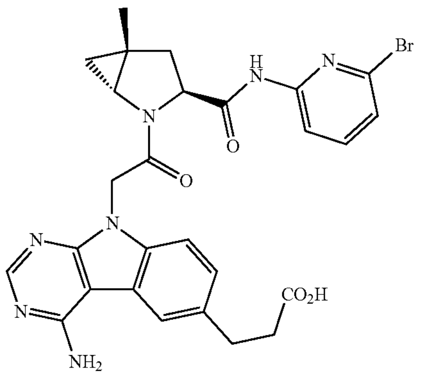 [SMILES: C[C@@]12C[C@@H](C(=O)Nc3cccc(Br)n3)N(C(=O)Cn3c4ccc(CCC(=O)O)cc4c4c(N)ncnc43)[C@@H]1C2] |
| 359c | 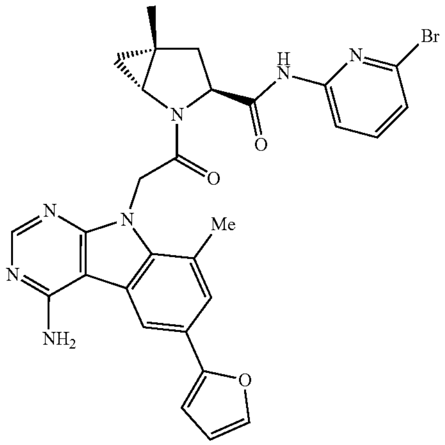 [SMILES: Cc1cc(-c2ccco2)cc2c3c(N)ncnc3n(CC(=O)N3[C@H](C(=O)Nc4cccc(Br)n4)C[C@@]4(C)C[C@@H]34)c12] | 213d | 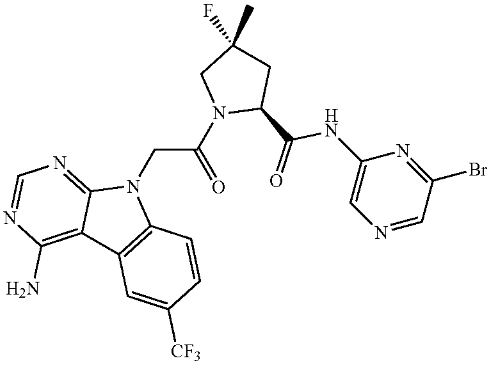 |
| 361a | 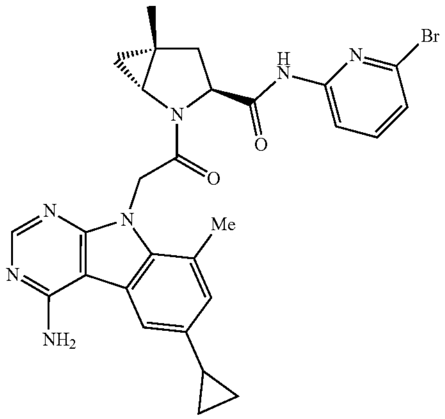 [SMILES: Cc1cc(C2CC2)cc2c3c(N)ncnc3n(CC(=O)N3[C@H](C(=O)Nc4cccc(Br)n4)C[C@@]4(C)C[C@@H]34)c12] | 215g | 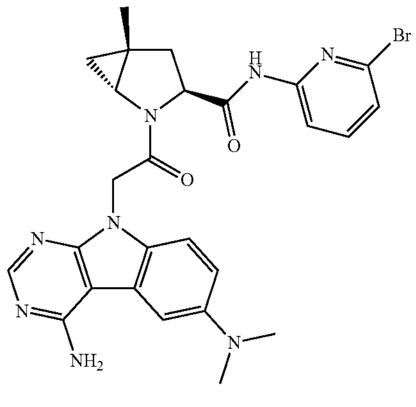 [SMILES: CN(C)c1ccc2c(c1)c1c(N)ncnc1n2CC(=O)N1[C@H](C(=O)Nc2cccc(Br)n2)C[C@@]2(C)C[C@@H]12] |

-continued
| # | Structure | # | Structure |
|---|---|---|---|
| 368a | 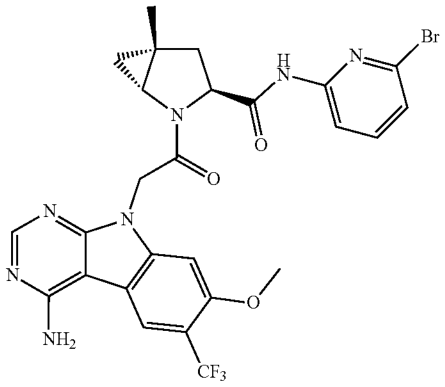 [SMILES: COc1cc2c(cc1C(F)(F)F)c1c(N)ncnc1n2CC(=O)N1[C@H](C(=O)Nc2cccc(Br)n2)C[C@@]2(C)C[C@@H]12] | 216g | 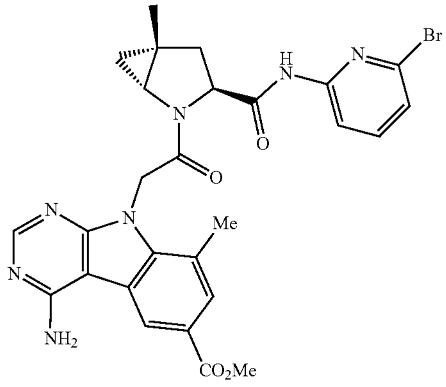 [SMILES: COC(=O)c1cc(C)c2c(c1)c1c(N)ncnc1n2CC(=O)N1[C@H](C(=O)Nc2cccc(Br)n2)C[C@@]2(C)C[C@@H]12] |
| 362f | 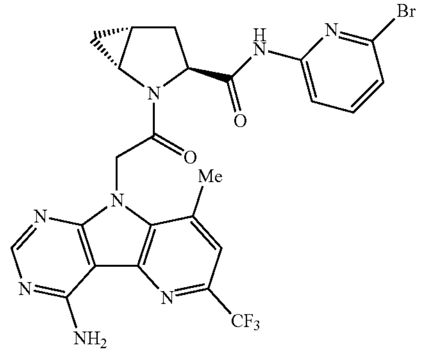 | 217a | 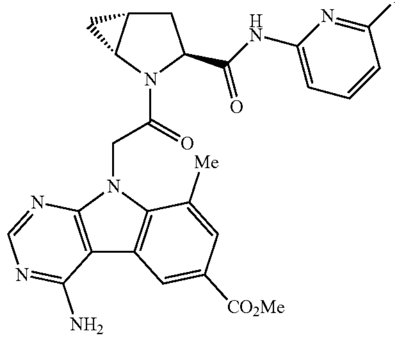 |
| 364e | 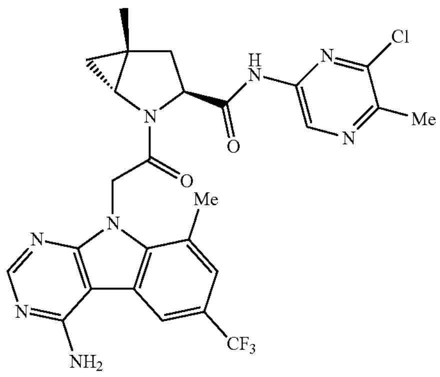 [SMILES: Cc1ncc(NC(=O)[C@@H]2C[C@@]3(C)C[C@H]3N2C(=O)Cn2c3ncnc(N)c3c3cc(C(F)(F)F)cc(C)c32)nc1Cl] | 220a | 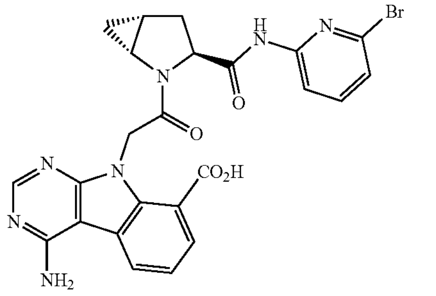 [SMILES: Nc1ncnc2c1c1cccc(C(=O)O)c1n2CC(=O)N1[C@@H]2C[C@@H]2C[C@H]1C(=O)Nc1cccc(Br)n1] |
| 381g | 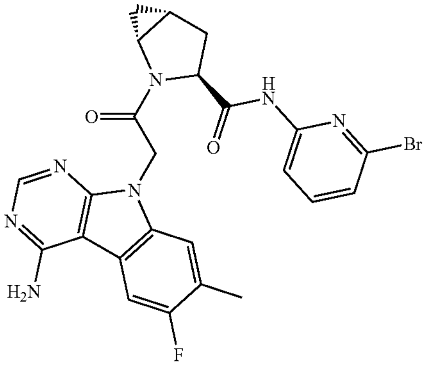 [SMILES: Cc1cc2c(cc1F)c1c(N)ncnc1n2CC(=O)N1[C@@H]2C[C@@H]2C[C@H]1C(=O)Nc1cccc(Br)n1] | 202a | 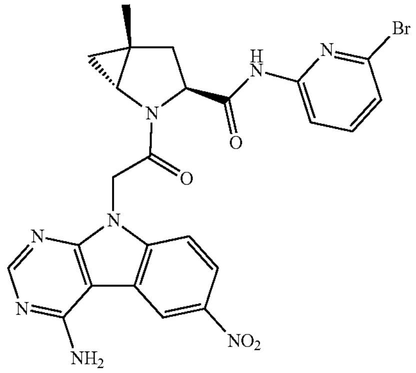 [SMILES: C[C@@]12C[C@@H](C(=O)Nc3cccc(Br)n3)N(C(=O)Cn3c4ccc([N+](=O)[O-])cc4c4c(N)ncnc43)[C@@H]1C2] |

-continued
| # | Structure | # | Structure |
| --- | --- | --- | --- |
| 385a | 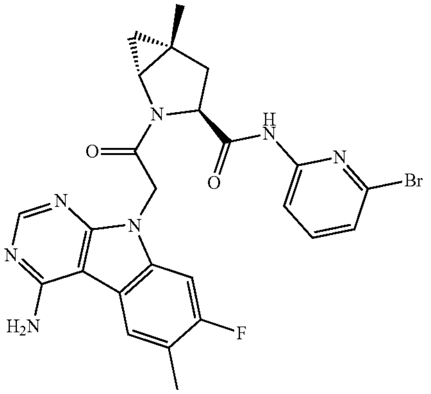 [SMILES: Cc1cc2c3c(N)ncnc3n(CC(=O)N3[C@H](C(=O)Nc4cccc(Br)n4)C[C@@]4(C)C[C@@H]34)c2cc1F] | 205c | 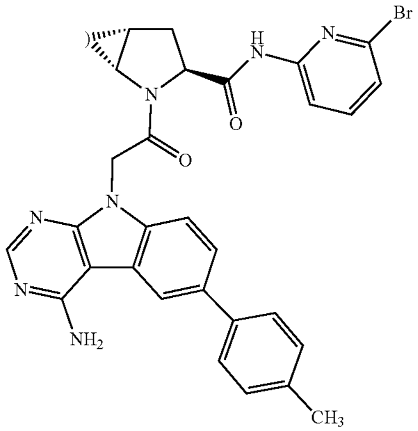 |
| 386g | 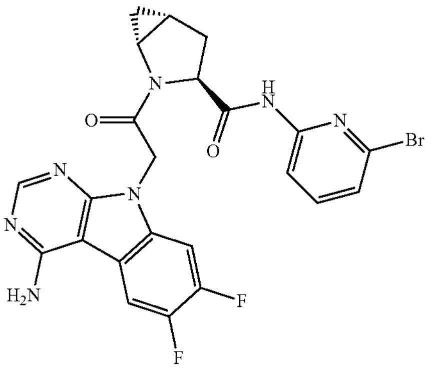 [SMILES: Nc1ncnc2c1c1cc(F)c(F)cc1n2CC(=O)N1[C@@H]2C[C@@H]2C[C@H]1C(=O)Nc1cccc(Br)n1] | 222a | 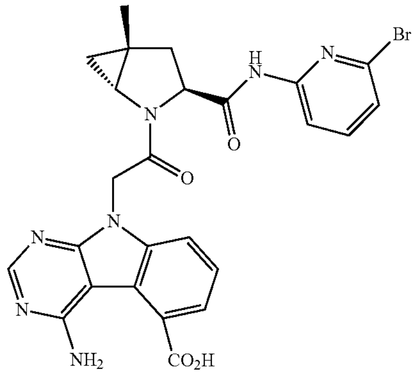 [SMILES: C[C@@]12C[C@@H](C(=O)Nc3cccc(Br)n3)N(C(=O)Cn3c4cccc(C(=O)O)c4c4c(N)ncnc43)[C@@H]1C2] |
| 383g | 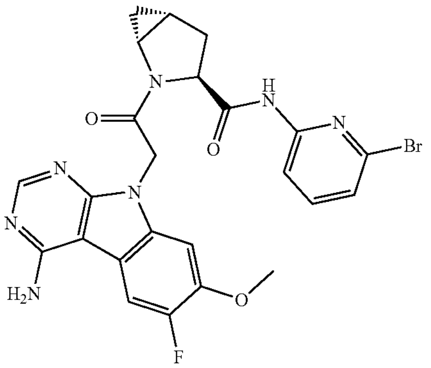 [SMILES: COc1cc2c(cc1F)c1c(N)ncnc1n2CC(=O)N1[C@@H]2C[C@@H]2C[C@H]1C(=O)Nc1cccc(Br)n1] | 236f | 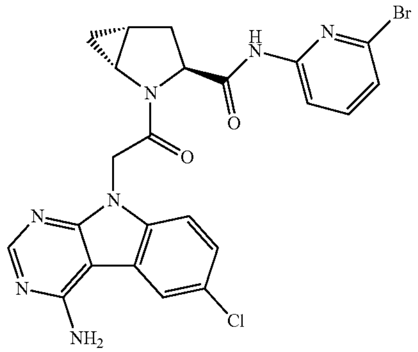 [SMILES: Nc1ncnc2c1c1cc(Cl)ccc1n2CC(=O)N1[C@@H]2C[C@@H]2C[C@H]1C(=O)Nc1cccc(Br)n1] |
| 389g | 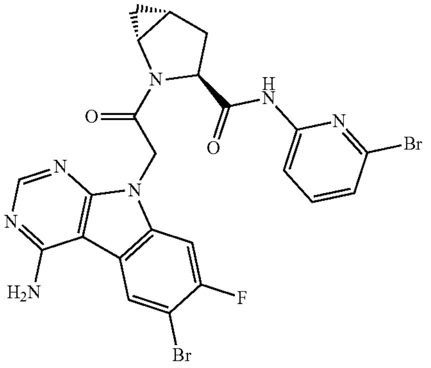 [SMILES: Nc1ncnc2c1c1cc(Br)c(F)cc1n2CC(=O)N1[C@@H]2C[C@@H]2C[C@H]1C(=O)Nc1cccc(Br)n1] | 237a | 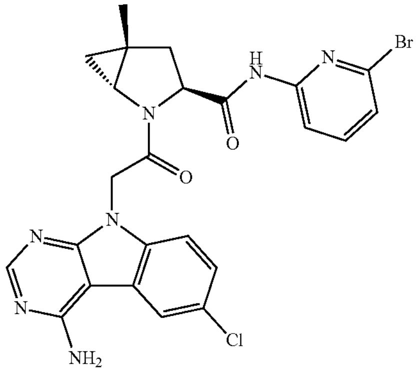 [SMILES: C[C@@]12C[C@@H](C(=O)Nc3cccc(Br)n3)N(C(=O)Cn3c4ccc(Cl)cc4c4c(N)ncnc43)[C@@H]1C2] |

-continued
| # | Structure | # | Structure |
|---|---|---|---|
| 376g | 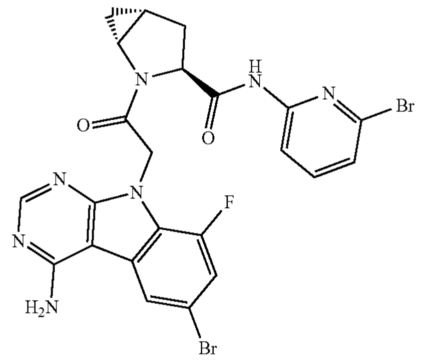 [SMILES: Nc1ncnc2c1c1cc(Br)cc(F)c1n2CC(=O)N1[C@@H]2C[C@@H]2C[C@H]1C(=O)Nc1cccc(Br)n1] | 238g | 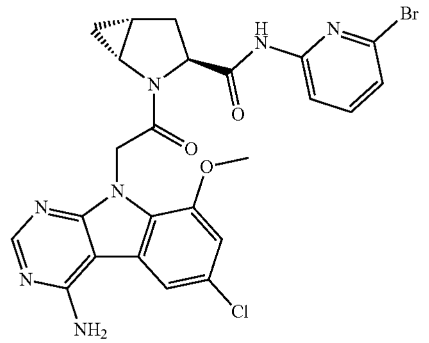 |
| 379h | 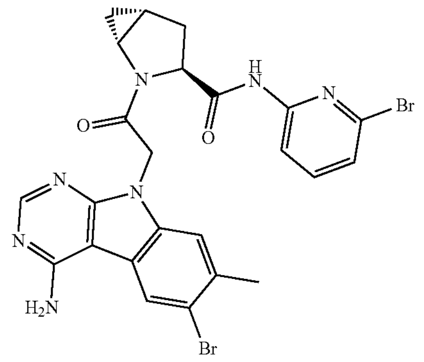 [SMILES: Cc1cc2c(cc1Br)c1c(N)ncnc1n2CC(=O)N1[C@@H]2C[C@@H]2C[C@H]1C(=O)Nc1cccc(Br)n1] | 239a | 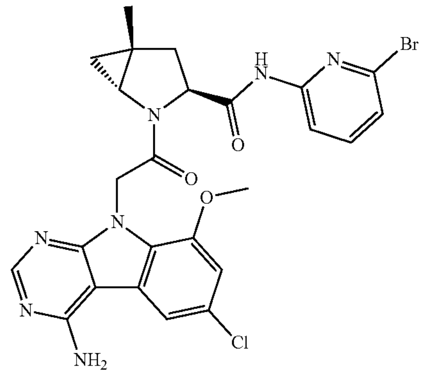 [SMILES: COc1cc(Cl)cc2c3c(N)ncnc3n(CC(=O)N3[C@H](C(=O)Nc4cccc(Br)n4)C[C@@]4(C)C[C@@H]34)c12] |
| 374g | 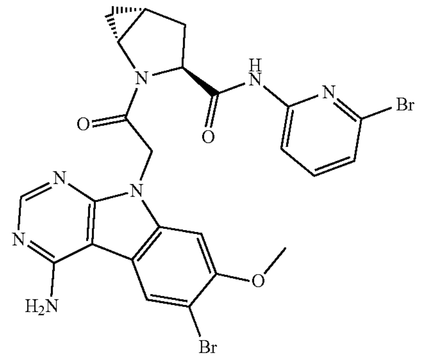 [SMILES: COc1cc2c(cc1Br)c1c(N)ncnc1n2CC(=O)N1[C@@H]2C[C@@H]2C[C@H]1C(=O)Nc1cccc(Br)n1] | 296a | 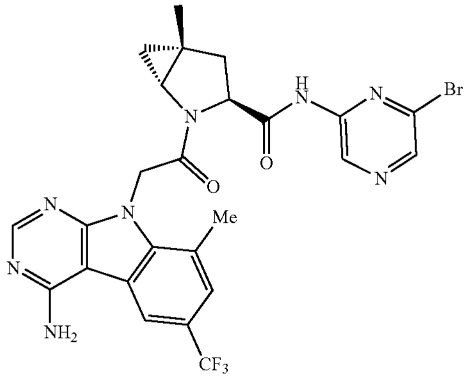 [SMILES: Cc1cc(C(F)(F)F)cc2c3c(N)ncnc3n(CC(=O)N3[C@H](C(=O)Nc4cncc(Br)n4)C[C@@]4(C)C[C@@H]34)c12] |
| 391g | 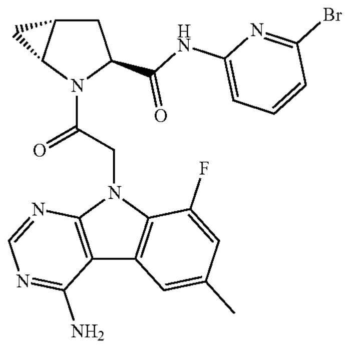 | 240g | 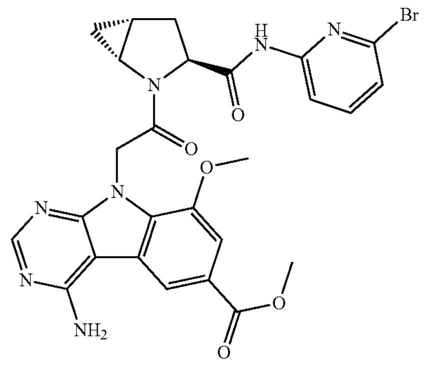 [SMILES: COC(=O)c1cc(OC)c2c(c1)c1c(N)ncnc1n2CC(=O)N1[C@@H]2C[C@@H]2C[C@H]1C(=O)Nc1cccc(Br)n1] |

-continued
| # | Structure | # | Structure |
|---|---|---|---|
| 370a | 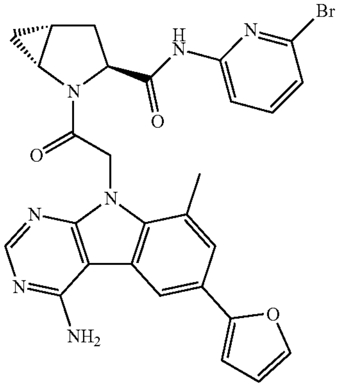 [SMILES: Cc1cc(-c2ccco2)cc2c3c(N)ncnc3n(CC(=O)N3[C@@H]4C[C@@H]4C[C@H]3C(=O)Nc3cccc(Br)n3)c12] | 241g | 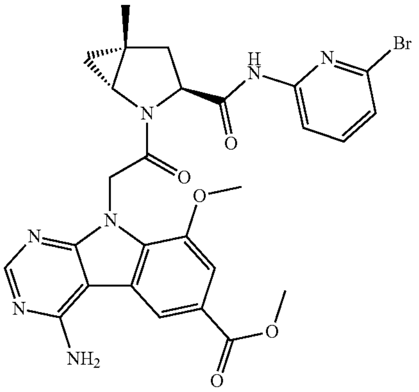 [SMILES: COC(=O)c1cc(OC)c2c(c1)c1c(N)ncnc1n2CC(=O)N1[C@H](C(=O)Nc2cccc(Br)n2)C[C@@]2(C)C[C@@H]12] |
| 371c | 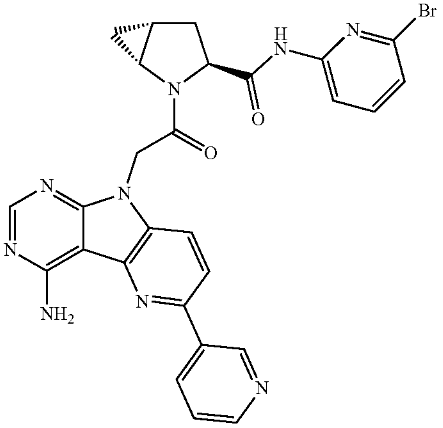 [SMILES: Nc1ncnc2c1c1nc(-c3cccnc3)ccc1n2CC(=O)N1[C@@H]2C[C@@H]2C[C@H]1C(=O)Nc1cccc(Br)n1] | 242a | 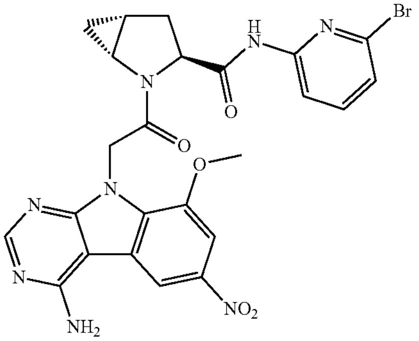 [SMILES: COc1cc([N+](=O)[O-])cc2c3c(N)ncnc3n(CC(=O)N3[C@@H]4C[C@@H]4C[C@H]3C(=O)Nc3cccc(Br)n3)c12] |
| 373a | 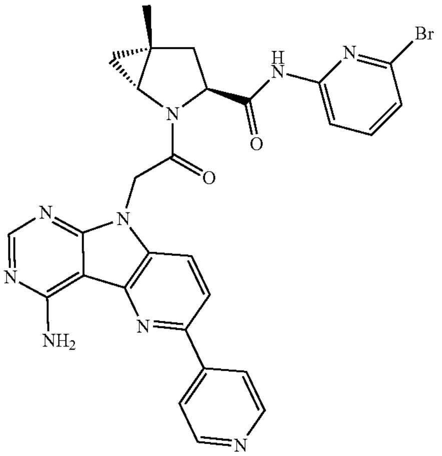 [SMILES: C[C@@]12C[C@@H](C(=O)Nc3cccc(Br)n3)N(C(=O)Cn3c4ccc(-c5ccncc5)nc4c4c(N)ncnc43)[C@@H]1C2] | 243a | 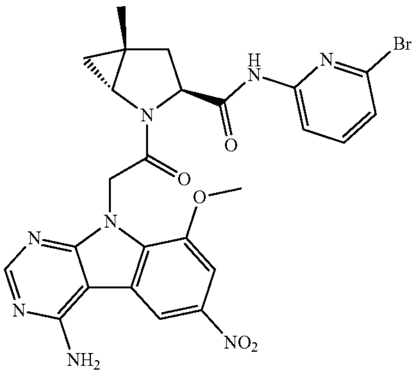 [SMILES: COc1cc([N+](=O)[O-])cc2c3c(N)ncnc3n(CC(=O)N3[C@H](C(=O)Nc4cccc(Br)n4)C[C@@]4(C)C[C@@H]34)c12] |

-continued
| # | Structure | # | Structure |
|---|---|---|---|
| 307c | 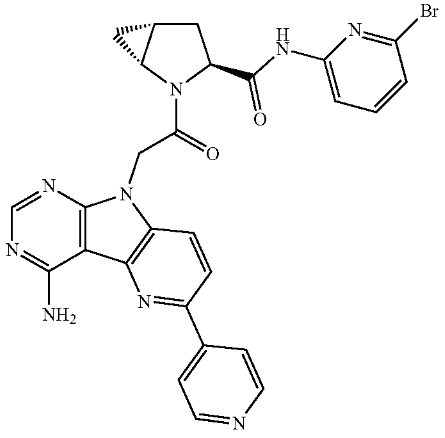 [SMILES: Nc1ncnc2c1c1nc(-c3ccncc3)ccc1n2CC(=O)N1[C@@H]2C[C@@H]2C[C@H]1C(=O)Nc1cccc(Br)n1] | 244d | 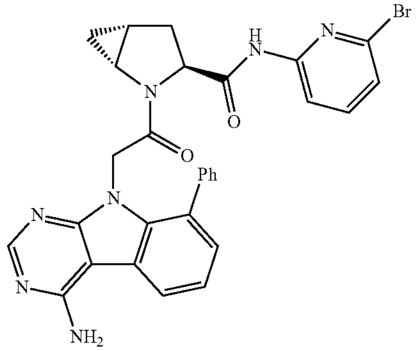 [SMILES: Nc1ncnc2c1c1cccc(-c3ccccc3)c1n2CC(=O)N1[C@@H]2C[C@@H]2C[C@H]1C(=O)Nc1cccc(Br)n1] |
| 305a | 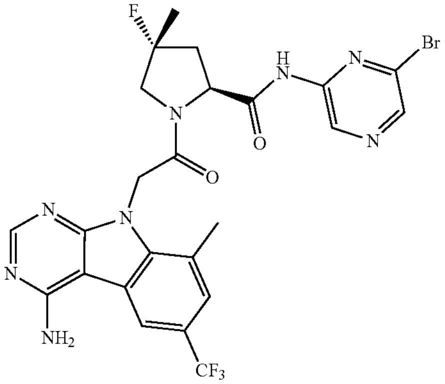 [SMILES: Cc1cc(C(F)(F)F)cc2c3c(N)ncnc3n(CC(=O)N3C[C@](C)(F)C[C@H]3C(=O)Nc3cncc(Br)n3)c12] | 245a | 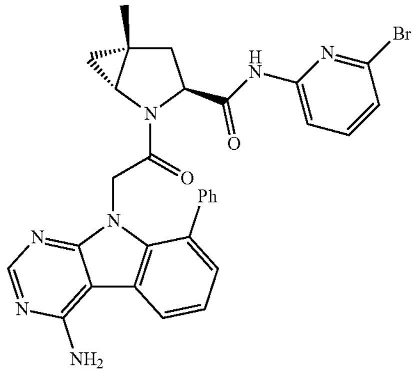 [SMILES: C[C@@]12C[C@@H](C(=O)Nc3cccc(Br)n3)N(C(=O)Cn3c4ncnc(N)c4c4cccc(-c5ccccc5)c43)[C@@H]1C2] |
| 309a | 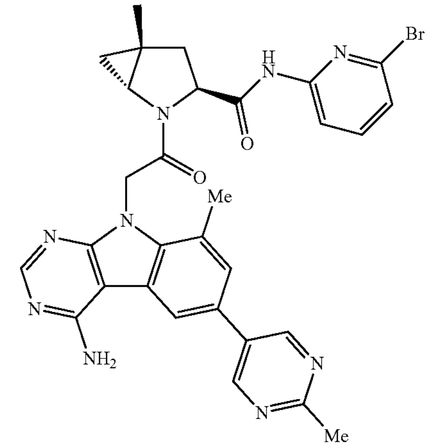 [SMILES: Cc1ncc(-c2cc(C)c3c(c2)c2c(N)ncnc2n3CC(=O)N2[C@H](C(=O)Nc3cccc(Br)n3)C[C@@]3(C)C[C@@H]23)cn1] | 42a | 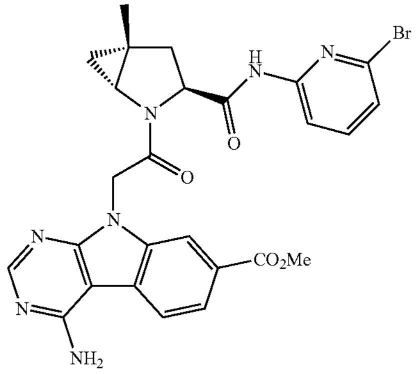 [SMILES: COC(=O)c1ccc2c3c(N)ncnc3n(CC(=O)N3[C@H](C(=O)Nc4cccc(Br)n4)C[C@@]4(C)C[C@@H]34)c2c1] |

-continued
| # | Structure | # | Structure |
|---|---|---|---|
| 311a | 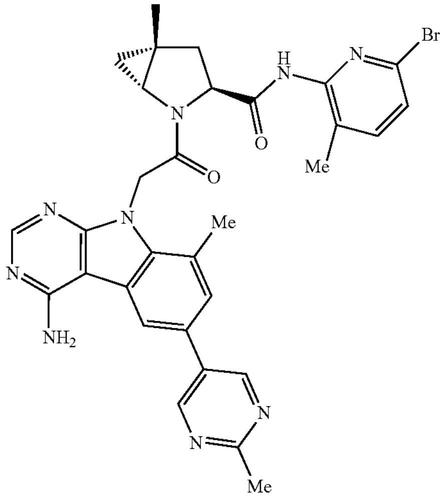 [SMILES: Cc1ncc(-c2cc(C)c3c(c2)c2c(N)ncnc2n3CC(=O)N2[C@H](C(=O)Nc3nc(Br)ccc3C)C[C@@]3(C)C[C@@H]23)cn1] | 16e | 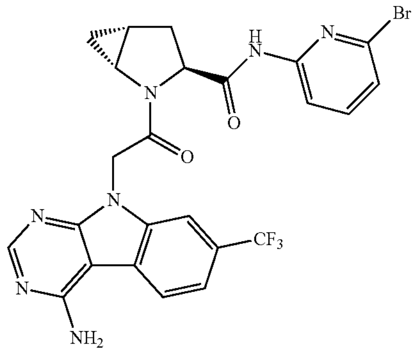 [SMILES: Nc1ncnc2c1c1ccc(C(F)(F)F)cc1n2CC(=O)N1[C@@H]2C[C@@H]2C[C@H]1C(=O)Nc1cccc(Br)n1] |
| 318c | 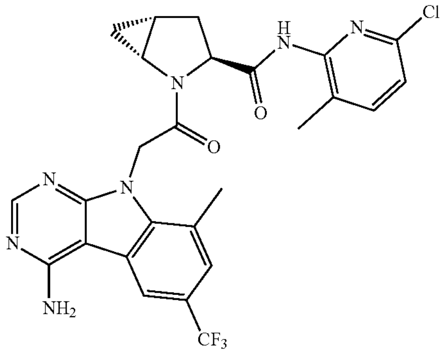 [SMILES: Cc1ccc(Cl)nc1NC(=O)[C@@H]1C[C@H]2C[C@H]2N1C(=O)Cn1c2ncnc(N)c2c2cc(C(F)(F)F)cc(C)c21] | 36e | 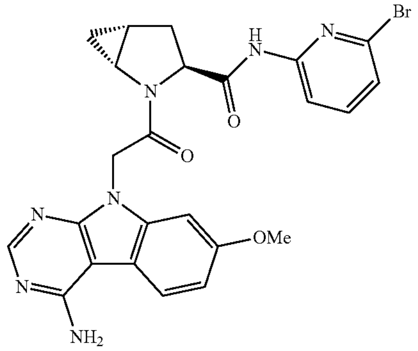 [SMILES: COc1ccc2c3c(N)ncnc3n(CC(=O)N3[C@@H]4C[C@@H]4C[C@H]3C(=O)Nc3cccc(Br)n3)c2c1] |
| 320c | 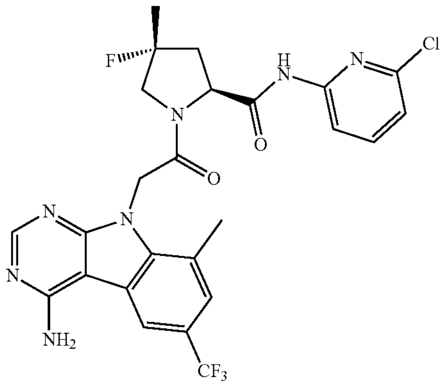 [SMILES: Cc1cc(C(F)(F)F)cc2c3c(N)ncnc3n(CC(=O)N3C[C@](C)(F)C[C@H]3C(=O)Nc3cccc(Cl)n3)c12] | 39f | 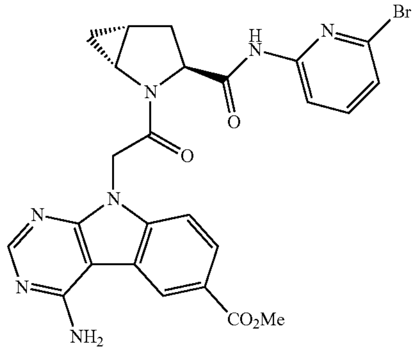 [SMILES: COC(=O)c1ccc2c(c1)c1c(N)ncnc1n2CC(=O)N1[C@@H]2C[C@@H]2C[C@H]1C(=O)Nc1cccc(Br)n1] |
| 322c | 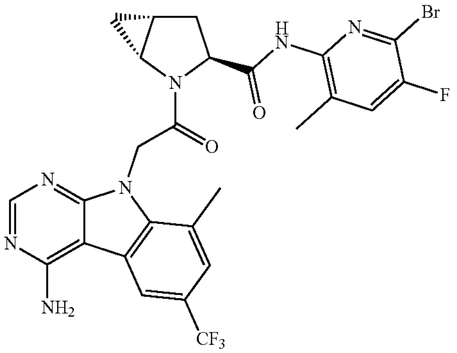 [SMILES: Cc1cc(F)c(Br)nc1NC(=O)[C@@H]1C[C@H]2C[C@H]2N1C(=O)Cn1c2ncnc(N)c2c2cc(C(F)(F)F)cc(C)c21] | 23f | 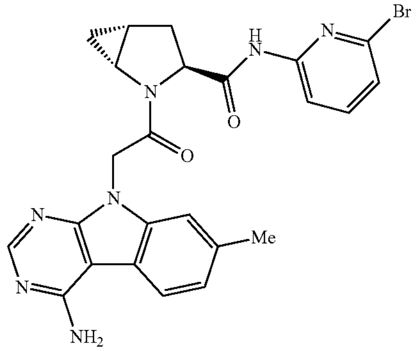 [SMILES: Cc1ccc2c3c(N)ncnc3n(CC(=O)N3[C@@H]4C[C@@H]4C[C@H]3C(=O)Nc3cccc(Br)n3)c2c1] |

-continued
| # | Structure | # | Structure |
|---|---|---|---|
| 335c | 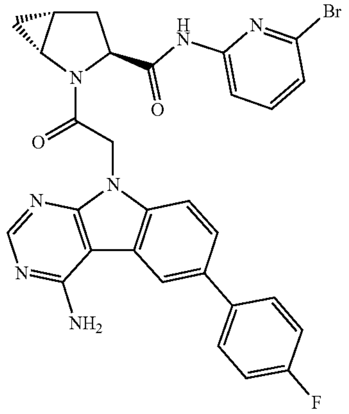 [SMILES: Nc1ncnc2c1c1cc(-c3ccc(F)cc3)ccc1n2CC(=O)N1[C@@H]2C[C@@H]2C[C@H]1C(=O)Nc1cccc(Br)n1] | 40a | 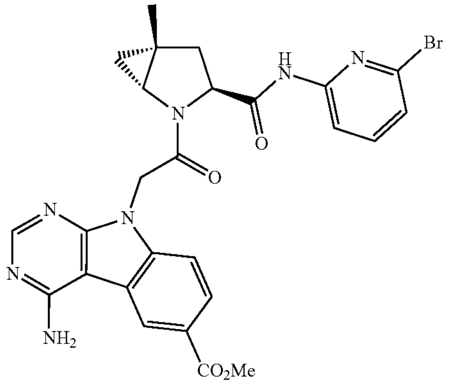 [SMILES: COC(=O)c1ccc2c(c1)c1c(N)ncnc1n2CC(=O)N1[C@H](C(=O)Nc2cccc(Br)n2)C[C@@]2(C)C[C@@H]12] |
| 314a | 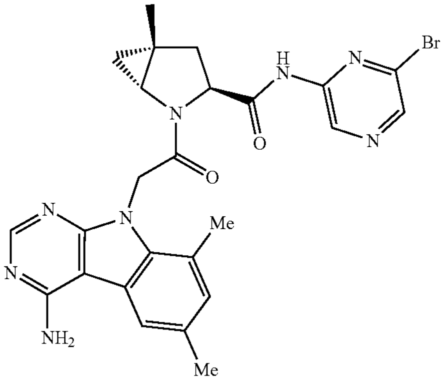 [SMILES: Cc1cc(C)c2c(c1)c1c(N)ncnc1n2CC(=O)N1[C@H](C(=O)Nc2cncc(Br)n2)C[C@@]2(C)C[C@@H]12] | | |
| 323a | 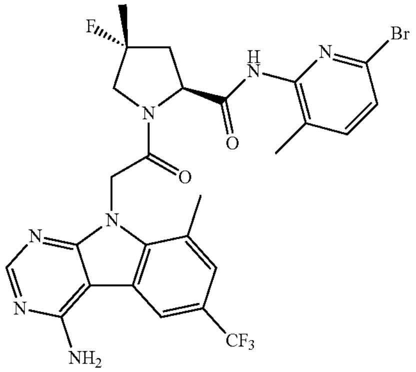 [SMILES: Cc1ccc(Br)nc1NC(=O)[C@@H]1C[C@@](C)(F)CN1C(=O)Cn1c2ncnc(N)c2c2cc(C(F)(F)F)cc(C)c21] | 45d | 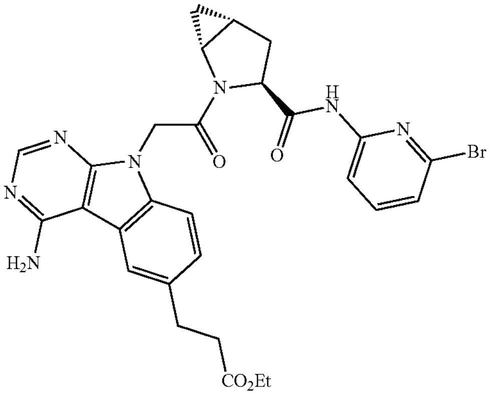 [SMILES: CCOC(=O)CCc1ccc2c(c1)c1c(N)ncnc1n2CC(=O)N1[C@@H]2C[C@@H]2C[C@H]1C(=O)Nc1cccc(Br)n1] |
| 306a | 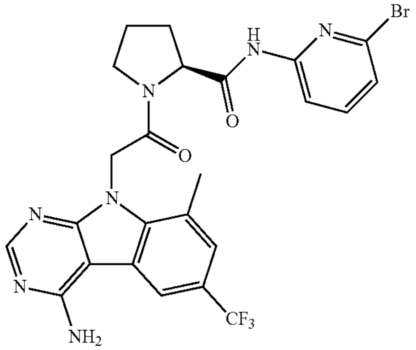 [SMILES: Cc1cc(C(F)(F)F)cc2c3c(N)ncnc3n(CC(=O)N3CCC[C@H]3C(=O)Nc3cccc(Br)n3)c12] | 41f | 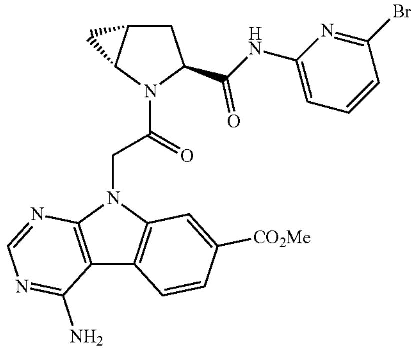 [SMILES: COC(=O)c1ccc2c3c(N)ncnc3n(CC(=O)N3[C@@H]4C[C@@H]4C[C@H]3C(=O)Nc3cccc(Br)n3)c2c1] |

-continued
| # | Structure | # | Structure |
|---|---|---|---|
| 326c | 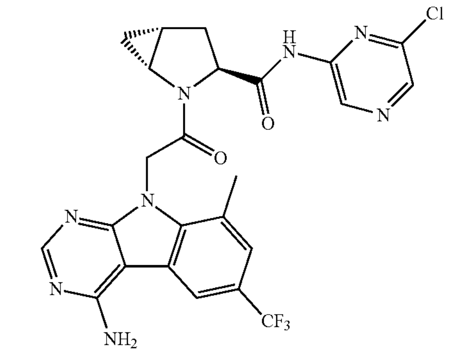 [SMILES: Cc1cc(C(F)(F)F)cc2c3c(N)ncnc3n(CC(=O)N3[C@@H]4C[C@@H]4C[C@H]3C(=O)Nc3cncc(Cl)n3)c12] | 221c | 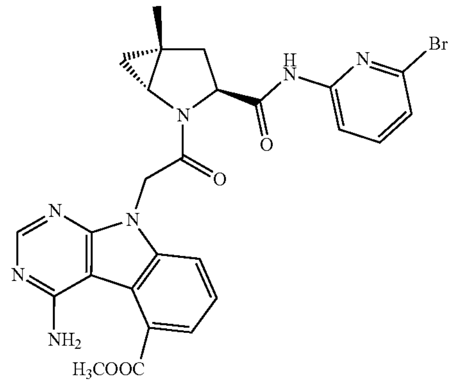 |
| 328f | 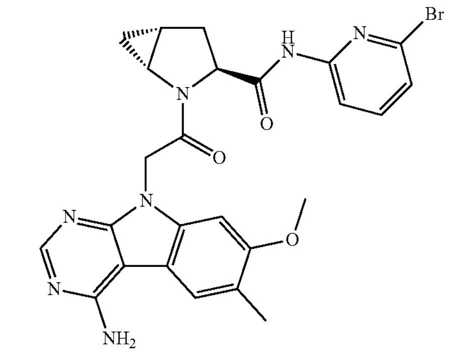 [SMILES: COc1cc2c(cc1C)c1c(N)ncnc1n2CC(=O)N1[C@@H]2C[C@@H]2C[C@H]1C(=O)Nc1cccc(Br)n1] | 250b | 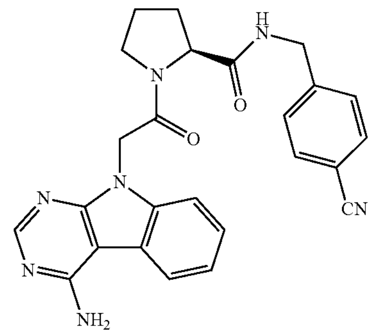 [SMILES: N#Cc1ccc(CNC(=O)[C@@H]2CCCN2C(=O)Cn2c3ccccc3c3c(N)ncnc32)cc1] |
| 330f | 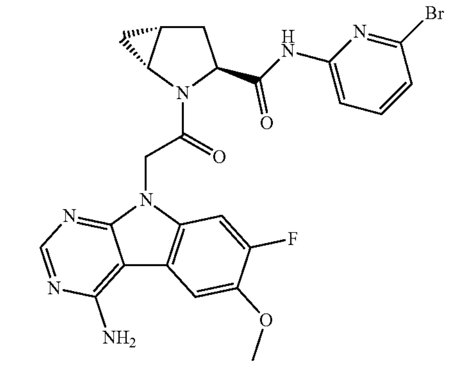 [SMILES: COc1cc2c3c(N)ncnc3n(CC(=O)N3[C@@H]4C[C@@H]4C[C@H]3C(=O)Nc3cccc(Br)n3)c2cc1F] | 270a | 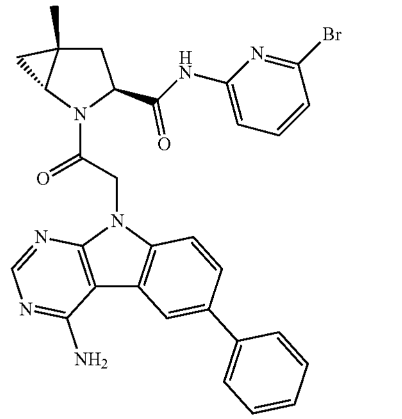 [SMILES: C[C@@]12C[C@@H](C(=O)Nc3cccc(Br)n3)N(C(=O)Cn3c4ccc(-c5ccccc5)cc4c4c(N)ncnc43)[C@@H]1C2] |
| 336c | 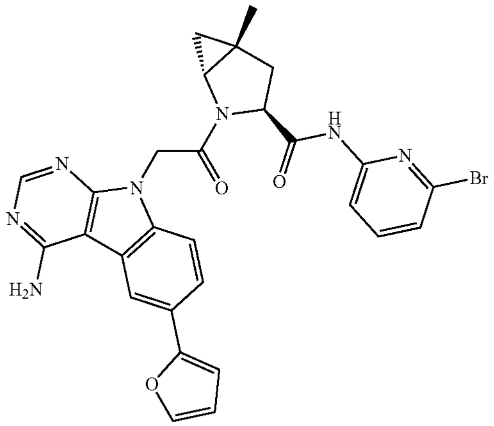 [SMILES: C[C@@]12C[C@@H](C(=O)Nc3cccc(Br)n3)N(C(=O)Cn3c4ccc(-c5ccco5)cc4c4c(N)ncnc43)[C@@H]1C2] | 271c | 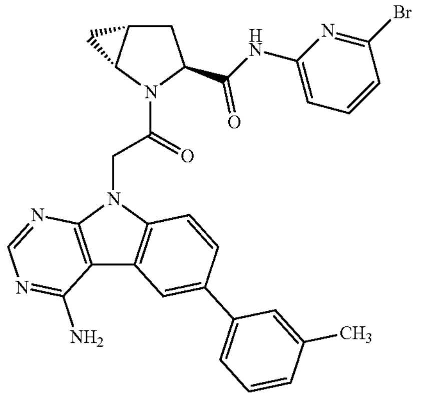 [SMILES: Cc1cccc(-c2ccc3c(c2)c2c(N)ncnc2n3CC(=O)N2[C@@H]3C[C@@H]3C[C@H]2C(=O)Nc2cccc(Br)n2)c1] |

-continued
| # | Structure | # | Structure |
|---|---|---|---|
| 315a | 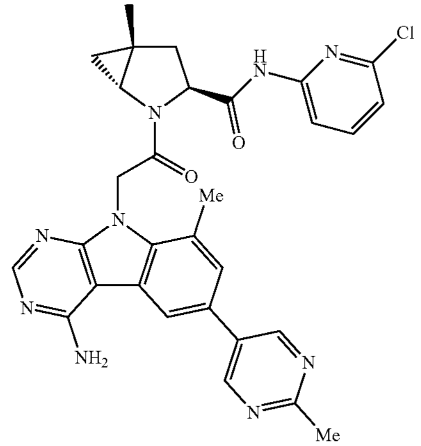 [SMILES: Cc1ncc(-c2cc(C)c3c(c2)c2c(N)ncnc2n3CC(=O)N2[C@H](C(=O)Nc3cccc(Cl)n3)C[C@@]3(C)C[C@@H]23)cn1] | 249a | 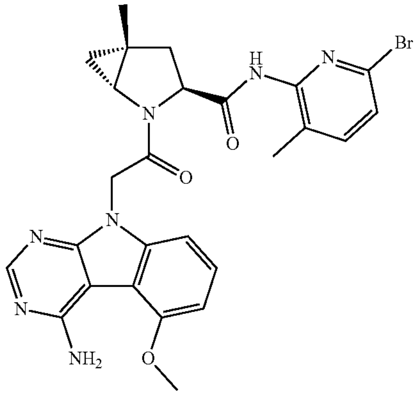 [SMILES: COc1cccc2c1c1c(N)ncnc1n2CC(=O)N1[C@H](C(=O)Nc2nc(Br)ccc2C)C[C@@]2(C)C[C@@H]12] |
| 343a | 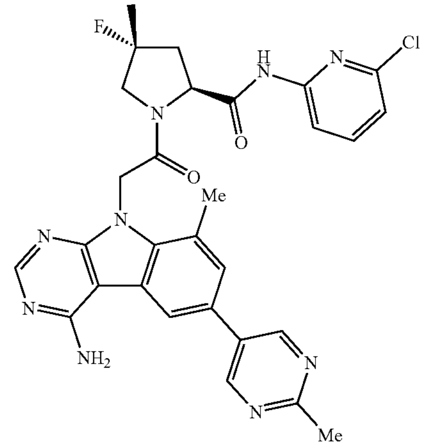 [SMILES: Cc1ncc(-c2cc(C)c3c(c2)c2c(N)ncnc2n3CC(=O)N2C[C@](C)(F)C[C@H]2C(=O)Nc2cccc(Cl)n2)cn1] | 252a | 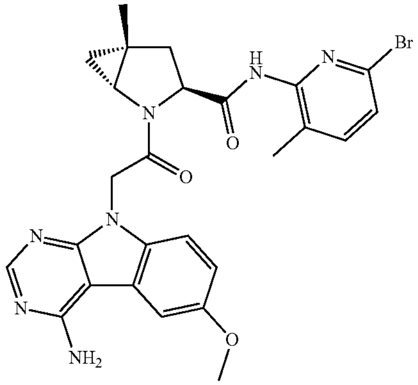 [SMILES: COc1ccc2c(c1)c1c(N)ncnc1n2CC(=O)N1[C@H](C(=O)Nc2nc(Br)ccc2C)C[C@@]2(C)C[C@@H]12] |
| 345c | 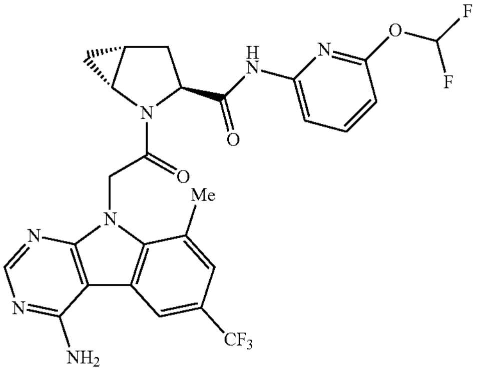 [SMILES: Cc1cc(C(F)(F)F)cc2c3c(N)ncnc3n(CC(=O)N3[C@@H]4C[C@@H]4C[C@H]3C(=O)Nc3cccc(OC(F)F)n3)c12] | 253a | 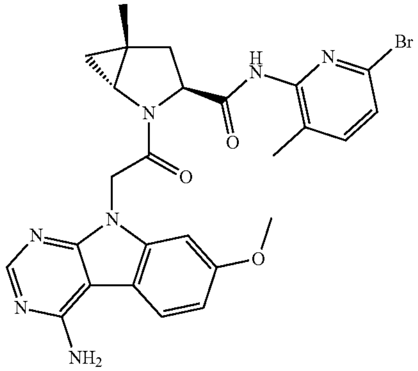 [SMILES: COc1ccc2c3c(N)ncnc3n(CC(=O)N3[C@H](C(=O)Nc4nc(Br)ccc4C)C[C@@]4(C)C[C@@H]34)c2c1] |

-continued
| # | Structure | # | Structure |
|---|---|---|---|
| 347a | 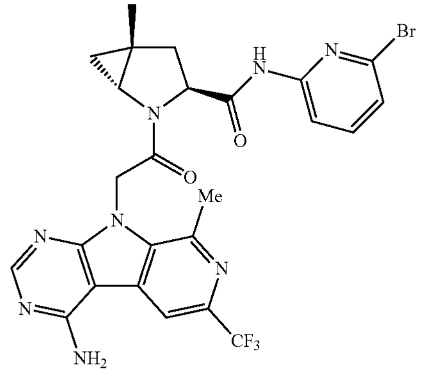 | 254a | 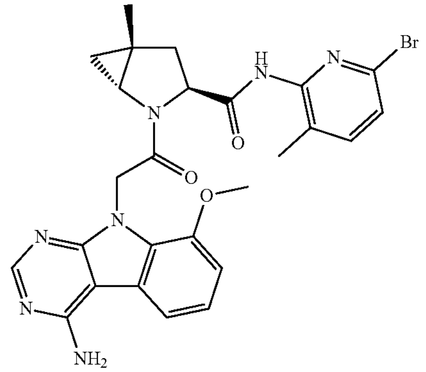 [SMILES: COc1cccc2c3c(N)ncnc3n(CC(=O)N3[C@H](C(=O)Nc4nc(Br)ccc4C)C[C@@]4(C)C[C@@H]34)c12] |
| 339g | 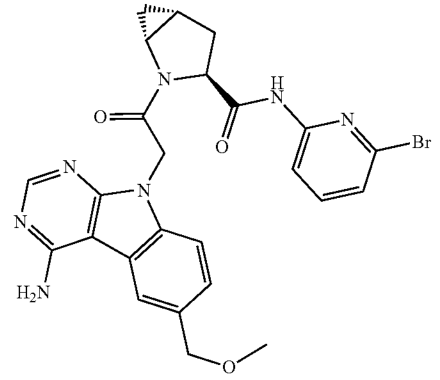 [SMILES: COCc1ccc2c(c1)c1c(N)ncnc1n2CC(=O)N1[C@@H]2C[C@@H]2C[C@H]1C(=O)Nc1cccc(Br)n1] | 263c | 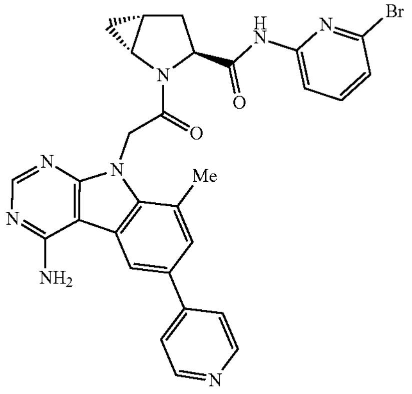 [SMILES: Cc1cc(-c2ccncc2)cc2c3c(N)ncnc3n(CC(=O)N3[C@@H]4C[C@@H]4C[C@H]3C(=O)Nc3cccc(Br)n3)c12] |
| 349c | 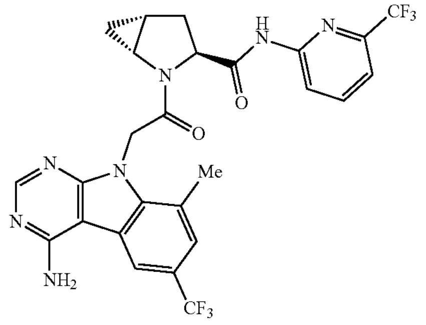 [SMILES: Cc1cc(C(F)(F)F)cc2c3c(N)ncnc3n(CC(=O)N3[C@@H]4C[C@@H]4C[C@H]3C(=O)Nc3cccc(C(F)(F)F)n3)c12] | 272c | 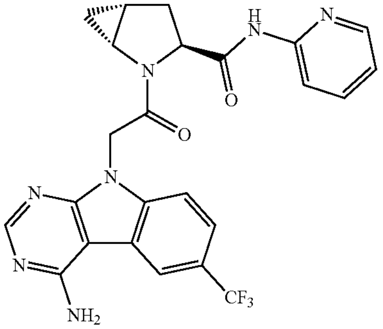 [SMILES: Nc1ncnc2c1c1cc(C(F)(F)F)ccc1n2CC(=O)N1[C@@H]2C[C@@H]2C[C@H]1C(=O)Nc1ccccn1] |
| 351a | 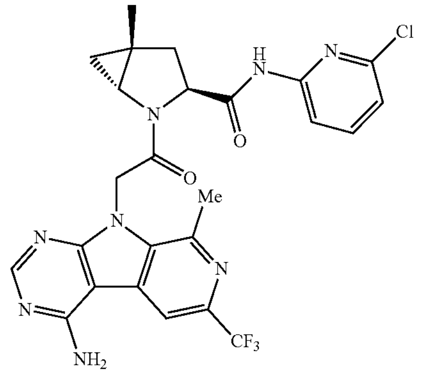 [SMILES: Cc1nc(C(F)(F)F)cc2c3c(N)ncnc3n(CC(=O)N3[C@H](C(=O)Nc4cccc(Cl)n4)C[C@@]4(C)C[C@@H]34)c12] | 255c | 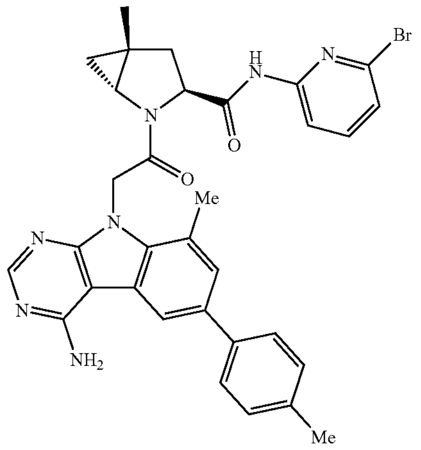 [SMILES: Cc1ccc(-c2cc(C)c3c(c2)c2c(N)ncnc2n3CC(=O)N2[C@H](C(=O)Nc3cccc(Br)n3)C[C@@]3(C)C[C@@H]23)cc1] |

-continued
| # | Structure | # | Structure |
|---|---|---|---|
| 333c | 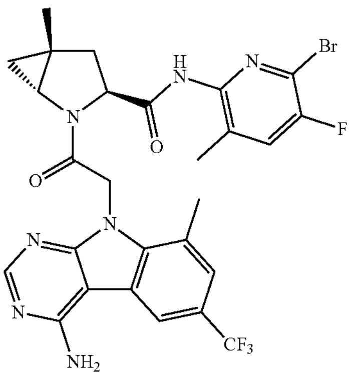 [SMILES: Cc1cc(F)c(Br)nc1NC(=O)[C@@H]1C[C@@]2(C)C[C@H]2N1C(=O)Cn1c2ncnc(N)c2c2cc(C(F)(F)F)cc(C)c21] | 256a | 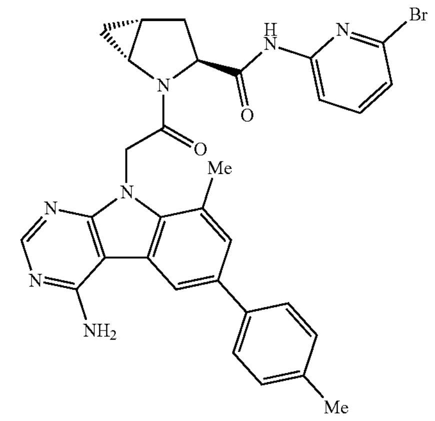 [SMILES: Cc1ccc(-c2cc(C)c3c(c2)c2c(N)ncnc2n3CC(=O)N2[C@@H]3C[C@@H]3C[C@H]2C(=O)Nc2cccc(Br)n2)cc1] |
| 366c | 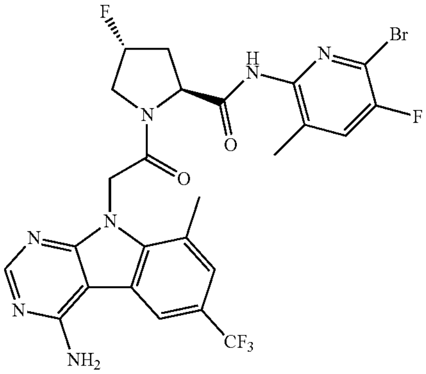 [SMILES: Cc1cc(F)c(Br)nc1NC(=O)[C@@H]1C[C@@H](F)CN1C(=O)Cn1c2ncnc(N)c2c2cc(C(F)(F)F)cc(C)c21] | 273c | 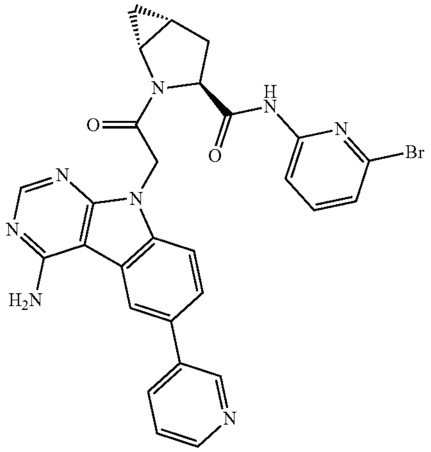 [SMILES: Nc1ncnc2c1c1cc(-c3cccnc3)ccc1n2CC(=O)N1[C@@H]2C[C@@H]2C[C@H]1C(=O)Nc1cccc(Br)n1] |
| 353a | 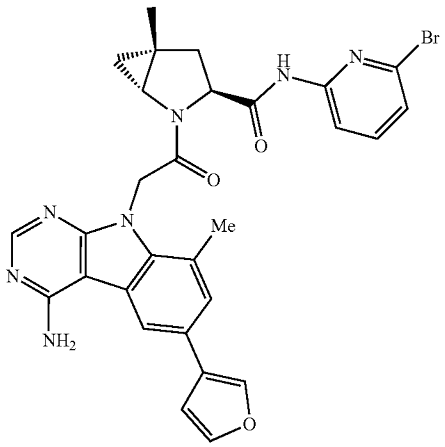 [SMILES: Cc1cc(-c2ccoc2)cc2c3c(N)ncnc3n(CC(=O)N3[C@H](C(=O)Nc4cccc(Br)n4)C[C@@]4(C)C[C@@H]34)c12] | 257g | 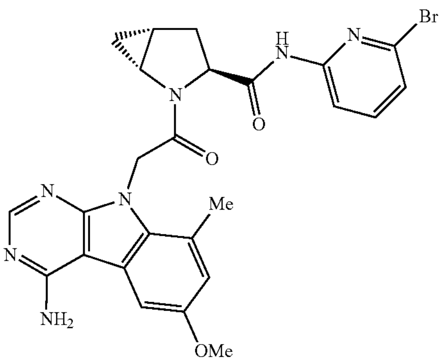 [SMILES: COc1cc(C)c2c(c1)c1c(N)ncnc1n2CC(=O)N1[C@@H]2C[C@@H]2C[C@H]1C(=O)Nc1cccc(Br)n1] |

-continued
| # | Structure | # | Structure |
|---|---|---|---|
| 355a | 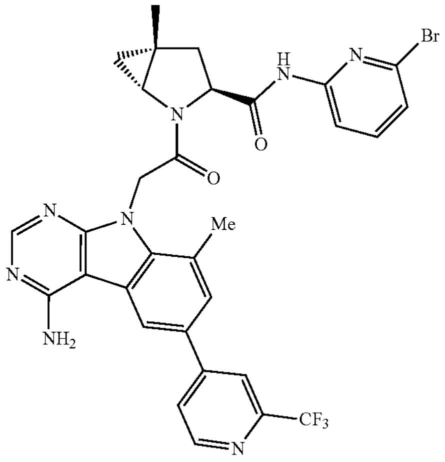 [SMILES: Cc1cc(-c2ccnc(C(F)(F)F)c2)cc2c3c(N)ncnc3n(CC(=O)N3[C@H](C(=O)Nc4cccc(Br)n4)C[C@@]4(C)C[C@@H]34)c12] | 258a | 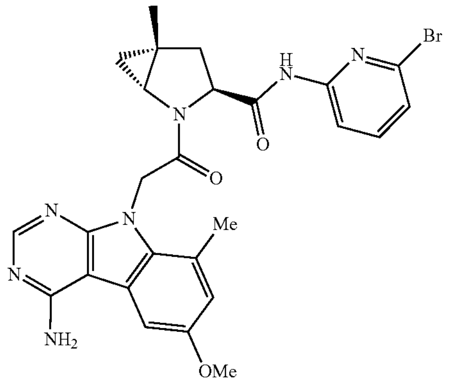 [SMILES: COc1cc(C)c2c(c1)c1c(N)ncnc1n2CC(=O)N1[C@H](C(=O)Nc2cccc(Br)n2)C[C@@]2(C)C[C@@H]12] |
| 341c | 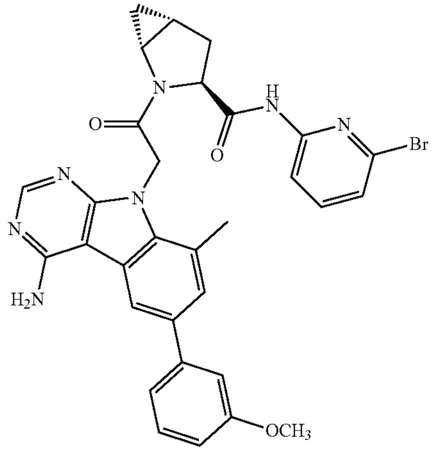 [SMILES: COc1cccc(-c2cc(C)c3c(c2)c2c(N)ncnc2n3CC(=O)N2[C@@H]3C[C@@H]3C[C@H]2C(=O)Nc2cccc(Br)n2)c1] | 259d | 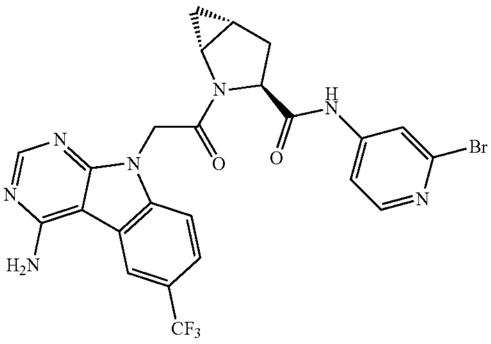 [SMILES: Nc1ncnc2c1c1cc(C(F)(F)F)ccc1n2CC(=O)N1[C@@H]2C[C@@H]2C[C@H]1C(=O)Nc1ccnc(Br)c1] |
| 356c | 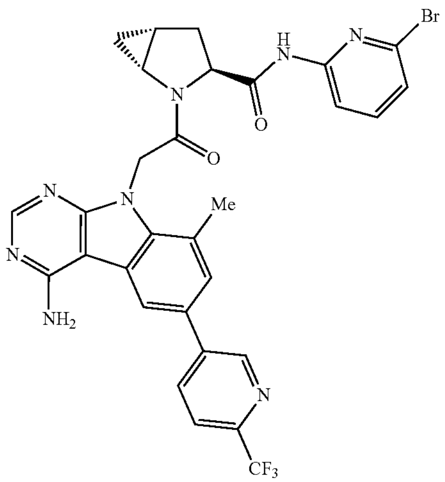 [SMILES: Cc1cc(-c2ccc(C(F)(F)F)nc2)cc2c3c(N)ncnc3n(CC(=O)N3[C@@H]4C[C@@H]4C[C@H]3C(=O)Nc3cccc(Br)n3)c12] | 260a | 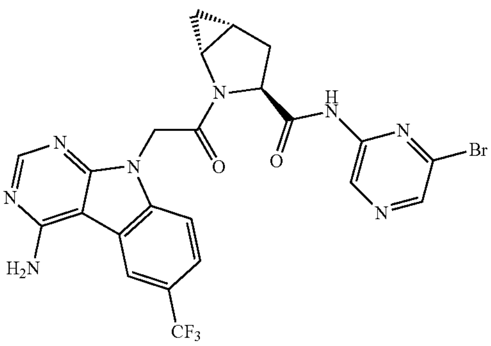 [SMILES: Nc1ncnc2c1c1cc(C(F)(F)F)ccc1n2CC(=O)N1[C@@H]2C[C@@H]2C[C@H]1C(=O)Nc1cncc(Br)n1] |

-continued
| # | Structure | # | Structure |
|---|---|---|---|
| 358c | 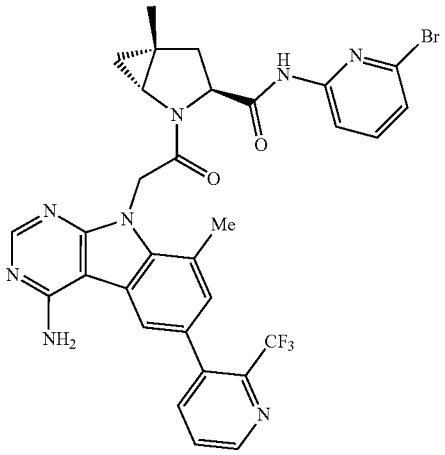 [SMILES: Cc1cc(-c2cccnc2C(F)(F)F)cc2c3c(N)ncnc3n(CC(=O)N3[C@H](C(=O)Nc4cccc(Br)n4)C[C@@]4(C)C[C@@H]34)c12] | 261d | 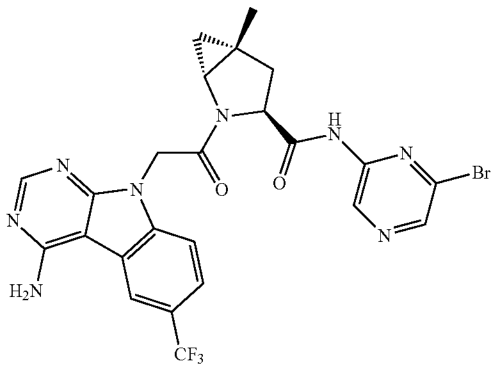 [SMILES: C[C@@]12C[C@@H](C(=O)Nc3cncc(Br)n3)N(C(=O)Cn3c4ccc(C(F)(F)F)cc4c4c(N)ncnc43)[C@@H]1C2] |
| 360c | 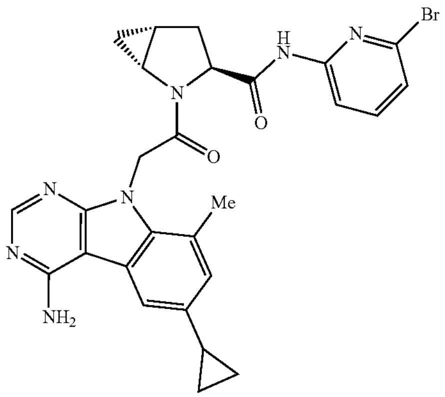 [SMILES: Cc1cc(C2CC2)cc2c3c(N)ncnc3n(CC(=O)N3[C@@H]4C[C@@H]4C[C@H]3C(=O)Nc3cccc(Br)n3)c12] | 262a | 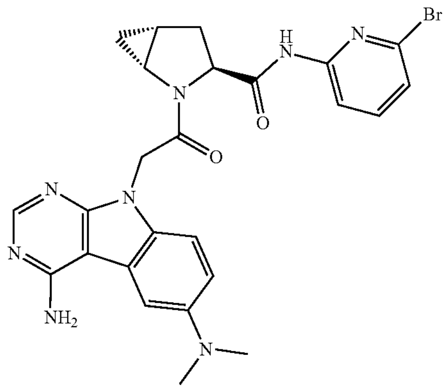 [SMILES: CN(C)c1ccc2c(c1)c1c(N)ncnc1n2CC(=O)N1[C@@H]2C[C@@H]2C[C@H]1C(=O)Nc1cccc(Br)n1] |
| 367g | 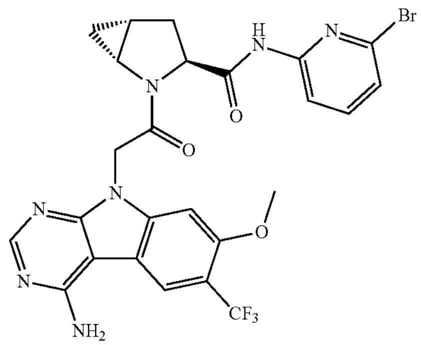 [SMILES: COc1cc2c(cc1C(F)(F)F)c1c(N)ncnc1n2CC(=O)N1[C@@H]2C[C@@H]2C[C@H]1C(=O)Nc1cccc(Br)n1] | 264a | 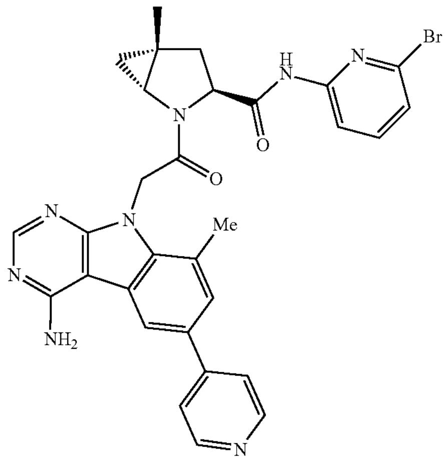 [SMILES: Cc1cc(-c2ccncc2)cc2c3c(N)ncnc3n(CC(=O)N3[C@H](C(=O)Nc4cccc(Br)n4)C[C@@]4(C)C[C@@H]34)c12] |

-continued
| # | Structure | # | Structure |
|---|---|---|---|
| 369g | 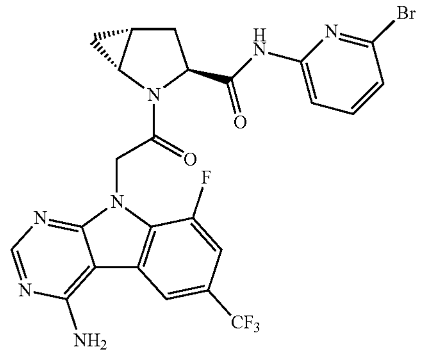 [SMILES: Nc1ncnc2c1c1cc(C(F)(F)F)cc(F)c1n2CC(=O)N1[C@@H]2C[C@@H]2C[C@H]1C(=O)Nc1cccc(Br)n1] | 265a | 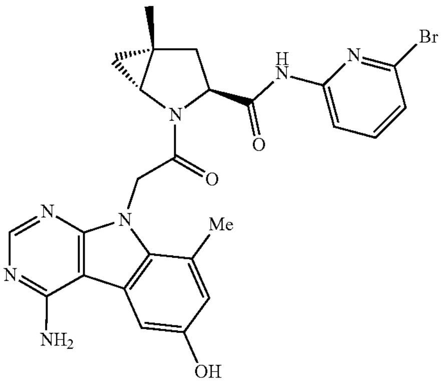 [SMILES: Cc1cc(O)cc2c3c(N)ncnc3n(CC(=O)N3[C@H](C(=O)Nc4cccc(Br)n4)C[C@@]4(C)C[C@@H]34)c12] |
| 363a | 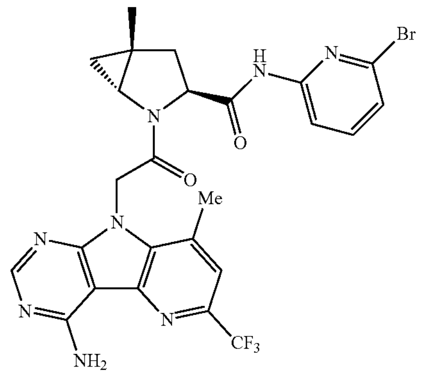 [SMILES: Cc1cc(C(F)(F)F)nc2c3c(N)ncnc3n(CC(=O)N3[C@H](C(=O)Nc4cccc(Br)n4)C[C@@]4(C)C[C@@H]34)c12] | 266b | 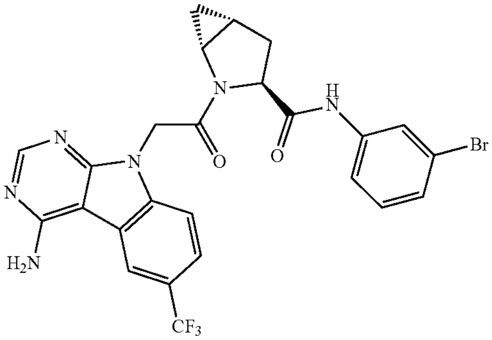 |
| 364d | 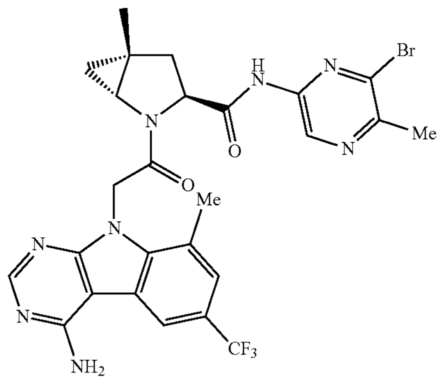 [SMILES: Cc1ncc(NC(=O)[C@@H]2C[C@@]3(C)C[C@H]3N2C(=O)Cn2c3ncnc(N)c3c3cc(C(F)(F)F)cc(C)c32)nc1Br] | 275c | 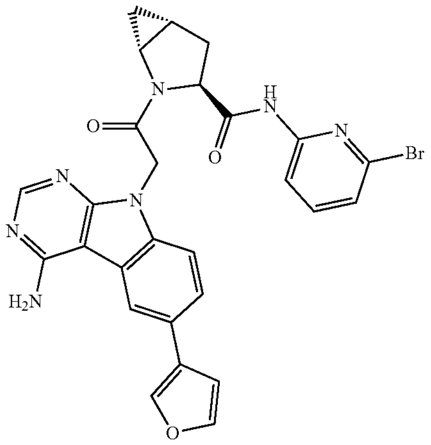 [SMILES: Nc1ncnc2c1c1cc(-c3ccoc3)ccc1n2CC(=O)N1[C@@H]2C[C@@H]2C[C@H]1C(=O)Nc1cccc(Br)n1] |
| 382a | 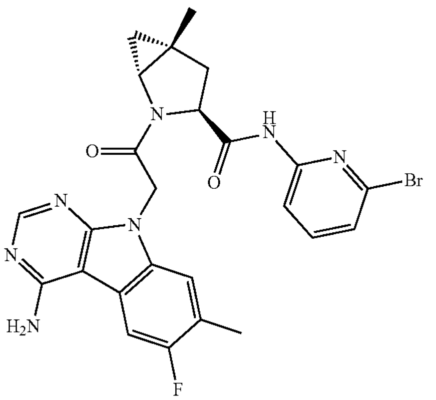 [SMILES: Cc1cc2c(cc1F)c1c(N)ncnc1n2CC(=O)N1[C@H](C(=O)Nc2cccc(Br)n2)C[C@@]2(C)C[C@@H]12] | 284a | 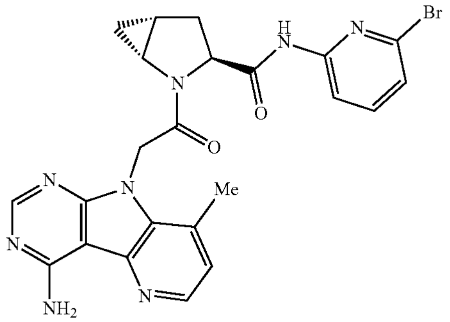 [SMILES: Cc1ccnc2c3c(N)ncnc3n(CC(=O)N3[C@@H]4C[C@@H]4C[C@H]3C(=O)Nc3cccc(Br)n3)c12] |

-continued
| # | Structure | # | Structure |
|---|---|---|---|
| 384g | 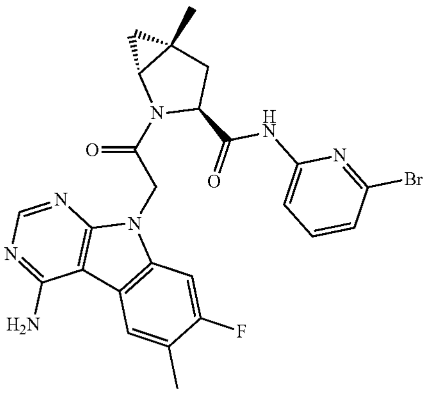 [SMILES: Cc1cc2c3c(N)ncnc3n(CC(=O)N3[C@H](C(=O)Nc4cccc(Br)n4)C[C@@]4(C)C[C@@H]34)c2cc1F] | 285g | 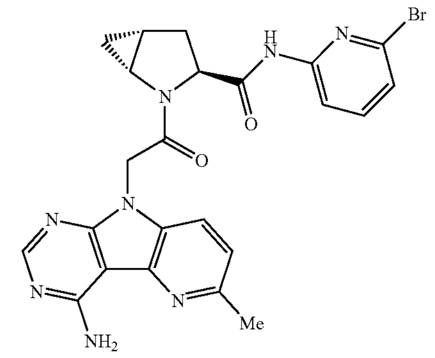 [SMILES: Cc1ccc2c(n1)c1c(N)ncnc1n2CC(=O)N1[C@@H]2C[C@@H]2C[C@H]1C(=O)Nc1cccc(Br)n1] |
| 387a | 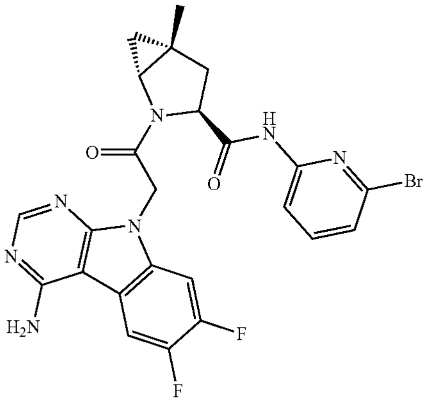 [SMILES: C[C@@]12C[C@@H](C(=O)Nc3cccc(Br)n3)N(C(=O)Cn3c4cc(F)c(F)cc4c4c(N)ncnc43)[C@@H]1C2] | 286a | 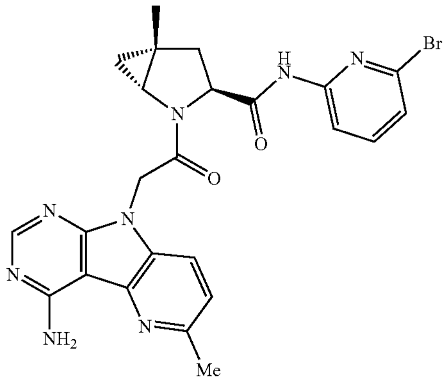 |
| 388a | 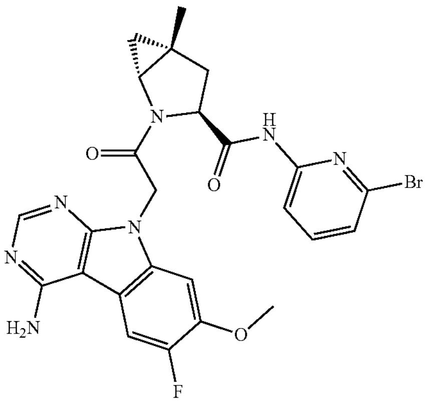 [SMILES: COc1cc2c(cc1F)c1c(N)ncnc1n2CC(=O)N1[C@H](C(=O)Nc2cccc(Br)n2)C[C@@]2(C)C[C@@H]12] | 287a | 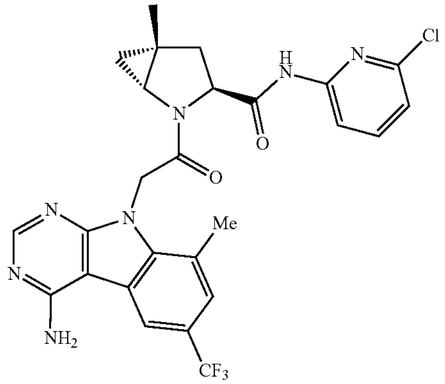 [SMILES: Cc1cc(C(F)(F)F)cc2c3c(N)ncnc3n(CC(=O)N3[C@H](C(=O)Nc4cccc(Cl)n4)C[C@@]4(C)C[C@@H]34)c12] |

-continued
| # | Structure | # | Structure |
|---|---|---|---|
| 390a | 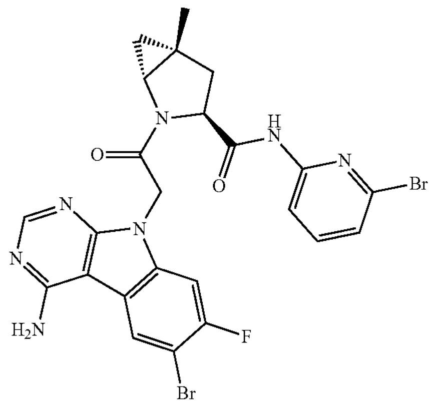 [SMILES: C[C@@]12C[C@@H](C(=O)Nc3cccc(Br)n3)N(C(=O)Cn3c4cc(F)c(Br)cc4c4c(N)ncnc43)[C@@H]1C2] | 288c | 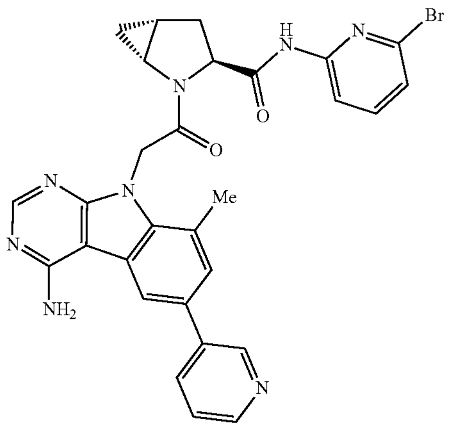 [SMILES: Cc1cc(-c2cccnc2)cc2c3c(N)ncnc3n(CC(=O)N3[C@@H]4C[C@@H]4C[C@H]3C(=O)Nc3cccc(Br)n3)c12] |
| 377a | 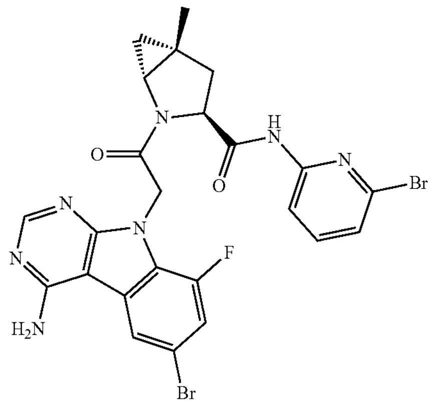 [SMILES: C[C@@]12C[C@@H](C(=O)Nc3cccc(Br)n3)N(C(=O)Cn3c4ncnc(N)c4c4cc(Br)cc(F)c43)[C@@H]1C2] | 289a | 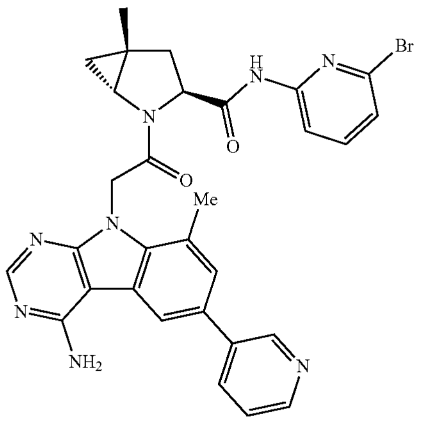 [SMILES: Cc1cc(-c2cccnc2)cc2c3c(N)ncnc3n(CC(=O)N3[C@H](C(=O)Nc4cccc(Br)n4)C[C@@]4(C)C[C@@H]34)c12] |
| 380a | 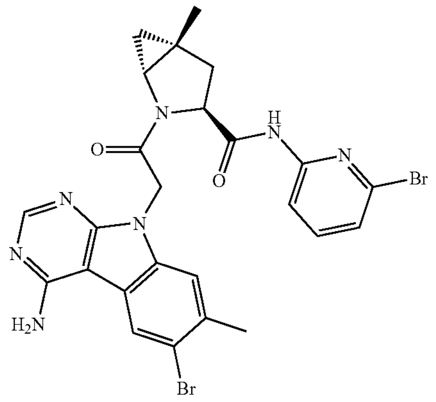 [SMILES: Cc1cc2c(cc1Br)c1c(N)ncnc1n2CC(=O)N1[C@H](C(=O)Nc2cccc(Br)n2)C[C@@]2(C)C[C@@H]12] | 290g | 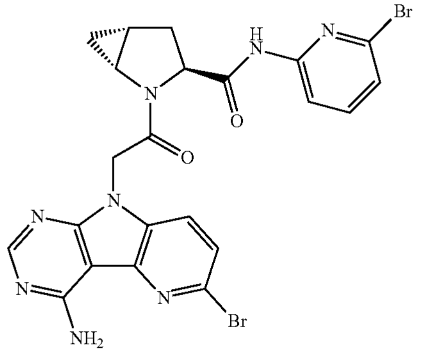 [SMILES: Nc1ncnc2c1c1nc(Br)ccc1n2CC(=O)N1[C@@H]2C[C@@H]2C[C@H]1C(=O)Nc1cccc(Br)n1] |

-continued
| # | Structure | # | Structure |
|---|---|---|---|
| 375a | 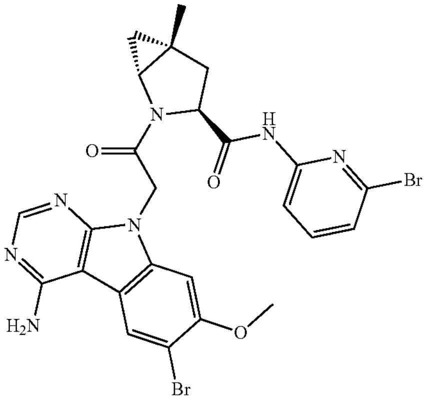 | 291a | 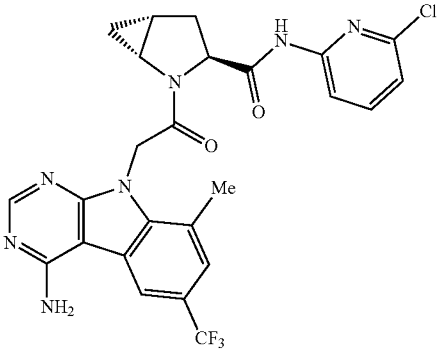 [SMILES: Cc1cc(C(F)(F)F)cc2c3c(N)ncnc3n(CC(=O)N3[C@@H]4C[C@@H]4C[C@H]3C(=O)Nc3cccc(Cl)n3)c12] |
| 392a | 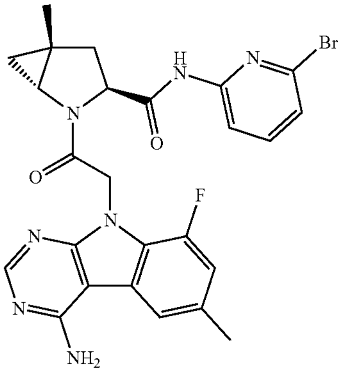 [SMILES: Cc1cc(F)c2c(c1)c1c(N)ncnc1n2CC(=O)N1[C@H](C(=O)Nc2cccc(Br)n2)C[C@@]2(C)C[C@@H]12] | 295a | 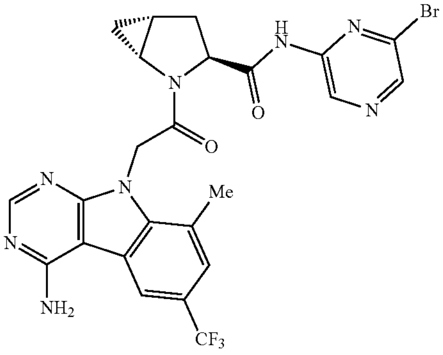 [SMILES: Cc1cc(C(F)(F)F)cc2c3c(N)ncnc3n(CC(=O)N3[C@@H]4C[C@@H]4C[C@H]3C(=O)Nc3cncc(Br)n3)c12] |
| 378c | 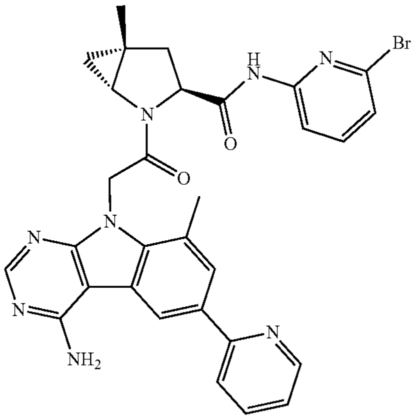 [SMILES: Cc1cc(-c2ccccn2)cc2c3c(N)ncnc3n(CC(=O)N3[C@H](C(=O)Nc4cccc(Br)n4)C[C@@]4(C)C[C@@H]34)c12] | 298c | 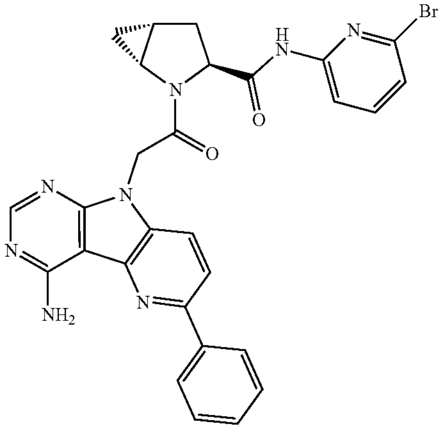 [SMILES: Nc1ncnc2c1c1nc(-c3ccccc3)ccc1n2CC(=O)N1[C@@H]2C[C@@H]2C[C@H]1C(=O)Nc1cccc(Br)n1] |

-continued

| # | Structure | # | Structure |
|---|---|---|---|
| 372a | 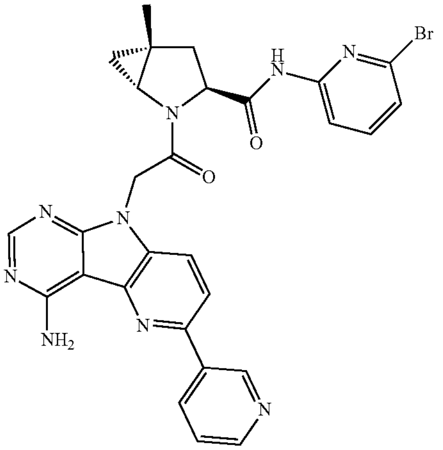 [SMILES: C[C@@]12C[C@@H](C(=O)Nc3cccc(Br)n3)N(C(=O)Cn3c4ccc(-c5cccnc5)nc4c4c(N)ncnc43)[C@@H]1C2] | 300a | 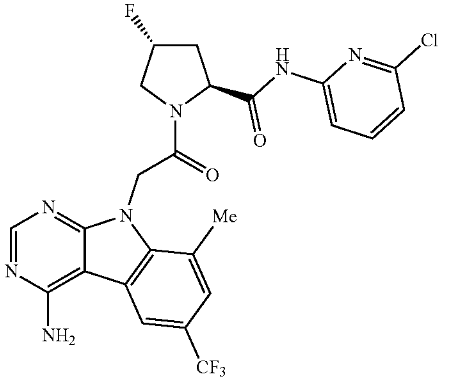 |
| | | 302a | 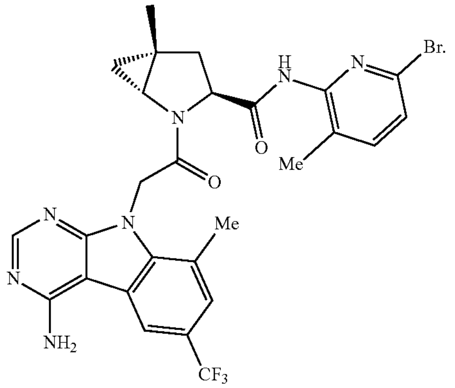 [SMILES: Cc1ccc(Br)nc1NC(=O)[C@@H]1C[C@@]2(C)C[C@H]2N1C(=O)Cn1c2ncnc(N)c2c2cc(C(F)(F)F)cc(C)c21] |

26. A pharmaceutical composition, comprising the compound of claim 1, or a pharmaceutically acceptable salt thereof; and a pharmaceutically acceptable carrier.

27. A method of treating e a disease or condition characterized by aberrant complement system activity, comprising administering to a subject in need thereof a therapeutically effective amount of a compound of claim 1, or a pharmaceutically acceptable salt thereof;

wherein the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, catastrophic antiphospholipid syndrome, adult respiratory distress syndrome, myocardial infarct, lung inflammation, sepsis, cardiopulmonary bypass, burns, asthma, restenosis, multiple organ dysfunction, Guillain-Barré syndrome, hemorrhagic shock, glomerulonephritis, systemic lupus erythematosus, rheumatoid arthritis, infertility, Alzheimer's disease, multiple sclerosis, platelet storage, hemodialysis, antineutrophil cytoplasmic antibody (ANCA)-associated vasculitis (AAV), warm autoimmune hemolytic anemia, IgA nephropathy, C3 glomerulonephritis, focal segmental glomerulosclerosis, macular degeneration, age-related macular degeneration (AMD), wet AMD, geographic atrophy, macular edema, diabetic macular edema, choroidal neovascularization (CNV), uveitis, Behcet's uveitis, proliferative diabetic retinopathy, non-proliferative diabetic retinopathy, glaucoma, hypertensive retinopathy, a corneal neovascularization disease, post-corneal transplant rejection, a corneal dystrophic disease, an autoimmune dry eye disease, Stevens-Johnson syndrome, Sjogren's syndrome, an environmental dry eye disease, Fuchs' endothelial dystrophy, retinal vein occlusion, post-operative inflammation, obesity, insulin resistance, diabetes, dyslipidemia, nephropathy, neuropathy, angioedema, hereditary angioedema or acquired angioedema, thrombotic microangiopathy, generalized myasthenia gravis, Parkinson's disease, schizophrenia, periodontitis, Crohn's disease, chronic obstructive pulmonary disease, acute respiratory distress syndrome, atherosclerosis, C3 glomerulopathy, membranous nephropathy, lupus nephritis, osteoarthritis, bullous pemphigoid, psoriasis, hidradenitis suppurativa, ischemia/reperfusion injury, acute kidney injury, organ transplantation, kidney transplant, systemic inflammatory response syndrome, septic shock, trauma, cancer, antibody-mediated rejection, antiphospholipid syndrome, Berger's disease, delayed graft function, granulomatosis with polyangiitis, graft versus host disease, hematopoietic stem cell transplant-related thrombotic microangiopathy, immune complex-mediated membranoproliferative glomerulonephritis, immune-mediated necrotizing myopathy, idiopathic polypoidal choroidal vasculopathy, microscopic polyangiitis, pyoderma gangrenosum, and Stargardt Disease 1.

28. A compound represented by Formula (I-b), or a pharmaceutically acceptable salt thereof:

(I-b)

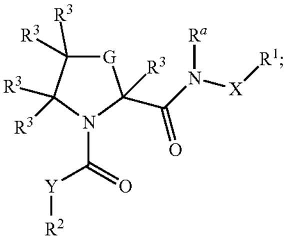

wherein, independently for each occurrence:

X is a bond or $C(R^X)_2$;

Y is a bond, $C(R^Y)_2$, or —$N(R^b)$—;

G is S or $C(R^3)_2$;

$R^a$ and $R^b$ are each independently H or $(C_1\text{-}C_6)$alkyl;

$R^1$ represents optionally substituted aryl or heteroaryl;

$R^2$ represents

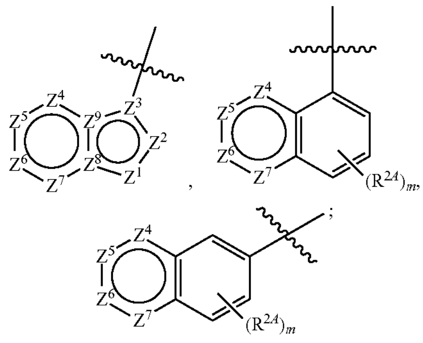

$R^3$ is independently for each occurrence H, halogen, —CN, —$NH_2$, —$CH_2NH_2$, $(C_1\text{-}C_6)$alkoxy or $(C_1\text{-}C_6)$ alkyl; or two vicinal occurrences of $R^3$ taken together with the carbon atoms to which they are bonded form an optionally substituted fused $(C_3\text{-}C_7)$cycloalkyl or $(C_6)$aryl; or two geminal occurrences of $R^3$ taken together with the carbon atom to which they are bonded form an optionally substituted spiro $(C_3\text{-}C_7)$cycloalkyl; or two hominal occurrences of $R^3$ taken together with the carbon atoms to which they are bonded form an optionally substituted bridged $(C_3\text{-}C_7)$cycloalkyl;

$R^X$ is independently for each occurrence H, $(C_1\text{-}C_6)$alkyl, or $(C_3\text{-}C_7)$cycloalkyl;

$R^Y$ is independently for each occurrence H, $(C_1\text{-}C_6)$alkyl, or $(C_3\text{-}C_7)$cycloalkyl;

optional substituents on $R^1$ each independently represent halogen, —CN, —$NO_2$, —$OR^{13}$, —$NR^{13}R^{14}$, —C(O)$R^{13}$, —C(O)$OR^{13}$, —C(O)$NR^{13}R^{14}$, —OC(O)$R^{13}$, —$NR^{13}C(O)R^{14}$, —OC(O)$NR^{13}R^{14}$, —OC(O)$OR^{13}$, —$NR^{13}C(O)OR^{14}$, —$NR^{13}C(O)NR^{13}R^{14}$, —$OS(O)_p(R^{13})$, —$SR^{13}$, —$NR^{13}S(O)_p(R^{14})$, or optionally substituted alkyl, alkenyl, alkynyl, haloalkyl, hydroxyalkyl, alkoxyalkyl, cycloalkoxyalkyl, aryloxyalkyl, aralkyl, heteroaralkyl, heteroaryl, aryl, aryloxy, cycloalkyl, (cycloalkyl)alkyl, heterocycloalkyl, or (heterocycloalkyl)alkyl;

or wherein two substituents on $R^1$, taken together with the intervening atoms, form a ring;

$R^{13}$ and $R^{14}$, independently for each occurrence, represent H or optionally substituted alkyl, haloalkyl, alkenyl, alkynyl, aryl, or heteroaryl;

p is 0, 1, or 2;

$Z^1$ represents N or $CR^{1Z}$;

$Z^2$ represents N or $CR^{2Z}$;

$Z^3$ represents N or C;

$Z^4$ represents N;

$Z^5$ represents N or $CR^{5Z}$;

$Z^6$ represents N;

$Z^7$ represents N or $CR^{7Z}$;

$Z^8$ represents C;

$Z^9$ represents N or C;

$R^{7Z}$ represents —$NR^{13}R^{14}$;

m is an integer selected from 1-3; and each occurrence of $R^{1Z}$, $R^{2Z}$, $R^{5Z}$, and $R^{2A}$ independently represents H, halogen, —CN, —$NO_2$, —$OR^{13}$, —$NR^{13}R^{14}$, —C(O)$R^{13}$, —C(O)$OR^{13}$, —C(O)$NR^{13}R^{14}$, —OC(O)$R^{13}$, —$NR^{13}C(O)R^{14}$, —OC(O)$NR^{13}R^{14}$, —OC(O)$OR^{13}$, —$NR^{13}C(O)OR^{14}$, —$NR^{13}C(O)NR^{13}R^{14}$, —$OS(O)_p(R^{13})$, —$SR^{13}$, —$NR^{13}S(O)_p(R^{14})$, or optionally substituted alkyl, alkenyl, alkynyl, haloalkyl, hydroxyalkyl, alkoxyalkyl, cycloalkoxyalkyl, aryloxyalkyl, aralkyl, heteroaralkyl, heteroaryl, aryl, aryloxy, cycloalkyl, (cycloalkyl)alkyl, heterocycloalkyl, or (heterocycloalkyl)alkyl; or wherein an occurrence of $R^Y$ and an occurrence of $R^{2Z}$ taken together with the intervening atoms form a ring.

29. The compound of claim 28, or a pharmaceutically acceptable salt thereof, selected from the following table:

| # | Structure |
|---|---|
| 75d | 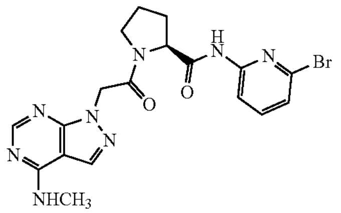 [SMILES: CNc1ncnc2c1cnn2CC(=O)N1CCC[C@H]1C(=O)Nc1cccc(Br)n1] |
| 76b | 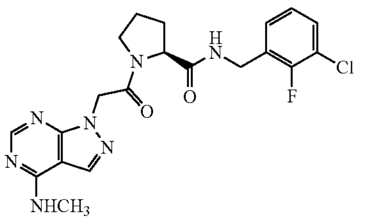 [SMILES: CNc1ncnc2c1cnn2CC(=O)N1CCC[C@H]1C(=O)NCc1cccc(Cl)c1F] |
| 158e | 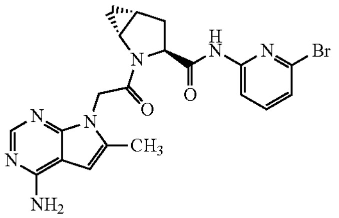 [SMILES: Cc1cc2c(N)ncnc2n1CC(=O)N1[C@@H]2C[C@@H]2C[C@H]1C(=O)Nc1cccc(Br)n1] |

-continued
| # | Structure |
|---|---|
| 77b | 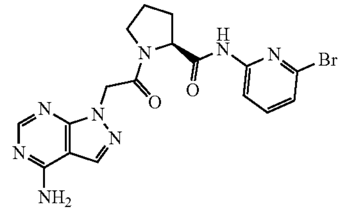 [SMILES: Nc1ncnc2c1cnn2CC(=O)N1CCC[C@H]1C(=O)Nc1cccc(Br)n1] |
| 78a | 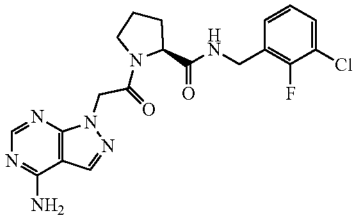 [SMILES: Nc1ncnc2c1cnn2CC(=O)N1CCC[C@H]1C(=O)NCc1cccc(Cl)c1F] |
| 79a | 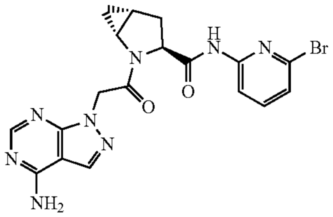 [SMILES: Nc1ncnc2c1cnn2CC(=O)N1[C@@H]2C[C@@H]2C[C@H]1C(=O)Nc1cccc(Br)n1] |
| 81a | 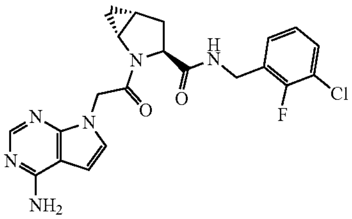 [SMILES: Nc1ncnc2c1ccn2CC(=O)N1[C@@H]2C[C@@H]2C[C@H]1C(=O)NCc1cccc(Cl)c1F] |
| 80a | 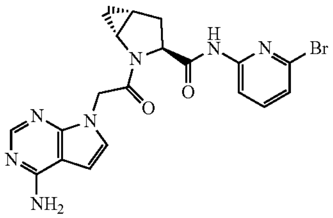 [SMILES: Nc1ncnc2c1ccn2CC(=O)N1[C@@H]2C[C@@H]2C[C@H]1C(=O)Nc1cccc(Br)n1] |
| 82a | 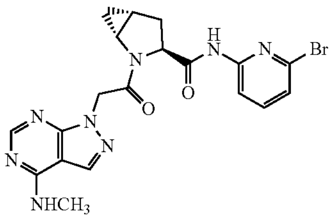 [SMILES: CNc1ncnc2c1cnn2CC(=O)N1[C@@H]2C[C@@H]2C[C@H]1C(=O)Nc1cccc(Br)n1] |
| 86b | 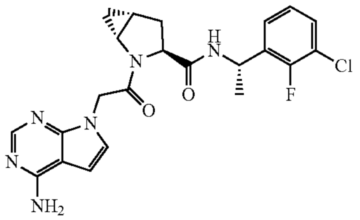 [SMILES: C[C@H](NC(=O)[C@@H]1C[C@H]2C[C@H]2N1C(=O)Cn1ccc2c(N)ncnc21)c1cccc(Cl)c1F] |
-continued
| # | Structure |
|---|---|
| 87f | 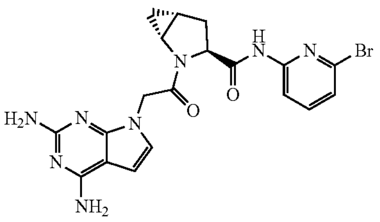 [SMILES: Nc1nc(N)c2ccn(CC(=O)N3[C@@H]4C[C@@H]4C[C@H]3C(=O)Nc3cccc(Br)n3)c2n1] |
| 84a | 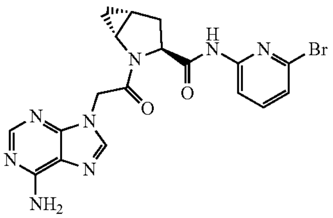 [SMILES: Nc1ncnc2c1ncn2CC(=O)N1[C@@H]2C[C@@H]2C[C@H]1C(=O)Nc1cccc(Br)n1] |
| 90d | 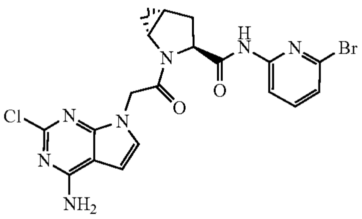 [SMILES: Nc1nc(Cl)nc2c1ccn2CC(=O)N1[C@@H]2C[C@@H]2C[C@H]1C(=O)Nc1cccc(Br)n1] |
| 101b | 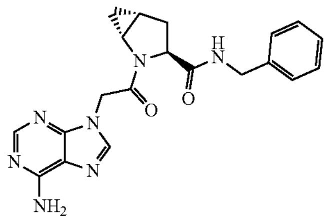 [SMILES: Nc1ncnc2c1ncn2CC(=O)N1[C@@H]2C[C@@H]2C[C@H]1C(=O)NCc1ccccc1] |
| 91a | 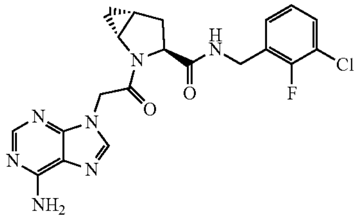 [SMILES: Nc1ncnc2c1ncn2CC(=O)N1[C@@H]2C[C@@H]2C[C@H]1C(=O)NCc1cccc(Cl)c1F] |
| 92b | 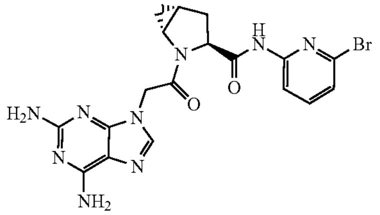 [SMILES: Nc1nc(N)c2ncn(CC(=O)N3[C@@H]4C[C@@H]4C[C@H]3C(=O)Nc3cccc(Br)n3)c2n1] |

-continued
| # | Structure |
|---|---|
| 93a | 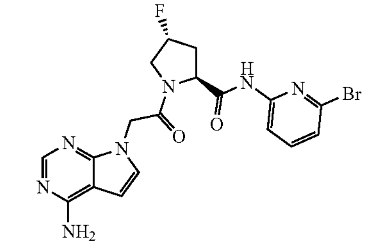 [SMILES: Nc1ncnc2c1ccn2CC(=O)N1C[C@H](F)C[C@H]1C(=O)Nc1cccc(Br)n1] |
| 104a | 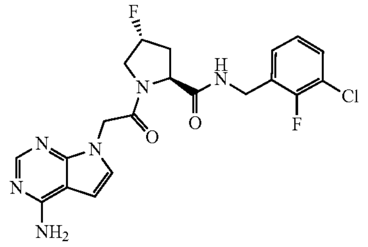 [SMILES: Nc1ncnc2c1ccn2CC(=O)N1C[C@H](F)C[C@H]1C(=O)NCc1cccc(Cl)c1F] |
| 105b | 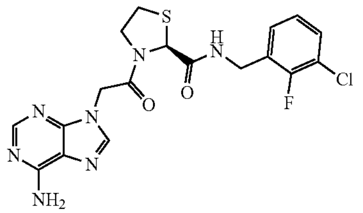 [SMILES: Nc1ncnc2c1ncn2CC(=O)N1CCS[C@H]1C(=O)NCc1cccc(Cl)c1F] |
| 96e | 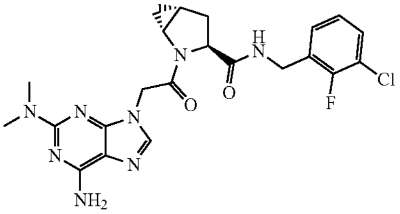 [SMILES: CN(C)c1nc(N)c2ncn(CC(=O)N3[C@@H]4C[C@@H]4C[C@H]3C(=O)NCc3cccc(Cl)c3F)c2n1] |
| 107b | 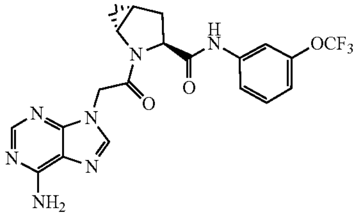 [SMILES: Nc1ncnc2c1ncn2CC(=O)N1[C@@H]2C[C@@H]2C[C@H]1C(=O)Nc1cccc(OC(F)(F)F)c1] |
| 108b | 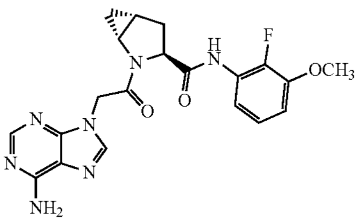 [SMILES: COc1cccc(NC(=O)[C@@H]2C[C@H]3C[C@H]3N2C(=O)Cn2cnc3c(N)ncnc32)c1F] |
-continued
| # | Structure |
|---|---|
| 109e | 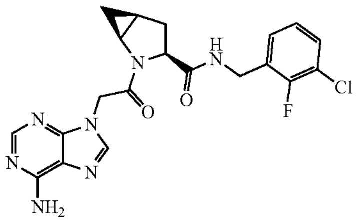 [SMILES: Nc1ncnc2c1ncn2CC(=O)N1[C@H](C(=O)NCc2cccc(Cl)c2F)C[C@@H]2C[C@@H]21] |
| 110d | 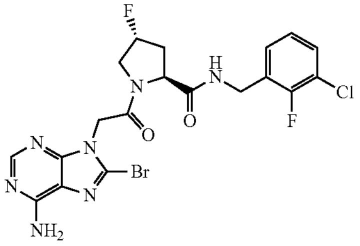 [SMILES: Nc1ncnc2c1nc(Br)n2CC(=O)N1C[C@H](F)C[C@H]1C(=O)NCc1cccc(Cl)c1F] |
| 123g | 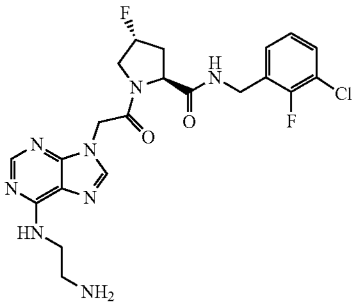 [SMILES: NCCNc1ncnc2c1ncn2CC(=O)N1C[C@H](F)C[C@H]1C(=O)NCc1cccc(Cl)c1F] |
| 112b | 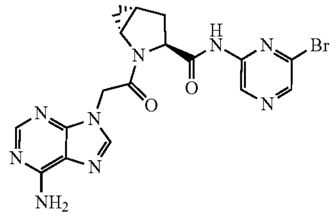 [SMILES: Nc1ncnc2c1ncn2CC(=O)N1[C@@H]2C[C@@H]2C[C@H]1C(=O)Nc1cncc(Br)n1] |
| 118a | 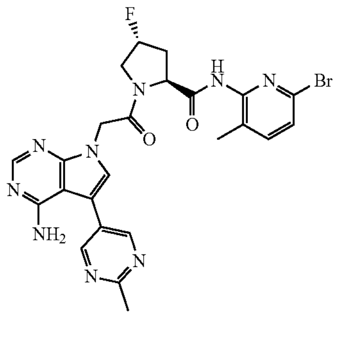 [SMILES: Cc1ncc(-c2cn(CC(=O)N3C[C@H](F)C[C@H]3C(=O)Nc3nc(Br)ccc3C)c3ncnc(N)c23)cn1] |
| 119a | 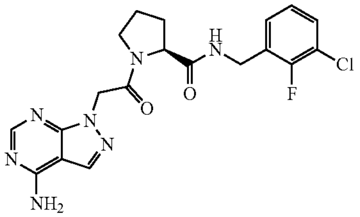 [SMILES: Nc1ncnc2c1cnn2CC(=O)N1CCC[C@H]1C(=O)NCc1cccc(Cl)c1F] |

| # | Structure |
|---|---|
| 117d | 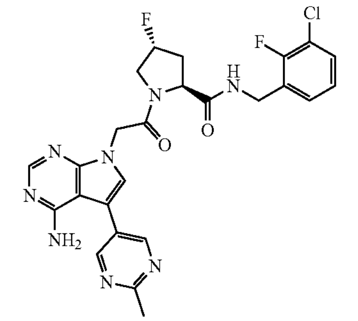 [SMILES: Cc1ncc(-c2cn(CC(=O)N3C[C@H](F)C[C@H]3C(=O)NCc3cccc(Cl)c3F)c3ncnc(N)c23)cn1] |
| 120c | 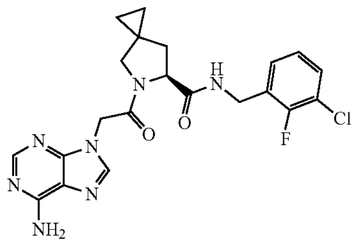 [SMILES: Nc1ncnc2c1ncn2CC(=O)N1CC2(CC2)C[C@H]1C(=O)NCc1cccc(Cl)c1F] |
| 116b | 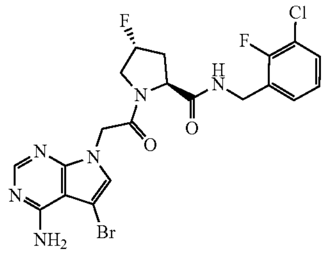 [SMILES: Nc1ncnc2c1c(Br)cn2CC(=O)N1C[C@H](F)C[C@H]1C(=O)NCc1cccc(Cl)c1F] |
| 121d | 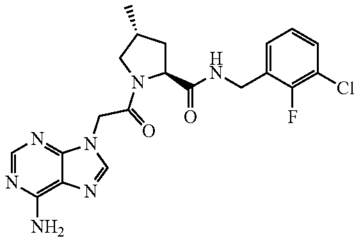 [SMILES: C[C@@H]1C[C@@H](C(=O)NCc2cccc(Cl)c2F)N(C(=O)Cn2cnc3c(N)ncnc32)C1] |
| 115e | 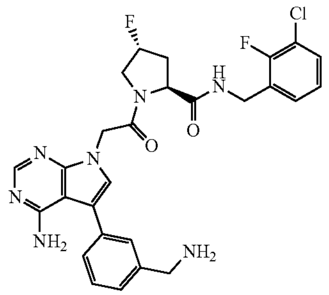 [SMILES: NCc1cccc(-c2cn(CC(=O)N3C[C@H](F)C[C@H]3C(=O)NCc3cccc(Cl)c3F)c3ncnc(N)c23)c1] |
| # | Structure |
|---|---|
| 122c | 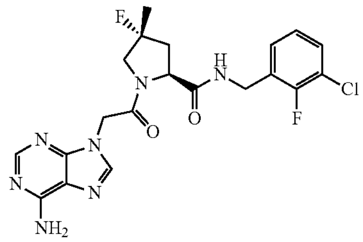 [SMILES: C[C@@]1(F)C[C@@H](C(=O)NCc2cccc(Cl)c2F)N(C(=O)Cn2cnc3c(N)ncnc32)C1] |
| 68a | 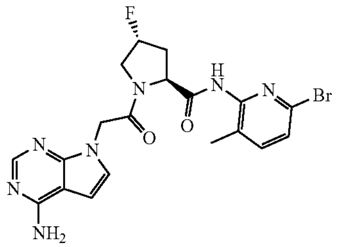 [SMILES: Cc1ccc(Br)nc1NC(=O)[C@@H]1C[C@@H](F)CN1C(=O)Cn1ccc2c(N)ncnc21] |
| 114f | 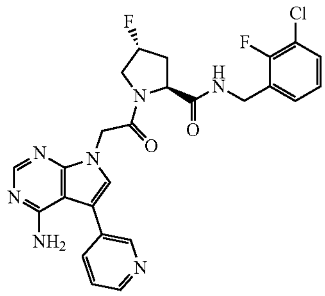 [SMILES: Nc1ncnc2c1c(-c1cccnc1)cn2CC(=O)N1C[C@H](F)C[C@H]1C(=O)NCc1cccc(Cl)c1F] |
| 67c | 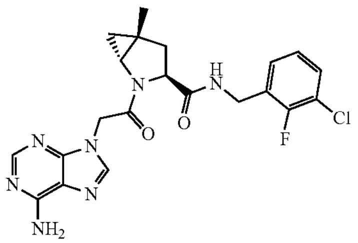 [SMILES: C[C@@]12C[C@@H](C(=O)NCc3cccc(Cl)c3F)N(C(=O)Cn3cnc4c(N)ncnc43)[C@@H]1C2] |
| 113a | 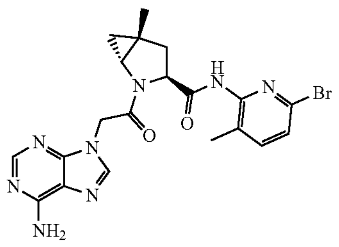 [SMILES: Cc1ccc(Br)nc1NC(=O)[C@@H]1C[C@@]2(C)C[C@H]2N1C(=O)Cn1cnc2c(N)ncnc21] |
| 65a | 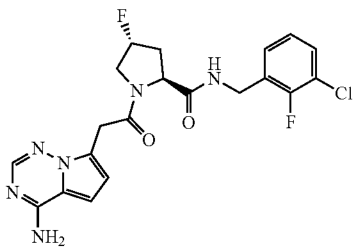 [SMILES: Nc1ncnn2c(CC(=O)N3C[C@H](F)C[C@H]3C(=O)NCc3cccc(Cl)c3F)ccc12] |

-continued
| # | Structure |
|---|---|
| 66b | 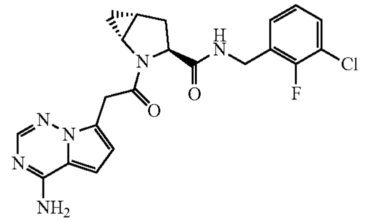 [SMILES: Nc1ncnn2c(CC(=O)N3[C@@H]4C[C@@H]4C[C@H]3C(=O)NCc3cccc(Cl)c3F)ccc12] |
| 64a | 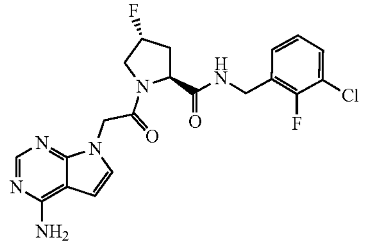 [SMILES: Nc1ncnc2c1ccn2CC(=O)N1C[C@H](F)C[C@H]1C(=O)NCc1cccc(Cl)c1F] |
| 124b | 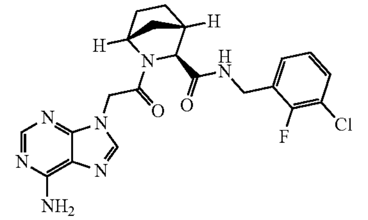 [SMILES: Nc1ncnc2c1ncn2CC(=O)N1[C@@H]2CC[C@@H](C2)[C@H]1C(=O)NCc1cccc(Cl)c1F] |
| 130e | 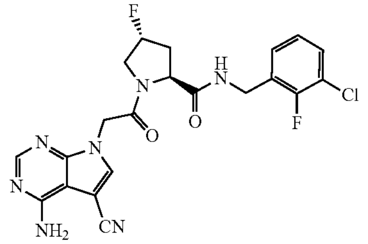 [SMILES: N#Cc1cn(CC(=O)N2C[C@H](F)C[C@H]2C(=O)NCc2cccc(Cl)c2F)c2ncnc(N)c12] |
| 132d | 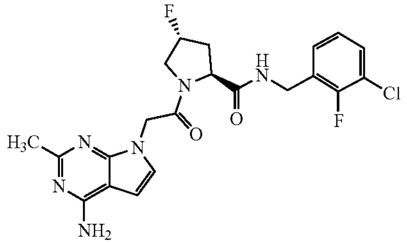 [SMILES: Cc1nc(N)c2ccn(CC(=O)N3C[C@H](F)C[C@H]3C(=O)NCc3cccc(Cl)c3F)c2n1] |
| 133b | 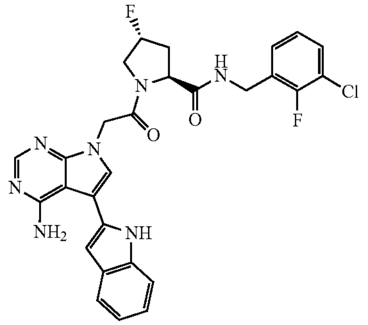 [SMILES: Nc1ncnc2c1c(-c1cc3ccccc3[nH]1)cn2CC(=O)N1C[C@H](F)C[C@H]1C(=O)NCc1cccc(Cl)c1F] |
-continued
| # | Structure |
|---|---|
| 138d | 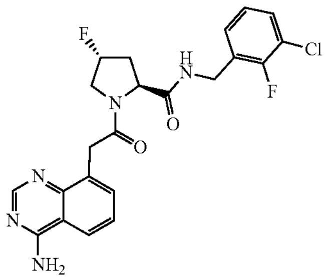 [SMILES: Nc1ncnc2c(CC(=O)N3C[C@H](F)C[C@H]3C(=O)NCc3cccc(Cl)c3F)cccc12] |
| 134b | 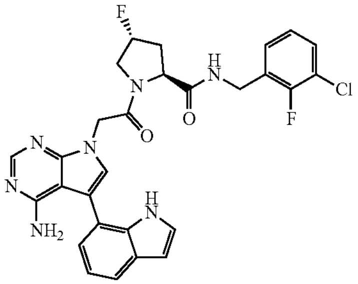 [SMILES: Nc1ncnc2c1c(-c1cccc3cc[nH]c13)cn2CC(=O)N1C[C@H](F)C[C@H]1C(=O)NCc1cccc(Cl)c1F] |
| 139b | 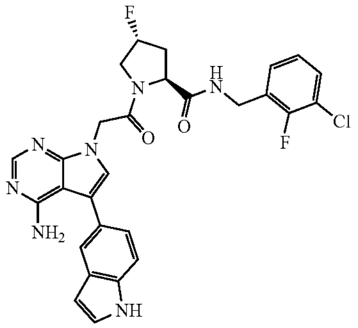 [SMILES: Nc1ncnc2c1c(-c1ccc3[nH]ccc3c1)cn2CC(=O)N1C[C@H](F)C[C@H]1C(=O)NCc1cccc(Cl)c1F] |
| 135a | 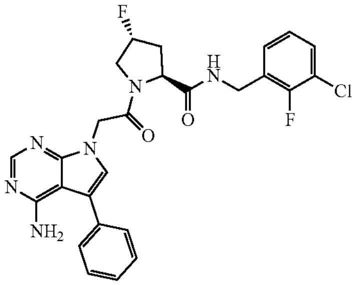 [SMILES: Nc1ncnc2c1c(-c1ccccc1)cn2CC(=O)N1C[C@H](F)C[C@H]1C(=O)NCc1cccc(Cl)c1F] |
| 125d | 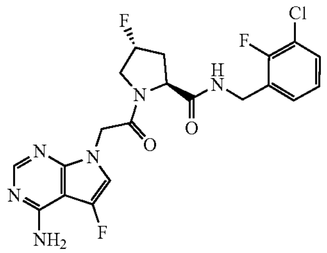 [SMILES: Nc1ncnc2c1c(F)cn2CC(=O)N1C[C@H](F)C[C@H]1C(=O)NCc1cccc(Cl)c1F] |

-continued
| # | Structure |
|---|---|
| 136a | 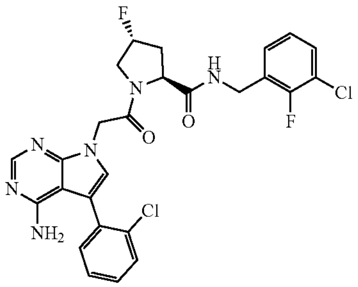 [SMILES: Nc1ncnc2c1c(-c1ccccc1Cl)cn2CC(=O)N1C[C@H](F)C[C@H]1C(=O)NCc1cccc(Cl)c1F] |
| 126f | 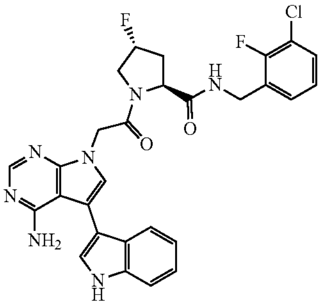 [SMILES: Nc1ncnc2c1c(-c1c[nH]c3ccccc13)cn2CC(=O)N1C[C@H](F)C[C@H]1C(=O)NCc1cccc(Cl)c1F] |
| 137b | 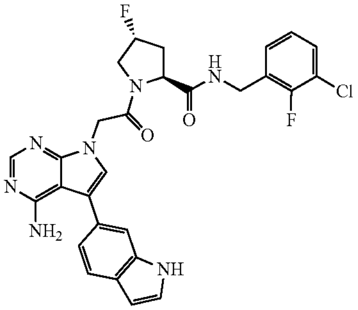 [SMILES: Nc1ncnc2c1c(-c1ccc3cc[nH]c3c1)cn2CC(=O)N1C[C@H](F)C[C@H]1C(=O)NCc1cccc(Cl)c1F] |
| 142d | 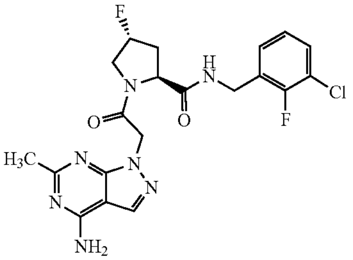 [SMILES: Cc1nc(N)c2cnn(CC(=O)N3C[C@H](F)C[C@H]3C(=O)NCc3cccc(Cl)c3F)c2n1] |
| 140a | 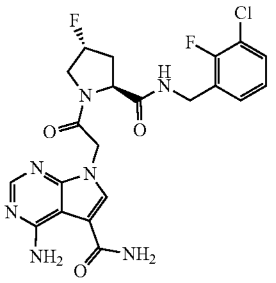 [SMILES: NC(=O)c1cn(CC(=O)N2C[C@H](F)C[C@H]2C(=O)NCc2cccc(Cl)c2F)c2ncnc(N)c12] |
-continued
| # | Structure |
|---|---|
| 143d | 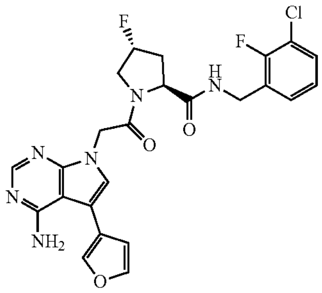 [SMILES: Nc1ncnc2c1c(-c1ccoc1)cn2CC(=O)N1C[C@H](F)C[C@H]1C(=O)NCc1cccc(Cl)c1F] |
| 141a | 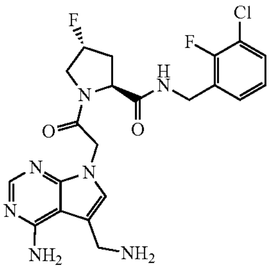 [SMILES: NCc1cn(CC(=O)N2C[C@H](F)C[C@H]2C(=O)NCc2cccc(Cl)c2F)c2ncnc(N)c12] |
| 148d | 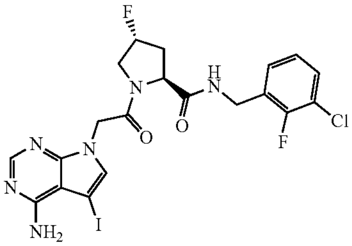 [SMILES: Nc1ncnc2c1c(I)cn2CC(=O)N1C[C@H](F)C[C@H]1C(=O)NCc1cccc(Cl)c1F] |
| 146a | 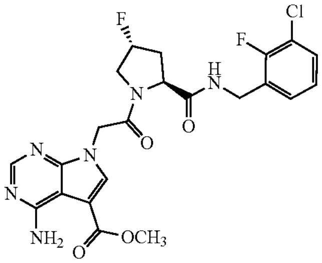 [SMILES: COC(=O)c1cn(CC(=O)N2C[C@H](F)C[C@H]2C(=O)NCc2cccc(Cl)c2F)c2ncnc(N)c12] |
| 149b | 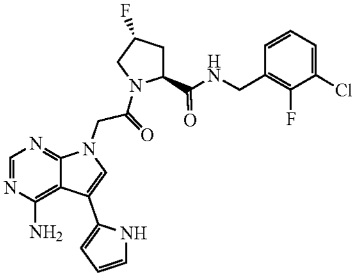 [SMILES: Nc1ncnc2c1c(-c1ccc[nH]1)cn2CC(=O)N1C[C@H](F)C[C@H]1C(=O)NCc1cccc(Cl)c1F] |

-continued
| # | Structure |
|---|---|
| 5e | 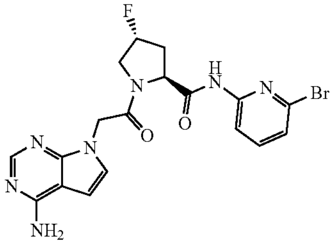 [SMILES: Nc1ncnc2c1ccn2CC(=O)N1C[C@H](F)C[C@H]1C(=O)Nc1cccc(Br)n1] |
| 150d | 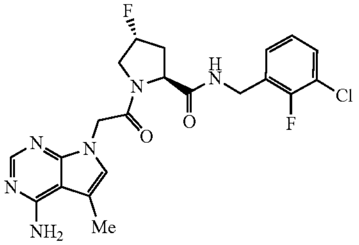 [SMILES: Cc1cn(CC(=O)N2C[C@H](F)C[C@H]2C(=O)NCc2cccc(Cl)c2F)c2ncnc(N)c12] |
| 152d | 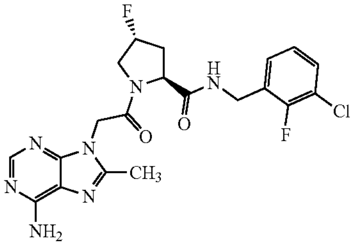 [SMILES: Cc1nc2c(N)ncnc2n1CC(=O)N1C[C@H](F)C[C@H]1C(=O)NCc1cccc(Cl)c1F] |
| 69a | 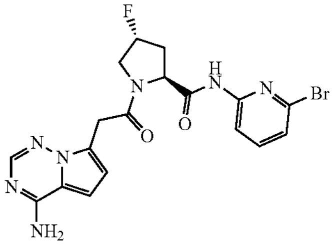 [SMILES: Nc1ncnn2c(CC(=O)N3C[C@H](F)C[C@H]3C(=O)Nc3cccc(Br)n3)ccc12] |
| 153a | 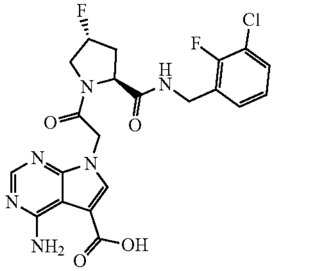 [SMILES: Nc1ncnc2c1c(C(=O)O)cn2CC(=O)N1C[C@H](F)C[C@H]1C(=O)NCc1cccc(Cl)c1F] |
| 70a | 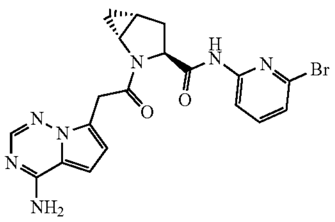 [SMILES: Nc1ncnn2c(CC(=O)N3[C@@H]4C[C@@H]4C[C@H]3C(=O)Nc3cccc(Br)n3)ccc12] |
-continued
| # | Structure |
|---|---|
| 2d | 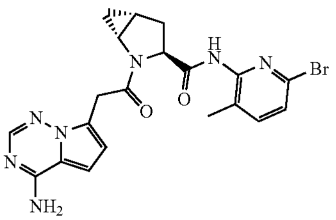 [SMILES: Cc1ccc(Br)nc1NC(=O)[C@@H]1C[C@H]2C[C@H]2N1C(=O)Cc1ccc2c(N)ncnn12] |
| 71a | 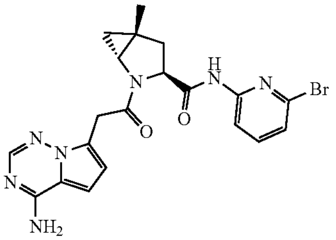 [SMILES: C[C@@]12C[C@@H](C(=O)Nc3cccc(Br)n3)N(C(=O)Cc3ccc4c(N)ncnn34)[C@@H]1C2] |
| 154e | 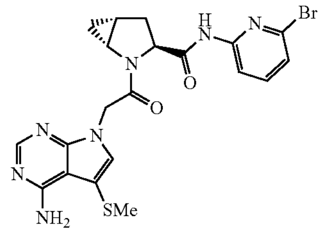 [SMILES: CSc1cn(CC(=O)N2[C@@H]3C[C@@H]3C[C@H]2C(=O)Nc2cccc(Br)n2)c2ncnc(N)c12] |
| 72a | 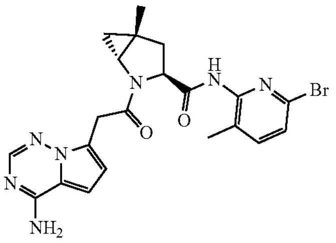 [SMILES: Cc1ccc(Br)nc1NC(=O)[C@@H]1C[C@@]2(C)C[C@H]2N1C(=O)Cc1ccc2c(N)ncnn12] |
| 73a | 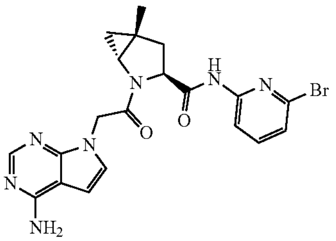 [SMILES: C[C@@]12C[C@@H](C(=O)Nc3cccc(Br)n3)N(C(=O)Cn3ccc4c(N)ncnc43)[C@@H]1C2] |
| 74a | 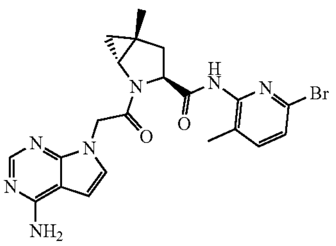 [SMILES: Cc1ccc(Br)nc1NC(=O)[C@@H]1C[C@@]2(C)C[C@H]2N1C(=O)Cn1ccc2c(N)ncnc21] |

-continued

| # | Structure |
| --- | --- |
| 233h | 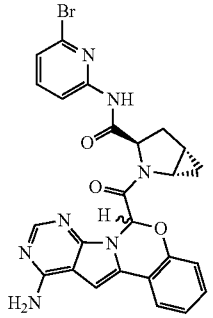 [SMILES: Nc1ncnc2c1cc1n2C(C(=O)N2[C@@H](C(=O)Nc3cccc(Br)n3)C[C@@H]3C[C@@H]32)Oc2ccccc2-1] |
| 293a and 293b | 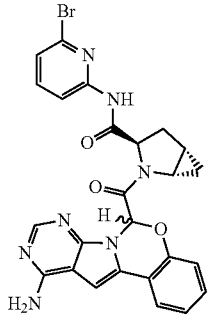 [SMILES: Nc1ncnc2c1cc1n2C(C(=O)N2[C@@H](C(=O)Nc3cccc(Br)n3)C[C@@H]3C[C@@H]32)Oc2ccccc2-1] |

30. The compound of claim 28, wherein Y represents $C(R^Y)_2$.

31. The compound of claim 28, wherein Y represents $CH_2$.

32. The compound of claim 28, wherein X represents a bond.

33. The compound of claim 28, wherein X represents $CH_2$.

34. The compound of claim 28, wherein $R^1$ represents optionally substituted heteroaryl.

35. The compound of claim 28, wherein $R^1$ represents optionally substituted phenyl (e.g., 3-halophenyl, or 2,3-dihalophenyl), pyridinyl (e.g., 6-halopyridin-2-yl), or pyrazinyl (e.g., 6-halopyrazin-2-yl).

36. The compound of claim 28, wherein $R^1$ represents

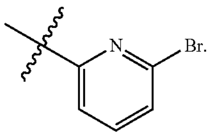 [SMILES: *c1cccc(Br)n1]

37. The compound of claim 28, wherein $R^1$ represents

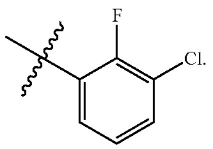 [SMILES: *c1cccc(Cl)c1F]

38. The compound of claim 28, wherein $R^2$ represents

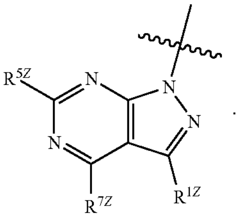

39. The compound of claim 28, wherein $R^2$ represents

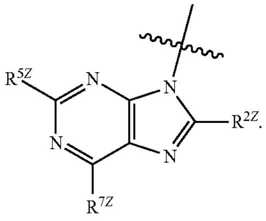

40. The compound of claim 28, wherein $R^2$ represents

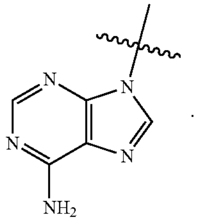

41. The compound of claim 28, wherein $R^2$ represents

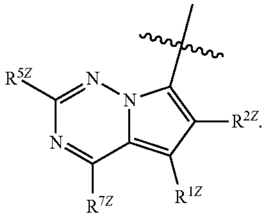

42. The compound of claim 28, wherein $R^2$ represents

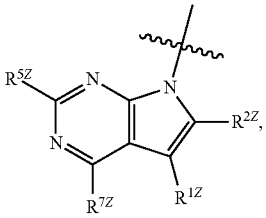

43. The compound of claim 42, wherein $R^2$ represents

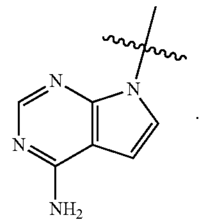 [SMILES: *n1ccc2c(N)ncnc21]

44. The compound of claim 28, wherein $R^{7Z}$ represents $—NH_2$.

45. The compound of claim 28, wherein $R^{5Z}$ represents alkyl, halo, or $—NR^{13}R^{14}$.

46. The compound of claim 28, wherein $R^{1Z}$ represents —CN, halo, haloalkyl, optionally substituted aryl, optionally substituted heteroaryl, optionally substituted alkyl, $—SR^{13}$, $—NR^{13}R^{14}$, $—OR^{13}$, or $—NR^{13}C(O)R^{14}$.

47. The compound of claim 28, wherein each occurrence of $R^{2A}$ independently represents —CN, $—NO_2$, halo, haloalkyl, optionally substituted aryl, optionally substituted heteroaryl, optionally substituted alkyl, optionally substituted alkenyl, optionally substituted hydroxyalkyl, $—C(O)R^{13}$, $—C(O)OR^{13}$, $—NR^{13}C(O)OR^{14}$, $—SR^{13}$, $—NR^{13}R^{14}$, $—OR^{13}$, $—C(O)NR^{13}R^{14}$, or $—NR^{13}C(O)R^{14}$.

48. The compound of claim 28, wherein G is $C(R^3)_2$.

49. The compound of claim 28, having the structure of formula (Ia):

(Ia)

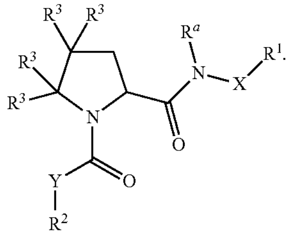

50. The compound of claim 28, wherein two vicinal occurrences of $R^3$ taken together with the carbon atoms to which they are bonded form an optionally substituted fused $C_3$-cycloalkyl.

51. The compound of claim 28, wherein at least one occurrence of $R^3$ is halo.

52. The compound of claim 28, wherein at least one occurrence of $R^3$ is methyl.

53. A pharmaceutical composition, comprising the compound of claim 28, or a pharmaceutically acceptable salt thereof; and a pharmaceutically acceptable carrier.

54. A method of treating a disease or condition characterized by aberrant complement system activity, comprising administering to a subject in need thereof a therapeutically effective amount of a compound of claim 28, or a pharmaceutically acceptable salt thereof;

wherein the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, catastrophic antiphospholipid syndrome, adult respiratory distress syndrome, myocardial infarct, lung inflammation, sepsis, cardiopulmonary bypass, burns, asthma, restenosis, multiple organ dysfunction, Guillain-Barré syndrome, hemorrhagic shock, glomerulonephritis, systemic lupus erythematosus, rheumatoid arthritis, infertility, Alzheimer's disease, multiple sclerosis, platelet storage, hemodialysis, antineutrophil cytoplasmic antibody (ANCA)-associated vasculitis (AAV), warm autoimmune hemolytic anemia, IgA nephropathy, C3 glomerulonephritis, focal segmental glomerulosclerosis, macular degeneration, age-related macular degeneration (AMD), wet AMD, geographic atrophy, macular edema, diabetic macular edema, choroidal neovascularization (CNV), uveitis, Behcet's uveitis, proliferative diabetic retinopathy, non-proliferative diabetic retinopathy, glaucoma, hypertensive retinopathy, a corneal neovascularization disease, post-corneal transplant rejection, a corneal dystrophic disease, an autoimmune dry eye disease, Stevens-Johnson syndrome, Sjogren's syndrome, an environmental dry eye disease, Fuchs' endothelial dystrophy, retinal vein occlusion, post-operative inflammation, obesity, insulin resistance, diabetes, dyslipidemia, nephropathy, neuropathy, angioedema, hereditary angioedema or acquired angioedema, thrombotic microangiopathy, generalized myasthenia gravis, Parkinson's disease, schizophrenia, periodontitis, Crohn's disease, chronic obstructive pulmonary disease, acute respiratory distress syndrome, atherosclerosis, C3 glomerulopathy, membranous nephropathy, lupus nephritis, osteoarthritis, bullous pemphigoid, psoriasis, hidradenitis suppurativa, ischemia/reperfusion injury, acute kidney injury, organ transplantation, kidney transplant, systemic inflammatory response syndrome, septic shock, trauma, cancer, antibody-mediated rejection, antiphospholipid syndrome, Berger's disease, delayed graft function, granulomatosis with polyangiitis, graft versus host disease, hematopoietic stem cell transplant-related thrombotic microangiopathy, immune complex-mediated membranoproliferative glomerulonephritis, immune-mediated necrotizing myopathy, idiopathic polypoidal choroidal vasculopathy, microscopic polyangiitis, pyoderma gangrenosum, and Stargardt Disease 1.

55. A compound or a pharmaceutically acceptable salt thereof, selected from the following table:

| # | Structure |
|---|---|
| 157a | 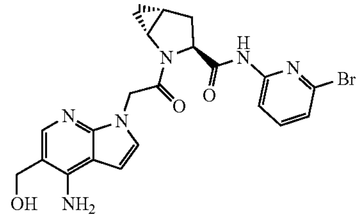 [SMILES: Nc1c(CO)cnc2c1ccn2CC(=O)N1[C@@H]2C[C@@H]2C[C@H]1C(=O)Nc1cccc(Br)n1] |
| 129f | 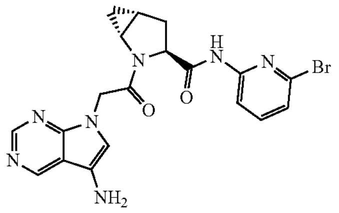 [SMILES: Nc1cn(CC(=O)N2[C@@H]3C[C@@H]3C[C@H]2C(=O)Nc2cccc(Br)n2)c2ncncc12] |

-continued
| # | Structure |
|---|---|
| 156e | 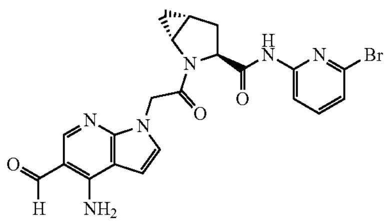 [SMILES: Nc1c(C=O)cnc2c1ccn2CC(=O)N1[C@@H]2C[C@@H]2C[C@H]1C(=O)Nc1cccc(Br)n1] |
| 144g | 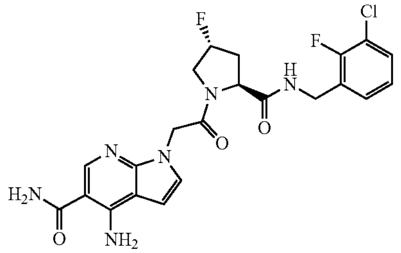 [SMILES: NC(=O)c1cnc2c(ccn2CC(=O)N2C[C@H](F)C[C@H]2C(=O)NCc2cccc(Cl)c2F)c1N] |
| 88f | 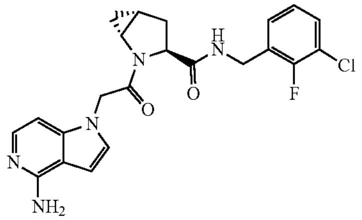 [SMILES: Nc1nccc2c1ccn2CC(=O)N1[C@@H]2C[C@@H]2C[C@H]1C(=O)NCc1cccc(Cl)c1F] |
| 85b | 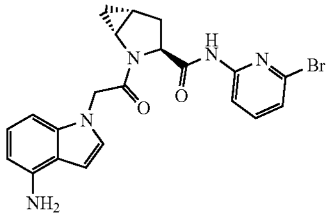 [SMILES: Nc1cccc2c1ccn2CC(=O)N1[C@@H]2C[C@@H]2C[C@H]1C(=O)Nc1cccc(Br)n1] |
| 89b | 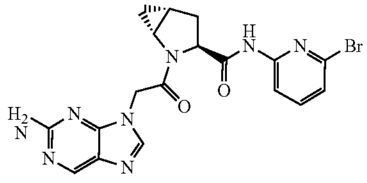 [SMILES: Nc1ncc2ncn(CC(=O)N3[C@@H]4C[C@@H]4C[C@H]3C(=O)Nc3cccc(Br)n3)c2n1] |
| 100b | 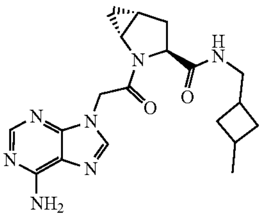 [SMILES: CC1CC(CNC(=O)[C@@H]2C[C@H]3C[C@H]3N2C(=O)Cn2cnc3c(N)ncnc32)C1] |
-continued
| # | Structure |
|---|---|
| 102b | 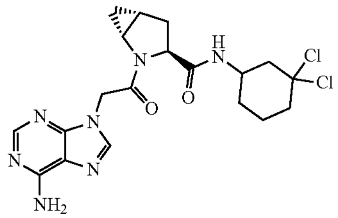 [SMILES: Nc1ncnc2c1ncn2CC(=O)N1[C@@H]2C[C@@H]2C[C@H]1C(=O)NC1CCCC(Cl)(Cl)C1] |
| 94b | 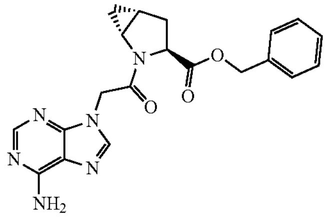 [SMILES: Nc1ncnc2c1ncn2CC(=O)N1[C@@H]2C[C@@H]2C[C@H]1C(=O)OCc1ccccc1] |
| 103b | 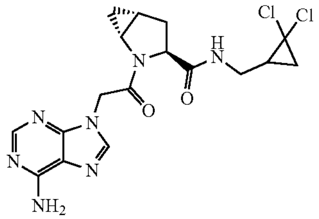 [SMILES: Nc1ncnc2c1ncn2CC(=O)N1[C@@H]2C[C@@H]2C[C@H]1C(=O)NCC1CC1(Cl)Cl] |
| 106b | 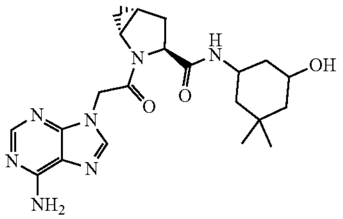 [SMILES: CC1(C)CC(O)CC(NC(=O)[C@@H]2C[C@H]3C[C@H]3N2C(=O)Cn2cnc3c(N)ncnc32)C1] |
| 95c | 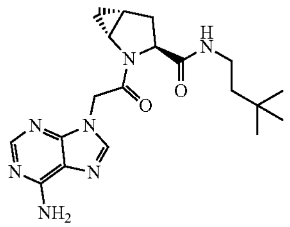 [SMILES: CC(C)(C)CCNC(=O)[C@@H]1C[C@H]2C[C@H]2N1C(=O)Cn1cnc2c(N)ncnc21] |
| 111b | 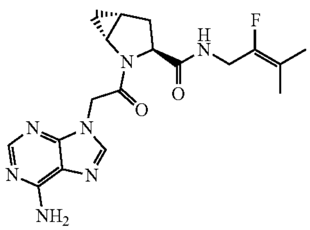 [SMILES: CC(C)=C(F)CNC(=O)[C@@H]1C[C@H]2C[C@H]2N1C(=O)Cn1cnc2c(N)ncnc21] |

| # | Structure |
|---|---|
| 97b | 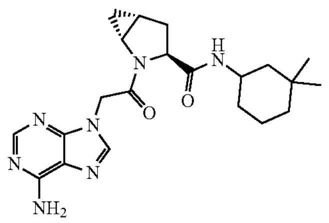 [SMILES: CC1(C)CCCC(NC(=O)[C@@H]2C[C@H]3C[C@H]3N2C(=O)Cn2cnc3c(N)ncnc32)C1] |
| 131e | 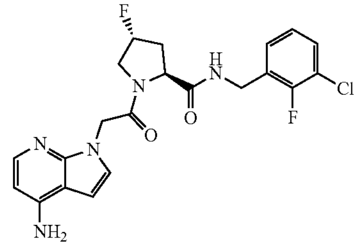 [SMILES: Nc1ccnc2c1ccn2CC(=O)N1C[C@H](F)C[C@H]1C(=O)NCc1cccc(Cl)c1F] |
| 98b | 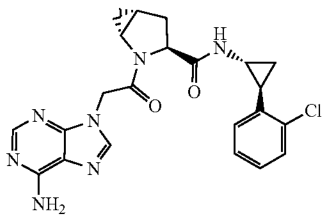 [SMILES: Nc1ncnc2c1ncn2CC(=O)N1[C@@H]2C[C@@H]2C[C@H]1C(=O)N[C@@H]1C[C@H]1c1ccccc1Cl] |
| 147a | 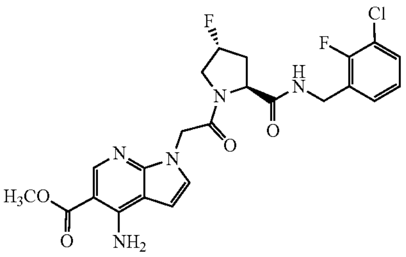 [SMILES: COC(=O)c1cnc2c(ccn2CC(=O)N2C[C@H](F)C[C@H]2C(=O)NCc2cccc(Cl)c2F)c1N] |
| 99b | 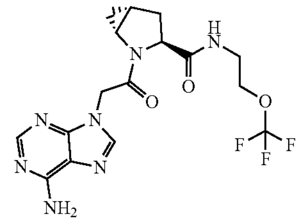 [SMILES: Nc1ncnc2c1ncn2CC(=O)N1[C@@H]2C[C@@H]2C[C@H]1C(=O)NCCOC(F)(F)F] |
| 145a | 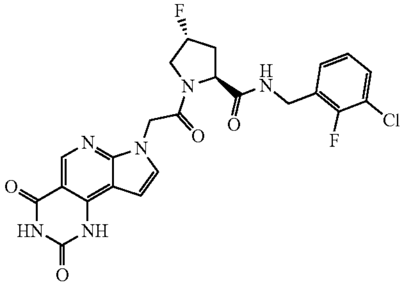 [SMILES: O=C(NCc1cccc(Cl)c1F)[C@@H]1C[C@@H](F)CN1C(=O)Cn1ccc2c3[nH]c(=O)[nH]c(=O)c3cnc21] |
| # | Structure |
|---|---|
| 235a | 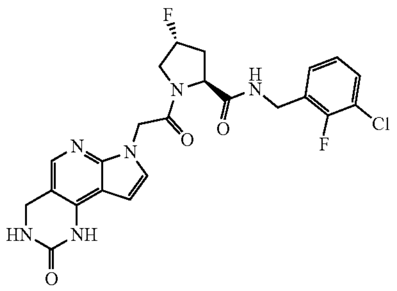 [SMILES: O=C1NCc2cnc3c(ccn3CC(=O)N3C[C@H](F)C[C@H]3C(=O)NCc3cccc(Cl)c3F)c2N1] |
| 151a | 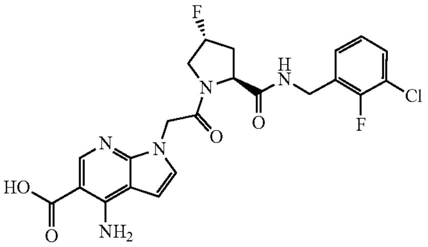 [SMILES: Nc1c(C(=O)O)cnc2c1ccn2CC(=O)N1C[C@H](F)C[C@H]1C(=O)NCc1cccc(Cl)c1F] |
| 127d | 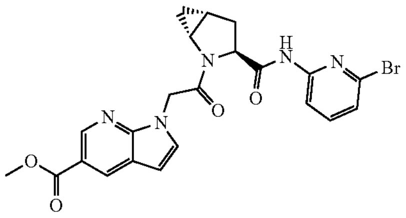 [SMILES: COC(=O)c1cnc2c(ccn2CC(=O)N2[C@@H]3C[C@@H]3C[C@H]2C(=O)Nc2cccc(Br)n2)c1] |
| 128a | 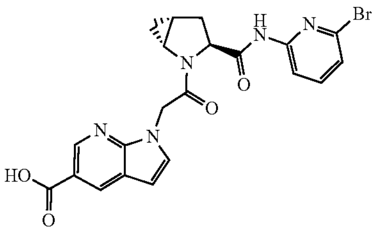 [SMILES: O=C(O)c1cnc2c(ccn2CC(=O)N2[C@@H]3C[C@@H]3C[C@H]2C(=O)Nc2cccc(Br)n2)c1] |
| 155f | 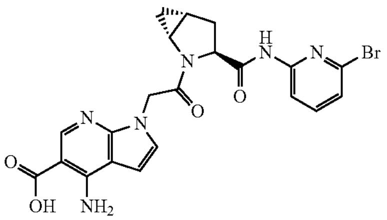 [SMILES: Nc1c(C(=O)O)cnc2c1ccn2CC(=O)N1[C@@H]2C[C@@H]2C[C@H]1C(=O)Nc1cccc(Br)n1] |
| 294c | 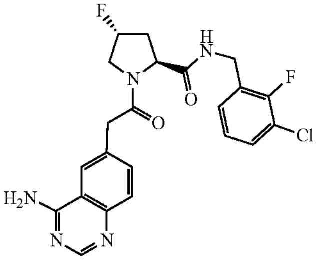 [SMILES: Nc1ncnc2ccc(CC(=O)N3C[C@H](F)C[C@H]3C(=O)NCc3cccc(Cl)c3F)cc12] |

-continued

| # | Structure |
|---|---|
| 83d | 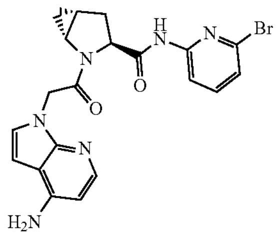 [SMILES: Nc1ccnc2c1ccn2CC(=O)N1[C@@H]2C[C@@H]2C[C@H]1C(=O)Nc1cccc(Br)n1] |
| 251f | 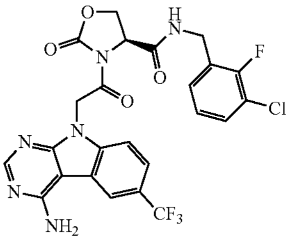 [SMILES: Nc1ncnc2c1c1cc(C(F)(F)F)ccc1n2CC(=O)N1C(=O)OC[C@H]1C(=O)NCc1cccc(Cl)c1F] |

56. A pharmaceutical composition, comprising the compound of claim 55, or a pharmaceutically acceptable salt thereof; and a pharmaceutically acceptable carrier.

57. A method of treating a disease or condition characterized by aberrant complement system activity, comprising administering to a subject in need thereof a therapeutically effective amount of a compound of claim 55, or a pharmaceutically acceptable salt thereof;

wherein the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, catastrophic antiphospholipid syndrome, adult respiratory distress syndrome, myocardial infarct, lung inflammation, sepsis, cardiopulmonary bypass, burns, asthma, restenosis, multiple organ dysfunction, Guillain-Barré syndrome, hemorrhagic shock, glomerulonephritis, systemic lupus erythematosus, rheumatoid arthritis, infertility, Alzheimer's disease, multiple sclerosis, platelet storage, hemodialysis, antineutrophil cytoplasmic antibody (ANCA)-associated vasculitis (AAV), warm autoimmune hemolytic anemia, IgA nephropathy, C3 glomerulonephritis, focal segmental glomerulosclerosis, macular degeneration, age-related macular degeneration (AMD), wet AMD, geographic atrophy, macular edema, diabetic macular edema, choroidal neovascularization (CNV), uveitis, Behcet's uveitis, proliferative diabetic retinopathy, non-proliferative diabetic retinopathy, glaucoma, hypertensive retinopathy, a corneal neovascularization disease, post-corneal transplant rejection, a corneal dystrophic disease, an autoimmune dry eye disease, Stevens-Johnson syndrome, Sjogren's syndrome, an environmental dry eye disease, Fuchs' endothelial dystrophy, retinal vein occlusion, post-operative inflammation, obesity, insulin resistance, diabetes, dyslipidemia, nephropathy, neuropathy, angioedema, hereditary angioedema or acquired angioedema, thrombotic microangiopathy, generalized myasthenia gravis, Parkinson's disease, schizophrenia, periodontitis, Crohn's disease, chronic obstructive pulmonary disease, acute respiratory distress syndrome, atherosclerosis, C3 glomerulopathy, membranous nephropathy, lupus nephritis, osteoarthritis, bullous pemphigoid, psoriasis, hidradenitis suppurativa, ischemia/reperfusion injury, acute kidney injury, organ transplantation, kidney transplant, systemic inflammatory response syndrome, septic shock, trauma, cancer, antibody-mediated rejection, antiphospholipid syndrome, Berger's disease, delayed graft function, granulomatosis with polyangiitis, graft versus host disease, hematopoietic stem cell transplant-related thrombotic microangiopathy, immune complex-mediated membranoproliferative glomerulonephritis, immune-mediated necrotizing myopathy, idiopathic polypoidal choroidal vasculopathy, microscopic polyangiitis, pyoderma gangrenosum, and Stargardt Disease 1.

* * * * *